United States Patent
Gordan et al.

(10) Patent No.: US 12,195,490 B2
(45) Date of Patent: Jan. 14, 2025

(54) STRAD-BINDING AGENTS AND USES THEREOF

(71) Applicants: The Regents of the University of California, Oakland, CA (US); ShangPharma Innovation Inc., South San Francisco, CA (US)

(72) Inventors: John Gordan, San Francisco, CA (US); Dominique Mitchell, San Francisco, CA (US); Richard Beresis, San Francisco, CA (US); Marc Adler, Orinda, CA (US)

(73) Assignees: The Regents of the University of California, Oakland, CA (US); ShangPharma Innovation Inc., South San Francisco, CA (US)

( * ) Notice: Subject to any disclaimer, the term of this patent is extended or adjusted under 35 U.S.C. 154(b) by 67 days.

(21) Appl. No.: 17/161,275

(22) Filed: Jan. 28, 2021

(65) Prior Publication Data
US 2021/0261587 A1    Aug. 26, 2021

Related U.S. Application Data

(60) Provisional application No. 63/028,242, filed on May 21, 2020, provisional application No. 62/967,811, filed on Jan. 30, 2020.

(51) Int. Cl.
| | |
|---|---|
| *C07D 241/26* | (2006.01) |
| *C07D 401/12* | (2006.01) |
| *C07D 403/04* | (2006.01) |
| *C07D 403/10* | (2006.01) |
| *C07D 403/12* | (2006.01) |
| *C07D 405/12* | (2006.01) |
| *C07D 409/04* | (2006.01) |
| *C07D 413/12* | (2006.01) |
| *C07D 417/12* | (2006.01) |
| *C07F 9/6509* | (2006.01) |

(52) U.S. Cl.
CPC ...... *C07F 9/650952* (2013.01); *C07D 241/26* (2013.01); *C07D 401/12* (2013.01); *C07D 403/04* (2013.01); *C07D 403/10* (2013.01); *C07D 403/12* (2013.01); *C07D 405/12* (2013.01); *C07D 409/04* (2013.01); *C07D 413/12* (2013.01); *C07D 417/12* (2013.01)

(58) Field of Classification Search
None
See application file for complete search history.

(56) References Cited

U.S. PATENT DOCUMENTS

| | | |
|---|---|---|
| 8,841,308 B2 | 9/2014 | Charrier et al. |
| 2008/0204608 A1 | 8/2008 | Takano et al. |
| 2010/0160356 A1 | 6/2010 | Heinrich et al. |
| 2012/0122991 A1 | 5/2012 | Cantley et al. |
| 2014/0316137 A1 | 10/2014 | Inouye et al. |
| 2015/0093398 A1 | 4/2015 | Wang et al. |
| 2016/0096824 A1 | 4/2016 | Arnold et al. |
| 2018/0170922 A1 | 6/2018 | Charrier et al. |
| 2018/0339978 A1 | 11/2018 | Brasca et al. |

FOREIGN PATENT DOCUMENTS

| | | |
|---|---|---|
| WO | WO-02/092599 A1 | 11/2002 |
| WO | WO-2005/010174 | 2/2005 |
| WO | WO-2011/029915 A1 | 3/2011 |
| WO | WO-2018/121228 A1 | 7/2017 |
| WO | WO-2021/155004 A1 | 8/2021 |

OTHER PUBLICATIONS

Database Registry Chemical Abstracts Service, Columbus, Ohio, Accession No. RN 1232410-60-4. Entered STN: Jul. 16, 2010.*
Database Registry Chemical Abstracts Service, Columbus, Ohio, Accession No. RN 1232423-21-0. Entered STN: Jul. 16, 2010.*
Database Registry Chemical Abstracts Service, Columbus, Ohio, Accession No. RN 1903809-63-1. Entered STN: May 4, 2016.*
Cokorinos, E.C. et al. (May 2, 2017). "Activation of Skeletal Muscle AMPK Promotes Glucose Disposal and Glucose Lowering in Non-human Primates and Mice," *Cell Metab.* 25(5):1147-1159.
Hammarén, H.M. et al. (2016). "Nucleotide-binding mechanisms in pseudokinases," Bioscience Reports 36(1):e00282.
International Search Report mailed on Apr. 15, 2021, for PCT Application No. PCT/US2021/015503, filed Jan. 28, 2021, 8 pages.
Jeppesen, J. et al. (May 2013). "LKB1 regulates lipid oxidation during exercise independently of AMPK," *Diabetes* 62(5):1490-1499.
Mitchell, D.C. et al. (Jan. 27-31, 2019). "Small molecule activation of LKB1 reveals multiphasic Hippo pathway signal buffering," Keystone Symposium: Signaling Dynamics, 1 page.
Mitchell, D.C. et al. (Aug. 15, 2020). Abstract 5228, "Small molecule activation of the LKB1 tumor suppressor," Poster Presentations—Proffered Abstracts, *Cancer Research* 80(16_Supplement): 5228, 2 pages.
Myers, R.W. et al. (Aug. 4, 2017). "Systemic pan-AMPK activator MK-8722 improves glucose homeostasis but induces cardiac hypertrophy," *Science* 2017 357(6350):507-511.
Written Opinion mailed on Apr. 15, 2021, for PCT Application No. PCT/US2021/015503, filed Jan. 28, 2021, 22 pages.
Zeqiraj, et al. (Dec. 18, 2009). "Structure of the LKB1-STRAD-MO25 complex reveals an allosteric mechanism of kinase activation," *Science* 326(5960):1707-1711.
Zeqiraj, E. et al. (Jun. 2009). "ATP and MO25α Regulate the Conformational State of the STRADα Pseudokinase and Activation of the LKB1 Tumour Suppressor," *PLoS Biology* 7(6):e1000126.
Byrne, D.P. et al. (Jan. 2017). "Pseudokinases: update on their functions and evaluation as new drug targets," *Future Medicinal Chemistry* 9(2):245-265.
Extended European Search Report mailed on Mar. 15, 2024, for EP Patent Application No. 21747178.8, 11 pages.

(Continued)

*Primary Examiner* — Samantha L Shterengarts
(74) *Attorney, Agent, or Firm* — Mintz, Levin, Cohn, Ferris, Glovsky and Popeo, P.C.

(57) ABSTRACT

Disclosed herein, inter alia, are compounds for binding STRAD pseudokinase and uses thereof.

14 Claims, 13 Drawing Sheets

Specification includes a Sequence Listing.

(56) References Cited

OTHER PUBLICATIONS

Widler, L. et al. (Mar. 26, 2001). "7-Alkyl- and 7-Cycloalkyl-5-aryl-pyrrolo[2,3-*d*]pyrimidines—potent inhibitors of the tyrosine kinase c-Src," *Bioorganic & Medicinal Chemistry Letters* 11(6):849-852.

Shaw, R. J. et al. (Dec. 9, 2005). "The kinase LKB1 mediates glucose homeostasis in liver and therapeutic effects of metformin," *Science* 310(5754):1642-1646.

* cited by examiner

SU20668-0197

LKB1 EC50 ~200 uM
LKB1 %Act - 255
Met. Stab. %rem/45min 26%

Metabolism    Cell Cycle    Polarity

STRAD-BINDING AGENTS AND USES THEREOF

CROSS-REFERENCES TO RELATED APPLICATIONS

This application claims the benefit of U.S. Provisional Application No. 62/967,811, filed Jan. 30, 2020, and U.S. Provisional Application No. 63/028,242, filed May 21, 2020, which are incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048536-666001US_Sequence_Listing_ST25.txt, created Jan. 21, 2021, 31,835 bytes, machine format IBM-PC, MS Windows operating system, is hereby incorporated by reference.

BACKGROUND

STRAD pseudokinase is a component of the LKB1-STRAD-MO25 trimer. Binding the STRAD pseudokinase may result in activation of the kinase LKB1. LKB1 is a tumor suppressor in multiple cancers, most notably lung, uterine, pancreatic and various squamous cell cancers. LKB1 activates a diverse signaling response, with effects on cellular metabolism, the hippo tumor suppressor and other regulators of cellular proliferation including p53. Disclosed herein, inter alia, are solutions to these and other problems known in the art.

BRIEF SUMMARY

In an aspect is provided a compound having the formula:

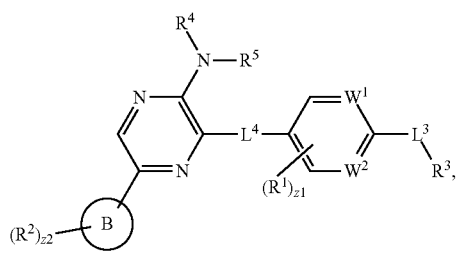

(I)

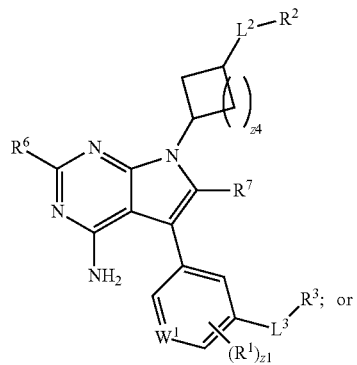

(II)

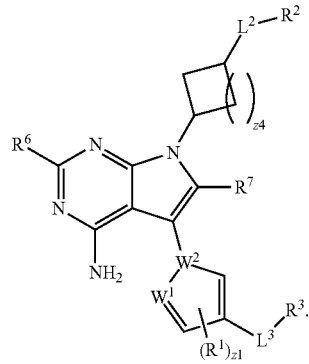

(III)

$W^1$ is N, CH, or $CR^1$.
$W^2$ is N, CH, or $CR^1$.
R is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NR^{1C}R^{1A}R^{1B}$, $-ONR^{1A}R^{1B}$, $-NHC(O)NR^{1C}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl.
z1 is an integer from 0 to 4.
Ring B is aryl or heteroaryl.
$L^2$ is a bond, $-NH-$, $-O-$, $-S-$, $-C(O)-$, $-C(O)NH-$, $-NHC(O)-$, $-NHC(O)NH-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.
$R^2$ is independently oxo, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl.
z2 is an integer from 0 to 6.
$L^3$ is a bond, $-NH-$, $-O-$, $-C(O)-$, $-C(O)NH-$, $-NHC(O)-$, $-NHC(O)NH-$, $-C(O)O-$, $-OC(O)-$, $-S(O)-$, $-SO_2-$, $P(O)-$, $-P(O)_2-$, $-P(S)-$, $-NHSO_2-$, $-SO_2NH-$, $-SO_2CH_2-$, $-SO_2CH_2P(O)-$, substituted or unsubstituted alkylene, or substituted or unsubstituted heteroalkylene.
$R^3$ is independently a polar moiety.
$L^4$ is $-C(O)NH-$ or $-NHC(O)-$.

R$^4$ and R$^5$ are independently hydrogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^4$ and R$^5$ substituents bonded to the same nitrogen may optionally be joined to form a substituted or unsubstituted heterocycloalkyl or substituted or unsubstituted heteroaryl.

R$^6$ is independently hydrogen, halogen, —CX$^6_3$, —CHX$^6_2$, —CH$_2$X$^6$, —OCX$^6_3$, —OCH$_2$X$^6$, —OCHX$^6_2$, —CN, —SO$_{n6}$H, —SO$_{v6}$NH$_2$, —NHNH$_2$, —ONH$_2$, —NHC(O)NHNH$_2$, —NHC(O)NH$_2$, —N(O)$_{m6}$, —NH$_2$, —C(O)H, —COOH, —C(O)NH$_2$, —OH, —NHSO$_2$H, —NHC(O)H, —NHC(O)OH, —NHOH, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^7$ is independently hydrogen halogen, —CX$^7_3$, —CHX$^7_2$, —CH$_2$X$^7$, —OCX$^7_3$, —OCH$_2$X$^7$, —OCHX$^7_2$, —CN, —SO$_{n7}$H, —SO$_{v7}$NH, —NHNH$_2$, —ONH$_2$, —NHC(O)NHNH$_2$, —NHC(O)NH$_2$, —N(O)$_{m7}$, —NH$_2$, —C(O)H, —COOH, —C(O)NH$_2$, —OH, —NHSO$_2$H, —NHC(O)H, —NHC(O)OH, —NHOH, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{1A}$, R$^{1B}$, R$^{1C}$, R$^{1D}$, R$^{2A}$, R$^{2B}$, R$^{2C}$, and R$^{2D}$ are independently hydrogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl.

z4 is 1 or 2.

X$^1$, X$^2$, X$^6$, and X$^7$ are independently —F, —Cl, —Br, or —I.

n1, n2, n6, and n7 are independently an integer from 0 to 4.

m1, m2, v1, v2, m6, v6, m7, and v7 are independently 1 or 2.

In an aspect is provided a pharmaceutical composition including a compound as described herein and a pharmaceutically acceptable excipient.

In an aspect is provided a method of increasing the level of LKB1 activity in a subject, the method including administering a compound as described herein to said subject.

In an aspect is provided a method of increasing the level of LKB1 activity in a cell, the method including contacting the cell with a compound as described herein.

In an aspect is provided a method of increasing the level of AMPK1, AMPK2, BRSK1, BRSK2, MARK1, MARK2, MARK3, MARK4, NUAK1, NUAK2, SIK1, SIK2, SIK3, SNRK, or TP53 activity in a subject, the method including administering a compound as described herein to the subject.

In an aspect is provided a method of decreasing the level of mTOR or cAMP-regulated transcriptional coactivator 2 (CRTC2), transcriptional coactivator 1 (CRTC1), or transcriptional coactivator 3 (CRTC3) activity in a subject, the method including administering a compound as described herein to the subject.

In an aspect is provided a method of increasing the level of Hippo pathway activity in a subject, the method including administering a compound as described herein to the subject.

In an aspect is provided a method of increasing the level of fatty acid oxidation activity in a subject, the method including administering a compound as described herein to the subject.

In an aspect is provided a method of increasing the level of AMPK1, AMPK2, BRSK1, BRSK2, MARK1, MARK2, MARK3, MARK4, NUAK1, NUAK2, SIK1, SIK2, SIK3, SNRK, or TP53 activity in a cell, the method including contacting said cell with a compound as described herein.

In an aspect is provided a method of decreasing the level of mTOR or cAMP-regulated transcriptional coactivator 2 (CRTC2), transcriptional coactivator 1 (CRTC1), or transcriptional coactivator 3 (CRTC3) activity in a cell, the method including contacting the cell with a compound as described herein.

In an aspect is provided a method of increasing the level of Hippo pathway activity in a cell, the method including contacting the cell with a compound as described herein.

In an aspect is provided a method of increasing the level of fatty acid oxidation activity in a cell, the method including contacting the cell with a compound as described herein.

In an aspect is provided a method of treating a cancer in a subject in need thereof, the method including administering to the subject in need thereof an effective amount of a compound as described herein.

In an aspect is provided a method of treating diabetes in a subject in need thereof, the method including administering to the subject in need thereof an effective amount of a compound as described herein.

In an aspect is provided a method of treating a cancer in a subject in need thereof, the method including administering to the subject in need thereof an effective amount of a pseudo-kinase STRADα stabilizing compound, wherein the pseudo-kinase STRADα stabilizing compound binds pseudo-kinase STRADα within the pseudo-kinase STRADα ATP binding pocket.

In an aspect is provided a method of treating diabetes in a subject in need thereof, the method including administering to the subject in need thereof an effective amount of a pseudo-kinase STRADα stabilizing compound, wherein the pseudo-kinase STRADα stabilizing compound binds pseudo-kinase STRADα within the pseudo-kinase STRADα ATP binding pocket.

BRIEF DESCRIPTION OF THE DRAWINGS

FIG. 7A. Cell viability screen performed on 42 cancer cell lines. Sensitivity to treatment with SU-329 was measured after 5 days with Cell Titer-Glo. Sensitivity was stratified by EC50 and depth of response. FIG. 7B. Bar graph of genetic profiles of cancer cell lines sensitive and resistant to LKB1 stimulation. PI3K pathway activity is enriched in sensitive lines and dampened in resistant lines. The terms SU-329 and SU20668-0329-01 refer to the same compound.

DETAILED DESCRIPTION

I. Definitions

Figure 1:
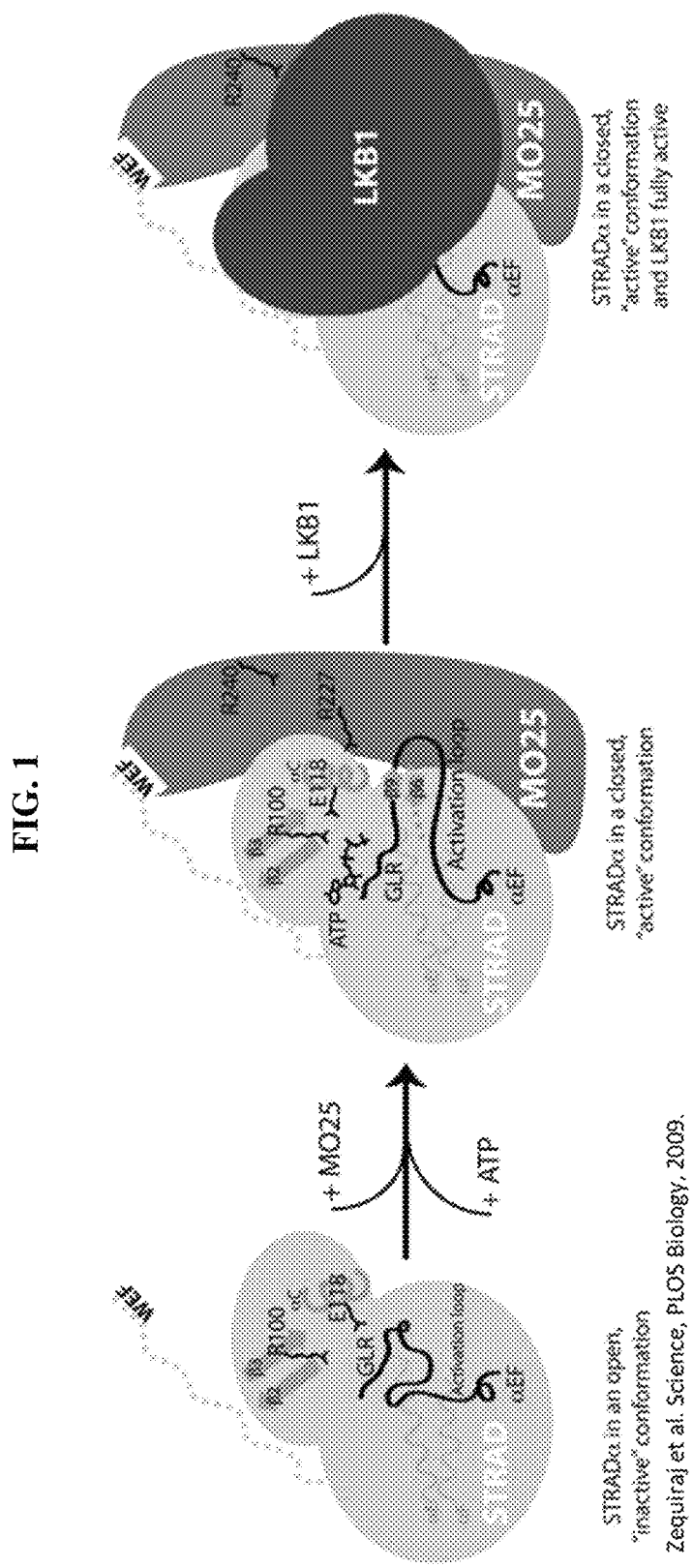
FIG. 1. Targeting STRAD mechanistic overview; The pseudo-kinase STRADα (Ste20-related adaptor, also named LYK5) binds ATP but is not phospho-transfer capable; STRAD activates LKB1 by forming a heterotrimeric complex with LKB1 and the scaffolding protein MO25, the association of STRAD with ATP and MO25 is essential for LKB1 activation wherein the interaction of ATP and MO25 with STRAD directly controls LKB1 activity.
Figure 2:
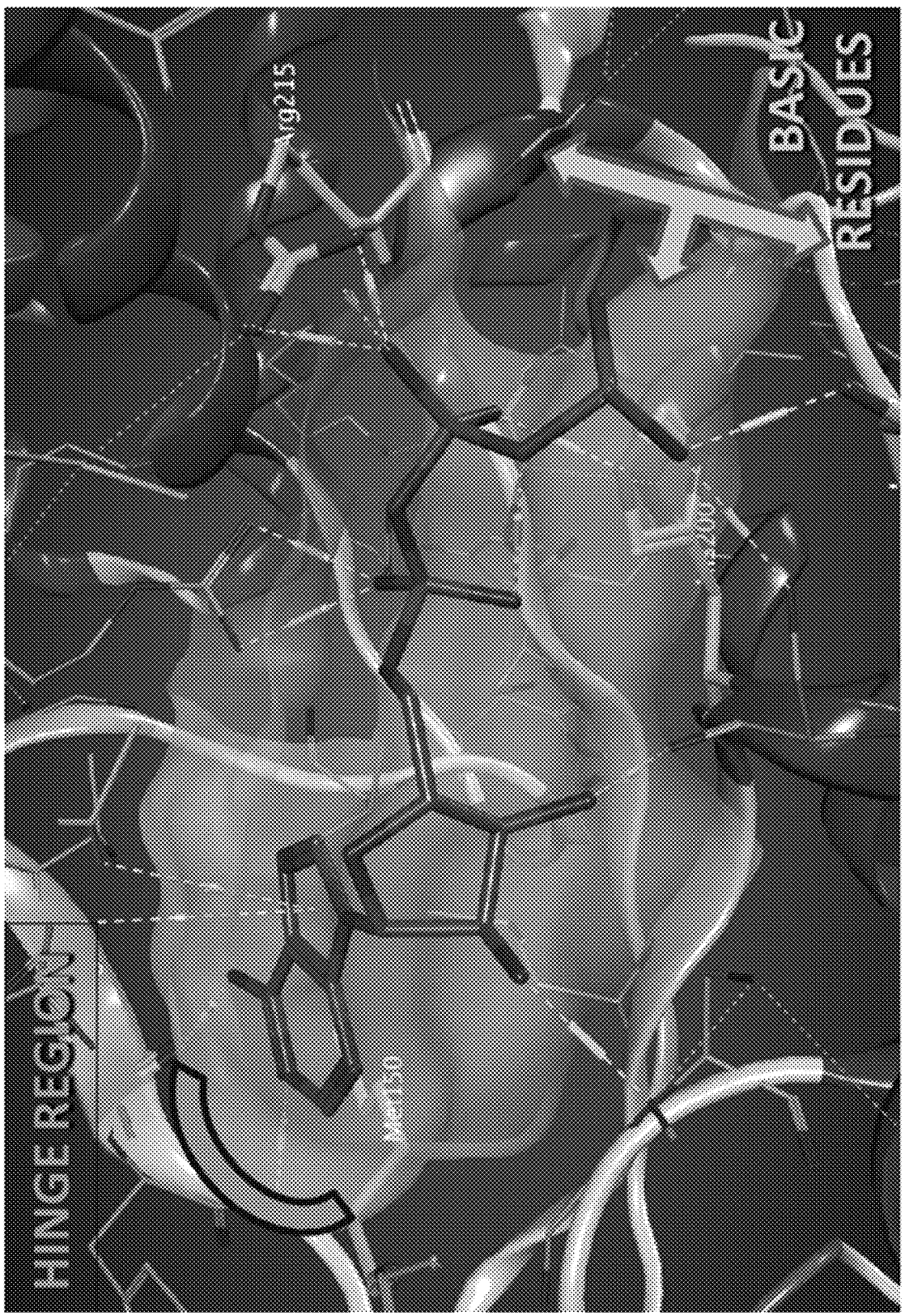
FIG. 2. The pseudo kinase STRAD lacks the key phospho-transfer functioning catalytic residues but maintains good kinase active site shape homology in an Mg ion independent manner. The most striking features are the absence of the highly conserved Asp residue in the Asp-Phe-Gly motif of the kinase domain which is normally key in coordinating ATP phosphate groups as well as the replacement of the catalytic Lysine with an Arginine (van Aalten, 2009, incorporated by reference in its entirety for all purposes). However, the classic Hinge region interaction, ability to bind ATP, and active conformation 3D geometry is maintained thus allowing STRAD to be targeted. Compounds include a Hinge binding region-Core region/linker region-acidic region (for binding basic residues new ATP phosphate binding site).
Figure 2:
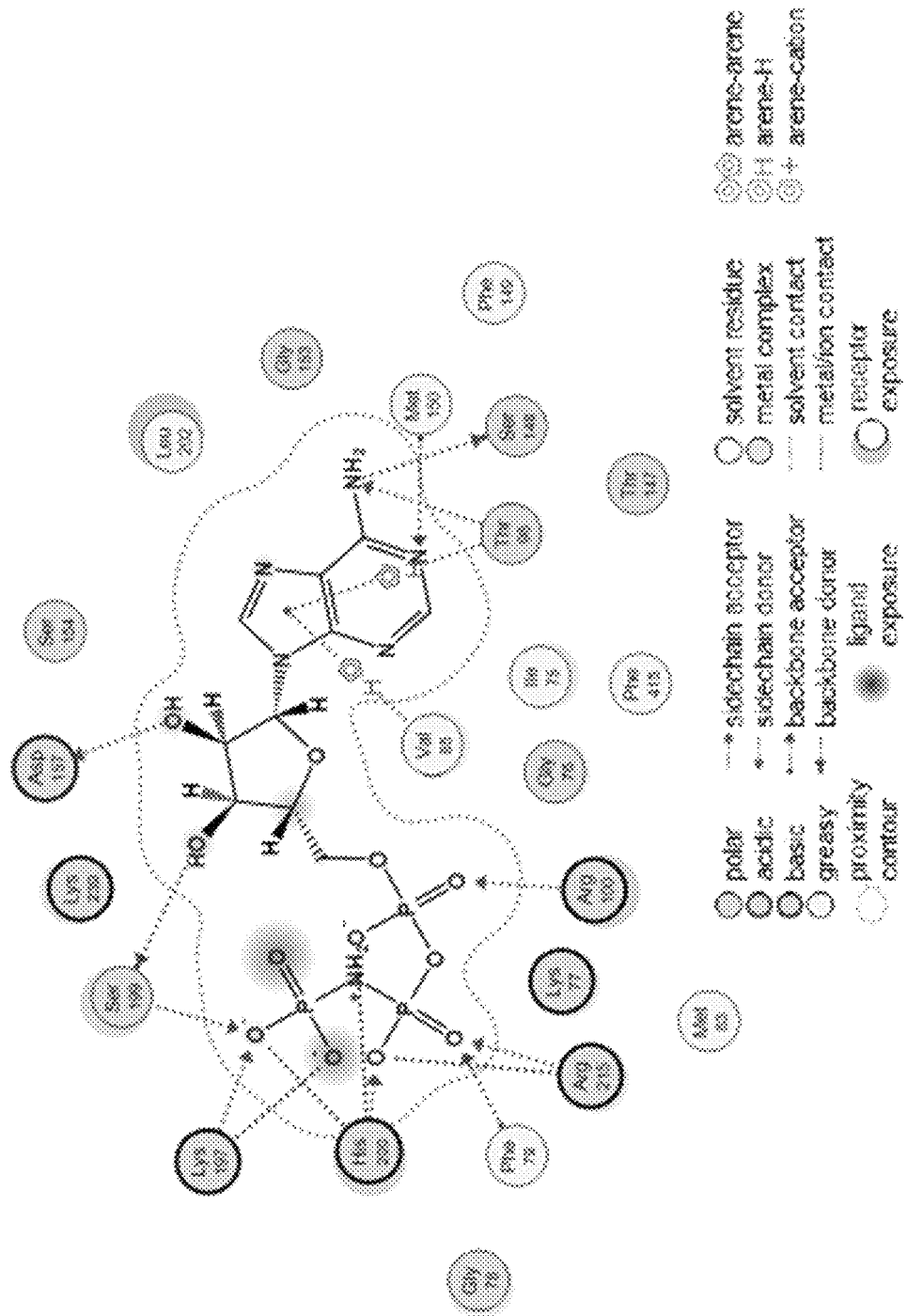
Figure 3:
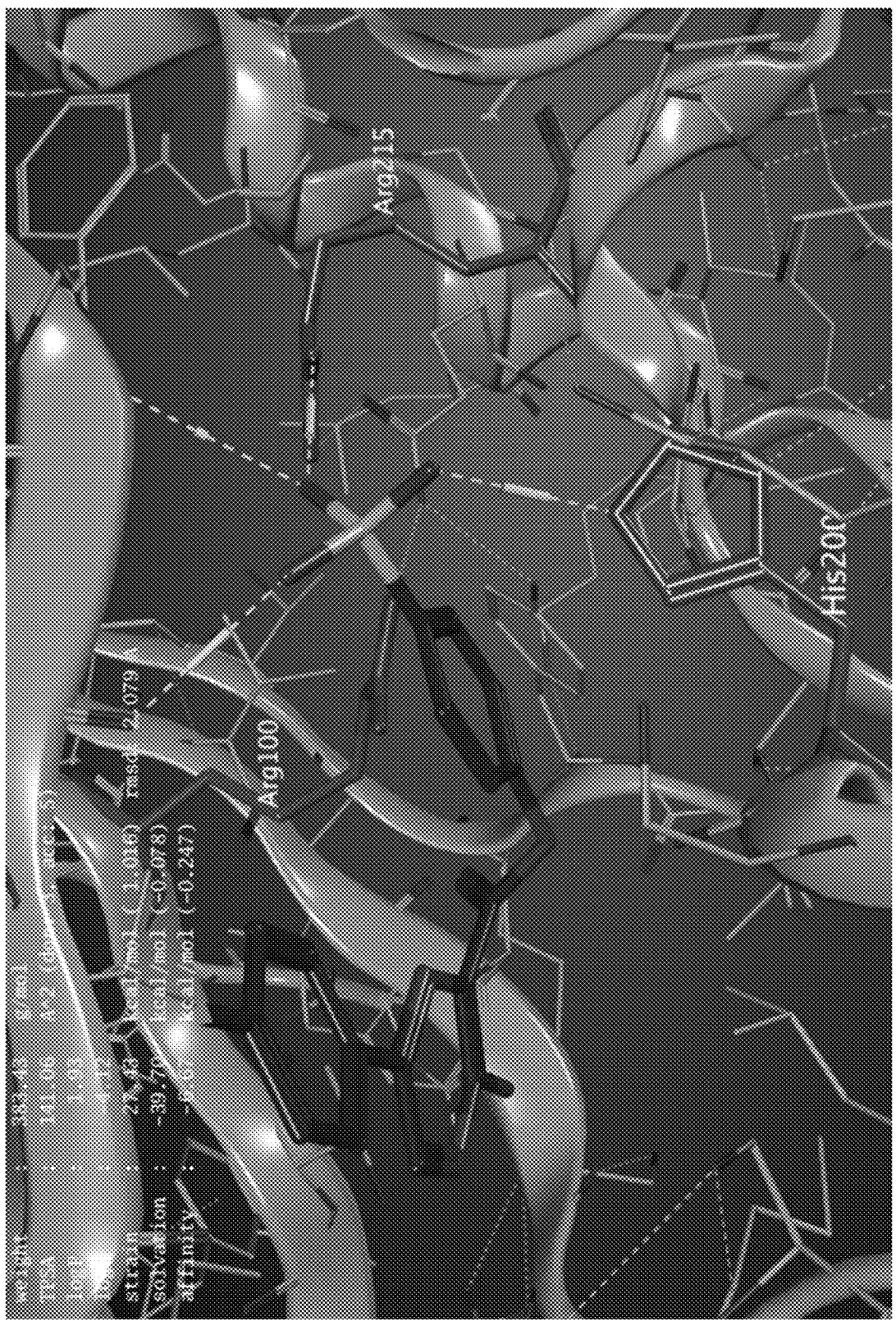
FIG. 3. SU206668-197 is representative of the novel hinge binding functionality identified in the STRAD-kinase ATP binding site homology computational analysis. The terminal Me-phenyl does not clash with Phe415/Phe149 but still fills the hinge-binding region and the sulfonamide is modeled to make beneficial desired interaction with STRAD's unique acidic phosphate-binding residues.
Figure 3:
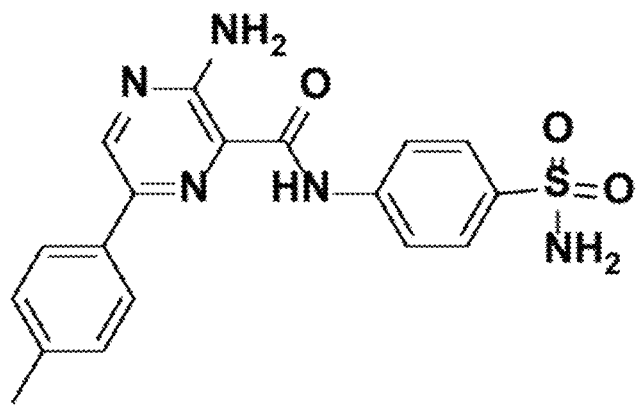
Figure 4:
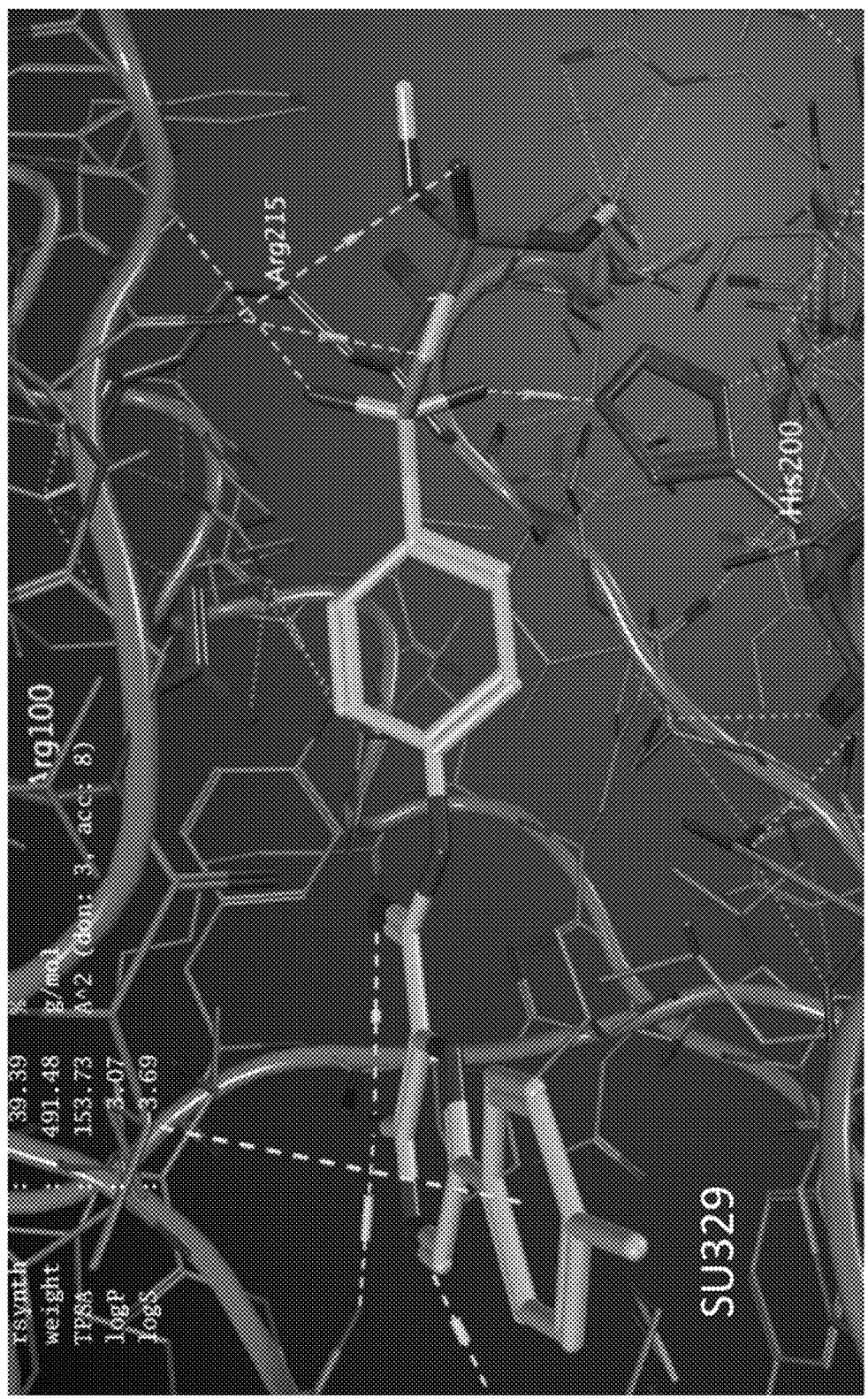
FIG. 4. Phenyl para-position polar phosphate mimetic substitutions are beneficial for activity. The second tertiary center (sulfonamide or phosphonate) with one atom spacer is postulated to mimic the bound phosphate chain of ATP contributing to superior activity. These polar substitutions differ from known hinge-binding motifs.
Figure 4:
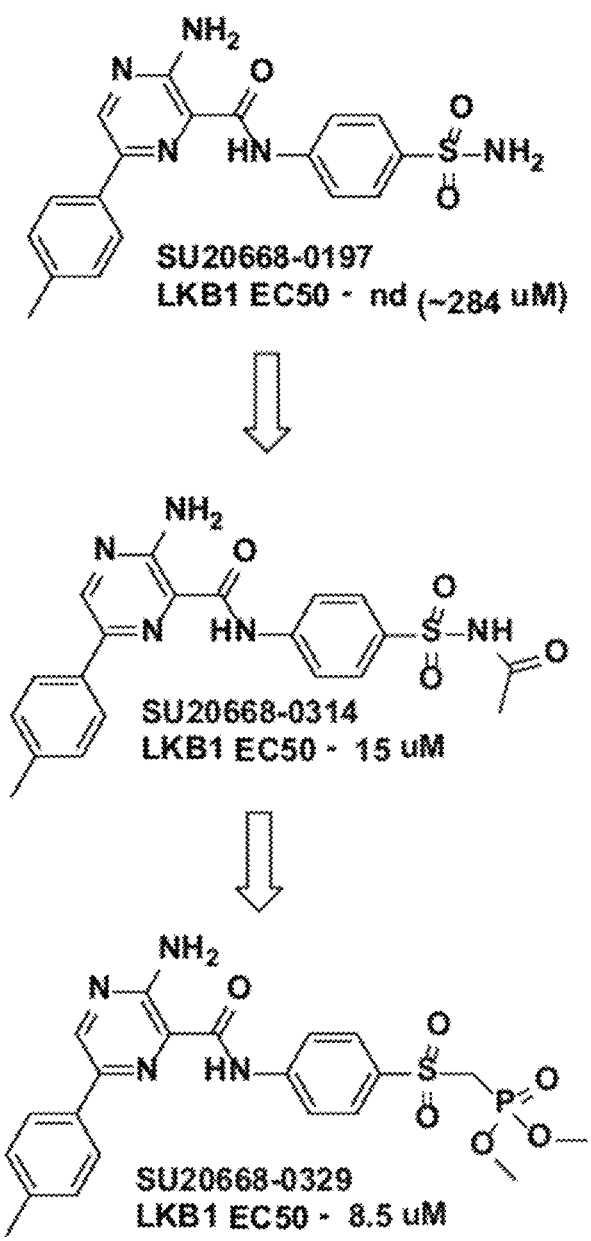
Figure 5:
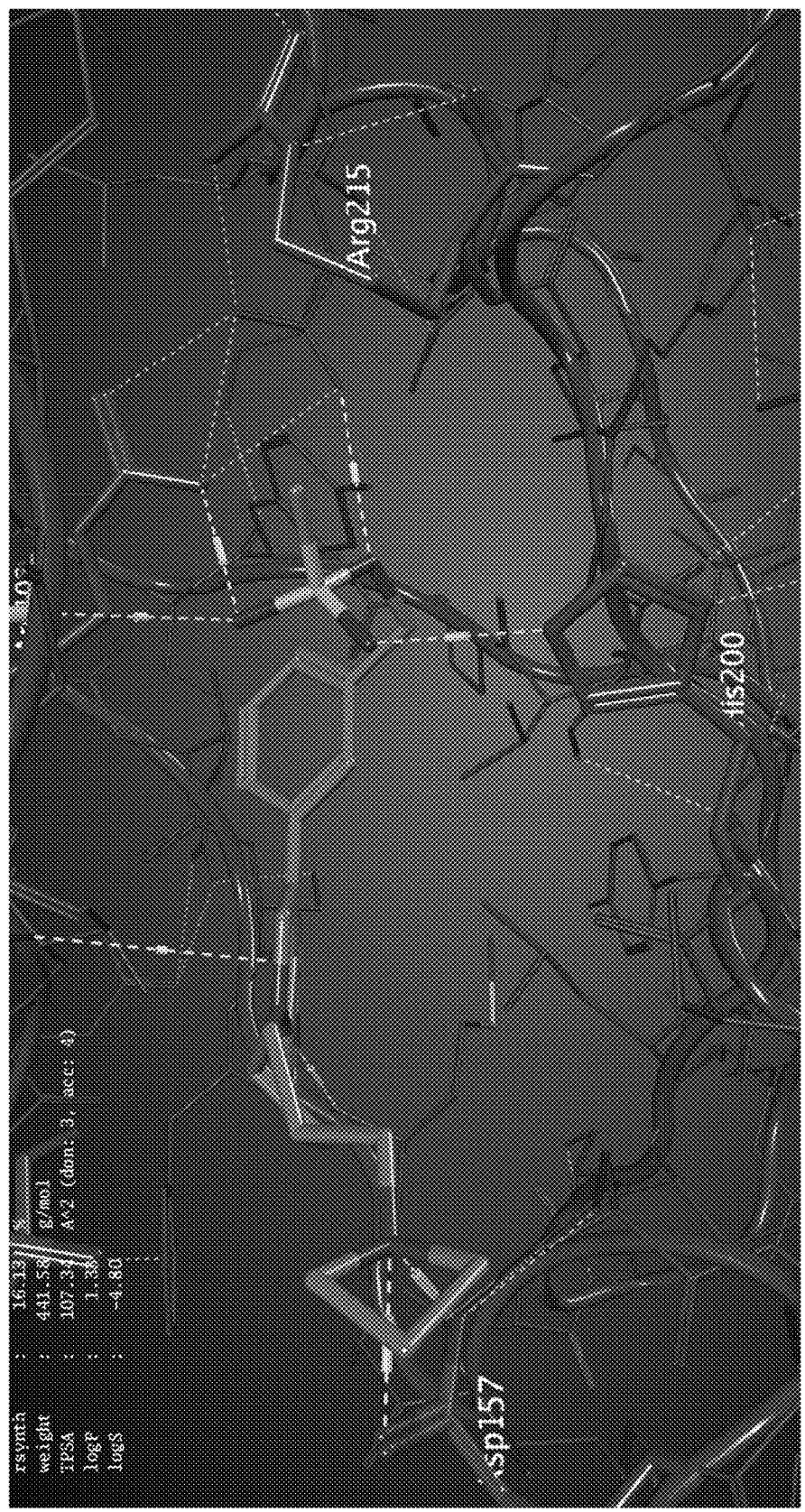
FIG. 5. The tetrahedral sulfonamide geometry is modeled to make beneficial H-bonding interactions with STRAD's unique basic residues.
Figure 5:
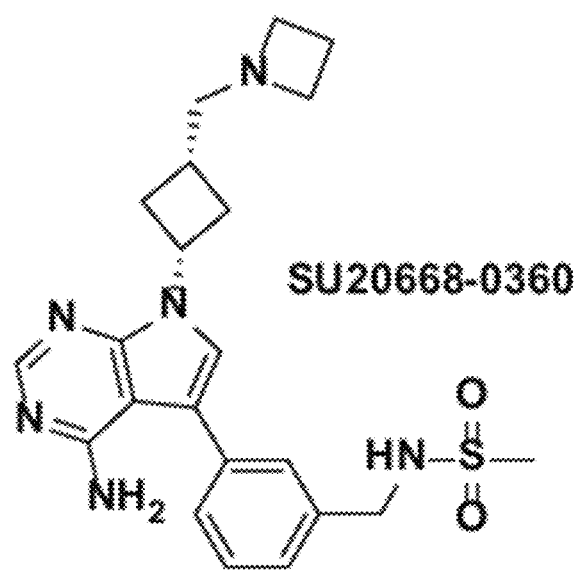
Figure 6:
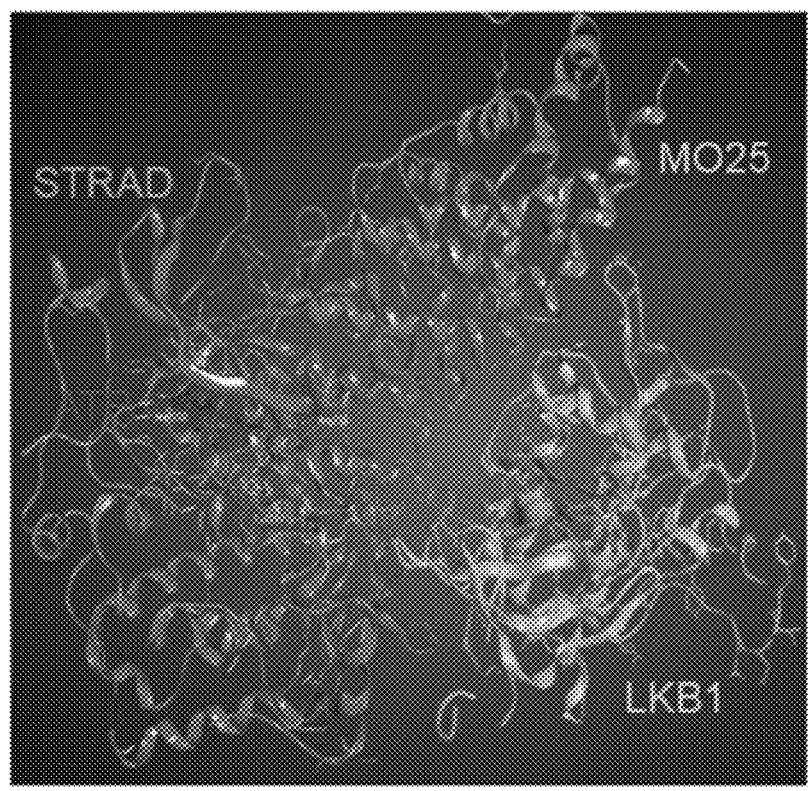
FIG. 6. The protein structure of the STRAD-MO25-LKB1 trimeric complex and the protein interaction pathway.
Figure 6:
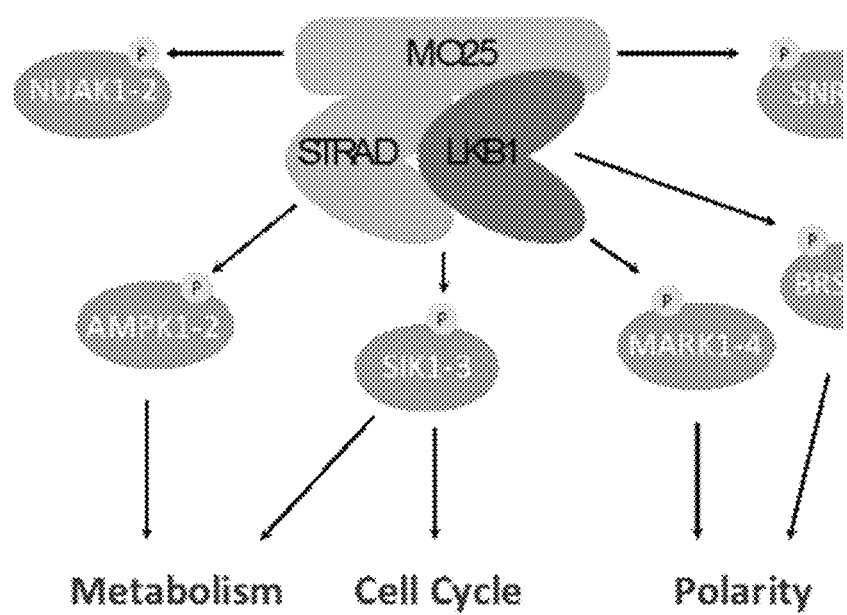
Figure 7A:
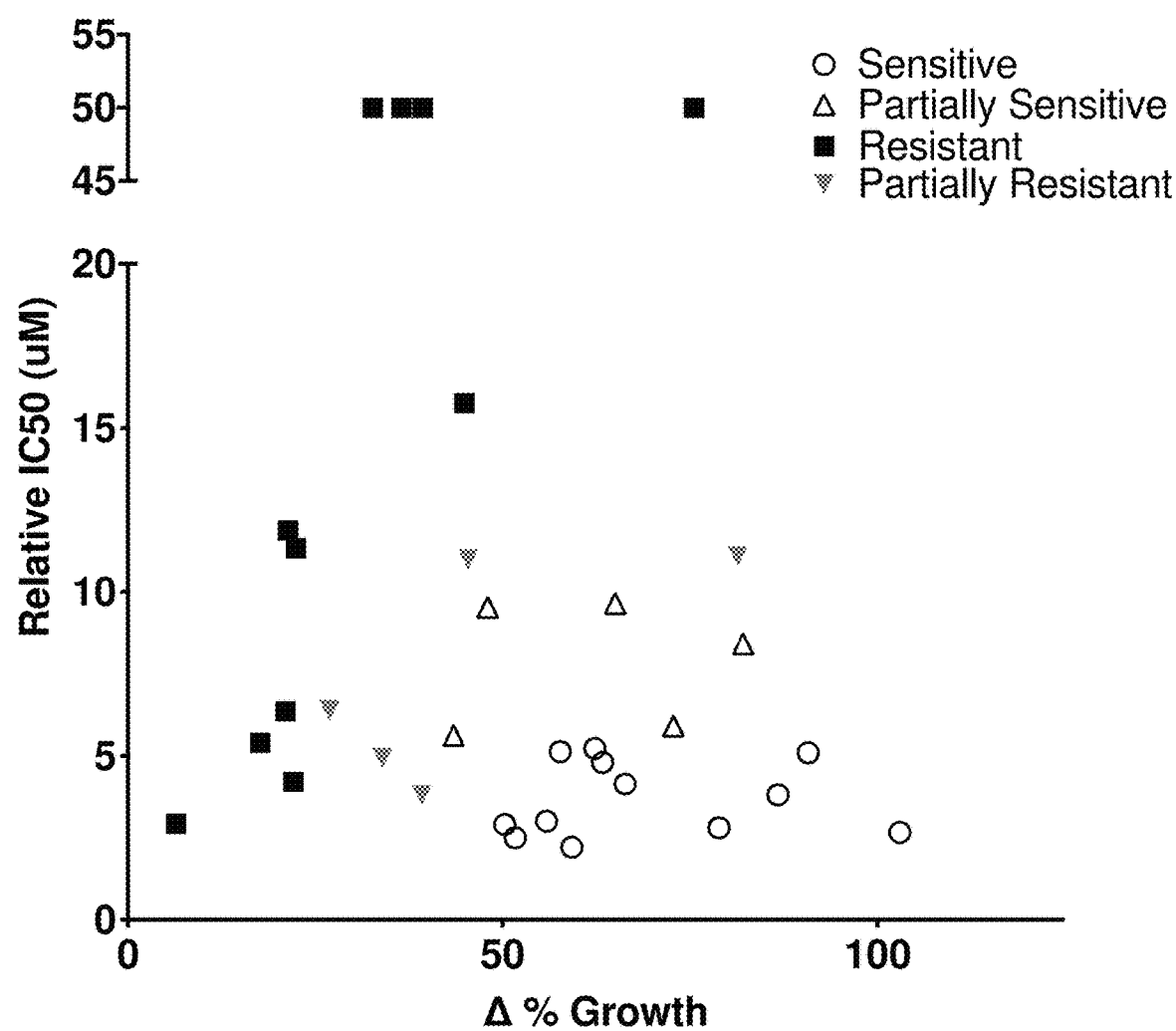
FIGS. 7A-7B. Viability screen identifies cell lines sensitive to small molecule activation of LKB1.
Figure 7B:
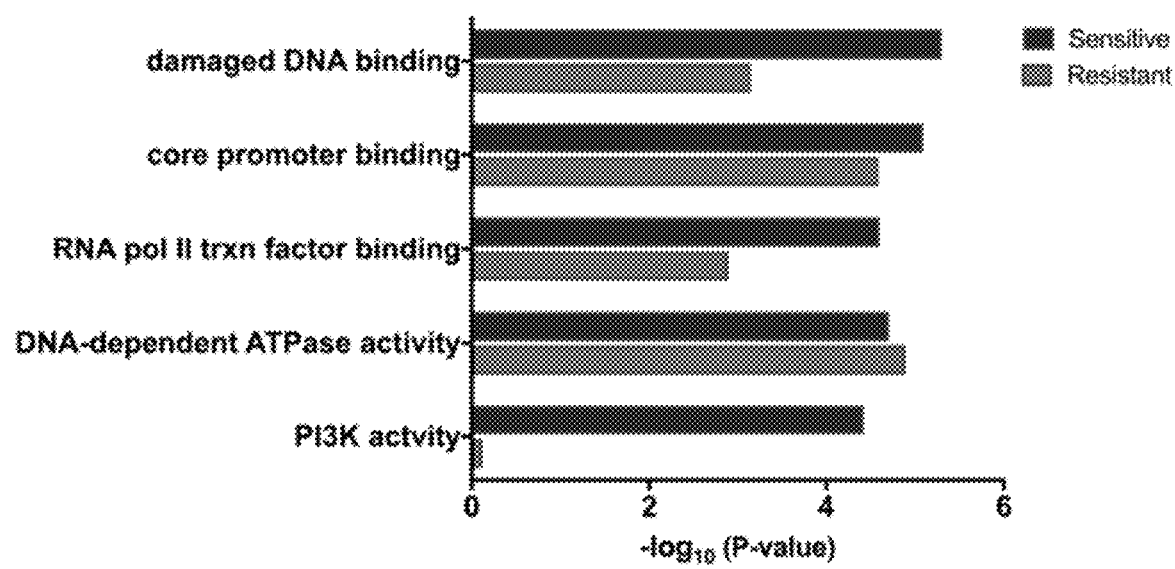

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). In embodiments, the alkyl is fully saturated. In embodiments, the alkyl is monounsaturated. In embodiments, the alkyl is polyunsaturated. Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. In embodiments, an alkenyl includes one or more double bonds. An alkynyl may include more than one triple bond and/or one or more double bonds in addition to the one or more triple bonds. In embodiments, an alkynyl includes one or more triple bonds The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. In embodiments, the alkylene is fully saturated. In embodiments, the alkylene is monounsaturated. In embodiments, the alkylene is polyunsaturated. In embodiments, an alkenylene includes one or more double bonds. In embodiments, an alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N(CH_3)—$CH_3$, —$CH_2$—S—$CH_2$—$CH_3$, —$CH_2$—$CH_2$—S—$CH_2$, —S(O)—$CH_3$, —$CH_2$—$CH_2$—S(O)_2—$CH_3$, —CH=CHO—$CH_3$, —Si(CH_3)_3, —$CH_2$—CH=N—$OCH_3$, —CH=CH—N(CH_3)—$CH_3$, —O—CH₃, —O—CH₂—CH₃, and —CN. Up to two or three heteroatoms may be consecutive, such as, for example, —CH₂—NH—OCH₃ and —CH₂—O—Si(CH₃)₃. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated.

Similarly, the term "heteroalkylene," by itself or as part of another substituent, means, unless otherwise stated, a divalent radical derived from heteroalkyl, as exemplified, but not limited by, —CH₂—CH₂—S—CH₂—CH₂— and —CH₂—S—CH₂—CH₂—NH—CH₂—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)₂R'— represents both —C(O)₂R'— and —R'C(O)₂—. As described above, heteroalkyl groups, as used herein, include those groups that are attached to the remainder of the molecule through a heteroatom, such as —C(O)R', —C(O)NR', —NR'R", —OR', —SR', and/or —SO₂R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like. In embodiments, the term "heteroalkenylene," by itself or as part of another substituent, means, unless otherwise stated, a divalent radical derived from a heteroalkene. In embodiments, the term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. In embodiments, a heteroalkenylene includes one or more double bonds. In embodiments, a heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form (CH₂)$_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thio. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thio. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl. In embodiments, a bicyclic or multicyclic cycloalkyl ring system refers to multiple rings fused together wherein at least one of the fused rings is a cycloalkyl ring and wherein the multiple rings are attached to the parent molecular moiety through any carbon atom contained within a cycloalkyl ring of the multiple rings.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thio. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl. In embodiments, a bicyclic or multicyclic cycloalkenyl ring system refers to multiple rings fused together wherein at least one of the fused rings is a cycloalkenyl ring and wherein the multiple rings are attached to the parent molecular moiety through any carbon atom contained within a cycloalkenyl ring of the multiple rings.

In embodiments, a heterocycloalkyl is a heterocyclyl. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thio. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thio. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl. In embodiments, the term "heterocycloalkyl" means a monocyclic, bicyclic, or a multicyclic heterocycloalkyl ring system. In embodiments, heterocycloalkyl groups are fully saturated. In embodiments, a bicyclic or multicyclic heterocycloalkyl ring system refers to multiple rings fused together wherein at least one of the fused rings is a heterocycloalkyl ring and wherein the multiple rings are attached to the parent molecular moiety through any atom contained within a heterocycloalkyl ring of the multiple rings.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. In embodiments, a fused ring aryl refers to multiple rings fused together wherein at least one of the fused rings is an aryl ring and wherein the multiple rings are attached to the parent molecular moiety through any carbon atom contained within an aryl ring of the multiple rings. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). In embodiments, the term "heteroaryl" includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings. In embodiments, a fused ring heteroaryl group is multiple rings fused together wherein at least one of the fused rings is a heteroaromatic ring and wherein the multiple rings are attached to the parent molecular moiety through any atom contained within a heteroaromatic ring of the multiple rings. A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl, benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol " $\sim$ " denotes the point of attachment of a chemical moiety to the remainder of a molecule or chemical formula.

The term "oxo," as used herein, means an oxygen that is double bonded to a carbon atom.

The term "alkylsulfonyl," as used herein, means a moiety having the formula —S(O$_2$)—R', where R' is a substituted or unsubstituted alkyl group as defined above. R' may have a specified number of carbons (e.g., "C$_1$-C$_4$ alkylsulfonyl").

The term "alkylarylene" as an arylene moiety covalently bonded to an alkylene moiety (also referred to herein as an alkylene linker). In embodiments, the alkylarylene group has the formula:

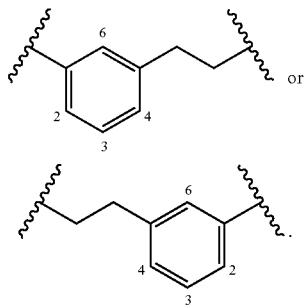

or

An alkylarylene moiety may be substituted (e.g. with a substituent group) on the alkylene moiety or the arylene linker (e.g. at carbons 2, 3, 4, or 6) with halogen, oxo, —N$_3$, —CF$_3$, —CCl$_3$, —CBr$_3$, —CI$_3$, —CN, —CHO, —OH, —NH$_2$, —COOH, —CONH$_2$, —NO$_2$, —SH, —SO$_2$CH$_3$— SO$_3$H, —OSO$_3$H, —SO$_2$NH$_2$, —NHNH$_2$, —ONH$_2$, —NHC(O)NHNH$_2$, substituted or unsubstituted C$_1$-C$_5$ alkyl or substituted or unsubstituted 2 to 5 membered heteroalkyl). In embodiments, the alkylarylene is unsubstituted.

Each of the above terms (e.g., "alkyl," "heteroalkyl," "cycloalkyl," "heterocycloalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_{20}$ alkyl, C$_1$-C$_{12}$ alkyl, C$_1$-C$_8$ alkyl, C$_1$-C$_6$ alkyl, C$_1$-C$_4$ alkyl, or C$_1$-C$_2$ alkyl), heteroalkyl (e.g., 2 to 20 membered heteroalkyl, 2 to 12 membered heteroalkyl, 2 to 8 membered heteroalkyl, 2 to 6 membered heteroalkyl, 4 to 6 membered heteroalkyl, 2 to 3 membered heteroalkyl, or 4 to 5 membered heteroalkyl), cycloalkyl (e.g., C$_3$-C$_{10}$ cycloalkyl, C$_3$-C$_8$ cycloalkyl, C$_3$-C$_6$ cycloalkyl, C$_4$-C$_6$ cycloalkyl, or C$_5$-C$_6$ cycloalkyl), heterocycloalkyl (e.g., 3 to 10 membered heterocycloalkyl, 3 to 8 membered heterocycloalkyl, 3 to 6 membered heterocycloalkyl, 4 to 6 membered heterocycloalkyl, 4 to 5 membered heterocycloalkyl, or 5 to 6 membered heterocycloalkyl), aryl (e.g., C$_6$-C$_{12}$ aryl, C$_6$-C$_{10}$ aryl, or phenyl), or heteroaryl (e.g., 5 to 12 membered heteroaryl, 5 to 10 membered heteroaryl, 5 to 9 membered heteroaryl, or 5 to 6 membered heteroaryl), substituted with at least one substituent selected from:

(i) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_1$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_{20}$ alkyl, C$_1$-C$_{12}$ alkyl, C$_1$-C$_8$ alkyl, C$_1$-C$_6$ alkyl, C$_1$-C$_4$ alkyl, or C$_1$-C$_2$ alkyl), heteroalkyl (e.g., 2 to 20 membered heteroalkyl, 2 to 12 membered heteroalkyl, 2 to 8 membered heteroalkyl, 2 to 6 membered heteroalkyl, 4 to 6 membered heteroalkyl, 2 to 3 membered heteroalkyl, or 4 to 5 membered heteroalkyl), cycloalkyl (e.g., C$_3$-C$_{10}$ cycloalkyl, C$_3$-C$_8$ cycloalkyl, C$_3$-C$_6$ cycloalkyl, C$_4$-C$_6$ cycloalkyl, or C$_1$-C$_6$ cycloalkyl), heterocycloalkyl (e.g., 3 to 10 membered heterocycloalkyl, 3 to 8 membered heterocycloalkyl, 3 to 6 membered heterocycloalkyl, 4 to 6 membered heterocycloalkyl, 4 to 5 membered heterocycloalkyl, or 5 to 6 membered heterocycloalkyl), aryl (e.g., C$_6$-C$_{12}$ aryl, C$_6$-C$_{10}$ aryl, or phenyl), or heteroaryl (e.g., 5 to 12 membered heteroaryl, 5 to 10 membered heteroaryl, 5 to 9 membered heteroaryl, or 5 to 6 membered heteroaryl), substituted with at least one substituent selected from:

(a) oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_1$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_{20}$ alkyl, $C_1$-$C_{12}$ alkyl, $C_1$-$C_8$ alkyl, $C_1$-$C_6$ alkyl, $C_1$-$C_4$ alkyl, or $C_1$-$C_2$ alkyl), heteroalkyl (e.g., 2 to 20 membered heteroalkyl, 2 to 12 membered heteroalkyl, 2 to 8 membered heteroalkyl, 2 to 6 membered heteroalkyl, 4 to 6 membered heteroalkyl, 2 to 3 membered heteroalkyl, or 4 to 5 membered heteroalkyl), cycloalkyl (e.g., $C_3$-$C_{10}$ cycloalkyl, $C_3$-$C_8$ cycloalkyl, $C_3$-$C_6$ cycloalkyl, $C_4$-$C_6$ cycloalkyl, or $C_1$-$C_6$ cycloalkyl), heterocycloalkyl (e.g., 3 to 10 membered heterocycloalkyl, 3 to 8 membered heterocycloalkyl, 3 to 6 membered heterocycloalkyl, 4 to 6 membered heterocycloalkyl, 4 to 5 membered heterocycloalkyl, or 5 to 6 membered heterocycloalkyl), aryl (e.g., $C_6$-$C_{12}$ aryl, $C_6$-$C_{10}$ aryl, or phenyl), or heteroaryl (e.g., 5 to 12 membered heteroaryl, 5 to 10 membered heteroaryl, 5 to 9 membered heteroaryl, or 5 to 6 membered heteroaryl), substituted with at least one substituent selected from: oxo, halogen, —$CCl_3$, —$CBr_3$, —$CF_3$, —$CI_3$, —$CHCl_2$, —$CHBr_2$, —$CHF_2$, —$CHI_2$, —$CH_2Cl$, —$CH_2Br$, —$CH_2F$, —$CH_2I$, —$CN$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth herein, for example in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In a recited claim or chemical formula description herein, each R substituent or L linker that is described as being "substituted" without reference as to the identity of any chemical moiety that composes the "substituted" group (also referred to herein as an "open substitution" on a R substituent or L linker or an "openly substituted" R substituent or L linker), the recited R substituent or L linker may, in embodiments, be substituted with one or more first substituent groups as defined below.

The first substituent group is denoted with a corresponding first decimal point numbering system such that, for example, $R^1$ may be substituted with one or more first substituent groups denoted by $R^{1.1}$, $R^2$ may be substituted with one or more first substituent groups denoted by $R^{2.1}$, $R^3$ may be substituted with one or more first substituent groups denoted by $R^{3.1}$, $R^4$ may be substituted with one or more first substituent groups denoted by $R^{4.1}$, $R^5$ may be substituted with one or more first substituent groups denoted by $R^{5.1}$, and the like up to or exceeding an $R^{100}$ that may be substituted with one or more first substituent groups denoted by $R^{100.1}$. As a further example, $R^{1A}$ may be substituted with one or more first substituent groups denoted by $R^{1A.1}$, $R^{2A}$ may be substituted with one or more first substituent groups denoted by $R^{2A.1}$, $R^{3A}$ may be substituted with one or more first substituent groups denoted by $R^{3A.1}$, $R^{4A}$ may be substituted with one or more first substituent groups denoted by $R^{4A.1}$, $R^{5A}$ may be substituted with one or more first substituent groups denoted by $R^{5A.1}$ and the like up to or exceeding an $R^{100A}$ may be substituted with one or more first substituent groups denoted by $R^{100A.1}$. As a further example, $L^1$ may be substituted with one or more first substituent groups denoted by $R^{L1.1}$, $L^2$ may be substituted with one or more first substituent groups denoted by $R^{L2.1}$, $L^3$ may be substituted with one or more first substituent groups denoted by $R^{L3.1}$ $L^4$ may be substituted with one or more first substituent groups denoted by $R^{L4.1}$, $L^5$ may be substituted with one or more first substituent groups denoted by $R^{L5.1}$ and the like up to or exceeding an $L^{100}$ which may be substituted with one or more first substituent groups denoted by $R^{L100.1}$. Thus, each numbered R group or L group (alternatively referred to herein as $R^{WW}$ or $L^{WW}$ wherein "WW" represents the stated superscript number of the subject R group or L group) described herein may be substituted with one or more first substituent groups referred to herein generally as $R^{WW.1}$ or $R^{LWW.1}$, respectively. In turn, each first substituent group (e.g. $R^{1.1}$, $R^{2.1}$, $R^{3.1}$, $R^{4.1}$, $R^{5.1}$ ... $R^{100.1}$; $R^{1A.1}$, $R^{2A.1}$, $R^{3A.1}$, $R^{4A.1}$, $R^{5A.1}$ ... $R^{100A.1}$; $R^{L1.1}$, $R^{L2.1}$, $R^{L3.1}$, $R^{L4.1}$, $R^{L5.1}$ ... $R^{L100.1}$) may be further substituted with one or more second substituent groups (e.g. $R^{1.1}$, $R^{2.2}$, $R^{3.2}$, $R^{4.2}$, $R^{5.2}$ ... $R^{100.2}$; $R^{1A.2}$, $R^{2A.2}$, $R^{3A.2}$, $R^{4A.2}$, $R^{5A.2}$ ... $R^{100A.2}$; $R^{L1.2}$, $R^{L2.2}$, $R^{L3.2}$, $R^{L4.2}$, $R^{L5.2}$ ... $R^{L100.2}$, respectively). Thus, each first substituent group, which may alternatively be represented herein as $R^{WW.1}$ as described above, may be further substituted with one or more second substituent groups, which may alternatively be represented herein as $R^{WW.2}$.

Finally, each second substituent group (e.g. $R^{1.2}$, $R^{2.2}$, $R^{3.2}$, $R^{4.2}$, $R^{5.2}$ ... $R^{100.2}$; $R^{1A.2}$, $R^{2A.2}$, $R^{3A.2}$, $R^{4A.2}$, $R^{5A.2}$ ... $R^{100A.2}$; $R^{L1.2}$, $R^{L2.2}$, $R^{L3.2}$, $R^{L4.2}$, $R^{L5.2}$ ... $R^{L100.2}$) may be further substituted with one or more third substituent groups (e.g $R^{1.3}$, $R^{2.3}$, $R^{3.3}$, $R^{4.3}$, $R^{5.3}$ ... $R^{100.3}$; $R^{1A.3}$, $R^{2A.3}$, $R^{3A.3}$, $R^{4A.3}$, $R^{5A.3}$ ... $R^{100A.3}$; $R^{L1.3}$, $R^{L2.3}$, $R^{L3.3}$, $R^{L4.3}$, $R^{L5.3}$ ... $R^{L100.3}$; respectively). Thus, each second substituent group, which may alternatively be represented herein as $R^{WW.2}$ as described above, may be further substituted with one or more third substituent groups, which may alternatively be represented herein as $R^{WW.3}$. Each of the first substituent groups may be optionally different. Each of the second substituent groups may be optionally different. Each of the third substituent groups may be optionally different.

Thus, as used herein, $R^{WW}$ represents a substituent recited in a claim or chemical formula description herein which is openly substituted. "WW" represents the stated superscript number of the subject R group (1, 2, 3, 1A, 2A, 3A, 1B, 2B, 3B. etc.). Likewise, $L^{WW}$ is a linker recited in a claim or chemical formula description herein which is openly substituted. Again, "WW" represents the stated superscript number of the subject L group (1, 2, 3, 1A, 2A, 3A, 1B, 2B, 3B etc.). As stated above, in embodiments, each $R^{WW}$ may be unsubstituted or independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group may be unsubstituted or independently substituted with one or more third substituent groups, referred to herein as $R^{WW.3}$. Similarly, each $L^{WW}$ linker may be unsubstituted or independently substituted with one or more first substituent groups, referred to herein as $R^{LWW.1}$; each first substituent group, $R^{LWW.1}$, may be unsubstituted or independently substituted with one or more second substituent groups, referred to herein as $R^{LWW.2}$; and each second substituent group may be unsubstituted or independently substituted with one or more third substituent groups, referred to herein as $R^{LWW.3}$. Each first substituent group is optionally different. Each second substituent group is optionally different. Each third substituent group is optionally different. For example, if $R^{WW}$ is phenyl, the said phenyl group is optionally substituted by one or more $R^{WW.1}$ groups as defined herein below, e.g. when $R^{WW.1}$ is $R^{WW.2}$-substituted alkyl, examples of groups so formed include but are not limited to itself optionally substituted by 1 or more $R^{WW.2}$, which $R^{WW.2}$ is optionally substituted by one or more $R^{WW.3}$. By way of example when $R^{WW.1}$ is alkyl, groups that could be formed, include but are not limited to:

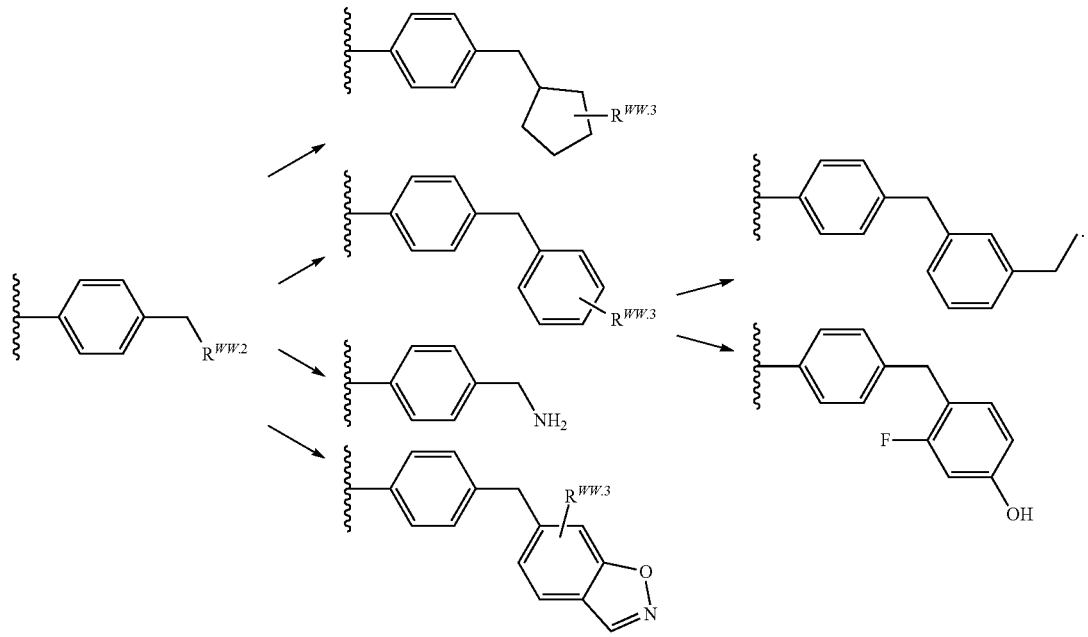

$R^{WW.1}$ is independently oxo, halogen, $-CX^{WW.1}_3$, $-CHX^{WW.1}_2$, $-CH_2X^{WW.1}$, $-OCX^{WW.1}_3$, $-OCH_2X^{WW.1}$, $-OCHX^{WW.1}_2$, $-CN$, $-OH$, $-NH_2$, $-COOH$, $-CONH_2$, $-NO_2$, $-SH$, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)$—$OH$, —$NHOH$, —$N_3$, $R^{WW.2}$-substituted or unsubstituted alkyl (e.g., $C_1$-$C_8$, $C_1$-$C_6$, $C_1$-$C_4$, or $C_1$-$C_2$), $R^{WW.2}$-substituted or unsubstituted heteroalkyl (e.g., 2 to 8 membered, 2 to 6 membered, 4 to 6 membered, 2 to 3 membered, or 4 to 5 membered), $R^{WW.2}$-substituted or unsubstituted cycloalkyl (e.g., $C_3$-$C_8$, $C_3$-$C_6$, $C_4$-$C_6$, or $C_5$-$C_6$), $R^{WW.2}$-substituted or unsubstituted heterocycloalkyl (e.g., 3 to 8 membered, 3 to 6 membered, 4 to 6 membered, 4 to 5 membered, or 5 to 6 membered), $R^{WW.2}$-substituted or unsubstituted aryl (e.g., $C_6$-$C_{12}$, $C_6$-$C_{10}$, or phenyl), or $R^{WW.2}$-substituted or unsubstituted heteroaryl (e.g., 5 to 12 membered, 5 to 10 membered, 5 to 9 membered, or 5 to 6 membered). In embodiments, $R^{WW.1}$ is independently oxo, halogen, —$CX^{WW.1}_3$, —$CHX^{WW.1}_2$, —$CH_2X^{WW.1}$, —$OCX^{WW.1}_3$, —$OCH_2X^{WW.1}$, —$OCHX^{WW.1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)$—$OH$, —$NHOH$, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.1}$ is independently —F, —Cl, —Br, or —I.

$R^{WW.2}$ is independently oxo, halogen, —$CX^{WW.2}_3$, —$CHX^{WW.2}_2$, —$CH_2X^{WW.2}$, —$OCX^{WW.2}_3$, —$OCH_2X^{WW.2}$, —$OCHX^{WW.2}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)$—$OH$, —$NHOH$, —$N_3$, $R^{WW.3}$-substituted or unsubstituted alkyl (e.g., $C_1$-$C_8$, $C_1$-$C_6$, $C_1$-$C_4$, or $C_1$-$C_2$), $R^{WW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{WW.3}$-substituted or unsubstituted heterocycloalkyl (e.g., 3 to 8 membered, 3 to 6 membered, 4 to 6 membered, 4 to 5 membered, or 5 to 6 membered), $R^{WW.3}$-substituted or unsubstituted aryl (e.g., $C_6$-$C_{12}$, $C_6$-$C_{10}$, or phenyl), or $R^{WW.3}$-substituted or unsubstituted heteroaryl (e.g., 5 to 12 membered, 5 to 10 membered, 5 to 9 membered, or 5 to 6 membered). In embodiments, $R^{WW.2}$ is independently oxo, halogen, —$CX^{WW.2}_3$, —$CHX^{WW.2}_2$, —$CH_2X^{WW.2}$, —$OCX^{WW.2}_3$, —$OCH_2X^{WW.2}$, —$OCHX^{WW.2}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)$—$OH$, —$NHOH$, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.2}$ is independently —F, —Cl, —Br, or —I.

$R^{WW.3}$ is independently oxo, halogen, —$CX^{WW.3}_3$, —$CHX^{WW.3}_2$, —$CH_2X^{WW.3}$, —$OCX^{WW.3}_3$, —$OCH_2X^{WW.3}$, —$OCHX^{WW.3}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)$—$OH$, —$NHOH$, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.3}$ is independently —F, —Cl, —Br, or —I.

Where two different $R^{WW}$ substituents are joined together to form an openly substituted ring (e.g. substituted cycloalkyl, substituted heterocycloalkyl, substituted aryl or substituted heteroaryl), in embodiments the openly substituted ring may be independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group, $R^{WW.2}$, may be unsubstituted or independently substituted with one or more third substituent groups, referred to herein as $R^{WW.3}$; and each third substituent group, $R^{WW.3}$, is unsubstituted. Each first substituent group is optionally different. Each second substituent group is optionally different. Each third substituent group is optionally different. In the context of two different $R^{WW}$ substituents joined together to form an openly substituted ring, the "WW" symbol in the $R^{WW.1}$, $R^{WW.2}$ and $R^{WW.3}$ refers to the designated number of one of the two different $R^{WW}$ substituents. For example, in embodiments where $R^{100A}$ and $R^{100B}$ are optionally joined together to form an openly substituted ring, $R^{WW.1}$ is $R^{100A.1}$, $R^{WW.2}$ is $R^{100A.2}$, and $R^{WW.3}$ is $R^{100A.3}$. Alternatively, in embodiments where $R^{100A}$ and $R^{100B}$ are optionally joined together to form an openly substituted ring, $R^{WW.1}$ is $R^{100B.1}$, $R^{WW.2}$ is $R^{100B.2}$, and $R^{WW.3}$ is $R^{100B.3}$. $R^{WW.1}$, $R^{WW.2}$ and $R^{WW.3}$ in this paragraph are as defined in the preceding paragraphs.

$R^{LWW.1}$ is independently oxo, halogen, —$CX^{LWW.1}_3$, —$CHX^{LWW.1}_2$, —$CH_2X^{LWW.1}$, —$OCX^{LWW.1}_3$, —$OCH_2X^{LWW.1}$, —$OCHX^{LWW.1}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —$NHC(O)$—$OH$, —$NHOH$, —$N_3$, $R^{LWW.2}$-substituted or unsubstituted alkyl (e.g., $C_1$-$C_8$, $C_1$-$C_6$, $C_1$-$C_4$, or $C_1$-$C_2$), $R^{LWW.2}$-substituted or unsubstituted heteroalkyl (e.g., 2 to 8 membered, 2 to 6 membered, 4 to 6 membered, 2 to 3 membered, or 4 to 5 membered), $R^{LWW.2}$-substituted or unsubstituted cycloalkyl (e.g., $C_3$-$C_8$, $C_3$-$C_6$, $C_4$-$C_6$, or $C_5$-$C_6$), $R^{LWW.2}$-substituted or unsubstituted heterocycloalkyl (e.g., 3 to 8 membered, 3 to 6 membered, 4 to 6 membered, 4 to 5 membered, or 5 to 6 membered), $R^{LWW.2}$-substituted or unsubstituted aryl (e.g., $C_6$-$C_{12}$, $C_6$-$C_{10}$, or phenyl), or $R^{LWW.2}$-substituted or unsubstituted heteroaryl (e.g., 5 to 12 membered, 5 to 10 membered, 5 to 9 membered, or 5 to 6 membered). In embodiments, $R^{LWW.1}$ is independently oxo, halogen, $-CX^{LWW.1}_3$, $-CHX^{LWW.1}_2$, $-CH_2X^{LWW.1}$, $-OCX^{LWW.1}_3$, $-OCH_2X^{LWW.1}$, $-OCHX^{LWW.1}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.1}$ is independently $-F$, $-Cl$, $-Br$, or $-I$.

$R^{LWW.2}$ is independently oxo, halogen, $-CX^{LWW.2}_3$, $-CHX^{LWW.2}_2$, $-CH_2X^{LWW.2}$, $-OCX^{LWW.2}_3$, $-OCH_2X^{LWW.2}$, $-OCHX^{LWW.2}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{LWW.3}$-substituted or unsubstituted alkyl (e.g., $C_1$-$C_8$, $C_1$-$C_6$, $C_1$-$C_4$, or $C_1$-$C_2$), $R^{LWW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{LWW.3}$-substituted or unsubstituted heterocycloalkyl (e.g., 3 to 8 membered, 3 to 6 membered, 4 to 6 membered, 4 to 5 membered, or 5 to 6 membered), $R^{LWW.3}$-substituted or unsubstituted aryl (e.g., $C_6$-$C_{12}$, $C_6$-$C_{10}$, or phenyl), or $R^{LWW.3}$-substituted or unsubstituted heteroaryl (e.g., 5 to 12 membered, 5 to 10 membered, 5 to 9 membered, or 5 to 6 membered). In embodiments, $R^{LWW.2}$ is independently oxo, halogen, $-CX^{LWW.2}_3$, $-CHX^{LWW.2}_2$, $-CH_2X^{LWW.2}$, $-OCX^{LWW.2}_3$, $-OCH_2X^{LWW.2}$, $-OCHX^{LWW.2}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.2}$ is independently $-F$, $-Cl$, $-Br$, or $-I$.

$R^{LWW.3}$ is independently oxo, halogen, $-CX^{LWW.3}_3$, $-CHX^{LWW.3}_2$, $-CH_2X^{LWW.3}$, $-OCX^{LWW.3}_3$, $-OCH_2X^{LWW.3}$, $-OCHX^{LWW.3}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.3}$ is independently $-F$, $-Cl$, $-Br$, or $-I$.

In the event that any R group recited in a claim or chemical formula description set forth herein ($R^{WW}$ substituent) is not specifically defined in this disclosure, then that R group ($R^{WW}$ group) is hereby defined as independently oxo, halogen, $-CX^{WW}_3$, $-CHX^{WW}_2$, $-CH_2X^{WW}$, $-OCX^{WW}_3$, $-OCH_2X^{WW}$, $-OCHX^{WW}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-N_3$, $R^{WW.1}$-substituted or unsubstituted alkyl (e.g., $C_1$-$C_8$, $C_1$-$C_6$, $C_1$-$C_4$, or $C_1$-$C_2$), $R^{WW.1}$-substituted or unsubstituted heteroalkyl (e.g., 2 to 8 membered, 2 to 6 membered, 4 to 6 membered, 2 to 3 membered, or 4 to 5 membered), $R^{WW.1}$-substituted or unsubstituted cycloalkyl (e.g., $C_3$-$C_8$, $C_3$-$C_6$, $C_4$-$C_6$, or $C_5$-$C_6$), $R^{WW.1}$-substituted or unsubstituted heterocycloalkyl (e.g., 3 to 8 membered, 3 to 6 membered, 4 to 6 membered, 4 to 5 membered, or 5 to 6 membered), $R^{WW.1}$-substituted or unsubstituted aryl (e.g., $C_6$-$C_{12}$, $C_6$-$C_{10}$, or phenyl), or $R^{WW.1}$-substituted or unsubstituted heteroaryl (e.g., 5 to 12 membered, 5 to 10 membered, 5 to 9 membered, or 5 to 6 membered). $X^{WW}$ is independently $-F$, $-Cl$, $-Br$, or $-I$. Again, "WW" represents the stated superscript number of the subject R group (e.g. 1, 2, 3, 1A, 2A, 3A, 1, 2B, 3B. etc.). $R^{WW.1}$, $R^{WW.2}$, and $R^{WW.3}$, are as defined above.

In the event that any L linker group recited in a claim or chemical formula description set forth herein (i.e. an $L^{WW}$ substituent) is not explicitly defined, then that L group ($L^{WW}$ group) is herein defined as independently a bond, $-O-$, $-NH-$, $-C(O)-$, $-C(O)NH-$, $-NHC(O)-$, $-NHC(O)NH-$, $-C(O)O-$, $-OC(O)-$, $-S-$, $-SO_2NH-$, $R^{LWW.1}$-substituted or unsubstituted alkylene (e.g., $C_1$-$C_8$, $C_1$-$C_6$, $C_1$-$C_4$, or $C_1$-$C_2$), $R^{LWW.1}$-substituted or unsubstituted heteroalkylene (e.g., 2 to 8 membered, 2 to 6 membered, 4 to 6 membered, 2 to 3 membered, or 4 to 5 membered), $R^{LWW.1}$-substituted or unsubstituted cycloalkylene (e.g., $C_3$-$C_8$, $C_3$-$C_6$, $C_4$-$C_6$, or $C_5$-$C_6$), $R^{LWW.1}$ substituted or unsubstituted heterocycloalkylene (e.g., 3 to 8 membered, 3 to 6 membered, 4 to 6 membered, 4 to 5 membered, or 5 to 6 membered), $R^{LWW.1}$-substituted or unsubstituted arylene (e.g., $C_6$-$C_{12}$, $C_6$-$C_{10}$, or phenyl), or $R^{LWW.1}$-substituted or unsubstituted heteroarylene (e.g., 5 to 12 membered, 5 to 10 membered, 5 to 9 membered, or 5 to 6 membered). Again, "WW" represents the stated superscript number of the subject L group (1, 2, 3, 1A, 2A, 3A, 1B, 2B, 3B. etc.). $R^{LWW.1}$, as well as $R^{LWW.2}$ and $R^{LWW.3}$, are as defined above.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present disclosure, whether radioactive or not, are encompassed within the scope of the present disclosure.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the terms "bioconjugate" and "bioconjugate linker" refer to the resulting association between atoms or molecules of "bioconjugate reactive groups" or "bioconjugate reactive moieties". The association can be direct or indirect. For example, a conjugate between a first bioconjugate reactive group (e.g., —NH2, —C(O)OH, —N-hydroxysuccinimide, or -maleimide) and a second bioconjugate reactive group (e.g., sulfhydryl, sulfur-containing amino acid, amine, amine sidechain containing amino acid, or carboxylate) provided herein may be bound, for example, by covalent bond, linker (e.g. a first linker of second linker), or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions, and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

Useful bioconjugate reactive moieties used for bioconjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido or maleimide groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold, or react with maleimides;

(h) amine or sulfhydryl groups (e.g., present in cysteine), which can be, for example, acylated, alkylated or oxidized;

(i) alkenes, which can undergo, for example, cycloadditions, acylation, Michael addition, etc;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds;

(n) azides coupled to alkynes using copper catalyzed cycloaddition click chemistry; and (o) biotin conjugate can react with avidin or strepavidin to form a avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13.A}$, $R^{13.B}$, $R^{13.C}$, $R^{13.D}$, etc., wherein each of $R^{13.A}$, $R^{13.B}$, $R^{13.C}$, $R^{13.D}$ etc. is defined within the scope of the definition of $R^{13}$ and optionally differently.

A "detectable agent" or "detectable moiety" is a composition, substance, element, or compound; or moiety thereof; detectable by appropriate means such as spectroscopic, photochemical, biochemical, immunochemical, chemical, magnetic resonance imaging, or other physical means. For example, useful detectable agents include $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$Ir, $^{198}$Au, $^{199}$Au, $^{211}$At, $^{211}$Pb, $^{212}$Bi, $^{212}$Pb, $^{213}$Bi, $^{223}$Ra, $^{225}$Ac, Cr, V, Mn, Fe, Co, Ni, Cu, La, Ce, Pr, Nd, Pm, Sm, Eu, Gd, Tb, Dy, Ho, Er, Tm, Yb, Lu, $^{32}$P, fluorophore (e.g. fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g. carbon-11, nitrogen-13, oxygen-15, fluorine-18, rubidium-82), fluorodeoxyglucose (e.g. fluorine-18 labeled), any gamma ray emitting radionuclides, positron-emitting radionuclide, radiolabeled glucose, radiolabeled water, radiolabeled ammonia, biocolloids, microbubbles (e.g. including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g. iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide or antibody specifically reactive with a target peptide. A detectable moiety is a monovalent detectable agent or a detectable agent capable of forming a bond with another composition, substance, element, or compound.

Radioactive substances (e.g., radioisotopes) that may be used as imaging and/or labeling agents in accordance with the embodiments of the disclosure include, but are not limited to, $^{18}$F, $^{32}$P, $^{33}$P, $^{45}$Ti, $^{47}$Sc, $^{52}$Fe, $^{59}$Fe, $^{62}$Cu, $^{64}$Cu, $^{67}$Cu, $^{67}$Ga, $^{68}$Ga, $^{77}$As, $^{86}$Y, $^{90}$Y, $^{89}$Sr, $^{89}$Zr, $^{94}$Tc, $^{94}$Tc, $^{99m}$Tc, $^{99}$Mo, $^{105}$Pd, $^{105}$Rh, $^{111}$Ag, $^{111}$In, $^{123}$I, $^{124}$I, $^{125}$I, $^{131}$I, $^{142}$Pr, $^{143}$Pr, $^{149}$Pm, $^{153}$Sm, $^{154\text{-}158}$Gd, $^{161}$Tb, $^{166}$Dy, $^{166}$Ho, $^{169}$Er, $^{175}$Lu, $^{177}$Lu, $^{186}$Re, $^{188}$Re, $^{189}$Re, $^{194}$I, $^{198}$Au, $^{199}$Au, $^{211}$At, $^{211}$Pb, $^{212}$Bi, $^{212}$Pb, $^{213}$Bi, $^{223}$Ra and $^{225}$Ac. Paramagnetic ions that may be used as additional imaging agents in accordance with the embodiments of the disclosure include, but are not limited to, ions of transition and lanthanide metals (e.g. metals having atomic numbers of 21-29, 42, 43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or —CH₃). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

The term "exogenous" refers to a molecule or substance (e.g., a compound, nucleic acid or protein) that originates from outside a given cell or organism. For example, an "exogenous promoter" as referred to herein is a promoter that does not originate from the plant it is expressed by. Conversely, the term "endogenous" or "endogenous promoter" refers to a molecule or substance that is native to, or originates within, a given cell or organism.

A charged moiety refers to a functional group possessing an abundance of electron density (i.e. electronegative) or is deficient in electron density (i.e. electropositive). Non-limiting examples of a charged moiety includes carboxylic acid, alcohol, phosphate, aldehyde, and sulfonamide. In embodiments, a charged moiety is capable of forming hydrogen bonds.

The term "solution" is used in accor and refers to a liquid mixture in which the minor component (e.g., a solute or compound) is uniformly distributed within the major component (e.g., a solvent).

The term "organic solvent" as used herein is used in accordance with its ordinary meaning in chemistry and refers to a solvent which includes carbon. Non-limiting examples of organic solvents include acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol, dimethyl ether), 1,2-dimethoxyethane (glyme, DME), dimethylformamide (DMF), dimethyl sulfoxide (DMSO), 1,4-dioxane, ethanol, ethyl acetate, ethylene glycol, glycerin, heptane, hexamethylphosphoramide (HMPA), hexamethylphosphorous, triamide (HMPT), hexane, methanol, methyl t-butyl ether (MTBE), methylene chloride, N-methyl-2-pyrrolidinone (NMP), nitromethane, pentane, petroleum ether (ligroine), 1-propanol, 2-propanol, pyridine, tetrahydrofuran (THF), toluene, triethyl amine, o-xylene, m-xylene, or p-xylene. In embodiments, the organic solvent is or includes chloroform, dichloromethane, methanol, ethanol, tetrahydrofuran, or dioxane.

The terms "bind" and "bound" as used herein is used in accordance with its plain and ordinary meaning and refers to the association between atoms or molecules. The association can be direct or indirect. For example, bound atoms or molecules may be bound, for example, by covalent bond, linker (e.g. a first linker or second linker), or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions, and the like).

The term "capable of binding" as used herein refers to a moiety (e.g. a compound as described herein) that is able to measurably bind to a target (e.g., STRAD pseudokinase). In embodiments, where a moiety is capable of binding a target, the moiety is capable of binding with a Kd of less than about 10 μM, 5 μM, 1 μM, 500 nM, 250 nM, 100 nM, 75 nM, 50 nM, 25 nM, 15 nM, 10 nM, 5 nM, 1 nM, or about 0.1 nM.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

The term "EC50" or "half maximal effective concentration" as used herein refers to the concentration of a molecule (e.g., an LKB1 activator) capable of inducing a response which is halfway between the baseline response and the maximum response after a specified exposure time. In embodiments, the EC50 is the concentration of a molecule (e.g., an LKB1 activator) that produces 50% of the maximal possible effect of that molecule.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

An "LKB1 activator" refers to a compound (e.g. a compound described herein) that increases the activity of LKB1 when compared to a control, such as absence of the compound or a compound with known inactivity.

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "STRAD", "STRAD-α", "LYK5", or "STE20-Related Adaptor protein" refers to the protein kinase LYK5. In embodiments, the term "STRADα" or "pseudo-kinase STRADα" are equivalent to "STRAD", "STRAD-α", "LYK5", or "STE20-Related Adaptor protein". Endogenous LKB1 and STRADα form a complex in which STRADα activates LKB1, resulting in phosphorylation of both partners. STRAD pseudokinase is a component of the LKB1-STRAD-MO25 trimer. The term includes any recombinant or naturally-occurring form of STRAD variants thereof that maintain STRAD function or activity (e.g., within at least 30%, 40%, 50%, 60%, 70%, 80%, 90%, 95%, or 100% function or activity compared to wildtype STRAD). In embodiments, STRAD is encoded by the STRAD gene. In embodiments, STRAD has the amino acid sequence set forth in or corresponding to Entrez 92335, UniProt Q7RTN6, or RefSeq (protein) NP_0010037871. In embodiments, STRAD has the amino acid sequence set forth in or corresponding to Entrez 92335, UniProt Q7RTN6, or RefSeq (protein) NP_001003787.1.

In embodiments, STRAD has the sequence:

```
                                            (SEQ ID NO: 1)
MSFLVSKPERIRRWVSEKFIVEGLRDLELFGEQPPGDTRRKTNDASSES

IASFSKQEVMSSFLPEGGCYELLTVIGKGFEDLMTVNLARYKPTGEYVT

VRRINLEACSNEMVTFLQGELHVSKLFNHPNIVPYRATFIADNELWVVT

SFMAYGSAKDLICTHFMDGMNELAIAYILQGVLKALDYIHHMGYVHRSV

KASHILISVDGKVYLSGLRSNLSMISHGQRQRVVHDFPKYSVKVLPWLS

PEVLQQNLQGYDAKSDIYSVGITACELANGHVPFKDMPATQMLLEKLNG

TVPCLLDTSTIPAEELTMSPSRSVANSGLSDSLTTSTPRPSNGDSPSHP

YHRTFPHFHHFVEQCLQRNPDARPSASTLLNHSFFKQIKRRASEALPEL

LRPVTPITNFEGSQSQDHSGIFGLVNLEELEVDDWEF.
```

In embodiments, STRAD has the sequence:

```
                                            (SEQ ID NO: 2)
MSFLVSKPERIRRWVSEKFIVEGLRDLELFGEQPPGDTRRKTNDASSESIASFSKQEVMSSFLPEGGCYE

LLTVIGKGFEDLMTVNLARYKPTGEYVTVRRINLEACSNEMVTFLQGELHVSKLENHPNIVPYRATFIAD

NELWVVTSFMAYGSAKDLICTHEMDGMNELAIAYILQGVLKALDYIHHMGYVHRSVKASHILISVDGKVY

LSGLRSNLSMISHGQRQRVVHDFPKYSVKVLPWLSPEVLQQNLQGYDAKSDIYSVGITACELANGHVPFK

DMPATQMLLEKLNGTVPCLLDTSTIPAEELTMSPSRSVANSGLSDSLTTSTPRPSNGDSPSHPYHRTESP

HFHHFVEQCLQRNPDARPSASTLLNHSFFKQIKRRASEALPELLRPVTPITNFEGSQSQDHSGIFGLVTN

LEELEVDDWEF
```

```
                                            (SEQ ID NO: 2)
   1 msflvskper irrwvsekfi veglrdlelf geqppgdtrr ktndassesi asfskqevms 61 sflpeggcye lltvigkgfe dlmtvnlary kptgeyvtvr rinleacsne mvtflqgelh 121 vsklinhpni vpyratfiad nelwvvtsfm aygsakdlic thfmdgmnel aiayilqgvl 181 kaldyihhmg yvhrsvkash ilisvdgkvy lsglrsnlsm ishgqrqrvv hdfpkysvkv 241 lpwlspevlq qnlqgydaks diysvgitac elanghvpfk dmpatqmlle klngtvpcll 301 dtstipaeel tmspsrsvan sglsdsltts tprpsngdsp shpyhrtfsp hfhhfveqcl 361 qrnpdarpsa stlinhsffk qikrraseal pellrpvtpi tnfegsqsqd hsgifglvtn 421 leelevddwe f
```

The term "LKB1" or "STK11" refers to serine/threonine kinase 11, also known as liver kinase B1 or renal carcinoma antigen NY-REN-19. LKB1 is activated allosterically by binding to the pseudokinase STRAD and the adaptor protein MO25. The LKB1-STRAD-MO25 heterotrimeric complex represents the biologically active unit that is capable of phosphorylating and activating AMPK as well as selected other kinases that belong to the AMPK-related kinase family. The term includes any recombinant or naturally-occurring form of LKB1 variants thereof that maintain LKB1 function or activity (e.g., within at least 30%, 40%, 50%, 60%, 70%, 80%, 90%, 95%, or 100% function or activity compared to wildtype LKB1). In embodiments, LKB1 is encoded by the LKB1 or STK11 gene. In embodiments, LKB1 has the amino acid sequence set forth in or corresponding to Entrez 6794, UniProt Q15831, RefSeq (protein) NP_000446 or RefSeq (protein) NP_000446.1.

In embodiments, LKB1 has the sequence:

```
                                            (SEQ ID NO: 3)
MEVVDPQQLGMFTEGELMSVGMDTFIHRIDSTEVIYQPRRKRAKLIGKY

LMGDLLGEGSYGKVKEVLDSETLCRRAVKILKKKLRRIPNGEANVKKE

IQLLRRLRHKNVIQLVDVLYNEEKQKMYMVMEYCVCGMQEMLDSVPEKR

FPVCQAHGYFCQLIDGLEYLHSQGIVHKDIKPGNLLLTTGGTLKISDLG

VAEALHPFAADDTCRTSQGSPAFQPPEIANGLDTFSGFKVDIWSAGVTL

YNITTGLYPFEGDNIYKLFENIGKGSYAIPGDCGPPLSDLLKGMLEYEP
```

```
AKRFSIRQIRQHSWFRKKHPPAEAPVPIPPSPDTKDRWRSMTVVPYLED

LHGADEDEDLFDIEDDIIYTQDFTVPGQVPEEEASHNGQRRGLPKAVCM

NGTEAAQLSTKSRAEGRAPNPARKACSASSKIRRLSACKQQ.
```

The term "MO25" or "CAB39" refers to calcium-binding protein 39. The protein encoded by this gene associates with LKB1 and STRAD. MO25 enhances formation of LKB1/STRAD complexes and stimulates LKB1 catalytic activity. MO25 may function as a scaffolding component of the LKB1/STRAD complex and regulates LKB1 activity and cellular localization. The term includes any recombinant or naturally-occurring form of MO25 variants thereof that maintain MO25 function or activity (e.g., within at least 30%, 40%, 50%, 60%, 70%, 80%, 90%, 95%, or 100% function or activity compared to wildtype MO25). In embodiments, MO25 is encoded by the CAB39 gene. In embodiments, MO25 has the amino acid sequence set forth in or corresponding to Entrez 51719, UniProt Q9Y376, RefSeq (protein) NP_001124321, RefSeq (protein) NP_001124322, or RefSeq (protein) NP_057373. In embodiments, MO25 has the sequence:

```
                                        (SEQ ID NO: 4)
MPFPFGKSHKSPADIVKNLKESMAVLEKQDISDKKAEKATEEVSKNLVA

MKEILYGTNEKEPQTEAVAQLAQELYNSGLLSTLVADLQLIDFEGKKDV

AQIFNNILRRQIGTRTPTVEYICTQQNILFMLLKGYESPEIALNCGIML

RECIRHEPLAKIILWSEQFYDFFRYVEMSTFDIASDAFATFKDLLTRHK

LLSAEFLEQHYDRFFSEYEKLLHSENYVTKRQSLKLLGELLLDRHNFTI

MTKYISKPENLKLMMNLLRDKSRNIQFEAFHVFKVFVANPNKTQPILDI

LLKNQAKLIEFLSKFQNDRTEDEQFNDEKTYLVKQIRDLKRPAQQEA.
```

The term "CRTC2" or "TORC2" refers to CREB regulated transcription coactivator 2. CRTC2, initially called TORC2, is a transcriptional coactivator for the transcription factor CREB and a central regulator of gluconeogenic gene expression in response to cAMP. CRTC2 may drive tumorigenesis in LKB1-null non-small cell lung cancers (NSCLC). The term includes any recombinant or naturally-occurring form of CRTC2 variants thereof that maintain CRTC2 function or activity (e.g., within at least 30%, 40%, 50%, 60%, 70%, 80%, 90%, 95%, or 100% function or activity compared to wildtype CRTC2). In embodiments, CRTC2 is encoded by the CRTC2 gene. In embodiments, CRTC2 has the amino acid sequence set forth in or corresponding to Entrez 200186, UniProt Q53ET0, RefSeq (protein) NP_859066, or RefSeq (protein) NP_859066.1. In embodiments, CRTC2 has the sequence:

```
                                        (SEQ ID NO: 5)
MATSGANGPGSATASASNPRKFSEKIALQKQRQAEETAAFEEVMMDIGS

TRLQAQKLRLAYTRSSHYGGSLPNVNQIGSGLAEFQSPLHSPLDSSRST

RHHGLVERVQRDPRRMVSPLRRYTRHIDSSPYSPAYLSPPPESSWRRTM

AWGNFPAEKGQLFRLPSALNRTSSDSALHTSVMNPSPQDTYPGPTPPSI

LPSRRGGILDGEMDPKVPAIEENLLDDKHLLKPWDAKKLSSSSSRPRSC

EVPGINIFPSPDQPANVPVLPPAMNTGGSLPDLTNLHFPPPLPTPLDPE

ETAYPSLSGGNSTSNLTHTMTHLGISRGMGLGPGYDAPGLHSPLSHPSL

QSSLSNPNLQASLSSPQPQLQGSHSHPSLPASSLARHVLPTTSLGHPSL

SAPALSSSSSSSSTSSPVLGAPSYPASTPGASPHHRRVPLSPLSLLAGP

ADARRSQQQLPKQFSPTMSPTLSSITQGVPLDTSKLSTDQRLPPYPYSS

PSLVLPTQPHTPKSLQQPGLPSQSCSVQSSGGQPPGRQSHYGTPYPPGP

SGHGQQSYHRPMSDFNLGNLEQFSMESPSASLVLDPPGFSEGPGFLGGE

GPMGGPQDPHTFNHQNLTHCSRHGSGPNIILTGDSSPGFSKEIAAALAG

VPGFEVSAAGLELGLGLEDELRMEPLGLEGLNMLSDPCALLPDPAVEES

FRSDRLQ.
```

The term "CRTC1" or "TORC1" refers to CREB regulated transcription coactivator 1. CRTC1, initially called TORC1, is a transcriptional coactivator for the transcription factor CREB. The term includes any recombinant or naturally-occurring form of CRTC1 variants thereof that maintain CRTC1 function or activity (e.g., within at least 30%, 40%, 50%, 60%, 70%, 80%, 90%, 95%, or 100% function or activity compared to wildtype CRTC1). In embodiments, CRTC1 is encoded by the CRTC1 gene. In embodiments, CRTC1 has the amino acid sequence set forth in or corresponding to Entrez 23373, UniProt Q6UUV9, RefSeq (protein) NP_001091952, or RefSeq (protein) NP_001091952.1. In embodiments, CRTC1 has the sequence:

```
                                        (SEQ ID NO: 6)
MATSNNPRKFSEKIALHNQKQAEETAAFEEVMKDLSLTRAARLQLQKSQ

YLQLGPSRGQYYGGSLPNVNQIGSGTMDLPFQPSGFLGEALAAAPVSLT

PFQSSGLDTSRTTRHHGLVDRVYRERGRLGSPHRRPLSVDKHGRQADSC

PYGTMYLSPPADTSWRRTNSDSALHQSTMTPTQPESFSSGSQDVHQKRV

LLLTVPGMEETTSEADKNLSKQAWDTKKTGSRPKSCEVPGINIFPSADQ

ENTTALIPATHNTGGSLPDLTNIHFPSPLPTPLDPEEPTFPALSSSSST

GNLAANLTHLGIGGAGQGMSTPGSSPQHRPAGVSPLSLSTEARRQQASP

TLSPLSPITQAVAMDALSLEQQLPYAFFTQAGSQQPPPQPQPPPPPPPA

SQQPPPPPPPQAPVRLPPGGPLLPSASLTRGPQPPPLAVTVPSSLPQSP

PENPGQPSMGIDIASAPALQQYRTSAGSPANQSPTSPVSNQGFSPGSSP

QHTSTLGSVFGDAYYEQQMAARQANALSHQLEQFNMMENAISSSSLYSP

GSTLNYSQAAMMGLTGSHGSLPDSQQLGYASHSGIPNIILTVTGESPPS

LSKELTSSLAGVGDVSFDSDSQFPLDELKIDPLTLDGLHMLNDPDMVLA

DPATEDTFRMDRL.
```

The term "CRTC3" or "TORC3" refers to CREB regulated transcription coactivator 3. CRTC3, initially called TORC3, is a transcriptional coactivator for the transcription factor CREB. The term includes any recombinant or naturally-occurring form of CRTC2 variants thereof that maintain CRTC3 function or activity (e.g., within at least 30%, 40%, 50%, 60%, 70%, 80%, 90%, 95%, or 100% function or activity compared to wildtype CRTC3). In embodiments, CRTC3 is encoded by the CRTC3 gene. In embodiments, CRTC3 has the amino acid sequence set forth in or corresponding to Entrez 64784, UniProt Q6UUV7, RefSeq (protein) NP_073606, or RefSeq (protein) NP_073606.1. In embodiments, CRTC3 has the sequence:

(SEQ ID NO: 7)
MAASPGSGSANPRKFSEKIALHTQRQAEETRAFEQLMTDLTLSRVQFQK

LQQLRLTQYHGGSLPNVSQLRSSASEFQPSFHQADNVRGTRHHGLVERP

SRNRFHPLHRRSGDKPGRQFDGSAFGANYSSQPLDESWPRQQPPWKDEK

HPGFRLTSALNRTNSDSALHTSALSTKPQDPYGGGGQSAWPAPYMGFCD

GENNGHGEVASFPGPLKEENLLNVPKPLPKQLWETKEIQSLSGRPRSCD

VGGGNAFPHNGQNLGLSPFLGTLNTGGSLPDLTNLHYSTPLPASLDTTD

HHFGSMSVGNSVNNIPAAMTHLGIRSSSGLQSSRSNPSIQATLNKTVLS

SSLNNHPQTSVPNASALHPSLRLFSLSNPSLSTTNLSGPSRRRQPPVSP

LTLSPGPEAHQGFSRQLSSTSPLAPYPTSQMVSSDRSQLSFLPTEAQAQ

VSPPPPYPAPQELTQPLLQQPRAPEAPAQQPQAASSLPQSDFQLLPAQG

SSLTNFFPDVGFDQQSMRPGPAFPQQVPLVQQGSRELQDSFHLRPSPYS

NCGSLPNTILPEDSSTSLFKDLNSALAGLPEVSLNVDTPFPLEEELQIE

PLSLDGLNMLSDSSMGLLDPSVEETFRADRL.

The term "hippo pathway" refers to the Hippo signaling pathway, also known as the Salvador-Warts-Hippo (SWH) pathway, controls organ size in animals through the regulation of cell proliferation and apoptosis. The pathway takes its name from one of its key signaling components—the protein kinase Hippo (Hpo). The Hippo pathway consists of a core kinase cascade in which Hpo phosphorylates the protein kinase Warts (Wts). Hpo (MST1/2 in mammals) is a member of the Ste-20 family of protein kinases. This highly conserved group of serine/threonine kinases regulates several cellular processes, including cell proliferation, apoptosis, and various stress responses.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. The terms "corresponds", "corresponds to", or "corresponding to" when referring to an amino acid residue in a protein means the given residue occupies the same essential structural position within the protein as the given residue. For example, a selected residue in a selected protein corresponds to K197 of human STRADα protein when the selected residue occupies the same essential spatial or other structural relationship as K197 of human STRADα protein. In some embodiments, where a selected protein is aligned for maximum homology with the human STRADα protein, the position in the aligned selected protein aligning with K197 is said to correspond to K197. Instead of a primary sequence alignment, a three dimensional structural alignment can also be used, e.g., where the structure of the selected protein is aligned for maximum correspondence with the human STRADα protein and the overall structures compared. In this case, an amino acid that occupies the same essential position as K197 in the structural model is said to correspond to the K197 residue.

The term "insulin resistance" or "IR" is a pathological condition in which cells fail to respond normally to the hormone insulin.

The term "diabetes therapeutic agent" refers to an agent (e.g. compound, small molecule, protein, nucleic acid) that can be administered to a subject in a therapeutically effective amount to treat diabetes. In embodiments, the diabetes therapeutic agent is a biguanide, sulfonylurea, meglitinide, thiazolidinedione, alpha-glucosidase inhibitor, incretin, GLP-1 analogue, DPP-4 inhibitor, GLP-1 receptor agonist, amylin agonist, or insulin analogue.

The term "polar moiety" refers to a portion or functional group of a molecule that is polar. The polar moiety may have an electric dipole moment, with a negatively charged end and a positively charged end. Polar moieties may contain polar bonds due to a difference in electronegativity between the bonded atoms. Non-limiting examples of a polar moiety include a moiety that contains an unsaturated carbonyl (e.g, carboxylic acid, carboxylate, ester, ketone, or amide) or an unsaturated oxide of sulfur (e.g., sulfone or sulfoxide) or phosphorus (e.g., phosphate or phosphonate). In embodiments, the polar moiety has the chemical formula:

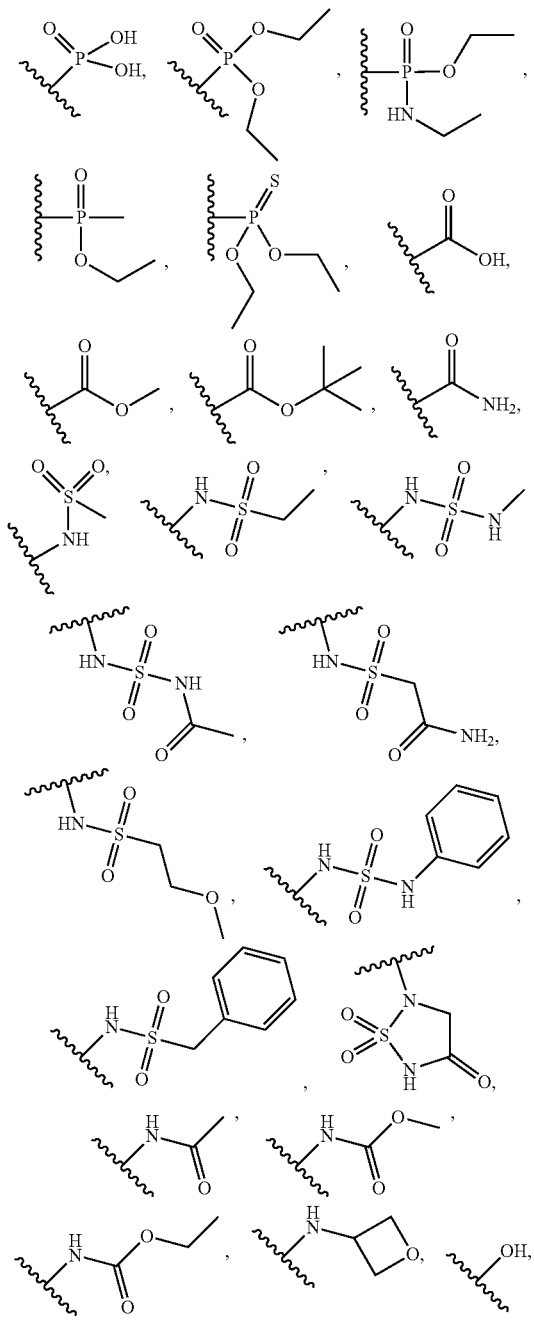

-continued
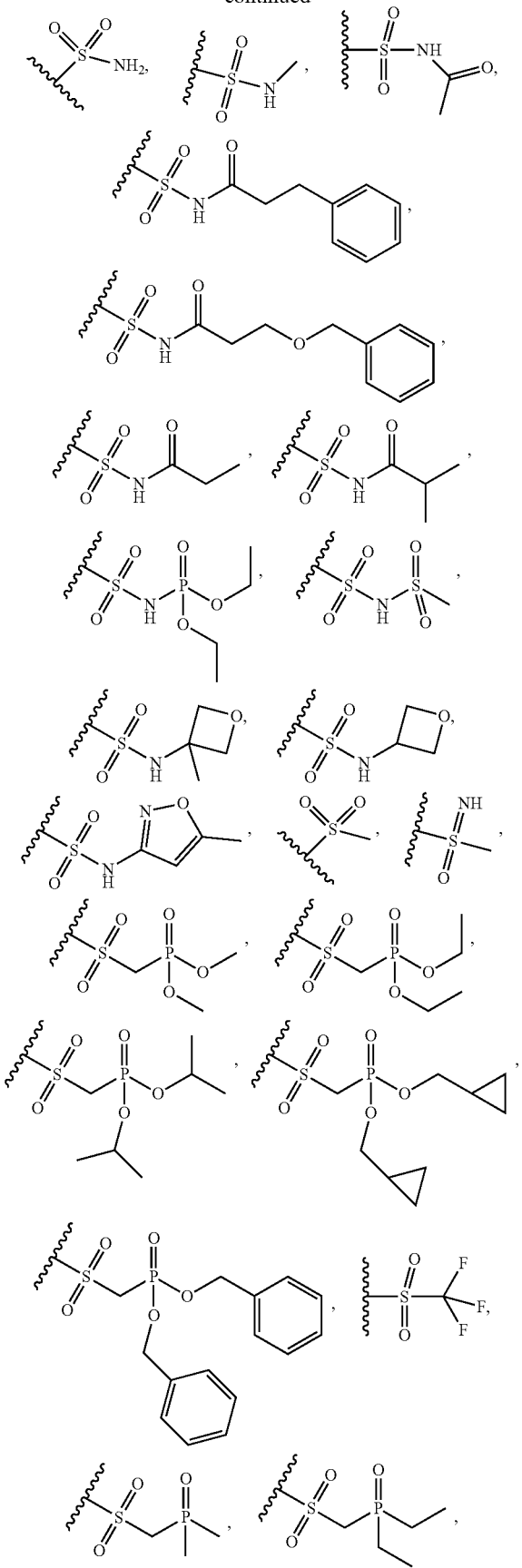
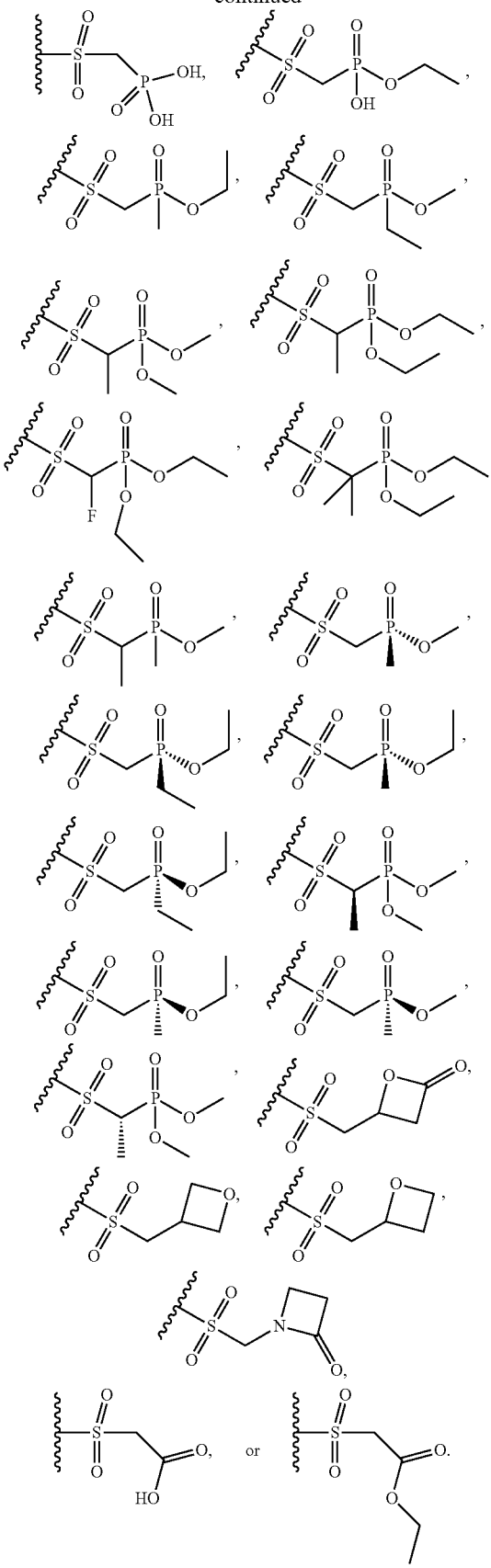

In embodiments, a polar moiety is capable of forming hydrogen bonds. In embodiments, a polar moiety may be a charged moiety (e.g., the polar moiety forms or is a cation or anion).

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator. In some embodiments, a STRAD associated disease modulator is a compound that reduces the severity of one or more symptoms of a disease associated with STRAD (e.g. cancer, an inflammatory disease, or an autoimmune disease). A STRAD modulator is a compound that increases or decreases the activity or function or level of activity or level of function of STRAD. In some embodiments, an LKB1 associated disease modulator is a compound that reduces the severity of one or more symptoms of a disease associated with LKB1 (e.g. cancer, an inflammatory disease, or an autoimmune disease). An LKB1 modulator is a compound that increases or decreases the activity or function or level of activity or level of function of LKB1.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease, a cancer associated with STRAD activity, STRAD associated cancer, STRAD associated disease (e.g., cancer, an inflammatory disease, or an autoimmune disease)) means that the disease (e.g. cancer, an inflammatory disease, or an autoimmune disease) is caused by (in whole or in part), or a symptom of the disease is caused by (in whole or in part) the substance or substance activity or function. For example, a cancer associated with STRAD activity or function may be a cancer that results (entirely or partially) from aberrant STRAD function (e.g. enzyme activity, protein-protein interaction, signaling pathway) or a cancer wherein a particular symptom of the disease is caused (entirely or partially) by aberrant STRAD activity or function. As used herein, what is described as being associated with a disease, if a causative agent, could be a target for treatment of the disease. For example, a cancer associated with STRAD activity or function or a STRAD associated disease (e.g., cancer, an inflammatory disease, or an autoimmune disease), may be treated with a STRAD modulator or STRAD inhibitor, in the instance where increased STRAD activity or function (e.g. signaling pathway activity) causes the disease (e.g., cancer, an inflammatory disease, or an autoimmune disease). A cancer associated with STRAD activity or function or a STRAD associated disease (e.g., cancer, an inflammatory disease, or an autoimmune disease), may be treated with a STRAD modulator or STRAD activator, in the instance where decreased STRAD activity or function (e.g. signaling pathway activity) causes the disease (e.g., cancer, an inflammatory disease, or an autoimmune disease). In embodiments, the term "associated" or "associated with" in the context of a substance or substance activity or function associated with a disease (e.g. a protein associated disease, a cancer associated with LKB1 activity, LKB1 associated cancer, LKB1 associated disease (e.g., cancer, an inflammatory disease, or an autoimmune disease)) means that the disease (e.g. cancer, an inflammatory disease, or an autoimmune disease) is caused by (in whole or in part), or a symptom of the disease is caused by (in whole or in part) the substance or substance activity or function. For example, a cancer associated with LKB1 activity or function may be a cancer that results (entirely or partially) from aberrant LKB1 function (e.g. enzyme activity, protein-protein interaction, signaling pathway) or a cancer wherein a particular symptom of the disease is caused (entirely or partially) by aberrant LKB1 activity or function. As used herein, what is described as being associated with a disease, if a causative agent, could be a target for treatment of the disease. For example, a cancer associated with LKB1 activity or function or a LKB1 associated disease (e.g., cancer, an inflammatory disease, or an autoimmune disease), may be treated with a LKB1 modulator or LKB1 inhibitor, in the instance where increased LKB1 activity or function (e.g. signaling pathway activity) causes the disease (e.g., cancer, an inflammatory disease, or an autoimmune disease). A cancer associated with LKB1 activity or function or a LKB1 associated disease (e.g., cancer, an inflammatory disease, or an autoimmune disease), may be treated with a LKB1 modulator or LKB1 activator, in the instance where decreased LKB1 activity or function (e.g. signaling pathway activity) causes the disease (e.g., cancer, an inflammatory disease, or an autoimmune disease).

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propagated to other signaling pathway components. For example, binding of a STRAD with a compound as described herein may reduce the level of a product of the STRAD catalyzed reaction or the level of a downstream derivative of the product or binding may reduce the interactions between the STRAD enzyme or a STRAD reaction product and downstream effectors or signaling pathway components, resulting in changes in cell growth, proliferation, or survival. For example, binding of a LKB1 with a compound as described herein may reduce the level of a product of the LKB1 catalyzed reaction or the level of a downstream derivative of the product or binding may reduce the interactions between the LKB1 enzyme or a LKB1 reaction product and downstream effectors or signaling pathway components, resulting in changes in cell growth, proliferation, or survival. Alternatively, binding of a STRAD with a compound as described herein may increase the level of a product of the STRAD catalyzed reaction or the level of a downstream derivative of the product or binding may increase the interactions between the STRAD enzyme or a STRAD reaction product and downstream effectors or signaling pathway components, resulting in changes in cell growth, proliferation, or survival. Alternatively, binding of a LKB1 with a compound as described herein may increase the level of a product of the LKB1 catalyzed reaction or the level of a downstream derivative of the product or binding may increase the interactions between the LKB1 enzyme or a LKB1 reaction product and downstream effectors or signaling pathway components, resulting in changes in cell growth, proliferation, or survival.

In this disclosure, "comprises," "comprising," "containing" and "having" and the like can have the meaning ascribed to them in U.S. patent law and can mean "includes," "including," and the like. "Consisting essentially of or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

The terms "disease" or "condition" refer to a state of being or health status of a patient or subject capable of being treated with the compounds or methods provided herein. The disease may be a cancer. The disease may be an autoimmune disease. The disease may be an inflammatory disease. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "inflammatory disease" refers to a disease or condition characterized by aberrant inflammation (e.g. an increased level of inflammation compared to a control such as a healthy person not suffering from a disease). Examples of inflammatory diseases include autoimmune diseases, traumatic brain injury, arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, allergic asthma, acne vulgaris, celiac disease, chronic prostatitis, inflammatory bowel disease, pelvic inflammatory disease, reperfusion injury, ischemia reperfusion injury, stroke, sarcoidosis, transplant rejection, interstitial cystitis, atherosclerosis, scleroderma, and atopic dermatitis.

As used herein, the term "cancer" refers to all types of cancer, neoplasm or malignant tumors found in mammals (e.g. humans), including leukemias, lymphomas, carcinomas and sarcomas. Exemplary cancers that may be treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Exemplary cancers that may be treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

As used herein, the term "autoimmune disease" refers to a disease or condition in which a subject's immune system has an aberrant immune response against a substance that does not normally elicit an immune response in a healthy subject. Examples of autoimmune diseases that may be treated with a compound, pharmaceutical composition, or method described herein include Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal or neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with *Streptococcus*), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatica, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, or Wegener's granulomatosis (i.e., Granulomatosis with Polyangiitis (GPA).

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms (e.g., ocular pain, seeing halos around lights, red eye, very high intraocular pressure), fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is not prophylactic treatment (e.g., the patient has a disease, the patient suffers from a disease).

The term "prevent" refers to a decrease in the occurrence of STRAD associated disease symptoms or LKB1 associated disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In embodiments, an anticancer agent as used herein refers to a molecule (e.g. compound, peptide, protein, nucleic acid) used to treat cancer through destruction or inhibition of cancer cells or tissues. In embodiments, the anticancer agent is a compound. Anticancer agents may be selective for certain cancers or certain tissues. In embodiments, anticancer agents herein may include epigenetic inhibitors and multi-kinase inhibitors. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/ AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin I1 (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxo™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-AABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-*pseudomonas* exotoxin conjugate, etc.), immunotherapy (e.g., cellular immunotherapy, antibody therapy, cytokine therapy, combination immunotherapy, etc.), radioimmunotherapy (e.g., anti-CD20 monoclonal antibody conjugated to $^{111}$In, $^{90}$Y, or $^{131}$I, etc.), immune checkpoint inhibitors (e.g., CTLA4 blockade, PD-1 inhibitors, PD-L1 inhibitors, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™) afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

The term "irreversible covalent bond" is used in accordance with its plain ordinary meaning in the art and refers to the resulting association between atoms or molecules of (e.g., electrophilic chemical moiety and nucleophilic moiety) wherein the probability of dissociation is low. In embodiments, the irreversible covalent bond does not easily dissociate under normal biological conditions. In embodiments, the irreversible covalent bond is formed through a chemical reaction between two species (e.g., electrophilic chemical moiety and nucleophilic moiety).

The term "pseudo-kinase STRADα stabilizing compound" refers to a compound that stabilizes the LKB1-STRAD-MO25 trimer (e.g., relative to absence of the compound). In embodiments, the compound increases stability of the trimer by at least 1.1-fold, 1.2, 1.3, 1.4, 1.5, 1.6, 1.7, 1.8, 1.9, 2.0, 5.0, 10, 50, 100, 1000, or 10,000-fold in equilibrium concentration of trimer at a fixed concentration of each component of the trimer compared to absence of the compound.

The term "pseudo-kinase STRADα ATP binding pocket" refers to region of the pseudo-kinase STRADα that binds ATP. The pseudo-kinase STRADα ATP binding pocket is lined with pseudo-kinase STRADα amino acids capable of contacting ATP when ATP binds the pseudo-kinase STRADα (e.g., contacts pseudo-kinase STRADα in an active and/or productive complex). In embodiments, the pseudo-kinase STRADα ATP binding pocket includes (is lined with) amino acids corresponding to human pseudo-kinase STRADα Lys 197, His 200, Arg 215, Lys 77, Arg 100, Ser199, Lys 239, Asp 157, Ser 154, Leu 202, Gly 153, Met 150, Phe 149, Ser 148, Thr 98, Thr 147, Ile 75, Val 85, Gly 76, Phe 415, Met 83, Phe 79, or Gly 78. In embodiments, the pseudo-kinase STRADα ATP binding pocket includes (is lined with) amino acids corresponding to human pseudo-kinase STRADα Lys 197, His 200, Arg 215, Lys 77, Arg 100, Ser199, Lys 239, Asp 157, Ser 154, Leu 202, Gly 153, Met 150, Phe 149, Ser 148, Thr 98, Thr 147, Ile 75, Val 85, Gly 76, Phe 415, Met 83, Phe 79, and Gly 78. In embodiments, the pseudo-kinase STRADα ATP binding pocket includes (is lined with) amino acids corresponding to human pseudo-kinase STRADα Lys 197, His 200, Arg 215, Lys 77, Arg 100, Ser199, Asp 157, Met 150, Ser 148, Thr 98, Val 85, or Phe 79. In embodiments, the pseudo-kinase STRADα ATP binding pocket includes (is lined with) amino acids corresponding to human pseudo-kinase STRADα Lys 197, His 200, Arg 215, Lys 77, Arg 100, Ser199, Asp 157, Met 150, Ser 148, Thr 98, Val 85, and Phe 79. In embodiments, the pseudo-kinase STRADα ATP binding pocket includes (is lined with) amino acids corresponding to human pseudo-kinase STRADα Lys 197, His 200, Arg 215, Lys 77, Arg 100, or Ser199. In embodiments, the pseudo-kinase STRADα ATP binding pocket includes (is lined with) amino acids corresponding to human pseudo-kinase STRADα Lys 197, His 200, Arg 215, Lys 77, Arg 100, and Ser199.

The term "LKB1-STRADα-Mo25 trimer complex association" refers to the degree to which the LKB1-STRADα-Mo25 trimer complex is associated.

II. Compounds

In an aspect is provided a compound having the formula:

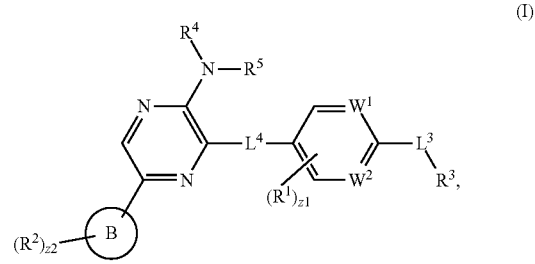

(I)

-continued

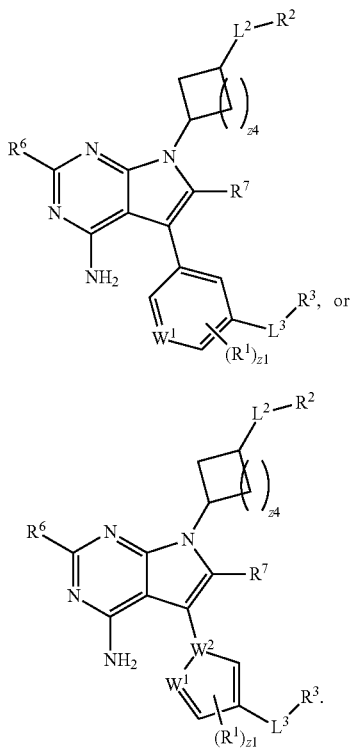

$W^1$ is N, CH, or $CR^1$.
$W^2$ is N, CH, or $CR^1$.
$R^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NR^{1C}NR^{1A}R^{1B}$, —$ONR^{1A}R^{1B}$, —$NHC(O)NR^{1C}NR^{1A}R^{1B}$, —$NHC(O)NR^{1A}R^{1B}$, —$N(O)_{m1}$, —$NR^{1A}R^{1B}$, —$C(O)R^{1C}$, —$C(O)OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$—$NR^{1A}OR^{1C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl.

z1 is an integer from 0 to 4.
Ring B is aryl or heteroaryl.
$L^2$ is a bond, —NH—, —O—, —S—, —C(O)—, —C(O)NH—, —NHC(O)—, —NHC(O)NH—, —C(O)O—, —OC(O)—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

$R^2$ is independently oxo, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, $SO_2NR^{2A}R^{2B}$, —$NR^{2C}NR^{2A}R^{2B}$, —$ONR^{2A}R^{2B}$, —$NHC(O)NR^{2C}NR^{2A}R^{2B}$, —$NHC(O)NR^{2A}R^{2B}$, —$N(O)_{m2}$, —$NR^{2A}R^{2B}$, —$C(O)R^{2C}$, —$C(O)OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl.

z2 is an integer from 0 to 6.
$L^3$ is a bond, —NH—, —O—, —C(O)—, —C(O)NH—, —NHC(O)—, —NHC(O)NH—, —C(O)O—, —OC(O)—, —S(O)—, —$SO_2$—, P(O)—, —$P(O)_2$—, —P(S)—, —$NHSO_2$—, —$SO_2NH$—, —$SO_2CH_2$—, —$SO_2CH_2P(O)$—, substituted or unsubstituted alkylene, or substituted or unsubstituted heteroalkylene.

$R^3$ is independently a polar moiety.
$L^4$ is —C(O)NH— or —NHC(O)—.
$R^4$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ and $R^5$ substituents bonded to the same nitrogen may optionally be joined to form a substituted or unsubstituted heterocycloalkyl or substituted or unsubstituted heteroaryl.

$R^6$ is independently hydrogen, halogen, —$CX^6_3$, —$CHX^6_2$, —$CH_2X^6$, —$OCX^6_3$, —$OCH_2X^6$, —$OCHX^6_2$, —CN, —$SO_{n6}H$, —$SO_{v6}NH_2$, —$NHNH_2$, —$ONH_2$, —$NHC(O)NHNH_2$, —$NHC(O)NH_2$, —$N(O)_{m6}$, —$NH_2$, —C(O)H, —COOH, —$C(O)NH_2$, —OH, —$NHSO_2H$, —NHC(O)H, —NHC(O)OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^7$ is independently hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}H$, —$SO_{v7}NH$, —$NHNH_2$, —$ONH_2$, —NHC(O)$NHNH_2$, —$NHC(O)NH_2$, —$N(O)_{m7}$, —$NH_2$, —C(O)H, —COOH, —$C(O)NH_2$, —OH, —$NHSO_2H$, —NHC(O)H, —NHC(O)OH, —NHOH, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^{1A}$, $R^{1B}$, $R^{1C}$, $R^{1D}$, $R^{2A}$, $R^{2B}$, $R^{2C}$, and $R^{2D}$ are independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl.

z4 is 1 or 2.

$X^1$, $X^2$, $X^6$, and $X^7$ are independently —F, —Cl, —Br, or —I.

n1, n2, n6, and n7 are independently an integer from 0 to 4.

m1, m2, v1, v2, m6, v6, m7, and v7 are independently 1 or 2.

In embodiments, $L^3$ is a bond. In embodiments, $L^3$ is —NH—. In embodiments, $L^3$ is —O—. In embodiments, $L^3$ is —C(O)—. In embodiments, $L^3$ is —C(O)NH—. In embodiments, $L^3$ is —NHC(O)—. In embodiments, $L^3$ is —NHC(O)NH—. In embodiments, $L^3$ is —C(O)O—. In embodiments, $L^3$ is —OC(O)—. In embodiments, $L^3$ is —S(O)—. In embodiments, $L^3$ is —SO$_2$—. In embodiments, $L^3$ is P(O)—. In embodiments, $L^3$ is —P(O)$_2$—. In embodiments, $L^3$ is —P(S)—. In embodiments, $L^3$ is —NHSO$_2$—. In embodiments, $L^3$ is —SO$_2$NH—. In embodiments, $L^3$ is —SO$_2$CH$_2$—. In embodiments, $L^3$ is —SO$_2$CH$_2$P(O)—. In embodiments, $L^3$ is substituted or unsubstituted alkylene. In embodiments, $L^3$ is substituted or unsubstituted heteroalkylene.

In embodiments, $L^3$ is a —S(O)—, —SO$_2$—, P(O)—, —P(O)$_2$—, —P(S)—, —NHSO$_2$—, —SO$_2$NH—, —SO$_2$CH$_2$—, or —SO$_2$CH$_2$P(O)—. In embodiments, $L^3$ is a —S(O)—, —SO$_2$—, —SO$_2$NH—, —SO$_2$CH$_2$—, or —SO$_2$CH$_2$P(O)—.

In embodiments, $L^3$ is a bond, —NH—, —O—, —C(O)—, —C(O)NH—, —NHC(O)—, —NHC(O)NH—, —C(O)O—, —OC(O)—, substituted or unsubstituted alkylene, or substituted or unsubstituted heteroalkylene.

In embodiments, $L^2$ is a bond, —NH—, —O—, —S—, —C(O)—, —C(O)NH—, —NHC(O)—, —NHC(O)NH—, —C(O)O—, or —OC(O)—. In embodiments, $L^2$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^2$ is a bond. In embodiments, $L^2$ is —NH—. In embodiments, $L^2$ is —O—. In embodiments, $L^2$ is —S—. In embodiments, $L^2$ is —C(O)—. In embodiments, $L^2$ is —C(O)NH—. In embodiments, $L^2$ is —NHC(O)—. In embodiments, $L^2$ is —NHC(O)NH—. In embodiments, $L^2$ is —C(O)O—. In embodiments, $L^2$ is —OC(O)—. In embodiments, $L^2$ is substituted or unsubstituted alkylene. In embodiments, $L^2$ is substituted or unsubstituted heteroalkylene. In embodiments, $L^2$ is substituted or unsubstituted cycloalkylene. In embodiments, $L^2$ is substituted or unsubstituted heterocycloalkylene. In embodiments, $L^2$ is substituted or unsubstituted arylene. In embodiments, $L^2$ is substituted or unsubstituted heteroarylene. In embodiments, $L^2$ is a bond, substituted or unsubstituted alkylene, or substituted or unsubstituted heteroalkylene. In embodiments, $L^2$ is a bond substituted or unsubstituted alkylene, or substituted or unsubstituted heteroalkylene. In embodiments, $L^2$ is a bond, —CH$_2$—, —CH$_2$CH$_2$—, —CH$_2$CH$_2$CH$_2$—, —OCH$_2$—, —OCH$_2$CH$_2$—, or —OCH$_2$CH$_2$CH$_2$—. In embodiments, $L^2$ is —CH$_2$—, —CH$_2$CH$_2$—, or —CH$_2$CH$_2$CH$_2$—. In embodiments, $L^2$ is —OCH$_2$—, —OCH$_2$CH$_2$—, or —OCH$_2$CH$_2$CH$_2$—. In embodiments, $L^2$ is —CH$_2$—. In embodiments, $L^2$ is —CH$_2$CH$_2$—. In embodiments, $L^2$ is —CH$_2$CH$_2$CH$_2$—. In embodiments, $L^2$ is —OCH$_2$—. In embodiments, $L^2$ is —OCH$_2$CH$_2$—. In embodiments, $L^2$ is —OCH$_2$CH$_2$CH$_2$—. In embodiments, $L^2$ is a bond or —CH$_2$—.

In embodiments, $R^4$ is independently hydrogen, —CCl$_3$, —CBr$_3$, —CF$_3$, —CI$_3$, —CN, —OH, —NH$_2$, —COOH, —CONH$_2$, —OCCl$_3$, —OCF$_3$, —OCBr$_3$, —OCI$_3$, substituted or unsubstituted C$_1$-C$_3$ alkyl, substituted or unsubstituted 2 to 4 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is independently hydrogen. In embodiments, $R^4$ is independently —CCl$_3$. In embodiments, $R^4$ is independently —CBr$_3$. In embodiments, $R^4$ is independently —CF$_3$. In embodiments, $R^4$ is independently-CI$_3$. In embodiments, $R^4$ is independently —CN. In embodiments, $R^4$ is independently —OH. In embodiments, $R^4$ is independently —NH$_2$. In embodiments, $R^4$ is independently —COOH. In embodiments, $R^4$ is independently —CONH$_2$. In embodiments, $R^4$ is independently —OCCl$_3$. In embodiments, $R^4$ is independently —OCF$_3$. In embodiments, $R^4$ is independently —OCBr$_3$. In embodiments, $R^4$ is independently —OCI$_3$. In embodiments, $R^4$ is independently substituted or unsubstituted C$_1$-C$_3$ alkyl. In embodiments, $R^4$ is independently unsubstituted methyl. In embodiments, $R^4$ is independently unsubstituted ethyl. In embodiments, $R^4$ is independently unsubstituted propyl. In embodiments, $R^4$ is independently substituted or unsubstituted 2 to 4 membered heteroalkyl. In embodiments, $R^4$ is independently unsubstituted 2 to 4 membered heteroalkyl. In embodiments, $R^4$ is independently substituted or unsubstituted C$_3$-C$_6$ cycloalkyl. In embodiments, $R^4$ is independently unsubstituted C$_3$-C$_6$ cycloalkyl. In embodiments, $R^4$ is independently substituted or unsubstituted 3 to 6 membered heterocycloalkyl. In embodiments, $R^4$ is independently unsubstituted 3 to 6 membered heterocycloalkyl. In embodiments, $R^4$ is independently substituted or unsubstituted phenyl. In embodiments, $R^4$ is independently unsubstituted phenyl. In embodiments, $R^4$ is independently substituted or unsubstituted 5 to 6 membered heteroaryl. In embodiments, $R^4$ is independently unsubstituted 5 to 6 membered heteroaryl.

In embodiments, $R^5$ is independently hydrogen, —CCl$_3$, —CBr$_3$, —CF$_3$, —CI$_3$, —CN, —OH, —NH$_2$, —COOH, —CONH$_2$, —OCCl$_3$, —OCF$_3$, —OCBr$_3$, —OCI$_3$, substituted or unsubstituted C$_1$-C$_3$ alkyl, substituted or unsubstituted 2 to 4 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^5$ is independently hydrogen. In embodiments, $R^5$ is independently —CCl$_3$. In embodiments, $R^5$ is independently —CBr$_3$. In embodiments, $R^5$ is independently —CF$_3$. In embodiments, $R^5$ is independently —CI$_3$. In embodiments, $R^5$ is independently —CN. In embodiments, $R^5$ is independently —OH. In embodiments, $R^5$ is independently —NH$_2$. In embodiments, $R^5$ is independently —COOH. In embodiments, $R^5$ is independently —CONH$_2$. In embodiments, $R^5$ is independently —OCCl$_3$. In embodiments, $R^5$ is independently —OCF$_3$. In embodiments, $R^5$ is independently —OCBr$_3$. In embodiments, $R^5$ is independently —OCI$_3$. In embodiments, $R^5$ is independently substituted or unsubstituted $C_1$-$C_3$ alkyl. In embodiments, $R^5$ is independently unsubstituted methyl. In embodiments, $R^5$ is independently unsubstituted ethyl. In embodiments, $R^5$ is independently unsubstituted propyl. In embodiments, $R^5$ is independently substituted or unsubstituted 2 to 4 membered heteroalkyl. In embodiments, $R^5$ is independently unsubstituted 2 to 4 membered heteroalkyl. In embodiments, $R^5$ is independently substituted or unsubstituted $C_3$-$C_6$ cycloalkyl. In embodiments, $R^5$ is independently unsubstituted $C_3$-$C_6$ cycloalkyl. In embodiments, $R^5$ is independently substituted or unsubstituted 3 to 6 membered heterocycloalkyl. In embodiments, $R^5$ is independently unsubstituted 3 to 6 membered heterocycloalkyl. In embodiments, $R^5$ is independently substituted or unsubstituted phenyl. In embodiments, $R^5$ is independently unsubstituted phenyl. In embodiments, $R^5$ is independently substituted or unsubstituted 5 to 6 membered heteroaryl. In embodiments, $R^5$ is independently unsubstituted 5 to 6 membered heteroaryl.

In embodiments, $R^4$ and $R^5$ substituents bonded to the same nitrogen may optionally be joined to form a substituted or unsubstituted 3 to 6 membered heterocycloalkyl or substituted or unsubstituted 5 to 6 membered heteroaryl. In embodiments, $R^4$ and $R^5$ substituents bonded to the same nitrogen may optionally be joined to form an unsubstituted 3 to 6 membered heterocycloalkyl. In embodiments, $R^4$ and $R^5$ substituents bonded to the same nitrogen may optionally be joined to form an unsubstituted 5 to 6 membered heteroaryl.

In embodiments, $R^6$ is independently hydrogen. In embodiments, $R^6$ is independently halogen. In embodiments, $R^6$ is independently —$CCl_3$. In embodiments, $R^6$ is independently —$CBr_3$. In embodiments, $R^6$ is independently —$CF_3$. In embodiments, $R^6$ is independently —$CI_3$. In embodiments, $R^6$ is independently —CN. In embodiments, $R^6$ is independently —$SO_2H$. In embodiments, $R^6$ is independently —$SO_2NH$. In embodiments, $R^6$ is independently —$NHNH_2$. In embodiments, $R^6$ is independently —$ONH_2$. In embodiments, $R^6$ is independently —$NHC(O)NHNH_2$. In embodiments, $R^6$ is independently —$NHC(O)NH_2$. In embodiments, $R^6$ is independently —$N(O)_2$. In embodiments, $R^6$ is independently —$C(O)H$. In embodiments, $R^6$ is independently —OH. In embodiments, $R^6$ is independently —$NH_2$. In embodiments, $R^6$ is independently —COOH. In embodiments, $R^6$ is independently —$CONH_2$. In embodiments, $R^6$ is independently —$NHSO_2H$. In embodiments, $R^6$ is independently —$NHC(O)H$. In embodiments, $R^6$ is independently —$NHC(O)OH$. In embodiments, $R^6$ is independently —NHOH. In embodiments, $R^6$ is independently —$N_3$. In embodiments, $R^6$ is independently —$OCCl_3$. In embodiments, $R^6$ is independently —$OCF_3$. In embodiments, $R^6$ is independently —$OCBr_3$. In embodiments, $R^6$ is independently —$OCI_3$. In embodiments, $R^6$ is independently substituted or unsubstituted $C_1$-$C_3$ alkyl. In embodiments, $R^6$ is independently unsubstituted methyl. In embodiments, $R^6$ is independently unsubstituted ethyl. In embodiments, $R^6$ is independently unsubstituted propyl. In embodiments, $R^6$ is independently substituted or unsubstituted 2 to 4 membered heteroalkyl. In embodiments, $R^6$ is independently unsubstituted 2 to 4 membered heteroalkyl. In embodiments, $R^6$ is independently unsubstituted $C_3$-$C_6$ cycloalkyl. In embodiments, $R^6$ is independently unsubstituted 3 to 6 membered heterocycloalkyl. In embodiments, $R^6$ is independently unsubstituted phenyl. In embodiments, R is independently unsubstituted 5 to 6 membered heteroaryl.

In embodiments, $R^7$ is independently hydrogen. In embodiments, $R^7$ is independently halogen. In embodiments, $R^7$ is independently —$CCl_3$. In embodiments, $R^7$ is independently —$CBr_3$. In embodiments, $R^7$ is independently —$CF_3$. In embodiments, $R^7$ is independently —$CI_3$. In embodiments, $R^7$ is independently —CN. In embodiments, $R^7$ is independently —$SO_2H$. In embodiments, $R^7$ is independently —$SO_2NH$. In embodiments, $R^7$ is independently —$NHNH_2$. In embodiments, $R^7$ is independently —$ONH_2$. In embodiments, $R^7$ is independently —$NHC(O)NHNH_2$. In embodiments, $R^7$ is independently —$NHC(O)NH_2$. In embodiments, $R^7$ is independently —$N(O)_2$. In embodiments, $R^7$ is independently —$C(O)H$. In embodiments, $R^7$ is independently —OH. In embodiments, $R^7$ is independently —$NH_2$. In embodiments, $R^7$ is independently —COOH. In embodiments, $R^7$ is independently —$CONH_2$. In embodiments, $R^7$ is independently —$NHSO_2H$. In embodiments, $R^7$ is independently —$NHC(O)H$. In embodiments, $R^7$ is independently —$NHC(O)OH$. In embodiments, $R^7$ is independently —NHOH. In embodiments, $R^7$ is independently —$N_3$. In embodiments, $R^7$ is independently —$OCCl_3$. In embodiments, $R^7$ is independently —$OCF_3$. In embodiments, $R^7$ is independently —$OCBr_3$. In embodiments, $R^7$ is independently —$OCI_3$. In embodiments, $R^7$ is independently substituted or unsubstituted $C_1$-$C_3$ alkyl. In embodiments, $R^7$ is independently unsubstituted methyl. In embodiments, $R^7$ is independently unsubstituted ethyl. In embodiments, $R^7$ is independently unsubstituted propyl. In embodiments, $R^7$ is independently substituted or unsubstituted 2 to 4 membered heteroalkyl. In embodiments, $R^7$ is independently unsubstituted 2 to 4 membered heteroalkyl. In embodiments, $R^7$ is independently unsubstituted $C_3$-$C_6$ cycloalkyl. In embodiments, $R^7$ is independently unsubstituted 3 to 6 membered heterocycloalkyl. In embodiments, $R^7$ is independently unsubstituted phenyl. In embodiments, $R^7$ is independently unsubstituted 5 to 6 membered heteroaryl.

In embodiments, the compound has the formula:

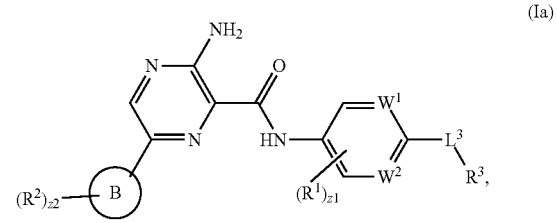

(Ia)

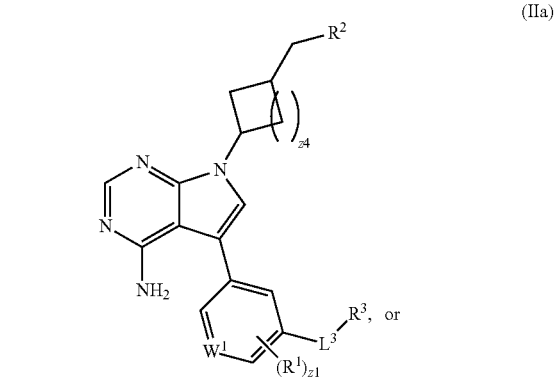

(IIa)

-continued

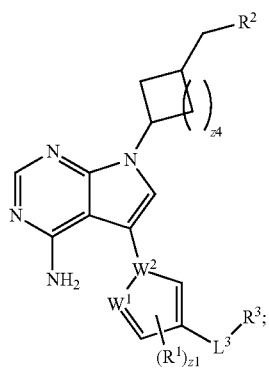

(IIIa)

wherein, $R^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NR^{1C}NR^{1A}R^{1B}$, —$ONR^{1A}R^{1B}$, —$NHC(O)NR^{1C}NR^{1A}R^{1B}$, —$NHC(O)NR^{1A}R^{1B}$, —$N(O)_{m1}$, —$NR^{1A}R^{1B}$, —$C(O)R^{1C}$, —C(O)—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; Ring B is phenyl or 5 to 10 membered heteroaryl; $R^2$ is independently oxo, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}N^{2A}R^{2B}$, —$ONR^{2A}R^{2B}$, —$NHC(O)NR^{2C}NR^{2A}R^{2B}$, —$NHC(O)NR^{2A}R^{2B}$, —$N(O)_{m2}$, —$NR^{2A}R^{2B}$, —$C(O)R^{2C}$, —C(O)—$OR^{2C}$, —$C(O)NR^{2A}R^{2B}$, —$OR^{2D}$, —$N^{2A}SO_2R^{2D}$, —$NR^{2A}C(O)R^{2C}$, —$NR^{2A}C(O)OR^{2C}$, —$NR^{2A}OR^{2C}$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; and $L^3$ is a bond, —NH—, —O—, —C(O)—, —C(O)NH—, —NHC(O)—, —NHC(O)NH—, —C(O)O—, —OC(O)—, substituted or unsubstituted $C_1$-$C_6$ alkylene, or substituted or unsubstituted 2 to 6 membered heteroalkylene.

In embodiments, $R^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NR^{1C}NR^{1A}R^{1B}$, —$ONR^{1A}R^{1B}$, —$NHC(O)NR^{1C}NR^{1A}R^{1B}$, —$NHC(O)NR^{1A}R^{1B}$, —$N(O)_{m1}$, —$NR^{1A}R^{1B}$, —$C(O)R^{1C}$, —C(O)—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 6 membered heterocycloalkyl, substituted or unsubstituted $C_6$-$C_{10}$ aryl, or substituted or unsubstituted 5 to 10 membered heteroaryl; two adjacent $R^1$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, $R^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1A}R^{1B}$, —$NR^{1C}NR^{1A}R^{1B}$, —$ONR^{1A}R^{1B}$, —$NHC(O)NR^{1C}NR^{1A}R^{1B}$, —$NHC(O)NR^{1A}R^{1B}$, —$N(O)_{m1}$, —$NR^{1A}R^{1B}$, —$C(O)R^{1C}$, —C(O)—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$N_3$.

In embodiments, $R^1$ is independently halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, or —$OCH_2F$.

In embodiments, $R^1$ is independently —F. In embodiments, $R^1$ is independently —$C_1$. In embodiments, $R^1$ is independently —Br. In embodiments, $R^1$ is independently —I. In embodiments, $R^1$ is independently —$CCl_3$. In embodiments, $R^1$ is independently —$CBr_3$. In embodiments, $R^1$ is independently —$CF_3$. In embodiments, $R^1$ is independently —$CI_3$. In embodiments, $R^1$ is independently —$CHCl_2$. In embodiments, $R^1$ is independently —$CHBr_2$. In embodiments, $R^1$ is independently —$CHF_2$. In embodiments, $R^1$ is independently —$CHI_2$. In embodiments, $R^1$ is independently —$CH_2Cl$. In embodiments, $R^1$ is independently —$CH_2Br$. In embodiments, $R^1$ is independently —$CH_2F$. In embodiments, $R^1$ is independently —$CH_2I$. In embodiments, $R^1$ is independently —CN. In embodiments, $R^1$ is independently —OH. In embodiments, $R^1$ is independently —$NH_2$. In embodiments, $R^1$ is independently —COOH. In embodiments, $R^1$ is independently —$CONH_2$. In embodiments, $R^1$ is independently —$OCCl_3$. In embodiments, $R^1$ is independently —$OCF_3$. In embodiments, $R^1$ is independently —$OCBr_3$. In embodiments, $R^1$ is independently —$OCI_3$. In embodiments, $R^1$ is independently —$OCHCl_2$. In embodiments, $R^1$ is independently —$OCHBr_2$. In embodiments, $R^1$ is independently —$OCHI_2$. In embodiments, $R^1$ is independently —$OCHF_2$. In embodiments, $R^1$ is independently —$OCH_2Cl$. In embodiments, $R^1$ is independently —$OCH_2Br$. In embodiments, $R^1$ is independently —$OCH_2I$. In embodiments, $R^1$ is independently —$OCH_2F$.

In embodiments, $R^1$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, $R^1$ is independently substituted or unsubstituted alkyl. In embodiments, $R^1$ is independently unsubstituted alkyl. In embodiments, $R^1$ is independently substituted or unsubstituted heteroalkyl. In embodiments, $R^1$ is independently substituted or unsubstituted cycloalkyl. In embodiments, $R^1$ is independently substituted or unsubstituted heterocycloalkyl. In embodiments, $R^1$ is independently substituted or unsubstituted aryl. In embodiments, $R^1$ is independently substituted or unsubstituted heteroaryl.

In embodiments, $R^1$ is independently halogen, —$CCl_3$, —$CBr_3$, —$CF_3$, —$CI_3$, $CHCl_2$, —$CHBr_2$, —$CHF_2$, —$CHI_2$, —CH$_2$Cl, —CH$_2$Br, —CH$_2$F, —CH$_2$I, —CN, —OH, —NH$_2$, —COOH, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted C$_1$-C$_6$ alkyl, or substituted or unsubstituted 2 to 6 membered heteroalkyl. In embodiments, R$^1$ is independently —F, —Cl, —Br, —I, unsubstituted methyl, unsubstituted ethyl, or unsubstituted propyl.

In embodiments, R$^1$ is independently substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted C$_6$-C$_{10}$ aryl, or substituted or unsubstituted 5 to 10 membered heteroaryl; two adjacent R$^1$ substituents may optionally be joined to form a substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, R$^1$ is independently substituted or unsubstituted C$_1$-C$_6$ alkyl. In embodiments, R$^1$ is independently unsubstituted methyl. In embodiments, R$^1$ is independently unsubstituted ethyl. In embodiments, R$^1$ is independently unsubstituted propyl. In embodiments, R$^1$ is independently substituted or unsubstituted 2 to 6 membered heteroalkyl. In embodiments, R$^1$ is independently substituted or unsubstituted C$_3$-C$_6$ cycloalkyl. In embodiments, R$^1$ is independently substituted or unsubstituted 3 to 6 membered heterocycloalkyl. In embodiments, R$^1$ is independently substituted or unsubstituted C$_6$-C$_{10}$ aryl. In embodiments, R$^1$ is independently substituted or unsubstituted 5 to 10 membered heteroaryl. In embodiments, two adjacent R$^1$ substituents may optionally be joined to form a substituted or unsubstituted C$_3$-C$_6$ cycloalkyl. In embodiments, two adjacent R$^1$ substituents may optionally be joined to form a substituted or unsubstituted 3 to 6 membered heterocycloalkyl. In embodiments, two adjacent R$^1$ substituents may optionally be joined to form a substituted or unsubstituted phenyl. In embodiments, two adjacent R$^1$ substituents may optionally be joined to form a substituted or unsubstituted 5 to 6 membered heteroaryl.

In embodiments, R$^2$ is independently oxo, halogen, —CX$^2_3$, —CHX$^2_2$, —CH$_2$X$^2$, —OCX$^2_3$, —OCH$_2$X$^2$, —OCHX$^2_2$, —CN, —SO$_{n2}$R$^{2D}$, —SO$_{v2}$NR$^{2A}$R$^{2B}$, —NR$^{2C}$NR$^{2A}$R$^{2B}$, —ONR$^{2A}$R$^{2B}$, —NHC(O)NR$^{2C}$NR$^{2A}$R$^{2B}$, —NHC(O)NR$^{2A}$R$^{2B}$, —N(O)$_{m2}$, —N$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO$_2$R$^{2D}$, —NR$^{2A}$C(O)R$^{2C}$, —NR$^{2A}$C(O)OR$^{2C}$, —NR$^{2A}$OR$^{2C}$, —N$_3$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl; two adjacent R$^2$ substituents may optionally be joined to form a substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl.

In embodiments, R$^2$ is independently oxo, halogen, —CX$^2_3$, —CHX$^2_2$, —CH$_2$X$^2$, —OCX$^2_3$, —OCH$_2$X$^2$, —OCHX$^2_2$, —CN, —SO$_{n2}$R$^{2D}$, —SO$_{v2}$NR$^{2A}$R$^{2B}$, —NR$^{2C}$NR$^{2A}$R$^{2B}$, —ONR$^{2A}$R$^{2B}$, —NHC(O)NR$^{2C}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO$_2$R$^{2D}$, —NR$^{2A}$C(O)R$^{2C}$, —NR$^{2A}$C(O)OR$^{2C}$, —NR$^{2A}$OR$^{2C}$, —N$_3$. In embodiments, R$^2$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —SO$_2$Me, —SO$_2$Et, —SO$_2$NH$_2$, —OH, —OCH$_3$, —NH$_2$, —COOH, —COCH$_3$, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$, or —OCH$_2$F. In embodiments, R$^2$ is independently oxo. In embodiments, R$^2$ is independently —F. In embodiments, R$^2$ is independently —C$_1$. In embodiments, R$^2$ is independently —Br. In embodiments, R$^2$ is independently —I. In embodiments, R$^2$ is independently —CCl$_3$. In embodiments, R$^2$ is independently —CBr$_3$. In embodiments, R$^2$ is independently —CF$_3$. In embodiments, R$^2$ is independently —CI$_3$. In embodiments, R$^2$ is independently —CHCl$_2$. In embodiments, R$^2$ is independently —CHBr$_2$. In embodiments, R$^2$ is independently —CHF$_2$. In embodiments, R$^2$ is independently —CHI$_2$. In embodiments, R$^2$ is independently —CH$_2$Cl. In embodiments, R$^2$ is independently —CH$_2$Br. In embodiments, R$^2$ is independently —CH$_2$F. In embodiments, R$^2$ is independently —CH$_2$I. In embodiments, R$^2$ is independently —CN. In embodiments, R$^2$ is independently —SO$_2$Me. In embodiments, R$^2$ is independently —SO$_2$Et. In embodiments, R$^2$ is independently —SO$_2$NH$_2$. In embodiments, R$^2$ is independently —OH. In embodiments, R$^2$ is independently —OCH$_3$. In embodiments, R$^2$ is independently —NH$_2$. In embodiments, R$^2$ is independently —COH. In embodiments, R$^2$ is independently —COCH$_3$. In embodiments, R$^2$ is independently —CONH$_2$. In embodiments, R$^2$ is independently —OCCl$_3$. In embodiments, R$^2$ is independently —OCF$_3$. In embodiments, R$^2$ is independently —OCBr$_3$. In embodiments, R$^2$ is independently —OCI$_3$. In embodiments, R$^2$ is independently —OCHCl$_2$. In embodiments, R$^2$ is independently —OCHBr$_2$. In embodiments, R$^2$ is independently —OCHI$_2$. In embodiments, R$^2$ is independently —OCHF$_2$. In embodiments, R$^2$ is independently —OCH$_2$Cl. In embodiments, R$^2$ is independently —OCH$_2$Br. In embodiments, R$^2$ is independently —OCH$_2$. In embodiments, R$^2$ is independently —OCH$_2$F.

In embodiments, R$^2$ is independently substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^2$ substituents may optionally be joined to form a substituted or unsubstituted cycloalkyl, substituted or unsubstituted heterocycloalkyl, substituted or unsubstituted aryl, or substituted or unsubstituted heteroaryl. In embodiments, R$^2$ is independently substituted or unsubstituted alkyl. In embodiments, R$^2$ is independently unsubstituted alkyl. In embodiments, R$^2$ is independently unsubstituted methyl. In embodiments, R$^2$ is independently unsubstituted ethyl. In embodiments, R$^2$ is independently unsubstituted propyl. In embodiments, R$^2$ is independently substituted or unsubstituted heteroalkyl. In embodiments, R$^2$ is independently unsubstituted heteroalkyl. In embodiments, R$^2$ is independently —CH$_2$N(CH$_3$)$_2$. In embodiments, R$^2$ is independently substituted or unsubstituted cycloalkyl. In embodiments, R$^2$ is independently substituted or unsubstituted heterocycloalkyl. In embodiments, R$^2$ is independently unsubstituted heterocycloalkyl. In embodiments, R$^2$ is independently substituted or unsubstituted aryl. In embodiments, R$^2$ is independently unsubstituted phenyl. In embodiments, R$^2$ is independently substituted or unsubstituted heteroaryl.

In embodiments, R$^2$ is independently substituted or unsubstituted 3 to 8 membered heterocycloalkyl, substituted or unsubstituted azetidinyl, substituted or unsubstituted azepanyl, substituted or unsubstituted morpholinyl, substituted or unsubstituted piperazinyl, substituted or unsubstituted piperidinyl, substituted or unsubstituted tetrahydrofuranyl, substituted or unsubstituted tetrahydrothienyl, or substituted or unsubstituted 2-oxa-6-azaspiro[3.3]heptanyl. In embodiments, $R^2$ is independently substituted or unsubstituted 4 to 7 membered heterocycloalkyl. In embodiments, $R^2$ is independently substituted or unsubstituted azetidinyl. In embodiments, $R^2$ is independently substituted or unsubstituted azepanyl. In embodiments, $R^2$ is independently substituted or unsubstituted morpholinyl. In embodiments, $R^2$ is independently substituted or unsubstituted piperazinyl. In embodiments, $R^2$ is independently substituted or unsubstituted piperidinyl. In embodiments, $R^2$ is independently substituted or unsubstituted tetrahydrofuranyl. In embodiments, $R^2$ is independently substituted or unsubstituted tetrahydrothienyl. In embodiments, $R^2$ is independently substituted or unsubstituted 2-oxa-6-azaspiro[3.3]heptanyl. In embodiments, $R^2$ is independently unsubstituted azetidinyl. In embodiments, $R^2$ is independently unsubstituted azepanyl. In embodiments, $R^2$ is independently unsubstituted morpholinyl. In embodiments, $R^2$ is independently unsubstituted piperazinyl. In embodiments, $R^2$ is independently unsubstituted piperidinyl. In embodiments, $R^2$ is independently unsubstituted tetrahydrofuranyl. In embodiments, $R^2$ is independently unsubstituted tetrahydrothienyl. In embodiments, $R^2$ is independently unsubstituted 2-oxa-6-azaspiro[3.3]heptanyl. In embodiments, $R^2$ is independently $R^{20}$-substituted or unsubstituted 4 to 7 membered heterocycloalkyl. In embodiments, $R^2$ is independently $R^{20}$-substituted or unsubstituted azetidinyl. In embodiments, $R^2$ is independently $R^{20}$-substituted or unsubstituted azepanyl. In embodiments, $R^2$ is independently $R^{20}$-substituted or unsubstituted morpholinyl. In embodiments, $R^2$ is independently $R^{20}$-substituted or unsubstituted piperazinyl. In embodiments, $R^2$ is independently $R^{20}$-substituted or unsubstituted piperidinyl. In embodiments, $R^2$ is independently $R^{20}$-substituted or unsubstituted tetrahydrofuranyl. In embodiments, $R^2$ is independently $R^{20}$-substituted or unsubstituted tetrahydrothienyl. In embodiments, $R^2$ is independently $R^{20}$-substituted or unsubstituted 2-oxa-6-azaspiro[3.3]heptanyl.

$R^{20}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted phenyl, or substituted or unsubstituted heteroaryl.

In embodiments, $R^{20}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl, unsubstituted heteroalkyl, unsubstituted cycloalkyl, unsubstituted heterocycloalkyl, unsubstituted phenyl, or unsubstituted heteroaryl.

In embodiments, $R^{20}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In embodiments, $L^3$ is a bond, —NH—, —O—, —C(O)—, —C(O)NH—, —NHC(O)—, —NHC(O)NH—, —C(O)O—, —OC(O)—, substituted or unsubstituted C$_1$-C$_6$ alkylene, or substituted or unsubstituted 2 to 6 membered heteroalkylene.

In embodiments, the compound has the formula:

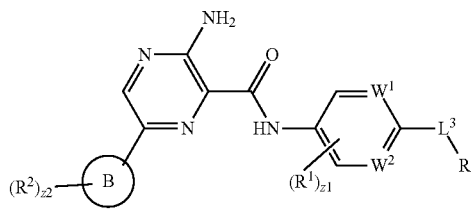

(Ia)

Ring B, $R^1$, $R^2$, $R^3$, $W^1$, $W^2$, $L^3$, z1 and z2 are as described herein, including in embodiments.

In embodiments, $R^3$ is independently —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO$_2$R$^{3D}$, —NR$^{3C}$SO$_2$NR$^{3A}$R$^{3B}$, —NR$^{3A}$R$^{3B}$, —NR$^{3A}$C(O)R$^{3C}$, —NR$^{3A}$C(O)OR$^{3C}$, —SO$_2$R$^{3C}$, —SO$_2$-L$^{3A}$-R$^{3C}$, —SO$_2$NR$^{3A}$R$^{3B}$, —SO$_2$NR$^{3A}$SO$_2$R$^{3C}$, —SO$_2$NR$^{3A}$P(O)(OR$^{3C}$)(OR$^{3D}$), —SO$_2$P(O)(OR$^{3C}$)(OR$^{3D}$), —SO$_2$CH$_2$P(O)(OR$^{3C}$)(OR$^{3D}$), —SO$_2$P(O)(OR$^{3D}$)(NR$^{3A}$R$^{3B}$), —SO$_2$P(O)(R$^{3C}$)(OR$^{3D}$), —SO$_2$P(O)(R$^{3C}$)(R$^{3D}$), —SO$_2$-L$^{3A}$-P(O)(OR$^{3C}$)(OR$^{3D}$), —SO$_2$-L$^{3A}$-P(O)(OR$^{3D}$)(NR$^{3A}$R$^{3B}$), —SO$_2$-L$^{3A}$-P(O)(R$^{3C}$)(OR$^{3D}$), —SO$_2$-L$^{3A}$-P(O)(R$^{3C}$)(R$^{3D}$), —S(O)(NR$^{3A}$)R$^{3C}$, —C(O)OR$^{3C}$, —C(O)NR$^{3A}$R$^{3B}$, —NR$^{3A}$C(O)OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $L^{3A}$ is independently substituted or unsubstituted alkylene, wherein a substituted $L^{3A}$ is substituted by one or more halogens; and $R^{3A}$, $R^{3B}$, $R^{3C}$, and $R^{3D}$ are independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{3A}$ and R$^{3D}$ substituents may optionally be joined to form a substituted or unsubstituted heterocycloalkyl or substituted or unsubstituted heteroaryl.

In embodiments, R$^3$ is independently —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO$_2$R$^{3D}$, —NR$^{3C}$SO$_2$NR$^{3A}$R$^{3B}$, —NR$^{3A}$R$^{3B}$, —NR$^{3A}$C(O)R$^{3C}$, —NR$^{3A}$C(O)OR$^{3C}$, —SO$_2$R$^{3C}$, —SO$_2$-L$^{3A}$-R$^{3C}$, —SO$_2$NR$^{3A}$R$^{3B}$, —SO$_2$NR$^{3A}$SO$_2$R$^{3C}$, —SO$_2$NR$^{3A}$P(O)(OR$^{3C}$)(OR$^{3D}$), —SO$_2$P(O)(OR$^{3C}$)(OR$^{3D}$), —SO$_2$CH$_2$P(O)(OR$^{3C}$)(OR$^{3D}$), —SO$_2$P(O)(OR$^{3D}$)(NR$^{3A}$R$^{3B}$), —SO$_2$P(O)(R$^{3C}$)(OR$^{3D}$), —SO$_2$P(O)(R$^{3C}$)(R$^{3D}$), —SO$_2$-L$^{3A}$-P(O)(OR$^{3C}$)(OR$^{3D}$), —SO$_2$-L$^{3A}$-P(O)(OR$^{3D}$)(NR$^{3A}$R$^{3B}$), —SO$_2$-L$^{3A}$-P(O)(R$^{3C}$)(OR$^{3D}$), —SO$_2$-L$^{3A}$-P(O)(R$^{3C}$)(R$^{3D}$), —S(O)(NR$^{3A}$)R$^{3C}$, —C(O)OR$^{3C}$, —C(O)NR$^{3A}$R$^{3B}$, or —NR$^{3A}$C(O)OR$^{3C}$; L$^{3A}$ is independently substituted or unsubstituted alkylene, wherein a substituted L$^{3A}$ is substituted by one or more halogens; and R$^{3A}$, R$^{3B}$, R$^{3C}$, and R$^{3D}$ are independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{3A}$ and R$^{3D}$ substituents may optionally be joined to form a substituted or unsubstituted heterocycloalkyl or substituted or unsubstituted heteroaryl.

In embodiments, R$^3$ is independently —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO$_2$R$^{3D}$, —NR$^{3C}$SO$_2$NR$^{3A}$R$^{3B}$, —NR$^{3A}$R$^{3B}$, —NR$^{3A}$C(O)R$^{3C}$, —NR$^{3A}$C(O)OR$^{3C}$, —SO$_2$R$^{3C}$, —SO$_2$-L$^{3A}$-R$^{3C}$, —SO$_2$NR$^{3A}$R$^{3B}$, —SO$_2$NR$^{3A}$SO$_2$R$^{3C}$, —SO$_2$NR$^{3A}$P(O)(OR$^{3C}$)(OR$^{3D}$), —SO$_2$P(O)(OR$^{3C}$)(OR$^{3D}$), —SO$_2$CH$_2$P(O)(OR$^{3C}$)(OR$^{3D}$), —SO$_2$P(O)(OR$^{3D}$)(NR$^{3A}$R$^{3B}$), —SO$_2$P(O)(R$^{3C}$)(OR$^{3D}$), —SO$_2$P(O)(R$^{3C}$)(R$^{3D}$), —SO$_2$-L$^{3A}$-P(O)(OR$^{3C}$)(OR$^{3D}$), —SO$_2$-L$^{3A}$-P(O)(OR$^{3D}$)(NR$^{3A}$R$^{3B}$), —SO$_2$-L$^{3A}$-P(O)(R$^{3C}$)(OR$^{3D}$), —SO$_2$-L$^{3A}$-P(O)(R$^{3C}$)(R$^{3D}$), —S(O)(NR$^{3A}$)R$^{3C}$, —C(O)OR$^{3C}$, —C(O)NR$^{3A}$R$^{3B}$, —NR$^{3A}$C(O)OR$^{3C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; L$^{3A}$ is independently —CH$_2$—, —CH(CH$_3$)—, —C(CH$_3$)$_2$—, —CH(X$^{3A}$)—, or —C(X$^{3A}$)$_2$—; X$^{3A}$ is independently —F, —Cl, —Br, or —I; and R$^{3A}$, R$^{3B}$, R$^{3C}$, and R$^{3D}$ are independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{3A}$ and R$^{3D}$ substituents may optionally be joined to form a substituted or unsubstituted heterocycloalkyl or substituted or unsubstituted heteroaryl.

In embodiments, R$^3$ is independently —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO$_2$R$^{3D}$, —NR$^{3C}$SO$_2$NR$^{3A}$R$^{3B}$, —NR$^{3A}$R$^{3B}$, —NR$^{3A}$C(O)R$^{3C}$, —NR$^{3A}$C(O)OR$^{3C}$, —SO$_2$R$^{3C}$, —SO$_2$-L$^{3A}$-R$^{3C}$, —SO$_2$NR$^{3A}$R$^{3B}$, —SO$_2$NR$^{3A}$SO$_2$R$^{3C}$, —SO$_2$NR$^{3A}$P(O)(OR$^{3C}$)(OR$^{3D}$), —SO$_2$P(O)(OR$^{3C}$)(OR$^{3D}$), —SO$_2$CH$_2$P(O)(OR$^{3C}$)(OR$^{3D}$), —SO$_2$P(O)(OR$^{3D}$)(NR$^{3A}$R$^{3B}$), —SO$_2$P(O)(R$^{3C}$)(OR$^{3D}$), —SO$_2$P(O)(R$^{3C}$)(R$^{3D}$), —SO$_2$-L$^{3A}$-P(O)(OR$^{3C}$)(OR$^{3D}$), —SO$_2$-L$^{3A}$-P(O)(OR$^{3D}$)(NR$^{3A}$R$^{3B}$), —SO$_2$-L$^{3A}$-P(O)(R$^{3C}$)(OR$^{3D}$), —SO$_2$-L$^{3A}$-P(O)(R$^{3C}$)(R$^{3D}$), —S(O)(NR$^{3A}$)R$^{3C}$, —C(O)OR$^{3C}$, —C(O)NR$^{3A}$R$^{3B}$, or —NR$^{3A}$C(O)OR$^{3C}$; L$^{3A}$ is independently —CH$_2$—, —CH(CH$_3$)—, —C(CH$_3$)$_2$—, —CH(X$^{3A}$)—, or —C(X$^{3A}$)$_2$—; X$^{3A}$ is independently —F, —Cl, —Br, or —I; and R$^{3A}$, R$^{3B}$, R$^{3C}$, and R$^{3D}$ are independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$C, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$C, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{3A}$ and $R^{3D}$ substituents may optionally be joined to form a substituted or unsubstituted heterocycloalkyl or substituted or unsubstituted heteroaryl.

In embodiments, $R^3$ is independently —OH, —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO$_2$R$^{3D}$, —NR$^{3C}$SO$_2$NR$^{3A}$R$^{3B}$, —NR$^{3A}$R$^{3B}$, —NR$^{3A}$C(O)R$^{3C}$, —NR$^{3A}$C(O)OR$^{3C}$, —SO$_2$R$^{3C}$, —SO$_2$-L$^{3A}$-R$^{3C}$, —SO$_2$NR$^{3A}$R$^{3B}$, —SO$_2$NR$^{3A}$SO$_2$R$^{3C}$, —SO$_2$NR$^{3A}$P(O)(OR$^{3C}$)(OR$^{3D}$), —SO$_2$P(O)(OR$^{3C}$)(OR$^{3D}$), —SO$_2$CH$_2$P(O)(OR$^{3C}$)(OR$^{3D}$), —SO$_2$P(O)(OR$^{3D}$)(NR$^{3A}$R$^{3B}$), —SO$_2$P(O)(R$^{3C}$)(OR$^{3D}$), —SO$_2$P(O)(R$^{3C}$)(R$^{3D}$), —SO$_2$-L$^{3A}$-P(O)(OR$^{3C}$)(OR$^{3D}$), —SO$_2$-L$^{3A}$-P(O)(OR$^{3D}$)(NR$^{3A}$R$^{3B}$), —SO$_2$-L$^{3A}$-P(O)(R$^{3C}$)(OR$^{3D}$), —SO$_2$-L$^{3A}$-P(O)(R$^{3C}$)(R$^{3D}$), —S(O)(NR$^{3A}$)R$^{3C}$, —C(O)OR$^{3C}$, —C(O)NR$^{3A}$R$^{3B}$, or —NR$^{3A}$C(O)OR$^{3C}$.

In embodiments, $R^3$ is independently —OH. In embodiments, $R^3$ is independently —P(O)(OR$^{3C}$)(OR$^{3D}$). In embodiments, $R^3$ is independently —P(O)(OR$^{3D}$)(NR$^{3A}$R$^{3B}$). In embodiments, $R^3$ is independently —P(O)(R$^{3C}$)(OR$^{3D}$). In embodiments, $R^3$ is independently —P(O)(R$^{3C}$)(R$^{3D}$). In embodiments, $R^3$ is independently —P(S)(OR$^{3C}$)(OR$^{3D}$). In embodiments, $R^3$ is independently —P(S)(OR$^{3D}$)(NR$^{3A}$R$^{3B}$). In embodiments, $R^3$ is independently —P(S)(R$^{3C}$)(OR$^{3D}$). In embodiments, $R^3$ is independently —P(S)(R$^{3C}$)(R$^{3D}$). In embodiments, $R^3$ is independently —NR$^{3A}$SO$_2$R$^{3D}$. In embodiments, $R^3$ is independently —NR$^{3C}$SO$_2$NR$^{3A}$R$^{3B}$. In embodiments, $R^3$ is independently —NR$^{3A}$R$^{3B}$. In embodiments, $R^3$ is independently —NR$^{3A}$C(O)R$^{3C}$. In embodiments, $R^3$ is independently —NR$^{3A}$C(O)OR$^{3C}$. In embodiments, $R^3$ is independently —SO$_2$R$^{3C}$. In embodiments, $R^3$ is independently —SO$_2$-L$^{3A}$-R$^{3C}$. In embodiments, $R^3$ is independently —SO$_2$NR$^{3A}$R$^{3B}$. In embodiments, $R^3$ is independently —SO$_2$NR$^{3A}$SO$_2$R$^{3C}$. In embodiments, $R^3$ is independently —SO$_2$NR$^{3A}$P(O)(OR$^{3C}$)(OR$^{3D}$). In embodiments, $R^3$ is independently —SO$_2$P(O)(OR$^{3C}$)(OR$^{3D}$). In embodiments, $R^3$ is independently —SO$_2$CH$_2$P(O)(OR$^{3C}$)(OR$^{3D}$). In embodiments, $R^3$ is independently —SO$_2$P(O)(OR$^{3D}$)(NR$^{3A}$R$^{3B}$). In embodiments, $R^3$ is independently —SO$_2$P(O)(R$^{3C}$)(OR$^{3D}$). In embodiments, $R^3$ is independently —SO$_2$P(O)(R$^{3C}$)(R$^{3D}$). In embodiments, $R^3$ is independently —SO$_2$-L$^{3A}$-P(O)(OR$^{3C}$)(OR$^{3D}$). In embodiments, $R^3$ is independently —SO$_2$-L$^{3A}$-P(O)(OR$^{3D}$)(NR$^{3A}$R$^{3B}$). In embodiments, $R^3$ is independently —SO$_2$-L$^{3A}$-P(O)(R$^{3C}$)(OR$^{3D}$). In embodiments, $R^3$ is independently —SO$_2$-L$^{3A}$-P(O)(R$^{3C}$)(R$^{3D}$). In embodiments, $R^3$ is independently —S(O)(NR$^{3A}$)R$^{3C}$, —C(O)OR$^{3C}$. In embodiments, $R^3$ is independently —C(O)NR$^{3A}$R$^{3B}$. In embodiments, $R^3$ is independently or —NR$^{3A}$C(O)OR$^{3C}$ In embodiments, $R^3$ is independently —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO$_2$R$^{3D}$, —NR$^{3C}$SO$_2$NR$^{3A}$R$^{3B}$, —NR$^{3A}$R$^{3B}$, —NR$^{3A}$C(O)R$^{3C}$, —NR$^{3A}$C(O)OR$^{3C}$, —SO$_2$R$^{3C}$, —SO$_2$-L$^{3A}$-R$^{3C}$, —SO$_2$NR$^{3A}$R$^{3B}$, —SO$_2$NR$^{3A}$SO$_2$R$^{3C}$, —SO$_2$NR$^{3A}$P(O)(OR$^{3C}$)(OR$^{3D}$), —SO$_2$P(O)(OR$^{3C}$)(OR$^{3D}$), —SO$_2$CH$_2$P(O)(OR$^{3C}$)(OR$^{3D}$), —SO$_2$P(O)(OR$^{3D}$)(NR$^{3A}$R$^{3B}$), —SO$_2$P(O)(R$^{3C}$)(OR$^{3D}$), —SO$_2$P(O)(R$^{3C}$)(R$^{3D}$), —SO$_2$-L$^{3A}$-P(O)(OR$^{3C}$)(OR$^{3D}$), —SO$_2$-L$^{3A}$-P(O)(OR$^{3D}$)(NR$^{3A}$R$^{3B}$), —SO$_2$-L$^{3A}$-P(O)(R$^{3C}$)(OR$^{3D}$), or —SO$_2$-L$^{3A}$-P(O)(R$^{3C}$)(R$^{3D}$). In embodiments, $R^3$ is independently —SO$_2$R$^{3C}$. In embodiments, $R^3$ is independently —SO$_2$-L$^{3A}$-R$^{3C}$. In embodiments, $R^3$ is independently —SO$_2$NR$^{3A}$R$^{3B}$. In embodiments, $R^3$ is independently —SO$_2$NR$^{3A}$SO$_2$R$^{3C}$. In embodiments, $R^3$ is independently —SO$_2$NR$^{3A}$P(O)(OR$^{3C}$)(OR$^{3D}$). In embodiments, $R^3$ is independently —SO$_2$P(O)(OR$^{3C}$)(OR$^{3D}$). In embodiments, $R^3$ is independently —SO$_2$CH$_2$P(O)(OR$^{3C}$)(OR$^{3D}$). In embodiments, $R^3$ is independently —SO$_2$P(O)(OR$^{3D}$)(NR$^{3A}$R$^{3B}$). In embodiments, $R^3$ is independently —SO$_2$P(O)(R$^{3C}$)(OR$^{3D}$). In embodiments, $R^3$ is independently —SO$_2$P(O)(R$^{3C}$)(R$^{3D}$). In embodiments, $R^3$ is independently —SO$_2$-L$^{3A}$-P(O)(OR$^{3C}$)(OR$^{3D}$). In embodiments, $R^3$ is independently —SO$_2$-L$^{3A}$-P(O)(OR$^{3D}$)(NR$^{3A}$R$^{3B}$). In embodiments, $R^3$ is independently —SO$_2$-L$^{3A}$-P(O)(R$^{3C}$)(OR$^{3D}$) In embodiments, $R^3$ is independently —SO$_2$-L$^{3A}$-P(O)(R$^{3C}$)(R$^{3D}$). In embodiments, $R^3$ is independently —S(O)(NR$^{3A}$)R$^{3C}$, —C(O)OR$^{3C}$, —C(O)NR$^{3A}$R$^{3B}$, or —NR$^{3A}$C(O)OR$^{3C}$ In embodiments, $L^{3A}$ is independently substituted or unsubstituted alkylene, wherein a substituted $L^{3A}$ is substituted by one or more halogens.

In embodiments, $L^{3A}$ is independently —CH$_2$—, —CH(CH$_3$)—, —C(CH$_3$)$_2$—, —CH(X$^{3A}$)—, or —C(X$^{3A}$)$_2$—. In embodiments, $L^{3A}$ is independently —CH$_2$—. In embodiments, $L^{3A}$ is independently —CH(CH$_3$)—. In embodiments, $L^{3A}$ is independently —C(CH$_3$)$_2$—. In embodiments, $L^{3A}$ is independently —CH(X$^{3A}$)—. In embodiments, $L^{3A}$ is independently —C(X$^{3A}$)$_2$—.

In embodiments, $X^{3A}$ is independently —F, —Cl, —Br, or —I.

In embodiments, $R^{3A}$, $R^{3B}$, $R^{3C}$, and $R^{3D}$ are independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{3A}$ and $R^{3D}$ substituents may optionally be joined to form a substituted or unsubstituted heterocycloalkyl or substituted or unsubstituted heteroaryl.

In embodiments, $R^{3A}$, $R^{3B}$, $R^{3C}$, and $R^{3D}$ are independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{3A}$ and $R^{3D}$ substituents may optionally be joined to form a substituted or unsubstituted heterocycloalkyl or substituted or unsubstituted heteroaryl.

In embodiments, $R^{3A}$, $R^{3B}$, $R^{3C}$, and $R^{3D}$ are independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted C$_6$-C$_{10}$ aryl, or substituted or unsubstituted 5 to 10 membered heteroaryl; $R^{3A}$ and $R^{3B}$ substituents bonded to the same nitrogen atom may optionally be joined to form a substituted or unsubstituted 3 to 6 membered heterocycloalkyl or substituted or unsubstituted 5 to 6 membered heteroaryl.

In embodiments, $R^{3A}$, $R^{3B}$, $R^{3C}$, and $R^{3D}$ are independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$C, —OCH$_2$Br, —OCH$_2$I, —OCH$_2$F, —N$_3$, —SO$_2$CH$_3$, —NHC(O)CH$_3$, —C(O)CH$_3$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted C$_6$-C$_{10}$ aryl, or substituted or unsubstituted 5 to 10 membered heteroaryl; $R^{3A}$ and $R^{3B}$ substituents bonded to the same nitrogen atom may optionally be joined to form a substituted or unsubstituted 3 to 6 membered heterocycloalkyl or substituted or unsubstituted 5 to 6 membered heteroaryl.

In embodiments, $R^3$ is independently —SO$_2$R$^{3C}$, —SO$_2$-L$^{3A}$-R$^{3C}$, —SO$_2$CH$_2$P(O)(OR$^{3C}$)(OR$^{3D}$), —SO$_2$-L$^{3A}$-P(O)(R$^{3C}$)(OR$^{3D}$), —SO$_2$-L$^{3A}$-P(O)(OR$^{3C}$)(OR$^{3D}$), —SO$_2$-L$^{3A}$-P(O)(R$^{3C}$)(R$^{3D}$), —SO$_2$NR$^{3A}$R$^{3B}$ or —SO$_2$NR$^{3A}$P(O)(OR$^{3C}$)(OR$^{3D}$). In embodiments, L$^{3A}$ is —CH$_2$—, —CH(CH$_3$)—, —C(CH$_3$)$_2$—, or —CH(X$^{3A}$)—. In embodiments, $R^{3A}$ and $R^{3B}$ are independently hydrogen, —C(O)CH$_3$, substituted or unsubstituted C$_1$-C$_6$ alkyl, or substituted or unsubstituted 4 to 6 membered heterocycloalkyl. In embodiments, $R^{3A}$ is independently substituted or unsubstituted oxetanyl, substituted or unsubstituted azetidinyl, or substituted or unsubstituted oxetanonyl. In embodiments, $R^{3A}$ is independently

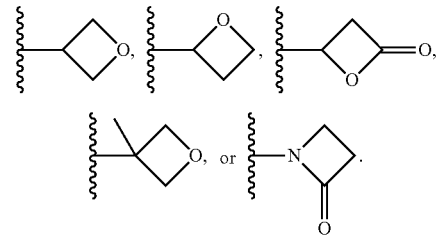

In embodiments $R^{3C}$ and $R^{3D}$ are independently hydrogen, —OH, —COOCH$_3$, —COOCH$_2$CH$_3$, unsubstituted C$_1$-C$_6$ alkyl, or substituted or unsubstituted 4 to 6 membered heterocycloalkyl. In embodiments, $R^{3C}$ is independently substituted or unsubstituted oxetanyl, substituted or unsubstituted azetidinyl, or substituted or unsubstituted oxetanonyl. In embodiments, $R^{3C}$ is independently

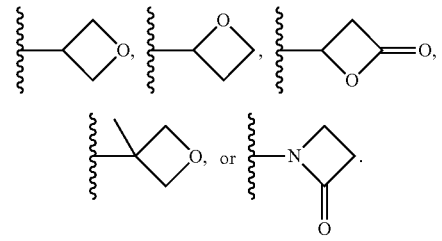

In embodiments, $R^{3C}$ is independently

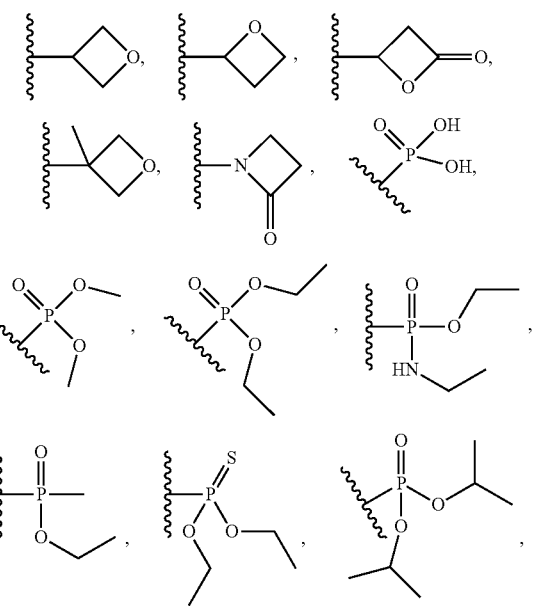

-continued

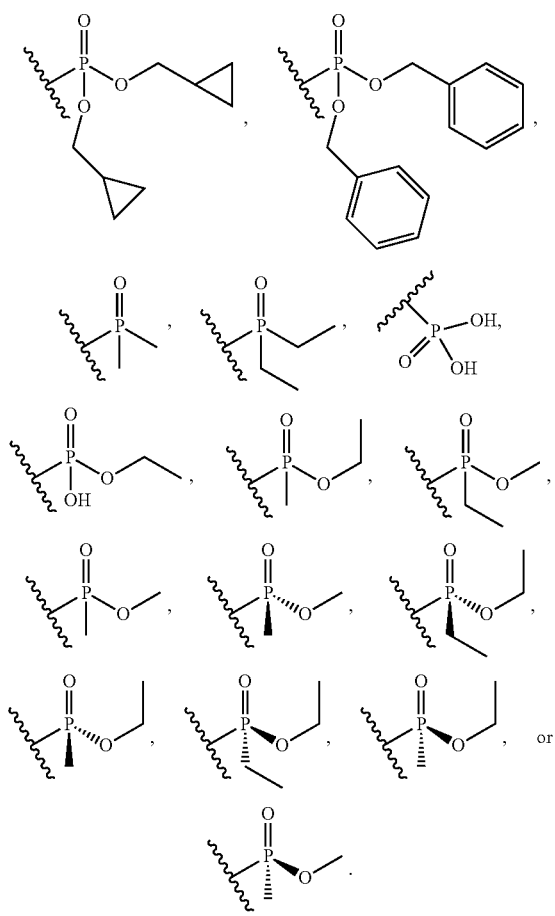

In embodiments $R^{3C}$ is

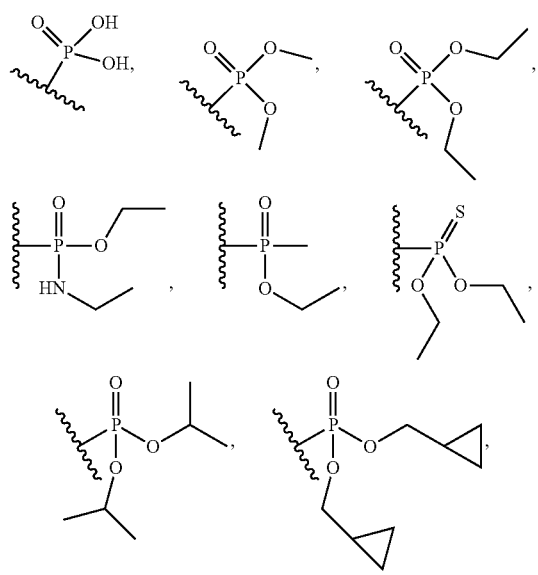

-continued

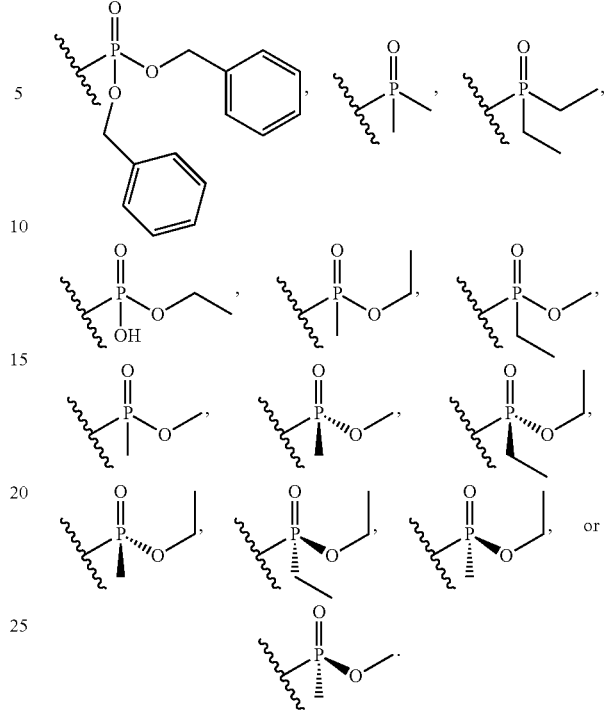

In embodiments, $R^{3C}$ is independently unsubstituted methyl, unsubstituted ethyl, or unsubstituted propyl. In embodiments, $R^3$ is independently unsubstituted methyl, unsubstituted ethyl, or unsubstituted propyl.

In embodiments, $R^3$ is independently —$SO_2R^{3C}$, —$SO_2$-$L^{3A}$-$R^{3C}$, —$SO_2CH_2P(O)(OR^{3C})(OR^{3D})$, —$SO_2$-$L^{3A}$-$P(O)$ $(R^{3C})(OR^{3D})$, —$SO_2$-$L^{3A}$-$P(O)(OR^{3C})(OR^{3D})$, —$SO_2$-$L^{3A}$-$P(O)(R^{3C})(R^{3D})$, —$SO_2NR^{3A}R^{3B}$ or —$SO_2NR^{3A}P(O)$ $(OR^{3C})(OR^{3D})$. In embodiments, $L^{3A}$ is —$CH_2$—, —$CH$ $(CH_3)$—, —$C(CH_3)_2$—, or —$CH(X^{3A})$—. In embodiments, $R^{3A}$ and $R^{3B}$ are independently hydrogen, —$C(O)CH_3$, substituted or unsubstituted $C_1$-$C_6$ alkyl, or substituted or unsubstituted 4 to 6 membered heterocycloalkyl. In embodiments, $R^{3A}$ is independently substituted or unsubstituted oxetanyl, substituted or unsubstituted azetidinyl, or substituted or unsubstituted oxetanonyl. In embodiments, $R^{3A}$ is independently

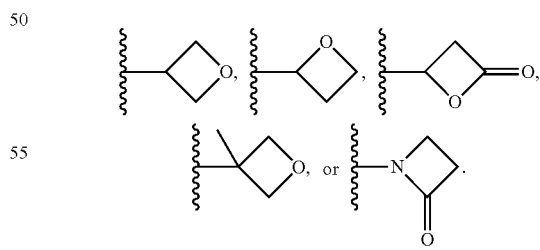

In embodiments, $R^{3C}$ and $R^{3D}$ are independently hydrogen, —OH, —$COOCH_3$, —$COOCH_2CH_3$, unsubstituted $C_1$-$C_6$ alkyl, or substituted or unsubstituted 4 to 6 membered heterocycloalkyl. In embodiments, $R^{3C}$ is independently substituted or unsubstituted oxetanyl, substituted or unsubstituted azetidinyl, or substituted or unsubstituted oxetanonyl. In embodiments, $R^{3C}$ is independently

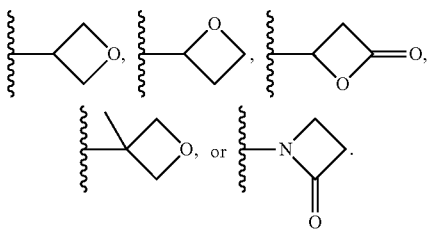

In embodiments, $R^{3C}$ is independently unsubstituted methyl, unsubstituted ethyl, or unsubstituted propyl. In embodiments, $R^{3D}$ is independently unsubstituted methyl, unsubstituted ethyl, or unsubstituted propyl.

In embodiments, $R^3$ is —SO$_2$R$^{3C}$ and $R^{3C}$ is independently —OH or unsubstituted $C_1$-$C_6$ alkyl. In embodiments, $R^3$ is —SO$_2$R$^{3C}$ and $R^{3C}$ is-OH. In embodiments, $R^3$ is —SO$_2$R$^{3C}$ and $R^{3C}$ is independently unsubstituted $C_1$-$C_6$ alkyl. In embodiments, $R^3$ is —SO$_2$-L$^{3A}$-R$^{3C}$, L$^{3A}$ is —CH$_2$—, and $R^{3C}$ is independently —COOCH$_3$ or —COOCH$_2$CH$_3$. In embodiments, $R^3$ is —SO$_2$-L$^{3A}$-R$^{3C}$, L$^{3A}$ is —CH$_2$—, and $R^{3C}$ is independently substituted or unsubstituted 4 to 6 membered heterocycloalkyl. In embodiments, $R^3$ is —SO$_2$-L$^{3A}$-R$^{3C}$, L$^{3A}$ is —CH$_2$—, and $R^{3C}$ is independently substituted or unsubstituted 4 membered heterocycloalkyl. In embodiments, $R^3$ is —SO$_2$-L$^{3A}$-P(O)(OR$^{3C}$)(OR$^{3D}$) and $R^{3C}$ and $R^{3D}$ are independently substituted or unsubstituted $C_1$-$C_6$ alkyl. In embodiments, $R^3$ is —SO$_2$-L$^{3A}$-P(O)(OR$^{3C}$)(OR$^{3D}$) L$^{3A}$ is —CH$_2$—, and $R^{3C}$ and $R^{3D}$ are independently substituted or unsubstituted $C_1$-$C_6$ alkyl. In embodiments, $R^3$ is —SO$_2$CH$_2$P(O)(OR$^{3C}$)(OR$^{3D}$) and $R^{3C}$ and $R^{3D}$ are independently substituted or unsubstituted $C_1$-$C_6$ alkyl. In embodiments, $R^3$ is —SO$_2$CH$_2$P(O)(OR$^{3C}$)(OR$^{3D}$) and $R^{3C}$ and $R^{3D}$ are independently unsubstituted $C_1$-$C_6$ alkyl. In embodiments, $R^3$ is —SO$_2$-L$^{3A}$-P(O)(R$^{3C}$)(OR$^{3D}$), L$^{3A}$ is —CH$_2$—, and $R^{3C}$ and $R^{3D}$ are independently hydrogen, —OH, or unsubstituted $C_1$-$C_6$ alkyl. In embodiments, $R^3$ is —SO$_2$-L$^{3A}$-P(O)(OR$^{3C}$)(OR$^{3D}$), L$^{3A}$ is —CH$_2$—, and $R^{3C}$ and $R^{3D}$ are independently hydrogen or unsubstituted $C_1$-$C_6$ alkyl. In embodiments, $R^3$ is —SO$_2$-L$^{3A}$-P(O)(R$^{3C}$)(OR$^{3D}$), L$^{3A}$ is —CH(CH$_3$)—, and $R^{3C}$ and $R^{3D}$ are independently hydrogen, —OH, or unsubstituted $C_1$-$C_6$ alkyl. In embodiments, $R^3$ is —SO$_2$-L$^{3A}$-P(O)(OR$^{3C}$)(OR$^{3D}$), L$^{3A}$ is —CH(CH$_3$)—, and $R^{3C}$ and $R^{3D}$ are independently hydrogen or unsubstituted $C_1$-$C_6$ alkyl. In embodiments, $R^3$ is —SO$_2$-L$^{3A}$-P(O)(R$^{3C}$)(OR$^{3D}$), L$^{3A}$ is —C(CH$_3$)$_2$—, and $R^{3C}$ and $R^{3D}$ are independently hydrogen, —OH, or unsubstituted $C_1$-$C_6$ alkyl. In embodiments, $R^3$ is —SO$_2$-L$^{3A}$-P(O)(OR$^{3C}$)(OR$^{3D}$) L$^{3A}$ is —C(CH$_3$)$_2$—, and $R^{3C}$ and $R^{3D}$ are independently hydrogen or unsubstituted $C_1$-$C_6$ alkyl. In embodiments, $R^3$ is —SO$_2$-L$^{3A}$-P(O)(R$^{3C}$)(OR$^{3D}$) L$^{3A}$ is —CH(X$^{3A}$)—, and $R^{3C}$ and $R^{3D}$ are independently hydrogen, —OH, or unsubstituted $C_1$-$C_6$ alkyl. In embodiments, $R^3$ is —SO$_2$-L$^{3A}$-P(O)(OR$^{3C}$)(OR$^{3D}$), L$^{3A}$ is —CH(X$^{3A}$)—, and $R^{3C}$ and $R^{3D}$ are independently hydrogen or unsubstituted $C_1$-$C_6$ alkyl. In embodiments, $R^3$ is —SO$_2$NR$^{3A}$R$^{3B}$ and $R^{3A}$ and $R^{3B}$ are independently hydrogen or substituted or unsubstituted 4 to 6 membered heterocycloalkyl. In embodiments, $R^3$ is —SO$_2$NR$^{3A}$R$^{3B}$ and $R^{3A}$ and $R^{3B}$ are independently hydrogen or substituted or unsubstituted $C_1$-$C_6$ alkyl. In embodiments, $R^3$ is —SO$_2$NR$^{3A}$R$^{3B}$ and $R^{3A}$ and $R^{3B}$ are independently hydrogen, —C(O)CH$_3$, or unsubstituted $C_1$-$C_6$ alkyl. In embodiments, $R^3$ is —SO$_2$NR$^{3A}$P(O)(OR$^{3C}$)(OR$^{3D}$), $R^{3A}$ is independently hydrogen or unsubstituted $C_1$-$C_6$ alkyl, and $R^{3C}$ and $R^{3D}$ are independently hydrogen or unsubstituted $C_1$-$C_6$ alkyl. In embodiments, $R^3$ is —SO$_2$-L$^{3A}$-P(O)(R$^{3C}$)(R$^{3D}$), and $R^{3C}$ and $R^{3D}$ are independently hydrogen or unsubstituted $C_1$-$C_6$ alkyl. In embodiments, $R^3$ is —SO$_2$-L$^{3A}$-P(O)(R$^{3C}$)(R$^{3D}$), L$^{3A}$ is —CH$_2$—, and $R^{3C}$ and $R^{3D}$ are independently hydrogen or unsubstituted $C_1$-$C_6$ alkyl. In embodiments, $R^{3A}$ is independently substituted or unsubstituted oxetanyl, substituted or unsubstituted azetidinyl, or substituted or unsubstituted oxetanonyl. In embodiments, $R^{3C}$ is independently substituted or unsubstituted oxetanyl, substituted or unsubstituted azetidinyl or substituted or unsubstituted oxetanonyl. In embodiments, $R^{3A}$ is independently

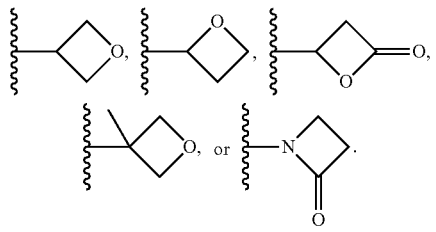

In embodiments, $R^{3C}$ is independently

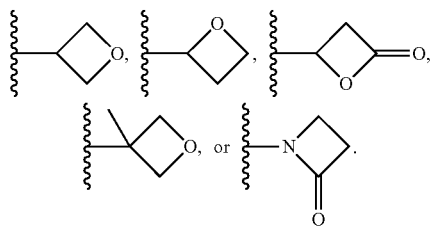

In embodiments, $R^{3C}$ is independently unsubstituted methyl, unsubstituted ethyl, or unsubstituted propyl. In embodiments, $R^{3D}$ is independently unsubstituted methyl, unsubstituted ethyl, or unsubstituted propyl.

In embodiments $R^3$ is —SO$_2$-L$^{3A}$-R$^{3C}$ L$^{3A}$ is —CH$_2$—, and $R^{3C}$ is independently

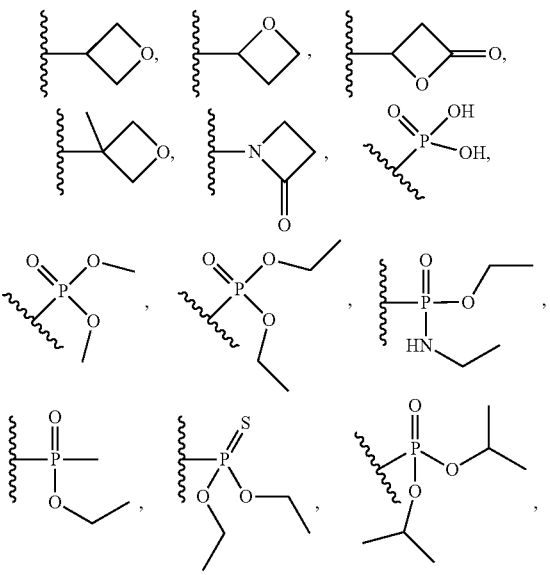

-continued

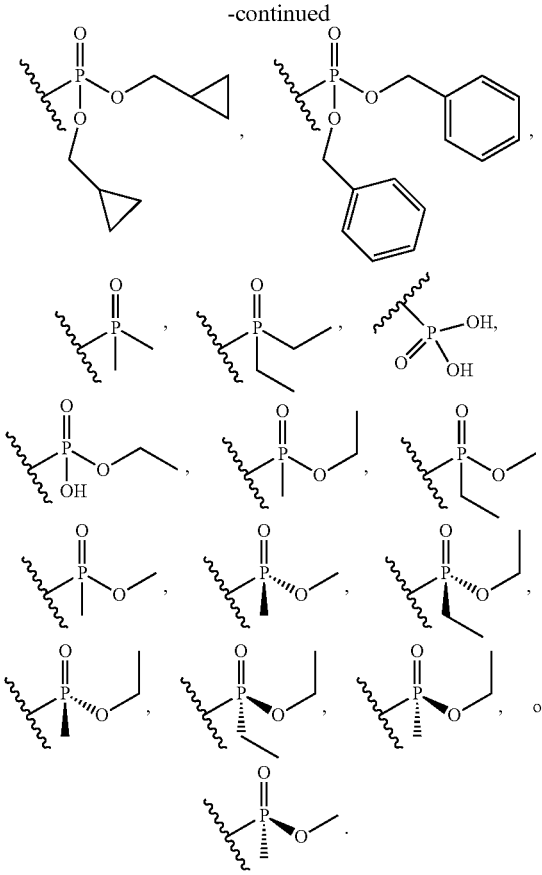

In embodiments, $R^{3A}$ is independently substituted or unsubstituted oxetanyl. In embodiments, $R^{3A}$ is independently substituted or unsubstituted azetidinyl. In embodiments, $R^{3A}$ is independently substituted or unsubstituted oxetanonyl. In embodiments, $R^{3C}$ is independently substituted or unsubstituted oxetanyl. In embodiments, $R^{3C}$ is independently unsubstituted azetidinyl. In embodiments, $R^{3C}$ is substituted or unsubstituted oxetanonyl. In embodiments, $R^{3A}$ is independently

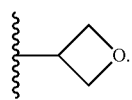

In embodiments, $R^{3A}$ is independently

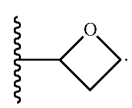 [SMILES: *C1CCO1]

In embodiments, $R^{3A}$ is independently

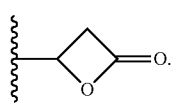 [SMILES: *C1CC(=O)O1]

In embodiments, $R^{3A}$ is independently

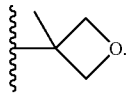

In embodiments, $R^{3A}$ is independently

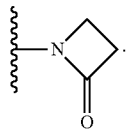

In embodiments, $R^{3C}$ is independently

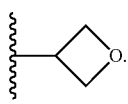

In embodiments, $R^{3C}$ is independently

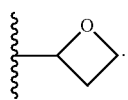

In embodiments, $R^{3C}$ is independently.

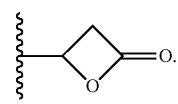

In embodiments, $R^{3C}$ is independently

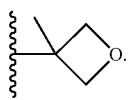 [SMILES: *C1(C)COC1]

In embodiments, $R^{3C}$ is independently

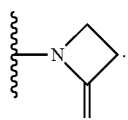

In embodiments, $R^{3C}$ is independently unsubstituted methyl. In embodiments, $R^{3C}$ is independently unsubstituted ethyl. In embodiments, $R^{3C}$ is independently unsubstituted propyl.

In embodiments, $R^{3D}$ is independently unsubstituted methyl. In embodiments, $R^{3D}$ is independently unsubstituted ethyl. In embodiments, $R^{3D}$ is independently unsubstituted propyl.

In embodiments, R$^{3B}$ is independently substituted or unsubstituted oxetanyl, substituted or unsubstituted azetidinyl, or substituted or unsubstituted oxetanonyl. In embodiments, R$^{3B}$ is independently

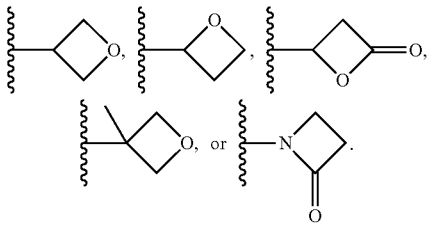

In embodiments, R$^{3B}$ is independently unsubstituted methyl, unsubstituted ethyl, or unsubstituted propyl. In embodiments, R$^{3B}$ is independently substituted or unsubstituted oxetanyl. In embodiments, R$^{3B}$ is independently substituted or unsubstituted azetidinyl. In embodiments, R$^{3B}$ is independently substituted or unsubstituted oxetanonyl. In embodiments, R$^{3B}$ is independently

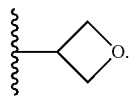

In embodiments, R$^{3B}$ is independently

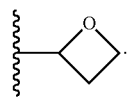 [SMILES: *C1CCO1]

In embodiments, R$^{3B}$ is independently

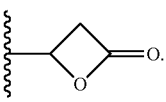 [SMILES: *C1CC(=O)O1]

In embodiments, R$^{3B}$ is independently

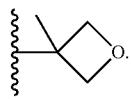

In embodiments, R$^{3B}$ is independently

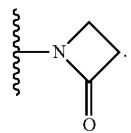 [SMILES: *N1CCC1=O]

In embodiments, R$^{3B}$ is independently unsubstituted methyl. In embodiments, R$^{3B}$ is independently unsubstituted ethyl. In embodiments, R$^{3B}$ is independently unsubstituted propyl.

In embodiments, R$^{3C}$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^{3C}$ is independently hydrogen. In embodiments, R$^{3C}$ is independently oxo. In embodiments, R$^{3C}$ is independently halogen. In embodiments, R$^{3C}$ is independently —CCl$_3$. In embodiments, R$^{3C}$ is independently —CBr$_3$. In embodiments, R$^{3C}$ is independently —CF$_3$. In embodiments, R$^{3C}$ is independently —CI$_3$. In embodiments, R$^{3C}$ is independently CHCl$_2$. In embodiments, R$^{3C}$ is independently —CHBr$_2$. In embodiments, R$^{3C}$ is independently —CHF$_2$. In embodiments, R$^{3C}$ is independently —CHI$_2$. In embodiments, R$^{3C}$ is independently —CH$_2$Cl. In embodiments, R$^{3C}$ is independently —CH$_2$Br. In embodiments, R$^{3C}$ is independently —CH$_2$F. In embodiments, R$^{3C}$ is independently —CH$_2$I. In embodiments, R$^{3C}$ is independently —CN. In embodiments, R$^{3C}$ is independently —OH. In embodiments, R$^{3C}$ is independently —NH$_2$. In embodiments, R$^{3C}$ is independently —COOH. In embodiments, R$^{3C}$ is independently —CONH$_2$. In embodiments, R$^{3C}$ is independently —NO$_2$. In embodiments, R$^{3C}$ is independently —SH. In embodiments, R$^{3C}$ is independently —SO$_3$H. In embodiments, R$^{3C}$ is independently —SO$_4$H. In embodiments, R$^{3C}$ is independently —SO$_2$NH$_2$. In embodiments, R$^{3C}$ is independently —NHNH$_2$. In embodiments, R$^{3C}$ is independently —ONH$_2$. In embodiments, R$^{3C}$ is independently —NHC(O)NHNH$_2$. In embodiments, R$^{3C}$ is independently —NHC(O)NH$_2$. In embodiments, R$^{3C}$ is independently —NHSO$_2$H. In embodiments, R$^{3C}$ is independently —NHC(O)H. In embodiments, R$^{3C}$ is independently —NHC(O)OH. In embodiments, R$^{3C}$ is independently —NHOH. In embodiments, R$^{3C}$ is independently —OCCl$_3$. In embodiments, R$^{3C}$ is independently —OCF$_3$. In embodiments, R$^{3C}$ is independently —OCBr$_3$. In embodiments, R$^{3C}$ is independently —OCI$_3$. In embodiments, R$^{3C}$ is independently —OCHCl$_2$. In embodiments, R$^{3C}$ is independently —OCHBr$_2$. In embodiments, R$^{3C}$ is independently —OCHI$_2$. In embodiments, R$^{3C}$ is independently —OCHF$_2$. In embodiments, R$^{3C}$ is independently —OCH$_2$Cl. In embodiments, R$^{3C}$ is independently —OCH$_2$Br. In embodiments, R$^{3C}$ is independently —OCH$_2$I. In embodiments, R$^{3C}$ is independently —OCH$_2$F. In embodiments, R$^{3C}$ is independently —N$_3$. In embodiments, R$^{3C}$ is independently —SO$_2$CH$_3$. In embodiments, R$^{3C}$ is independently —NHC(O)CH$_3$. In embodiments, R$^{3C}$ is independently —C(O)CH$_3$. In embodiments, R$^{3C}$ is independently substituted or unsubstituted alkyl. In embodiments, R$^{3C}$ is independently substituted or unsubstituted heteroalkyl. In embodiments, R$^{3C}$ is independently substituted or unsubstituted cycloalkyl. In embodiments, R$^{3C}$ is independently substituted or unsubstituted heterocycloalkyl. In embodiments, R$^{3C}$ is independently substituted or unsubstituted aryl. In embodiments, R$^{3C}$ is independently substituted or unsubstituted heteroaryl.

In embodiments, R$^3$ is independently —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO$_2$R$^{3D}$, —NR$^{3C}$SO$_2$NR$^{3A}$R$^{3B}$, —NR$^{3A}$R$^{3B}$, —NR$^{3A}$C(O)R$^{3C}$, —NR$^{3A}$C(O)OR$^{3C}$, —SO$_2$R$^{3C}$, —SO$_2$-L$^{3A}$R$^{3C}$, —SO$_2$NR$^{3A}$R$^{3B}$, —SO$_2$NR$^{3A}$SO$_2$R$^{3C}$, —SO$_2$NR$^{3A}$P(O)(OR$^{3C}$)(OR$^{3D}$), —SO$_2$P(O)(OR$^{3C}$)(OR$^{3D}$), —SO$_2$CH$_2$P(O)(OR$^{3C}$)(OR$^{3D}$), —SO$_2$P(O)(OR$^{3D}$)(NR$^{3A}$R$^{3B}$), —SO$_2$P(O)(R$^{3C}$)(OR$^{3D}$), —SO$_2$P(O)(R$^{3C}$)(R$^{3D}$)—SO$_2$-L$^{3A}$-P(O)(OR$^{3C}$)(OR$^{3D}$), —SO$_2$-L$^{3A}$-P(O)(OR$^{3D}$)(NR$^{3A}$R$^{3B}$), —SO$_2$-L$^{3A}$-P(O)(R$^{3C}$)(OR$^{3D}$), —SO$_2$-L$^{3A}$-P(O)(R$^{3C}$)(R$^{3D}$), —S(O)(NR$^{3A}$)R$^{3C}$, —C(O)OR$^{3C}$, —C(O)NR$^{3A}$R$^{3B}$, —NR$^{3A}$C(O)OR$^{3C}$, R$^{30}$-substituted or unsubstituted alkyl, R$^{30}$-substituted or unsubstituted heteroalkyl, R$^{30}$-substituted or unsubstituted cycloalkyl, R$^{30}$-substituted or unsubstituted heterocycloalkyl, R$^{30}$-substituted or unsubstituted aryl, or R$^{30}$-substituted or unsubstituted heteroaryl.

R$^{30}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted phenyl, or substituted or unsubstituted heteroaryl.

In embodiments, R$^{30}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl, unsubstituted heteroalkyl, unsubstituted cycloalkyl, unsubstituted heterocycloalkyl, unsubstituted phenyl, or unsubstituted heteroaryl.

In embodiments, R$^{30}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted C$_1$-C$_6$ alkyl, unsubstituted 2 to 6 membered heteroalkyl, unsubstituted C$_3$-C$_6$ cycloalkyl, unsubstituted 3 to 6 membered heterocycloalkyl, unsubstituted phenyl, or unsubstituted 5 to 6 membered heteroaryl.

In embodiments, R$^{3A}$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, R$^3$-substituted or unsubstituted alkyl, R$^{30}$-substituted or unsubstituted heteroalkyl, R$^{30}$-substituted or unsubstituted cycloalkyl, R$^{30}$-substituted or unsubstituted heterocycloalkyl, R$^{30}$-substituted or unsubstituted aryl, or R$^{30}$-substituted or unsubstituted heteroaryl; R$^{3A}$ and R$^{3B}$ substituents bonded to the same nitrogen atom may optionally be joined to form a R$^{30}$-substituted or unsubstituted heterocycloalkyl or R$^{30}$-substituted or unsubstituted heteroaryl; R$^{3A}$ and R$^{3D}$ substituents may optionally be joined to form a R$^{30}$-substituted or unsubstituted heterocycloalkyl or R$^{30}$-substituted or unsubstituted heteroaryl.

In embodiments, R$^{3B}$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, R$^3$-substituted or unsubstituted alkyl, R$^{31}$-substituted or unsubstituted heteroalkyl, R$^{31}$-substituted or unsubstituted cycloalkyl, R$^{31}$-substituted or unsubstituted heterocycloalkyl, R$^{31}$-substituted or unsubstituted aryl, or R$^{31}$-substituted or unsubstituted heteroaryl; R$^{3A}$ and R$^{3B}$ substituents bonded to the same nitrogen atom may optionally be joined to form a R$^3$-substituted or unsubstituted heterocycloalkyl or R$^{31}$-substituted or unsubstituted heteroaryl.

R$^{31}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, substituted or unsubstituted alkyl, substituted or unsubstituted heteroalkyl, substituted or unsubstituted cycloalkyl, substituted or unsubstituted heterocycloalkyl, substituted or unsubstituted phenyl, or substituted or unsubstituted heteroaryl.

In embodiments, R$^{31}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted alkyl, unsubstituted heteroalkyl, unsubstituted cycloalkyl, unsubstituted heterocycloalkyl, unsubstituted phenyl, or unsubstituted heteroaryl.

In embodiments, R$^{31}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted C$_1$-C$_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{3C}$ is independently hydrogen, oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SO_2CH_3$, —$NHC(O)CH_3$, —$C(O)CH_3$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl.

$R^{32}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted phenyl, or substituted or unsubstituted heteroaryl.

In embodiments, $R^{32}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl, unsubstituted heteroalkyl, unsubstituted cycloalkyl, unsubstituted heterocycloalkyl, unsubstituted phenyl, or unsubstituted heteroaryl.

In embodiments, $R^{32}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, R" is independently hydrogen, oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SO_2CH_3$, —$NHC(O)CH_3$, —$C(O)CH_3$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl; $R^{34}$ and $R^{3D}$ substituents may optionally be joined to form a $R^{33}$-substituted or unsubstituted heterocycloalkyl or $R^{33}$-substituted or unsubstituted heteroaryl.

$R^{33}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted phenyl, or substituted or unsubstituted heteroaryl.

In embodiments, $R^{33}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted alkyl, unsubstituted heteroalkyl, unsubstituted cycloalkyl, unsubstituted heterocycloalkyl, unsubstituted phenyl, or unsubstituted heteroaryl.

In embodiments, $R^{33}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{3C}$ is independently

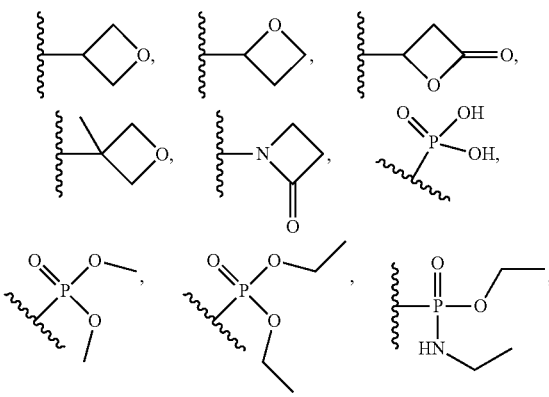

-continued
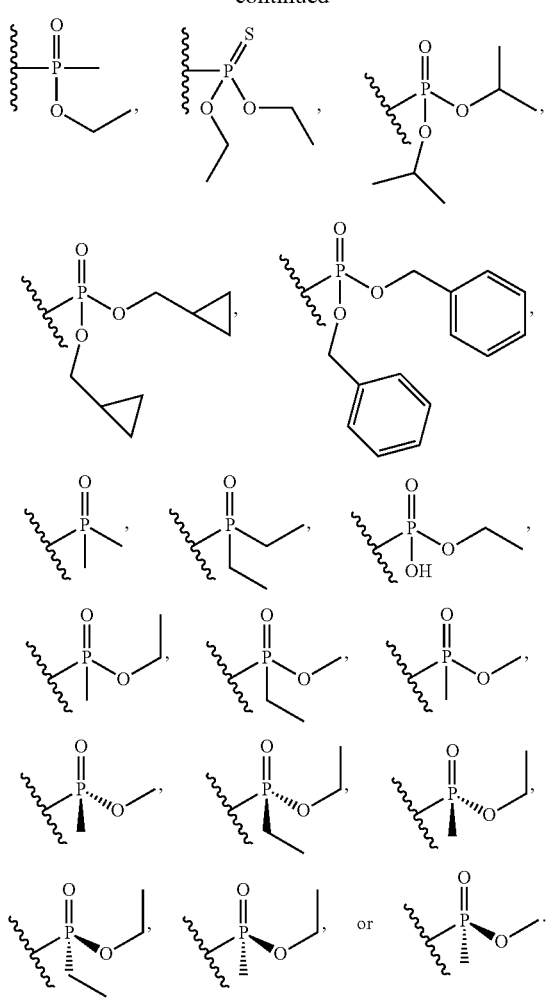
In embodiments, $R^{3C}$ is
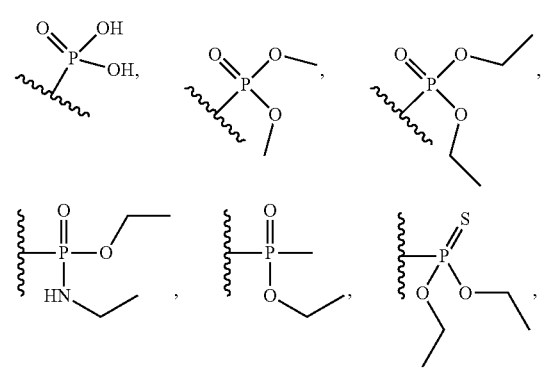
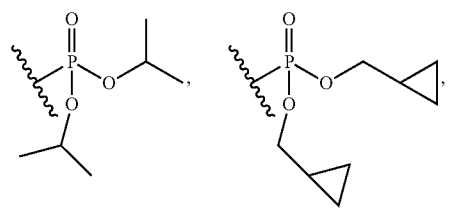
-continued
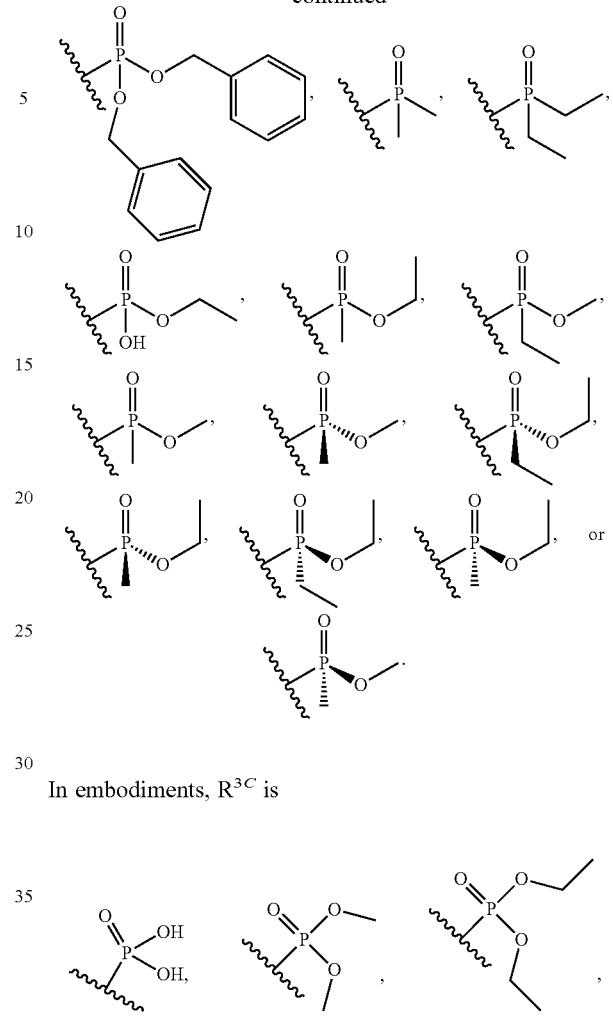
In embodiments, $R^{3C}$ is
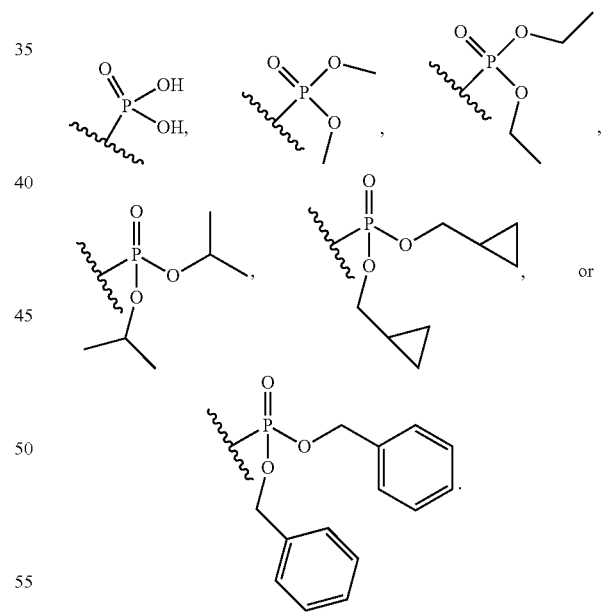
In embodiments, $R^{3C}$ is
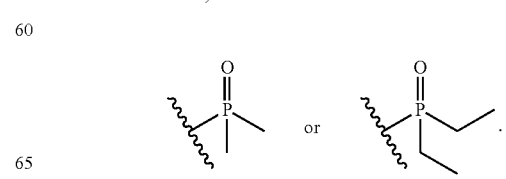

In embodiments, R³ᶜ is

[chemical structures of phosphonate groups with various substituents including ethyl, methyl, methoxy, ethoxy groups with stereochemistry]

or

[phosphonate structure]

In embodiments, R³ᶜ is

[phosphonic acid structure with two OH groups]

In embodiments, R³ᶜ is

[dimethyl phosphonate structure]

In embodiments, R³ᶜ is

[diethyl phosphonate structure]

In embodiments, R³ᶜ is

[ethyl phosphonate with NH-ethyl group]

In embodiments, R³ᶜ is

[methyl phosphinate with ethoxy group]

In embodiments, R³ᶜ is

[thiophosphonate with two ethoxy groups]

In embodiments R³ᶜ is

[diisopropyl phosphonate]

In embodiments, R³ᶜ is

[phosphonate with two cyclopropylmethoxy groups]

In embodiments, R³ᶜ is

[dibenzyl phosphonate]

In embodiments, R³ᶜ is

[dimethyl phosphine oxide]

In embodiments, $R^{3C}$ is
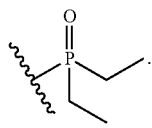 [SMILES: *P(=O)(CC)CC]
In embodiments $R^{3C}$ is
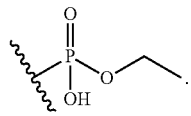 [SMILES: *P(=O)(O)OCC]
In embodiments, $R^{3C}$ is
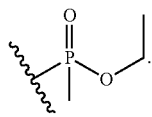 [SMILES: *P(C)(=O)OCC]
In embodiments, $R^{3C}$ is
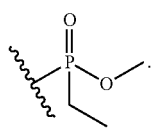 [SMILES: *P(=O)(CC)OC]
In embodiments, $R^{3C}$ is
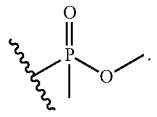 [SMILES: *P(C)(=O)OC]
In embodiments, $R^{3C}$ is
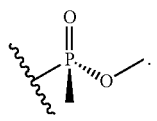 [SMILES: *[P@](C)(=O)OC]
In embodiments, $R^{3C}$ is
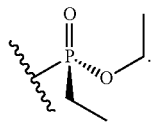 [SMILES: *[P@@](=O)(CC)OCC]
In embodiments, $R^{3C}$ is
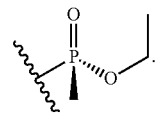 [SMILES: *[P@](C)(=O)OCC]
In embodiments $R^{3C}$ is
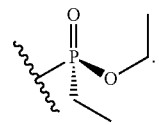 [SMILES: *[P@](=O)(CC)OCC]
In embodiments $R^{3C}$ is
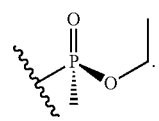 [SMILES: *[P@@](C)(=O)OCC]
In embodiments $R^{3C}$ is
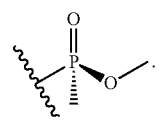 [SMILES: *[P@@](C)(=O)OC]
In embodiments, $R^3$ is
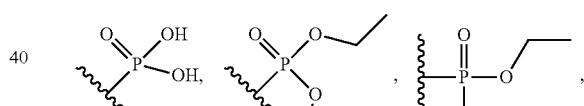
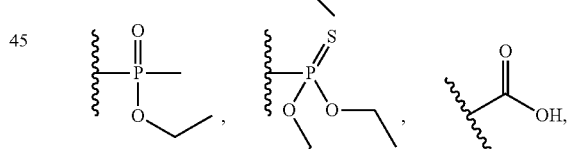
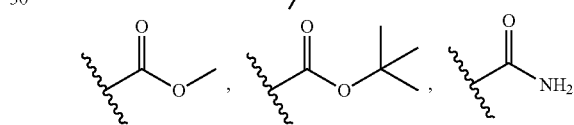
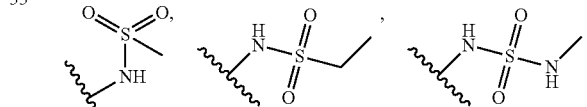
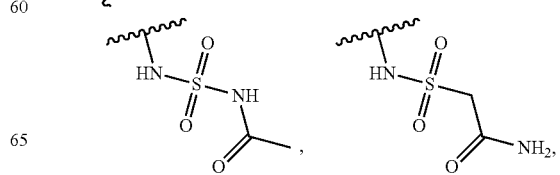

-continued
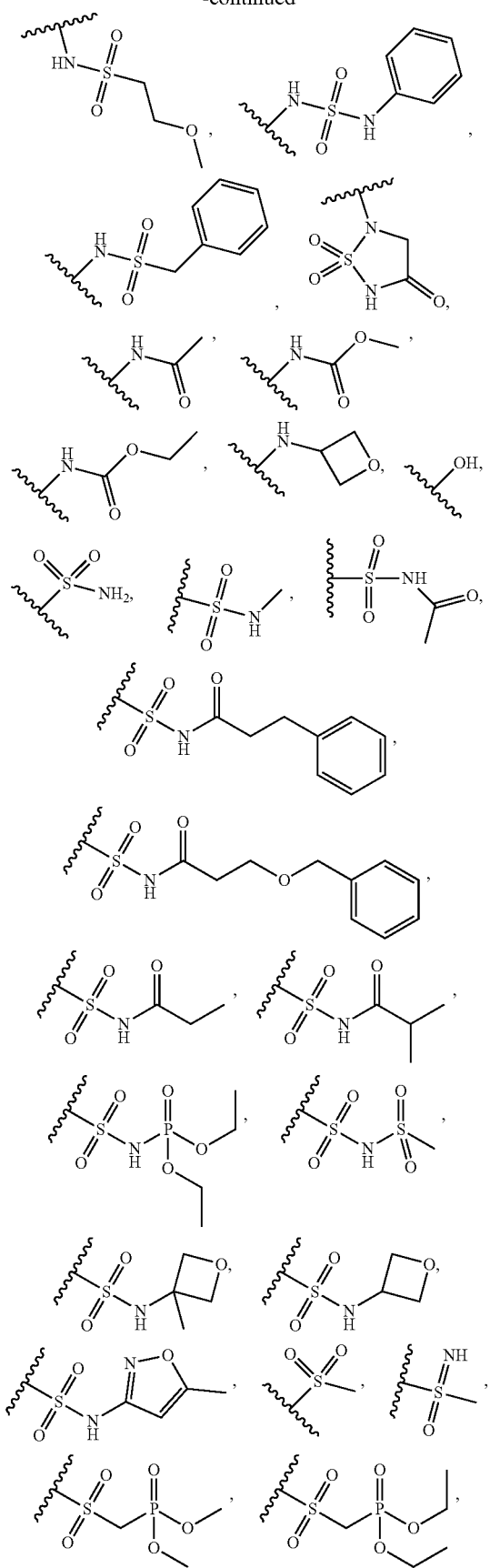
-continued
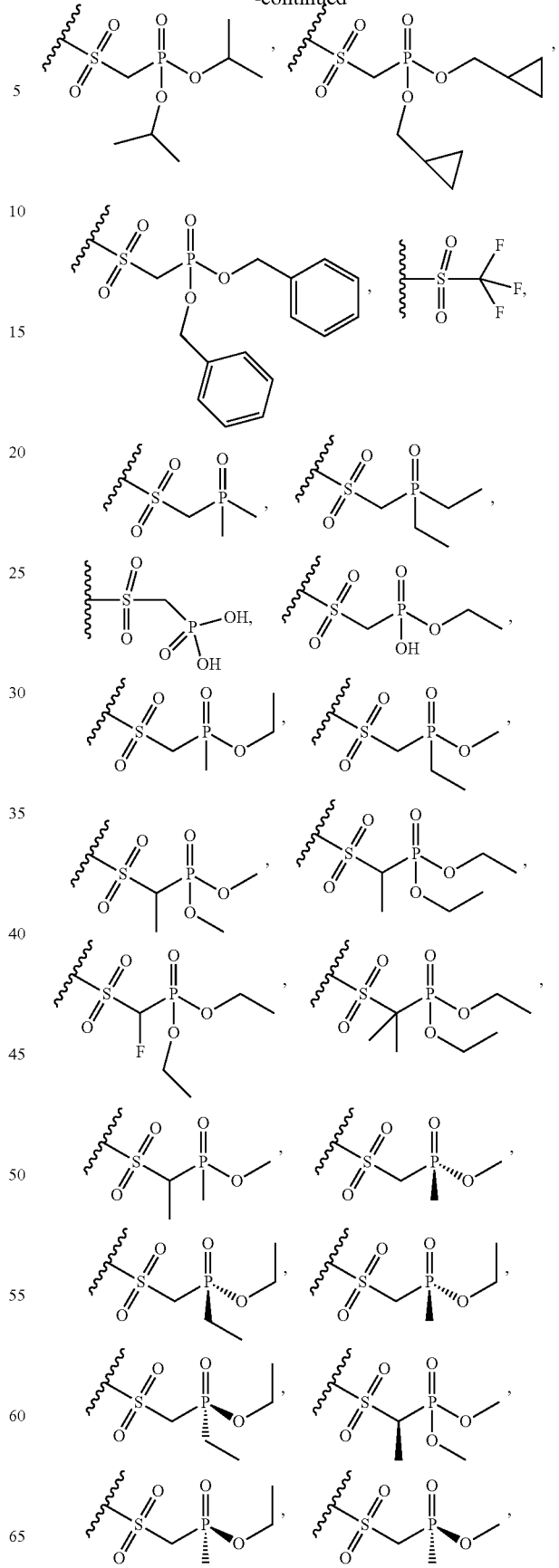

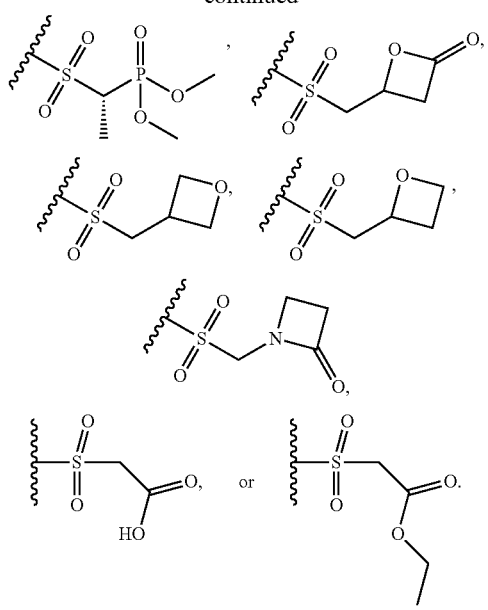
In embodiments R³ is
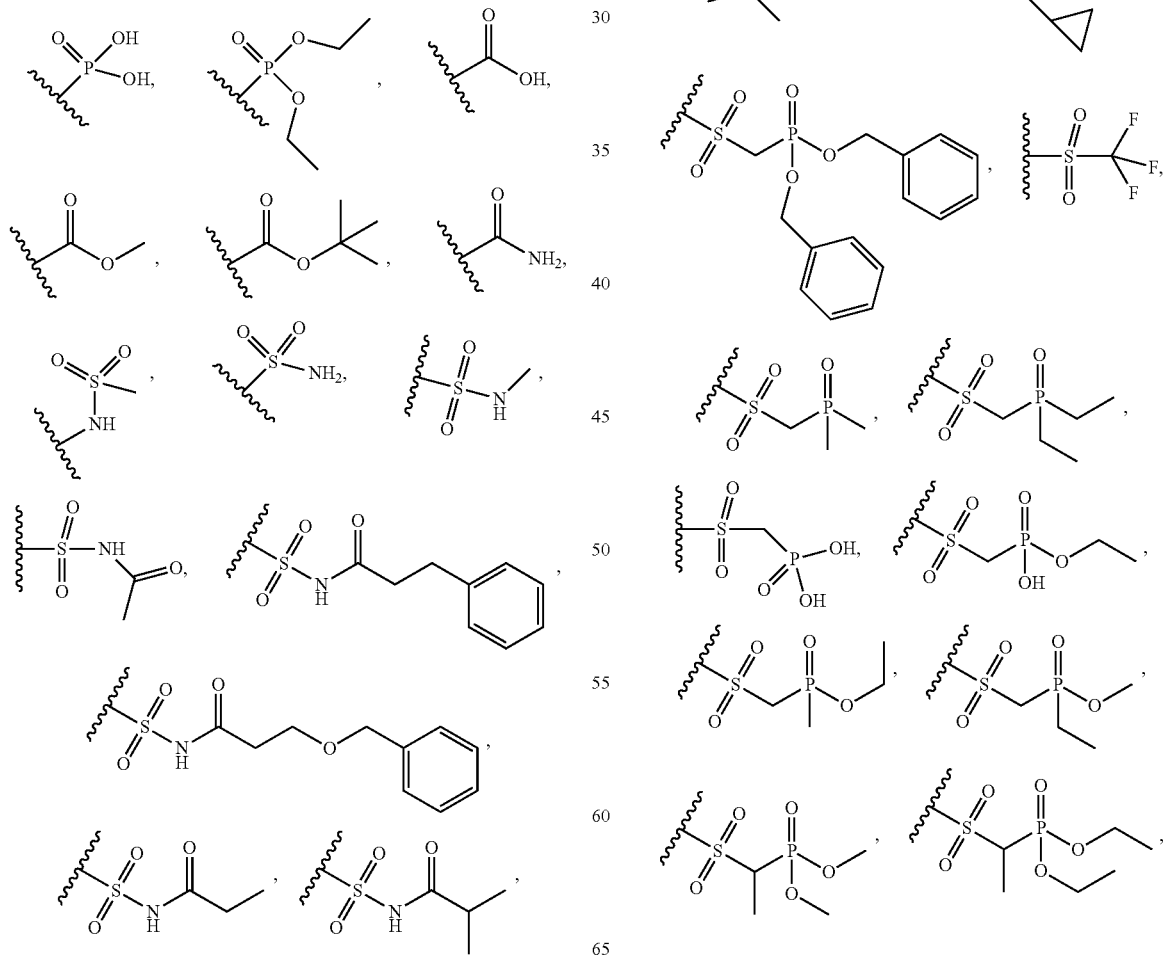
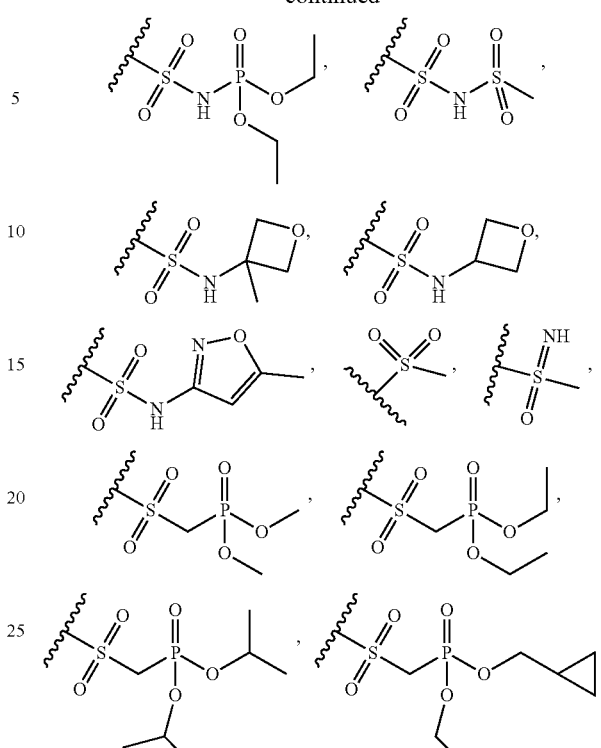

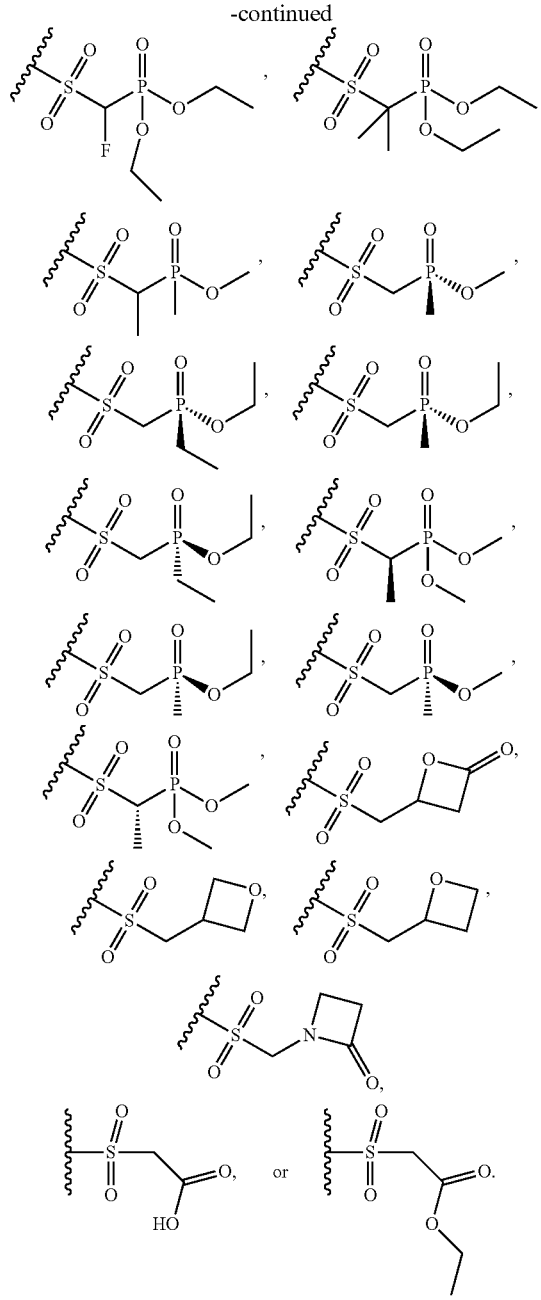
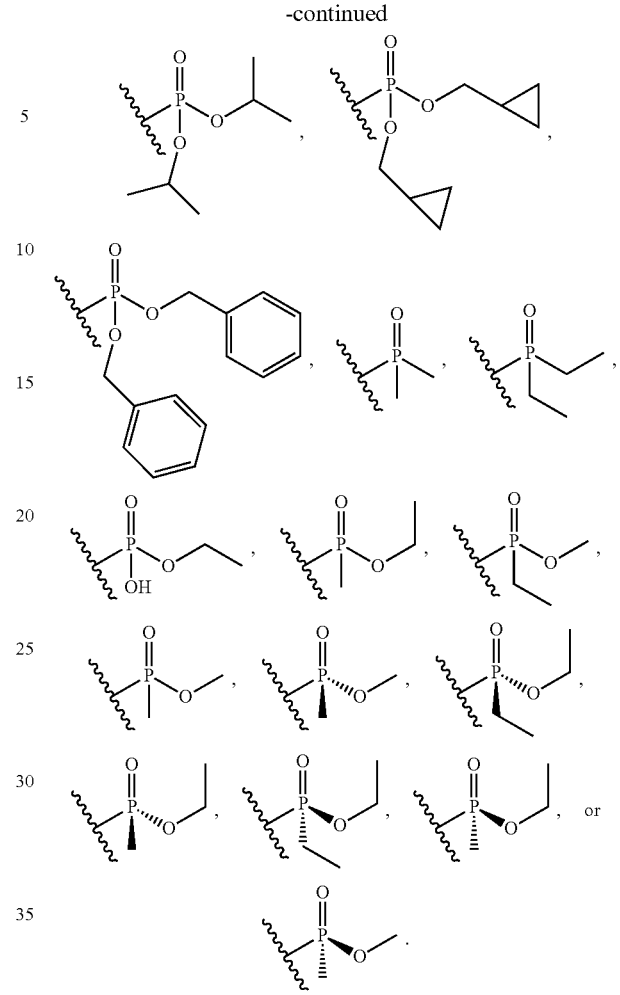
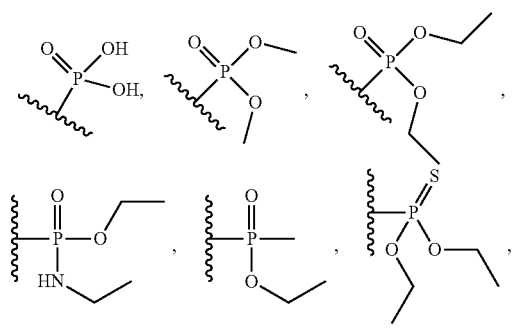
In embodiments, R³ is
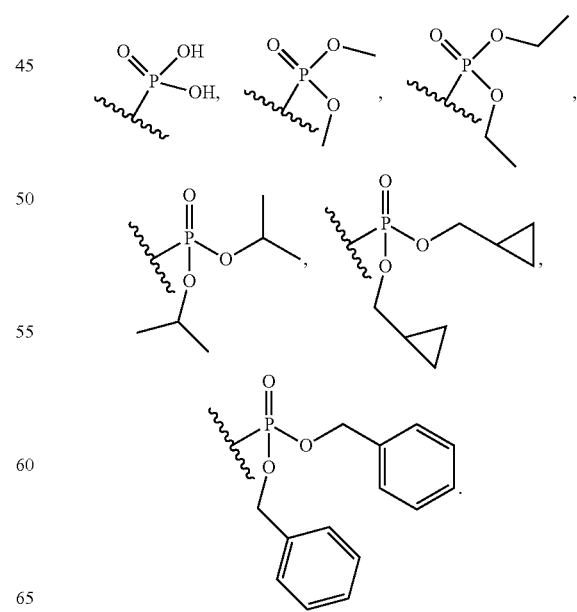

In embodiments, R³ is
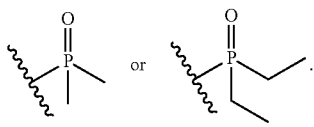 or
In embodiments, R³ is
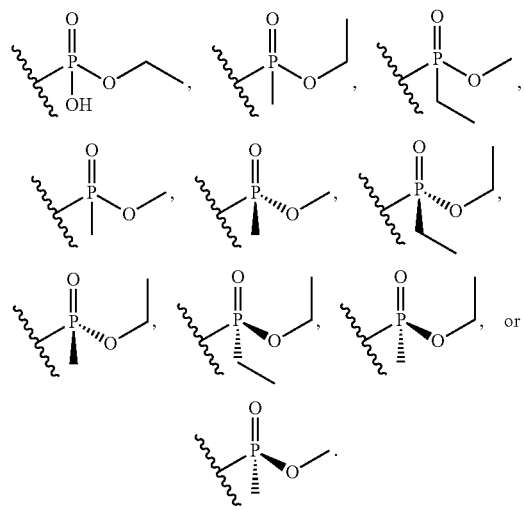 or
In embodiments, R³ is
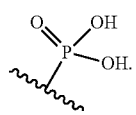
In embodiments, R³ is
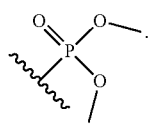
In embodiments, R³ is
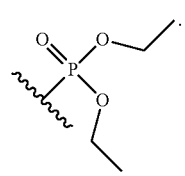 [SMILES: *P(=O)(OCC)OCC]
In embodiments, R³ is
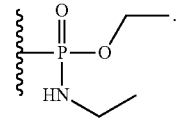
In embodiments, R³ is
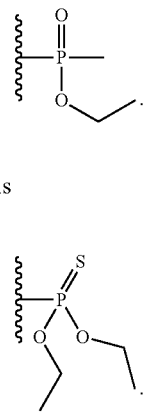
In embodiments, R³ is
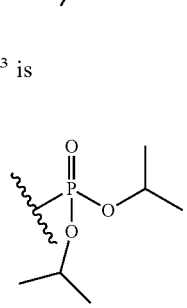
In embodiments, R³ is
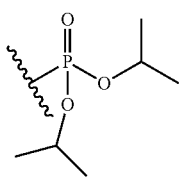
In embodiments, R³ is
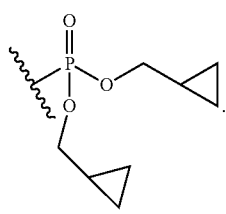 [SMILES: *P(=O)(OCC1CC1)OCC1CC1]
In embodiments, R³ is
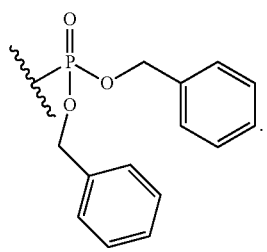 [SMILES: *P(=O)(OCc1ccccc1)OCc1ccccc1]

In embodiments, R³ is
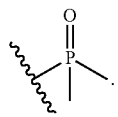
In embodiments, R³ is
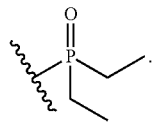 [SMILES: *P(=O)(CC)CC]
In embodiments, R³ is
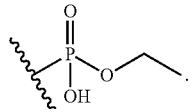
In embodiments, R³ is
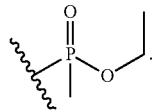
In embodiments, R³ is
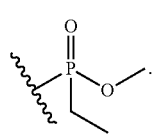
In embodiments, R³ is
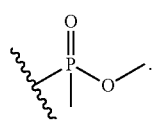 [SMILES: *P(C)(=O)OC]
In embodiments R³ is
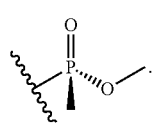
In embodiments, R³ is
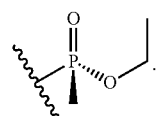
In embodiments, R³ is
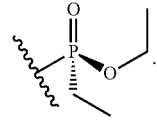
In embodiments, R³ is
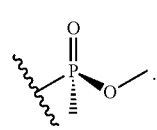
In embodiments, R³ is
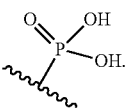
In embodiments, R is
In embodiments, R³ is
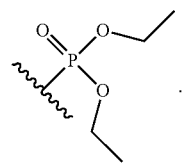 [SMILES: *P(=O)(OCC)OCC]
In embodiments, R³ is In embodiments, R³ is
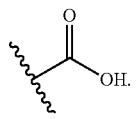 [SMILES: *C(=O)O]
In embodiments, R³ is
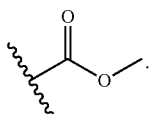 [SMILES: *C(=O)OC]
In embodiments, R³ is
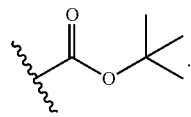 [SMILES: *C(=O)OC(C)(C)C]
In embodiments, R³ is
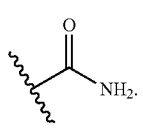
In embodiments, R³ is
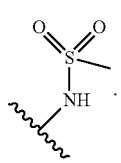
In embodiments, R³ is
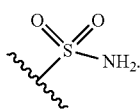
In embodiments, R³ is
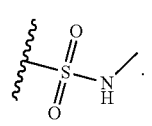
In embodiments, R³ is
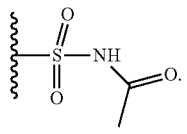
In embodiments, R³ is
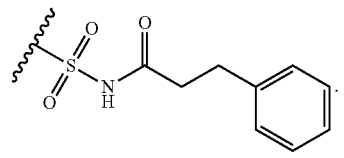 [SMILES: *S(=O)(=O)NC(=O)CCc1ccccc1]
In embodiments, R³ is
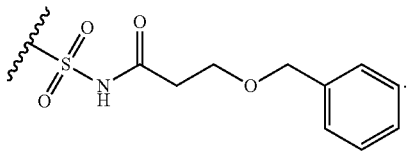 [SMILES: *S(=O)(=O)NC(=O)CCOCc1ccccc1]
In embodiments, R³ is
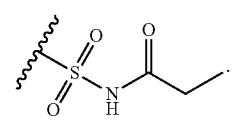 [SMILES: *S(=O)(=O)NC(=O)CC]
In embodiments, R³ is
In embodiments, R³ is
In embodiments, R³ is
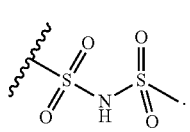 [SMILES: *S(=O)(=O)NS(C)(=O)=O]

In embodiments R³ is
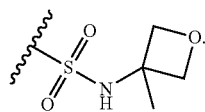
In embodiments, R³ is
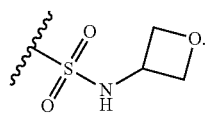 [SMILES: *S(=O)(=O)NC1COC1]
In embodiments, R³ is
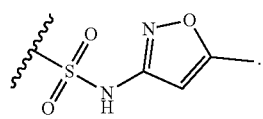 [SMILES: *S(=O)(=O)Nc1cc(C)on1]
In embodiments, R³ is
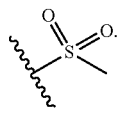
In embodiments, R³ is
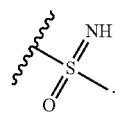
In embodiments, R³ is
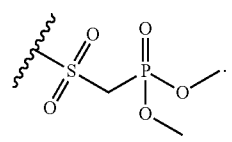 [SMILES: *S(=O)(=O)CP(=O)(OC)OC]
In embodiments, R³ is
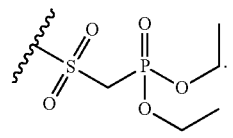 [SMILES: *S(=O)(=O)CP(=O)(OCC)OCC]
In embodiments, R³ is
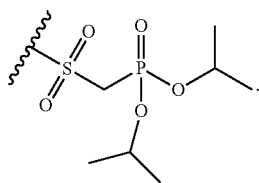 [SMILES: *S(=O)(=O)CP(=O)(OC(C)C)OC(C)C]
In embodiments R³ is
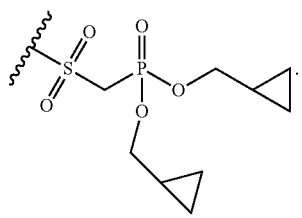 [SMILES: *S(=O)(=O)CP(=O)(OCC1CC1)OCC1CC1]
In embodiments, R³ is
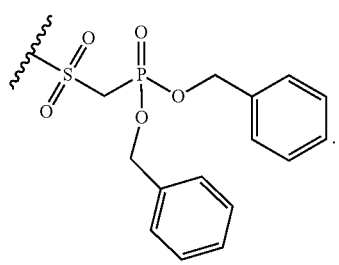 [SMILES: *S(=O)(=O)CP(=O)(OCc1ccccc1)OCc1ccccc1]
In embodiments, R³ is
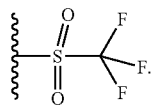
In embodiments, R³ is
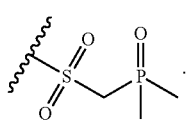 [SMILES: *S(=O)(=O)CP(C)(C)=O]
In embodiments, R³ is
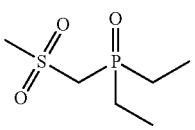

In embodiments, R³ is
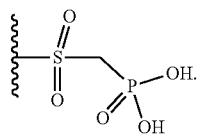 [SMILES: *S(=O)(=O)CP(=O)(O)O]
In embodiments, R³ is
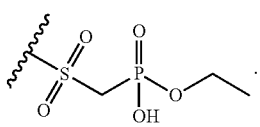 [SMILES: *S(=O)(=O)CP(=O)(O)OCC]
In embodiments, R³ is
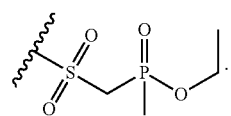
In embodiments, R³ is
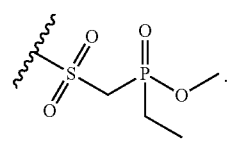 [SMILES: *S(=O)(=O)CP(=O)(CC)OC]
In embodiments R³ is
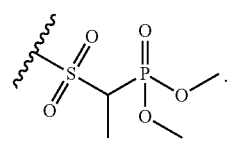 [SMILES: *S(=O)(=O)C(C)P(=O)(OC)OC]
In embodiments, R³ is
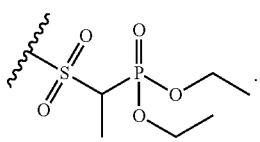 [SMILES: *S(=O)(=O)C(C)P(=O)(OCC)OCC]
In embodiments R³ is
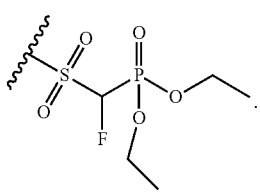 [SMILES: *S(=O)(=O)C(F)P(=O)(OCC)OCC]
In embodiments, R³ is
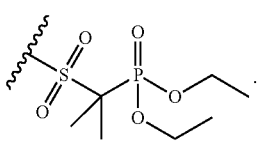 [SMILES: *S(=O)(=O)C(C)(C)P(=O)(OCC)OCC]
In embodiments, R³ is
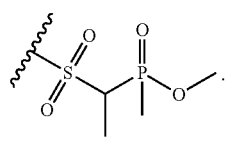 [SMILES: *S(=O)(=O)C(C)P(C)(=O)OC]
In embodiments, R³ is
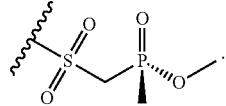 [SMILES: *S(=O)(=O)C[P@](C)(=O)OC]
In embodiments, R³ is
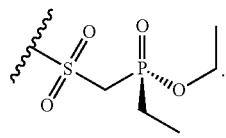
In embodiments, R³ is
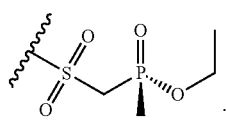 [SMILES: *S(=O)(=O)C[P@](C)(=O)OCC]
In embodiments R³ is
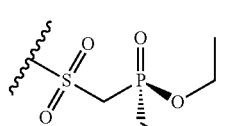
In embodiments, R³ is
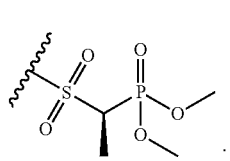 [SMILES: *S(=O)(=O)[C@H](C)P(=O)(OC)OC]

In embodiments, R³ is
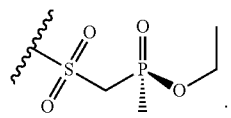 [SMILES: *S(=O)(=O)C[P@@](C)(=O)OCC]
In embodiments, R³ is
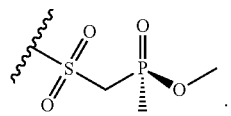 [SMILES: *S(=O)(=O)C[P@@](C)(=O)OC]
In embodiments R³ is
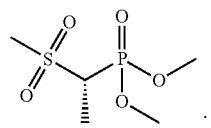
In embodiments, R³ is
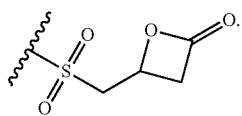 [SMILES: *S(=O)(=O)CC1CC(=O)O1]
In embodiments, R³ is
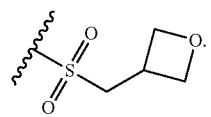 [SMILES: *S(=O)(=O)CC1COC1]
In embodiments, R³ is
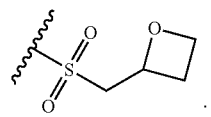
In embodiments R³ is
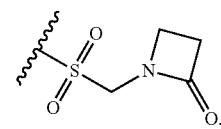 [SMILES: *S(=O)(=O)CN1CCC1=O]
In embodiments, R³ is
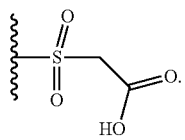 [SMILES: *S(=O)(=O)CC(=O)O]
In embodiments, R³ is
In embodiments, R³ is
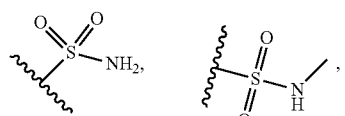
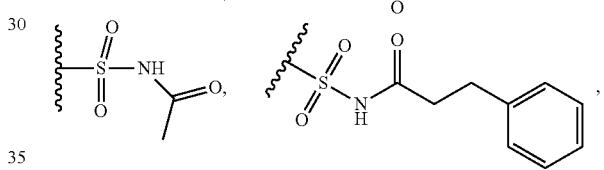
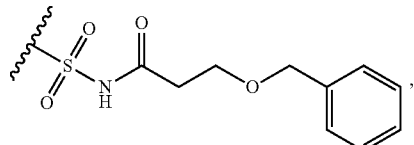
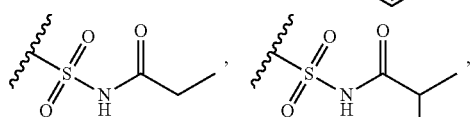
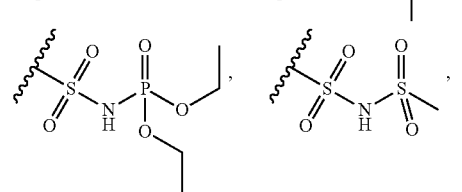
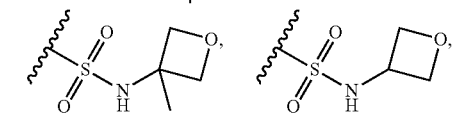
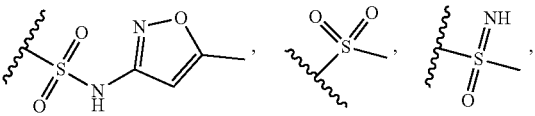
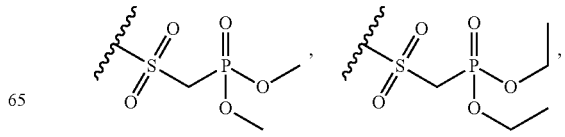

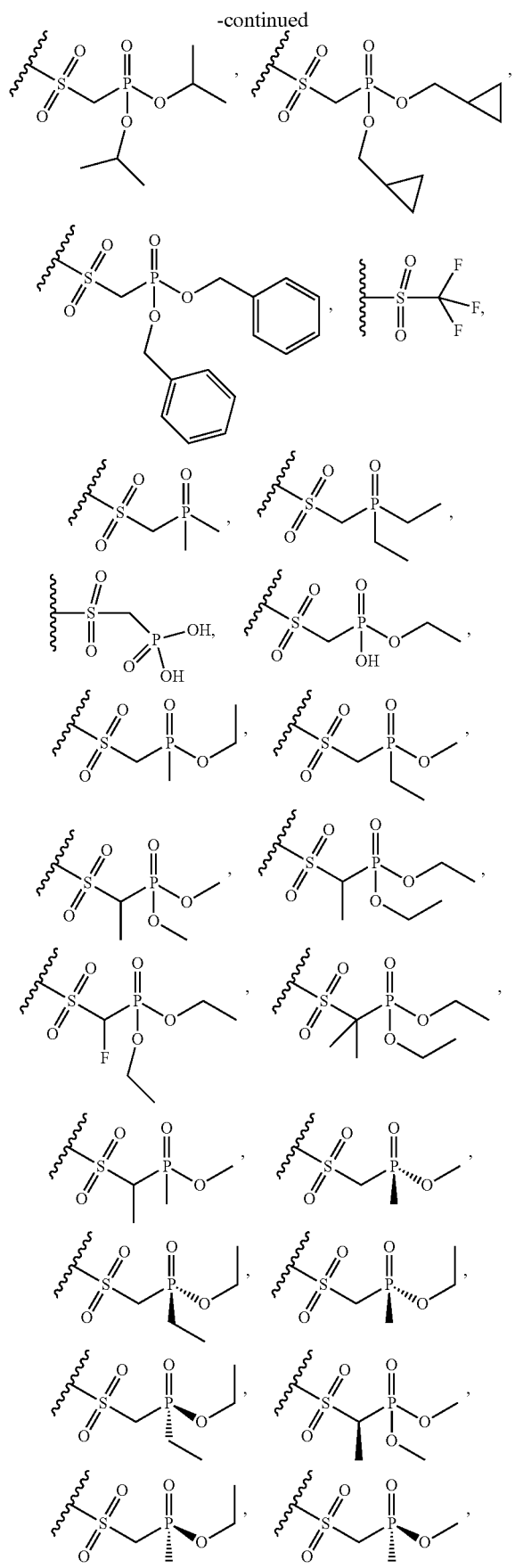
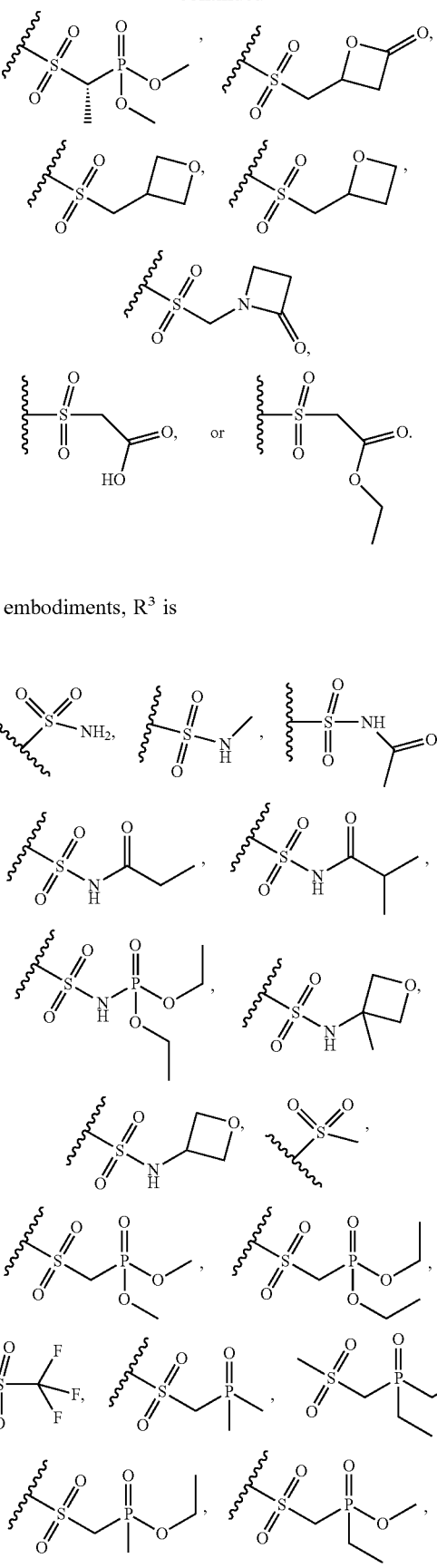
In embodiments, $R^3$ is

-continued

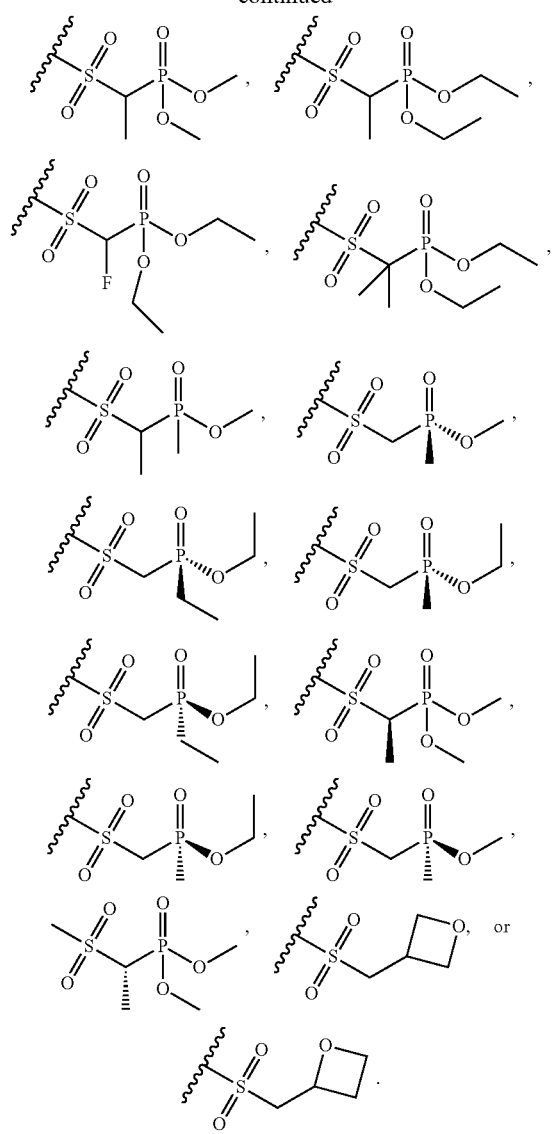

In embodiments, R³ is

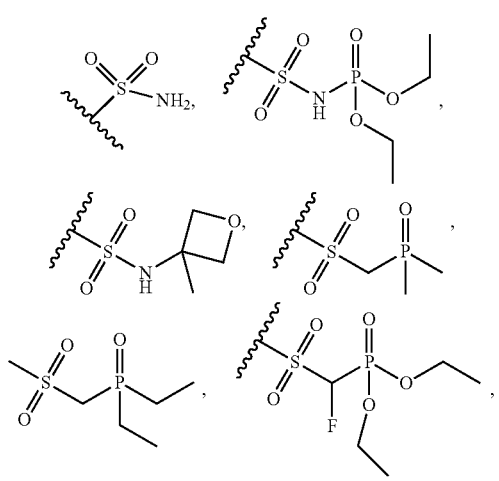

-continued

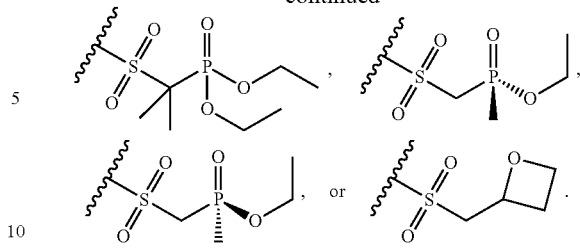

In embodiments R³ is

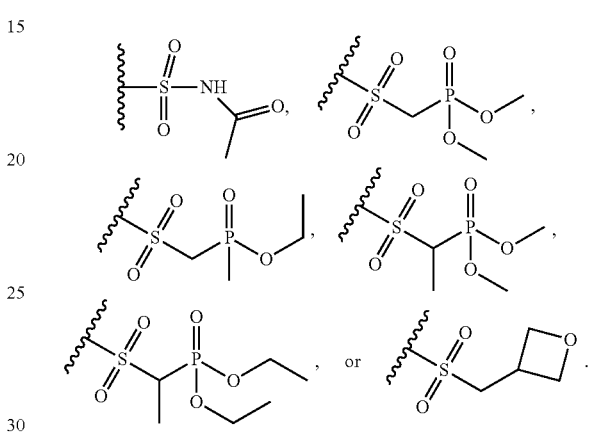

In embodiments, L³ is a bond. In embodiments, L³ is —NH—. In embodiments, L³ is —O—. In embodiments, L³ is —C(O)—. In embodiments, L³ is —C(O)NH—. In embodiments, L³ is —NHC(O)—. In embodiments, L³ is —NHC(O)NH—. In embodiments, L³ is —C(O)O—. In embodiments, L³ is —OC(O)—. In embodiments, L³ is substituted or unsubstituted alkylene. In embodiments, L³ is substituted or unsubstituted heteroalkylene. In embodiments, L³ is a bond, substituted or unsubstituted alkylene, or substituted or unsubstituted heteroalkylene. In embodiments, L³ is a bond unsubstituted alkylene, or unsubstituted heteroalkylene. In embodiments, L³ is a bond, —CH₂—, —CH₂CH₂—, —CH₂CH₂CH₂—, —OCH₂—, —OCH₂CH₂—, or —OCH₂CH₂CH₂—. In embodiments, L³ is a bond. In embodiments, L³ is —CH₂—. In embodiments, L³ is —CH₂CH₂—. In embodiments, L³ is —CH₂CH₂CH₂—. In embodiments, L³ is —OCH₂—. In embodiments, L³ is —OCH₂CH₂—. In embodiments, L³ is —OCH₂CH₂CH₂—.

In embodiments, L³ is a bond or —CH₂—.

In embodiments, Ring B is phenyl or 5 to 10 membered heteroaryl.

In embodiments, Ring B is phenyl. In embodiments, Ring B is independently pyrrolyl, pyrazolyl, pyridazinyl, triazinyl, pyrimidinyl, imidazolyl, pyrazinyl, oxazolyl, isoxazolyl, thiazolyl, furyl, thienyl, pyridyl, pyrimidyl, benzothiazolyl, benzoxazoyl, benzimidazolyl, benzofuran, benzothienyl, isobenzofuranyl, indazolyl, indolyl, or isoindolyl. In embodiments, Ring B is independently pyrrolyl. In embodiments, Ring B is independently pyrazolyl. In embodiments, Ring B is independently pyridazinyl. In embodiments, Ring B is independently triazinyl. In embodiments, Ring B is independently pyrimidinyl. In embodiments, Ring B is independently imidazolyl. In embodiments, Ring B is independently pyrazinyl. In embodiments, Ring B is independently oxazolyl. In embodiments, Ring B is independently isoxazolyl. In embodiments, Ring B is independently thiazolyl. In embodiments, Ring B is independently furyl. In embodiments, Ring B is independently thienyl. In embodiments, Ring B is independently pyridyl. In embodiments, Ring B is independently pyrimidyl. In embodiments, Ring B is independently benzothiazolyl. In embodiments, Ring B is independently benzoxazoyl. In embodiments, Ring B is independently benzimidazolyl. In embodiments, Ring B is independently benzofuran. In embodiments, Ring B is independently benzothienyl. In embodiments, Ring B is independently isobenzofuranyl. In embodiments, Ring B is independently indazolyl. In embodiments, Ring B is independently indolyl. In embodiments, Ring B is independently isoindolyl.

In embodiments, Ring B is phenyl, thienyl, indazolyl, indolyl, pyrazolyl, pyrimidinyl, pyridyl, or benzothienyl. In embodiments, Ring B is thienyl, pyrazolyl, pyrimidinyl, or pyridyl. In embodiments, Ring B is indazolyl, indolyl, or benzothienyl.

In embodiments, the compound has the formula:

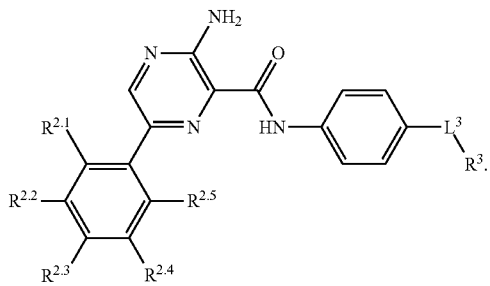

$R^{2.1}$, $R^{2.2}$, $R^{2.3}$, $R^{2.4}$, and $R^{2.5}$ are independently hydrogen or any value of $R^2$ as described herein, including in embodiments. $R^3$ and $L^3$ are as described herein, including in embodiments.

In embodiments, the compound has the formula:

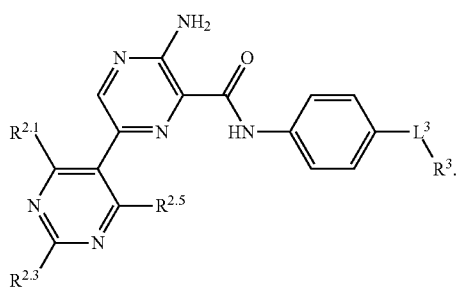

$R^{2.1}$, $R^{2.3}$, $R^{2.5}$, $R^3$ and $L^3$ are as described herein, including in embodiments.

In embodiments, the compound has the formula:

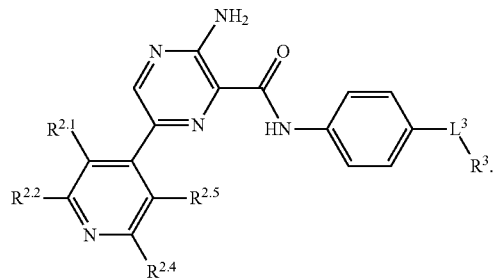

$R^{2.1}$, $R^{2.2}$, $R^{2.4}$, $R^{2.5}$, $R^3$ and $L^3$ areas described herein, including in embodiments.

In embodiments, the compound has the formula:

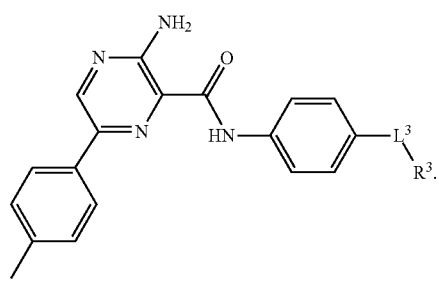

(Ib)

$R^3$ and $L^3$ are as described herein, including in embodiments.

In embodiments, the compound has the formula:

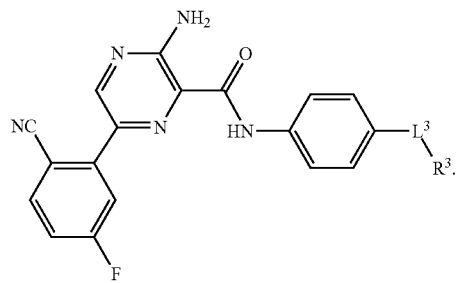

$R^3$ and $L^3$ are as described herein, including in embodiments.

In embodiments, the compound has the formula:

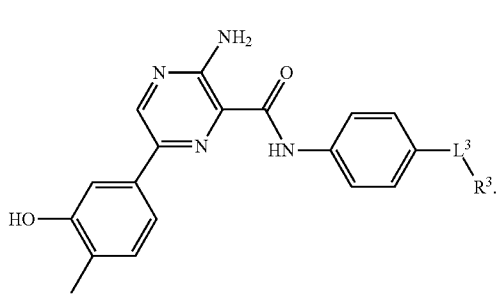

(Ib)

$R^3$ and $L^3$ are as described herein, including in embodiments.

In embodiments, the compound has the formula:

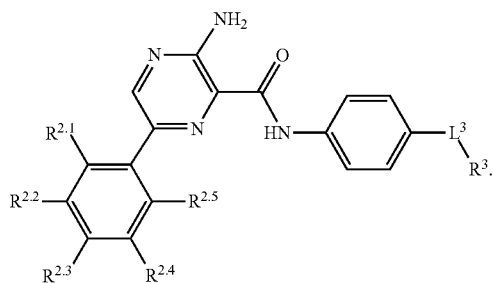

$R^{2.1}$, $R^{2.2}$, $R^{2.3}$, $R^{2.4}$, $R^{2.5}$, and $L^3$ are as described herein, including in embodiments. In embodiments, $L^3$ is —SO$_2$-$L^{3.A}$-$R^{3C}$. $L^{3.A}$ and $R^{3C}$ are as described herein, including in embodiments. In embodiments, $L^{3.A}$ is —CH$_2$—. In embodiments, $R^{3C}$ is independently

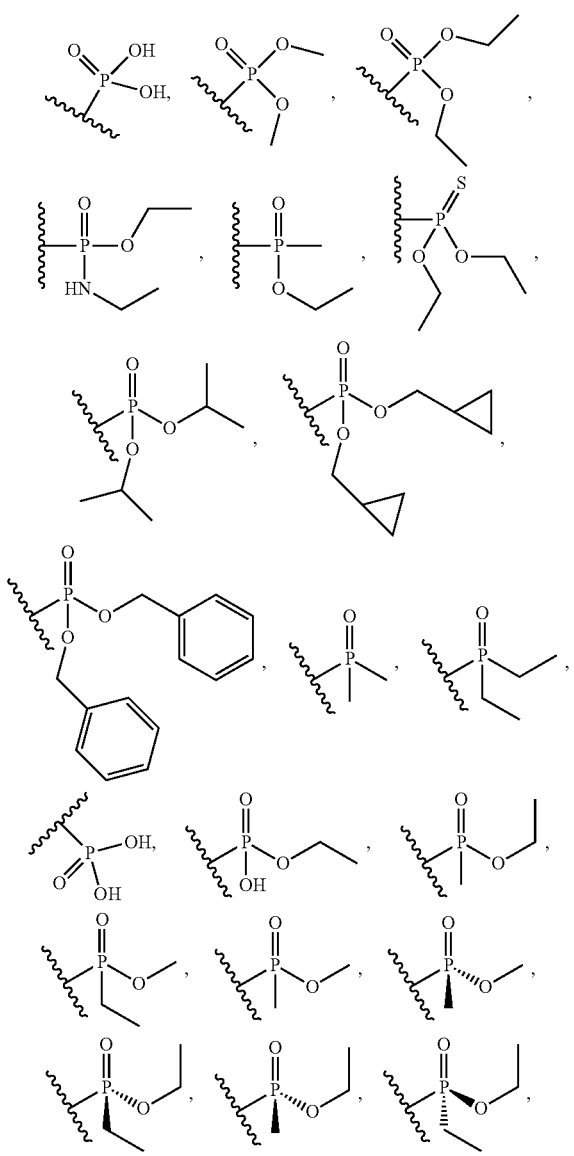

-continued

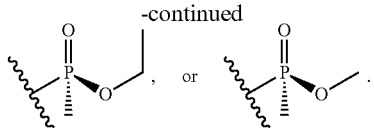

In embodiments, the compound has the formula:

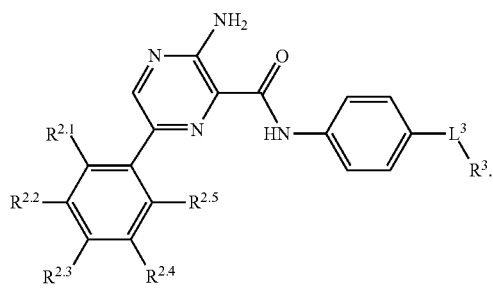

$R^{2.1}$, $R^{2.2}$, $R^{2.3}$, $R^{2.4}$, and $R^{2.5}$ are as described herein, including in embodiments. $L^3$ is —SO$_2$-$L^{3.A}$-$R^{3C}$. $L^{3.A}$ and $R^{3C}$ are as described herein, including in embodiments. In embodiments, $L^{3.A}$ is —CH$_2$—. In embodiments, $R^{3C}$ is independently

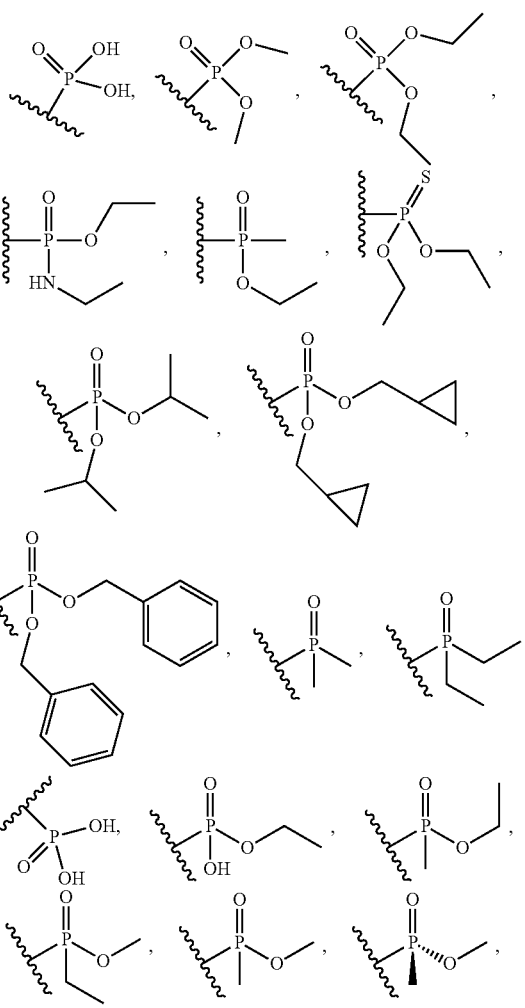

-continued
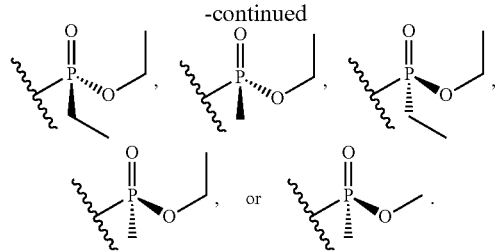
In embodiments, the compound has the formula:
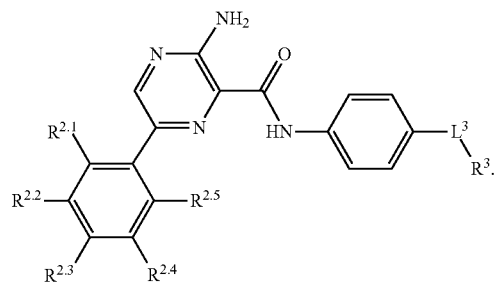
$R^{2.1}$, $R^{2.2}$, $R^{2.3}$, $R^{2.4}$, $R^{2.5}$, and $L^3$ are as described herein, including in embodiments. In embodiments, $L^3$ is a bond. $R^3$ is independently
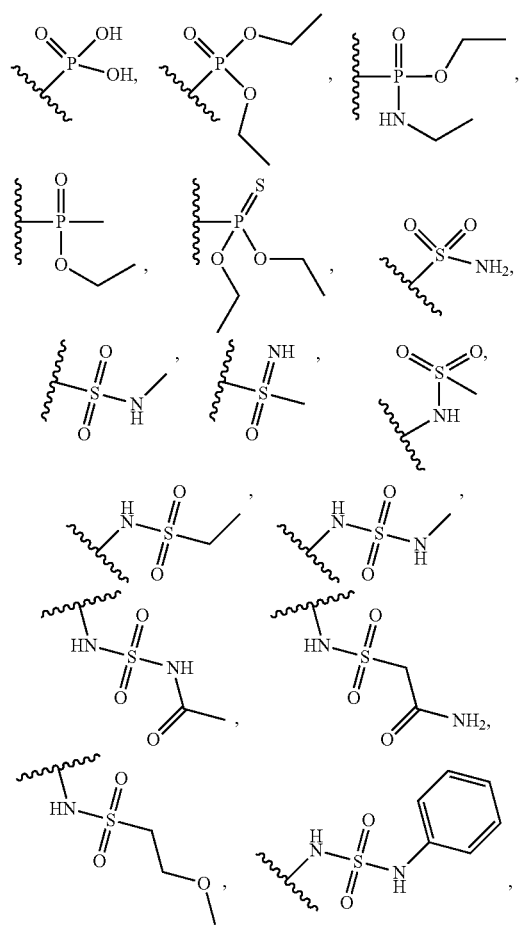
-continued
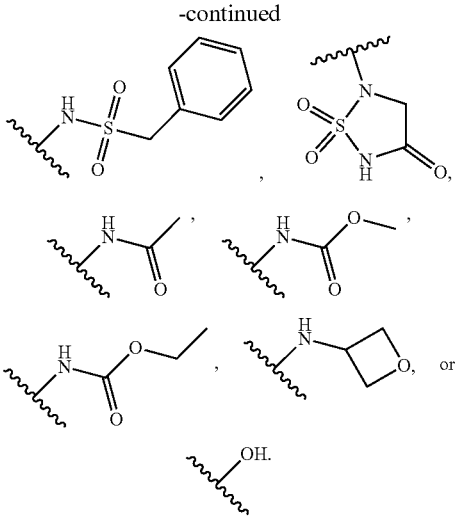
In embodiments, the compound has the formula:
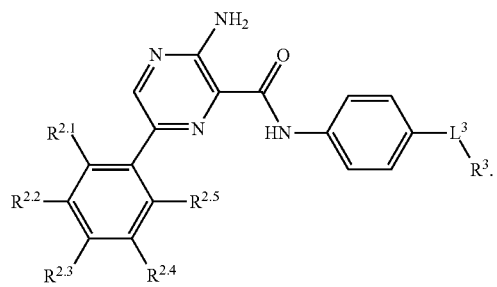
$R^{2.1}$, $R^{2.2}$, $R^{2.3}$, $R^{2.4}$, and $R^{2.5}$ are as described herein, including in embodiments. $L^3$ is a bond. $R^3$ is independently
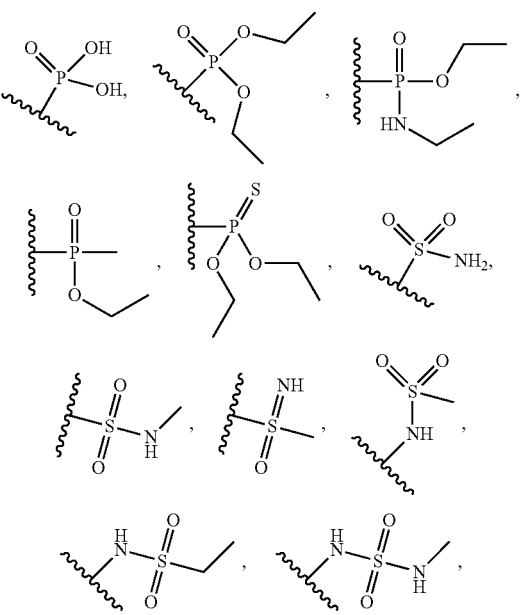

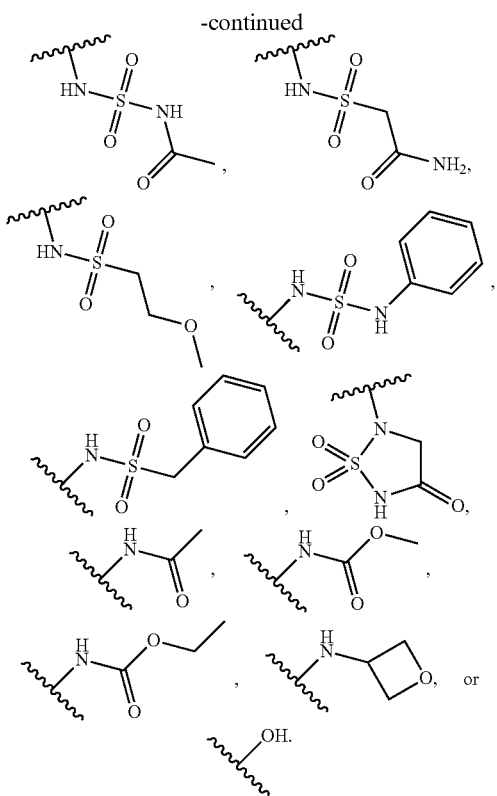

In embodiments, R$^{2.1}$ is independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CH$_2$OH, —CH$_2$NH$_2$, —CH$_2$NH(CH$_3$), —CH$_2$N(CH$_3$)$_2$, —CN, —SO$_2$Me, —SO$_2$Et, —SO$_2$NH$_2$, —OH, —OCH$_3$, —NH$_2$, —NHC(O)CH$_3$, —COOH, —COCH$_3$, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^{2.1}$ is independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CH$_2$OH, —CH$_2$NH$_2$, —CH$_2$NH(CH$_3$), —CH$_2$N(CH$_3$)$_2$, —CN, —SO$_2$Me, —SO$_2$Et, —SO$_2$NH$_2$, —OH, —OCH$_3$, —NH$_2$, —NHC(O)CH$_3$, —COOH, —COCH$_3$, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, or —OCH$_2$F. In embodiments, R$^{2.1}$ is independently hydrogen. In embodiments, R$^{2.1}$ is independently —F. In embodiments, R$^{2.1}$ is independently —Cl. In embodiments, R$^{2.1}$ is independently —Br. In embodiments, R$^{2.1}$ is independently —I. In embodiments, R$^{2.1}$ is independently —CCl$_3$. In embodiments, R$^{2.1}$ is independently —CBr$_3$. In embodiments, R$^{2.1}$ is independently —CF$_3$. In embodiments, R$^{2.1}$ is independently —CI$_3$. In embodiments, R$^{2.1}$ is independently —CHCl$_2$. In embodiments, R$^{2.1}$ is independently —CHBr$_2$. In embodiments, R$^{2.1}$ is independently —CHF$_2$. In embodiments, R$^{2.1}$ is independently —CHI$_2$. In embodiments, R$^{2.1}$ is independently —CH$_2$Cl. In embodiments, R$^{2.1}$ is independently —CH$_2$Br. In embodiments, R$^{2.1}$ is independently —CH$_2$F. In embodiments, R$^{2.1}$ is independently —CH$_2$I. In embodiments, R$^{2.1}$ is independently —CH$_2$OH. In embodiments, R$^{2.1}$ is independently —CH$_2$NH$_2$. In embodiments, R$^{2.1}$ is independently —CH$_2$NH(CH$_3$). In embodiments, R$^{2.1}$ is independently —CH$_2$N(CH$_3$)$_2$. In embodiments, R$^{2.1}$ is independently —CN. In embodiments, R$^{2.1}$ is independently —SO$_2$Me. In embodiments, R$^{2.1}$ is independently —SO$_2$Et. In embodiments, R$^{2.1}$ is independently —SO$_2$NH$_2$. In embodiments, R$^{2.1}$ is independently —OH. In embodiments, R$^{2.1}$ is independently —OCH$_3$. In embodiments, R$^{2.1}$ is independently —NH$_2$. In embodiments, R$^{2.1}$ is independently —NHC(O)CH$_3$. In embodiments, R$^{2.1}$ is independently —COOH. In embodiments, R$^{2.1}$ is independently —COCH$_3$. In embodiments, R$^{2.1}$ is independently —CONH$_2$. In embodiments, R$^{2.1}$ is independently —OCCl$_3$. In embodiments, R$^{2.1}$ is independently —OCF$_3$. In embodiments, R$^{2.1}$ is independently —OCBr$_3$. In embodiments, R$^{2.1}$ is independently —OCI$_3$. In embodiments, R$^{2.1}$ is independently —OCHCl$_2$. In embodiments, R$^{2.1}$ is independently —OCHBr$_2$. In embodiments, R$^{2.1}$ is independently —OCHI$_2$. In embodiments, R$^{2.1}$ is independently —OCHF$_2$. In embodiments, R$^{2.1}$ is independently —OCH$_2$Cl. In embodiments, R$^{2.1}$ is independently —OCH$_2$Br. In embodiments, R$^{2.1}$ is independently —OCH$_2$I. In embodiments, R$^{2.1}$ is independently —OCH$_2$F. In embodiments, R$^{2.1}$ is substituted or unsubstituted alkyl. In embodiments, R$^{2.1}$ is substituted or unsubstituted C$_1$-C$_6$ alkyl. In embodiments, R$^{2.1}$ is substituted or unsubstituted methyl. In embodiments, R$^{2.1}$ is substituted or unsubstituted ethyl. In embodiments, R$^{2.1}$ is substituted or unsubstituted propyl. In embodiments, R$^{2.1}$ is unsubstituted alkyl. In embodiments, R$^{2.1}$ is unsubstituted C$_1$-C$_6$ alkyl. In embodiments, R$^{2.1}$ is unsubstituted methyl. In embodiments, R$^{2.1}$ is unsubstituted ethyl. In embodiments, R$^{2.1}$ is unsubstituted propyl. In embodiments, R$^{2.1}$ is independently piperazinyl. In embodiments, R$^{2.1}$ is independently 4-methylpiperazin-1-yl. In embodiments, R$^{2.1}$ is independently morpholinyl. In embodiments, R$^{2.1}$ is independently 4-morpholinyl.

In embodiments, R$^{2.2}$ is independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CH$_2$OH, —CH$_2$NH$_2$, —CH$_2$NH(CH$_3$), —CH$_2$N(CH$_3$)$_2$, —CN, —SO$_2$Me, —SO$_2$Et, —SO$_2$NH$_2$, —OH, —OCH$_3$, —NH$_2$, —NHC(O)CH$_3$, —COOH, —COCH$_3$, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^{2.2}$ is independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CH$_2$OH, —CH$_2$NH$_2$, —CH$_2$NH(CH$_3$), —CH$_2$N(CH$_3$)$_2$, —CN, —SO$_2$Me, —SO$_2$Et, —SO$_2$NH$_2$, —OH, —OCH$_3$, —NH$_2$, —NHC(O)CH$_3$, —COOH, —COCH$_3$, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, or —OCH$_2$F. In embodiments, R$^{2.2}$ is independently hydrogen. In embodiments, R$^{2.2}$ is independently —F. In embodiments, R$^{2.2}$ is independently —C$_1$. In embodiments, R$^{2.2}$ is independently —Br. In embodiments, R$^{2.2}$ is independently —I. In embodiments, R$^{2.2}$ is independently —CCl$_3$. In embodiments, R$^{2.2}$ is independently —CBr$_3$. In embodiments, R$^{2.2}$ is independently —CF$_3$. In embodiments, R$^{2.2}$ is independently —CI$_3$. In embodiments, R$^{2.2}$ is independently —CHCl$_2$. In embodiments, R$^{2.2}$ is independently —CHBr$_2$. In embodiments, $R^{2.2}$ is independently —CHF$_2$. In embodiments, $R^{2.2}$ is independently —CHI$_2$. In embodiments, $R^{2.2}$ is independently —CH$_2$Cl. In embodiments, $R^{2.2}$ is independently —CH$_2$Br. In embodiments, $R^{2.2}$ is independently —CH$_2$F. In embodiments, $R^{2.2}$ is independently —CH$_2$I. In embodiments, $R^{2.2}$ is independently —CH$_2$OH. In embodiments, $R^{2.2}$ is independently —CH$_2$NH$_2$. In embodiments, $R^{2.2}$ is independently —CH$_2$NH(CH$_3$). In embodiments, $R^{2.2}$ is independently —CH$_2$N(CH$_3$)$_2$. In embodiments, $R^{2.2}$ is independently —CN. In embodiments, $R^{2.2}$ is independently —SO$_2$Me. In embodiments, $R^{2.2}$ is independently —SO$_2$Et. In embodiments, $R^{2.2}$ is independently —SO$_2$NH$_2$. In embodiments, $R^{2.2}$ is independently —OH. In embodiments, $R^{2.2}$ is independently —OCH$_3$. In embodiments, $R^{2.2}$ is independently —NH$_2$. In embodiments, $R^{2.2}$ is independently —NHC(O)CH$_3$. In embodiments, $R^{2.2}$ is independently —COOH. In embodiments, $R^{2.2}$ is independently —COCH$_3$. In embodiments, $R^{2.2}$ is independently —CONH$_2$. In embodiments, $R^{2.2}$ is independently —OCCl$_3$. In embodiments, $R^{2.2}$ is independently —OCF$_3$. In embodiments, $R^{2.2}$ is independently —OCBr$_3$. In embodiments, $R^{2.2}$ is independently —OCI$_3$. In embodiments, $R^{2.2}$ is independently —OCHCl$_2$. In embodiments, $R^{2.2}$ is independently —OCHBr$_2$. In embodiments, $R^{2.2}$ is independently —OCHI$_2$. In embodiments, $R^{2.2}$ is independently —OCHF$_2$. In embodiments, $R^{2.2}$ is independently —OCH$_2$Cl. In embodiments, $R^{2.2}$ is independently —OCH$_2$Br. In embodiments, $R^{2.2}$ is independently —OCH$_2$I. In embodiments, $R^{2.2}$ is independently —OCH$_2$F. In embodiments, $R^{2.2}$ is substituted or unsubstituted alkyl. In embodiments, $R^{2.2}$ is substituted or unsubstituted $C_1$-$C_6$ alkyl. In embodiments, $R^{2.2}$ is substituted or unsubstituted methyl. In embodiments, $R^{2.2}$ is substituted or unsubstituted ethyl. In embodiments, $R^{2.2}$ is substituted or unsubstituted propyl. In embodiments, $R^{2.2}$ is unsubstituted alkyl. In embodiments, $R^{2.2}$ is unsubstituted $C_1$-$C_6$ alkyl. In embodiments, $R^{2.2}$ is unsubstituted methyl. In embodiments, $R^{2.2}$ is unsubstituted ethyl. In embodiments, $R^{2.2}$ is unsubstituted propyl. In embodiments, $R^{2.2}$ is independently piperazinyl. In embodiments, $R^{2.2}$ is independently 4-methylpiperazin-1-yl. In embodiments, $R^{2.2}$ is independently morpholinyl. In embodiments, $R^{2.2}$ is independently 4-morpholinyl.

In embodiments, $R^{2.3}$ is independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CH$_2$OH, —CH$_2$NH$_2$, —CH$_2$NH(CH$_3$), —CH$_2$N(CH$_3$)$_2$, —CN, —SO$_2$Me, —SO$_2$Et, —SO$_2$NH$_2$, —OH, —OCH$_3$, —NH2, —NHC(O)CH$_3$, —COOH, —COCH$_3$, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$C, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{2.3}$ is independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CH$_2$OH, —CH$_2$NH$_2$, —CH$_2$NH(CH$_3$), —CH$_2$N(CH$_3$)$_2$, —CN, —SO$_2$Me, —SO$_2$Et, —SO$_2$NH$_2$, —OH, —OCH$_3$, —NH$_2$, —NHC(O) CH$_3$, —COOH, —COCH$_3$, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, or —OCH$_2$F. In embodiments, $R^{2.3}$ is independently hydrogen. In embodiments, $R^{2.3}$ is independently —F. In embodiments, $R^{2.3}$ is independently —Cl. In embodiments, $R^{2.3}$ is independently —Br. In embodiments, $R^{2.3}$ is independently —I. In embodiments, $R^{2.3}$ is independently —CCl$_3$. In embodiments, $R^{2.3}$ is independently —CBr$_3$. In embodiments, $R^{2.3}$ is independently —CF$_3$. In embodiments, $R^{2.3}$ is independently —CI$_3$. In embodiments, $R^{2.3}$ is independently —CHCl$_2$. In embodiments, $R^{2.3}$ is independently —CHBr$_2$. In embodiments, $R^{2.3}$ is independently —CHF$_2$. In embodiments, $R^{2.3}$ is independently —CHI$_2$. In embodiments, $R^{2.3}$ is independently —CH$_2$Cl. In embodiments, $R^{2.3}$ is independently —CH$_2$Br. In embodiments, $R^{2.3}$ is independently —CH$_2$F. In embodiments, $R^{2.3}$ is independently —CH$_2$I. In embodiments, $R^{2.3}$ is independently —CH$_2$OH. In embodiments, $R^{2.3}$ is independently —CH$_2$NH$_2$. In embodiments, $R^{2.3}$ is independently —CH$_2$NH(CH$_3$). In embodiments, $R^{2.3}$ is independently —CH$_2$N(CH$_3$)$_2$. In embodiments, $R^{2.3}$ is independently —CN. In embodiments, $R^{2.3}$ is independently —SO$_2$Me. In embodiments, $R^{2.3}$ is independently —SO$_2$Et. In embodiments, $R^{2.3}$ is independently —SO$_2$NH$_2$. In embodiments, $R^{2.3}$ is independently —OH. In embodiments, $R^{2.3}$ is independently —OCH$_3$. In embodiments, $R^{2.3}$ is independently —NH$_2$. In embodiments, $R^{2.3}$ is independently —NHC(O)CH$_3$. In embodiments, $R^{2.3}$ is independently —COOH. In embodiments, $R^{2.3}$ is independently —COCH$_3$. In embodiments, $R^{2.3}$ is independently —CONH$_2$. In embodiments, $R^{2.3}$ is independently —OCCl$_3$. In embodiments, $R^{2.3}$ is independently —OCF$_3$. In embodiments, $R^{2.3}$ is independently —OCBr$_3$. In embodiments, $R^{2.3}$ is independently —OCI$_3$. In embodiments, $R^{2.3}$ is independently —OCHCl$_2$. In embodiments, $R^{2.3}$ is independently —OCHBr$_2$. In embodiments, $R^{2.3}$ is independently —OCHI$_2$. In embodiments, $R^{2.3}$ is independently —OCHF$_2$. In embodiments, $R^{2.3}$ is independently —OCH$_2$Cl. In embodiments, $R^{2.3}$ is independently —OCH$_2$Br. In embodiments, $R^{2.3}$ is independently —OCH$_2$I. In embodiments, $R^{2.3}$ is independently —OCH$_2$F. In embodiments, $R^{2.3}$ is substituted or unsubstituted alkyl. In embodiments, $R^{2.3}$ is substituted or unsubstituted $C_1$-$C_6$ alkyl. In embodiments, $R^{2.3}$ is substituted or unsubstituted methyl. In embodiments, $R^{2.3}$ is substituted or unsubstituted ethyl. In embodiments, $R^{2.3}$ is substituted or unsubstituted propyl. In embodiments, $R^{2.3}$ is unsubstituted alkyl. In embodiments, $R^{2.3}$ is unsubstituted $C_1$-$C_6$ alkyl. In embodiments, $R^{2.3}$ is unsubstituted methyl. In embodiments, $R^{2.3}$ is unsubstituted ethyl. In embodiments, $R^{2.3}$ is unsubstituted propyl. In embodiments, $R^{2.3}$ is independently piperazinyl. In embodiments, $R^{2.3}$ is independently 4-methylpiperazin-1-yl. In embodiments, $R^{2.3}$ is independently morpholinyl. In embodiments, $R^{2.3}$ is independently 4-morpholinyl.

In embodiments, $R^{2.4}$ is independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CH$_2$OH, —CH$_2$NH$_2$, —CH$_2$NH(CH$_3$), —CH$_2$N(CH$_3$)$_2$, —CN, —SO$_2$Me, —SO$_2$Et, —SO$_2$NH$_2$, —OH, —OCH$_3$, —NH$_2$, —NHC(O)CH$_3$, —COOH, —COCH$_3$, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$C, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, $R^{2.4}$ is independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CH$_2$OH, —CH$_2$NH$_2$, —CH$_2$NH(CH$_3$), —CH$_2$N(CH$_3$)$_2$, —CN, —SO$_2$Me, —SO$_2$Et, —SO$_2$NH$_2$, —OH, —OCH$_3$, —NH$_2$, —NHC(O) CH$_3$, —COOH, —COCH$_3$, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, or —OCH$_2$F. In embodiments, R$^{2.4}$ is independently hydrogen. In embodiments, R$^{2.4}$ is independently —F. In embodiments, R$^{2.4}$ is independently —Cl. In embodiments, R$^{2.4}$ is independently —Br. In embodiments, R$^{2.4}$ is independently —I. In embodiments, R$^{2.4}$ is independently —CCl$_3$. In embodiments, R$^{2.4}$ is independently —CBr$_3$. In embodiments, R$^{2.4}$ is independently —CF$_3$. In embodiments, R$^{2.4}$ is independently-CI$_3$. In embodiments, R$^{2.4}$ is independently —CHCl$_2$. In embodiments, R$^{2.4}$ is independently —CHBr$_2$. In embodiments, R$^{2.4}$ is independently —CHF$_2$. In embodiments, R$^{2.4}$ is independently —CHI$_2$. In embodiments, R$^{2.4}$ is independently —CH$_2$Cl. In embodiments, R$^{2.4}$ is independently —CH$_2$Br. In embodiments, R$^{2.4}$ is independently —CH$_2$F. In embodiments, R$^{2.4}$ is independently —CH$_2$I. In embodiments, R$^{2.4}$ is independently —CH$_2$OH. In embodiments, R$^{2.4}$ is independently —CH$_2$NH$_2$. In embodiments, R$^{2.4}$ is independently —CH$_2$NH(CH$_3$). In embodiments, R$^{2.4}$ is independently —CH$_2$N(CH$_3$)$_2$. In embodiments, R$^{2.4}$ is independently —CN. In embodiments, R$^{2.4}$ is independently —SO$_2$Me. In embodiments, R$^{2.4}$ is independently —SO$_2$Et. In embodiments, R$^{2.4}$ is independently —SO$_2$NH$_2$. In embodiments, R$^{2.4}$ is independently —OH. In embodiments, R$^{2.4}$ is independently —OCH$_3$. In embodiments, R$^{2.4}$ is independently —NH$_2$. In embodiments, R$^{2.4}$ is independently —NHC(O)CH$_3$. In embodiments, R$^{2.4}$ is independently —COOH. In embodiments, R$^{2.4}$ is independently —COCH$_3$. In embodiments, R$^{2.4}$ is independently —CONH$_2$. In embodiments, R$^{2.4}$ is independently —OCCl$_3$. In embodiments, R$^{2.4}$ is independently —OCF$_3$. In embodiments, R$^{2.4}$ is independently —OCBr$_3$. In embodiments, R$^{2.4}$ is independently —OCI$_3$. In embodiments, R$^{2.4}$ is independently —OCHCl$_2$. In embodiments, R$^{2.4}$ is independently —OCHBr$_2$. In embodiments, R$^{2.4}$ is independently —OCHI$_2$. In embodiments, R$^{2.4}$ is independently —OCHF$_2$. In embodiments, R$^{2.4}$ is independently —OCH$_2$Cl. In embodiments, R$^{2.4}$ is independently —OCH$_2$Br. In embodiments, R$^{2.4}$ is independently —OCH$_2$I. In embodiments, R$^{2.4}$ is independently —OCH$_2$F. In embodiments, R$^{2.4}$ is substituted or unsubstituted alkyl. In embodiments, R$^{2.4}$ is substituted or unsubstituted C$_1$-C$_6$ alkyl. In embodiments, R$^{2.4}$ is substituted or unsubstituted methyl. In embodiments, R$^{2.4}$ is substituted or unsubstituted ethyl. In embodiments, R$^{2.4}$ is substituted or unsubstituted propyl. In embodiments, R$^{2.4}$ is unsubstituted alkyl. In embodiments, R$^{2.4}$ is unsubstituted C$_1$-C$_6$ alkyl. In embodiments, R$^{2.4}$ is unsubstituted methyl. In embodiments, R$^{2.4}$ is unsubstituted ethyl. In embodiments, R$^{2.4}$ is unsubstituted propyl. In embodiments, R$^{2.4}$ is independently piperazinyl. In embodiments, R$^{2.4}$ is independently 4-methylpiperazin-1-yl. In embodiments, R$^{2.4}$ is independently morpholinyl. In embodiments, R$^{2.4}$ is independently 4-morpholinyl.

In embodiments, R$^{2.5}$ is independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CH$_2$OH, —CH$_2$NH$_2$, —CH$_2$NH(CH$_3$), —CH$_2$N(CH$_3$)$_2$, —CN, —SO$_2$Me, —SO$_2$Et, —SO$_2$NH$_2$, —OH, —OCH$_3$, —NH$_2$, —NHC(O)CH$_3$, —COOH, —COCH$_3$, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In embodiments, R$^{2.5}$ is independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CH$_2$OH, —CH$_2$NH$_2$, —CH$_2$NH(CH$_3$), —CH$_2$N(CH$_3$)$_2$, —CN, —SO$_2$Me, —SO$_2$Et, —SO$_2$NH$_2$, —OH, —OCH$_3$, —NH$_2$, —NHC(O)CH$_3$, —COOH, —COCH$_3$, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, or —OCH$_2$F. In embodiments, R$^{2.5}$ is independently hydrogen. In embodiments, R$^{2.5}$ is independently —F. In embodiments, R$^{2.5}$ is independently —Cl. In embodiments, R$^{2.5}$ is independently —Br. In embodiments, R$^{2.5}$ is independently —I. In embodiments, R$^{2.5}$ is independently —CCl$_3$. In embodiments, R$^{2.5}$ is independently —CBr$_3$. In embodiments, R$^{2.5}$ is independently —CF$_3$. In embodiments, R$^{2.5}$ is independently —CI$_3$. In embodiments, R$^{2.5}$ is independently —CHCl$_2$. In embodiments, R$^{2.5}$ is independently —CHBr$_2$. In embodiments, R$^{2.5}$ is independently —CHF$_2$. In embodiments, R$^{2.5}$ is independently —CHI$_2$. In embodiments, R$^{2.5}$ is independently —CH$_2$Cl. In embodiments, R$^{2.5}$ is independently —CH$_2$Br. In embodiments, R$^{2.5}$ is independently —CH$_2$F. In embodiments, R$^{2.5}$ is independently —CH$_2$I. In embodiments, R$^{2.5}$ is independently —CH$_2$OH. In embodiments, R$^{2.5}$ is independently —CH$_2$NH$_2$. In embodiments, R$^{2.5}$ is independently —CH$_2$NH(CH$_3$). In embodiments, R$^{2.5}$ is independently —CH$_2$N(CH$_3$)$_2$. In embodiments, R$^{2.5}$ is independently —CN. In embodiments, R$^{2.5}$ is independently —SO$_2$Me. In embodiments, R$^{2.5}$ is independently —SO$_2$Et. In embodiments, R$^{2.5}$ is independently —SO$_2$NH$_2$. In embodiments, R$^{2.5}$ is independently —OH. In embodiments, R$^{2.5}$ is independently —OCH$_3$. In embodiments, R$^{2.5}$ is independently —NH$_2$. In embodiments, R$^{2.5}$ is independently —NHC(O)CH$_3$. In embodiments, R$^{2.5}$ is independently —COOH. In embodiments, R$^{2.5}$ is independently —COCH$_3$. In embodiments, R$^{2.5}$ is independently —CONH$_2$. In embodiments, R$^{2.5}$ is independently —OCCl$_3$. In embodiments, R$^{2.5}$ is independently —OCF$_3$. In embodiments, R$^{2.5}$ is independently —OCBr$_3$. In embodiments, R$^{2.5}$ is independently —OCI$_3$. In embodiments, R$^{2.5}$ is independently —OCHCl$_2$. In embodiments, R$^{2.5}$ is independently —OCHBr$_2$. In embodiments, R$^{2.5}$ is independently —OCHI$_2$. In embodiments, R$^{2.5}$ is independently —OCHF$_2$. In embodiments, R$^{2.5}$ is independently —OCH$_2$Cl. In embodiments, R$^{2.5}$ is independently —OCH$_2$Br. In embodiments, R$^{2.5}$ is independently —OCH$_2$I. In embodiments, R$^{2.5}$ is independently —OCH$_2$F. In embodiments, R$^{2.5}$ is substituted or unsubstituted alkyl. In embodiments, R$^{2.5}$ is substituted or unsubstituted C$_1$-C$_6$ alkyl. In embodiments, R$^{2.5}$ is substituted or unsubstituted methyl. In embodiments, R$^{2.5}$ is substituted or unsubstituted ethyl. In embodiments, R$^{2.5}$ is substituted or unsubstituted propyl. In embodiments, R$^{2.5}$ is unsubstituted alkyl. In embodiments, R$^{2.5}$ is unsubstituted C$_1$-C$_6$ alkyl. In embodiments, R$^{2.5}$ is unsubstituted methyl. In embodiments, R$^{2.5}$ is unsubstituted ethyl. In embodiments, R$^{2.5}$ is unsubstituted propyl. In embodiments, R$^{2.5}$ is independently piperazinyl. In embodiments, R$^{2.5}$ is independently 4-methylpiperazin-1-yl. In embodiments, R$^{2.5}$ is independently morpholinyl. In embodiments, R$^{2.5}$ is independently 4-morpholinyl.

In embodiments, R$^{2.1}$ is hydrogen. In embodiments, R$^{2.2}$ is hydrogen. In embodiments, R$^{2.3}$ is substituted or unsubstituted C$_1$-C$_6$ alkyl. In embodiments, R$^{2.4}$ is hydrogen. In embodiments, R$^{2.5}$ is hydrogen. In embodiments, R$^{2.3}$ is unsubstituted methyl and R$^{2.1}$, R$^{2.2}$, R$^{2.4}$, and R$^{2.5}$ are hydrogen. In embodiments, R$^{2.3}$ is —SO$_2$Me and R$^{2.1}$, R$^{2.2}$, R$^{2.4}$, and R$^{2.5}$ are hydrogen. In embodiments, R$^{23}$ is —CH$_2$N(CH$_3$)$_2$ and R$^{2.1}$, R$^{2.2}$, R$^{2.4}$, and R$^{2.5}$ are hydrogen. In embodiments, R$^{23}$ is —CONH$_2$ and R$^{2.1}$, R$^{2.2}$, R$^{2.4}$, and R$^{2.5}$ are hydrogen. In embodiments, R$^{2.3}$ is —NH$_2$ and R$^{2.1}$, R$^{2.2}$, $R^{2.4}$, and $R^{2.5}$ are hydrogen. In embodiments, $R^{2.3}$ is —NHC(O)CH$_3$ and $R^{2.1}$, $R^{2.2}$, $R^{2.4}$, and $R^{2.5}$ are hydrogen. In embodiments, $R^{2.3}$ is 4-methylpiperazin-1-yl and $R^{2.1}$, $R^{2.2}$, $R^{2.4}$, and $R^{2.5}$ are hydrogen. In embodiments, $R^{2.3}$ is —CH$_2$OH and $R^{2.1}$, $R^{2.2}$, $R^{2.4}$, and $R^{2.5}$ are hydrogen. In embodiments, $R^{2.2}$ is —NH$_2$ and $R^{2.1}$, $R^{2.3}$, $R^{2.4}$, and $R^{2.5}$ are hydrogen. In embodiments, $R^{2.3}$ is —SO$_2$NH$_2$ and $R^{2.1}$, $R^{2.2}$, $R^{2.4}$, and $R^{2.5}$ are hydrogen. In embodiments, $R^{2.1}$ is —CN, $R^{2.4}$ is —F and $R^{2.2}$, $R^{2.3}$, and $R^{2.5}$ are hydrogen. In embodiments, $R^{2.3}$ is —NH$_2$ and $R^{2.1}$, $R^{2.2}$, $R^{2.4}$, and $R^{2.5}$ are hydrogen. In embodiments, $R^{2.2}$ is —SO$_2$Et and $R^{2.1}$, $R^{2.3}$, $R^{2.4}$, and $R^{2.5}$ are hydrogen. In embodiments, $R^{2.1}$ is —F and $R^{2.2}$, $R^{2.3}$, $R^{2.4}$, and $R^{2.5}$ are hydrogen. In embodiments, $R^{2.1}$ is —F, $R^{2.5}$ is —F, $R^{2.3}$ is —OCH$_3$, and $R^{2.2}$ and $R^{2.4}$ are hydrogen. In embodiments, $R^{2.2}$ is 4-morpholinyl and $R^{2.1}$, $R^{2.3}$, $R^{2.4}$, and $R^{2.5}$ are hydrogen. In embodiments, $R^{2.2}$ is —F, $R^{2.3}$ is —CH$_3$ and $R^{2.1}$, $R^{2.4}$, and $R^{2.5}$ are hydrogen. In embodiments, $R^{2.3}$ is —Cl and $R^{2.1}$, $R^{2.2}$, $R^{2.4}$, and $R^{2.5}$ are hydrogen. In embodiments, $R^{2.3}$ is —OCF$_3$ and $R^{2.1}$, $R^{2.2}$, $R^{2.4}$, and $R^{2.5}$ are hydrogen. In embodiments, $R^{2.1}$ is —Cl, $R^{2.4}$ is —F, and $R^{2.2}$, $R^{2.3}$, and $R^{2.5}$ are hydrogen. In embodiments, $R^{2.1}$ is —CH$_3$, $R^{2.3}$ is —CH$_3$, and $R^{2.2}$, $R^{2.4}$, and $R^{2.5}$ are hydrogen. In embodiments, $R^{2.3}$ is —CF$_3$ and $R^{2.1}$, $R^{2.2}$, $R^{2.4}$, and $R^{2.5}$ are hydrogen. In embodiments, $R^{2.2}$ is —OH, $R^{2.3}$ is —CH$_3$, and $R^{2.1}$, $R^{2.4}$, and $R^{2.5}$ are hydrogen. In embodiments, $R^{2.2}$ is —CONH$_2$, $R^{2.3}$ is —CH$_3$, and $R^{2.1}$, $R^{2.4}$, and $R^{2.5}$ are hydrogen.

In embodiments, the compound has the formula:

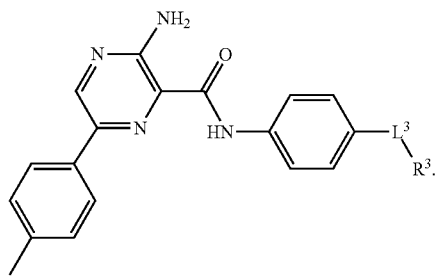

(Ib)

$R^3$ and $L^3$ are as described herein, including in embodiments.

In embodiments, the compound has the formula:

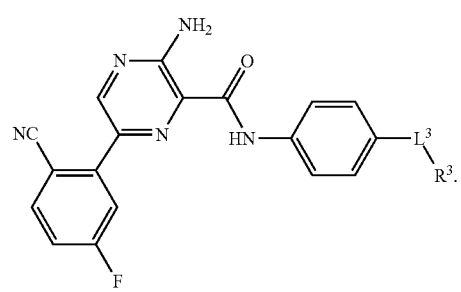

(Ib)

$R^3$ and $L^3$ are as described herein, including in embodiments.

In embodiments, the compound has the formula:

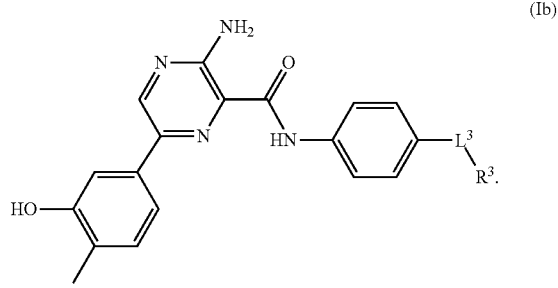

(Ib)

$R^3$ and $L^3$ are as described herein, including in embodiments.

In embodiments, the compound has the formula:

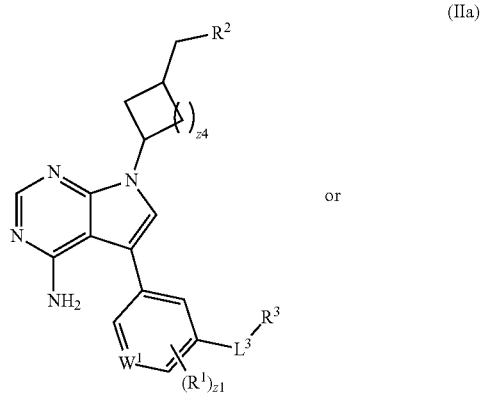

(IIa)

or

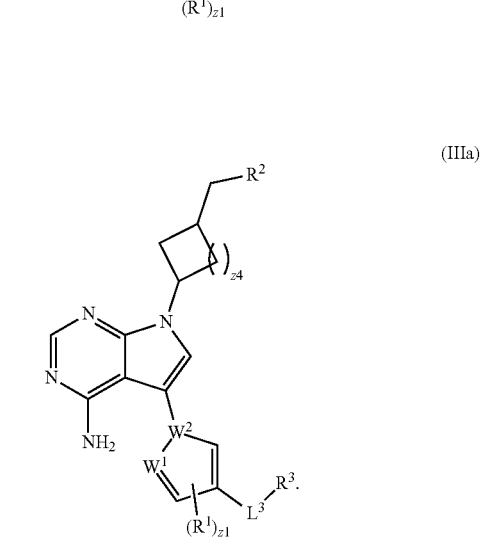

(IIIa)

$R^1$, $R^2$, $R^3$, $W^1$, $W^2$, $L^3$, z1 and z4 are as described herein, including embodiments. In embodiments, the compound has the formula:

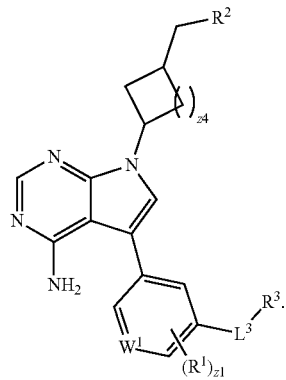

(IIa)

$R^1$, $R^2$, $R^3$, $W^1$, $L^3$, z1 and z4 are as described herein, including embodiments. In embodiments, the compound has the formula:

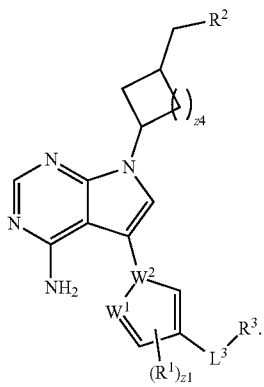

(IIIa)

$R^1$, $R^2$, $R^3$, $W^1$, $W^2$, $L^3$, z1 and z4 are as described herein, including embodiments.

In embodiments, the compound has the formula:

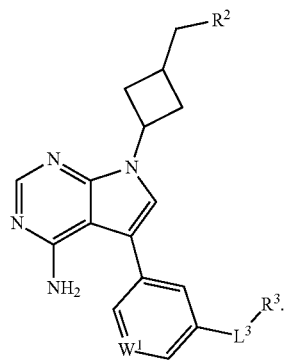

(IIb)

$W^1$, $L^3$, and $R^3$ are as described herein, including embodiments. $R^2$ is independently —$NR^{2A}R^{2B}$ or —OH; $R^{2A}$ and $R^{2B}$ are independently hydrogen or $R^{20}$-substituted or unsubstituted $C_1$-$C_6$ alkyl; or $R^{2A}$ and $R^{2B}$ substituents bonded to the same nitrogen atom may optionally be joined to form an $R^{20}$-substituted or unsubstituted 4 to 7 membered heterocycloalkyl.

In embodiments, the compound has the formula:

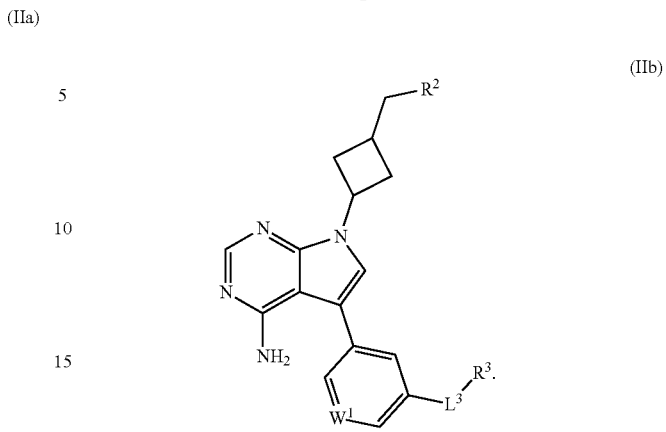

(IIb)

$W^1$, $L^3$, and $R^3$ are as described herein, including embodiments. $R^2$ is independently —$NR^{2A}R^{2B}$ or —OH; $R^{2A}$ and $R^{2B}$ are independently hydrogen or $R^{20}$-substituted or unsubstituted $C_1$-$C_6$ alkyl; or $R^{2A}$ and $R^{2B}$ substituents bonded to the same nitrogen atom may optionally be joined to form an $R^{20}$-substituted or unsubstituted 4 to 7 membered heterocycloalkyl; and $R^{20}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, the compound has the formula:

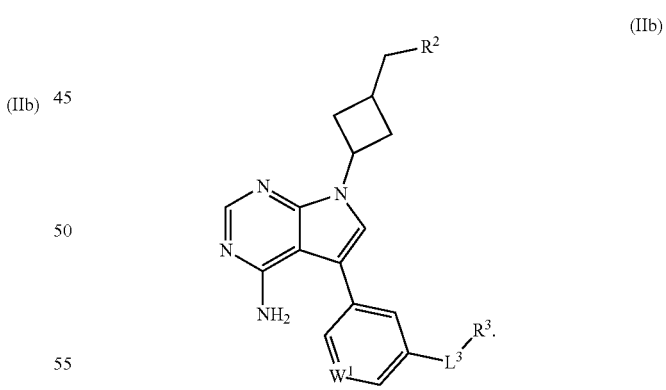

(IIb)

$R^2$, $R^3$, $W^1$, and $L^3$ are as described herein, including embodiments.

In embodiments, $R^2$ is independently —$NR^{2A}R^{2B}$ or —OH.

In embodiments, $R^{2A}$ and $R^{2B}$ substituents bonded to the same nitrogen atom are joined to form a substituted or unsubstituted heterocycloalkyl. In embodiments, $R^{2A}$ and $R^{2B}$ substituents bonded to the same nitrogen atom are joined to form a substituted or unsubstituted heteroaryl. In embodiments, $R^{2A}$ and $R^{2B}$ substituents bonded to the same nitrogen atom are joined to form a substituted or unsubstituted 4 to 7 membered heterocycloalkyl. In embodiments, $R^{2A}$ and $R^{2B}$ substituents bonded to the same nitrogen atom are joined to form a substituted or unsubstituted 5 to 6 membered heteroaryl.

In embodiments, $R^{2A}$ and $R^{2B}$ are independently hydrogen or $R^{20}$-substituted or unsubstituted $C_1$-$C_6$ alkyl; or $R^{2A}$ and $R^{2B}$ substituents bonded to the same nitrogen atom may optionally be joined to form an $R^{20}$-substituted or unsubstituted 4 to 7 membered heterocycloalkyl.

In embodiments, $R^{20}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, or —N$_3$. In embodiments, $R^{20}$ is independently unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl. In embodiments, $R^{20}$ is independently halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, unsubstituted $C_1$-$C_6$ alkyl, or unsubstituted 2 to 6 membered heteroalkyl.

In embodiments, $R^{20}$ is independently oxo. In embodiments, $R^{20}$ is independently halogen. In embodiments, $R^{20}$ is independently —F. In embodiments, $R^{20}$ is independently —Cl. In embodiments, $R^{20}$ is independently —Br. In embodiments, $R^{20}$ is independently —I. In embodiments, $R^{20}$ is independently —CCl$_3$. In embodiments, $R^{20}$ is independently —CBr$_3$. In embodiments, $R^{20}$ is independently —CF$_3$. In embodiments, $R^{20}$ is independently —CI$_3$. In embodiments, $R^{20}$ is independently CHCl$_2$. In embodiments, $R^{20}$ is independently —CHBr$_2$. In embodiments, $R^{20}$ is independently —CHF$_2$. In embodiments, $R^{20}$ is independently —CHI$_2$. In embodiments, $R^{20}$ is independently —CH$_2$Cl. In embodiments, $R^{20}$ is independently —CH$_2$Br. In embodiments, $R^{20}$ is independently —CH$_2$F. In embodiments, $R^{20}$ is independently —CH$_2$I. In embodiments, $R^{20}$ is independently —CN. In embodiments, $R^{20}$ is independently —OH. In embodiments, $R^{20}$ is independently —NH$_2$. In embodiments, $R^{20}$ is independently —COOH. In embodiments, $R^{20}$ is independently —CONH$_2$. In embodiments, $R^{20}$ is independently —NO$_2$. In embodiments, $R^{20}$ is independently —SH. In embodiments, $R^{20}$ is independently —SO$_3$H. In embodiments, $R^{20}$ is independently —SO$_4$H. In embodiments, $R^{20}$ is independently —SO$_2$NH$_2$. In embodiments, $R^{20}$ is independently —NHNH$_2$. In embodiments, $R^{20}$ is independently —ONH$_2$. In embodiments, $R^{20}$ is independently —NHC(O)NHNH$_2$. In embodiments, $R^{20}$ is independently —NHC(O)NH$_2$. In embodiments, $R^{20}$ is independently —NHSO$_2$H. In embodiments, $R^{20}$ is independently —NHC(O)H. In embodiments, $R^{20}$ is independently —NHC(O)OH. In embodiments, $R^{20}$ is independently —NHOH. In embodiments, $R^{20}$ is independently —OCCl$_3$. In embodiments, $R^{20}$ is independently —OCF$_3$. In embodiments, $R^{20}$ is independently —OCBr$_3$. In embodiments, $R^{20}$ is independently —OCI$_3$. In embodiments, $R^{20}$ is independently —OCHCl$_2$. In embodiments, $R^{20}$ is independently —OCHBr$_2$. In embodiments, $R^{20}$ is independently —OCHI$_2$. In embodiments, $R^{20}$ is independently —OCHF$_2$. In embodiments, $R^{20}$ is independently —OCH$_2$Cl, —OCH$_2$Br, —OCH$_2$I, —OCH$_2$F, —N$_3$. In embodiments, $R^{20}$ is independently unsubstituted $C_1$-$C_6$ alkyl. In embodiments, $R^{20}$ is independently unsubstituted methyl. In embodiments, $R^{20}$ is independently ethyl. In embodiments, $R^{20}$ is independently propyl. In embodiments, $R^{20}$ is independently unsubstituted 2 to 6 membered heteroalkyl. In embodiments, $R^{20}$ is independently unsubstituted $C_3$-$C_6$ cycloalkyl. In embodiments, $R^{20}$ is independently unsubstituted 3 to 6 membered heterocycloalkyl. In embodiments, $R^{20}$ is independently unsubstituted phenyl. In embodiments, $R^{20}$ is independently unsubstituted 5 to 6 membered heteroaryl.

In embodiments, the compound has the formula:

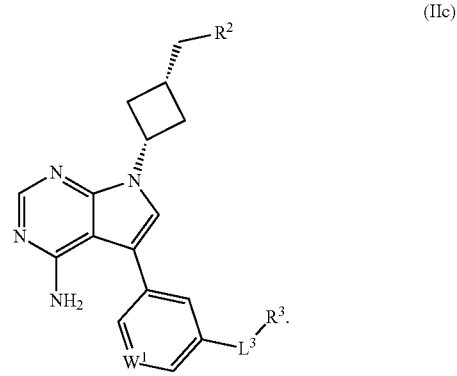

(IIc)

$R^2$, $R^3$, $W^1$, and $L^3$ are as described herein, including embodiments. In embodiments, the compound has the formula:

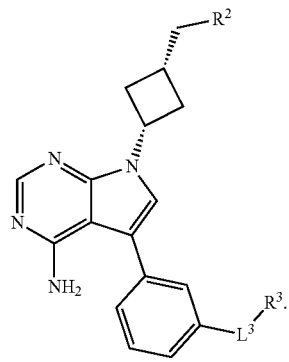

$R^2$, $R^3$, and $L^3$ are as described herein, including embodiments.

In embodiments, the compound has the formula:

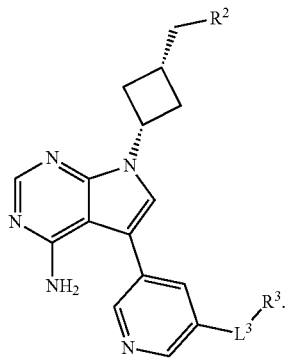

$R^2$, $R^3$, and $L^3$ are as described herein, including embodiments.

In embodiments, the compound has the formula:

(IIIb)

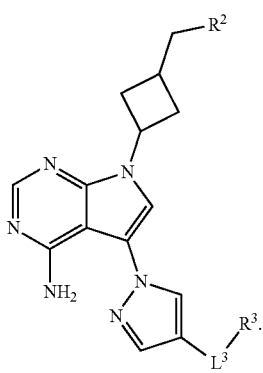

$L^3$ and $R^3$ are as described herein, including embodiments. $R^2$ is independently —$NR^{2A}R^{2B}$; $R^{2A}$ and $R^{2B}$ are independently hydrogen or $R^{20}$-substituted or unsubstituted $C_1$-$C_6$ alkyl; or $R^{2A}$ and $R^{2B}$ substituents bonded to the same nitrogen atom may optionally be joined to form an $R^{20}$-substituted or unsubstituted 4 to 7 membered heterocycloalkyl; and $R^{20}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, the compound has the formula:

(IIIc)

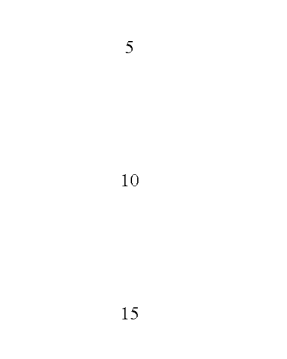

$R^2$, $R^3$, and $L^3$ are as described herein, including embodiments.

In embodiments, $R^{2A}$ and $R^{2B}$ substituents bonded to the same nitrogen atom are joined to form an $R^{20}$-substituted or unsubstituted 4 to 7 membered heterocycloalkyl; and $R^{20}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCl_3$, —$OCHCl_2$, —$OCHBr_2$, —$OCHI_2$, —$OCHF_2$, —$OCH_2C$, —$OCH_2Br$, —$OCH_2I$, —$OCH_2F$, —$N_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

In embodiments, $R^{2A}$ and $R^{2B}$ substituents bonded to the same nitrogen atom are joined to form an $R^{20}$-substituted or unsubstituted 4 to 7 membered heterocycloalkyl. In embodiments, $R^{2A}$ and $R^{2B}$ substituents bonded to the same nitrogen atom are joined to form an $R^{20}$-substituted or unsubstituted azetidinyl. In embodiments, $R^{2A}$ and $R^{2B}$ substituents bonded to the same nitrogen atom are joined to form an $R^{20}$-substituted or unsubstituted azepanyl. In embodiments, $R^{2A}$ and $R^{2B}$ substituents bonded to the same nitrogen atom are joined to form an $R^{20}$-substituted or unsubstituted morpholinyl. In embodiments, $R^{2A}$ and $R^{2B}$ substituents bonded to the same nitrogen atom are joined to form an $R^{20}$-substituted or unsubstituted piperazinyl. In embodiments, $R^{2A}$ and $R^{2B}$ substituents bonded to the same nitrogen atom are joined to form an $R^{20}$-substituted or unsubstituted piperidinyl. In embodiments, $R^{2A}$ and $R^{2B}$ substituents bonded to the same nitrogen atom are joined to form an $R^{20}$-substituted or unsubstituted tetrahydrofuranyl. In embodiments, $R^{2A}$ and $R^{2B}$ substituents bonded to the same nitrogen atom are joined to form an $R^{20}$-substituted or unsubstituted tetrahydrothienyl. In embodiments, $R^{2A}$ and $R^{2B}$ substituents bonded to the same nitrogen atom are joined to form an $R^{20}$-substituted or unsubstituted 2-oxa-6-azaspiro[3.3]heptanyl.

In embodiments, $R^{2A}$ and $R^{2B}$ substituents bonded to the same nitrogen atom are joined to form

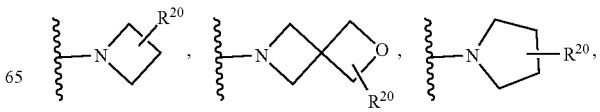

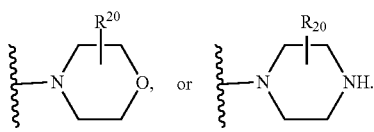

In embodiments, R[2A] and R[2B] substituents bonded to the same nitrogen atom are joined to form

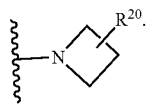

In embodiments, R[2A] and R[2B] substituents bonded to the same nitrogen atom are joined to form

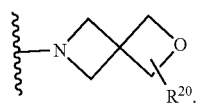

In embodiments, R[2A] and R[2B] substituents bonded to the same nitrogen atom are joined to form

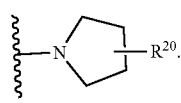

In embodiments, R[2A] and R[2B] substituents bonded to the same nitrogen atom are joined to form

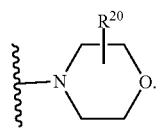

In embodiments, R[2A] and R[2B] substituents bonded to the same nitrogen atom are joined to form

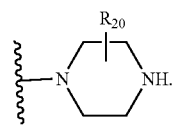

In embodiments, R[2A] and R[2B] substituents bonded to the same nitrogen atom are joined to form

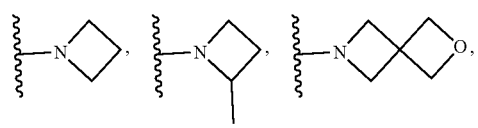

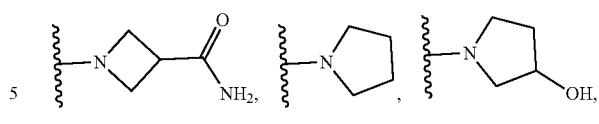

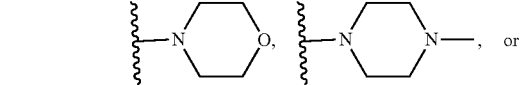

In embodiments, R[2A] and R[2B] substituents bonded to the same nitrogen atom are joined to form

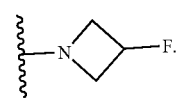

In embodiments, R[2A] and R[2B] substituents bonded to the same nitrogen atom are joined to form

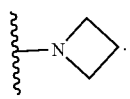

In embodiments, R[2A] and R[2B] substituents bonded to the same nitrogen atom are joined to form

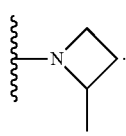

In embodiments, R[2A] and R[2B] substituents bonded to the same nitrogen atom are joined to form

In embodiments, R[2A] and R[2B] substituents bonded to the same nitrogen atom are joined to form

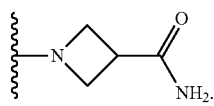

In embodiments, R[2A] and R[2B] substituents bonded to the same nitrogen atom are joined to form

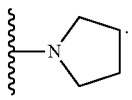

In embodiments, R[2A] and R[2B] substituents bonded to the same nitrogen atom are joined to form

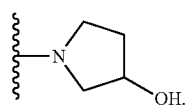 [SMILES: *N1CCC(O)C1]

In embodiments, $R^{2A}$ and $R^{2B}$ substituents bonded to the same nitrogen atom are joined to form

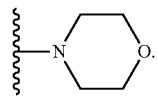

In embodiments, $R^{2A}$ and $R^{2B}$ substituents bonded to the same nitrogen atom are joined to form

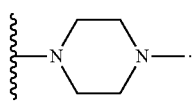

In embodiments, $R^{2A}$ and $R^{2B}$ substituents bonded to the same nitrogen atom are joined to form

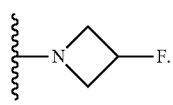

In embodiments, the compound has the formula:

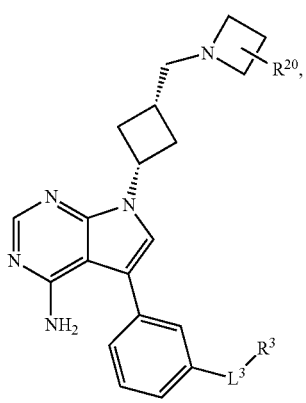

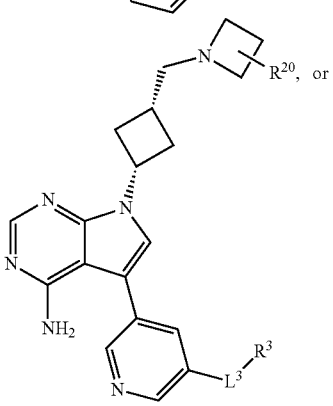

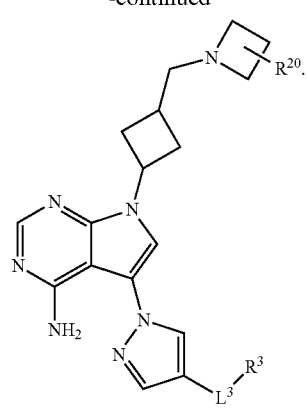

$R^{20}$, $R^3$, and $L^3$ are as described herein, including embodiments. In embodiments, the compound has the formula:

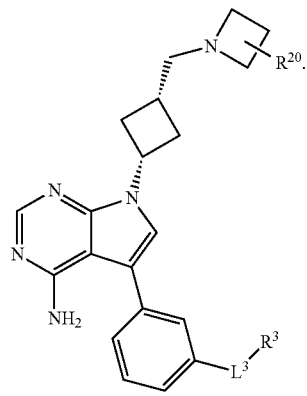

$R^{20}$, $R^3$, and $L^3$ areas described herein, including embodiments. In embodiments, the compound has the formula:

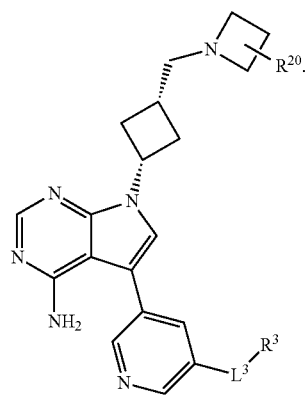

$R^{20}$, $R^3$, and $L^3$ are as described herein, including embodiments. In embodiments, the compound has the formula:

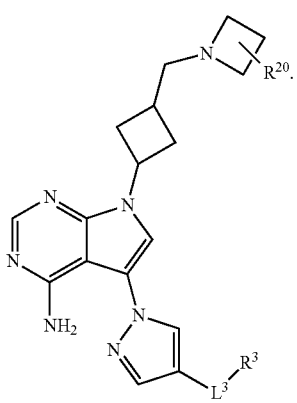

$R^{20}$, $R^3$, and $L^3$ are as described herein, including embodiments. In embodiments, the compound has the formula:

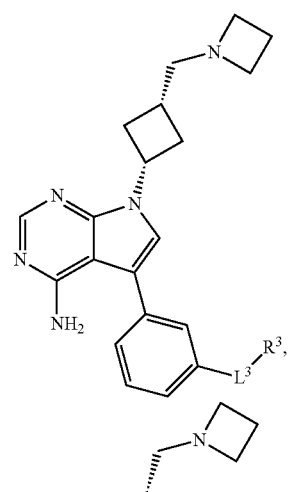

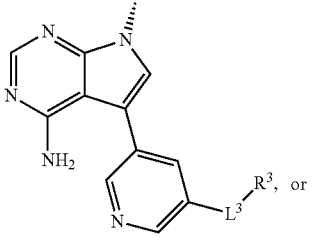

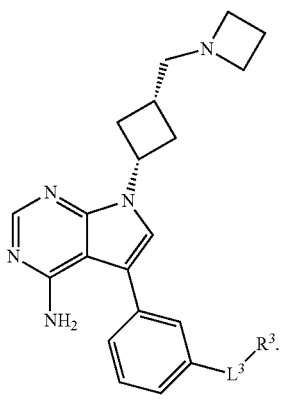

$R^3$ and $L^3$ are as described herein, including embodiments. In embodiments, the compound has the formula:

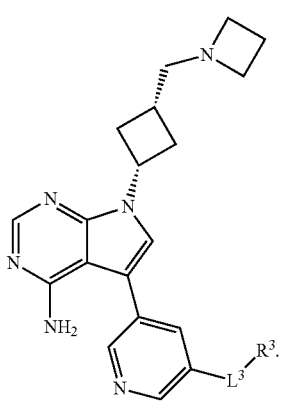

$R^3$ and $L^3$ are as described herein, including embodiments. In embodiments, the compound has the formula:

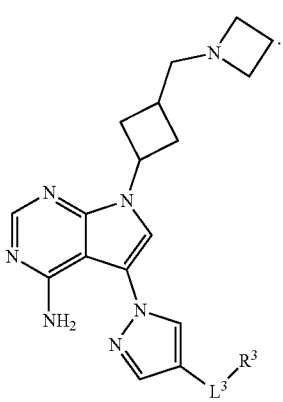

$R^3$ and $L^3$ are as described herein, including embodiments.

In embodiments, $L^3$ is a bond, —$CH_2$—, —$CH_2CH_2$—, —$CH_2CH_2CH_2$—, —$OCH_2$—, —$OCH_2CH_2$—, or —$OCH_2CH_2CH_2$—; $R^3$ is independently —OH, —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO$_2$R$^{3D}$, —NR$^{3A}$SO$_2$L$^{3A}$R$^{3D}$, —NR$^{3C}$SO$_2$NR$^{3A}$R$^{3B}$, —NR$^{3A}$R$^{3B}$, —NR$^{3A}$C(O)R$^{3C}$, —NR$^{3A}$C(O)OR$^{3C}$, —SO$_2$R$^{3C}$, —SO$_2$NR$^{3A}$R$^{3B}$, —SO$_2$P(O)(OR$^{3C}$)(OR$^{3D}$), —SO$_2$CH$_2$P(O)(OR$^{3C}$)(OR$^{3D}$), —SO$_2$P(O)(OR$^{3D}$)(NR$^{3A}$R$^{3B}$), —SO$_2$P(O)(R$^{3C}$)(OR$^{1D}$), —SO$_2$P(O)(R$^{3C}$)(R$^{3D}$), —S(O)(NR$^{3A}$)R$^{3C}$, —C(O)OR$^{3C}$, —C(O)NR$^{3A}$R$^{3B}$, —NR$^{3A}$C(O)OR$^{3C}$; L$^{3A}$ is independently —CH$_2$—, —CH(CH$_3$)—, or —C(CH$_3$)$_2$—; and R$^{3A}$, R$^{3B}$, R$^{3C}$, and R$^{3D}$ are independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{3A}$ and R$^{3D}$ substituents may optionally be joined to form a substituted or unsubstituted heterocycloalkyl or substituted or unsubstituted heteroaryl.

In embodiments, L$^3$ is a bond, —CH$_2$—, —CH$_2$CH$_2$—, —CH$_2$CH$_2$CH$_2$—, —OCH$_2$—, —OCH$_2$CH$_2$—, or —OCH$_2$CH$_2$CH$_2$—.

In embodiments, R$^3$ is independently —OH, —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO$_2$R$^{3D}$, —NR$^{3A}$SO$_2$L$^{3A}$R$^{3D}$, —NR$^{3C}$SO$_2$NR$^{3A}$R$^{3B}$, —NR$^{3A}$R$^{3B}$, —NR$^{3A}$C(O)R$^{3C}$, —NR$^{3A}$C(O)OR$^{3C}$, —SO$_2$R$^{3C}$, —SO$_2$NR$^{3A}$R$^{3B}$, —SO$_2$P(O)(OR$^{3C}$)(OR$^{3D}$), —SO$_2$CH$_2$P(O)(OR$^{3C}$)(OR$^{3D}$), —SO$_2$P(O)(OR$^{3D}$)(NR$^{3A}$R$^{3B}$), —SO$_2$P(O)(R$^{3C}$)(OR$^{3D}$), —SO$_2$P(O)(R$^{3C}$)(R$^{3D}$), —S(O)(NR$^{3A}$)R$^{3C}$, —C(O)OR$^{3C}$, —C(O)NR$^{3A}$R$^{3B}$ or —NR$^{3A}$C(O)OR$^{3C}$.

In embodiments, L$^{3A}$ is independently —CH$_2$—, —CH(CH$_3$)—, or —C(CH$_3$)$_2$—.

In embodiments, R$^{3A}$, R$^{3B}$, R$^{3C}$, and R$^{3D}$ are independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{3A}$ and R$^{3D}$ substituents may optionally be joined to form a substituted or unsubstituted heterocycloalkyl or substituted or unsubstituted heteroaryl.

In embodiments, R$^{3A}$, R$^{3B}$, R$^{3C}$, and R$^{3D}$ are independently hydrogen, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{3A}$ and R$^{3D}$ substituents may optionally be joined to form a substituted or unsubstituted heterocycloalkyl or substituted or unsubstituted heteroaryl.

In embodiments, W$^1$ is CH.
In embodiments, W$^1$ is N.
In embodiments, W$^1$ is CR$^1$; and R$^1$ is independently halogen, —CX$^1_3$, —CHX$^1_2$, —CH$_2$X$^1$, or unsubstituted C$_1$-C$_4$ alkyl.
In embodiments, W$^2$ is CH.
In embodiments, W$^2$ is N.
In embodiments, W$^2$ is CR$^1$; and R$^1$ is independently halogen, —CX$^1_3$, —CHX$^1_2$, —CH$_2$X$^1$, or unsubstituted C$_1$-C$_4$ alkyl.
In embodiments, L$^4$ is —C(O)NH—. In embodiments, L$^4$ is —NHC(O)—.
In embodiments, R$^3$ is

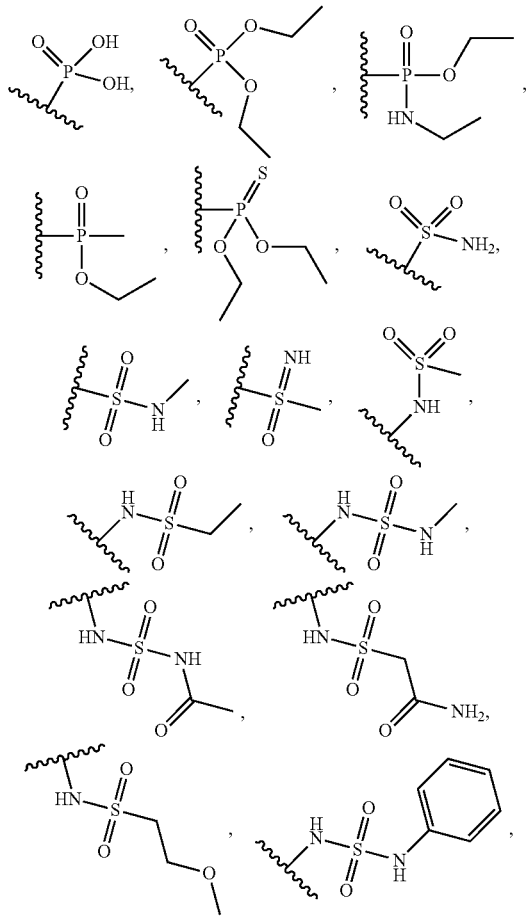

-continued

[chemical structures: benzylsulfonamide; cyclic sulfamide with oxo group; acetamide; methyl carbamate; ethyl carbamate; oxetanyl amine; hydroxyl]

In embodiments, R³ is

[phosphonic acid structure]

In embodiments, R³ is

[diethyl phosphonate]

In embodiments, R³ is

[ethyl P-aminoethyl phosphonate]

In embodiments, R³ is

[methyl ethyl phosphonate]

In embodiments, R³ is

[diethyl thiophosphonate]

In embodiments, R³ is

[sulfonamide -S(O)₂NH₂]

In embodiments, R³ is

[N-methyl sulfonamide]

In embodiments, R³ is

[sulfonimidamide, NH imine]

In embodiments, R³ is

[methanesulfonyl]

In embodiments, R³ is

[NH-sulfonyl methyl]

In embodiments, R³ is

[NH-SO₂-ethyl]

In embodiments, R³ is

[sulfamide, -NH-S(O)₂-NH-methyl]

In embodiments, R³ is

[HN-S(O)₂-NH-C(O)-methyl, acyl sulfamide]

In embodiments, R³ is

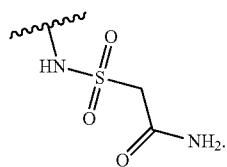 [SMILES: *NS(=O)(=O)CC(N)=O]

In embodiments, R³ is

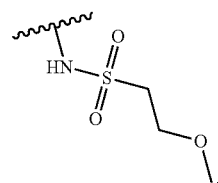 [SMILES: *NS(=O)(=O)CCOC]

In embodiments, R³ is

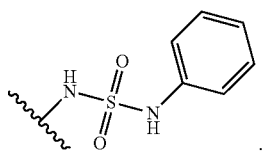 [SMILES: *NS(=O)(=O)Nc1ccccc1]

In embodiments, R³ is

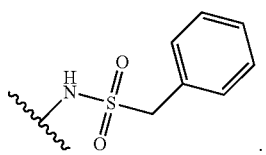 [SMILES: *NS(=O)(=O)Cc1ccccc1]

In embodiments, R³ is

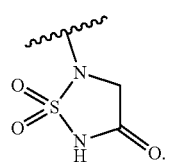

In embodiments, R³ is

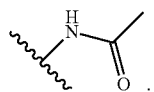

In embodiments, R³ is

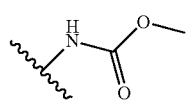

In embodiments, R³ is

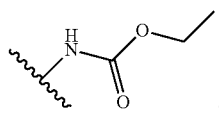

In embodiments, R³ is

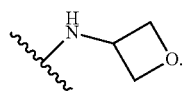

In embodiments, R³ is

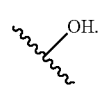

In embodiments, $R^{1A}$ is independently hydrogen, —CCl₃, —CBr₃, —CF₃, —CI₃, CHCl₂, —CHBr₂, —CHF₂, —CHI₂, —CH₂Cl, —CH₂Br, —CH₂F, —CH₂I, substituted or unsubstituted $C_1$-$C_4$ alkyl, or substituted or unsubstituted 2 to 4 membered heteroalkyl. In embodiments, $R^{1A}$ is independently hydrogen, substituted or unsubstituted $C_1$-$C_4$ alkyl, or substituted or unsubstituted 2 to 4 membered heteroalkyl. In embodiments, $R^{1A}$ is independently hydrogen. In embodiments, $R^{1A}$ is independently substituted or unsubstituted $C_1$-$C_4$ alkyl. In embodiments, $R^{1A}$ is independently substituted or unsubstituted 2 to 4 membered heteroalkyl. In embodiments, $R^{1A}$ is independently unsubstituted methyl.

In embodiments, $R^{1B}$ is independently hydrogen, —CCl₃, —CBr₃, —CF₃, —CI₃, CHCl₂, —CHBr₂, —CHF₂, —CHI₂, —CH₂Cl, —CH₂Br, —CH₂F, —CH₂I, substituted or unsubstituted $C_1$-$C_4$ alkyl, or substituted or unsubstituted 2 to 4 membered heteroalkyl. In embodiments, $R^{1B}$ is independently hydrogen, substituted or unsubstituted $C_1$-$C_4$ alkyl, or substituted or unsubstituted 2 to 4 membered heteroalkyl. In embodiments, $R^{1B}$ is independently hydrogen. In embodiments, $R^{1B}$ is independently substituted or unsubstituted $C_1$-$C_4$ alkyl. In embodiments, $R^{1B}$ is independently substituted or unsubstituted 2 to 4 membered heteroalkyl. In embodiments, $R^{1B}$ is independently unsubstituted methyl.

In embodiments, $R^{1C}$ is independently hydrogen, —CCl₃, —CBr₃, —CF₃, —CI₃, CHCl₂, —CHBr₂, —CHF₂, —CHI₂, —CH₂Cl, —CH₂Br, —CH₂F, —CH₂I, substituted or unsubstituted $C_1$-$C_4$ alkyl, or substituted or unsubstituted 2 to 4 membered heteroalkyl. In embodiments, $R^{1C}$ is independently hydrogen, substituted or unsubstituted $C_1$-$C_4$ alkyl, or substituted or unsubstituted 2 to 4 membered heteroalkyl. In embodiments, $R^{1C}$ is independently hydrogen. In embodiments, $R^{1C}$ is independently substituted or unsubstituted $C_1$-$C_4$ alkyl. In embodiments, $R^{1C}$ is independently substituted or unsubstituted 2 to 4 membered heteroalkyl. In embodiments, $R^{1C}$ is independently unsubstituted methyl.

In embodiments, $R^{1D}$ is independently hydrogen, —CCl₃, —CBr₃, —CF₃, —CI₃, CHCl₂, —CHBr₂, —CHF₂, —CHI₂, —CH₂Cl, —CH₂Br, —CH₂F, —CH₂I, substituted or unsubstituted $C_1$-$C_4$ alkyl, or substituted or unsubstituted 2 to 4 membered heteroalkyl. In embodiments, $R^{1D}$ is independently hydrogen, substituted or unsubstituted $C_1$-$C_4$ alkyl, or substituted or unsubstituted 2 to 4 membered heteroalkyl. In embodiments, $R^{1D}$ is independently hydrogen. In embodiments, $R^{1D}$ is independently substituted or unsubstituted $C_1$-$C_4$ alkyl. In embodiments, $R^{1D}$ is independently substituted or unsubstituted 2 to 4 membered heteroalkyl. In embodiments, $R^{1D}$ is independently unsubstituted methyl.

In embodiments, $R^{2A}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, substituted or unsubstituted $C_1$-$C_4$ alkyl, or substituted or unsubstituted 2 to 4 membered heteroalkyl. In embodiments, $R^{2A}$ is independently hydrogen, substituted or unsubstituted $C_1$-$C_4$ alkyl, or substituted or unsubstituted 2 to 4 membered heteroalkyl. In embodiments, $R^{2A}$ is independently hydrogen. In embodiments, $R^{2A}$ is independently substituted or unsubstituted $C_1$-$C_4$ alkyl. In embodiments, $R^{2A}$ is independently substituted or unsubstituted 2 to 4 membered heteroalkyl. In embodiments, $R^{2A}$ is independently unsubstituted methyl.

In embodiments, $R^{2B}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, substituted or unsubstituted $C_1$-$C_4$ alkyl, or substituted or unsubstituted 2 to 4 membered heteroalkyl. In embodiments, $R^{2B}$ is independently hydrogen, substituted or unsubstituted $C_1$-$C_4$ alkyl, or substituted or unsubstituted 2 to 4 membered heteroalkyl. In embodiments, $R^{2B}$ is independently hydrogen. In embodiments, $R^{2B}$ is independently substituted or unsubstituted $C_1$-$C_4$ alkyl. In embodiments, $R^{2B}$ is independently substituted or unsubstituted 2 to 4 membered heteroalkyl. In embodiments, $R^{2B}$ is independently unsubstituted methyl.

In embodiments, R" is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, substituted or unsubstituted $C_1$-$C_4$ alkyl, or substituted or unsubstituted 2 to 4 membered heteroalkyl. In embodiments, $R^{2C}$ is independently hydrogen, substituted or unsubstituted $C_1$-$C_4$ alkyl, or substituted or unsubstituted 2 to 4 membered heteroalkyl. In embodiments, $R^{2C}$ is independently hydrogen. In embodiments, $R^{2C}$ is independently substituted or unsubstituted $C_1$-$C_4$ alkyl. In embodiments, $R^{2C}$ is independently substituted or unsubstituted 2 to 4 membered heteroalkyl. In embodiments, $R^{2C}$ is independently unsubstituted methyl.

In embodiments, $R^{2D}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, substituted or unsubstituted $C_1$-$C_4$ alkyl, or substituted or unsubstituted 2 to 4 membered heteroalkyl. In embodiments, $R^{2D}$ is independently hydrogen, substituted or unsubstituted $C_1$-$C_4$ alkyl, or substituted or unsubstituted 2 to 4 membered heteroalkyl. In embodiments, $R^{2D}$ is independently hydrogen. In embodiments, $R^{2D}$ is independently substituted or unsubstituted $C_1$-$C_4$ alkyl. In embodiments, $R^{2D}$ is independently substituted or unsubstituted 2 to 4 membered heteroalkyl. In embodiments, $R^{2D}$ is independently unsubstituted methyl.

In embodiments, $R^{3A}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, substituted or unsubstituted $C_1$-$C_4$ alkyl, or substituted or unsubstituted 2 to 4 membered heteroalkyl. In embodiments, $R^{3A}$ is independently hydrogen, substituted or unsubstituted $C_1$-$C_4$ alkyl, or substituted or unsubstituted 2 to 4 membered heteroalkyl. In embodiments, $R^{3A}$ is independently hydrogen. In embodiments, $R^{3A}$ is independently substituted or unsubstituted $C_1$-$C_4$ alkyl. In embodiments, $R^{3A}$ is independently substituted or unsubstituted 2 to 4 membered heteroalkyl. In embodiments, $R^{3A}$ is independently unsubstituted methyl.

In embodiments, $R^{3B}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, substituted or unsubstituted $C_1$-$C_4$ alkyl, or substituted or unsubstituted 2 to 4 membered heteroalkyl. In embodiments, $R^{3B}$ is independently hydrogen, substituted or unsubstituted $C_1$-$C_4$ alkyl, or substituted or unsubstituted 2 to 4 membered heteroalkyl. In embodiments, $R^{3B}$ is independently hydrogen. In embodiments, $R^{3B}$ is independently substituted or unsubstituted $C_1$-$C_4$ alkyl. In embodiments, $R^{3B}$ is independently substituted or unsubstituted 2 to 4 membered heteroalkyl. In embodiments, R" is independently unsubstituted methyl.

In embodiments, $R^{3C}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, substituted or unsubstituted $C_1$-$C_4$ alkyl, or substituted or unsubstituted 2 to 4 membered heteroalkyl. In embodiments, $R^{3C}$ is independently hydrogen, substituted or unsubstituted $C_1$-$C_4$ alkyl, or substituted or unsubstituted 2 to 4 membered heteroalkyl. In embodiments, $R^{3C}$ is independently hydrogen. In embodiments, $R^{3C}$ is independently substituted or unsubstituted $C_1$-$C_4$ alkyl. In embodiments, $R^{3C}$ is independently substituted or unsubstituted 2 to 4 membered heteroalkyl. In embodiments, $R^{3C}$ is independently unsubstituted methyl.

In embodiments, $R^{3D}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, substituted or unsubstituted $C_1$-$C_4$ alkyl, or substituted or unsubstituted 2 to 4 membered heteroalkyl. In embodiments, $R^{3D}$ is independently hydrogen, substituted or unsubstituted $C_1$-$C_4$ alkyl, or substituted or unsubstituted 2 to 4 membered heteroalkyl. In embodiments, $R^{3D}$ is independently hydrogen. In embodiments, $R^{3D}$ is independently substituted or unsubstituted $C_1$-$C_4$ alkyl. In embodiments, $R^{3D}$ is independently substituted or unsubstituted 2 to 4 membered heteroalkyl. In embodiments, $R^{3D}$ is independently unsubstituted methyl.

In embodiments, z1 is an integer from 0 to 4. In embodiments, z1 is 0. In embodiments, z1 is 1. In embodiments, z1 is 2. In embodiments, z1 is 3. In embodiments, z1 is 4. In embodiments, z2 is an integer from 0 to 6. In embodiments, z2 is 0. In embodiments, z2 is 1. In embodiments, z2 is 2. In embodiments, z2 is 3. In embodiments, z2 is 4. In embodiments, z2 is 5. In embodiments, z2 is 6. In embodiments, z4 is 1 or 2. In embodiments, z4 is 1. In embodiments, z4 is 2.

In embodiments, n1, n2, n6, and n7 are independently an integer from 0 to 4. In embodiments, n1 is independently an integer from 0 to 4. In embodiments, n1 is independently 0. In embodiments, n1 is independently 1. In embodiments, n1 is independently 2. In embodiments, n1 is independently 3. In embodiments, n1 is independently 4. In embodiments, n2 is independently an integer from 0 to 4. In embodiments, n2 is independently 0. In embodiments, n2 is independently 1. In embodiments, n2 is independently 2. In embodiments, n2 is independently 3. In embodiments, n2 is independently 4. In embodiments, n6 is independently an integer from 0 to 4. In embodiments, n6 is independently 0. In embodiments, n6 is independently 1. In embodiments, n6 is independently 2. In embodiments, n6 is independently 3. In embodiments, n6 is independently 4. In embodiments, n7 is independently an integer from 0 to 4. In embodiments, n7 is independently 0. In embodiments, n7 is independently 1. In embodiments, n7 is independently 2. In embodiments, n7 is independently 3. In embodiments, n7 is independently 4. In embodiments, m1, m2, v, v2, m6, v6, m7, and v7 are independently 1 or 2. In embodiments, m1 is independently 1. In embodiments, m1 is independently 2. In embodiments, m2 is independently 1. In embodiments, m2 is independently 2. In embodiments, v1 is independently 1. In embodiments, v1 is independently 2. In embodiments, v2 is independently 1. In embodiments, v2 is independently 2. In embodiments, m6 is independently 1. In embodiments, m6 is independently 2. In embodiments, m7 is independently 1. In embodiments, m7 is independently 2. In embodiments, v6 is independently 1. In embodiments, v6 is independently 2. In embodiments, v7 is independently 1. In embodiments, v7 is independently 2.

In embodiments, $X^1$, $X^2$, $X^6$, and $X^7$ are independently —F, —Cl, —Br, or —I. In embodiments, $X^1$ is independently —F, —Cl, —Br, or —I. In embodiments, $X^1$ is independently —F. In embodiments, $X^1$ is independently —Cl. In embodiments, $X^1$ is independently —Br. In embodiments, $X^1$ is independently —I. In embodiments, $X^2$ is independently —F, —Cl, —Br, or —I. In embodiments, $X^2$ is independently —F. In embodiments, $X^2$ is independently —Cl. In embodiments, $X^2$ is independently —Br. In embodiments, $X^2$ is independently —I. In embodiments, $X^6$ is independently —F, —Cl, —Br, or —I. In embodiments, $X^7$ is independently —F, —Cl, —Br, or —I. In embodiments, $X^6$ is independently —F. In embodiments, $X^6$ is independently —Cl. In embodiments, $X^6$ is independently —Br. In embodiments, $X^6$ is independently —I. In embodiments, $X^7$ is independently —F. In embodiments, $X^7$ is independently —Cl. In embodiments, $X^7$ is independently —Br. In embodiments, $X^7$ is independently —I. In embodiments, $X^{3A}$ is independently —F, —Cl, —Br, or —I. In embodiments, $X^{3A}$ is independently —F. In embodiments, $X^{3A}$ is independently —Cl. In embodiments, $X^{3A}$ is independently —Br. In embodiments, $X^{3A}$ is independently —I.

In embodiments, when $R^1$ is substituted, $R^1$ is substituted with one or more first substituent groups denoted by $R^{1.1}$ as explained in the definitions section above in the description of "first substituent group(s)". In embodiments, when an $R^{1.1}$ substituent group is substituted, the $R^{1.1}$ substituent group is substituted with one or more second substituent groups denoted by $R^{1.2}$ as explained in the definitions section above in the description of "first substituent group(s)". In embodiments, when an $R^{1.2}$ substituent group is substituted, the $R^{1.2}$ substituent group is substituted with one or more third substituent groups denoted by $R^3$ as explained in the definitions section above in the description of "first substituent group(s)". In the above embodiments, $R^1$, $R^{1.1}$, $R^{1.2}$ and $R^{1.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^1$, $R^{1.1}$, $R^{1.2}$, and $R^{1.3}$, respectively.

In embodiments, when two adjacent $R^1$ substituents are optionally joined to forma moiety that is substituted (e.g., a substituted cycloalkyl, substituted heterocycloalkyl, substituted aryl, or substituted heteroaryl), the moiety is substituted with one or more first substituent groups denoted by $R^{1.1}$ as explained in the definitions section above in the description of "first substituent group(s)". In embodiments, when an $R^{1.1}$ substituent group is substituted, the $R^{1.1}$ substituent group is substituted with one or more second substituent groups denoted by $R^{1.2}$ as explained in the definitions section above in the description of "first substituent group(s)". In embodiments, when an $R^{1.2}$ substituent group is substituted, the $R^{1.2}$ substituent group is substituted with one or more third substituent groups denoted by $R^{1.3}$ as explained in the definitions section above in the description of "first substituent group(s)". In the above embodiments, $R^1$, $R^{1.1}$, $R^{1.2}$, and $R^{1.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^1$, $R^{1.1}$, $R^{1.2}$, and $R^{1.3}$, respectively.

In embodiments, when $R^{1A}$ is substituted, $R^{1A}$ is substituted with one or more first substituent groups denoted by $R^{1A.1}$ as explained in the definitions section above in the description of "first substituent group(s)". In embodiments, when an $R^{1A.1}$ substituent group is substituted, the $R^{1A.1}$ substituent group is substituted with one or more second substituent groups denoted by $R^{1A.2}$ as explained in the definitions section above in the description of "first substituent group(s)". In embodiments, when an $R^{1A.2}$ substituent group is substituted, the $R^{1A.2}$ substituent group is substituted with one or more third substituent groups denoted by $R^{1A.3}$ as explained in the definitions section above in the description of "first substituent group(s)". In the above embodiments, $R^{1A}$ $R^{1A.1}$, $R^{1A.2}$, and $R^{1A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1A}$, $R^{1A.1}$, $R^{1A.2}$, and $R^{1A.3}$ respectively.

In embodiments, when $R^{1B}$ is substituted, $R^{1B}$ is substituted with one or more first substituent groups denoted by $R^{1B}$ as explained in the definitions section above in the description of "first substituent group(s)". In embodiments, when an $R^{1B.1}$ substituent group is substituted, the $R^{1B.1}$ substituent group is substituted with one or more second substituent groups denoted by $R^{1B.2}$ as explained in the definitions section above in the description of "first substituent group(s)". In embodiments, when an $R^{1B.2}$ substituent group is substituted, the $R^{1B.2}$ substituent group is substituted with one or more third substituent groups denoted by $R^{1B.3}$ as explained in the definitions section above in the description of "first substituent group(s)". In the above embodiments, $R^{1B}$ $R^{1B.1}$, $R^{1B.2}$, and $R^{1B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1B}$, $R^{1B.1}$, $R^{1B.2}$, and $R^{1B.3}$ respectively.

In embodiments, when $R^{1A}$ and $R^{1B}$ substituents that are bonded to the same nitrogen atom are joined to form a moiety that is substituted (e.g., a substituted heterocycloalkyl or substituted heteroaryl), the moiety is substituted with one or more first substituent groups denoted by $R^{1A.1}$ as explained in the definitions section above in the description of "first substituent group(s)". In embodiments, when an $R^{1A.1}$ substituent group is substituted, the $R^{1A.1}$ substituent group is substituted with one or more second substituent groups denoted by $R^{1A.2}$ as explained in the definitions section above in the description of "first substituent group(s)". In embodiments, when an $R^{1A.2}$ substituent group is substituted, the $R^{1A.2}$ substituent group is substituted with one or more third substituent groups denoted by $R^{1A.3}$ as explained in the definitions section above in the description of "first substituent group(s)". In the above embodiments, $R^{1A}$, $R^{1A.1}$, $R^{1A.2}$, and $R^{1A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1A}$, $R^{1A.1}$, $R^{1A.2}$, and $R^{1A.3}$, respectively.

In embodiments, when $R^{1A}$ and $R^{1B}$ substituents that are bonded to the same nitrogen atom are joined to form a moiety that is substituted (e.g., a substituted heterocycloalkyl or substituted heteroaryl), the moiety is substituted with one or more first substituent groups denoted by $R^{1B.1}$ as explained in the definitions section above in the description of "first substituent group(s)". In embodiments, when an $R^{1B.1}$ substituent group is substituted, the $R^{1B.1}$ substituent group is substituted with one or more second substituent groups denoted by $R^{1B.2}$ as explained in the definitions section above in the description of "first substituent group(s)". In embodiments, when an $R^{1B.2}$ substituent group is substituted, the $R^{1B.2}$ substituent group is substituted with one or more third substituent groups denoted by $R^{1B.3}$ as explained in the definitions section above in the description of "first substituent group(s)". In the above embodiments, $R^{1B}$, $R^{1B.1}$, $R^{1B.2}$, and $R^{1B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1B}$, $R^{1B.1}$, $R^{1B.2}$, and $R^{1B.3}$, respectively.

In embodiments, when $R^{1C}$ is substituted, $R^{1C}$ is substituted with one or more first substituent groups denoted by $R^{1C.1}$ as explained in the definitions section above in the description of "first substituent group(s)". In embodiments, when an $R^{1C.1}$ substituent group is substituted, the $R^{1C.1}$ substituent group is substituted with one or more second substituent groups denoted by $R^{1C.2}$ as explained in the definitions section above in the description of "first substituent group(s)". In embodiments, when an $R^{1C.2}$ substituent group is substituted, the $R^{1C.2}$ substituent group is substituted with one or more third substituent groups denoted by $R^{1C.3}$ as explained in the definitions section above in the description of "first substituent group(s)". In the above embodiments, $R^{1C}$, $R^{1C.1}$, $R^{1C.2}$, and $R^{1C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1C}$, $R^{1C.1}$, $R^{1C.2}$, and $R^{1C.3}$, respectively.

In embodiments, when $R^{1D}$ is substituted, $R^{1D}$ is substituted with one or more first substituent groups denoted by $R^{1D}$ as explained in the definitions section above in the description of "first substituent group(s)". In embodiments, when an $R^{1D.1}$ substituent group is substituted, the $R^{1D.1}$ substituent group is substituted with one or more second substituent groups denoted by $R^{1D.2}$ as explained in the definitions section above in the description of "first substituent group(s)". In embodiments, when an $R^{1D.2}$ substituent group is substituted, the $R^{1D.2}$ substituent group is substituted with one or more third substituent groups denoted by $R^{1D.3}$ as explained in the definitions section above in the description of "first substituent group(s)". In the above embodiments, $R^{1D}$, $R^{1D.1}$, $R^{1D.2}$, and $R^{1D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1D}$, $R^{1D.1}$, $R^{1D.2}$, and $R^{1D.3}$ respectively.

In embodiments, when $R^2$ is substituted, $R^2$ is substituted with one or more first substituent groups denoted by $R^{2.1}$ as explained in the definitions section above in the description of "first substituent group(s)". In embodiments, when an $R^{2.1}$ substituent group is substituted, the $R^{2.1}$ substituent group is substituted with one or more second substituent groups denoted by $R^{2.2}$ as explained in the definitions section above in the description of "first substituent group(s)". In embodiments, when an $R^{2.2}$ substituent group is substituted, the $R^{2.2}$ substituent group is substituted with one or more third substituent groups denoted by $R^{2.3}$ as explained in the definitions section above in the description of "first substituent group(s)". In the above embodiments, $R^2$, $R^{2.1}$, $R^{2.2}$ and $R^{2.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^2$, $R^{2.1}$, $R^{2.2}$, and $R^{2.3}$, respectively.

In embodiments, when two adjacent $R^2$ substituents are optionally joined to form a moiety that is substituted (e.g., a substituted cycloalkyl, substituted heterocycloalkyl, substituted aryl, or substituted heteroaryl), the moiety is substituted with one or more first substituent groups denoted by $R^{2.1}$ as explained in the definitions section above in the description of "first substituent group(s)". In embodiments, when an $R^{2.1}$ substituent group is substituted, the $R^{2.1}$ substituent group is substituted with one or more second substituent groups denoted by $R^{2.2}$ as explained in the definitions section above in the description of "first substituent group(s)". In embodiments, when an $R^{2.2}$ substituent group is substituted, the $R^{2.2}$ substituent group is substituted with one or more third substituent groups denoted by $R^{2.3}$ as explained in the definitions section above in the description of "first substituent group(s)". In the above embodiments, $R^2$, $R^{2.1}$, $R^{2.2}$, and $R^{2.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^2$, $R^{2.1}$, $R^{2.2}$, and $R^{2.3}$, respectively.

In embodiments, when $R^{2A}$ is substituted, $R^{2A}$ is substituted with one or more first substituent groups denoted by $R^{2A.1}$ as explained in the definitions section above in the description of "first substituent group(s)". In embodiments, when an $R^{2A.1}$ substituent group is substituted, the $R^{2A.1}$ substituent group is substituted with one or more second substituent groups denoted by $R^{2A.2}$ as explained in the definitions section above in the description of "first substituent group(s)". In embodiments, when an $R^{2A.2}$ substituent group is substituted, the $R^{2A.2}$ substituent group is substituted with one or more third substituent groups denoted by $R^{2A.3}$ as explained in the definitions section above in the description of "first substituent group(s)". In the above embodiments, $R^{2A}R^{2A.1}R^{2A.2}$, and $R^{2A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2A}$, $R^{2A.1}$, $R^{2A.2}$, and $R^{2A.3}$ respectively.

In embodiments, when $R^{2B}$ is substituted, $R^{2B}$ is substituted with one or more first substituent groups denoted by $R^{2B.1}$ as explained in the definitions section above in the description of "first substituent group(s)". In embodiments, when an $R^{2B.1}$ substituent group is substituted, the $R^{2B.1}$ substituent group is substituted with one or more second substituent groups denoted by $R^{2B}.2$ as explained in the definitions section above in the description of "first substituent group(s)". In embodiments, when an $R^{2B.2}$ substituent group is substituted, the $R^{2B.2}$ substituent group is substituted with one or more third substituent groups denoted by $R^{2B.3}$ as explained in the definitions section above in the description of "first substituent group(s)". In the above embodiments, $R^{2B}R^{2B}.1$, $R^{2B.2}$, and $R^{2B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2B}$, $R^{2B.1}$, $R^{2B.2}$, and $R^{2B.3}$, respectively.

In embodiments, when $R^{2A}$ and $R^{2B}$ substituents that are bonded to the same nitrogen atom are joined to form a moiety that is substituted (e.g., a substituted heterocycloalkyl or substituted heteroaryl), the moiety is substituted with one or more first substituent groups denoted by $R^{2A.1}$ as explained in the definitions section above in the description of "first substituent group(s)". In embodiments, when an $R^{2A.1}$ substituent group is substituted, the $R^{2A.1}$ substituent group is substituted with one or more second substituent groups denoted by $R^{2A.2}$ as explained in the definitions section above in the description of "first substituent group(s)". In embodiments, when an $R^{2A.2}$ substituent group is substituted, the $R^{2A.2}$ substituent group is substituted with one or more third substituent groups denoted by $R^{2A.3}$ as explained in the definitions section above in the description of "first substituent group(s)". In the above embodiments, $R^{2A}$, $R^{2A.1}$, $R^{2A.2}$, and $R^{2A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2A}$, $R^{2A.1}$, $R^{2A.2}$, and $R^{2A.3}$, respectively.

In embodiments, when $R^{2A}$ and $R^{2B}$ substituents that are bonded to the same nitrogen atom are joined to form a moiety that is substituted (e.g., a substituted heterocycloalkyl or substituted heteroaryl), the moiety is substituted with one or more first substituent groups denoted by $R^{2B}$ as explained in the definitions section above in the description of "first substituent group(s)". In embodiments, when an $R^{2B.1}$ substituent group is substituted, the $R^{2B.1}$ substituent group is substituted with one or more second substituent groups denoted by $R^{2B.2}$ as explained in the definitions section above in the description of "first substituent group(s)". In embodiments, when an $R^{2B.2}$ substituent group is substituted, the $R^{2B.2}$ substituent group is substituted with one or more third substituent groups denoted by $R^{2B.3}$ as explained in the definitions section above in the description of "first substituent group(s)". In the above embodiments, $R^{2B}$, $R^{2B.1}$, $R^{2B.2}$, and $R^{2B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2B}$, $R^{2B.1}$, $R^{2B.2}$, and $R^{2B.3}$, respectively.

In embodiments, when $R^{2C}$ is substituted, $R^{2C}$ is substituted with one or more first substituent groups denoted by $R^{2C.1}$ as explained in the definitions section above in the description of "first substituent group(s)". In embodiments, when an $R^{2C.1}$ substituent group is substituted, the $R^{2C.1}$ substituent group is substituted with one or more second substituent groups denoted by $R^{2C.2}$ as explained in the definitions section above in the description of "first substituent group(s)". In embodiments, when an $R^{2C.2}$ substituent group is substituted, the $R^{2C.2}$ substituent group is substituted with one or more third substituent groups denoted by $R^{2C.3}$ as explained in the definitions section above in the description of "first substituent group(s)". In the above embodiments, $R^{2C}$, $R^{2C.1}$, $R^{2C.2}$, and $R^{2C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2C}$, $R^{2C.1}$, $R^{2C.2}$, and $R^{2C.3}$ respectively.

In embodiments, when $R^{2D}$ is substituted, $R^{2D}$ is substituted with one or more first substituent groups denoted by $R^{2D.1}$ as explained in the definitions section above in the description of "first substituent group(s)". In embodiments, when an $R^{2D.1}$ substituent group is substituted, the $R^{2D.1}$ substituent group is substituted with one or more second substituent groups denoted by $R^{2D.2}$ as explained in the definitions section above in the description of "first substituent group(s)". In embodiments, when an $R^{2D.2}$ substituent group is substituted, the $R^{2D.2}$ substituent group is substituted with one or more third substituent groups denoted by $R^{2D.3}$ as explained in the definitions section above in the description of "first substituent group(s)". In the above embodiments, $R^{2D}$, $R^{2D.1}$, $R^{2D.2}$, and $R^{2D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2D}$, $R^{2D.1}$, $R^{2D.2}$, and $R^{2D.3}$ respectively.

In embodiments, when $R^{3A}$ is substituted, $R^{3A}$ is substituted with one or more first substituent groups denoted by $R^{3A.1}$ as explained in the definitions section above in the description of "first substituent group(s)". In embodiments, when an $R^{3A.1}$ substituent group is substituted, the $R^{3A.1}$ substituent group is substituted with one or more second substituent groups denoted by $R^{3A.2}$ as explained in the definitions section above in the description of "first substituent group(s)". In embodiments, when an $R^{3A.2}$ substituent group is substituted, the $R^{3A.2}$ substituent group is substituted with one or more third substituent groups denoted by $R^{3A.3}$ as explained in the definitions section above in the description of "first substituent group(s)". In the above embodiments, $R^{3A}$, $R^{3A.1}$, $R^{3A.2}$, and $R^{3A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3A}$, $R^{3A.1}$, $R^{3A.2}$, and $R^{3A.3}$ respectively.

In embodiments, when $R^{3B}$, is substituted, $R^{3B}$ is substituted with one or more first substituent groups denoted by $R^{3B.1}$ as explained in the definitions section above in the description of "first substituent group(s)". In embodiments, when an $R^{3B.1}$ substituent group is substituted, the $R^{3B.1}$ substituent group is substituted with one or more second substituent groups denoted by $R^{3B.2}$ as explained in the definitions section above in the description of "first substituent group(s)". In embodiments, when an $R^{3B.2}$ substituent group is substituted, the $R^{3B.2}$ substituent group is substituted with one or more third substituent groups denoted by $R^{3B.3}$ as explained in the definitions section above in the description of "first substituent group(s)". In the above embodiments, $R^{3B}$, $R^{3B.1}$, $R^{3B.2}$, and $R^{3B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3B}$, $R^{3B.1}$, $R^{3B.2}$, and $R^{3B.3}$ respectively.

In embodiments, when $R^{3A}$ and $R^{3B}$ substituents that are bonded to the same nitrogen atom are joined to form a moiety that is substituted (e.g., a substituted heterocycloalkyl or substituted heteroaryl), the moiety is substituted with one or more first substituent groups denoted by $R^{3A.1}$ as explained in the definitions section above in the description of "first substituent group(s)". In embodiments, when an $R^{3A.1}$ substituent group is substituted, the $R^{3A.1}$ substituent group is substituted with one or more second substituent groups denoted by $R^{3A.2}$ as explained in the definitions section above in the description of "first substituent group(s)". In embodiments, when an $R^{3A.2}$ substituent group is substituted, the $R^{3A.2}$ substituent group is substituted with one or more third substituent groups denoted by $R^{3A.3}$ as explained in the definitions section above in the description of "first substituent group(s)". In the above embodiments, $R^{3A}$, $R^{3A.1}$, $R^{3A.2}$, and $R^{3A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3A}$, $R^{3A.1}$, $R^{3A.2}$, and $R^{3A.3}$, respectively.

In embodiments, when $R^{3A}$ and $R^{3B}$ substituents that are bonded to the same nitrogen atom are joined to form a moiety that is substituted (e.g., a substituted heterocycloalkyl or substituted heteroaryl), the moiety is substituted with one or more first substituent groups denoted by $R^{3B.1}$ as explained in the definitions section above in the description of "first substituent group(s)". In embodiments, when an $R^{3B.1}$ substituent group is substituted, the $R^{3B.1}$ substituent group is substituted with one or more second substituent groups denoted by $R^{3B.2}$ as explained in the definitions section above in the description of "first substituent group(s)". In embodiments, when an $R^{3B.2}$ substituent group is substituted, the $R^{3B.2}$ substituent group is substituted with one or more third substituent groups denoted by $R^{3B.3}$ as explained in the definitions section above in the description of "first substituent group(s)". In the above embodiments, $R^{3B}$, $R^{3B.1}$, $R^{3B.2}$, and $R^{3B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3B}$, $R^{3B.1}$, $R^{3B.2}$, and $R^{3B.3}$, respectively.

In embodiments, when $R^{3A}$ and $R^{3D}$ substituents that are bonded to the same nitrogen atom are joined to form a moiety that is substituted (e.g., a substituted heterocycloalkyl or substituted heteroaryl), the moiety is substituted with one or more first substituent groups denoted by $R^{3A.1}$ as explained in the definitions section above in the description of "first substituent group(s)". In embodiments, when an $R^{3A.1}$ substituent group is substituted, the $R^{3A.1}$ substituent group is substituted with one or more second substituent groups denoted by $R^{3A.2}$ as explained in the definitions section above in the description of "first substituent group(s)". In embodiments, when an $R^{3A.2}$ substituent group is substituted, the $R^{3A.2}$ substituent group is substituted with one or more third substituent groups denoted by $R^{3A.3}$ as explained in the definitions section above in the description of "first substituent group(s)". In the above embodiments, $R^{3A}$, $R^{3A.1}$ $R^{3A.2}$, and $R^{3A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3A}$, $R^{3A.1}$, $R^{3A.2}$, and $R^{3A.3}$, respectively.

In embodiments, when $R^{3A}$ and $R^{3D}$ substituents that are bonded to the same nitrogen atom are joined to form a moiety that is substituted (e.g., a substituted heterocycloalkyl or substituted heteroaryl), the moiety is substituted with one or more first substituent groups denoted by $R^{3D.1}$ as explained in the definitions section above in the description of "first substituent group(s)". In embodiments, when an $R^{3D.1}$ substituent group is substituted, the $R^{3D.1}$ substituent group is substituted with one or more second substituent groups denoted by $R^{3D.2}$ as explained in the definitions section above in the description of "first substituent group(s)". In embodiments, when an $R^{3D.2}$ substituent group is substituted, the $R^{3D.2}$ substituent group is substituted with one or more third substituent groups denoted by $R^{3D.3}$ as explained in the definitions section above in the description of "first substituent group(s)". In the above embodiments, $R^{3D}$, $R^{3D.1}$ $R^{3D.2}$, and $R^{3D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3D}$, $R^{3D.1}$, $R^{3D.2}$, and $R^{3D.3}$, respectively.

In embodiments, when $R^{3C}$ is substituted, $R^{3C}$ is substituted with one or more first substituent groups denoted by $R^{3C.1}$ as explained in the definitions section above in the description of "first substituent group(s)". In embodiments, when an $R^{3C.1}$ substituent group is substituted, the $R^{3C.1}$ substituent group is substituted with one or more second substituent groups denoted by $R^{3C.2}$ as explained in the definitions section above in the description of "first substituent group(s)". In embodiments, when an $R^{3C.2}$ substituent group is substituted, the $R^{3C.2}$ substituent group is substituted with one or more third substituent groups denoted by $R^{3C.3}$ as explained in the definitions section above in the description of "first substituent group(s)". In the above embodiments, $R^{3C}$, $R^{3C.1}$, $R^{3C.2}$, and $R^{3C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3C}$, $R^{3C.1}$, $R^{3C.2}$, and $R^{3C.3}$, respectively.

In embodiments, when $R^{3D}$ is substituted, $R^{3D}$ is substituted with one or more first substituent groups denoted by $R^{3D.1}$ as explained in the definitions section above in the description of "first substituent group(s)". In embodiments, when an $R^{3D.1}$ substituent group is substituted, the $R^{3D.1}$ substituent group is substituted with one or more second substituent groups denoted by $R^{3D.2}$ as explained in the definitions section above in the description of "first substituent group(s)". In embodiments, when an $R^{3D.2}$ substituent group is substituted, the $R^{3D.2}$ substituent group is substituted with one or more third substituent groups denoted by $R^{3D.3}$ as explained in the definitions section above in the description of "first substituent group(s)". In the above embodiments, $R^{3D}$ $R^{3D.1}$, $R^{3D.2}$, and $R^{3D.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3D}$, $R^{3D.1}$, $R^{3D.2}$, and $R^{3D.3}$ respectively.

In embodiments, when $R^4$ is substituted, $R^4$ is substituted with one or more first substituent groups denoted by $R^{4.1}$ as explained in the definitions section above in the description of "first substituent group(s)". In embodiments, when an $R^{4.1}$ substituent group is substituted, the $R^{4.1}$ substituent group is substituted with one or more second substituent groups denoted by $R^{4.2}$ as explained in the definitions section above in the description of "first substituent group(s)". In embodiments, when an $R^{4.2}$ substituent group is substituted, the $R^{4.2}$ substituent group is substituted with one or more third substituent groups denoted by $R^{4.3}$ as explained in the definitions section above in the description of "first substituent group(s)". In the above embodiments, $R^4$, $R^{4.1}$, $R^{4.2}$ and $R^{4.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^4$, $R^{4.1}$, $R^{4.2}$, and $R^{4.3}$, respectively.

In embodiments, when $R^5$ is substituted, $R^5$ is substituted with one or more first substituent groups denoted by $R^{5.1}$ as explained in the definitions section above in the description of "first substituent group(s)". In embodiments, when an $R^{5.1}$ substituent group is substituted, the $R^{5.1}$ substituent group is substituted with one or more second substituent groups denoted by $R^{5.2}$ as explained in the definitions section above in the description of "first substituent group(s)". In embodiments, when an $R^{5.2}$ substituent group is substituted, the $R^{5.2}$ substituent group is substituted with one or more third substituent groups denoted by $R^{5.3}$ as explained in the definitions section above in the description of "first substituent group(s)". In the above embodiments, $R^5$, $R^{5.1}$, $R^{5.2}$ and $R^{5.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^5$, $R^{5.1}$, $R^{5.2}$, and $R^{5.3}$, respectively.

In embodiments, when two $R^4$ and $R^5$ substituents bonded to the same nitrogen are joined to form a moiety that is substituted (e.g., a substituted heterocycloalkyl or substituted heteroaryl), the moiety is substituted with one or more first substituent groups denoted by $R^{4.1}$ as explained in the definitions section above in the description of "first substituent group(s)". In embodiments, when an $R^{4.1}$ substituent group is substituted, the $R^{4.1}$ substituent group is substituted with one or more second substituent groups denoted by $R^{4.2}$ as explained in the definitions section above in the description of "first substituent group(s)". In embodiments, when an $R^{4.2}$ substituent group is substituted, the $R^{4.2}$ substituent group is substituted with one or more third substituent groups denoted by $R^{4.3}$ as explained in the definitions section above in the description of "first substituent group(s)". In the above embodiments, $R^4$, $R^{4.1}$, $R^{4.2}$, and $R^{4.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^4$, $R^{4.1}$, $R^{4.2}$, and $R^{4.3}$, respectively.

In embodiments, when two $R^4$ and $R^5$ substituents bonded to the same nitrogen are joined to form a moiety that is substituted (e.g., a substituted heterocycloalkyl or substituted heteroaryl), the moiety is substituted with one or more first substituent groups denoted by $R^{5.1}$ as explained in the definitions section above in the description of "first substituent group(s)". In embodiments, when an $R^{5.1}$ substituent group is substituted, the $R^{5.1}$ substituent group is substituted with one or more second substituent groups denoted by $R^{5.2}$ as explained in the definitions section above in the description of "first substituent group(s)". In embodiments, when an $R^{5.2}$ substituent group is substituted, the $R^{5.2}$ substituent group is substituted with one or more third substituent groups denoted by $R^{5.3}$ as explained in the definitions section above in the description of "first substituent group(s)". In the above embodiments, $R^5$, $R^{5.1}$, $R^{5.2}$, and $R^{5.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^5$, $R^{5.1}$, $R^{5.2}$, and $R^{5.3}$, respectively.

In embodiments, when $R^6$ is substituted, $R^6$ is substituted with one or more first substituent groups denoted by $R^{6.1}$ as explained in the definitions section above in the description of "first substituent group(s)". In embodiments, when an $R^{6.1}$ substituent group is substituted, the $R^{6.1}$ substituent group is substituted with one or more second substituent groups denoted by $R^{6.2}$ as explained in the definitions section above in the description of "first substituent group(s)". In embodiments, when an $R^{6.2}$ substituent group is substituted, the $R^{6.2}$ substituent group is substituted with one or more third substituent groups denoted by $R^{6.3}$ as explained in the definitions section above in the description of "first substituent group(s)". In the above embodiments, $R^6$, $R^{6.1}$, $R^{6.2}$ and $R^{6.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^6$, $R^{6.1}$, $R^{6.2}$, and $R^{6.3}$, respectively.

In embodiments, when $R^7$ is substituted, $R^7$ is substituted with one or more first substituent groups denoted by $R^{7.1}$ as explained in the definitions section above in the description of "first substituent group(s)". In embodiments, when an $R^{7.1}$ substituent group is substituted, the $R^{7.1}$ substituent group is substituted with one or more second substituent groups denoted by $R^{7.2}$ as explained in the definitions section above in the description of "first substituent group(s)". In embodiments, when an $R^{7.2}$ substituent group is substituted, the $R^{7.2}$ substituent group is substituted with one or more third substituent groups denoted by $R^{7.3}$ as explained in the definitions section above in the description of "first substituent group(s)". In the above embodiments, $R^7$, $R^{7.1}$, $R^{7.2}$ and $R^{7.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^7$, $R^{7.1}$, $R^{7.2}$, and $R^{7.3}$, respectively.

In embodiments, when $R^{20}$ is substituted, $R^{20}$ is substituted with one or more first substituent groups denoted by $R^{20.1}$ as explained in the definitions section above in the description of "first substituent group(s)". In embodiments, when an $R^{20.1}$ substituent group is substituted, the $R^{20.1}$ substituent group is substituted with one or more second substituent groups denoted by $R^{20.2}$ as explained in the definitions section above in the description of "first substituent group(s)". In embodiments, when an $R^{20.2}$ substituent group is substituted, the $R^{20.2}$ substituent group is substituted with one or more third substituent groups denoted by $R^{20.3}$ as explained in the definitions section above in the description of "first substituent group(s)". In the above embodiments, $R^{20}$, $R^{20.1}$, $R^{20.2}$, and $R^{20.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{20}$, $R^{20.1}$, $R^{20.2}$, and $R^{20.3}$ respectively.

In embodiments, when $L^2$ is substituted, $L^2$ is substituted with one or more first substituent groups denoted by $R^{L2.1}$ as explained in the definitions section above in the description of "first substituent group(s)". In embodiments, when an $R^{L2.1}$ substituent group is substituted, the $R^{L2.1}$ substituent group is substituted with one or more second substituent groups denoted by $R^{L2.2}$ as explained in the definitions section above in the description of "first substituent group(s)". In embodiments, when an $R^{L2.2}$ substituent group is substituted, the $R^{L2.2}$ substituent group is substituted with one or more third substituent groups denoted by $R^{L2.3}$ as explained in the definitions section above in the description of "first substituent group(s)". In the above embodiments, $L^2$, $R^{L2.1}$, $R^{L2.2}$, and $R^{L2.3}$ have values corresponding to the values of $L^{WW}$, $R^{LWW.1}$, $R^{LWW.2}$, and $R^{LWW.3}$ respectively, as explained in the definitions section above in the description of "first substituent group(s)", wherein $L^{WW}$, $R^{LWW.1}$, $R^{LWW.2}$, and $R^{LWW.3}$ are $L^2$, $R^{L2.1}$, $R^{L2.2}$, and $R^{L2.3}$, respectively.

In embodiments, when $L^3$ is substituted, $L^3$ is substituted with one or more first substituent groups denoted by $R^{L3.1}$ as explained in the definitions section above in the description of "first substituent group(s)". In embodiments, when an $R^{L3.1}$ substituent group is substituted, the $R^{L3.1}$ substituent group is substituted with one or more second substituent groups denoted by $R^{L3.2}$ as explained in the definitions section above in the description of "first substituent group(s)". In embodiments, when an $R^{L3.2}$ substituent group is substituted, the $R^{L3.2}$ substituent group is substituted with one or more third substituent groups denoted by $R^{L3.3}$ as explained in the definitions section above in the description of "first substituent group(s)". In the above embodiments, $L^3$, $R^{L3.1}$, $R^{L3.2}$, and $R^{L3.3}$ have values corresponding to the values of $L^{WW}$, $R^{LWW.1}$, $R^{LWW.2}$, and $R^{LWW.3}$ respectively, as explained in the definitions section above in the description of "first substituent group(s)", wherein $L^{WW}$, $R^{LWW.1}$, $R^{LWW.2}$, and $R^{LWW.3}$ are $L^3$, $R^{L3.1}$, $R^{L3.2}$, and $R^{L3.3}$, respectively.

In embodiments, $R^1$ is independently halogen, —$CX^1_3$, —$CHX^1_2$, —$CH_2X^1$, —$OCX^1_3$, —$OCH_2X^1$, —$OCHX^1_2$, —CN, —$SO_{n1}R^{1D}$, —$SO_{v1}NR^{1C}R^{1B}$, —$NR^{1C}NR^{1A}R^{1B}$, —$ONR^{1A}R^{1B}$, —$NHC(O)NR^{1C}NR^{1A}R^{1B}$, —$NHC(O)NR^{1A}R^{1B}$, $N(O)_{m1}$, —$NR^{1A}R^{1B}$, —$C(O)R^{1C}$, —$C(O)$—$OR^{1C}$, —$C(O)NR^{1A}R^{1B}$, —$OR^{1D}$, —$NR^{1A}SO_2R^{1D}$, —$NR^{1A}C(O)R^{1C}$, —$NR^{1A}C(O)OR^{1C}$, —$NR^{1A}OR^{1C}$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^1$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group.

In embodiments, two adjacent $R^1$ substituents may optionally be joined to form a substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, when two adjacent $R^1$ substituents are joined to form a moiety that is substituted (e.g., a substituted cycloalkyl, substituted heterocycloalkyl, substituted aryl, or substituted heteroaryl), the moiety is substituted with at least one substituent group, size-limited substituent group, or lower substituent group; wherein if the substituted ring formed when two adjacent $R^1$ substituents are joined is substituted with a plurality of groups selected from substituent groups, size-limited substituent groups, and lower substituent groups; each substituent group, size-limited substituent group, and/or lower substituent group may optionally be different. In embodiments, when the ring formed when two adjacent $R^1$ substituents are joined is substituted, it is substituted with at least one substituent group. In embodiments, when the ring formed when two adjacent $R^1$ substituents are joined is substituted, it is substituted with at least one size-limited substituent group. In embodiments, when the ring formed when two adjacent $R^1$ substituents are joined is substituted, it is substituted with at least one lower substituent group.

In embodiments, $R^{1A}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{1A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1A}$ is substituted with a plurality of groups selected from substituent groups, size-limited substituent groups, and lower substituent groups; each substituent group, size-limited substituent group, and/or lower substituent group may optionally be different. In embodiments, when $R^{1A}$ is substituted, it is substituted with at least one substituent group. In embodiments, when $R^{1A}$ is substituted, it is substituted with at least one size-limited substituent group. In embodiments, when $R^{1A}$ is substituted, it is substituted with at least one lower substituent group.

In embodiments, $R^{1B}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{1B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1B}$ is substituted with a plurality of groups selected from substituent groups, size-limited substituent groups, and lower substituent groups; each substituent group, size-limited substituent group, and/or lower substituent group may optionally be different. In embodiments, when $R^{1B}$ is substituted, it is substituted with at least one substituent group. In embodiments, when $R^{1B}$ is substituted, it is substituted with at least one size-limited substituent group. In embodiments, when Rm is substituted, it is substituted with at least one lower substituent group.

In embodiments, $R^{1A}$ and $R^{1B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

In embodiments, a substituted ring formed when $R^{1A}$ and $R^{1B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{1A}$ and $R^{1B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{1A}$ and $R^{1B}$ substituents bonded to the same nitrogen atom are joined is substituted, it is substituted with at least one substituent group. In embodiments, when the substituted ring formed when $R^{1A}$ and $R^{1B}$ substituents bonded to the same nitrogen atom are joined is substituted, it is substituted with at least one size-limited substituent group. In embodiments, when the substituted ring formed when $R^{1A}$ and $R^{1B}$ substituents bonded to the same nitrogen atom are joined is substituted, it is substituted with at least one lower substituent group.

In embodiments, $R^{1C}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted R (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1C}$ is substituted with a plurality of groups selected from substituent groups, size-limited substituent groups, and lower substituent groups; each substituent group, size-limited substituent group, and/or lower substituent group may optionally be different. In embodiments, when $R^{1C}$ is substituted, it is substituted with at least one substituent group. In embodiments, when $R^{1C}$ is substituted, it is substituted with at least one size-limited substituent group. In embodiments, when $R^{1C}$ is substituted, it is substituted with at least one lower substituent group.

In embodiments, $R^{1D}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_2$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{1D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{1D}$ is substituted with a plurality of groups selected from substituent groups, size-limited substituent groups, and lower substituent groups; each substituent group, size-limited substituent group, and/or lower substituent group may optionally be different. In embodiments, when $R^{1D}$ is substituted, it is substituted with at least one substituent group. In embodiments, when $R^{1D}$ is substituted, it is substituted with at least one size-limited substituent group. In embodiments, when $R^{1D}$ is substituted, it is substituted with at least one lower substituent group.

In embodiments, $R^2$ is independently oxo, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_{v2}NR^{2A}R^{2B}$, —$NR^{2C}NR^{2A}R^{2B}$, —$ONR^{2A}R^{2B}$, —$NHC(O)NR^{2C}NR^{2A}R^{2B}$, —$NHC(O)NR^{2A}R^{2B}$, —$N(O)_{m2}$, —$NR^{2A}R^{2B}$, —$C(O)R^{2C}$, —$C(O)$—$OR^{2C}$, —$C(O)NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^2$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group;

wherein if the substituted $R^2$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^2$ is substituted, it is substituted with at least one lower substituent group.

In embodiments, two adjacent $R^2$ substituents may optionally be joined to form a substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, when two adjacent $R^2$ substituents are joined to form a moiety that is substituted (e.g., a substituted cycloalkyl, substituted heterocycloalkyl, substituted aryl, or substituted heteroaryl), the moiety is substituted with at least one substituent group, size-limited substituent group, or lower substituent group; wherein if the substituted ring formed when two adjacent $R^2$ substituents are joined is substituted with a plurality of groups selected from substituent groups, size-limited substituent groups, and lower substituent groups; each substituent group, size-limited substituent group, and/or lower substituent group may optionally be different. In embodiments, when the ring formed when two adjacent $R^2$ substituents are joined is substituted, it is substituted with at least one substituent group. In embodiments, when the ring formed when two adjacent $R^2$ substituents are joined is substituted, it is substituted with at least one size-limited substituent group. In embodiments, when the ring formed when two adjacent $R^2$ substituents are joined is substituted, it is substituted with at least one lower substituent group.

In embodiments, $R^{2A}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{2A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2A}$ is substituted with a plurality of groups selected from substituent groups, size-limited substituent groups, and lower substituent groups; each substituent group, size-limited substituent group, and/or lower substituent group may optionally be different. In embodiments, when $R^{2A}$ is substituted, it is substituted with at least one substituent group. In embodiments, when $R^{1A}$ is substituted, it is substituted with at least one size-limited substituent group. In embodiments, when $R^{2A}$ is substituted, it is substituted with at least one lower substituent group.

In embodiments, $R^{2B}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{2B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2B}$ is substituted with a plurality of groups selected from substituent groups, size-limited substituent groups, and lower substituent groups; each substituent group, size-limited substituent group, and/or lower substituent group may optionally be different. In embodiments, when $R^{2B}$ is substituted, it is substituted with at least one substituent group. In embodiments, when $R^{2B}$ is substituted, it is substituted with at least one size-limited substituent group. In embodiments, when $R^{2B}$ is substituted, it is substituted with at least one lower substituent group.

In embodiments, $R^{2A}$ and $R^{2B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

In embodiments, a substituted ring formed when $R^{2A}$ and $R^{2B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{2A}$ and $R^{2B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{2A}$ and $R^{2B}$ substituents bonded to the same nitrogen atom are joined is substituted, it is substituted with at least one substituent group. In embodiments, when the substituted ring formed when $R^{2A}$ and $R^{2B}$ substituents bonded to the same nitrogen atom are joined is substituted, it is substituted with at least one size-limited substituent group. In embodiments, when the substituted ring formed when $R^{2A}$ and $R^{2B}$ substituents bonded to the same nitrogen atom are joined is substituted, it is substituted with at least one lower substituent group.

In embodiments, $R^{2C}$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —NH$_2$, —COOH, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, a substituted $R^{2C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2C}$ is substituted with a plurality of groups selected from substituent groups, size-limited substituent groups, and lower substituent groups; each substituent group, size-limited substituent group, and/or lower substituent group may optionally be different. In embodiments, when $R^{2C}$ is substituted, it is substituted with at least one substituent group. In embodiments, when $R^{2C}$ is substituted, it is substituted with at least one size-limited substituent group. In embodiments, when $R^{2C}$ is substituted, it is substituted with at least one lower substituent group.

In embodiments, $R^{2D}$ is independently hydrogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_5$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, a substituted $R^{2D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{2D}$ is substituted with a plurality of groups selected from substituent groups, size-limited substituent groups, and lower substituent groups; each substituent group, size-limited substituent group, and/or lower substituent group may optionally be different. In embodiments, when $R^{2D}$ is substituted, it is substituted with at least one substituent group. In embodiments, when $R^{2D}$ is substituted, it is substituted with at least one size-limited substituent group. In embodiments, when $R^{2D}$ is substituted, it is substituted with at least one lower substituent group.

In embodiments, $R^{3A}$ is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_1$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, a substituted $R^{3A}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3A}$ is substituted with a plurality of groups selected from substituent groups, size-limited substituent groups, and lower substituent groups; each substituent group, size-limited substituent group, and/or lower substituent group may optionally be different. In embodiments, when $R^{3A}$ is substituted, it is substituted with at least one substituent group. In embodiments, when $R^{3A}$ is substituted, it is substituted with at least one size-limited substituent group. In embodiments, when $R^{3A}$ is substituted, it is substituted with at least one lower substituent group.

In embodiments, $R^{3B}$, is independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl (e.g., C$_1$-C$_8$, C$_1$-C$_6$, C$_1$-C$_4$, or C$_1$-C$_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., C$_3$-C$_8$, C$_3$-C$_6$, C$_4$-C$_6$, or C$_1$-C$_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., C$_6$-C$_{10}$ or phenyl), or substituted or unsubstituted heteroaryl (e.g., 5 to 10 membered, 5 to 9 membered, or 5 to 6 membered).

In embodiments, a substituted $R^{3B}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3B}$ is substituted with a plurality of groups selected from substituent groups, size-limited substituent groups, and lower substituent groups; each substituent group, size-limited substituent group, and/or lower substituent group may optionally be different. In embodiments, when $R^{3B}$ is substituted, it is substituted with at least one substituent group. In embodiments, when $R^{3B}$ is substituted, it is substituted with at least one size-limited substituent group. In embodiments, when $R^{3B}$ is substituted, it is substituted with at least one lower substituent group.

In embodiments, $R^{3A}$ and $R^{3B}$ substituents bonded to the same nitrogen atom may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

In embodiments, a substituted ring formed when $R^{3A}$ and $R^{3B}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{3A}$ and $R^{3B}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{3A}$ and $R^{3B}$ substituents bonded to the same nitrogen atom are joined is substituted, it is substituted with at least one substituent group. In embodiments, when the substituted ring formed when $R^{3A}$ and $R^{3B}$ substituents bonded to the same nitrogen atom are joined is substituted, it is substituted with at least one size-limited substituent group. In embodiments, when the substituted ring formed when $R^{3A}$ and $R^{3B}$ substituents bonded to the same nitrogen atom are joined is substituted, it is substituted with at least one lower substituent group.

In embodiments, $R^{3A}$ and $R^{3D}$ substituents may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

In embodiments, a substituted ring formed when $R^{3A}$ and $R^{3D}$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^{3A}$ and $R^{3D}$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^{3A}$ and $R^{3D}$ substituents bonded to the same nitrogen atom are joined is substituted, it is substituted with at least one substituent group. In embodiments, when the substituted ring formed when $R^{3A}$ and $R^{3D}$ substituents bonded to the same nitrogen atom are joined is substituted, it is substituted with at least one size-limited substituent group. In embodiments, when the substituted ring formed when $R^{3A}$ and $R^{3D}$ substituents bonded to the same nitrogen atom are joined is substituted, it is substituted with at least one lower substituent group.

In embodiments, $R^{3C}$ is independently hydrogen, oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —$CN$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SO_2CH_3$, —$NHC(O)CH_3$, —$C(O)CH_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_1$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{3C}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3C}$ is substituted with a plurality of groups selected from substituent groups, size-limited substituent groups, and lower substituent groups; each substituent group, size-limited substituent group, and/or lower substituent group may optionally be different. In embodiments, when $R^{3C}$ is substituted, it is substituted with at least one substituent group. In embodiments, when $R^{3C}$ is substituted, it is substituted with at least one size-limited substituent group. In embodiments, when $R^{3C}$ is substituted, it is substituted with at least one lower substituent group.

In embodiments, $R^{3D}$ is independently hydrogen, oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —$CN$, —$OH$, —$NH_2$, —$COOH$, —$CONH_2$, —$NO_2$, —$SH$, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —$NHOH$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SO_2CH_3$, —$NHC(O)CH_3$, —$C(O)CH_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_1$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^{3D}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{3D}$ is substituted with a plurality of groups selected from substituent groups, size-limited substituent groups, and lower substituent groups; each substituent group, size-limited substituent group, and/or lower substituent group may optionally be different. In embodiments, when $R^{3D}$ is substituted, it is substituted with at least one substituent group. In embodiments, when $R^{3D}$ is substituted, it is substituted with at least one size-limited substituent group. In embodiments, when $R^{3D}$ is substituted, it is substituted with at least one lower substituent group.

In embodiments, $R^4$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —$CN$, —$OH$, —$NH_2$, —$COOH$, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^4$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^4$ is substituted with a plurality of groups selected from substituent groups, size-limited substituent groups, and lower substituent groups; each substituent group, size-limited substituent group, and/or lower substituent group may optionally be different. In embodiments, when $R^4$ is substituted, it is substituted with at least one substituent group. In embodiments, when $R^4$ is substituted, it is substituted with at least one size-limited substituent group. In embodiments, when $R^4$ is substituted, it is substituted with at least one lower substituent group.

In embodiments, $R^5$ is independently hydrogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_5$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^5$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^5$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

In embodiments, $R^4$ and $R^5$ substituents bonded to the same nitrogen may optionally be joined to form a substituted or unsubstituted heterocycloalkyl (e.g., 3 to 8 membered, 3 to 6 membered, 4 to 6 membered, 4 to 5 membered, or 5 to 6 membered) or substituted or unsubstituted heteroaryl (e.g., 5 to 10 membered, 5 to 9 membered, or 5 to 6 membered).

In embodiments, a substituted ring formed when $R^4$ and $R^5$ substituents bonded to the same nitrogen atom are joined (e.g., substituted heterocycloalkyl and/or substituted heteroaryl) is substituted with at least one substituent group, size-limited substituent group, or lower substituent group; wherein if the substituted ring formed when $R^4$ and $R^5$ substituents bonded to the same nitrogen atom are joined is substituted with a plurality of groups selected from substituent groups, size-limited substituent groups, and lower substituent groups; each substituent group, size-limited substituent group, and/or lower substituent group may optionally be different. In embodiments, when the substituted ring formed when $R^4$ and $R^5$ substituents bonded to the same nitrogen atom are joined is substituted, it is substituted with at least one substituent group. In embodiments, when the substituted ring formed when $R^4$ and $R^5$ substituents bonded to the same nitrogen atom are joined is substituted, it is substituted with at least one size-limited substituent group. In embodiments, when the substituted ring formed when $R^4$ and $R^5$ substituents bonded to the same nitrogen atom are joined is substituted, it is substituted with at least one lower substituent group.

In embodiments, $R^6$ is independently hydrogen, halogen, —$CX^6_3$, —$CHX^6_2$, —$CH_2X^6$, —$OCX^6_3$, —$OCH_2X^6$, —$OCHX^6_2$, —CN, —$SO_{n6}H$, —$SO_{v6}NH_2$, —$NHNH_2$, —$ONH_2$, —$NHC(O)NHNH_2$, —$NHC(O)NH_2$, —$N(O)_{m6}$, —$NH_2$, —$C(O)H$, —COOH, —$C(O)NH_2$, —OH, —$NHSO_2H$, —$NHC(O)H$, —$NHC(O)OH$, —NHOH, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_1$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^6$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^6$ is substituted with a plurality of groups selected from substituent groups, size-limited substituent groups, and lower substituent groups; each substituent group, size-limited substituent group, and/or lower substituent group may optionally be different. In embodiments, when $R^6$ is substituted, it is substituted with at least one substituent group. In embodiments, when $R^6$ is substituted, it is substituted with at least one size-limited substituent group. In embodiments, when $R^6$ is substituted, it is substituted with at least one lower substituent group.

In embodiments, $R^7$ is independently hydrogen halogen, —$CX^7_3$, —$CHX^7_2$, —$CH_2X^7$, —$OCX^7_3$, —$OCH_2X^7$, —$OCHX^7_2$, —CN, —$SO_{n7}H$, —$SO_{v7}NH$, —$NHNH_2$, —$ONH_2$, —$NHC(O)NHNH_2$, —$NHC(O)NH_2$, —$N(O)_{m7}$, —$NH_2$, —$C(O)H$, —COOH, —$C(O)NH_2$, —OH, —$NHSO_2H$, —$NHC(O)H$, —$NHC(O)OH$, —NHOH, —$N_3$, substituted or unsubstituted alkyl (e.g., $C_1$-$C_8$, $C_1$-$C_6$, $C_1$-$C_4$, or $C_1$-$C_2$), substituted or unsubstituted heteroalkyl (e.g., 2 to 8 membered, 2 to 6 membered, 4 to 6 membered, 2 to 3 membered, or 4 to 5 membered), substituted or unsubstituted cycloalkyl (e.g., $C_3$-$C_8$, $C_3$-$C_6$, $C_4$-$C_6$, or $C_1$-$C_6$), substituted or unsubstituted heterocycloalkyl (e.g., 3 to 8 membered, 3 to 6 membered, 4 to 6 membered, 4 to 5 membered, or 5 to 6 membered), substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered).

In embodiments, a substituted $R^7$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^7$ is substituted with a plurality of groups selected from substituent groups, size-limited substituent groups, and lower substituent groups; each substituent group, size-limited substituent group, and/or lower substituent group may optionally be different. In embodiments, when $R^7$ is substituted, it is substituted with at least one substituent group. In embodiments, when $R^7$ is substituted, it is substituted with at least one size-limited substituent group. In embodiments, when $R^7$ is substituted, it is substituted with at least one lower substituent group.

In embodiments, $R^{20}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted C$_1$-C$_6$ alkyl (e.g., C$_1$-C$_6$, C$_1$-C$_4$, or C$_1$-C$_2$), unsubstituted 2 to 6 membered heteroalkyl (e.g., 2 to 6 membered, 4 to 6 membered, 2 to 3 membered, or 4 to 5 membered), unsubstituted C$_3$-C$_6$ cycloalkyl (e.g., C$_3$-C$_6$, C$_4$-C$_6$, or C$_1$-C$_6$), unsubstituted 3 to 6 membered heterocycloalkyl (e.g., 3 to 6 membered, 4 to 6 membered, 4 to 5 membered, or 5 to 6 membered), unsubstituted phenyl, or unsubstituted 5 to 6 membered heteroaryl.

In embodiments, a substituted $R^{20}$ (e.g., substituted alkyl, substituted heteroalkyl, substituted cycloalkyl, substituted heterocycloalkyl, substituted aryl, and/or substituted heteroaryl) is substituted with at least one substituent group, size-limited substituent group, or lower substituent group; wherein if the substituted $R^{20}$ is substituted with a plurality of groups selected from substituent groups, size-limited substituent groups, and lower substituent groups; each substituent group, size-limited substituent group, and/or lower substituent group may optionally be different. In embodiments, when $R^{20}$ is substituted, it is substituted with at least one substituent group. In embodiments, when $R^{20}$ is substituted, it is substituted with at least one size-limited substituent group. In embodiments, when $R^{20}$ is substituted, it is substituted with at least one lower substituent group.

In embodiments, $L^2$ is a bond, —NH—, —O—, —S—, —C(O)—, —C(O)NH—, —NHC(O)—, —NHC(O)NH—, —C(O)O—, —OC(O)—, substituted or unsubstituted alkylene (e.g., C$_1$-C$_{10}$, C$_1$-C$_8$, C$_1$-C$_6$, C$_1$-C$_4$, C$_1$-C$_2$, C$_2$-C$_{10}$, C$_2$-C$_8$, C$_2$-C$_6$, or C$_2$-C$_4$), substituted or unsubstituted heteroalkylene (e.g., 2 to 8 membered, 2 to 6 membered, 4 to 6 membered, 2 to 3 membered, or 4 to 5 membered), substituted or unsubstituted cycloalkylene (e.g., C$_3$—CI, C$_3$-C$_8$, C$_3$-C$_6$, C$_4$-C$_6$, or C$_1$-C$_6$), substituted or unsubstituted heterocycloalkylene (e.g., 3 to 8 membered, 3 to 6 membered, 4 to 6 membered, 4 to 5 membered, or 5 to 6 membered), substituted or unsubstituted arylene (e.g., C$_6$-C$_1$ or phenylene), or substituted or unsubstituted heteroarylene (e.g., 5 to 10 membered, 5 to 9 membered, or 5 to 6 membered).

In embodiments, a substituted $L^2$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^2$ is substituted with a plurality of groups selected from substituent groups, size-limited substituent groups, and lower substituent groups; each substituent group, size-limited substituent group, and/or lower substituent group may optionally be different. In embodiments, when $L^2$ is substituted, it is substituted with at least one substituent group. In embodiments, when $L^2$ is substituted, it is substituted with at least one size-limited substituent group. In embodiments, when $L^2$ is substituted, it is substituted with at least one lower substituent group.

In embodiments, $L^3$ is a bond, —NH—, —O—, —C(O)—, —C(O)NH—, —NHC(O)—, —NHC(O)NH—, —C(O)O—, —OC(O)—, —S(O)—, —SO$_2$—, P(O)—, —P(O)$_2$—, —P(S)—, —NHSO$_2$—, —SO$_2$NH—, —SO$_2$CH$_2$—, —SO$_2$CH$_2$P(O)—, substituted or unsubstituted alkylene (e.g., C$_1$-C$_{10}$, C$_1$-C$_8$, C$_1$-C$_6$, C$_1$-C$_4$, C$_1$-C$_2$, C$_2$-C$_{10}$, C$_2$-C$_8$, C$_2$-C$_6$, or C$_2$-C$_4$), or substituted or unsubstituted heteroalkylene (e.g., 2 to 8 membered, 2 to 6 membered, 4 to 6 membered, 2 to 3 membered, or 4 to 5 membered).

In embodiments, a substituted $L^3$ (e.g., substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted $L^3$ is substituted with a plurality of groups selected from substituent groups, size-limited substituent groups, and lower substituent groups; each substituent group, size-limited substituent group, and/or lower substituent group may optionally be different. In embodiments, when $L^3$ is substituted, it is substituted with at least one substituent group. In embodiments, when $L^3$ is substituted, it is substituted with at least one size-limited substituent group. In embodiments, when $L^3$ is substituted, it is substituted with at least one lower substituent group.

In embodiments, the compound is a compound described herein. In embodiments, the compound, or salt (e.g., pharmaceutically acceptable salt) thereof, is the compound. In embodiments, the compound, or a salt (e.g., pharmaceutically acceptable salt) thereof, is the salt (e.g., pharmaceutically acceptable salt) of the compound. In embodiments, the compound, or a salt (e.g., pharmaceutically acceptable salt) thereof, is the pharmaceutically acceptable salt of the compound.

In embodiments, the compound is:

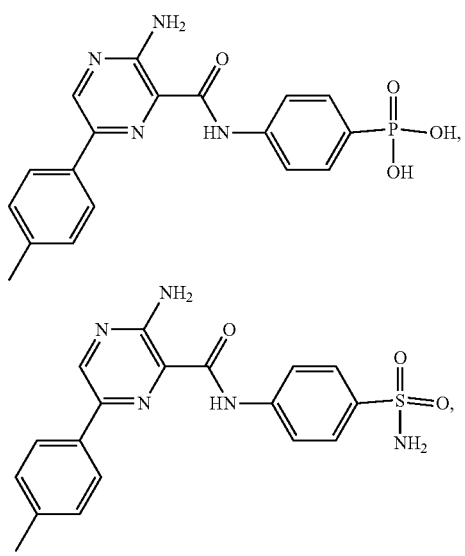

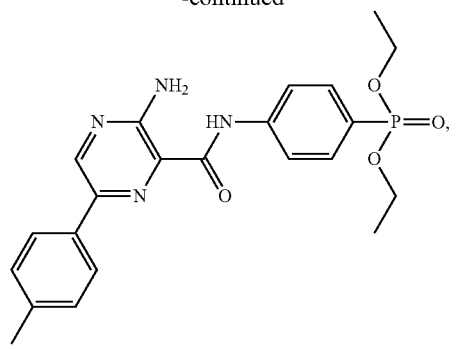
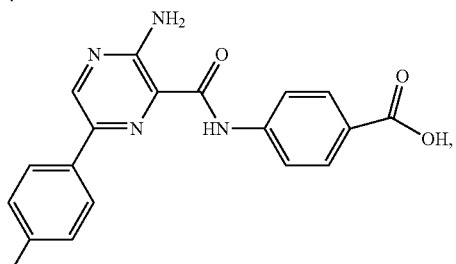
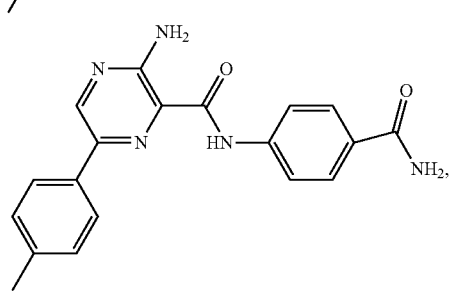
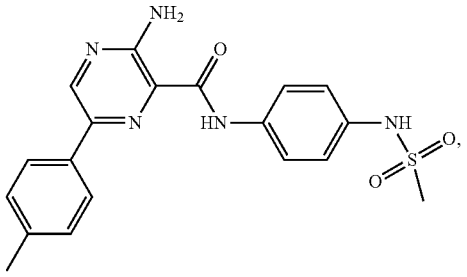
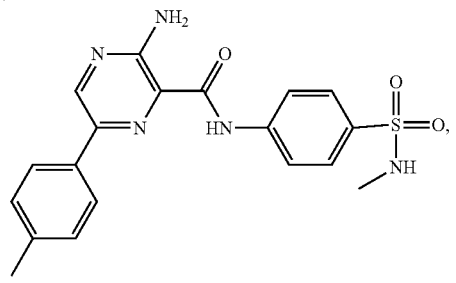
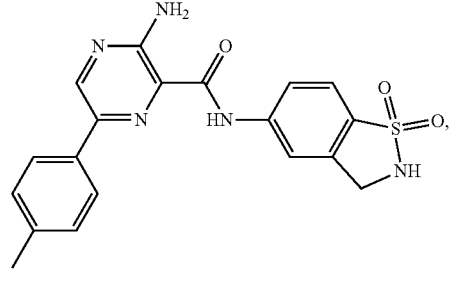
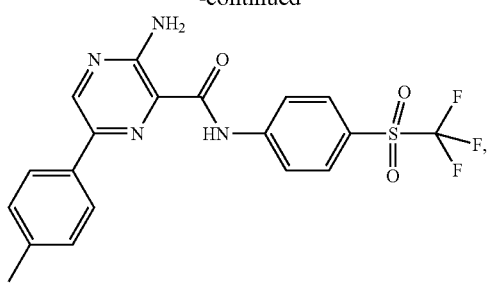
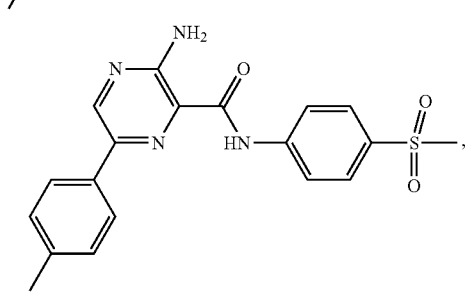
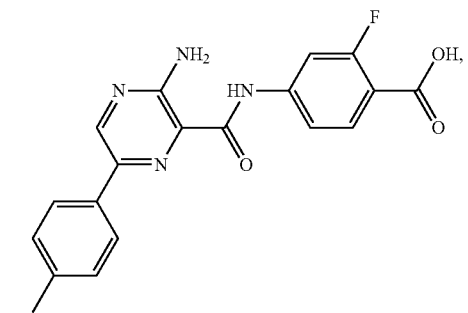
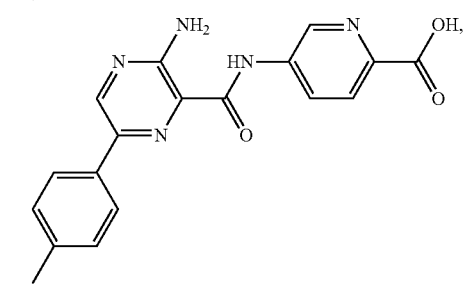
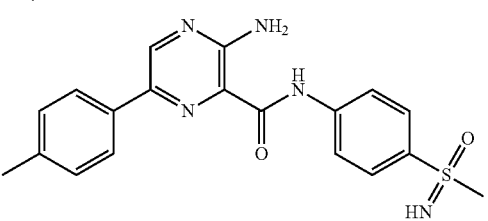
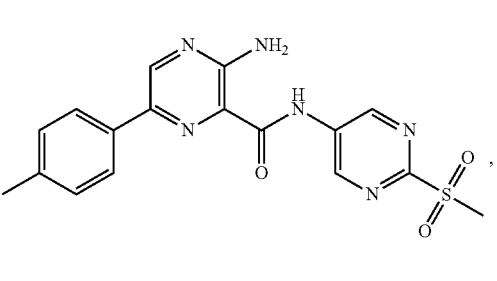

-continued
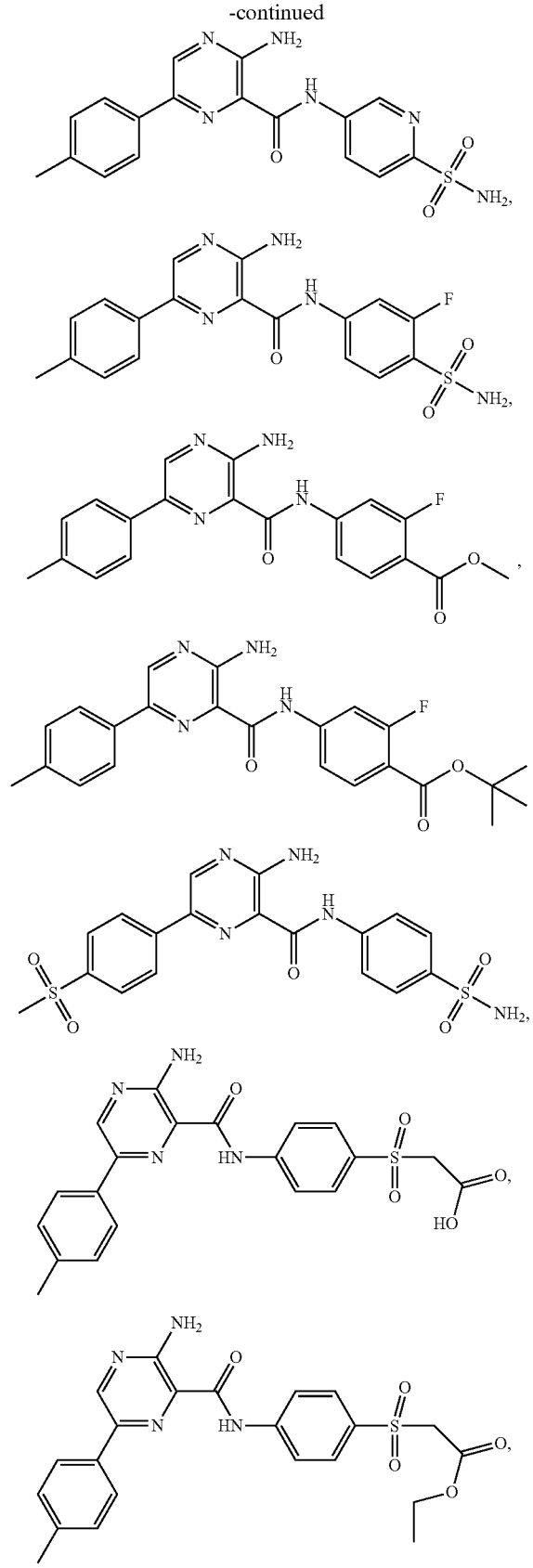
-continued
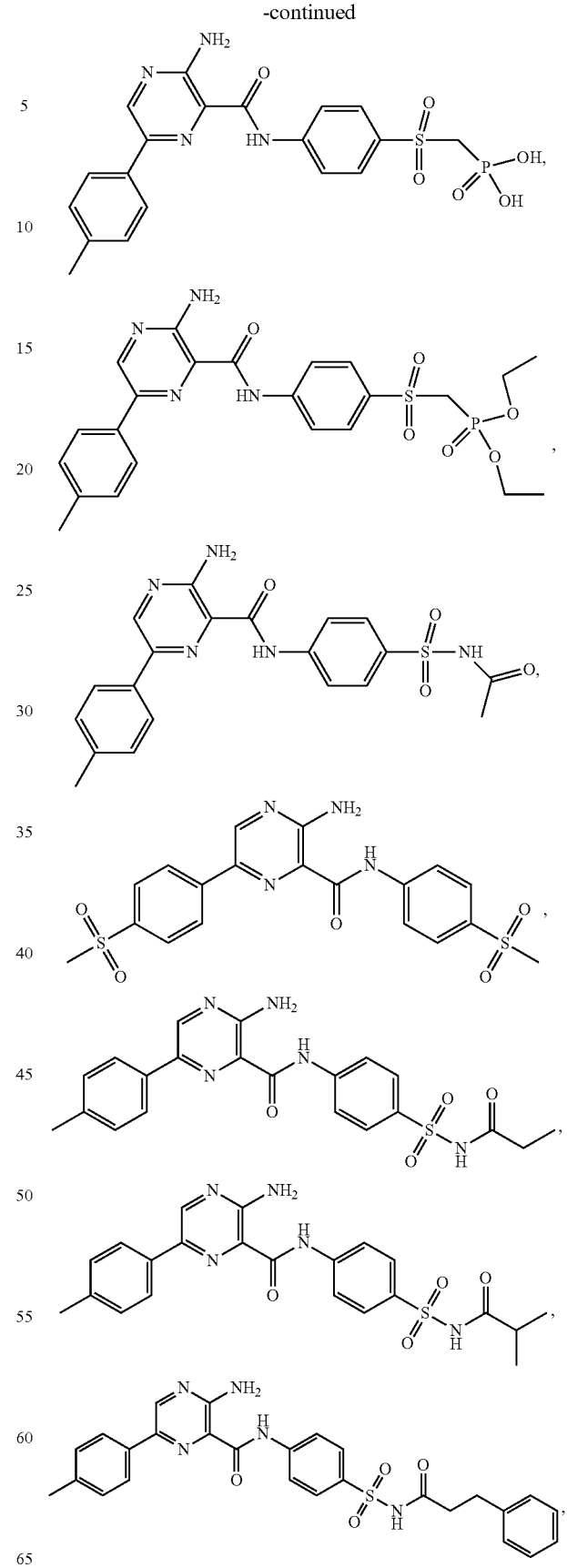

-continued
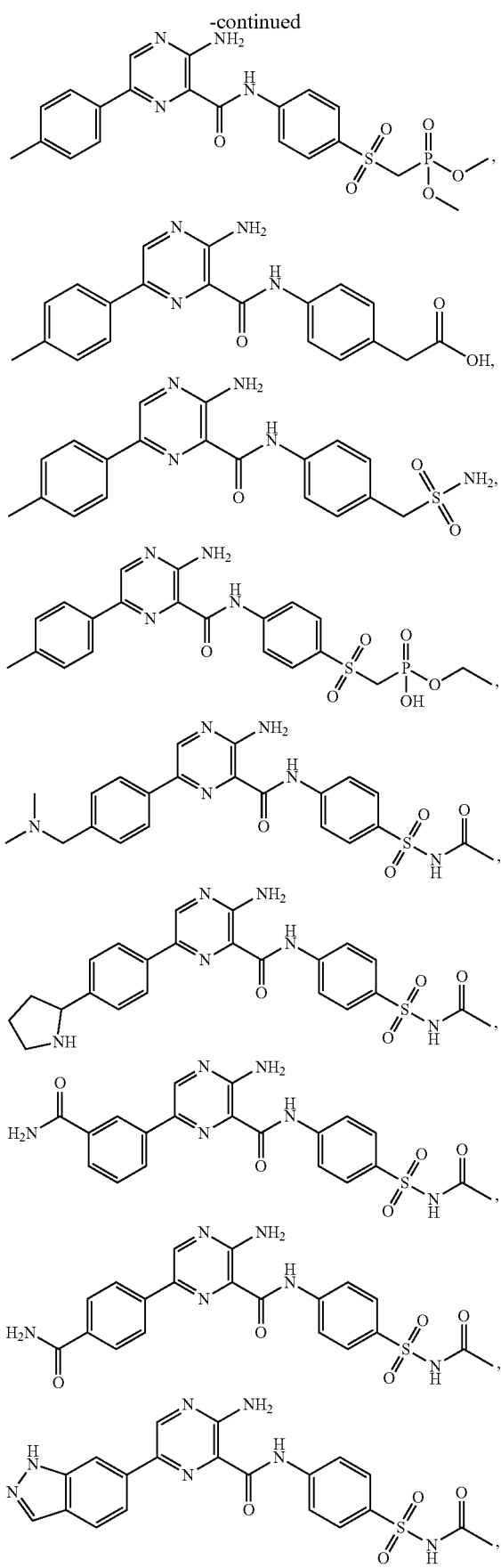
-continued
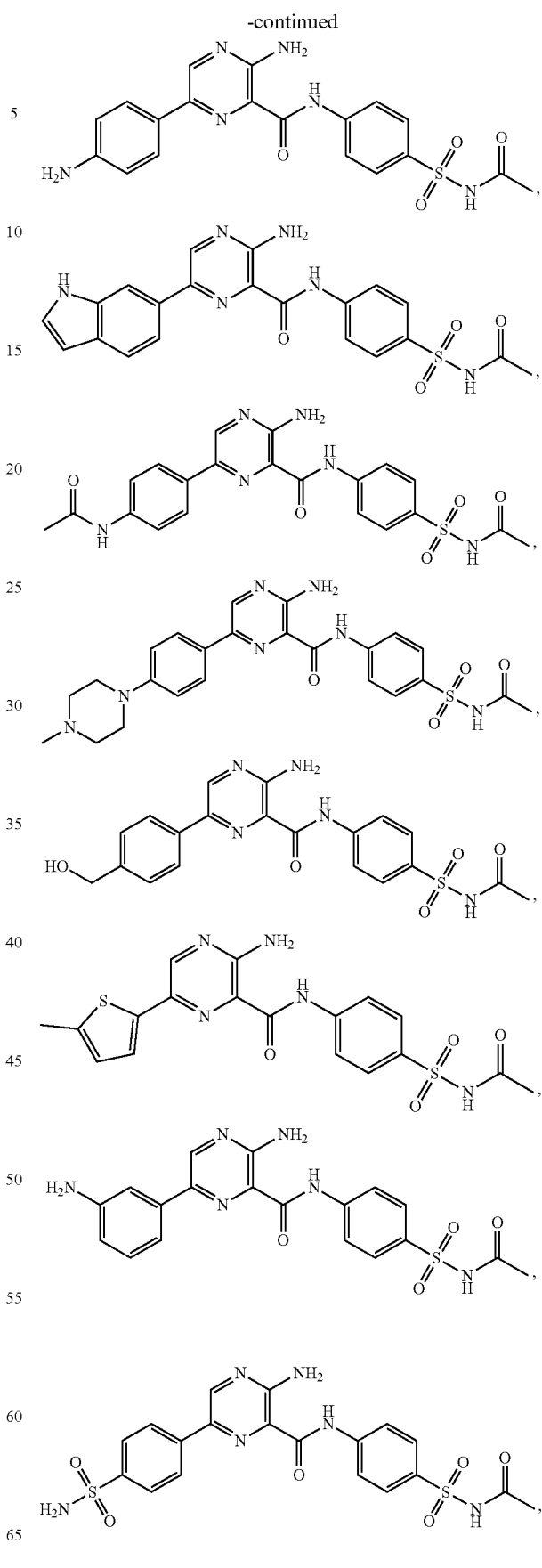

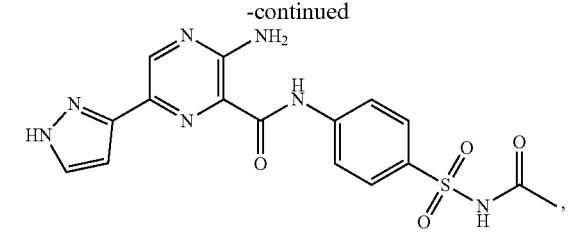
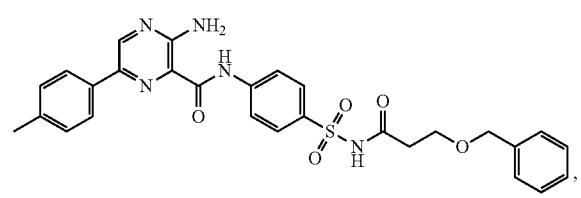
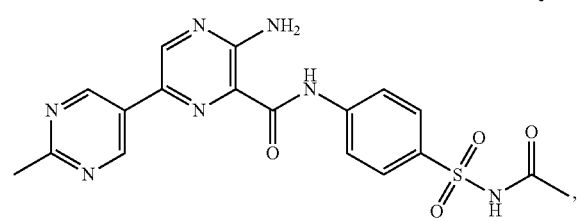
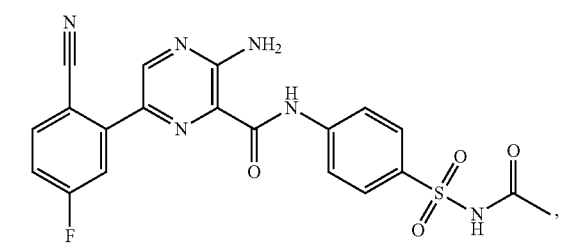
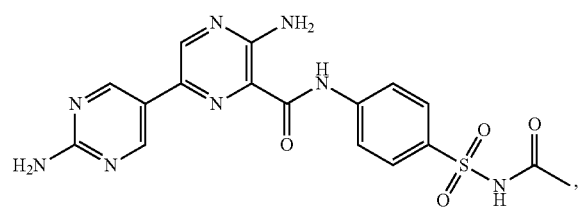
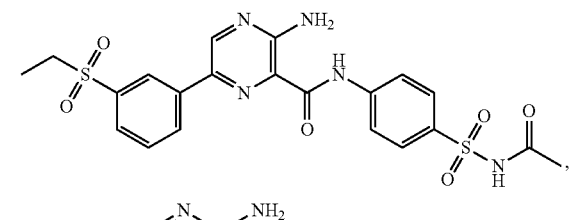
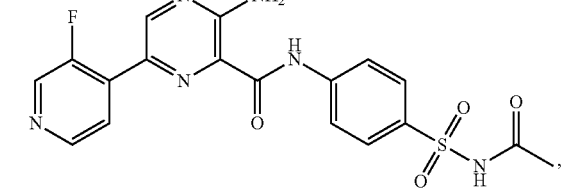
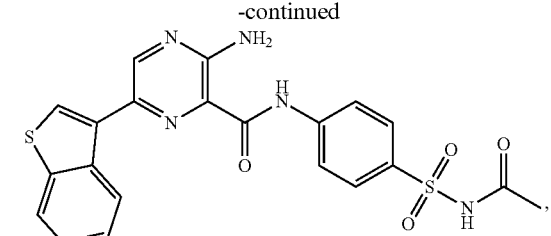
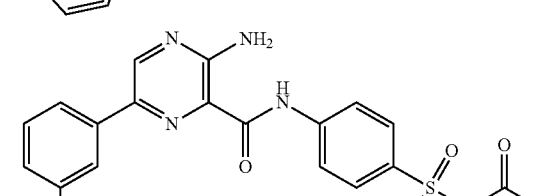
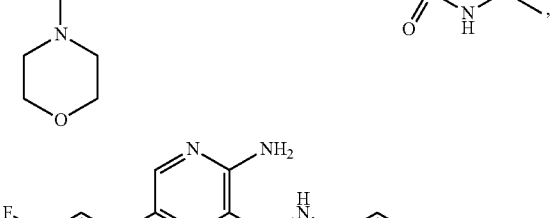
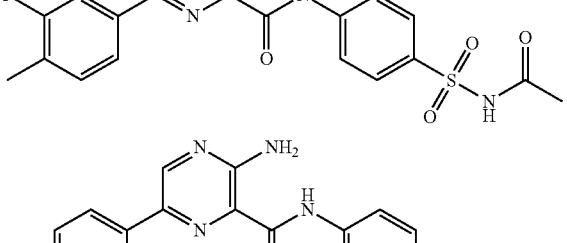
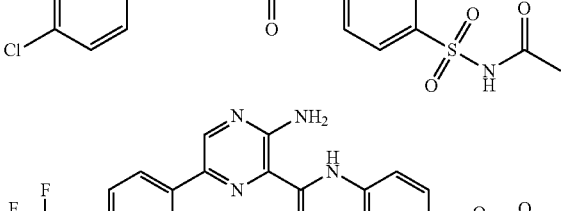
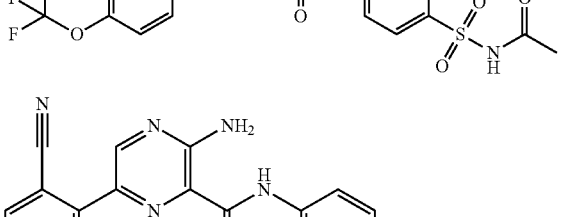
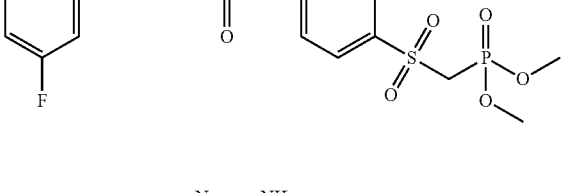
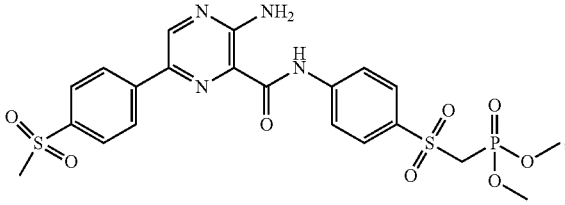

181
-continued
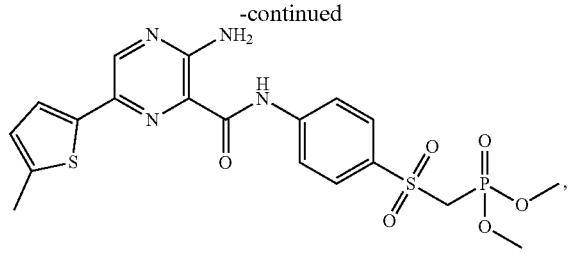
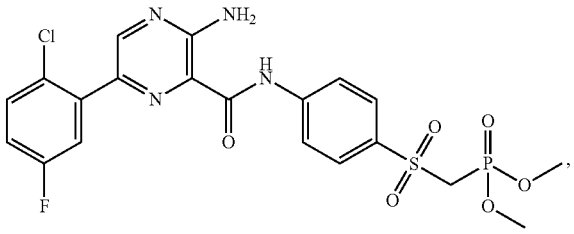
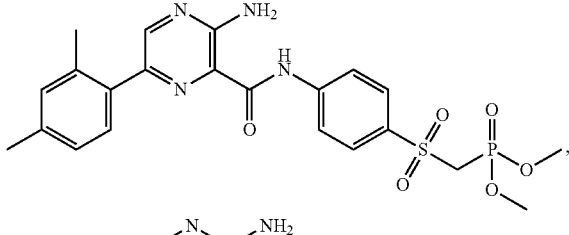
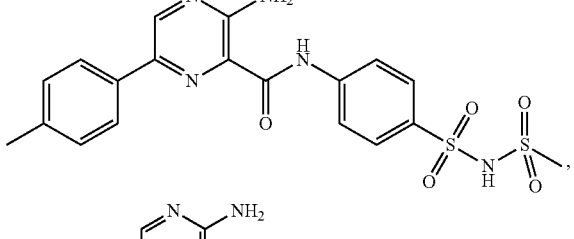
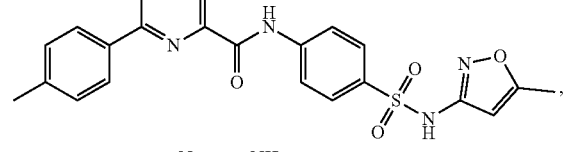
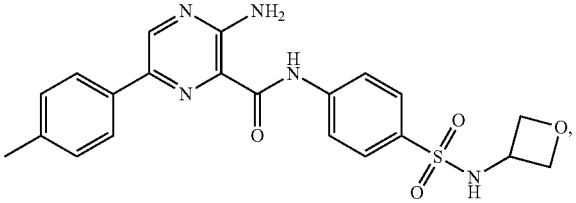
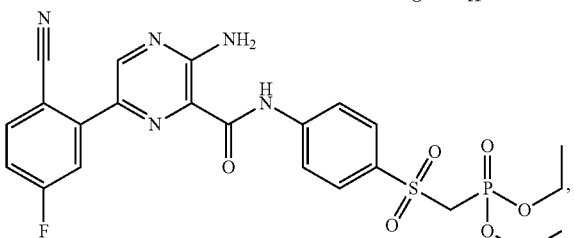
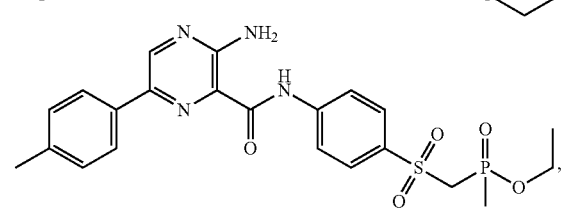
182
-continued
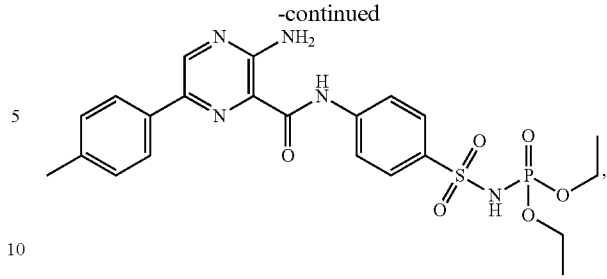
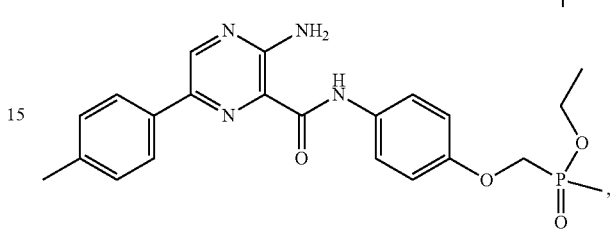
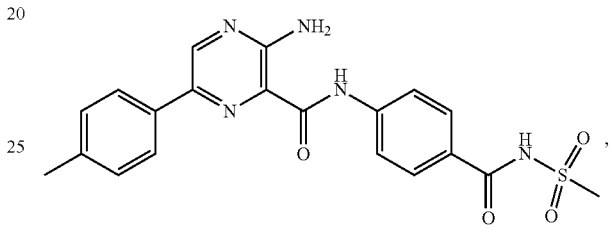

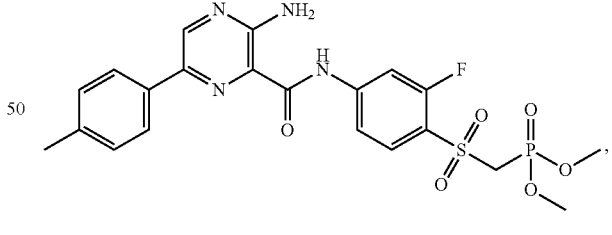
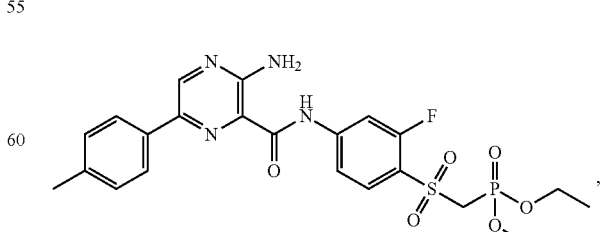
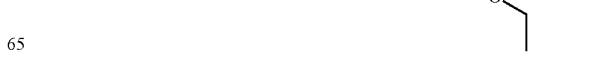

-continued
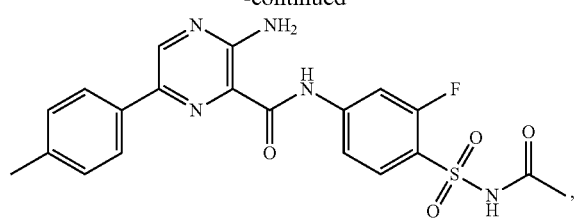
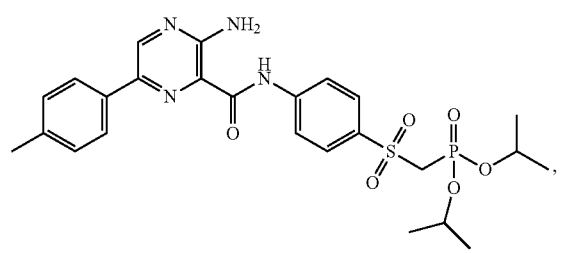
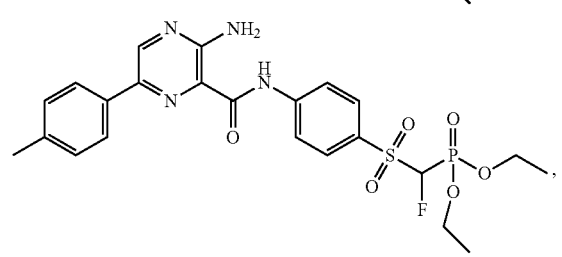
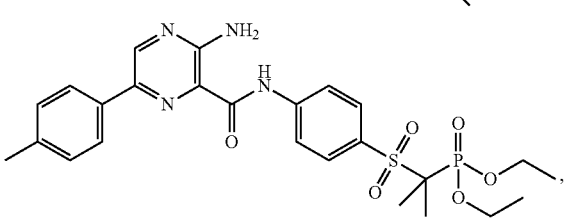
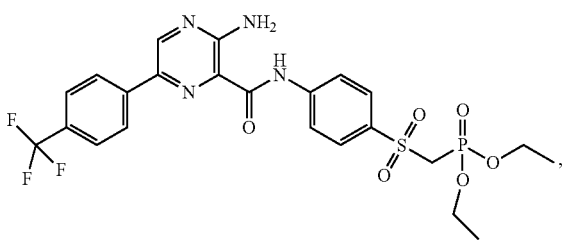
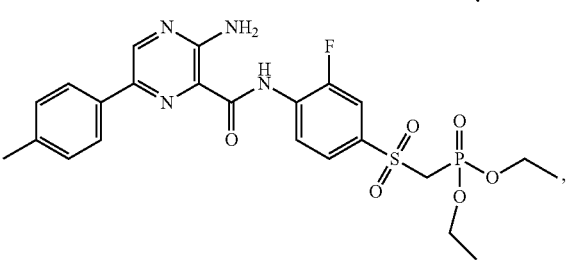
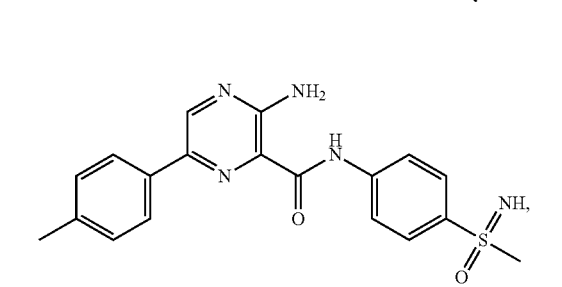
-continued
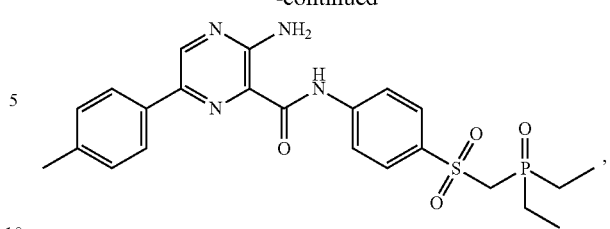
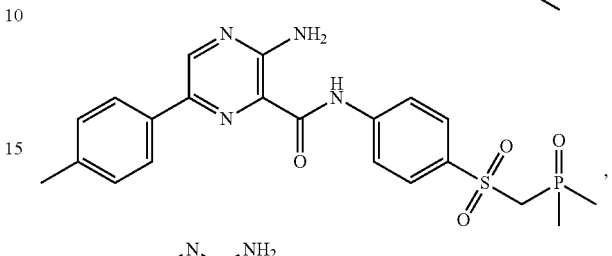
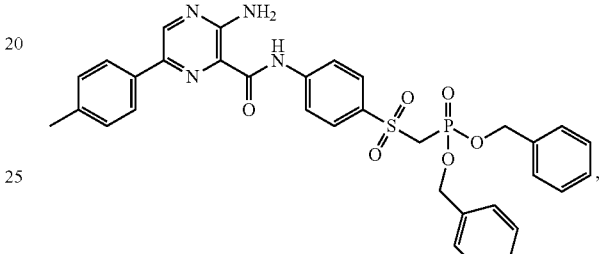
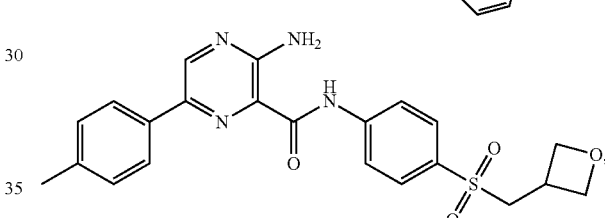
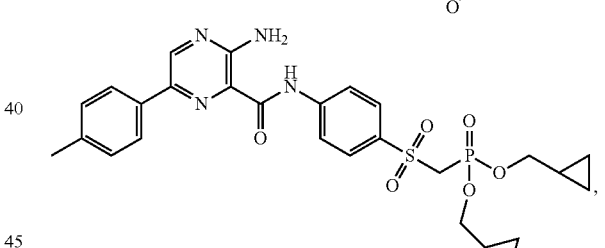
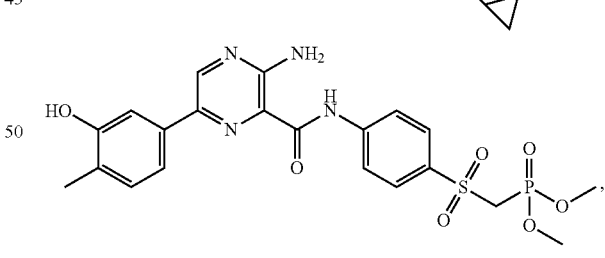
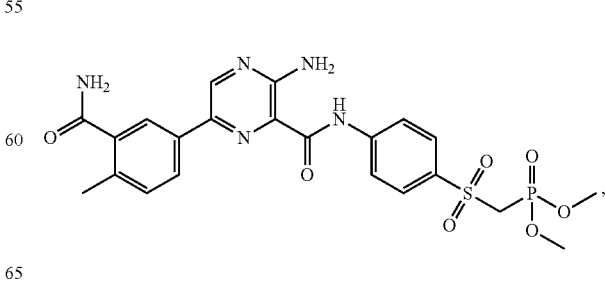

-continued
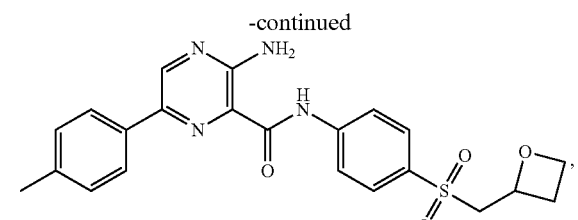
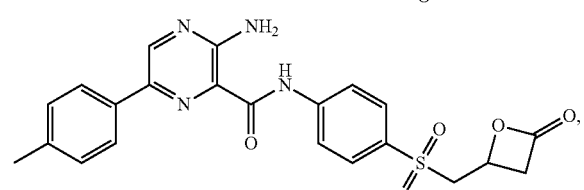
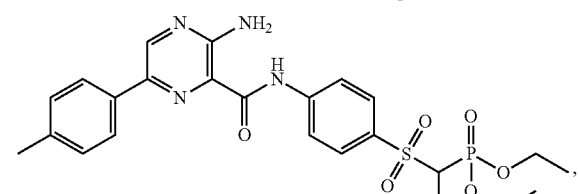
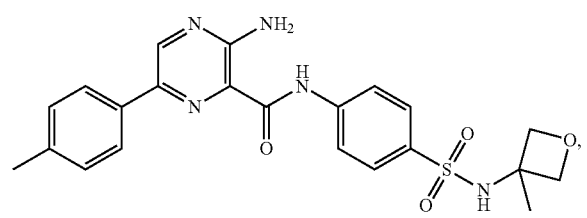
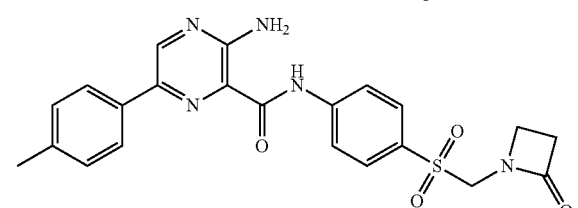
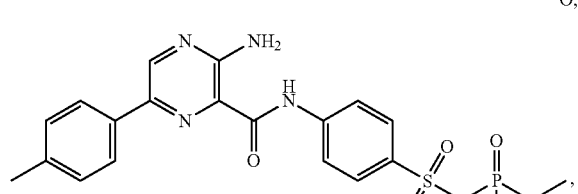

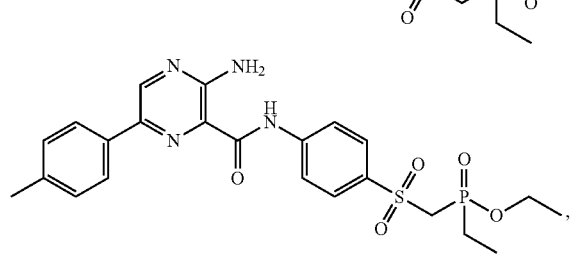
-continued
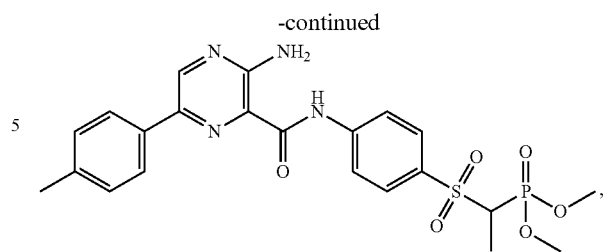
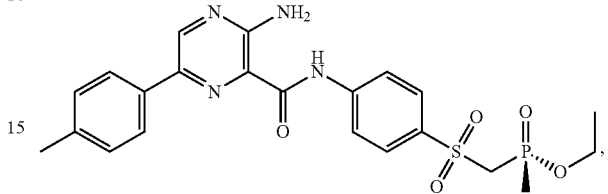
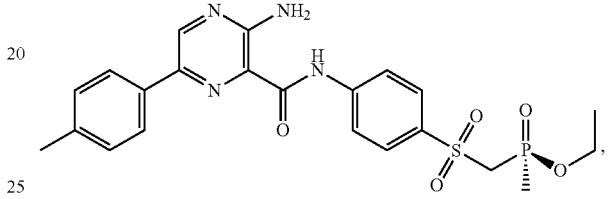
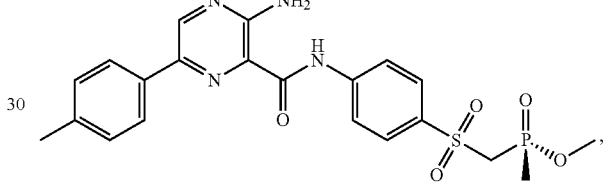
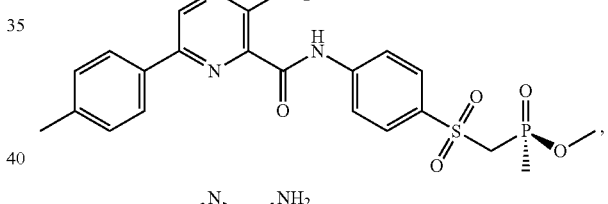
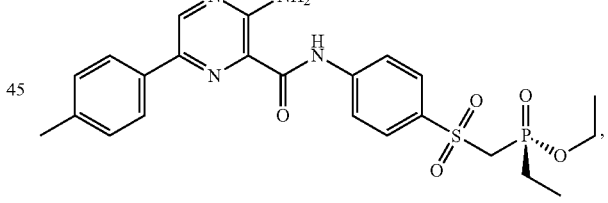
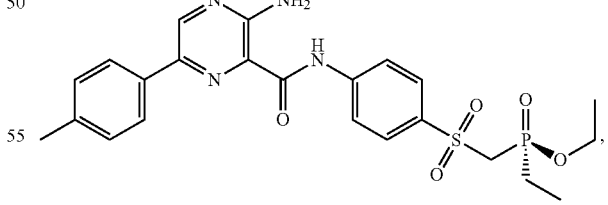
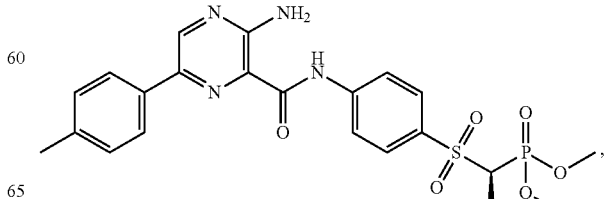

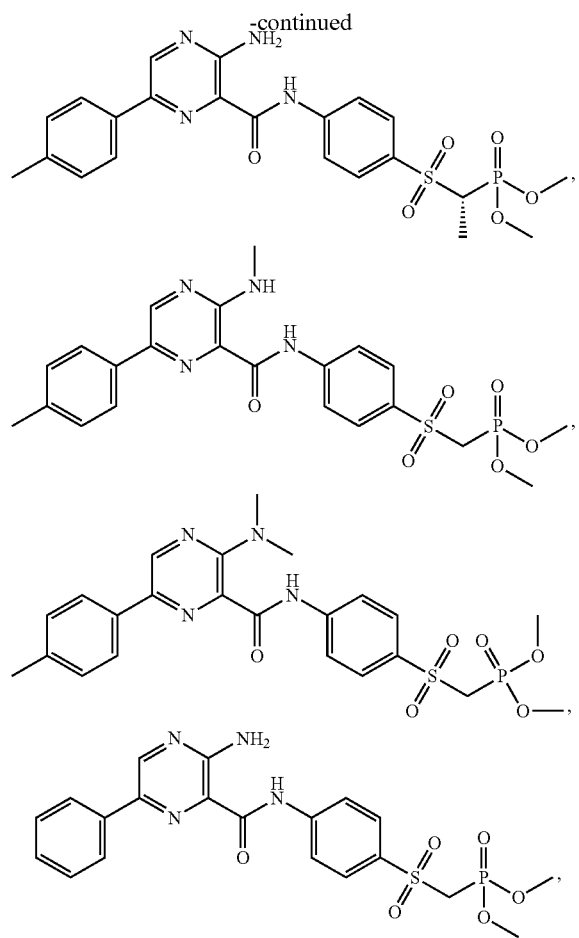
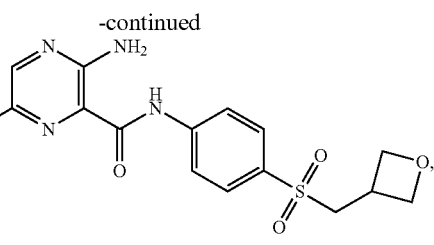
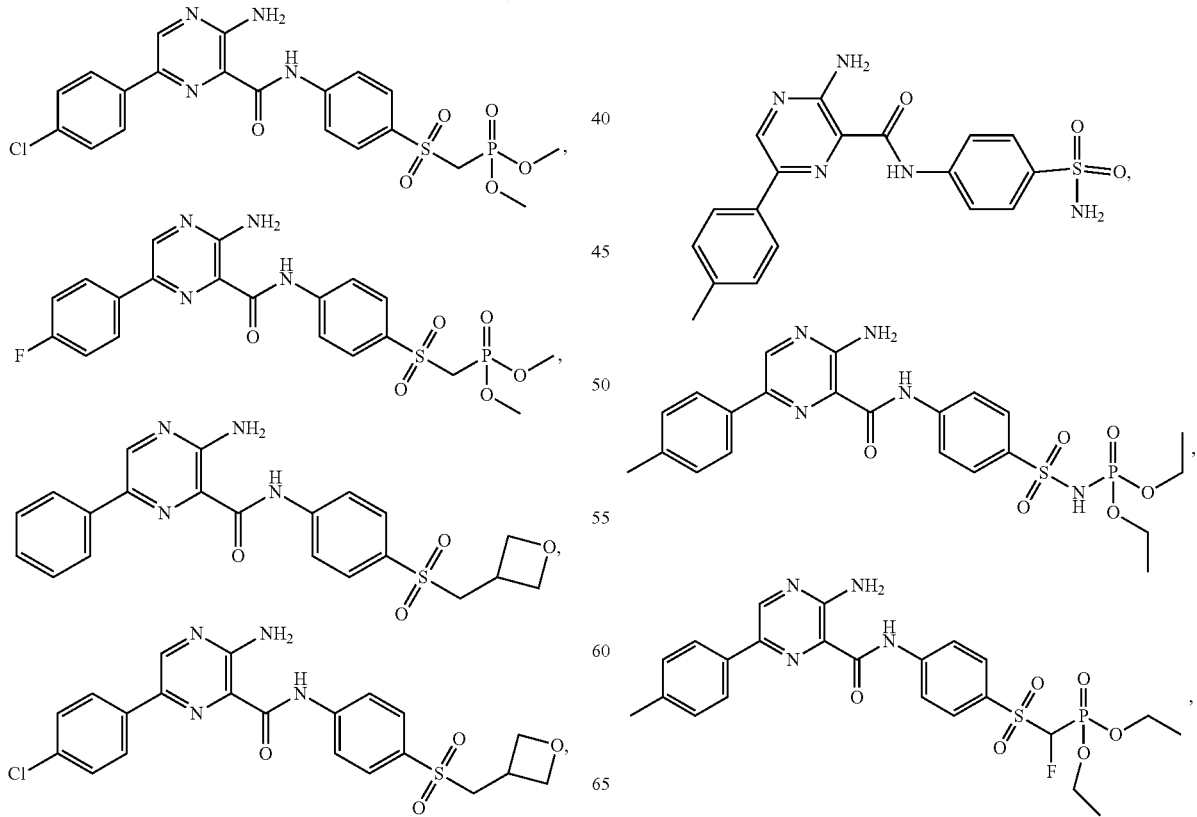
In embodiments, the compound is:

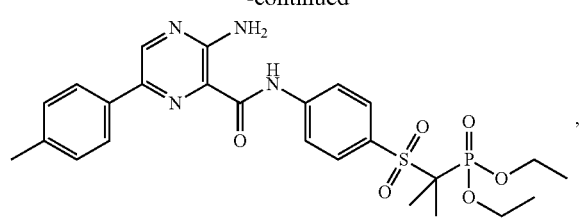
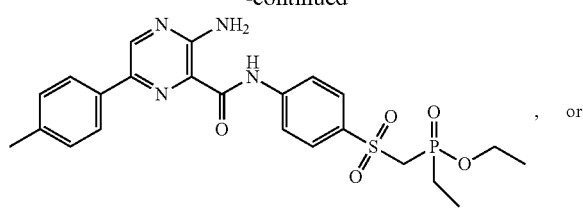
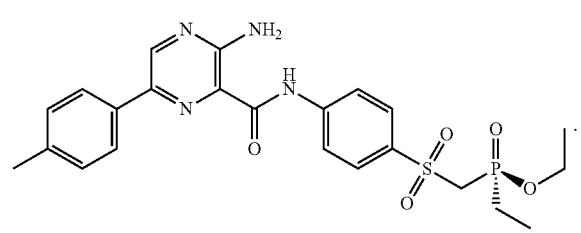
In embodiments, the compound is:
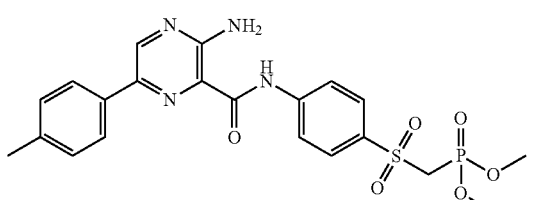
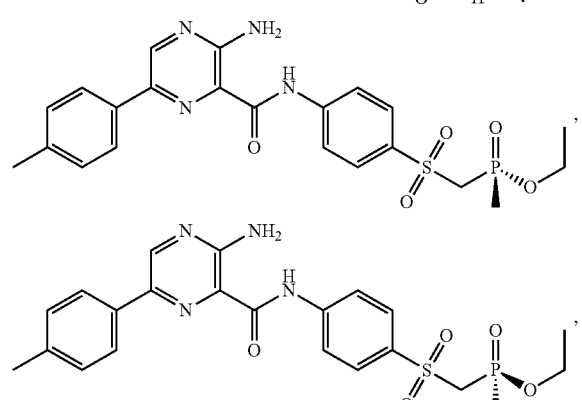
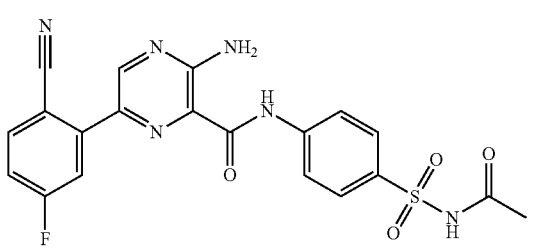
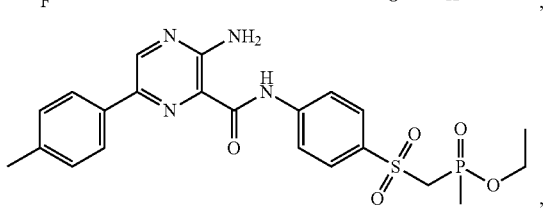
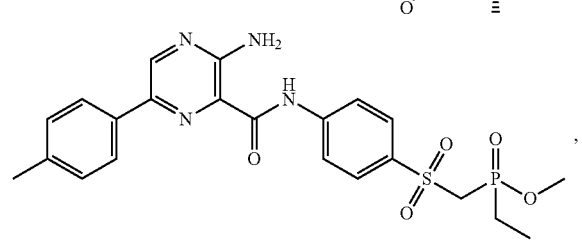
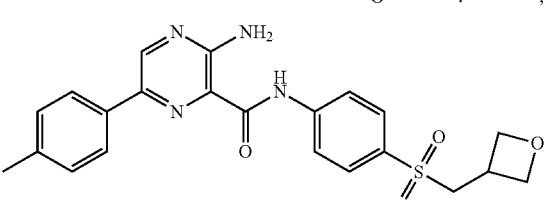

-continued
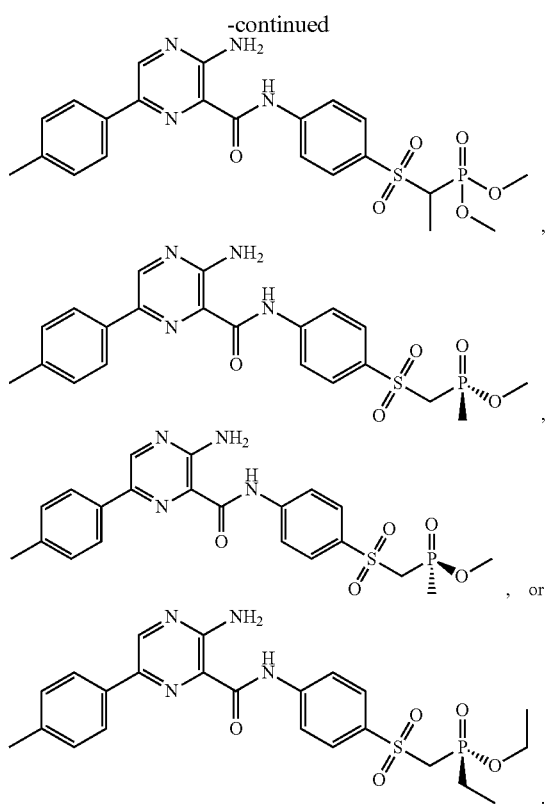
In embodiments, the compound is:
-continued
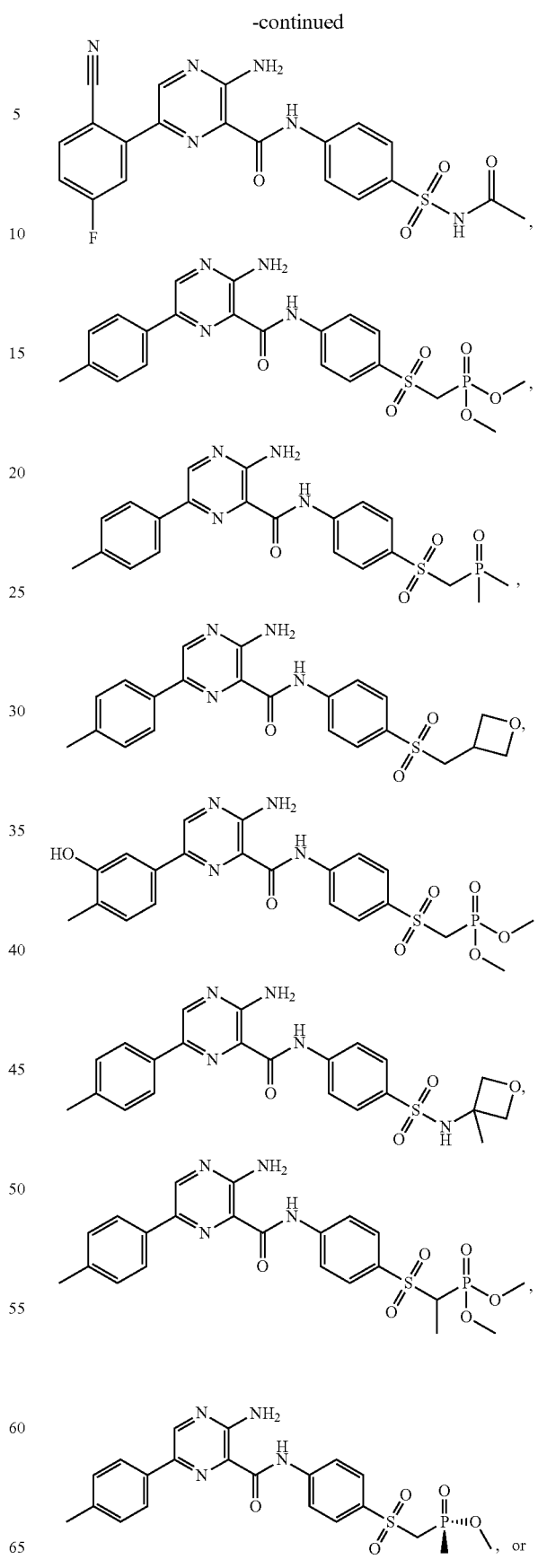

-continued
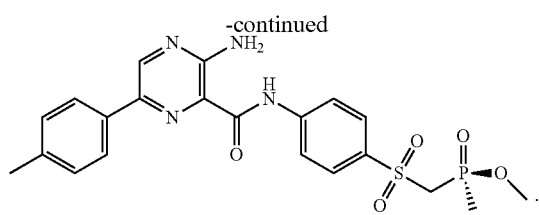
In embodiments, the compound is:
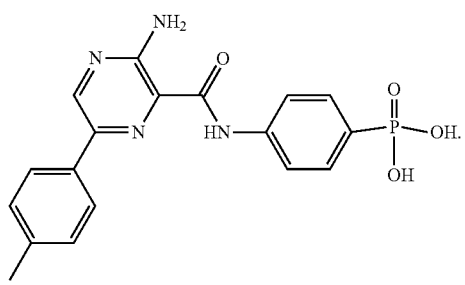 [SMILES: Cc1ccc(-c2cnc(N)c(C(=O)Nc3ccc(P(=O)(O)O)cc3)n2)cc1]
In embodiments, the compound is:
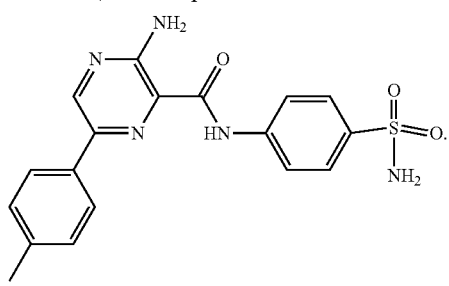
In embodiments, the compound is:
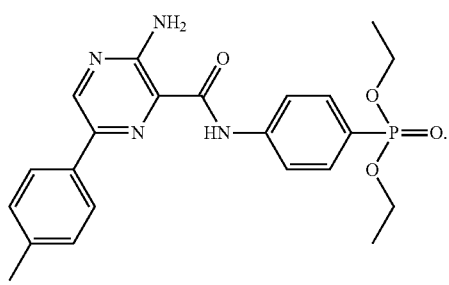 [SMILES: CCOP(=O)(OCC)c1ccc(NC(=O)c2nc(-c3ccc(C)cc3)cnc2N)cc1]
In embodiments, the compound is:
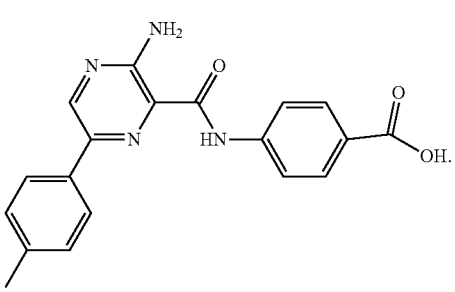 [SMILES: Cc1ccc(-c2cnc(N)c(C(=O)Nc3ccc(C(=O)O)cc3)n2)cc1]
In embodiments, the compound is:
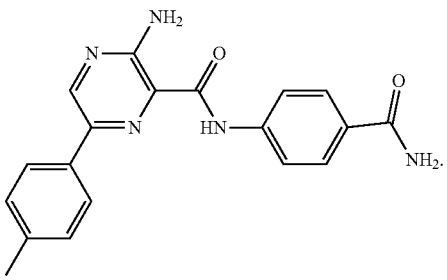 [SMILES: Cc1ccc(-c2cnc(N)c(C(=O)Nc3ccc(C(N)=O)cc3)n2)cc1]
In embodiments, the compound is:
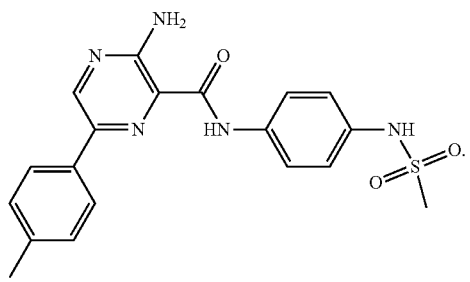 [SMILES: Cc1ccc(-c2cnc(N)c(C(=O)Nc3ccc(NS(C)(=O)=O)cc3)n2)cc1]
In embodiments, the compound is:
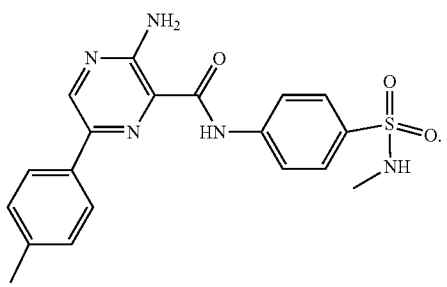 [SMILES: CNS(=O)(=O)c1ccc(NC(=O)c2nc(-c3ccc(C)cc3)cnc2N)cc1]
In embodiments, the compound is:
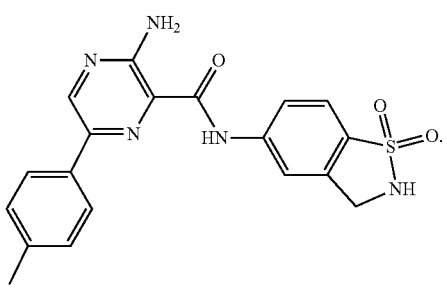 [SMILES: Cc1ccc(-c2cnc(N)c(C(=O)Nc3ccc4c(c3)CNS4(=O)=O)n2)cc1]

In embodiments, the compound is:
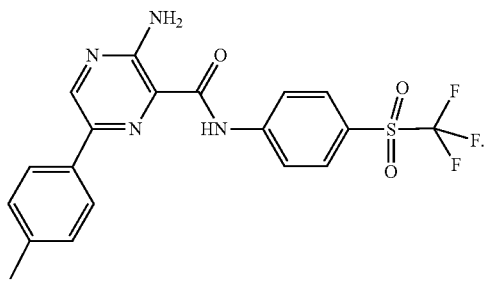 [SMILES: Cc1ccc(-c2cnc(N)c(C(=O)Nc3ccc(S(=O)(=O)C(F)(F)F)cc3)n2)cc1]
In embodiments, the compound is:
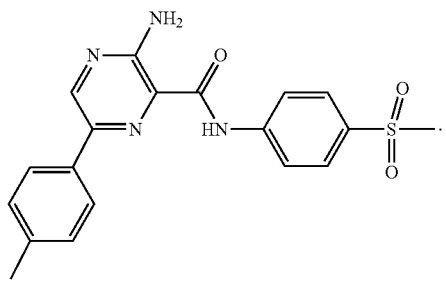 [SMILES: Cc1ccc(-c2cnc(N)c(C(=O)Nc3ccc(S(C)(=O)=O)cc3)n2)cc1]
In embodiments, the compound is:
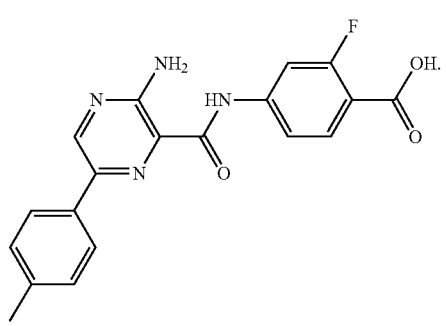 [SMILES: Cc1ccc(-c2cnc(N)c(C(=O)Nc3ccc(C(=O)O)c(F)c3)n2)cc1]
In embodiments, the compound is:
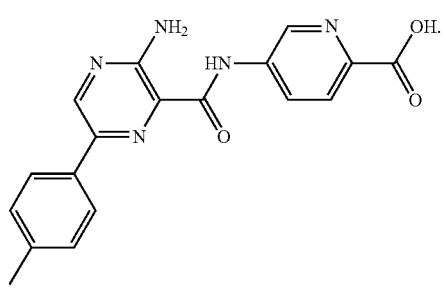 [SMILES: Cc1ccc(-c2cnc(N)c(C(=O)Nc3ccc(C(=O)O)nc3)n2)cc1]
In embodiments, the compound is:
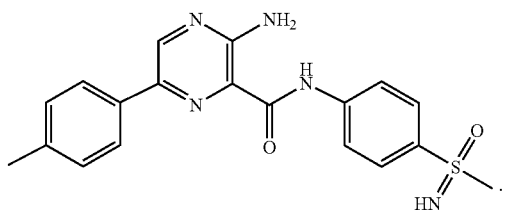
In embodiments, the compound is:
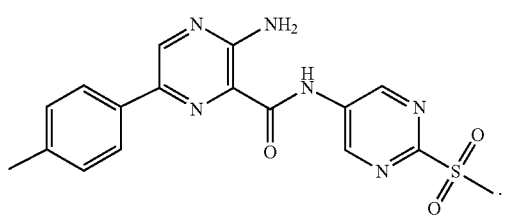
In embodiments, the compound is:
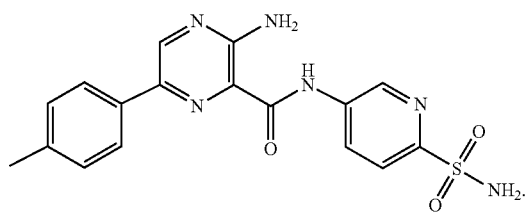 [SMILES: Cc1ccc(-c2cnc(N)c(C(=O)Nc3ccc(S(N)(=O)=O)nc3)n2)cc1]
In embodiments, the compound is:
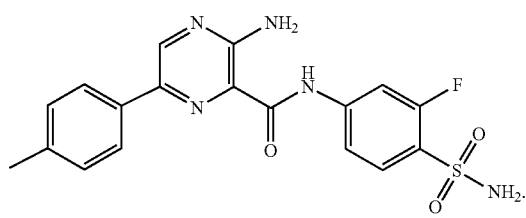 [SMILES: Cc1ccc(-c2cnc(N)c(C(=O)Nc3ccc(S(N)(=O)=O)c(F)c3)n2)cc1]
In embodiments, the compound is:
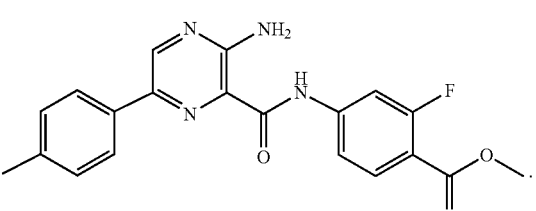

In embodiments, the compound is:
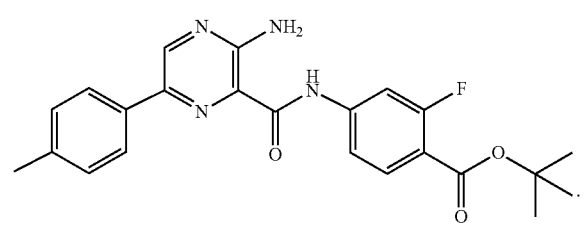 [SMILES: Cc1ccc(-c2cnc(N)c(C(=O)Nc3ccc(C(=O)OC(C)(C)C)c(F)c3)n2)cc1]
In embodiments, the compound is:
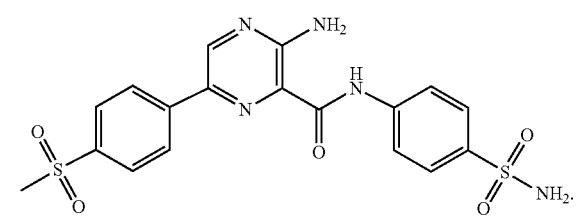 [SMILES: CS(=O)(=O)c1ccc(-c2cnc(N)c(C(=O)Nc3ccc(S(N)(=O)=O)cc3)n2)cc1]
In embodiments, the compound is:
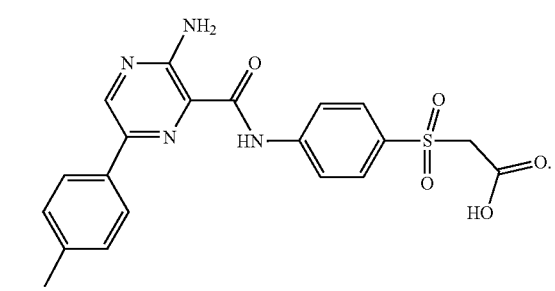 [SMILES: Cc1ccc(-c2cnc(N)c(C(=O)Nc3ccc(S(=O)(=O)CC(=O)O)cc3)n2)cc1]
In embodiments, the compound is:
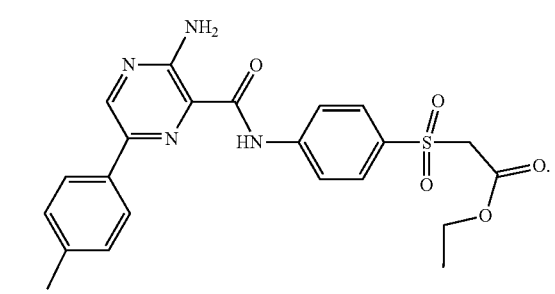 [SMILES: CCOC(=O)CS(=O)(=O)c1ccc(NC(=O)c2nc(-c3ccc(C)cc3)cnc2N)cc1]
In embodiments, the compound is:
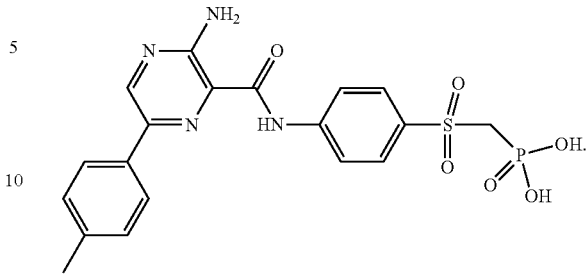
In embodiments, the compound is:
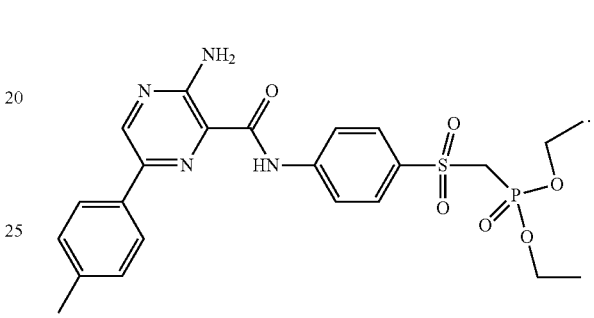
In embodiments, the compound is:
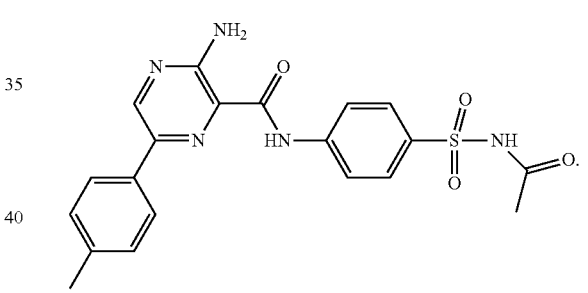
In embodiments, the compound is:
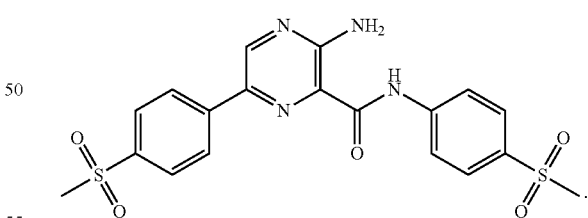
In embodiments, the compound is:
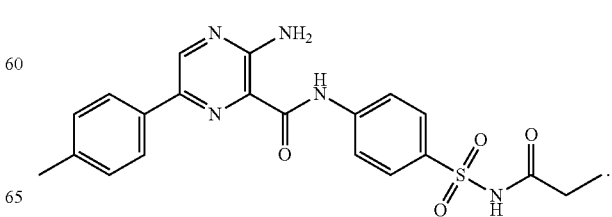

In embodiments, the compound is:
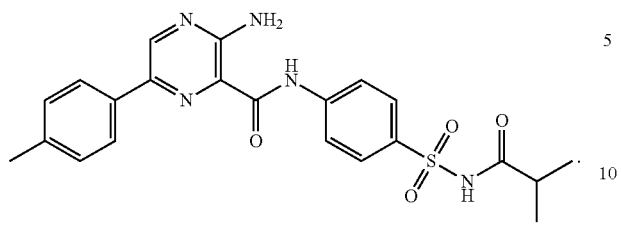
In embodiments, the compound is:
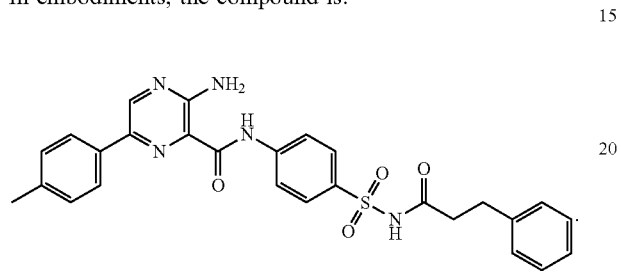
In embodiments, the compound is:
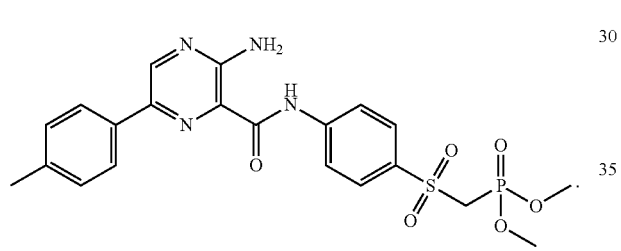
In embodiments, the compound is:
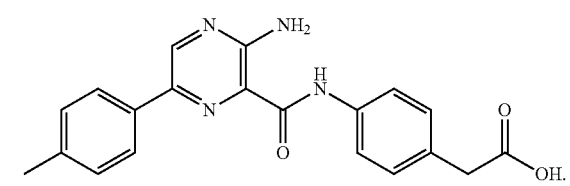 [SMILES: Cc1ccc(-c2cnc(N)c(C(=O)Nc3ccc(CC(=O)O)cc3)n2)cc1]
In embodiments, the compound is:
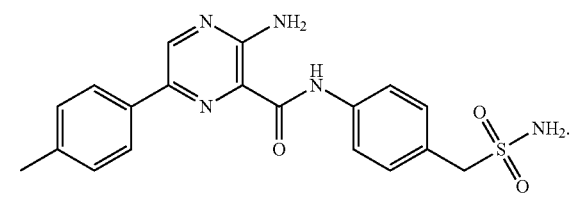 [SMILES: Cc1ccc(-c2cnc(N)c(C(=O)Nc3ccc(CS(N)(=O)=O)cc3)n2)cc1]
In embodiments, the compound is:
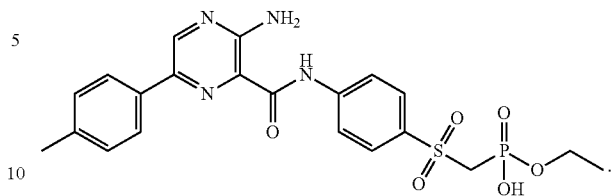
In embodiments, the compound is:
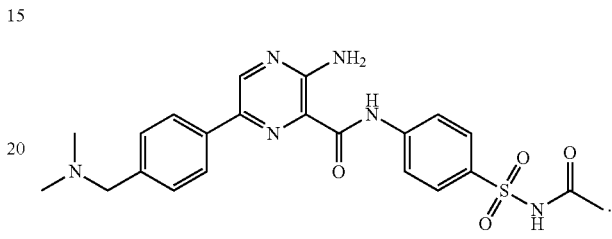
In embodiments, the compound is:
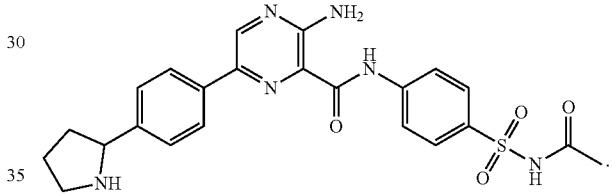
In embodiments, the compound is:
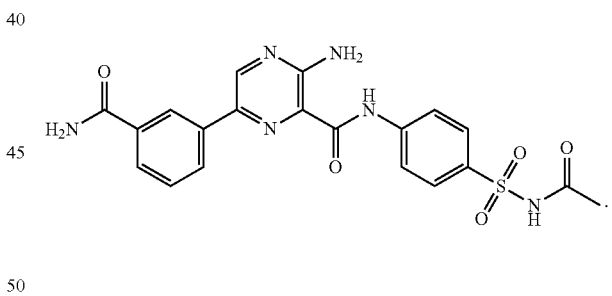
In embodiments, the compound is:
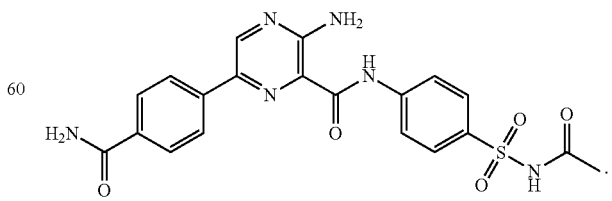

In embodiments, the compound is:
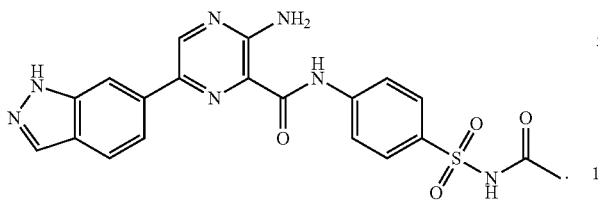
In embodiments, the compound is:
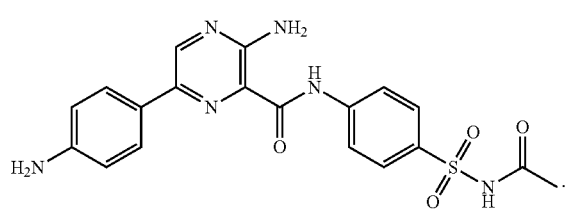 [SMILES: CC(=O)NS(=O)(=O)c1ccc(NC(=O)c2nc(-c3ccc(N)cc3)cnc2N)cc1]
In embodiments, the compound is:
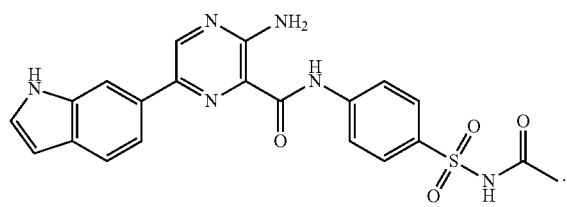 [SMILES: CC(=O)NS(=O)(=O)c1ccc(NC(=O)c2nc(-c3ccc4cc[nH]c4c3)cnc2N)cc1]
In embodiments, the compound is:
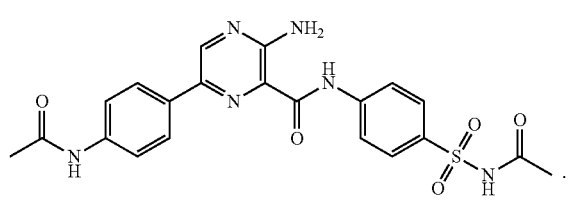 [SMILES: CC(=O)Nc1ccc(-c2cnc(N)c(C(=O)Nc3ccc(S(=O)(=O)NC(C)=O)cc3)n2)cc1]
In embodiments, the compound is:
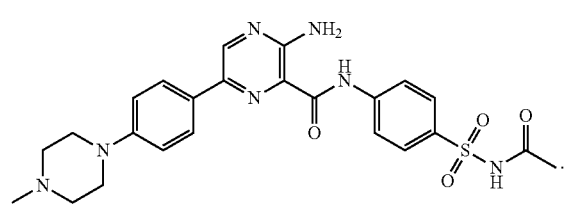 [SMILES: CC(=O)NS(=O)(=O)c1ccc(NC(=O)c2nc(-c3ccc(N4CCN(C)CC4)cc3)cnc2N)cc1]
In embodiments, the compound is:
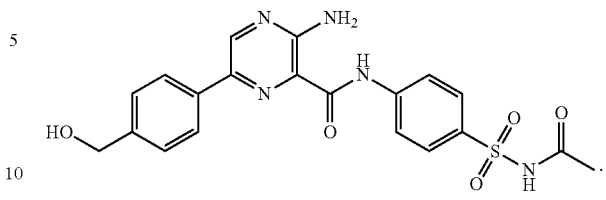
In embodiments, the compound is:
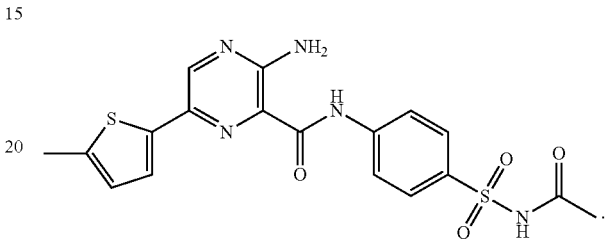
In embodiments, the compound is:
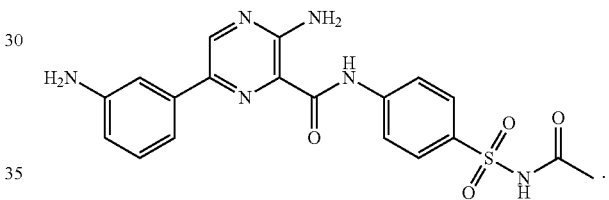
In embodiments, the compound is:
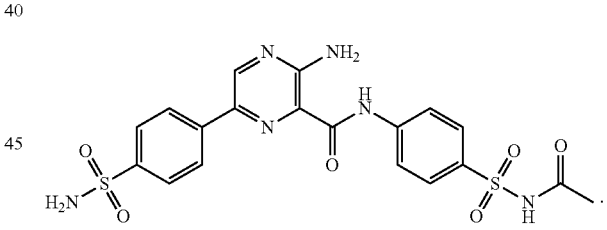
In embodiments, the compound is:
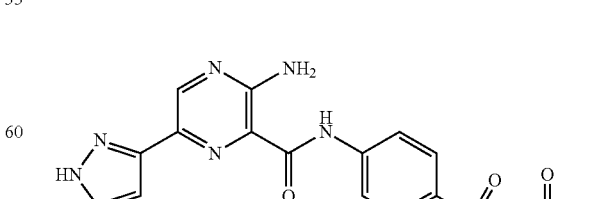

In embodiments, the compound is:
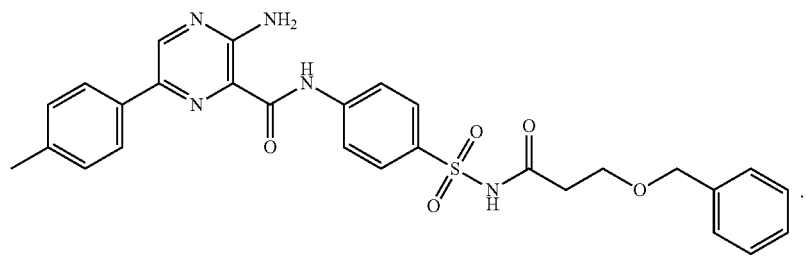 [SMILES: Cc1ccc(-c2cnc(N)c(C(=O)Nc3ccc(S(=O)(=O)NC(=O)CCOCc4ccccc4)cc3)n2)cc1]
In embodiments, the compound is:
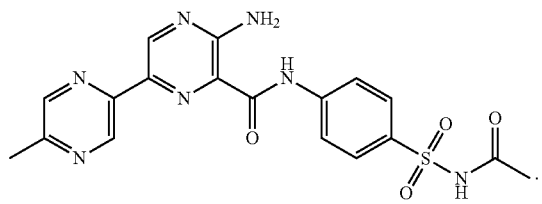 [SMILES: CC(=O)NS(=O)(=O)c1ccc(NC(=O)c2nc(-c3cnc(C)cn3)cnc2N)cc1]
In embodiments, the compound is:
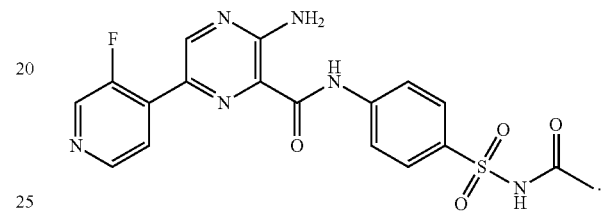
In embodiments, the compound is:
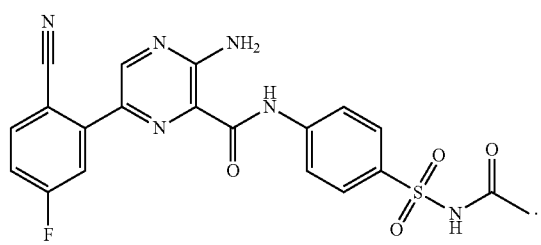 [SMILES: CC(=O)NS(=O)(=O)c1ccc(NC(=O)c2nc(-c3cc(F)ccc3C#N)cnc2N)cc1]
In embodiments, the compound is:
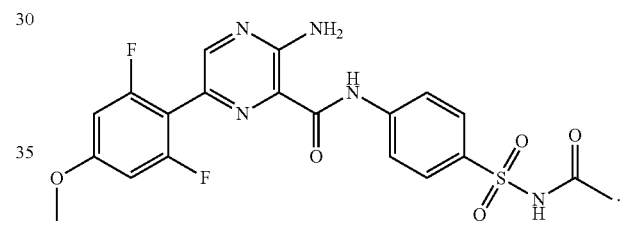
In embodiments, the compound is:
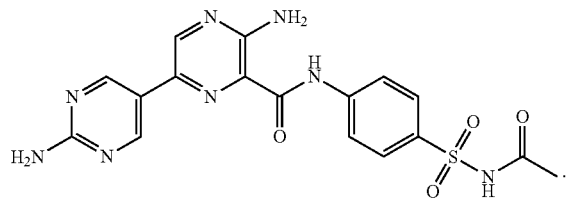 [SMILES: CC(=O)NS(=O)(=O)c1ccc(NC(=O)c2nc(-c3cnc(N)nc3)cnc2N)cc1]
In embodiments, the compound is:
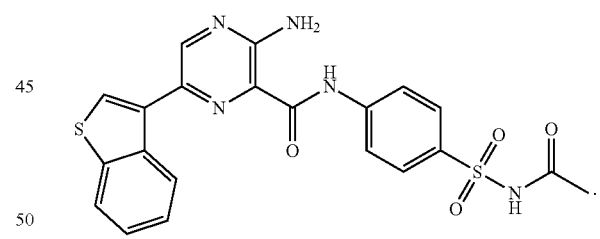
In embodiments, the compound is:
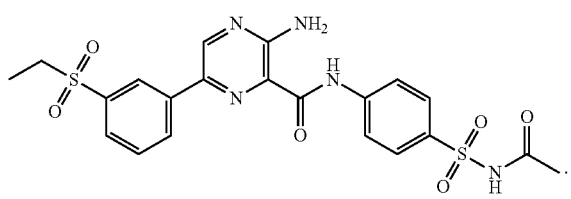 [SMILES: CCS(=O)(=O)c1cccc(-c2cnc(N)c(C(=O)Nc3ccc(S(=O)(=O)NC(C)=O)cc3)n2)c1]
In embodiments, the compound is:
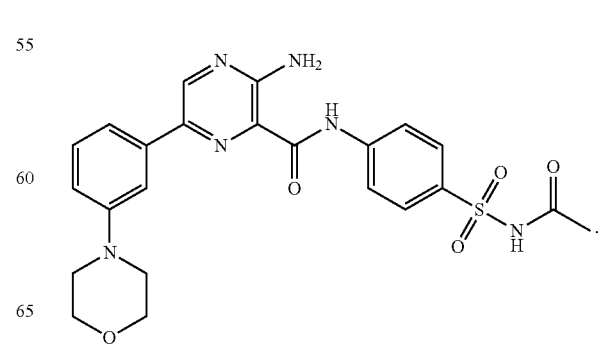

In embodiments, the compound is:
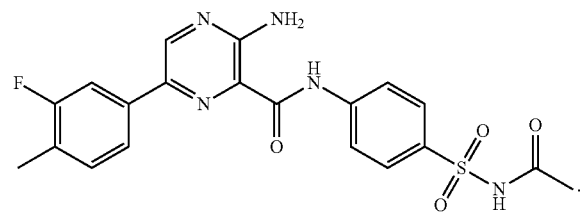 [SMILES: CC(=O)NS(=O)(=O)c1ccc(NC(=O)c2nc(-c3ccc(C)c(F)c3)cnc2N)cc1]
In embodiments, the compound is:
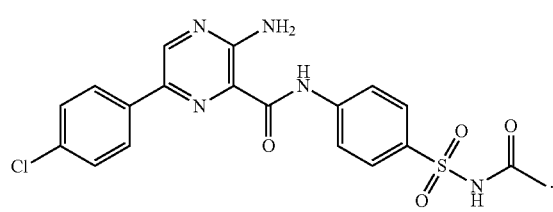 [SMILES: CC(=O)NS(=O)(=O)c1ccc(NC(=O)c2nc(-c3ccc(Cl)cc3)cnc2N)cc1]
In embodiments, the compound is:
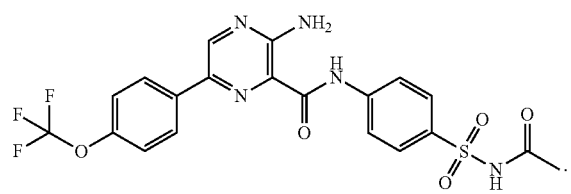 [SMILES: CC(=O)NS(=O)(=O)c1ccc(NC(=O)c2nc(-c3ccc(OC(F)(F)F)cc3)cnc2N)cc1]
In embodiments, the compound is:
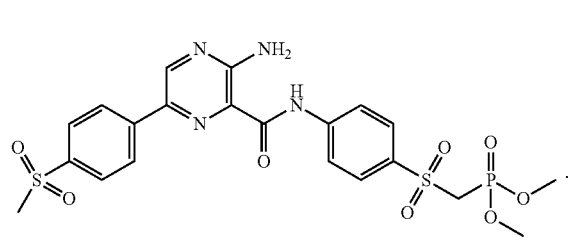 [SMILES: COP(=O)(CS(=O)(=O)c1ccc(NC(=O)c2nc(-c3ccc(S(C)(=O)=O)cc3)cnc2N)cc1)OC]
In embodiments, the compound is:
In embodiments, the compound is:
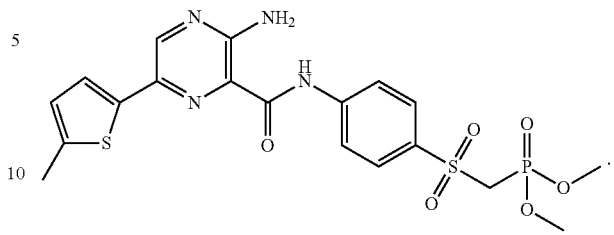
In embodiments, the compound is:
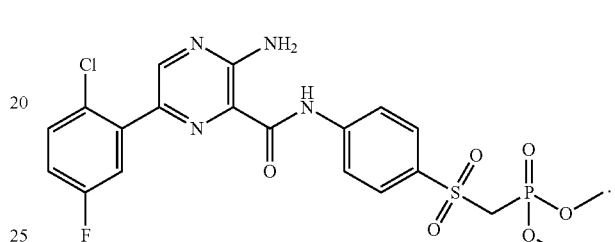
In embodiments, the compound is:
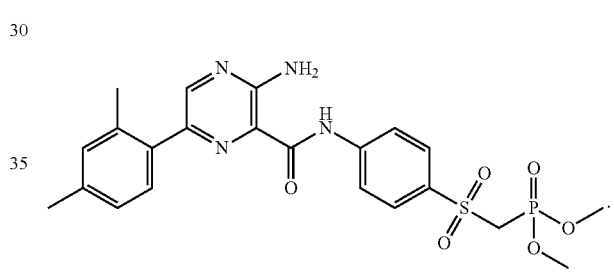
In embodiments, the compound is:
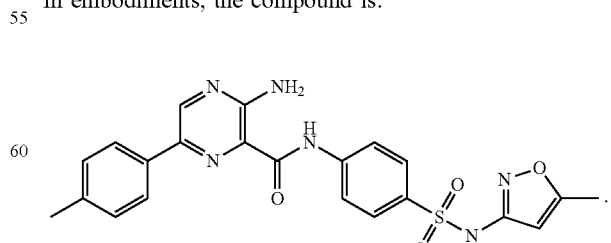
In embodiments, the compound is:

In embodiments, the compound is:
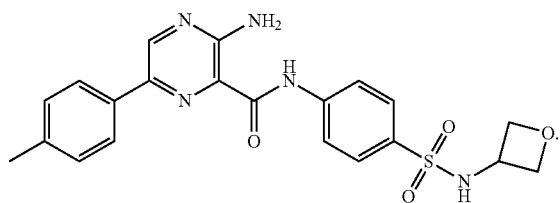 [SMILES: Cc1ccc(-c2cnc(N)c(C(=O)Nc3ccc(S(=O)(=O)NC4COC4)cc3)n2)cc1]
In embodiments, the compound is:
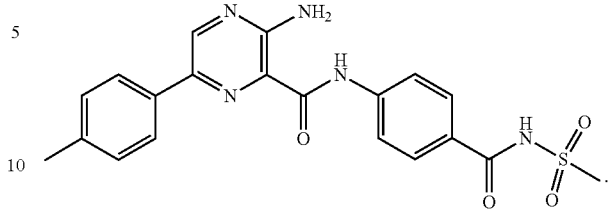
In embodiments, the compound is:
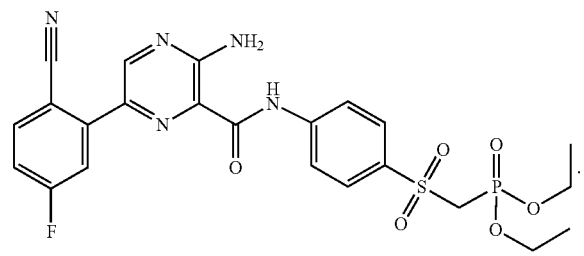 [SMILES: CCOP(=O)(CS(=O)(=O)c1ccc(NC(=O)c2nc(-c3cc(F)ccc3C#N)cnc2N)cc1)OCC]
In embodiments, the compound is:
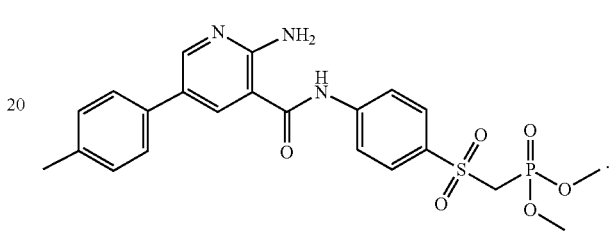
In embodiments, the compound is:
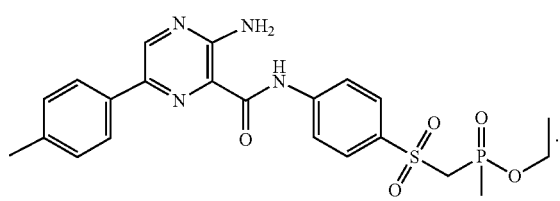 [SMILES: CCOP(C)(=O)CS(=O)(=O)c1ccc(NC(=O)c2nc(-c3ccc(C)cc3)cnc2N)cc1]
In embodiments, the compound is:
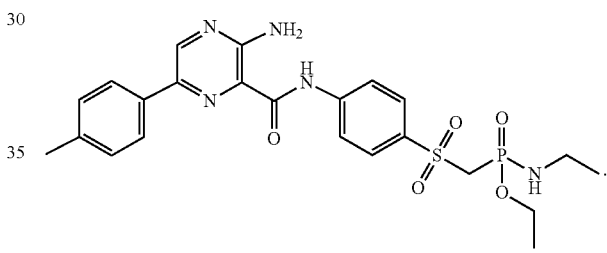
In embodiments, the compound is:
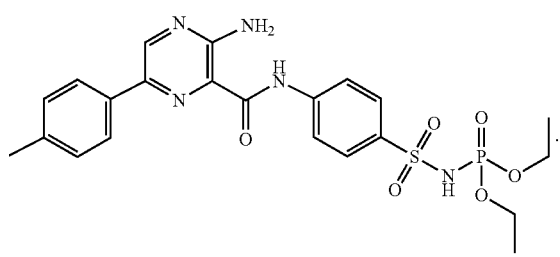 [SMILES: CCOP(=O)(NS(=O)(=O)c1ccc(NC(=O)c2nc(-c3ccc(C)cc3)cnc2N)cc1)OCC]
In embodiments, the compound is:
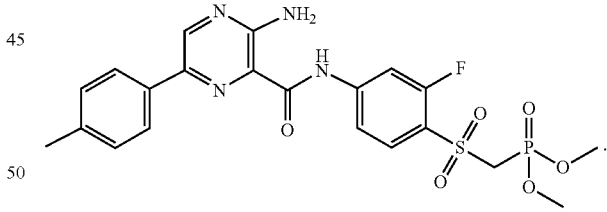
In embodiments, the compound is:
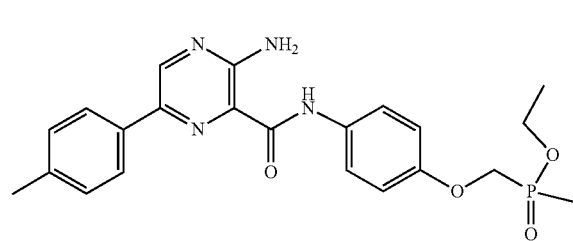
In embodiments, the compound is:
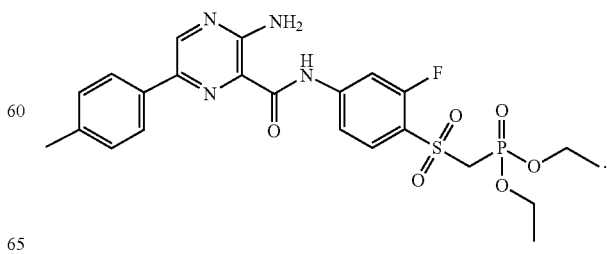

In embodiments, the compound is:
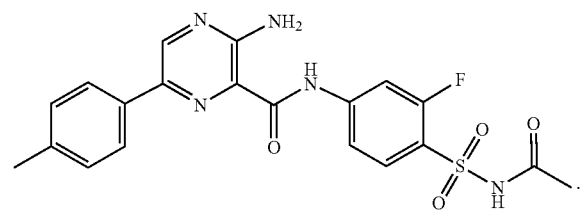 [SMILES: CC(=O)NS(=O)(=O)c1ccc(NC(=O)c2nc(-c3ccc(C)cc3)cnc2N)cc1F]
In embodiments, the compound is:
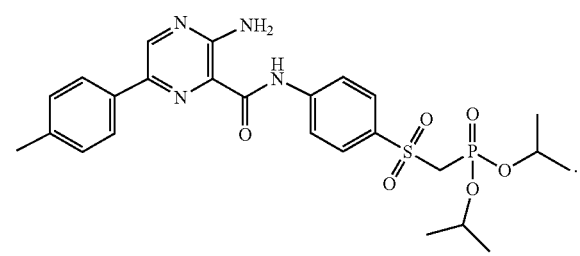 [SMILES: Cc1ccc(-c2cnc(N)c(C(=O)Nc3ccc(S(=O)(=O)CP(=O)(OC(C)C)OC(C)C)cc3)n2)cc1]
In embodiments, the compound is:
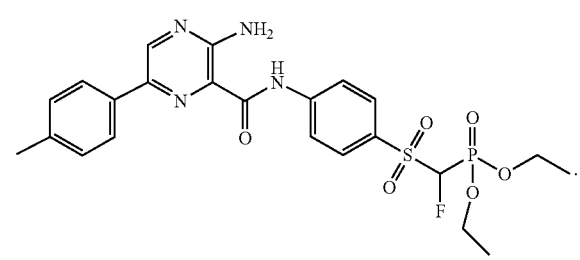 [SMILES: CCOP(=O)(OCC)C(F)S(=O)(=O)c1ccc(NC(=O)c2nc(-c3ccc(C)cc3)cnc2N)cc1]
In embodiments, the compound is:
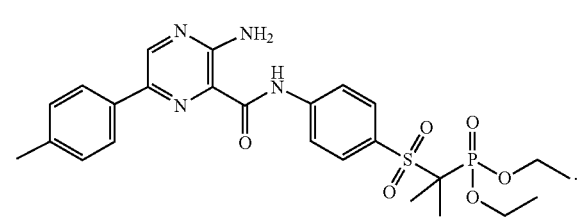 [SMILES: CCOP(=O)(OCC)C(C)(C)S(=O)(=O)c1ccc(NC(=O)c2nc(-c3ccc(C)cc3)cnc2N)cc1]
In embodiments, the compound is:
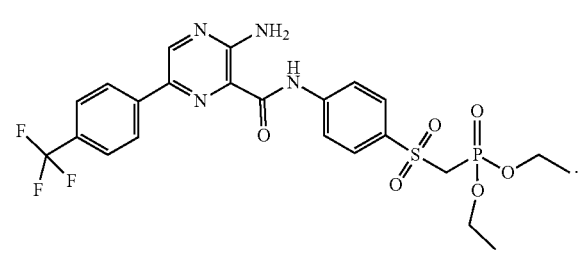 [SMILES: CCOP(=O)(CS(=O)(=O)c1ccc(NC(=O)c2nc(-c3ccc(C(F)(F)F)cc3)cnc2N)cc1)OCC]
In embodiments, the compound is:
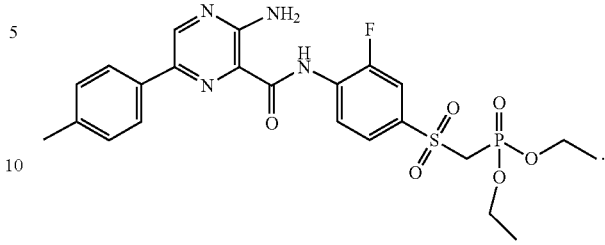
In embodiments, the compound is:
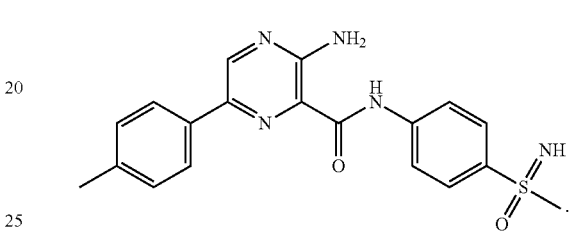
In embodiments, the compound is:
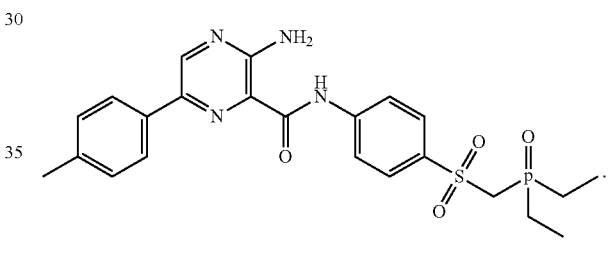
In embodiments, the compound is:
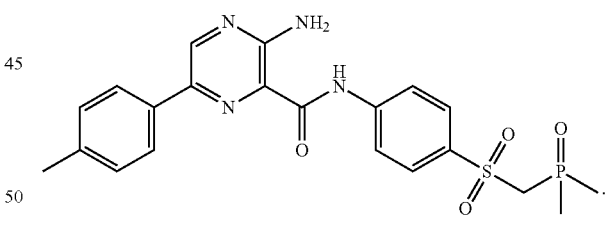
In embodiments, the compound is:
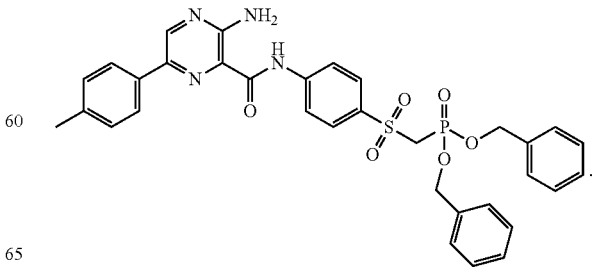

In embodiments, the compound is:
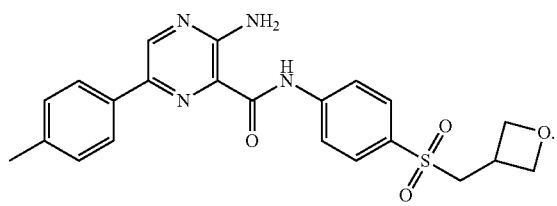 [SMILES: Cc1ccc(-c2cnc(N)c(C(=O)Nc3ccc(S(=O)(=O)CC4COC4)cc3)n2)cc1]
In embodiments, the compound is:
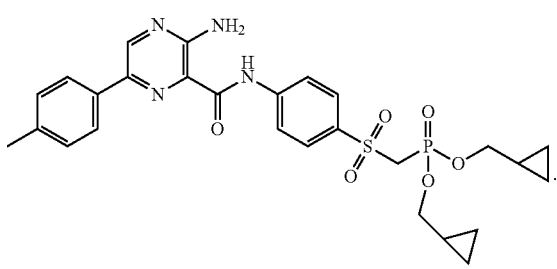 [SMILES: Cc1ccc(-c2cnc(N)c(C(=O)Nc3ccc(S(=O)(=O)CP(=O)(OCC4CC4)OCC4CC4)cc3)n2)cc1]
In embodiments, the compound is:
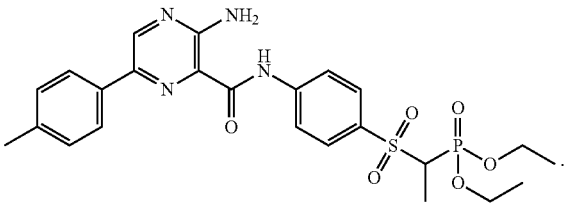
In embodiments, the compound is:
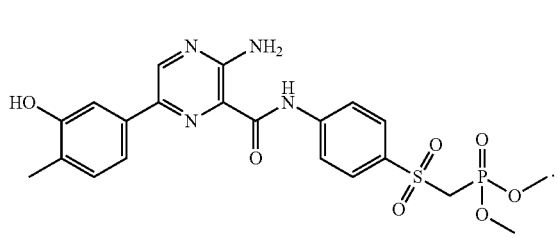 [SMILES: COP(=O)(CS(=O)(=O)c1ccc(NC(=O)c2nc(-c3ccc(C)c(O)c3)cnc2N)cc1)OC]
In embodiments, the compound is:
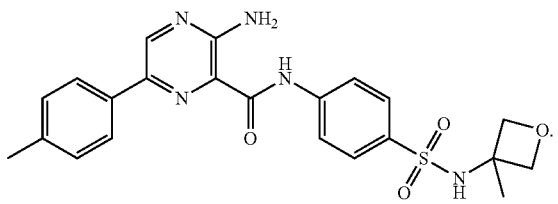
In embodiments, the compound is:
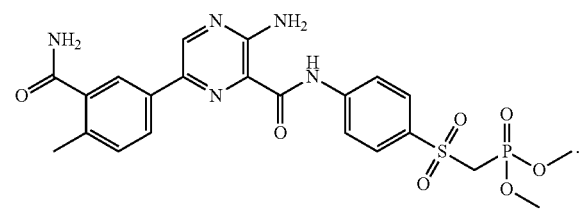 [SMILES: COP(=O)(CS(=O)(=O)c1ccc(NC(=O)c2nc(-c3ccc(C)c(C(N)=O)c3)cnc2N)cc1)OC]
In embodiments, the compound is:
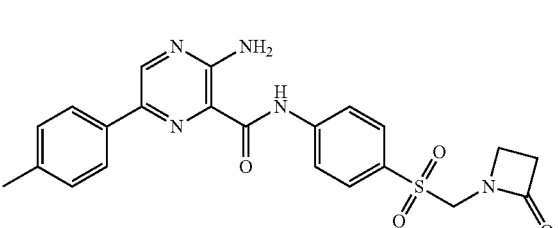
In embodiments, the compound is:
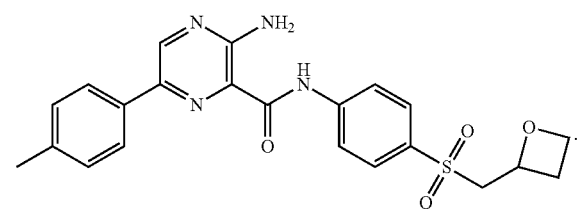 [SMILES: Cc1ccc(-c2cnc(N)c(C(=O)Nc3ccc(S(=O)(=O)CC4CCO4)cc3)n2)cc1]
In embodiments, the compound is:
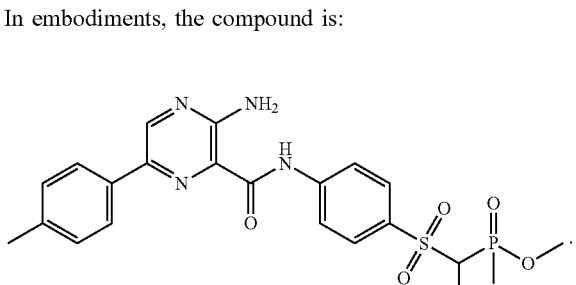

In embodiments, the compound is:
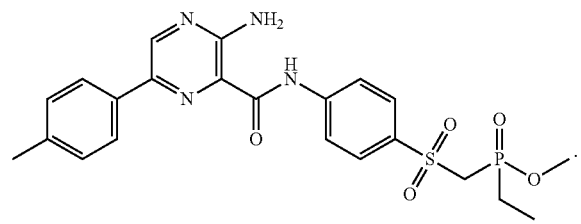
In embodiments, the compound is:
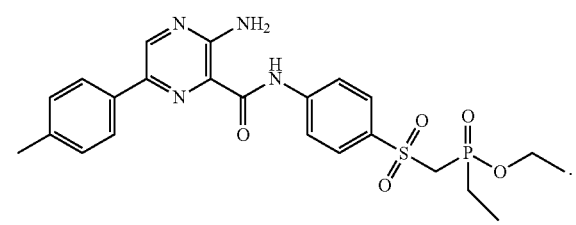 [SMILES: CCOP(=O)(CC)CS(=O)(=O)c1ccc(NC(=O)c2nc(-c3ccc(C)cc3)cnc2N)cc1]
In embodiments, the compound is:
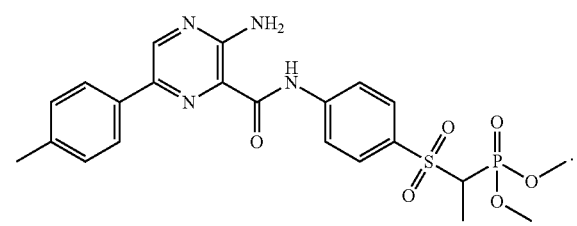
In embodiments, the compound is:
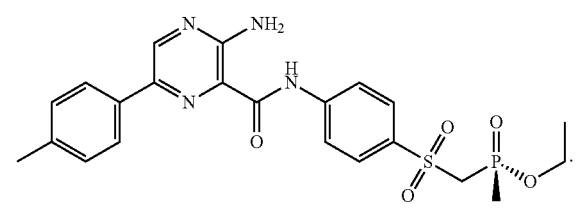 [SMILES: CCO[P@@](C)(=O)CS(=O)(=O)c1ccc(NC(=O)c2nc(-c3ccc(C)cc3)cnc2N)cc1]
In embodiments, the compound is:
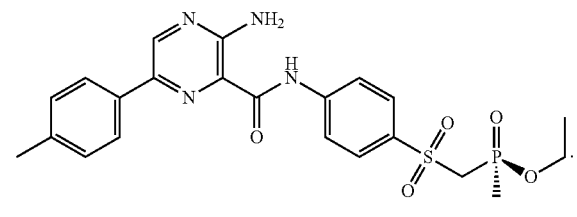 [SMILES: CCO[P@](C)(=O)CS(=O)(=O)c1ccc(NC(=O)c2nc(-c3ccc(C)cc3)cnc2N)cc1]
In embodiments, the compound is:
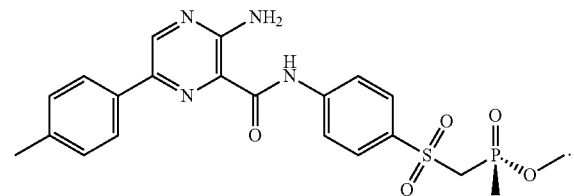
In embodiments, the compound is:
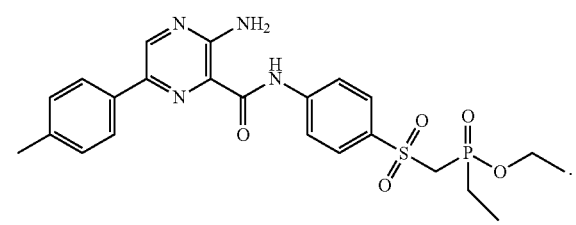 [SMILES: CCOP(=O)(CC)CS(=O)(=O)c1ccc(NC(=O)c2nc(-c3ccc(C)cc3)cnc2N)cc1]
In embodiments, the compound is:
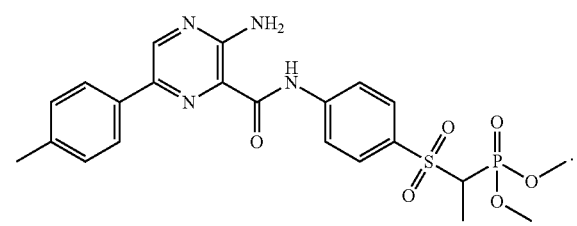
In embodiments, the compound is:
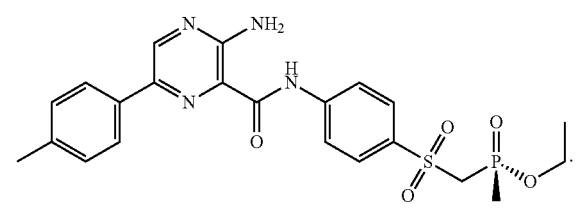 [SMILES: CCO[P@@](C)(=O)CS(=O)(=O)c1ccc(NC(=O)c2nc(-c3ccc(C)cc3)cnc2N)cc1]
In embodiments, the compound is:
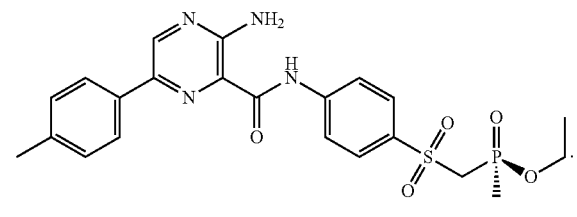 [SMILES: CCO[P@](C)(=O)CS(=O)(=O)c1ccc(NC(=O)c2nc(-c3ccc(C)cc3)cnc2N)cc1]

In embodiments, the compound is:
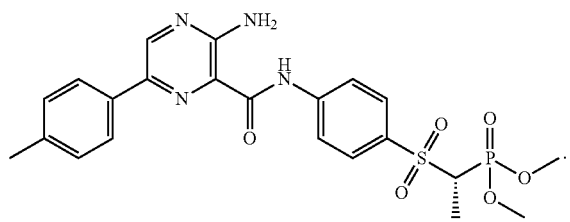
In embodiments, the compound is:
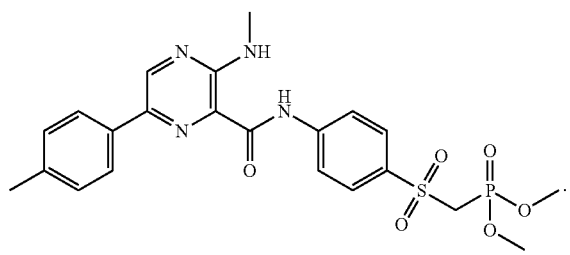
In embodiments, the compound is:
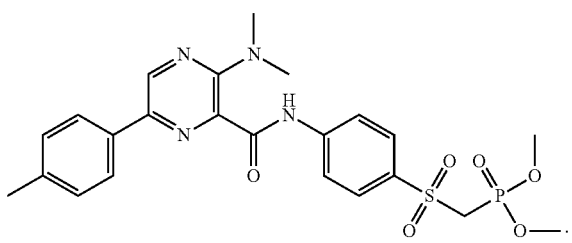
In embodiments, the compound is:
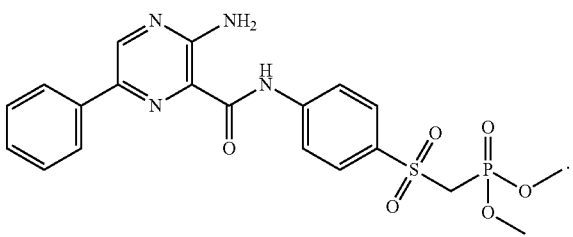 [SMILES: COP(=O)(CS(=O)(=O)c1ccc(NC(=O)c2nc(-c3ccccc3)cnc2N)cc1)OC]
In embodiments, the compound is:
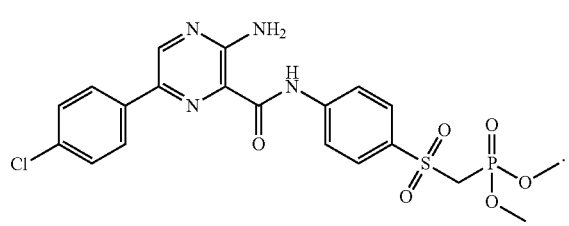 [SMILES: COP(=O)(CS(=O)(=O)c1ccc(NC(=O)c2nc(-c3ccc(Cl)cc3)cnc2N)cc1)OC]
In embodiments, the compound is:
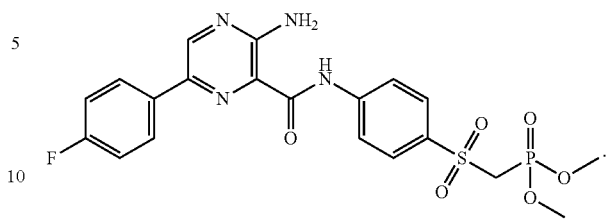 [SMILES: COP(=O)(CS(=O)(=O)c1ccc(NC(=O)c2nc(-c3ccc(CF)cc3)cnc2N)cc1)OC]
In embodiments, the compound is:
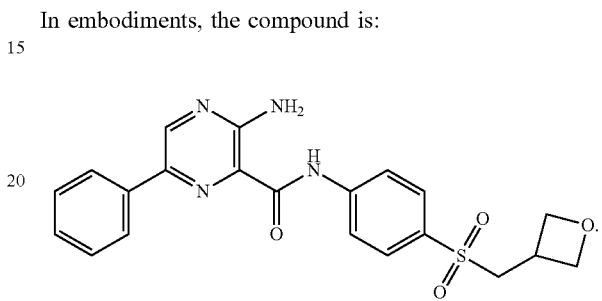
In embodiments, the compound is:
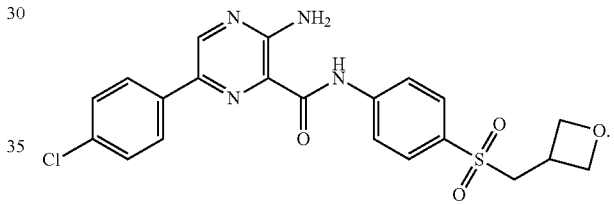
In embodiments, the compound is:
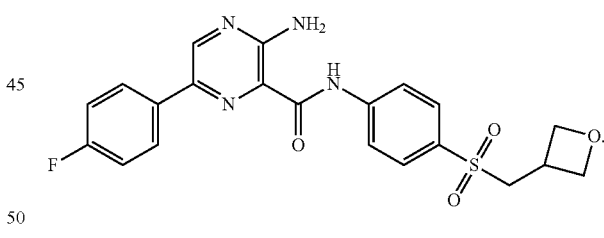
In embodiments, the compound is:
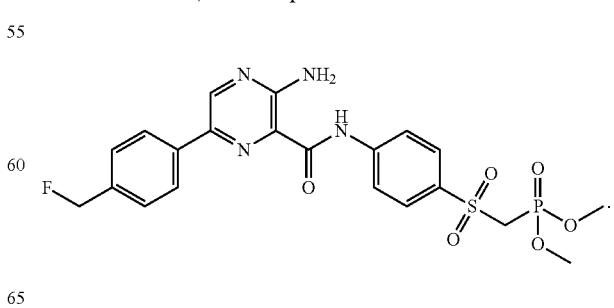

In embodiments, the compound is:
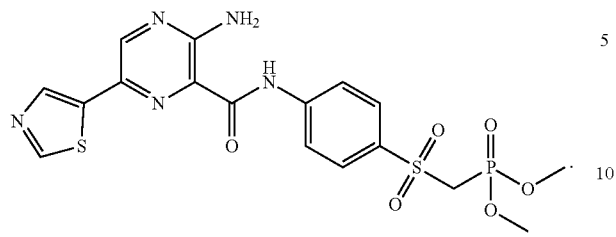
In embodiments, the compound is:
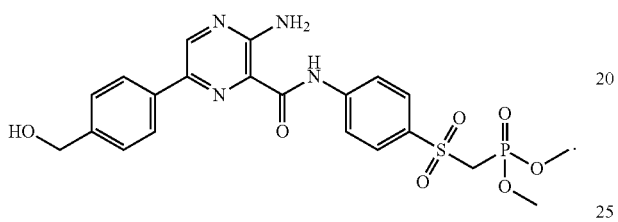
In embodiments, the compound is:
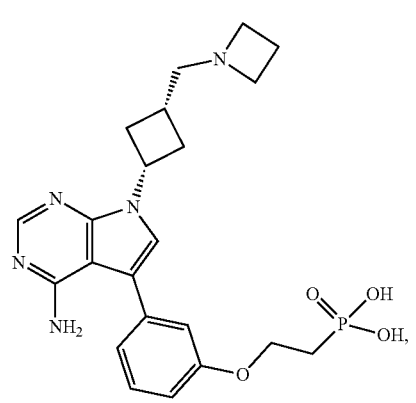
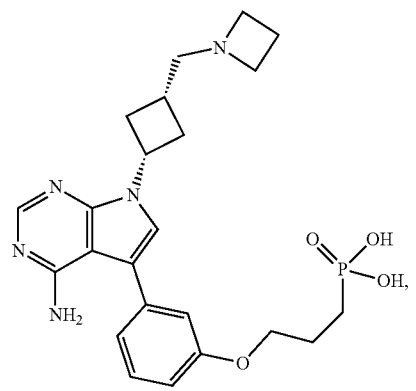
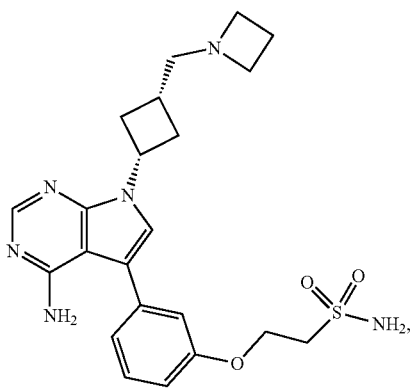
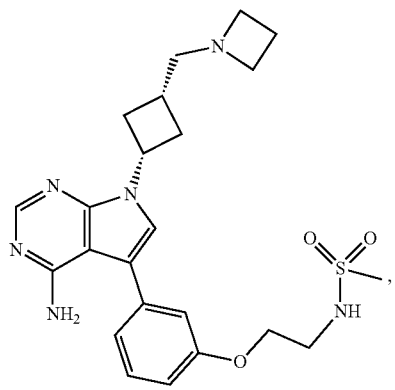
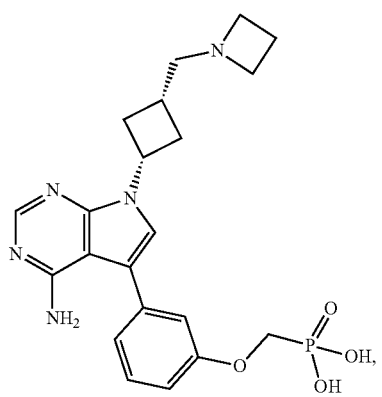
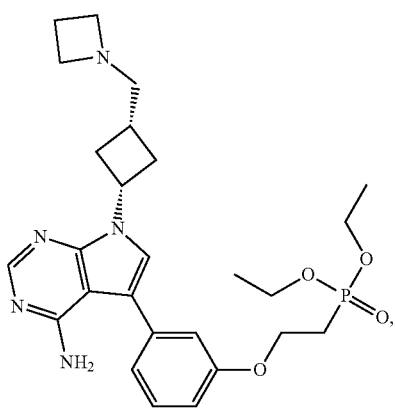

219
-continued
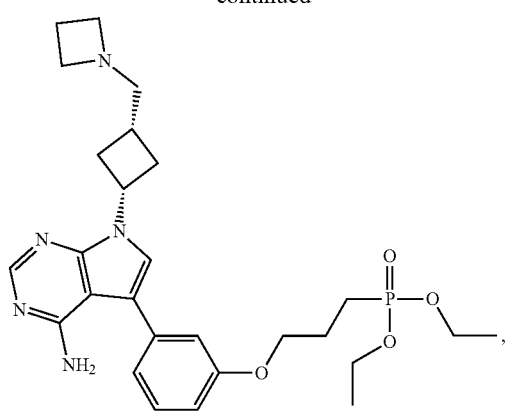
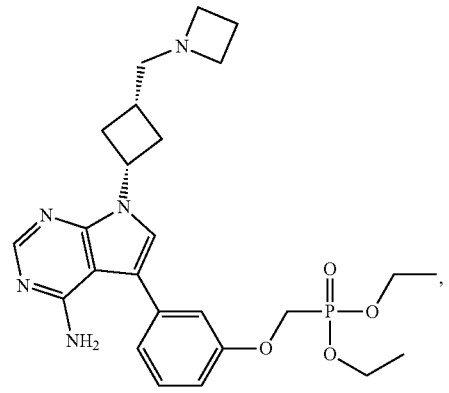
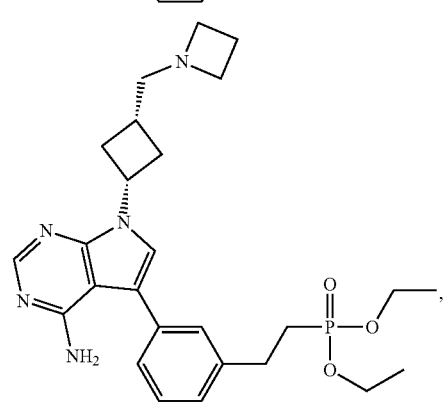

220
-continued
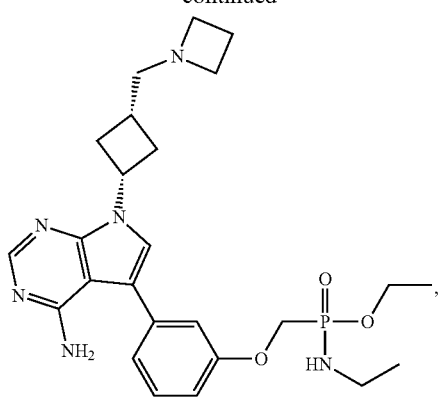

221
-continued

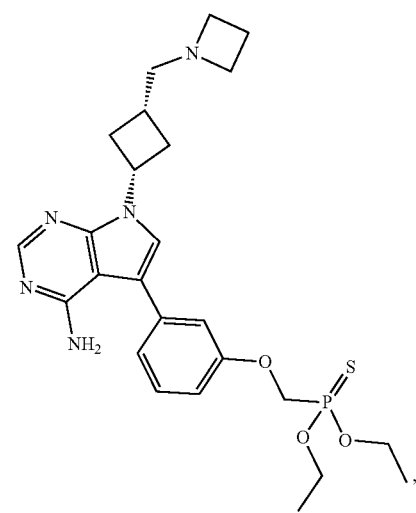
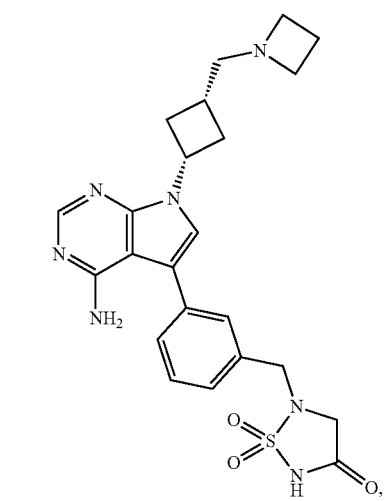
222
-continued
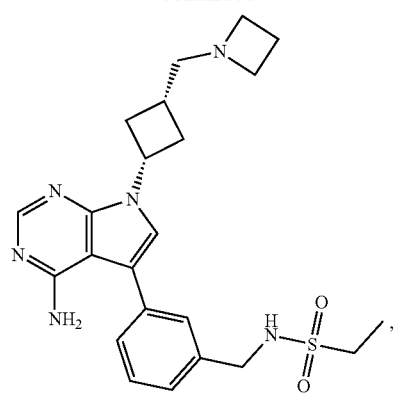
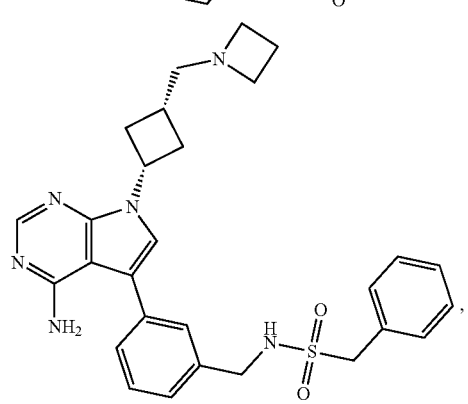
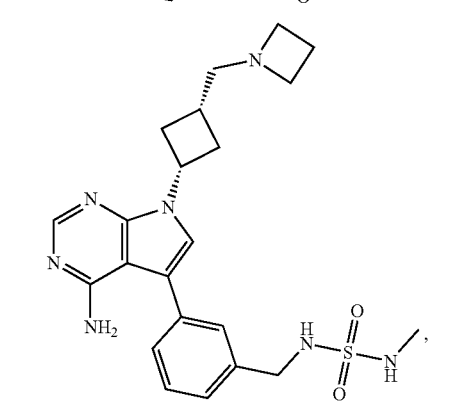
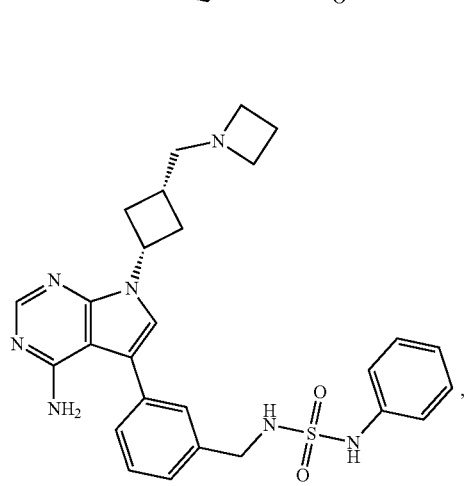

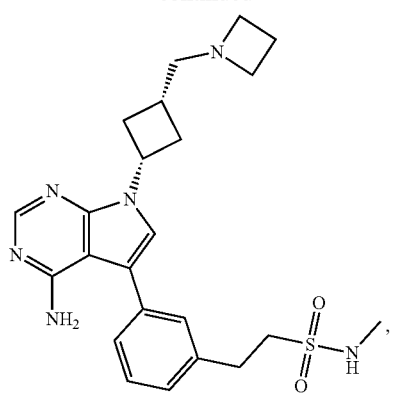
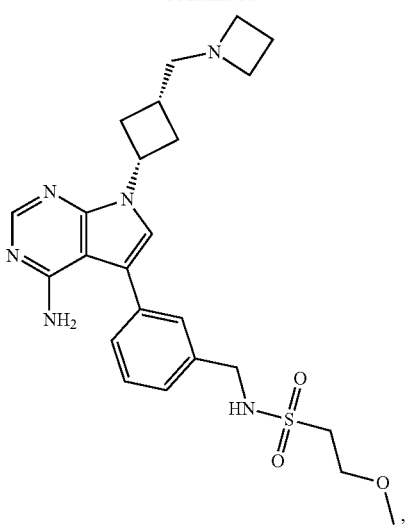
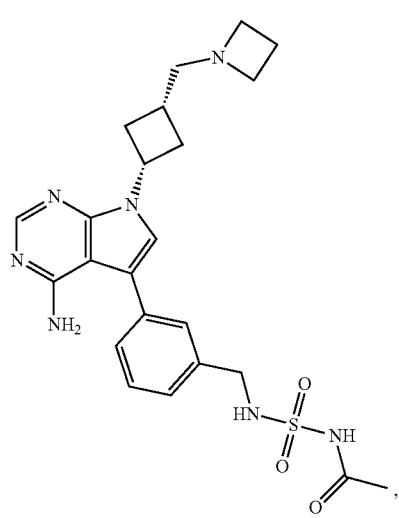
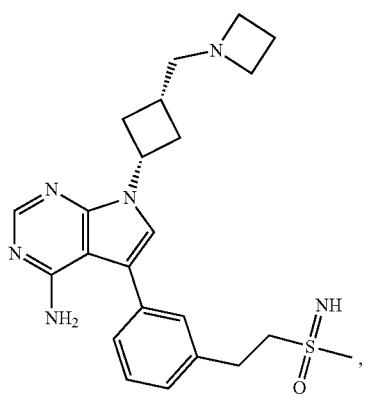
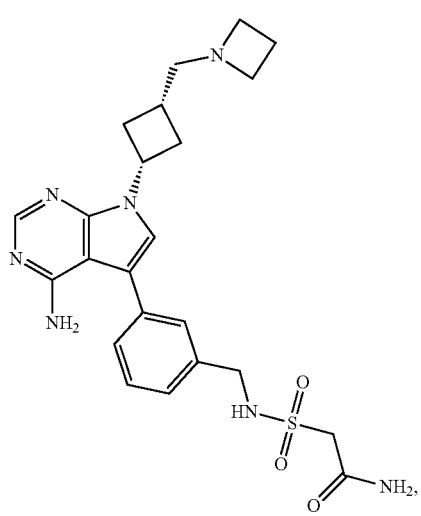
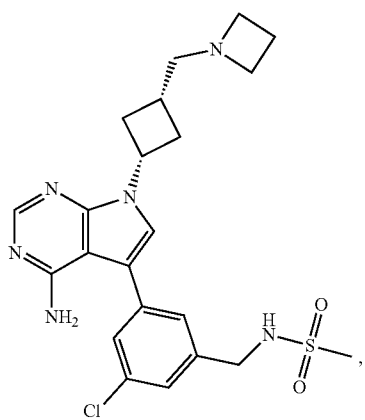

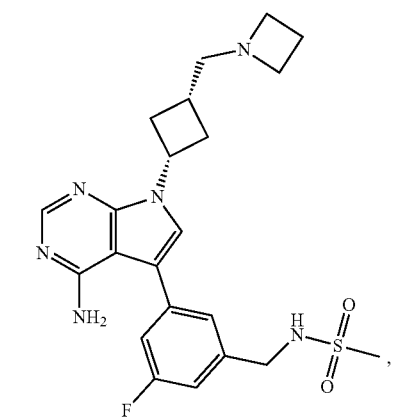
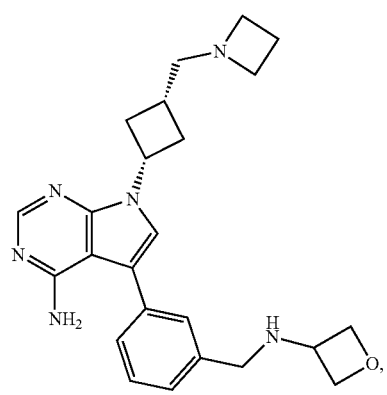
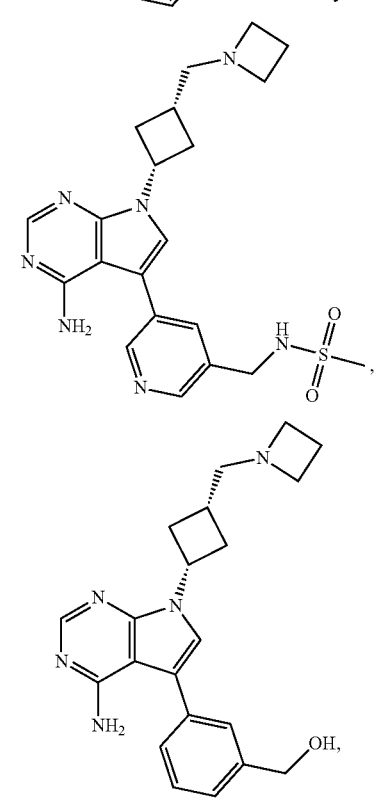
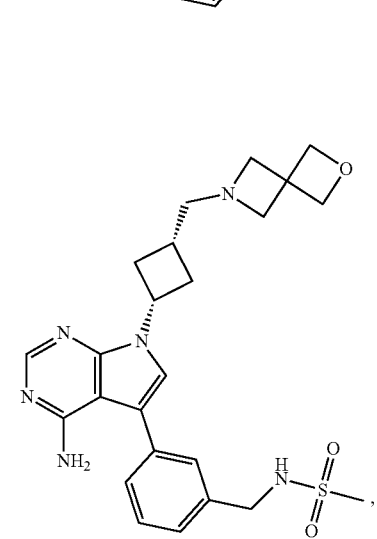

227
-continued
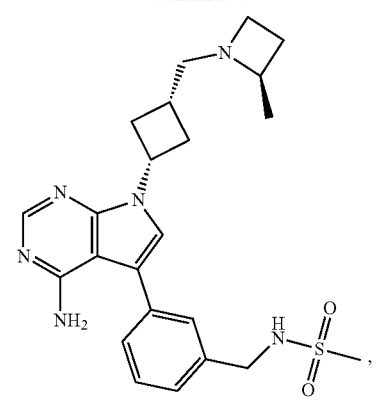
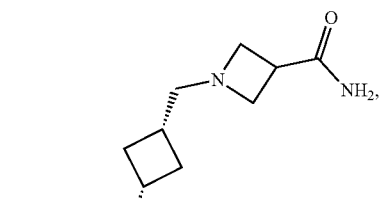
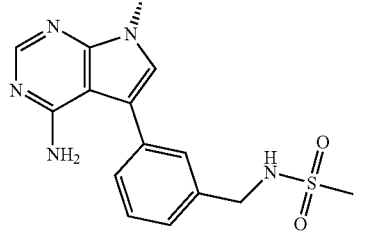
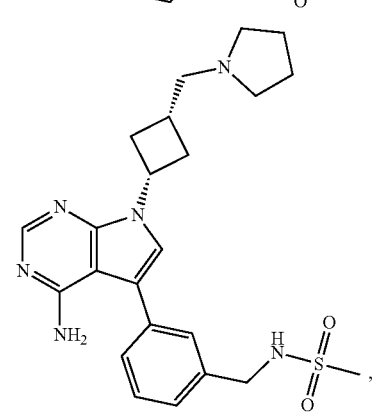
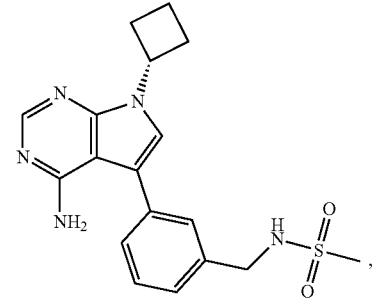
228
-continued
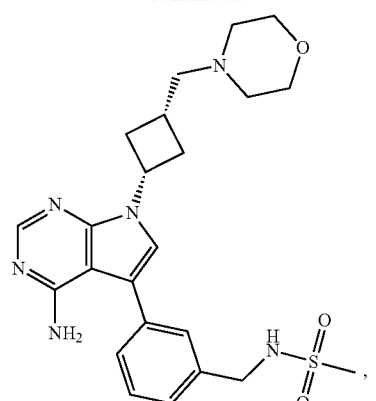
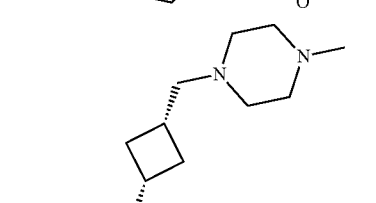
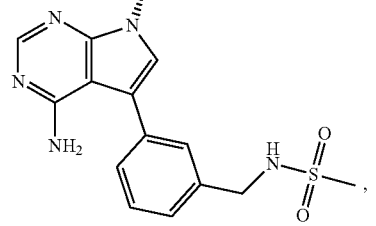
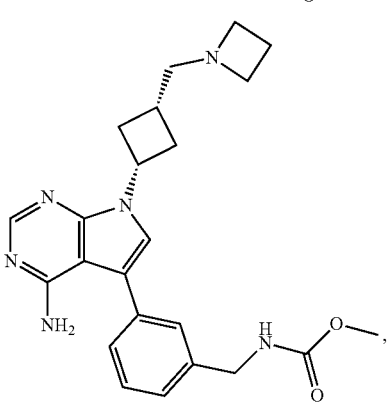
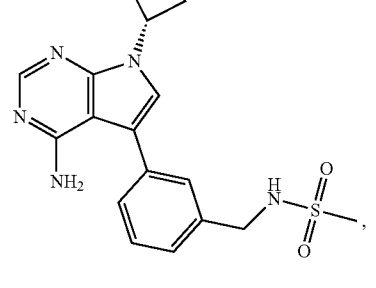

229
-continued
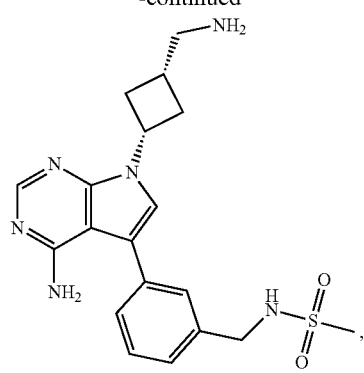
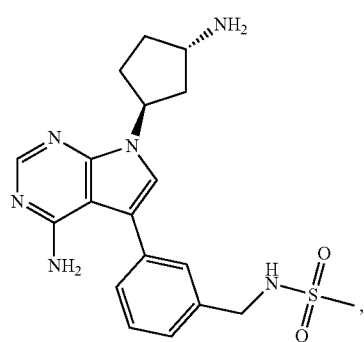
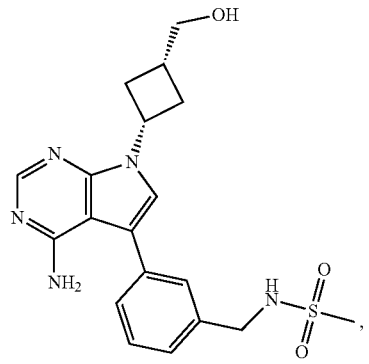
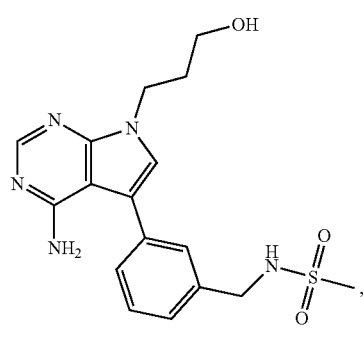
230
-continued
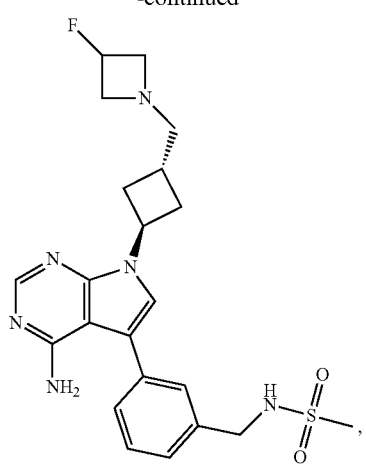
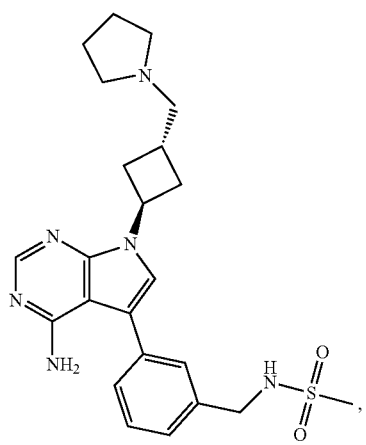
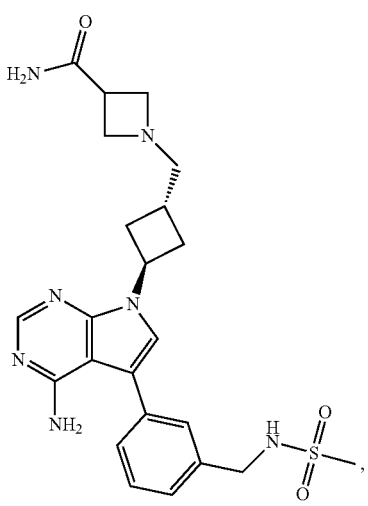

231
-continued
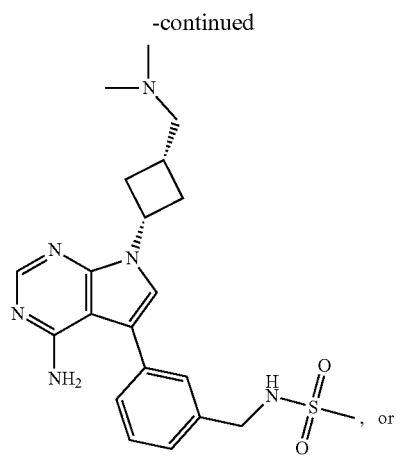
, or
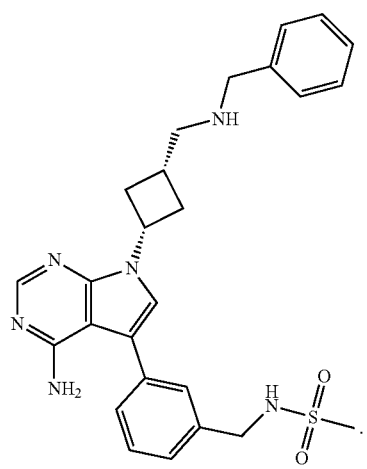
.
In embodiments, the compound is:
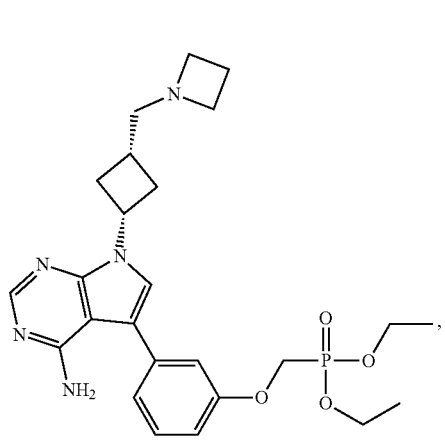
,
232
-continued
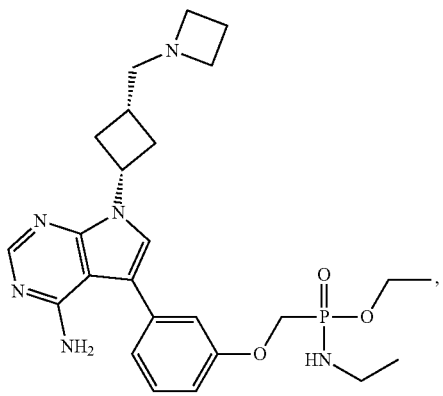
,
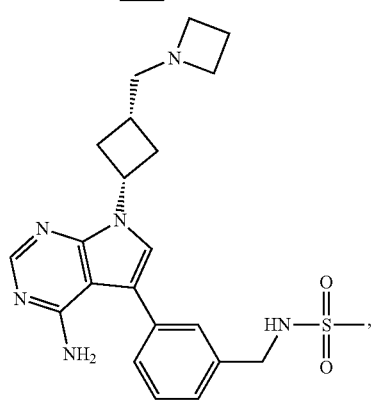
,
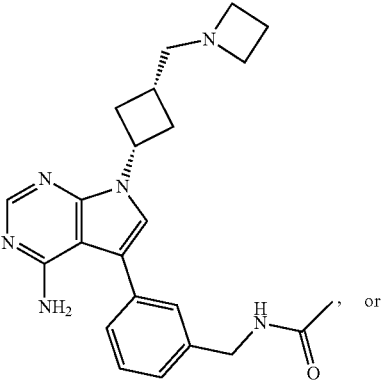
, or
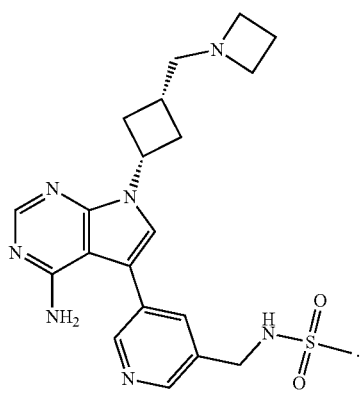 [SMILES: CS(=O)(=O)NCc1cncc(-c2cn([C@H]3C[C@@H](CN4CCC4)C3)c3ncnc(N)c23)c1]
.

In embodiments, the compound is:
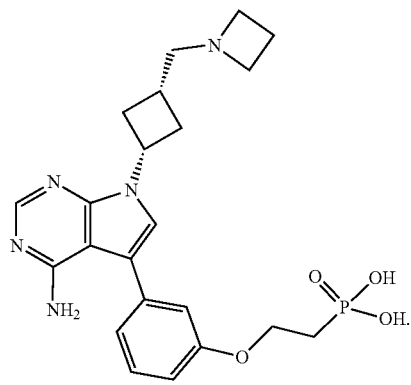 [SMILES: Nc1ncnc2c1c(-c1cccc(OCCP(=O)(O)O)c1)cn2[C@H]1C[C@@H](CN2CCC2)C1]
In embodiments, the compound is:
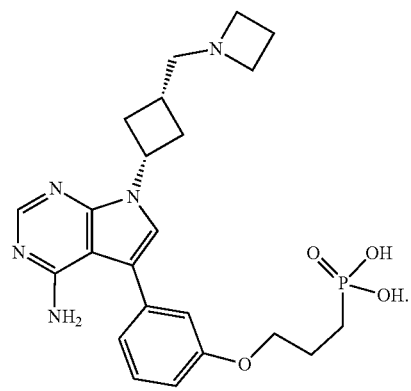 [SMILES: Nc1ncnc2c1c(-c1cccc(OCCCP(=O)(O)O)c1)cn2[C@H]1C[C@@H](CN2CCC2)C1]
In embodiments, the compound is:
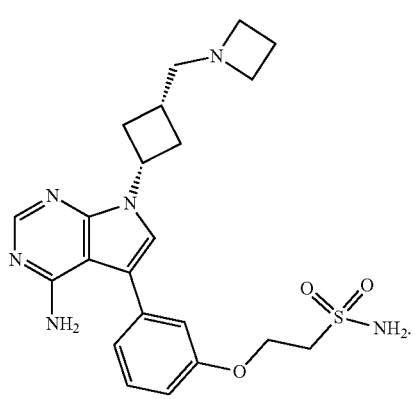 [SMILES: Nc1ncnc2c1c(-c1cccc(OCCS(N)(=O)=O)c1)cn2[C@H]1C[C@@H](CN2CCC2)C1]
In embodiments, the compound is:
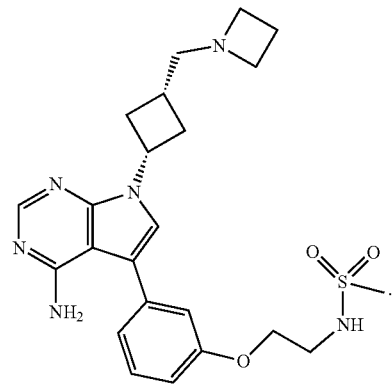 [SMILES: CS(=O)(=O)NCCOc1cccc(-c2cn([C@H]3C[C@@H](CN4CCC4)C3)c3ncnc(N)c23)c1]
In embodiments, the compound is:
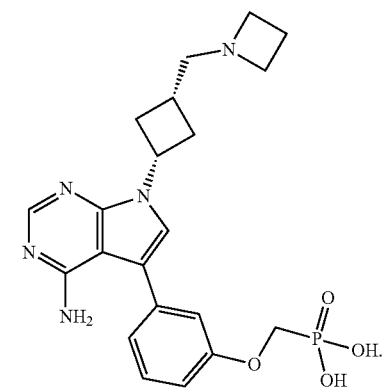 [SMILES: Nc1ncnc2c1c(-c1cccc(OCP(=O)(O)O)c1)cn2[C@H]1C[C@@H](CN2CCC2)C1]
In embodiments, the compound is:
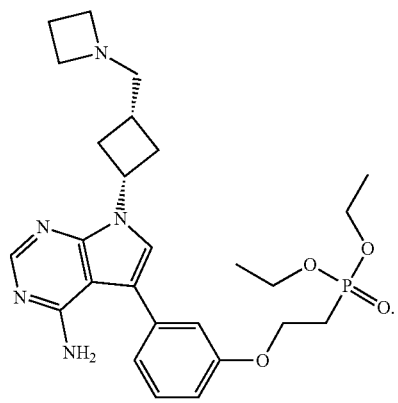 [SMILES: CCOP(=O)(CCOc1cccc(-c2cn([C@H]3C[C@@H](CN4CCC4)C3)c3ncnc(N)c23)c1)OCC]

In embodiments, the compound is:
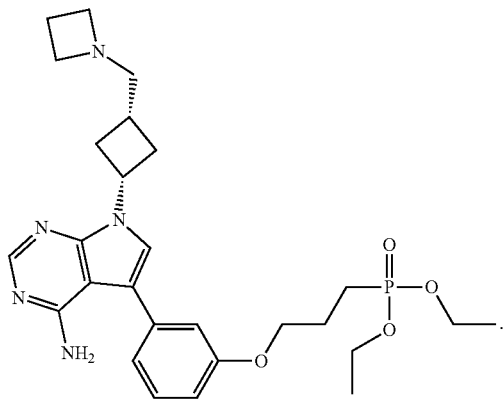 [SMILES: CCOP(=O)(CCCOc1cccc(-c2cn([C@H]3C[C@@H](CN4CCC4)C3)c3ncnc(N)c23)c1)OCC]
In embodiments, the compound is:
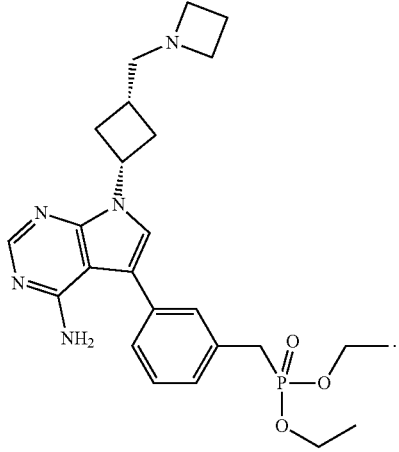
In embodiments, the compound is:
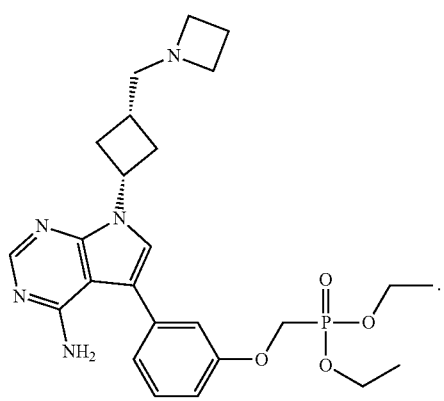 [SMILES: CCOP(=O)(COc1cccc(-c2cn([C@H]3C[C@@H](CN4CCC4)C3)c3ncnc(N)c23)c1)OCC]
In embodiments, the compound is:
In embodiments, the compound is:
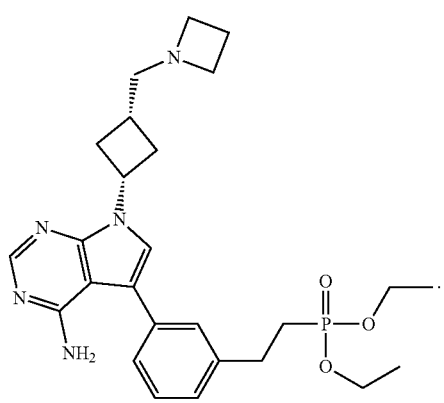 [SMILES: CCOP(=O)(CCc1cccc(-c2cn([C@H]3C[C@@H](CN4CCC4)C3)c3ncnc(N)c23)c1)OCC]
In embodiments, the compound is:
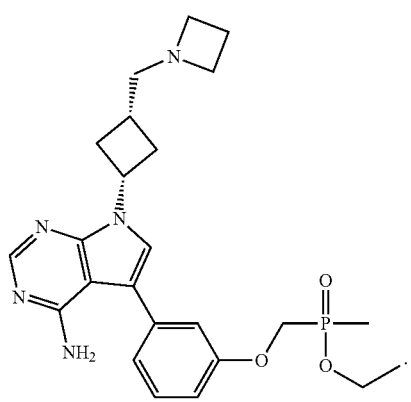 [SMILES: CCOP(C)(=O)COc1cccc(-c2cn([C@H]3C[C@@H](CN4CCC4)C3)c3ncnc(N)c23)c1]

In embodiments, the compound is:
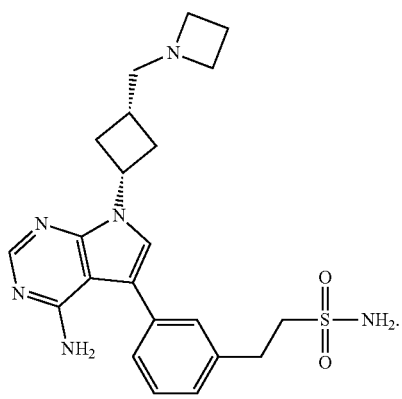 [SMILES: Nc1ncnc2c1c(-c1cccc(CCS(N)(=O)=O)c1)cn2[C@H]1C[C@@H](CN2CCC2)C1]
In embodiments, the compound is:
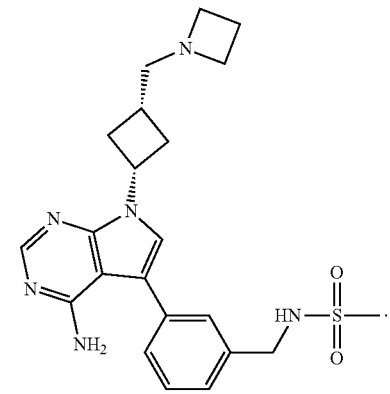 [SMILES: CS(=O)(=O)NCc1cccc(-c2cn([C@H]3C[C@@H](CN4CCC4)C3)c3ncnc(N)c23)c1]
In embodiments, the compound is:
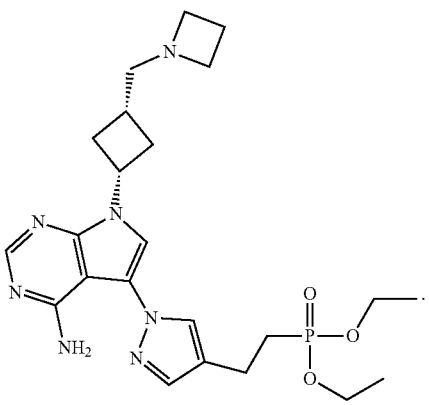 [SMILES: CCOP(=O)(CCc1cnn(-c2cn([C@H]3C[C@@H](CN4CCC4)C3)c3ncnc(N)c23)c1)OCC]
In embodiments, the compound is:
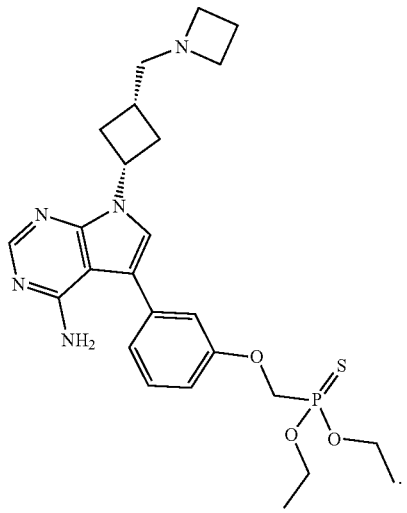 [SMILES: CCOP(=S)(COc1cccc(-c2cn([C@H]3C[C@@H](CN4CCC4)C3)c3ncnc(N)c23)c1)OCC]
In embodiments, the compound is:
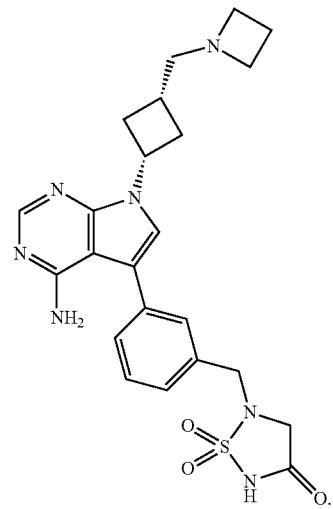 [SMILES: Nc1ncnc2c1c(-c1cccc(CN3CC(=O)NS3(=O)=O)c1)cn2[C@H]1C[C@@H](CN2CCC2)C1]
In embodiments, the compound is:
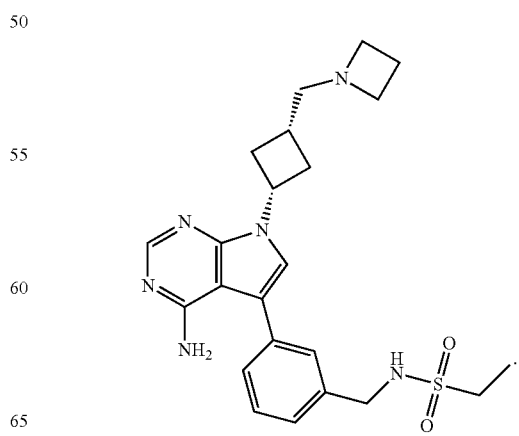

In embodiments, the compound is:
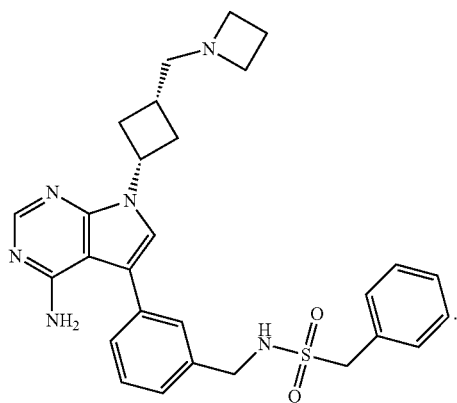 [SMILES: Nc1ncnc2c1c(-c1cccc(CNS(=O)(=O)Cc3ccccc3)c1)cn2[C@H]1C[C@@H](CN2CCC2)C1]
In embodiments, the compound is:
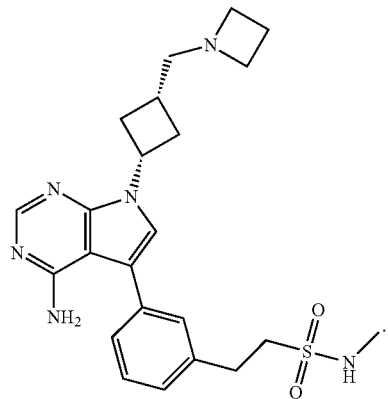
In embodiments, the compound is:
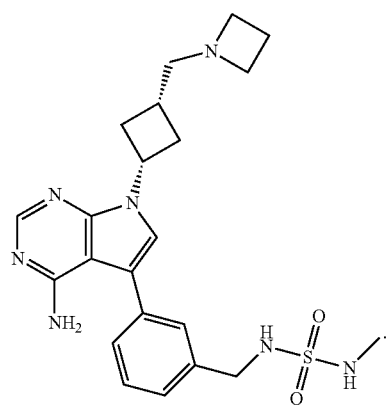 [SMILES: CNS(=O)(=O)NCc1cccc(-c2cn([C@H]3C[C@@H](CN4CCC4)C3)c3ncnc(N)c23)c1]
In embodiments, the compound is:
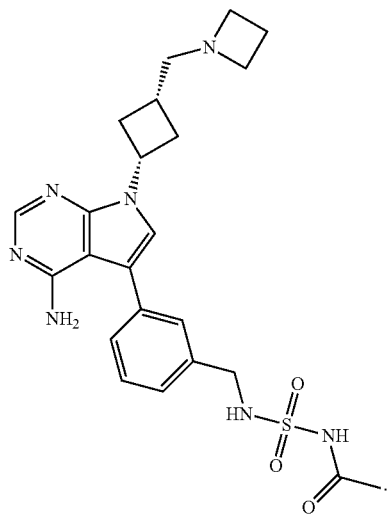
In embodiments, the compound is:
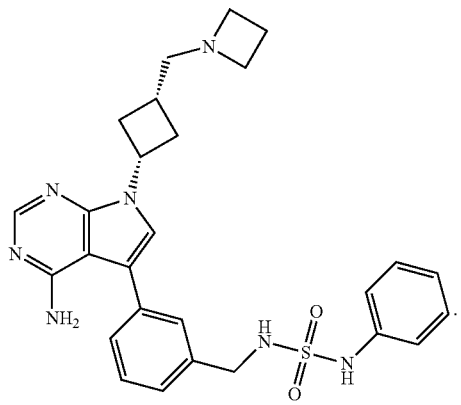 [SMILES: Nc1ncnc2c1c(-c1cccc(CNS(=O)(=O)Nc3ccccc3)c1)cn2[C@H]1C[C@@H](CN2CCC2)C1]
In embodiments, the compound is:
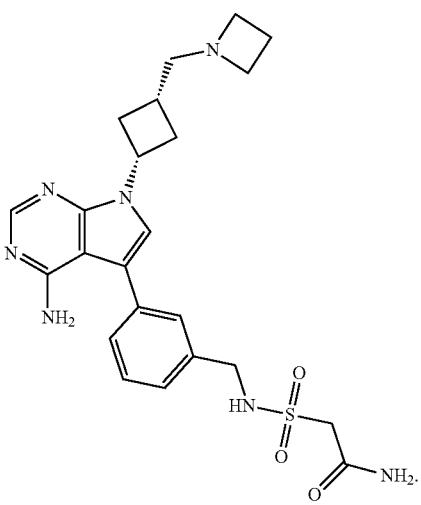 [SMILES: NC(=O)CS(=O)(=O)NCc1cccc(-c2cn([C@H]3C[C@@H](CN4CCC4)C3)c3ncnc(N)c23)c1]

In embodiments, the compound is:
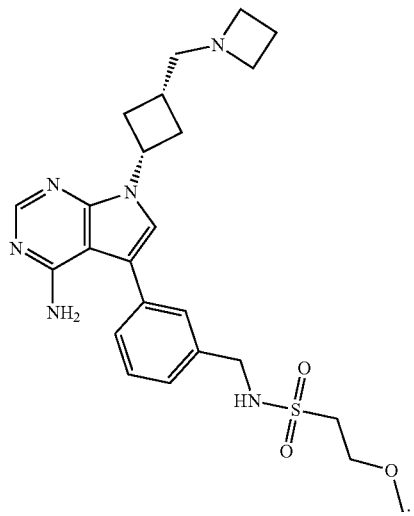 [SMILES: COCCS(=O)(=O)NCc1cccc(-c2cn([C@H]3C[C@@H](CN4CCC4)C3)c3ncnc(N)c23)c1]
In embodiments, the compound is:
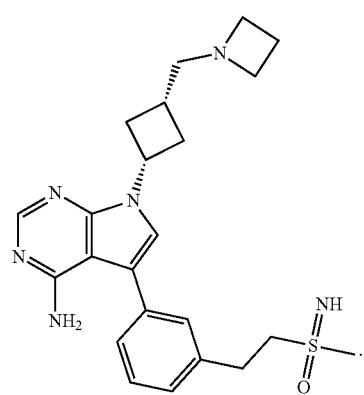 [SMILES: CS(=N)(=O)CCc1cccc(-c2cn([C@H]3C[C@@H](CN4CCC4)C3)c3ncnc(N)c23)c1]
In embodiments, the compound is:
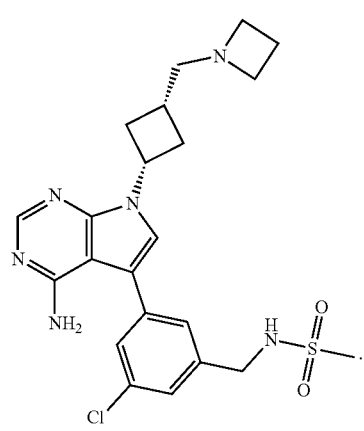
In embodiments, the compound is:
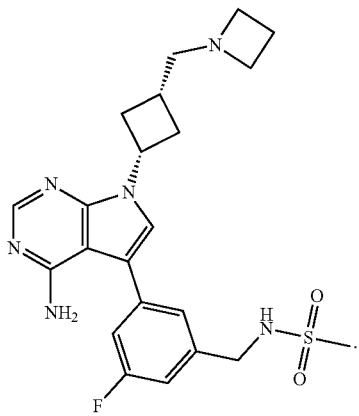 [SMILES: CS(=O)(=O)NCc1cc(Cl)cc(-c2cn([C@H]3C[C@@H](CN4CCC4)C3)c3ncnc(N)c23)c1]
In embodiments, the compound is:
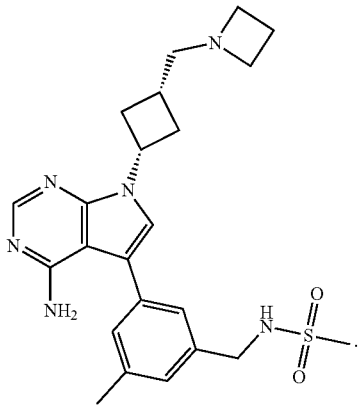 [SMILES: Cc1cc(CNS(C)(=O)=O)cc(-c2cn([C@H]3C[C@@H](CN4CCC4)C3)c3ncnc(N)c23)c1]
In embodiments, the compound is:
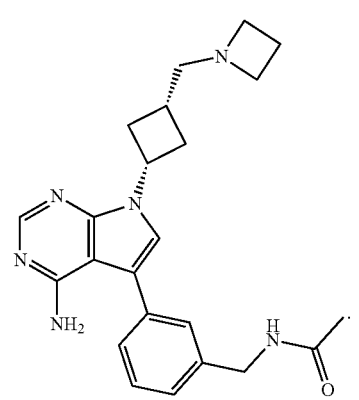 [SMILES: CC(=O)NCc1cccc(-c2cn([C@H]3C[C@@H](CN4CCC4)C3)c3ncnc(N)c23)c1]

In embodiments, the compound is:
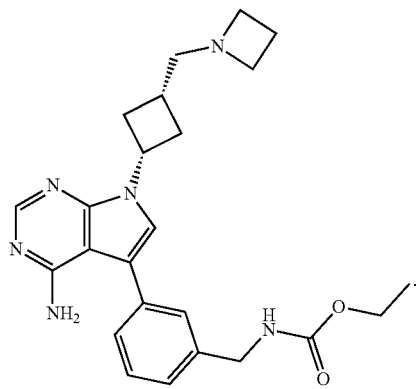 [SMILES: CCOC(=O)NCc1cccc(-c2cn([C@H]3C[C@@H](CN4CCC4)C3)c3ncnc(N)c23)c1]
In embodiments, the compound is:
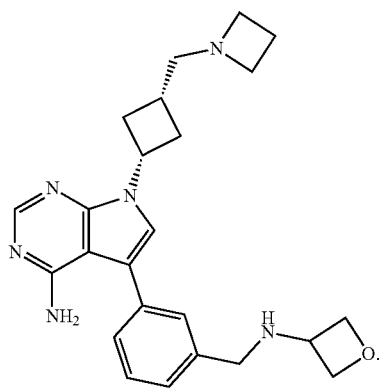 [SMILES: Nc1ncnc2c1c(-c1cccc(CNC3COC3)c1)cn2[C@H]1C[C@@H](CN2CCC2)C1]
In embodiments, the compound is:
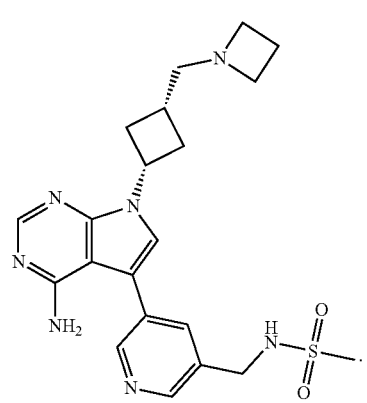 [SMILES: CS(=O)(=O)NCc1cncc(-c2cn([C@H]3C[C@@H](CN4CCC4)C3)c3ncnc(N)c23)c1]
In embodiments, the compound is:
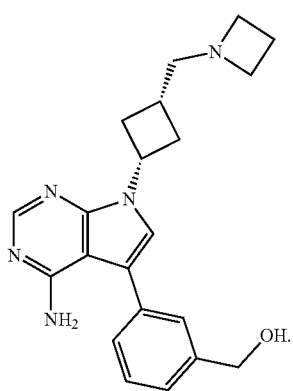 [SMILES: Nc1ncnc2c1c(-c1cccc(CO)c1)cn2[C@H]1C[C@@H](CN2CCC2)C1]
In embodiments, the compound is:
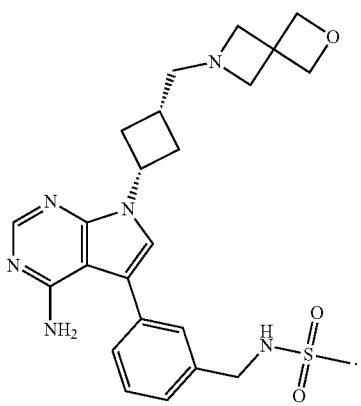 [SMILES: CS(=O)(=O)NCc1cccc(-c2cn([C@H]3C[C@@H](CN4CC5(COC5)C4)C3)c3ncnc(N)c23)c1]
In embodiments, the compound is:
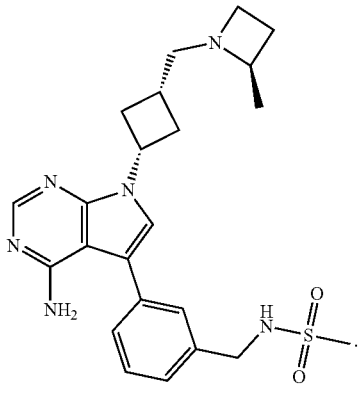 [SMILES: C[C@@H]1CCN1C[C@H]1C[C@@H](n2cc(-c3cccc(CNS(C)(=O)=O)c3)c3c(N)ncnc32)C1]

In embodiments, the compound is:
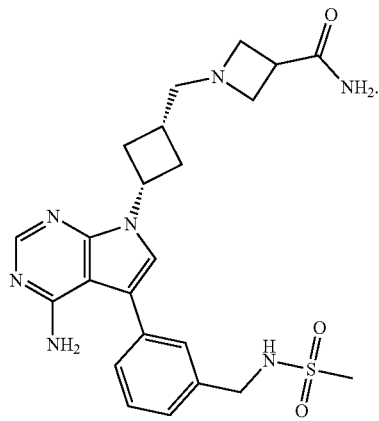 [SMILES: CS(=O)(=O)NCc1cccc(-c2cn([C@H]3C[C@@H](CN4CC(C(N)=O)C4)C3)c3ncnc(N)c23)c1]
In embodiments, the compound is:
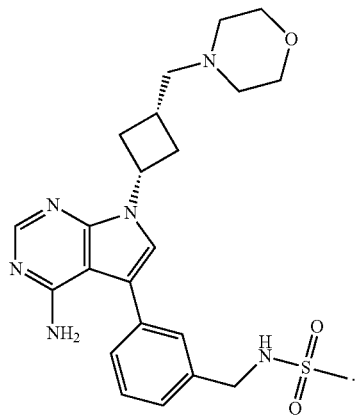
In embodiments, the compound is:
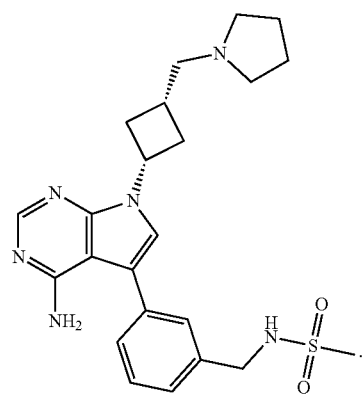 [SMILES: CS(=O)(=O)NCc1cccc(-c2cn([C@H]3C[C@@H](CN4CCCC4)C3)c3ncnc(N)c23)c1]
In embodiments, the compound is:
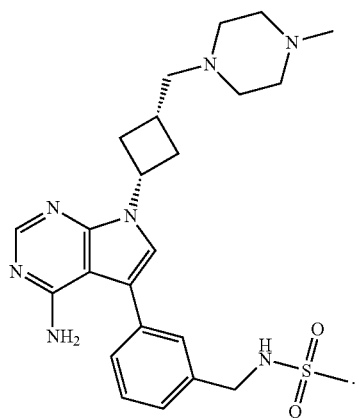
In embodiments, the compound is:
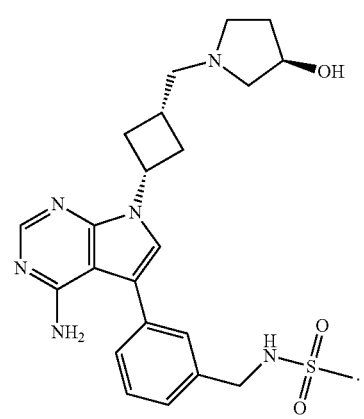 [SMILES: CS(=O)(=O)NCc1cccc(-c2cn([C@H]3C[C@@H](CN4CC[C@@H](O)C4)C3)c3ncnc(N)c23)c1]
In embodiments, the compound is:
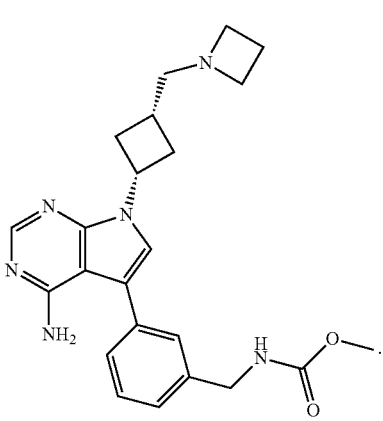 [SMILES: COC(=O)NCc1cccc(-c2cn([C@H]3C[C@@H](CN4CCC4)C3)c3ncnc(N)c23)c1]

In embodiments, the compound is:
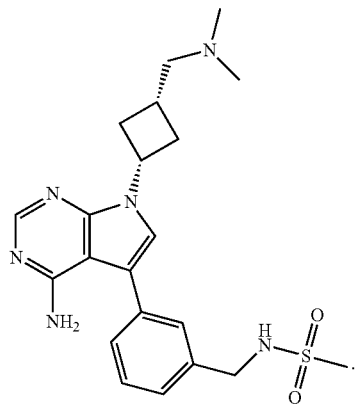 [SMILES: CN(C)C[C@H]1C[C@@H](n2cc(-c3cccc(CNS(C)(=O)=O)c3)c3c(N)ncnc32)C1]
In embodiments, the compound is:
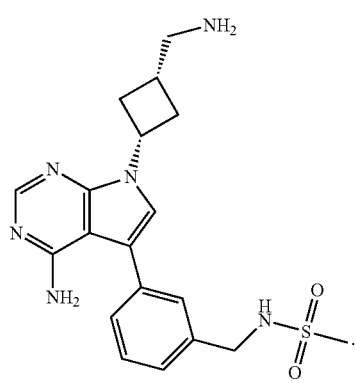
In embodiments, the compound is:
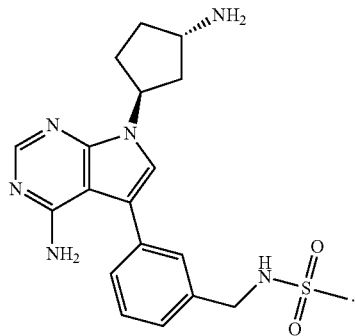 [SMILES: CS(=O)(=O)NCc1cccc(-c2cn([C@H]3CC[C@H](N)C3)c3ncnc(N)c23)c1]
In embodiments, the compound is:
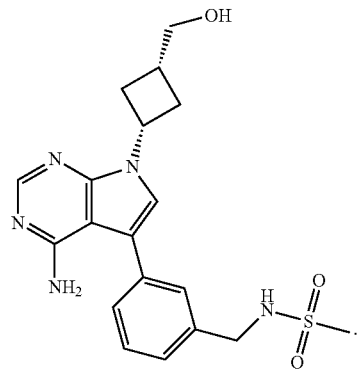 [SMILES: CS(=O)(=O)NCc1cccc(-c2cn([C@H]3C[C@@H](CO)C3)c3ncnc(N)c23)c1]
In embodiments, the compound is:
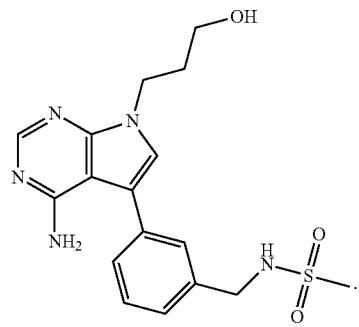 [SMILES: CS(=O)(=O)NCc1cccc(-c2cn(CCCO)c3ncnc(N)c23)c1]
In embodiments, the compound is:
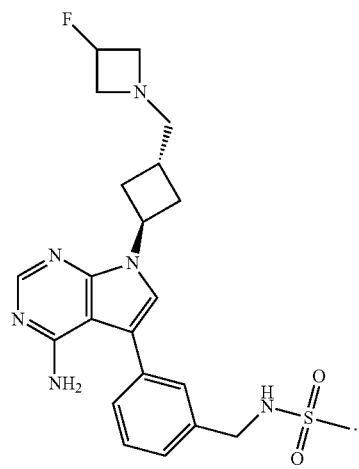 [SMILES: CS(=O)(=O)NCc1cccc(-c2cn([C@H]3C[C@H](CN4CC(F)C4)C3)c3ncnc(N)c23)c1]

In embodiments, the compound is:

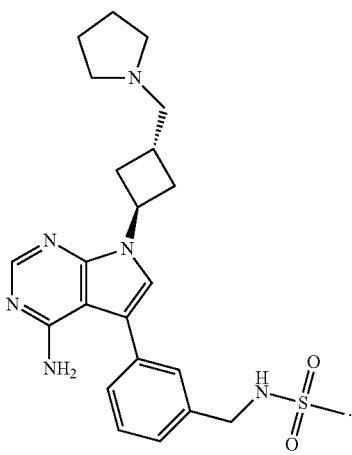 [SMILES: CS(=O)(=O)NCc1cccc(-c2cn([C@H]3C[C@H](CN4CCCC4)C3)c3ncnc(N)c23)c1]

In embodiments, the compound is:

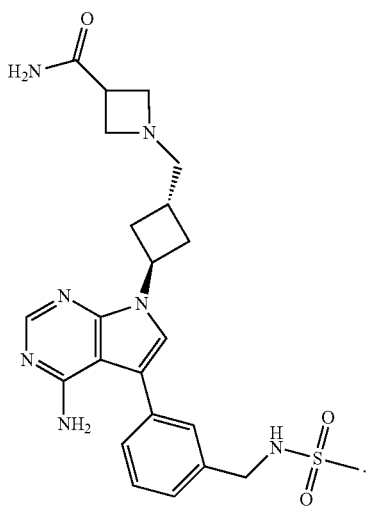 [SMILES: CS(=O)(=O)NCc1cccc(-c2cn([C@H]3C[C@H](CN4CC(C(N)=O)C4)C3)c3ncnc(N)c23)c1]

In embodiments, the compound is:

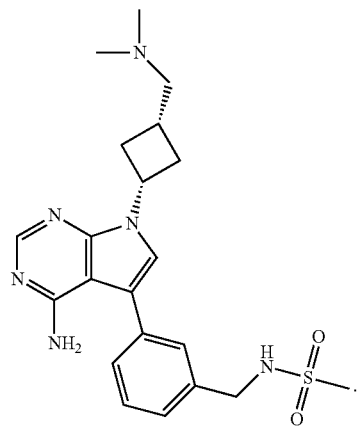 [SMILES: CN(C)C[C@H]1C[C@@H](n2cc(-c3cccc(CNS(C)(=O)=O)c3)c3c(N)ncnc32)C1]

In embodiments, the compound is:

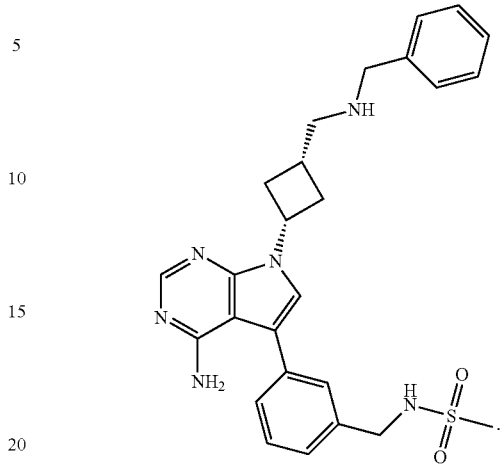

In embodiments, the compound is useful as a comparator compound. In embodiments, the comparator compound can be used to assess the activity of a test compound in an assay (e.g., an assay as described herein, for example in the examples section, figures, or tables).

In embodiments, the compound is a compound described herein (e.g., in an aspect, embodiment, example, table, figure, or claim).

III. Pharmaceutical Compositions

In an aspect is provided a pharmaceutical composition including a compound as described herein, including embodiments, and a pharmaceutically acceptable excipient. In embodiments, the compound as described herein is included in a therapeutically effective amount.

In embodiments of the pharmaceutical compositions, the compound, or pharmaceutically acceptable salt thereof, is included in a therapeutically effective amount.

In embodiments of the pharmaceutical compositions, the pharmaceutical composition includes a second agent (e.g. therapeutic agent). In embodiments of the pharmaceutical compositions, the pharmaceutical composition includes a second agent (e.g. therapeutic agent) in a therapeutically effective amount. In embodiments of the pharmaceutical compositions, the second agent is an agent for treating cancer. In embodiments of the pharmaceutical compositions, the second agent is an agent for treating an inflammatory disease. In embodiments of the pharmaceutical compositions, the second agent is an agent for treating an autoimmune disease. In embodiments, the administering does not include administration of any active agent other than the recited active agent (e.g., a compound described herein).

IV. Methods of Use

In an aspect is provided a method of increasing the level of LKB1 activity in a subject, the method including administering a compound as described herein to the subject. In embodiments, the compound is administered in an effective amount.

In an aspect is provided a method of increasing the level of LKB1 activity in a cell, the method including contacting said cell with a compound as described herein. In embodiments, the compound is administered in an effective amount.

In embodiments, the compound contacts a STRAD protein. In embodiments, the compound contacts an LKB1 protein. In embodiments, the compound contacts an MO25 protein. In embodiments, the compound contacts the LKB1-STRAD complex. In embodiments, the compound contacts an MO25 protein. In embodiments, the compound contacts the LKB1-STRAD-MO25 trimer complex.

In an aspect is provided a method of increasing the level of AMPK1, AMPK2, BRSK1, BRSK2, MARK1, MARK2, MARK3, MARK4, NUAK1, NUAK2, SIK1, SIK2, SIK3, SNRK, or TP53 activity in a subject, the method including administering a compound as described herein to the subject. In embodiments, the method increases the level of AMPK1, AMPK2, BRSK1, BRSK2, MARK1, MARK2, MARK3, MARK4, NUAK1, NUAK2, SIK1, SIK2, SIK3, SNRK, or TP53 protein. In embodiments, the compound is administered in an effective amount.

In an aspect is provided a method of modulating the level of AMPK1, AMPK2, BRSK1, BRSK2, MARK1, MARK2, MARK3, MARK4, NUAK1, NUAK2, SIK1, SIK2, SIK3, SNRK, or TP53 activity in a subject, the method including administering a compound as described herein to the subject. In embodiments, the method modulates the level of AMPK1, AMPK2, BRSK1, BRSK2, MARK1, MARK2, MARK3, MARK4, NUAK1, NUAK2, SIK1, SIK2, SIK3, SNRK, or TP53 protein. In embodiments, the compound is administered in an effective amount. In embodiments, the method increases the level of AMPK1, AMPK2, BRSK1, BRSK2, MARK1, MARK2, MARK3, MARK4, NUAK1, NUAK2, SIK1, SIK2, SIK3, SNRK, or TP53 activity in a subject, the method including administering a compound as described herein to the subject. In embodiments, the method increases the level of AMPK1, AMPK2, BRSK1, BRSK2, MARK1, MARK2, MARK3, MARK4, NUAK1, NUAK2, SIK1, SIK2, SIK3, SNRK, or TP53 protein. In embodiments, the compound is administered in an effective amount.

In an aspect is provided a method of modulating the level of a RAS/MAPK pathway activity in a subject, the method including administering a compound as described herein to the subject. In embodiments, the compound is administered in an effective amount. In embodiments, the method increases the level of a RAS/MAPK pathway activity in a subject. In embodiments, the method decreases the level of a RAS/MAPK pathway activity in a subject. In an aspect is provided a method of modulating the level of PIK3CA activity in a subject, the method including administering a compound as described herein to the subject. In embodiments, the compound is administered in an effective amount. In embodiments, the method increases the level of PIK3CA activity in a subject. In embodiments, the method decreases the level of PIK3CA activity in a subject. In an aspect is provided a method of modulating (e.g., increasing or decreasing) the level of 5' AMP-activated protein kinase 1 (AMPK1), 5' AMP-activated protein kinase 2 (AMPK2), Brain-specific serine/threonine kinase 1 (BRSK1), Brain-specific serine/threonine kinase 2 (BRSK2), Serine/threonine-protein kinase MARK1 (MARK1), Serine/threonine-protein kinase MARK2 (MARK2), Serine/threonine-protein kinase MARK3 (MARK3), Serine/threonine-protein kinase MARK4 (MARK4), NUAK family SNF1-like kinase 1 (NUAK1), NUAK family SNF1-like kinase 2 (NUAK2), salt inducible kinase 1 (SIK1), salt inducible kinase 2 (SIK2), salt inducible kinase 3 (SIK3), SNF-related serine/threonine-protein kinase (SNRK), or Tumor protein p53 (TP53) activity in a subject, the method including administering to the subject an effective amount of a compound as described herein. In embodiments, the method modulates (e.g., increases or decreases) the level of 5' AMP-activated protein kinase 1 (AMPK1), 5' AMP-activated protein kinase 2 (AMPK2), Brain-specific serine/threonine kinase 1 (BRSK1), Brain-specific serine/threonine kinase 2 (BRSK2), Serine/threonine-protein kinase MARK1 (MARK1), Serine/threonine-protein kinase MARK2 (MARK2), Serine/threonine-protein kinase MARK3 (MARK3), Serine/threonine-protein kinase MARK4 (MARK4), NUAK family SNF1-like kinase 1 (NUAK1), NUAK family SNF1-like kinase 2 (NUAK2), salt inducible kinase 1 (SIK1), salt inducible kinase 2 (SIK2), salt inducible kinase 3 (SIK3), SNF-related serine/threonine-protein kinase (SNRK), or Tumor protein p53 (TP53).

In an aspect is provided a method of decreasing the level of mTOR or cAMP-regulated transcriptional coactivator 2 (CRTC2), transcriptional coactivator 1 (CRTC1), or transcriptional coactivator 3 (CRTC3) activity in a subject, the method including administering a compound as described herein to the subject. In embodiments, the method decreases the level of mTOR or cAMP-regulated transcriptional coactivator 2 (CRTC2) activity in a subject. In embodiments, the method decreases the level of mTOR or cAMP-regulated transcriptional coactivator 1 (CRTC1) activity in a subject. In embodiments, the method decreases the level of mTOR or cAMP-regulated transcriptional coactivator 3 (CRTC3) activity in a subject. In embodiments, the method decreases the level of mTOR or cAMP-regulated transcriptional coactivator 2 protein. In embodiments, the compound is administered in an effective amount.

In an aspect is provided a method of increasing the level of mTOR or cAMP-regulated transcriptional coactivator 2 (CRTC2), transcriptional coactivator 1 (CRTC1), or transcriptional coactivator 3 (CRTC3) activity in a subject, the method including administering a compound as described herein to the subject. In embodiments, the method increases the level of mTOR or cAMP-regulated transcriptional coactivator 2 (CRTC2) activity in a subject. In embodiments, the method increases the level of mTOR or cAMP-regulated transcriptional coactivator 1 (CRTC1) activity in a subject. In embodiments, the method increases the level of mTOR or cAMP-regulated transcriptional coactivator 3 (CRTC3) activity in a subject. In embodiments, the method increases the level of mTOR or cAMP-regulated transcriptional coactivator 2 protein. In embodiments, the compound is administered in an effective amount.

In an aspect is provided a method of increasing the level of Hippo pathway activity in a subject, the method including administering a compound as described herein to the subject. In embodiments, the compound is administered in an effective amount.

In an aspect is provided a method of increasing the level of fatty acid oxidation activity in a subject, the method including administering a compound as described herein to the subject. In embodiments, the compound is administered in an effective amount.

In embodiments, the method includes increasing the level of LKB1 activity in the subject.

In an aspect is provided a method of increasing the level of 5' AMP-activated protein kinase 1 (AMPK1), 5' AMP-activated protein kinase 2 (AMPK2), Brain-specific serine/threonine kinase 1 (BRSK1), Brain-specific serine/threonine kinase 2 (BRSK2), Serine/threonine-protein kinase MARK1 (MARK1), Serine/threonine-protein kinase MARK2 (MARK2), Serine/threonine-protein kinase MARK3 (MARK3), Serine/threonine-protein kinase MARK4 (MARK4), NUAK family SNF1-like kinase 1 (NUAK1), NUAK family SNF1-like kinase 2 (NUAK2), salt inducible kinase 1 (SIK1), salt inducible kinase 2 (SIK2), salt inducible kinase 3 (SIK3), SNF-related serine/threonine-protein kinase (SNRK), or Tumor protein p53 (TP53) activity in a cell, the method including contacting the cell with a compound as described herein. In embodiments, the method increases the level of 5' AMP-activated protein kinase 1 (AMPK1), 5' AMP-activated protein kinase 2 (AMPK2), Brain-specific serine/threonine kinase 1 (BRSK1), Brain-specific serine/threonine kinase 2 (BRSK2), Serine/threonine-protein kinase MARK1 (MARK1), Serine/threonine-protein kinase MARK2 (MARK2), Serine/threonine-protein kinase MARK3 (MARK3), Serine/threonine-protein kinase MARK4 (MARK4), NUAK family SNF1-like kinase 1 (NUAK1), NUAK family SNF1-like kinase 2 (NUAK2), salt inducible kinase 1 (SIK1), salt inducible kinase 2 (SIK2), salt inducible kinase 3 (SIK3), SNF-related serine/threonine-protein kinase (SNRK), or Tumor protein p53 (TP53). In embodiments, the compound is administered in an effective amount.

In an aspect is provided a method of modulating the level of a RAS/MAPK pathway activity in a cell, the method including administering a compound as described herein to the cell. In embodiments, the compound is administered in an effective amount. In embodiments, the method increases the level of a RAS/MAPK pathway activity in a cell. In embodiments, the method decreases the level of a RAS/MAPK pathway activity in a cell. In an aspect is provided a method of modulating the level of PIK3CA activity in a cell, the method including administering a compound as described herein to the cell. In embodiments, the compound is administered in an effective amount. In embodiments, the method increases the level of PIK3CA activity in a cell. In embodiments, the method decreases the level of PIK3CA activity in a cell. In an aspect is provided a method of modulating (e.g., increasing or decreasing) the level of 5' AMP-activated protein kinase 1 (AMPK1), 5' AMP-activated protein kinase 2 (AMPK2), Brain-specific serine/threonine kinase 1 (BRSK1), Brain-specific serine/threonine kinase 2 (BRSK2), Serine/threonine-protein kinase MARK1 (MARK1), Serine/threonine-protein kinase MARK2 (MARK2), Serine/threonine-protein kinase MARK3 (MARK3), Serine/threonine-protein kinase MARK4 (MARK4), NUAK family SNF1-like kinase 1 (NUAK1), NUAK family SNF1-like kinase 2 (NUAK2), salt inducible kinase 1 (SIK1), salt inducible kinase 2 (SIK2), salt inducible kinase 3 (SIK3), SNF-related serine/threonine-protein kinase (SNRK), or Tumor protein p53 (TP53) activity in a cell, the method including contacting the cell with a compound as described herein. In embodiments, the method modulates (e.g., increases or decreases) the level of 5' AMP-activated protein kinase 1 (AMPK1), 5' AMP-activated protein kinase 2 (AMPK2), Brain-specific serine/threonine kinase 1 (BRSK1), Brain-specific serine/threonine kinase 2 (BRSK2), Serine/threonine-protein kinase MARK (MARK1), Serine/threonine-protein kinase MARK2 (MARK2), Serine/threonine-protein kinase MARK3 (MARK3), Serine/threonine-protein kinase MARK4 (MARK4), NUAK family SNF1-like kinase 1 (NUAK1), NUAK family SNF1-like kinase 2 (NUAK2), salt inducible kinase 1 (SIK1), salt inducible kinase 2 (SIK2), salt inducible kinase 3 (SIK3), SNF-related serine/threonine-protein kinase (SNRK), or Tumor protein p53 (TP53).

In an aspect is provided a method of decreasing the level of mTOR or cAMP-regulated transcriptional coactivator 2 (CRTC2), transcriptional coactivator 1 (CRTC1), or transcriptional coactivator 3 (CRTC3) activity in a cell, the method including contacting the cell with a compound as described herein. In embodiments, the method decreases the level of mTOR or cAMP-regulated transcriptional coactivator 2 (CRTC2) activity in a cell. In embodiments, the method decreases the level of mTOR or cAMP-regulated transcriptional coactivator 1 (CRTC1) activity in a cell. In embodiments, the method decreases the level of mTOR or cAMP-regulated transcriptional coactivator 3 (CRTC3) activity in a cell. In embodiments, the method decreases the level of mTOR or cAMP-regulated transcriptional coactivator 2 protein. In embodiments, an effective amount of the compound contacts the cell.

In an aspect is provided a method of increasing the level of mTOR or cAMP-regulated transcriptional coactivator 2 (CRTC2), transcriptional coactivator 1 (CRTC1), or transcriptional coactivator 3 (CRTC3) activity in a cell, the method including contacting the cell with a compound as described herein. In embodiments, the method increases the level of mTOR or cAMP-regulated transcriptional coactivator 2 (CRTC2) activity in a cell. In embodiments, the method increases the level of mTOR or cAMP-regulated transcriptional coactivator 1 (CRTC1) activity in a cell. In embodiments, the method increases the level of mTOR or cAMP-regulated transcriptional coactivator 3 (CRTC3) activity in a cell. In embodiments, the method increases the level of mTOR or cAMP-regulated transcriptional coactivator 2 protein. In embodiments, an effective amount of the compound contacts the cell.

In an aspect is provided a method of increasing the level of Hippo pathway activity in a cell, the method including contacting the cell with a compound as described herein. In embodiments, an effective amount of the compound contacts the cell.

In an aspect is provided a method of increasing the level of fatty acid oxidation activity in a cell, the method including contacting the cell with a compound as described herein. In embodiments, an effective amount of the compound contacts the cell.

In embodiments, the method includes increasing the level of LKB1 activity in the cell.

In embodiments, the compound contacts a STRAD protein. In embodiments, the compound contacts an LKB1 protein. In embodiments, the compound contacts an MO25 protein. In embodiments, the compound contacts the LKB1-STRAD complex. In embodiments, the compound contacts an MO25 protein. In embodiments, the compound contacts the LKB1-STRAD-MO25 trimer complex.

In an aspect is provided a method of treating a cancer in a subject in need thereof, the method including administering to the subject in need thereof an effective amount of a compound as described herein.

In embodiments, the cancer is pancreatic cancer, lung cancer, uterine cancer, renal cancer, colon cancer, soft tissue sarcoma, or a squamous cell cancer. In embodiments, the cancer is pancreatic cancer. In embodiments, the cancer is lung cancer. In embodiments, the cancer is uterine cancer. In embodiments, the cancer is renal cancer. In embodiments, the cancer is colon cancer. In embodiments, the cancer is soft tissue sarcoma. In embodiments, the cancer is a squamous cell cancer. In embodiments, the cancer is papillary renal carcinoma (PPRC). In embodiments, the cancer is non-small-cell lung carcinoma (NSCLC). In embodiments, the cancer includes a RAS/MAPK pathway mutation. In embodiments, the cancer includes a PIK3CA mutation.

In embodiments, the method further includes co-administering an anti-cancer agent to said subject in need.

In embodiments, the anti-cancer agent is a KRAS inhibitor, ERK inhibitor, MEK inhibitor, BRAF inhibitor, mTOR inhibitor, PD1 inhibitor, PDL1 inhibitor, or CTLA4 inhibitor. In embodiments, the anti-cancer agent is a KRAS inhibitor. In embodiments, the anti-cancer agent is an ERK inhibitor. In embodiments, the anti-cancer agent is a MEK inhibitor. In embodiments, the anti-cancer agent is a BRAF inhibitor. In embodiments, the anti-cancer agent is an mTOR inhibitor. In embodiments, the anti-cancer agent is a PD1 inhibitor. In embodiments, the anti-cancer agent is a PDL1 inhibitor. In embodiments, the anti-cancer agent is a CTLA4 inhibitor. In embodiments, the anti-cancer agent is a PIK3CA inhibitor. In embodiments, the method further includes co-administering an anti-cancer agent described herein.

In an aspect is provided a method of treating diabetes in a subject in need thereof, the method including administering to the subject in need thereof an effective amount of a compound as described herein.

In embodiments, the method includes reducing the level of blood glucose in the subject in need. In embodiments, the method reduces the amount of blood glucose at least (equal to or more than), e.g. 1 mg/dl, 5 mg/dl, 10 mg/dl, 15 mg/dl, 20 mg/dl, 25 mg/dl, 30 mg/dl, 35 mg/dl, 40 mg/dl, 45 mg/dl, 50 mg/dl, 60 mg/dl, 70 mg/dl, 70 mg/dl, 90 mg/dl, or 100 mg/dl.

In embodiments, the method includes reducing the level of insulin resistance in the subject in need.

In embodiments, the method further including co-administering a diabetes therapeutic agent to the subject in need.

In embodiments, the diabetes therapeutic agent is a biguanide, sulfonylurea, meglitinide, thiazolidinedione, alpha-glucosidase inhibitor, incretin, GLP-1 analogue, DPP-4 inhibitor, GLP-1 receptor agonist, amylin agonist, or insulin analogue. In embodiments, the diabetes therapeutic agent is a biguanide. In embodiments, the diabetes therapeutic agent is a sulfonylurea. In embodiments, the diabetes therapeutic agent is a meglitinide. In embodiments, the diabetes therapeutic agent is a thiazolidinedione. In embodiments, the diabetes therapeutic agent is an alpha-glucosidase inhibitor. In embodiments, the diabetes therapeutic agent is an incretin. In embodiments, the diabetes therapeutic agent is a GLP-1 analogue. In embodiments, the diabetes therapeutic agent is a DPP-4 inhibitor. In embodiments, the diabetes therapeutic agent is a GLP-1 receptor agonist. In embodiments, the diabetes therapeutic agent is an amylin agonist. In embodiments, the diabetes therapeutic agent is an insulin analogue.

In an aspect is provided a method of treating a cancer in a subject in need thereof, the method including administering to the subject in need thereof an effective amount of a pseudo-kinase STRADα stabilizing compound, wherein the pseudo-kinase STRADα stabilizing compound binds pseudo-kinase STRADα within the pseudo-kinase STRADα ATP binding pocket.

In an aspect is provided a method of treating diabetes in a subject in need thereof, the method including administering to the subject in need thereof an effective amount of a pseudo-kinase STRADα stabilizing compound, wherein the pseudo-kinase STRADα stabilizing compound binds pseudo-kinase STRADα within the pseudo-kinase STRADα ATP binding pocket.

In embodiments, the pseudo-kinase STRADα stabilizing compound contacts an amino acid within (lining) the pseudo-kinase STRADα ATP binding pocket corresponding to human STRADα Lys 197, His 200, Arg 215, Lys 77, or Arg 100. In embodiments, the pseudo-kinase STRADα stabilizing compound contacts amino acids within (lining) the pseudo-kinase STRADα ATP binding pocket corresponding to human STRADα Lys 197, His 200, Arg 215, Lys 77, and Arg 100. In embodiments, the pseudo-kinase STRADα stabilizing compound contacts one or more amino acids within (lining) the pseudo-kinase STRADα ATP binding pocket corresponding to human STRADα Lys 197, His 200, Arg 215, Lys 77, and/or Arg 100. In embodiments, the pseudo-kinase STRADα stabilizing compound contacts one or more amino acids within (lining) the pseudo-kinase STRADα ATP binding pocket corresponding to human STRADα Lys 197, His 200, Arg 215, Lys 77, Arg 100, Ser199, Lys 239, Asp 157, Ser 154, Leu 202, Gly 153, Met 150, Phe 149, Ser 148, Thr 98, Thr 147, Ile 75, Val 85, Gly 76, Phe 415, Met 83, Phe 79, and/or Gly 78. In embodiments, the pseudo-kinase STRADα stabilizing compound contacts one or more amino acids within (lining) the pseudo-kinase STRADα ATP binding pocket corresponding to human STRADα Lys 197, His 200, Arg 215, Lys 77, Arg 100, Ser199, Asp 157, Met 150, Ser 148, Thr 98, Val 85, and/or Phe 79. In embodiments, the pseudo-kinase STRADα stabilizing compound contacts one or more amino acids within (lining) the pseudo-kinase STRADα ATP binding pocket corresponding to human STRADα Lys 197, His 200, Arg 215, Lys 77, Arg 100, and/or Ser199. In embodiments, the pseudo-kinase STRADα stabilizing compound contacts one or more amino acids within (lining) the pseudo-kinase STRADα ATP binding pocket corresponding to human STRADα Lys 197. In embodiments, the pseudo-kinase STRADα stabilizing compound contacts one or more amino acids within (lining) the pseudo-kinase STRADα ATP binding pocket corresponding to human STRADα His 200. In embodiments, the pseudo-kinase STRADα stabilizing compound contacts one or more amino acids within (lining) the pseudo-kinase STRADα ATP binding pocket corresponding to human STRADα Arg 215. In embodiments, the pseudo-kinase STRADα stabilizing compound contacts one or more amino acids within (lining) the pseudo-kinase STRADα ATP binding pocket corresponding to human STRADα Lys 77. In embodiments, the pseudo-kinase STRADα stabilizing compound contacts one or more amino acids within (lining) the pseudo-kinase STRADα ATP binding pocket corresponding to human STRADα Arg 100. In embodiments, the pseudo-kinase STRADα stabilizing compound contacts one or more amino acids within (lining) the pseudo-kinase STRADα ATP binding pocket corresponding to human STRADα Ser199. In embodiments, the pseudo-kinase STRADα stabilizing compound contacts one or more amino acids within (lining) the pseudo-kinase STRADα ATP binding pocket corresponding to human STRADα Lys 239. In embodiments, the pseudo-kinase STRADα stabilizing compound contacts one or more amino acids within (lining) the pseudo-kinase STRADα ATP binding pocket corresponding to human STRADα Asp 157. In embodiments, the pseudo-kinase STRADα stabilizing compound contacts one or more amino acids within (lining) the pseudo-kinase STRADα ATP binding pocket corresponding to human STRADα Ser 154. In embodiments, the pseudo-kinase STRADα stabilizing compound contacts one or more amino acids within (lining) the pseudo-kinase STRADα ATP binding pocket corresponding to human STRADα Leu 202. In embodiments, the pseudo-kinase STRADα stabilizing compound contacts one or more amino acids within (lining) the pseudo-kinase STRADα ATP binding pocket corresponding to human STRADα Gly 153. In embodiments, the pseudo-kinase STRADα stabilizing compound contacts one or more amino acids within (lining) the pseudo-kinase STRADα ATP binding pocket corresponding to human STRADα Met 150. In embodiments, the pseudo-kinase STRADα stabilizing compound contacts one or more amino acids within (lining) the pseudo-kinase STRADα

ATP binding pocket corresponding to human STRADα Phe 149. In embodiments, the pseudo-kinase STRADα stabilizing compound contacts one or more amino acids within (lining) the pseudo-kinase STRADα ATP binding pocket corresponding to human STRADα Ser 148. In embodiments, the pseudo-kinase STRADα stabilizing compound contacts one or more amino acids within (lining) the pseudo-kinase STRADα ATP binding pocket corresponding to human STRADα Thr 98. In embodiments, the pseudo-kinase STRADα stabilizing compound contacts one or more amino acids within (lining) the pseudo-kinase STRADα ATP binding pocket corresponding to human STRADα Thr 147. In embodiments, the pseudo-kinase STRADα stabilizing compound contacts one or more amino acids within (lining) the pseudo-kinase STRADα ATP binding pocket corresponding to human STRADα Ile 75. In embodiments, the pseudo-kinase STRADα stabilizing compound contacts one or more amino acids within (lining) the pseudo-kinase STRADα ATP binding pocket corresponding to human STRADα Val 85. In embodiments, the pseudo-kinase STRADα stabilizing compound contacts one or more amino acids within (lining) the pseudo-kinase STRADα ATP binding pocket corresponding to human STRADα Gly 76. In embodiments, the pseudo-kinase STRADα stabilizing compound contacts one or more amino acids within (lining) the pseudo-kinase STRADα ATP binding pocket corresponding to human STRADα Phe 415. In embodiments, the pseudo-kinase STRADα stabilizing compound contacts one or more amino acids within (lining) the pseudo-kinase STRADα ATP binding pocket corresponding to human STRADα Met 83. In embodiments, the pseudo-kinase STRADα stabilizing compound contacts one or more amino acids within (lining) the pseudo-kinase STRADα ATP binding pocket corresponding to human STRADα Phe 79. In embodiments, the pseudo-kinase STRADα stabilizing compound contacts one or more amino acids within (lining) the pseudo-kinase STRADα ATP binding pocket corresponding to human STRADα Gly 78. In embodiments, the pseudo-kinase STRADα stabilizing compound contacts one or more amino acids within (lining) the pseudo-kinase STRADα ATP binding pocket corresponding to human STRADα Lys 197, His 200, Arg 215, Lys 77, and/or Arg 100; and the pseudo-kinase STRADα stabilizing compound contacts one or more amino acids within (lining) the pseudo-kinase STRADα ATP binding pocket corresponding to human STRADα Ser199, Lys 239, Asp 157, Ser 154, Leu 202, Gly 153, Met 150, Phe 149, Ser 148, Thr 98, Thr 147, Ile 75, Val 85, Gly 76, Phe 415, Met 83, Phe 79, and/or Gly 78. In embodiments, the pseudo-kinase STRADα stabilizing compound contacts one or more amino acids within (lining) the pseudo-kinase STRADα ATP binding pocket corresponding to human STRADα Lys 197, His 200, Arg 215, Lys 77, and/or Arg 100; and the pseudo-kinase STRADα stabilizing compound contacts one or more amino acids within (lining) the pseudo-kinase STRADα ATP binding pocket corresponding to human STRADα Ser199, Asp 157, Met 150, Ser 148, Thr 98, Val 85, and/or Phe 79. In embodiments, the pseudo-kinase STRADα stabilizing compound is a compound described herein (e.g., including in embodiments).

In an aspect is provided a method of treating a cancer in a subject in need thereof, the method including administering to the subject in need thereof an effective amount of a pseudo-kinase STRADα stabilizing compound, wherein the pseudo-kinase STRADα stabilizing compound binds pseudo-kinase STRADα within the pseudo-kinase STRADα ATP binding pocket and contacts an amino acid within (lining) the pseudo-kinase STRADα ATP binding pocket corresponding to Lys 197, His 200, Arg 215, Lys 77, or Arg 100.

In an aspect is provided a method of treating diabetes in a subject in need thereof, the method including administering to the subject in need thereof an effective amount of a pseudo-kinase STRADα stabilizing compound, wherein the pseudo-kinase STRADα stabilizing compound binds pseudo-kinase STRADα within the pseudo-kinase STRADα ATP binding pocket and contacts an amino acid within (lining) the pseudo-kinase STRADα ATP binding pocket corresponding to Lys 197, His 200, Arg 215, Lys 77, or Arg 100.

In embodiments, the pseudo-kinase STRADα stabilizing compound contacts amino acids within (lining) the pseudo-kinase STRADα ATP binding pocket corresponding to Lys 197, His 200, Arg 215, Lys 77, and Arg 100. In embodiments, the pseudo-kinase STRADα stabilizing compound increases LKB1-STRADα-Mo25 trimer complex association. In embodiments, the pseudo-kinase STRADα stabilizing compound increases the rate of phosphorylation by LKB1. In embodiments, the pseudo-kinase STRADα stabilizing compound maintains biologically relevant downstream signaling for greater than 24 hours upon onetime pseudo-kinase STRADα stabilizing compound exposure. In embodiments, the pseudo-kinase STRADα stabilizing compound contacts an amino acid within (lining) the pseudo-kinase STRADα ATP binding pocket corresponding to Lys 197 of human pseudo-kinase STRADα. In embodiments, the pseudo-kinase STRADα stabilizing compound contacts an amino acid within (lining) the pseudo-kinase STRADα ATP binding pocket corresponding to His 200 of human pseudo-kinase STRADα. In embodiments, the pseudo-kinase STRADα stabilizing compound contacts an amino acid within (lining) the pseudo-kinase STRADα ATP binding pocket corresponding to Arg 215 of human pseudo-kinase STRADα. In embodiments, the pseudo-kinase STRADα stabilizing compound contacts an amino acid within (lining) the pseudo-kinase STRADα ATP binding pocket corresponding to Lys 77 of human pseudo-kinase STRADα. In embodiments, the pseudo-kinase STRADα stabilizing compound contacts an amino acid within (lining) the pseudo-kinase STRADα ATP binding pocket corresponding to Arg 100 of human pseudo-kinase STRADα.

In embodiments, the pseudo-kinase STRADα stabilizing compound induces desirable effects on pCRTC2 (e.g., increase amount, increase level of protein, increase level of activity, or increase activity), pS6 (e.g., decrease amount, decrease level of protein, decrease level of activity, or decrease activity), and/or pLATS (e.g., increase amount, increase level of protein, increase level of activity, or increase activity). In embodiments, the pseudo-kinase STRADα stabilizing compound induces desirable effects on NUAK1, NUAK2, AMPK1, AMPK2, SIK1, SIK2, SIK3, MARK1, MARK2, MARK3, MARK4, BRSK1, BRSK2, or SNRK.

In embodiments, the pseudo-kinase STRADα stabilizing compound selectively binds STRADα relative to LKB1, or relative to other kinases. In embodiments, the compound binds STRADα at least 1.1-fold, 1.2, 1.3, 1.4, 1.5, 1.6, 1.7, 1.8, 1.9, 2.0, 5.0, 10, 50, 100, 1000, or 10,000-fold stronger than the compound binds LKB1 at the same compound concentration (e.g., measured by dissociation constant). In embodiments, the compound binds STRADα at least 1.1-fold, 1.2, 1.3, 1.4, 1.5, 1.6, 1.7, 1.8, 1.9, 2.0, 5.0, 10, 50, 100, 1000, or 10,000-fold stronger than the compound binds other proteins (e.g., other kinases) at the same compound concentration (e.g., measured by dissociation constant). In embodiments, the compound binds STRADα at least 1.1-fold stronger than the compound binds LKB1 at the same compound concentration (e.g., measured by dissociation constant). In embodiments, the compound binds STRADα at least 1.2-fold stronger than the compound binds LKB1 at the same compound concentration (e.g., measured by dissociation constant). In embodiments, the compound binds STRADα at least 1.3-fold stronger than the compound binds LKB1 at the same compound concentration (e.g., measured by dissociation constant). In embodiments, the compound binds STRADα at least 1.4-fold stronger than the compound binds LKB1 at the same compound concentration (e.g., measured by dissociation constant). In embodiments, the compound binds STRADα at least 1.5-fold stronger than the compound binds LKB1 at the same compound concentration (e.g., measured by dissociation constant). In embodiments, the compound binds STRADα at least 1.6-fold stronger than the compound binds LKB1 at the same compound concentration (e.g., measured by dissociation constant). In embodiments, the compound binds STRADα at least 1.7-fold stronger than the compound binds LKB1 at the same compound concentration (e.g., measured by dissociation constant). In embodiments, the compound binds STRADα at least 1.8-fold stronger than the compound binds LKB1 at the same compound concentration (e.g., measured by dissociation constant). In embodiments, the compound binds STRADα at least 1.9-fold stronger than the compound binds LKB1 at the same compound concentration (e.g., measured by dissociation constant). In embodiments, the compound binds STRADα at least 2.0-fold stronger than the compound binds LKB1 at the same compound concentration (e.g., measured by dissociation constant). In embodiments, the compound binds STRADα at least 5.0-fold stronger than the compound binds LKB1 at the same compound concentration (e.g., measured by dissociation constant). In embodiments, the compound binds STRADα at least 10-fold stronger than the compound binds LKB1 at the same compound concentration (e.g., measured by dissociation constant). In embodiments, the compound binds STRADα at least 50-fold stronger than the compound binds LKB1 at the same compound concentration (e.g., measured by dissociation constant). In embodiments, the compound binds STRADα at least 100-fold stronger than the compound binds LKB1 at the same compound concentration (e.g., measured by dissociation constant). In embodiments, the compound binds STRADα at least 1000-fold stronger than the compound binds LKB1 at the same compound concentration (e.g., measured by dissociation constant). In embodiments, the compound binds STRADα at least 10,000-fold stronger than the compound binds LKB1 at the same compound concentration (e.g., measured by dissociation constant). In embodiments, the compound binds STRADα at least 1.1-fold stronger than the compound binds other proteins (e.g., other kinases) at the same compound concentration (e.g., measured by dissociation constant). In embodiments, the compound binds STRADα at least 1.2-fold stronger than the compound binds other proteins (e.g., other kinases) at the same compound concentration (e.g., measured by dissociation constant). In embodiments, the compound binds STRADα at least 1.3-fold stronger than the compound binds other proteins (e.g., other kinases) at the same compound concentration (e.g., measured by dissociation constant). In embodiments, the compound binds STRADα at least 1.4-fold stronger than the compound binds other proteins (e.g., other kinases) at the same compound concentration (e.g., measured by dissociation constant). In embodiments, the compound binds STRADα at least 1.5-fold stronger than the compound binds other proteins (e.g., other kinases) at the same compound concentration (e.g., measured by dissociation constant). In embodiments, the compound binds STRADα at least 1.6-fold stronger than the compound binds other proteins (e.g., other kinases) at the same compound concentration (e.g., measured by dissociation constant). In embodiments, the compound binds STRADα at least 1.7-fold stronger than the compound binds other proteins (e.g., other kinases) at the same compound concentration (e.g., measured by dissociation constant). In embodiments, the compound binds STRADα at least 1.8-fold stronger than the compound binds other proteins (e.g., other kinases) at the same compound concentration (e.g., measured by dissociation constant). In embodiments, the compound binds STRADα at least 1.9-fold stronger than the compound binds other proteins (e.g., other kinases) at the same compound concentration (e.g., measured by dissociation constant). In embodiments, the compound binds STRADα at least 2.0-fold stronger than the compound binds other proteins (e.g., other kinases) at the same compound concentration (e.g., measured by dissociation constant). In embodiments, the compound binds STRADα at least 5.0-fold stronger than the compound binds other proteins (e.g., other kinases) at the same compound concentration (e.g., measured by dissociation constant). In embodiments, the compound binds STRADα at least 10-fold stronger than the compound binds other proteins (e.g., other kinases) at the same compound concentration (e.g., measured by dissociation constant). In embodiments, the compound binds STRADα at least 50-fold stronger than the compound binds other proteins (e.g., other kinases) at the same compound concentration (e.g., measured by dissociation constant). In embodiments, the compound binds STRADα at least 100-fold stronger than the compound binds other proteins (e.g., other kinases) at the same compound concentration (e.g., measured by dissociation constant). In embodiments, the compound binds STRADα at least 1000-fold stronger than the compound binds other proteins (e.g., other kinases) at the same compound concentration (e.g., measured by dissociation constant). In embodiments, the compound binds STRADα at least 10,000-fold stronger than the compound binds other proteins (e.g., other kinases) at the same compound concentration (e.g., measured by dissociation constant).

In embodiments, the pseudo-kinase STRADα stabilizing compound contacts an amino acid within (lining) the pseudo-kinase STRADα ATP binding pocket through a chemical moiety selected from carboxylic acid, ether, sulfone, sulfonamide, nitrile, hetero-cycle, alcohol, sulfonic acid, amide, ester, urea, and/or sulfonyl urea. In embodiments, the pseudo-kinase STRADα stabilizing compound contacts an amino acid within (lining) the pseudo-kinase STRADα ATP binding pocket through a carboxylic acid. In embodiments, the pseudo-kinase STRADα stabilizing compound contacts an amino acid within (lining) the pseudo-kinase STRADα ATP binding pocket through an ether. In embodiments, the pseudo-kinase STRADα stabilizing compound contacts an amino acid within (lining) the pseudo-kinase STRADα ATP binding pocket through a sulfone. In embodiments, the pseudo-kinase STRADα stabilizing compound contacts an amino acid within (lining) the pseudo-kinase STRADα ATP binding pocket through a sulfonamide. In embodiments, the pseudo-kinase STRADα stabilizing compound contacts an amino acid within (lining) the pseudo-kinase STRADα ATP binding pocket through a nitrile. In embodiments, the pseudo-kinase STRADα stabilizing compound contacts an amino acid within (lining) the pseudo-kinase STRADα ATP binding pocket through a hetero-cycle. In embodiments, the pseudo-kinase STRADα stabilizing compound contacts an amino acid within (lining) the pseudo-kinase STRADα ATP binding pocket through an alcohol. In embodiments, the pseudo-kinase STRADα stabilizing compound contacts an amino acid within (lining) the pseudo-kinase STRADα ATP binding pocket through a sulfonic acid. In embodiments, the pseudo-kinase STRADα stabilizing compound contacts an amino acid within (lining) the pseudo-kinase STRADα ATP binding pocket through an amide. In embodiments, the pseudo-kinase STRADα stabilizing compound contacts an amino acid within (lining) the pseudo-kinase STRADα ATP binding pocket through an ester. In embodiments, the pseudo-kinase STRADα stabilizing compound contacts an amino acid within (lining) the pseudo-kinase STRADα ATP binding pocket through a urea. In embodiments, the pseudo-kinase STRADα stabilizing compound contacts an amino acid within (lining) the pseudo-kinase STRADα ATP binding pocket through a sulfonyl urea. In embodiments, the pseudo-kinase STRADα stabilizing compound contacts an amino acid within (lining) the pseudo-kinase STRADα ATP binding pocket that contacts a phosphate of ATP when ATP contacts the pseudo-kinase STRADα, through a chemical moiety selected from carboxylic acid, ether, sulfone, sulfonamide, nitrile, hetero-cycle, alcohol, sulfonic acid, amide, ester, urea, and/or sulfonyl urea. In embodiments, the pseudo-kinase STRADα stabilizing compound contacts an amino acid within (lining) the pseudo-kinase STRADα ATP binding pocket that contacts a phosphate of ATP when ATP contacts the pseudo-kinase STRADα, through a carboxylic acid. In embodiments, the pseudo-kinase STRADα stabilizing compound contacts an amino acid within (lining) the pseudo-kinase STRADα ATP binding pocket that contacts a phosphate of ATP when ATP contacts the pseudo-kinase STRADα, through an ether. In embodiments, the pseudo-kinase STRADα stabilizing compound contacts an amino acid within (lining) the pseudo-kinase STRADα ATP binding pocket that contacts a phosphate of ATP when ATP contacts the pseudo-kinase STRADα, through a sulfone. In embodiments, the pseudo-kinase STRADα stabilizing compound contacts an amino acid within (lining) the pseudo-kinase STRADα ATP binding pocket that contacts a phosphate of ATP when ATP contacts the pseudo-kinase STRADα, through a sulfonamide. In embodiments, the pseudo-kinase STRADα stabilizing compound contacts an amino acid within (lining) the pseudo-kinase STRADα ATP binding pocket that contacts a phosphate of ATP when ATP contacts the pseudo-kinase STRADα, through a nitrile. In embodiments, the pseudo-kinase STRADα stabilizing compound contacts an amino acid within (lining) the pseudo-kinase STRADα ATP binding pocket that contacts a phosphate of ATP when ATP contacts the pseudo-kinase STRADα, through a hetero-cycle. In embodiments, the pseudo-kinase STRADα stabilizing compound contacts an amino acid within (lining) the pseudo-kinase STRADα ATP binding pocket that contacts a phosphate of ATP when ATP contacts the pseudo-kinase STRADα, through an alcohol. In embodiments, the pseudo-kinase STRADα stabilizing compound contacts an amino acid within (lining) the pseudo-kinase STRADα ATP binding pocket that contacts a phosphate of ATP when ATP contacts the pseudo-kinase STRADα, through a sulfonic acid. In embodiments, the pseudo-kinase STRADα stabilizing compound contacts an amino acid within (lining) the pseudo-kinase STRADα ATP binding pocket that contacts a phosphate of ATP when ATP contacts the pseudo-kinase STRADα, through an amide. In embodiments, the pseudo-kinase STRADα stabilizing compound contacts an amino acid within (lining) the pseudo-kinase STRADα ATP binding pocket that contacts a phosphate of ATP when ATP contacts the pseudo-kinase STRADα, through an ester. In embodiments, the pseudo-kinase STRADα stabilizing compound contacts an amino acid within (lining) the pseudo-kinase STRADα ATP binding pocket that contacts a phosphate of ATP when ATP contacts the pseudo-kinase STRADα, through a urea. In embodiments, the pseudo-kinase STRADα stabilizing compound contacts an amino acid within (lining) the pseudo-kinase STRADα ATP binding pocket that contacts a phosphate of ATP when ATP contacts the pseudo-kinase STRADα, through a sulfonyl urea.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

V. Embodiments

Embodiment 1. A compound having the formula:

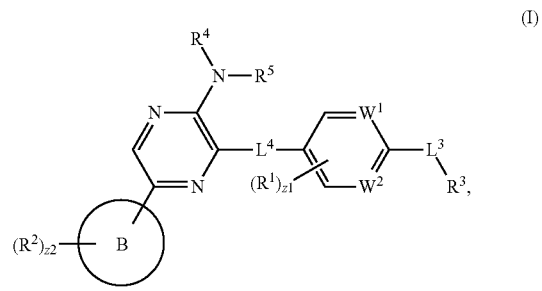

(I)

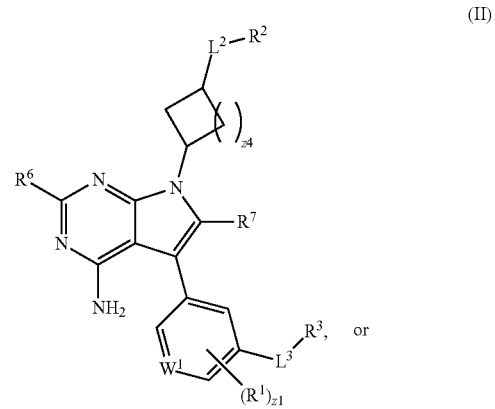

(II)

or

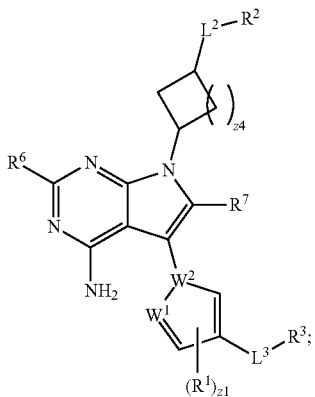

(III)

wherein, $W^1$ is N, CH, or $CR^1$; $W^2$ is N, CH, or $CR^1$; $R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NR^{1C}NR^{1A}R^{1B}$, $-ONR^{1A}R^{1B}$, $-NHC(O)NR^{1C}NR^{1A}R^{1B}$, $-NHC(O)NR^{1A}R^{1B}$, $N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; z1 is an integer from 0 to 4; Ring B is aryl or heteroaryl; $L^2$ is a bond, $-NH-$, $-O-$, $-S-$, $-C(O)-$, $-C(O)NH-$, $-NHC(O)-$, $-NHC(O)NH-$, $-C(O)O-$, $-OC(O)-$, substituted or unsubstituted alkylene, substituted or unsubstituted heteroalkylene, substituted or unsubstituted cycloalkylene substituted or unsubstituted heterocycloalkylene, substituted or unsubstituted arylene, or substituted or unsubstituted heteroarylene; $R^2$ is independently oxo, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl; z2 is an integer from 0 to 6; $L^3$ is a bond, $-NH-$, $-O-$, $-C(O)-$, $-C(O)NH-$, $-NHC(O)-$, $-NHC(O)NH-$, $-C(O)O-$, $-OC(O)-$, substituted or unsubstituted alkylene, or substituted or unsubstituted heteroalkylene; $R^3$ is independently a polar moiety; $L^4$ is $-C(O)NH-$ or $-NHC(O)-$; $R^4$ and $R^5$ are independently hydrogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ and $R^5$ substituents bonded to the same nitrogen may optionally be joined to form a substituted or unsubstituted heterocycloalkyl or substituted or unsubstituted heteroaryl; $R^6$ is independently hydrogen, halogen, $-CX^6_3$, $-CHX^6_2$, $-CH_2X^6$, $-OCX^6_3$, $OCH_2X^6$, $-OCHX^6_2$, $-CN$, $-SO_{n6}H$, $-SO_{v6}NH_2$, $-NHNH_2$, $-ONH_2$, $-NHC(O)NHNH_2$, $-NHC(O)NH_2$, $-N(O)_{m6}$, $-NH_2$, $-C(O)H$, $-COOH$, $-C(O)NH_2$, $-OH$, $-NHSO_2H$, $-NHC(O)H$, $-NHC(O)OH$, $-NHOH$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ is independently hydrogen, halogen, $-CX^7_3$, $-CHX^7_2$, $-CH_2X^7$, $-OCX^7_3$, $-OCH_2X^7$, $-OCHX^7_2$, $-CN$, $-SO_{n7}H$, $-SO_{v7}NH$, $-NHNH_2$, $-ONH_2$, $-NHC(O)NHNH_2$, $-NHC(O)NH_2$, $-N(O)_{m7}$, $-NH_2$, $-C(O)H$, $-COOH$, $-C(O)NH_2$, $-OH$, $-NHSO_2H$, $-NHC(O)H$, $-NHC(O)OH$, $-NHOH$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}R^{1B}$, $R^{1C}$, $R^{1D}$, $R^{2A}$, $R^{2B}$, $R^{2C}$, and $R^{2D}$ are independently hydrogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; z4 is 1 or 2; $X^1$, $X^2$, $X^6$, and $X^7$ are independently $-F$, $-Cl$, $-Br$, or $-I$; n1, n2, n6, and n7 are independently an integer from 0 to 4; and m1, m2, v1, v2, m6, v6, m7, and v7 are independently 1 or 2.

Embodiment 2 The compound of embodiment 1, having the formula:

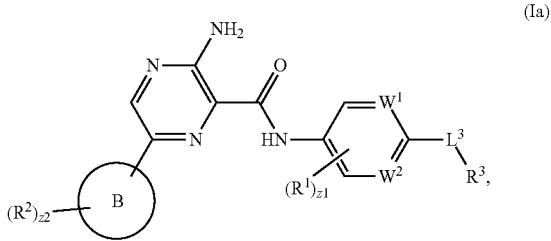

(Ia)

-continued

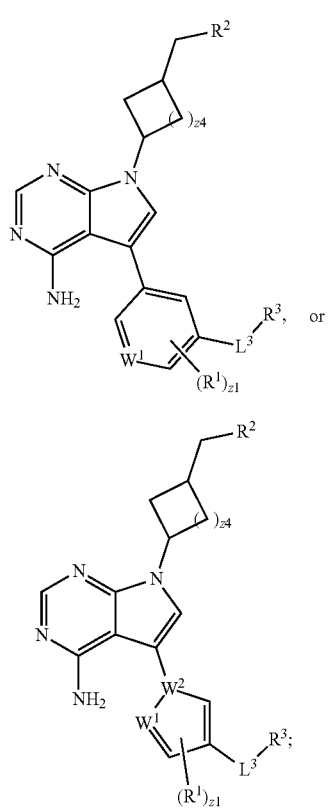

(IIa)

(IIIa)

wherein,

R¹ is independently halogen, —CX¹₃, —CHX¹₂, —CH₂X¹, —OCX¹₃, —OCH₂X¹, —OCHX¹₂, —CN, —SO$_{n1}$R$^{1D}$, —SO$_{v1}$NR$^{1A}$R$^{1B}$, —NR$^{1C}$NR$^{1A}$R$^{1B}$, —ONR$^{1A}$R$^{1B}$, —NHC(O)NR$^{1C}$NR$^{1A}$R$^{1B}$, —NHC(O)NR$^{1A}$R$^{1B}$, N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO₂R$^{1D}$, —NR$^{1A}$C(O)R$^{1C}$, —NR$^{1A}$C(O)OR$^{1C}$, —NR$^{1A}$OR$^{1C}$, —SF₅, —N₃, substituted or unsubstituted C₁-C₆ alkyl, substituted or unsubstituted 2 to 6 membered heteroalkyl, substituted or unsubstituted C₃-C₆ cycloalkyl, substituted or unsubstituted 3 to 6 membered heterocycloalkyl, substituted or unsubstituted C₆-C₁₀ aryl, or substituted or unsubstituted 5 to 10 membered heteroaryl; two adjacent R¹ substituents may optionally be joined to form a substituted or unsubstituted C₃-C₆ cycloalkyl, substituted or unsubstituted 3 to 6 membered heterocycloalkyl, substituted or unsubstituted phenyl, or substituted or unsubstituted 5 to 6 membered heteroaryl; Ring B is phenyl or 5 to 10 membered heteroaryl; R² is independently oxo, halogen, —CX²₃, —CHX²₂, —CH₂X², —OCX²₃, —OCH₂X², —OCHX²₂, —CN, —SO$_{n2}$R$^{2D}$, —SO$_{v2}$NR$^{2A}$R$^{2B}$, —NR$^{2C}$NR$^{2A}$R$^{2B}$, —ONR$^{2A}$R$^{2B}$, —NHC(O)NR$^{2C}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO₂R$^{2D}$, —NR$^{2A}$C(O)R$^{2C}$, —NR$^{2A}$C(O)OR$^{2C}$, —NR$^{2A}$OR$^{2C}$, —SF₅, —N₃, substituted or unsubstituted C₁-C₆ alkyl, substituted or unsubstituted 2 to 6 membered heteroalkyl, substituted or unsubstituted C₃-C₆ cycloalkyl, substituted or unsubstituted 3 to 8 membered heterocycloalkyl, substituted or unsubstituted C₆-C₁₀ aryl, or substituted or unsubstituted 5 to 10 membered heteroaryl; two adjacent R² substituents may optionally be joined to form a substituted or unsubstituted C₃-C₆ cycloalkyl, substituted or unsubstituted 3 to 6 membered heterocycloalkyl, substituted or unsubstituted phenyl, or substituted or unsubstituted 5 to 6 membered heteroaryl; and L³ is a bond, —NH—, —O—, —C(O)—, —C(O)NH—, —NHC(O)—, —NHC(O)NH—, —C(O)O—, —OC(O)—, substituted or unsubstituted C₁-C₆ alkylene, or substituted or unsubstituted 2 to 6 membered heteroalkylene.

Embodiment 3. The compound of one of embodiments 1 to 2, having the formula:

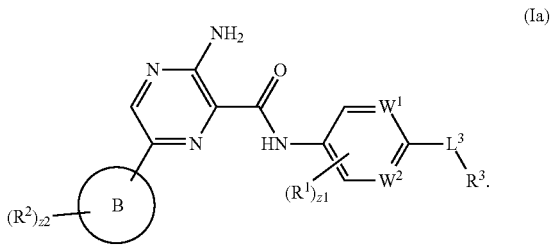

(Ia)

Embodiment 4. The compound of one of embodiments 1 to 3, wherein

R³ is independently —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO₂R$^{3D}$, —NR$^{3C}$SO₂NR$^{3A}$R$^{3B}$, —NR$^{3A}$R$^{3B}$, —NR$^{3A}$C(O)R$^{3C}$, —NR$^{3A}$C(O)OR$^{3C}$, —SO₂R$^{3C}$, —SO₂-L$^{3A}$-R$^{3C}$, —SO₂NR$^{3A}$R$^{3B}$, —SO₂NR$^{3A}$SO₂R$^{3C}$, —SO₂NR$^{3A}$P(O)(OR$^{3C}$)(OR$^{3D}$), —SO₂P(O)(OR$^{3C}$)(OR$^{3D}$), —SO₂CH₂P(O)(OR$^{3C}$)(OR$^{3D}$), —SO₂P(O)(OR$^{3D}$)(NR$^{3A}$R$^{3B}$), —SO₂P(O)(R$^{3C}$)(OR$^{3D}$), —SO₂P(O)(R$^{3C}$)(R$^{3D}$), —SO₂-L$^{3A}$-P(O)(OR$^{3C}$)(OR$^{3D}$), —SO₂-L$^{3A}$-P(O)(OR$^{3D}$)(NR$^{3A}$R$^{3B}$), —SO₂-L$^{3A}$-P(O)(R$^{3C}$)(OR$^{3D}$), —SO₂-L$^{3A}$-P(O)(R$^{3C}$)(R$^{3D}$), —S(O)(NR$^{3A}$)R$^{3C}$, —C(O)OR$^{3C}$, —C(O)NR$^{3A}$R$^{3B}$, or —NR$^{3A}$C(O)OR$^{3C}$; L$^{3A}$ is independently —CH₂—, —CH(CH₃)—, —C(CH₃)₂—, —CH(X$^{3A}$)—, or —C(X$^{3A}$)₂—; X$^{3A}$ is —F, —Cl, —Br, or —I; and R$^{3A}$, R$^{3B}$, R$^{3C}$, and R$^{3D}$ are independently hydrogen, oxo, halogen, —CCl₃, —CBr₃, —CF₃, —CI₃, CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SO₂CH₃, —NHC(O)CH₃, —C(O)CH₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{3A}$ and R$^{3D}$ substituents may optionally be joined to form a substituted or unsubstituted heterocycloalkyl or substituted or unsubstituted heteroaryl.

Embodiment 5. The compound of one of embodiments 1 to 4, wherein $R^3$ is —$SO_2$-$L^{3A}$-$R^{3C}$ and $R^{3C}$ is independently —$COOCH_3$ or —$COOCH_2CH_3$.
Embodiment 6. The compound of one of embodiments 1 to 5, wherein $R^3$ is,
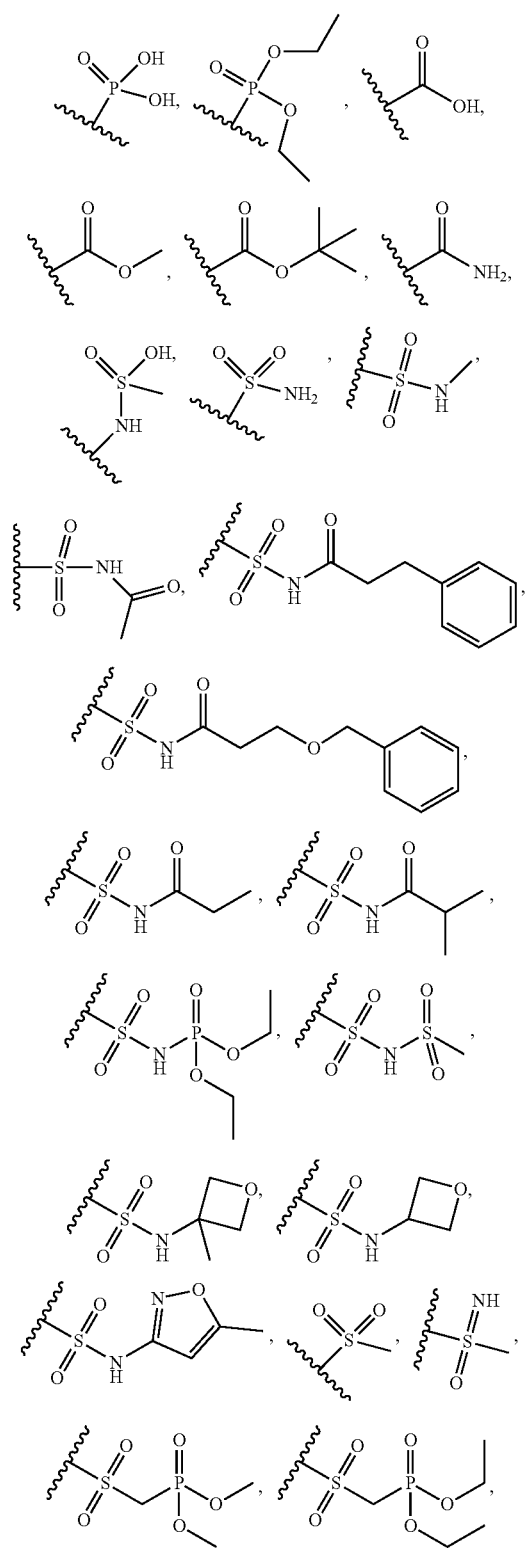
-continued
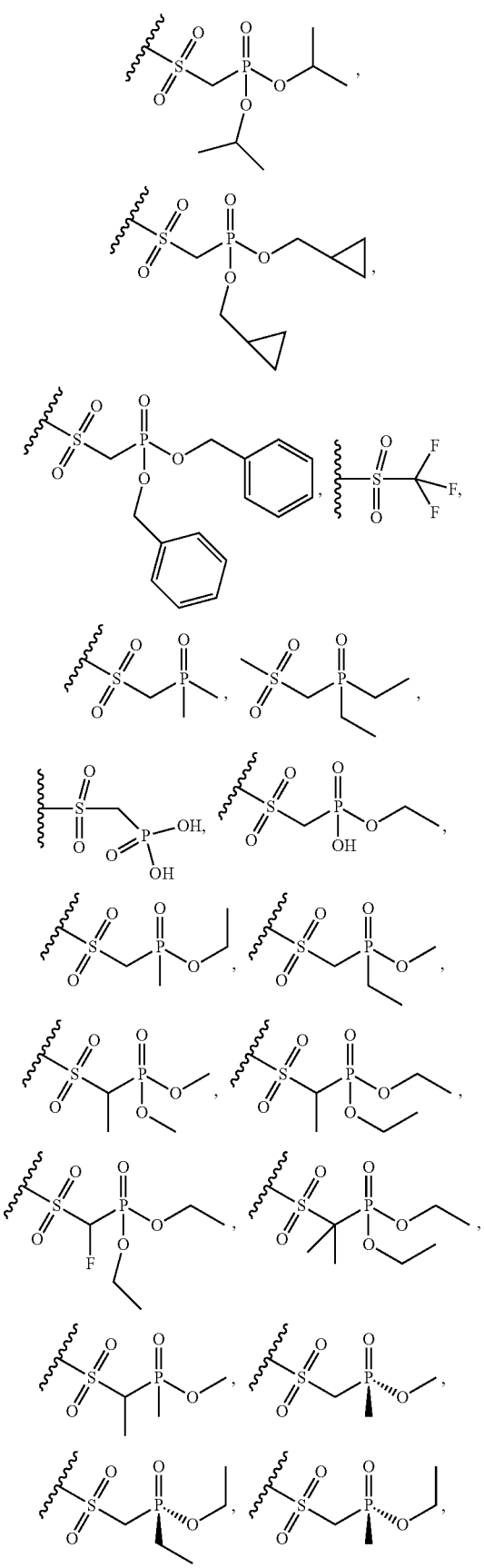

-continued

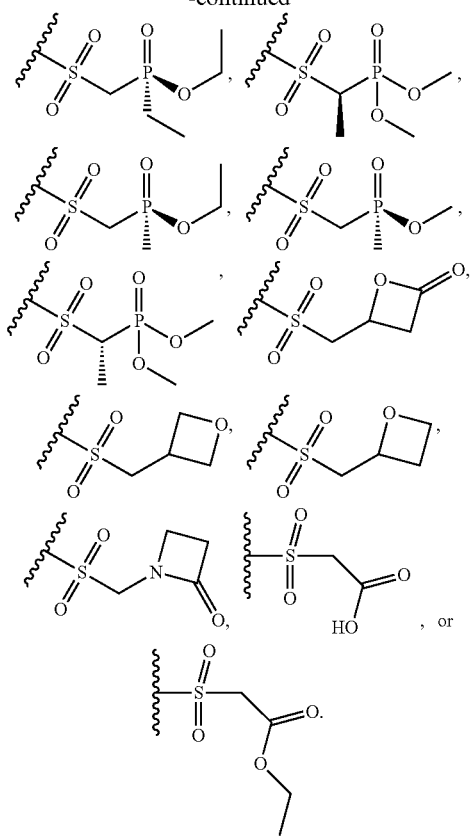

Embodiment 7. The compound of one of embodiments 1 to 6, wherein L³ is a bond or —CH₂—.

Embodiment 8. The compound of one of embodiments 1 to 7, wherein Ring B is phenyl, thienyl, indazolyl, indolyl, pyrazolyl, pyrimidinyl, pyridyl, or benzothienyl.

Embodiment 9. The compound of one of embodiments 1 to 7, having the formula:

(Ib)

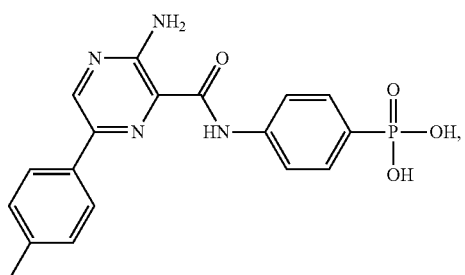

Embodiment 10. The compound of embodiment 1, having the formula:

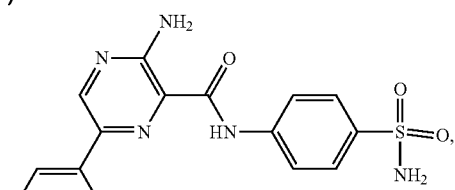

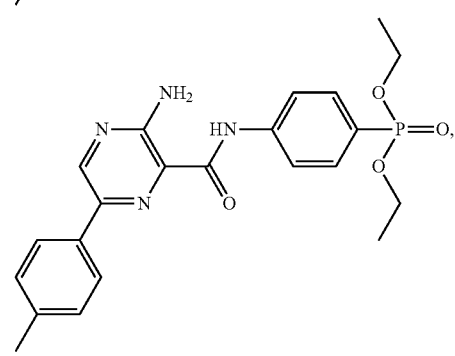

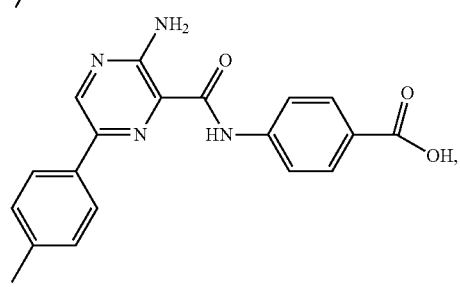

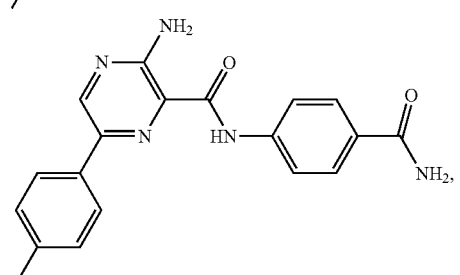

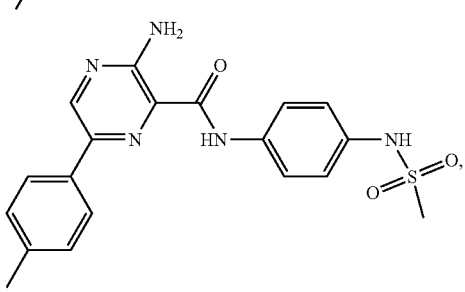

271
-continued
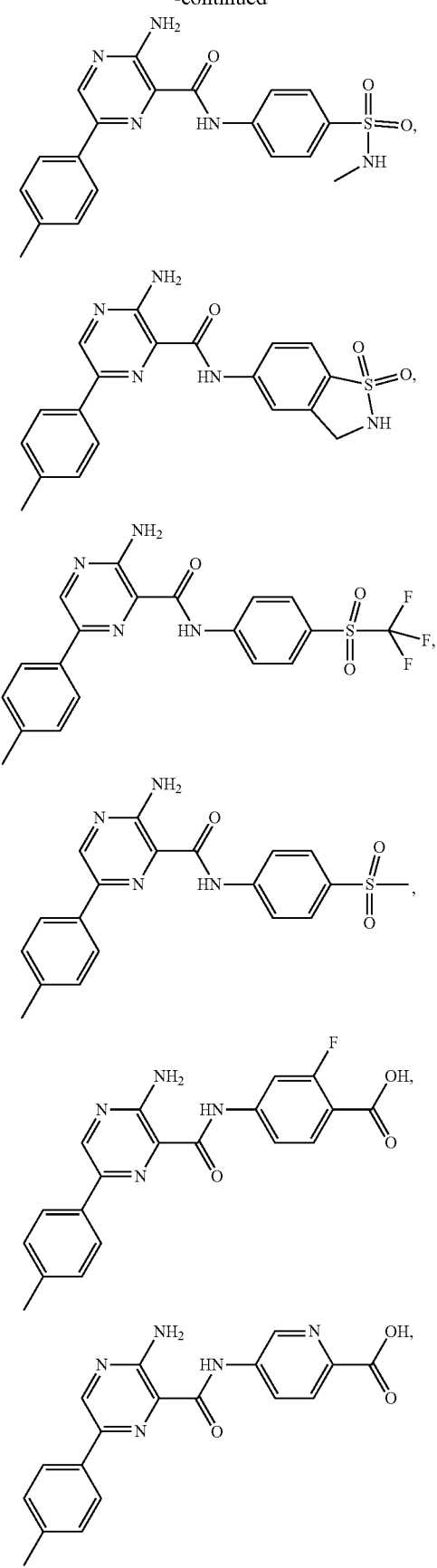
272
-continued
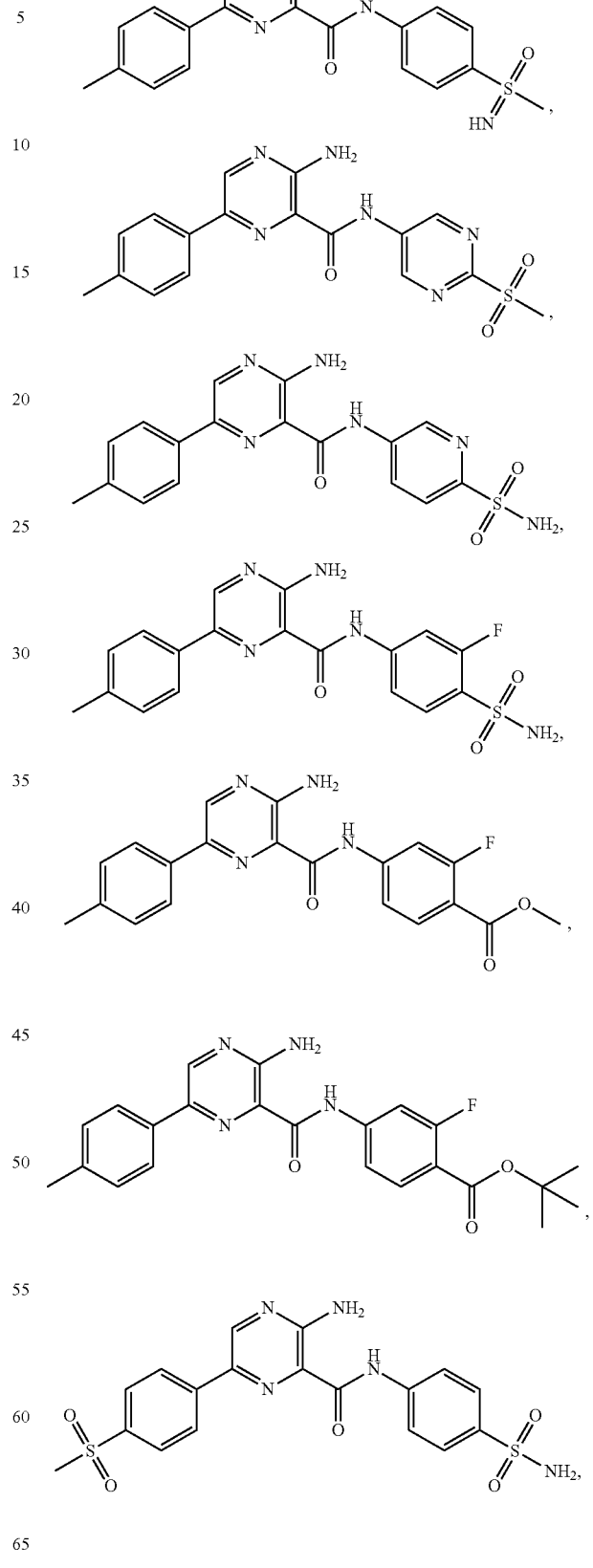

-continued
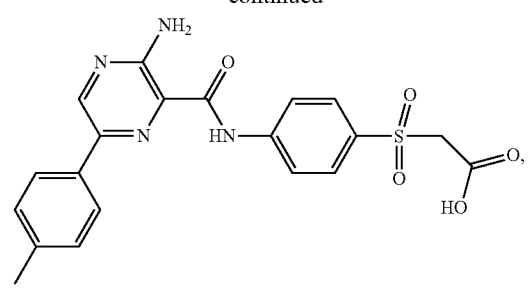
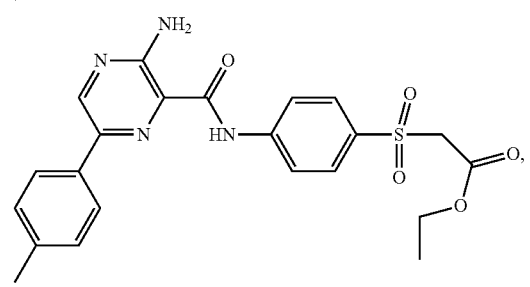
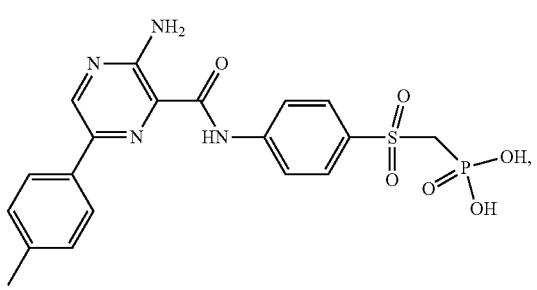
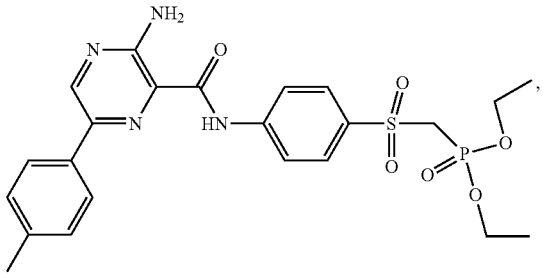
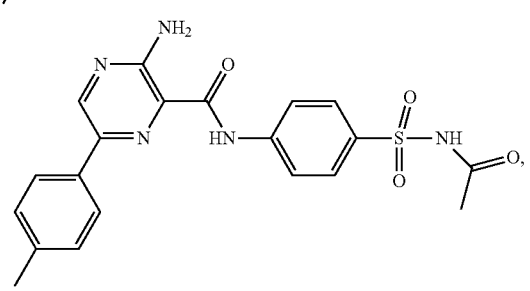
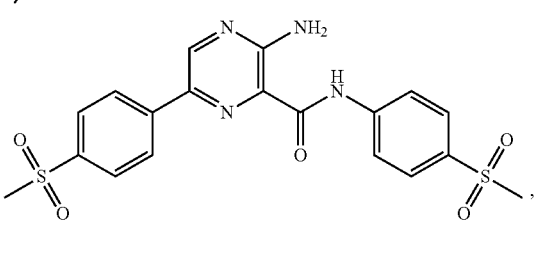
-continued

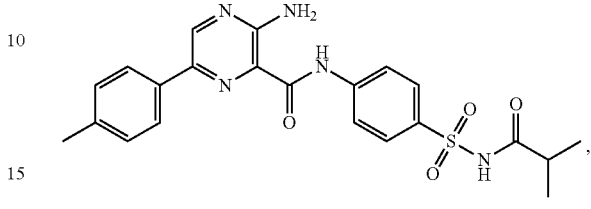
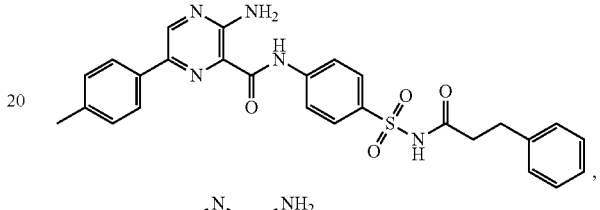
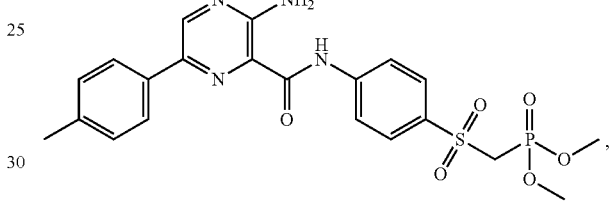
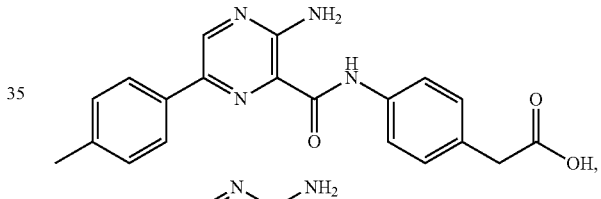
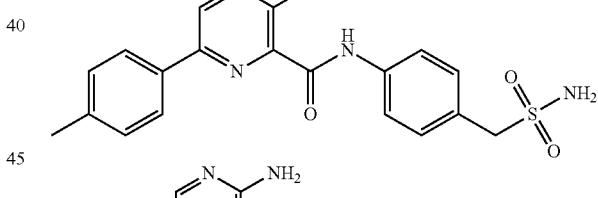
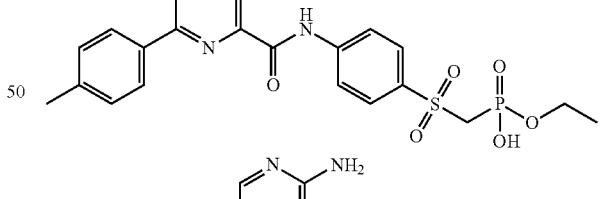
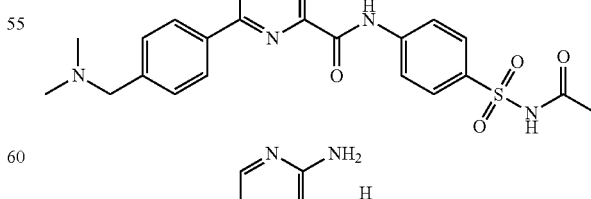
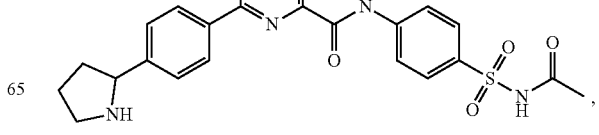

275
-continued
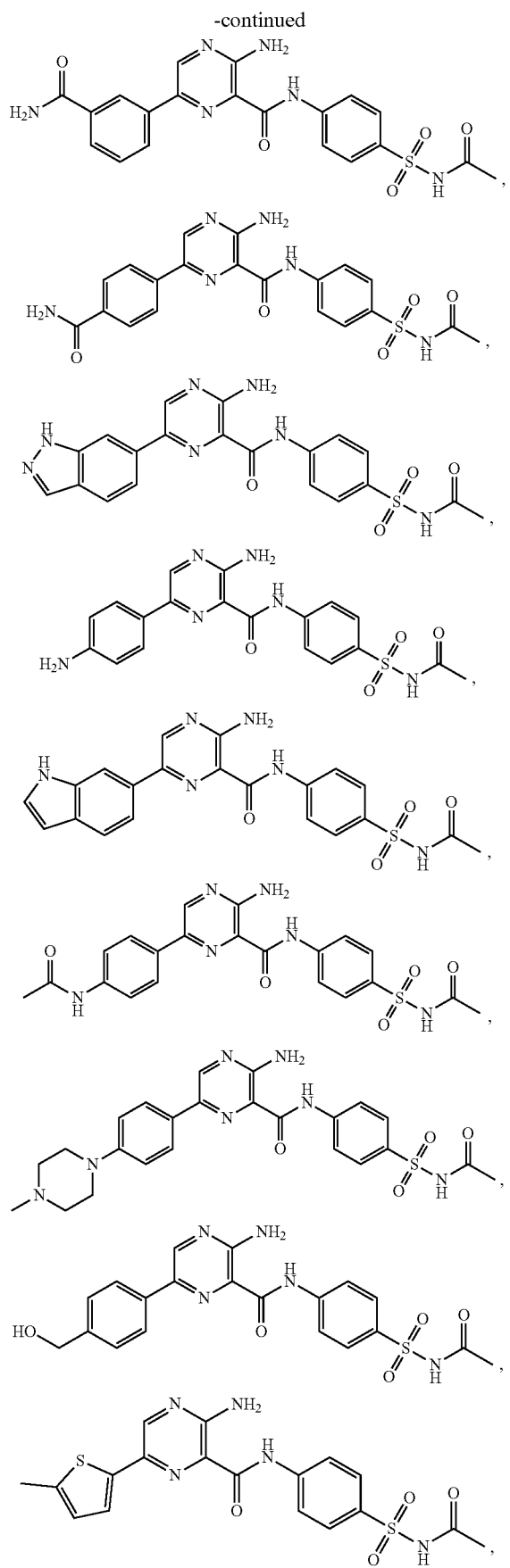
276
-continued
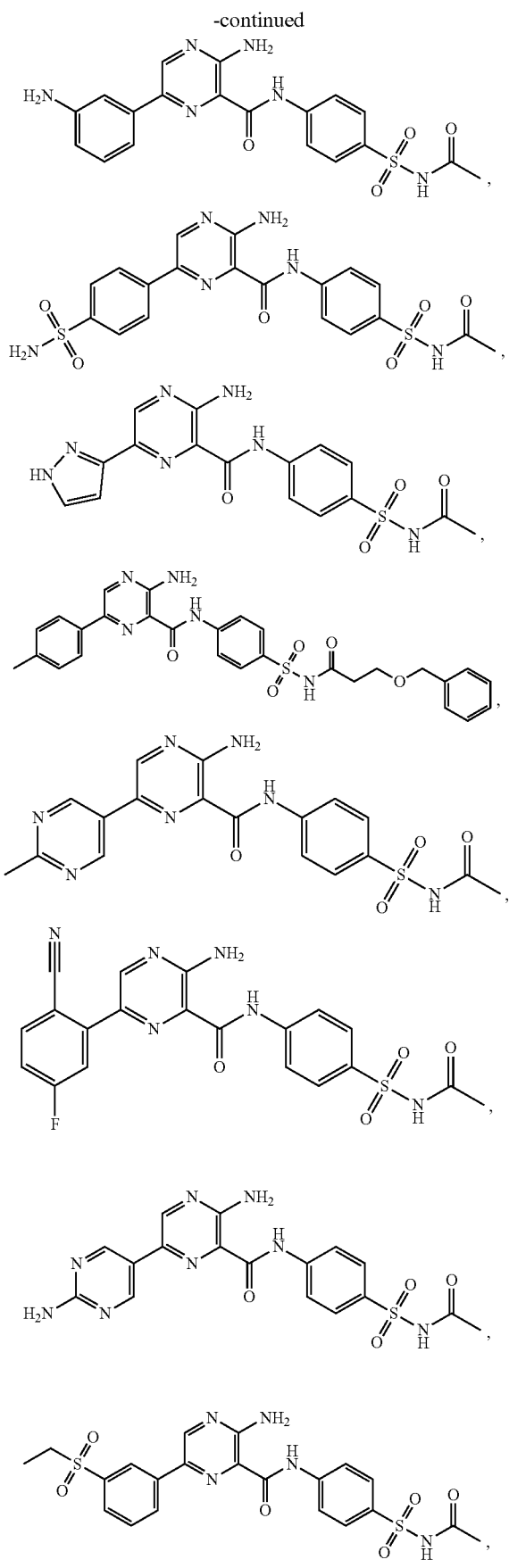

277
-continued
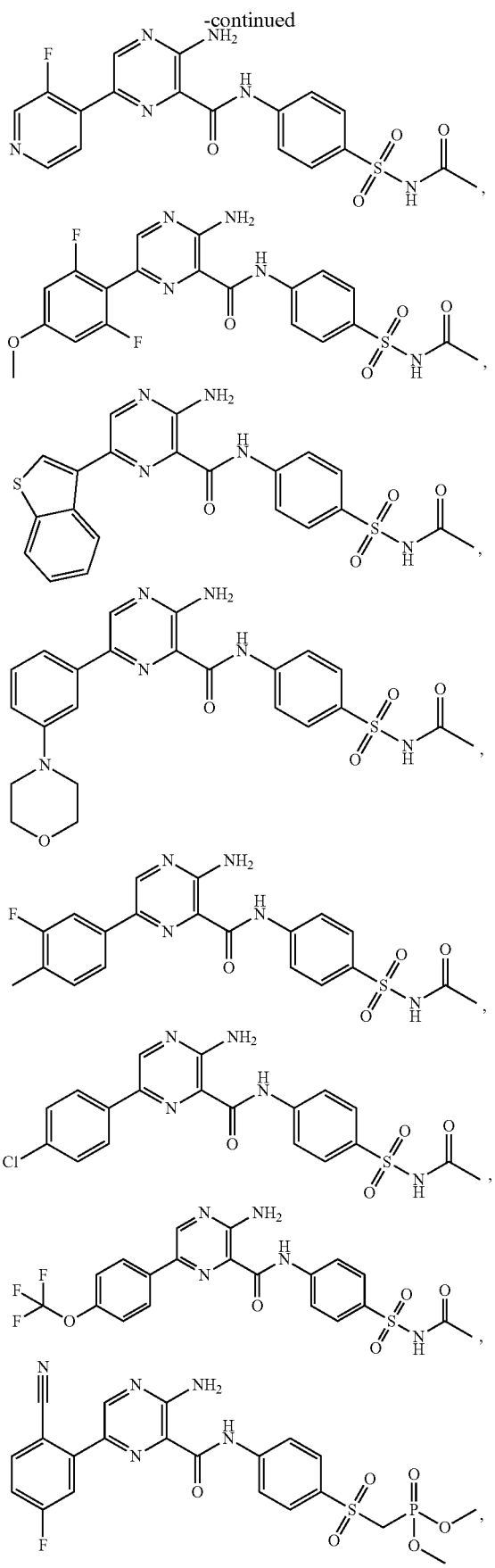
278
-continued
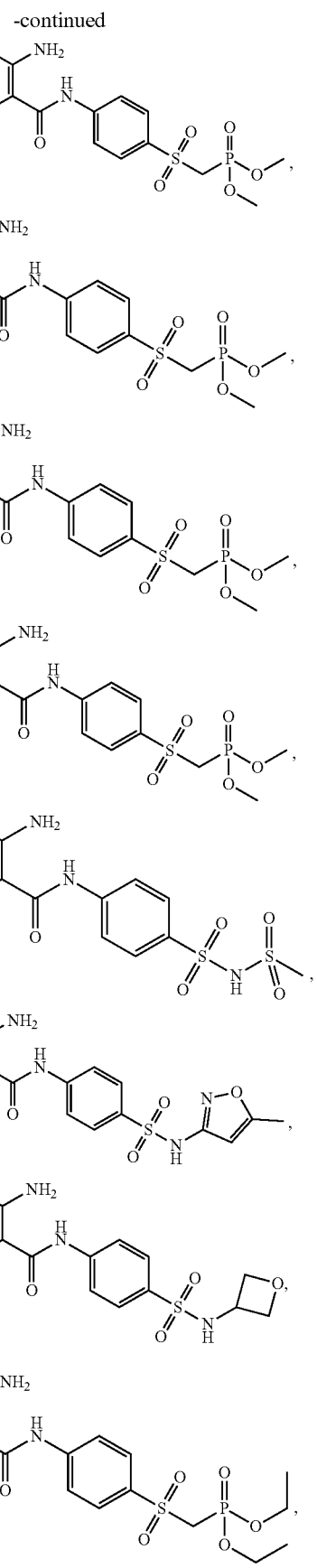

279
-continued
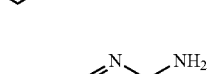
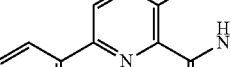
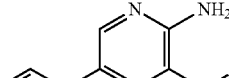
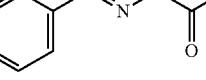
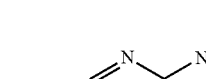
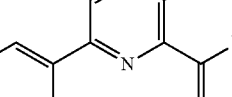
280
-continued
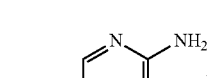
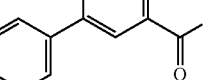
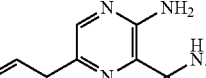
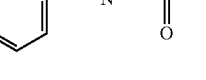
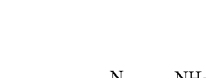
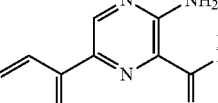

281
-continued
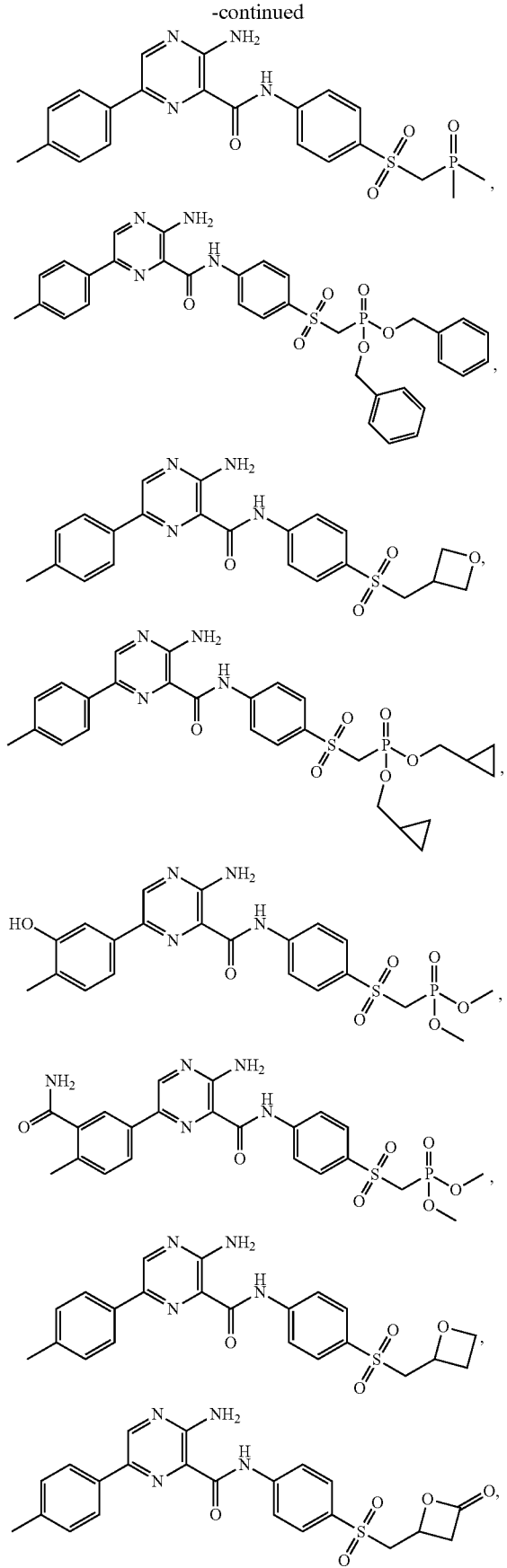
282
-continued
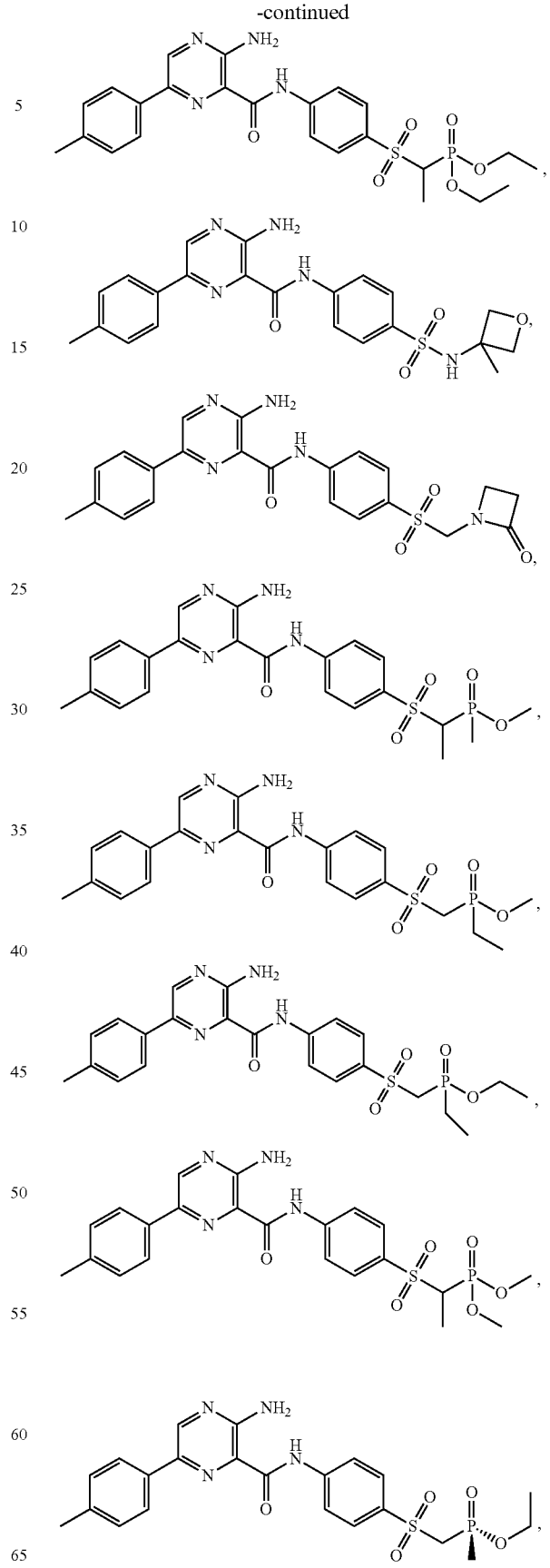

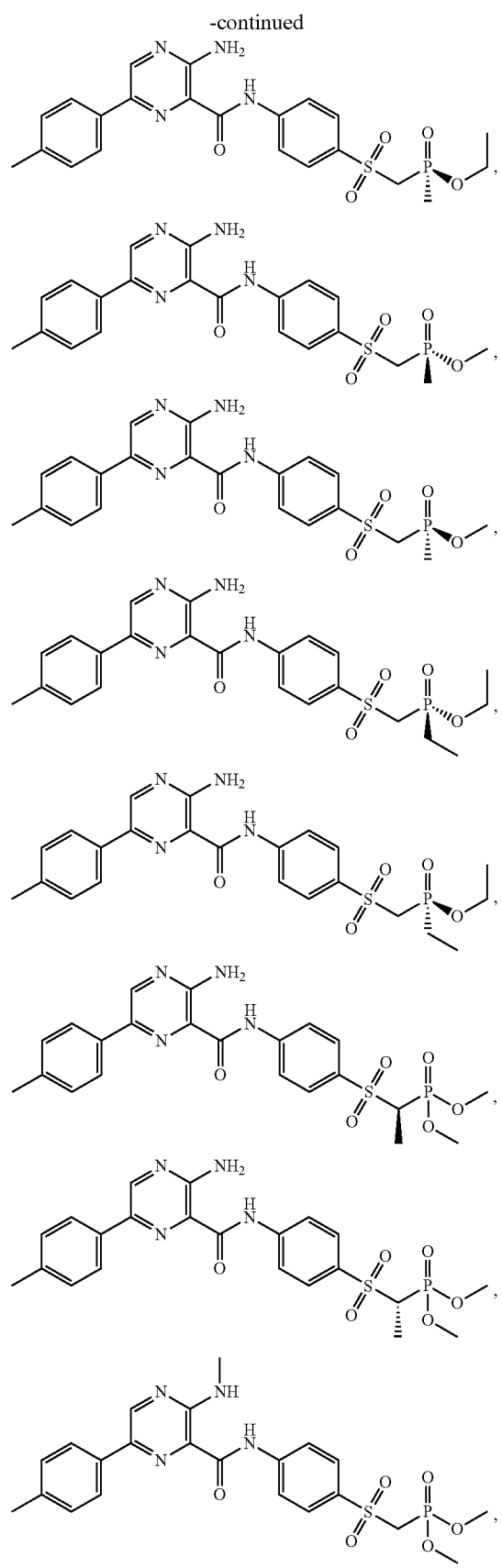
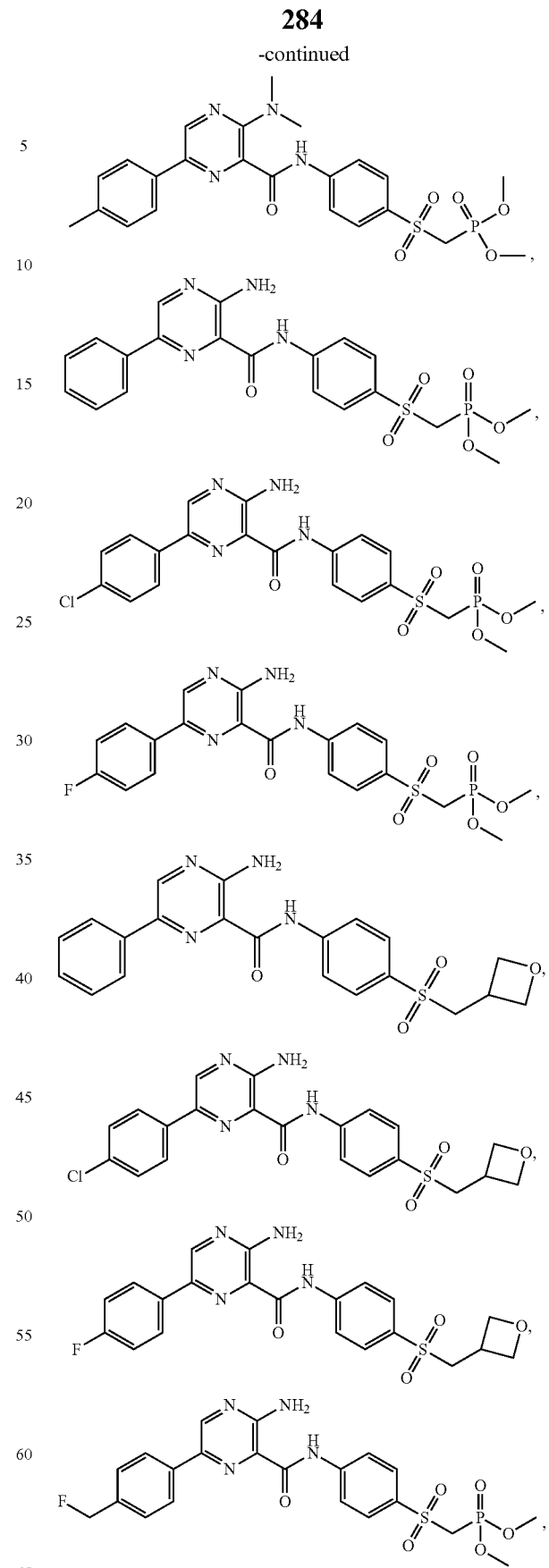

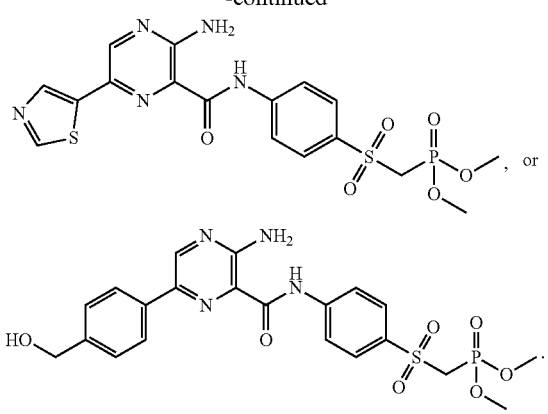
Embodiment 11. The compound of embodiment 1, having the formula:
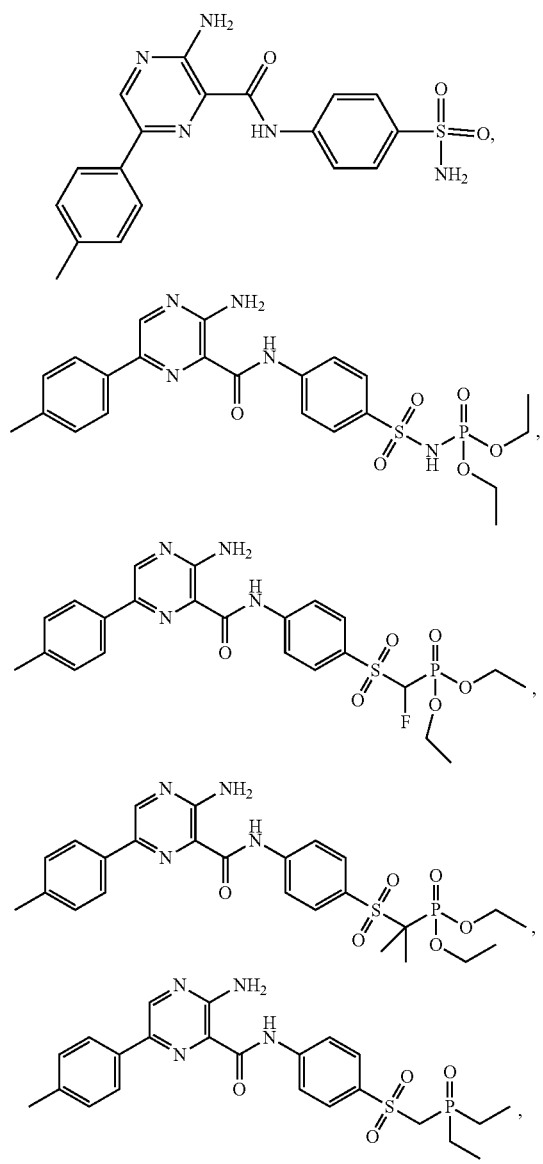
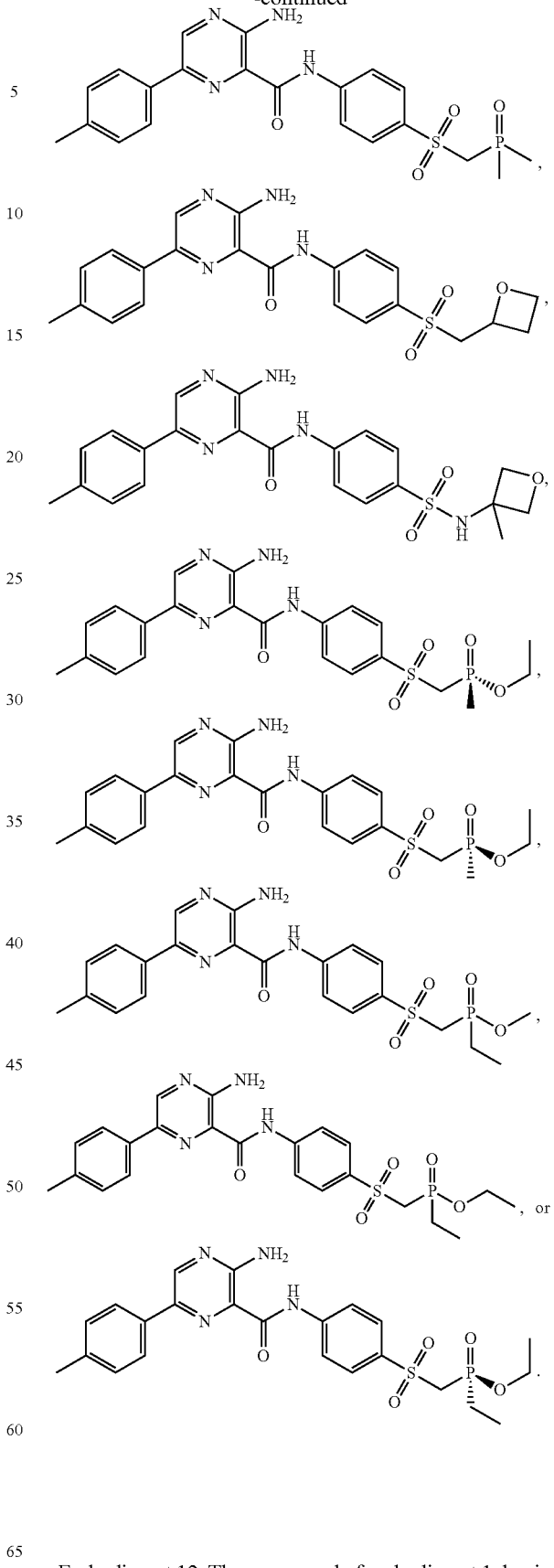
Embodiment 12. The compound of embodiment 1, having the formula:

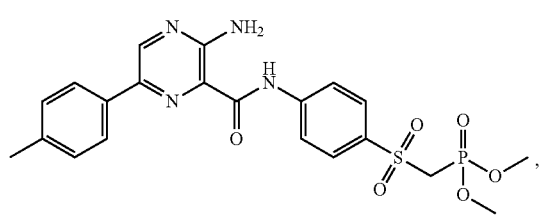
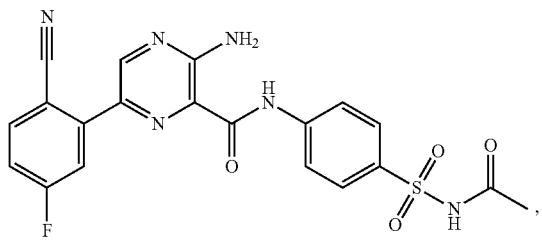
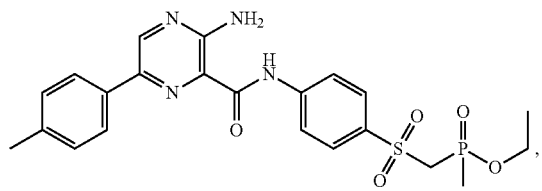
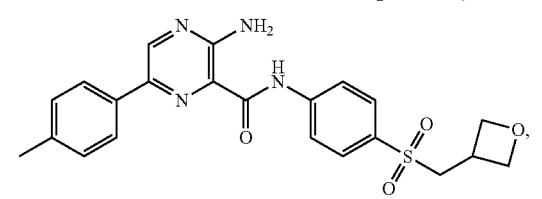
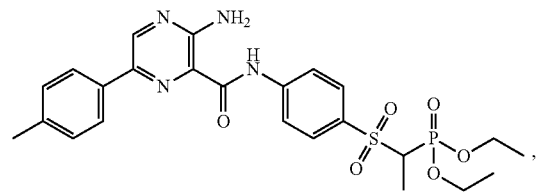
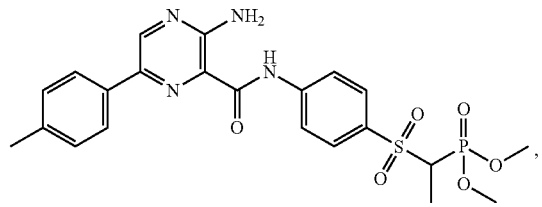
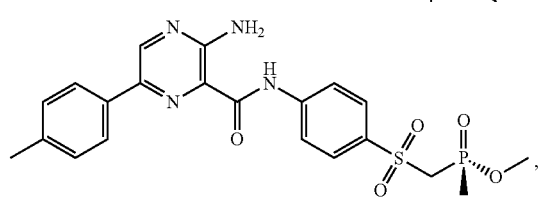
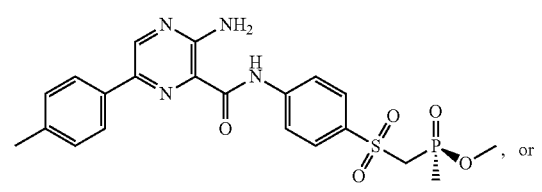
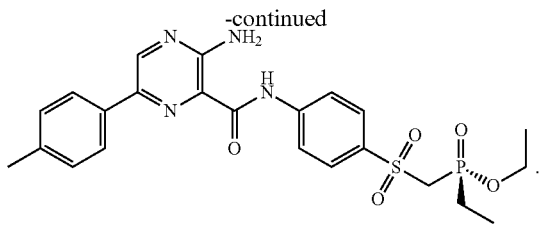
Embodiment 13. The compound of one of embodiments 1 to 2, having the formula.
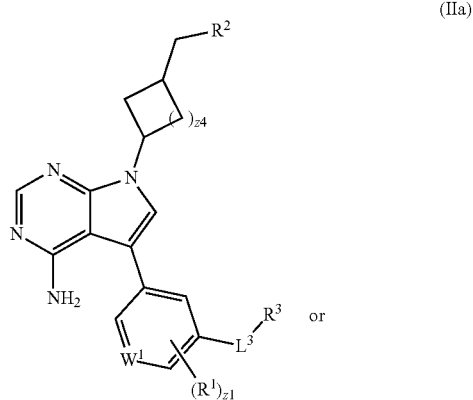
(IIa)
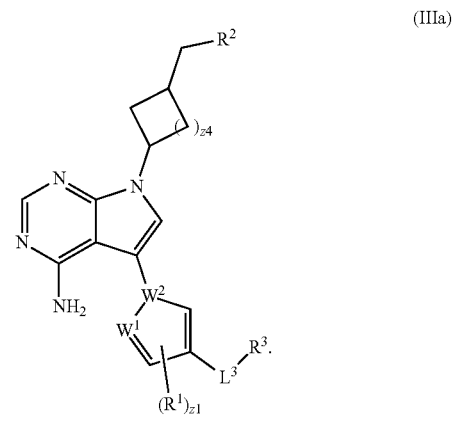
(IIIa)
Embodiment 14. The compound of embodiment 13, having the formula:
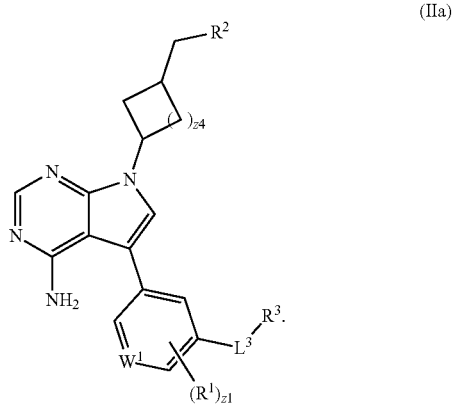
(IIa)

Embodiment 15. The compound of embodiment 13, having the formula:

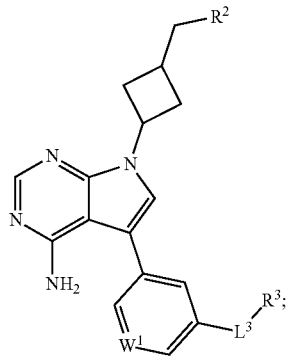

(IIb)

wherein $R^2$ is independently —$NR^{2A}R^{2B}$ or —OH; $R^{2A}$ and $R^{2B}$ are independently hydrogen or $R^{20}$-substituted or unsubstituted $C_1$-$C_6$ alkyl; or $R^{2A}$ and $R^{2B}$ substituents bonded to the same nitrogen atom may optionally be joined to form an $R^{20}$-substituted or unsubstituted 4 to 7 membered heterocycloalkyl; and $R^{20}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment 16. The compound of embodiment 15, having the formula:

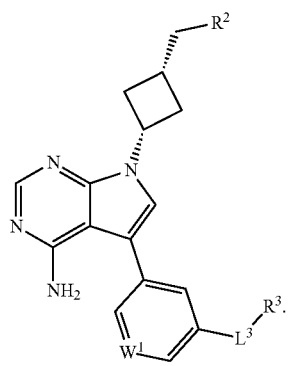

(IIc)

Embodiment 17. The compound of embodiment 13, having the formula:

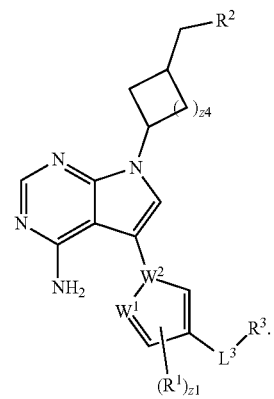

(IIIa)

Embodiment 18. The compound of embodiment 13, having the formula:

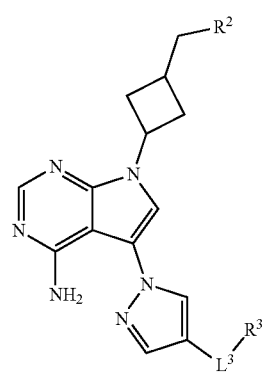

(IIIb)

wherein $R^2$ is independently —$NR^{2A}R^{2B}$; $R^{2A}$ and $R^{2B}$ are independently hydrogen or $R^{20}$-substituted or unsubstituted $C_1$-$C_6$ alkyl; or $R^{2A}$ and $R^{2B}$ substituents bonded to the same nitrogen atom may optionally be joined to form an $R^{20}$-substituted or unsubstituted 4 to 7 membered heterocycloalkyl; and $R^{20}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment 19. The compound of embodiment 18, having the formula:

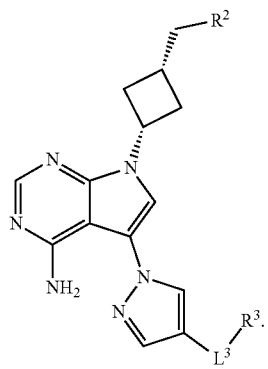

(IIIc)

Embodiment 20. The compound of one of embodiments 13 to 19, wherein
$R^{2A}$ and $R^{2B}$ substituents bonded to the same nitrogen atom are joined to form an $R^2$-substituted or unsubstituted 4 to 7 membered heterocycloalkyl; and
$R^{2O}$ is independently oxo, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment 21. The compound of embodiment 20, wherein
$R^{2A}$ and $R^{2B}$ substituents bonded to the same nitrogen atom are joined to form

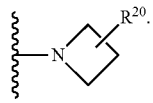

Embodiment 22. The compound of embodiment 20, wherein
$R^{2A}$ and $R^{2B}$ substituents bonded to the same nitrogen atom are joined to form

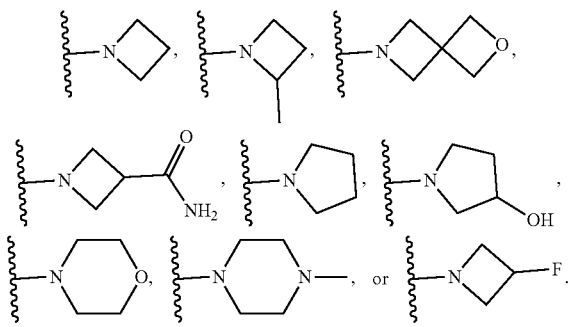

Embodiment 23. The compound of one of embodiments 13 to 22, wherein
$L^3$ is a bond, $-CH_2-$, $-CH_2CH_2-$, $-CH_2CH_2CH_2-$, $-OCH_2-$, $-OCH_2CH_2-$, or $-OCH_2CH_2CH_2-$;
$R^3$ is independently $-OH$, $-P(O)(OR^{3C})(OR^{3D})$, $-P(O)(OR^{3D})(NR^{3A}R^{3B})$, $-P(O)(R^{3C})(OR^{3D})$, $-P(O)(R^{3C})(R^{3D})$, $-P(S)(OR^{3C})(OR^{3D})$, $-P(S)(OR^{3D})(NR^{3A}R^{3B})$, $-P(S)(R^{3C})(OR^{3D})$, $-P(S)(R^{3C})(R^{3D})$, $-NR^{3A}SO_2R^{3D}$, $-NR^{3A}SO_2L^{3A}R^{3D}$, $-NR^{3C}SO_2NR^{3A}R^{3B}$, $-NR^{3A}R^{3B}$, $-NR^{3A}C(O)R^{3C}$, $-NR^{3A}C(O)OR^{3C}$, $-SO_2R^{3C}$, $-SO_2NR^{3A}R^{3B}$, $-SO_2P(O)(OR^{3C})(OR^{3D})$, $-SO_2CH_2P(O)(OR^{3C})(OR^{3D})$, $-SO_2P(O)(OR^{3D})(NR^{3A}R^{3B})$, $-SO_2P(O)(R^{3C})(OR^{3D})$, $-SO_2P(O)(R^{3C})(R^{3D})$, $-S(O)(NR^{3A})R^{3C}$, $-C(O)OR^{3C}$, $-C(O)NR^{3A}R^{3B}$, $-NR^{3A}C(O)OR^{3C}$;
$L^{3A}$ is independently $-CH_2-$, $-CH(CH_3)-$, or $-C(CH_3)_2-$; and
$R^{3A}$, $R^{3B}$, $R^{3C}$, and $R^{3D}$ are independently hydrogen, oxo, halogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC(O)NHNH_2$, $-NHC(O)NH_2$, $-NHSO_2H$, $-NHC(O)H$, $-NHC(O)OH$, $-NHOH$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, $-N_3$, $-SO_2CH_3$, $-NHC(O)CH_3$, $-C(O)CH_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3A}$ and $R^{3B}$, substituents bonded to the same nitrogen atom may optionally be joined to form a substituted or unsubstituted heterocycloalkyl or substituted or unsubstituted heteroaryl; $R^{3A}$ and $R^{3D}$ substituents may optionally be joined to form a substituted or unsubstituted heterocycloalkyl or substituted or unsubstituted heteroaryl.

Embodiment 24. The compound of one of embodiments 13 to 23, wherein $W^1$ is CH.

Embodiment 25. The compound of one of embodiments 13 to 23, wherein $W^1$ is N.

Embodiment 26. The compound of one of embodiments 13 to 23, wherein $W^1$ is $CR^1$; and
$R^1$ is independently halogen, $-CX^1_3$, $-CHX^1_2$, $-CH_2X^1$, or unsubstituted $C_1$-$C_4$ alkyl.

Embodiment 27. The compound of one of embodiments 1 to 4 or 13 to 26, wherein $R^3$ is

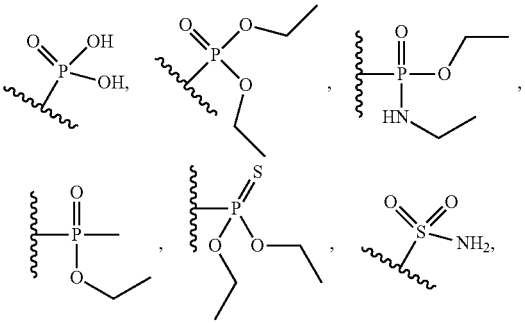

293
-continued
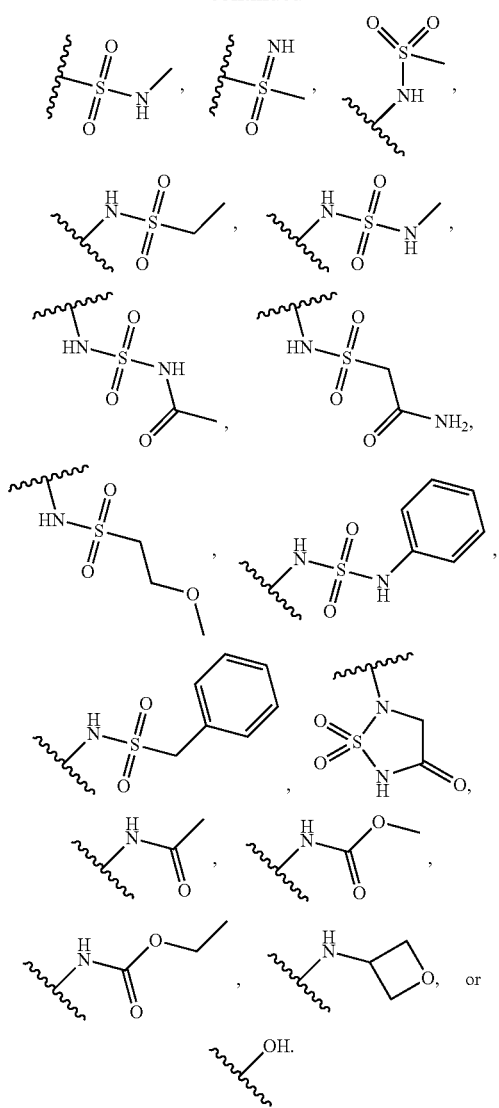
Embodiment 28. The compound of embodiment 1, having the formula:
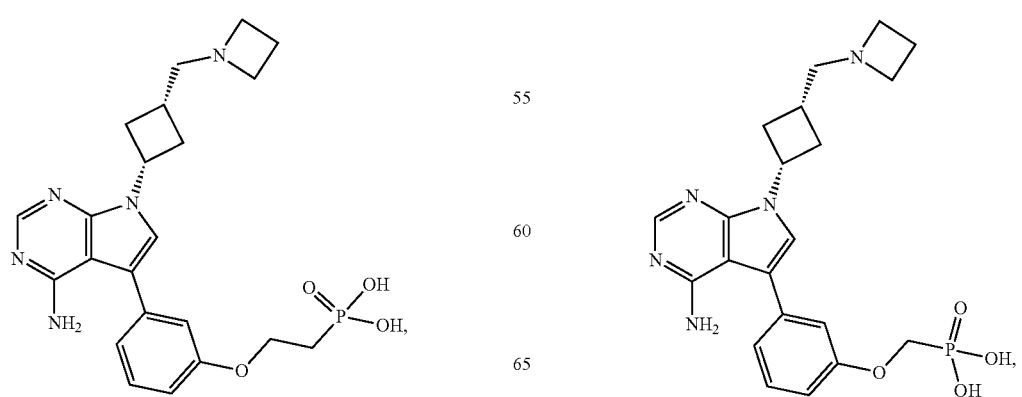
294
-continued
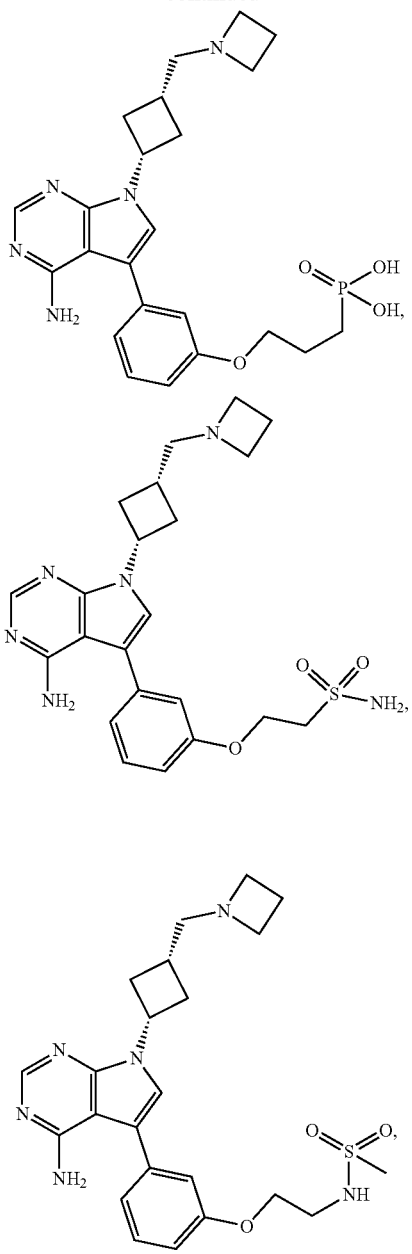

295
-continued
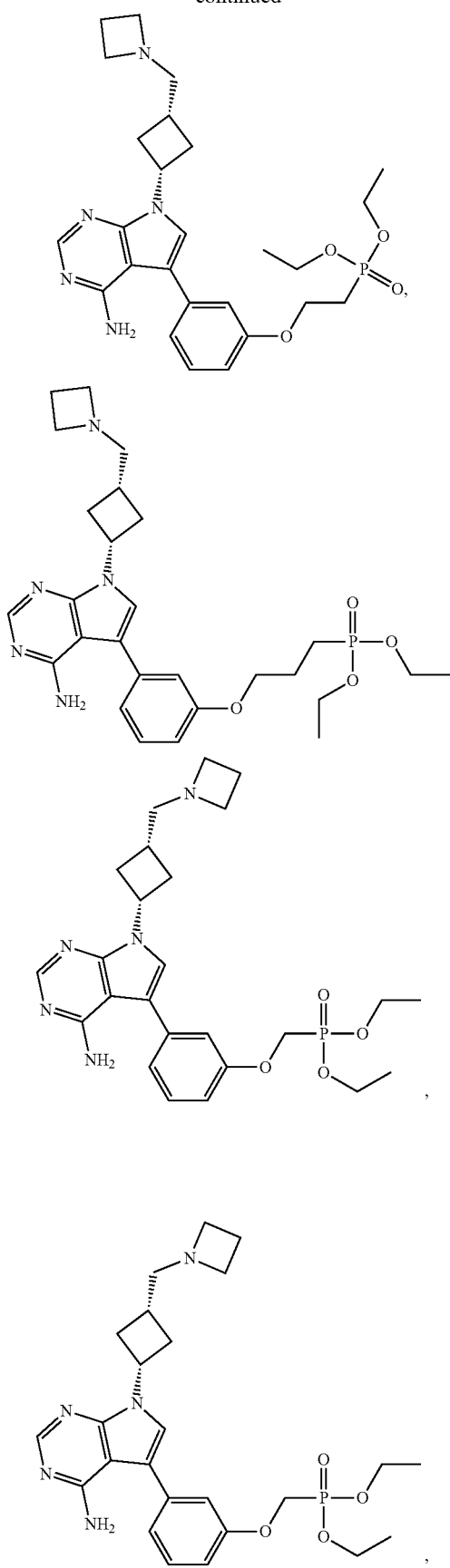
296
-continued
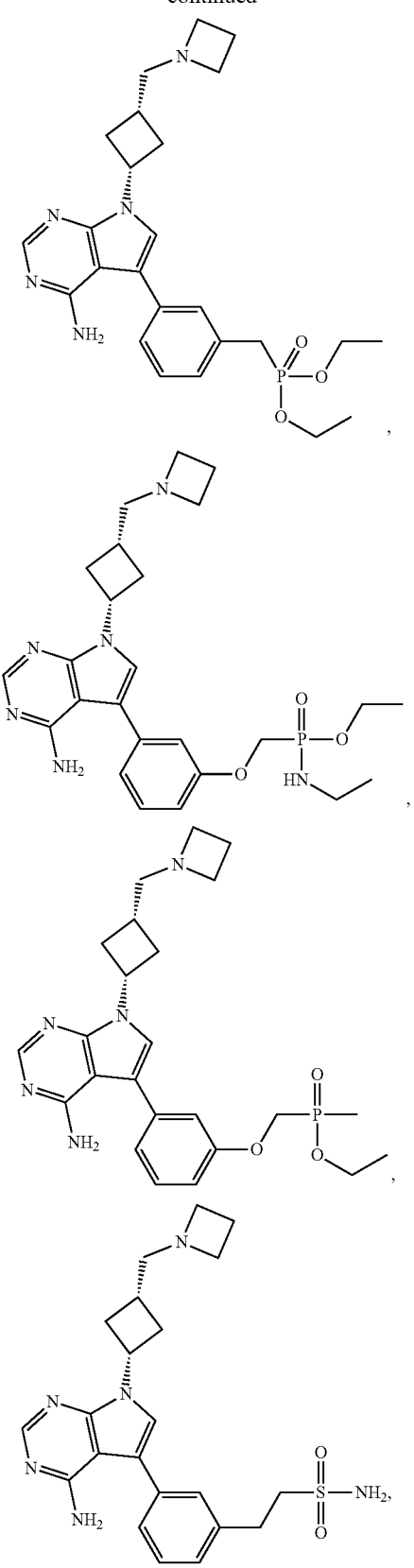

297
-continued
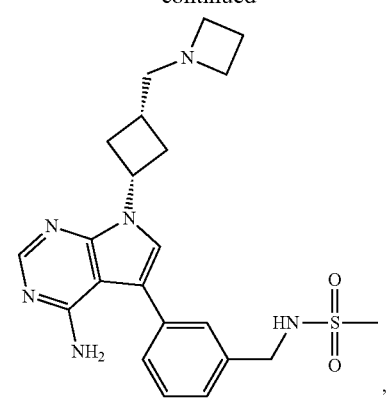
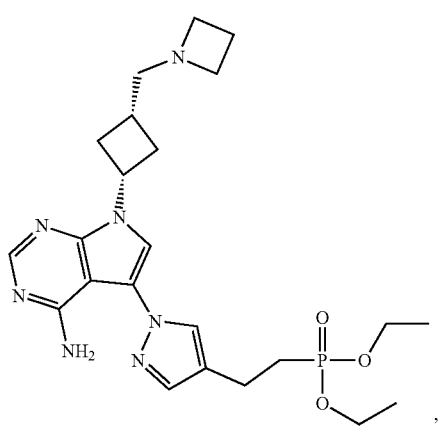
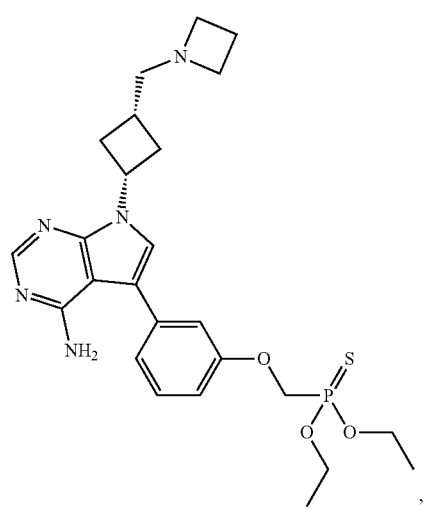
298
-continued
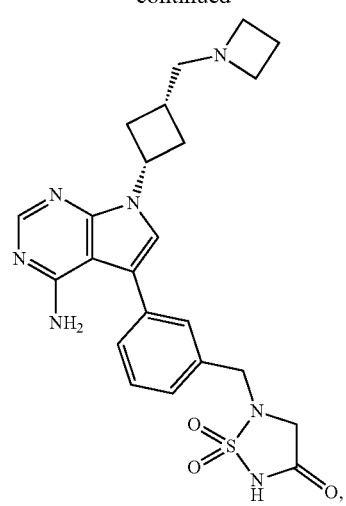
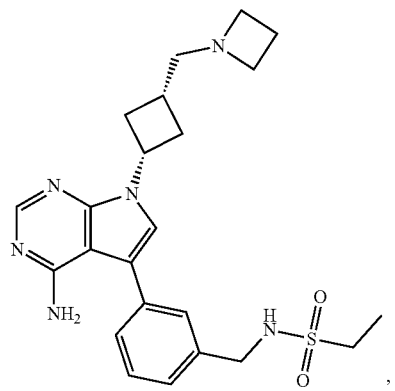
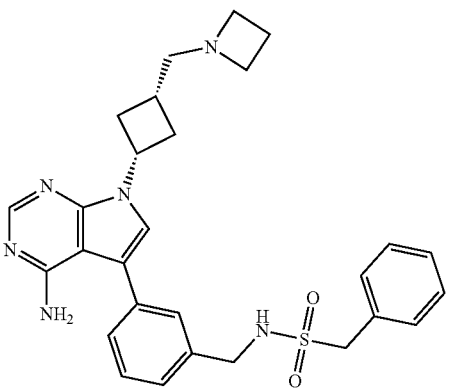
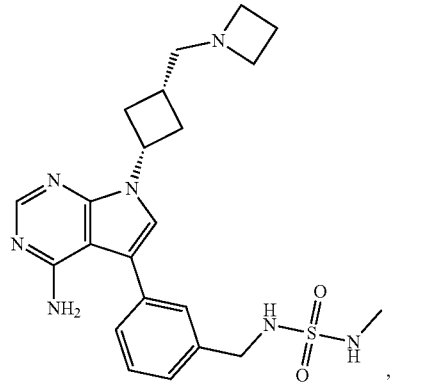

299
-continued
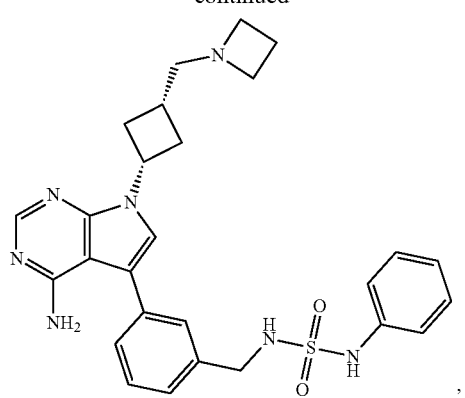
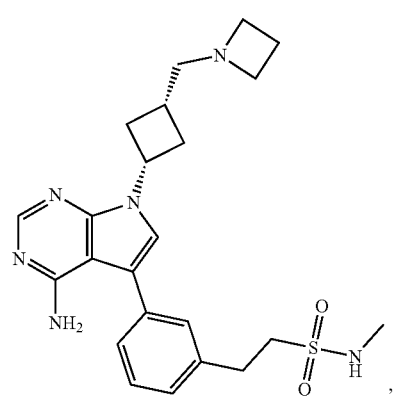
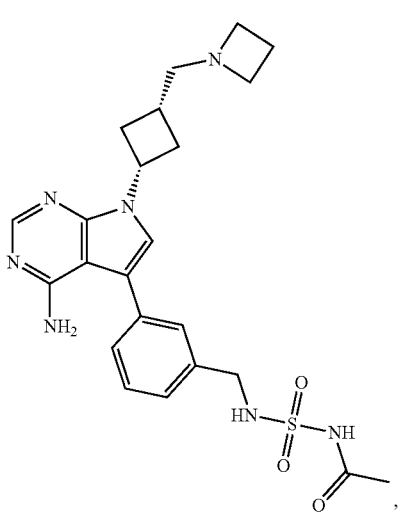
300
-continued
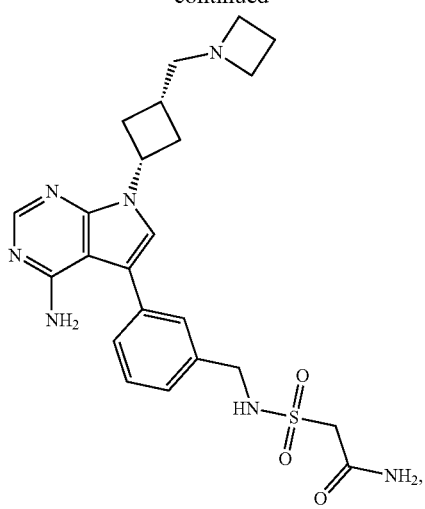
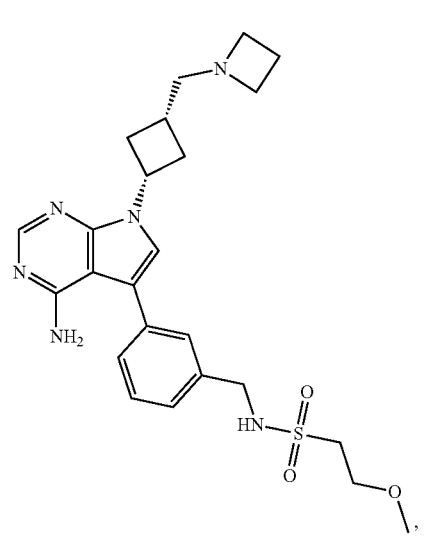
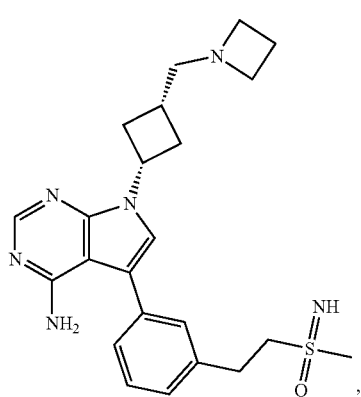

301
-continued
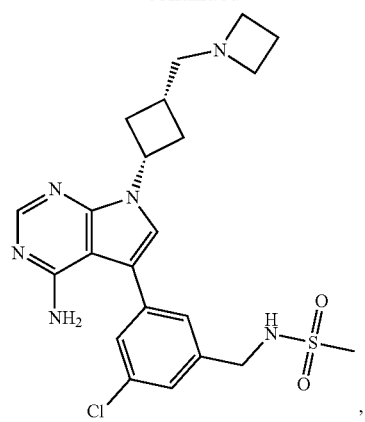
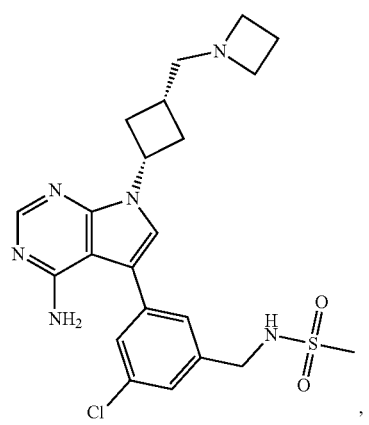
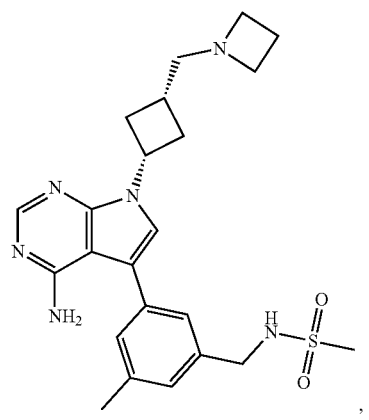
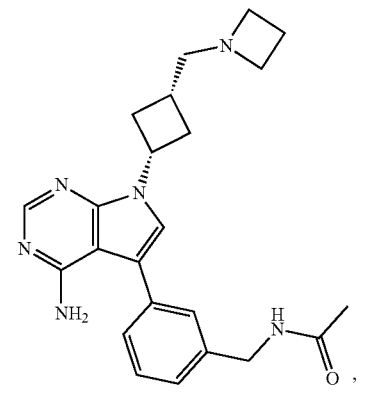
302
-continued
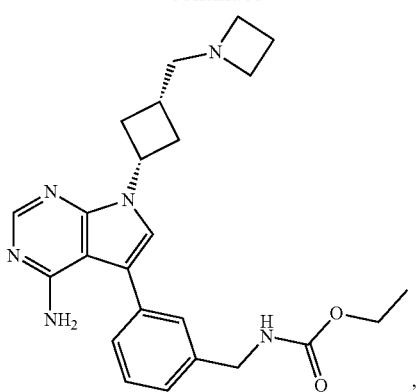
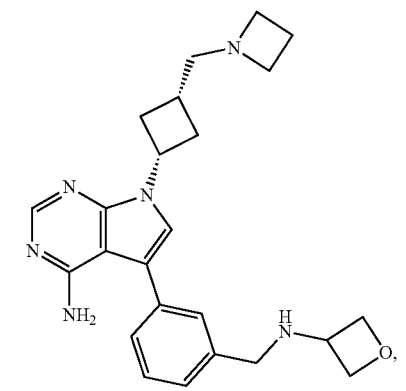
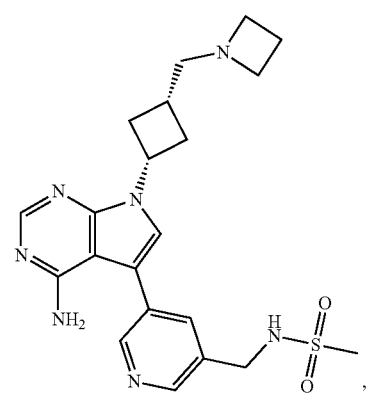
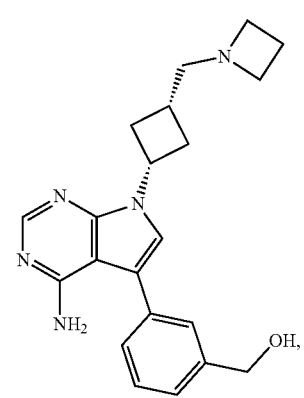

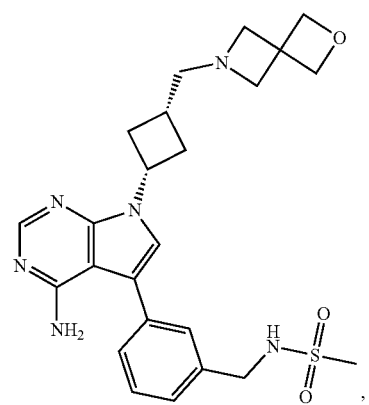
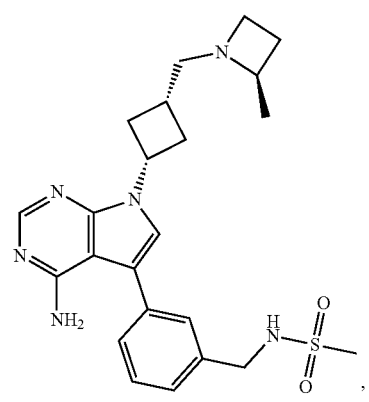
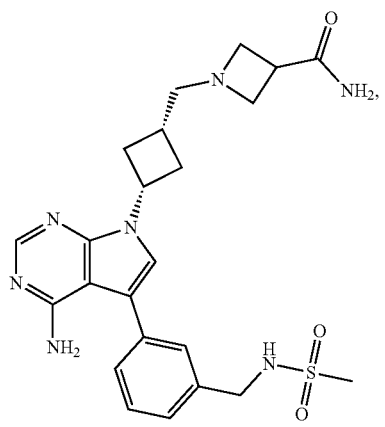
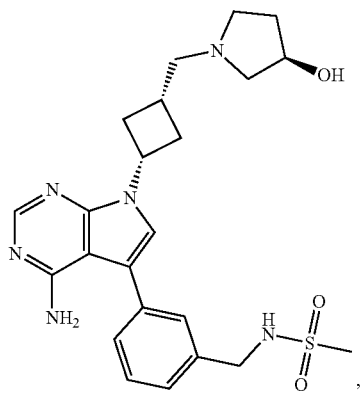

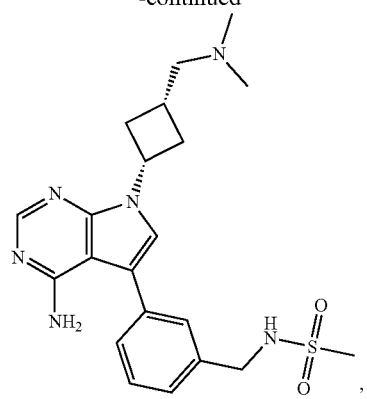
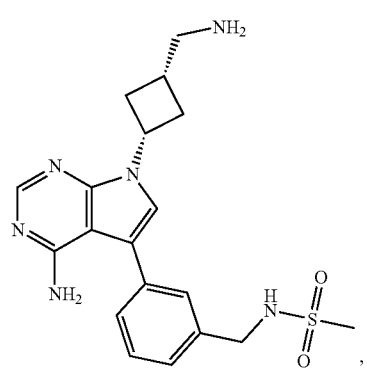
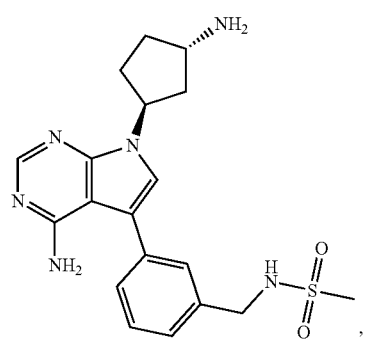
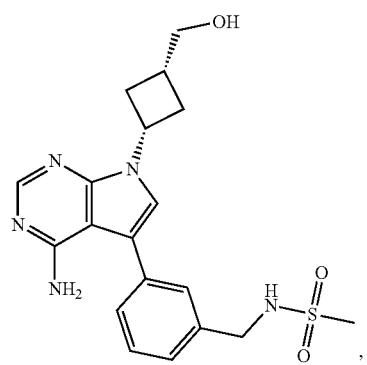
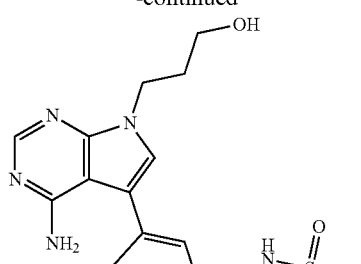
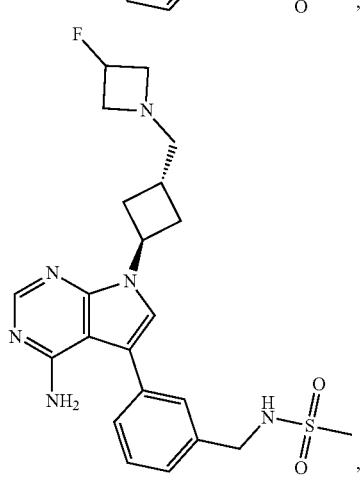
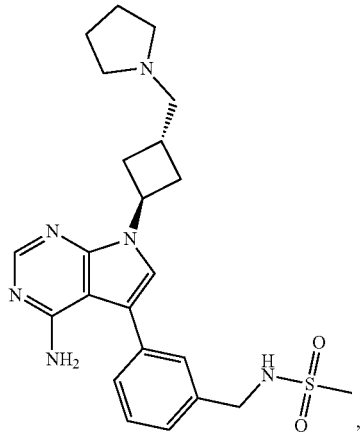
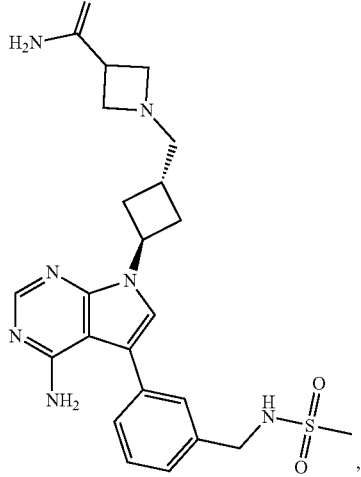

-continued

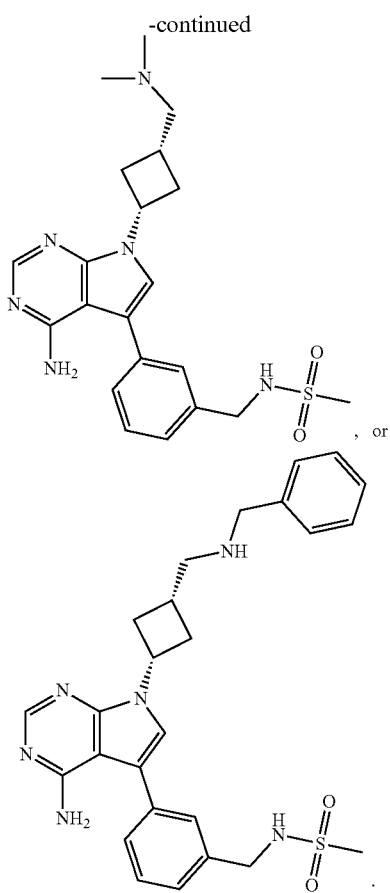

, or

Embodiment 29. A pharmaceutical composition comprising the compound of any one of embodiments 1 to 28 and a pharmaceutically acceptable excipient.

Embodiment 30. A method of increasing the level of LKB1 activity in a subject, said method comprising administering a compound of one of embodiments 1 to 28 to said subject.

Embodiment 31. A method of increasing the level of LKB1 activity in a cell, said method comprising contacting said cell with a compound of one of embodiments 1 to 28.

Embodiment 32. The method of one of embodiments 30 to 31, wherein the compound contacts a STRAD protein.

Embodiment 33. A method of increasing the level of AMPK1, AMPK2, BRSK1, BRSK2, MARK1, MARK2, MARK3, MARK4, NUAK1, NUAK2, SIK1, SIK2, SIK3, SNRK, or TP53 activity in a subject, said method comprising administering a compound of one of embodiments 1 to 28 to said subject.

Embodiment 34. A method of decreasing the level of mTOR or cAMP-regulated transcriptional coactivator 2 (CRTC2) activity in a subject, said method comprising administering a compound of one of embodiments 1 to 28 to said subject.

Embodiment 35. A method of increasing the level of Hippo pathway activity in a subject, said method comprising administering a compound of one of embodiments 1 to 28 to said subject.

Embodiment 36. A method of increasing the level of fatty acid oxidation activity in a subject, said method comprising administering a compound of one of embodiments 1 to 28 to said subject.

Embodiment 37. The method of one of embodiments 33 to 36, comprising increasing the level of LKB1 activity in said subject.

Embodiment 38. A method of increasing the level of AMPK1, AMPK2, BRSK1, BRSK2, MARK1, MARK2, MARK3, MARK4, NUAK1, NUAK2, SIK1, SIK2, SIK3, SNRK, or TP53 activity in a cell, said method comprising contacting said cell with a compound of one of embodiments 1 to 28.

Embodiment 39. A method of decreasing the level of mTOR or cAMP-regulated transcriptional coactivator 2 (CRTC2) activity in a cell, said method comprising contacting said cell with a compound of one of embodiments 1 to 28.

Embodiment 40. A method of increasing the level of Hippo pathway activity in a cell, said method comprising contacting said cell with a compound of one of embodiments 1 to 28.

Embodiment 41. A method of increasing the level of fatty acid oxidation activity in a cell, said method comprising contacting said cell with a compound of one of embodiments 1 to 28.

Embodiment 42. The method of one of embodiments 38 to 41, comprising increasing the level of LKB1 activity in said cell.

Embodiment 43. The method of one of embodiments 33 to 42, wherein the compound contacts a STRAD protein.

Embodiment 44. A method of treating a cancer in a subject in need thereof, said method comprising administering to the subject in need thereof an effective amount of a compound of one of embodiments 1 to 28.

Embodiment 45. The method of embodiment 44, wherein the cancer is pancreatic cancer, lung cancer, uterine cancer, renal cancer, colon cancer, soft tissue sarcoma, or a squamous cell cancer.

Embodiment 46. The method of one of embodiments 44 to 45, further comprising co-administering an anti-cancer agent to said subject in need.

Embodiment 47. The method of embodiment 46, wherein the anti-cancer agent is a KRAS inhibitor, ERK inhibitor, MEK inhibitor, BRAF inhibitor, mTOR inhibitor, PD1 inhibitor, PDL1 inhibitor, or CTLA4 inhibitor.

Embodiment 48. A method of treating diabetes in a subject in need thereof, said method comprising administering to the subject in need thereof an effective amount of a compound of one of embodiments 1 to 28.

Embodiment 49. The method of embodiment 48, comprising reducing the level of blood glucose in said subject in need.

Embodiment 50. The method of embodiment 48, comprising reducing the level of insulin resistance in said subject in need.

Embodiment 51. The method of one of embodiments 48 to 50, further comprising co-administering diabetes therapeutic agent to said subject in need.

Embodiment 52. The method of embodiment 51, wherein the diabetes therapeutic agent is a biguanide, sulfonylurea, meglitinide, thiazolidinedione, alpha-glucosidase inhibitor, incretin, GLP-1 analogue, DPP-4 inhibitor, insulin, GLP-1 receptor agonist, amylin agonist, or insulin analogue.

VI. Additional Embodiments

Embodiment P1. A compound having the formula:

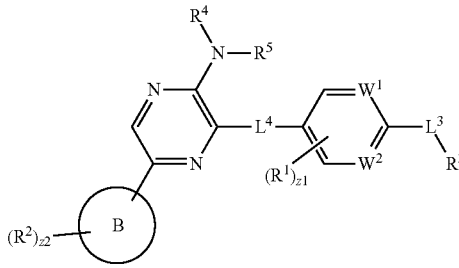

(I)

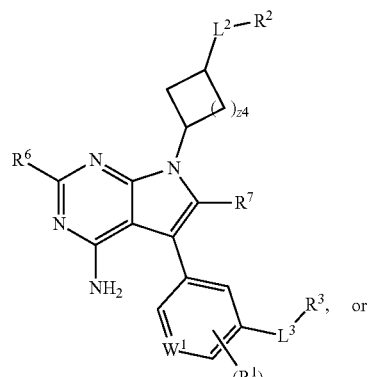

(II)

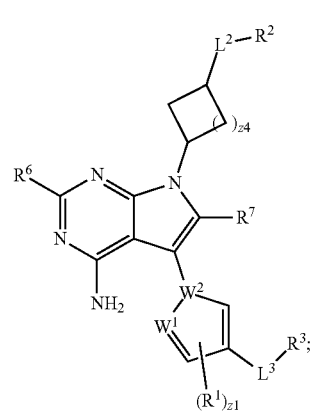

(III)

$W^1$ is N, CH, or $CR^1$;
$W^2$ is N, CH, or $CR^1$;
$R^1$ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NR^{1C}NR^{1A}R^{1B}$, $-ONR^{1A}R^{1B}$, $-NHC(O)NR^{1C}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 4;
Ring B is aryl or heteroaryl;
$L^2$ is a bond, $-NH-$, $-O-$, $-S-$, $-C(O)-$, $-C(O)NH-$, $-NHC(O)-$, $-NHC(O)NH-$, $-C(O)O-$, $-OC(O)-$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;
$R^2$ is independently oxo, halogen, $-CX^2_3$, $-CHX^2_2$, $-CH_2X^2$, $-OCX^2_3$, $-OCH_2X^2$, $-OCHX^2_2$, $-CN$, $-SO_2R^{2D}$, $-SO_{v2}NR^{2A}R^{2B}$, $-NR^{2C}NR^{2A}R^{2B}$, $-ONR^{2A}R^{2B}$, $-NHC(O)NR^{2C}NR^{2A}R^{2B}$, $-NHC(O)NR^{2A}R^{2B}$, $-N(O)_{m2}$, $-NR^{2A}R^{2B}$, $-C(O)R^{2C}$, $-C(O)-OR^{2C}$, $-C(O)NR^{2A}R^{2B}$, $-OR^{2D}$, $-NR^{2A}SO_2R^{2D}$, $-NR^{2A}C(O)R^{2C}$, $-NR^{2A}C(O)OR^{2C}$, $-NR^{2A}OR^{2C}$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl;
z2 is an integer from 0 to 6;
$L^3$ is a bond, $-NH-$, $-O-$, $-C(O)-$, $-C(O)NH-$, $-NHC(O)-$, $-NHC(O)NH-$, $-C(O)O-$, $-OC(O)-$, substituted or unsubstituted alkylene, or substituted or unsubstituted heteroalkylene;
$R^3$ is independently a polar moiety;
$L^4$ is $-C(O)NH-$ or $-NHC(O)-$;
$R^4$ and $R^5$ are independently hydrogen, $-CCl_3$, $-CBr_3$, $-CF_3$, $-CI_3$, $CHCl_2$, $-CHBr_2$, $-CHF_2$, $-CHI_2$, $-CH_2Cl$, $-CH_2Br$, $-CH_2F$, $-CH_2I$, $-CN$, $-OH$, $-NH_2$, $-COOH$, $-CONH_2$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ and $R^5$ substituents bonded to the same nitrogen may optionally be joined to form a substituted or unsubstituted heterocycloalkyl or substituted or unsubstituted heteroaryl;
$R^6$ is independently hydrogen, halogen, $-CX^6_3$, $-CHX^6_2$, $-CH_2X^6$, $-OCX^6_3$, $-OCH_2X^6$, $-OCHX^6_2$, $-CN$, $-SO_{n6}H$, $-SO_{v6}NH_2$, $-NHNH_2$, $-ONH_2$, $-NHC(O)NHNH_2$, $-NHC(O)NH_2$, $-N(O)_{m6}$, $-NH_2$, $-C(O)H$, $-COOH$, $-C(O)NH_2$, $-OH$, $-NHSO_2H$, $-NHC(O)H$, $-NHC(O)OH$, $-NHOH$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^7$ is independently hydrogen, halogen, $-CX^7_3$, $-CHX^7_2$, $-CH_2X^7$, $-OCX^7_3$, $-OCH_2X^7$, $-OCHX^7_2$, $-CN$, $-SO_{n7}H$, $-SO_{v7}NH$, $-NHNH_2$, $-ONH_2$, $-NHC(O)NHNH_2$, $-NHC(O)NH_2$, $-N(O)_{m7}$, $-NH_2$, $-C(O)H$, $-COOH$, $-C(O)NH_2$, $-OH$, $-NHSO_2H$, $-NHC(O)H$, $-NHC(O)OH$, $-NHOH$, $-SF_5$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, and $R^{2D}$ are independently hydrogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl;

z4 is 1 or 2;

$X^1$, $X^2$, $X^6$, and $X^7$ are independently —F, —Cl, —Br, or —I;

n1, n2, n6, and n7 are independently an integer from 0 to 4; and m1, m2, v1, v2, m6, v6, m7, and v7 are independently 1 or 2.

Embodiment P2. The compound of embodiment P1 having the formula:

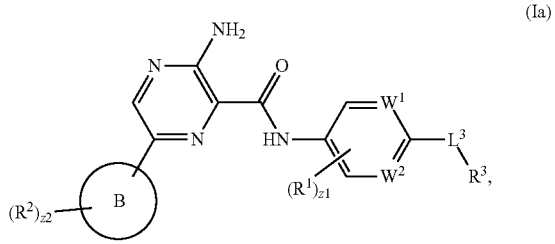

(Ia)

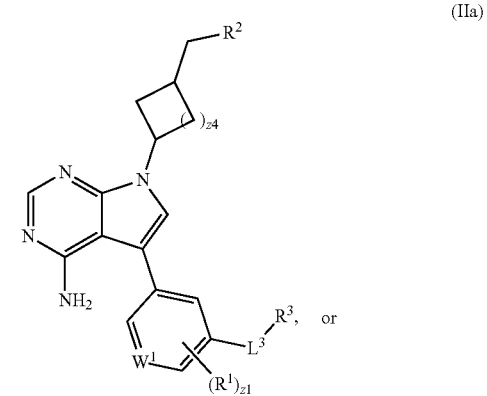

(IIa)

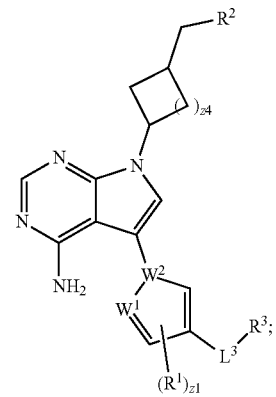

(IIIa)

wherein, $R^1$ is independently halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —R$^{1C}$NR$^{1A}$R$^{1B}$, —ONR$^{1A}$R$^{1B}$, —NHC(O)NR$^{1C}$NR$^{1A}$R$^{1B}$, —NHC(O)NR$^{1A}$R$^{1B}$, N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, —SF$_5$, —N$_3$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted C$_6$-C$_{10}$ aryl, or substituted or unsubstituted 5 to 10 membered heteroaryl; two adjacent $R^1$ substituents may optionally be joined to form a substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl;

Ring B is phenyl or 5 to 10 membered heteroaryl;

$R^2$ is independently oxo, halogen, —CX$^2_3$, —CHX$^2_2$, —CH$_2$X$^2$, —OCX$^2_3$, —OCH$_2$X$^2$, —OCHX$^2_2$, —CN, —SO$_{n2}$R$^{2D}$, —SO$_{v2}$NR$^{2A}$R$^{2B}$, —NR$^{2C}$NR$^{2A}$R$^{2B}$, —ONR$^{2A}$R$^{2B}$, —NHC(O)NR$^{2C}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO$_2$R$^{2D}$, —NR$^{2A}$C(O)R$^{2C}$, —NR$^{2A}$C(O)OR$^{2C}$, —NR$^{2A}$OR$^{2C}$, —SF$_5$, —N$_3$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl; two adjacent $R^2$ substituents may optionally be joined to form a substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl; and $L^3$ is a bond, —NH—, —O—, —C(O)—, —C(O)NH—, —NHC(O)—, —NHC(O)NH—, —C(O)O—, —OC(O)—, substituted or unsubstituted C$_1$-C$_6$ alkylene, or substituted or unsubstituted 2 to 6 membered heteroalkylene.

Embodiment P3. The compound of one of embodiments P1 to P2, having the formula:

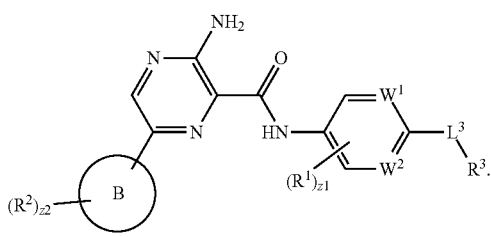

(Ia)

Embodiment P4. The compound of one of claims 1 to 3, wherein

R$^3$ is independently —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO$_2$R$^{3D}$, —NR$^{3C}$SO$_2$NR$^{3A}$R$^{3B}$, —NR$^{3A}$R$^{3B}$, —NR$^{3A}$C(O)R$^{3C}$, —NR$^{3A}$C(O)OR$^{3C}$, —SO$_2$R$^{3C}$, —SO$_2$-L$^{3A}$-R$^{3C}$, —SO$_2$NR$^{3A}$R$^{3B}$, —SO$_2$NR$^{3A}$SO$_2$R$^{3C}$, —SO$_2$NR$^{3A}$P(O)(OR$^{3C}$)(OR$^{3D}$), —SO$_2$P(O)(OR$^{3C}$)(OR$^{3D}$), —SO$_2$CH$_2$P(O)(OR$^{3C}$)(OR$^{3D}$), —SO$_2$P(O)(OR$^{3D}$)(NR$^{3A}$R$^{3B}$), —SO$_2$P(O)(R$^{3C}$)(OR$^{3D}$), —SO$_2$P(O)(R$^{3C}$)(R$^{3D}$), —SO$_2$-L$^{3A}$-P(O)(OR$^{3C}$)(OR$^{3D}$), —SO$_2$-L$^{3A}$-P(O)(OR$^{3D}$)(NR$^{3A}$R$^{3B}$), —SO$_2$-L$^{3A}$-P(O)(R$^3$)(OR$^{3D}$), —SO$_2$-L$^{3A}$-P(O)(R$^{3C}$)(R$^{3D}$), —S(O)(NR$^{3A}$)R$^{3C}$, —C(O)OR$^{3C}$, —C(O)NR$^{3A}$R$^{3B}$, or —NR$^{3A}$C(O)OR$^{3C}$;

L$^{3A}$ is independently —CH$_2$—, —CH(CH$_3$)—, —C(CH$_3$)$_2$—, —CH(X$^{3A}$)—, or —C(X$^{3A}$)$_2$—;

X$^{3A}$ is —F, —Cl, —Br, or —I; and

R$^{3A}$, R$^{3B}$, R$^{3C}$, and R$^{3D}$ are independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{3A}$ and R$^{3D}$ substituents may optionally be joined to form a substituted or unsubstituted heterocycloalkyl or substituted or unsubstituted heteroaryl.

Embodiment P5. The compound of one of embodiments P1 to P4, wherein R$^3$ is —SO$_2$-L$^{3A}$-R$^{3C}$ and R$^{3C}$ is independently —COOCH$_3$ or —COOCH$_2$CH$_3$.

Embodiment P6 The compound of one of embodiments P1 to P5, wherein R$^3$ is

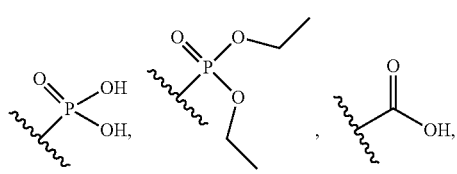

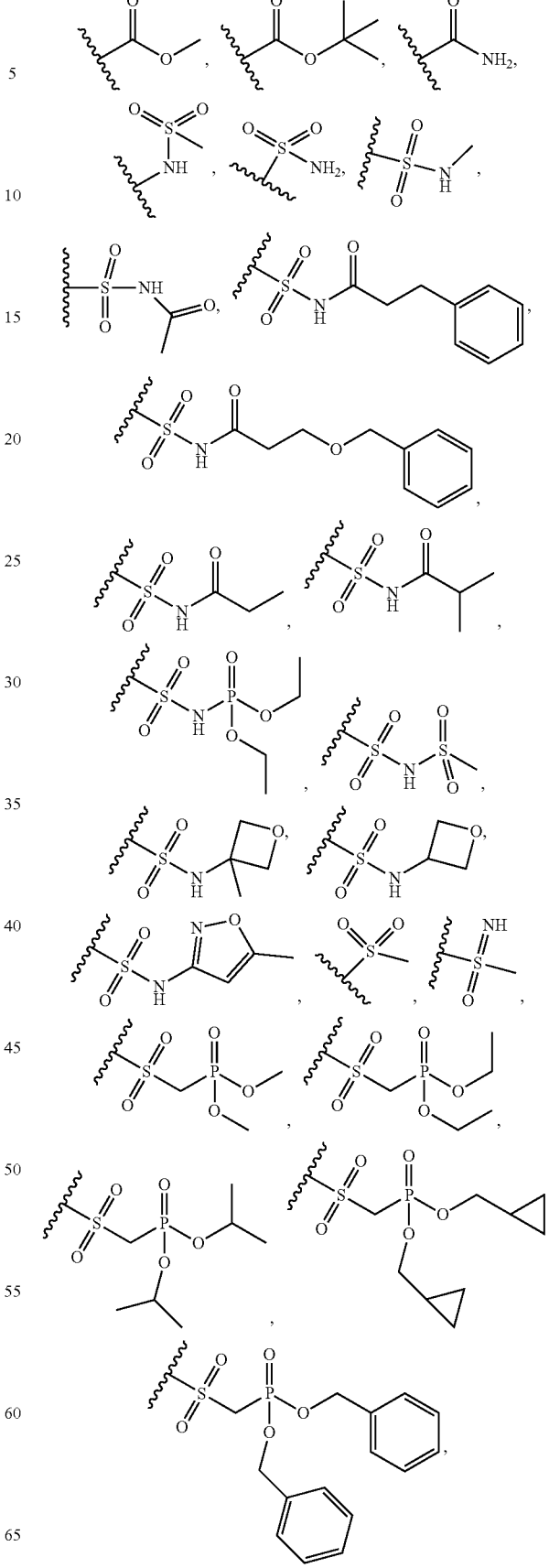

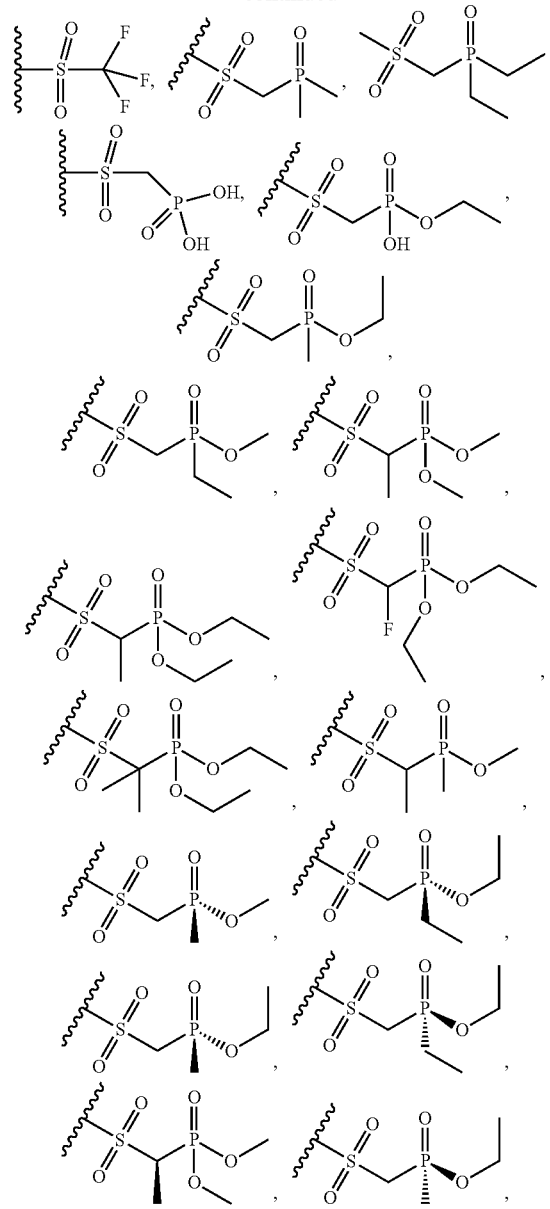
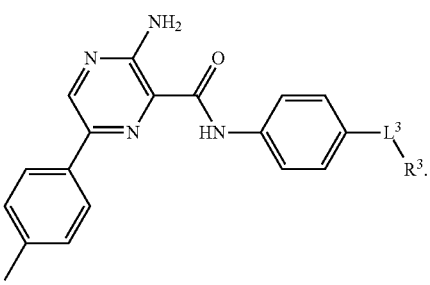

Embodiment P7. The compound of one of embodiments P1 to P6, wherein $L^3$ is a bond or —$CH_2$—.

Embodiment P8. The compound of one of embodiments P1 to P7, wherein Ring B is phenyl, thienyl, indazolyl, indolyl, pyrazolyl, pyrimidinyl, pyridyl, or benzothienyl.

Embodiment P9. The compound of one of embodiments P1 to P7, having the formula:

(Ib)

Embodiment P10. The compound of embodiment P1, having the formula:

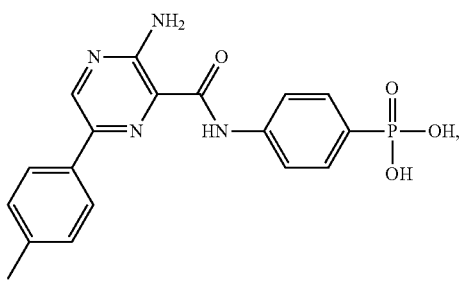
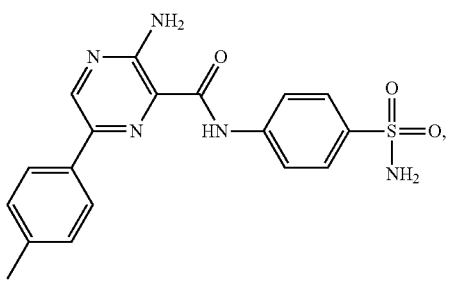

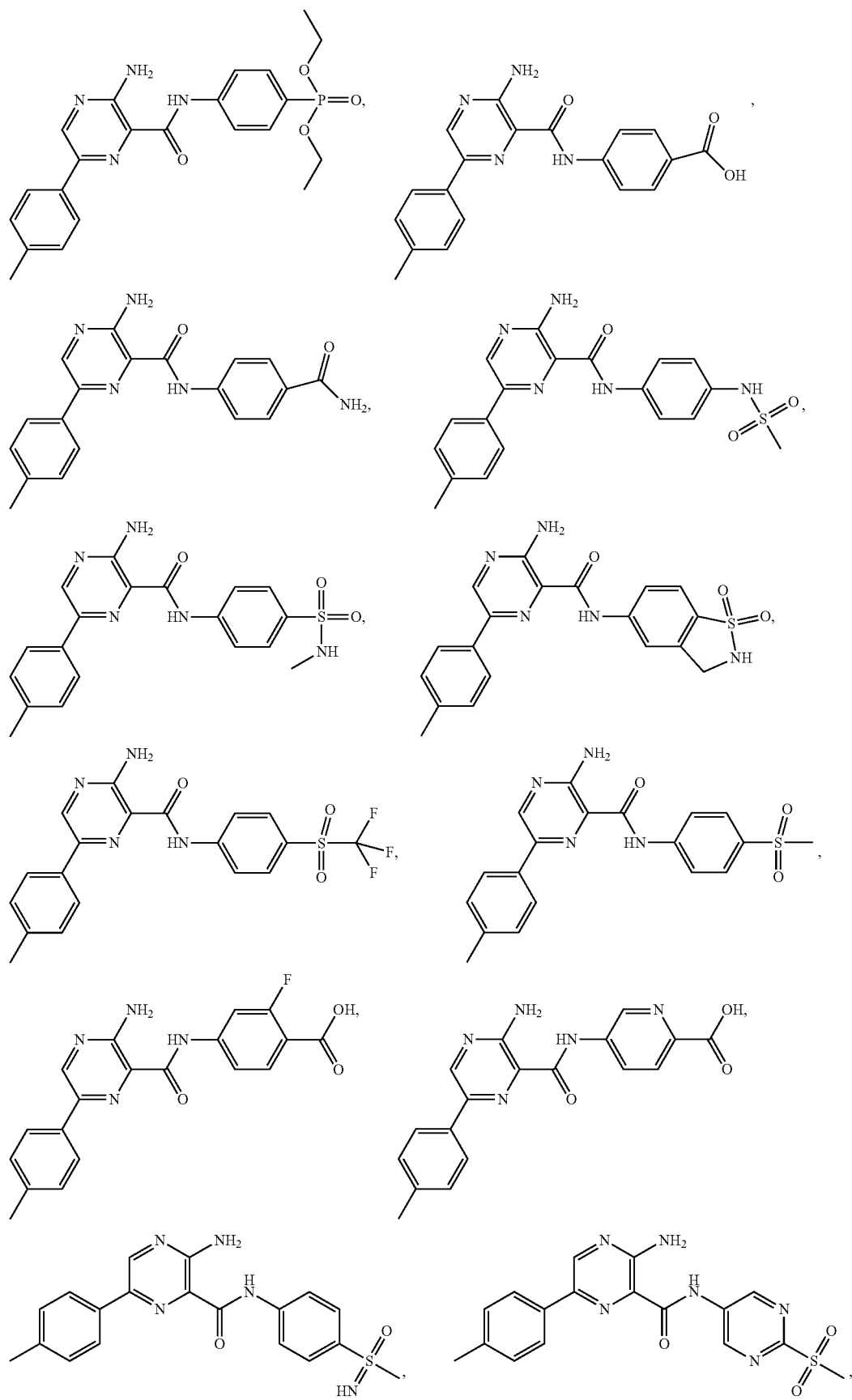

319
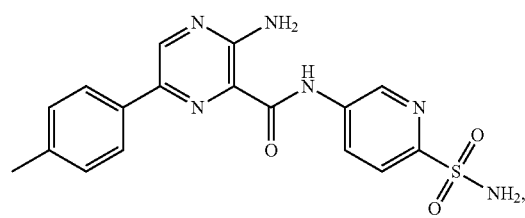
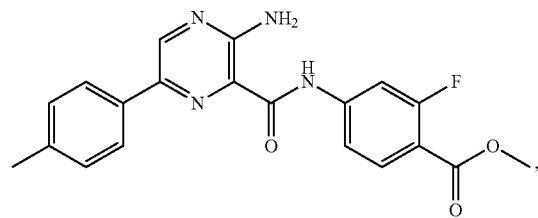
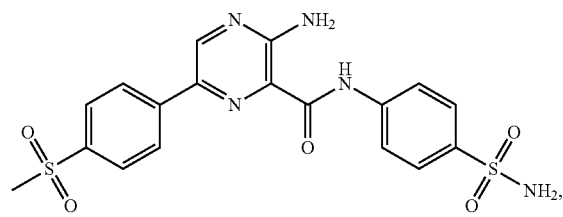
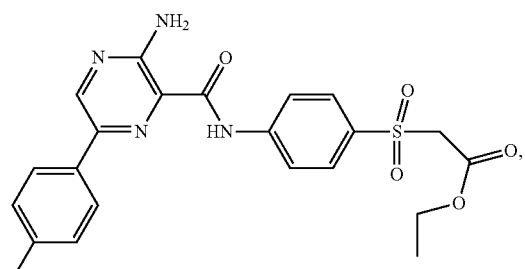
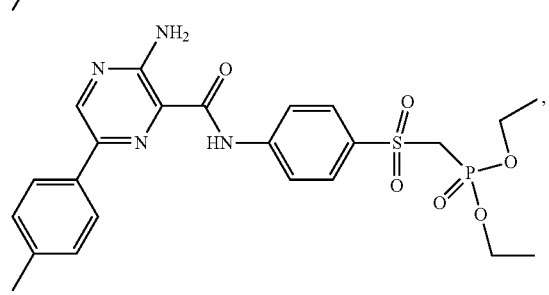
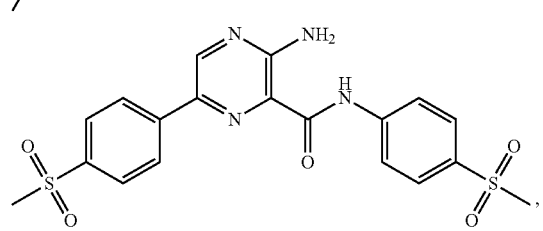
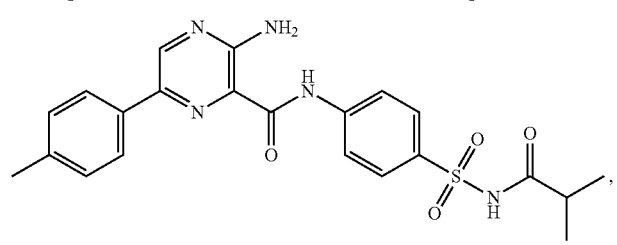
320
-continued
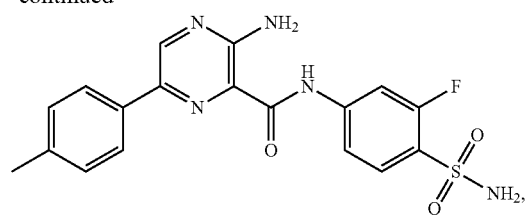
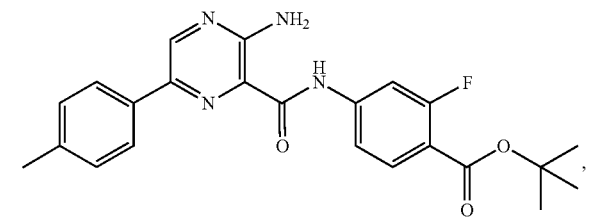
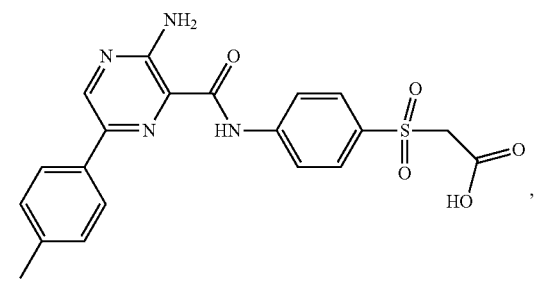
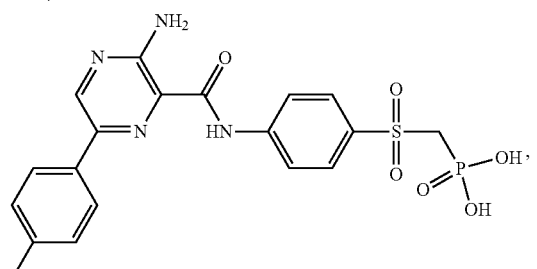
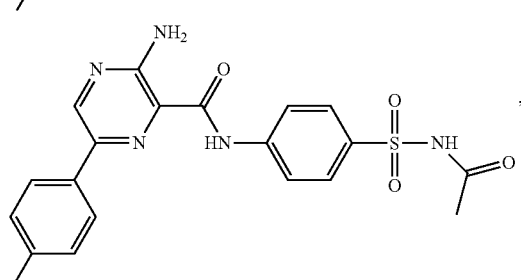
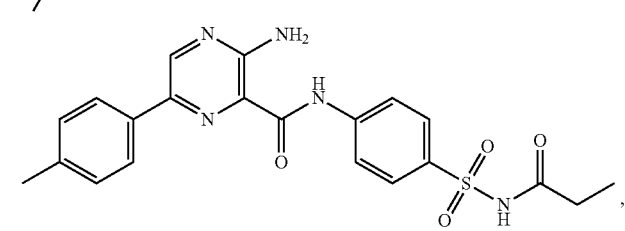

321
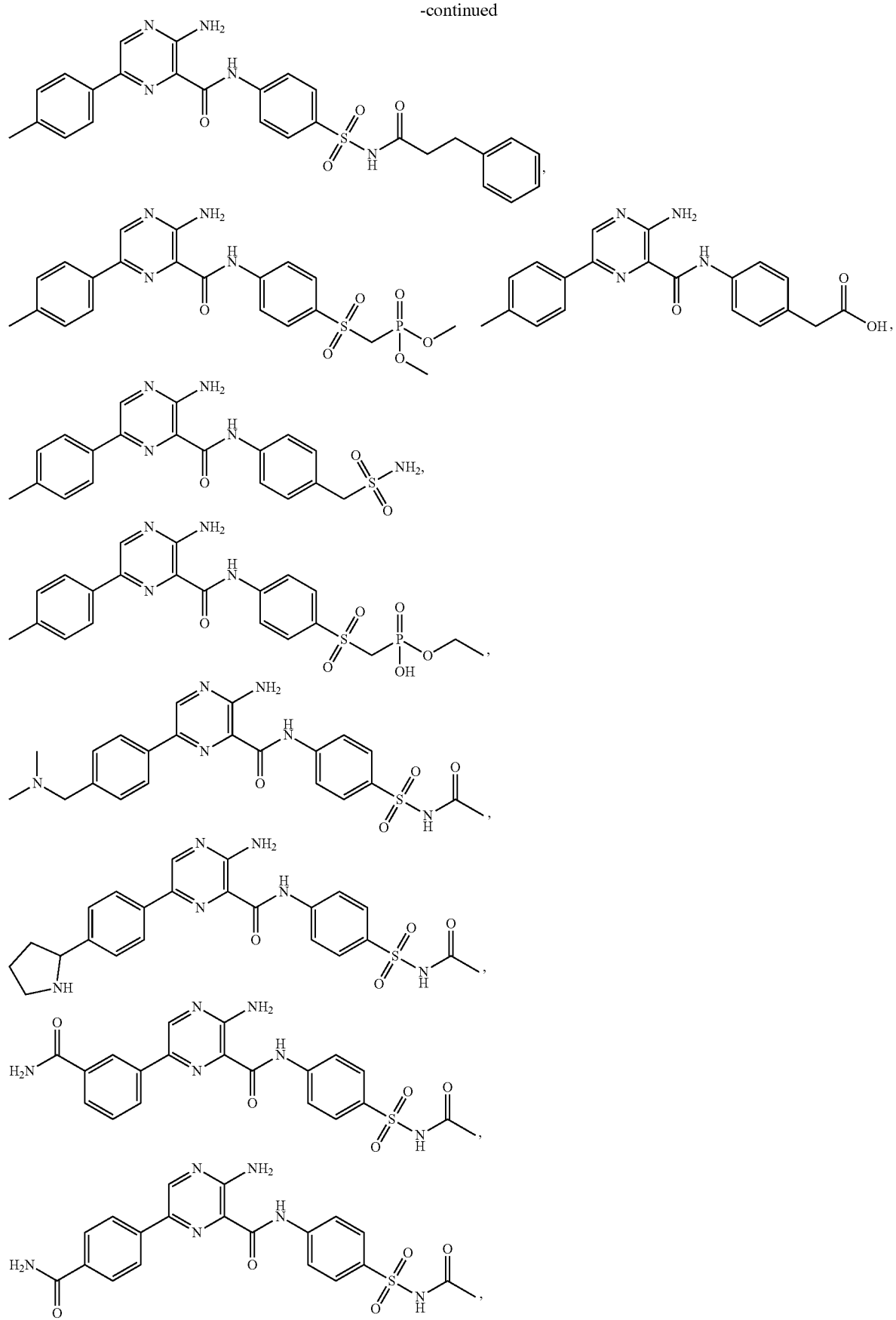
322

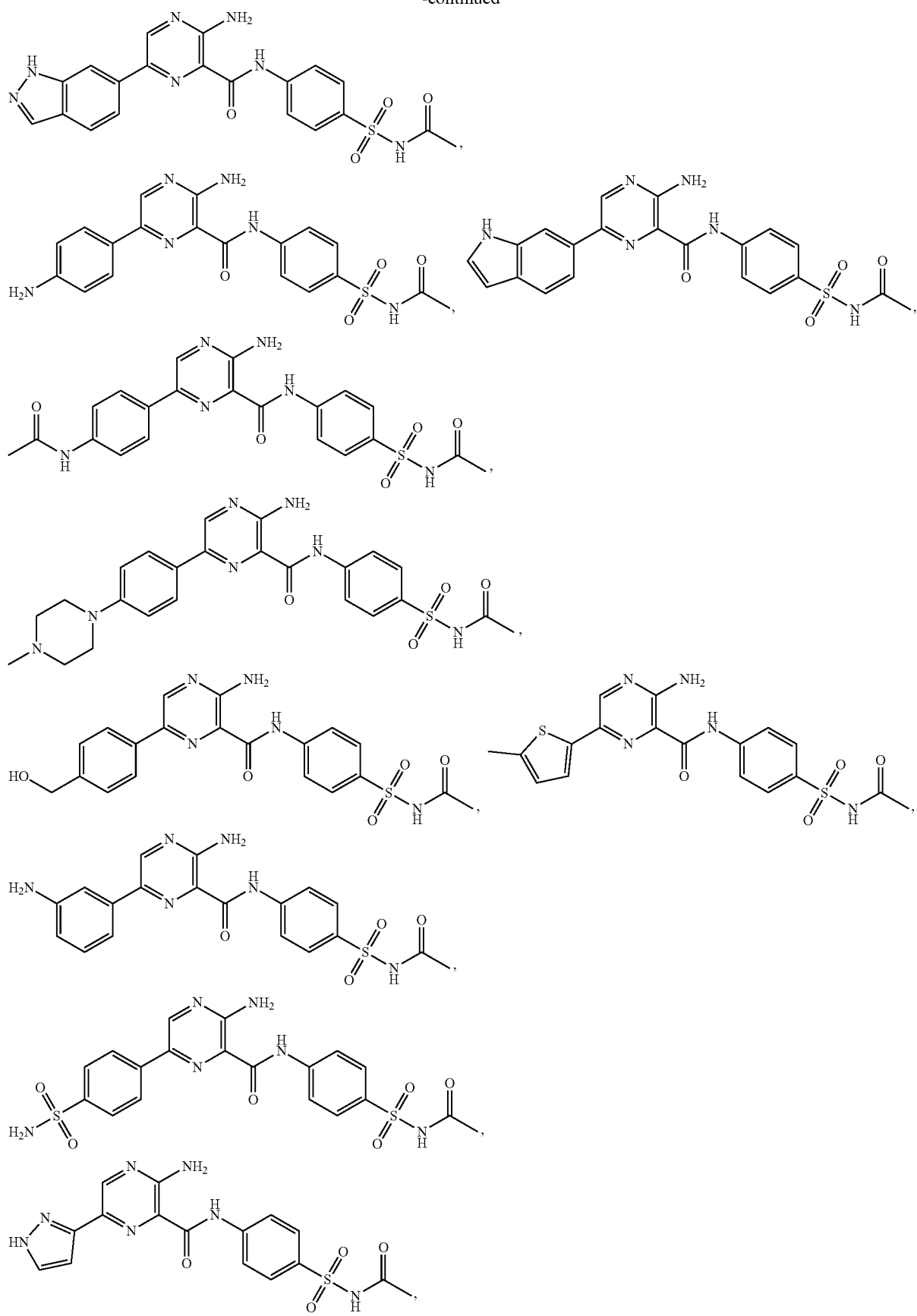

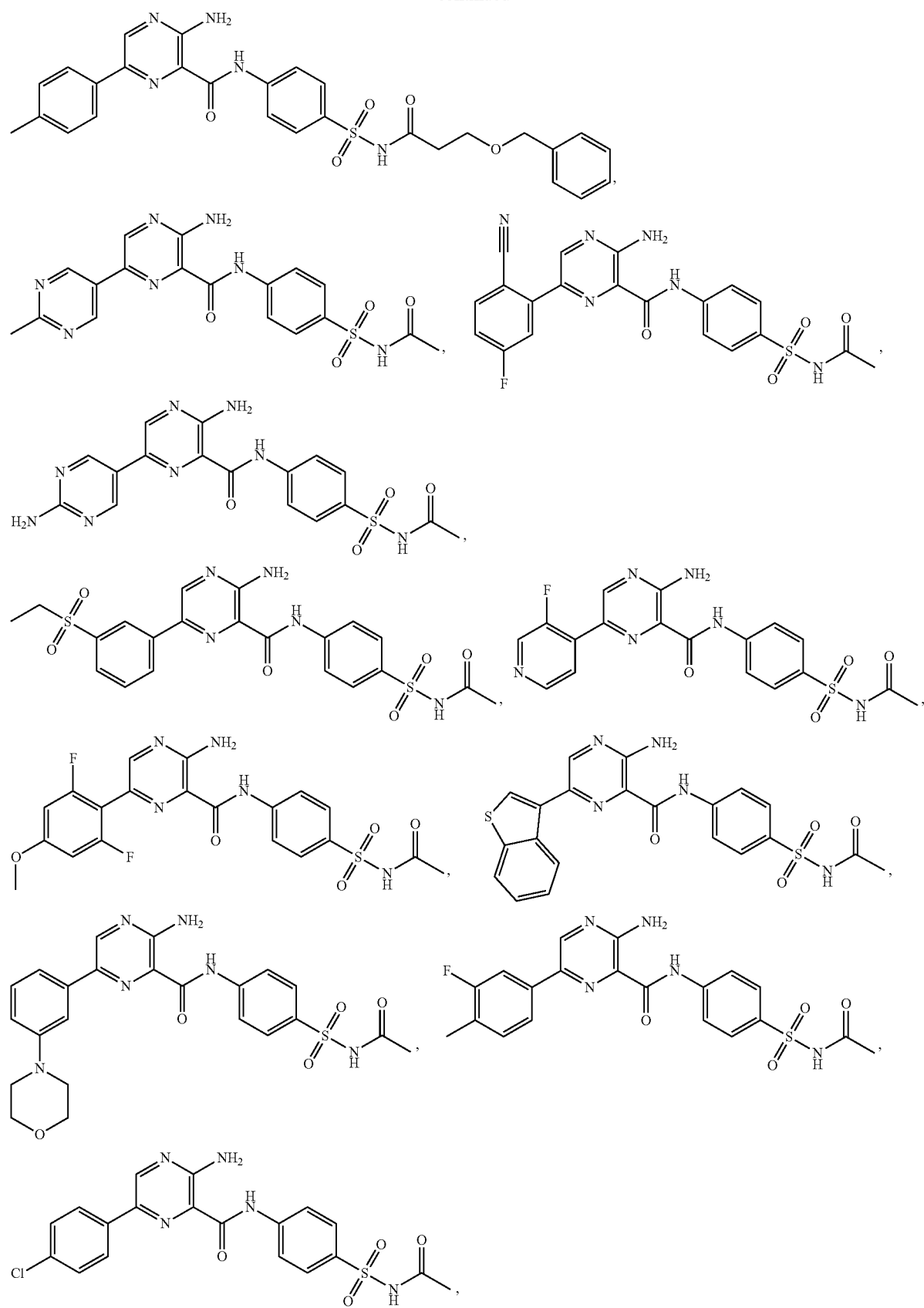

-continued
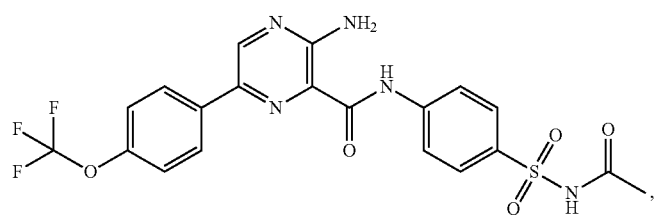
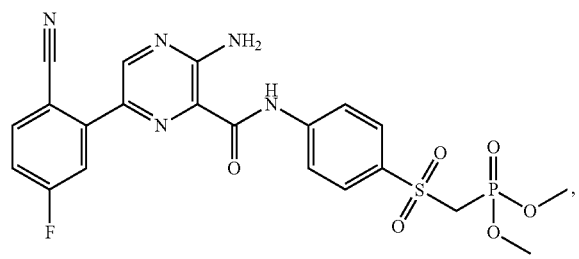
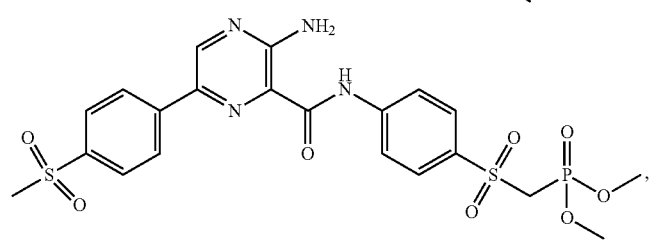
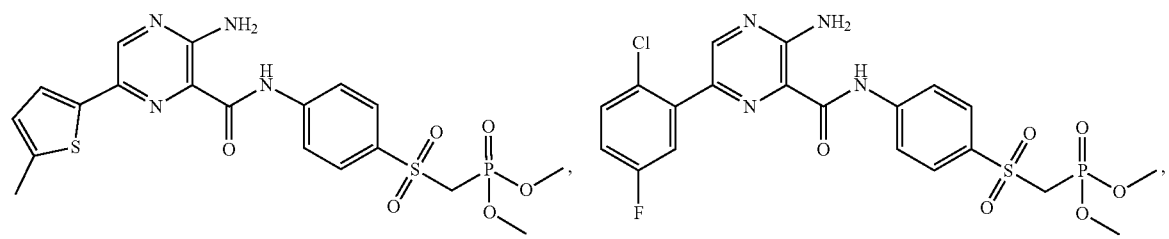
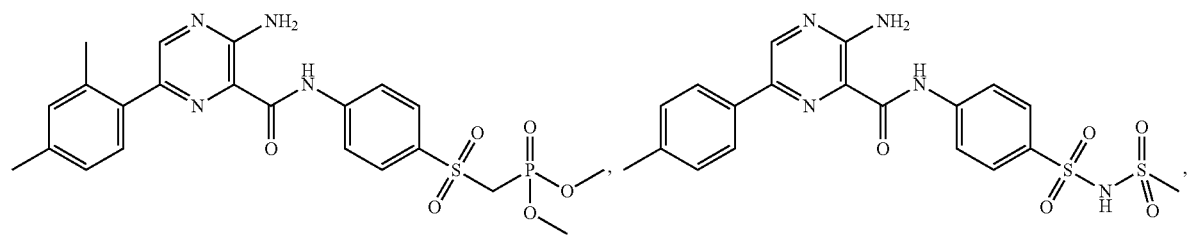
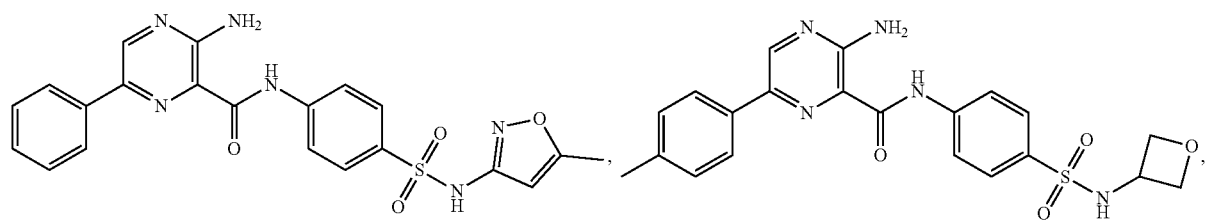
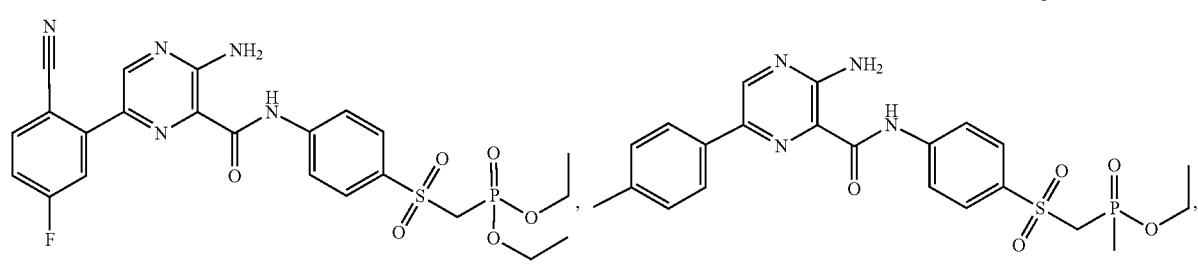

329
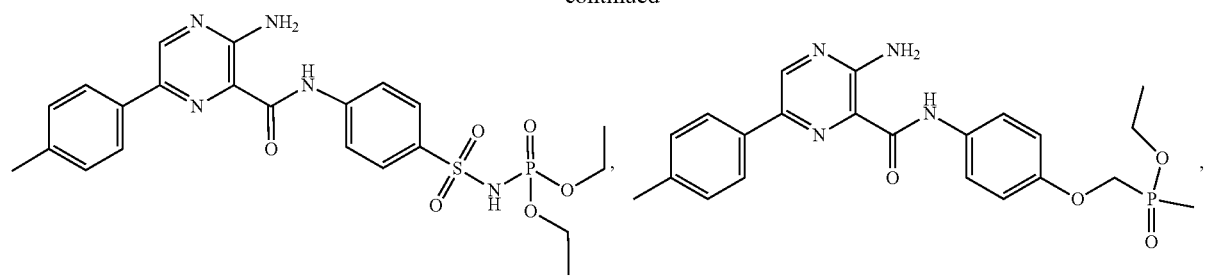
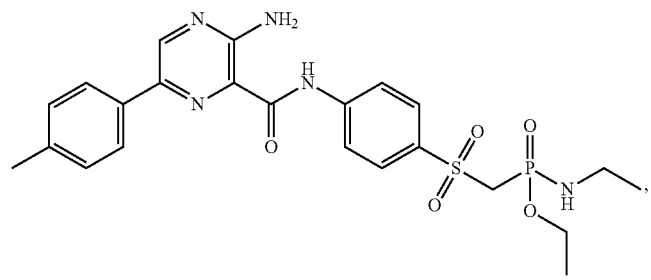
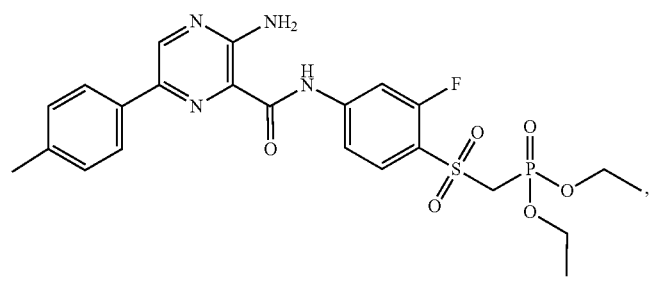
330
-continued
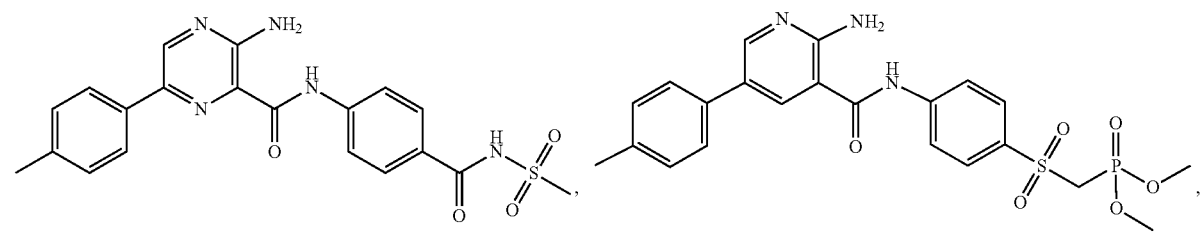
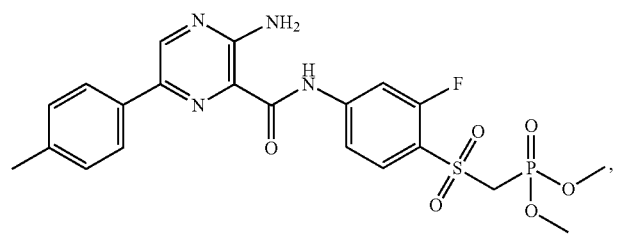
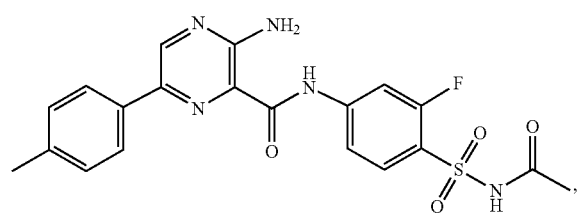

-continued
331
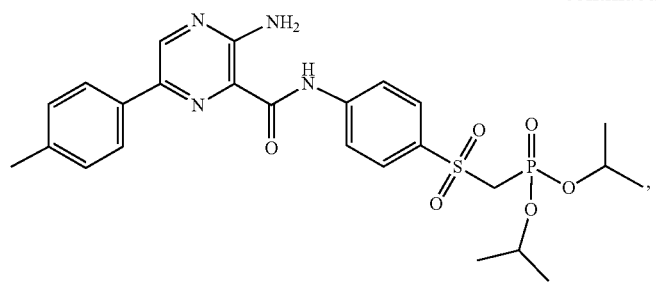
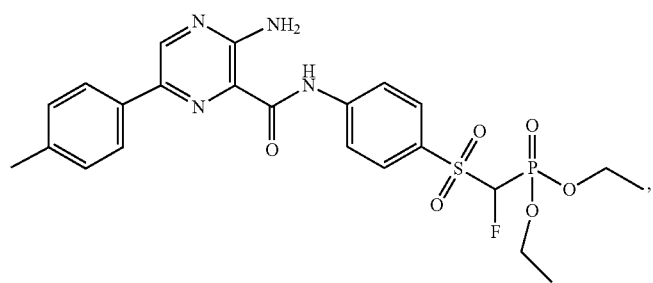
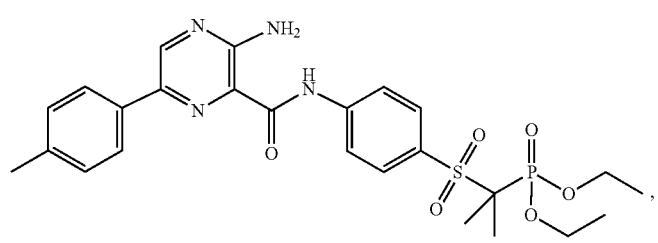
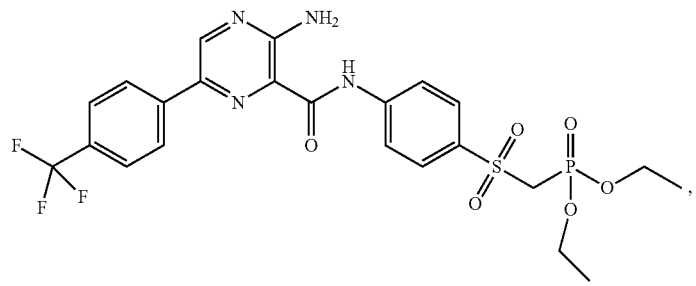
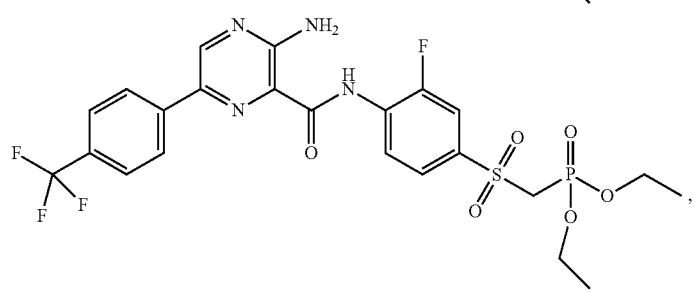
332
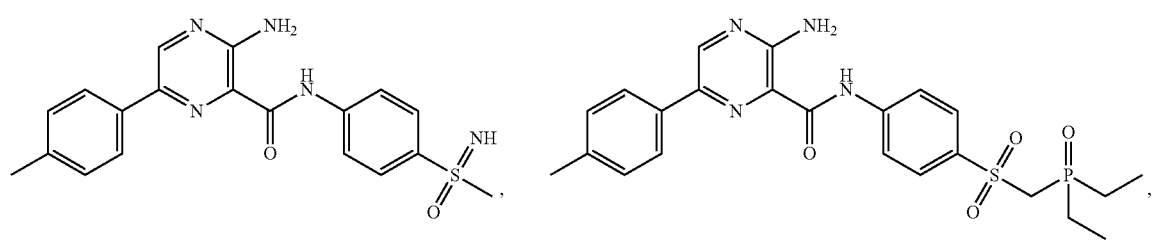

-continued
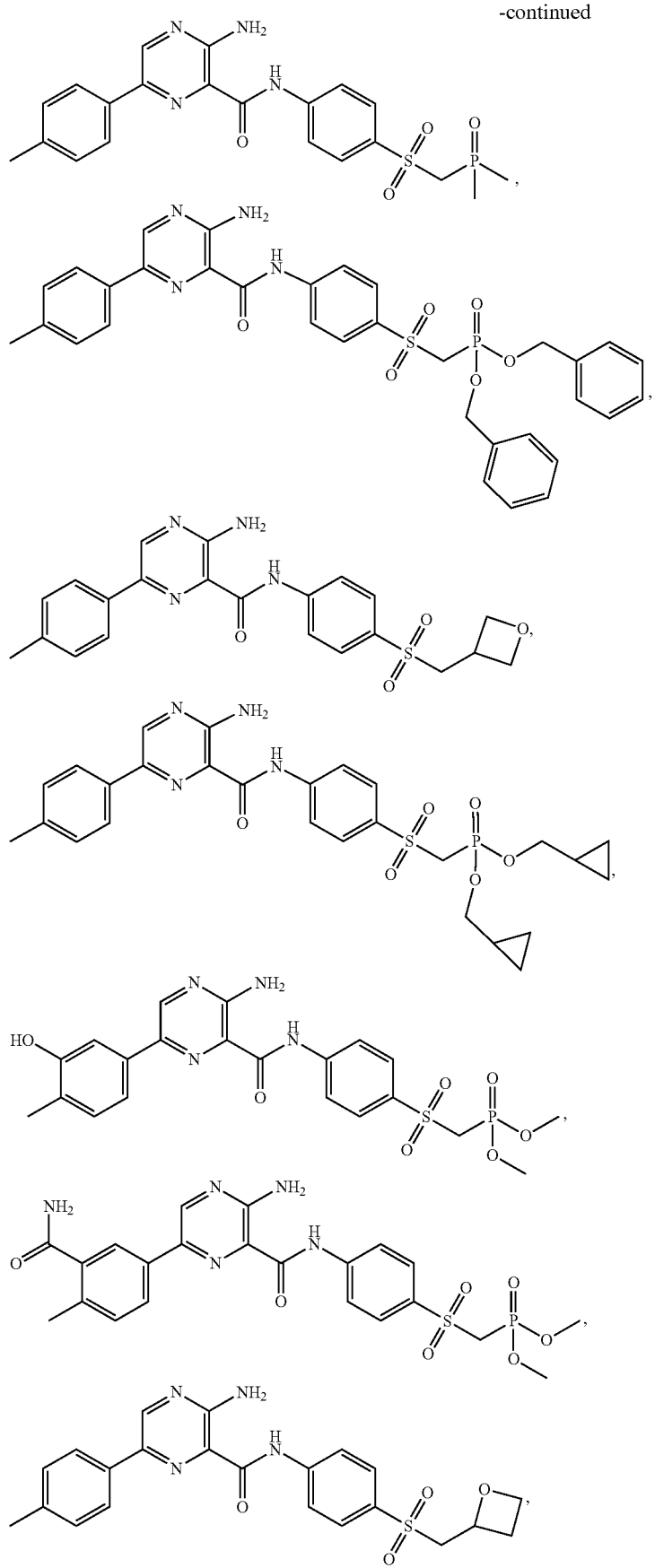

-continued
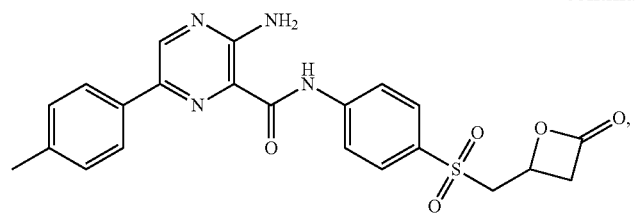
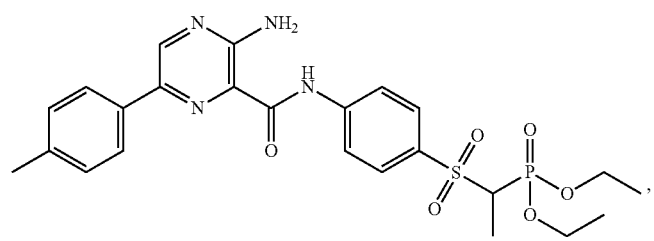
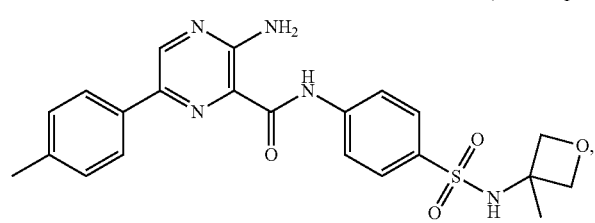
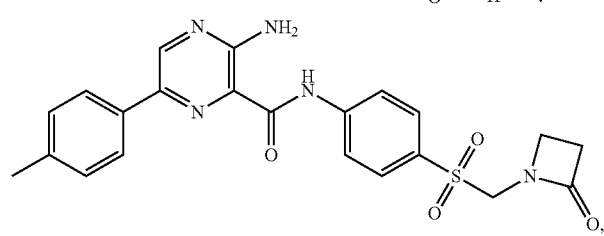
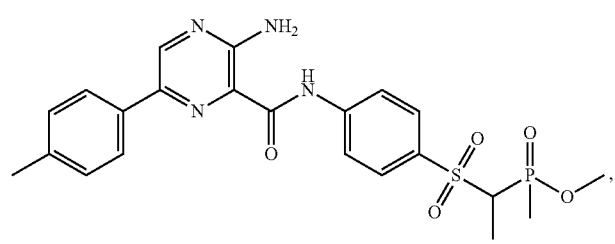
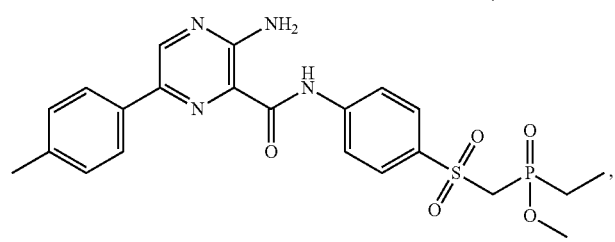
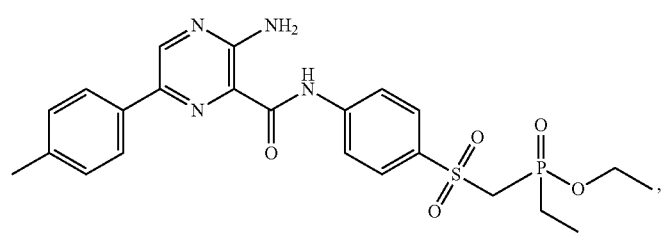

-continued
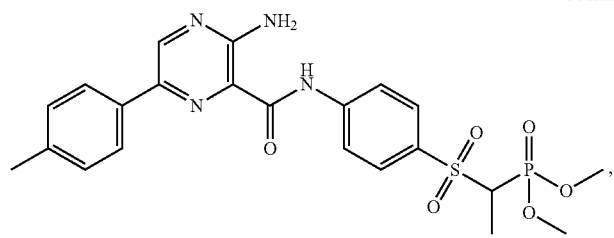
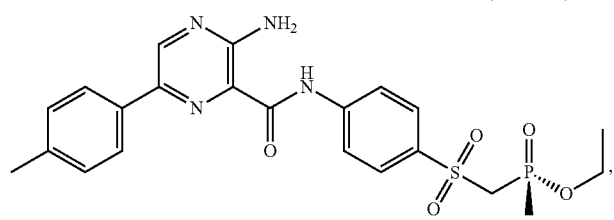
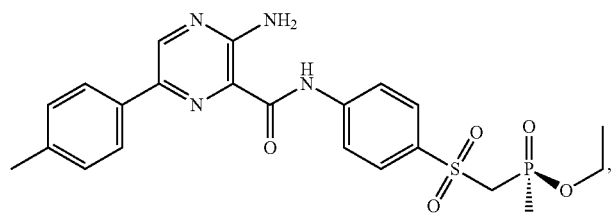
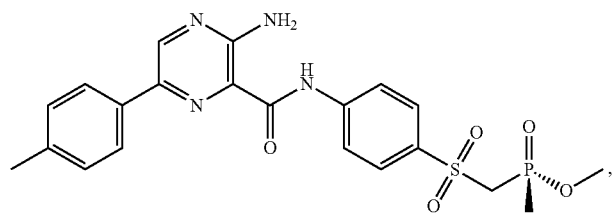
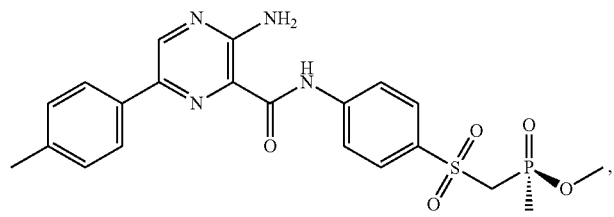
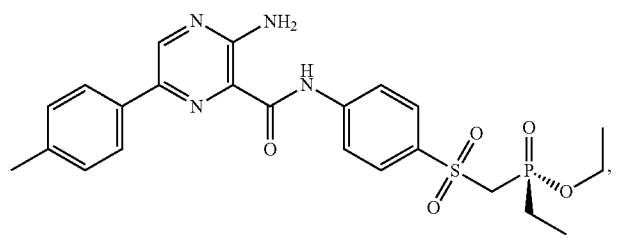
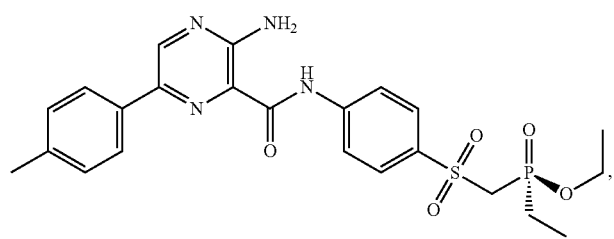

-continued
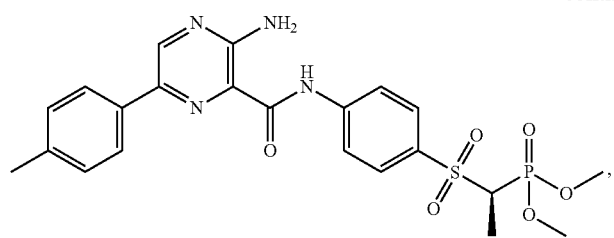
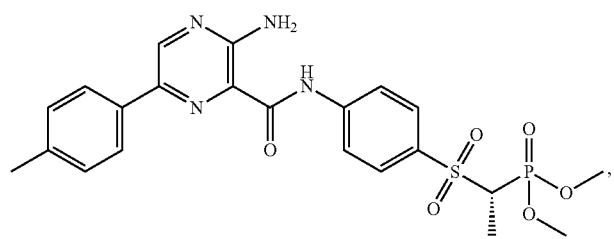
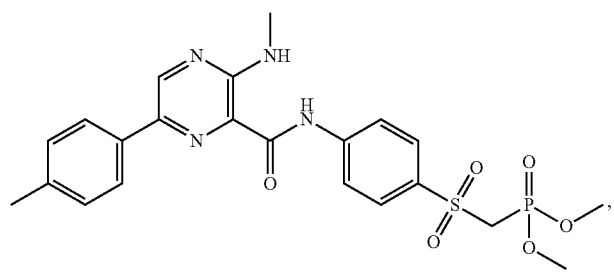
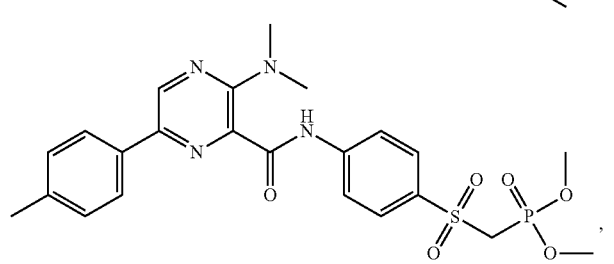
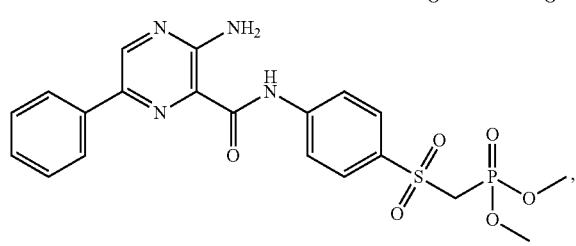
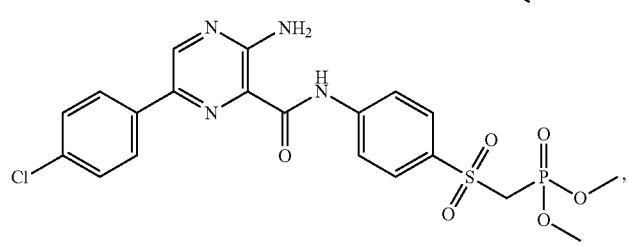
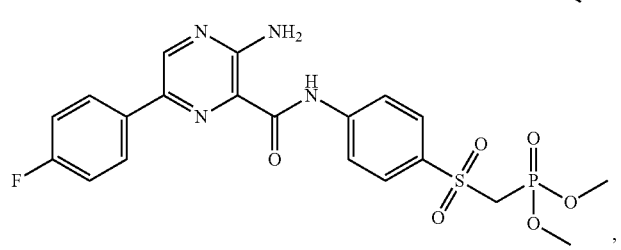

341
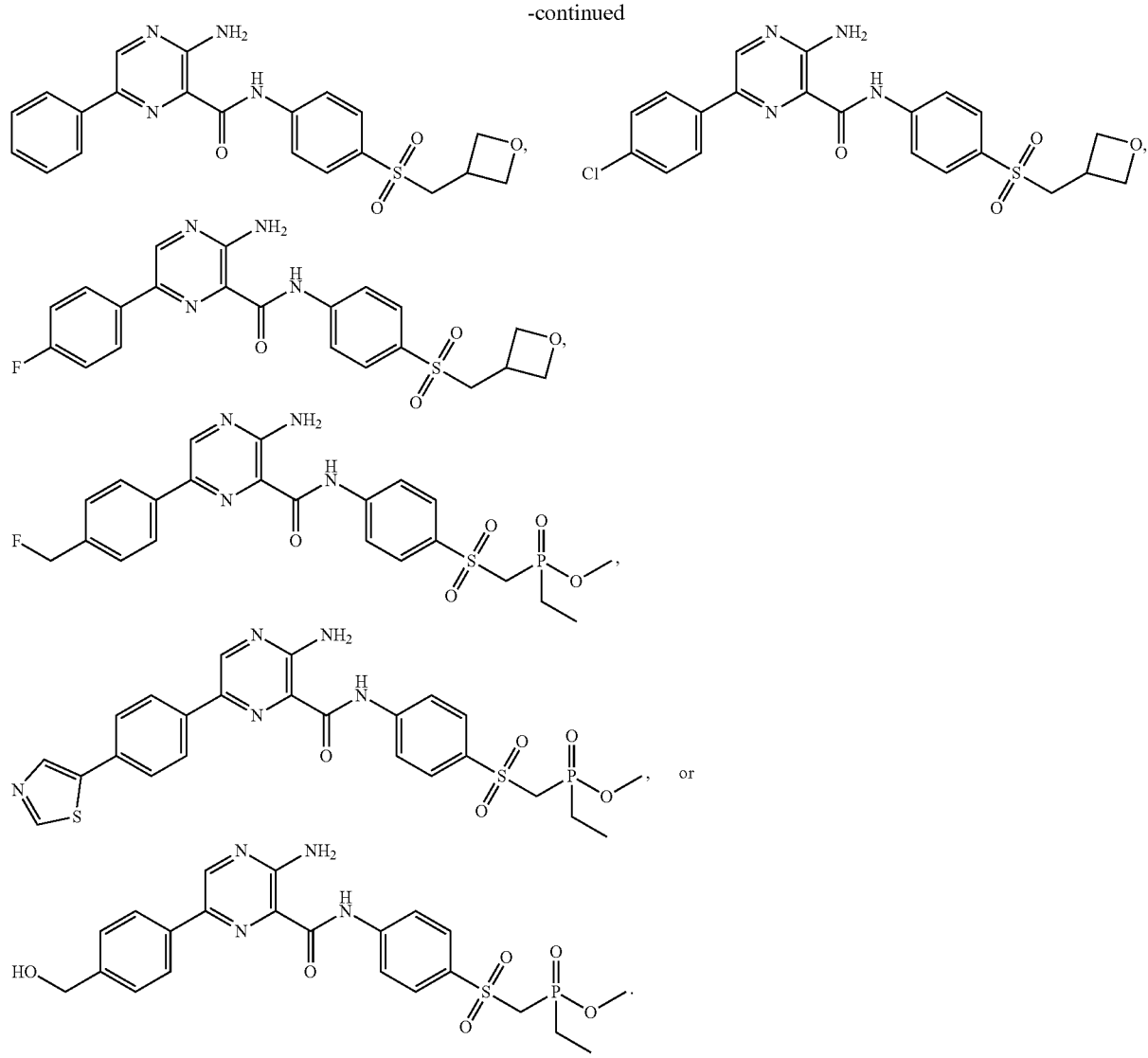
-continued
342
Embodiment P11. The compound of embodiment P1, having the formula:
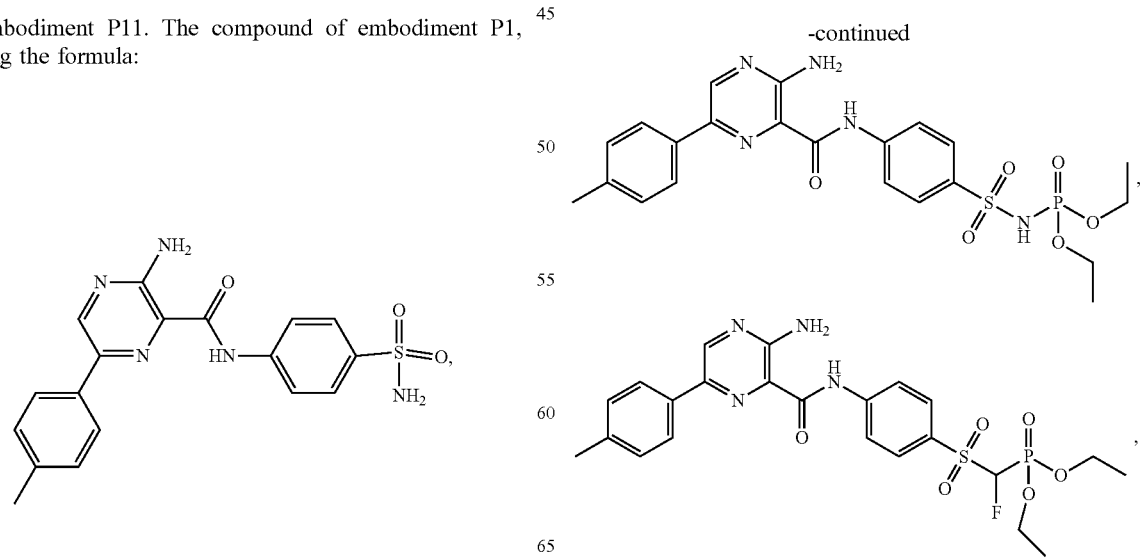

-continued
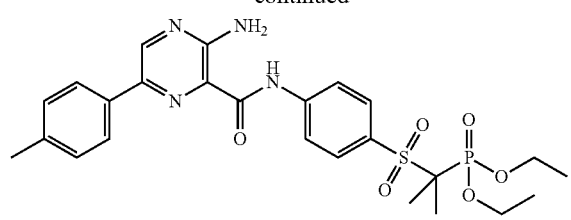
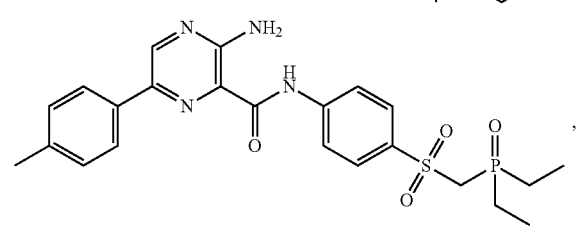
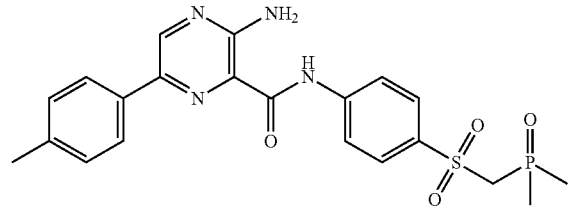
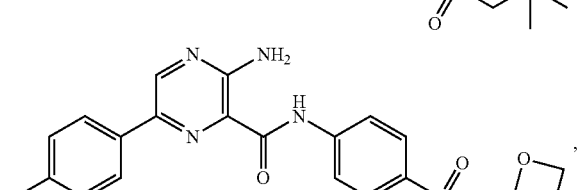
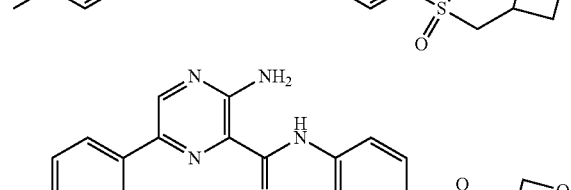
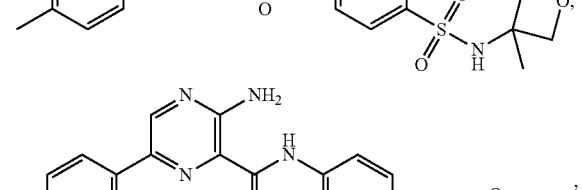
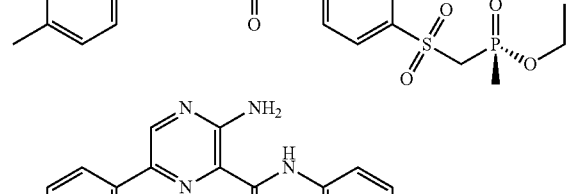
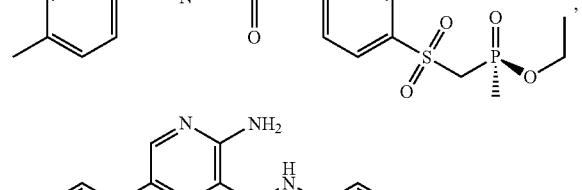
-continued
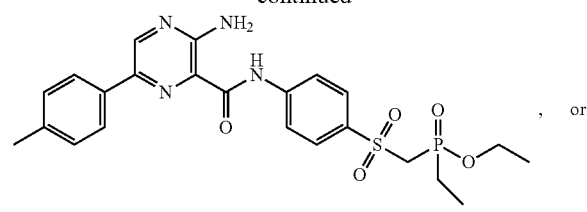, or
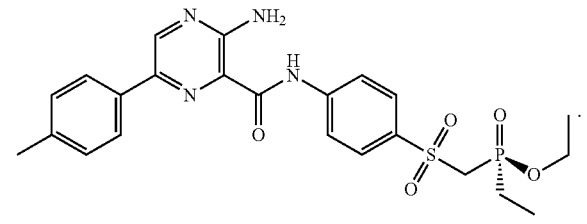
Embodiment P12. The compound of embodiment P1, having the formula:
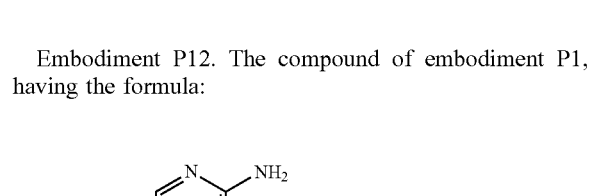
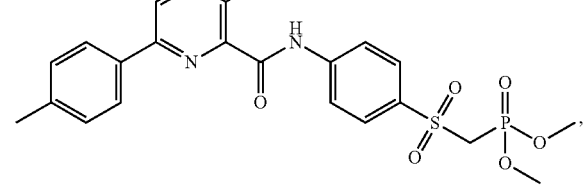
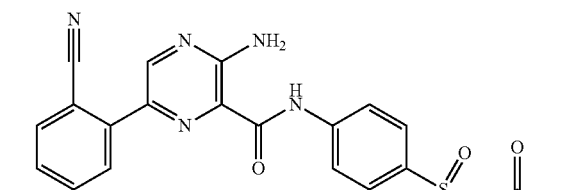
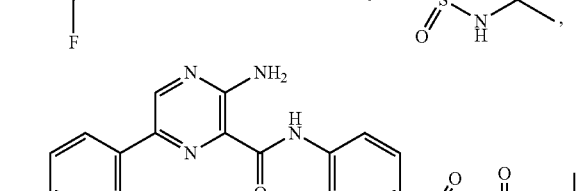
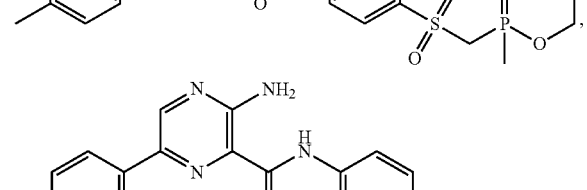
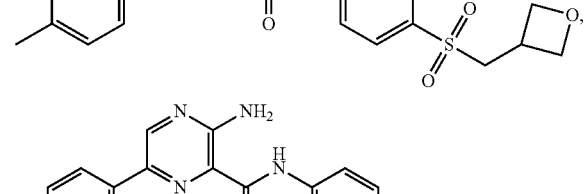

-continued

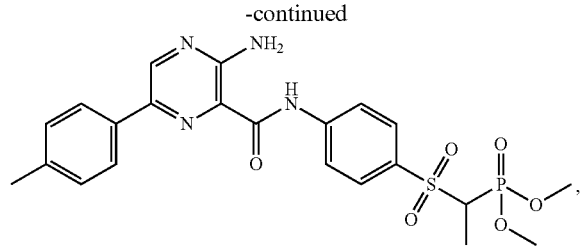

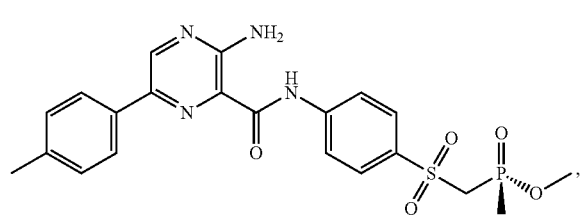

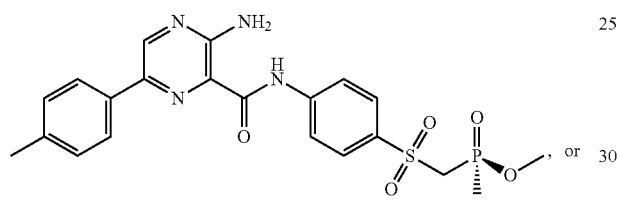

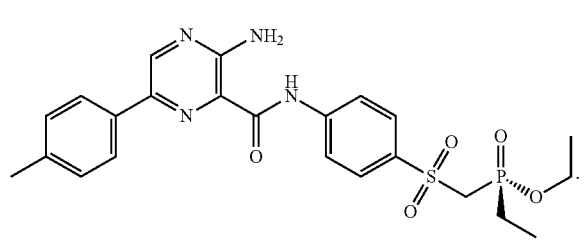

Embodiment P13. The compound of one of embodiments P1 to P2, having the formula:

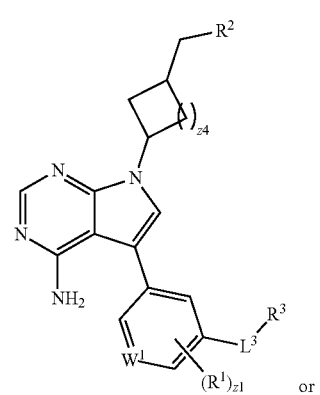
(IIa)

-continued

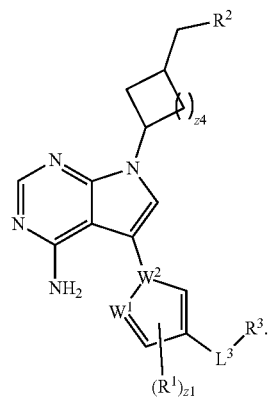
(IIIa)

Embodiment P14. The compound of embodiment P13, having the formula:

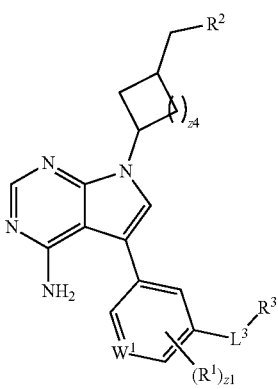
(IIa)

Embodiment P15. The compound of embodiment P13, having the formula:

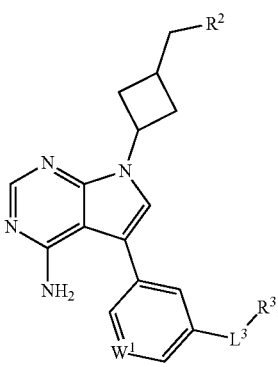
(IIb)

wherein
R$^2$ is independently —NR$^{2A}$R$^{2B}$ or —OH;
R$^{2A}$ and R$^{2B}$ are independently hydrogen or R$^{20}$-substituted or unsubstituted C$_1$-C$_6$ alkyl; or R$^{2A}$ and R$^{2B}$ substituents bonded to the same nitrogen atom may optionally be joined to form an R$^{20}$-substituted or unsubstituted 4 to 7 membered heterocycloalkyl; and
R$^{20}$ is independently oxo, halogen, —CCl$_3$, —CBr$_3$, —CF$_3$, —CI$_3$, CHCl$_2$, —CHBr$_2$, —CHF$_2$, —CHI$_2$, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, unsubstituted C₁-C₆ alkyl, unsubstituted 2 to 6 membered heteroalkyl, unsubstituted C₃-C₆ cycloalkyl, unsubstituted 3 to 6 membered heterocycloalkyl, unsubstituted phenyl, or unsubstituted 5 to 6 membered heteroaryl.

Embodiment P16. The compound of embodiment P15, having the formula:

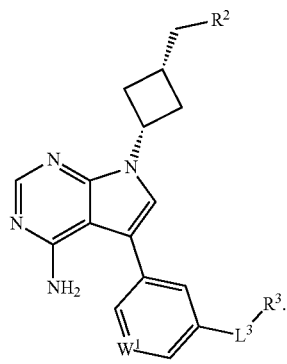

(IIc)

Embodiment P17. The compound of embodiment P13, having the formula:

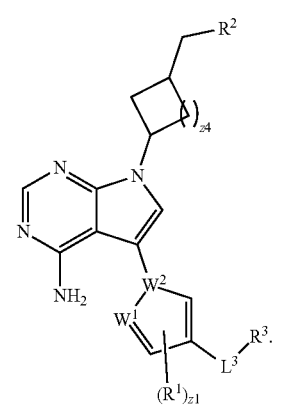

(IIIa)

Embodiment P18. The compound of embodiment P13, having the formula:

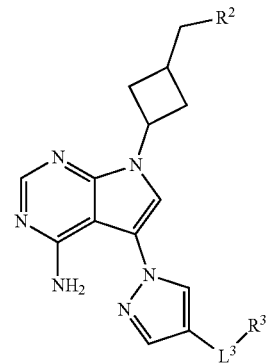

(IIIb)

wherein
R² is independently —NR²ᴬR²ᴮ;
R²ᴬ and R²ᴮ are independently hydrogen or R²⁰-substituted or unsubstituted C₁-C₆ alkyl; or R²ᴬ and R²ᴮ substituents bonded to the same nitrogen atom may optionally be joined to form an R²⁰-substituted or unsubstituted 4 to 7 membered heterocycloalkyl; and
R²⁰ is independently oxo, halogen, —CCl₃, —CBr₃, —CF₃, —CI₃, CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, unsubstituted C₁-C₆ alkyl, unsubstituted 2 to 6 membered heteroalkyl, unsubstituted C₃-C₆ cycloalkyl, unsubstituted 3 to 6 membered heterocycloalkyl, unsubstituted phenyl, or unsubstituted 5 to 6 membered heteroaryl.

Embodiment P19. The compound of embodiment P18, having the formula:

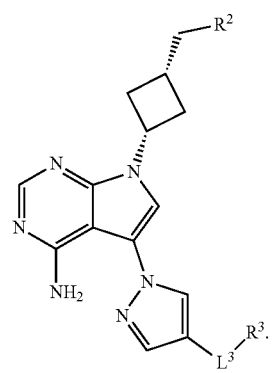

(IIIc)

Embodiment P20. The compound of one of embodiments P13 to P19, wherein
R²ᴬ and R²ᴮ substituents bonded to the same nitrogen atom are joined to form an R20-substituted or unsubstituted 4 to 7 membered heterocycloalkyl; and
R²⁰ is independently oxo, halogen, —CCl₃, —CBr₃, —CF₃, —CI₃, CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, unsubstituted C₁-C₆ alkyl, unsubstituted 2 to 6 membered heteroalkyl, unsubstituted C₃-C₆ cycloalkyl, unsubstituted 3 to 6 membered heterocycloalkyl, unsubstituted phenyl, or unsubstituted 5 to 6 membered heteroaryl.

Embodiment P21. The compound of embodiment P20, wherein
R²ᴬ and R²ᴮ substituents bonded to the same nitrogen atom are joined to form

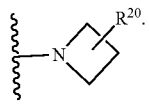

Embodiment P22. The compound of embodiment P20, wherein
R²ᴬ and R²ᴮ substituents bonded to the same nitrogen atom are joined to form

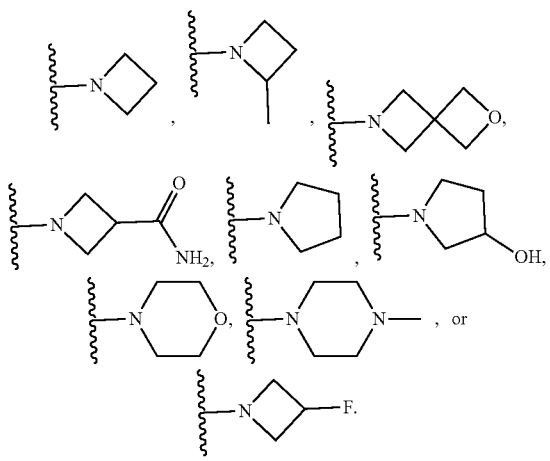

Embodiment P23. The compound of one of embodiments P13 to P22, wherein
L³ is a bond, —CH₂—, —CH₂CH₂—, —CH₂CH₂CH₂—, —OCH₂—, —OCH₂CH₂—, or —OCH₂CH₂CH₂—;
R³ is independently —OH, —P(O)(OR³ᶜ)(OR³ᴰ), —P(O)(OR³ᴰ)(NR³ᴬR³ᴮ), —P(O)(R³ᶜ)(OR³ᴰ), —P(O)(R³ᶜ)(R³ᴰ), —P(S)(OR³ᶜ)(OR³ᴰ), —P(S)(OR³ᴰ)(NR³ᴬR³ᴮ), —P(S)(R³ᶜ)(OR³ᴰ), —P(S)(R³ᶜ)(R³ᴰ), —NR³ᴬSO₂R³ᴰ, —NR³ᴬSO₂L³ᴬR³ᴰ, —NR³ᶜSO₂NR³ᴬR³ᴮ, —NR³ᴬR³ᴮ, —NR³ᴬC(O)R³ᶜ, —NR³ᴬC(O)OR³ᶜ, —SO₂R³ᶜ, —SO₂NR³ᴬR³ᴮ, —SO₂P(O)(OR³ᶜ)(OR³ᴰ), —SO₂CH₂P(O)(OR³ᶜ)(OR³ᴰ), —SO₂P(O)(OR³ᴰ)(NR³ᴬR³ᴮ), —SO₂P(O)(R³ᶜ)(OR³ᴰ), —SO₂P(O)(R³ᶜ)(R³ᴰ), —S(O)(NR³ᴬ)R³ᶜ, —C(O)OR³ᶜ, —C(O)NR³ᴬR³ᴮ, —NR³ᴬC(O)OR³ᶜ;
L³ᴬ is independently —CH₂—, —CH(CH₃)—, or —C(CH₃)₂—; and
R³ᴬ, R³ᴮ, R³ᶜ, and R³ᴰ are independently hydrogen, oxo, halogen, —CCl₃, —CBr₃, —CF₃, —CI₃, —CHCl₂, —CHBr₂, —CHF₂, —CHI₂, —CH₂Cl, —CH₂Br, —CH₂F, —CH₂I, —CN, —OH, —NH₂, —COOH, —CONH₂, —NO₂, —SH, —SO₃H, —SO₄H, —SO₂NH₂, —NHNH₂, —ONH₂, —NHC(O)NHNH₂, —NHC(O)NH₂, —NHSO₂H, —NHC(O)H, —NHC(O)OH, —NHOH, —OCCl₃, —OCF₃, —OCBr₃, —OCI₃, —OCHCl₂, —OCHBr₂, —OCHI₂, —OCHF₂, —OCH₂Cl, —OCH₂Br, —OCH₂I, —OCH₂F, —N₃, —SO₂CH₃, —NHC(O)CH₃, —C(O)CH₃, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R³ᴬ and R³ᴮ substituents bonded to the same nitrogen atom may optionally be joined to form a substituted or unsubstituted heterocycloalkyl or substituted or unsubstituted heteroaryl; R³ᴬ and R³ᴰ substituents may optionally be joined to form a substituted or unsubstituted heterocycloalkyl or substituted or unsubstituted heteroaryl.

Embodiment P24. The compound of one of embodiments P13 to P23, wherein W¹ is CH.

Embodiment P25. The compound of one of embodiments P13 to P23, wherein W¹ is N.

Embodiment P26. The compound of one of embodiments P13 to P23, wherein W¹ is CR¹; and
R¹ is independently halogen, —CX¹₃, —CHX¹₂, —CH₂X¹, or unsubstituted C₁-C₄ alkyl.

Embodiment P27. The compound of one of embodiments P1 to P4 or P13 to P26, wherein R³ is

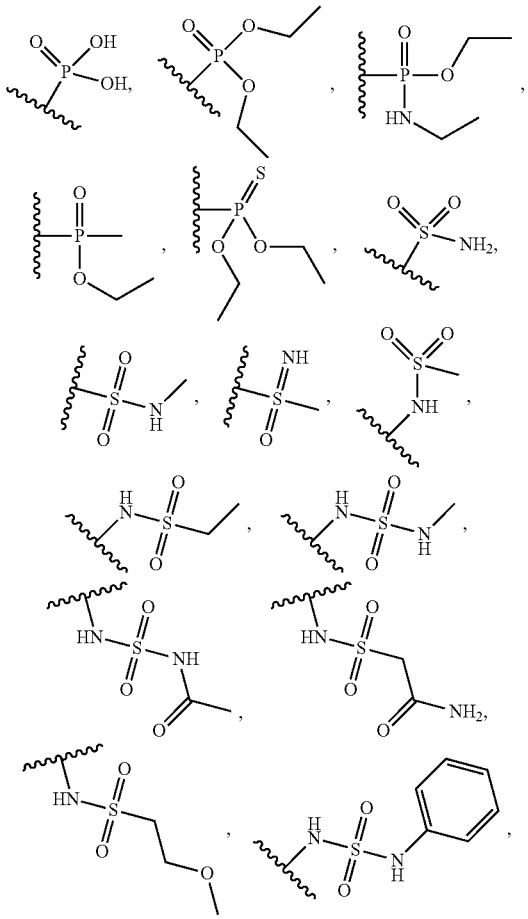

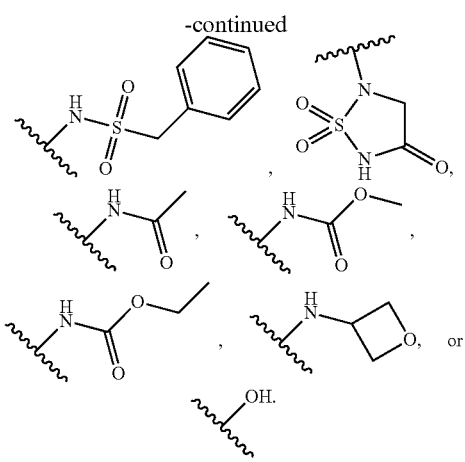
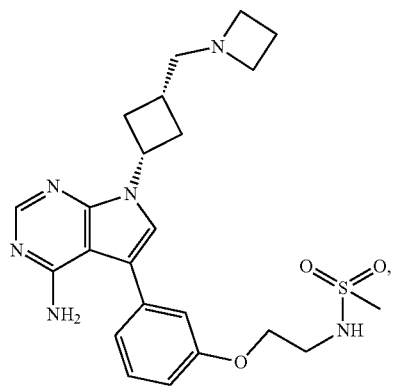
Embodiment P28. The compound of claim 1, having the formula:
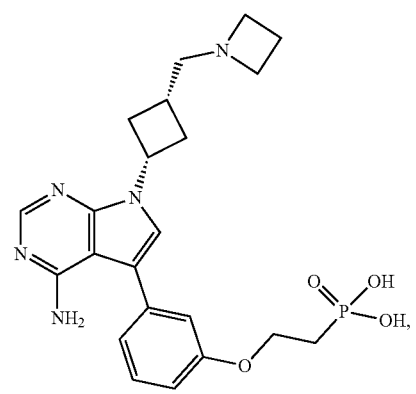
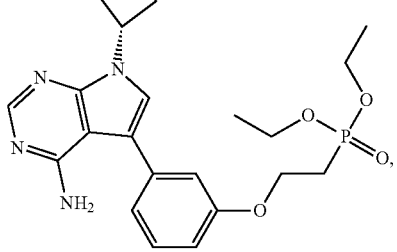
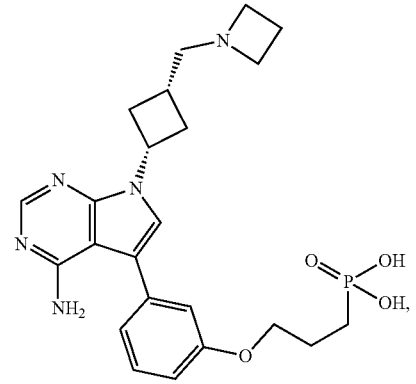
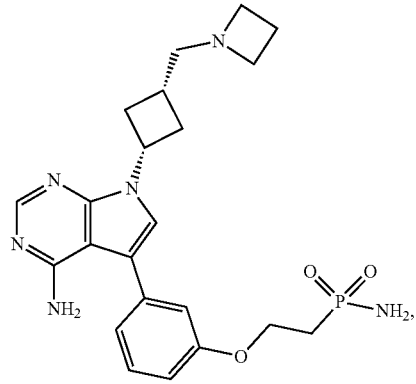
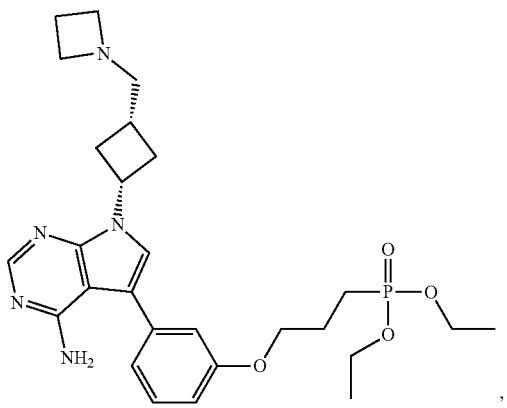

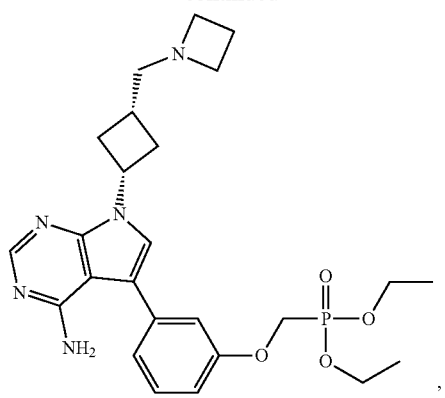,
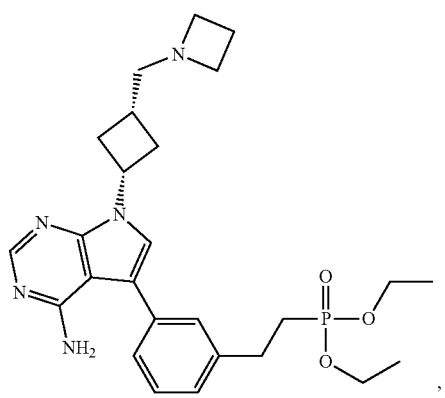,
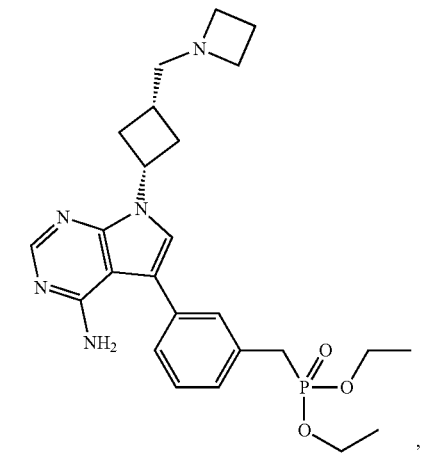,
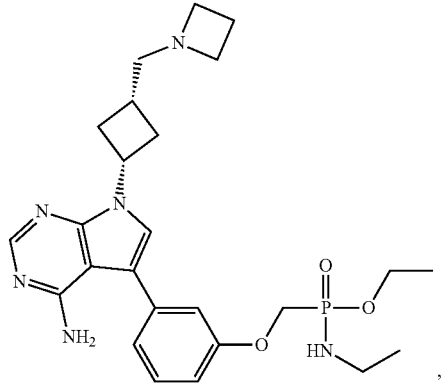,
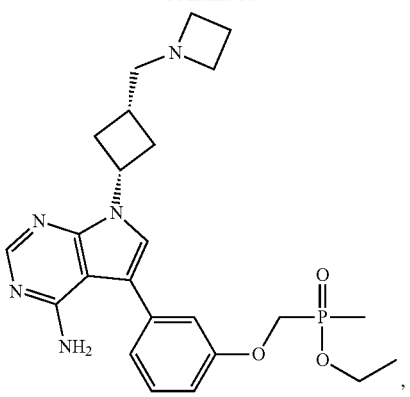,
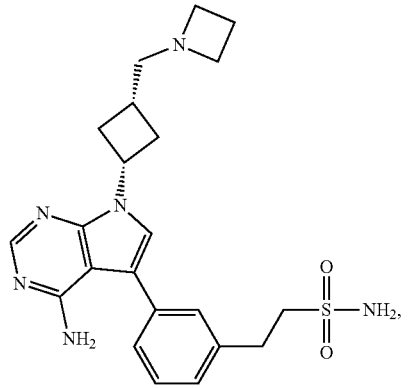,
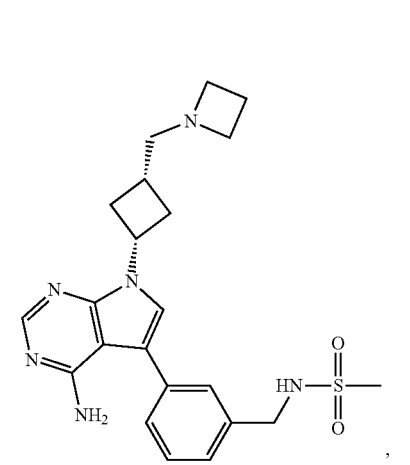,
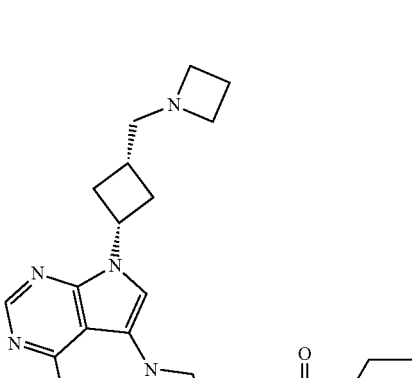, 355
-continued
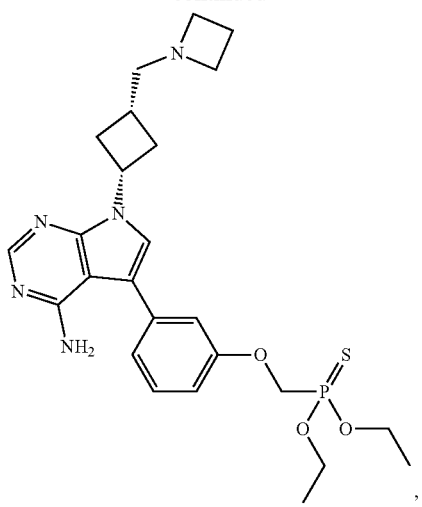
,
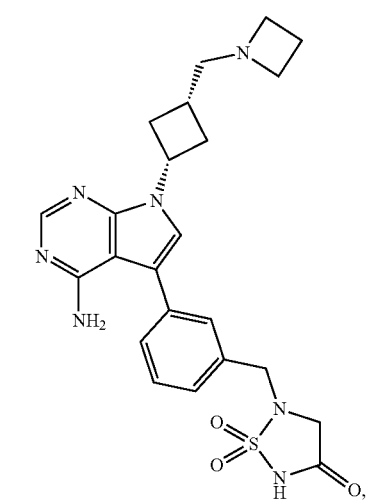
,
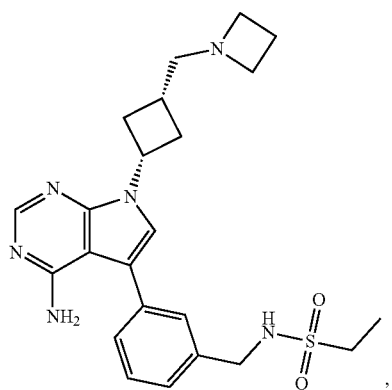
,
356
-continued
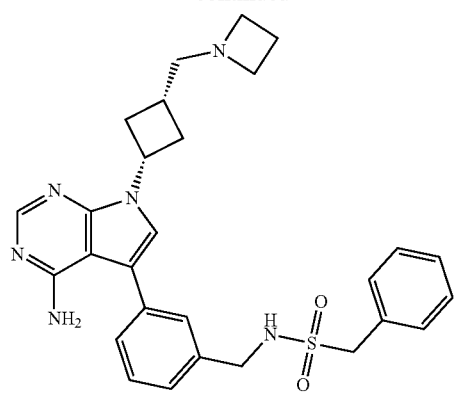
,
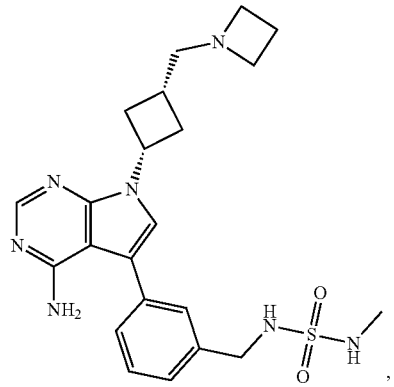
,
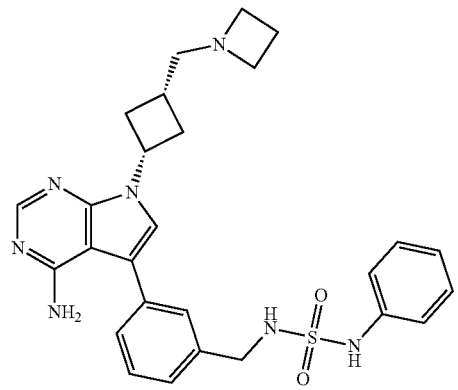
, 357
-continued
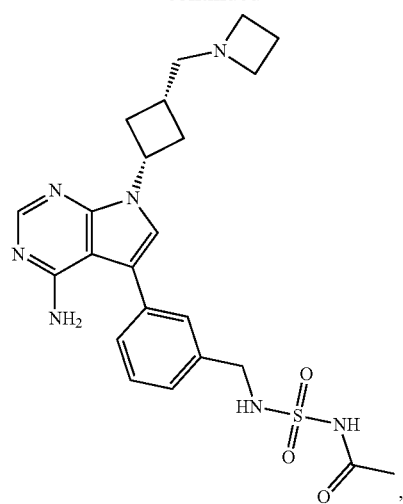
358
-continued
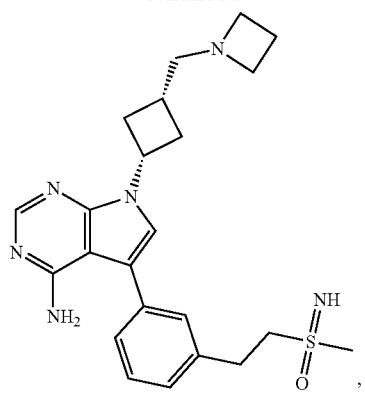
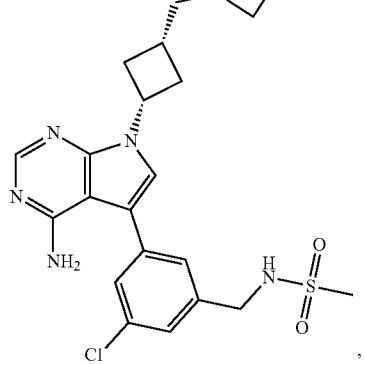
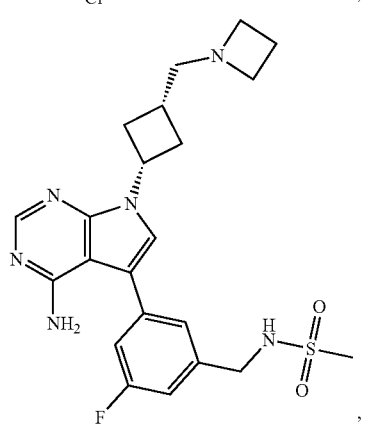
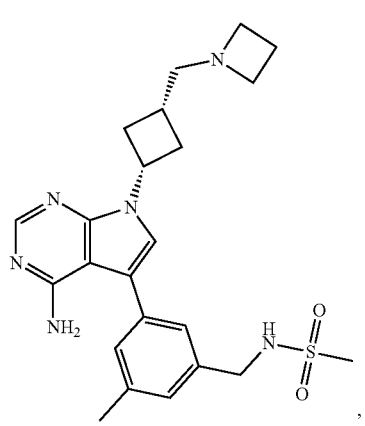

359
-continued
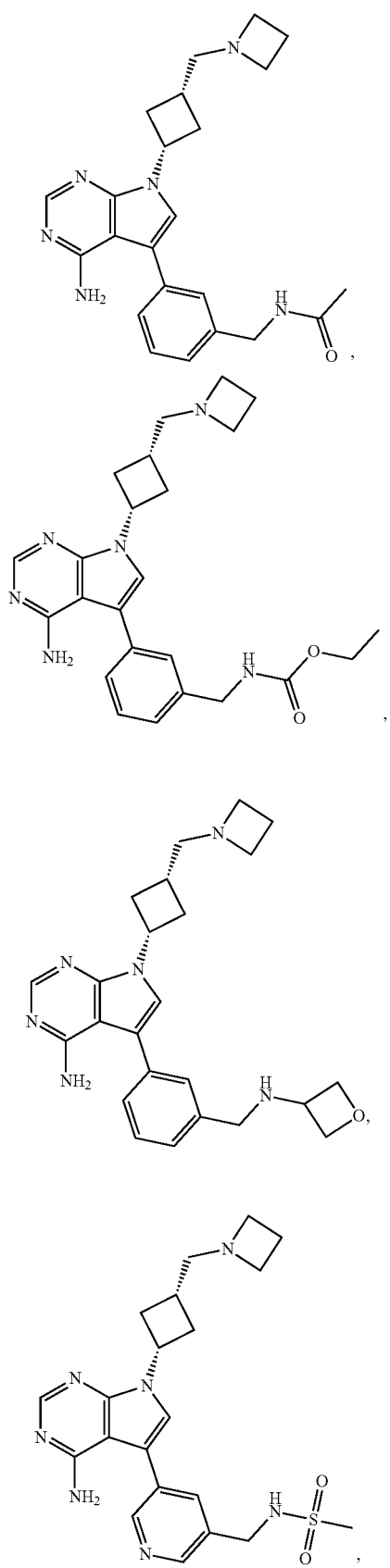
360
-continued
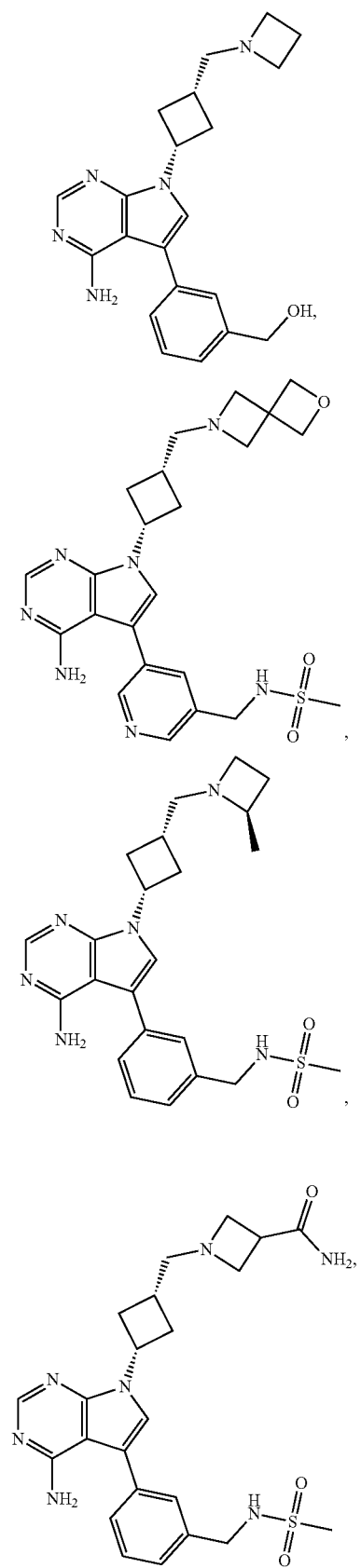

-continued
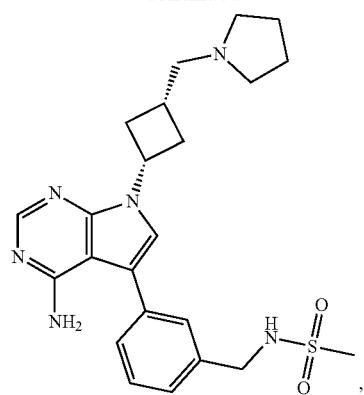
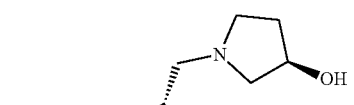
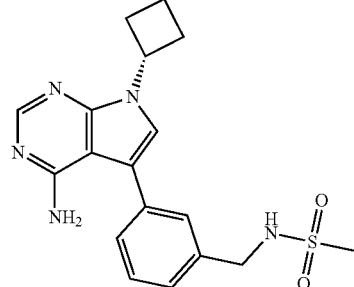
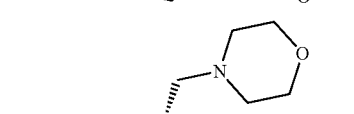
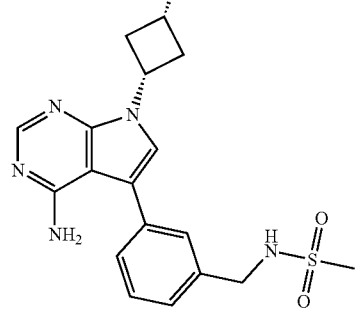
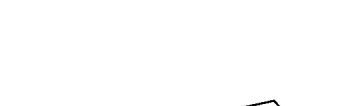
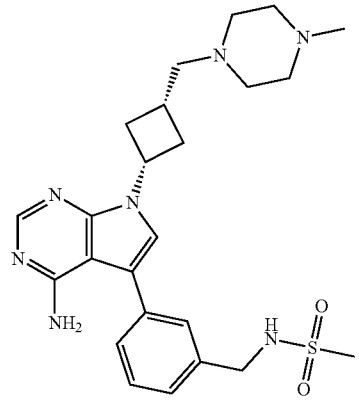
-continued
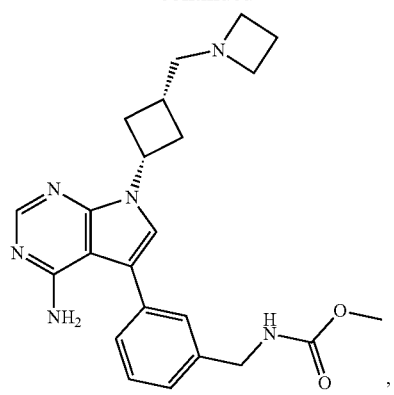
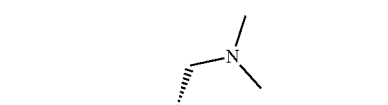
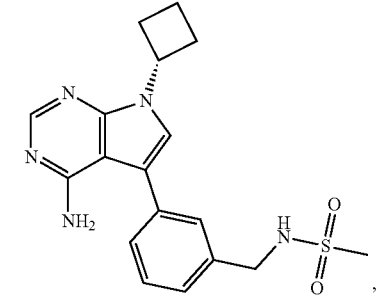
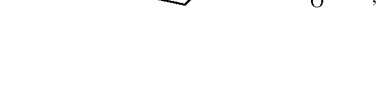
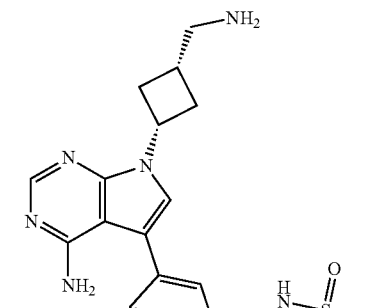
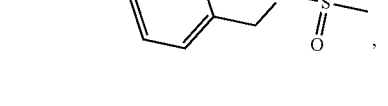
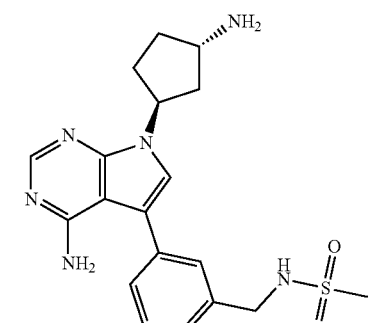

363
-continued

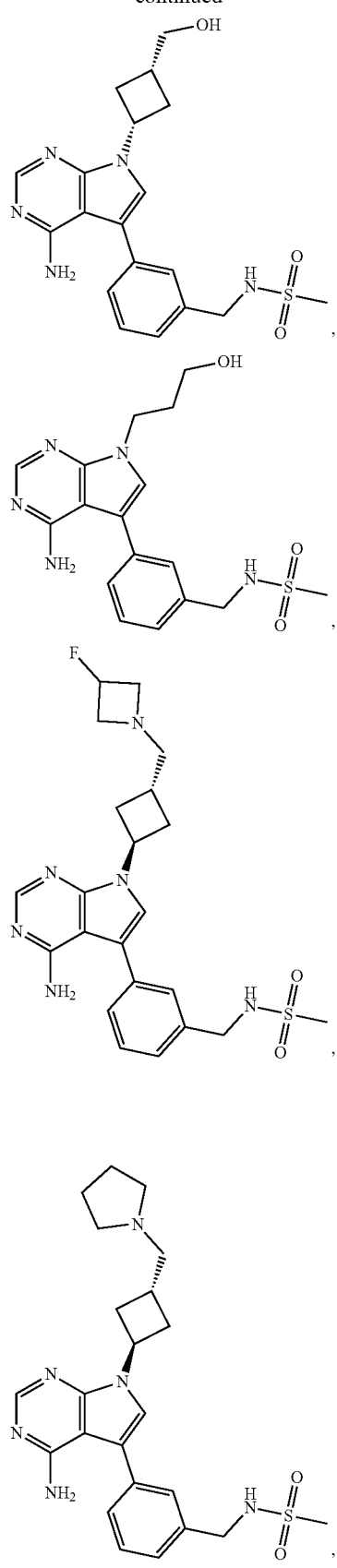

364
-continued

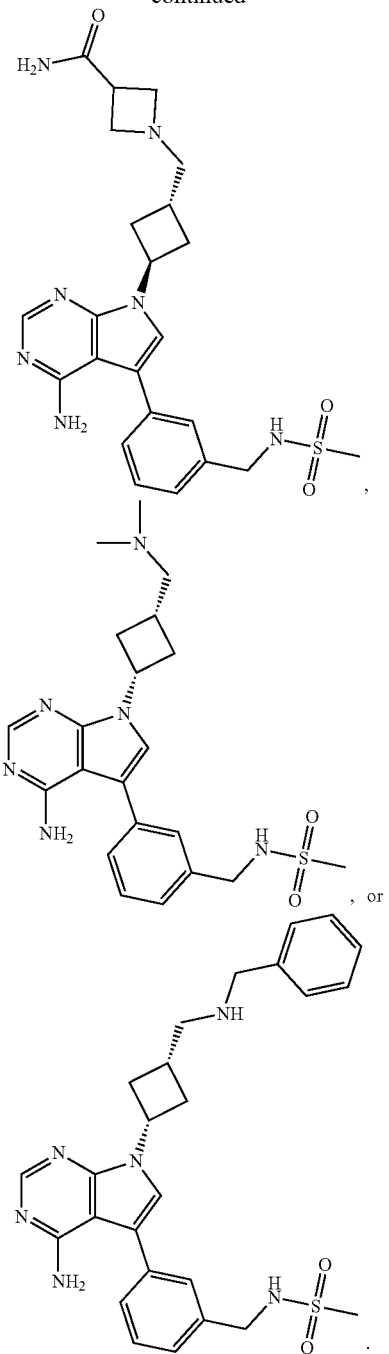

Embodiment P29. A pharmaceutical composition comprising the compound of any one of embodiments P1 to P28 and a pharmaceutically acceptable excipient.

Embodiment P30. A method of increasing the level of LKB1 activity in a subject, said method comprising administering a compound of one of embodiments P1 to P28 to said subject.

Embodiment P31. A method of increasing the level of LKB1 activity in a cell, said method comprising contacting said cell with a compound of one of embodiments P1 to P28.

Embodiment P32. The method of one of embodiments P30 to P31, wherein the compound contacts a STRAD protein.

Embodiment P33. A method of increasing the level of AMPK1, AMPK2, BRSK1, BRSK2, MARK1, MARK2, MARK3, MARK4, NUAK1, NUAK2, SIK1, SIK2, SIK3, SNRK, or TP53 activity in a subject, said method comprising administering a compound of one of embodiments P1 to P28 to said subject.

Embodiment P34. A method of decreasing the level of mTOR or cAMP-regulated transcriptional coactivator 2 (CRTC2) activity in a subject, said method comprising administering a compound of one of embodiments P1 to P28 to said subject.

Embodiment P35. A method of increasing the level of Hippo pathway activity in a subject, said method comprising administering a compound of one of embodiments P1 to P28 to said subject.

Embodiment P36. A method of increasing the level of fatty acid oxidation activity in a subject, said method comprising administering a compound of one of embodiments P1 to P28 to said subject.

Embodiment P37. The method of one of embodiments P33 to P36, comprising increasing the level of LKB1 activity in said subject.

Embodiment P38. A method of increasing the level of AMPK1, AMPK2, BRSK1, BRSK2, MARK1, MARK2, MARK3, MARK4, NUAK1, NUAK2, SIK1, SIK2, SIK3, SNRK, or TP53 activity in a cell, said method comprising contacting said cell with a compound of one of embodiments P1 to P28.

Embodiment P39. A method of decreasing the level of mTOR or cAMP-regulated transcriptional coactivator 2 (CRTC2) activity in a cell, said method comprising contacting said cell with a compound of one of embodiments P1 to P28.

Embodiment P40. A method of increasing the level of Hippo pathway activity in a cell, said method comprising contacting said cell with a compound of one of embodiments P1 to P28.

Embodiment P41. A method of increasing the level of fatty acid oxidation activity in a cell, said method comprising contacting said cell with a compound of one of embodiments P1 to P28.

Embodiment P42. The method of one of embodiments P38 to P41, comprising increasing the level of LKB1 activity in said cell.

Embodiment P43. The method of one of embodiments P33 to P42, wherein the compound contacts a STRAD protein.

Embodiment P44. A method of treating a cancer in a subject in need thereof, said method comprising administering to the subject in need thereof an effective amount of a compound of one of embodiments P1 to P28.

Embodiment P45. The method of embodiment P44, wherein the cancer has a RAS/MAPK pathway mutation or a PIK3CA mutation.

Embodiment P46. The method of embodiment P44, wherein the cancer is pancreatic cancer, lung cancer, uterine cancer, renal cancer, colon cancer, soft tissue sarcoma, or a squamous cell cancer.

Embodiment P47. The method of one of embodiments P44 to P46, further comprising co-administering an anti-cancer agent to said subject in need.

Embodiment P48. The method of embodiment P47, wherein the anti-cancer agent is a KRAS inhibitor, ERK inhibitor, MK inhibitor, BRAF inhibitor, PIK3CA inhibitor mTOR inhibitor, PD1 inhibitor, PDL1 inhibitor, or CTLA4 inhibitor.

Embodiment P49. A method of treating diabetes in a subject in need thereof, said method comprising administering to the subject in need thereof an effective amount of a compound of one of embodiments P1 to P28.

Embodiment P50. The method of embodiment P49, comprising reducing the level of blood glucose in said subject in need.

Embodiment P51. The method of embodiment P49, comprising reducing the level of insulin resistance in said subject in need.

Embodiment P52. The method of one of embodiments P49 to P51, further comprising co-administering diabetes therapeutic agent to said subject in need.

Embodiment P53. The method of embodiment P52, wherein the diabetes therapeutic agent is a biguanide, sulfonylurea, meglitinide, thiazolidinedione, alpha-glucosidase inhibitor, incretin, GLP-1 analogue, DPP-4 inhibitor, insulin, GLP-1 receptor agonist, amylin agonist, or insulin analogue.

Embodiment P54. A method of treating a cancer in a subject in need thereof, said method comprising administering to the subject in need thereof an effective amount of a pseudo-kinase STRADα stabilizing compound, wherein said pseudo-kinase STRADα stabilizing compound binds pseudo-kinase STRADα within the pseudo-kinase STRADα ATP binding pocket and contacts an amino acid within said pseudo-kinase STRADα ATP binding pocket corresponding to Lys 197, His 200, Arg 215, Lys 77, or Arg 100.

Embodiment P55. A method of treating diabetes in a subject in need thereof, said method comprising administering to the subject in need thereof an effective amount of a pseudo-kinase STRADα stabilizing compound, wherein said pseudo-kinase STRADα stabilizing compound binds pseudo-kinase STRADα within the pseudo-kinase STRADα ATP binding pocket and contacts an amino acid within said pseudo-kinase STRADα ATP binding pocket corresponding to Lys 197, His 200, Arg 215, Lys 77, or Arg 100.

Embodiment P56. The method of one of embodiments P54 to P55, wherein said pseudo-kinase STRADα stabilizing compound contacts amino acids within said pseudo-kinase STRADα ATP binding pocket corresponding to Lys 197, His 200, Arg 215, Lys 77, and Arg 100.

Embodiment P57. The method of one of embodiments P54 to P56, wherein said pseudo-kinase STRADα stabilizing compound increases LKB1-STRADα-Mo25 trimer complex association.

Embodiment P58. The method of one of embodiments P54 to P57, wherein said pseudo-kinase STRADα stabilizing compound increases the rate of phosphorylation by LKB1.

Embodiment P59. The method of one of embodiments P54 to P58, wherein said pseudo-kinase STRADα stabilizing compound maintains biologically relevant downstream signaling for greater than 24 hours upon onetime pseudo-kinase STRADα stabilizing compound exposure.

Embodiment P60. The method of one of embodiments P54 to P59, wherein said pseudo-kinase STRADα stabilizing compound induces desirable effects on pCRTC2, pS6, and/or pLATS.

Embodiment P61. The method of one of claims 62 to 68, wherein said pseudo-kinase STRADα stabilizing compound selectively binds STRADα relative to LKB1, or relative to other kinases.

VII. Further Embodiments

Embodiment F1. A compound having the formula:

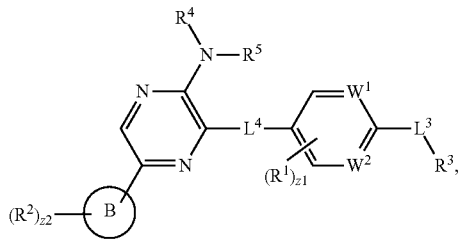
(I)

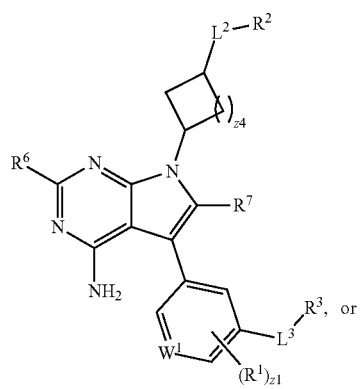
(II)

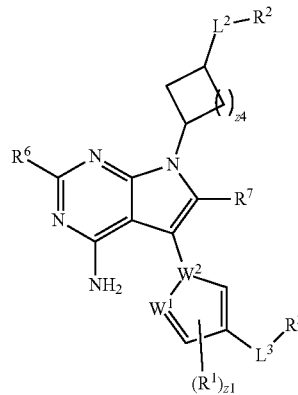
(III)

wherein, $W^1$ is N, CH, or $CR^1$;

$W^2$ is N, CH, or $CR^1$;

$R^1$ is independently halogen, $—CX^1{_3}$, $—CHX^1{_2}$, $—CH_2X^1$, $—OCX^1{_3}$, $—OCH_2X^1$, $—OCHX^1{_2}$, $—CN$, $—SO_{n1}R^{1D}$, $—SO_{v1}NR^{1A}R^{1B}$, $—NR^{1C}NR^{1A}R^{1B}$, $—ONR^{1A}R^{1B}$, $—NHC(O)NR^{1C}NR^{1A}R^{1B}$, $—NHC(O)NR^{1A}R^{1B}$, $N(O)_{m1}$, $—NR^{1A}R^{1B}$, $—C(O)R^{1C}$, $—C(O)—OR^{1C}$, $—C(O)NR^{1A}R^{1B}$, $—OR^{1D}$, $—NR^{1A}SO_2R^{1D}$, $—NR^{1A}C(O)R^{1C}$, $—NR^{1A}C(O)OR^{1C}$, $—NR^{1A}OR^{1C}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 4;

Ring B is aryl or heteroaryl;

$L^2$ is a bond, $—NH—$, $—O—$, $—S—$, $—C(O)—$, $—C(O)NH—$, $—NHC(O)—$, $—NHC(O)NH—$, $—C(O)O—$, $—OC(O)—$, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

$R^2$ is independently oxo, halogen, $—CX^2{_3}$, $—CHX^2{_2}$, $—CH_2X^2$, $—OCX^2{_3}$, $—OCH_2X^2$, $—OCHX^2{_2}$, $—CN$, $—SO_{n2}R^{2D}$, $—SO_{v2}NR^{2A}R^{2B}$, $—NR^{2C}NR^{2A}R^{2B}$, $—ONR^{2A}R^{2B}$, $—NHC(O)NR^{2C}NR^{2A}R^{2B}$, $—NHC(O)NR^{2A}R^{2B}$, $—N(O)_{m2}$, $—NR^{2A}R^{2B}$, $—C(O)R^{2C}$, $—C(O)—OR^{2C}$, $—C(O)NR^{2A}R^{2B}$, $—OR^{2D}$, $—NR^{2A}SO_2R^{2D}$, $—NR^{2A}C(O)R^{2C}$, $—NR^{2A}C(O)OR^{2C}$, $—NR^{2A}OR^{2C}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

z2 is an integer from 0 to 6;

$L^3$ is a bond, $—NH—$, $—O—$, $—C(O)—$, $—C(O)NH—$, $—NHC(O)—$, $—NHC(O)NH—$, $—C(O)O—$, $—OC(O)—$, substituted or unsubstituted alkylene, or substituted or unsubstituted heteroalkylene;

$R^3$ is independently a polar moiety;

$L^4$ is $—C(O)NH—$ or $—NHC(O)—$;

$R^4$ and $R^5$ are independently hydrogen, $—CCl_3$, $—CBr_3$, $—CF_3$, $—CI_3$, $CHCl_2$, $—CHBr_2$, $—CHF_2$, $—CHI_2$, $—CH_2Cl$, $—CH_2Br$, $—CH_2F$, $—CH_2I$, $—CN$, $—OH$, $—NH_2$, $—COOH$, $—CONH_2$, $—OCCl_3$, $—OCF_3$, $—OCBr_3$, $—OCI_3$, $—OCHCl_2$, $—OCHBr_2$, $—OCHI_2$, $—OCHF_2$, $—OCH_2Cl$, $—OCH_2Br$, $—OCH_2I$, $—OCH_2F$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ and $R^5$ substituents bonded to the same nitrogen may optionally be joined to form a substituted or unsubstituted heterocycloalkyl or substituted or unsubstituted heteroaryl;

$R^6$ is independently hydrogen, halogen, $—CX^6{_3}$, $—CHX^6{_2}$, $—CH_2X^6$, $—OCX^6{_3}$, $OCH_2X^6$, $—OCHX^6{_2}$, $—CN$, $—SO_{n6}H$, $—SO_{v6}NH_2$, $—NHNH_2$, $—ONH_2$, $—NHC(O)NHNH_2$, $—NHC(O)NH_2$, $—N(O)_{m6}$, $—NH_2$, $—C(O)H$, $—COOH$, $—C(O)NH_2$, $—OH$, $—NHSO_2H$, $—NHC(O)H$, $—NHC(O)OH$, $—NHOH$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^7$ is independently hydrogen, halogen, $—CX^7{_3}$, $—CHX^7{_2}$, $—CH_2X^7$, $—OCX^7{_3}$, $—OCH_2X^7$, $—OCHX^7{_2}$, $—CN$, $—SO_{n7}H$, $—SO_{v7}NH$, $—NHNH_2$, $—ONH_2$, $—NHC(O)NHNH_2$, $—NHC(O)NH_2$, $—N(O)_{m1}$, $—NH_2$, $—C(O)H$, $—COOH$, $—C(O)NH_2$, $—OH$, $—NHSO_2H$, $—NHC(O)H$, $—NHC(O)OH$, $—NHOH$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$, $R^{1B}$, $R^{1C}$, $R^{1D}$, $R^{2A}$, $R^{2B}$, $R^{2C}$, and $R^{2D}$ are independently hydrogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl;

z4 is 1 or 2;

$X^1$, $X^2$, $X^6$, and $X^7$ are independently —F, —Cl, —Br, or —I;

n1, n2, n6, and n7 are independently an integer from 0 to 4; and m1, m2, v1, v2, m6, v6, m7, and v7 are independently 1 or 2.

Embodiment F2. The compound of embodiment F1, having the formula:

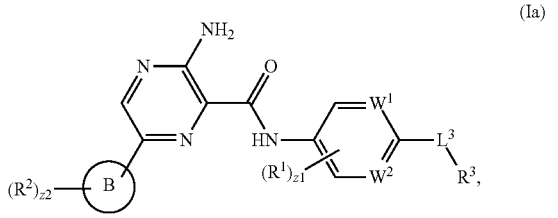

(Ia)

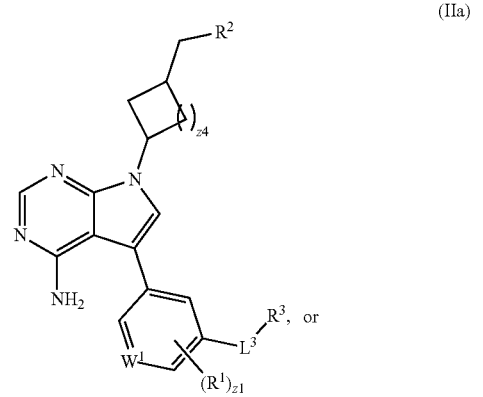

(IIa)

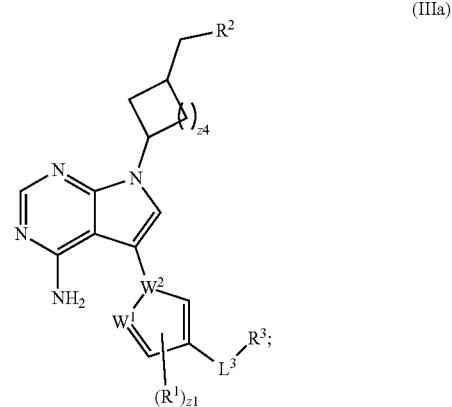

(IIIa)

wherein, $R^1$ is independently halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NR$^{1C}$NR$^{1A}$R$^{1B}$, —ONR$^{1A}$R$^{1B}$, —NHC(O)NR$^{1C}$NR$^{1A}$R$^{1B}$, —NHC(O)NR$^{1A}$R$^{1B}$, N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^A$OR$^{1C}$, —N$_3$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted C$_6$-C$_{10}$ aryl, or substituted or unsubstituted 5 to 10 membered heteroaryl; two adjacent R$^1$ substituents may optionally be joined to form a substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl;

Ring B is phenyl or 5 to 10 membered heteroaryl;

$R^2$ is independently oxo, halogen, —CX$^2_3$, —CHX$^2_2$, —CH$_2$X$^2$, —OCX$^2_3$, —OCH$_2$X$^2$, —OCHX$^2_2$, —CN, —SO$_{n2}$R$^{2D}$, —SO$_{v2}$NR$^{2A}$R$^{2B}$, —NR$^{2C}$NR$^{2A}$R$^{2B}$, —ONR$^{2A}$R$^{2B}$, —NHC(O)NR$^{2C}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO$_2$R$^{2D}$, —NR$^{2A}$C(O)R$^{2C}$, —NR$^{2A}$C(O)OR$^{2C}$, —NR$^{2A}$OR$^{2C}$, —N$_3$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl; two adjacent R$^2$ substituents may optionally be joined to form a substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl; and L$^3$ is a bond, —NH—, —O—, —C(O)—, —C(O)NH—, —NHC(O)—, —NHC(O)NH—, —C(O)O—, —OC(O)—, substituted or unsubstituted C$_1$-C$_6$ alkylene, or substituted or unsubstituted 2 to 6 membered heteroalkylene.

Embodiment F3. The compound of one of embodiments F1 to F2, having the formula:

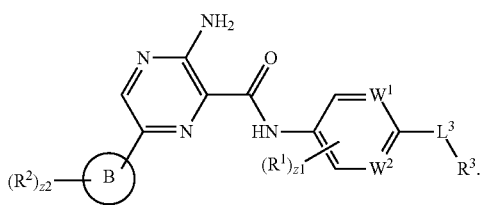

(Ia)

Embodiment F4. The compound of one of embodiments F1 to F3, wherein

R$^3$ is independently —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO$_2$R$^{3D}$, —NR$^{3C}$SO$_2$NR$^{3A}$R$^{3B}$, —NR$^{3A}$R$^{3B}$, —NR$^{3A}$C(O)R$^{3C}$, —NR$^{3A}$C(O)OR$^{3C}$, —SO$_2$R$^{3C}$, —SO$_2$-L$^{3A}$-R$^{3C}$, —SO$_2$NR$^{3A}$R$^{3B}$, —SO$_2$NR$^{3A}$SO$_2$R$^{3C}$, —SO$_2$NR$^{3A}$P(O)(OR$^{3C}$)(OR$^{3D}$), —SO$_2$P(O)(OR$^{3C}$)(OR$^{3D}$), —SO$_2$CH$_2$P(O)(OR$^{3C}$)(OR$^{3D}$), —SO$_2$P(O)(OR$^{3D}$)(NR$^{3A}$R$^{3B}$), —SO$_2$P(O)(R$^{3C}$)(OR$^{3D}$), —SO$_2$P(O)(R$^{3C}$)(R$^{3D}$), —SO$_2$-L$^{3A}$-P(O)(OR$^{3C}$)(OR$^{3D}$), —SO$_2$-L$^{3A}$-P(O)(OR$^{3D}$)(NR$^{3A}$R$^{3B}$), —SO$_2$-L$^{3A}$-P(O)(R$^{3}$)(OR$^{3D}$), —SO$_2$-L$^{3A}$-P(O)(R$^{3C}$)(R$^{3D}$), —S(O)(NR$^{3A}$)R$^{3C}$, —C(O)OR$^{3C}$, —C(O)NR$^{3A}$R$^{3B}$, or —NR$^{3A}$C(O)OR$^{3C}$;

L$^{3A}$ is independently —CH$_2$—, —CH(CH$_3$)—, —C(CH$_3$)$_2$—, —CH(X$^{3A}$)—, or —C(X$^{3A}$)$_2$—;

X$^{3A}$ is —F, —Cl, —Br, or —I; and

R$^{3A}$, R$^{3B}$, R$^{3C}$, and R$^{3D}$ are independently hydrogen, oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCl$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{3A}$ and R$^{3D}$ substituents may optionally be joined to form a substituted or unsubstituted heterocycloalkyl or substituted or unsubstituted heteroaryl.

Embodiment F5. The compound of one of embodiments F1 to F4, wherein R$^3$ is —SO$_2$-L$^{3A}$-R$^{3C}$ and R$^{3C}$ is independently —COOCH$_3$ or —COOCH$_2$CH$_3$.

Embodiment F6. The compound of one of embodiments F1 to F5, wherein R$^3$ is

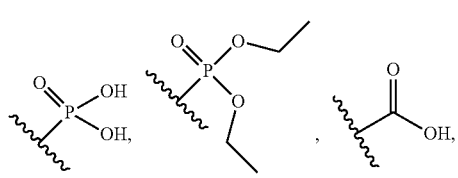

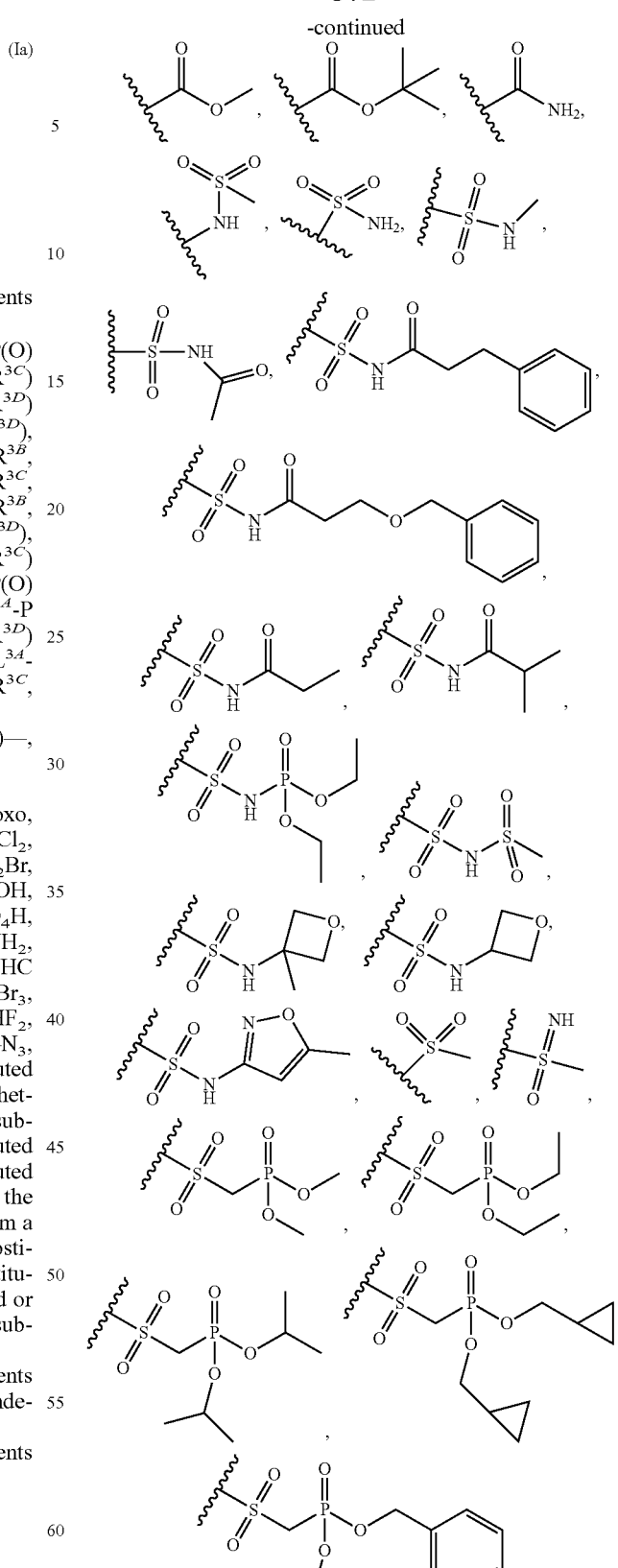

-continued

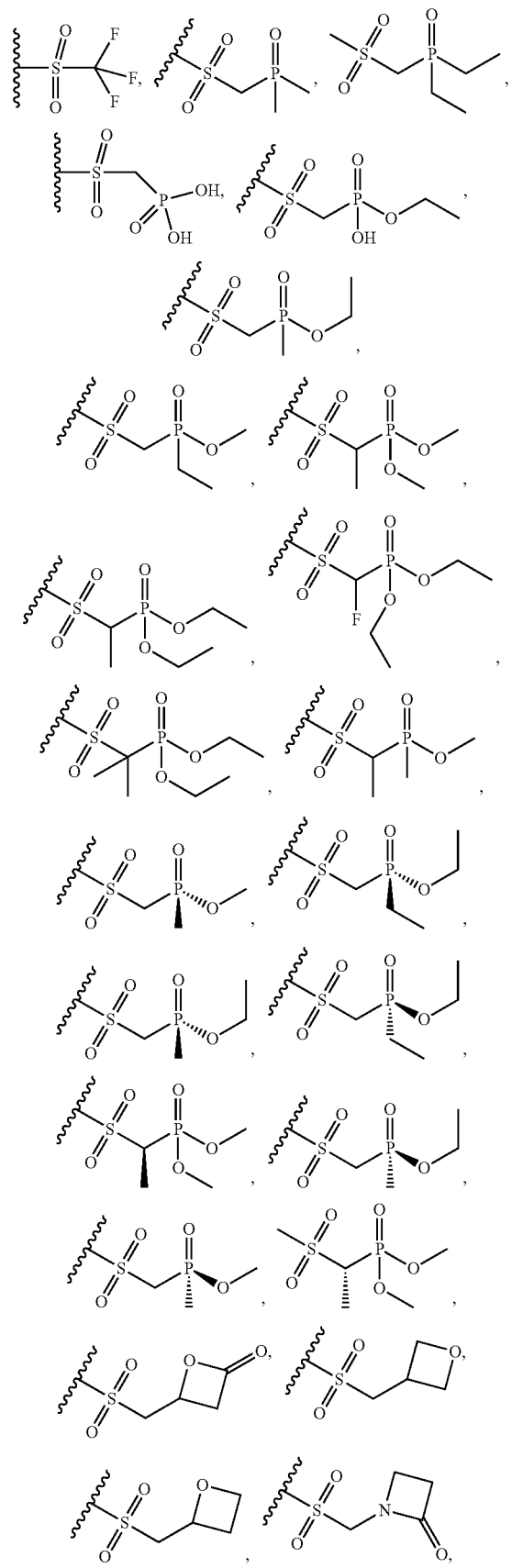

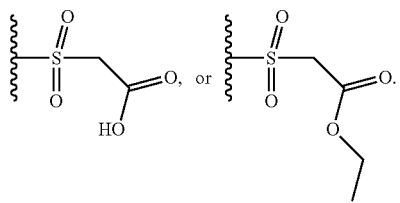

Embodiment F7. The compound of one of embodiments F1 to F6, wherein $L^3$ is a bond or —$CH_2$—.

Embodiment F8. The compound of one of embodiments F1 to F7, wherein Ring B is phenyl, thienyl, indazolyl, indolyl, pyrazolyl, pyrimidinyl, pyridyl, or benzothienyl.

Embodiment F9. The compound of one of embodiments F1 to F7, having the formula:

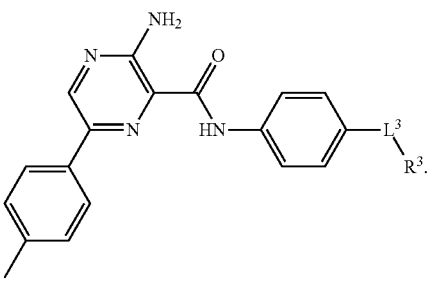

(Ib)

Embodiment F10. The compound of embodiment F1, having the formula:

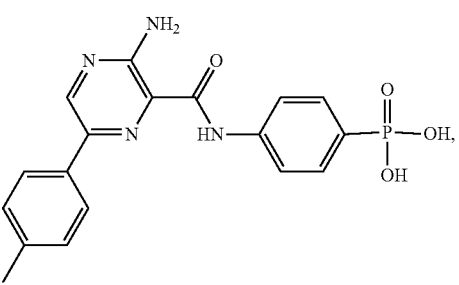

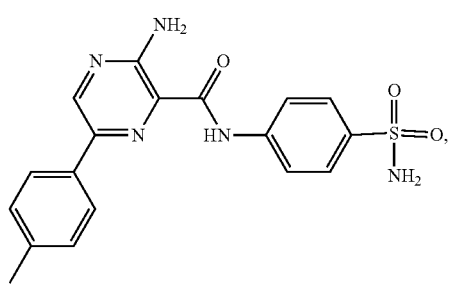

375
-continued
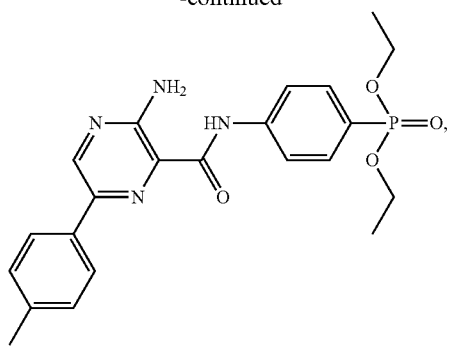
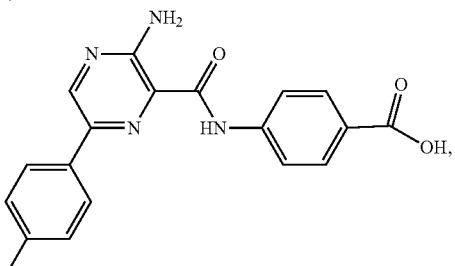
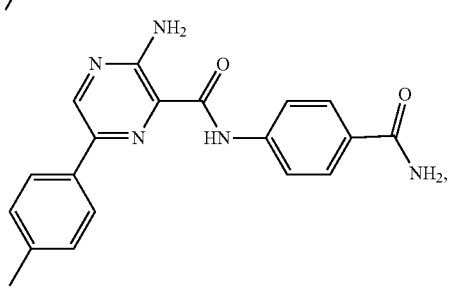
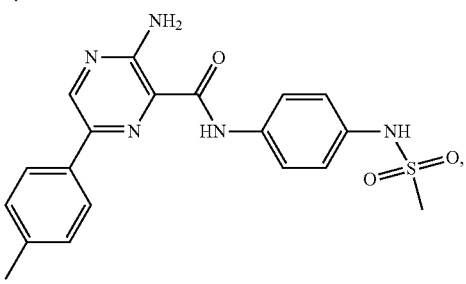
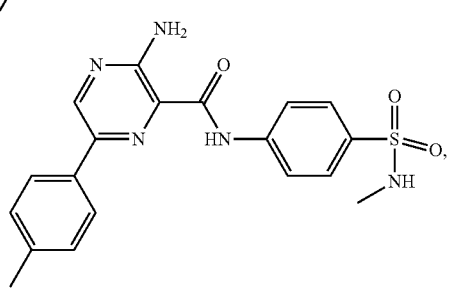
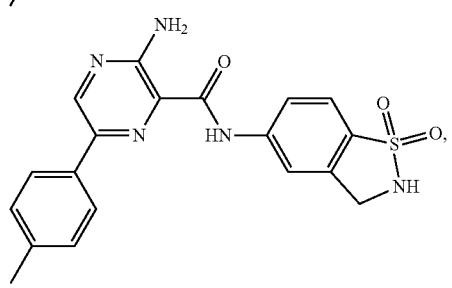
376
-continued
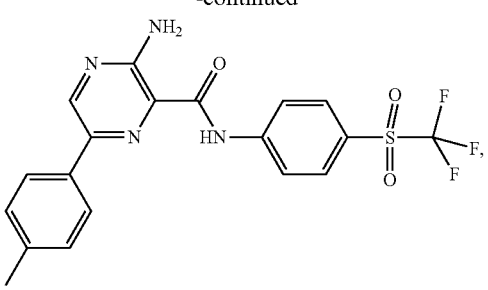
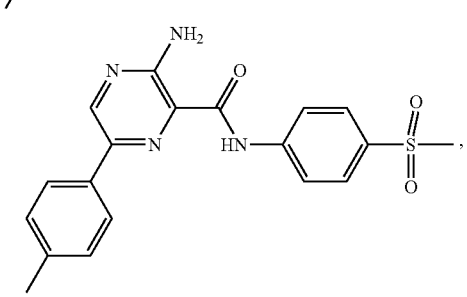
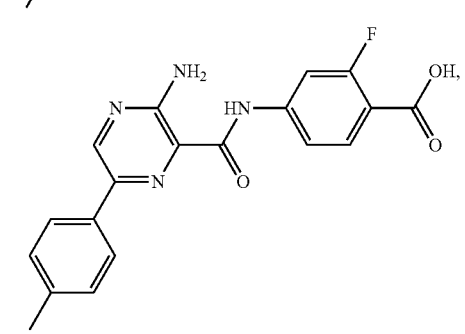
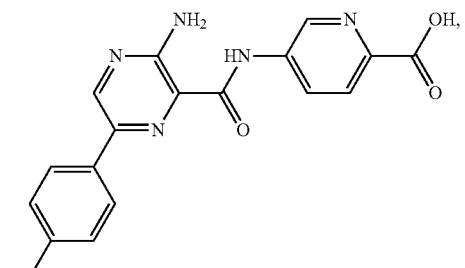
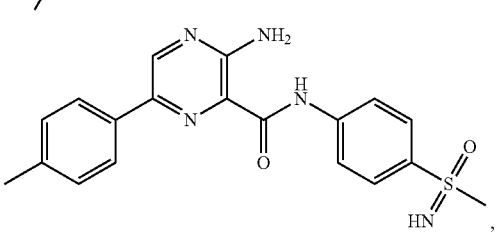
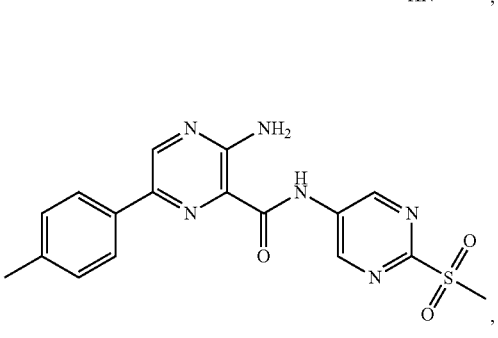

377
-continued
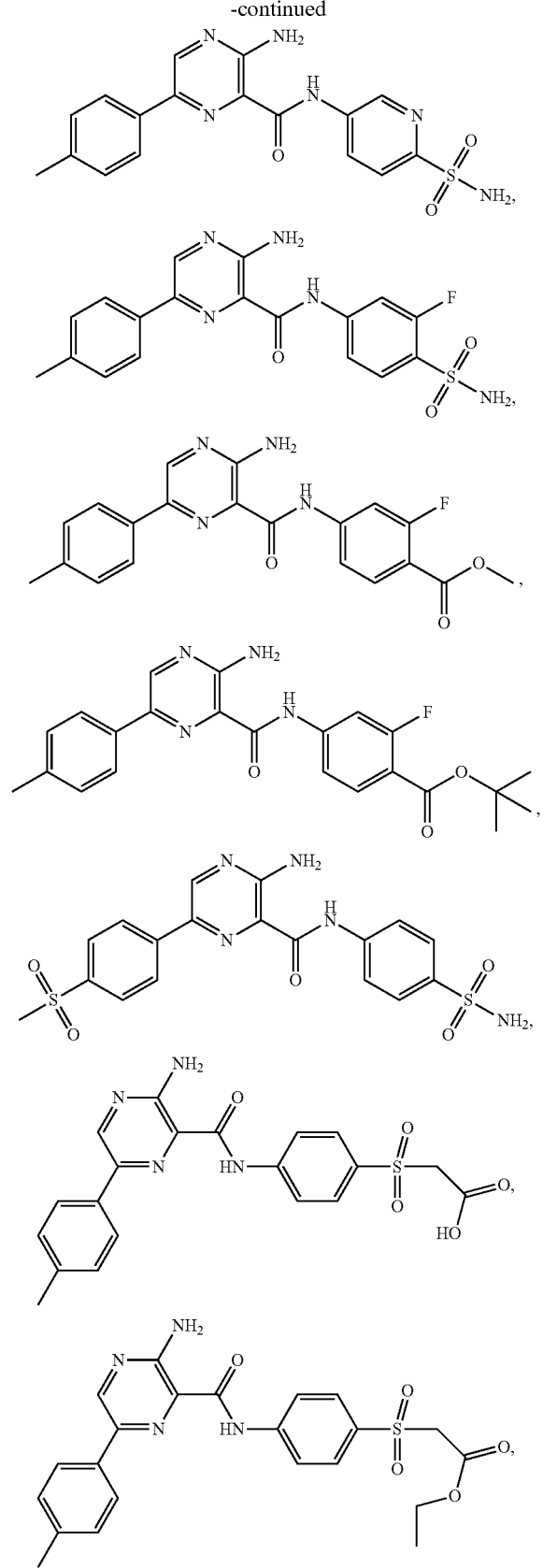
378
-continued
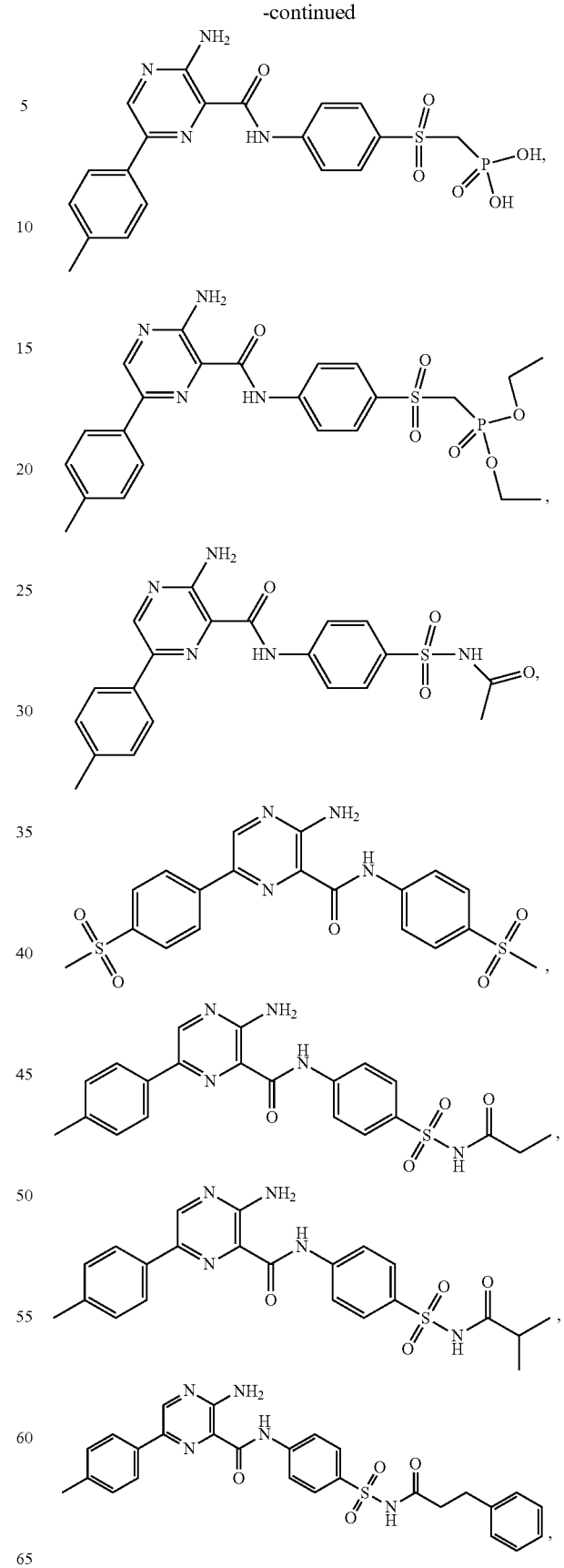

-continued
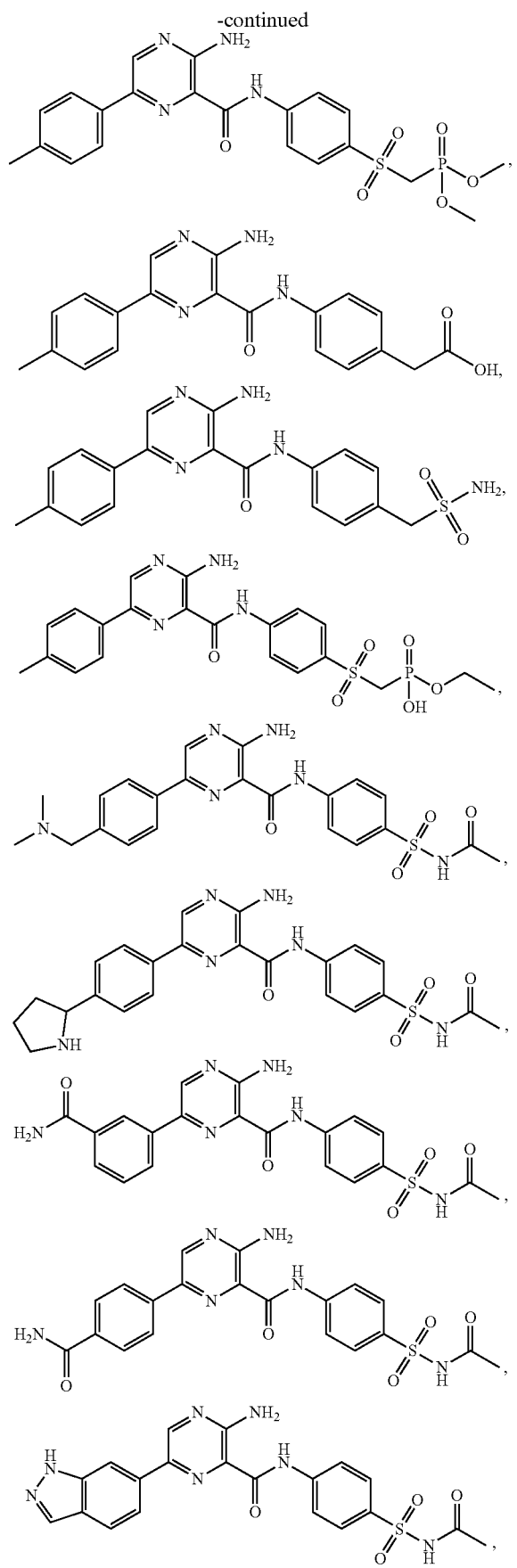
-continued
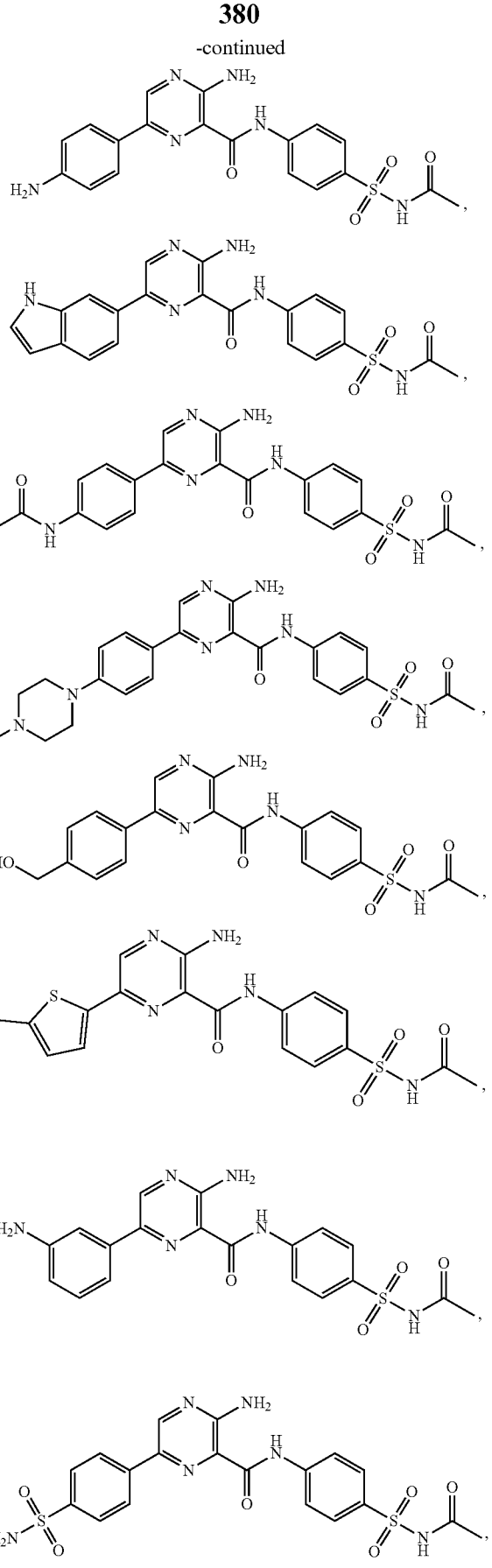

381
-continued
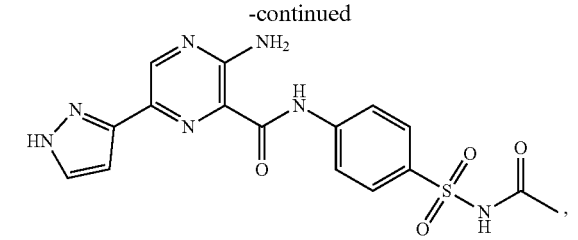
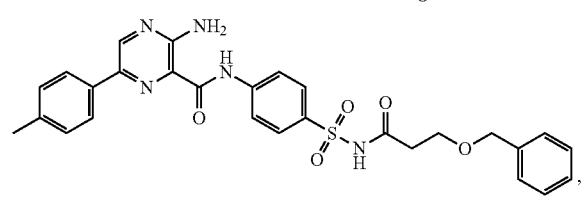
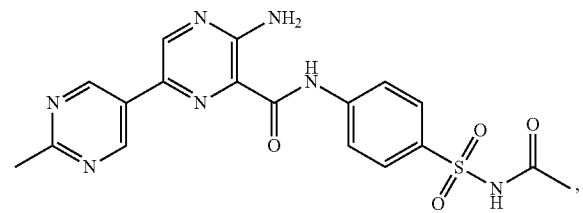
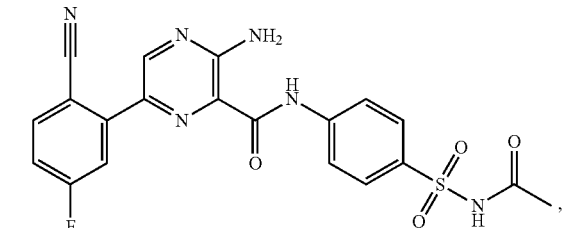
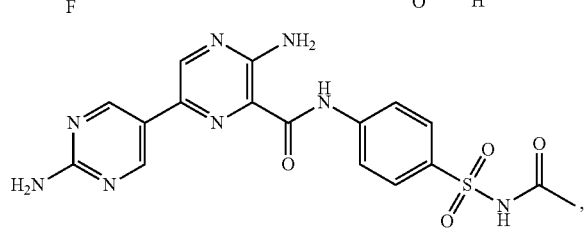
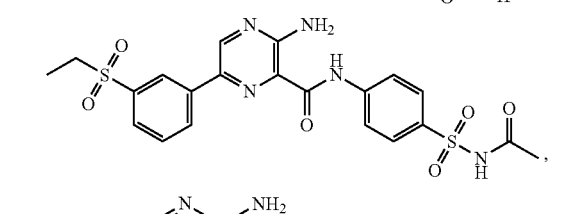
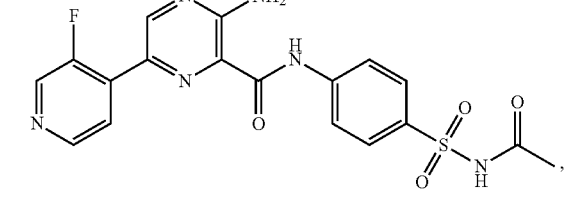
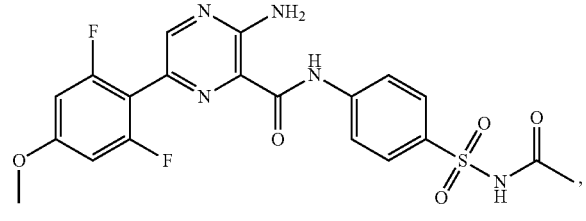
382
-continued
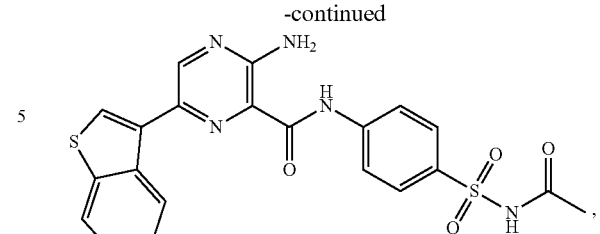
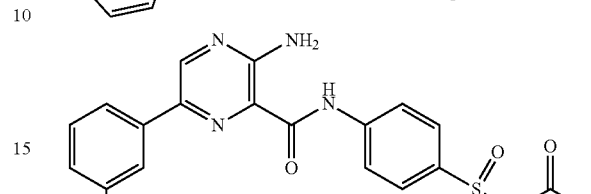
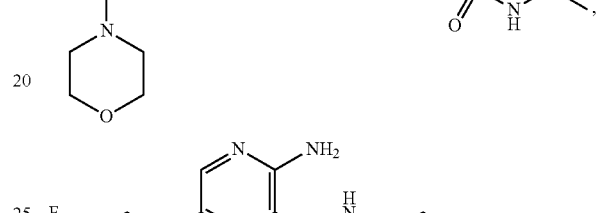
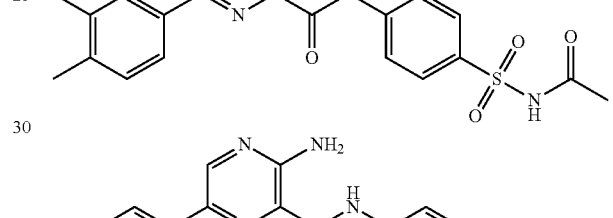
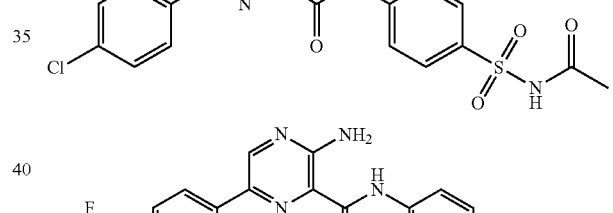
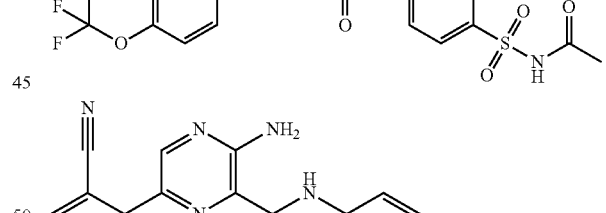
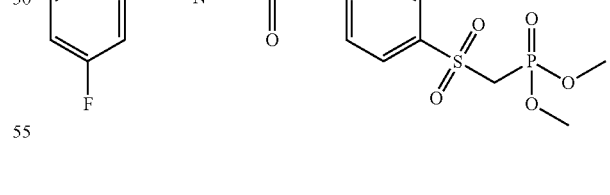
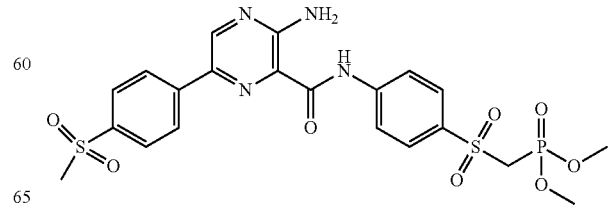

383
-continued
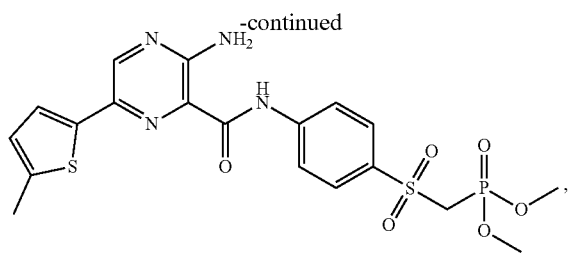
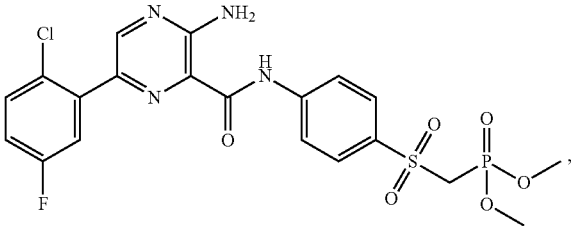
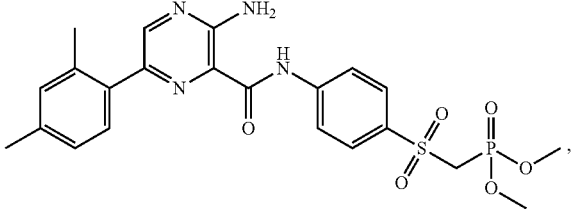

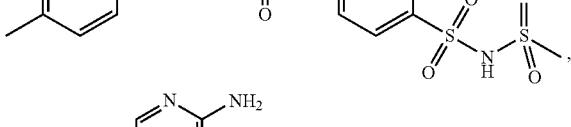
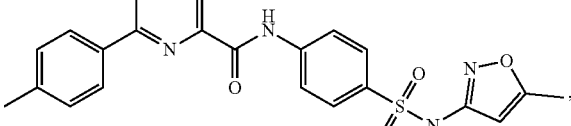

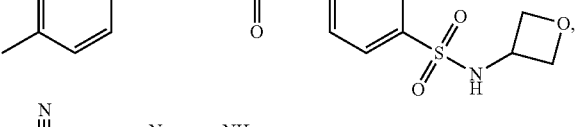
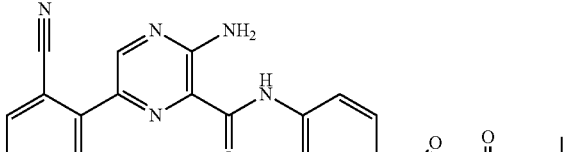
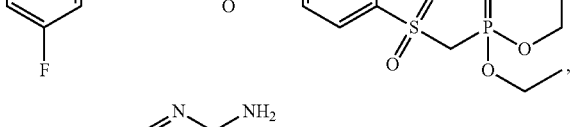
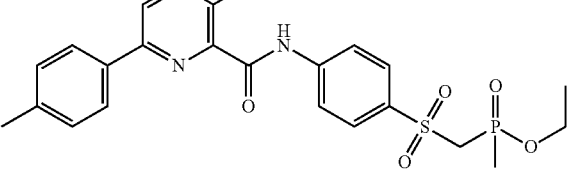
384
-continued
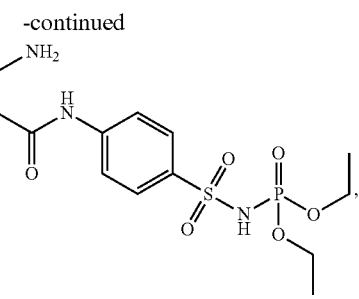
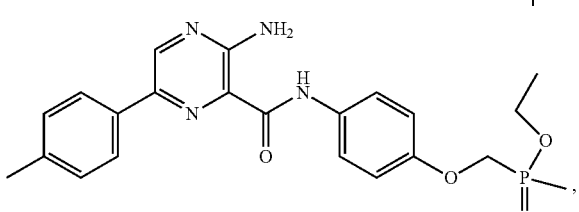
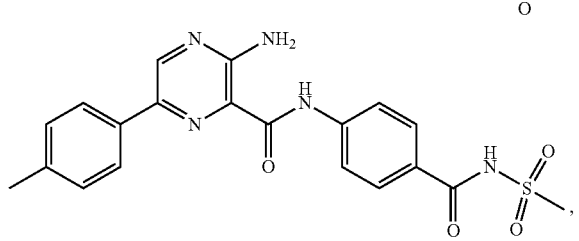
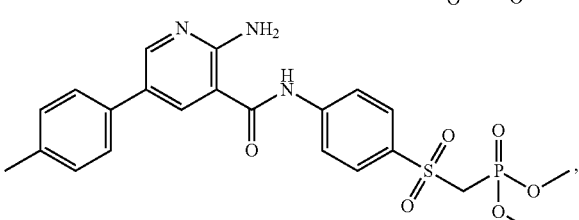
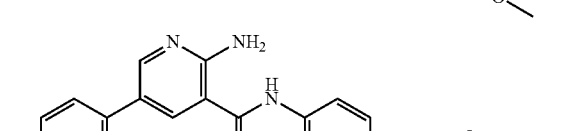
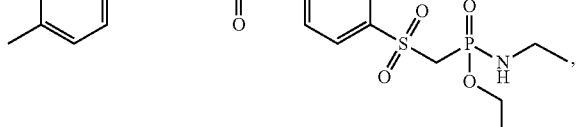
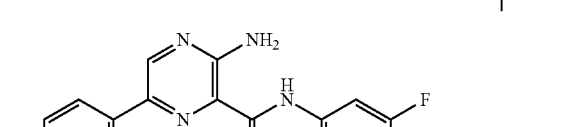
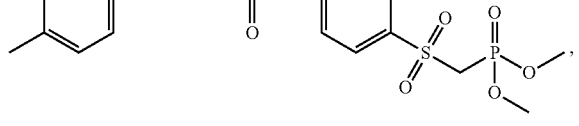
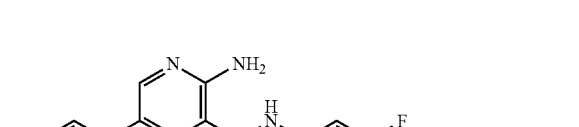
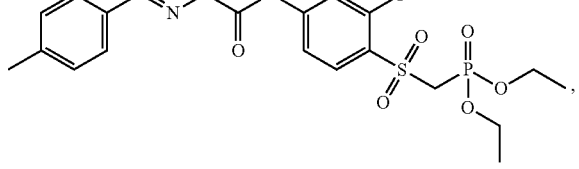

385
-continued
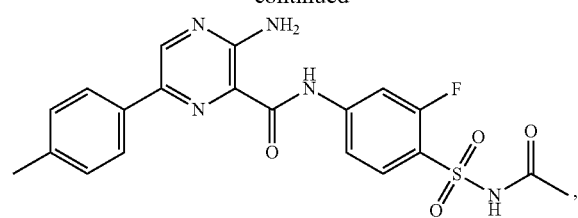
386
-continued
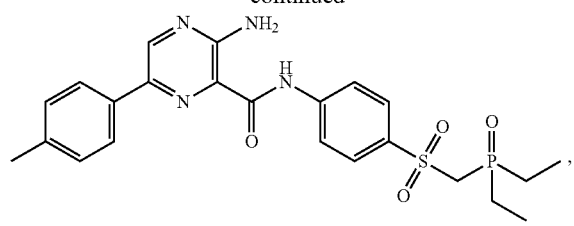

387
-continued
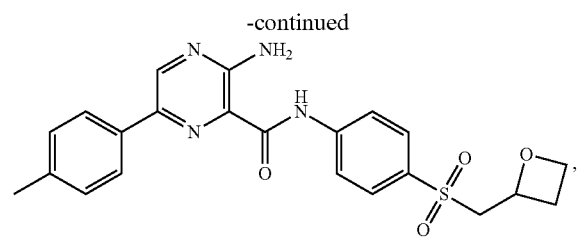
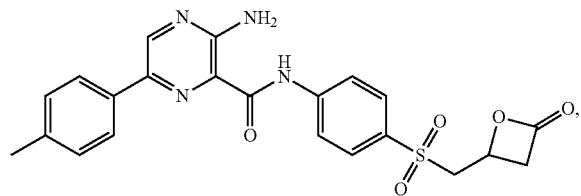
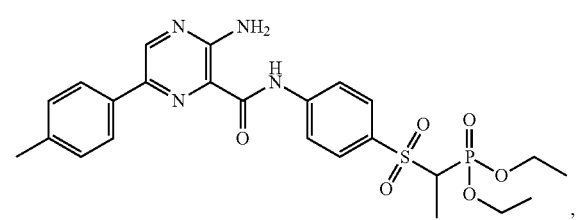
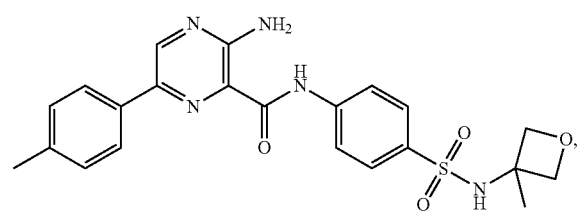
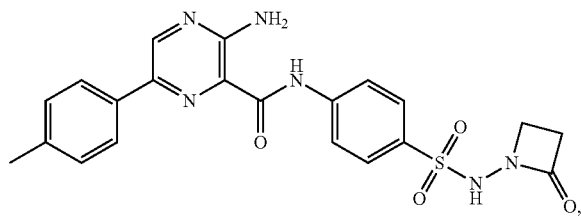
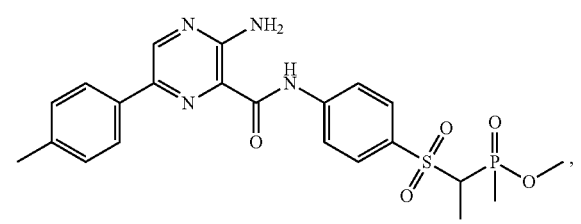
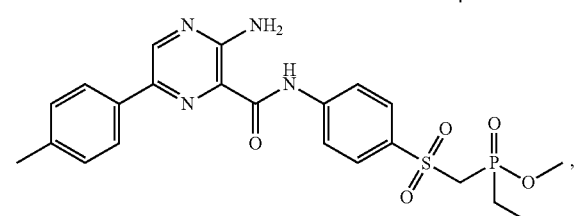
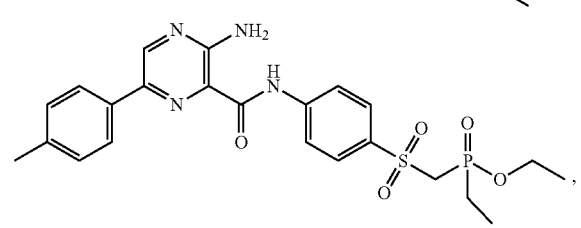
388
-continued
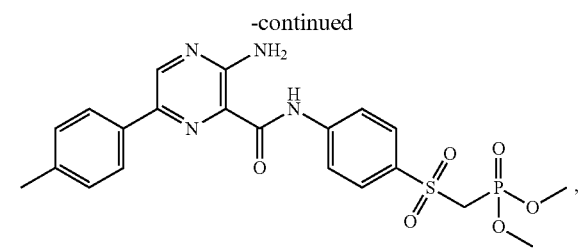
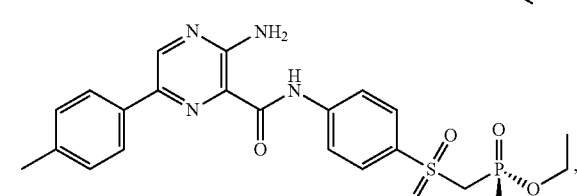
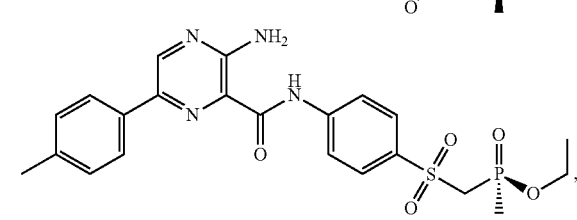
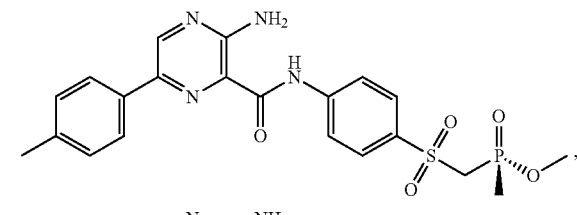
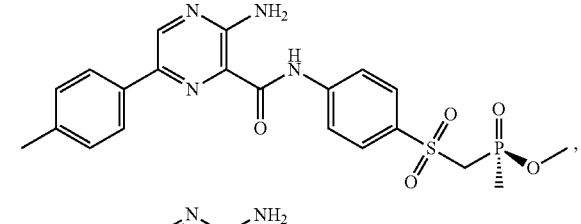
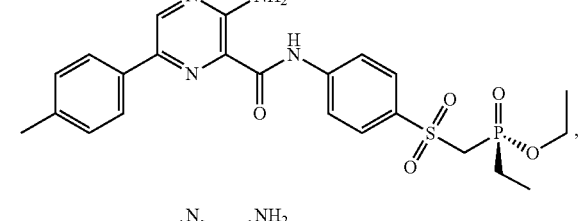
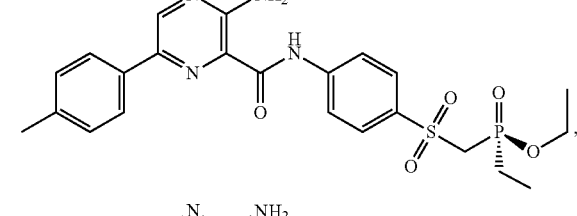
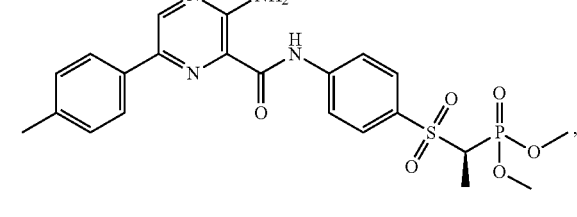

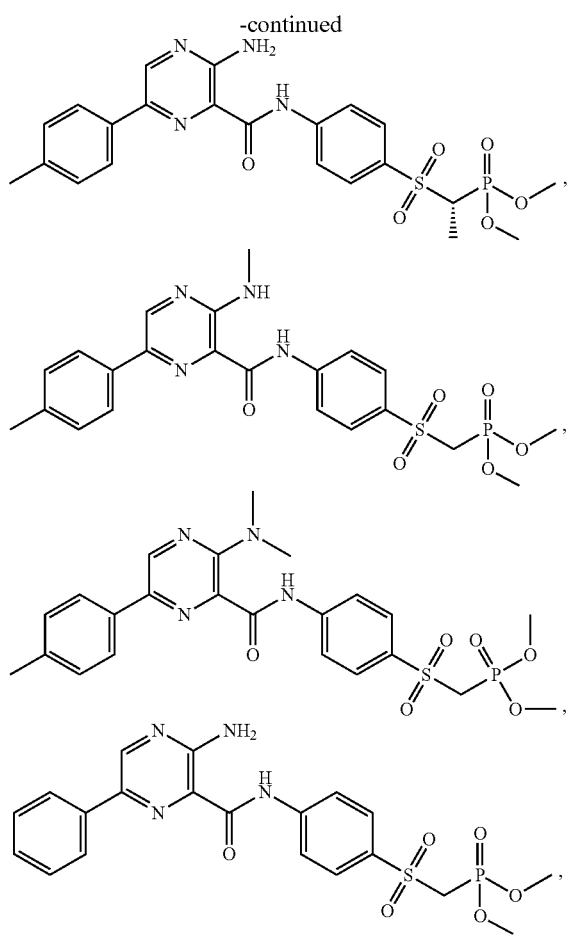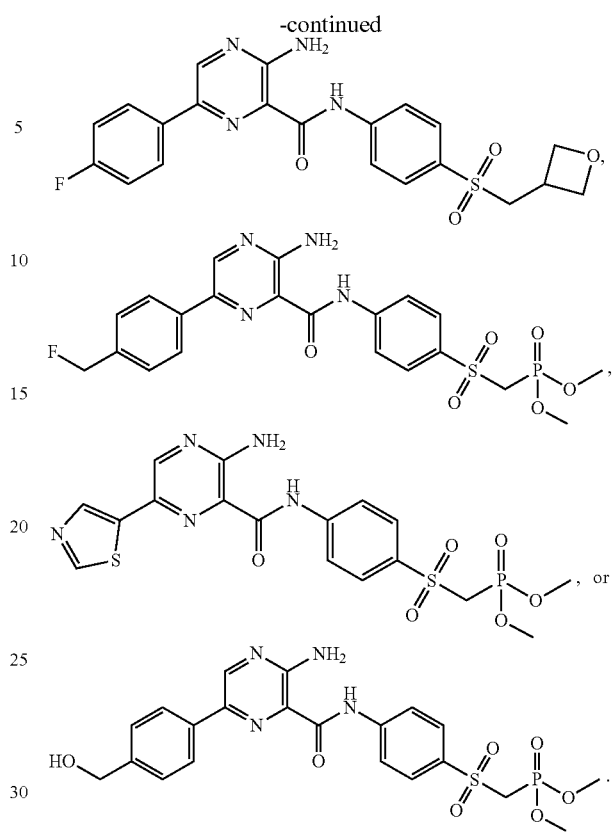
Embodiment F11. The compound of embodiment F1, having the formula:
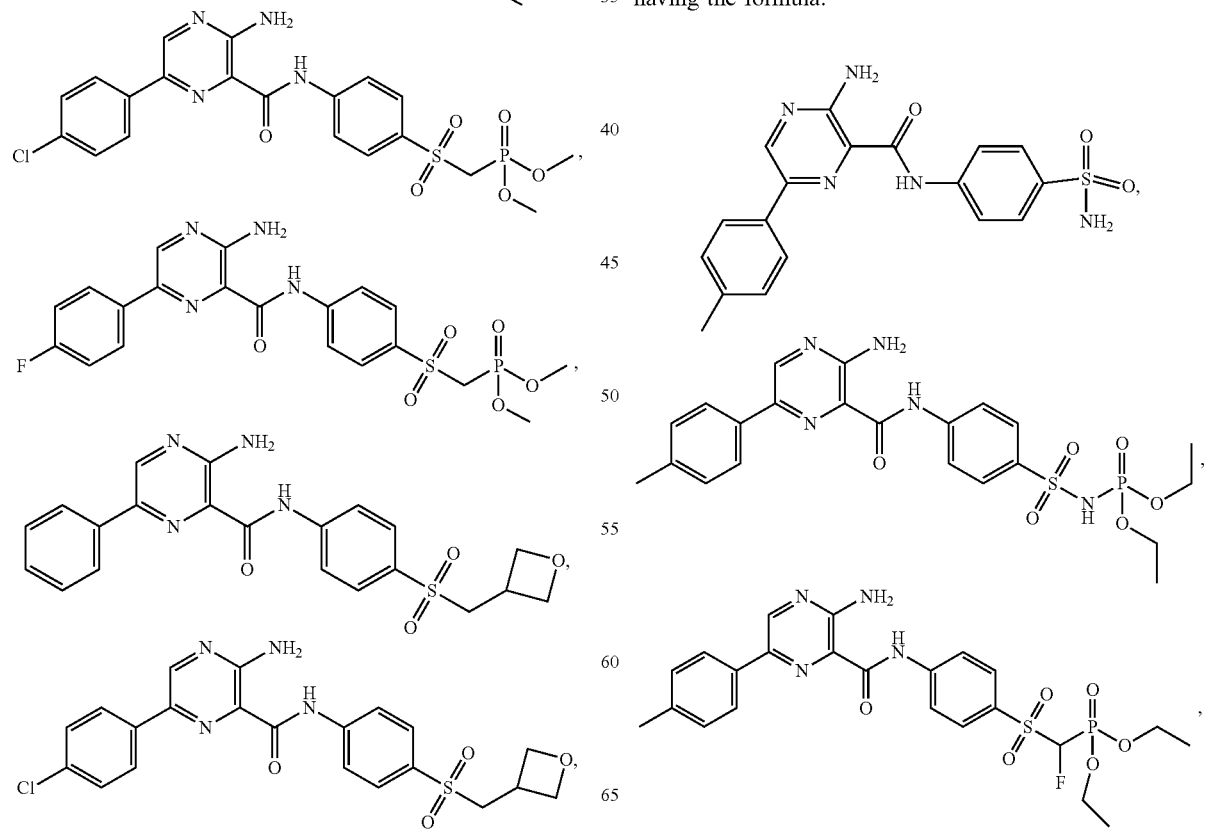

391
-continued
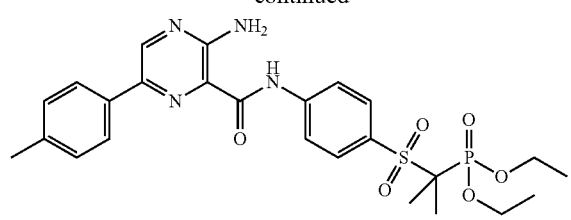
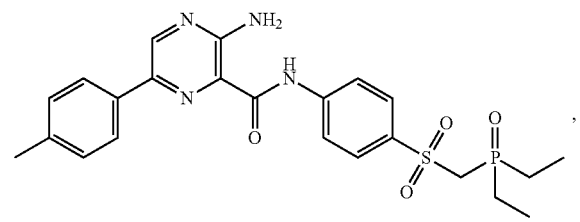
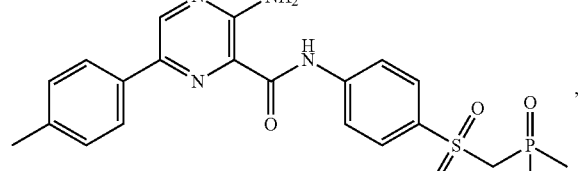
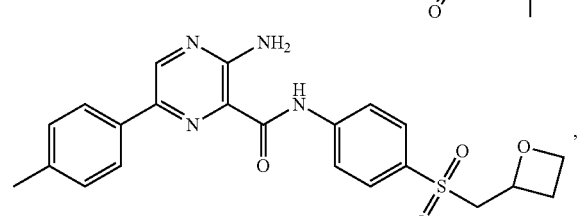
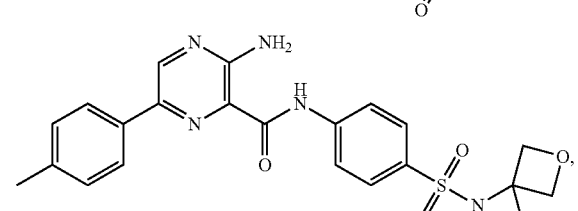
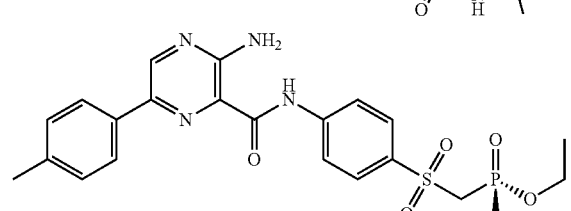
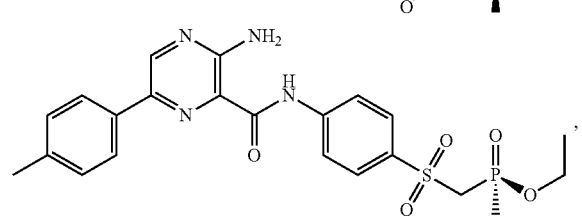
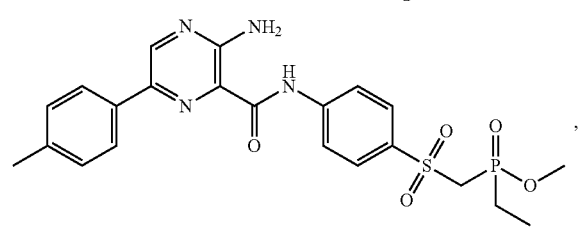
392
-continued
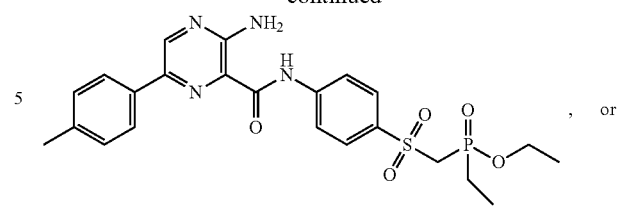, or
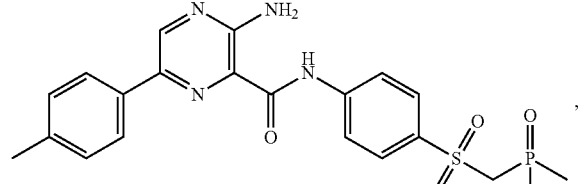
Embodiment F12. The compound of embodiment F1, having the formula:
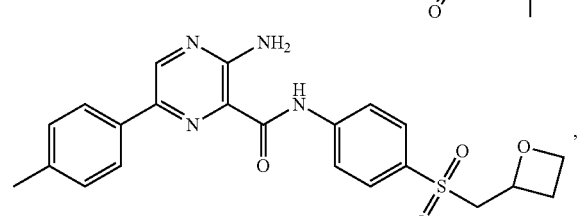
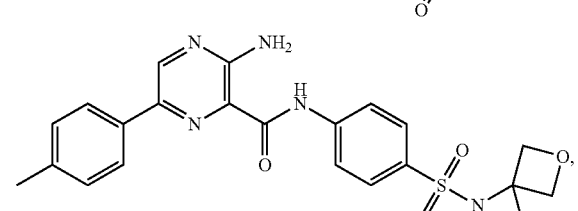
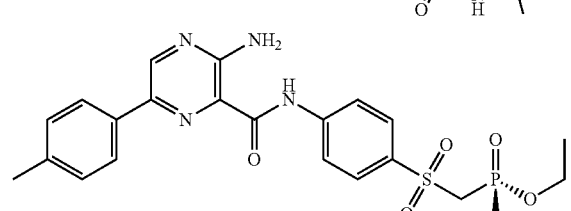,
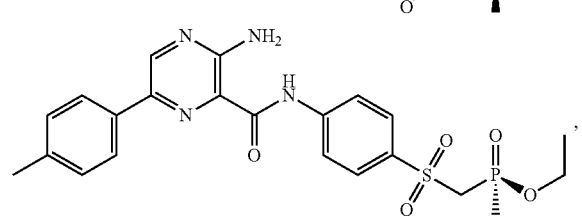
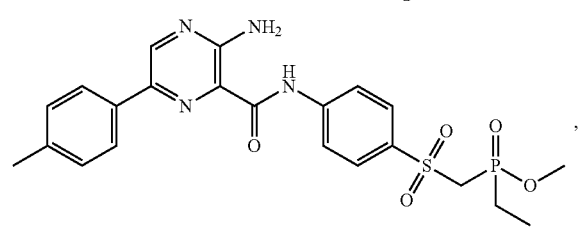,

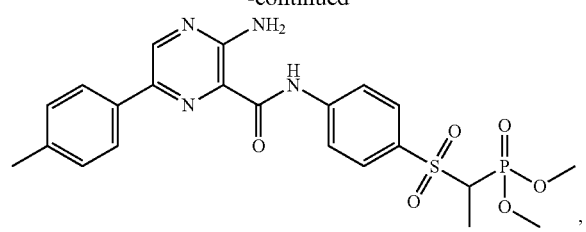
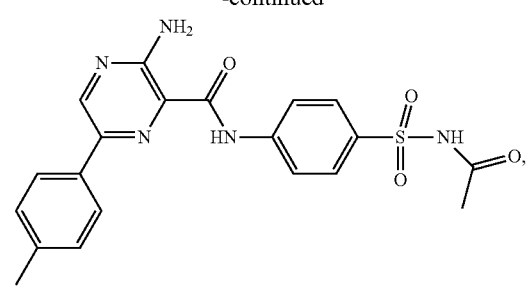
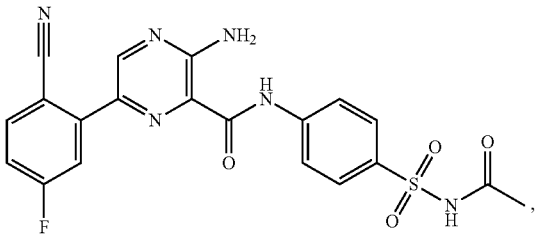

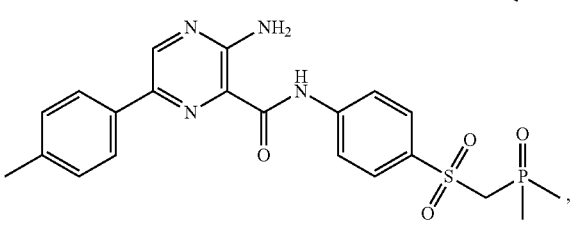
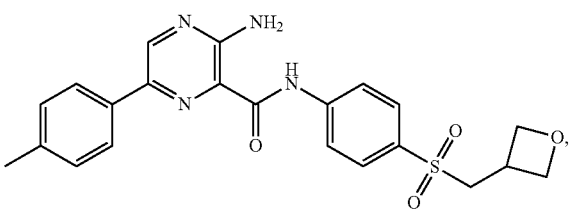
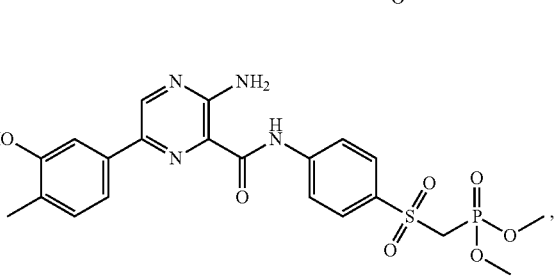
Embodiment F13. The compound of embodiment F1, having the formula:
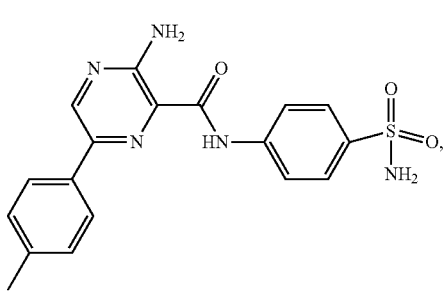
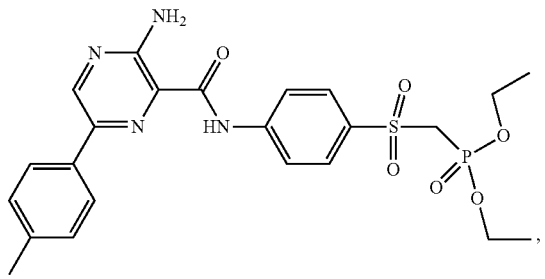

-continued

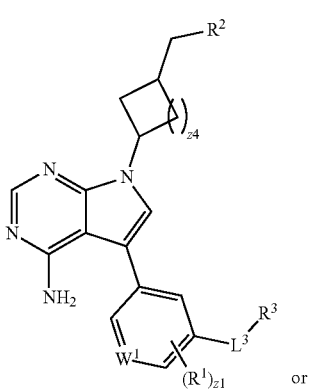

Embodiment F14. The compound of one of embodiments F1 to F2, having the formula:

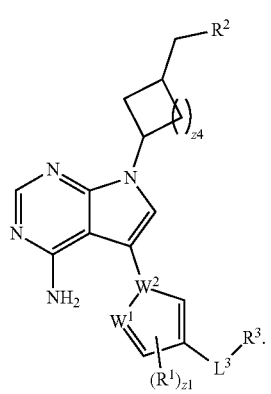

Embodiment F15. The compound of embodiment F14, having the formula:

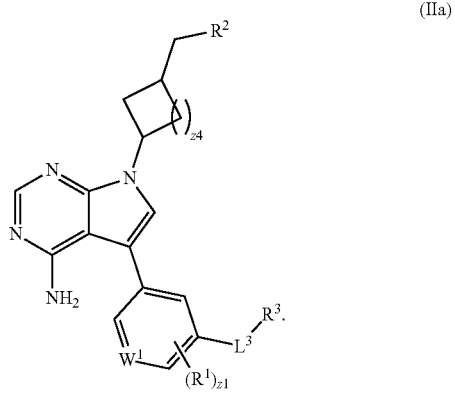

(IIa)

Embodiment F16. The compound of embodiment F14, having the formula:

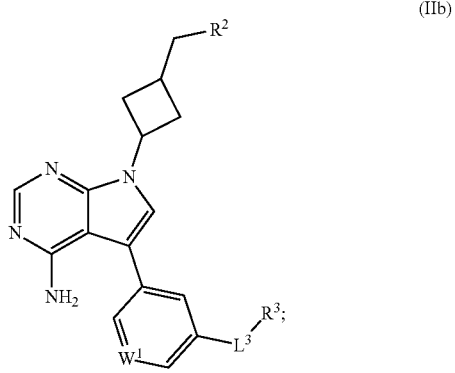

(IIb)

wherein $R^2$ is independently —NR$^{2A}$R$^{2B}$ or —OH;

$R^{2A}$ and $R^{2B}$ are independently hydrogen or $R^{20}$-substituted or unsubstituted $C_1$-$C_6$ alkyl; or $R^{2A}$ and $R^{2B}$ substituents bonded to the same nitrogen atom may optionally be joined to form an $R^{20}$-substituted or unsubstituted 4 to 7 membered heterocycloalkyl; and $R^{20}$ is independently oxo, halogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O) NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment F17. The compound of embodiment F16, having the formula:

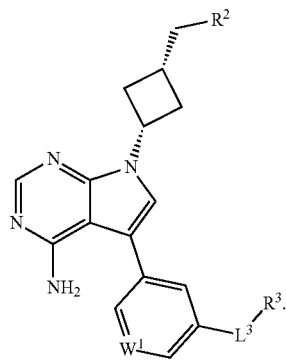

Embodiment F18. The compound of embodiment F14, having the formula:

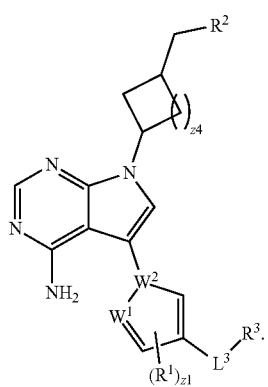

Embodiment F19. The compound of embodiment F14, having the formula:

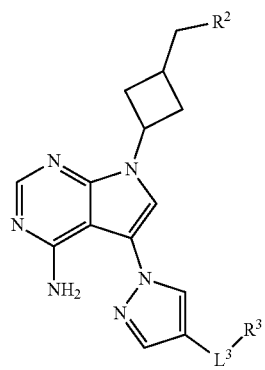

wherein
$R^2$ is independently —$NR^{2A}R^{2B}$;
$R^{2A}$ and $R^{2B}$ are independently hydrogen or $R^{20}$-substituted or unsubstituted $C_1$-$C_6$ alkyl; or $R^{2A}$ and $R^{2B}$ substituents bonded to the same nitrogen atom may optionally be joined to form an $R^{20}$-substituted or unsubstituted 4 to 7 membered heterocycloalkyl; and
$R^{20}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment F20. The compound of embodiment F19, having the formula:

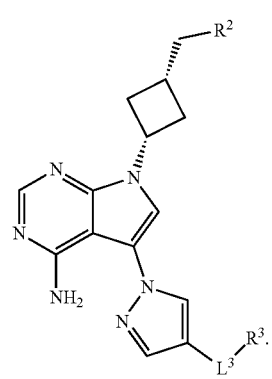

Embodiment F21. The compound of one of embodiments F14 to F20, wherein
$R^{2A}$ and $R^{2B}$ substituents bonded to the same nitrogen atom are joined to form an R20-substituted or unsubstituted 4 to 7 membered heterocycloalkyl; and
$R^{20}$ is independently oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC(O)$NHNH_2$, —NHC(O)$NH_2$, —$NHSO_2H$, —NHC(O)H, —NHC(O)OH, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, unsubstituted $C_1$-$C_6$ alkyl, unsubstituted 2 to 6 membered heteroalkyl, unsubstituted $C_3$-$C_6$ cycloalkyl, unsubstituted 3 to 6 membered heterocycloalkyl, unsubstituted phenyl, or unsubstituted 5 to 6 membered heteroaryl.

Embodiment F22. The compound of embodiment 21, wherein
$R^{2A}$ and $R^{2B}$ substituents bonded to the same nitrogen atom are joined to form

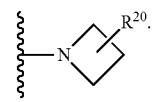

Embodiment F23. The compound of embodiment F21, wherein
$R^{2A}$ and $R^{2B}$ substituents bonded to the same nitrogen atom are joined to form

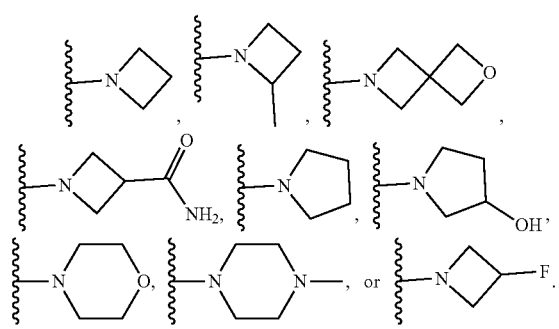

Embodiment F24. The compound of one of embodiments F14 to F23, wherein $L^3$ is a bond, —$CH_2$—, —$CH_2CH_2$—, —$CH_2CH_2CH_2$—, —$OCH_2$—, —$OCH_2CH_2$—, or —$OCH_2CH_2CH_2$—;

$R^3$ is independently —OH, —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO$_2$R$^{3D}$, —NR$^{3A}$SO$_2$L$^{3A}$R$^{3D}$, —NR$^{3C}$SO$_2$NR$^{3A}$R$^{3B}$, —NR$^{3A}$R$^{3B}$, —NR$^{3A}$C(O)R$^{3C}$, —NR$^{3A}$C(O)OR$^{3C}$, —SO$_2$R$^{3C}$, —SO$_2$NR$^{3A}$R$^{3B}$, —SO$_2$P(O)(OR$^{3C}$)(OR$^{3D}$), —SO$_2$CH$_2$P(O)(OR$^{3C}$)(OR$^{3D}$), —SO$_2$P(O)(OR$^{3D}$)(NR$^{3A}$R$^{3B}$), —SO$_2$P(O)(R$^{3C}$)(OR$^{3D}$), —SO$_2$P(O)(R$^{3C}$)(R$^{3D}$), —S(O)(NR$^{3A}$)R$^{3C}$, —C(O)OR$^{3C}$, —C(O)NR$^{3A}$R$^{3B}$, —NR$^{3A}$C(O)OR$^{3C}$;

$L^{3A}$ is independently —$CH_2$—, —$CH(CH_3)$—, or —$C(CH_3)_2$—; and $R^{3A}$, $R^{3B}$, $R^{3C}$, and $R^{3D}$ are independently hydrogen, oxo, halogen, —$CCl_3$, —$CBr_3$, —$CF_3$, —$CI_3$, $CHCl_2$, —$CHBr_2$, —$CHF_2$, —$CHI_2$, —$CH_2Cl$, —$CH_2Br$, —$CH_2F$, —$CH_2I$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC(O)NHNH_2$, —$NHC(O)NH_2$, —$NHSO_2H$, —$NHC(O)H$, —$NHC(O)OH$, —NHOH, —$OCCl_3$, —$OCF_3$, —$OCBr_3$, —$OCI_3$, —$OCHCl_2$, —$OCHBr_2$, —$OCHI_2$, —$OCHF_2$, —$OCH_2Cl$, —$OCH_2Br$, —$OCH_2I$, —$OCH_2F$, —$N_3$, —$SO_2CH_3$, —$NHC(O)CH_3$, —$C(O)CH_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{3A}$ and $R^{3B}$ substituents bonded to the same nitrogen atom may optionally be joined to form a substituted or unsubstituted heterocycloalkyl or substituted or unsubstituted heteroaryl; $R^{3A}$ and $R^{3D}$ substituents may optionally be joined to form a substituted or unsubstituted heterocycloalkyl or substituted or unsubstituted heteroaryl.

Embodiment F25. The compound of one of embodiments F14 to F24, wherein $W^1$ is CH.

Embodiment F26. The compound of one of embodiments F14 to F24, wherein $W^1$ is N.

Embodiment F27. The compound of one of embodiments F14 to F24, wherein $W^1$ is CR$^1$; and $R^1$ is independently halogen, —$CX^1_3$, —$CHX^1_2$, —$CH_2X^1$, or unsubstituted $C_1$-$C_4$ alkyl.

Embodiment F28. The compound of one of embodiments F1 to F4 or F14 to F27, wherein $R^3$ is

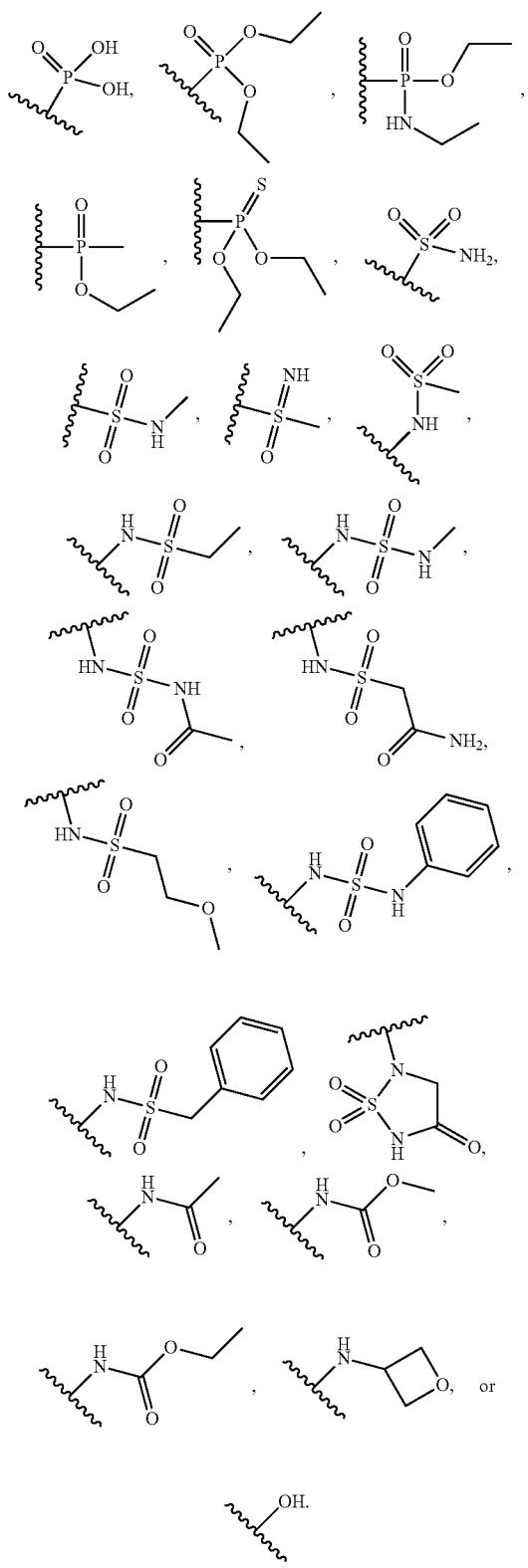

Embodiment F29. The compound of embodiment F1, having the formula:

401
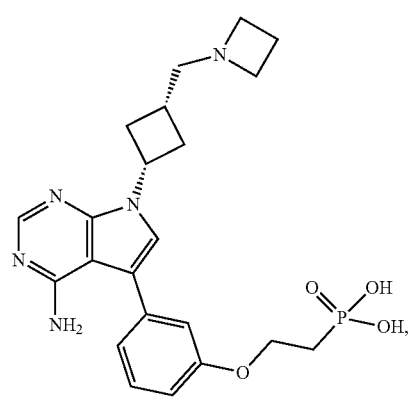
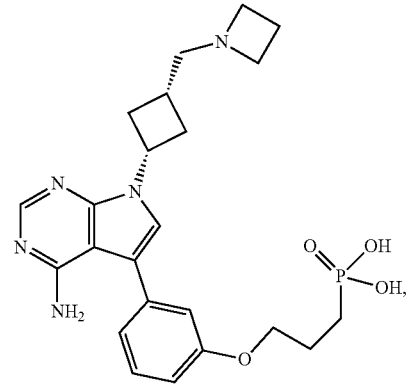
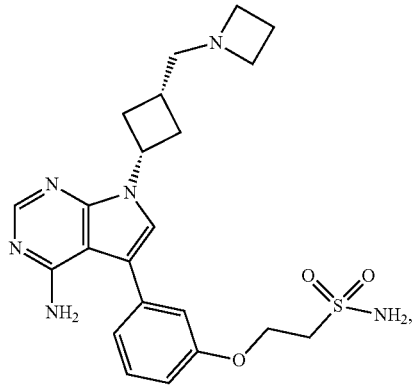
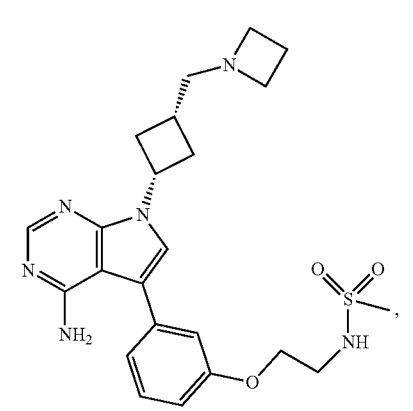
402
-continued
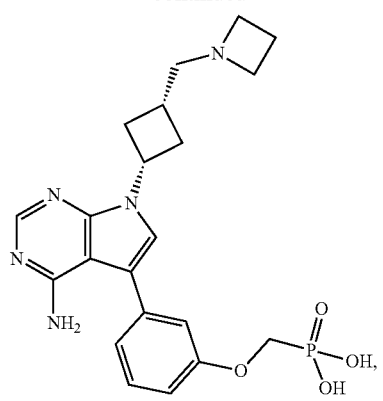
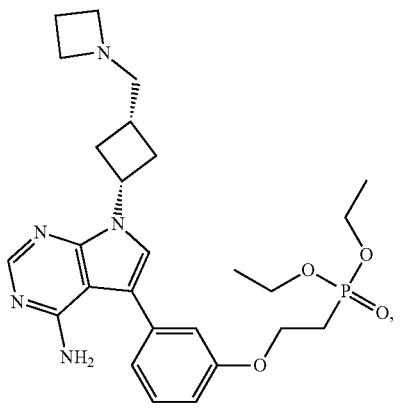
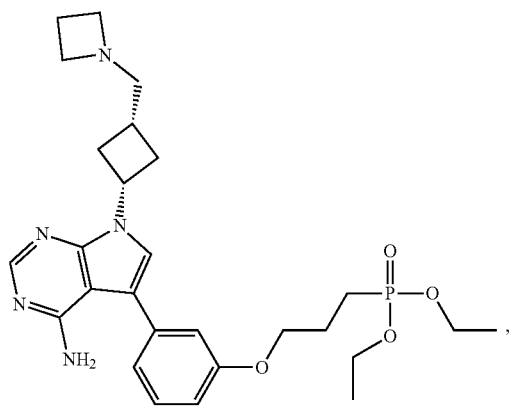
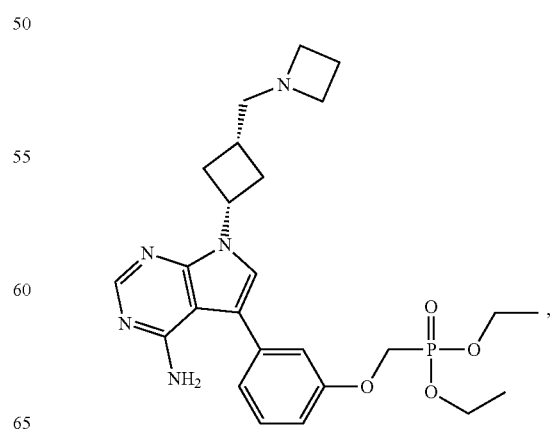

403
-continued
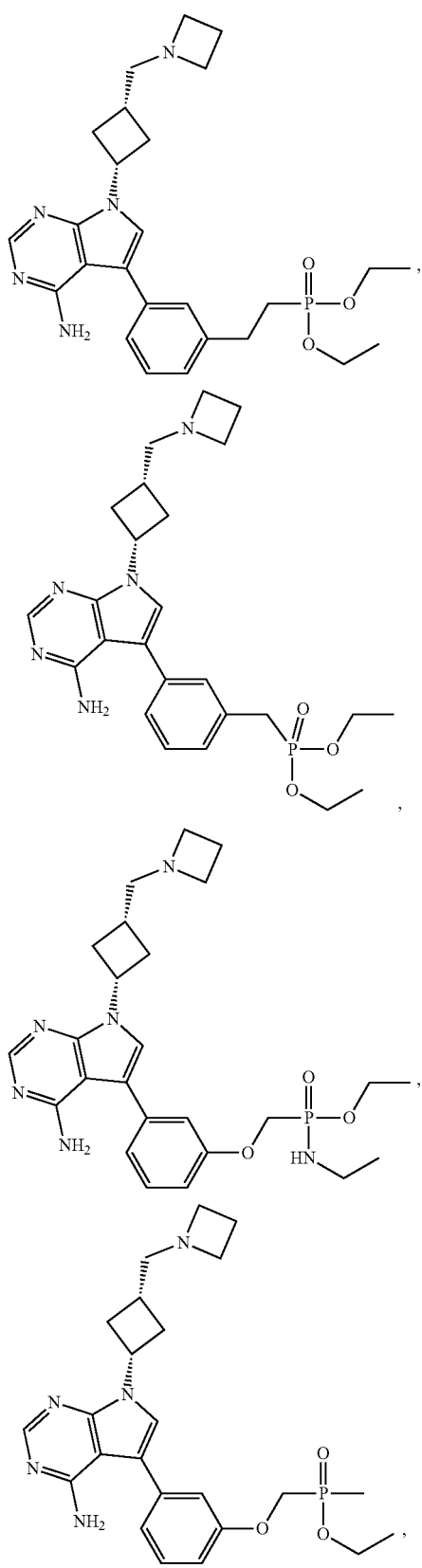
404
-continued
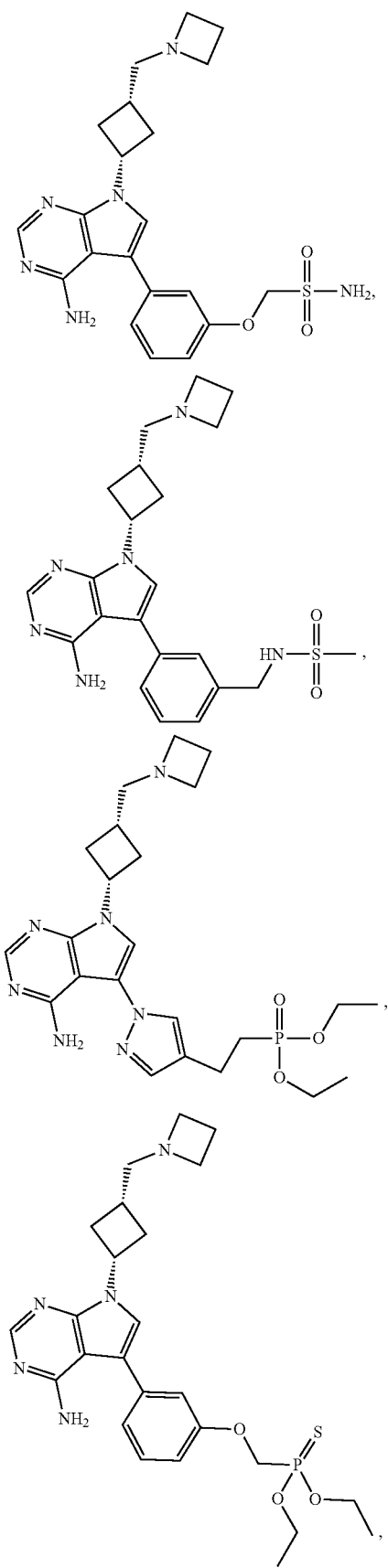

405
-continued
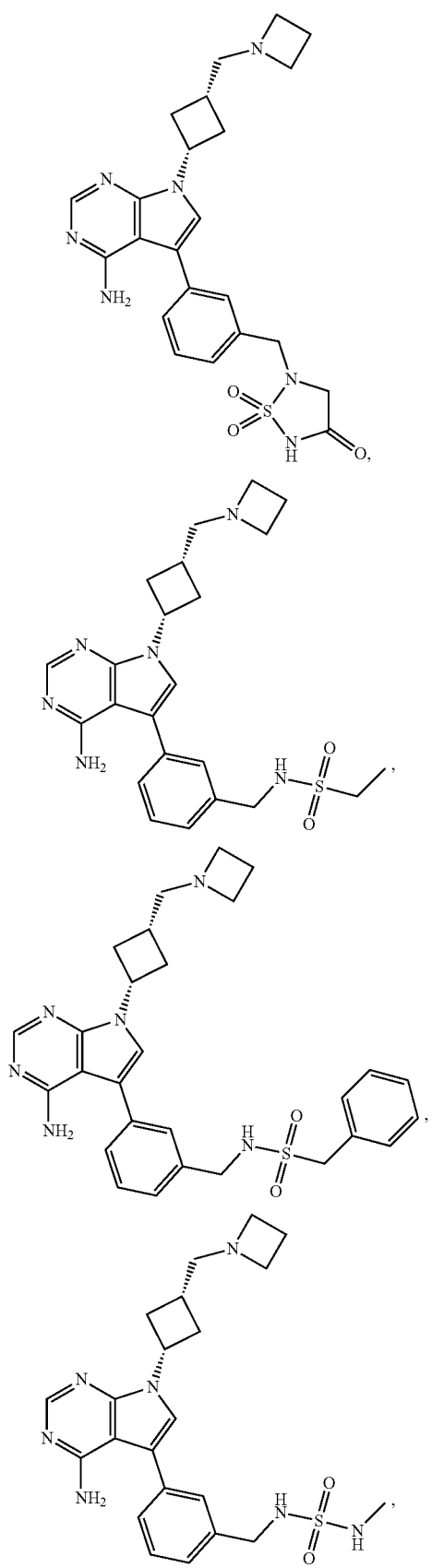
406
-continued
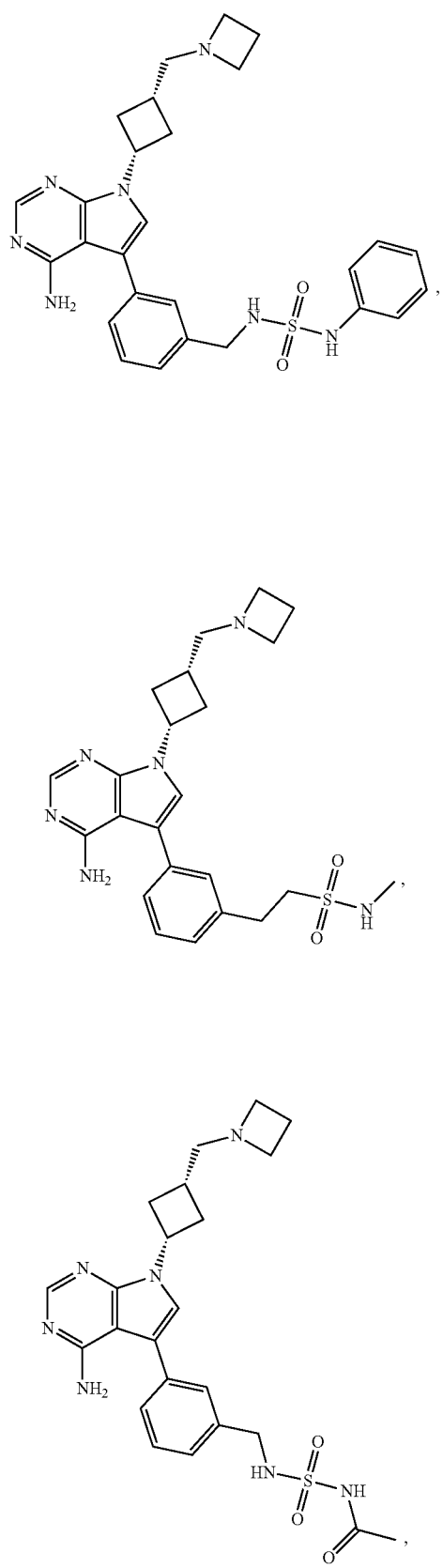

407
-continued
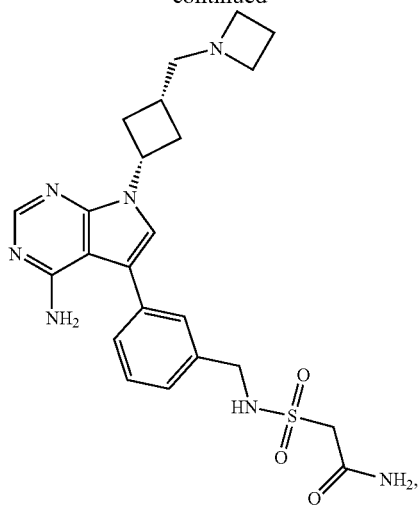
408
-continued
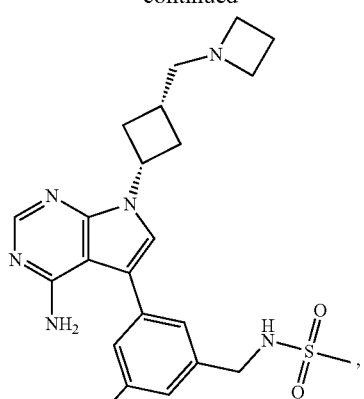
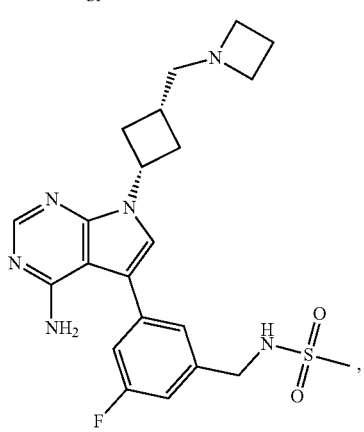
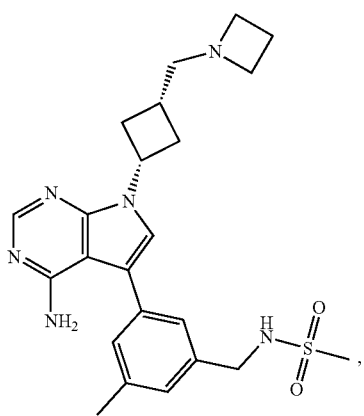
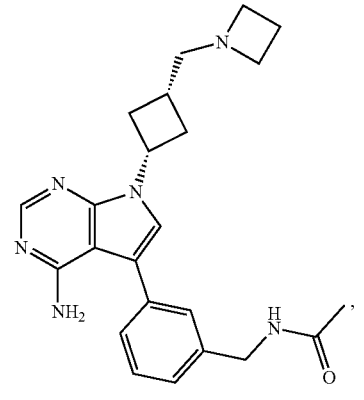

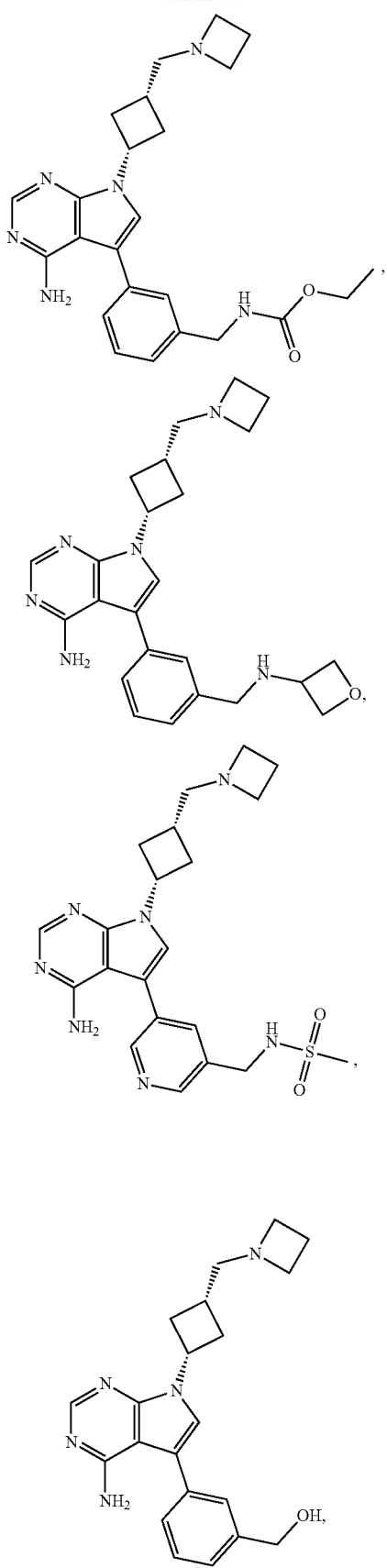
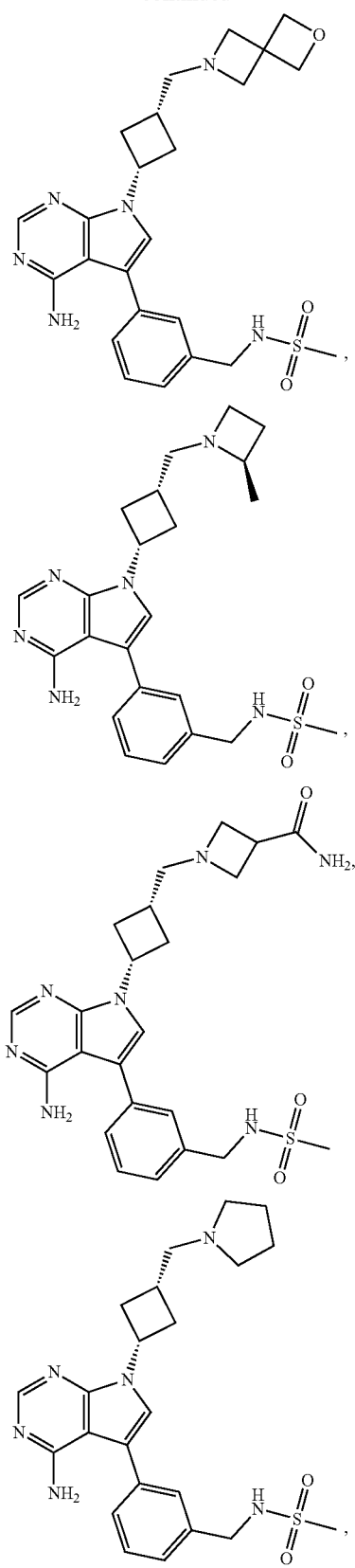

411
-continued
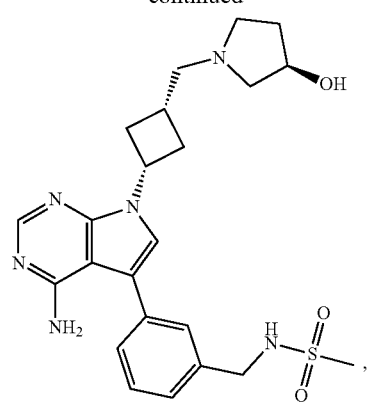
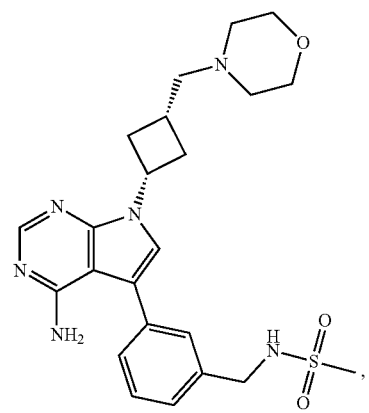
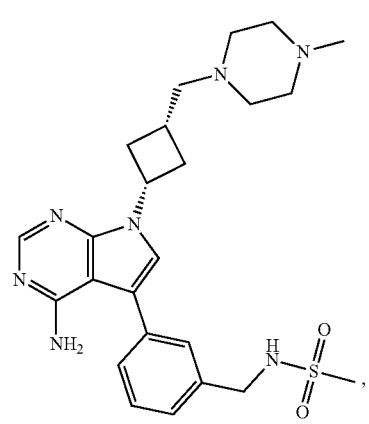
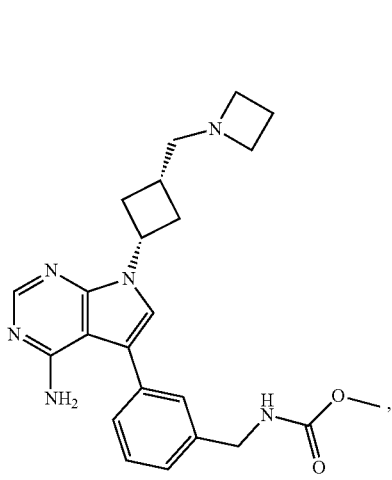
412
-continued
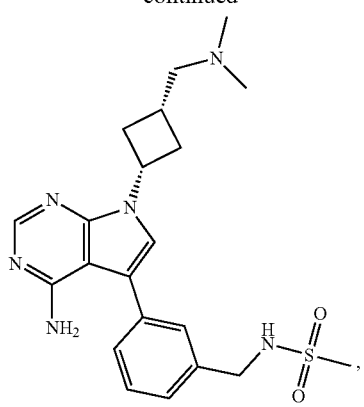
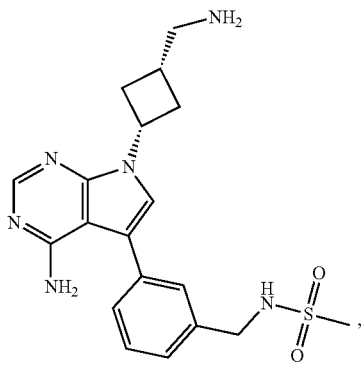
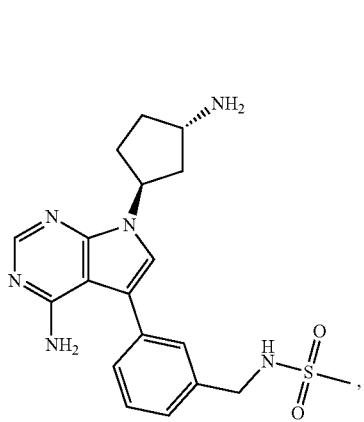
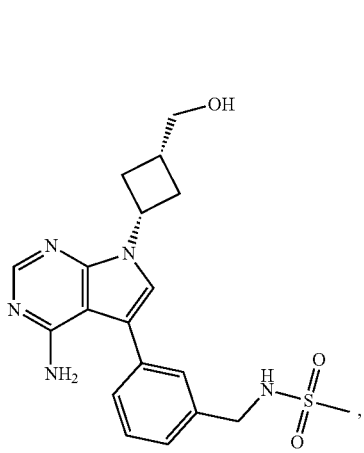

413
-continued
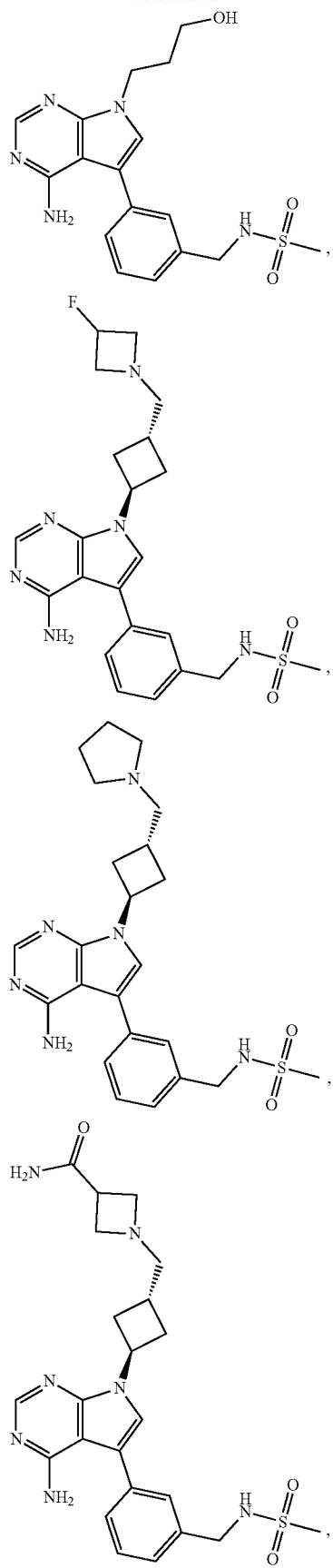
414
-continued
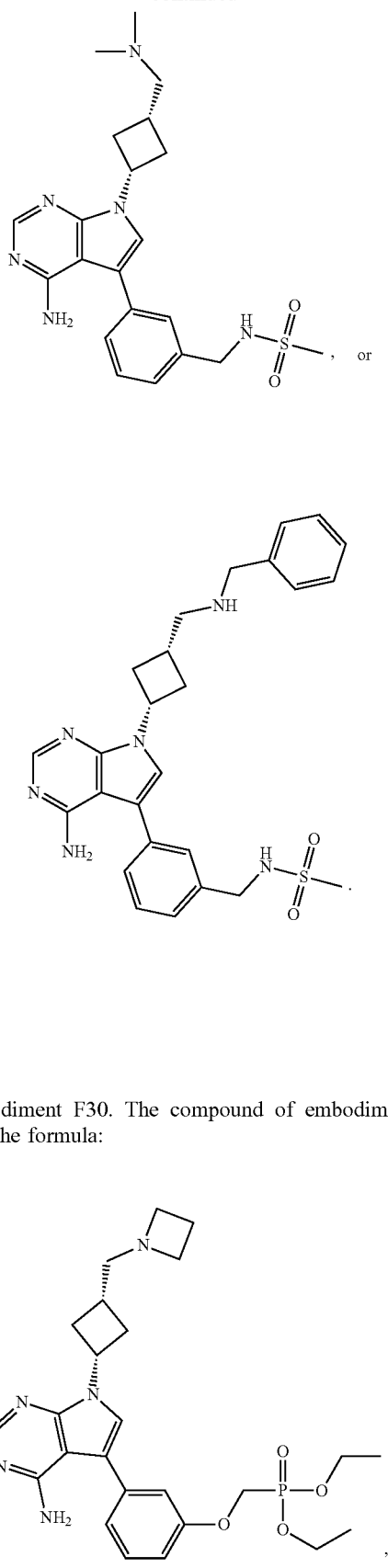
Embodiment F30. The compound of embodiment F1, having the formula:

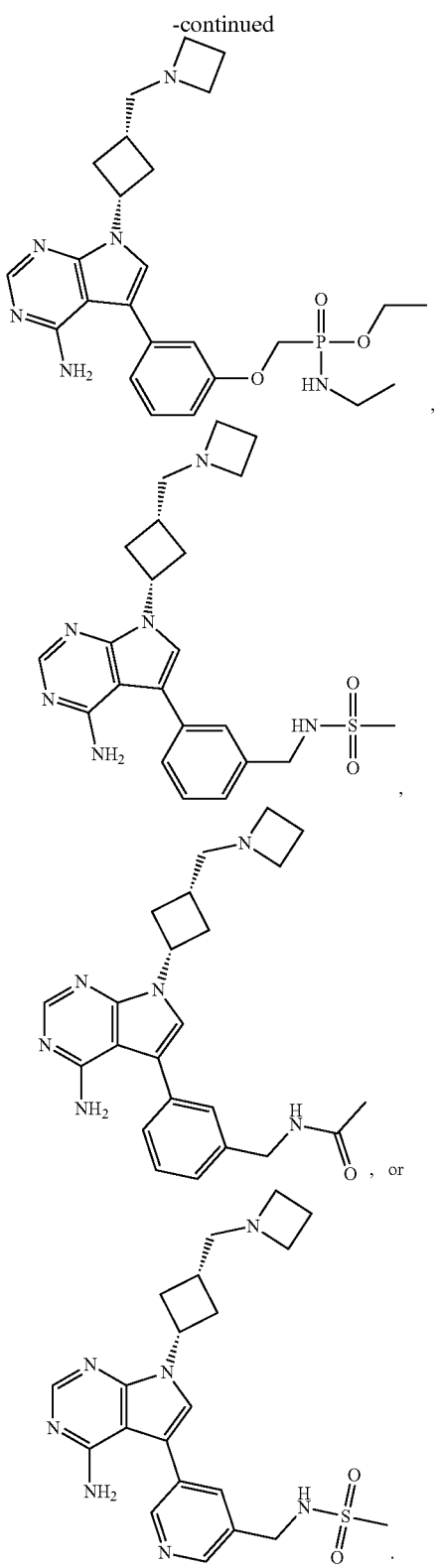

Embodiment 31. A pharmaceutical composition comprising the compound of any one of embodiments F1 to F30 and a pharmaceutically acceptable excipient.

Embodiment F32. A method of increasing the level of LKB1 activity in a subject, said method comprising administering a compound of one of embodiments F1 to F30 to said subject.

Embodiment F33. A method of increasing the level of LKB1 activity in a cell, said method comprising contacting said cell with a compound of one of embodiments F1 to F30.

Embodiment F34. The method of one of embodiments F32 to F33, wherein the compound contacts a STRAD protein.

Embodiment F35. A method of increasing the level of AMPK1, AMPK2, BRSK1, BRSK2, MARK1, MARK2, MARK3, MARK4, NUAK1, NUAK2, SIK1, SIK2, SIK3, SNRK, or TP53 activity in a subject, said method comprising administering a compound of one of embodiments F1 to F30 to said subject.

Embodiment F36. A method of decreasing the level of mTOR or cAMP-regulated transcriptional coactivator 2 (CRTC2) activity in a subject, said method comprising administering a compound of one of embodiments F1 to F30 to said subject.

Embodiment F37. A method of increasing the level of Hippo pathway activity in a subject, said method comprising administering a compound of one of embodiments F1 to F30 to said subject.

Embodiment F38. A method of increasing the level of fatty acid oxidation activity in a subject, said method comprising administering a compound of one of embodiments F1 to F30 to said subject.

Embodiment F39. The method of embodiment F35, comprising increasing the level of LKB1 activity in said subject.

Embodiment F40. The method of embodiment F36, comprising increasing the level of LKB1 activity in said subject.

Embodiment F41. The method of embodiment F37, comprising increasing the level of LKB1 activity in said subject.

Embodiment F42. The method of embodiment F38, comprising increasing the level of LKB1 activity in said subject.

Embodiment F43. A method of increasing the level of AMPK1, AMPK2, BRSK1, BRSK2, MARK1, MARK2, MARK3, MARK4, NUAK1, NUAK2, SIK1, SIK2, SIK3, SNRK, or TP53 activity in a cell, said method comprising contacting said cell with a compound of one of embodiments F1 to F30.

Embodiment F44. A method of decreasing the level of mTOR or cAMP-regulated transcriptional coactivator 2 (CRTC2) activity in a cell, said method comprising contacting said cell with a compound of one of embodiments F1 to F30.

Embodiment F45. A method of increasing the level of Hippo pathway activity in a cell, said method comprising contacting said cell with a compound of one of embodiments F1 to F30.

Embodiment F46. A method of increasing the level of fatty acid oxidation activity in a cell, said method comprising contacting said cell with a compound of one of embodiments F1 to F30.

Embodiment F47. The method of embodiment F43, comprising increasing the level of LKB1 activity in said cell.

Embodiment F48. The method of embodiment F44, comprising increasing the level of LKB1 activity in said cell Embodiment F49. The method of embodiment F45, comprising increasing the level of LKB1 activity in said cell.

Embodiment F50. The method of embodiment F45, comprising increasing the level of LKB1 activity in said cell.

Embodiment F51. The method of one of embodiments F35 to F50, wherein the compound contacts a STRAD protein.

Embodiment F52. A method of treating a cancer in a subject in need thereof, said method comprising administering to the subject in need thereof an effective amount of a compound of one of embodiments F1 to F30.

Embodiment F53. The method of embodiment F52, wherein the cancer has a RAS/MAPK pathway mutation or a PIK3CA mutation.

Embodiment F54. The method of embodiment F52, wherein the cancer is pancreatic cancer, lung cancer, uterine cancer, renal cancer, colon cancer, soft tissue sarcoma, or a squamous cell cancer.

Embodiment F55. The method of one of claims F52 to F54, further comprising co-administering an anti-cancer agent to said subject in need.

Embodiment F56. The method of embodiment F55, wherein the anti-cancer agent is a KRAS inhibitor, ERK inhibitor, MEK inhibitor, BRAF inhibitor, PIK3CA inhibitor, mTOR inhibitor, PD1 inhibitor, PDL1 inhibitor, or CTLA4 inhibitor.

Embodiment F57. A method of treating diabetes in a subject in need thereof, said method comprising administering to the subject in need thereof an effective amount of a compound of one of embodiments F1 to F30.

Embodiment F58. The method of embodiment F57, comprising reducing the level of blood glucose in said subject in need.

Embodiment F59. The method of embodiment F58, comprising reducing the level of insulin resistance in said subject in need.

Embodiment F60. The method of one of embodiments F57 to F59, further comprising co-administering diabetes therapeutic agent to said subject in need.

Embodiment F61. The method of embodiment F60, wherein the diabetes therapeutic agent is a biguanide, sulfonylurea, meglitinide, thiazolidinedione, alpha-glucosidase inhibitor, incretin, GLP-1 analogue, DPP-4 inhibitor, insulin, GLP-1 receptor agonist, amylin agonist, or insulin analogue.

Embodiment F62. A method of treating a cancer in a subject in need thereof, said method comprising administering to the subject in need thereof an effective amount of a pseudo-kinase STRADα stabilizing compound, wherein said pseudo-kinase STRADα stabilizing compound binds pseudo-kinase STRADα within the pseudo-kinase STRADα ATP binding pocket and contacts an amino acid within said pseudo-kinase STRADα ATP binding pocket corresponding to Lys 197, His 200, Arg 215, Lys 77, or Arg 100.

Embodiment F63. A method of treating diabetes in a subject in need thereof, said method comprising administering to the subject in need thereof an effective amount of a pseudo-kinase STRADα stabilizing compound, wherein said pseudo-kinase STRADα stabilizing compound binds pseudo-kinase STRADα within the pseudo-kinase STRADα ATP binding pocket and contacts an amino acid within said pseudo-kinase STRADα ATP binding pocket corresponding to Lys 197, His 200, Arg 215, Lys 77, or Arg 100.

Embodiment F64. The method of one of embodiments F62 to F63, wherein said pseudo-kinase STRADα stabilizing compound contacts amino acids within said pseudo-kinase STRADα ATP binding pocket corresponding to Lys 197, His 200, Arg 215, Lys 77, and Arg 100.

Embodiment F65. The method of one of embodiments F62 to F64, wherein said pseudo-kinase STRADα stabilizing compound increases LKB1-STRADα-Mo25 trimer complex association.

Embodiment F66. The method of one embodiments F62 to F65, wherein said pseudo-kinase STRADα stabilizing compound increases the rate of phosphorylation by LKB1.

Embodiment F67. The method of one embodiments F62 to F66, wherein said pseudo-kinase STRADα stabilizing compound maintains biologically relevant downstream signaling for greater than 24 hours upon onetime pseudo-kinase STRADα stabilizing compound exposure.

Embodiment F68. The method of one of embodiments F62 to F67, wherein said pseudo-kinase STRADα stabilizing compound induces desirable effects on pCRTC2, pS6, and/or pLATS.

Embodiment F69. The method of one of embodiments F62 to F68, wherein said pseudo-kinase STRADα stabilizing compound selectively binds STRADα relative to LKB1, or relative to other kinases.

EXAMPLES

Example 1: Synthetic Methods for APA Analogs

The pseudo-kinase STRADα (Ste20-related adaptor, also named LYK5) binds ATP but is not phospho-transfer capable. STRAD activates LKB1 via the formation of a heterotrimeric complex with LKB1 and the scaffolding protein MO25. The association of STRAD with ATP and MO25 is essential for LKB1 activation wherein the interaction of these binding partners drives allosteric changes necessary for LKB1 activity.

The active kinase LKB1 signals as part of this trimeric complex to suppress oncogenesis via effector pathways with effects on metabolism, the cell cycle, and polarity. LKB1 activation directly influences cell growth pathways through effects on SIK kinases and the Hippo target YAP. LKB1 is mutated in Peutz-Jeghers syndrome as well as lung, GI, cervical, and uterine cancers and LKB1 downregulation is associated with resistance to targeted and immune therapies and worse clinical outcomes.

Thus, small molecule activation/stabilization of the novel target STRAD and subsequent LKB1 activation is expected to afford therapeutic benefit for the treatment of cancer in combination or as a mono-therapy. Via a focused Structure-Based-Drug-Design effort centered on the STRAD ATP binding site utilizing a computational modeling based disclosed crystal structures of the trimer, we have developed compounds that target the intact LKB1 complex to increase its kinase activity.

Single digit micro-molar LKB1 in vitro activation was achieved for APA Series members such as SU-329 and tractable SAR emerged for this series in subsequent biological assays. Screening in human cancer cell lines has identified cell lines responsive to LKB1 activation and predictive biomarkers for compound development have been determined. Installation of a novel polar functionality specifically designed to target STRAD's unique phosphate-binding residues led to the identification of compound SU-329 which is currently progressing through efficacy models evaluating tumor growth inhibition. The terms SU-329 and SU20668-0329-01 refer to the same compound.

Small Molecule Activation of the LKB1 Tumor Suppressor. Cancer treatment has been considerably advanced by the relatively recent development of small molecules capable of inhibiting oncogenic kinase signaling, but exogenous enhancement of tumor suppressive signaling remains elusive. Here, we sought to design small molecules capable of activating the tumor suppressor kinase LKB1. Designing compounds capable of increasing kinase activity has been more structurally challenging than those aimed at inhibiting them: apart from the ATP-binding pocket, there is rarely a site that would be conducive to binding a small molecule. Unlike most protein kinases, LKB1 signals as part of an obligate trimer consisting of itself, a scaffolding protein (MO25), and a pseudokinase (STRAD). As part of its mechanism of activation, LKB1 must bind to an ATP-bound STRAD to take on its active kinase conformation. Targeting STRAD provides a unique opportunity to allosterically stabilize and enhance LKB1 kinase activity. Using a structure-based drug design, we developed compounds that are able to selectively bind STRAD's ATP-binding pocket. We confirmed that our STRAD targeting small molecules are able to enhance the activity of recombinant LKB1 in a kinase assay. The observed increase in LKB1's kinase activity corresponds to increased association of complex components after drug treatment, as suggested by immunoprecipitation of the trimer. To understand the clinical contexts in which our compounds might be most effective, we performed a viability screen across multiple histologies to determine which cancer cells could be sensitive to LKB1 activation. Sensitive cells were used to investigate the mechanism of action of exogenous LKB1 stimulation. LKB1 signals through members of the AMPK-related kinase family to carry out its tumor suppressive functions in the cell. Thus, we used western blot analysis of LKB1 proximal and distal mediators to assess changes in downstream signaling. We found that activation of multiple LKB1 effectors was dose dependent and occurred rapidly, with signal enhancement seen in more tumor-relevant low adherence cell culture conditions. Real-time microscopy confirmed that our compounds slowed cell proliferation in a dose-dependent manner. This work demonstrates that targeting a pseudokinase with a small molecule to allosterically activate of a tumor suppressor kinase is possible, therapeutically effective in vitro, and triggers multiple downstream signaling pathways to decrease cancer cell proliferation.

General information: All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All NMR spectra were recorded on a Bruker 400 (400 MHz) spectrometer. $^1$H chemical shifts are reported in δ values in ppm with the deuterated solvent as the internal standard. Data are reported as follows: chemical shift, multiplicity (s=singlet, d=doublet, t=triplet, q=quartet, br=broad, m=multiplet), coupling constant (Hz), integration. LCMS spectra were obtained on an Agilent 1200 series 6110 or 6120 mass spectrometer with electrospray ionization and excepted as otherwise indicated, the general LCMS condition was as follows: Waters X Bridge C18 column (50 mm×4.6 mm×3.5 um), Flow Rate: 2.0 ml/min, the column temperature: 40° C.

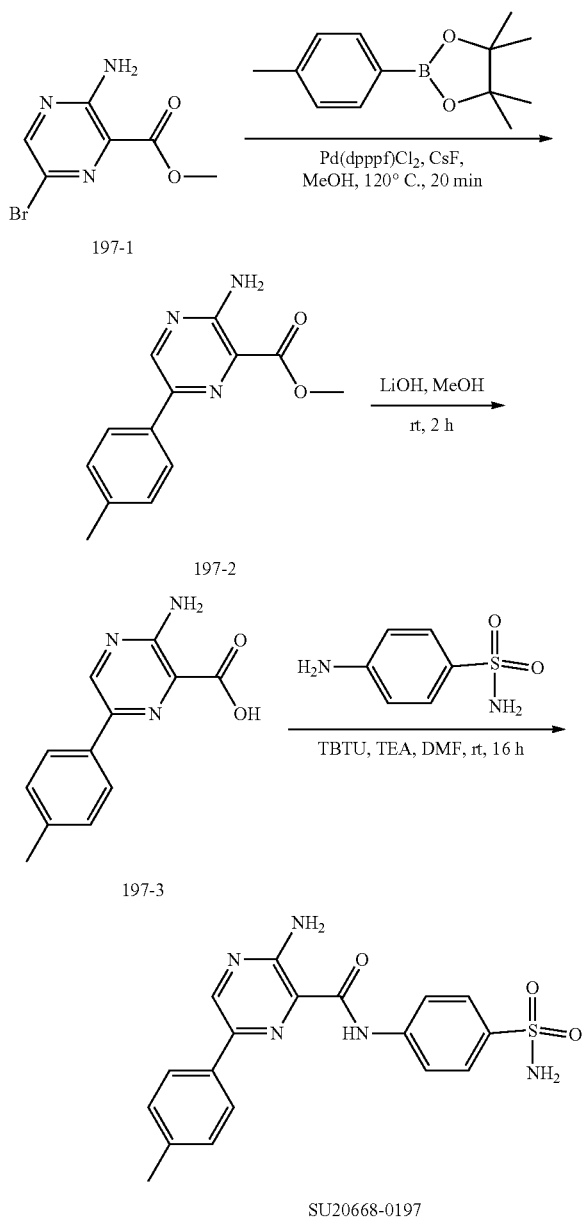

Scheme 1 Route for SU20668-0197

The Synthesis of methyl 3-amino-6-p-tolylpyrazine-2-carboxylate (197-2)

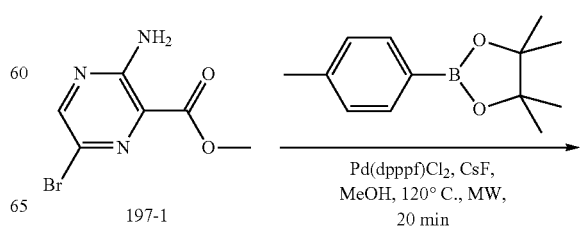

-continued

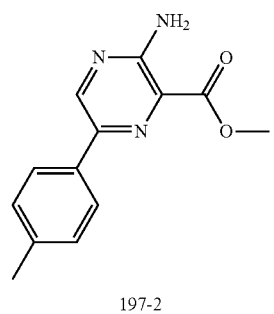

197-2

To a stirred solution of compound 197-1 (12.0 g, 51.7 mmol) in MeOH (50 mL) were added CsF (15.7 g, 103.4 mmol), 4,4,5,5-tetramethyl-2-p-tolyl-1,3,2-dioxaborolane (13.5 g, 62.1 mmol) and Pd(dppf)Cl$_2$ (10%, 1.2 g). The resulting reaction mixture was irradiated with microwave radiation at 120° C. for 20 min under Ar atmosphere. Then water (80 mL) was added, extracted with EA (3×200 mL) and the organic phase was dried over Na$_2$SO$_4$ and the crude was purified by TLC (EA:PE=5:1) get the desired product 197-2 (9.7 g, yield: 78%) as a yellow solid.

The Synthesis of
3-amino-6-p-tolylpyrazine-2-carboxylic acid (197-3)

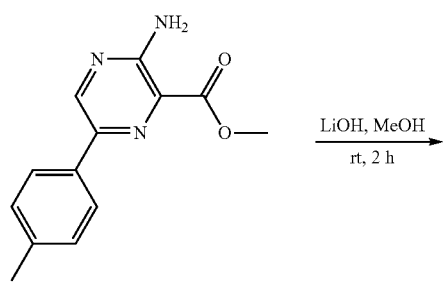

To a solution of compound 197-2 (9.7 g, 39.9 mmoL) in MeOH (150 mL) was added LiOH (3.4 g, 79.8 g). The mixture was stirred at rt for 2 h. After the consumption of starting material (by LCMS), the solvent was removed, water (10 mL) was added to residue and the pH value was adjusted to ~6.0 with dilute hydrochloric acid. The mixture was filtered, and the filtrate was concentrated in vacuo to give the desired product 197-3 (7.9 g, yield: 86%) as a yellow solid.

The Synthesis of 3-amino-N-(4-sulfamoylphenyl)-6-p-tolylpyrazine-2-carboxamide (SU20668-0197)

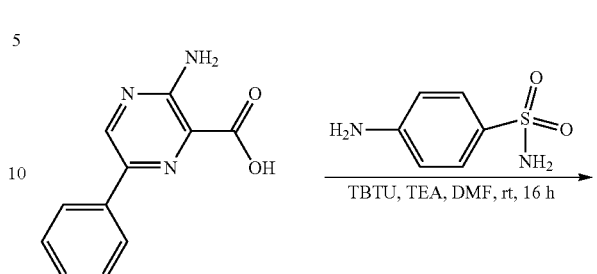

197-3

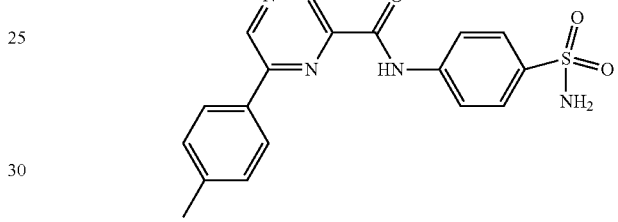

SU20668-0197

To a stirred solution of compound 197-3 (115 mg, 0.5 mmol) was added TBTU (326 mg, 1 mmol), TEA (101 mg, 1 mmol) and 4-aminobenzenesulfonamide (86 mg, 0.5 mmol). The resulting reaction mixture was stirred at rt for 16 h. Then water (50 mL) was added, extracted with EA (3×100 mL) and the organic phase was dried over Na$_2$SO$_4$. Purified by prep-HPLC to give the desired product SU20668-0197 (20 mg, yield: 13%) as a yellow solid. LC-MS (Agilent LCMS 1200-6120, Column: Waters X-Bridge C18 (30 mm×4.6 mm×2.7 m); Column Temperature: 40° C.; Flow Rate: 3.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 0.8 min, then under this condition for 0.4 min, finally changed to 95% [water+0.05% TFA] and 5% [CH$_3$CN+0.05%] in 0.01 min. Purity: 97.14%, Rt=1.740 min; MS Calcd.: 383.4; MS Found: 384.4 [M+H]$^+$. Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min. Purity: 99.41%, Rt=8.817 min. $^1$H NMR (400 MHz, DMSO) δ 10.61 (s, 1H), 8.90 (s, 1H), 8.11 (d, J=8.0 Hz, 2H), 8.01 (d, J=8.8 Hz, 2H), 7.82 (d, J=8.8 Hz, 2H), 7.64 (s, 2H), 7.28-7.29 (m, 4H), 2.35 (s, 3H)

Scheme 2: Route for SU20668-0279

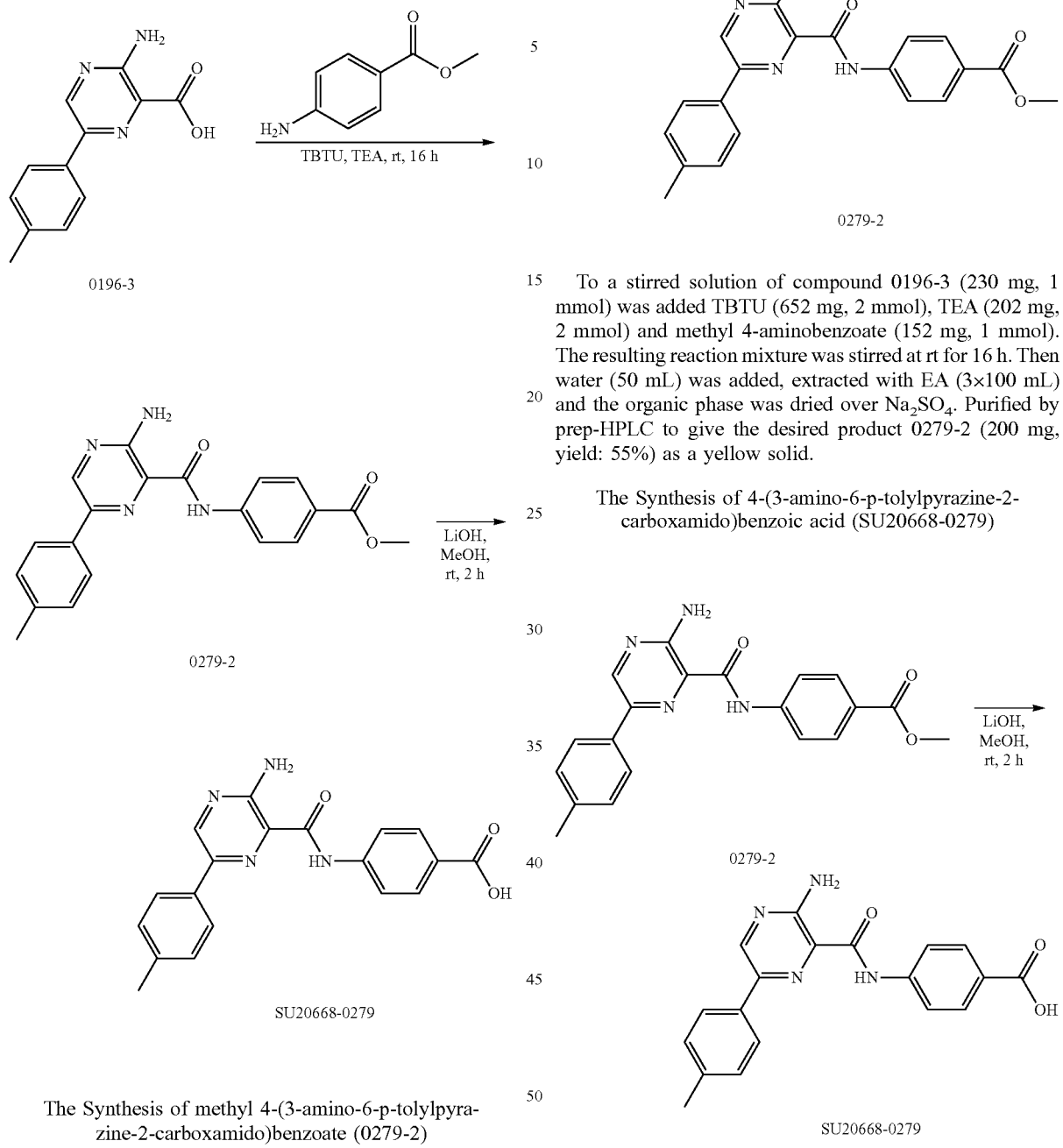

The Synthesis of methyl 4-(3-amino-6-p-tolylpyrazine-2-carboxamido)benzoate (0279-2)

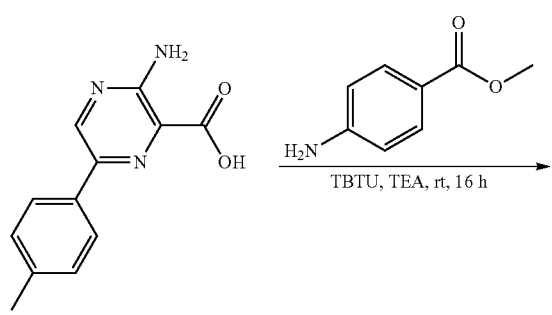

To a stirred solution of compound 0196-3 (230 mg, 1 mmol) was added TBTU (652 mg, 2 mmol), TEA (202 mg, 2 mmol) and methyl 4-aminobenzoate (152 mg, 1 mmol). The resulting reaction mixture was stirred at rt for 16 h. Then water (50 mL) was added, extracted with EA (3×100 mL) and the organic phase was dried over $Na_2SO_4$. Purified by prep-HPLC to give the desired product 0279-2 (200 mg, yield: 55%) as a yellow solid.

The Synthesis of 4-(3-amino-6-p-tolylpyrazine-2-carboxamido)benzoic acid (SU20668-0279)

To a solution of compound 0279-2 (200 mg, 0.6 mmoL) in MeOH (50 mL) was added LiOH (50 mg, 1.2 mmol). The mixture was stirred at rt for 2 h. After the consumption of starting material (by LCMS), the solvent was removed, water (10 mL) was added to residue and the pH value was adjusted to ~6.0 with dilute hydrochloric acid. The mixture was filtered, and the filtrate was concentrated in vacuo to give the desired product SU20668-0279 (46 mg, yield: 24%) as a yellow solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 99.21%, Rt=1.498 min; MS Calcd.: 348.4; MS Found: 349.4 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 99.62%, Rt=6.673 min. $^1$H NMR (400 MHz, DMSO-d$_6$) δ 12.82 (s, 1H), 10.60 (s, 1H), 8.92 (s, 1H), 8.12 (d, J=8.2 Hz, 2H), 7.83-8.02 (m, 4H), 7.65 (s, 2H), 7.31 (d, J=8.0 Hz, 2H), 2.37 (s, 3H).

The Synthesis of methyl 4-(3-amino-6-p-tolylpyrazine-2-carboxamido)benzoate (0279-2)

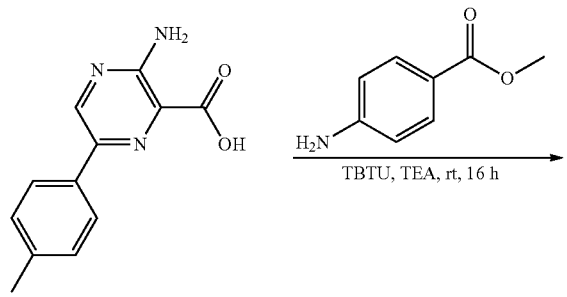

0196-3

0279-2

To a stirred solution of compound 0196-3 (230 mg, 1 mmol) was added TBTU (652 mg, 2 mmol), TEA (202 mg, 2 mmol) and methyl 4-aminobenzoate (152 mg, 1 mmol). The resulting reaction mixture was stirred at rt for 16 h. Then water (50 mL) was added, extracted with EA (3×100 mL) and the organic phase was dried over Na$_2$SO$_4$. Purified by prep-HPLC to give the desired product 0279-2 (200 mg, yield: 55%) as a yellow solid.

The Synthesis of 4-(3-amino-6-p-tolylpyrazine-2-carboxamido)benzoic acid (SU20668-0279)

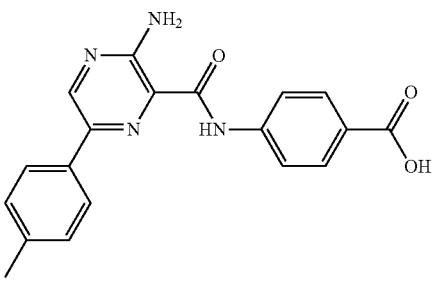

SU20668-0279

To a solution of compound 0279-2 (200 mg, 0.6 mmoL) in MeOH (50 mL) was added LiOH (50 mg, 1.2 mmol). The mixture was stirred at rt for 2 h. After the consumption of starting material (by LCMS), the solvent was removed, water (10 mL) was added to residue and the pH value was adjusted to ~6.0 with dilute hydrochloric acid. The mixture was filtered, and the filtrate was concentrated in vacuo to give the desired product SU20668-0279 (46 mg, yield: 24%) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 99.21%, Rt=1.498 min; MS Calcd.: 348.4; MS Found: 349.4 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 99.62%, Rt=6.673 min. $^1$H NMR (400 MHz, DMSO-d$_6$) δ 12.82 (s, 1H), 10.60 (s, 1H), 8.92 (s, 1H), 8.12 (d, J=8.2 Hz, 2H), 7.83-8.02 (m, 4H), 7.65 (s, 2H), 7.31 (d, J=8.0 Hz, 2H), 2.37 (s, 3H).

Scheme 3: Route for SU20668-0281

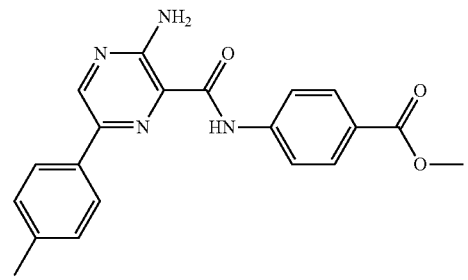

0279-2

0196-3

-continued

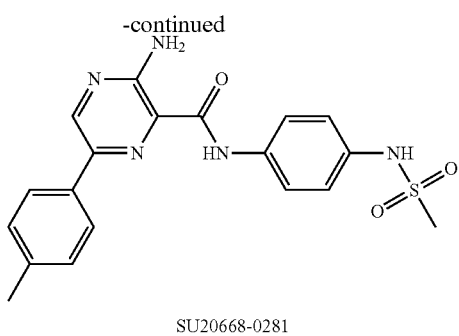

SU20668-0281

The Synthesis of methyl 4-(3-amino-6-p-tolylpyrazine-2-carboxamido)benzoate (SU20668-0281)

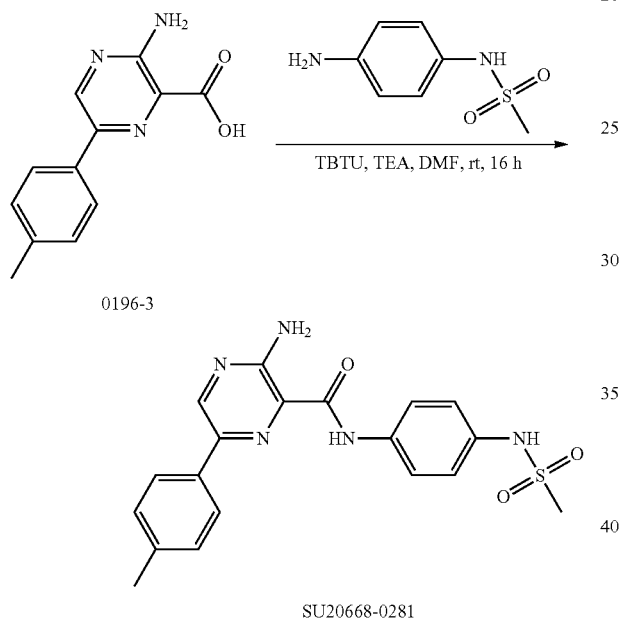

To a stirred solution of compound 0196-3 (230 mg, 1 mmol) was added TBTU (652 mg, 2 mmol), TEA (202 mg, 2 mmol), methyl 4-aminobenzoate (186 mg, 1 mmol). The resulting reaction mixture was stirred at rt for 16 h. Then water (50 mL) was added, extracted with EA (3×100 mL) and the organic phase was dried over $Na_2SO_4$. Purified by prep-HPLC to give the desired product SU20668-0281 (80 mg, yield: 20%) as a yellow solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min Purity: 99.36%, Rt=2.00 min; MS Calcd.: 397.5; MS Found: 398.4 [M+H]$^+$. Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min Purity: 98.31%, Rt=9.328 min. $^1$H NMR (400 MHz, DMSO-$d_6$) δ 10.38 (s, 1H), 9.67 (s, 1H), 8.88 (s, 1H), 8.11 (d, J=8.2 Hz, 2H), 7.77 (d, J=7.2 Hz, 2H), 7.63 (s, 2H), 7.30 (d, J=8.0 Hz, 2H), 7.24 (d, J=8.8 Hz, 2H), 2.98 (s, 3H), 2.37 (s, 3H).

Scheme 4: Route for SU20668-0293

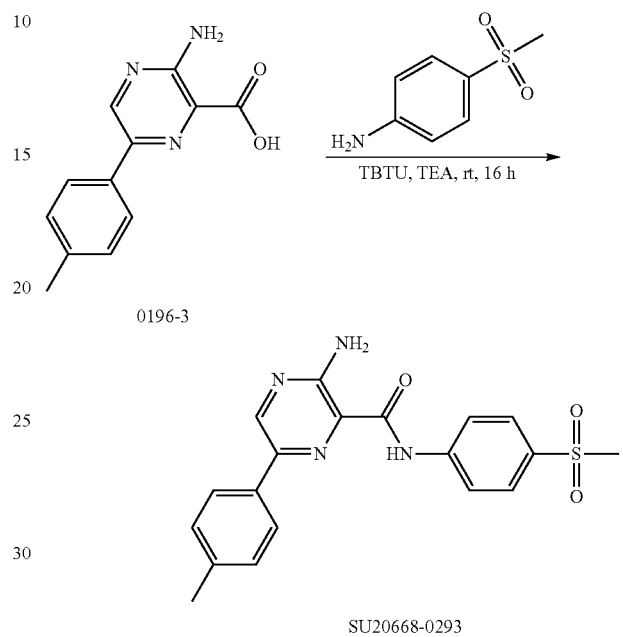

The Synthesis of 3-amino-N-(4-(methylsulfonyl)phenyl)-6-p-tolylpyrazine-2-carboxamide (SU20668-0293)

To a stirred solution of compound 0196-3 (230 mg, 1 mmol) was added HATU (760 mg, 2 mmol), TEA (202 mg, 2 mmol), 4-(methylsulfonyl)aniline (171 mg, 1 mmol). The resulting reaction mixture was stirred at rt for 16 h. Then water (50 mL) was added, extracted with EA (3×100 mL) and the organic phase was dried over $Na_2SO_4$. Purified by prep-HPLC to give the desired product SU20668-0293 (286 mg, yield: 75%) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 95.85%, Rt=2.051 min; MS Calcd.: 382.4; MS Found: 383.4 $[M+H]^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 98.99%, Rt=9.580 min. $^1$H NMR (400 MHz, DMSO-$d_6$) δ 10.72 (s, 1H), 8.93 (s, 1H), 8.22-8.07 (m, 4H), 7.95 (d, J=8.8 Hz, 2H), 7.66 (s, 2H), 7.31 (d, J=8.0 Hz, 2H), 3.22 (s, 3H), 2.37 (s, 3H).

Scheme 5: Route for SU20668-0299-01

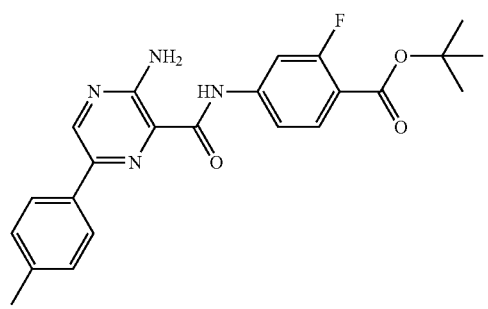

SU20668-0308-01

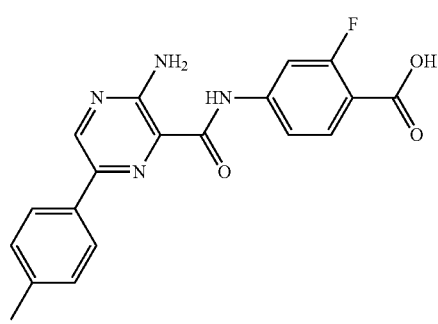

SU20668-0299-01

The Synthesis of 4-(3-amino-6-p-tolylpyrazine-2-carboxamido)-2-fluorobenzoic acid (SU20668-0299-01)

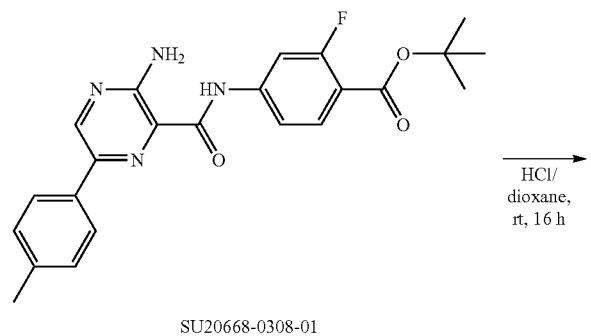

SU20668-0308-01

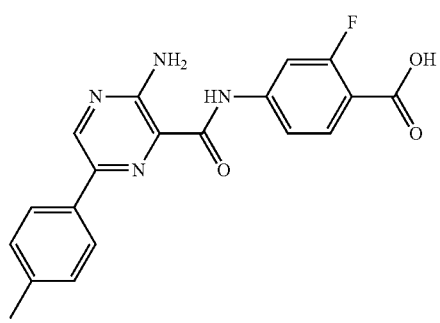

SU20668-0299-01

To a stirred solution of compound SU20668-0308-01 (200 mg, 0.47 mmol) in dioxane (1.0 mL) was added HCl/dioxane (4M, 3.0 mL) at rt. The resulting reaction mixture was further stirred for 16 h at rt, then concentrated in vacuo and further purified by prep-HPLC to give the desired product SU20668-0299-01 (137 mg, yield: 71%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 97.36%, Rt=1.539 min; MS Calcd.: 366.1; MS Found: 367.2 $[M+H]^+$.

HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 97.45%, Rt=6.711 min. $^1$H NMR (400 MHz, DMSO-$d_6$) δ 10.54 (s, 1H), 8.91 (s, 1H), 8.11 (d, J=8.0 Hz, 2H), 7.74-7.83 (m, 2H), 7.62-7.64 (m, 3H), 7.30 (d, J=8.0 Hz, 2H), 2.37 (s, 3H).

Scheme 6: Route for SU20668-0300-01

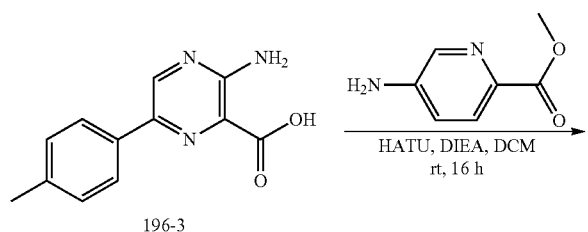

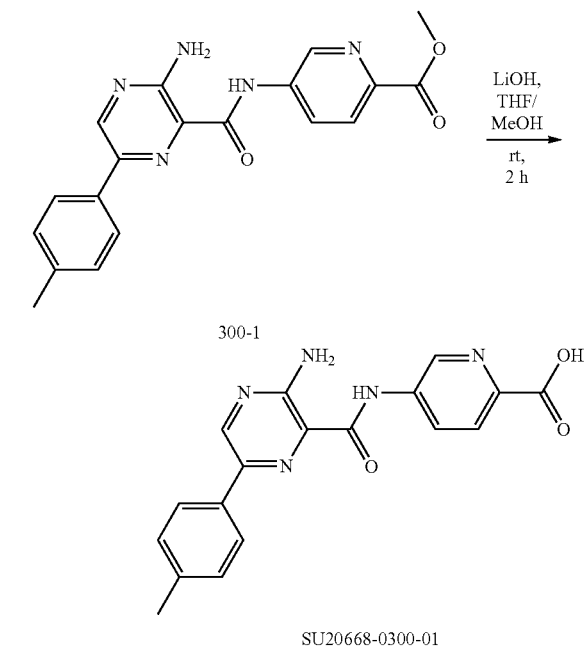

The Synthesis of methyl 5-(3-amino-6-p-tolylpyrazine-2-carboxamido)picolinate (300-1)

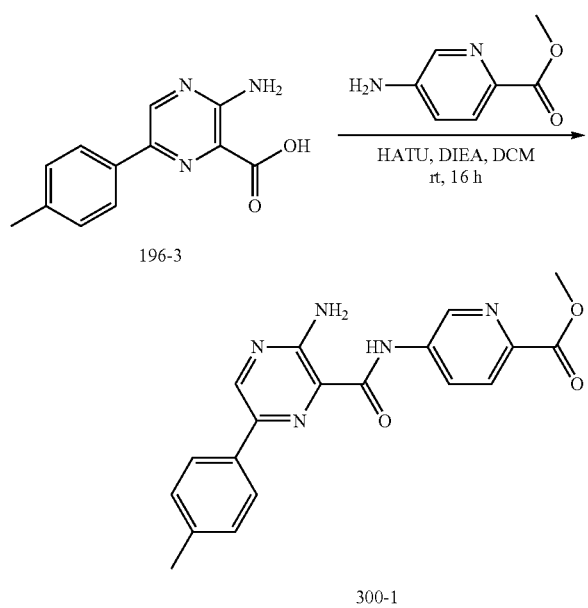

To a solution of compound 196-3 (200 mg, 0.87 mmol) in DMF (4 mL) was added methyl 5-aminopicolinate (132 mg, 0.87 mmol), DIEA (194 mg, 1.5 mmol), HATU (430 mg, 1.13 mmol). The resulting reaction mixture was stirred for 16 h at rt. Then the mixture was purified by prep-HPLC to give the desired product 300-1 (250 mg, yield: 78.9%) as a yellow solid.

The Synthesis of 5-(3-amino-6-p-tolylpyrazine-2-carboxamido)picolinic acid (SU20668-0300-01)

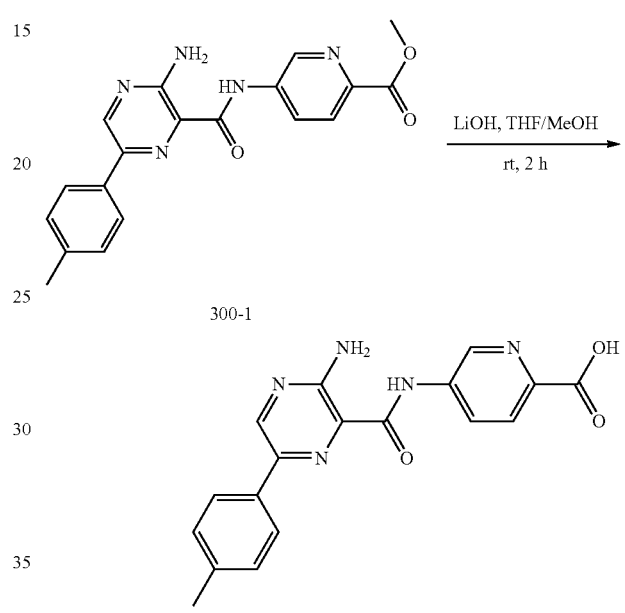

The mixture of 300-1 (250 mg, 0.69 mmol) and LiOH (84 mg, 2.0 mmol) in methanol/THF (1:1, 5.0 mL) was stirred at room temperature for 2 hours. Then the reaction mixture was acidified with HCl (1N) till pH=3~4. Collected the solid by filtration to afford SU20668-0300-01 (48 mg, yield: 16.7%) a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 100%, Rt=1.627 min; MS Calcd.: 349.1; MS Found: 350.0 [M+H]$^+$. HPLC (Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 96.83%, Rt=8.058 min. $^1$H NMR (400 MHz, DMSO-$d_6$) δ 10.77 (s, 1H), 9.11 (d, J=2.0 Hz, 1H), 8.93 (s, 1H), 8.39 (dd, J=14 Hz, 8.8 Hz, 1H), 8.14 (d, J=8.0 Hz, 2H), 8.08 (d, J=8.4 Hz, 1H), 7.66 (s, 2H), 7.31 (d, J=8.0 Hz, 2H), 2.37 (s, 3H).

Scheme 7: Route for SU20668-0303-01

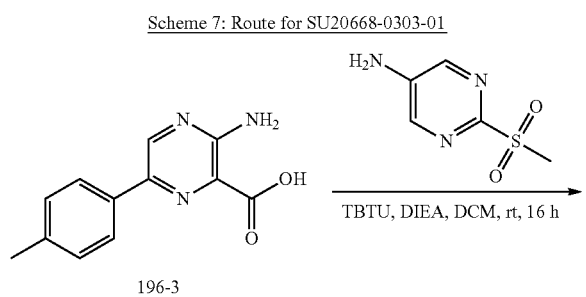

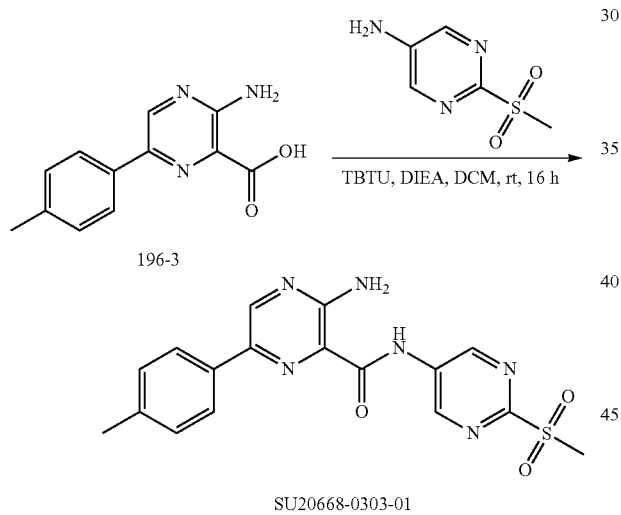

The Synthesis of 3-amino-N-(2-(methylsulfonyl)pyrimidin-5-yl)-6-p-tolylpyrazine-2-carboxamide (SU20668-0303-01)

To a solution of compound 196-3 (200 mg, 0.87 mmol) in DCM (4 mL) was added 2-(methylsulfonyl)pyrimidin-5-amine (151 mg, 0.87 mmol), DIEA (224 mg, 1.74 mmol) and TBTU (362 mg, 1.13 mmol). The resulting reaction mixture was stirred for 16 h at rt. Then the mixture was purified by prep-HPLC to give the desired product SU20668-0303-01 (40 mg, yield: 11.9%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 96.71%, Rt=1.959 min; MS Calcd.: 384.1; MS Found: 385.3 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 97.91%, Rt=8.924 min. $^1$H NMR (400 MHz, DMSO-d$_6$) δ11.02 (s, 1H), 9.49 (s, 2H), 8.98 (s, 1H), 8.15 (d, J=8.0 Hz, 2H), 7.70 (s, 2H), 7.32 (d, J=8.0 Hz, 2H), 3.42 (s, 3H), 2.38 (s, 3H).

Scheme 8: Route for SU20668-0304-01

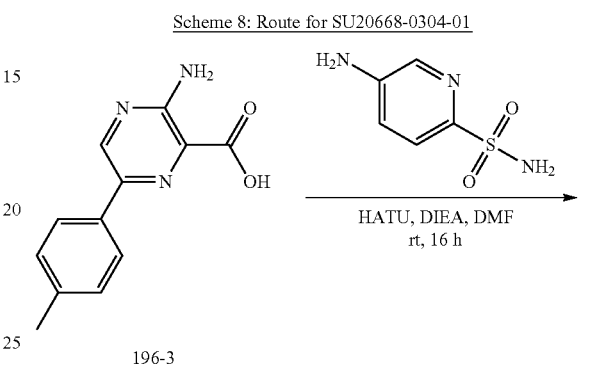

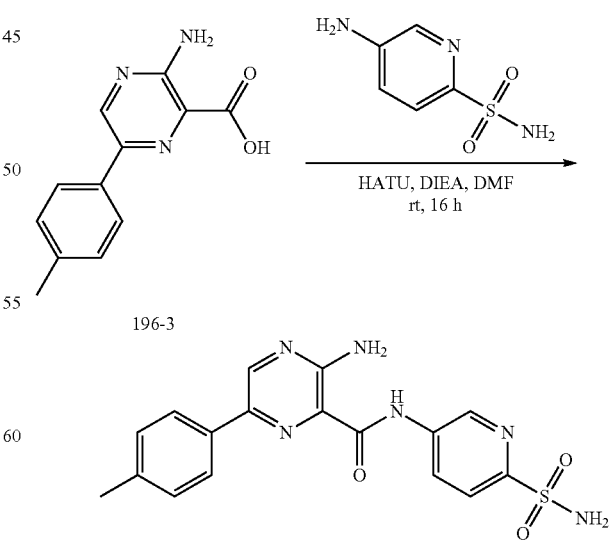

The Synthesis of 3-amino-N-(6-sulfamoylpyridin-3-yl)-6-p-tolylpyrazine-2-carboxamide (SU20668-0304-01)

To a solution of compound 196-3 (200 mg, 0.87 mmol) in DMF (4 mL) was added 5-aminopyridine-2-sulfonamide (151 mg, 0.87 mmol), DIEA (194 mg, 1.5 mmol) and HATU (430 mg, 1.13 mmol). The resulting reaction mixture was stirred for 16 h at rt. Then the mixture was purified by prep-HPLC to give the desired product SU20668-0304-01 (45 mg, yield: 13.4%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 99.27%, Rt=1.851 min; MS Calcd.: 384.1; MS Found: 385.0 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 96.03%, Rt=8.474 min. $^H$ NMR (400 MHz, DMSO-$d_6$) δ 10.82 (s, 1H), 9.14 (d, J=2.4 Hz, 1H), 8.94 (s, 1H), 8.48 (dd, J=8.4 Hz, 2.4 Hz, 1H), 8.14 (d, J=8.0 Hz, 2H), 7.97 (d, J=8.4 Hz, 1H), 7.66 (s, 2H), 7.43 (s, 2H), 7.31 (d, J=8.0 Hz, 2H), 2.37 (s, 3H).

Scheme 9: Route for SU20668-0305-01

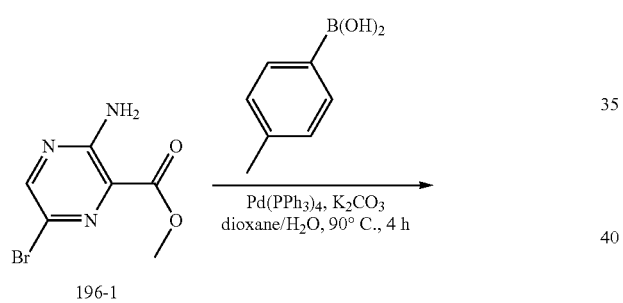

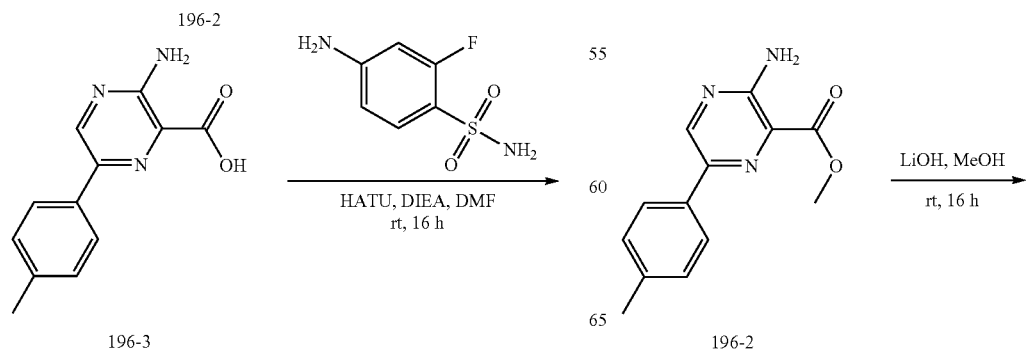

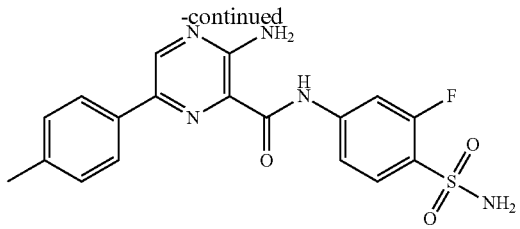

SU20668-0305-01

The Synthesis of methyl 3-amino-6-p-tolylpyrazine-2-carboxylate (196-2)

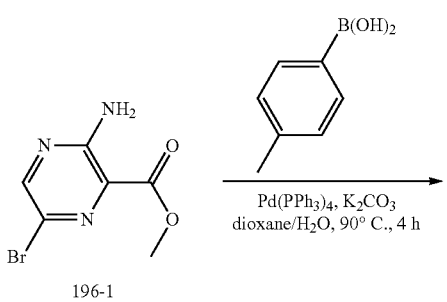

The mixture of 196-1 (16 g, 69 mmol), p-tolylboronic acid (11.3 g, 83 mmol), Pd(PPh$_3$)$_4$ (1.5 g, 1.3 mmol) and K$_2$CO$_3$ (19.3 g, 140 mmol) in dioxane/H$_2$O (200 mL, 4/1) was stirred at 90° C. under N$_2$ atmosphere for 4 hours. Then the mixture was concentrated to dryness. The residue was purified by silica-gel column (DCM) to give 196-2 (13 g, 77.6% yield) as a yellow solid.

The Synthesis of 3-amino-6-p-tolylpyrazine-2-carboxylic acid (196-3)

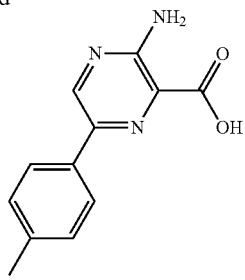

196-3

The mixture of 196-2 (13 g, 53.4 mmol) and LiOH (6.7 g, 160 mmol) in methanol (150 mL) was stirred at room temperature for 16 hours. Then the reaction mixture was concentrated to ~50 mL and acidified with HCl (1N) till pH=3~4. The solid was collected by filtration to afford 196-3 (10.5 g, yield: 86.1%) a yellow solid.

The Synthesis of 3-amino-N-(3-fluoro-4-sulfamoylphenyl)-6-p-tolylpyrazine-2-carboxamide (SU20668-0305-01)

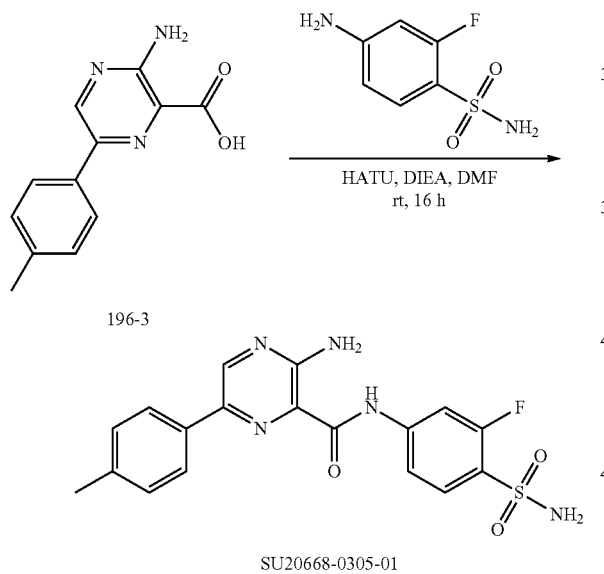

To a solution of compound 196-3 (200 mg, 0.87 mmol) in DMF (4 mL) was added 4-amino-2-fluorobenzenesulfonamide (166 mg, 0.87 mmol), DIEA (194 mg, 1.5 mmol) and HATU (430 mg, 1.13 mmol). The resulting reaction mixture was stirred for 16 h at rt. Then the mixture was purified by prep-HPLC to give the desired product SU20668-0305-01 (19 mg, yield: 5.4%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=1.970 min; MS Calcd.: 401.1; MS Found: 402.0 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 93.54%, Rt=9.235 min. $^1$H NMR (400 MHz, DMSO-d$_6$) δ 10.73 (s, 1H), 8.93 (s, 1H), 8.13 (d, J=8.4 Hz, 2H), 8.01 (dd, J=12.8 Hz, 1.6 Hz, 1H), 7.79-7.83 (m, 2H), 7.58-7.66 (m, 4H), 7.31 (d, J=8.0 Hz, 2H), 2.37 (s, 3H).

Scheme 10: Route for SU20668-0308-01

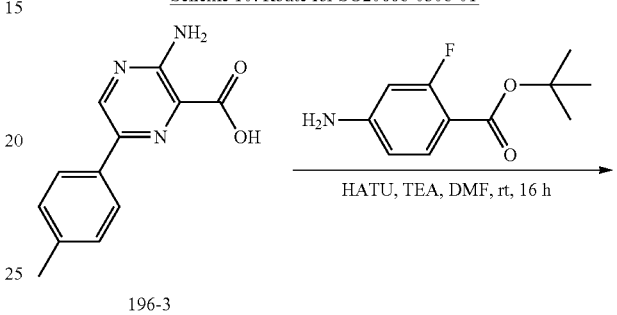

196-3

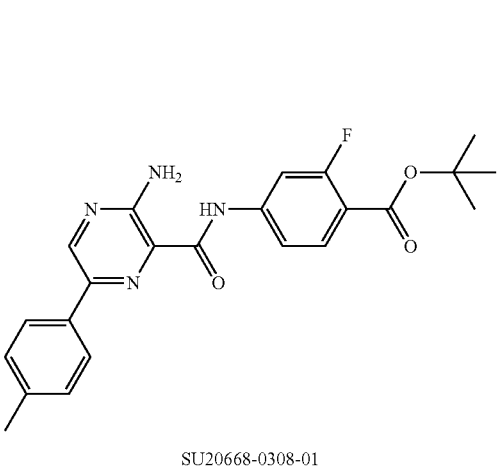

SU20668-0308-01

The Synthesis of tert-butyl 4-(3-amino-6-p-tolylpyrazine-2-carboxamido)-2-fluorobenzoate (SU20668-0308-01)

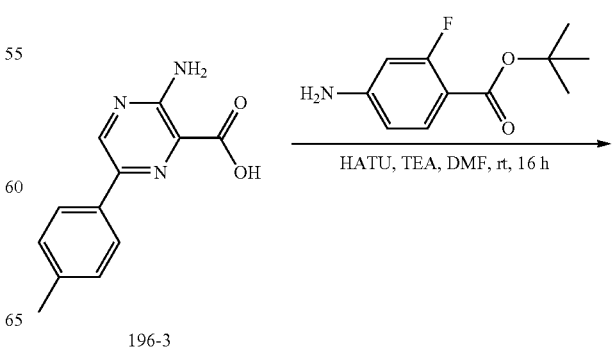

196-3

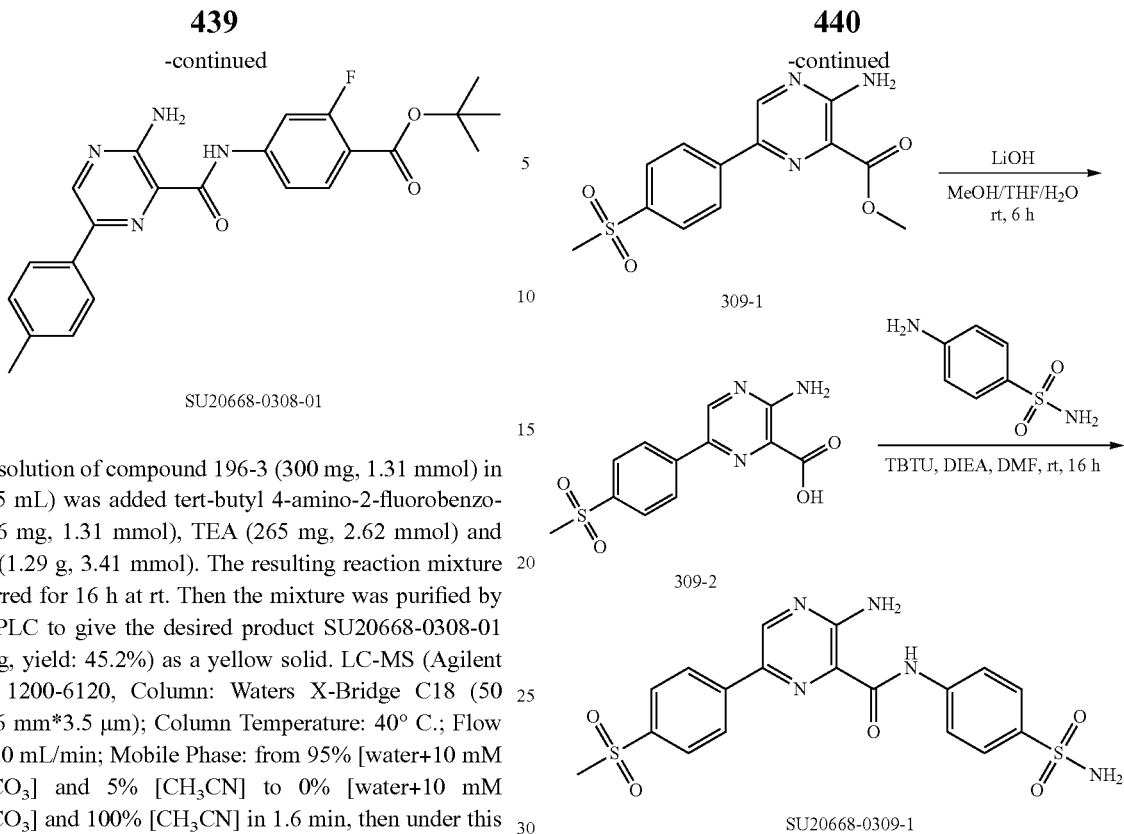

SU20668-0308-01

To a solution of compound 196-3 (300 mg, 1.31 mmol) in DMF (5 mL) was added tert-butyl 4-amino-2-fluorobenzoate (276 mg, 1.31 mmol), TEA (265 mg, 2.62 mmol) and HATU (1.29 g, 3.41 mmol). The resulting reaction mixture was stirred for 16 h at rt. Then the mixture was purified by prep-HPLC to give the desired product SU20668-0308-01 (250 mg, yield: 45.2%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 97.95%, Rt=2.574 min; MS Calcd.: 422.1; MS Found: 423.0 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 95.75%, Rt=12.226 min. $^1$H NMR (400 MHz, DMSO-$d_6$) δ 10.70 (s, 1H), 8.93 (s, 1H), 8.12 (d, J=8.0 Hz, 2H), 7.95 (dd, J=13.6 Hz, 1.6 Hz, 1H), 7.78-7.87 (m, 2H), 7.64 (s, 2H), 7.31 (d, J=8.0 Hz, 2H), 2.37 (s, 3H), 1.55 (s, 9H).

Scheme 11: Route for SU20668-0309-1

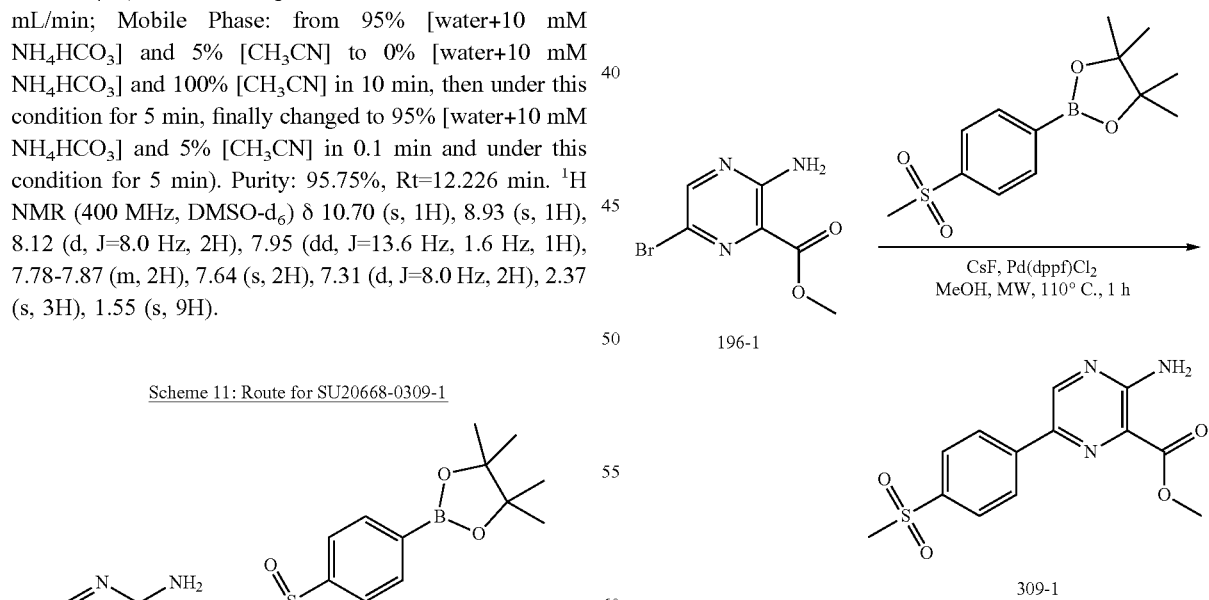

The Synthesis of methyl 3-amino-6-(4-(methylsulfonyl)phenyl)pyrazine-2-carboxylate (309-1)

The mixture of 196-1 (1.1 g, 4.8 mmol), 4,4,5,5-tetramethyl-2-(4-(methylsulfonyl)phenyl)-1,3,2-dioxaborolane (1.6 g, 5.7 mmol), Pd(dppf)Cl$_2$ (100 mg) and CsF (1.5 g, 9.6 mmol) in MeOH (10 mL). The resulting reaction mixture was irradiated with microwave radiation at 110° C. for 1 h under Ar atmosphere. Then mixture was concentrated to dryness. The residue was purified by silica-gel column (DCM) to give 309-1 (0.9 g, yield: 61.6%) as a yellow solid.

The Synthesis of 3-amino-6-(4-(methylsulfonyl) phenyl)pyrazine-2-carboxylic acid (309-2)

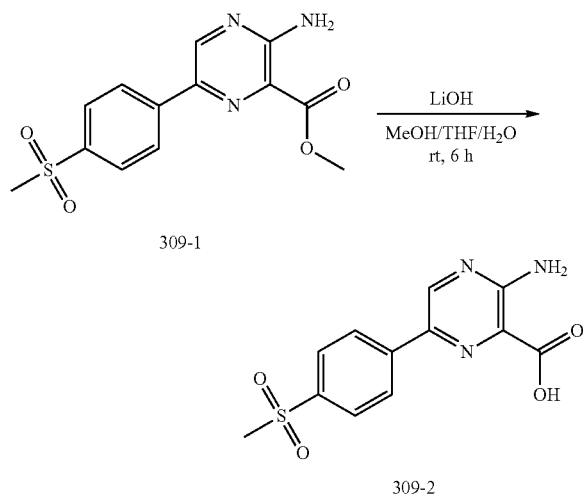

309-1

309-2

The mixture of 309-1 (900 mg, 2.93 mmol) and LiOH (369 mg, 8.79 mmol) in methanol/THF/H₂O (1:1:1, 15 mL) was stirred at room temperature for 6 hours. Then the reaction mixture was concentrated to ~5 mL and acidified with HCl (1N) till pH=3~4. The solid was collected by filtration to afford 309-2 (700 mg, yield: 81.4%) a yellow solid.

The Synthesis of 3-amino-6-(4-(methylsulfonyl) phenyl)-N-(4-sulfamoylphenyl)pyrazine-2-carboxamide (SU20668-0309-1)

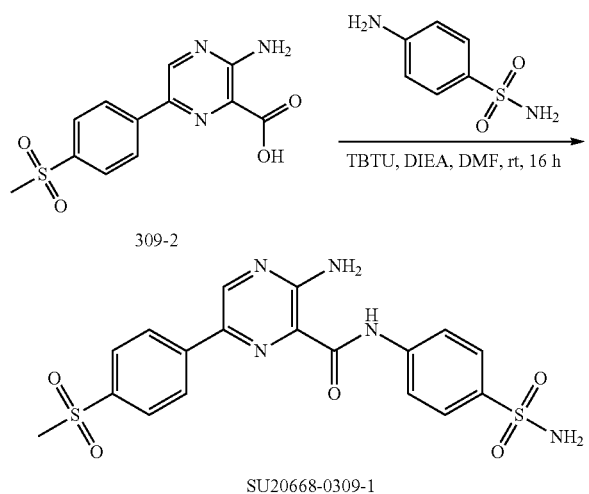

309-2

SU20668-0309-1

To a solution of compound 309-2 (300 mg, 1.02 mmol) in DMF (4 mL) was added 4-aminobenzenesulfonamide (176 mg, 1.02 mmol), DIEA (258 mg, 2.0 mmol) and TBTU (417 mg, 1.3 mmol). The resulting reaction mixture was stirred for 16 h at rt. Then the mixture was purified by prep-HPLC to give the desired product SU20668-0309-01 (13 mg, yield: 2.8%) as a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 98.69%, Rt=1.502 min; MS Calcd.: 447.0; MS Found: 465.2 [M+18]⁺. HPLC (Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min). Purity: 96.94%, Rt=7.045 min. ¹H NMR (400 MHz, DMSO-d₆) δ10.69 (bs, 1H), 9.06 (s, 1H), 8.51 (d, J=8.4 Hz, 2H), 8.02 (t, J=8.0 Hz, 4H), 7.89 (s, 2H), 7.85 (d, J=6.8 Hz, 2H), 7.31 (s, 2H), 3.27 (s, 3H).

Scheme 12: Route for SU20668-0314-01

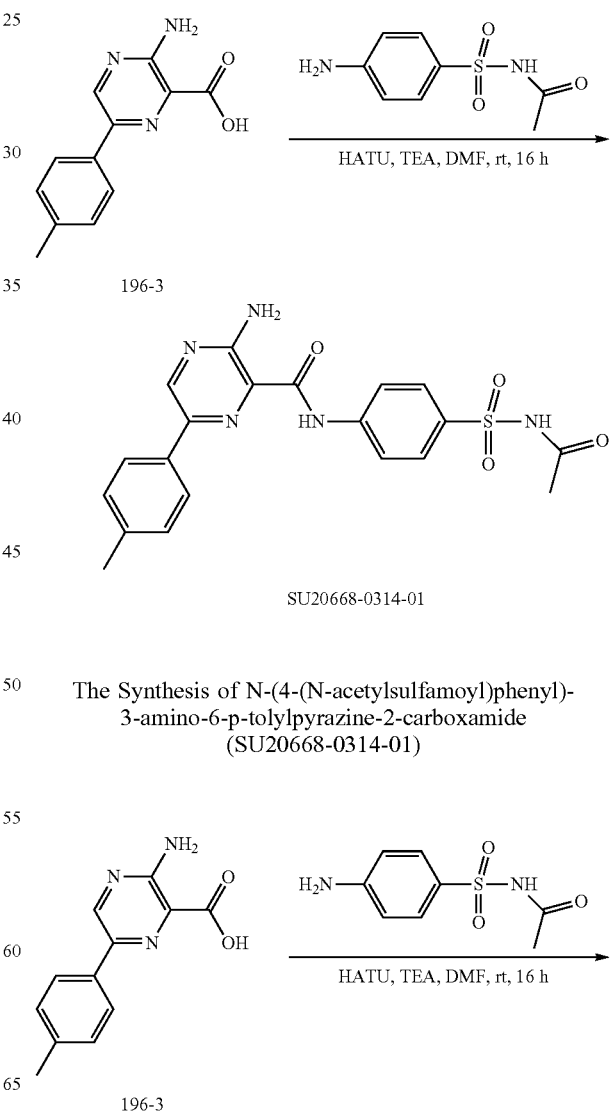

196-3

SU20668-0314-01

The Synthesis of N-(4-(N-acetylsulfamoyl)phenyl)-3-amino-6-p-tolylpyrazine-2-carboxamide (SU20668-0314-01)

196-3

443

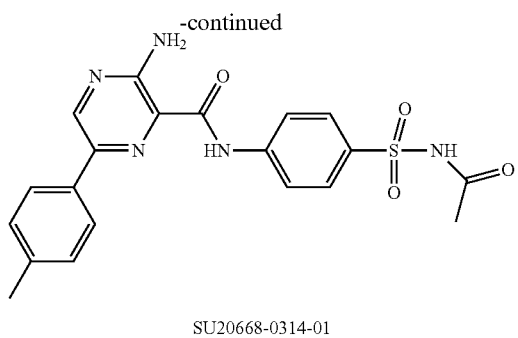

SU20668-0314-01

To a solution of compound 196-3 (120 mg, 0.52 mmol) in DMF (4 mL) was added N-(4-aminophenylsulfonyl)acetamide (112 mg, 0.52 mmol), TEA (101 mg, 1.0 mmol) and HATU (256 mg, 0.67 mmol). The resulting reaction mixture was stirred for 16 h at rt. Then the mixture was purified by prep-HPLC to give the desired product SU20668-0314-01 (30 mg, yield: 13.5%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 98.31%, Rt=1.556 min; MS Calcd.: 425.1; MS Found: 426.0 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 99.33%, Rt=6.800 min. $^1$H NMR (400 MHz, DMSO-d$_6$) δ12.04 (bs, 1H), 10.67 (s, 1H), 8.92 (s, 1H), 8.11 (d, J=8.4 Hz, 2H), 8.04 (d, J=8.8 Hz, 2H), 7.90 (d, J=9.2 Hz, 2H), 7.64 (s, 2H), 7.31 (d, J=8.0 Hz, 2H), 2.37 (s, 3H), 1.89 (s, 3H).

Scheme 13: Route for SU20668-0317-01

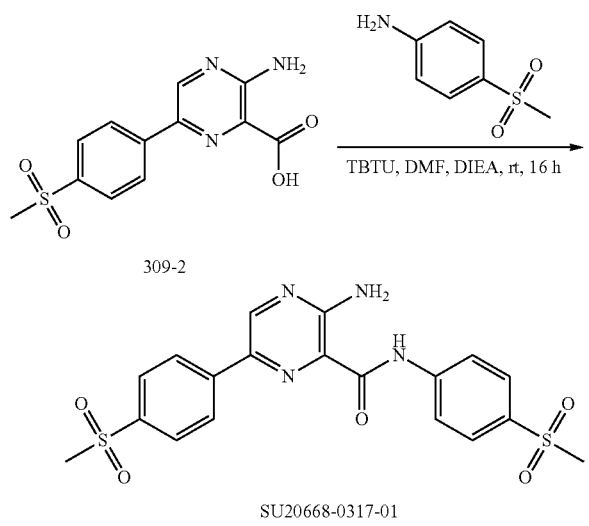

444

The Synthesis of methyl 3-amino-N,6-bis(4-(methylsulfonyl)phenyl)pyrazine-2-carboxamide (SU20668-0317-01)

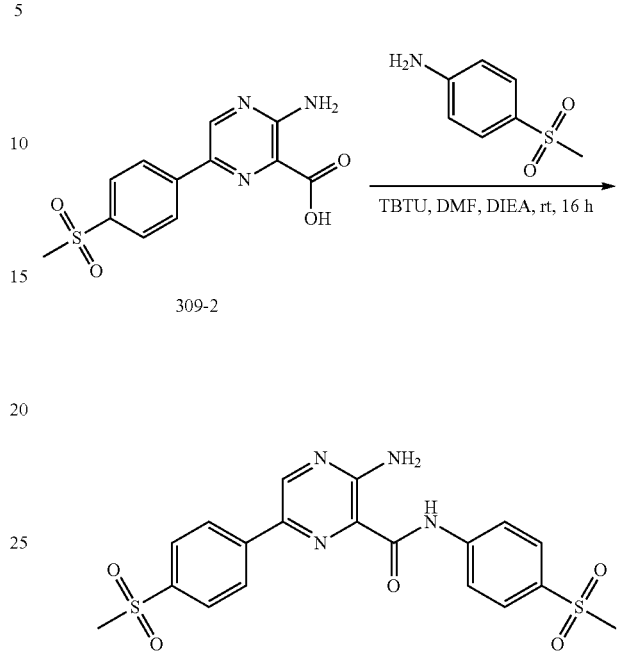

To a solution of compound 309-2 (230 mg, 0.78 mmol) in DMF (4 mL) was added 4-(methylsulfonyl)aniline (134 mg, 0.78 mmol), DIEA (206 mg, 1.6 mmol) and TBTU (321 mg, 1.0 mmol). The resulting reaction mixture was stirred for 16 h at rt. Then the mixture was purified by prep-HPLC to give the desired product SU20668-0317-01 (245 mg, yield: 70%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 99.43%, Rt=1.754 min; MS Calcd.: 446.0; MS Found: 464.2 [M+18]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 99.27%, Rt=7.672 min. $^1$H NMR (400 MHz, DMSO-d$_6$) δ10.77 (s, 1H), 9.07 (s, 1H), 8.51 (d, J=8.8 Hz, 2H), 8.13 (d, J=6.8 Hz, 2H), 8.02 (d, J=8.4 Hz, 2H), 7.96 (d, J=8.0 Hz, 2H), 7.89 (s, 2H), 3.27 (s, 3H), 3.22 (s, 3H).

Scheme 14: Route for SU20668-0339-01

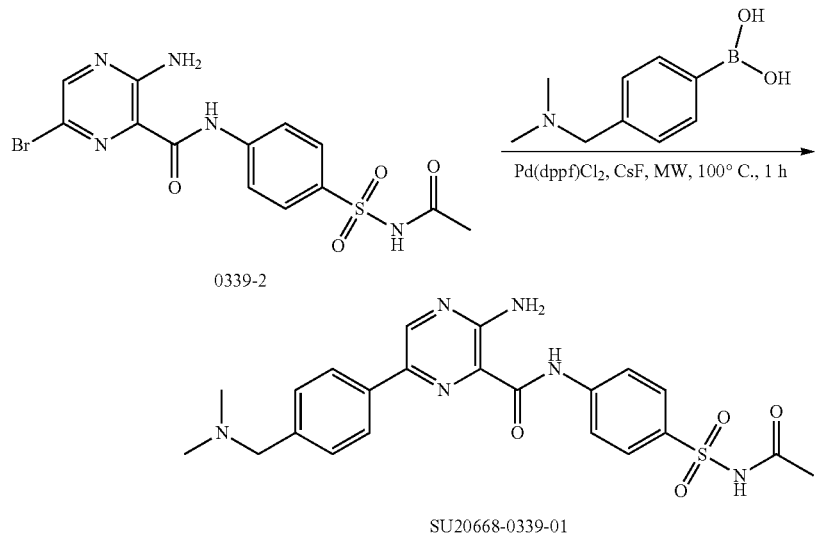

The Synthesis of N-(4-(N-acetylsulfamoyl)phenyl)-3-amino-6-(4-((dimethylamino)methyl)phenyl)pyrazine-2-carboxamide (SU20668-0339-01)

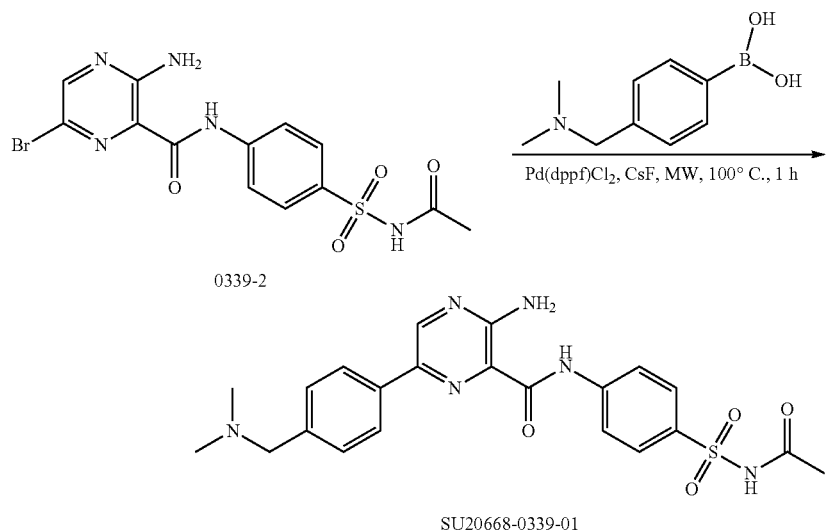

To a stirred solution of compound 0339-2 (140 mg, 0.34 mmol), 4-((dimethylamino)methyl)phenylboronic acid (74 mg, 0.41 mmol) and CsF (120 mg, 1 mmol) in MeOH (4 mL) was added Pd(dppf)Cl$_2$ (10%, 25 mg). The resulting reaction mixture was irradiated with microwave radiation at 100° C. for 1 h under Ar atmosphere (1.0 atm). After the consumption of starting material (by LCMS), the mixture was filtered, and the filtrate was concentrated in vacuo, purified by prep-HPLC to give the desired product SU20668-0339-01 (75 mg, yield: 46.8%) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 100%, Rt=1.285 min; MS Calcd.: 468.2; MS Found: 469.2 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 98.09%, Rt=5.578 min. $^1$H NMR (400 MHz, DMSO-d$_6$) δ 10.67 (s, 1H), 8.95 (s, 1H), 8.21 (d, J=8.4 Hz, 2H), 8.02 (d, J=8.8 Hz, 2H), 7.88 (d, J=8.4 Hz, 2H), 7.69 (s, 2H), 7.45 (d, J=8.0 Hz, 2H), 3.66 (s, 2H), 2.32 (s, 6H), 1.87 (s, 3H).

Scheme 15: Route for SU20668-0375

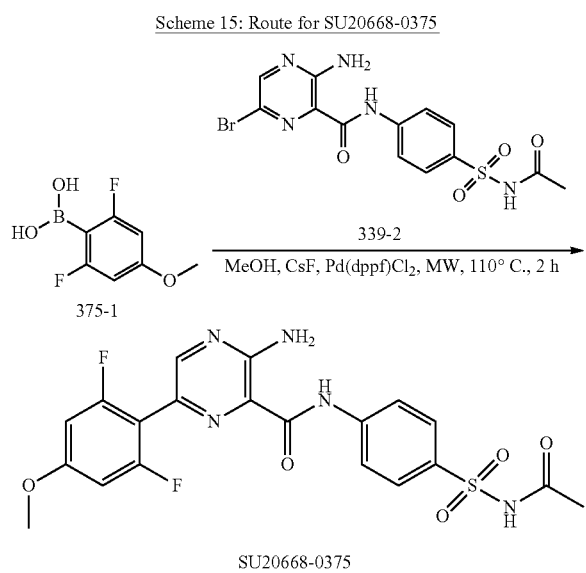

The Synthesis of N-(4-(N-acetylsulfamoyl)phenyl)-3-amino-6-(2,6-difluoro-4-methoxyphenyl)pyrazine-2-carboxamide (SU20668-0375)

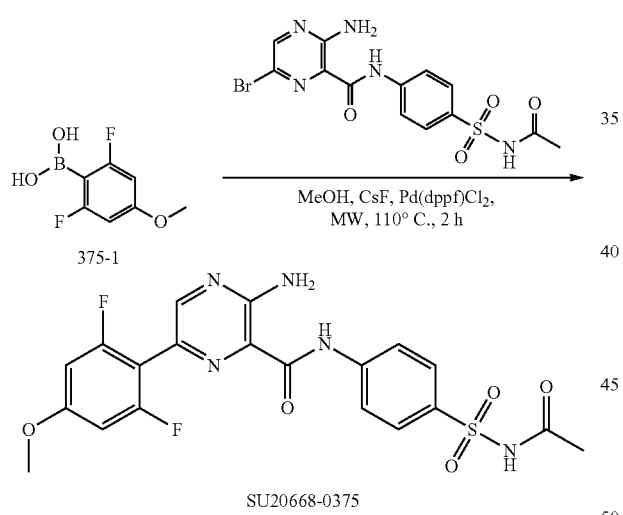

To a stirred solution of compound 375-1 (109 mg, 0.58 mmol) in MeOH (3 mL) was added 339-2 (200 mg, 0.48 mmol), CsF (182 mg, 1.2 mmol), Pd(dppf)Cl$_2$ (21 mg, 0.05 mmol). The resulting reaction mixture was heated to 120° C. in M.W. and stirred for 2 h and concentrated in vacuo to remove the solvent, then added water, the aqueous phase was extracted with dichloromethane, the combined organic phases were dried over anhydrous sodium sulfate, filtered, and concentrated, the crude was purified by prep-HPLC to give the desired product SU20668-0375 (31 mg, yield: 11.2%) as a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100.00%, Rt=1.671 min; MS Calcd.: 477.09; MS Found: 478.2 [M+H]$^+$. HPLC (Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 98.96%, Rt=6.967 min. $^1$H NMR (400 MHz, DMSO-d$_6$) δ 8.44 (s, 1H), 8.00 (d, J=8.8 Hz, 2H), 7.90 (d, J=8.8 Hz, 2H), 6.90 (d, J=9.6 Hz, 2H), 3.85 (s, 3H), 1.93 (s, 3H).

Scheme 16: Route for SU20668-0376-01

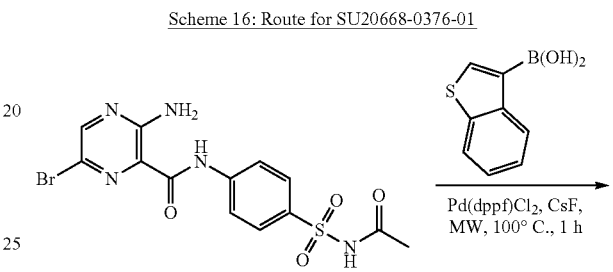

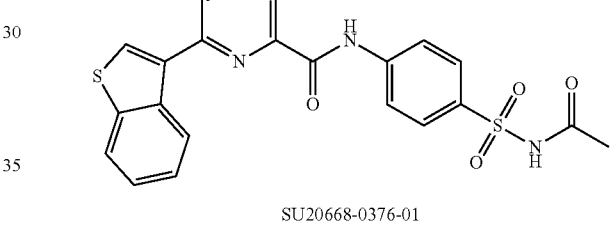

The Synthesis of N-(4-(N-acetylsulfamoyl)phenyl)-3-amino-6-(benzo[b]thiophen-3-yl)pyrazine-2-carboxamide (SU20668-0376-01)

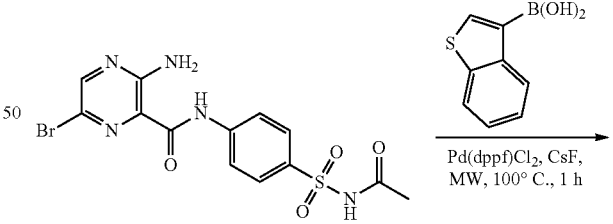

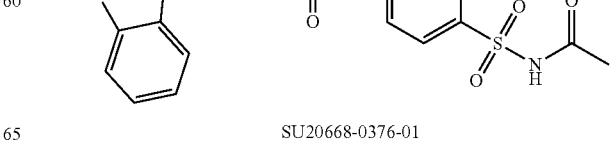

To a stirred solution of compound 0339-2 (140 mg, 0.34 mmol), benzo[b]thiophen-3-ylboronic acid (73 mg, 0.41 mmol) and CsF (150 mg, 1.02 mmol) in MeOH (4 mL) was added Pd(dppf)Cl$_2$ (10%, 25 mg). The resulting reaction mixture was irradiated with microwave radiation at 100° C. for 1 h under Ar atmosphere. After the consumption of starting material (by LCMS), the mixture was filtered, and the filtrate was concentrated in vacuo, purified by prep-HPLC to give the desired product SU20668-0376 (46 mg, 29% yield) as a yellow solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 98.98%, Rt=1.698 min; MS Calcd.: 467.52; MS Found: 468.3 [M+H]$^+$. Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 96.15%, Rt=7.202 min. $^1$H NMR (400 MHz, DMSO-d$_6$) δ 10.59 (s, 1H), 8.84 (s, 1H), 8.43 (d, J=8.0 Hz, 1H), 8.38 (s, 1H), 8.10 (d, J=7.6 Hz, 1H), 7.96 (d, J=8.8 Hz, 2H), 7.86 (d, J=8.8 Hz, 2H), 7.72 (s, 2H), 7.44-7.54 (m, 2H), 1.85 (s, 3H).

Scheme 17: Route for SU20668-0377

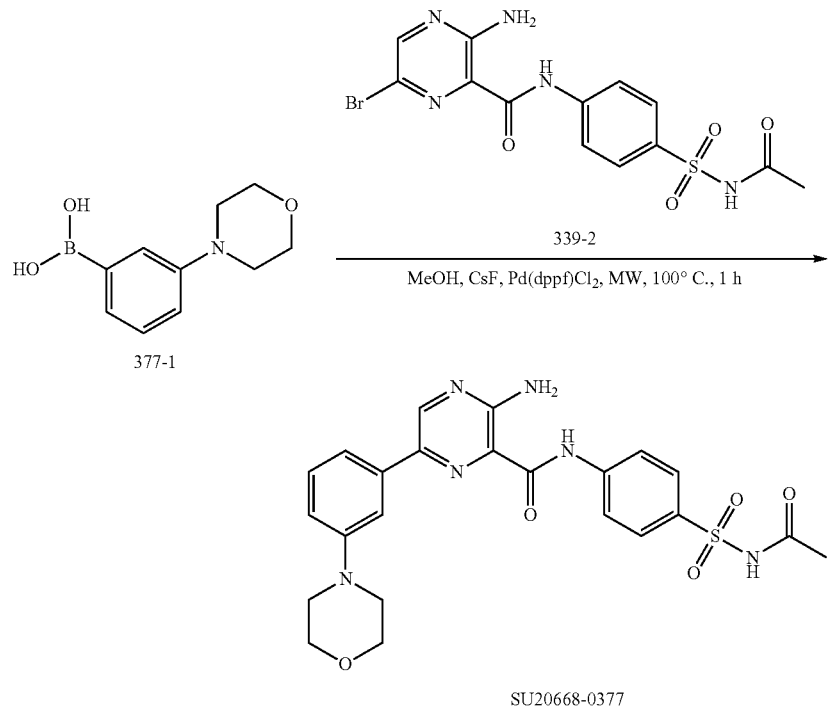

SU20668-0377

The Synthesis of N-(4-(N-acetylsulfamoyl)phenyl)-3-amino-6-(3-morpholinophenyl)pyrazine-2-carboxamide (SU20668-0377)

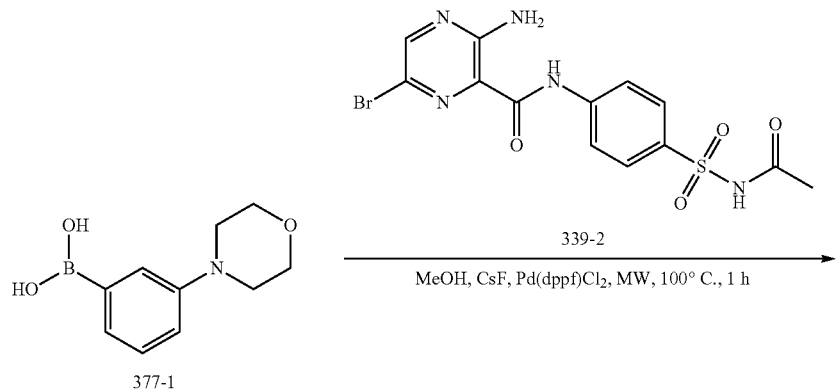

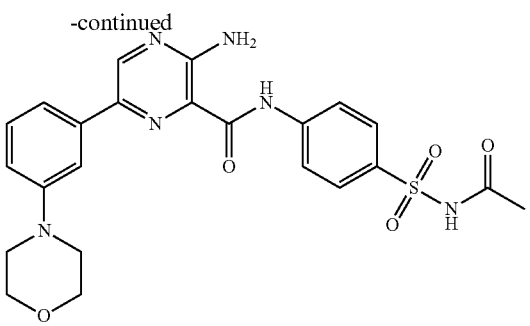

SU20668-0377

To a stirred solution of compound 377-1 (120 mg, 0.58 mmol) in MeOH (3 mL) was added 339-2 (200 mg, 0.48 mmol), CsF (182 mg, 1.2 mmol), Pd(dppf)Cl$_2$ (21 mg, 0.05 mmol). The resulting reaction mixture was heated to 100° C. in M.W. and stirred for 1 h and concentrated in vacuo to remove the solvent, then added water, the aqueous phase was extracted with dichloromethane, the combined organic phases were dried over anhydrous sodium sulfate, filtered, and concentrated, the crude was purified by prep-HPLC to give the desired product SU20668-0377 (35 mg, yield: 12.2%) as a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 98.01%, Rt=1.566 min; MS Calcd.: 496.15; MS Found: 497.3 [M+H]$^+$. HPLC (Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 98.24%, Rt=6.554 min. $^1$H NMR (400 MHz, DMSO-d$_6$) δ 12.06 (s, 1H), 10.71 (s, 1H), 8.95 (s, 1H), 8.02 (d, J=8.8 Hz, 2H), 7.89 (d, J=8.8 Hz, 2H), 7.64-7.69 (m, 4H), 7.35 (t, J=7.8 Hz, 1H), 6.99 (d, J=10.0 Hz, 1H), 3.77-3.80 (m, 4H), 3.23-3.26 (m, 4H), 1.88 (s, 3H).

Scheme 18: Route for SU20668-0390-01

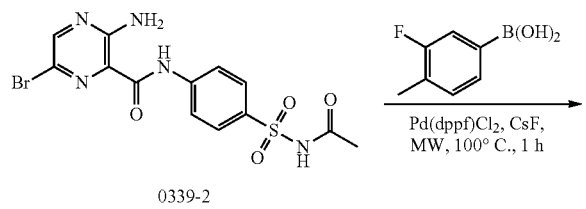

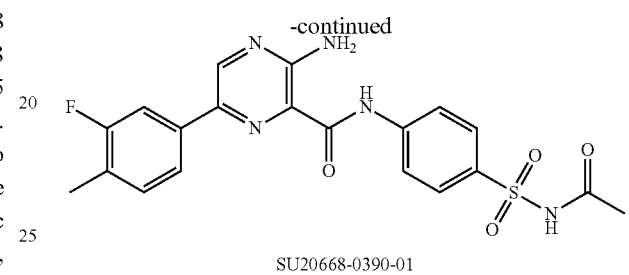

SU20668-0390-01

The Synthesis of N-(4-(N-acetylsulfamoyl)phenyl)-3-amino-6-(3-fluoro-4-methylphenyl)pyrazine-2-carboxamide (SU20668-0390-01)

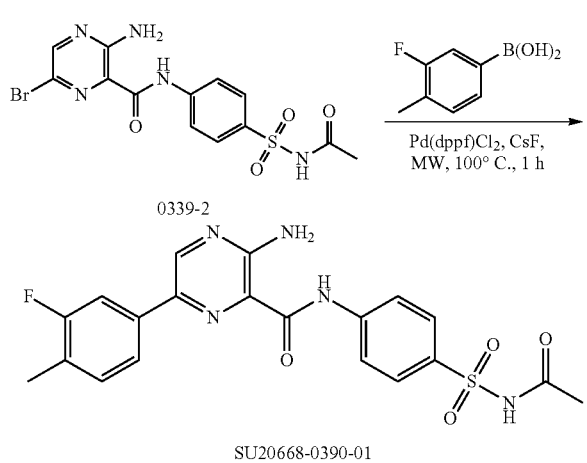

SU20668-0390-01

To a stirred solution of compound 0339-2 (140 mg, 0.34 mmol), 3-fluoro-4-methylphenylboronic acid (63 mg, 0.41 mmol) and CsF (150 mg, 1.02 mmol) in MeOH (4 mL) was added Pd(dppf)Cl$_2$ (10%, 25 mg). The resulting reaction mixture was irradiated with microwave radiation at 100° C. for 1 h under Ar atmosphere. After the consumption of starting material (by LCMS), the mixture was filtered, and the filtrate was concentrated in vacuo, purified by prep-HPLC to give the desired product SU20668-0390-01 (36 mg, 24% yield) as a yellow solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100%

[CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 99.92%, Rt=1.680 min; MS Calcd.: 443.45; MS Found: 444.2 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 98.29%, Rt=7.149 min. $^1$H NMR (400 MHz, DMSO-d$_6$) δ 10.69 (s, 1H), 8.97 (s, 1H), 8.13 (d, J=11.6 Hz, 1H), 8.03-7.94 (m, 3H), 7.89 (d, J=8.8 Hz, 2H), 7.75 (s, 2H), 7.39 (t, J=8.0 Hz, 1H), 2.29 (s, 3H), 1.87 (s, 3H).

Scheme 19: Route for SU20668-0391-01

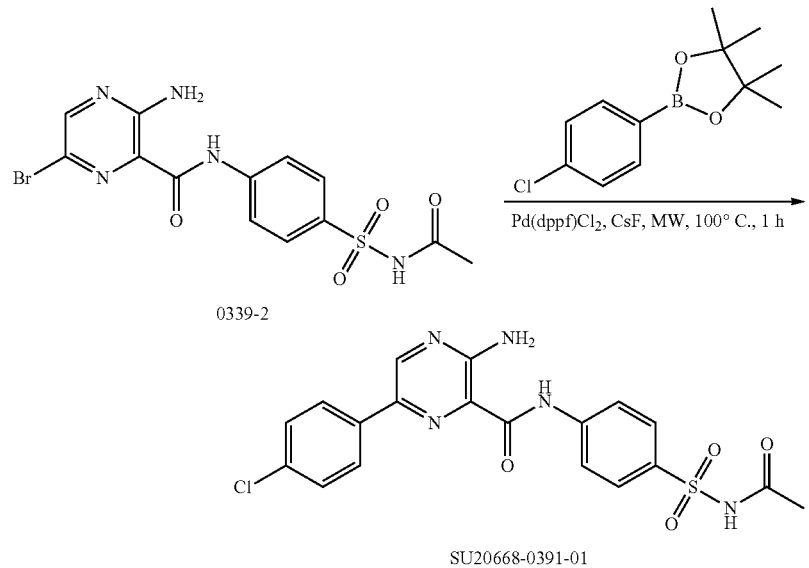

The Synthesis of N-(4-(N-acetylsulfamoyl)phenyl)-3-amino-6-(4-chlorophenyl)pyrazine-2-carboxamide (SU20668-0391-01)

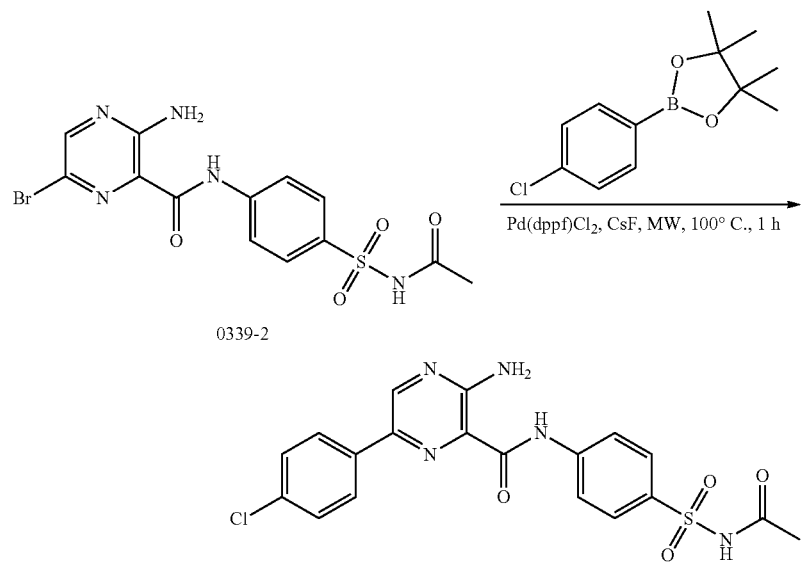

To a stirred solution of compound 0339-2 (140 mg, 0.34 mmol), 2-(4-chlorophenyl)-4,4,5,5-tetramethyl-1,3,2-dioxaborolane (98 mg, 0.41 mmol) and CsF (150 mg, 1.02 mmol) in MeOH (4 mL) was added Pd(dppf)Cl$_2$ (10%, 25 mg). The resulting reaction mixture was irradiated with microwave radiation at 100° C. for 1h under Ar atmosphere. After the consumption of starting material (by LCMS), the mixture was filtered, and the filtrate was concentrated in vacuo, purified by prep-HPLC to give the desired product SU20668-0391-01 (27 mg, 18% yield) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 99.30%, Rt=1.689 min; MS Calcd.: 445.88; MS Found: 446.2 [M+H]$^+$. Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 98.14%, Rt=7.161 min. $^1$H NMR (400 MHz, DMSO-d$_6$) δ 10.70 (s, 1H), 8.97 (s, 1H), 8.27-8.29 (m, 2H), 8.02 (d, J=8.8 Hz, 2H), 7.89 (d, J=8.8 Hz, 2H), 7.76 (s, 2H), 7.55 (d, J=8.8 Hz, 2H), 1.87 (s, 3H).

Scheme 20: Route for SU20668-0491-01

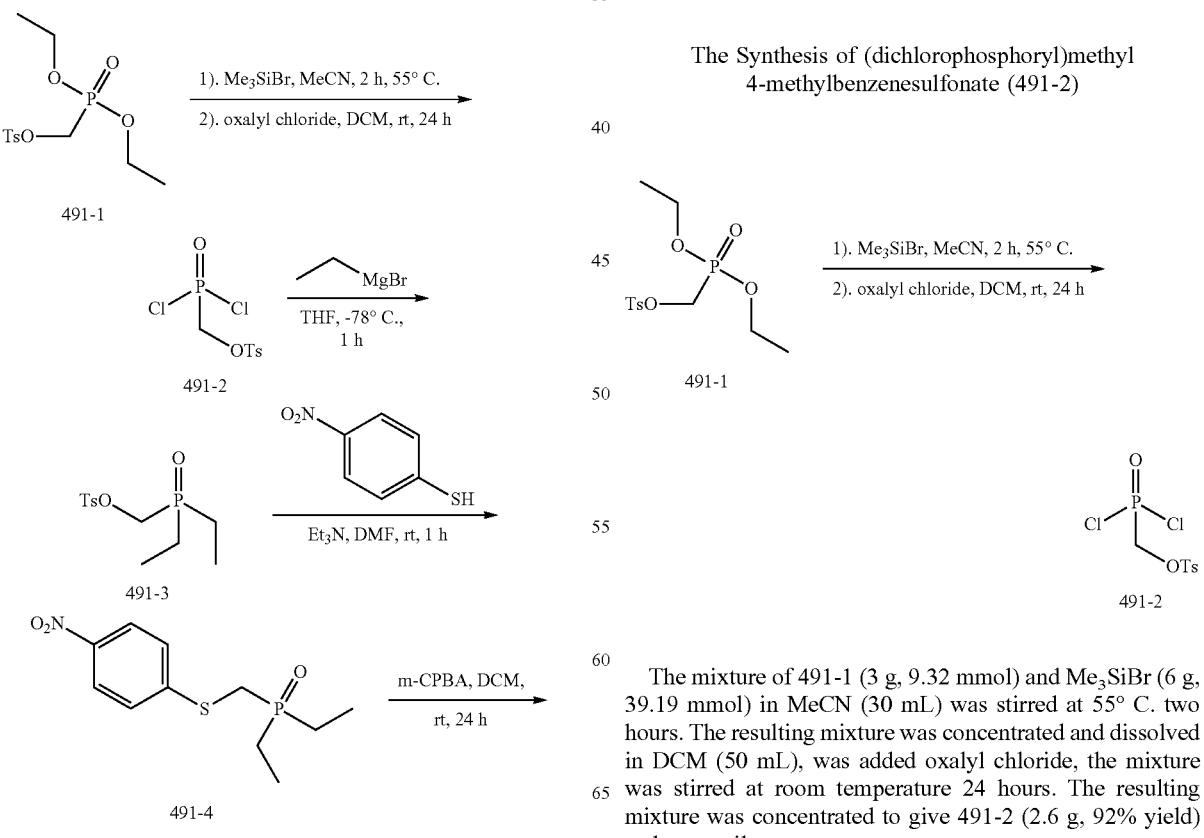

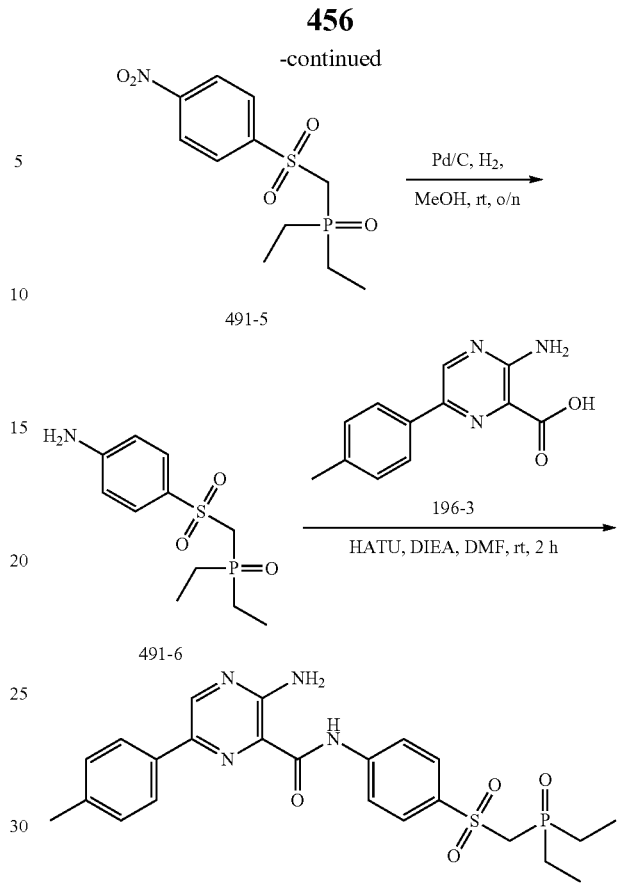

The Synthesis of (dichlorophosphoryl)methyl 4-methylbenzenesulfonate (491-2)

The mixture of 491-1 (3 g, 9.32 mmol) and Me$_3$SiBr (6 g, 39.19 mmol) in MeCN (30 mL) was stirred at 55° C. two hours. The resulting mixture was concentrated and dissolved in DCM (50 mL), was added oxalyl chloride, the mixture was stirred at room temperature 24 hours. The resulting mixture was concentrated to give 491-2 (2.6 g, 92% yield) as brown oil.

The Synthesis of (diethylphosphoryl)methyl 4-methylbenzenesulfonate (0491-3)

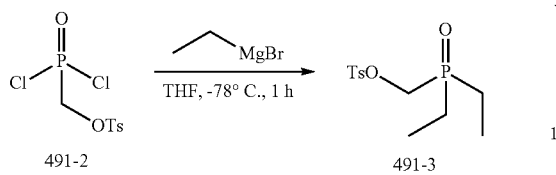

To a stirred solution of compound 491-2 (2.6 g, 8.58 mmol) in THF (20 mL) was added ethylmagnesium bromide (3M in ethyl ether, 21.00 mmol) at −78° C. The resulting reaction mixture was stirred for 1 h, then added water, the aqueous phase was extracted with EA, the combined organic phases were dried over anhydrous sodium sulfate, filtered, and concentrated, the crude was purified by prep-HPLC to give the desired product 491-3 (2.2 g, yield: 88%) as yellow oil.

The Synthesis of 1-(diethylphosphorylmethylsulfanyl)-4-nitro-benzene (491-4)

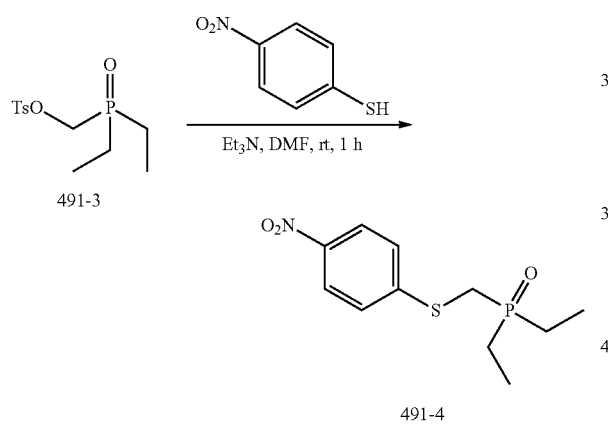

To a stirred solution of 491-3 (2.2 g, 7.58 mmol) in DMF (10 ml) was added 4-nitrobenzenethiol (1.3 g, 8.38 mmol) and TEA (1.09 g, 10.76 mmol). The resulting reaction mixture was stirred for 1 h at rt. Then added water, the aqueous phase was extracted with EA, the combined organic phases were dried over anhydrous sodium sulfate, filtered, and concentrated in vacuo to give the desired product 491-4 (2.0 g, yield: 96.57%) as yellow oil.

The Synthesis of methyl 1-(diethylphosphorylmethylsulfonyl)-4-nitro-benzene (491-5)

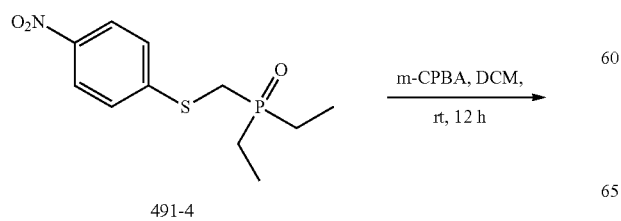

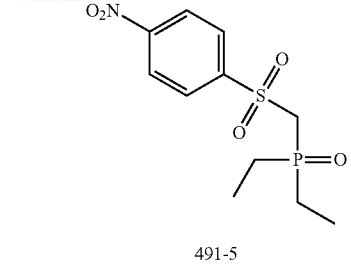

To a stirred solution of compound 491-4 (1 g, 3.66 mmol) in DCM (10 mL) was added 3-chlorobenzenecarboperoxoic acid (1.5 g, 8.69 mmol) at 0° C. The resulting reaction mixture was further stirred for 12 h at rt, then added water and $Na_2SO_3$. The aqueous phase was extracted with EA, the combined organic phases were dried over anhydrous sodium sulfate, filtered, and concentrated, the crude was purified by prep-HPLC to give the desired product 491-5 (500 mg, yield: 44.76%) as yellow oil.

The Synthesis of 4-(diethylphosphorylmethylsulfonyl)aniline (491-6)

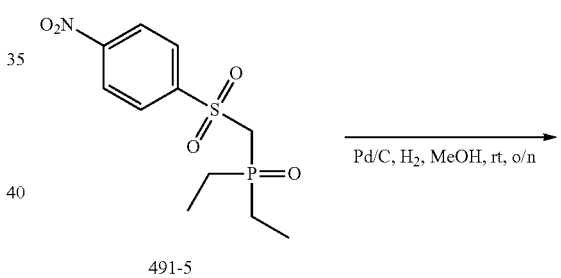

To a solution of 491-5 (500 mg, 1.64 mmol) in MeOH (5 mL) was added Pd/C (10%, 50 mg), the mixture was stirred at rt for o/n under $H_2$ atmosphere (1.0 atm). The mixture was filtered and concentrated in vacuo to give crude product, which was purified by pre-HPLC to afford compound 491-6 (150 mg, yield: 33.22%) as a yellow solid.

459

The Synthesis of 3-amino-N-(4-((diethylphosphoryl)methylsulfonyl)phenyl)-6-p-tolylpyrazine-2-carboxamide (SU20668-0491)

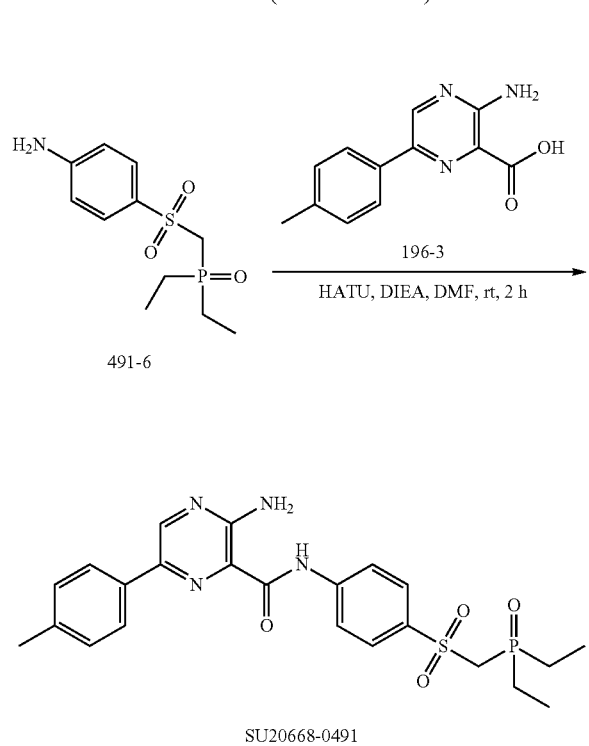

To a solution of compound 491-6 (150 mg, 0.54 mmol) in DMF (2 mL) was added 196-3 (150 mg, 0.65 mmol), DIEA (200 mg, 1.55 mmol) and HATU (249 mg, 0.65 mmol). The resulting reaction mixture was stirred for 2 h at rt, then added water, the aqueous phase was extracted with EA, the combined organic phases were dried over anhydrous sodium sulfate, filtered, and concentrated, the crude was purified by prep-HPLC to give the desired product SU20668-0491 (33 mg, yield: 12%) as a yellow solid. LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 5% [water+0.05% TFA] and 95% [water+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min). Purity: 99.53%, Rt=1.945 min; MS Calcd.: 486.1; MS Found: 487.0 [M+H]$^+$. HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 5% [water+0.05% TFA] and 95% [water+0.05% TFA] in 10 min, then under this condition for 5 min, finally changed to 95% [water+0.05% TFA] and 5% [CH$_3$CN+0.05% TFA] in 0.1 min and under this condition for 5 min). Purity:100.00%, Rt=9.306 min. $^1$H NMR (400 MHz, DMSO-d$_6$) δ 10.70 (s, 1H), 8.91 (s, 1H), 8.07-8.12 (m, 4H), 7.95 (d, J=8.8 Hz, 2H), 7.64 (s, 2H), 7.29 (d, J=8.0 Hz, 2H), 4.21 (d, J=10.4 Hz, 2H), 2.35 (s, 1H), 1.80-1.89 (m, 4H), 1.00-1.09 (m, 6H).

460

Scheme 21: Route for SU20668-0292-01

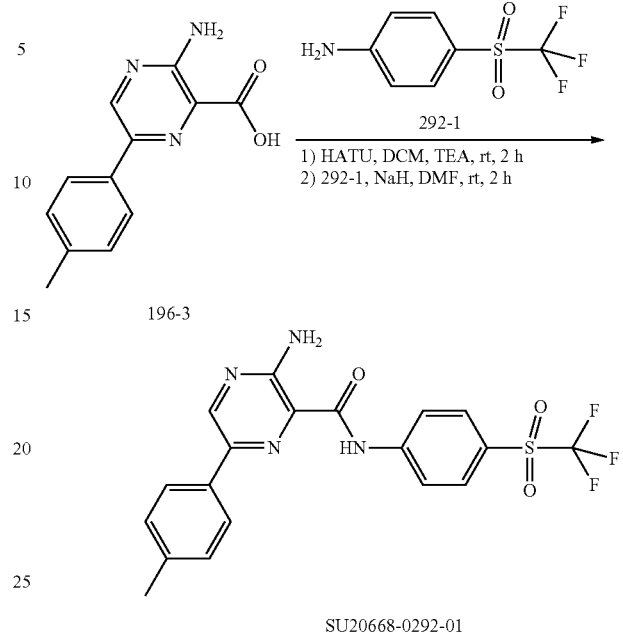

The Synthesis of 3-amino-6-p-tolyl-N-(4-(trifluoromethylsulfonyl)phenyl)pyrazine-2-carboxamide (SU20668-0292-01)

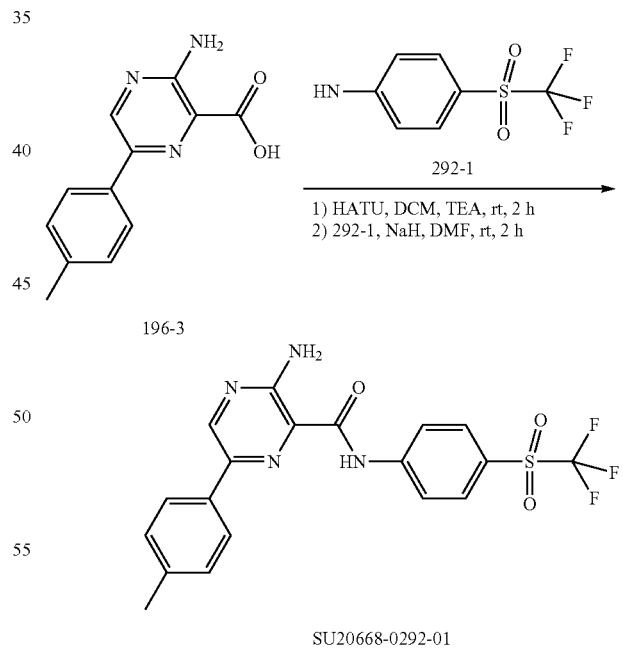

Step 1: To a solution of 196-3 (200 mg, 0.87 mmol) in DCM (5.0 mL) was added HATU (380 mg, 1.0 mmol) and TEA (200 mg, 2.0 mmol). The resulting reaction mixture was stirred for 2 h at rt, then it was concentrated to dryness. Step 2: To a solution of 292-1 (225 mg, 1.00 mmol) in DMF (4 mL) was added NaH (50 mg, 1.25 mmol) and the mixture was stirred at rt for 2 hours. Then the reaction mixture was added the crude intermediate from step 1 and further stirred for 2 h at rt. The reaction mixture was purified by prep-HPLC to give the desired product SU20668-0292-01 (35 mg, yield: 9.2%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 96.65%, Rt=2.426 min; MS Calcd.: 436.0; MS Found: 436.9 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 95.92%, Rt=11.542 min. $^1$H NMR (400 MHz, DMSO-d$_6$) δ10.96 (s, 1H), 8.95 (s, 1H), 8.33 (d, J=8.8 Hz, 2H), 8.14 (t, J=9.2 Hz, 4H), 7.67 (s, 2H), 7.31 (d, J=8.0 Hz, 2H), 2.37 (s, 3H).

Scheme 22: Route for SU20668-0310

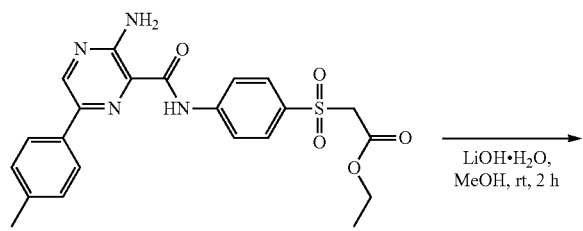

SU20668-0311

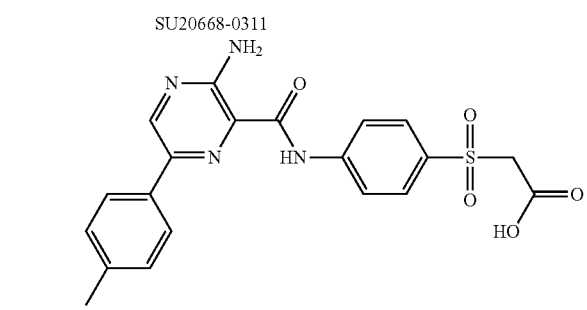

SU20668-0310

The Synthesis of 2-(4-(3-amino-6-p-tolylpyrazine-2-carboxamido)phenylsulfonyl)acetic acid (SU20668-0310)

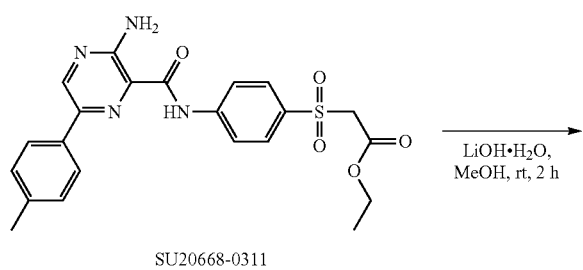

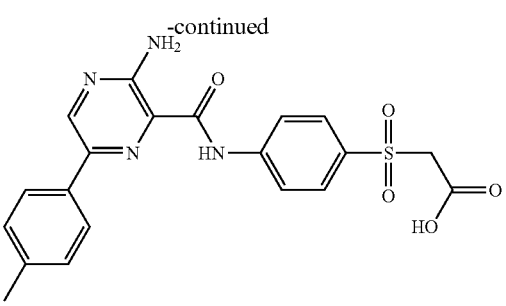

SU20668-0310

To a solution of SU20668-0311 (30 mg, 0.066 mmol) in MeOH (3 mL) was added LiOH·H$_2$O (28 mg, 0.66 mmol), the mixture was stirred at rt for 2 h. The mixture was cooled to 0° C. and acidified with 1N HCl solution to pH=4.0. After the reaction mixture was filtered and washed with H$_2$O. Then concentrated in vacuo to give SU20668-0310 (12 mg, 43% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min), Purity: 94.97%, Rt=1.572 min; MS Calcd.: 426.1; MS Found: 427.0 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min), Purity: 97.29%, Rt=6.878 min. $^1$H NMR (400 MHz, DMSO-d$_6$) δ 13.52 (brs., 1H), 10.73 (s, 1H), 8.93 (s, 1H), 8.11-8.14 (m, 4H), 7.93 (d, J=8.8 Hz, 2H), 7.66 (s., 2H), 7.32 (d, J=8.0 Hz, 2H), 4.46 (s, 2H), 2.37 (s, 3H).

Scheme 23: Route for SU20668-0311

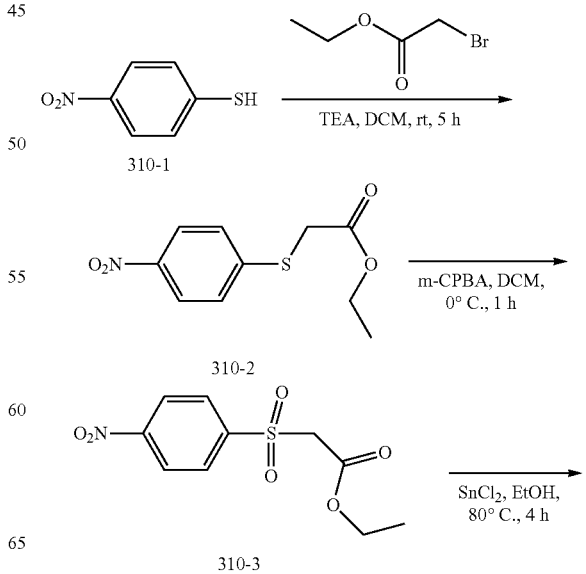

463

-continued

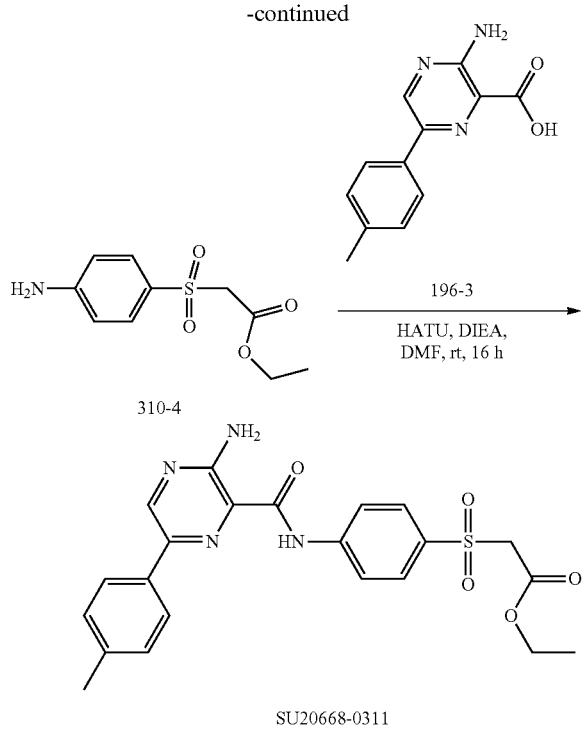

310-4

196-3
HATU, DIEA,
DMF, rt, 16 h

SU20668-0311

The Synthesis of ethyl 2-(4-nitrophenylthio)acetate (310-2)

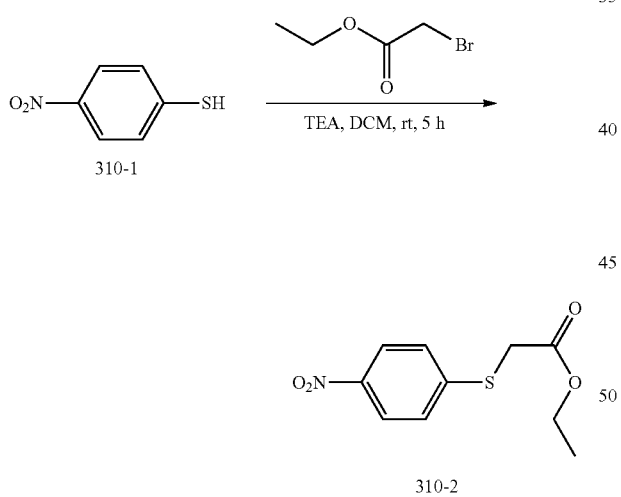

310-1 ethyl 2-bromoacetate
TEA, DCM, rt, 5 h 310-2

To a stirred solution of 310-1 (3.0 g, 19.4 mmol) in DCM (20 ml) was added ethyl 2-bromoacetate (3.54 g, 21.3 mmol) and TEA (5.88 g, 58.2 mmol). The resulting reaction mixture was stirred for 5 h at rt. Then added water, the aqueous phase was extracted with EA, the combined organic phases were dried over anhydrous sodium sulfate, filtered, and concentrated in vacuo to give the desired product 310-2 (4.0 g, yield: 91%) as a yellow solid.

464

The Synthesis of ethyl 2-(4-nitrophenylsulfonyl)acetate (310-3)

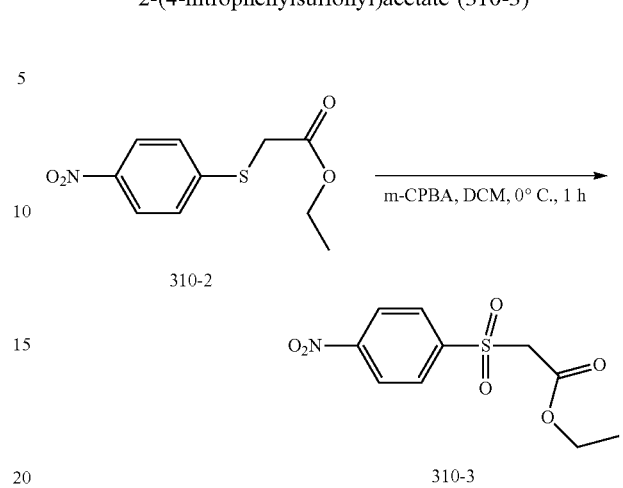

310-2 m-CPBA, DCM, 0° C., 1 h 310-3

To a stirred solution of compound 310-2 (4.0 g, 16.6 mmol) in DCM (40 mL) was added 3-chlorobenzenecarboperoxoic acid (11.5 g, 66.3 mmol) at 0° C. The resulting reaction mixture was further stirred for 1 h at 0° C., then added water and aq. $Na_2S_2O_5$. The aqueous phase was extracted with DCM, the combined organic phases were dried over anhydrous sodium sulfate, filtered, and concentrated, the crude was purified by prep-HPLC to give the desired product 310-3 (3.6 g, yield: 79%) as a yellow solid.

The Synthesis of ethyl 2-(4-aminophenylsulfonyl)acetate (310-4)

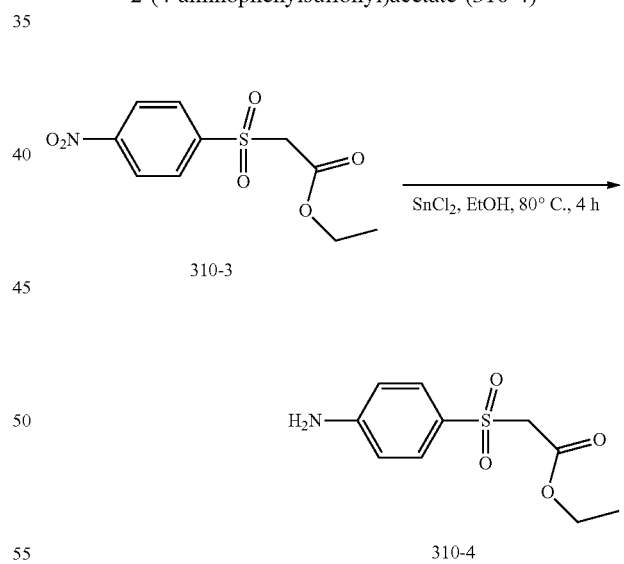

310-3

$SnCl_2$, EtOH, 80° C., 4 h 310-4

To a stirred solution of compound 310-3 (1.8 g, 6.59 mmol) in EtOH (20 mL) was added $SnCl_2$ (1.7 g, 29.7 mmol). The resulting reaction mixture was further stirred for 4 h at 80° C., then cooled to rt. The solvent was removed. The residue was partitioned between EA and water. The organic layer was separated. The aqueous phase was extracted with EA, the combined organic phases were dried over anhydrous sodium sulfate, filtered, and concentrated, the crude was purified by prep-HPLC to give the desired product 310-4 (1.2 g, yield: 75%) as a yellow solid.

465

The Synthesis of ethyl 2-(4-(3-amino-6-p-tolylpyrazine-2-carboxamido)phenylsulfonyl)acetate (SU20668-0311)

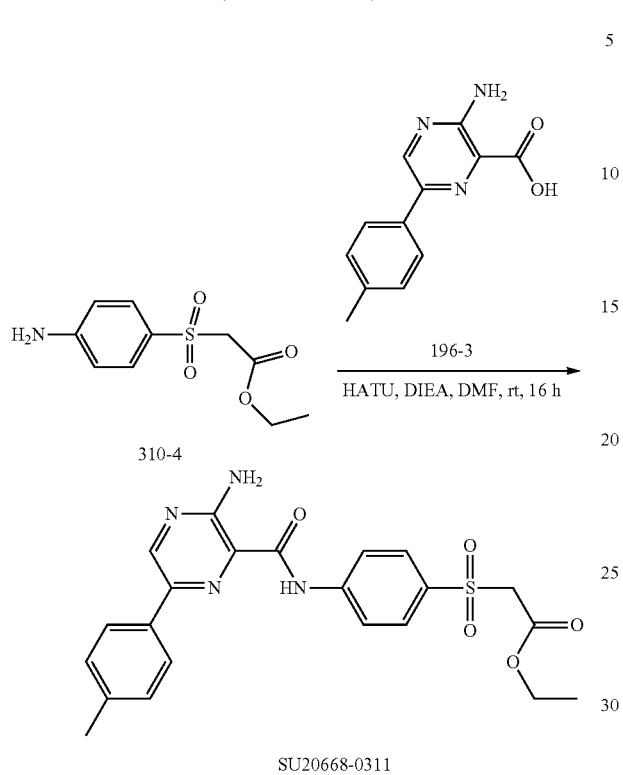

To a solution of compound 310-4 (150 mg, 0.62 mmol) in DMF (10 mL) was added 196-3 (141 mg, 0.62 mmol), DIEA (240 mg, 1.86 mmol) and HATU (471 mg, 1.24 mmol). The resulting reaction mixture was stirred for 16 h at rt, then added water, the aqueous phase was extracted with EA, the combined organic phases were dried over anhydrous sodium sulfate, filtered, and concentrated, the crude was purified by prep-HPLC to give the desired product SU20668-0311 (60 mg, yield: 21%) as a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min), Purity: 98.40%, Rt=2.174 min; MS Calcd.: 454.1; MS Found: 455.0 [M+H]$^+$. HPLC (Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min), Purity: 100.0%, Rt=10.228 min. $^1$H NMR (400 MHz, DMSO-d$_6$) δ 10.75 (s, 1H), 8.93 (s, 1H), 8.12-8.15 (m, 4H), 7.93 (d, J=8.8 Hz, 2H), 7.66 (s., 2H), 7.32 (d, J=8.0 Hz, 2H), 4.60 (s, 2H), 4.05 (q, J=7.2 Hz, 2H), 2.38 (s, 3H), 1.09 (d, J=7.2 Hz, 3H).

466

Scheme 24: Route for SU20668-0312-01

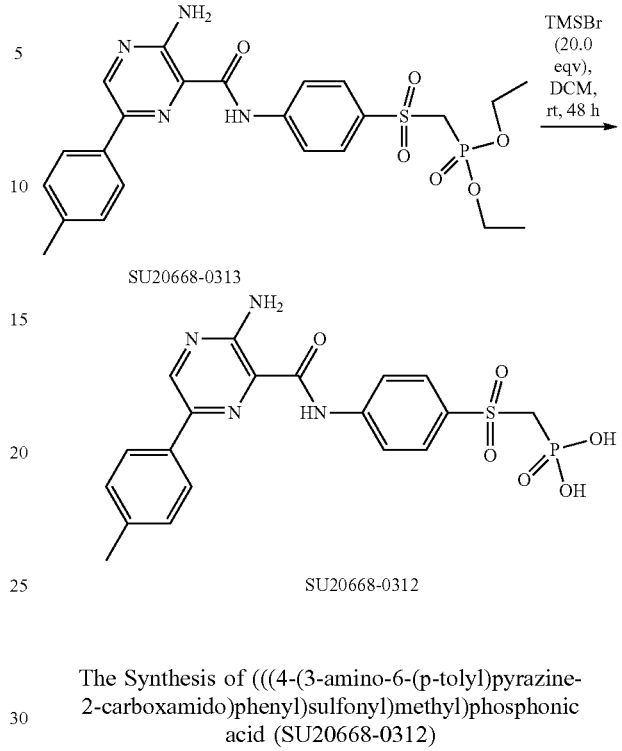

The Synthesis of (((4-(3-amino-6-(p-tolyl)pyrazine-2-carboxamido)phenyl)sulfonyl)methyl)phosphonic acid (SU20668-0312)

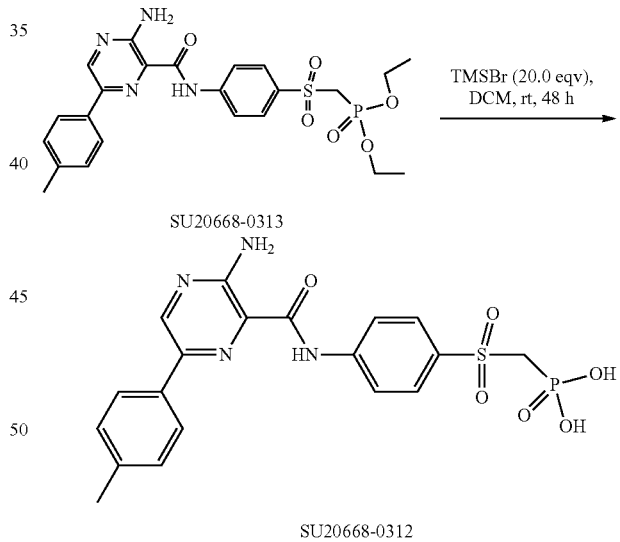

To a solution of SU20668-0313 (180 mg, 0.35 mmol) in dichloromethane (10 mL), was added Me$_3$SiBr (1.0M, 7.0 mL, 7.0 mmol) and the mixture was stirred at rt for 48 h, then added water, the aqueous phase was extracted with DCM, the combined organic phases were dried over anhydrous sodium sulfate, filtered, and concentrated, the crude was purified by prep-HPLC to give the desired product SU20668-0312 (60 mg, yield: 37%) as a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 96.2%, Rt=1.461 min; MS Calcd.: 462.1; MS Found: 462.9 [M+H]⁺. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min). Purity: 97.2%, Rt=6.091 min. ¹H NMR (400 MHz, DMSO-d₆) δ 10.69 (s, 1H), 8.93 (s, 1H), 8.08-8.14 (m, 4H), 7.94 (d, J=8.8 Hz, 2H), 7.66 (brs., 2H), 7.31 (d, J=8.0 Hz, 2H), 3.89 (d, J=16.4 Hz, 2H), 2.37 (s, 3H).

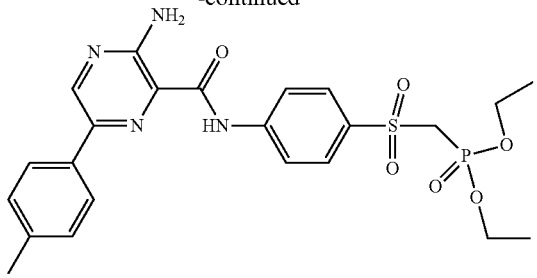

SU20668-0313

The Synthesis of diethyl ((((4-nitrophenyl)thio)methyl)phosphonate (313-2)

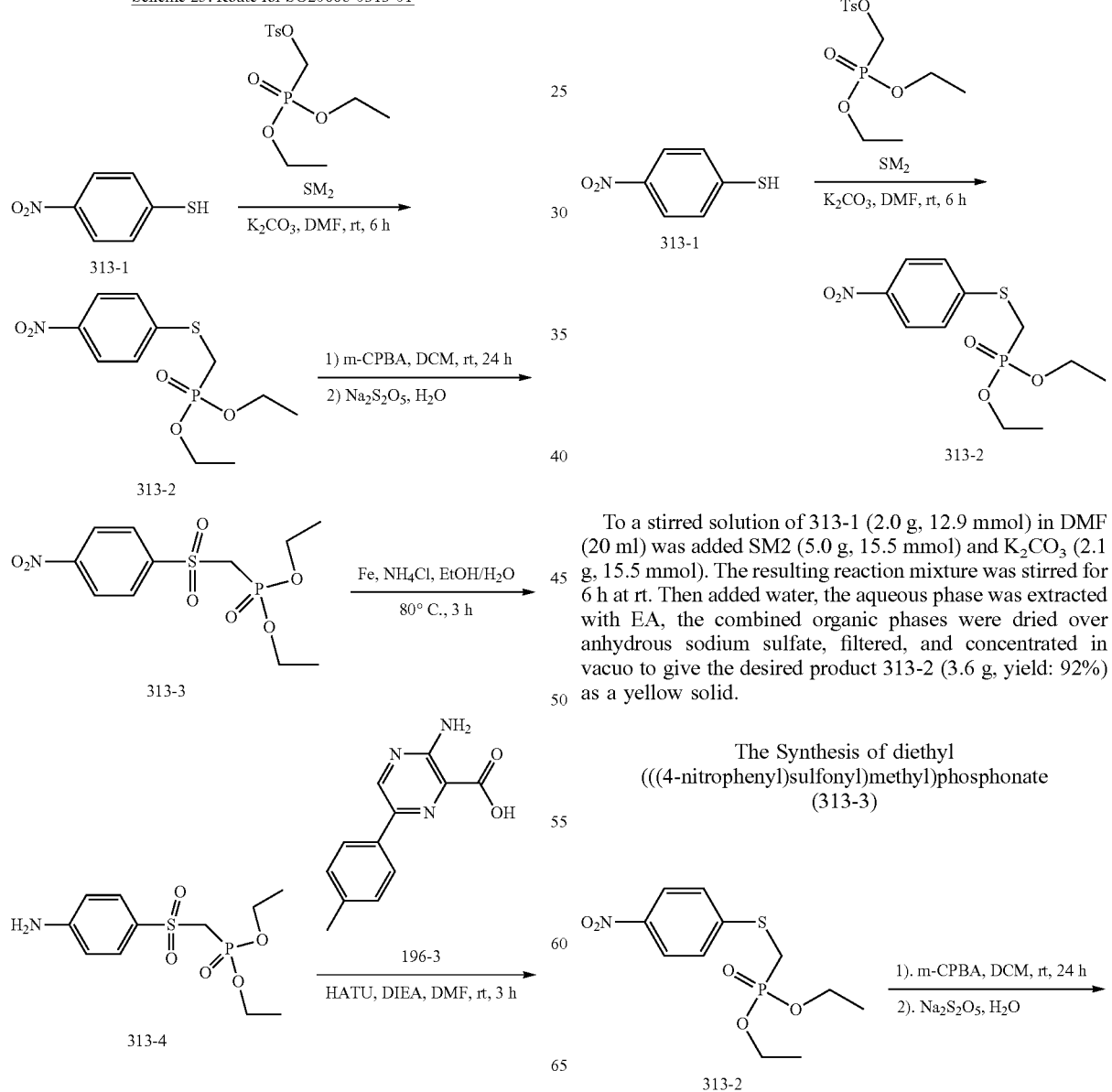

To a stirred solution of 313-1 (2.0 g, 12.9 mmol) in DMF (20 ml) was added SM2 (5.0 g, 15.5 mmol) and K₂CO₃ (2.1 g, 15.5 mmol). The resulting reaction mixture was stirred for 6 h at rt. Then added water, the aqueous phase was extracted with EA, the combined organic phases were dried over anhydrous sodium sulfate, filtered, and concentrated in vacuo to give the desired product 313-2 (3.6 g, yield: 92%) as a yellow solid.

The Synthesis of diethyl ((((4-nitrophenyl)sulfonyl)methyl)phosphonate (313-3)

-continued

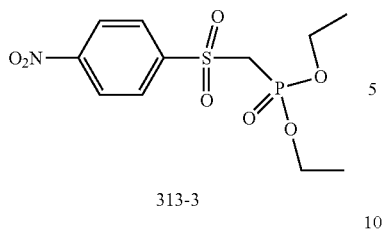

313-3

To a stirred solution of compound 313-2 (2.0 g, 6.5 mmol) in DCM (40 mL) was added 3-chlorobenzenecarboperoxoic acid (4.5 g, 26.0 mmol) at 0° C. The resulting reaction mixture was further stirred for 24 h at rt, then added water and $Na_2S_2O_5$. The aqueous phase was extracted with EA, the combined organic phases were dried over anhydrous sodium sulfate, filtered, and concentrated, the crude was purified by prep-HPLC to give the desired product 313-3 (1.6 g, yield: 73%) as a yellow solid.

The Synthesis of diethyl (((4-aminophenyl)sulfonyl)methyl)phosphonate (313-4)

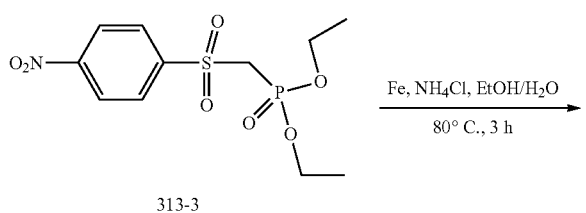

To a stirred solution of compound 313-3 (1.0 g, 3.0 mmol) in $EtOH/H_2O$ (20 mL/4 mL) was added Fe powder (1.7 g, 29.7 mmol) and $NH_4Cl$ (1.6 g, 29.7 mmol) at 0° C. The resulting reaction mixture was further stirred for 3 h at 80° C., then cooled to rt. The aqueous phase was extracted with EA, the combined organic phases were dried over anhydrous sodium sulfate, filtered, and concentrated, the crude was purified by prep-HPLC to give the desired product 313-4 (0.56 g, yield: 62%) as a yellow solid.

The Synthesis of diethyl (((4-(3-amino-6-(p-tolyl)pyrazine-2-carboxamido)phenyl)sulfonyl)methyl)phosphonate(SU20668-0313-01)

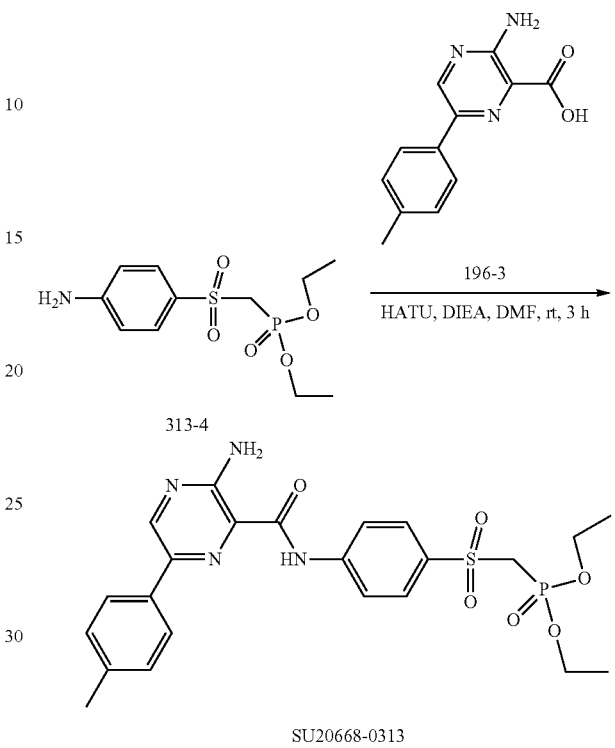

To a solution of compound 313-4 (200 mg, 0.65 mmol) in DMF (10 mL) was added 196-3 (150 mg, 0.65 mmol), DIEA (250 mg, 1.95 mmol) and HATU (500 mg, 1.30 mmol). The resulting reaction mixture was stirred for 3 h at rt, then added water, the aqueous phase was extracted with EA, the combined organic phases were dried over anhydrous sodium sulfate, filtered, and concentrated, the crude was purified by prep-HPLC to give the desired product SU20668-0313 (180 mg, yield: 53%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 97.42%, Rt=2.117 min; MS Calcd.: 518.1; MS Found: 519.1 $[M+H]^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 95.4%, Rt=9.831 min. $^1H$ NMR (400 MHz, DMSO-$d_6$) δ 10.72 (s, 1H), 8.93 (s, 1H), 8.11-8.14 (m, 4H), 7.95 (d, J=8.8 Hz, 2H), 7.66 (s, 2H), 7.32 (d, J=8.4 Hz, 2H), 4.42 (d, J=16.8 Hz, 2H), 3.98-4.04 (m, 4H), 2.37 (s, 3H), 1.18 (t, J=7.2 Hz, 6H), Scheme 26: Route for SU20668-0325-01

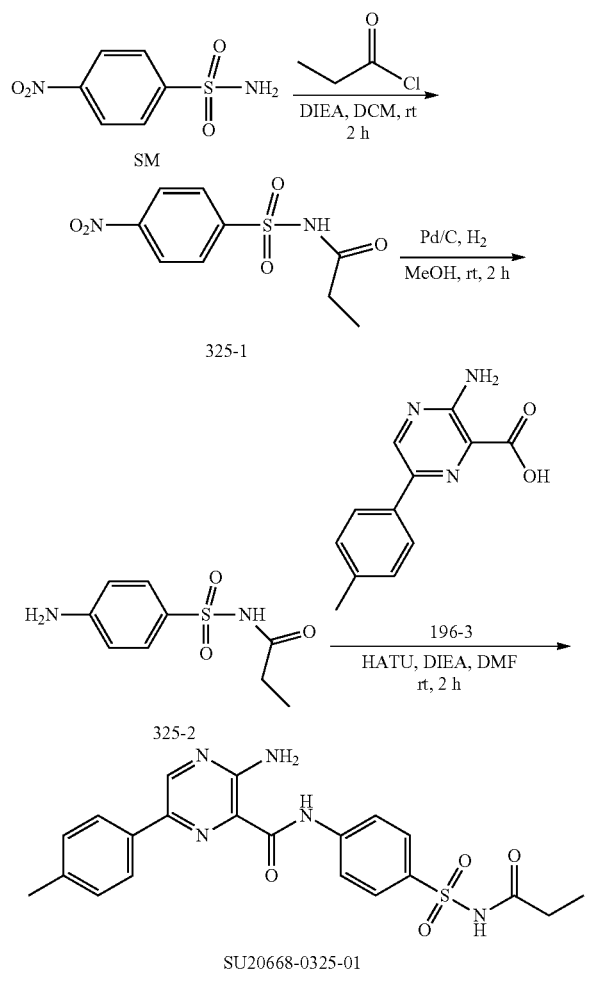

The Synthesis of
N-(4-nitrophenylsulfonyl)propionamide (325-1)

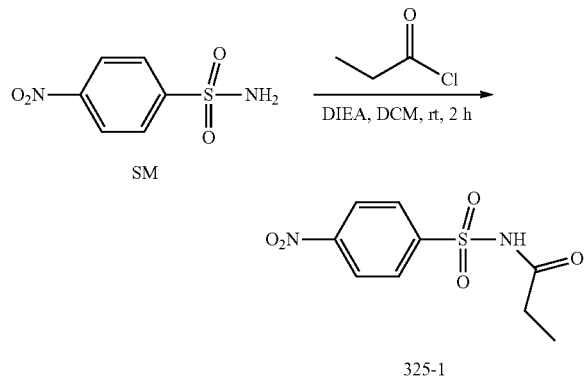

To a solution of 4-nitrobenzenesulfonamide (1.0 g, 4.99 mmol) and DIEA (1.29 g, 10 mmol) in DCM (15 mL) was added propionyl chloride (460 mg, 5.0 mmol). The resulting reaction solution was stirred for 2 h at rt. Then the mixture was concentrated to dryness. The crude product was purified by silica-gel column (DCM:MeOH=100:1) to afford 325-1 (500 mg, yield: 39%) as a yellow solid.

The Synthesis of
N-(4-aminophenylsulfonyl)propionamide (325-2)

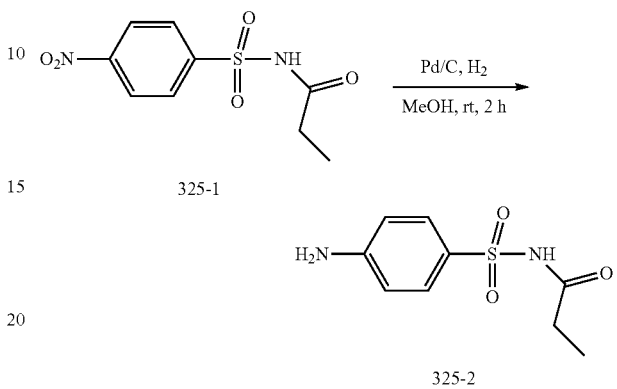

To a solution of 325-1 (500 mg, 1.94 mmol) in MeOH (10 mL) was added Pd/C (10%, 40 mg), the mixture was stirred at rt for 2 h under $H_2$ atmosphere (1.0 atm). Then the reaction mixture was filtered and concentrated in vacuo to afford compound 325-2 (440 mg, yield: 100%) as a yellow solid.

The Synthesis of 3-amino-N-(4-(N-propionylsulfamoyl)phenyl)-6-p-tolylpyrazine-2-carboxamide (SU20668-0325-01)

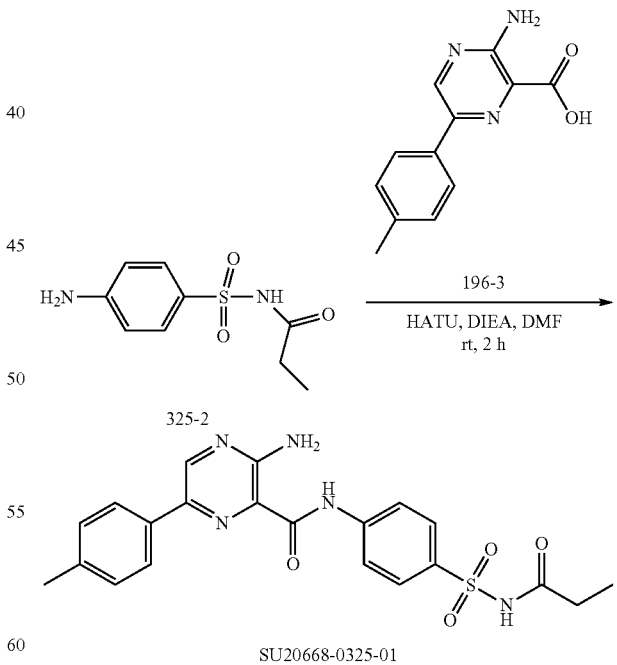

To a solution of compound 325-2 (150 mg, 0.66 mmol) in DMF (4 mL) was added 196-3 (150 mg, 0.66 mmol), DIEA (170 mg, 1.32 mmol) and HATU (300 mg, 0.80 mmol). The resulting reaction mixture was stirred for 2 h at rt. Then it was purified by prep-HPLC to give the desired product SU20668-0325-01 (53 mg, yield: 18.4%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 98.37%, Rt=1.613 min; MS Calcd.: 439.1; MS Found: 440.3 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 98.95%, Rt=7.066 min. $^1$H NMR (400 MHz, DMSO-d$_6$) δ10.66 (s, 1H), 8.92 (s, 1H), 8.12 (d, J=8.4 Hz, 2H), 8.03 (d, J=8.4 Hz, 2H), 7.89 (d, J=8.8 Hz, 2H), 7.64 (s, 2H), 7.31 (d, J=8.0 Hz, 2H), 2.37 (s, 3H), 2.17 (q, J=7.6 Hz, 2H), 0.88 (t, J=7.6 Hz, 3H).

Scheme 27 Route for SU20668-0327-01

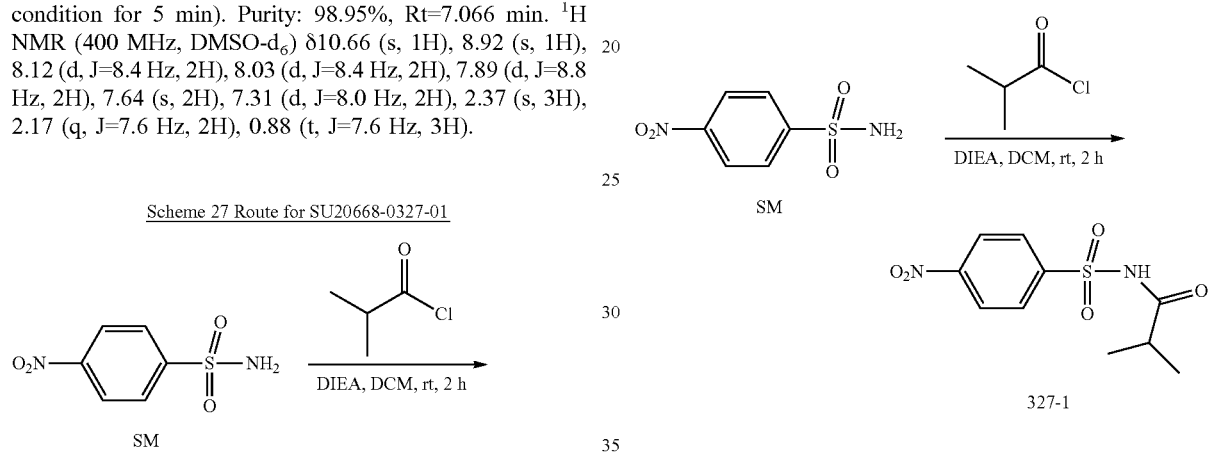

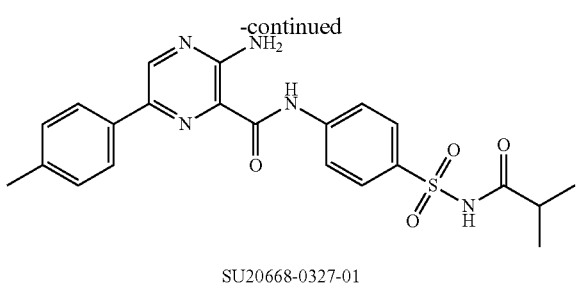

SU20668-0327-01

The Synthesis of N-(4-nitrophenylsulfonyl)isobutyramide (327-1)

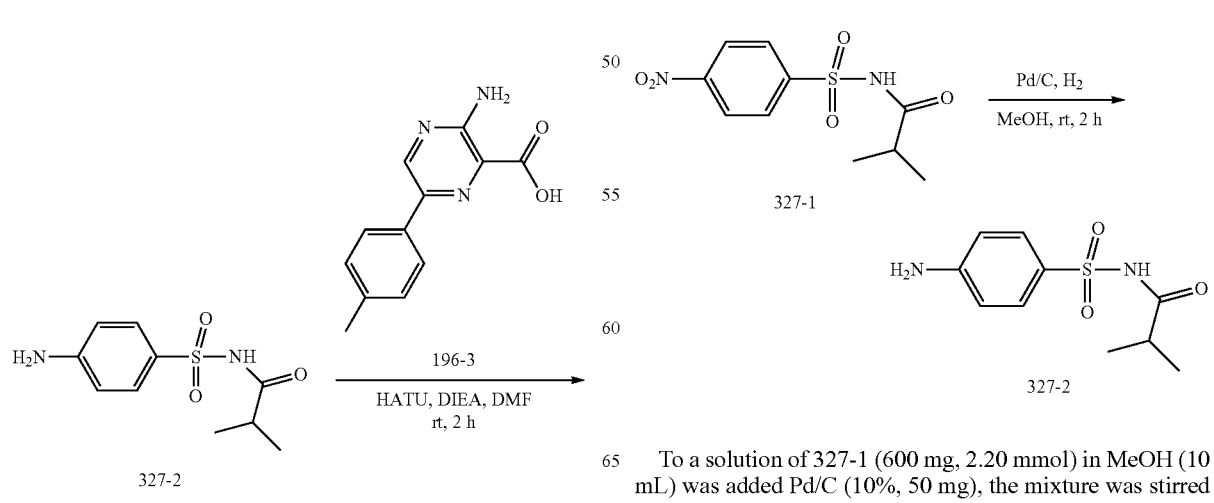

To a solution of 4-nitrobenzenesulfonamide (1.0 g, 4.99 mmol) and DIEA (1.29 g, 10 mmol) in DCM (15 mL) was added isobutyryl chloride (530 mg, 5.0 mmol). The resulting reaction solution was stirred for 2 h at rt. Then the mixture was concentrated to dryness. The crude product was purified by silica-gel column (DCM:MeOH=100:1) to afford 327-1 (600 mg, yield: 44.0%) as a yellow solid.

The Synthesis of N-(4-aminophenylsulfonyl)isobutyramide (327-2)

To a solution of 327-1 (600 mg, 2.20 mmol) in MeOH (10 mL) was added Pd/C (10%, 50 mg), the mixture was stirred at rt for 2 h under H$_2$ atmosphere (1.0 atm). Then the reaction mixture was filtered and concentrated in vacuo to afford compound 327-2 (440 mg, yield: 93.8%) as a yellow solid.

The Synthesis of 3-amino-N-(4-(N-isobutyrylsulfamoyl)phenyl)-6-p-tolylpyrazine-2-carboxamide (SU20668-0327-01)

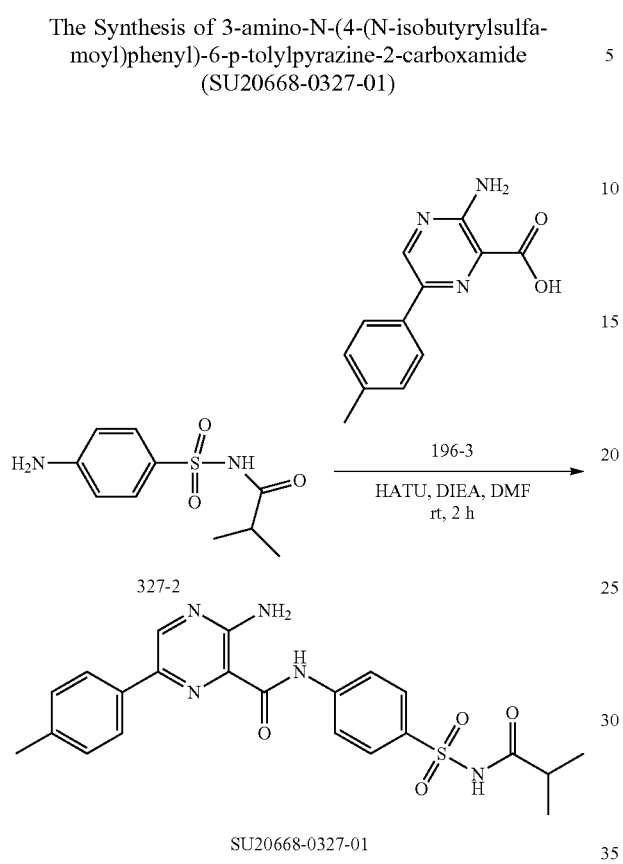

To a solution of compound 327-2 (150 mg, 0.62 mmol) in DMF (4 mL) was added 196-3 (142 mg, 0.62 mmol), DIEA (160 mg, 1.24 mmol) and HATU (300 mg, 0.80 mmol). The resulting reaction mixture was stirred for 2 h at rt. Then it was purified by prep-HPLC to give the desired product SU20668-0327-01 (40 mg, yield: 14.3%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 100%, Rt=1.666 min; MS Calcd.: 453.1; MS Found: 454.3 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 95.84%, Rt=7.350 min. $^1$H NMR (400 MHz, DMSO-$d_6$) δ11.98 (s, 1H), 10.71 (s, 1H), 8.93 (s, 1H), 8.12 (d, J=8.4 Hz, 2H), 8.06 (d, J=8.4 Hz, 2H), 7.91 (d, J=8.0 Hz, 2H), 7.64 (s, 2H), 7.31 (d, J=8.0 Hz, 2H), 2.44-2.49 (m, 1H), 2.37 (s, 3H), 0.94 (d, J=6.8 Hz, 6H).

Scheme 28 Route for SU20668-0328-01

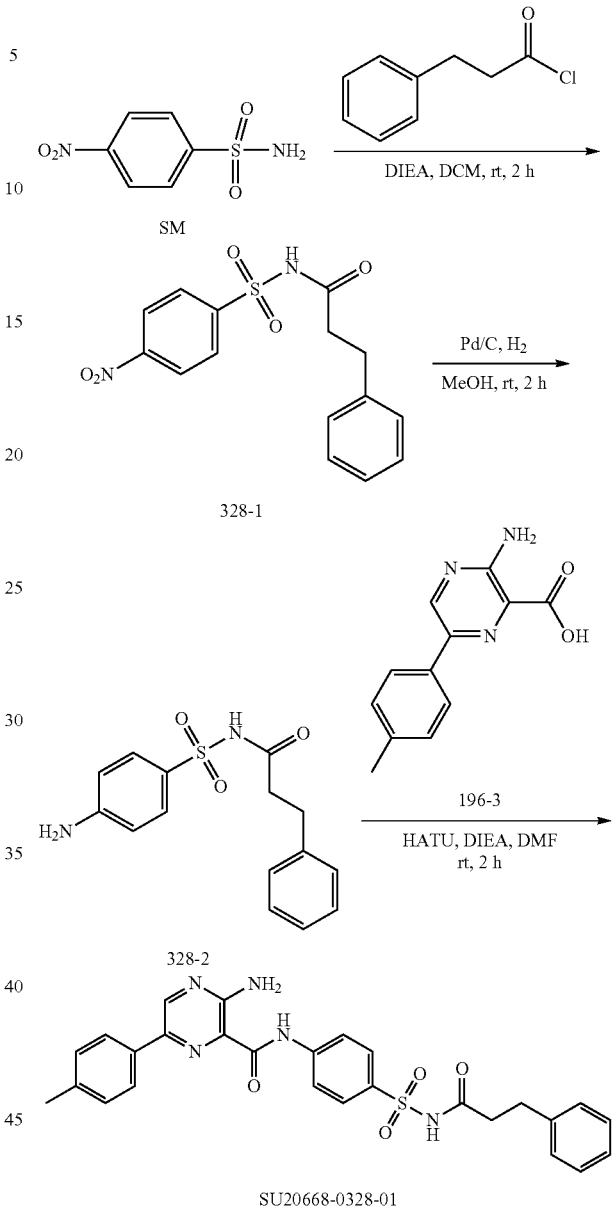

The Synthesis of N-(4-nitrophenylsulfonyl)-3-phenylpropanamide (328-1)

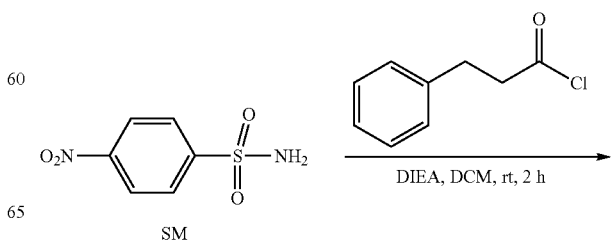

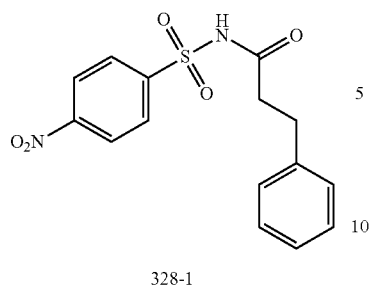

328-1

To a solution of 4-nitrobenzenesulfonamide (1.0 g, 4.99 mmol) and DIEA (1.29 g, 10 mmol) in DCM (15 mL) was added isobutyryl chloride (840 mg, 5.0 mmol). The resulting reaction solution was stirred for 2 h at rt. Then the mixture was concentrated to dryness. The crude product was purified by silica-gel column (DCM:MeOH=100:1) to afford 328-1 (900 mg, yield: 54.5%) as a yellow solid.

The Synthesis of
N-(4-aminophenylsulfonyl)-3-phenylpropanamide
(328-2)

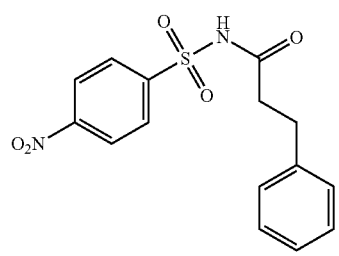

328-1

Pd/C, H$_2$
MeOH, rt, 2 h

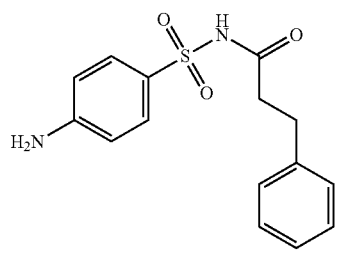

328-2

To a solution of 328-1 (500 mg, 2.20 mmol) in MeOH (10 mL) was added Pd/C (10%, 50 mg), the mixture was stirred at rt for 2 h under H$_2$ atmosphere (1.0 atm). Then the reaction mixture was filtered and concentrated in vacuo to afford compound 328-2 (450 mg, yield: 98.9%) as a yellow solid.

The Synthesis of 3-amino-N-(4-(N-(3-phenylpropanoyl)sulfamoyl)phenyl)-6-p-tolylpyrazine-2-carboxamide (SU20668-0328-01)

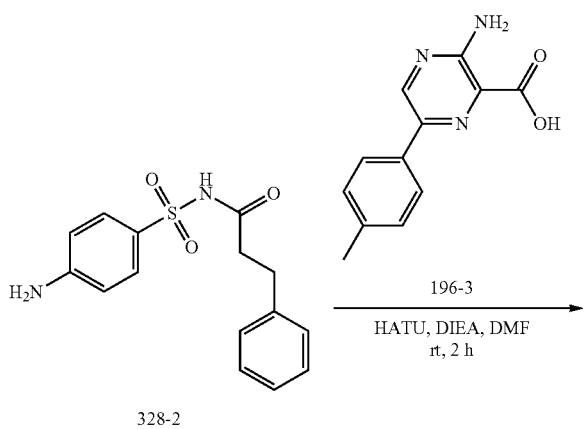

328-2

196-3
HATU, DIEA, DMF
rt, 2 h

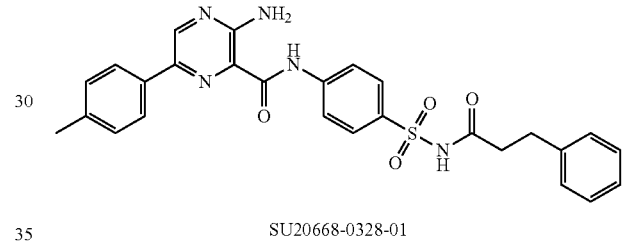

SU20668-0328-01

To a solution of compound 328-2 (150 mg, 0.49 mmol) in DMF (4 mL) was added 196-3 (113 mg, 0.49 mmol), DIEA (129 mg, 1.00 mmol) and HATU (243 mg, 0.64 mmol). The resulting reaction mixture was stirred for 2 h at rt. Then it was purified by prep-HPLC to give the desired product SU20668-0328-01 (35 mg, yield: 13.8%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=1.790 min; MS Calcd.: 515.1; MS Found: 516.3 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 98.12%, Rt=8.039 min. $^1$H NMR (400 MHz, DMSO-d$_6$) δ12.05 (s, 1H), 10.71 (s, 1H), 8.93 (s, 1H), 8.13 (d, J=8.4 Hz, 2H), 8.07 (d, J=9.2 Hz, 2H), 7.90 (d, J=8.8 Hz, 2H), 7.66 (s, 2H), 7.31 (d, J=8.0 Hz, 2H), 7.09-7.23 (m, 5H), 2.70-2.74 (m, 2H), 2.49-2.53 (m, 2H), 2.37 (s, 3H).

Scheme 29 Route for SU20668-0329-01

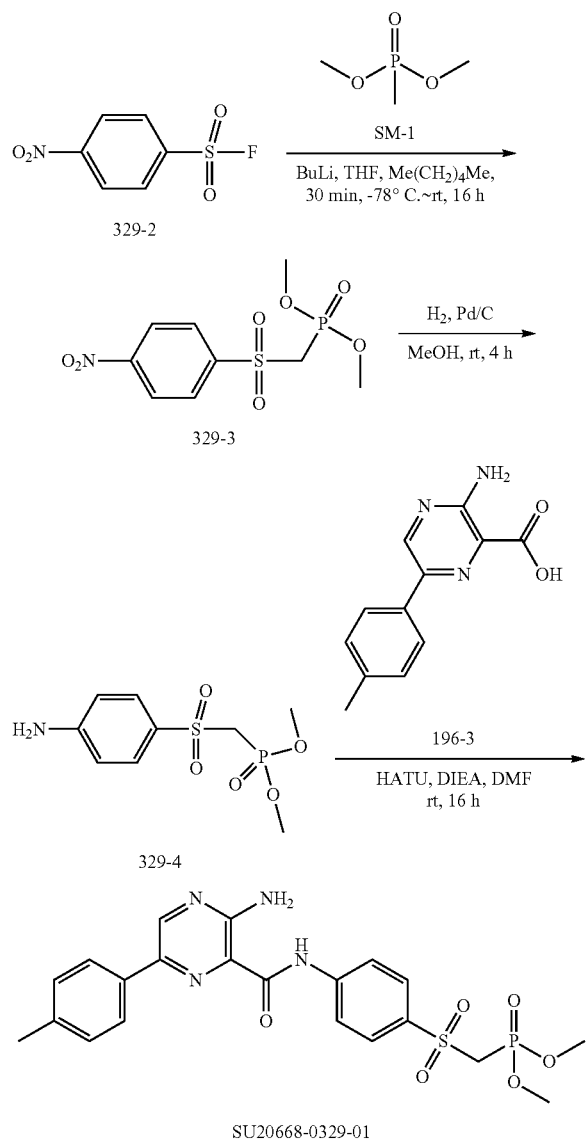

The Synthesis of dimethyl (4-nitrophenylsulfonyl)methylphosphonate (329-3)

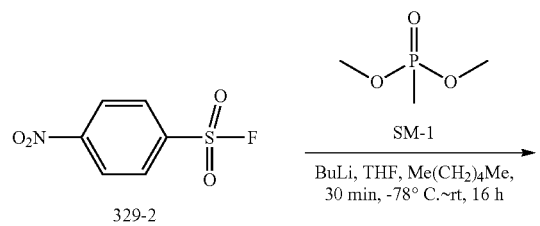

To a stirred solution of SM-1 (2.42 g, 19.50 mmol) in THF (25 mL) was added n-BuLi (23.40 mmol) dropwise at −78° C., the solution was stirred at −78° C. for 30 min, 329-2 (4 g, 19.50 mmol) dissolved in THF was added dropwise, the mixture was warmed to room temperature naturally, and stirred for 16 h, poured into water, extracted with EA, the combined organic phases were dried over anhydrous sodium sulfate, filtered, and concentrated in vacuo and purified by CC. and SFC to give 329-3 (0.5 g, 8.29% yield) as a white solid.

The Synthesis of dimethyl (4-aminophenylsulfonyl)methylphosphonate (329-4)

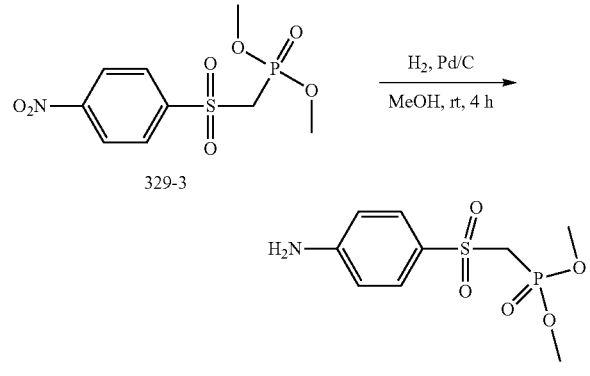

To a solution of 329-3 (900 mg, 2.91 mmol) in MeOH (70 mL) was added Pd/C (200 mg), the mixture was stirred under hydrogen atmosphere (1 atm) at room temperature for 4 h, filtrated, concentrated to give 329-4 (684 mg, 84.16% yield) as brown oil.

The Synthesis of dimethyl (4-(3-amino-6-p-tolylpyrazine-2-carboxamido)phenylsulfonyl)methylphosphonate (SU20668-0329-01)

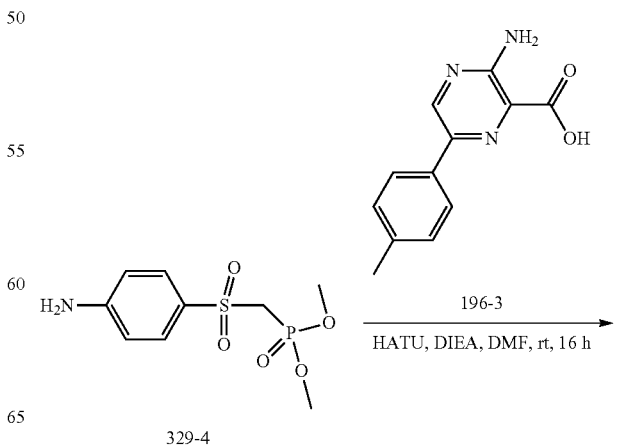

-continued

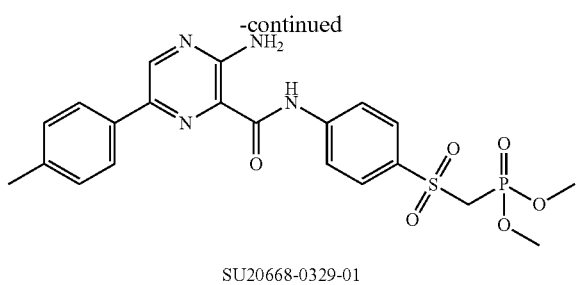

SU20668-0329-01

To a stirred solution of 329-4 (200 mg, 716.21 umol) in DMF (8 mL) was added 196-3 (164.18 mg, 716.21 umol), DIPEA (277.69 mg, 2.15 mmol) and HATU (408.48 mg, 1.07 mmol). The resulting reaction mixture was stirred at rt for 16 h. Then it was purified by prep-HPLC to give SU20668-0329-01 (149 mg, 42.42% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=1.898 min; MS Calcd.: 490.11; MS Found: 491.0 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM AcONH$_4$) water/CH$_3$CN=900/100 (v/v)] and 10% [total 10 mM AcONH$_4$) water/CH$_3$CN=100/900 (v/v)] to 15% [total 10 mM AcONH$_4$) water/CH$_3$CN=900/100 (v/v)] and 85% [total 10 mM AcONH$_4$) water/CH$_3$CN=100/900 (v/v)] in 5 min, then under this condition for 10 min, finally changed to 90% [(total 10 mM AcONH$_4$) water/CH$_3$CN=900/100 (v/v)] and 10% [(total 10 mM AcONH$_4$) water/CH$_3$CN=100/900 (v/v)] in 0.1 min and under this condition for 5 min). Purity: 92.67%, Rt=8.939 min. $^1$H NMR (400 MHz, DMSO-d$_6$) δ 10.73 (s, 1H), 8.94 (s, 1H), 8.12-8.14 (m, 4H), 7.95-7.97 (m, 2H), 7.67 (s, 2H), 7.31 (d, J=8 Hz, 2H), 4.50 (d, J=17.2 Hz, 2H), 3.64 (d, J=11.2 Hz, 6H), 2.38 (s, 3H).

Scheme 30: Route for SU20668-0330-01

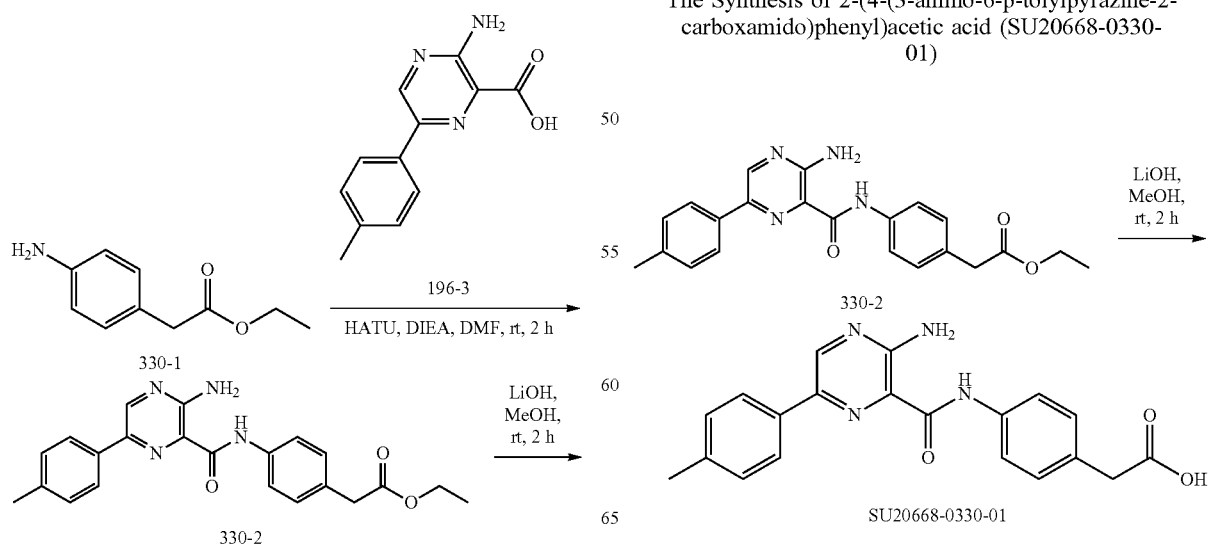

-continued

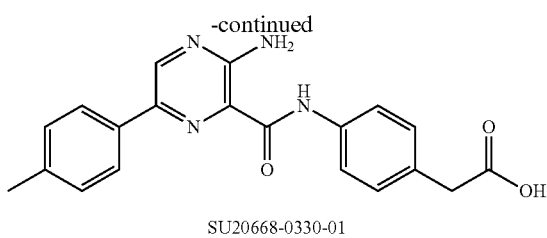

SU20668-0330-01

The Synthesis of ethyl 2-(4-(3-amino-6-p-tolylpyrazine-2-carboxamido)phenyl)acetate (330-2)

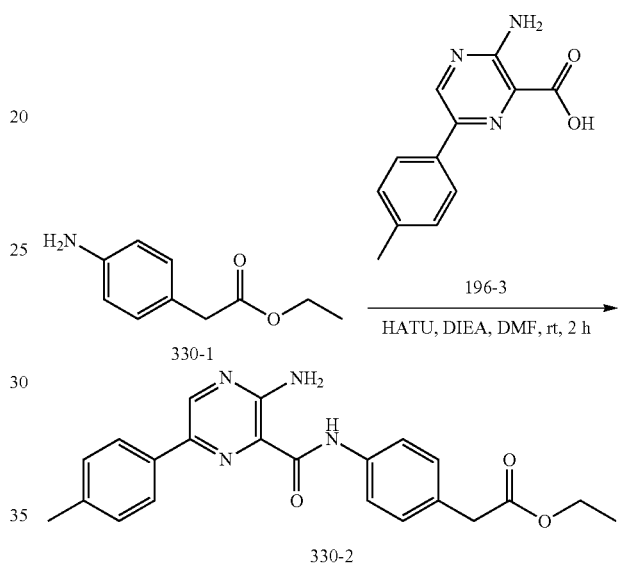

To a solution of compound 330-1 (200 mg, 1.12 mmol) in DMF (4 mL) was added 196-3 (255 mg, 1.12 mmol), DIEA (290 mg, 2.24 mmol) and HATU (533 mg, 1.4 mmol). The resulting reaction mixture was stirred for 2 h at rt. Then it was purified by prep-HPLC to give the desired product 330-2 (230 mg, yield: 52.9%) as a yellow solid.

The Synthesis of 2-(4-(3-amino-6-p-tolylpyrazine-2-carboxamido)phenyl)acetic acid (SU20668-0330-01)

The mixture of 330-2 (180 mg, 0.46 mmol) and LiOH (60 mg, 1.38 mmol) in methanol (50 mL) was stirred at room temperature for 2 hours. Then the reaction mixture was acidified with HCl (1N) till pH=3~4. The solid was collected by filtration to afford SU20668-0330-01 (100 mg, yield: 59.9%) as a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 98.53%, Rt=1.559 min; MS Calcd.: 362.1; MS Found: 363.4 $[M+H]^+$. HPLC (Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 97.34%, Rt=6.764 min. $^1$H NMR (400 MHz, DMSO-$d_6$) δ12.31 (s, 1H), 10.36 (s, 1H), 8.88 (s, 1H), 8.11 (d, J=8.4 Hz, 2H), 7.75 (d, J=8.4 Hz, 2H), 7.63 (s, 2H), 7.28 (t, J=9.2 Hz, 4H), 3.56 (s, 2H), 2.37 (s, 3H).

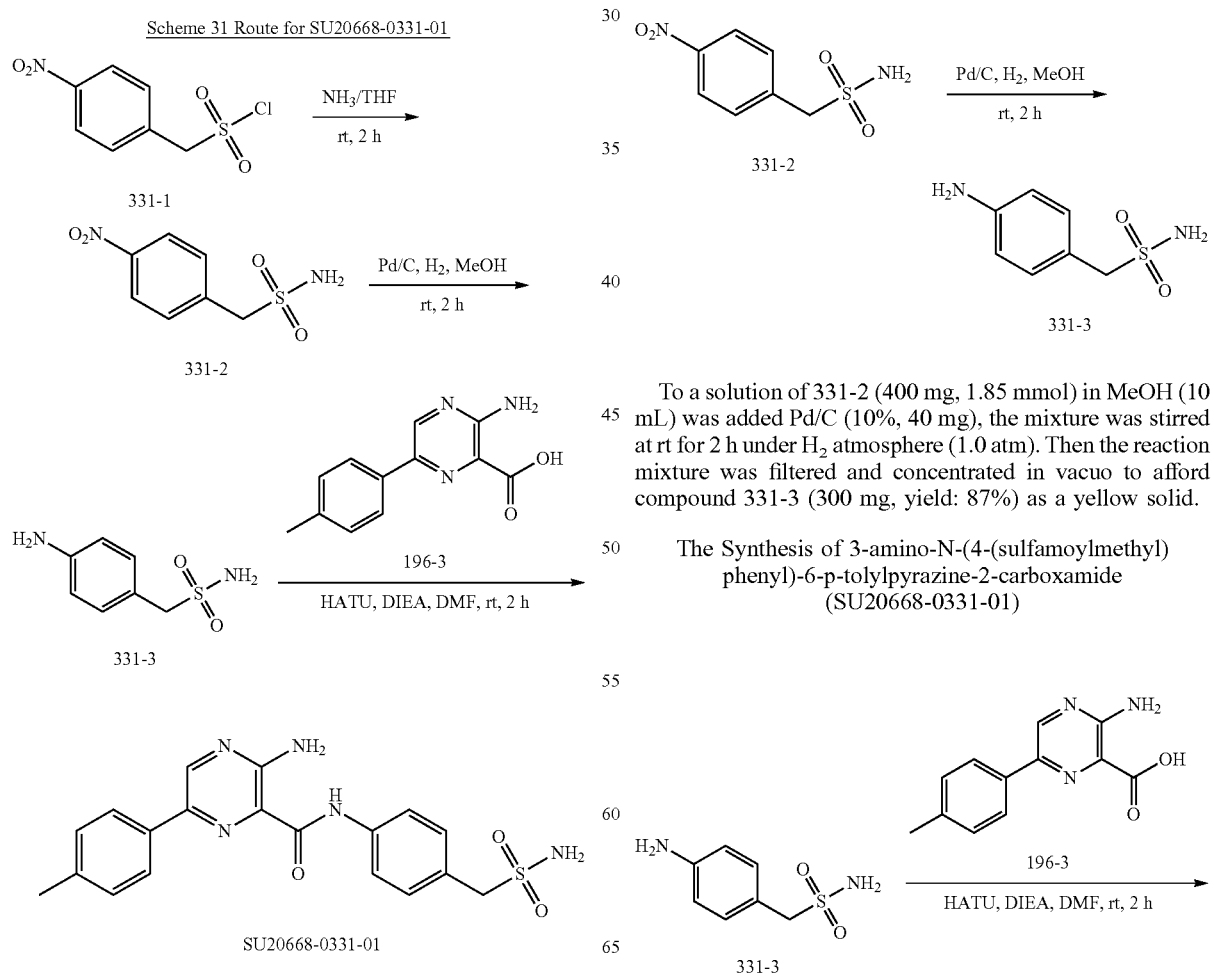

The Synthesis of methyl (4-nitrophenyl)methanesulfonamide (331-2)

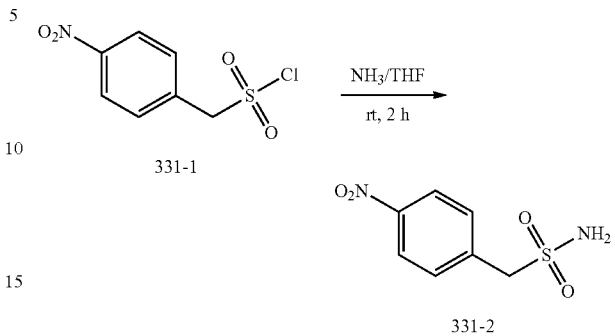

To a solution of (4-nitrophenyl)methanesulfonyl chloride (500 mg, 2.13 mmol) in THF (4 mL) was added $NH_3$/THF (7N, 5 mL). The resulting reaction solution was stirred for 2 h at rt. Then the mixture was concentrated to dryness. The crude product was washed by methanol (3 mL) to afford 331-2 (400 mg, yield: 87%) as a yellow solid.

The Synthesis of (4-aminophenyl)methanesulfonamide (331-3)

To a solution of 331-2 (400 mg, 1.85 mmol) in MeOH (10 mL) was added Pd/C (10%, 40 mg), the mixture was stirred at rt for 2 h under $H_2$ atmosphere (1.0 atm). Then the reaction mixture was filtered and concentrated in vacuo to afford compound 331-3 (300 mg, yield: 87%) as a yellow solid.

The Synthesis of 3-amino-N-(4-(sulfamoylmethyl)phenyl)-6-p-tolylpyrazine-2-carboxamide (SU20668-0331-01)

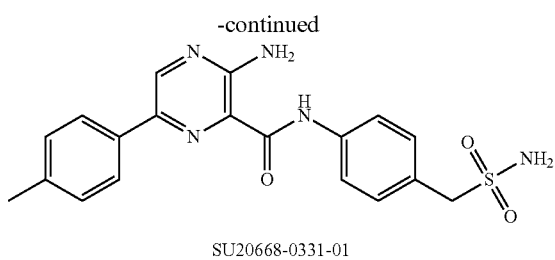

SU20668-0331-01

To a solution of compound 331-3 (170 mg, 0.91 mmol) in DMF (4 mL) was added 196-3 (209 mg, 0.91 mmol), DIEA (234 mg, 1.82 mmol) and HATU (450 mg, 1.18 mmol). The resulting reaction mixture was stirred for 2 h at rt. Then it was purified by prep-HPLC to give the desired product SU20668-0331-01 (50 mg, yield: 13.8%) as a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=1.941 min; MS Calcd.: 397.1; MS Found: 398.3 [M+H]$^+$. HPLC (Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 99.84%, Rt=8.979 min. $^1$H NMR (400 MHz, DMSO-d$_6$) δ10.41 (s, 1H), 8.89 (s, 1H), 8.11 (d, J=8.0 Hz, 2H), 7.83 (d, J=8.4 Hz, 2H), 7.63 (s, 2H), 7.38 (d, J=8.4 Hz, 2H), 7.30 (d, J=8.0 Hz, 2H), 6.84 (s, 2H), 4.26 (s, 2H), 2.37 (s, 3H).

Scheme 32: Route for SU20668-0338-01

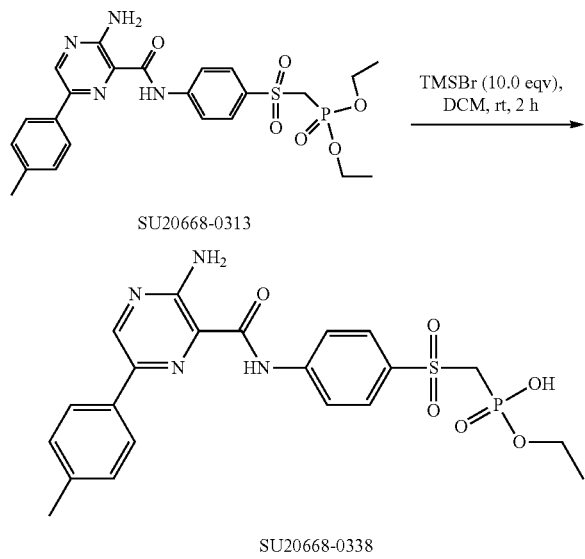

The Synthesis of ethyl hydrogen (((4-(3-amino-6-(p-tolyl)pyrazine-2-carboxamido)phenyl)sulfonyl)methyl)phosphonate (SU20668-0338)

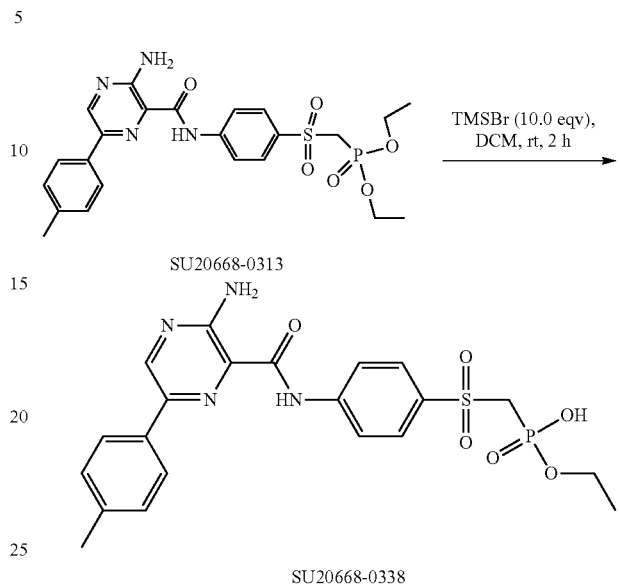

To a solution of SU20668-0313 (150 mg, 0.29 mmol) in dichloromethane (10 mL), was added Me$_3$SiBr (1.0M, 2.9 mL, 2.9 mmol) and the mixture was stirred at rt for 48 h, then added water, the aqueous phase was extracted with DCM, the combined organic phases were dried over anhydrous sodium sulfate, filtered, and concentrated, the crude was purified by prep-HPLC to give the desired product SU20668-0338 (15 mg, yield: 10%) as a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 96.2%, Rt=1.504 min; MS Calcd.: 490.1; MS Found: 490.2 [M+H]$^+$. HPLC (Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 100%, Rt=7.037 min. $^1$H NMR (400 MHz, DMSO-d$_6$) δ 10.65 (s, 1H), 8.92 (s, 1H), 8.12 (d, J=8.0 Hz, 2H), 8.05 (d, J=8.8 Hz, 2H), 7.93 (d, J=8.8 Hz, 2H), 7.65 (brs., 2H), 3.66-3.70 (m, 2H), 3.43-3.49 (m, 2H), 2.37 (s, 3H), 1.03 (t, J=7.2 Hz, 3H).

Scheme 33 Route for SU20668-0392-01

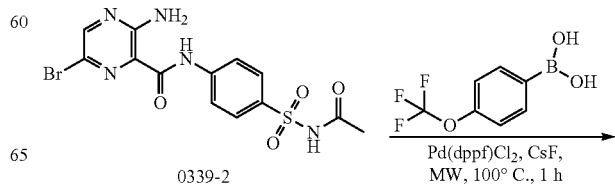

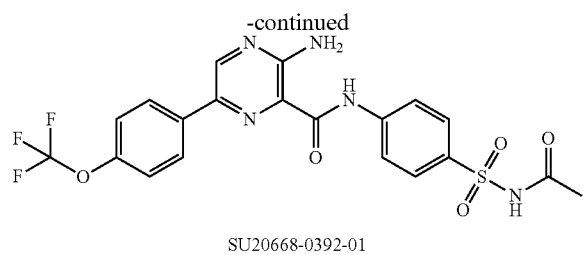

SU20668-0392-01

The Synthesis of N-(4-(N-acetylsulfamoyl)phenyl)-3-amino-6-(4-(trifluoromethoxy)phenyl)pyrazine-2-carboxamide (SU20668-0392-01)

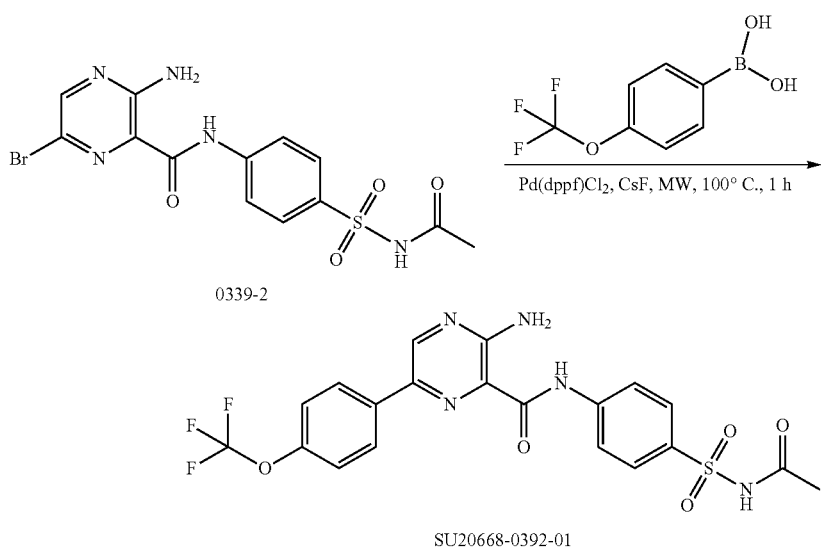

To a stirred solution of compound 0339-2 (140 mg, 0.34 mmol), 4-(trifluoromethoxy)phenylboronic acid (85 mg, 0.41 mmol) and CsF (150 mg, 1.02 mmol) in MeOH (4 mL) was added Pd(dppf)Cl$_2$ (10%, 25 mg). The resulting reaction mixture was irradiated with microwave radiation at 100° C. for 1 h under Ar atmosphere (1.0 atm). After the consumption of starting material (by LCMS), the mixture was filtered, and the filtrate was concentrated in vacuo, purified by prep-HPLC to give the desired product SU20668-0392-01 (77 mg, 46% yield) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 98.54%, Rt=1.771 min; MS Calcd.: 495.43; MS Found: 446.2 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 98.00%, Rt=7.558 min. $^1$H NMR (400 MHz, DMSO-d$_6$) δ 8.98 (s, 1H), 8.36 (d, J=8.4 Hz, 2H), 8.08 (d, J=8.8 Hz, 2H), 7.93 (d, J=8.4 Hz, 2H), 7.49 (d, J=8.0 Hz, 2H), 1.93 (s, 3H).

Scheme 34: Route for SU20668-0446-01

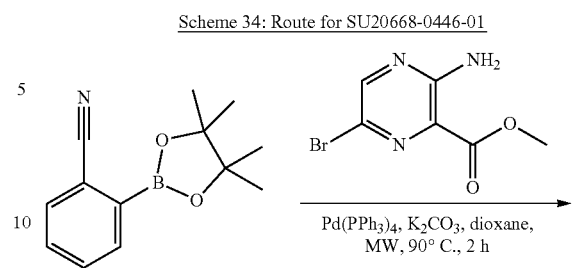

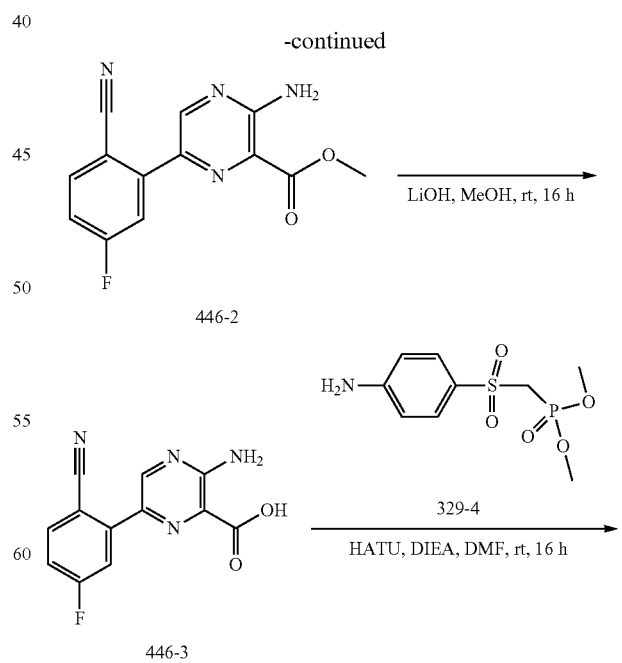

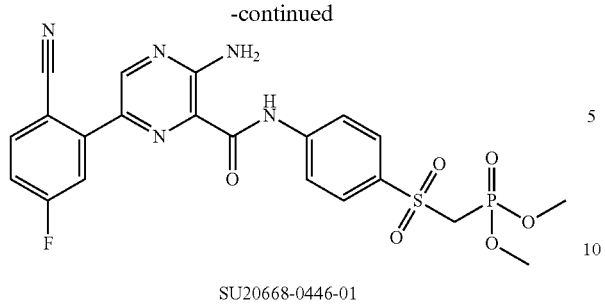

SU20668-0446-01

The Synthesis of methyl 3-amino-6-(2-cyano-5-fluorophenyl)pyrazine-2-carboxylate (446-2)

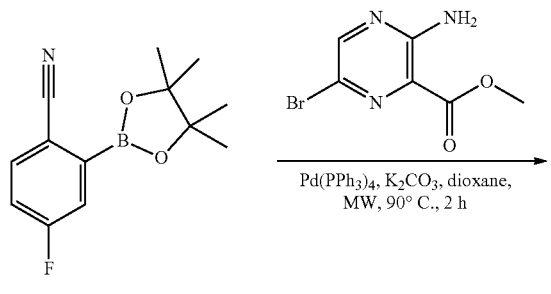

446-1

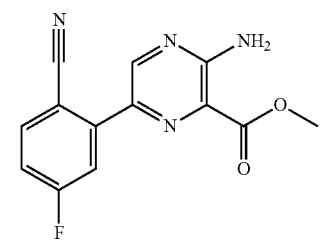

446-2

To a stirred solution of compound 446-1 (500 mg, 2.02 mmol) in Dioxane (16 mL) was added methyl 3-amino-6-bromopyrazine-2-carboxylate (375 mg, 1.62 mmol), K₂CO₃ (558 mg, 4.04 mmol), Pd(PPh₃)₄ (115 mg, 0.1 mmol). The resulting reaction mixture was heated to 90° C. in M.W. and stirred for 2 h, then, concentrated in vacuo to remove the solvent, added water, the aqueous phase was extracted with dichloromethane, the combined organic phases were dried over anhydrous sodium sulfate, filtered, and concentrated, the crude was purified by C.C. to give 446-2 (400 mg, yield: 72.8%) as a yellow solid.

The Synthesis of 3-amino-6-(2-cyano-5-fluorophenyl)pyrazine-2-carboxylic acid (446-3)

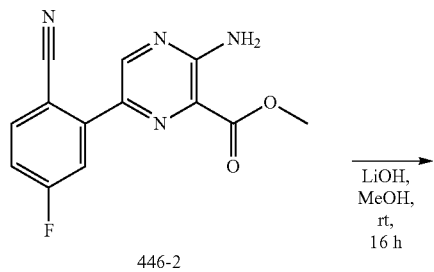

446-2

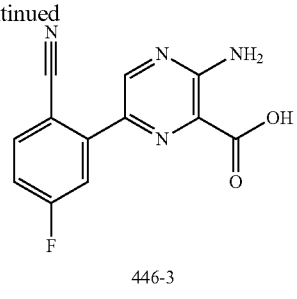

446-3

To a solution of 446-2 (400 mg, 1.47 mmol) in MeOH (10 mL) was added LiOH (616 mg, 14.7 mmol), the mixture was stirred at rt for 16 h. The mixture was cooled to 0° C. and acidified with 1N HCl solution to pH 4.0. After the reaction mixture was filtered and washed with MeOH. Then concentrated in vacuo to give 446-3 (100 mg, 26% yield) as yellow solid.

The Synthesis of dimethyl (4-(3-amino-6-(2-cyano-5-fluorophenyl)pyrazine-2-carboxamido)phenylsulfonyl)methylphosphonate (SU20668-0446-01)

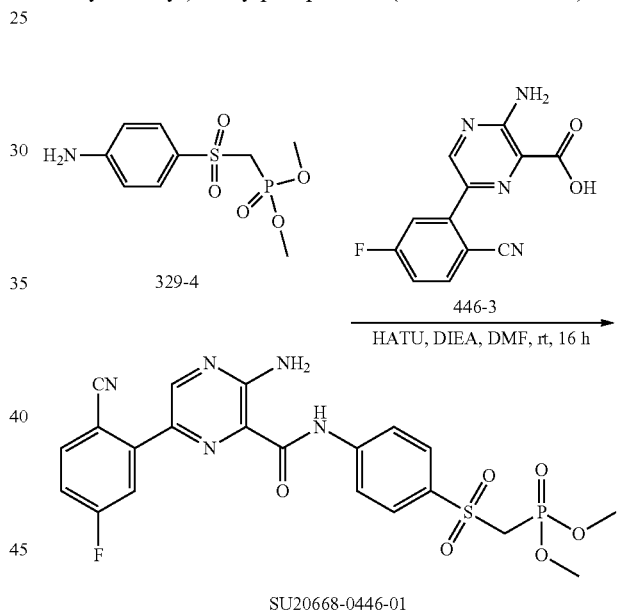

SU20668-0446-01

To a stirred solution of 329-4 (110 mg, 393.91 umol) in DMF (4 mL) was added 446-3 (101.71 mg, 393.91 umol), DIPEA (152.73 mg, 1.18 mmol) and HATU (224.67 mg, 590.87 umol). The resulting reaction mixture was stirred at rt for 16 h. Then it was purified by prep-HPLC to give SU20668-0446-01 (27 mg, 13.20% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 94.1%, Rt=1.888 min; MS Calcd.: 519.08; MS Found: 520.2 [M+H]⁺. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM AcONH₄) water/CH₃CN=900/100 (v/v)] and 10% [total 10 mM AcONH₄) water/CH₃CN=100/900 (v/v)] to 15% [total 10 mM AcONH₄) water/CH₃CN=900/100 (v/v)] and 85% [total 10 mM AcONH₄) water/CH₃CN=100/900 (v/v)] in 5 min, then under this condition for 10 min, finally changed to 90% [(total 10 mM AcONH₄) water/CH₃CN=900/100 (v/v)] and 10% [total 10 mM AcONH₄) water/CH₃CN=100/900 (v/v)] in 0.1 min and under this condition for 5 min). Purity:95.97%, Rt=8.781 min. ¹H NMR (400 MHz, DMSO-d₆) δ 10.49 (s, 1H), 9.03 (s, 1H), 8.02-8.19 (m, 6H), 7.93-7.95 (m, 2H), 7.48 (t, J=8.4 Hz, 1H), 4.46 (d, J=16.8 Hz, 2H), 3.61 (d, J=10.0 Hz, 6H).

Scheme 35 Route for SU20668-0447-01

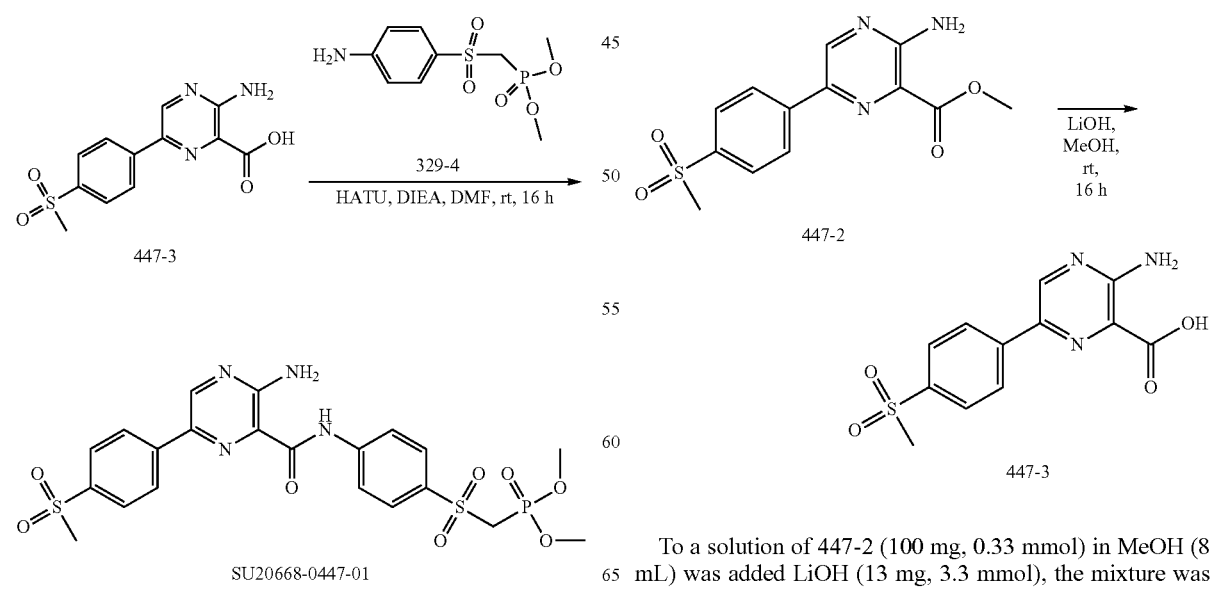

The Synthesis of methyl 3-amino-6-(4-(methylsulfonyl)phenyl)pyrazine-2-carboxylate (447-2)

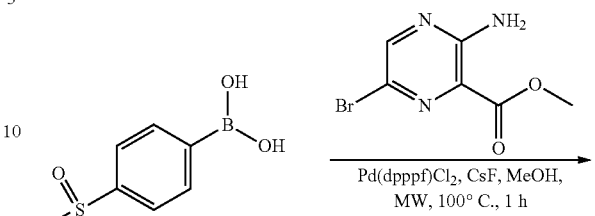

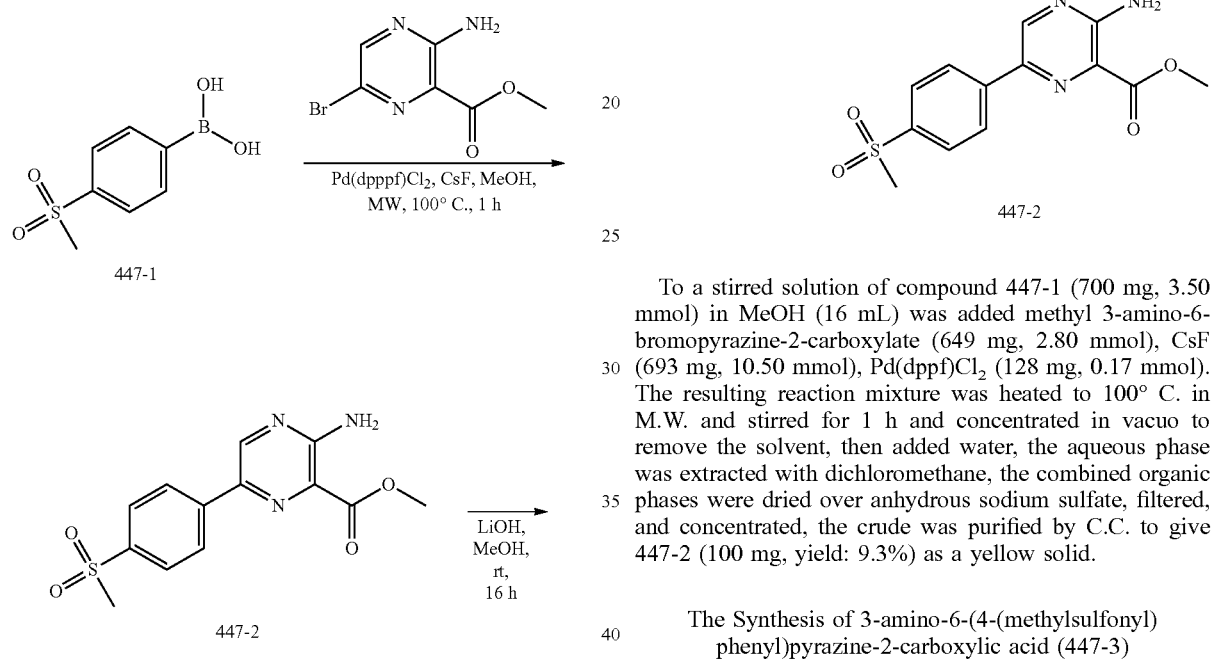

To a stirred solution of compound 447-1 (700 mg, 3.50 mmol) in MeOH (16 mL) was added methyl 3-amino-6-bromopyrazine-2-carboxylate (649 mg, 2.80 mmol), CsF (693 mg, 10.50 mmol), Pd(dppf)Cl₂ (128 mg, 0.17 mmol). The resulting reaction mixture was heated to 100° C. in M.W. and stirred for 1 h and concentrated in vacuo to remove the solvent, then added water, the aqueous phase was extracted with dichloromethane, the combined organic phases were dried over anhydrous sodium sulfate, filtered, and concentrated, the crude was purified by C.C. to give 447-2 (100 mg, yield: 9.3%) as a yellow solid.

The Synthesis of 3-amino-6-(4-(methylsulfonyl)phenyl)pyrazine-2-carboxylic acid (447-3)

To a solution of 447-2 (100 mg, 0.33 mmol) in MeOH (8 mL) was added LiOH (13 mg, 3.3 mmol), the mixture was stirred at rt for 16 h. The mixture was cooled to 0° C. and acidified with 1N HCl solution to pH 4.0. After the reaction mixture was filtered and washed with MeOH. Then concentrated in vacuo to give 447-3 (80 mg, 83.3% yield) as yellow oil.

The Synthesis of dimethyl (4-(3-amino-6-(4-(methylsulfonyl)phenyl)pyrazine-2-carboxamido)phenylsulfonyl)methylphosphonate (SU20668-0447-01)

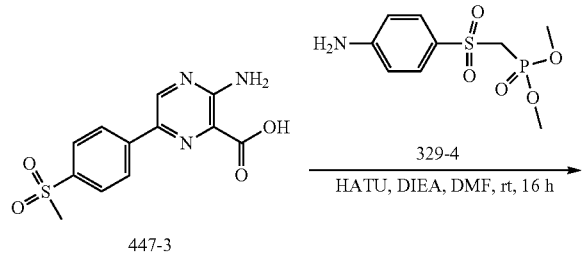

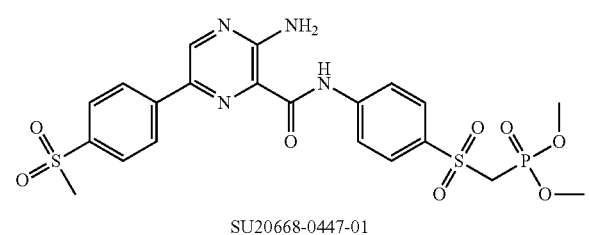

To a stirred solution of 329-4 (80 mg, 286.48 umol) in DMF (4 mL) was added 447-3 (84.02 mg, 286.48 umol), DIPEA (111.07 mg, 859.45 umol) and HATU (163.39 mg, 429.72 umol). The resulting reaction mixture was stirred at rt for 16 h. Then the crude was purified by prep-HPLC to give SU20668-0447-01 (26 mg, 16.37% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 92.54%, Rt=1.651 min; MS Calcd.: 554.07; MS Found: 555.2 [M+H]⁺. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM $AcONH_4$) water/$CH_3CN$=900/100 (v/v)] and 10% [total 10 mM $AcONH_4$) water/$CH_3CN$=100/900 (v/v)] to 15% [total 10 mM $AcONH_4$) water/$CH_3CN$=900/100 (v/v)] and 85% [total 10 mM $AcONH_4$) water/$CH_3CN$=100/900 (v/v)] in 5 min, then under this condition for 10 min, finally changed to 90% [(total 10 mM $AcONH_4$) water/$CH_3CN$=900/100 (v/v)] and 10% [total 10 mM $AcONH_4$) water/$CH_3CN$=100/900 (v/v)] in 0.1 min and under this condition for 5 min). Purity: 95.73%, Rt=7.595 min. ¹H NMR (400 MHz, DMSO-$d_6$) δ 10.77 (s, 1H), 9.05 (s, 1H), 8.49 (d, J=8.8 Hz, 2H), 8.09-8.12 (m, 2H), 7.94-8.01 (m, 4H), 7.88 (s, 2H), 4.48 (d, J=17.2 Hz, 2H), 3.62 (d, J=11.6 Hz, 6H), 3.25 (s, 3H).

Scheme 36 Route for SU20668-0448-01

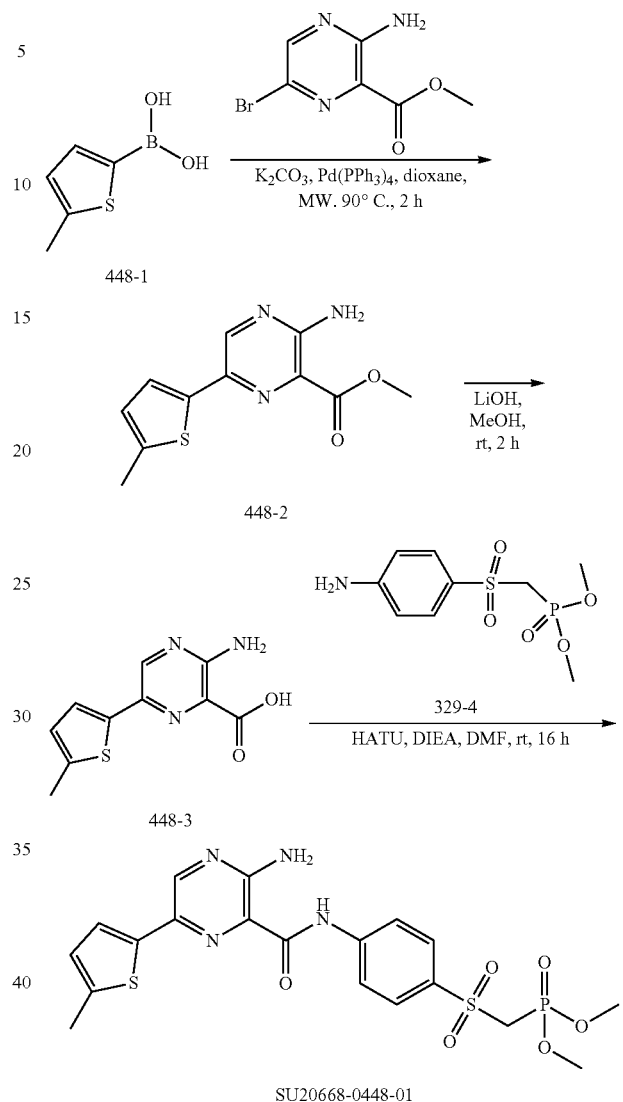

The Synthesis of methyl 3-amino-6-(5-methylthiophen-2-yl)pyrazine-2-carboxylate (448-2)

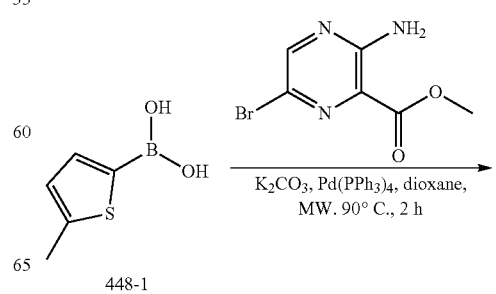

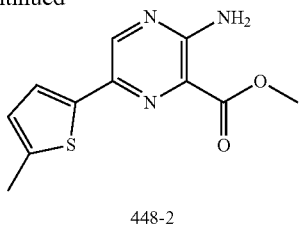

448-2

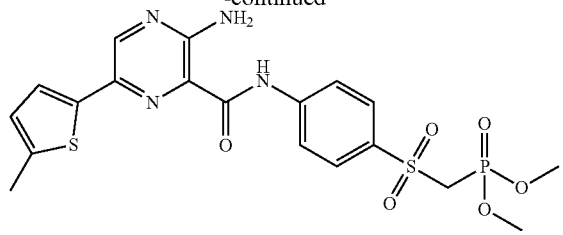

SU20668-0448-01

To a stirred solution of compound 448-1 (400 mg, 2.82 mmol) in Dioxane (8 mL) was added methyl 3-amino-6-bromopyrazine-2-carboxylate (523 mg, 2.25 mmol), $K_2CO_3$ (971 mg, 7.04 mmol), $Pd(PPh_3)_4$ (162 mg, 0.14 mmol). The resulting reaction mixture was heated to 90° C. in M.W. and stirred for 2 h and concentrated in vacuo to remove the solvent, then added water, the aqueous phase was extracted with dichloromethane, the combined organic phases were dried over anhydrous sodium sulfate, filtered, and concentrated, the crude was purified by C.C. to give 448-2 (600 mg, yield: 85.5%) as a yellow solid.

The Synthesis of 3-amino-6-(5-methylthiophen-2-yl)pyrazine-2-carboxylic acid (448-3)

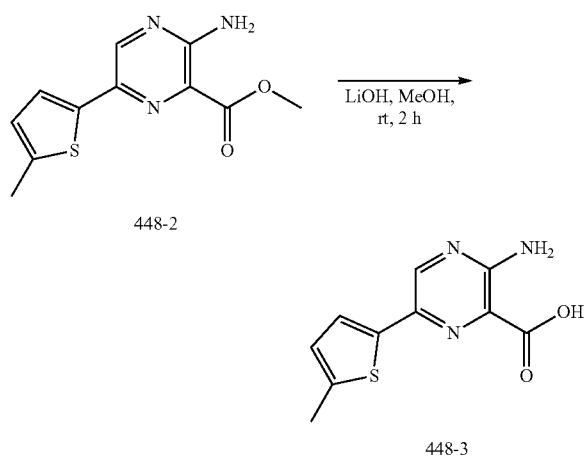 [SMILES: COC(=O)c1nc(-c2ccc(C)s2)cnc1N ; Cc1ccc(-c2cnc(N)c(C(=O)O)n2)s1]

To a solution of 448-2 (600 mg, 2.41 mmol) in MeOH (10 mL) was added LiOH (101 mg, 24.1 mmol), the mixture was stirred at rt for 2 h. The mixture was cooled to 0° C. and acidified with 1N HCl solution to pH 4.0. After the reaction mixture was filtered and washed with MeOH. Then concentrated in vacuo to give 448-3 (200 mg, 35.3% yield) as yellow oil.

The Synthesis of dimethyl (4-(3-amino-6-(5-methylthiophen-2-yl)pyrazine-2-carboxamido)phenylsulfonyl)methylphosphonate (SU20668-0448-01)

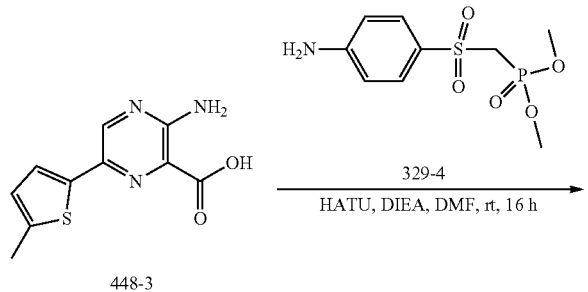

To a stirred solution of 329-4 (80 mg, 286.48 umol) in DMF (4 mL) was added 448-3 (67.40 mg, 286.48 umol), DIPEA (111.07 mg, 859.45 umol) and HATU (163.39 mg, 429.72 umol). The resulting reaction mixture was stirred at rt for 16 h. Then it was purified by prep-HPLC to give SU20668-0448-01 (42 mg, 29.53% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 98.68%, Rt=1.953 min; MS Calcd.: 496.06; MS Found: 497.2 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM $AcONH_4$) water/$CH_3CN$=900/100 (v/v)] and 10% [total 10 mM $AcONH_4$) water/$CH_3CN$=100/900 (v/v)] to 15% [total 10 mM $AcONH_4$) water/$CH_3CN$=900/100 (v/v)] and 85% [total 10 mM $AcONH_4$) water/$CH_3CN$=100/900 (v/v)] in 5 min, then under this condition for 10 min, finally changed to 90% [(total 10 mM $AcONH_4$) water/$CH_3CN$=900/100 (v/v)] and 10% [total 10 mM $AcONH_4$) water/$CH_3CN$=100/900 (v/v)] in 0.1 min and under this condition for 5 min). Purity: 98.77%, Rt=9.156 min. $^1H$ NMR (400 MHz, DMSO-$d_6$) δ 10.47 (s, 1H), 8.77 (s, 1H), 8.05 (d, J=9.2 Hz, 2H), 7.93 (d, J=8.8 Hz, 2H), 7.62-7.63 (m, 3H), 6.85 (m, 1H), 4.47 (d, J=17.2 Hz, 2H), 3.61 (d, J=11.6 Hz, 6H), 2.48 (s, 3H).

Scheme 37 Route for SU20668-0446-01

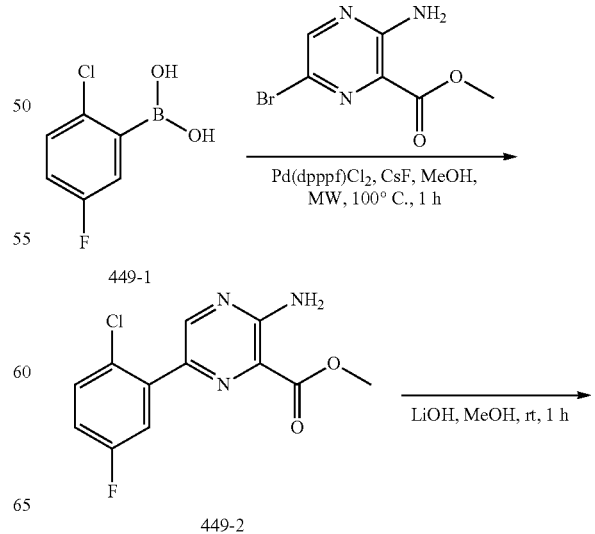

497

-continued

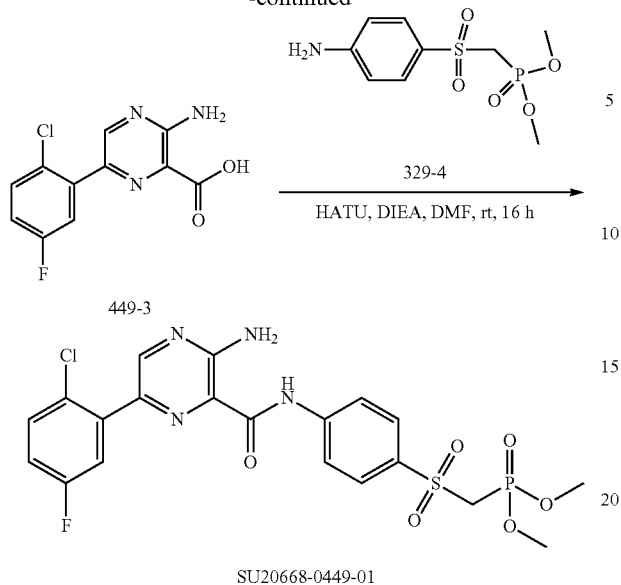

The Synthesis of methyl 3-amino-6-(2-chloro-5-fluorophenyl)pyrazine-2-carboxylate (449-2)

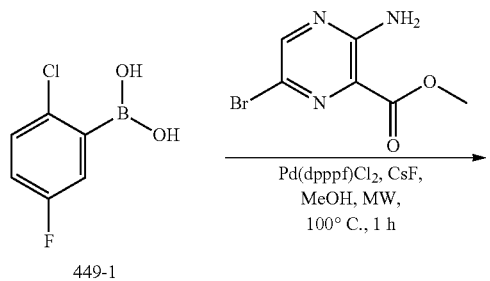

To a stirred solution of compound 449-1 (500 mg, 2.87 mmol) in MeOH (10 mL) was added methyl 3-amino-6-bromopyrazine-2-carboxylate (532 mg, 2.29 mmol), CsF (568 mg, 8.6 mmol), Pd(dppf)Cl₂ (165 mg, 0.14 mmol). The resulting reaction mixture was heated to 100° C. in M.W. and stirred for 1 h and concentrated in vacuo to remove the solvent, then added water, the aqueous phase was extracted with dichloromethane, the combined organic phases were dried over anhydrous sodium sulfate, filtered, and concentrated, the crude was purified by C.C. to give 449-2 (600 mg, yield: 74.4%) as a yellow solid.

498

The Synthesis of 3-amino-6-(2-chloro-5-fluorophenyl)pyrazine-2-carboxylic acid (449-3)

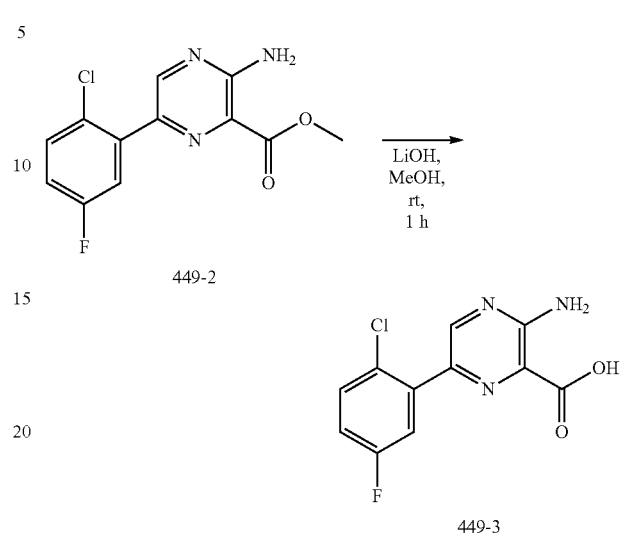

To a solution of 449-2 (600 mg, 2.1 mmol) in MeOH (16 mL) was added LiOH (884 mg, 21.1 mmol), the mixture was stirred at rt for 1 h. The mixture was cooled to 0° C. and acidified with 1N HCl solution to pH 4.0. After the reaction mixture was filtered and washed with MeOH. Then concentrated in vacuo to give 449-3 (200 mg, 35.7% yield) as a yellow solid.

The Synthesis of dimethyl (4-(3-amino-6-(2-chloro-5-fluorophenyl)pyrazine-2-carboxamido)phenylsulfonyl)methylphosphonate (SU20668-0449-01)

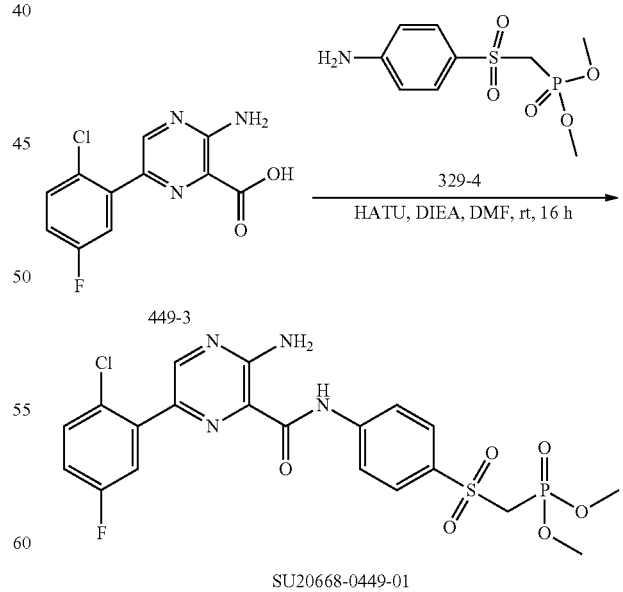

To a stirred solution of 329-4 (80 mg, 286.48 umol) in DMF (4 mL) was added 446-3 (76.68 mg, 286.48 umol), DIPEA (111.08 mg, 859.45 umol) and HATU (163.39 mg, 429.72 umol). The resulting reaction mixture was stirred at rt for 16 h. Then it was purified by prep-HPLC to give SU20668-0449-01 (58 mg, 38.28% yield) as a light-yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 96.95%, Rt=1.988 min; MS Calcd.: 528.04; MS Found: 529.2 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM AcONH$_4$) water/$CH_3CN$=900/100 (v/v)] and 10% [total 10 mM AcONH$_4$) water/$CH_3CN$=100/900 (v/v)] to 15% [total 10 mM AcONH$_4$) water/$CH_3CN$=900/100 (v/v)] and 85% [total 10 mM AcONH$_4$) water/$CH_3CN$=100/900 (v/v)] in 5 min, then under this condition for 10 min, finally changed to 90% [(total 10 mM AcONH$_4$) water/$CH_3CN$=900/100 (v/v)] and 10% [total 10 mM AcONH$_4$) water/$CH_3CN$=100/900 (v/v)] in 0.1 min and under this condition for 5 min). Purity: 99.31%, Rt=9.332 min. $^1$H NMR (400 MHz, DMSO-d$_6$) δ 10.69 (s, 1H), 8.69 (s, 1H), 8.07 (d, J=8.8 Hz, 2H), 7.93 (d, J=9.2 Hz, 2H), 7.80-7.85 (m, 3H), 7.64-7.67 (m, 1H), 7.34-7.38 (m, 1H), 4.48 (d, J=17.2 Hz, 2H), 3.63 (d, J=11.2 Hz, 6H).

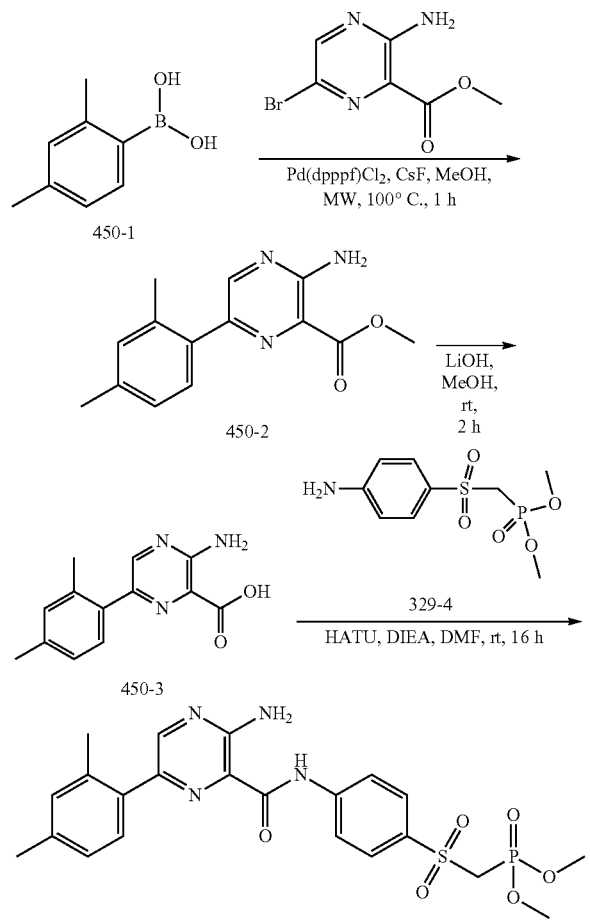

Scheme 38 Route for SU20668-0450-01

The Synthesis of methyl 3-amino-6-(2,4-dimethylphenyl)pyrazine-2-carboxylate (450-2)

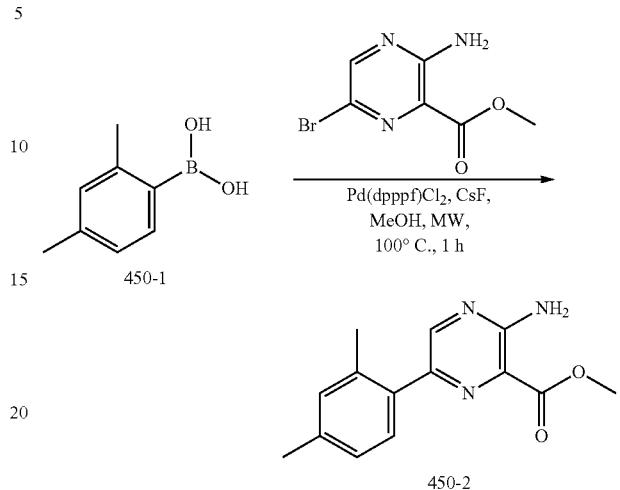

To a stirred solution of compound 450-1 (400 mg, 2.67 mmol) in MeOH (10 mL) was added methyl 3-amino-6-bromopyrazine-2-carboxylate (495 mg, 2.13 mmol), CsF (528 mg, 8.0 mmol), Pd(dppf)Cl$_2$ (150 mg, 0.13 mmol). The resulting reaction mixture was heated to 100° C. in M.W. and stirred for 1 h and concentrated in vacuo to remove the solvent, then added water, the aqueous phase was extracted with dichloromethane, the combined organic phases were dried over anhydrous sodium sulfate, filtered, and concentrated, the crude was purified by C.C. to give 450-2 (500 mg, yield: 72.9%) as a yellow solid.

The Synthesis of 3-amino-6-(2,4-dimethylphenyl) pyrazine-2-carboxylic acid (450-3)

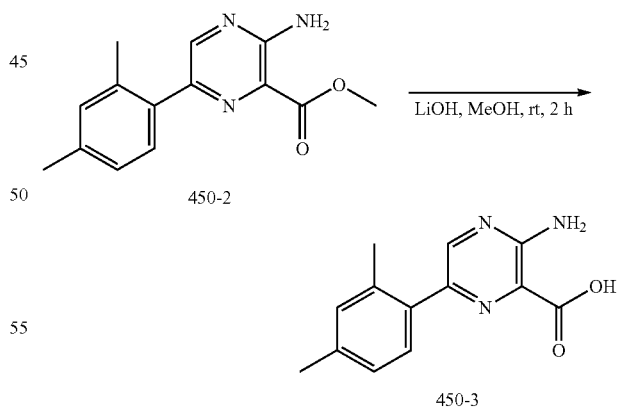

To a solution of 450-2 (500 mg, 2.06 mmol) in MeOH (16 mL) was added LiOH (863 mg, 20.6 mmol), the mixture was stirred at rt for 2 h. The mixture was cooled to 0° C. and acidified with 1N HCl solution to pH 4.0. After the reaction mixture was filtered and washed with MeOH. Then concentrated in vacuo to give 450-3 (250 mg, 50.0% yield) as yellow oil.

The Synthesis of dimethyl (4-(3-amino-6-(2,4-dimethylphenyl)pyrazine-2-carboxamido)phenylsulfonyl)methylphosphonate (SU20668-0450-01)

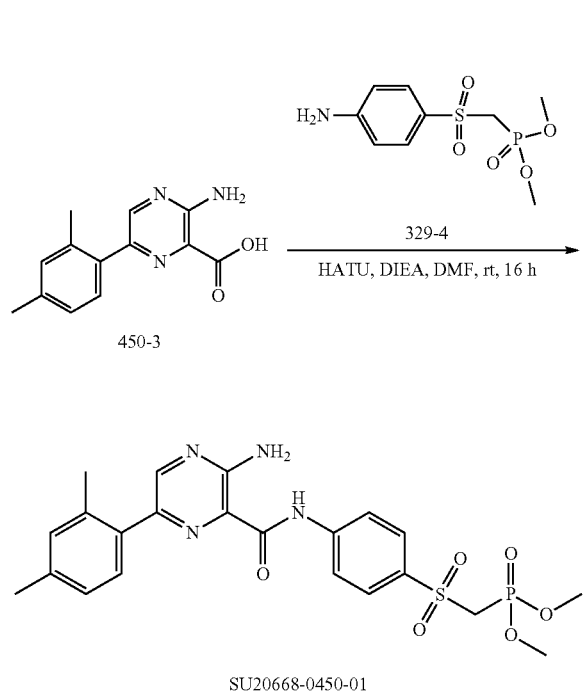

To a stirred solution of 329-4 (110 mg, 393.91 umol) in DMF (4 mL) was added 450-3 (95.82 mg, 393.91 umol), DIPEA (152.73 mg, 1.18 mmol) and HATU (224.67 mg, 590.87 umol). The resulting reaction mixture was stirred at rt for 16 h. Then it was purified by prep-HPLC to give SU20668-0450-01 (61 mg, 30.70% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 98.93%, Rt=2.047 min; MS Calcd.: 504.12; MS Found: 505.2 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM $AcONH_4$) water/$CH_3CN$=900/100 (v/v)] and 10% [total 10 mM $AcONH_4$) water/$CH_3CN$=100/900 (v/v)] to 15% [total 10 mM $AcONH_4$) water/$CH_3CN$=900/100 (v/v)] and 85% [total 10 mM $AcONH_4$) water/$CH_3CN$=100/900 (v/v)] in 5 min, then under this condition for 10 min, finally changed to 90% [(total 10 mM $AcONH_4$) water/$CH_3CN$=900/100 (v/v)] and 10% [total 10 mM $AcONH_4$) water/$CH_3CN$=100/900 (v/v)] in 0.1 min and under this condition for 5 min). Purity: 98.73%, Rt=9.648 min. $^H$ NMR (400 MHz, DMSO-$d_6$) δ 10.63 (s, 1H), 8.47 (s, 1H), 8.06 (d, J=8.8 Hz, 2H), 7.89 (d, J=8.8 Hz, 2H), 7.63 (s, 2H), 7.45 (d, J=7.6 Hz, 1H), 7.11-7.14 (m, 2H), 4.45 (d, J=17.2 Hz, 2H), 3.61 (d, J=11.6 Hz, 6H), 2.38 (s, 3H), 2.32 (s, 3H).

Scheme 39: Route for SU20668-0467-01

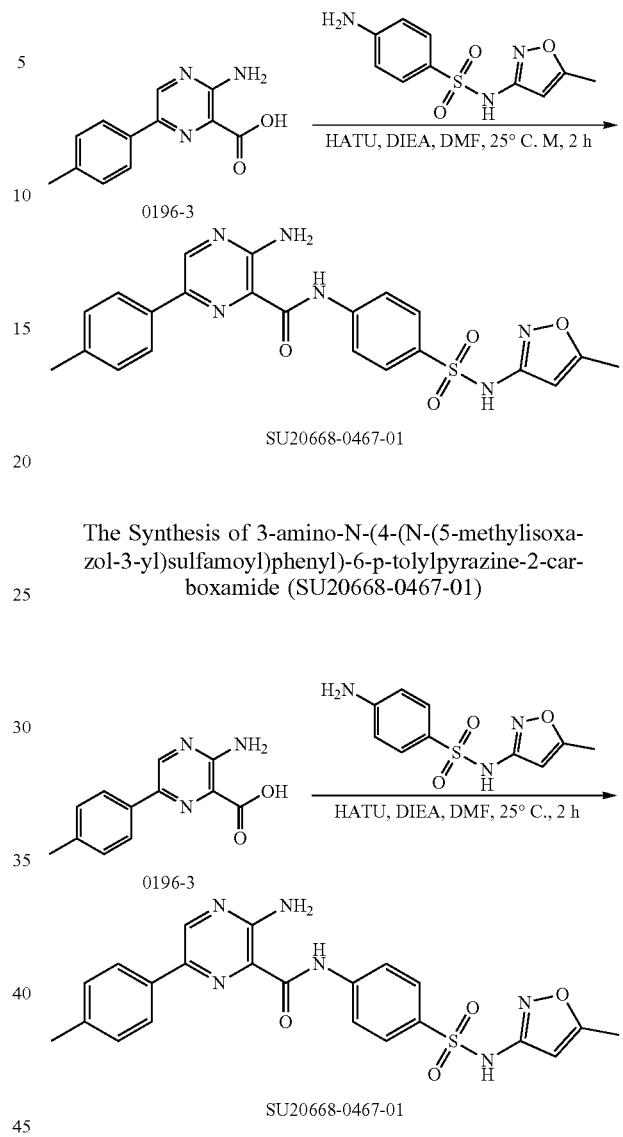

The Synthesis of 3-amino-N-(4-(N-(5-methylisoxazol-3-yl)sulfamoyl)phenyl)-6-p-tolylpyrazine-2-carboxamide (SU20668-0467-01)

To a stirred solution of compound 4-amino-N-(5-methylisoxazol-3-yl)benzenesulfonamide (133 mg, 0.53 mmol) in DMF (5 ml) was added 0196-3 (100 mg, 0.44 mmol), HATU (250 mg, 0.66 mmol) and DIEA (170 mg, 1.32 mmol). The resulting reaction mixture was stirred at rt for 2 h. The mixture was concentrated in vacuo, purified by prep-HPLC to give SU20668-0467-01 (30 mg, yield: 14.8%) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 97.81%, Rt=1.812 min; MS Calcd.: 464.50; MS Found: 465.2 [M+H]$^+$. Agilent HPLC 1200, Column: L-column 2 ODS (150 mm*4.6 mm*5.0 μm); Column Temperature: 40° C.; Flow Rate: 1.5 mL/min; Mobile Phase: from 90% [(total 10 mM $AcONH_4$) water/$CH_3CN$=900/100 (v/v)] and 10% [total 10 mM $AcONH_4$) water/$CH_3CN$=100/900 (v/v)] to 15% [total 10 mM AcONH$_4$) water/CH$_3$CN=900/100 (v/v)] and 85% [total 10 mM AcONH$_4$) water/CH$_3$CN=100/900 (v/v)] in 5 min, then under this condition for 10 min, finally changed to 90% [(total 10 mM AcONH$_4$) water/CH$_3$CN=900/100 (v/v)] and 10% [total 10 mM AcONH$_4$) water/CH$_3$CN=100/900 (v/v)] in 0.1 min and under this condition for 5 min. Purity: 97.69%, Rt=8.121 min. $^1$H NMR (400 MHz, DMSO-d$_6$) δ 11.36 (brs, 1H), 10.63 (s, 1H), 8.89 (s, 1H), 8.09 (d, J=8.0 Hz, 2H), 8.00 (d, J=8.8 Hz, 2H), 7.83 (d, J=8.4 Hz, 2H), 7.61 (s, 2H), 7.27 (d, J=8.0 Hz, 2H), 6.10 (s, 1H), 2.34 (s, 3H), 2.26 (s, 3H).

Scheme 40: Route for SU20668-0468-01

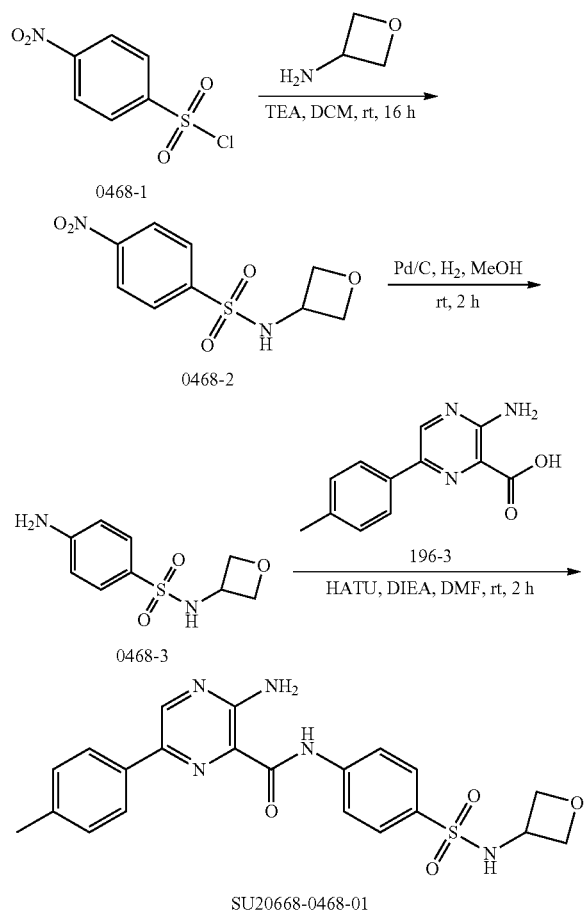

The Synthesis of 4-nitro-N-(oxetan-3-yl)benzenesulfonamide (0468-2)

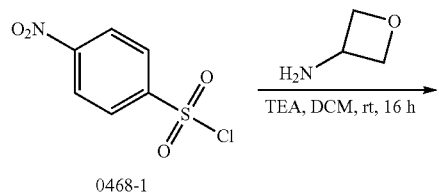

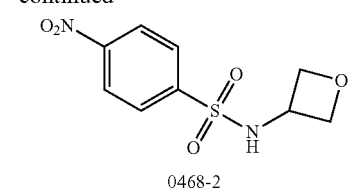

To a solution of compound 0468-1 (400 mg, 1.81 mmol) in DCM (10 mL) was added oxetan-3-amine (146 mg, 2.00 mmol) and DIEA (516 mg, 4.00 mmol). The resulting reaction mixture was stirred for 16 h at rt. Then it was concentrated to dryness and purified by silica-gel column (DCM:MeOH=100:1) to give the desired product 0468-2 (300 mg, yield: 64.2%) as a yellow solid.

The Synthesis of 4-amino-N-(oxetan-3-yl)benzenesulfonamide (0468-3)

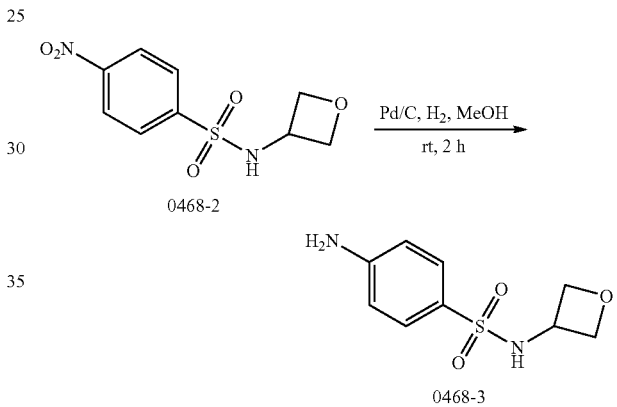

To a solution of 0468-2 (300 mg, 1.16 mmol) in MeOH (10 mL) was added Pd/C (10%, 40 mg), the mixture was stirred at rt for 2 h under H$_2$ atmosphere (1.0 atm). Then the reaction mixture was filtered and concentrated in vacuo to afford compound 0468-3 (230 mg, yield: 87.8%) as a light yellow solid.

The Synthesis of 3-amino-N-(4-(N-oxetan-3-ylsulfamoyl)phenyl)-6-p-tolylpyrazine-2-carboxamide (SU20668-0468-01)

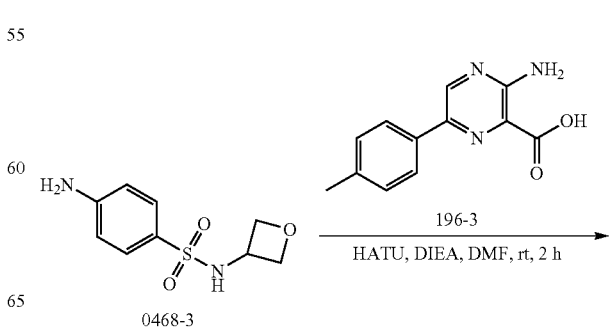

505

-continued

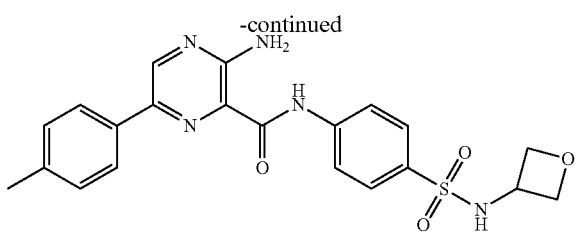

SU20668-0468-01

506

-continued

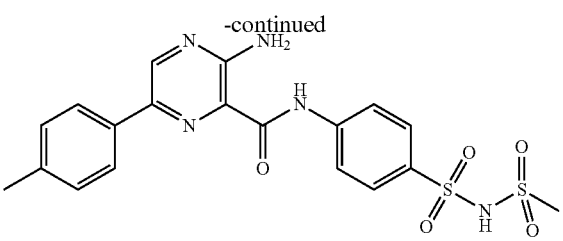

SU20668-0470-01

To a solution of compound 0468-3 (80 mg, 0.35 mmol) in DMF (4 mL) was added 196-3 (80 mg, 0.35 mmol), DIEA (90 mg, 0.70 mmol) and HATU (182 mg, 0.48 mmol). The resulting reaction mixture was stirred for 2 h at rt. Then it was purified by prep-HPLC to give the desired product SU20668-0468-01 (49 mg, yield: 31.8%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 98.38%, Rt=2.046 min; MS Calcd.: 439.1; MS Found: 440.2 [M+H]+. HPLC (Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 98.51%, Rt=9.576 min. $^1$H NMR (400 MHz, DMSO-d$_6$) δ10.65 (s, 1H), 8.90 (s, 1H), 8.46 (s, 1H), 8.10 (d, J=8.0 Hz, 2H), 8.04 (d, J=7.2 Hz, 2H), 7.77 (d, J=8.0 Hz, 2H), 7.62 (s, 2H), 7.28 (d, J=8.0 Hz, 2H), 4.47-4.51 (m, 2H), 4.35-4.39 (m, 1H), 4.22-4.25 (m, 2H), 2.35 (s, 3H).

The Synthesis of N-(methylsulfonyl)-4-nitrobenzenesulfonamide (0470-2)

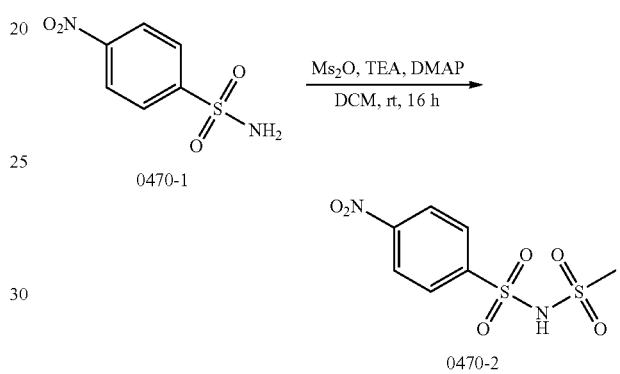

To a solution of compound 0470-1 (400 mg, 1.99 mmol) in DCM (10 mL) was added TEA (606 mg, 6.00 mmol), DMAP (25 mg, 0.20 mmol) and Ms$_2$O (348 mg, 2.00 mmol). The resulting reaction mixture was stirred for 16 h at rt. Then it was concentrated to dryness and purified by silica-gel column (DCM:MeOH=100:1) to give the desired product 0470-2 (460 mg, yield: 83.0%) as a yellow solid.

The Synthesis of 4-amino-N-(methylsulfonyl)benzenesulfonamide (470-3)

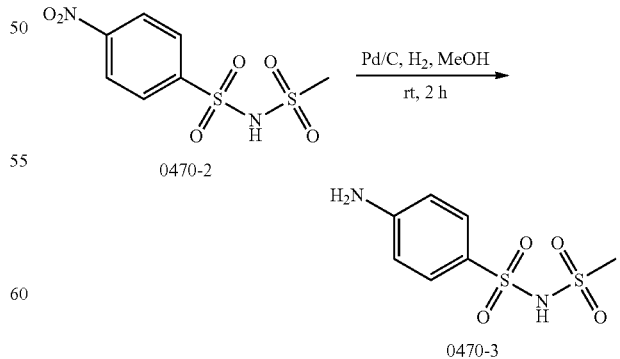

To a solution of 0470-2 (460 mg, 1.64 mmol) in MeOH (10 mL) was added Pd/C (10%, 50 mg), the mixture was stirred at rt for 2 h under H$_2$ atmosphere (1.0 atm). Then the Scheme 41: Route for SU20668-0468-01

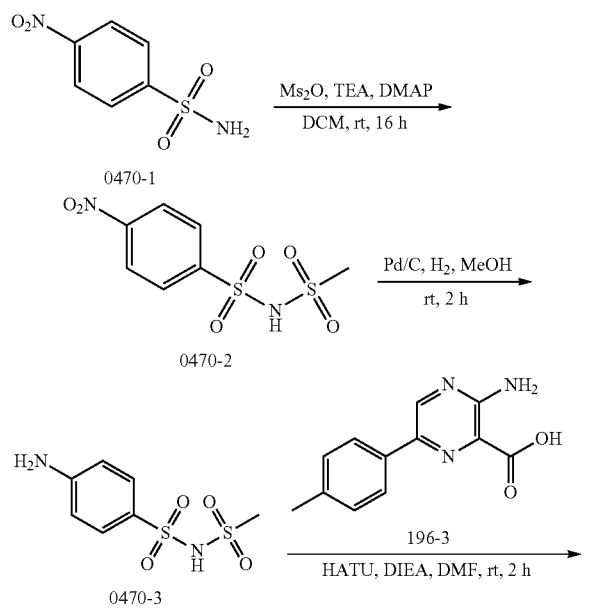

The Synthesis of 3-amino-N-(4-(N-(methylsulfonyl)sulfamoyl)phenyl)-6-p-tolylpyrazine-2-carboxamide (SU20668-0470-01)

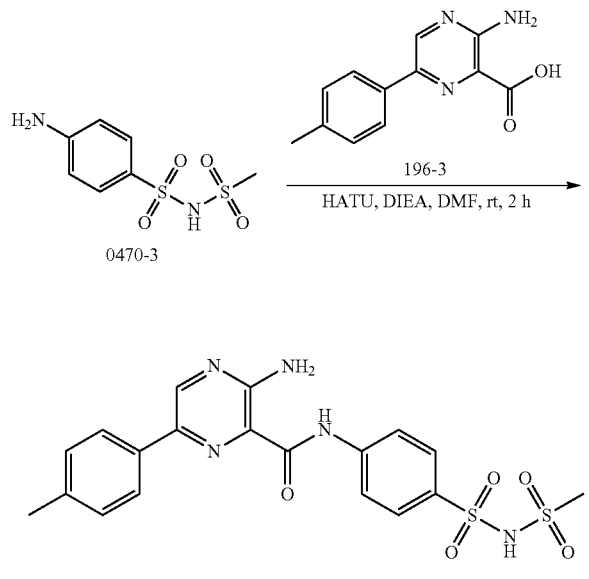

Scheme 42: Route for SU20668-0471-01

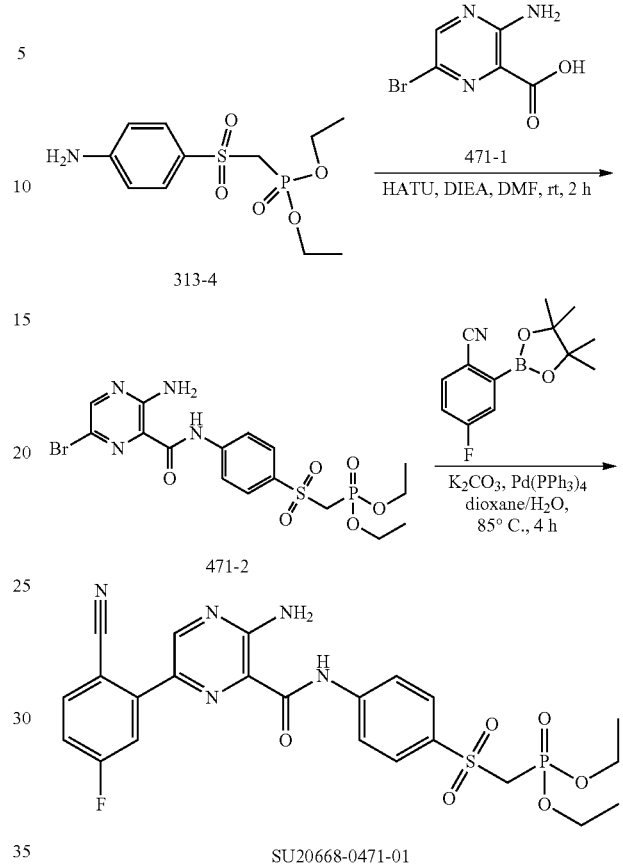

To a solution of compound 0470-3 (400 mg, 1.60 mmol) in DMF (8 mL) was added 196-3 (366 mg, 1.60 mmol), DIEA (412 mg, 3.20 mmol) and HATU (760 mg, 2.00 mmol). The resulting reaction mixture was stirred for 2 h at rt. Then it was purified by prep-HPLC to give the desired product SU20668-0470-01 (53 mg, yield: 7.2%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 99.55%, Rt=1.647 min; MS Calcd.: 461.1; MS Found: 462.2 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 99.70%, Rt=7.475 min. $^1$H NMR (400 MHz, DMSO-d$_6$) δ10.48 (s, 1H), 8.87 (s, 1H), 8.10 (d, J=8.0 Hz, 2H), 7.84 (d, J=8.4 Hz, 2H), 7.70 (d, J=8.4 Hz, 2H), 7.62 (s, 1H), 7.29 (d, J=8.0 Hz, 2H), 7.03 (s, 2H), 2.73 (s, 3H), 2.35 (s, 3H).

The Synthesis of diethyl (4-(3-amino-6-bromopyrazine-2-carboxamido)phenylsulfonyl)methylphosphonate (471-2)

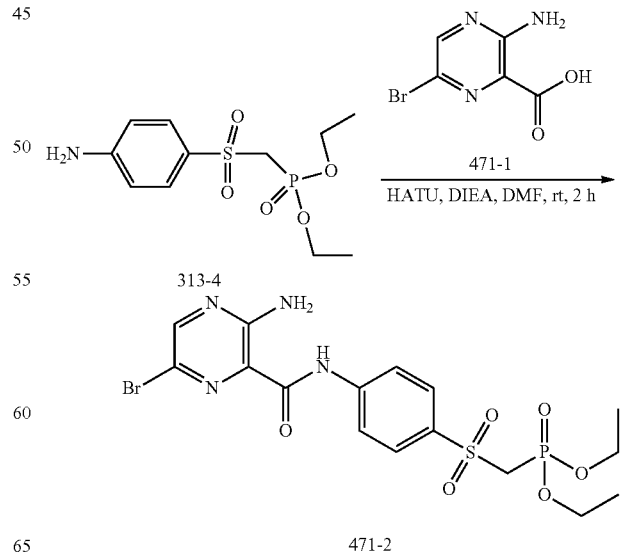

To a solution of compound 313-4 (200 mg, 0.64 mmol) in DMF (4 mL) was added 471-1 (140 mg, 0.16 mmol), DIEA (165 mg, 1.28 mmol) and HATU (300 mg, 0.80 mmol). The resulting reaction mixture was stirred for 2 h at rt. Then it was purified by prep-HPLC to give the desired product 471-2 (240 mg, yield: 72.7%) as a yellow solid.

The Synthesis of diethyl (4-(3-amino-6-(2-cyano-5-fluorophenyl)pyrazine-2-carboxamido)phenylsulfonyl)methylphosphonate (SU20668-0471-01)

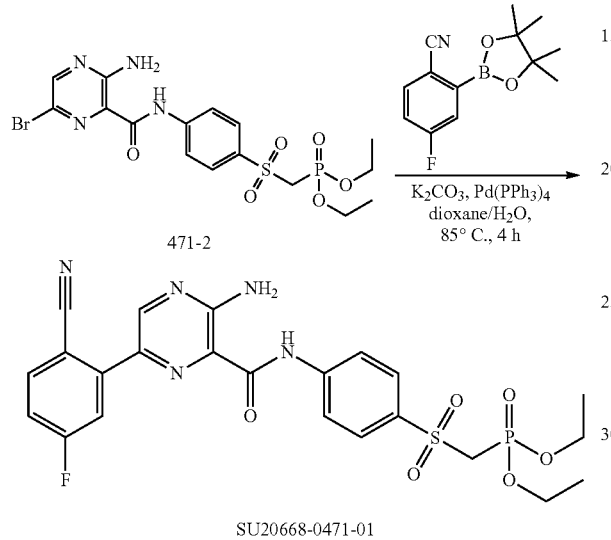

The mixture of 471-2 (240 mg, 0.47 mmol), 4-fluoro-2-(4,4,5,5-tetramethyl-1,3,2-dioxaborolan-2-yl)benzonitrile (124 mg, 0.50 mmol), Pd(PPh$_3$)$_4$ (25 mg) and K$_2$CO$_3$ (124 mg, 0.90 mmol) in dioxane/H$_2$O (4:1, 4 mL) was stirred at 85° C. under N$_2$ atmosphere for 4 hours. Then mixture was concentrated to dryness. The residue was purified by prep-HPLC to give SU20668-0471-01 (132 mg, yield: 51.0%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 98.96%, Rt=2.011 min; MS Calcd.: 547.1; MS Found: 548.1 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 98.92%, Rt=9.395 min. $^1$H NMR (400 MHz, DMSO-d$_6$) δ10.50 (s, 1H), 9.05 (s, 1H), 8.17-8.21 (m, 2H), 8.03-8.14 (m, 4H), 7.94-7.96 (m, 2H), 7.47-7.51 (m, 1H), 4.42 (d, J=16.8 Hz, 2H), 3.95-4.03 (m, 4H), 1.17 (t, J=6.8 Hz, 6H).

Scheme 43: Route for SU-20668-0476-01

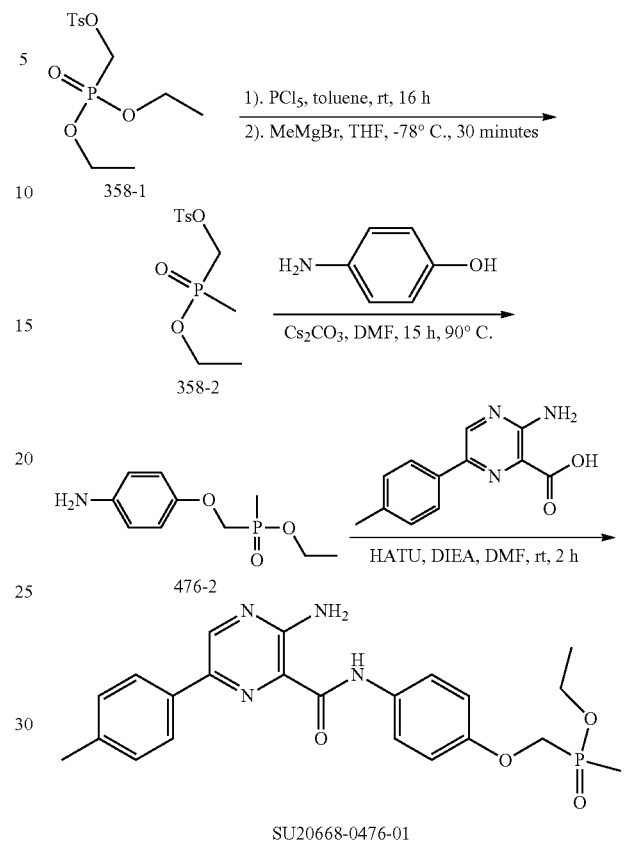

The Synthesis of (ethoxy(methyl)phosphoryl)methyl 4-methylbenzenesulfonate (358-2)

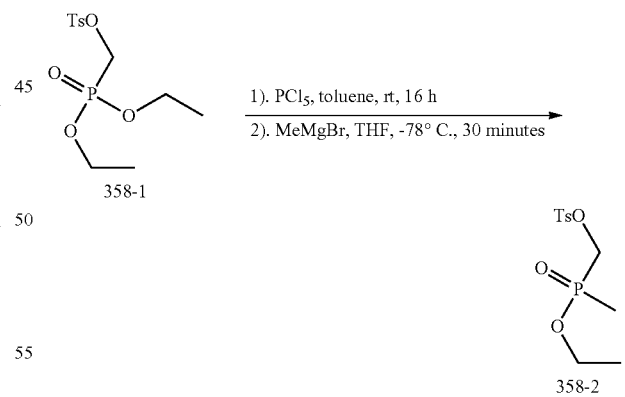

To a stirred solution of 358-1 (5 g, 15.5 mmol) in toluene (30 mL) was added PCl$_5$ (4.85 g, 23.3 mmol) and the reaction mixture was stirred at 0° C. until homogenous, then stirred at rt overnight. The solvent was removed. To the crude in dry THF (25 mL) at −78° C. was added MeMgBr (5.6 mL, 3.0M in diethyl ether). The mixture solution was stirred for 30 min. The reaction was quenched with aqueous NH$_4$Cl. The mixture was diluted with ethyl acetate and H$_2$O, the organic layer was washed with H$_2$O. The organic layer was concentrated, purified by column to afford the product 358-2 (2 g, 44% yield) as a white solid.

The Synthesis of ethyl (4-aminophenoxy)methyl(methyl)phosphinate (476-2)

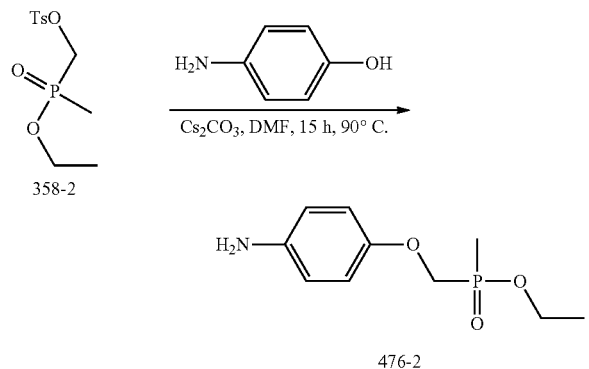

To a stirred solution of 358-2 (250 mg, 0.86 mmol), 4-aminophenol (112 mg, 1.03 mmol) and $Cs_2CO_3$ (336 mg, 1.03 mmol) in DMF (10 mL), was stirred at 90° C. overnight. After the consumption of starting material (by LCMS), the mixture was concentrated, purified by column to afford the product 476-2 (110 mg, 57% yield) as brown oil.

The Synthesis of ethyl (4-(3-amino-6-p-tolylpyrazine-2-carboxamido henoxy)methyl(methyl)phosphinate(SU20668-0476-01)

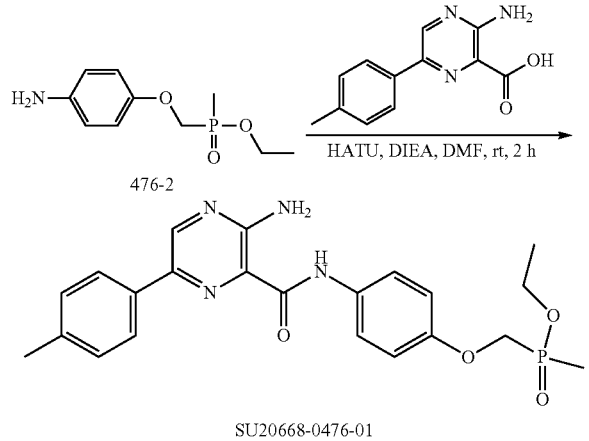

To a stirred solution of compound 476-2 (110 mg, 0.48 mmol) in DMF (5 ml) was added 3-amino-6-p-tolylpyrazine-2-carboxylic acid (110 mg, 0.48 mmol), HATU (274 mg, 0.72 mmol) and DIEA (186 mg, 1.44 mmol). The resulting reaction mixture was stirred at rt for 2 h. The mixture was concentrated in vacuo, purified by prep-HPLC to give SU20668-0476-01 (40 mg, 19% yield) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 99.67%, Rt=2.079 min; MS Calcd.: 440.43; MS Found: 441.4 [M+H]$^+$. Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM $AcONH_4$) water/$CH_3CN$=900/100 (v/v)] and 10% [total 10 mM $AcONH_4$) water/$CH_3CN$=100/900 (v/v)] to 15% [total 10 mM $AcONH_4$) water/$CH_3CN$=900/100 (v/v)] and 85% [total 10 mM $AcONH_4$) water/$CH_3CN$=100/900 (v/v)] in 5 min, then under this condition for 10 min, finally changed to 90% [(total 10 mM $AcONH_4$) water/$CH_3CN$=900/100 (v/v)] and 10% [total 10 mM $AcONH_4$) water/$CH_3CN$=100/900 (v/v)] in 0.1 min and under this condition for 5 min. Purity: 100%, Rt=9.682 min. $^1$H NMR (400 MHz, DMSO-$d_6$) δ 10.31 (s, 1H), 8.85 (s, 1H), 8.09 (d, J=8.4 Hz, 2H), 7.70-7.73 (m, 2H), 7.60 (s, 2H), 7.27 (d, J=8.0 Hz, 2H), 7.03-7.06 (m, 2H), 4.26-4.38 (m, 2H), 3.98-4.09 (m, 2H), 2.34 (s, 3H), 1.52 (d, J=14.4 Hz, 3H), 1.22 (t, J=7.2 Hz, 3H).

Scheme 44: Route for SU20688-0478-01

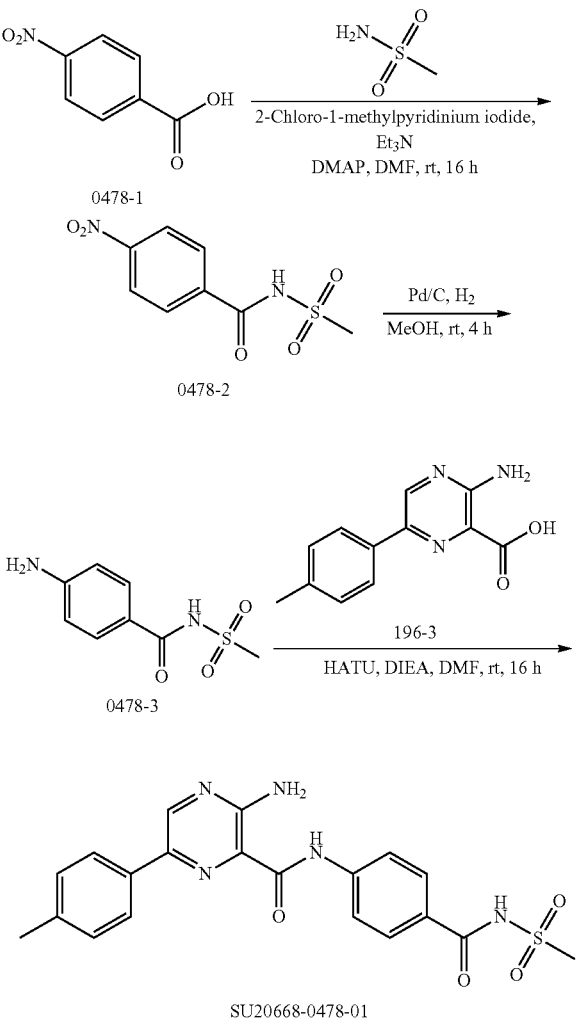

The Synthesis of N-(methylsulfonyl)-4-nitrobenzamide (0478-2)

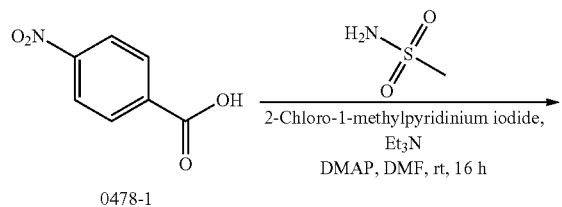

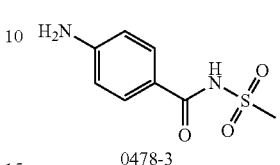

To a stirred solution of methanesulfonamide (136.60 mg, 1.44 mmol) in DMF (6 mL) was added 0478-1 (200 mg, 1.20 mmol), TEA (363.30 mg, 3.59 mmol), 2-Chloro-1-methylpyridinium iodide (458.62 mg, 1.80 mmol) and DMAP (160.83 mg, 1.32 mmol) at rt. The resulting reaction mixture was stirred at rt for 16 h. Then purified by prep-HPLC to give 0478-2 (250 mg, 85.54% yield) as a white solid.

The Synthesis of 4-amino-N-(methylsulfonyl)benzamide (0478-3)

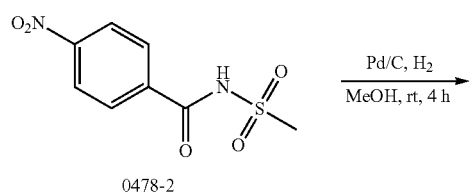

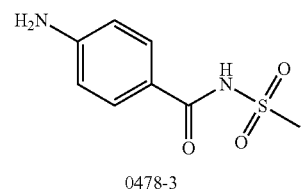

To a solution of 0478-2 (110 mg, 450.41 umol) in MeOH (11 mL) was added Pd/C (30 mg), the mixture was stirred under hydrogen atmosphere (1 atm) at room temperature for 4 h, filtrated, concentrated to give 0478-3 (96 mg, 99.49% yield) as brown oil.

The Synthesis of 3-amino-N-(4-(methylsulfonylcarbamoyl)phenyl)-6-p-tolylpyrazine-2-carboxamide (SU20668-0478-01)

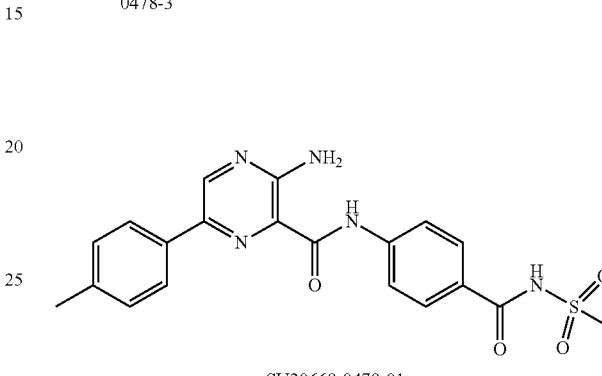

To a stirred solution of 0478-3 (96 mg, 448.09 umol) in DMF (3 mL) was added 196-3 (102.72 mg, 448.09 umol), DIPEA (173.73 mg, 1.34 mmol) and HATU (255.57 mg, 672.14 umol). The resulting reaction mixture was stirred at rt for 16 h. Then it was purified by prep-HPLC to give SU20668-0478-01 (63 mg, 33.05% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 97.84%, Rt=1.678 min; MS Calcd.: 425.12; MS Found: 426.2 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM $AcONH_4$) water/$CH_3CN$=900/100 (v/v)] and 10% [total 10 mM $AcONH_4$) water/$CH_3CN$=100/900 (v/v)] to 15% [total 10 mM $AcONH_4$) water/$CH_3CN$=900/100 (v/v)] and 85% [total 10 mM $AcONH_4$) water/$CH_3CN$=100/900 (v/v)] in 5 min, then under this condition for 10 min, finally changed to 90% [(total 10 mM $AcONH_4$) water/$CH_3CN$=900/100 (v/v)] and 10% [total 10 mM $AcONH_4$) water/$CH_3CN$=100/900 (v/v)] in 0.1 min and under this condition for 5 min). Purity: 97.96%, Rt=7.332 min. $^1$H NMR (400 MHz, DMSO-$d_6$) δ 12.04 (bs, 1H), 10.55 (s, 1H), 8.89 (s, 1H), 8.09-8.11 (m, 2H), 7.91-7.97 (m, 4H), 7.63 (s, 2H), 7.29 (d, J=8.0 Hz, 2H), 3.19 (s, 3H), 2.35 (s, 3H).

Scheme 45: Route for SU20668-0480-01

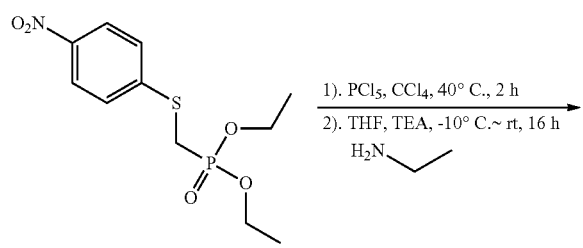

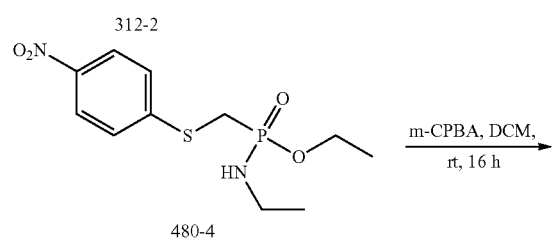

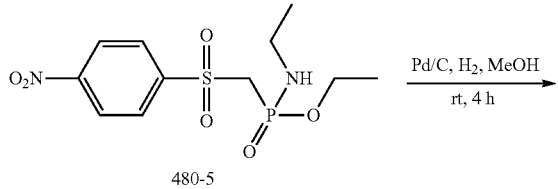

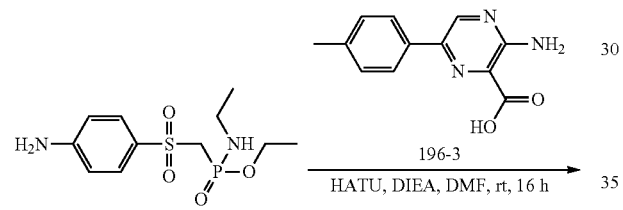

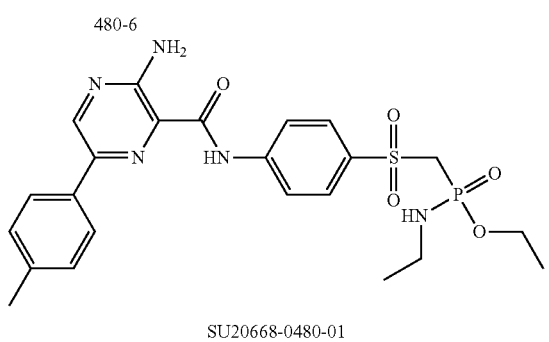

SU20668-0480-01

The Synthesis of ethyl N-ethyl-P-((4-nitrophenyl-thio)methyl)phosphonamidate (480-4)

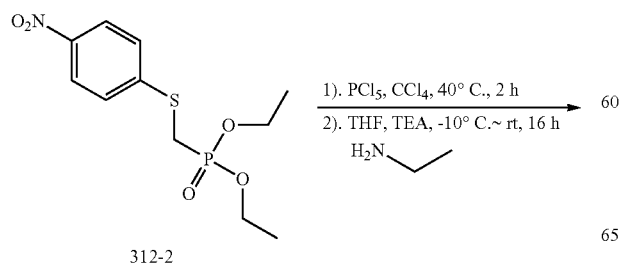

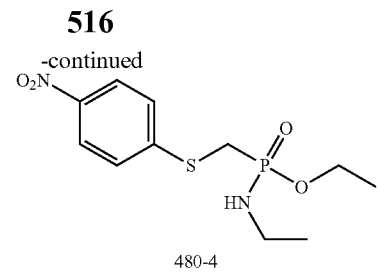

To a stirred solution of 312-2 (200 mg, 655.12 umol) in Carbon tetrachloride (6 mL) was added Phosphorus pentachloride (204.63 mg, 982.68 umol), the solution was stirred at 40° C. for 2 h, the solvent was removed by concentration, the residue was dissolved in THF (4 mL), added Triethylamine (331.46 mg, 3.28 mmol), cooled to −10° C., ethanamine (59.07 mg, 1.31 mmol) solution of THF (2 N) was added slowly, the mixture was warmed to rt, stirred for 16 h, concentrated and purified by pre-HPLC to give 480-4 (480 mg, 80.26% yield) as a brown solid.

The Synthesis of ethyl N-ethyl-P-((4-nitrophenylsulfonyl)methyl)phosphonamidate (480-5)

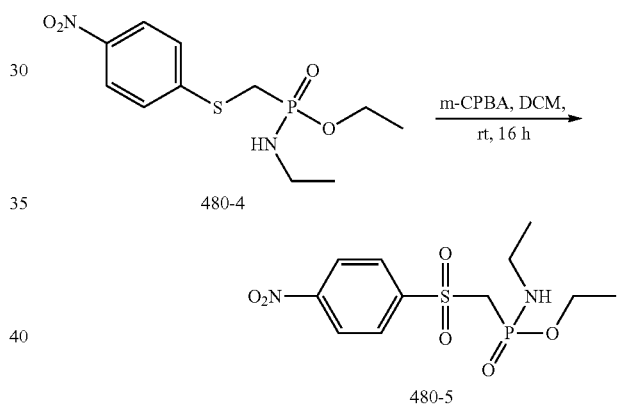

To a stirred solution of 480-4 (550 mg, 1.81 mmol) in DCM (16 mL) was added 3-Chloroperoxybenzoic acid (935.72 mg, 5.42 mmol), the mixture was stirred at rt for 16 h, poured into water, extracted with DCM, washed with Sodium carbonate solution, water, the combined organic phases were dried over anhydrous sodium sulfate, filtered, concentrated in vacuo and purified with pre-HPLC to give 480-5 (112 mg, 18.43% yield) as a white solid.

The Synthesis of ethyl P-(4-aminophenylsulfonyl)methyl-N-ethylphosphonamidate (480-6)

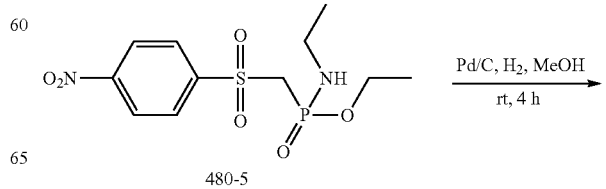

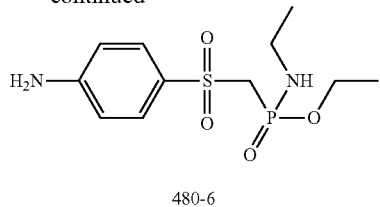

480-6

To a solution of 480-5 (60 mg, 178.41 umol) in MeOH (30 mL) was added Pd/C (20 mg), the mixture was stirred under hydrogen atmosphere (1 atm) at room temperature for 4 h, filtrated, concentrated to give 480-6 (52 mg, 95.15% yield) as brown oil.

The Synthesis of ethyl P-(4-(3-amino-6-p-tolylpyrazine-2-carboxamido)phenylsulfonyl)methyl-N-ethylphosphonamidate (SU20668-0480-01)

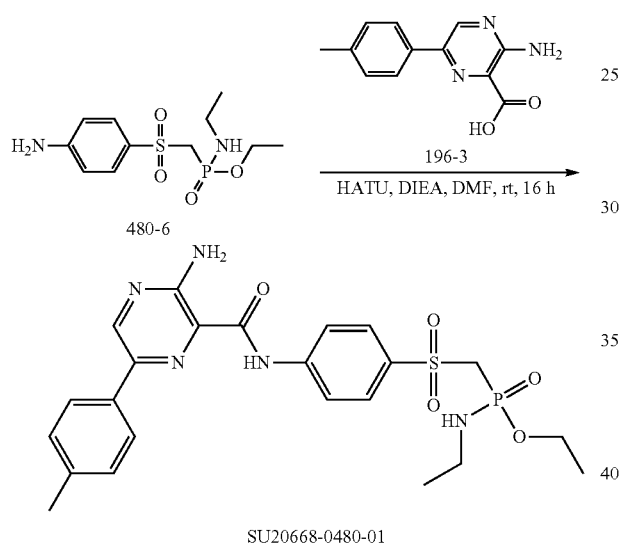

SU20668-0480-01

To a stirred solution of 480-6 (52 mg, 169.76 umol) in DMF (4 mL) was added 196-3 (42.81 mg, 186.73 umol), DIPEA (65.82 mg, 509.28 umol) and HATU (96.82 mg, 254.64 umol). The resulting reaction mixture was stirred at rt for 16 h. Then it was purified by prep-HPLC to give SU20668-0480-01 (31 mg, 35.28% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 100%, Rt=1.931 min; MS Calcd.: 517.15; MS Found: 518.2 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM $AcONH_4$) water/$CH_3CN$=900/100 (v/v)] and 10% [total 10 mM $AcONH_4$) water/$CH_3CN$=100/900 (v/v)] to 15% [total 10 mM $AcONH_4$) water/$CH_3CN$=900/100 (v/v)] and 85% [total 10 mM $AcONH_4$) water/$CH_3CN$=100/900 (v/v)] in 5 min, then under this condition for 10 min, finally changed to 90% [(total 10 mM $AcONH_4$) water/$CH_3CN$=900/100 (v/v)] and 10% [total 10 mM $AcONH_4$) water/$CH_3CN$=100/900 (v/v)] in 0.1 min and under this condition for 5 min). Purity: 96.87%, Rt=9.561 min. $^1$H NMR (400 MHz, DMSO-$d_6$ & $D_2O$) δ 8.89 (s, 1H), 8.07-8.09 (m, 4H), 7.92-7.94 (m, 2H), 7.30 (d, J=8.0 Hz, 2H), 3.82-3.89 (m, 2H), 2.76-2.80 (m, 2H), 2.35 (s, 3H) 1.11 (t, J=7.2 Hz, 3H), 0.99 (t, J=7.2 Hz, 3H).

Scheme 46: Route for SU20668-0484-01

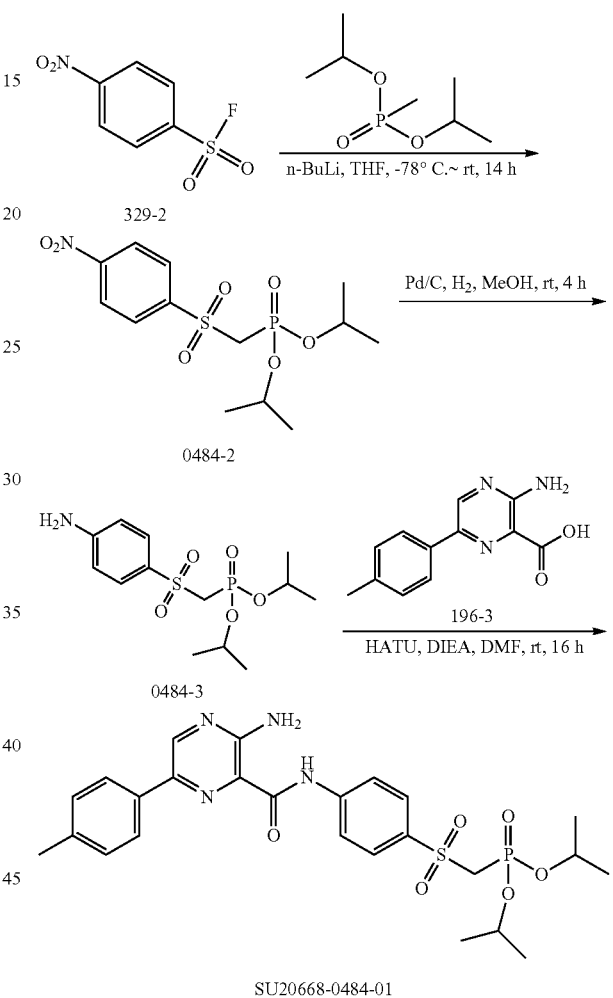

SU20668-0484-01

The Synthesis of diisopropyl (4-nitrophenylsulfonyl)methylphosphonate (0484-2)

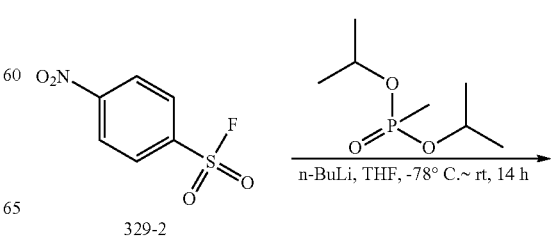

329-2

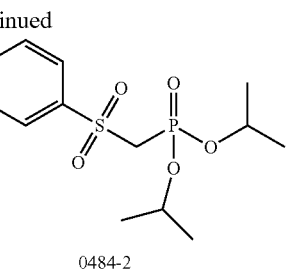

0484-2

To a stirred solution of diisopropyl methylphosphonate (1 g, 5.55 mmol) in THF (15 mL) was added n-BuLi (6.56 mmol) dropwise at −78° C., the solution was stirred at −78° C. for 30 min, 4-nitrobenzenesulfonyl fluoride (1.04 g, 5.05 mmol) was dissolved in THF and added slowly, the mixture was warmed to rt. and stirred for 14 h, poured into water, extracted with EA, the combined organic phases were dried over anhydrous sodium sulfate, filtered, and concentrated in vacuo and purified by C.C. to give 0484-2 (112 mg, 6.08% yield) as brown oil.

The Synthesis of diisopropyl (4-aminophenylsulfonyl)methylphosphonate (0484-3)

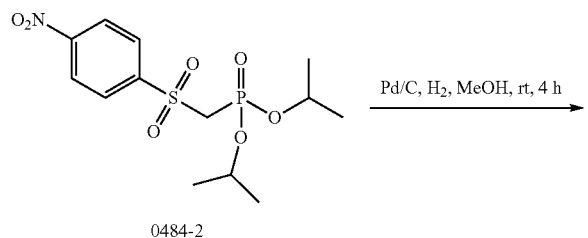

0484-2

Pd/C, H₂, MeOH, rt, 4 h

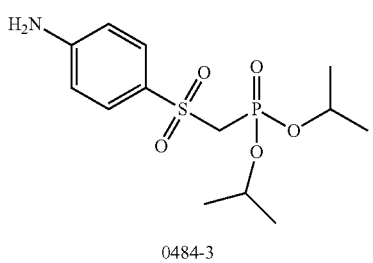

0484-3

To a solution of 0484-2 (110 mg, 301.09 umol) in MeOH (20 mL) was added Pd/C (20 mg), the mixture was stirred under hydrogen atmosphere (1 atm) at room temperature for 4 h, filtrated, concentrated to give 484-3 (94 mg, 93.1% yield) as brown oil.

The Synthesis of diisopropyl (4-(3-amino-6-p-tolylpyrazine-2-carboxamido)phenylsulfonyl)methylphosphonate (SU20668-0484-01)

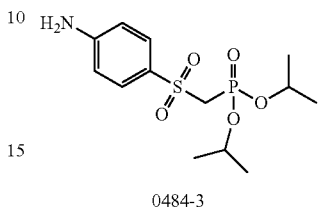 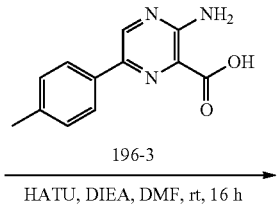

0484-3     196-3

HATU, DIEA, DMF, rt, 16 h

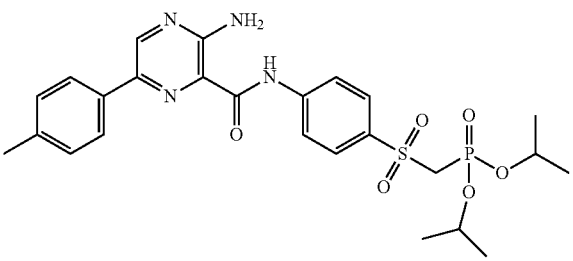

SU20668-0484-01

To a stirred solution of 0484-3 (128 mg, 381.68 umol) in DMF (4 mL) was added 196-3 (96.24 mg, 419.85 umol), DIPEA (147.99 mg, 1.15 mmol) and HATU (217.69 mg, 572.53 umol). The resulting reaction mixture was stirred at rt for 16 h. Then it was purified by prep-HPLC to give SU20668-0484-01 (110 mg, 52.73% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 100%, Rt=2.182 min; MS Calcd.: 546.17; MS Found: 547.2 [M+H]⁺. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM AcONH₄) water/CH₃CN=900/100 (v/v)] and 10% [total 10 mM AcONH₄) water/CH₃CN=100/900 (v/v)] to 15% [total 10 mM AcONH₄) water/CH₃CN=900/100 (v/v)] and 85% [total 10 mM AcONH₄) water/CH₃CN=100/900 (v/v)] in 5 min, then under this condition for 10 min, finally changed to 90% [(total 10 mM AcONH₄) water/CH₃CN=900/100 (v/v)] and 10% [total 10 mM AcONH₄) water/CH₃CN=100/900 (v/v)] in 0.1 min and under this condition for 5 min). Purity: 100%, Rt=10.528 min. ¹H NMR (400 MHz, DMSO-d₆) δ 10.69 (s, 1H), 8.89 (s, 1H), 8.07-8.11 (m, 4H), 7.90-7.93 (m, 2H), 7.66 (s, 2H), 7.29 (d, J=8.0 Hz, 2H), 4.55-4.64 (m, 2H), 4.29 (d, J=16.8 Hz, 2H), 2.34 (s, 3H), 1.19 (t, J=6.0 Hz, 12H).

Scheme 47: Route for SU20668-0485-01

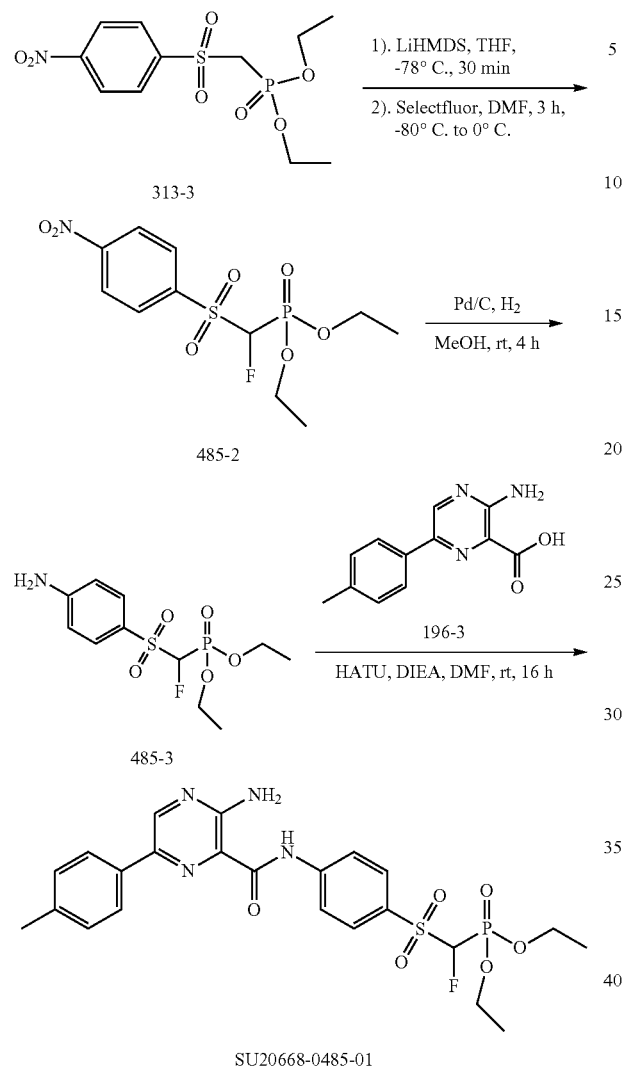

The Synthesis of diethyl fluoro(4-nitrophenylsulfonyl)methylphosphonate (485-2)

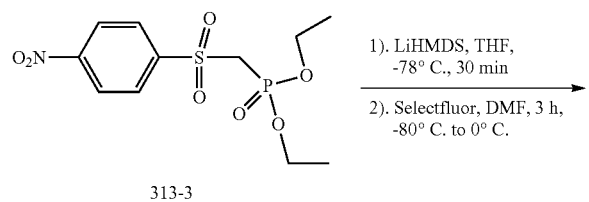

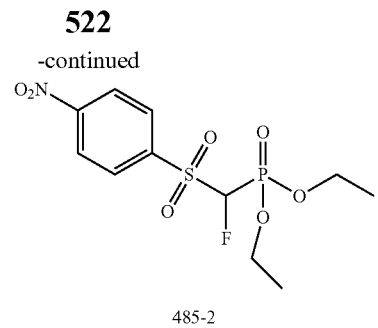

To a stirred solution of 313-3 (300 mg, 889.45 umol) in THF (1.8 mL) was added LDA (142.92 mg, 1.33 mmol) at −78° C. slowly, after stirred for 0.5 h at −78° C., Selectfluor (472.65 mg, 1.33 mmol) dissolved in THF (6 mL) was added dropwise, the mixture was warmed to rt, stirred for 3 h at rt, then added water, the aqueous phase was extracted with dichloromethane, the combined organic phases were dried over anhydrous sodium sulfate, filtered, concentrated in vacuo and purified with pre-HPLC to give 485-2 (112 mg, 35.44% yield) as brown oil.

The Synthesis of diethyl (4-aminophenylsulfonyl)fluoromethylphosphonate (485-3)

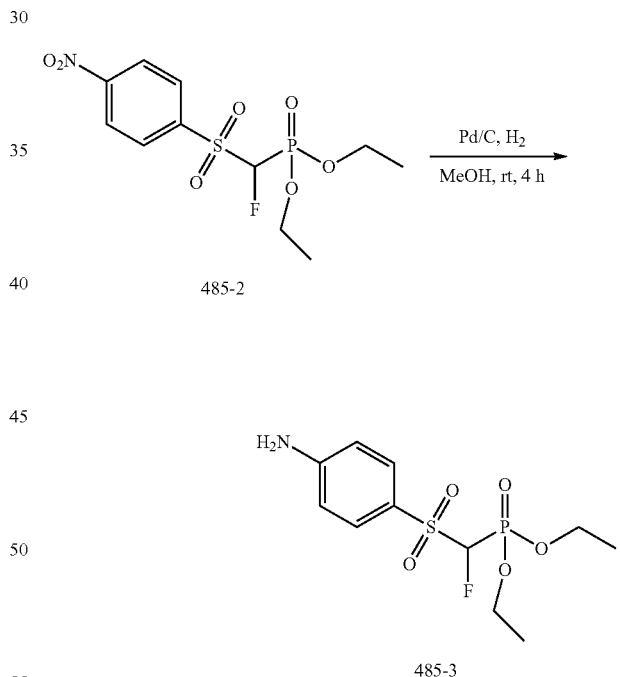

To a solution of 485-2 (110 mg, 0.309 mmol) in MeOH (20 mL) was added Pd/C (20 mg), the mixture was stirred under hydrogen atmosphere (1 atm) at room temperature for 4 h, filtrated, concentrated to give 485-3 (63 mg, 62.56% yield) as brown oil.

The Synthesis of diethyl (4-(3-amino-6-p-tolylpyrazine-2-carboxamido)phenylsulfonyl)fluoromethylphosphonate (SU20668-0485-01)

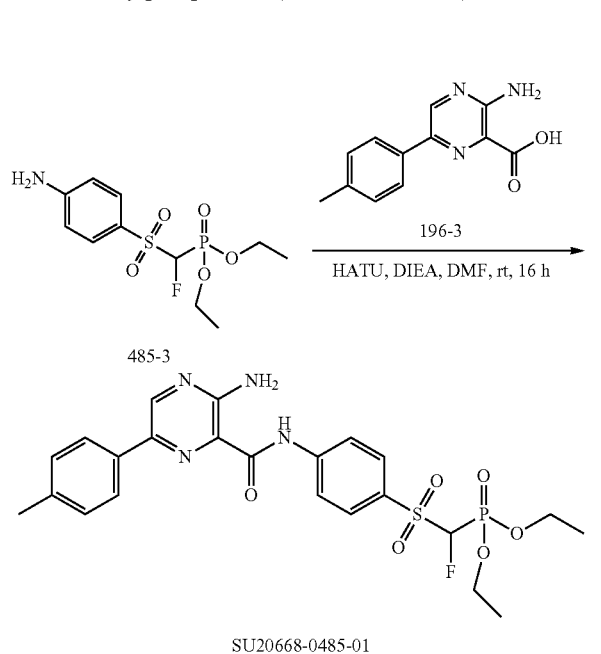

To a stirred solution of 485-3 (50 mg, 153.71 umol) in DMF (8 mL) was added 196-3 (38.76 mg, 169.08 umol), DIPEA (59.60 mg, 461.12 umol) and HATU (87.67 mg, 230.56 umol). The resulting reaction mixture was stirred at rt for 16 h. Then it was purified by prep-HPLC to give SU20668-0485-01 (25 mg, 30.32% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 100%, Rt=2.190 min; MS Calcd.: 536.13; MS Found: 537.1 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM $AcONH_4$) water/$CH_3CN$=900/100 (v/v)] and 10% [total 10 mM $AcONH_4$) water/$CH_3CN$=100/900 (v/v)] to 15% [total 10 mM $AcONH_4$) water/$CH_3CN$=900/100 (v/v)] and 85% [total 10 mM $AcONH_4$) water/$CH_3CN$=100/900 (v/v)] in 5 min, then under this condition for 10 min, finally changed to 90% [(total 10 mM $AcONH_4$) water/$CH_3CN$=900/100 (v/v)] and 10% [total 10 mM $AcONH_4$) water/$CH_3CN$=100/900 (v/v)] in 0.1 min and under this condition for 5 min). Purity: 99.17%, Rt=10.359 min. $^1$H NMR (400 MHz, DMSO-$d_6$) δ 10.77 (s, 1H), 8.88 (s, 1H), 8.08-8.14 (m, 4H), 7.89-7.91 (m, 2H), 7.68 (s, 2H), 7.29 (d, J=8.0 Hz, 2H), 6.54 (dd, J=43.2 Hz, 6.4 Hz, 1H), 4.13-4.18 (m, 4H), 2.35 (s, 3H), 1.20-1.25 (m, 6H).

Scheme 48: Route for SU20668-0492-01

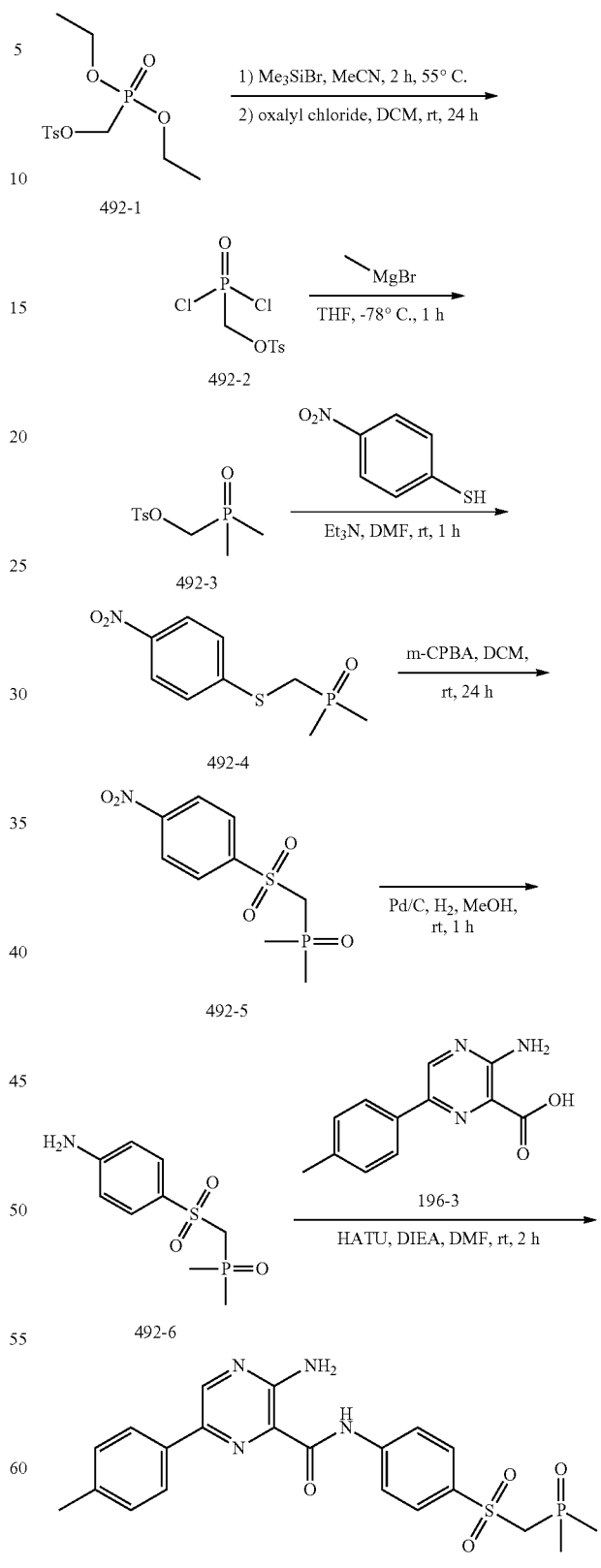

The Synthesis of (dichlorophosphoryl)methyl 4-methylbenzenesulfonate (492-2)

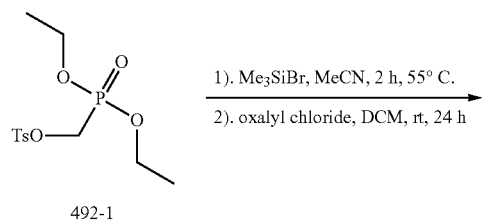

The mixture of 492-1 (3 g, 9.32 mmol) and Me₃SiBr (6 g, 39.19 mmol) in MeCN (30 mL) was stirred at 55° C. two hours. The resulting mixture was concentrated and dissolved in DCM (50 mL), was added oxalyl chloride (4 g, 31.51 mmol), the mixture was stirred at room temperature 24 hours. The resulting mixture was concentrated to give 492-2 (2.5 g, 88% yield) as brown oil.

The Synthesis of (dimethylphosphoryl)methyl-4-methylbenzenesulfonate (0492-3)

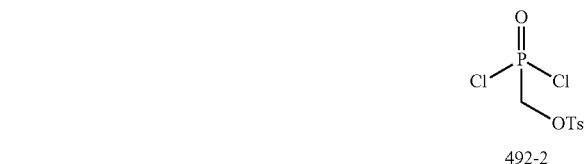

To a stirred solution of compound 492-2 (2.5 g, 8.25 mmol) in THF (25 mL) was added methylmagnesium bromide (3M in ethyl ether, 18.00 mmol) at −78° C. The resulting reaction mixture was stirred for 1 h, then added water, the aqueous phase was extracted with EA, the combined organic phases were dried over anhydrous sodium sulfate, filtered, and concentrated, the crude was purified by prep-HPLC to give the desired product 492-3 (1.8 g, yield: 83%) as yellow oil.

The Synthesis of 1-(dimethylphosphorylmethylsulfanyl)-4-nitro-benzene (492-4)

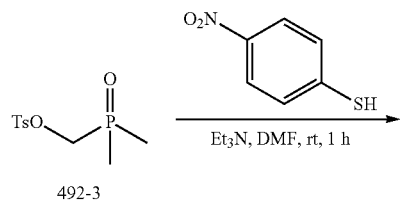

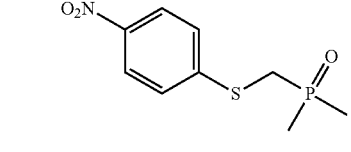

To a stirred solution of 492-3 (1.8 g, 6.86 mmol) in DMF (10 ml) was added 4-nitrobenzenethiol (1.1 g, 7.09 mmol) and TEA (717 mg, 7.09 mmol). The resulting reaction mixture was stirred for 1 h at rt. Then added water, the aqueous phase was extracted with EA, the combined organic phases were dried over anhydrous sodium sulfate, filtered, and concentrated in vacuo to give the desired product 492-4 (1.5 g, yield: 89%) as yellow oil.

The Synthesis of methyl 1-(dimethylphosphorylmethylsulfonyl)-4-nitro-benzene (492-5)

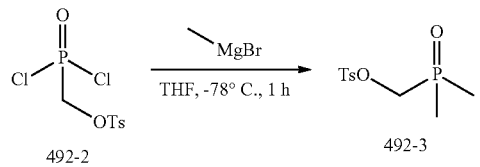

To a stirred solution of compound 492-4 (750 mg, 3.06 mmol) in DCM (15 mL) was added 3-chlorobenzenecarboperoxoic acid (1.2 g, 6.95 mmol) at 0° C. The resulting reaction mixture was further stirred for 24 h at rt, then added water and Na₂SO₃. The aqueous phase was extracted with EA, the combined organic phases were dried over anhydrous sodium sulfate, filtered, and concentrated, the crude was purified by prep-HPLC to give the desired product 492-5 (600 mg, yield: 71%) as yellow oil.

The Synthesis of 4-(dimethylphosphorylmethylsulfonyl)aniline (492-6)

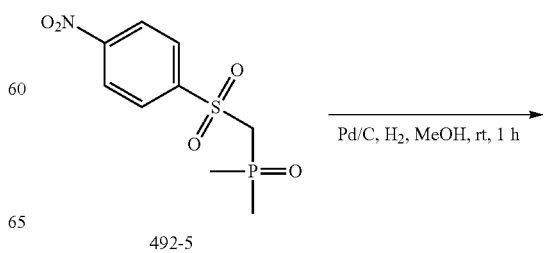

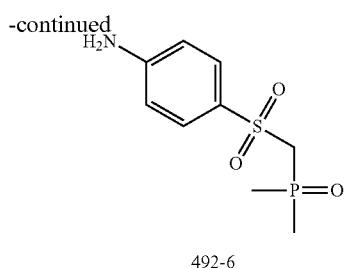

To a solution of 492-5 (600 mg, 2.16 mmol) in MeOH (6 mL) was added Pd/C (10%, 230 mg), the mixture was stirred at rt for 1 h under $H_2$ atmosphere (1.0 atm). The mixture was filtered and concentrated in vacuo to give crude product, which was purified by pre-HPLC to afford compound 492-6 (200 mg, 37%) as a yellow solid.

The Synthesis of 3-amino-N-[4-(dimethylphosphorylmethylsulfonyl)phenyl]-6-(p-tolyl)pyrazine-2-carboxamide (SU20668-0492)

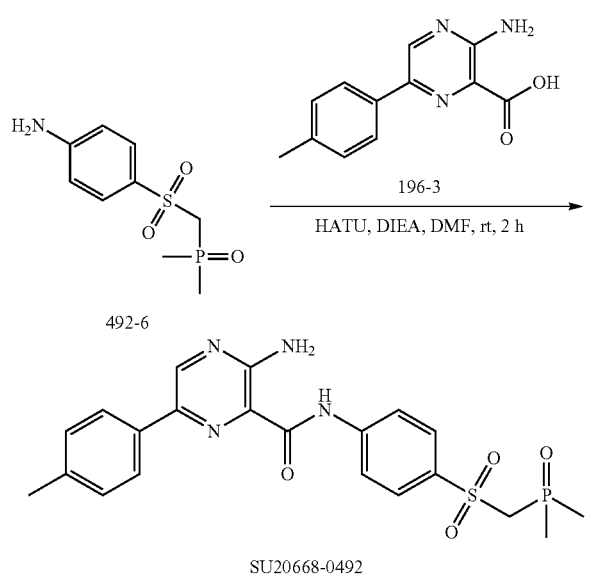

To a solution of compound 492-6 (200 mg, 0.81 mmol) in DMF (5 mL) was added 196-3 (200 mg, 0.87 mmol), DIEA (223 mg, 1.72 mmol) and HATU (320 mg, 0.84 mmol). The resulting reaction mixture was stirred for 2 h at rt, then added water, the aqueous phase was extracted with EA, the combined organic phases were dried over anhydrous sodium sulfate, filtered, and concentrated, the crude was purified by prep-HPLC to give the desired product SU20668-0492 (47 mg, yield: 13%) as a yellow solid. LC-MS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [$CH_3CN$+0.05% TFA] to 5% [water+0.05% TFA] and 95% [water+0.05% TFA] in 1.6 min, then under this condition for 1.4 min, finally changed to 95% [water+0.05% TFA] and 5% [$CH_3CN$+0.05% TFA] in 0.05 min and under this condition for 0.7 min). Purity: 95.10%, Rt=1.695 min; MS Calcd.: 458.1; MS Found: 459.2 [M+H]$^+$. HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [$CH_3CN$+0.05% TFA] to 5% [water+0.05% TFA] and 95% [water+0.05% TFA] in 10 min, then under this condition for 5 min, finally changed to 95% [water+0.05% TFA] and 5% [$CH_3CN$+0.05% TFA] in 0.1 min and under this condition for 5 min). Purity: 100.00%, Rt=8.799 min. H NMR (400 MHz, DMSO-$d_6$) δ 10.70 (s, 1H), 8.91 (s, 1H), 8.09-8.12 (m, 4H), 7.94 (d, J=8.8 Hz, 2H), 7.64 (s, 2H), 7.29 (d, J=8.0 Hz, 2H), 4.27 (d, J=11.6 Hz, 2H), 2.35 (s, 3H), 1.55 (d, J=14.0 Hz, 6H).

Scheme 49: Route for SU20668-0510-01

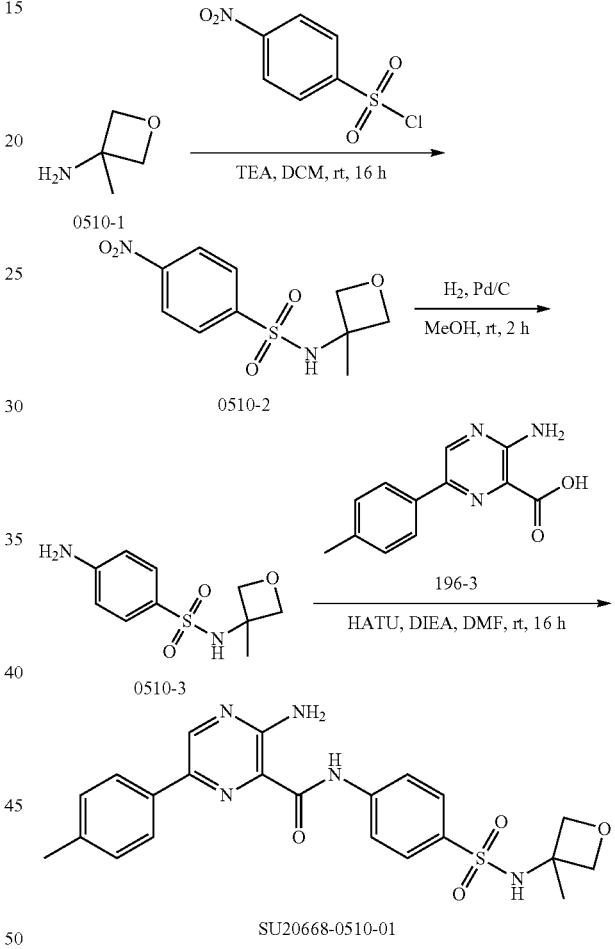

The Synthesis of N-(3-methyloxetan-3-yl)-4-nitrobenzenesulfonamide (0510-2)

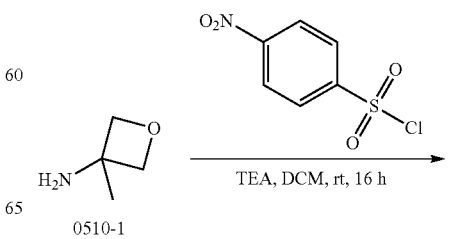

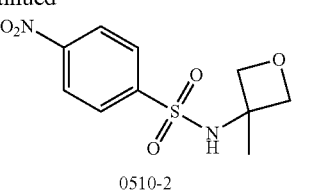

0510-2

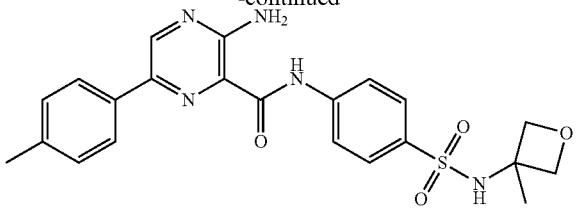

SU20668-0510-01

To a stirred solution of 0510-1 (200 mg, 2.30 mmol) in DCM (8 mL) was added TEA (696.90 mg, 6.89 mmol) and 4-nitrobenzenesulfonyl chloride (559.64 mg, 2.53 mmol) at rt. The resulting reaction mixture was stirred for 16 h at rt. Then added water, the aqueous phase was extracted with dichloromethane, the combined organic phases were dried over anhydrous sodium sulfate, filtered, and concentrated in vacuo to give 0510-2 (530 mg, 84.79% yield) as yellow oil.

The Synthesis of 4-amino-N-(3-methyloxetan-3-yl)benzenesulfonamide (0510-3)

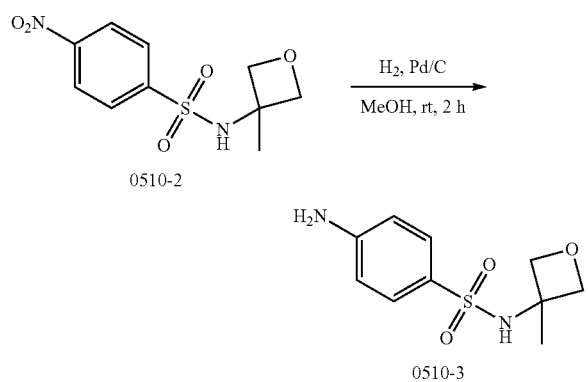

To a solution of 0510-2 (102 mg, 374.62 umol) in MeOH (20 mL) was added Pd/C (20 mg), the mixture was stirred under hydrogen atmosphere (1 atm) at room temperature for 2 h, filtrated, concentrated to give 0510-3 (86 mg, 94.75% yield) as brown oil.

The Synthesis of 3-amino-N-(4-(N-(3-methyloxetan-3-yl)sulfamoyl)phenyl)-6-p-tolylpyrazine-2-carboxamide (SU20668-0510-01)

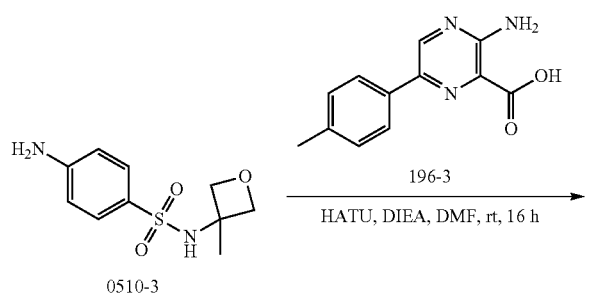

To a stirred solution of 0510-3 (86 mg, 354.94 umol) in DMF (3 mL) was added 196-3 (81.36 mg, 354.94 umol), DIPEA (137.62 mg, 1.06 mmol) and HATU (202.44 mg, 532.41 umol). The resulting reaction mixture was stirred at rt for 16 h. Then it was purified by prep-HPLC to give SU20668-0510-01 (76 mg, 47.21% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 100%, Rt=2.057 min; MS Calcd.: 453.15; MS Found: 454.1 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM $AcONH_4$) water/$CH_3CN$=900/100 (v/v)] and 10% [total 10 mM $AcONH_4$) water/$CH_3CN$=100/900 (v/v)] to 15% [total 10 mM $AcONH_4$) water/$CH_3CN$=900/100 (v/v)] and 85% [total 10 mM $AcONH_4$) water/$CH_3CN$=100/900 (v/v)] in 5 min, then under this condition for 10 min, finally changed to 90% [(total 10 mM $AcONH_4$) water/$CH_3CN$=900/100 (v/v)] and 10% [total 10 mM $AcONH_4$) water/$CH_3CN$=100/900 (v/v)] in 0.1 min and under this condition for 5 min). Purity: 99.17%, Rt=9.833 min. $^1$H NMR (400 MHz, DMSO-$d_6$) δ 10.66 (bs, 1H), 8.92 (s, 1H), 8.28 (bs, 1H), 8.13 (d, J=8.4 Hz, 2H), 8.06 (d, J=8.8 Hz, 2H), 7.83 (d, J=9.2 Hz, 2H), 7.65 (s, 2H), 7.31 (d, J=8.0 Hz, 2H), 4.55 (d, J=6.4 Hz, 2H), 4.11 (d, J=6.4 Hz, 2H), 2.37 (s, 3H), 1.43 (s, 3H).

Scheme 50: Route for SU20668-0196-01

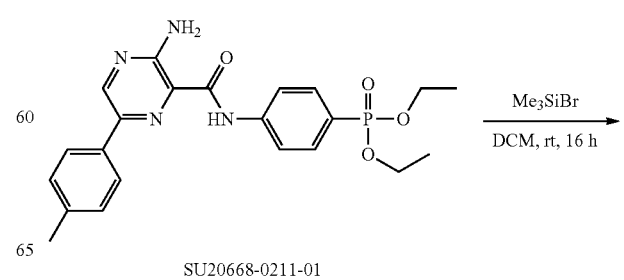

SU20668-0211-01

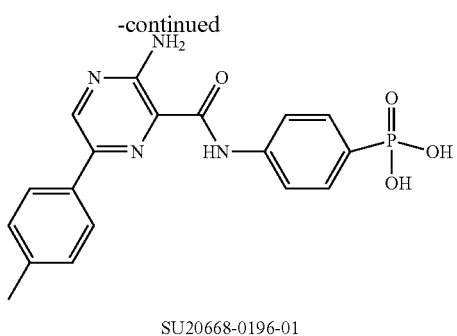

SU20668-0196-01

The Synthesis of 4-(3-amino-6-p-tolylpyrazine-2-carboxamido)phenylphosphonic acid (SU20668-0196-01)

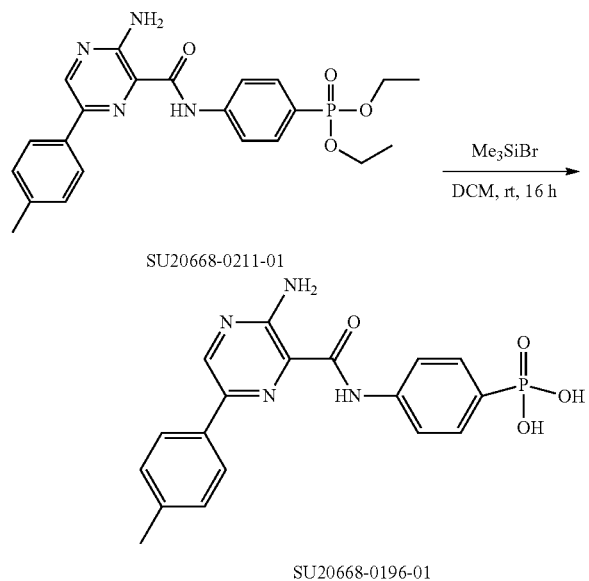

To a solution of SU20668-0211-01 (200 mg, 0.45 mmol) in DCM (10 mL) was added Me₃SiBr (70 mg, 0.45 mmol) at rt. Then it was stirred at rt for 16 hours. The reaction mixture was concentrated to dryness and purified by prep-HPLC to afford SU20668-0196-01 (30 mg, yield: 17.4%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=1.367 min; MS Calcd.: 384.1; MS Found: 385.3 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 98.65%, Rt=5.931 min. $^1$H NMR (400 MHz, DMSO-d$_6$) δ10.41 (s, 1H), 8.99 (s, 1H), 8.10 (d, J=8.0 Hz, 2H), 7.79-7.82 (m, 2H), 7.62-7.67 (m, 3H), 7.29 (d, J=8.0 Hz, 2H), 2.35 (s, 3H).

Scheme 51 Route for SU20668-0211-01

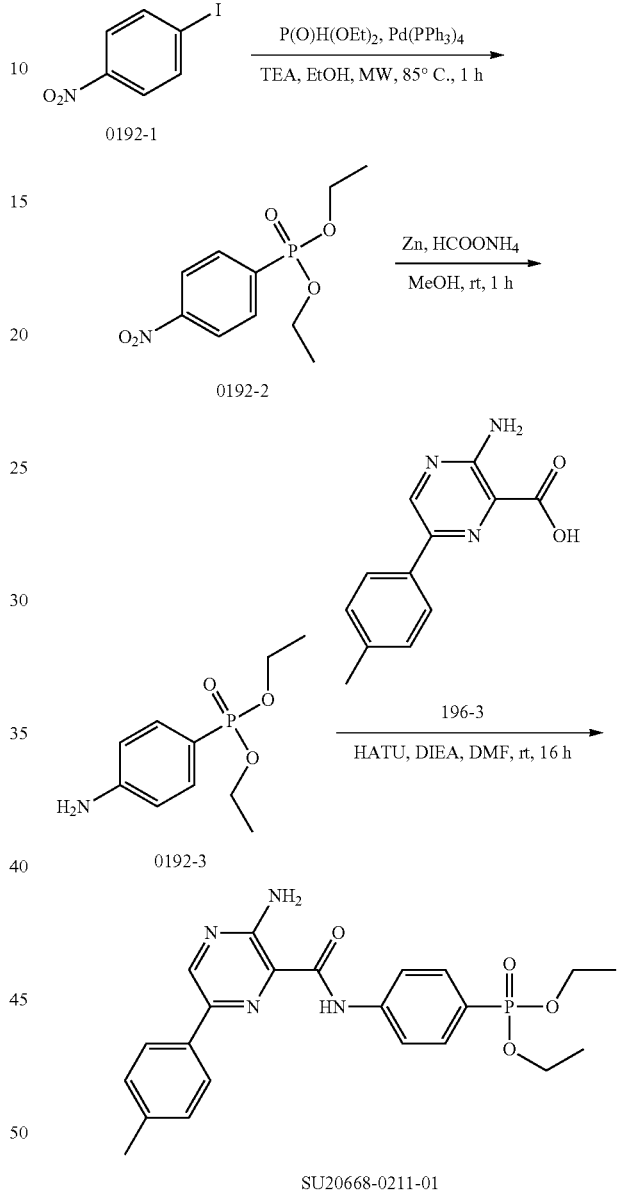

The Synthesis of diethyl 4-nitrophenylphosphonate (0192-2)

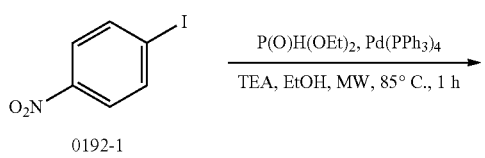

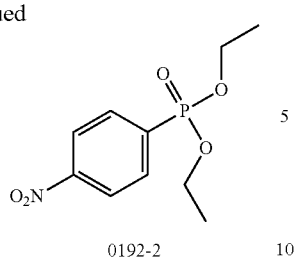

0192-2

To a solution of 1-iodo-4-nitrobenzene (4.0 g, 16.1 mmol) in ethanol (50 mL) was added diethyl phosphonate (4.1 g, 30 mmol), TEA (4.0 g, 40 mmol) and Pd(PPh$_3$)$_4$ (500 mg). Then it was heated to 85° C. by microwave under argon atmosphere and stirred for 1 h. The reaction mixture was concentrated to dryness to afford a crude product (5.5 g) as brown oil.

The Synthesis of diethyl 4-aminophenylphosphonate (0192-3)

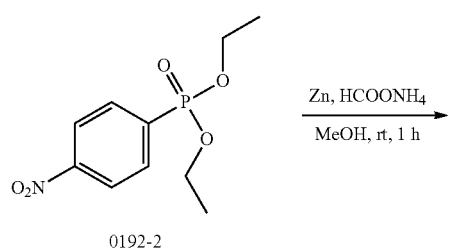

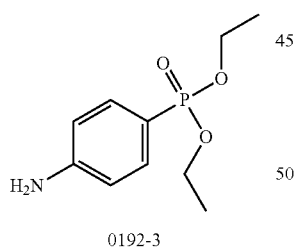

0192-3

To a solution of 0192-2 (5.5 g, crude) in MeOH (60 mL) was added zinc powder (6.5 g, 100 mmol) and HCOONH$_4$ (3.2 g, 50 mmol). The mixture was stirred at rt for 1 h. Then it was filtered and concentrated in vacuo. The residue was purified by silica-gel column to afford 0192-3 (1.5 g, total yield for 2 steps: 40.7%) as light yellow oil.

The Synthesis of diethyl 4-(3-amino-6-p-tolylpyrazine-2-carboxamido)phenylphosphonate (SU20668-0211-01)

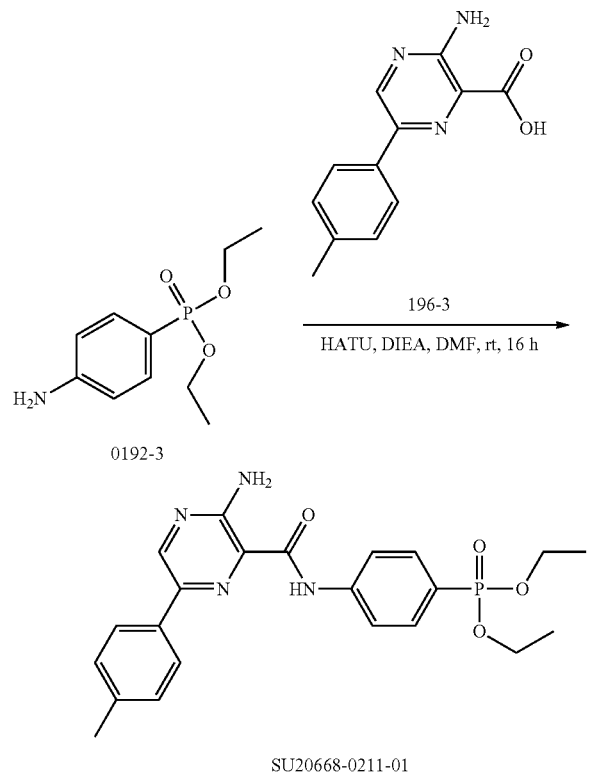

To a solution of compound 0192-3 (400 mg, 1.75 mmol) in DMF (6 mL) was added 196-3 (400 mg, 1.75 mmol), DIEA (450 mg, 3.50 mmol) and HATU (800 mg, 2.10 mmol). The resulting reaction mixture was stirred for 2 hours. Then it was purified by prep-HPLC to give the desired product SU20668-0211-01 (450 mg, yield: 58.5%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 99.14%, Rt=2.163 min; MS Calcd.: 440.1; MS Found: 441.3 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 100%, Rt=10.631 min. $^1$H NMR (400 MHz, DMSO-d$_6$) δ 10.60 (s, 1H), 8.92 (s, 1H), 8.12 (d, J=8.4 Hz, 2H), 8.01-8.04 (m, 2H), 7.70-7.76 (m, 2H), 7.65 (s, 2H), 7.31 (d, J=8.0 Hz, 2H), 3.99-4.03 (m, 4H), 2.37 (s, 3H), 1.24 (t, J=7.6 Hz, 6H).

Scheme 52: Route for SU20668-0280-01

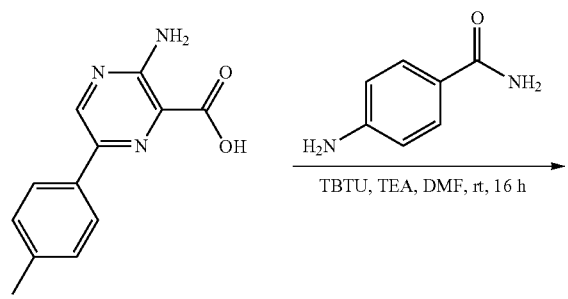

196-3 → SU20668-0280-01

The Synthesis of 3-amino-N-(4-carbamoylphenyl)-6-p-tolylpyrazine-2-carboxamide (SU20668-0280-01)

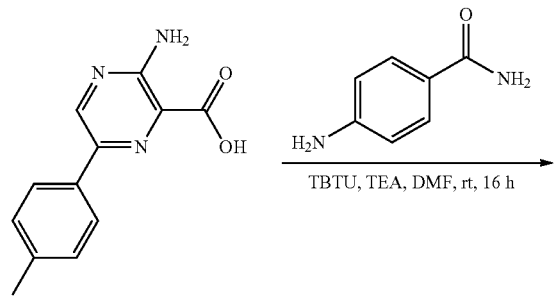

196-3

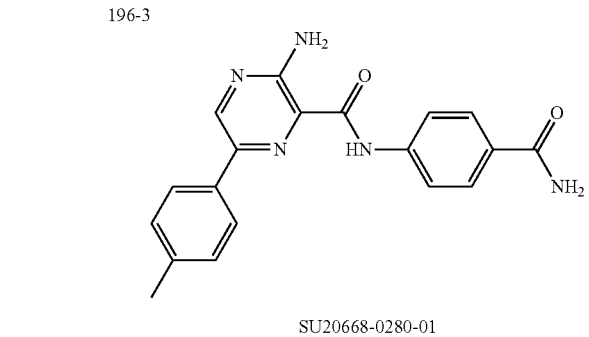

SU20668-0280-01

To a solution of compound 196-3 (250 mg, 1.09 mmol) in DMF (4 mL) was added 4-aminobenzamide (149 mg, 1.09 mmol), DIEA (258 mg, 2.00 mmol) and TBTU (482 mg, 1.50 mmol). The resulting reaction mixture was stirred for 16 h at rt. Then it was purified by prep-HPLC to give the desired product SU20668-0280-01 (110 mg, yield: 29.1%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 96.15%, Rt=1.850 min; MS Calcd.: 347.1; MS Found: 348.4 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 98.98%, Rt=8.554 min. $^1$H NMR (400 MHz, DMSO-$d_6$) δ 10.53 (s, 1H), 8.91 (s, 1H), 8.12 (d, J=8.0 Hz, 2H), 7.90-7.93 (m, 5H), 7.65 (s, 2H), 7.30-7.32 (m, 3H), 2.37 (s, 3H).

Scheme 53: Route for SU20668-0286-01

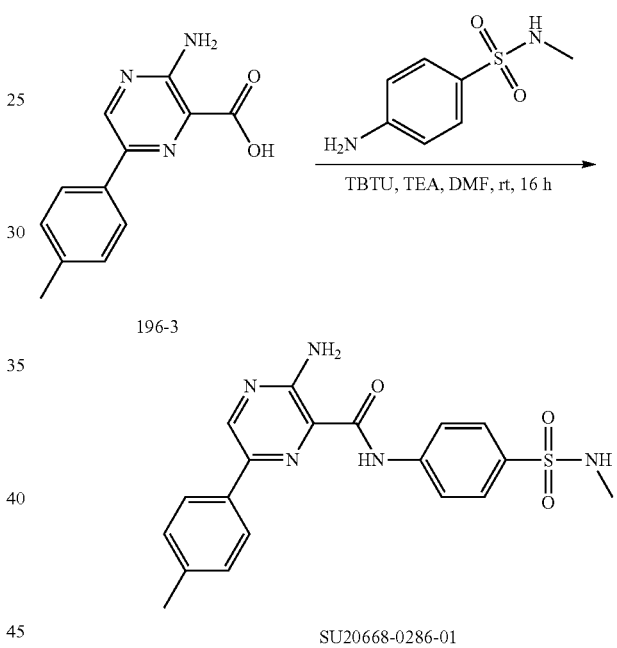

196-3 → SU20668-0286-01

The Synthesis of 3-amino-N-(4-(N-methylsulfamoyl)phenyl)-6-p-tolylpyrazine-2-carboxamide (SU20668-0286-01)

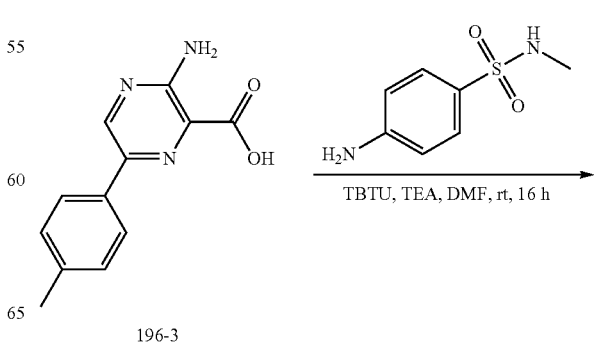

196-3

537

-continued

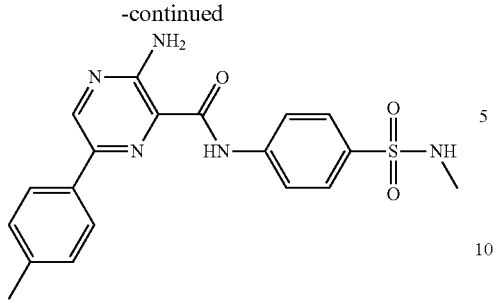

SU20668-0286-01

To a solution of compound 196-3 (250 mg, 1.09 mmol) in DMF (4 mL) was added 4-amino-N-methylbenzenesulfonamide (203 mg, 1.09 mmol), DIEA (258 mg, 2.00 mmol) and TBTU (482 mg, 1.50 mmol). The resulting reaction mixture was stirred for 16 h at rt. Then it was purified by prep-HPLC to give the desired product SU20668-0286-01 (32 mg, yield: 7.4%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 100%, Rt=2.053 min; MS Calcd.: 397.1; MS Found: 398.4 [M+H]+. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 99.07%, Rt=9.624 min. $^1$H NMR (400 MHz, DMSO-$d_6$) δ 10.66 (s, 1H), 8.92 (s, 1H), 8.12 (d, J=8.0 Hz, 2H), 8.07 (d, J=8.0 Hz, 2H), 7.79 (d, J=7.6 Hz, 2H), 7.65 (s, 2H), 7.37-7.38 (m, 1H), 7.31 (d, J=8.0 Hz, 2H), 2.50 (d, J=4.8 Hz, 3H), 2.37 (s, 3H).

Scheme 54: Route for SU20668-0288-01

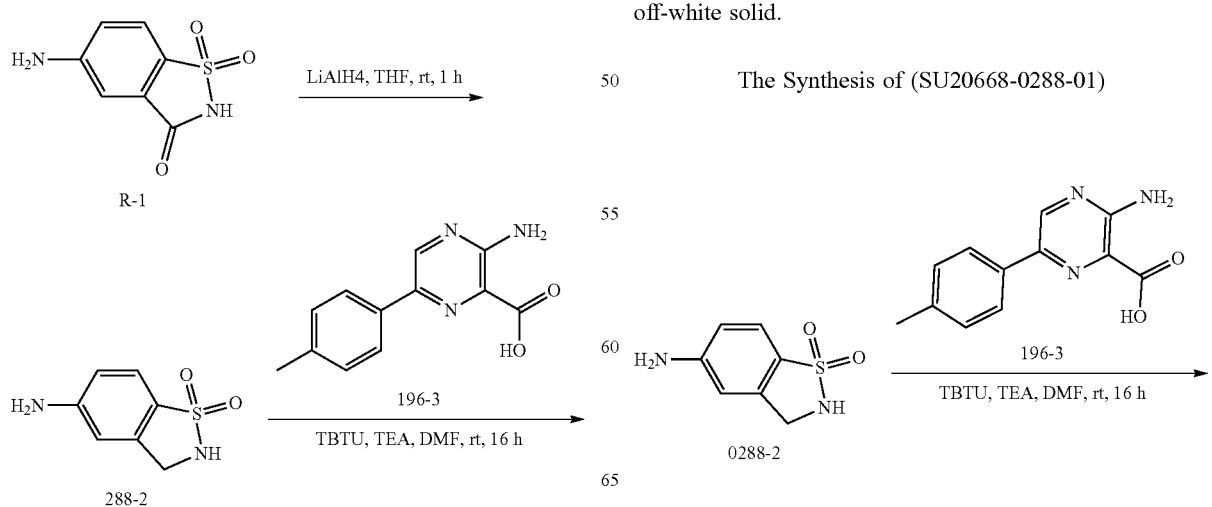

538

-continued

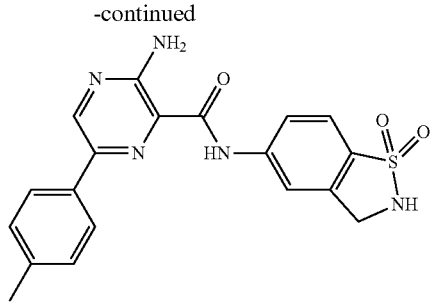

SU20668-0288-01

The Synthesis of 0288-2

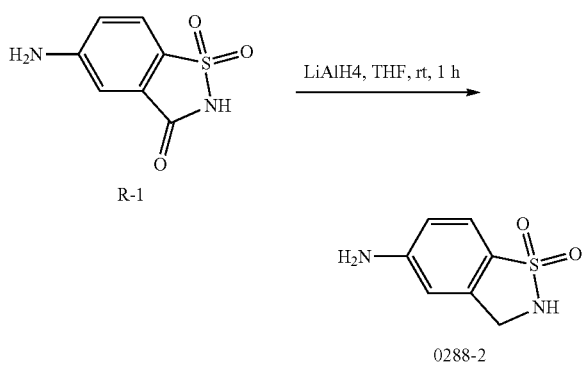

To a solution of R-1 (500 mg, 2.53 mmol) in THF was added LiAlH$_4$ (96 mg, 2.53 mmol) at 0° C. Then it was stirred at rt for 1 h. Water was added to quench the reaction. The mixture was concentrated to dryness and purified by prep-HPLC to afford 0288-2 (100 mg, yield: 21.5%) as an off-white solid.

The Synthesis of (SU20668-0288-01)

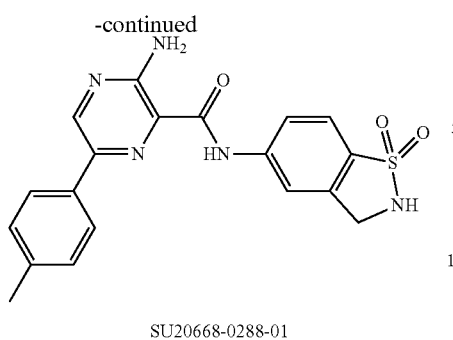

SU20668-0288-01

To a solution of compound 196-3 (124 mg, 0.54 mmol) in DMF (4 mL) was added 0288-2 (100 mg, 0.54 mmol), DIEA (130 mg, 1.00 mmol) and TBTU (240 mg, 0.75 mmol). The resulting reaction mixture was stirred for 16 h at rt. Then it was purified by prep-HPLC to give the desired product SU20668-0288-01 (40 mg, yield: 18.8%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=1.971 min; MS Calcd.: 395.1; MS Found: 396.2 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 99.32%, Rt=9.143 min. $^1$H NMR (400 MHz, DMSO-d$_6$) δ 10.69 (s, 1H), 8.92 (s, 1H), 8.37 (d, J=1.2 Hz, 1H), 8.14 (d, J=8.0 Hz, 2H), 8.09-8.12 (m, 1H), 7.86 (s, 1H), 7.65 (s, 2H), 7.58 (d, J=8.4 Hz, 1H), 7.31 (d, J=8.4 Hz, 2H), 4.40 (s, 2H), 2.37 (s, 3H).

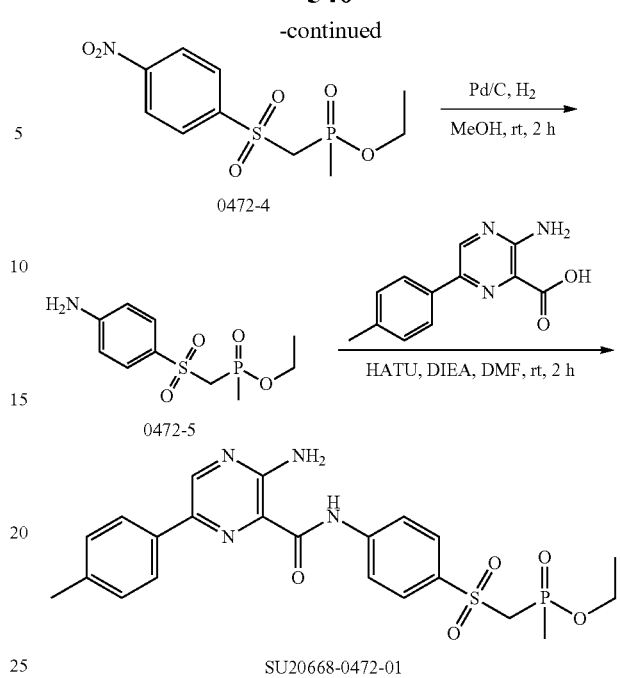

SU20668-0472-01

The Synthesis of (ethoxy(methyl)phosphoryl)methyl 4-methylbenzenesulfonate (0472-2)

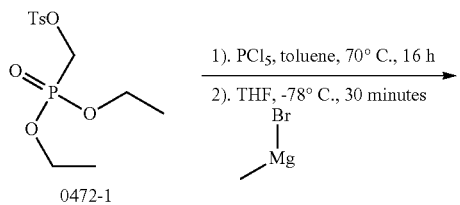

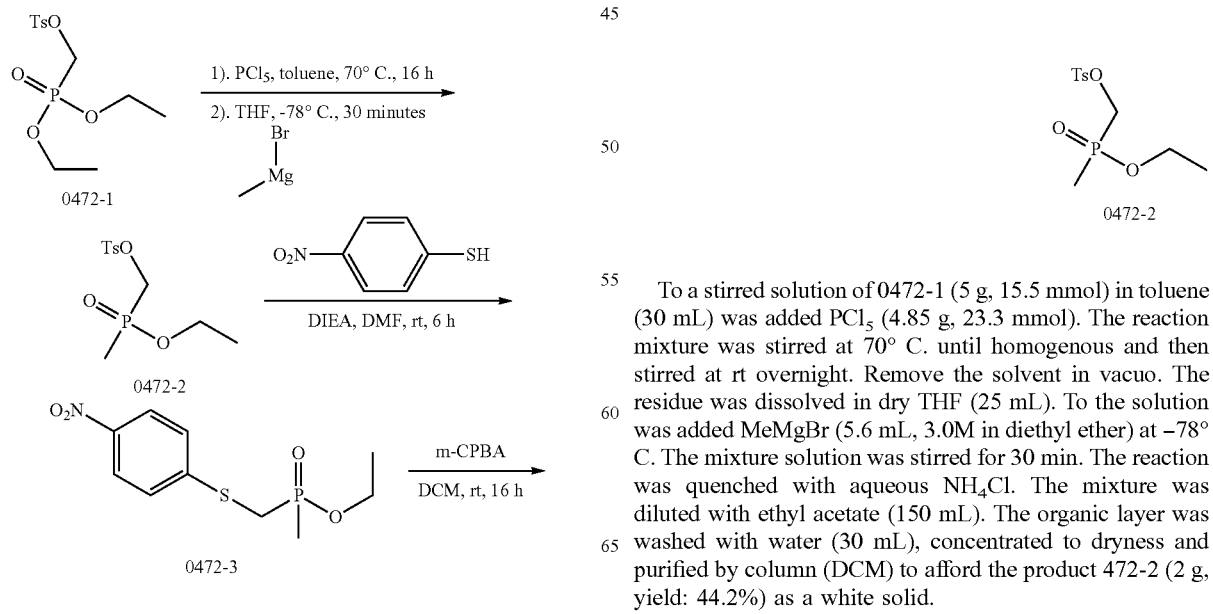

0472-2

To a stirred solution of 0472-1 (5 g, 15.5 mmol) in toluene (30 mL) was added PCl$_5$ (4.85 g, 23.3 mmol). The reaction mixture was stirred at 70° C. until homogenous and then stirred at rt overnight. Remove the solvent in vacuo. The residue was dissolved in dry THF (25 mL). To the solution was added MeMgBr (5.6 mL, 3.0M in diethyl ether) at −78° C. The mixture solution was stirred for 30 min. The reaction was quenched with aqueous NH$_4$Cl. The mixture was diluted with ethyl acetate (150 mL). The organic layer was washed with water (30 mL), concentrated to dryness and purified by column (DCM) to afford the product 472-2 (2 g, yield: 44.2%) as a white solid.

The Synthesis of ethyl methyl((4-nitrophenylthio)methyl)phosphinate (0472-3)

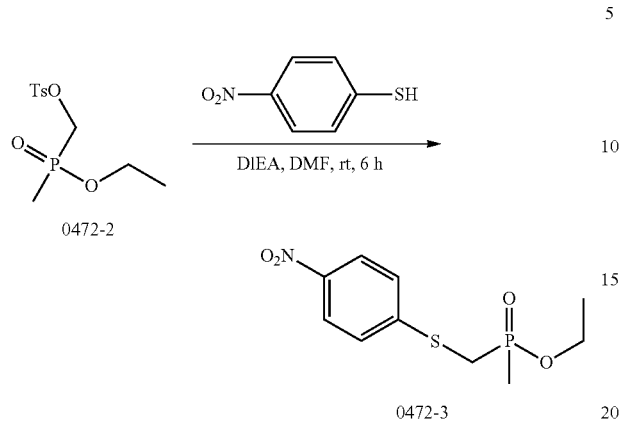

To a stirred solution of 4-nitrobenzenethiol (600 mg, 3.87 mmol) in DMF (10 ml) was added 0472-2 (1.13 g, 3.87 mmol) and DIEA (774 mg, 6.00 mmol). The resulting reaction mixture was stirred for 6 h at rt. Then water (50 mL) was added. The aqueous phase was extracted with EA (20 mL×3). The combined organic phases were dried over anhydrous sodium sulfate, filtered, and concentrated in vacuo to give the desired product 0472-3 (500 mg, yield: 47.0%) as a yellow solid.

The Synthesis of ethyl methyl((4-nitrophenylsulfonyl)methyl)phosphinate (0472-4)

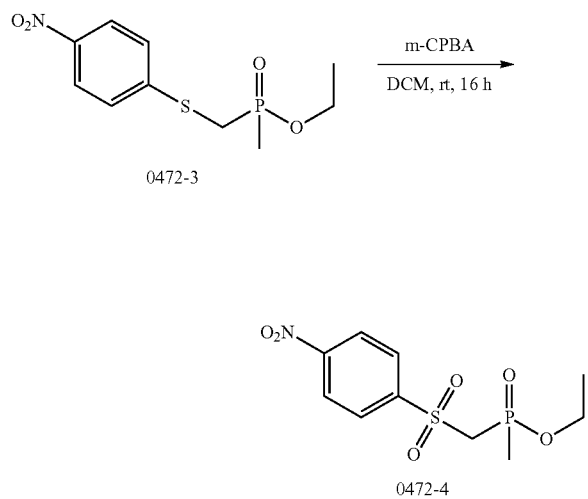

To a stirred solution of compound 0472-3 (400 mg, 1.30 mmol) in DCM (10 mL) was added 3-chlorobenzenecarboperoxoic acid (518 mg, 3.00 mmol) at 0° C. The resulting reaction mixture was further stirred for 24 h at rt, then added water (40 mL) and $Na_2SO_3$ (1.5 g). The aqueous phase was extracted with DCM (15 mL*3). The combined organic phases were dried over anhydrous sodium sulfate, filtered, concentrated and purified by prep-HPLC to give the desired product 0472-4 (300 mg, yield: 75.2%) as a yellow solid.

The Synthesis of ethyl (4-aminophenylsulfonyl)methyl(methyl)phosphinate (0472-5)

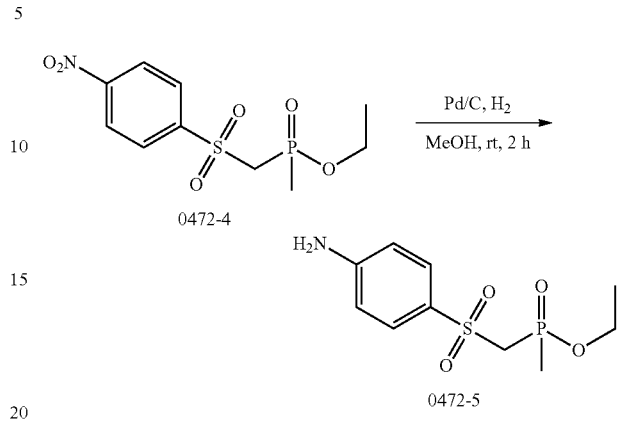

To a solution of 0472-4 (300 mg, 0.98 mmol) in MeOH (10 mL) was added Pd/C (10%, 40 mg). The mixture was stirred at rt for 2 h under $H_2$ atmosphere (1.0 atm). Then it was filtered and concentrated in vacuo to give 0472-5 (200 mg, yield: 73.7%) as an off-white solid.

The Synthesis of ethyl (4-(3-amino-6-p-tolylpyrazine-2-carboxamido)phenylsulfonyl)methyl(methyl)phosphinate (SU20668-0472-01)

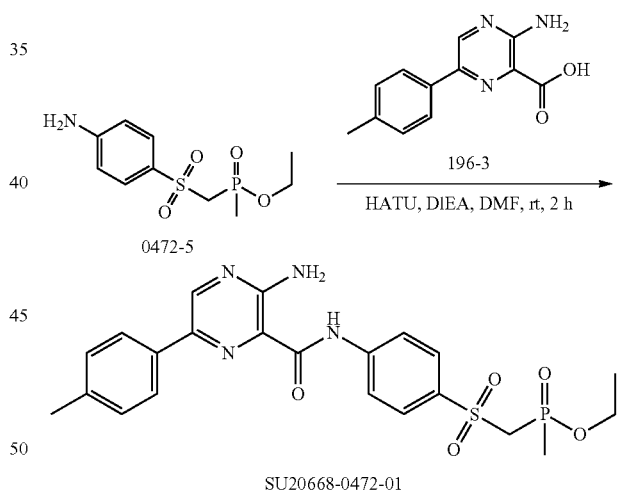

To a solution of compound 0472-5 (100 mg, 0.36 mmol) in DMF (4 mL) was added 196-3 (82 mg, 0.36 mmol), DIEA (93 mg, 0.72 mmol) and HATU (190 mg, 0.50 mmol). The resulting reaction mixture was stirred for 2 hours. Then it was purified by prep-HPLC to give the desired product SU20668-0472-01 (53 mg, yield: 30.2%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 100%, Rt=2.011 min; MS Calcd.: 488.1; MS Found: 489.4 [M+H]⁺. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 100%, Rt=9.396 min. ¹H NMR (400 MHz, DMSO-d$_6$) δ 10.70 (s, 1H), 8.90 (s, 1H), 8.10 (dd, J=8.0 Hz, J=1.6 Hz, 4H), 7.93 (d, J=6.8 Hz, 2H), 7.64 (s, 2H), 7.29 (d, J=8.0 Hz, 2H), 4.36 (d, J=14.0 Hz, 2H), 3.93-3.98 (m, 1H), 3.84-3.88 (m, 1H), 2.35 (s, 3H), 1.58 (d, J=15.6 Hz, 3H), 1.14 (t, J=7.6 Hz, 3H).

The Synthesis of 3-amino-N-(3-(methylsulfonamido)phenyl)-6-p-tolylpyrazine-2-carboxamide (SU20668-0289-01)

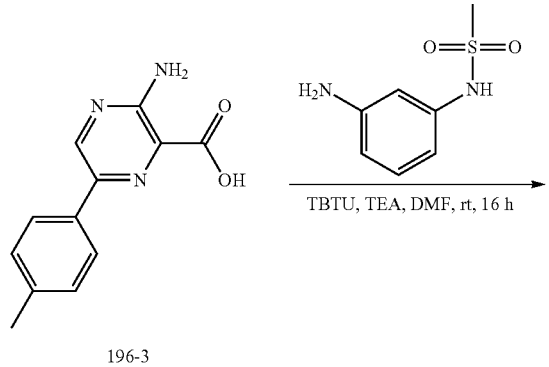

196-3

SU20668-0289

To a solution of compound 196-3 (250 mg, 1.09 mmol) in DMF (4 mL) was added N-(3-aminophenyl)methanesulfonamide (203 mg, 1.09 mmol), DIEA (258 mg, 2.00 mmol) and TBTU (482 mg, 1.50 mmol). The resulting reaction mixture was stirred for 16 h at rt. Then it was purified by prep-HPLC to give the desired product SU20668-0289-01 (63 mg, yield: 14.8%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=2.031 min; MS Calcd.: 397.1; MS Found: 398.2 [M+H]⁺. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 98.82%, Rt=9.533 min. ¹H NMR (400 MHz, DMSO-d$_6$) δ 10.42 (s, 1H), 9.81 (s, 1H), 8.89 (s, 1H), 8.10 (d, J=8.0 Hz, 2H), 7.75-7.76 (m, 1H), 7.62 (s, 2H), 7.51-7.53 (m, 1H), 7.29-7.36 (m, 3H), 7.00-7.02 (m, 1H), 3.03 (s, 3H), 2.37 (s, 3H).

Scheme 56: Route for SU20668-0475-01

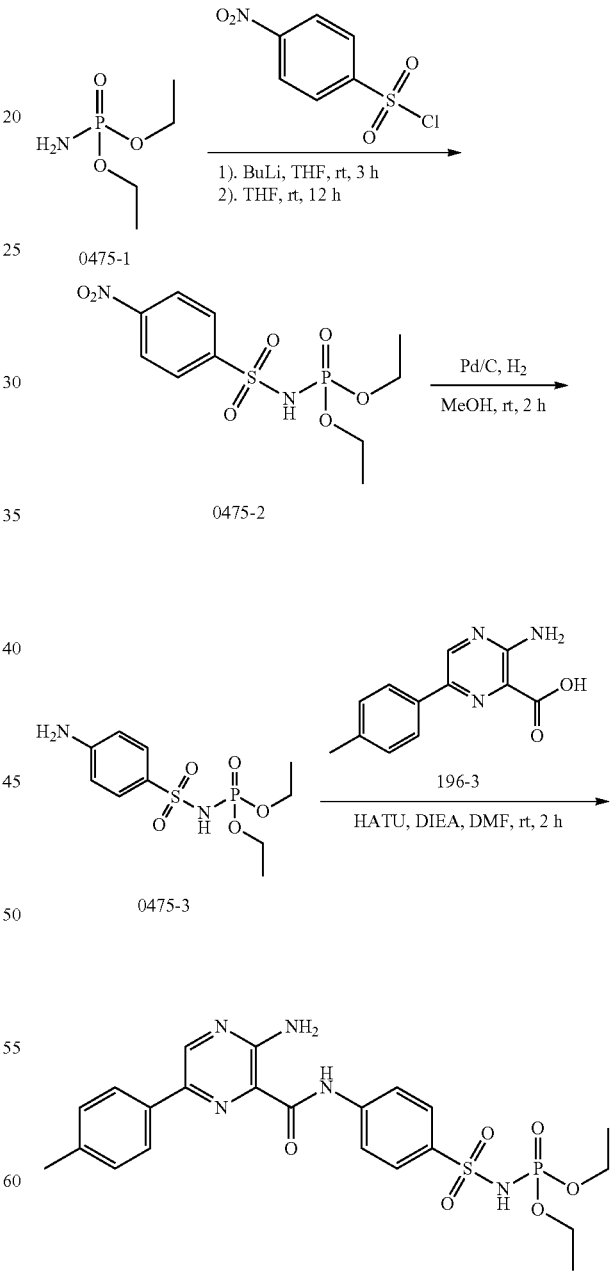

The Synthesis of diethyl 4-nitrophenylsulfonylphosphoramidate (0475-2)

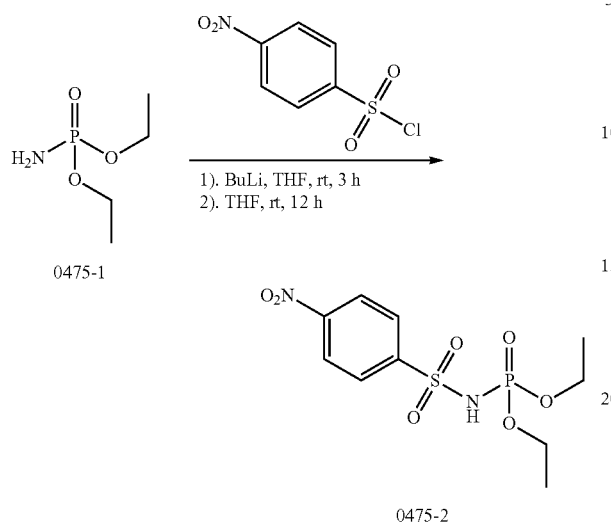

0475-1

0475-2

To a solution of 0475-1 (1.1 g, 7.2 mmol) in THF (20 mL) was added n-BuLi (3.2 mL, 2.5M, 8.0 mmol) at −78° C. Then the reaction mixture was stirred at −78° C. for 3 hours. The solution of 4-nitrobenzene-1-sulfonyl chloride (1.6 g, 7.2 mmol) in THF (5 mL) was added dropwise. The mixture was allowed to warm to rt and stirred for 12 hours. Water (100 mL) was added. The mixture was extracted with ethyl acetate (50 mL×3). The organic layer was washed with brine (30 mL), concentrated to dryness and purified by column (DCM) to afford the product 0475-2 (500 mg, yield: 20.5%) as a yellow solid.

The Synthesis of diethyl 4-aminophenylsulfonylphosphoramidate (0475-3)

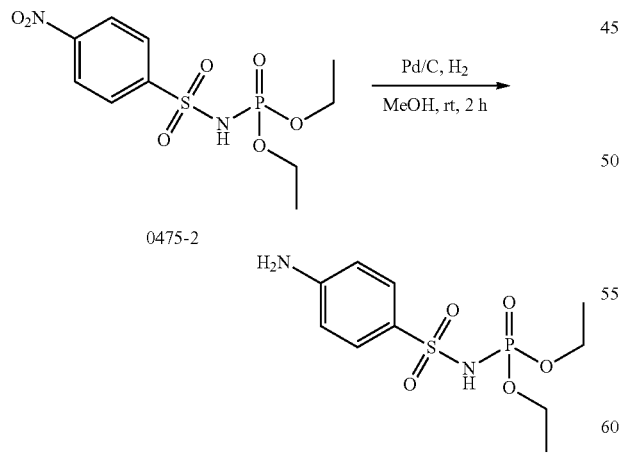

0475-2

0475-3

To a solution of 0475-2 (500 mg, 1.48 mmol) in MeOH (10 mL) was added Pd/C (10%, 50 mg). The mixture was stirred at rt for 2 h under H$_2$ atmosphere (1.0 atm). Then it was filtered and concentrated in vacuo to give 0475-3 (400 mg, yield: 87.9%) as an off-white solid.

The Synthesis of diethyl 4-(3-amino-6-p-tolylpyrazine-2-carboxamido)phenylsulfonylphosphoramidate (SU20668-0475-01)

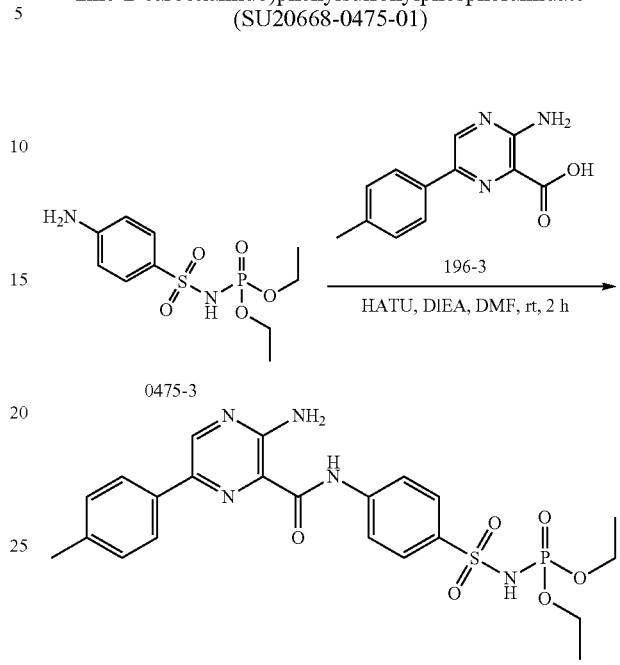

0475-3

SU20668-0475-01

To a solution of compound 0475-3 (100 mg, 0.32 mmol) in DMF (4 mL) was added 196-3 (74 mg, 0.32 mmol), DIEA (84 mg, 0.65 mmol) and HATU (170 mg, 0.45 mmol). The resulting reaction mixture was stirred for 2 h. Then it was purified by prep-HPLC to give the desired product SU20668-0475-01 (70 mg, yield: 41.7%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 99.26%, Rt=1.692 min; MS Calcd.: 519.1; MS Found: 520.3 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 100%, Rt=7.675 min. $^1$H NMR (400 MHz, DMSO-d$_6$) δ 8.85 (s, 1H), 8.07 (d, J=8.0 Hz, 2H), 7.72-7.80 (m, 4H), 7.28 (d, J=8.0 Hz, 2H), 3.69-3.73 (m, 4H), 2.33 (s, 3H), 1.06 (t, J=6.8 Hz, 6H).

Scheme 57: Route for SU20668-0482-01

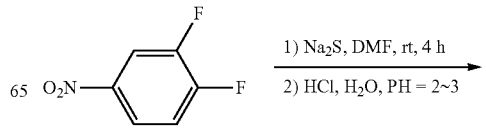

547
-continued

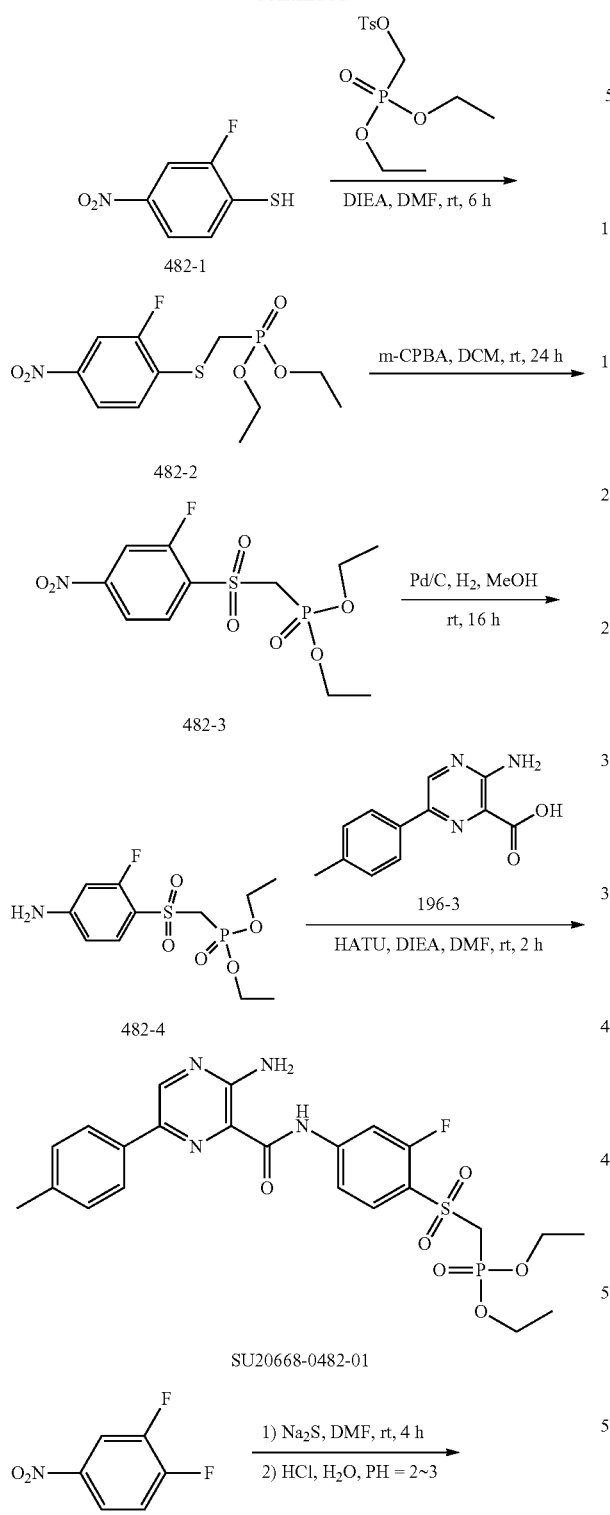

SU20668-0482-01

548

The Synthesis of 2-fluoro-4-nitrobenzenethiol
(0482-1)

To a solution of 1,2-difluoro-4-nitrobenzene (2.0 g, 12.6 mmol) in DMF (20 mL) was added Na₂S (1.4 g, 18.0 mmol). The mixture was stirred at rt for 4 hours. Water (100 mL) was added. The mixture was acidified to PH=23 with HCl (1N). Then it was extracted with EA (30 mL×3). The organic layer was washed with brine (25 mL), dried over anhydrous sodium sulfate, filtered, and concentrated in vacuo to give the desired product as a brown solid (1.5 g, yield: 68.9%).

The Synthesis of diethyl
(2-fluoro-4-nitrophenylthio)methylphosphonate
(0482-2)

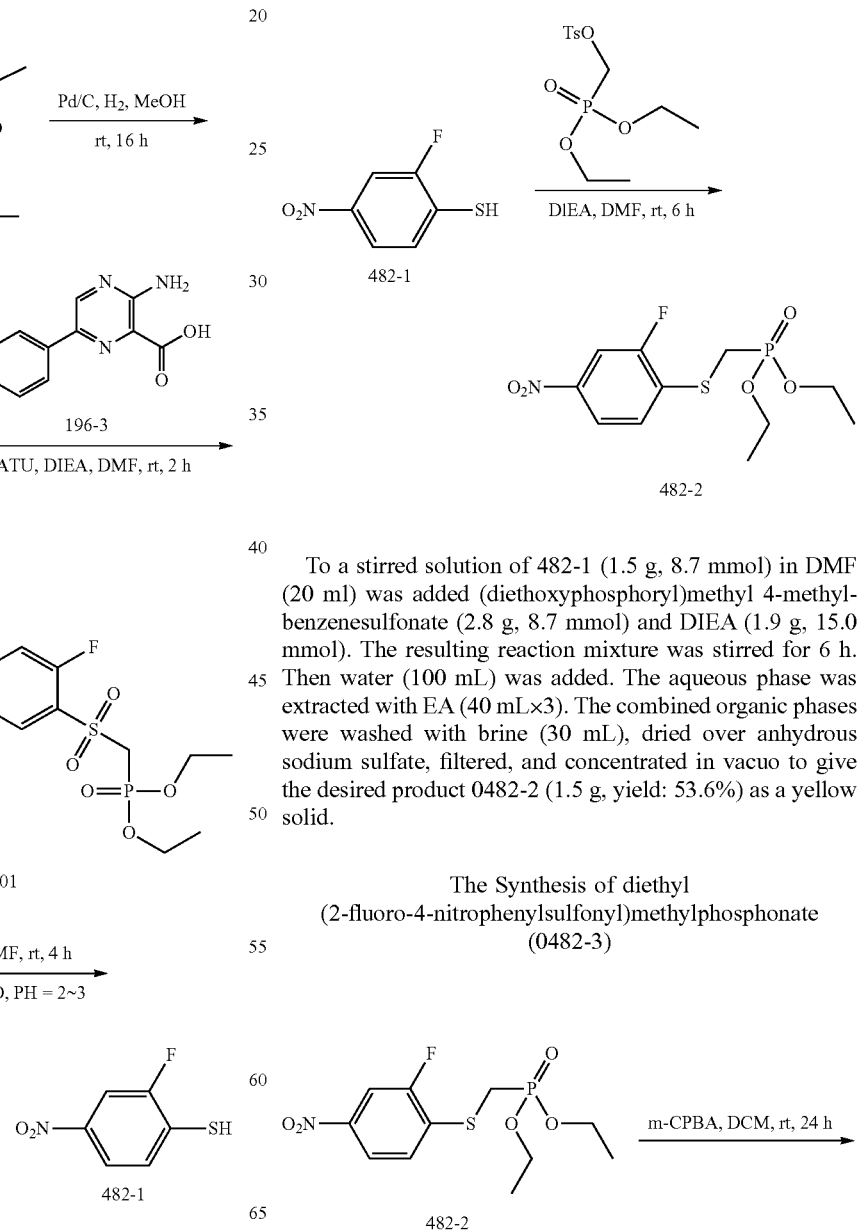

To a stirred solution of 482-1 (1.5 g, 8.7 mmol) in DMF (20 ml) was added (diethoxyphosphoryl)methyl 4-methylbenzenesulfonate (2.8 g, 8.7 mmol) and DIEA (1.9 g, 15.0 mmol). The resulting reaction mixture was stirred for 6 h. Then water (100 mL) was added. The aqueous phase was extracted with EA (40 mL×3). The combined organic phases were washed with brine (30 mL), dried over anhydrous sodium sulfate, filtered, and concentrated in vacuo to give the desired product 0482-2 (1.5 g, yield: 53.6%) as a yellow solid.

The Synthesis of diethyl
(2-fluoro-4-nitrophenylsulfonyl)methylphosphonate
(0482-3)

549

-continued

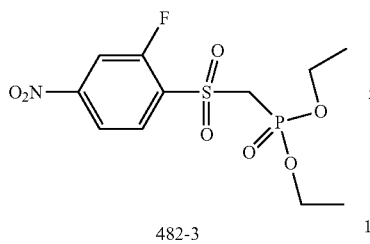

482-3

To a stirred solution of compound 0482-2 (800 mg, 2.48 mmol) in DCM (20 mL) was added 3-chlorobenzenecarboperoxoic acid (1.0 g, 6.00 mmol) at 0° C. The resulting reaction mixture was further stirred for 24 h at rt, then added water (40 mL) and $Na_2SO_3$ (2.0 g). The aqueous phase was extracted with DCM (20 mL×3). The combined organic phases were dried over anhydrous sodium sulfate, filtered, concentrated and purified by prep-HPLC to give the desired product 0482-3 (500 mg, yield: 56.8%) as a yellow solid.

The Synthesis of diethyl (4-amino-2-fluorophenylsulfonyl)methylphosphonate (0482-4)

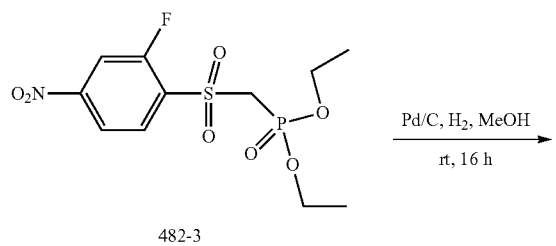

482-3

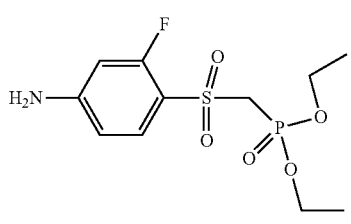

482-4

To a solution of 0482-3 (500 mg, 1.41 mmol) in MeOH (10 mL) was added Pd/C (10%, 50 mg). The mixture was stirred at rt for 2 h under $H_2$ atmosphere (1.0 atm). Then it was filtered and concentrated in vacuo to give 0482-4 (300 mg, yield: 65.6%) as an off-white solid.

550

The Synthesis of diethyl (4-(3-amino-6-p-tolylpyrazine-2-carboxamido)-2-fluorophenylsulfonyl)methylphosphonate (SU20668-0482-01)

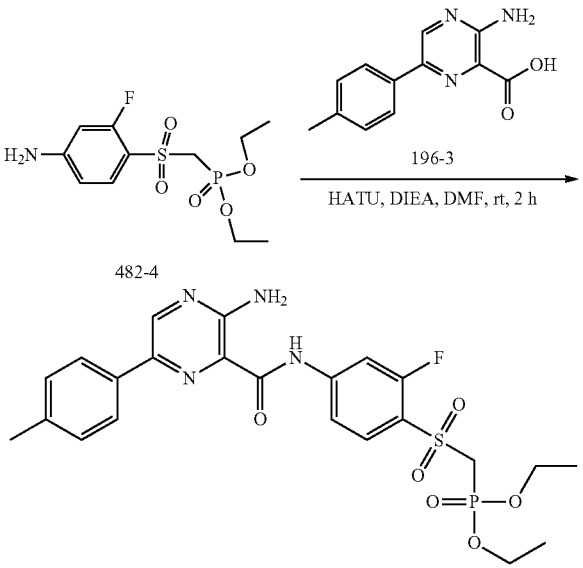

SU20668-0482-01

To a solution of compound 0482-4 (150 mg, 0.46 mmol) in DMF (4 mL) was added 196-3 (106 mg, 0.46 mmol), DIEA (120 mg, 0.92 mmol) and HATU (228 mg, 0.60 mmol). The resulting reaction mixture was stirred for 2 hours. Then it was purified by prep-HPLC to give the desired product SU20668-0482-01 (50 mg, yield: 20.2%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 100%, Rt=2.154 min; MS Calcd.: 536.1; MS Found: 537.3 [M+H]. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 100%, Rt=10.146 min. $^1$H NMR (400 MHz, DMSO-$d_6$) δ 10.82 (s, 1H), 8.90 (s, 1H), 8.05-8.10 (m, 3H), 7.81-7.87 (m, 2H), 7.66 (s, 2H), 7.29 (d, J=8.0 Hz, 2H), 4.38 (d, J=16.8 Hz, 2H), 3.95-4.02 (m, 4H), 2.35 (s, 3H), 1.16 (t, J=6.8 Hz, 6H).

Scheme 58 Route for SU20668-0483-01

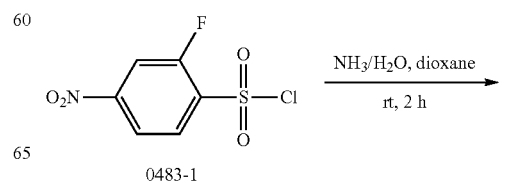

0483-1

551

-continued

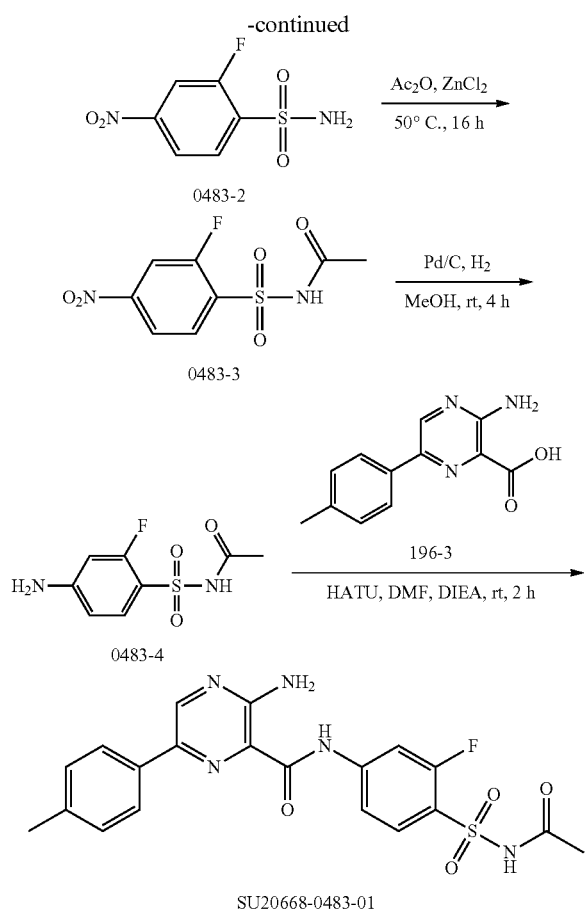

The Synthesis of 2-fluoro-4-nitrobenzenesulfonamide (0483-2)

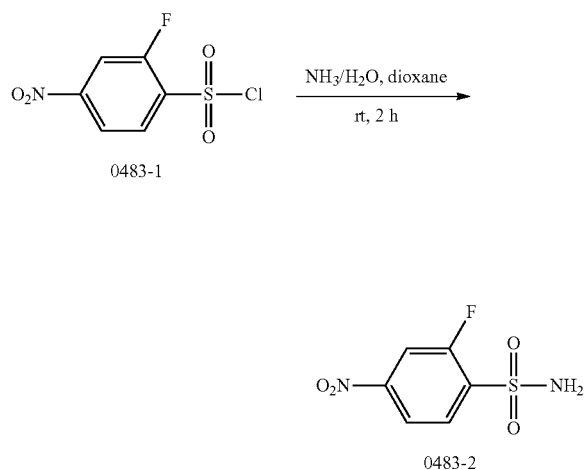

To a solution of 0483-1 (200 mg, 0.84 mmol) in dioxane (2.0 mL) was added ammonium hydroxide (2.0 mL). The mixture was stirred at rt for 2 h. The solvent was removed in vacuo to afford a crude product (250 mg) as a yellow solid.

552

The Synthesis of N-(2-fluoro-4-nitrophenylsulfonyl)acetamide (0483-3)

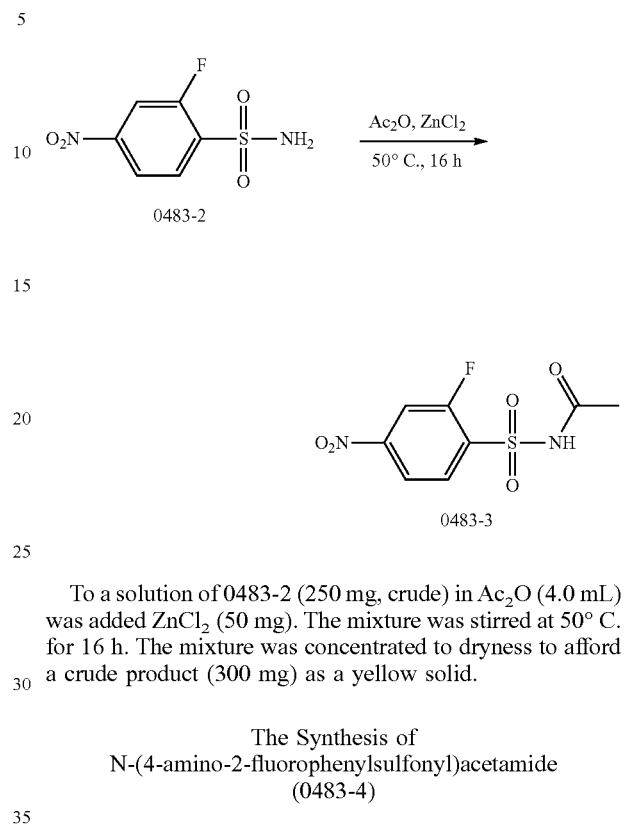

To a solution of 0483-2 (250 mg, crude) in Ac$_2$O (4.0 mL) was added ZnCl$_2$ (50 mg). The mixture was stirred at 50° C. for 16 h. The mixture was concentrated to dryness to afford a crude product (300 mg) as a yellow solid.

The Synthesis of N-(4-amino-2-fluorophenylsulfonyl)acetamide (0483-4)

To a solution of 0483-3 (300 mg, crude) in MeOH (6 mL) was added Pd/C (10%, 40 mg). The mixture was stirred at rt for 2 h under H$_2$ atmosphere (1.0 atm). Then it was filtered and concentrated in vacuo to give 0483-4 (200 mg, yield: 75.5%) as an off-white solid.

The Synthesis of diethyl N-(4-(N-acetylsulfamoyl)-3-fluorophenyl)-3-amino-6-p-tolylpyrazine-2-carboxamide (SU20668-0483-01)

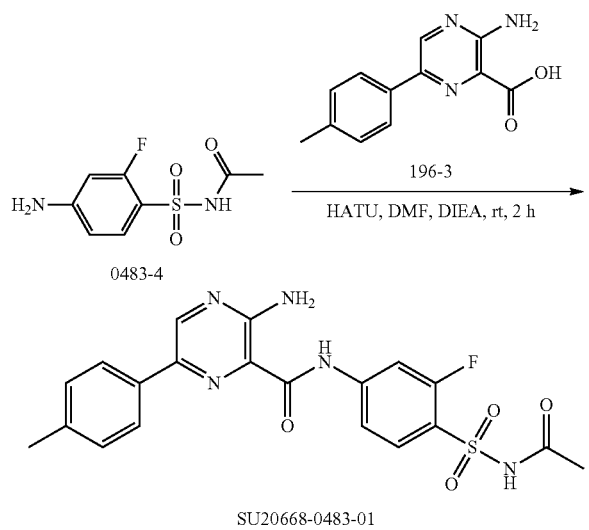

To a solution of compound 0483-4 (200 mg, 0.86 mmol) in DMF (4 mL) was added 196-3 (197 mg, 0.86 mmol), DIEA (220 mg, 1.7 mmol) and HATU (456 mg, 1.2 mmol). The resulting reaction mixture was stirred for 2 h. Then it was purified by prep-HPLC to give the desired product SU20668-0483-01 (40 mg, yield: 10.5%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 97.64%, Rt=1.563 min; MS Calcd.: 443.1; MS Found: 444.3 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 97.90%, Rt=7.253 min. $^1$H NMR (400 MHz, DMSO-$d_6$) δ 10.67 (s, 1H), 8.92 (s, 1H), 8.11 (d, J=8.4 Hz, 2H), 7.87-7.90 (m, 1H), 7.75-7.80 (m, 2H), 7.64 (s, 2H), 7.31 (d, J=8.0 Hz, 2H), 2.37 (s, 3H), 1.80 (s, 3H).

Scheme 59 Route for SU20668-0486-01

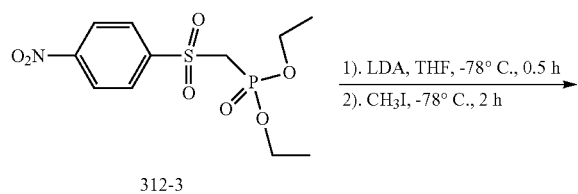

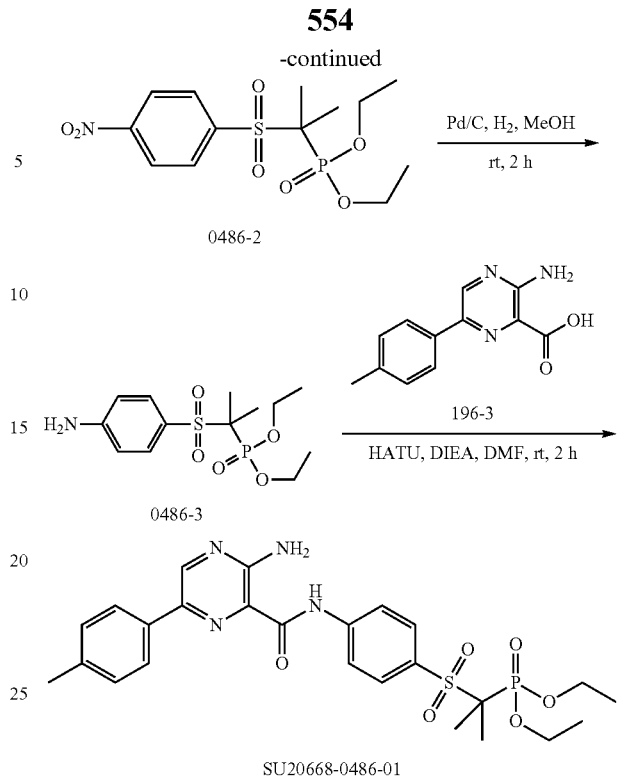

The synthesis of diethyl 2-(4-nitrophenylsulfonyl)propan-2-ylphosphonate (0486-2)

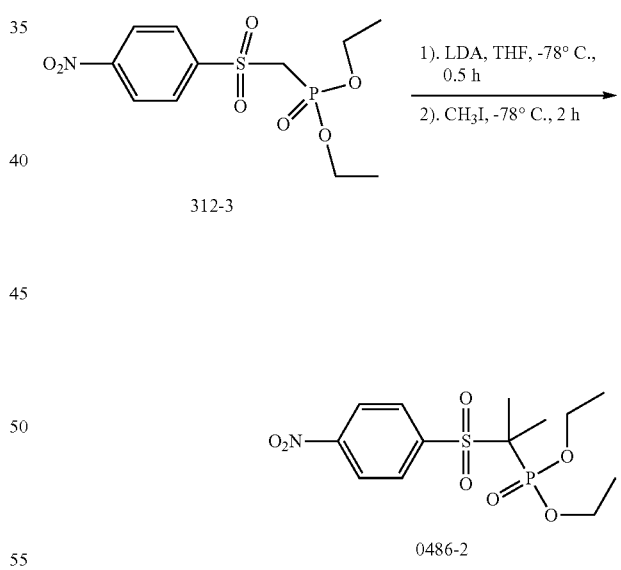

To a solution of 312-3 (500 mg, 1.5 mmol) in THF (10 mL) was added LDA (6 mL, 1.0M, 6.0 mmol) at −78° C. Then the reaction mixture was stirred at −78° C. for 30 minutes. The solution of $CH_3I$ (850 mg, 6.0 mmol) in THF (2 mL) was added dropwise. The mixture was stirred at −78° C. for 2 hours. Water (40 mL) was added. The mixture was extracted with ethyl acetate (20 mL*3). The organic layer was washed with brine (15 mL), concentrated to dryness and purified by column (DCM) to afford the product 0486-2 (280 mg, yield: 51.9%) as a yellow solid.

The Synthesis of diethyl 2-(4-aminophenylsulfonyl)propan-2-ylphosphonate (0486-3)

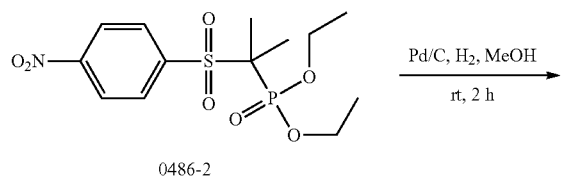

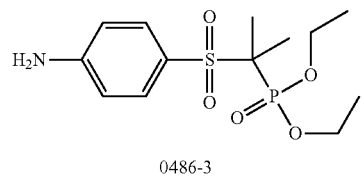

To a solution of 0486-2 (280 mg, 0.77 mmol) in MeOH (8 mL) was added Pd/C (10%, 40 mg). The mixture was stirred at rt for 2 h under H$_2$ atmosphere (1.0 atm). Then it was filtered and concentrated in vacuo to give 0486-3 (240 mg, yield: 93.8%) as an off-white solid.

The Synthesis of diethyl 2-(4-(3-amino-6-p-tolylpyrazine-2-carboxamido)phenylsulfonyl)propan-2-ylphosphonate (SU20668-0486-01)

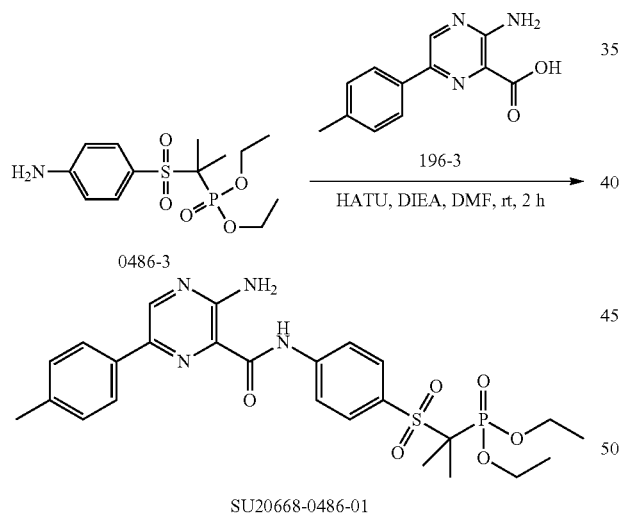

To a solution of compound 0486-3 (240 mg, 0.72 mmol) in DMF (4 mL) was added 196-3 (164 mg, 0.72 mmol), DIEA (194 mg, 1.50 mmol) and HATU (380 mg, 1.00 mmol). The resulting reaction mixture was stirred for 2 h. Then it was purified by prep-HPLC to give the desired product SU20668-0486-01 (50 mg, yield: 12.7%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=2.218 min; MS Calcd.: 546.1; MS Found: 547.3 [M+H]. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 99.3%, Rt=10.485 min. $^1$H NMR (400 MHz, DMSO-d$_6$) δ 10.73 (s, 1H), 8.89 (s, 1H), 8.07-8.10 (m, 4H), 7.86 (d, J=8.8 Hz, 2H), 7.66 (s, 2H), 7.29 (d, J=8.0 Hz, 2H), 3.98-4.09 (m, 4H), 2.35 (s, 3H), 1.43 (d, J=14.4 Hz, 6H), 1.18 (t, J=6.8 Hz, 6H).

Scheme 60 Route for SU20668-0488-01

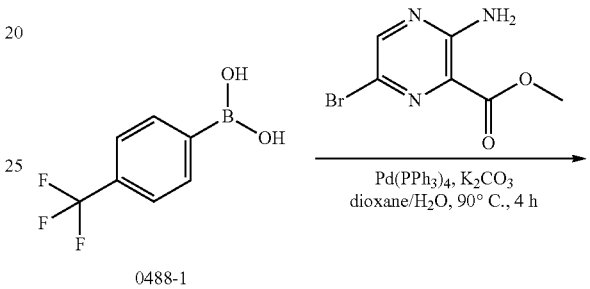

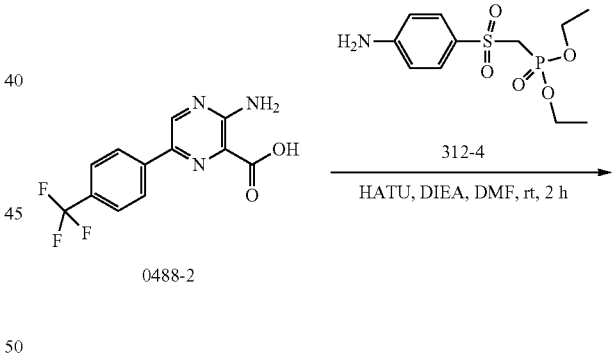

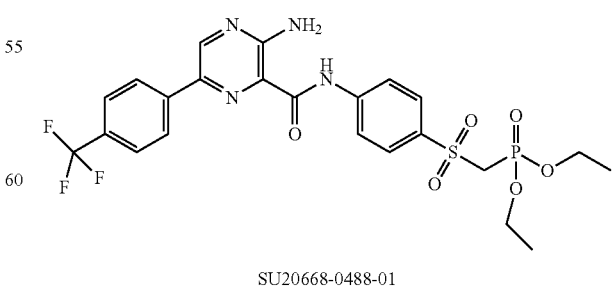

The Synthesis of 3-amino-6-(4-(trifluoromethyl)phenyl)pyrazine-2-carboxylic acid (0488-2)

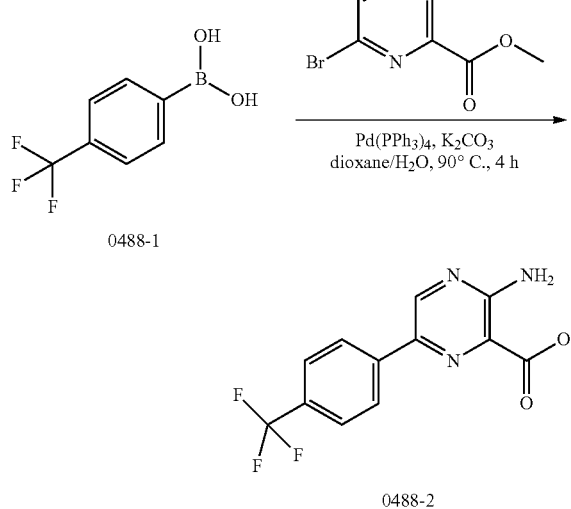

To a solution of 0488-1 (2.00 g, 10.52 mmol) in dioxane/H₂O (10 mL, 5/1) was added methyl 3-amino-6-bromopyrazine-2-carboxylate (2.91 g, 12.62 mmol), K₂CO₃ (4.36 g, 31.57 mmol) and Pd(PPh₃)₄ (1.21 g, 1.05 mmol). It was heated to 90° C. for 4 h. The reaction was cooled to room temperature and water (30 mL) was added, the residue was extracted with EA (30 mL×3). The organic layer was dried over Na₂SO₄, filtered and concentrated to give 0488-2 (2.60 g, 87%) as a white solid. Agilent LCMS 1200-6110, Column: Waters X-Bridge C18 (30 mm*4.6 mm*2.7 m); Column Temperature: 40° C.; Flow Rate: 3.0 mL/min; Mobile Phase: from 95% [water+0.05% TFA] and 5% [CH₃CN+0.05% TFA] to 0% [water+0.05% TFA] and 100% [CH₃CN+0.05% TFA] in 0.8 min, then under this condition for 0.4 min, finally changed to 95% [water+0.05% TFA] and 5% [CH₃CN+0.05% TFA] in 0.1 min. Purity: 100%, Rt=0.681 min; MS Calcd.: 283.1; MS Found: 284.4 [M+H]⁺.

The Synthesis of diethyl (4-(3-amino-6-(4-(trifluoromethyl)phenyl)pyrazine-2-carboxamido)phenylsulfonyl)methylphosphonate (SU20668-0488-01)

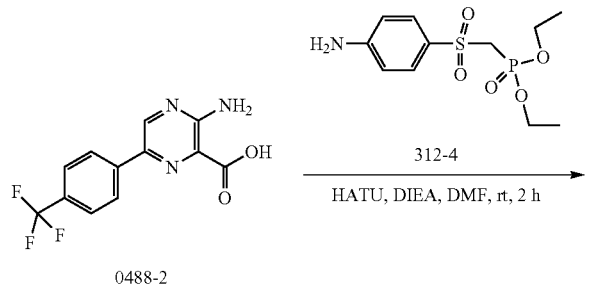

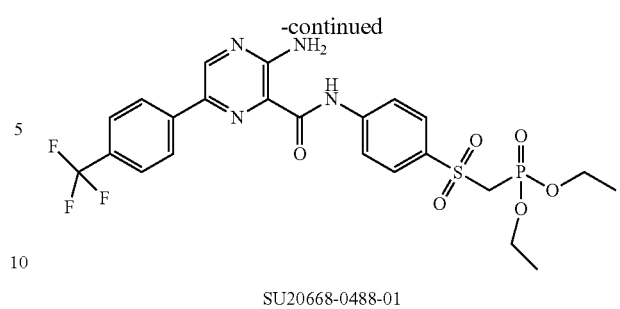

SU20668-0488-01

To a solution of 0488-2 (0.5 g, 1.76 mmol) in DMF (10 mL) was added 312-4 (0.65 g, 2.11 mmol). It was heated to 95° C. for 5 h. The reaction was cooled to room temperature and water (30 mL) was added, the residue was extracted with EA (30 mL×2). The organic layer was dried over Na₂SO₄, filtered and concentrated. The residue was purified by Prep-HPLC to give SU20667-0488-01 (200 mg, 20%) as a white solid. Agilent LCMS 1200-6120, Column: Waters X-Bridge C18 (50 mm*4.6 mm*3.5 μm); Column Temperature: 30° C.; Flow Rate: 2.0 mL/min; Mobile Phase: from 95% [water+0.01% NH₃ (7M in methanol)] and 5% [CH₃CN] to 0% [water+0.01% NH₃ (7M in methanol)] and 100% [CH₃CN] in 1.6 min, then under this condition for 1.4 min, finally changed to 95% [water+0.01% NH₃ (7M in methanol)] and 5% [CH₃CN] in 0.1 min and under this condition for 0.7 min. Purity: 97.55%, Rt=2.265 min; MS Calcd.: 572.1; MS Found: 573.2 [M+H]⁺. Agilent HPLC 1200, Column: Waters X-Bridge C18 (150 mm*4.6 mm*3.5 μm); Column Temperature: 30° C.; Flow Rate: 1.0 mL/min; Mobile Phase: from 95% [water+0.01% NH₃ (7M in methanol)] and 5% [CH₃CN] to 0% [water+0.01% NH₃ (7M in methanol)] and 100% [CH₃CN] in 10 min, then under this condition for 5 min, finally changed to 95% [water+0.01% NH₃ (7M in methanol)] and 5% [CH₃CN] in 0.1 min and under this condition for 5 min, Purity: 94.69%. 1H NMR (400 MHz, DMSO-d₆) δ 10.76 (s, 1H), 9.00 (s, 1H), 8.43 (d, J=8.4 Hz, 2H), 8.07 (d, J=8.8 Hz, 2H), 7.80-7.93 (m, 6H), 4.39 (d, J=16.8 Hz, 2H), 3.94-4.03 (m, 4H), 1.16 (t, J=6.8 Hz, 6H).

Scheme 61 Route for SU20667-0490-01

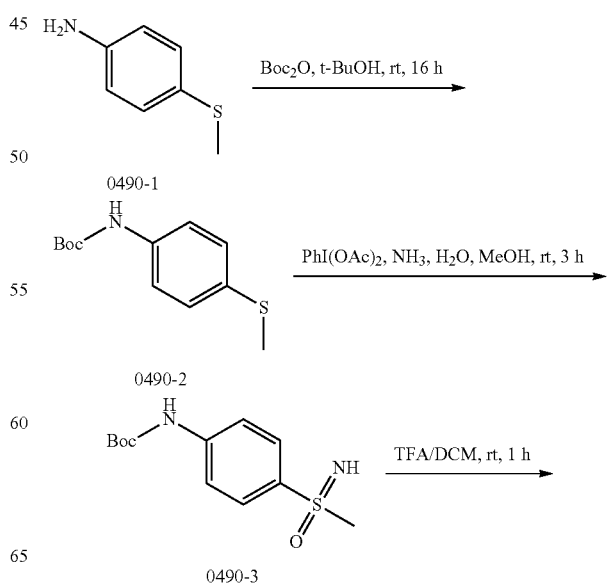

-continued

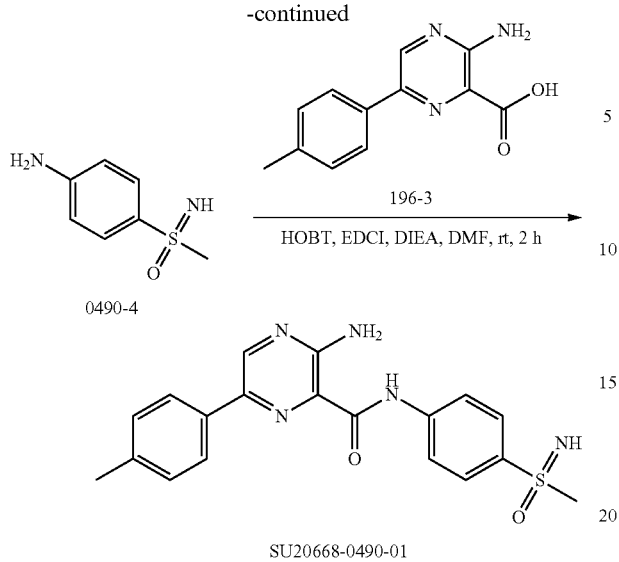

SU20668-0490-01

The Synthesis of tert-butyl 4-(methylthio)phenylcarbamate (0490-2)

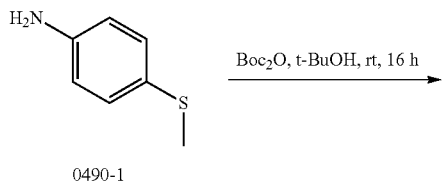

To a solution of 0490-1 (1.00 g, 7.19 mmol) in t-BuOH (10 mL) was added Boc₂O (1.73 g, 7.91 mmol). It was stirred at room temperature for 16 h. After the reaction was completed, the mixture was quenched with water, and then extracted with EA (30 mL×3). The organic layer was dried over Na$_2$SO$_4$, filtered and concentrated to give 0490-2 (1.60 g, 94%) as a brown solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 3.0 min, then under this condition for 1.0 min, finally changed to 95% [water+10 mM NH$_4$HCO$_3$] and 5% [CH$_3$CN] in 0.1 min and under this condition for 0.7 min. Purity: 96%, Rt=2.228 min; MS Calcd.: 239.1; MS Found: 184.3 [M-56+1]⁺.

The Synthesis of tert-butyl 4-(S-methylsulfonimidoyl)phenylcarbamate (0490-3)

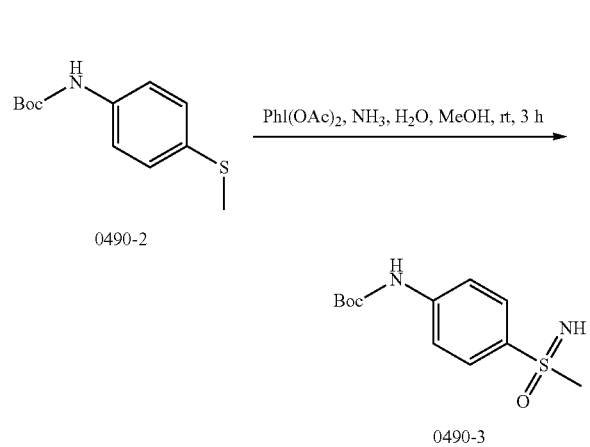

To a solution of 0490-2 (1.60 g, 6.69 mmol) in MeOH (10 mL) was added PhI(OAc)$_2$ (2.15 g, 6.69 mmol). It was stirred at room temperature for 3 h. After the reaction was completed, the mixture was quenched with water, and then extracted with EA (30 mL×3). The organic layer was dried over Na$_2$SO$_4$, filtered and concentrated. The residue was purified by Prep-HPLC to give 0490-3 (0.80 g, 44%) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 3.0 min, then under this condition for 1.0 min, finally changed to 95% [water+10 mM NH$_4$HCO$_3$] and 5% [CH$_3$CN] in 0.1 min and under this condition for 0.7 min. Purity: 96%, Rt=1.581 min; MS Calcd.: 270.1; MS Found: 271.4 [M+H]⁺.

The Synthesis of 4-(S-methylsulfonimidoyl)aniline (0490-4)

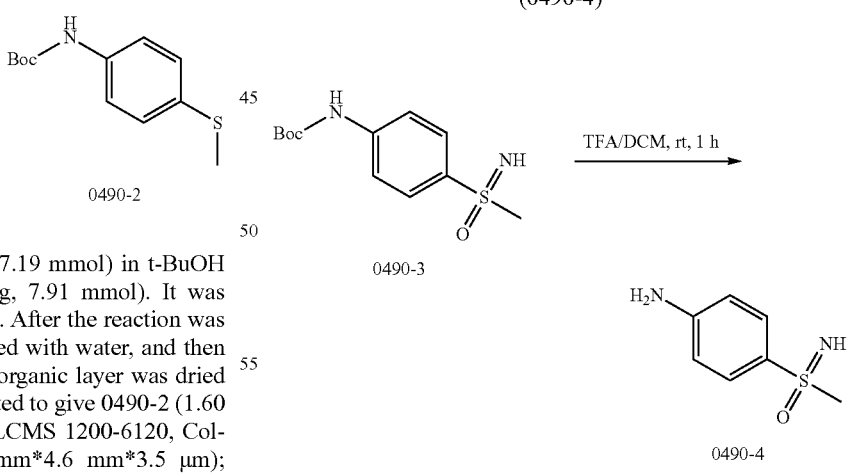

To a solution of 0490-3 (0.80 g, 2.96 mmol) in DCM (10 mL) was added TFA (0.43 g, 4.44 mmol). It was stirred at room temperature for 1 h. After the reaction was completed, the mixture was quenched with water, and then extracted with EA (30 mL×3). The organic layer was dried over Na$_2$SO$_4$, filtered and concentrated to give 0490-4 (0.48 g, 96%) as a yellow solid. Agilent LCMS 1200-6110, Column:

Waters X-Bridge C18 (30 mm*4.6 mm*2.7 m); Column Temperature: 40° C.; Flow Rate: 3.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 0.8 min, then under this condition for 0.4 min, finally changed to 95% [water+0.05% TFA] and 5% [CH$_3$CN+0.05% TFA] in 0.1 min. Purity: 87%, Rt=0.525 min; MS Calcd.: 170.1; MS Found: 171.1 [M+H]$^+$.

The Synthesis of 4-(S-methylsulfonimidoyl)aniline (SU20668-0490-01)

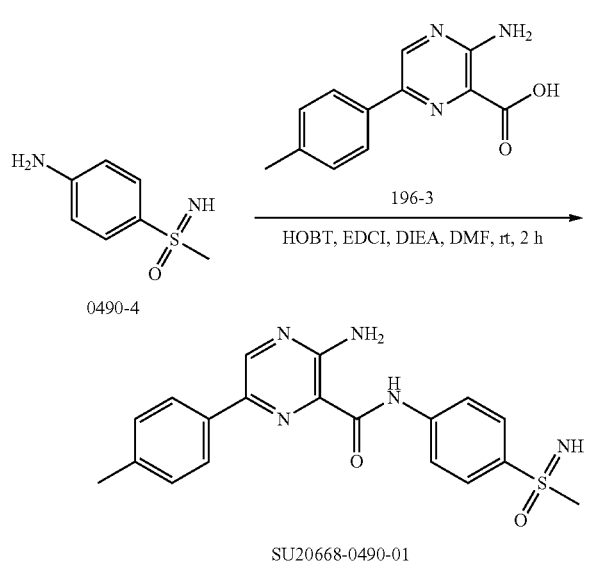

To a solution of 0490-4 (0.48 g, 2.82 mmol) in DMF (5 mL) was added HOBT (0.76 g, 5.64 mmol), EDCI (1.08 g, 5.64 mmol), 196-3 (0.71 g, 3.10 mmol) and DIEA (1.09 g, 8.46 mmol). It was stirred at room temperature for 2 h. After the reaction was completed, the mixture was quenched with water and filtered. The residue was purified by Prep-HPLC to give SU20668-0490-01 (0.11 g, 10%) as a yellow solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 96%, Rt=1.892 min; MS Calcd.: 381.1; MS Found: 382.3 [M+H]$^+$. Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min, Purity: 97%. 1H NMR (400 MHz, DMSO-d$_6$) δ 10.85 (s, 1H), 8.92 (s, 1H), 8.12 (d, J=8.4 Hz, 2H), 8.06-8.09 (m, 2H), 7.92-7.95 (m, 2H), 7.65 (s, 2H), 7.31 (d, J=9.2 Hz, 2H), 4.16 (s, 1H), 3.07 (s, 3H), 2.37 (s, 3H).

Scheme 62 Route for SU20668-0494-01

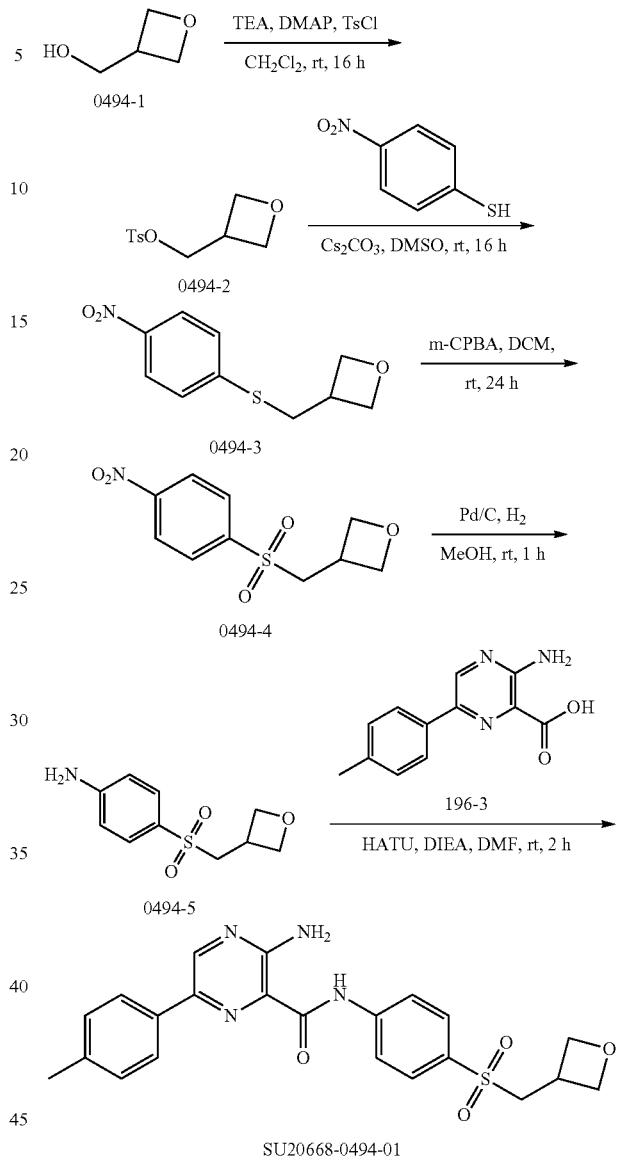

The Synthesis of oxetan-3-ylmethyl 4-methylbenzenesulfonate (0494-2)

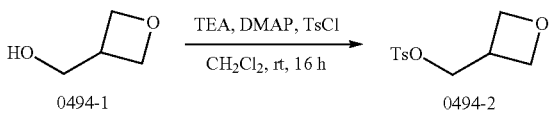

To a solution of 0494-1 (550 mg, 6.25 mmol) in DCM (20 mL) was added TEA (1.21 g, 12.0 mmol), DMAP (50 mg) and TsCl (1.4 g, 7.50 mmol). The mixture was stirred at rt for 16 hours. Water (60 mL) was added. The mixture was extracted with DCM (30 mL×3). The organic layer was washed with brine (30 mL) and concentrated to dryness to afford the product 0494-2 (800 mg, yield: 52.9%) as an off-white solid.

The Synthesis of 3-((4-nitrophenylthio)methyl)oxetane (0494-3)

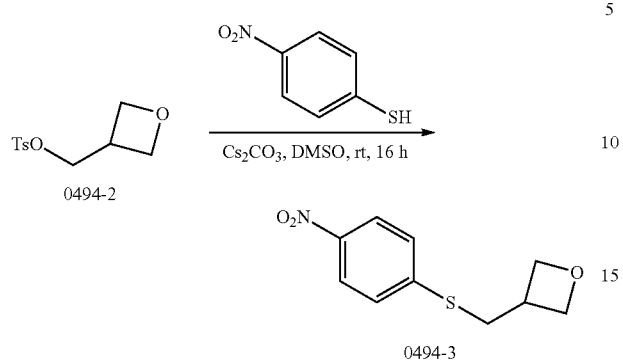

To a stirred solution of 0494-2 (800 mg, 3.31 mmol) in DMSO (15 ml) was added 4-nitrobenzenethiol (465 mg, 3.00 mmol) and $Cs_2CO_3$ (1.96 g, 6.00 mmol). The resulting reaction mixture was stirred for 16 h at rt. Then water (80 mL) was added. The aqueous phase was extracted with EA (40 mL×3). The combined organic phases were washed with brine (30 mL), dried over anhydrous sodium sulfate, filtered, and concentrated in vacuo to give the desired product 0494-3 (600 mg, yield: 88.9%) as a yellow solid.

The Synthesis of 3-((4-nitrophenylsulfonyl)methyl)oxetane (0494-4)

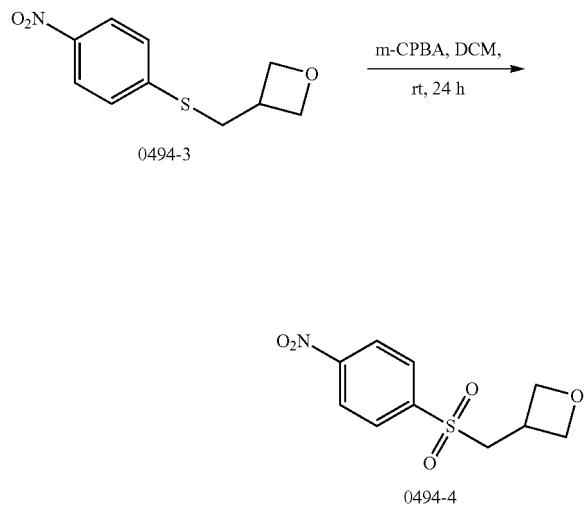

To a stirred solution of compound 0494-3 (600 mg, 2.67 mmol) in DCM (20 mL) was added 3-chlorobenzenecarboperoxoic acid (1.21 g, 7.00 mmol) at 0° C. The resulting reaction mixture was further stirred for 24 h at rt. Then water (60 mL) and $Na_2SO_3$ (2.0 g) were added. The aqueous phase was extracted with DCM (30 mL×3). The combined organic phases were dried over anhydrous sodium sulfate, filtered, concentrated and purified by silica-gel column to give the desired product 0494-4 (400 mg, yield: 58.3%) as a yellow solid.

The Synthesis of 4-(oxetan-3-ylmethylsulfonyl)aniline (0494-5)

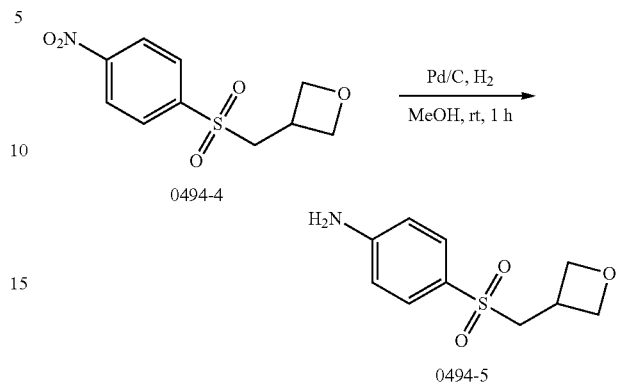

To a solution of 0494-4 (400 mg, 1.56 mmol) in MeOH (10 mL) was added Pd/C (10%, 40 mg). The mixture was stirred at rt for 2 h under $H_2$ atmosphere (1.0 atm). Then it was filtered and concentrated in vacuo to give 0494-5 (350 mg, yield: 99.1%) as an off-white solid.

The Synthesis of 3-amino-N-(4-(oxetan-3-ylmethylsulfonyl)phenyl)-6-p-tolylpyrazine-2-carboxamide (SU20668-0494-01)

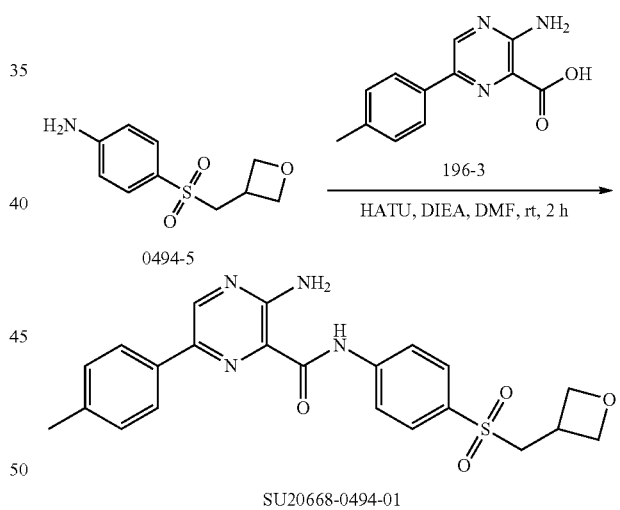

To a solution of compound 0494-5 (200 mg, 0.78 mmol) in DMF (4 mL) was added 196-3 (178 mg, 0.78 mmol), DIEA (193 mg, 1.50 mmol) and HATU (380 mg, 1.00 mmol). The resulting reaction mixture was stirred for 2 hours. Then it was purified by prep-HPLC to give the desired product SU20668-0494-01 (130 mg, yield: 33.8%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 95.75%, Rt=2.069 min; MS Calcd.: 438.1; MS Found: 439.4 [M+H]+. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 95.78%, Rt=9.698 min. $^1$H NMR (400 MHz, DMSO-$d_6$) δ 10.72 (s, 1H), 8.88 (s, 1H), 8.08-8.11 (m, 4H), 7.84 (d, J=8.8 Hz, 2H), 7.67 (s, 2H), 7.29 (d, J=8.0 Hz, 2H), 4.49-4.53 (m, 2H), 4.28 (t, J=6.4 Hz, 2H), 3.71 (d, J=7.6 Hz, 2H), 3.26-3.30 (m, 1H), 2.35 (s, 3H).

The Synthesis of 2-methyl-5-(4,4,5,5-tetramethyl-1,3,2-dioxaborolan-2-yl)phenol (0496-1)

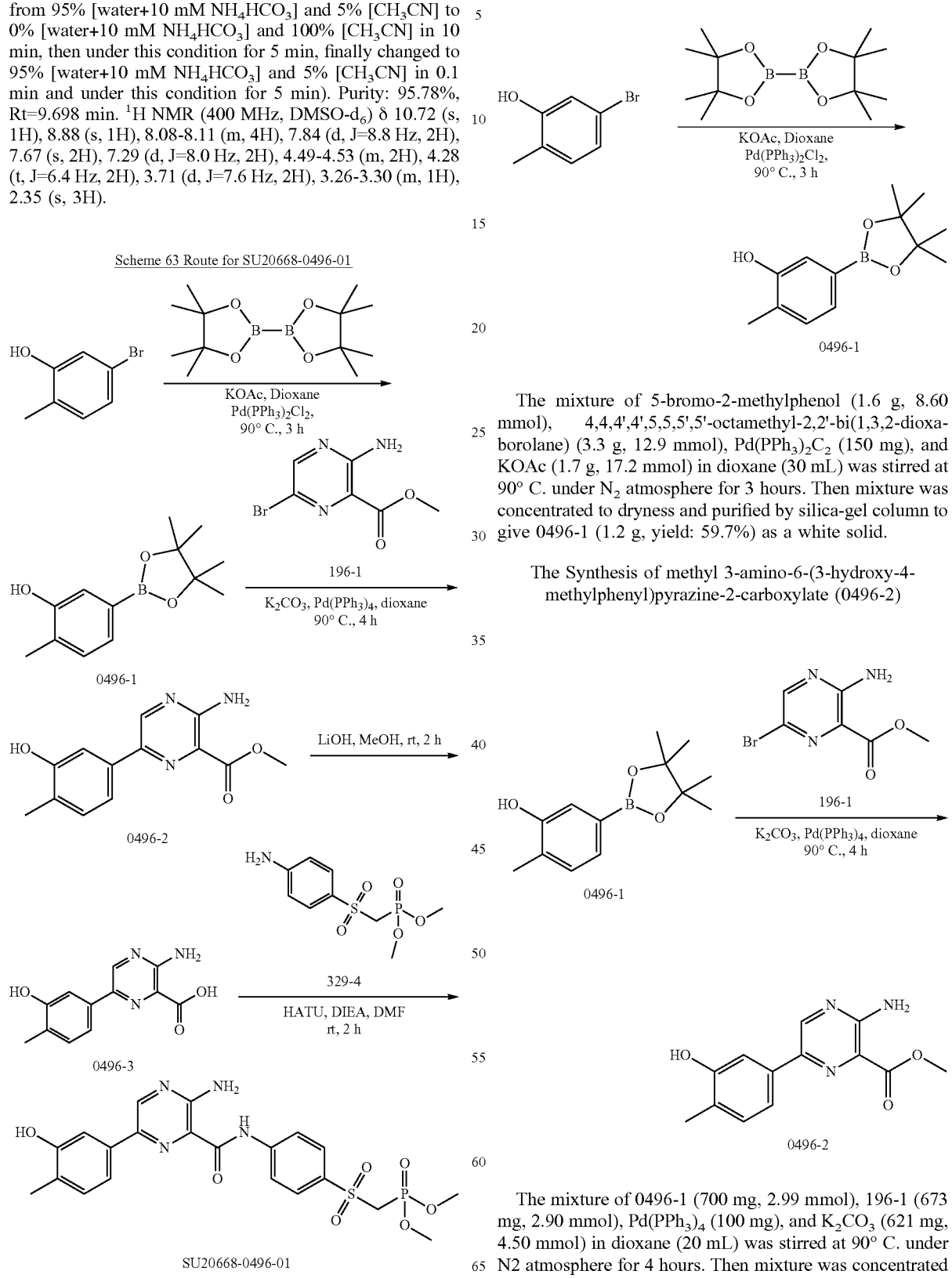

The mixture of 5-bromo-2-methylphenol (1.6 g, 8.60 mmol), 4,4,4',4',5,5,5',5'-octamethyl-2,2'-bi(1,3,2-dioxaborolane) (3.3 g, 12.9 mmol), Pd(PPh$_3$)$_2$C$_2$ (150 mg), and KOAc (1.7 g, 17.2 mmol) in dioxane (30 mL) was stirred at 90° C. under N$_2$ atmosphere for 3 hours. Then mixture was concentrated to dryness and purified by silica-gel column to give 0496-1 (1.2 g, yield: 59.7%) as a white solid.

The Synthesis of methyl 3-amino-6-(3-hydroxy-4-methylphenyl)pyrazine-2-carboxylate (0496-2)

The mixture of 0496-1 (700 mg, 2.99 mmol), 196-1 (673 mg, 2.90 mmol), Pd(PPh$_3$)$_4$ (100 mg), and K$_2$CO$_3$ (621 mg, 4.50 mmol) in dioxane (20 mL) was stirred at 90° C. under N2 atmosphere for 4 hours. Then mixture was concentrated to dryness and purified by silica-gel column to give 0496-2 (500 mg, yield: 64.6%) as a yellow solid.

The Synthesis of 3-amino-6-(3-hydroxy-4-methylphenyl)pyrazine-2-carboxylic acid (0496-3)

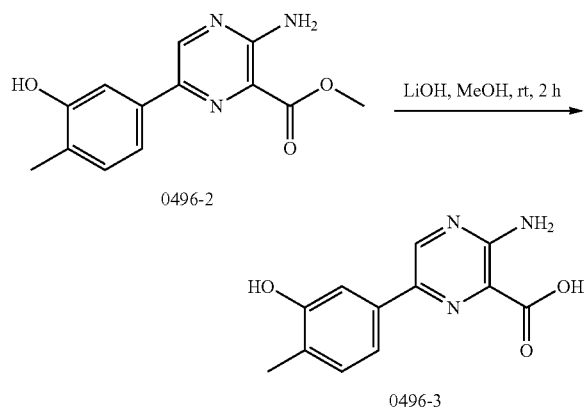

The mixture of 0496-2 (800 mg, 3.09 mmol) and LiOH (336 mg, 8.00 mmol) in methanol (15 mL) was stirred at room temperature for 2 hours. Then the reaction mixture was acidified with HCl (1N) till pH=3~4. The solid was collected by filtration to afford 0496-3 (450 mg, yield: 59.5%) as a yellow solid.

The Synthesis of dimethyl (4-(3-amino-6-(3-hydroxy-4-methylphenyl)pyrazine-2-carboxamido)phenylsulfonyl)methylphosphonate (SU20668-0496-01)

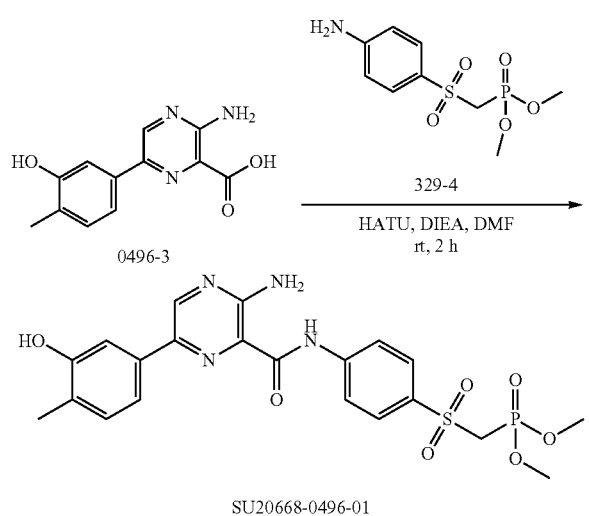

To a solution of compound 0496-3 (200 mg, 0.82 mmol) in DMF (4 mL) was added 196-3 (187 mg, 0.82 mmol), DIEA (193 mg, 1.50 mmol) and HATU (380 mg, 1.00 mmol). The resulting reaction mixture was stirred for 2 hours. Then it was purified by prep-HPLC to give the desired product SU20668-0496-01 (30 mg, yield: 7.3%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=1.795 min; MS Calcd.: 506.1; MS Found: 507.4 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 99.45%, Rt=8.378 min. $^1$H NMR (400 MHz, DMSO-d$_6$) δ 10.69 (s, 1H), 9.43 (s, 1H), 8.80 (s, 1H), 8.08-8.10 (m, 2H), 7.94-7.97 (m, 2H), 7.61 (s, 2H), 7.51-7.54 (m, 2H), 7.18 (d, J=8.0 Hz, 1H), 4.49 (d, J=16.8 Hz, 2H), 3.63 (d, J=11.2 Hz, 6H), 2.17 (s, 3H).

Scheme 64: Route for SU20668-0500-01

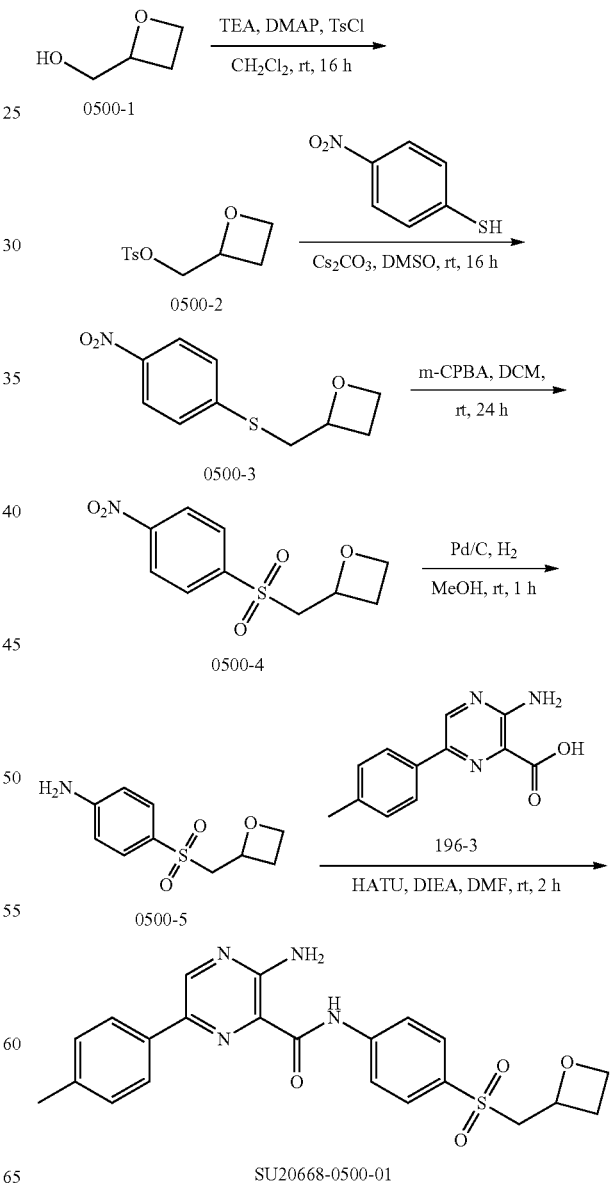

The Synthesis of oxetan-2-ylmethyl 4-methylbenzenesulfonate (0500-2)

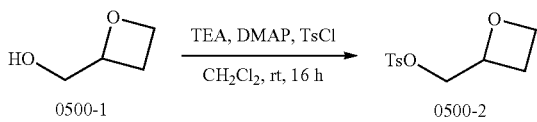

To a solution of 0500-1 (500 mg, 5.68 mmol) in DCM (20 mL) was added TEA (1.21 g, 12.0 mmol), DMAP (50 mg) and TsCl (1.3 g, 7.00 mmol). The mixture was stirred at rt for 16 hours. Water (60 mL) was added. The mixture was extracted with DCM (30 mL×3). The organic layer was washed with brine (30 mL) and concentrated to dryness to afford the product 0500-2 (900 mg, yield: 65.5%) as an off-white solid.

The Synthesis of 2-((4-nitrophenylthio)methyl)oxetane (0500-3)

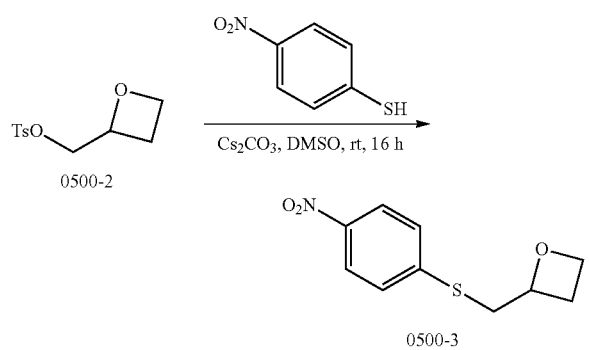

To a stirred solution of 0500-2 (600 mg, 2.48 mmol) in DMSO (12 mL) was added 4-nitrobenzenethiol (372 mg, 2.40 mmol) and $Cs_2CO_3$ (1.63 g, 5.00 mmol). The resulting reaction mixture was stirred for 16 h at rt. Then water (80 mL) was added. The aqueous phase was extracted with EA (40 mL×3). The combined organic phases were washed with brine (30 mL), dried over anhydrous sodium sulfate, filtered, and concentrated in vacuo to give the desired product 0500-3 (400 mg, yield: 71.7%) as a yellow solid.

The Synthesis of 2-((4-nitrophenylsulfonyl)methyl)oxetane (0500-4)

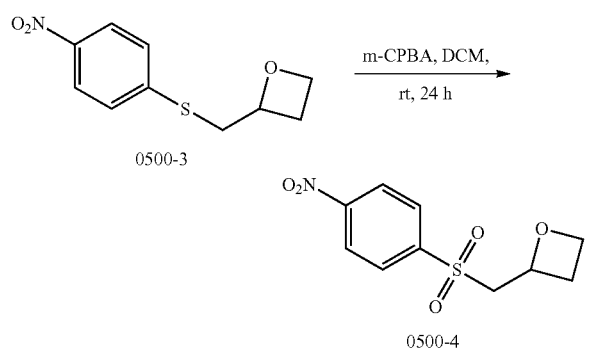

To a stirred solution of compound 0500-3 (400 mg, 1.78 mmol) in DCM (20 mL) was added 3-chlorobenzenecarboperoxoic acid (776 mg, 4.50 mmol) at 0° C. The resulting reaction mixture was further stirred for 24 h at rt. Then water (50 mL) and $Na_2SO_3$ (1.5 g) were added. The aqueous phase was extracted with DCM (25 mL×3). The combined organic phases were dried over anhydrous sodium sulfate, filtered, concentrated and purified by silica-gel column to give the desired product 0500-4 (300 mg, yield: 65.6%) as a yellow solid.

The Synthesis of 4-(oxetan-2-ylmethylsulfonyl)aniline (0500-5)

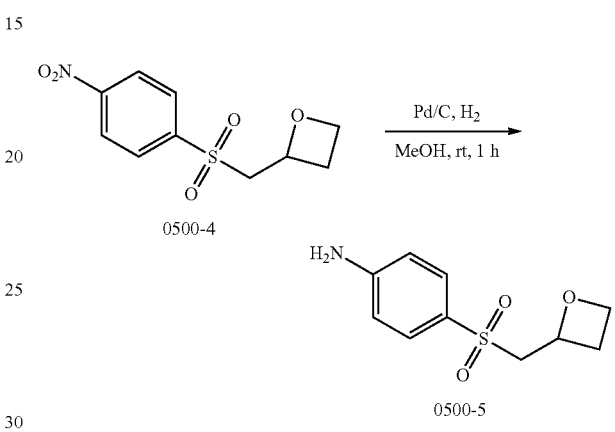

To a solution of 0500-4 (200 mg, 0.78 mmol) in MeOH (6 mL) was added Pd/C (10%, 30 mg). The mixture was stirred at rt for 2 h under $H_2$ atmosphere (1.0 atm). Then it was filtered and concentrated in vacuo to give 0500-5 (150 mg, yield: 84.7%) as an off-white solid.

The Synthesis of 3-amino-N-(4-(oxetan-2-ylmethylsulfonyl)phenyl)-6-p-tolylpyrazine-2-carboxamide (SU20668-0500-01)

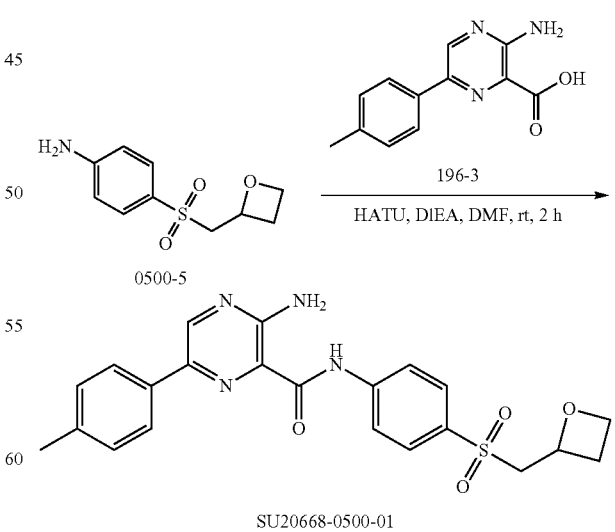

To a solution of compound 0500-5 (150 mg, 0.66 mmol) in DMF (4 mL) was added 196-3 (151 mg, 0.66 mmol), DIEA (155 mg, 1.20 mmol) and HATU (342 mg, 0.90 mmol). The resulting reaction mixture was stirred for 2 hours. Then it was purified by prep-HPLC to give the desired product SU20668-0500-01 (33 mg, yield: 11.4%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 99.13%, Rt=2.106 min; MS Calcd.: 438.1; MS Found: 439.4 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 94.2%, Rt=9.848 min. $^1$H NMR (400 MHz, DMSO-d$_6$) δ 10.70 (s, 1H), 8.90 (s, 1H), 8.08-8.11 (m, 4H), 7.86 (d, J=8.8 Hz, 2H), 7.63 (s, 2H), 7.29 (d, J=8.0 Hz, 2H), 4.95-4.99 (m, 1H), 4.40-4.44 (m, 1H), 4.33-4.37 (m, 1H), 3.74-3.86 (m, 2H), 2.49-2.64 (m, 1H), 2.30-2.47 (m, 4H).

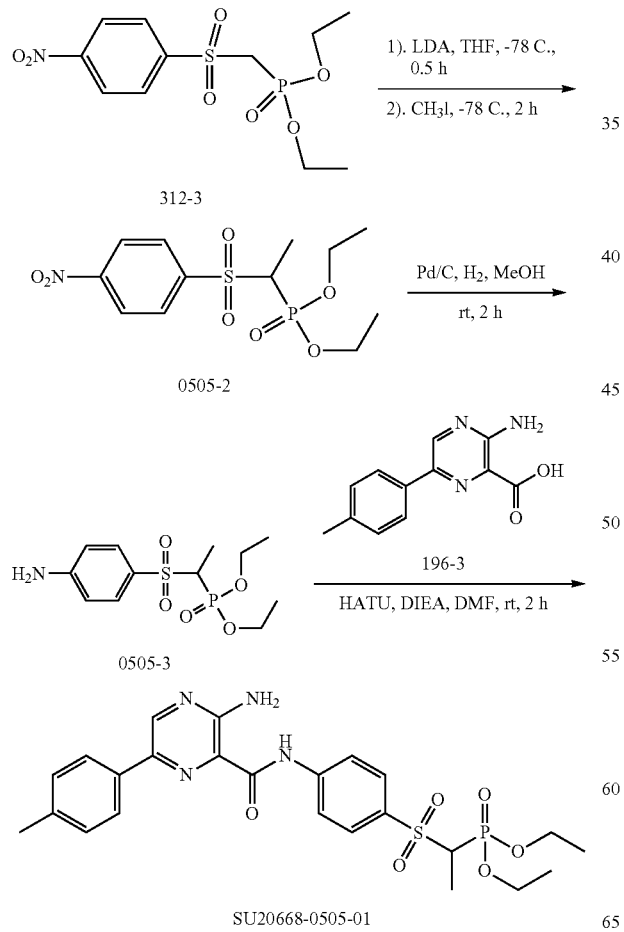

The Synthesis of diethyl 1-(4-nitrophenylsulfonyl)ethylphosphonate (0505-2)

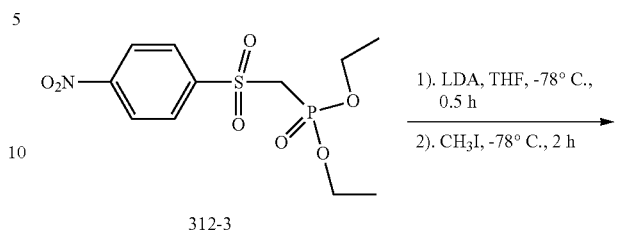

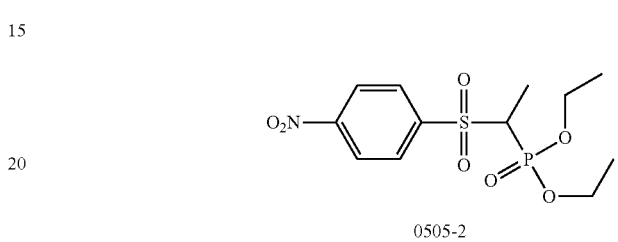

To a solution of 312-3 (500 mg, 1.5 mmol) in THF (10 mL) was added LDA (3 mL, 1.0M, 3.0 mmol) at −78° C. Then the reaction mixture was stirred at −78° C. for 30 minutes. The solution of CH$_3$I (284 mg, 2.0 mmol) in THF (2 mL) was added dropwise in 30 minutes. The mixture was stirred at −78° C. for 2 hours. Water (40 mL) was added. The mixture was extracted with ethyl acetate (20 mL×3). The organic layer was washed with brine (15 mL), concentrated to dryness and purified by column (DCM) to afford the product 0505-2 (130 mg, yield: 25.0%) as a yellow solid.

The Synthesis of diethyl 1-(4-aminophenylsulfonyl)ethylphosphonate (0505-3)

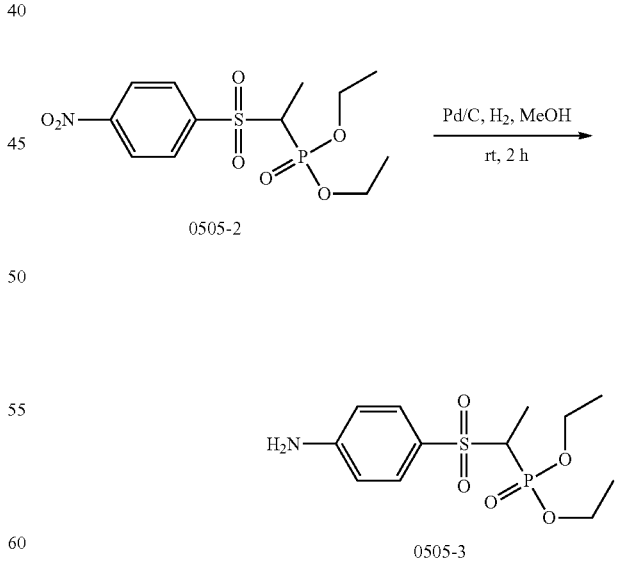

To a solution of 0505-2 (130 mg, 0.37 mmol) in MeOH (6 mL) was added Pd/C (10%, 30 mg). The mixture was stirred at rt for 2 h under H$_2$ atmosphere (1.0 atm). Then it was filtered and concentrated in vacuo to give 0505-3 (100 mg, yield: 84.0%) as an off-white solid.

The Synthesis of diethyl 1-(4-(3-amino-6-p-tolylpyrazine-2-carboxamido)phenylsulfonyl)ethylphosphonate (SU20668-0505-01)

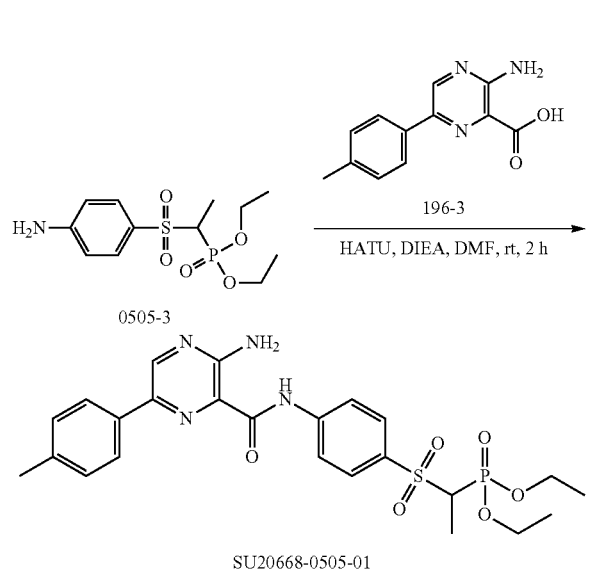

To a solution of compound 0505-3 (100 mg, 0.31 mmol) in DMF (4 mL) was added 196-3 (71 mg, 0.31 mmol), DIEA (80 mg, 0.62 mmol) and HATU (152 mg, 0.40 mmol). The resulting reaction mixture was stirred for 2 hours. Then it was purified by prep-HPLC to give the desired product SU20668-0505-01 (23 mg, yield: 13.9%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 97.64%, Rt=2.156 min; MS Calcd.: 532.1; MS Found: 533.3 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 100%, Rt=10.178 min. $^1$H NMR (400 MHz, DMSO-d$_6$) δ 10.71 (s, 1H), 8.91 (s, 1H), 8.09-8.11 (m, 4H), 7.89 (d, J=8.8 Hz, 2H), 7.63 (s, 2H), 7.29 (d, J=8.0 Hz, 2H), 4.25-4.32 (m, 1H), 3.97-4.04 (m, 4H), 2.35 (s, 3H), 1.34-1.39 (m, 3H), 1.15-1.19 (m, 6H).

Scheme 66: Route for SU20668-0508-01

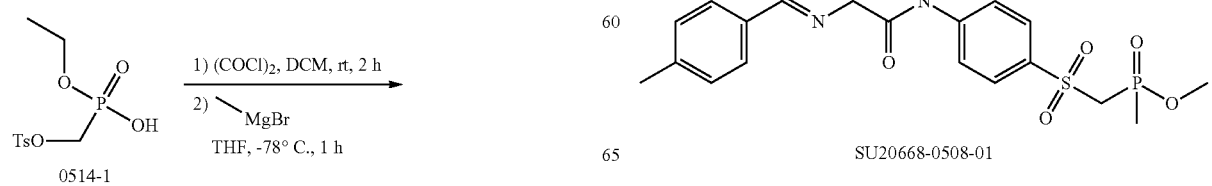

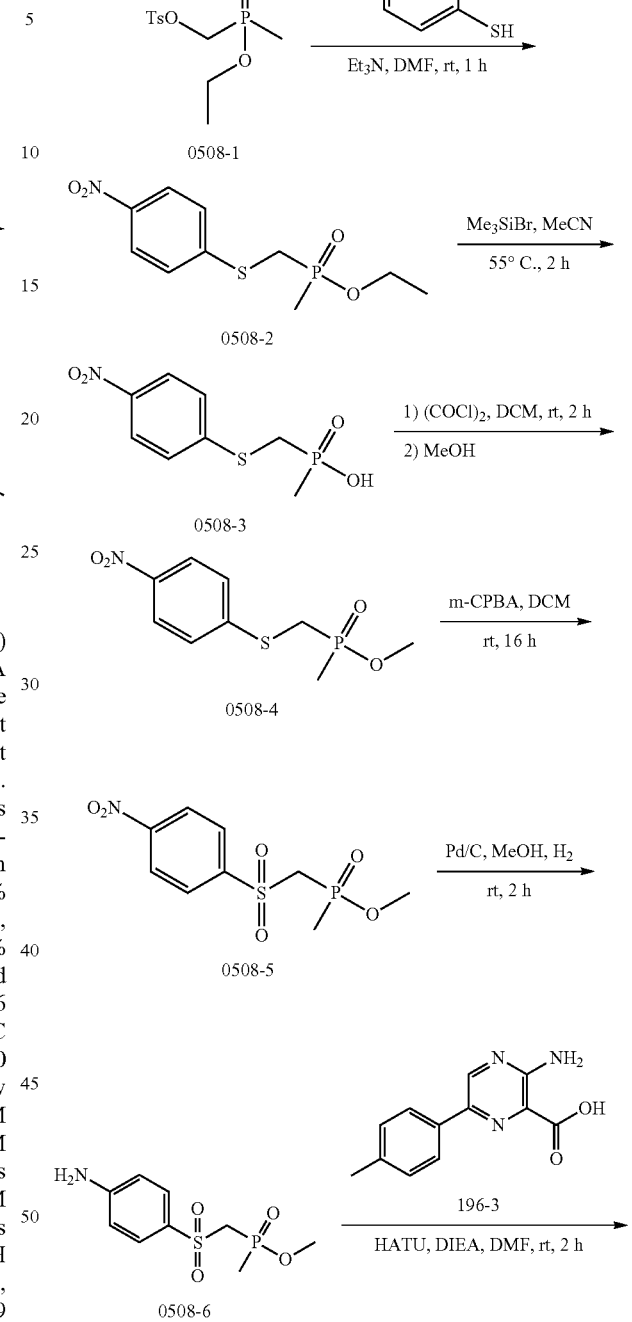

The Synthesis of (ethoxy(methyl)phosphoryl)methyl 4-methylbenzenesulfonate (0508-1)

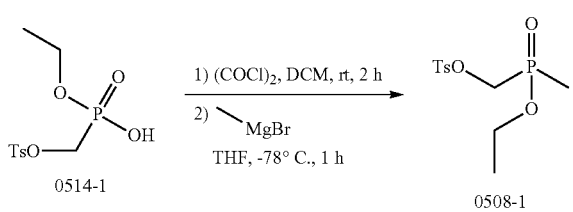

To a solution of 0514-1 (15.0 g, crude) in DCM (150 mL) was added oxalyl dichloride (7.5 mL) dropwise at 0° C. DMF (0.5 mL) was added. The mixture was stirred at rt for 2 h and then concentrated to dryness. The residue was dissolved in THF (150 mL). Then methylmagnesium bromide (17 mL, 3M, 51 mmol) was added dropwise at −78° C. The mixture was stirred at −78° C. for 1 hour. Water (300 mL) was added to quench the reaction. The mixture was extracted with EA (80 mL×3). The combined organic phases were washed with brine (80 mL), dried over anhydrous sodium sulfate, filtered, concentrated and purified by prep-HPLC to give the desired product 0508-1 (2.7 g, yield: 18.1%) as a yellow solid.

The Synthesis of ethyl methyl((4-nitrophenylthio)methyl)phosphinate (0508-2)

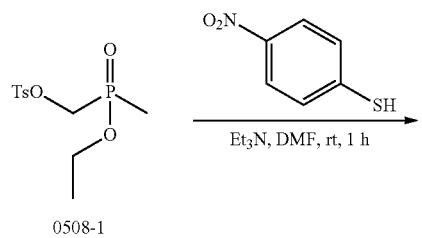

To a stirred solution of 0508-1 (2.7 g, 9.2 mmol) in DMF (30 mL) was added 4-nitrobenzenethiol (1.4 g, 9.2 mmol) and TEA (1.8 g, 18.0 mmol). The resulting reaction mixture was stirred for 1 h at rt. Then water (150 mL) was added. The aqueous phase was extracted with EA (80 mL×3). The combined organic phases were washed with brine (80 mL), dried over anhydrous sodium sulfate, filtered, and concentrated in vacuo to give the desired product 0508-2 (1.8 g, yield: 70.9%) as a yellow solid.

The Synthesis of methyl((4-nitrophenylthio)methyl)phosphinic acid (0508-3)

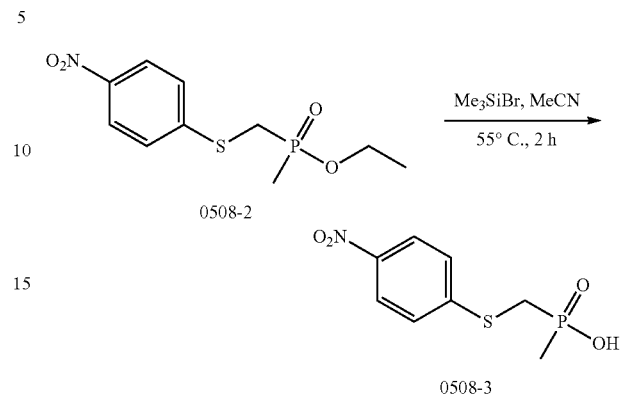

To a solution of 0508-2 (1.8 g, 6.5 mmol) in MeCN (25 mL) was added Me₃SiBr (1.1 g, 7.5 mmol) dropwise at rt. Then it was stirred at 55° C. for 2 hours. The reaction mixture was concentrated to dryness to afford 0508-3 (2.5 g, crude) as a yellow solid.

The Synthesis of methyl methyl((4-nitrophenylthio)methyl)phosphinate (0508-4)

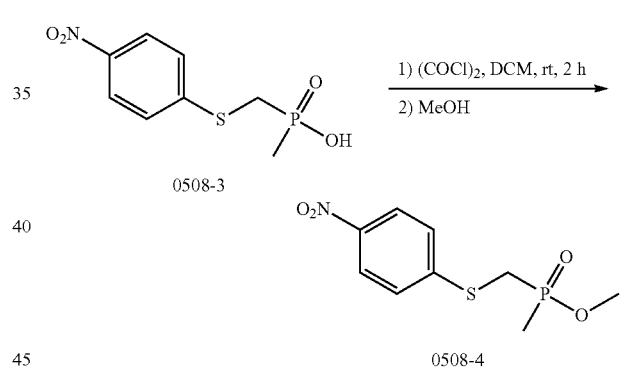

To a solution of 0508-3 (2.5 g, crude) in DCM (20 mL) was added oxalyl dichloride (3.0 mL) dropwise at 0° C. DMF (0.3 mL) was added. The mixture was stirred at rt for 2 h and then MeOH (5 mL) was added dropwise. The mixture was concentrated to dryness to afford 0508-4 (3.3 g, crude) as a yellow solid.

The Synthesis of methyl methyl((4-nitrophenylsulfonyl)methyl)phosphinate (0508-5)

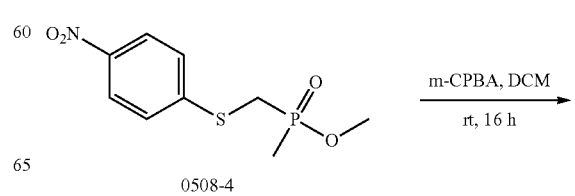

577

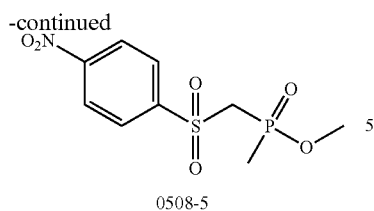

0508-5

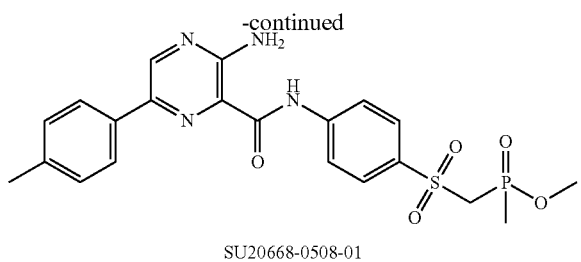

SU20668-0508-01

To a stirred solution of compound 0508-4 (3.3 g, crude) in DCM (35 mL) was added 3-chlorobenzenecarboperoxoic acid (2.6 g, 15.0 mmol) at 0° C. The resulting reaction mixture was further stirred for 16 h at rt. Then water (150 mL) and Na$_2$SO$_3$ (4.5 g) were added. The aqueous phase was extracted with DCM (70 mL×3). The combined organic phases were dried over anhydrous sodium sulfate, filtered, concentrated and purified by silica-gel column to give the desired product 0508-5 (800 mg, total yield for 3 steps: 41.7%) as a yellow solid.

The Synthesis of methyl (4-aminophenylsulfonyl)methyl(methyl)phosphinate (0508-6)

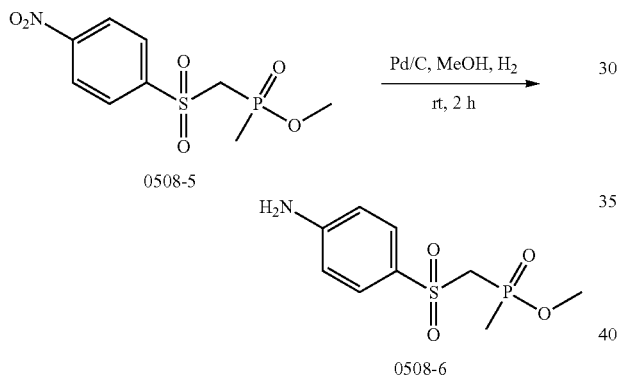

To a solution of 0508-5 (200 mg, 0.68 mmol) in MeOH (6 mL) was added Pd/C (10%, 30 mg). The mixture was stirred at rt for 2 h under H$_2$ atmosphere (1.0 atm). Then it was filtered and concentrated in vacuo to give 0508-6 (160 mg, yield: 89.5%) as an off-white solid.

The Synthesis of methyl (4-(3-amino-6-p-tolylpyrazine-2-carboxamido)phenylsulfonyl)methyl(methyl)phosphinate(SU20668-0508-01)

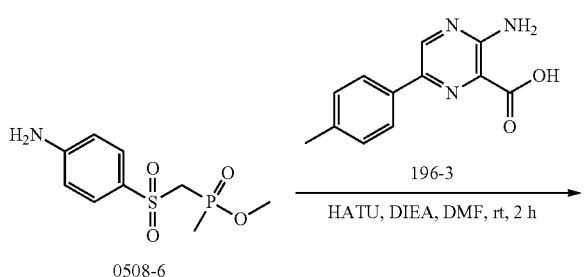

To a solution of compound 0508-6 (160 mg, 0.61 mmol) in DMF (4 mL) was added 196-3 (140 mg, 0.61 mmol), DIEA (155 mg, 1.20 mmol) and HATU (304 mg, 0.80 mmol). The resulting reaction mixture was stirred for 2 hours. Then it was purified by prep-HPLC to give the desired product SU20668-0508-01 (120 mg, yield: 41.5%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 98.27%, Rt=1.964 min; MS Calcd.: 474.1; MS Found: 475.2 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 100%, Rt=9.213 min. $^1$H NMR (400 MHz, DMSO-d$_6$) δ10.70 (s, 1H), 8.91 (s, 1H), 8.10 (d, J=8.8 Hz, 4H), 7.94 (d, J=8.8 Hz, 2H), 7.64 (s, 2H), 7.29 (d, J=8.0 Hz, 2H), 4.38 (d, J=14.0 Hz, 2H), 3.51 (d, J=11.2 Hz, 3H), 2.35 (s, 3H), 1.58 (d, J=15.6 Hz, 3H).

Scheme 67: Route for SU20668-0505-01

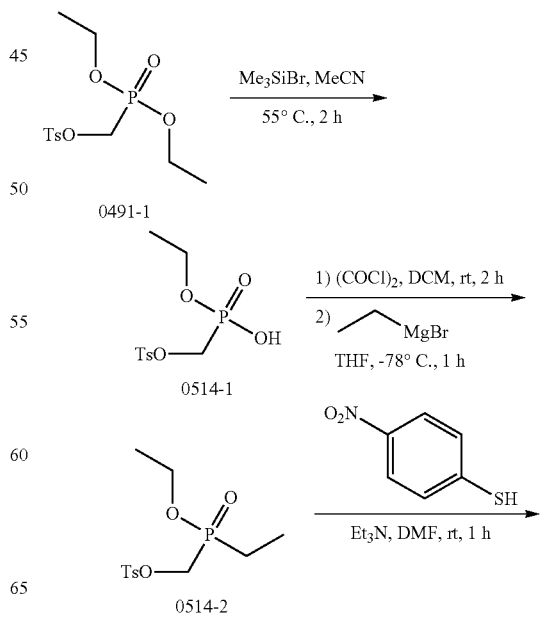

579

-continued

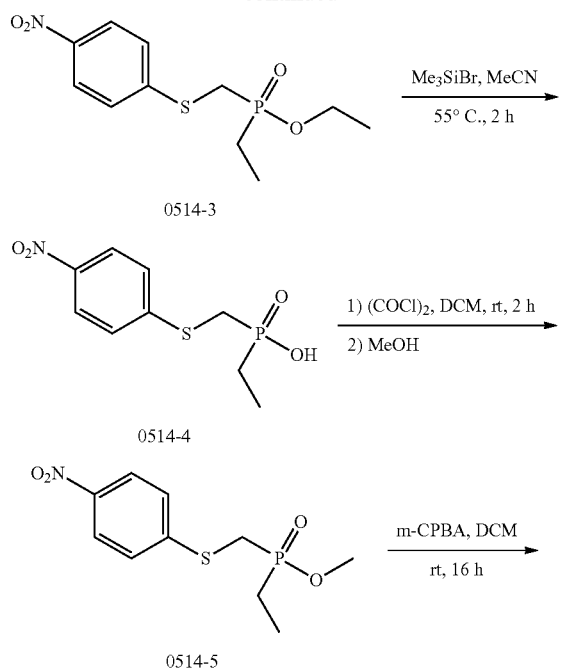

580

The Synthesis of (ethoxy(hydroxy)phosphoryl)methyl 4-methylbenzenesulfonate (0514-1)

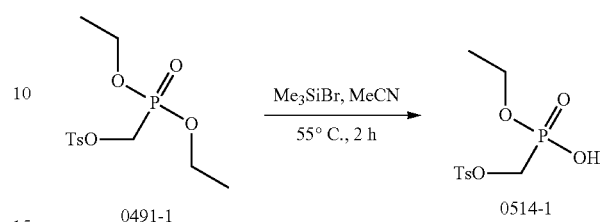

To a solution of 0491-1 (15 g, 46.6 mmol) in MeCN (150 mL) was added Me₃SiBr (7.13 g, 46.6 mmol) dropwise at rt. Then it was stirred at 55° C. for 2 hours. The reaction mixture was concentrated to dryness to afford 0514-1 (20 g, crude) as a colorless oil.

The Synthesis of (ethoxy(ethyl)phosphoryl)methyl 4-methylbenzenesulfonate (0514-2)

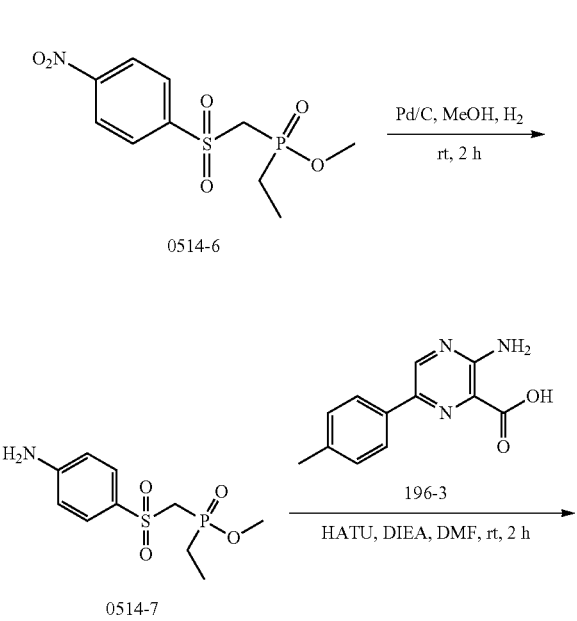

To a solution of 0514-1 (5.0 g, crude) in DCM (50 mL) was added oxalyl dichloride (2.5 mL) dropwise at 0° C. DMF (0.2 mL) was added. The mixture was stirred at rt for 2 h and then concentrated to dryness. The residue was dissolved in THF (50 mL). Then ethylmagnesium bromide (17 mL, 1M, 17 mmol) was added at −78° C. The mixture was stirred at −78° C. for 1 hour. Water (100 mL) was added to quench the reaction. The mixture was extracted with EA (30 mL×3). The combined organic phases were washed with brine (30 mL), dried over anhydrous sodium sulfate, filtered, concentrated and purified by prep-HPLC to give the desired product 0514-2 (850 mg, yield: 16.3%) as a yellow solid.

The Synthesis of ethyl ethyl((4-nitrophenylthio)methyl)phosphinate (0514-3)

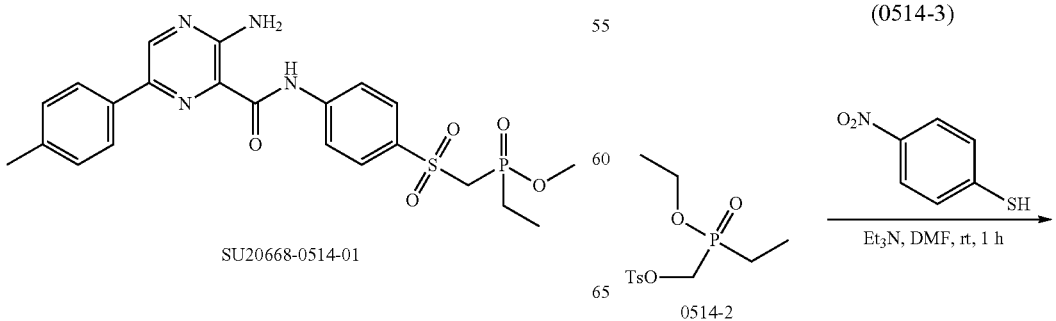

-continued

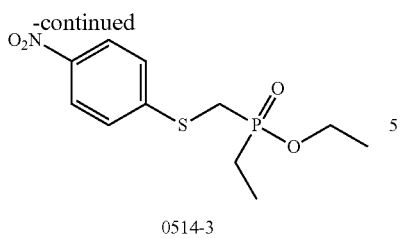

0514-3

To a stirred solution of 0514-2 (850 mg, 2.78 mmol) in DMF (10 mL) was added 4-nitrobenzenethiol (418 mg, 2.70 mmol) and TEA (1.63 g, 5.00 mmol). The resulting reaction mixture was stirred for 1 h at rt. Then water (60 mL) was added. The aqueous phase was extracted with EA (40 mL×3). The combined organic phases were washed with brine (30 mL), dried over anhydrous sodium sulfate, filtered, and concentrated in vacuo to give the desired product 0514-3 (450 mg, yield: 56.1%) as a yellow solid.

The Synthesis of ethyl((4-nitrophenylthio)methyl)phosphinic acid (0514-4)

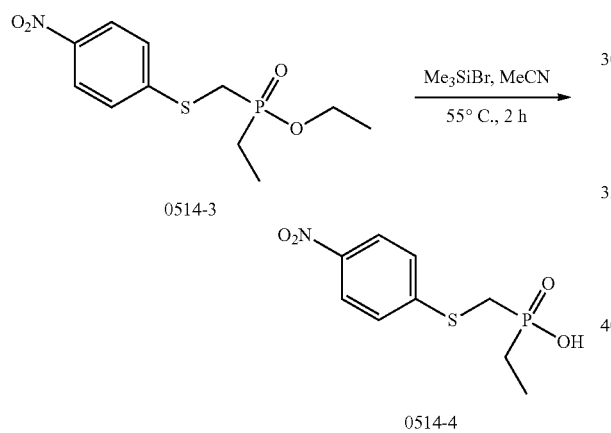

To a solution of 0514-3 (400 mg, 1.38 mmol) in MeCN (5 mL) was added Me₃SiBr (230 mg, 1.5 mmol) dropwise at rt. Then it was stirred at 55° C. for 2 hours. The reaction mixture was concentrated to dryness to afford 0514-4 (750 mg, crude) as a yellow solid.

The Synthesis of methyl ethyl((4-nitrophenylthio)methyl)phosphinate (0514-5)

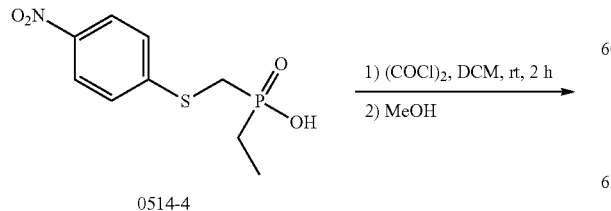

-continued

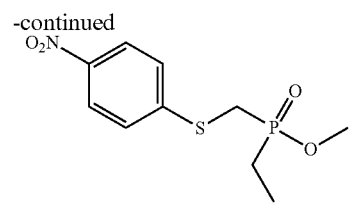

0514-5

To a solution of 0514-4 (750 mg, crude) in DCM (8 mL) was added oxalyl dichloride (1.0 mL) dropwise at 0° C. DMF (0.1 mL) was added. The mixture was stirred at rt for 2 h and then MeOH (3 mL) was added dropwise. The mixture was concentrated to dryness to afford 0514-5 (1.0 g, crude) as a yellow solid.

The Synthesis of methyl ethyl((4-nitrophenylsulfonyl)methyl)phosphinate (0514-6)

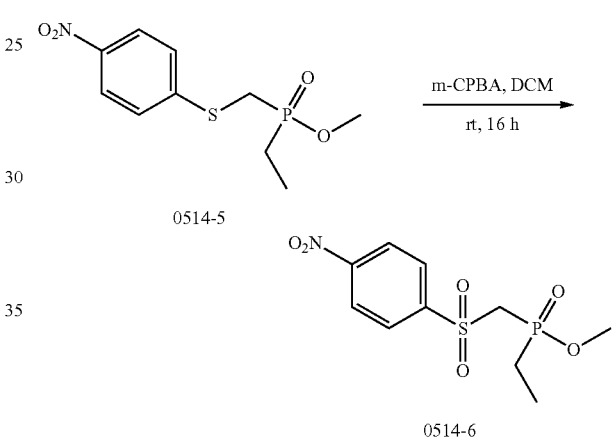

To a stirred solution of compound 0514-5 (1.0 g, crude) in DCM (15 mL) was added 3-chlorobenzenecarboperoxoic acid (863 mg, 5.00 mmol) at 0° C. The resulting reaction mixture was further stirred for 16 h at rt. Then water (50 mL) and Na₂SO₃ (1.5 g) were added. The aqueous phase was extracted with DCM (25 mL×3). The combined organic phases were dried over anhydrous sodium sulfate, filtered, concentrated and purified by silica-gel column to give the desired product 0514-6 (200 mg, total yield for 3 steps: 47.1%) as a yellow solid.

The Synthesis of methyl (4-aminophenylsulfonyl)methyl(ethyl)phosphinate (0514-7)

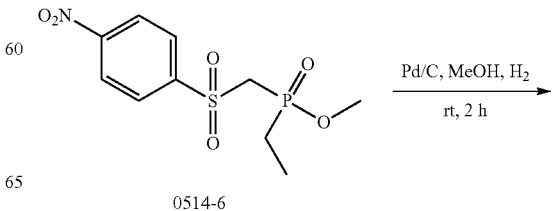

-continued

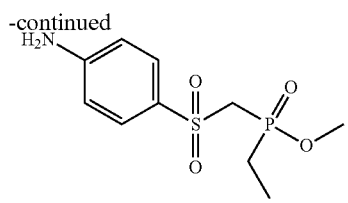

0514-7

To a solution of 0514-6 (200 mg, 0.65 mmol) in MeOH (6 mL) was added Pd/C (10%, 30 mg). The mixture was stirred at rt for 2 h under H$_2$ atmosphere (1.0 atm). Then it was filtered and concentrated in vacuo to give 0514-7 (150 mg, yield: 84.7%) as an off-white solid.

The Synthesis of methyl (4-(3-amino-6-p-tolylpyrazine-2-carboxamido)phenylsulfonyl)methyl(ethyl) phosphinate (SU20668-0514-01)

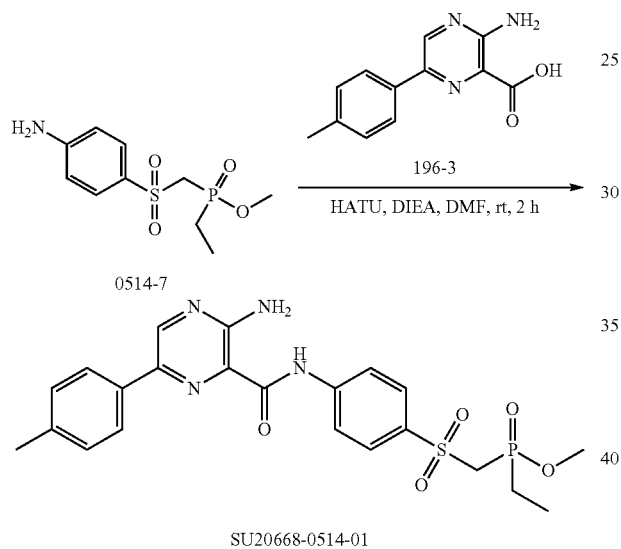

To a solution of compound 0514-7 (150 mg, 0.54 mmol) in DMF (4 mL) was added 196-3 (124 mg, 0.54 mmol), DIEA (129 mg, 1.00 mmol) and HATU (266 mg, 0.70 mmol). The resulting reaction mixture was stirred for 2 hours. Then it was purified by prep-HPLC to give the desired product SU20668-0514-01 (110 mg, yield: 41.8%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=1.987 min; MS Calcd.: 488.1; MS Found: 489.2 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 100%, Rt=9.433 min. $^1$H NMR (400 MHz, DMSO-d$_6$) δ 10.70 (s, 1H), 8.91 (s, 1H), 8.09-8.11 (m, 4H), 7.94 (d, J=8.8 Hz, 2H), 7.64 (s, 2H), 7.29 (d, J=8.0 Hz, 2H), 4.35 (d, J=13.2 Hz, 2H), 3.53 (d, J=11.2 Hz, 3H), 2.35 (s, 3H), 1.86-1.88 (m, 2H), 0.99-1.07 (m, 3H).

Scheme 68: Route for SU20668-0515-01

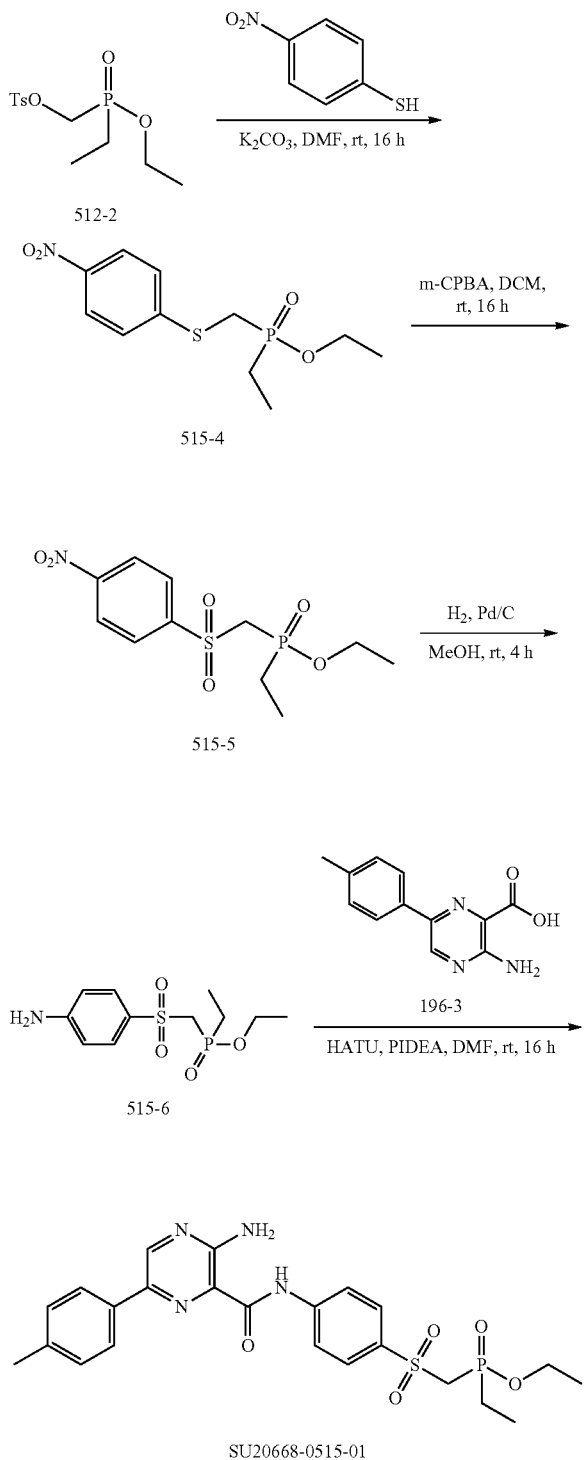

The Synthesis of ethyl ethyl((4-nitrophenylthio)methyl)phosphinate (515-4)

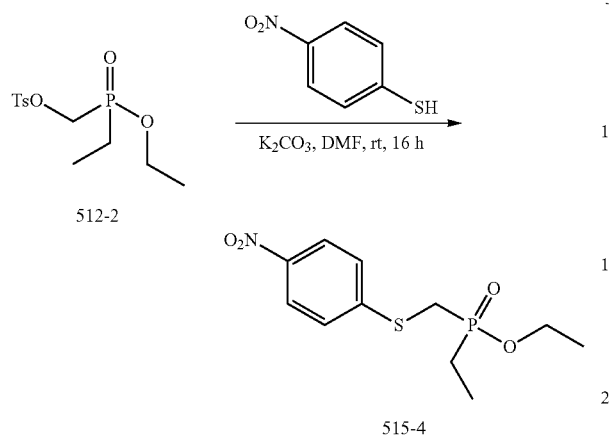

To a stirred solution of 512-2 in DMF (6 mL) was added 4-nitrobenzenethiol (121.58 mg, 783.51 umol) and Potassium carbonate (162.43 mg, 1.18 mmol), the mixture was stirred at rt for 16 h, poured into water, extracted with DCM, dried over anhydrous sodium sulfate, filtered, concentrated and purified with C.C to give 515-4 (176 mg, 608.39 umol) as brown oil.

The Synthesis of ethyl ethyl((4-nitrophenylsulfonyl)methyl)phosphinate (515-5)

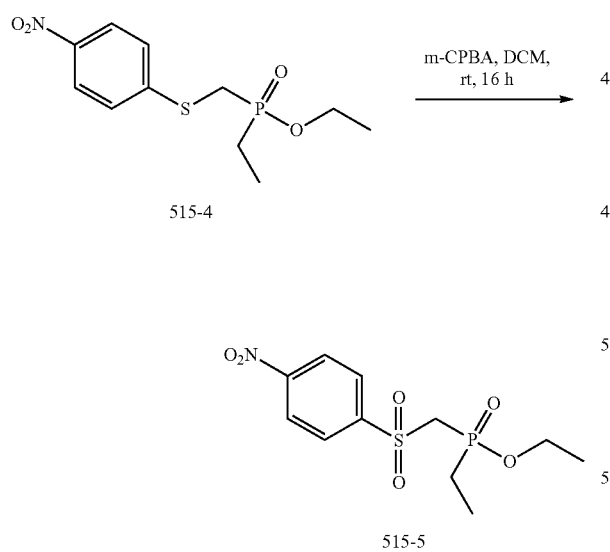

To a stirred solution of 515-4 (176 mg, 644.16 umol) in DCM (10 mL) was added 3-Chloroperoxybenzoic acid (166.75 mg, 966.25 umol), the mixture was stirred at rt for 16 h, poured into water, extracted with DCM, washed with Sodium carbonate solution, water, the combined organic phases were dried over anhydrous sodium sulfate, filtered, concentrated in vacuo and purified with pre-HPLC to give 515-5 (196 mg, 610.05 umol, 94.70% yield) as a white solid.

The Synthesis of ethyl (4-aminophenylsulfonyl)methyl(ethyl)phosphinate (515-6)

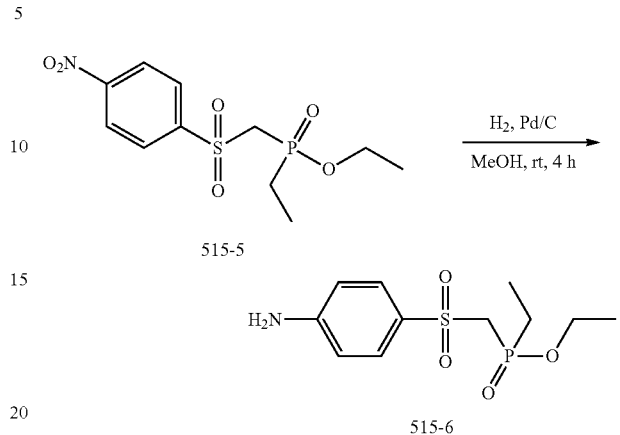

To a solution of 515-5 (120 mg, 373.49 umol) in MeOH (30 mL) was added Pd/C (20 mg), the mixture was stirred under hydrogen atmosphere (1 atm) at room temperature for 4 h, filtrated, concentrated to give 515-6 (104 mg, 95.60% yield) as brown oil.

The Synthesis of ethyl (4-(3-amino-6-p-tolylpyrazine-2-carboxamido)phenylsulfonyl)methyl(ethyl) phosphinate (SU20668-0515-01)

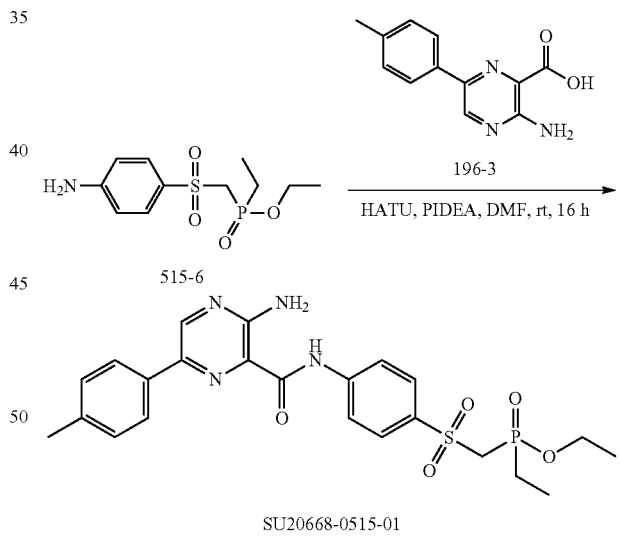

To a stirred solution of 515-6 (180 mg, 617.91 umol) in DMF (5 mL) was added 196-3 (141.65 mg, 617.91 umol), DIPEA (239.58 mg, 1.85 mmol) and HATU (352.42 mg, 926.87 umol). The resulting reaction mixture was stirred at rt for 16 h. Then it was purified by prep-HPLC to give SU20668-0515-01 (178 mg, 57.32% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM NH₄HCO₃] and 5% [CH₃CN] in 0.1 min and under this condition for 0.7 min). Purity: 100%, R$_t$=2.040 min; MS Calcd.: 502.14; MS Found: 503.1 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM AcONH₄) water/CH₃CN=900/100 (v/v)] and 10% [total 10 mM AcONH₄) water/CH₃CN=100/900 (v/v)] to 15% [total 10 mM AcONH₄) water/CH₃CN=900/100 (v/v)] and 85% [total 10 mM AcONH₄) water/CH₃CN=100/900 (v/v)] in 5 min, then under this condition for 10 min, finally changed to 90% [(total 10 mM AcONH₄) water/CH₃CN=900/100 (v/v)] and 10% [total 10 mM AcONH₄) water/CH₃CN=100/900 (v/v)] in 0.1 min and under this condition for 5 min). Purity: 99.69%, Rt=9.699 min. $^1$H NMR (400 MHz, DMSO-d$_6$) δ 10.70 (s, 1H), 8.91 (s, 1H), 8.09-8.11 (m, 4H), 7.93-7.95 (m, 2H), 7.64 (s, 2H), 7.29 (d, J=7.6 Hz, 2H), 4.33 (d, J=12.8 Hz, 2H), 3.95-4.01 (m, 1H), 3.82-3.88 (m, 1H), 2.35 (s, 3H), 1.82-1.89 (m, 2H), 1.14 (t, J=7.2 Hz, 3H), 0.99-1.08 (m, 3H).

The Synthesis of dimethyl 1-(4-aminophenylsulfonyl)ethylphosphonate (516-2)

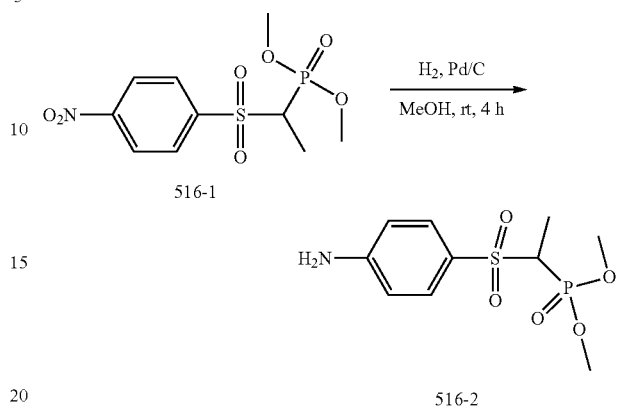

To a solution of 516-1 (100 mg, 309.35 umol) in MeOH (30 mL) was added Pd/C (30 mg), the mixture was stirred under hydrogen atmosphere (1 atm) at room temperature for 4 h, filtrated, concentrated to give 516-2 (84 mg, 92.61% yield) as brown oil.

The Synthesis of dimethyl 1-(4-(3-amino-6-p-tolylpyrazine-2-carboxamido)phenylsulfonyl)ethylphosphonate (SU20668-0516-01)

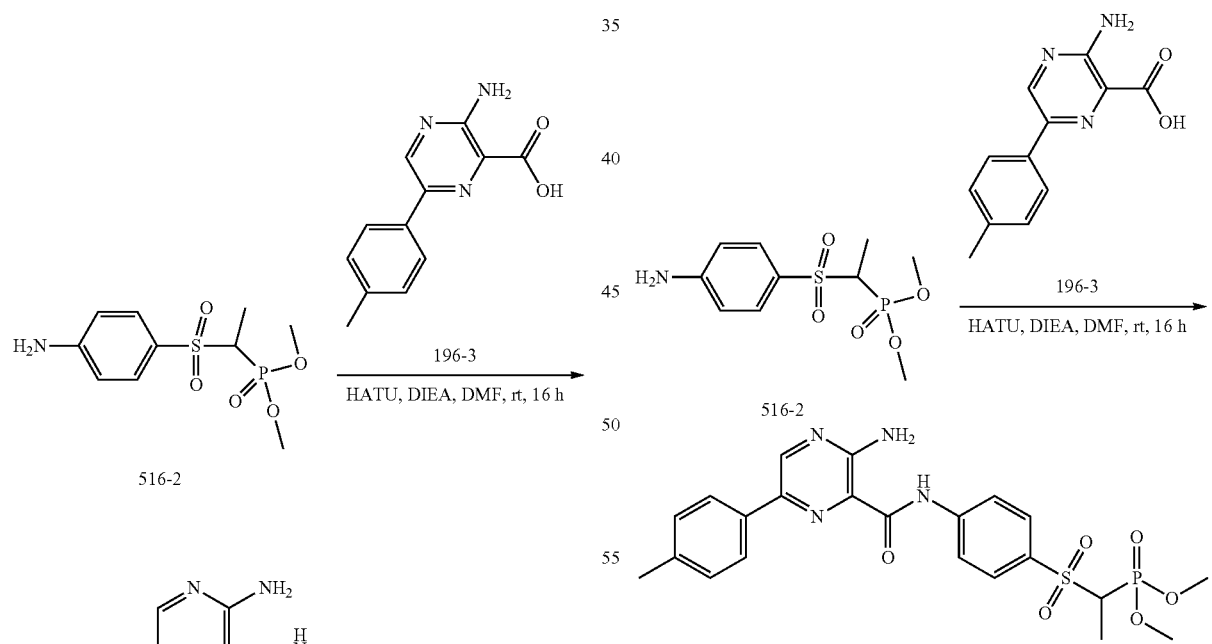

Scheme 69: Route for SU20668-0516-01

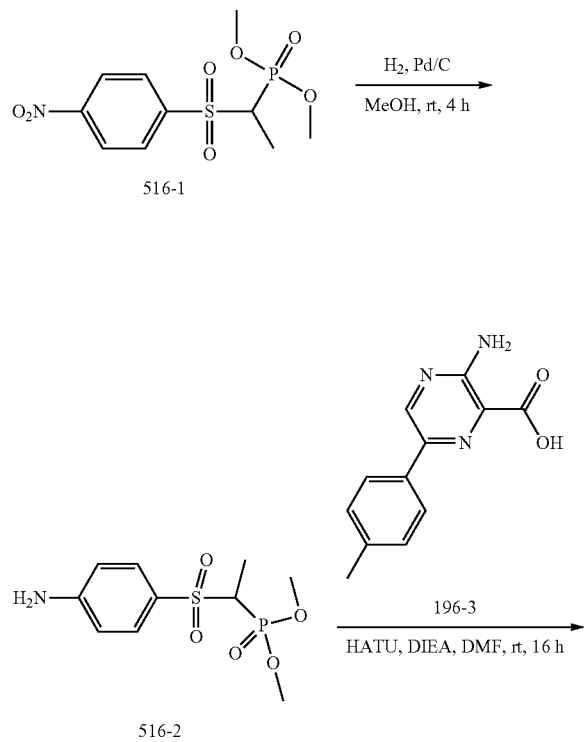

To a stirred solution of 516-2 (84 mg, 286.42 umol) in DMF (4 mL) was added 196-3 (65.66 mg, 286.42 umol), DIPEA (111.05 mg, 859.26 umol) and HATU (163.36 mg, 429.63 umol). The resulting reaction mixture was stirred at rt for 16 h. Then it was purified by prep-HPLC to give SU20668-0516-01 (63 mg, 43.60% yield) as a yellow solid.

LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, R$_t$=1.898 min; MS Calcd.: 490.11; MS Found: 491.0 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM AcONH$_4$) water/CH$_3$CN=900/100 (v/v)] and 10% [total 10 mM AcONH$_4$) water/CH$_3$CN=100/900 (v/v) to 15% [total 10 mM AcONH$_4$) water/CH$_3$CN=900/100 (v/v)] and 85% [total 10 mM AcONH$_4$) water/CH$_3$CN=100/900 (v/v)] in 5 min, then under this condition for 10 min, finally changed to 90% [(total 10 mM AcONH$_4$) water/CH$_3$CN=900/100 (v/v)] and 10% [total 10 mM AcONH$_4$) water/CH$_3$CN=100/900 (v/v)] in 0.1 min and under this condition for 5 min). Purity: 92.67%, Rt=8.939 min. $^1$H NMR (400 MHz, DMSO-d$_6$) δ 10.74 (s, 1H), 8.93 (s, 1H), 8.12-8.14 (m, 4H), 7.91-7.93 (m, 2H), 7.66 (s, 2H), 7.31 (d, J=7.6 Hz, 2H), 4.35-4.46 (m, 1H), 3.67 (t, J=10.4 Hz, 6H), 2.37 (s, 3H) 1.35-1.41 (m, 3H).

Scheme 70: Route for SU20667-0517-01 & SU20667-0518-01

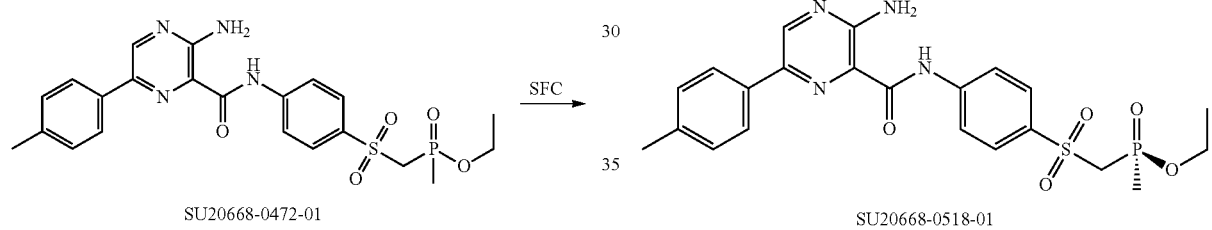

The Synthesis of (R)-ethyl (4-(3-amino-6-p-tolylpyrazine-2-carboxamido)phenylsulfonyl)methyl (methyl)phosphinate (SU20668-0517-01) and (S)-ethyl (4-(3-amino-6-p-tolylpyrazine-2-carboxamido) phenylsulfonyl)methyl(methyl)phosphinate (SU20668-0518-01)

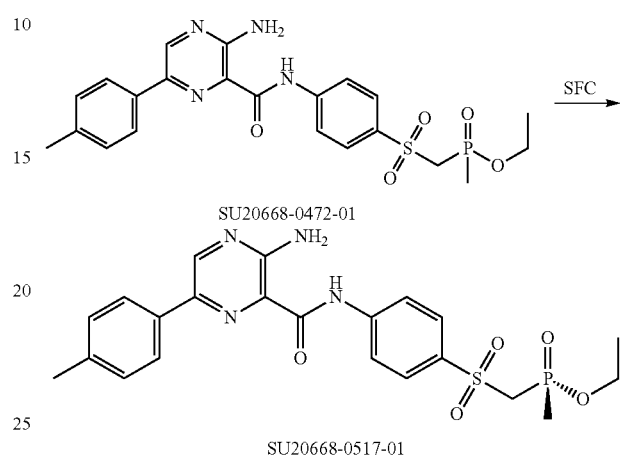

Chiral-HPLC on target SU20668-0472-01 to give SU20668-0517-01 (510 mg) as a yellow solid and SU20668-0518-01 (510 mg) as a yellow solid

SU20668-0517-01

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+ 10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 99%, Rt=2.002 min; MS Calcd.: 488.1; MS Found: 489.3 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min, Purity: 99%. 1H NMR (400 MHz, DMSO-d$_6$) δ 10.70 (s, 1H), 8.91 (s, 1H), 8.09-8.12 (m, 4H), 7.94 (d, J=8.8 Hz, 2H), 7.64 (s, 2H), 7.29 (d, J=8.0 Hz, 2H), 4.36 (d, J=13.6 Hz, 2H), 3.82-3.99 (m, 2H), 2.35 (s, 3H), 1.58 (d, J=15.6 Hz, 3H), 1.14 (t, J=7.2 Hz, 3H).

SU20668-0518-01

Agilent LCMS 1200-6120, Column: Waters X-Bridge C18 (50 mm*4.6 mm*3.5 μm); Column Temperature: 40°

C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 98%, Rt=1.992 min; MS Calcd.: 488.1; MS Found: 489.3 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min, Purity: 100%. 1H NMR (400 MHz, DMSO-d$_6$) δ 10.70 (s, 1H), 8.91 (s, 1H), 8.09-8.12 (m, 4H), 7.94 (d, J=8.8 Hz, 2H), 7.64 (s, 2H), 7.29 (d, J=8.0 Hz, 2H), 4.36 (d, J=14.0 Hz, 2H), 3.82-3.99 (m, 2H), 2.35 (s, 3H), 1.58 (d, J=15.6 Hz, 3H), 1.14 (t, J=7.2 Hz, 3H).

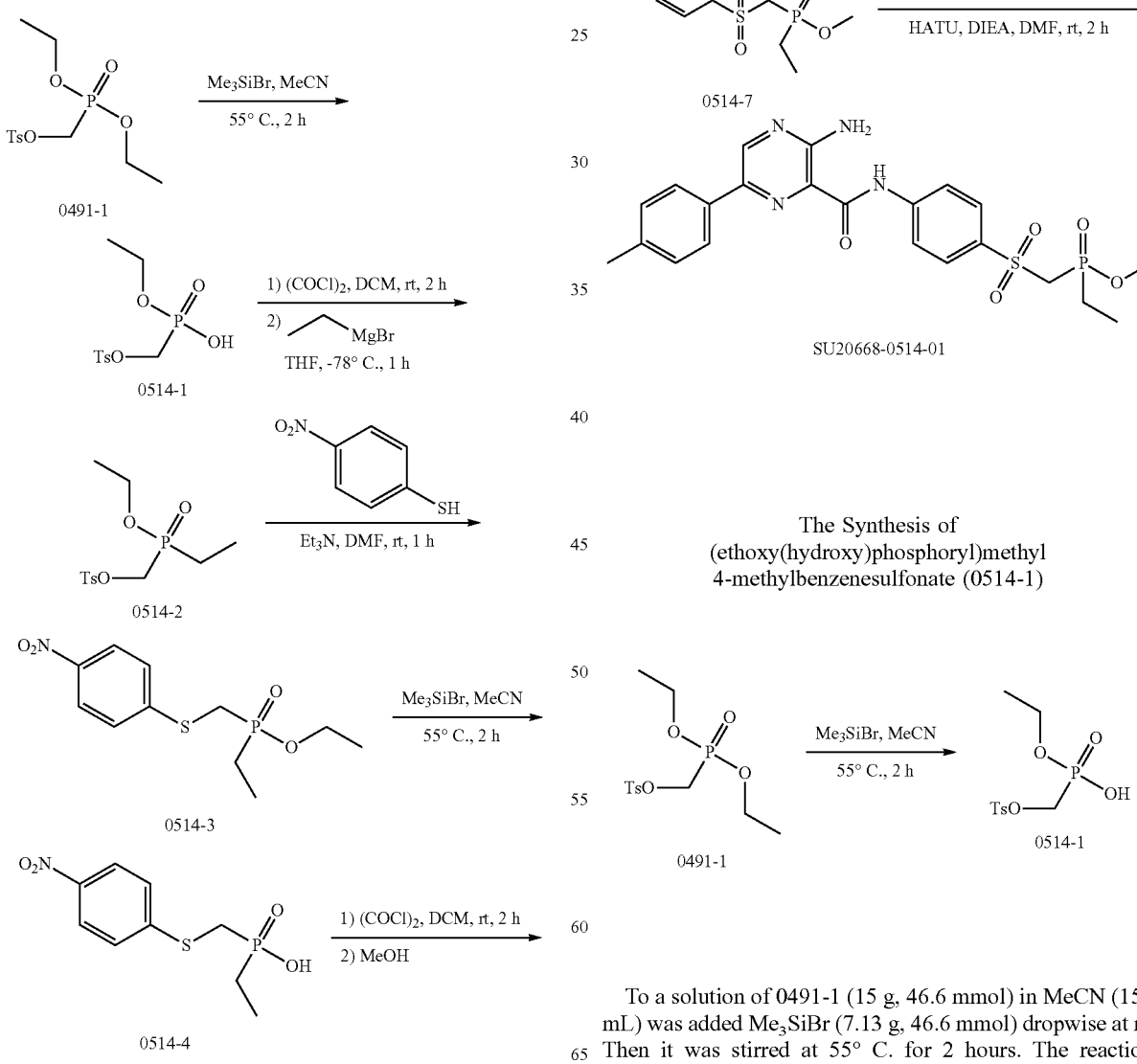

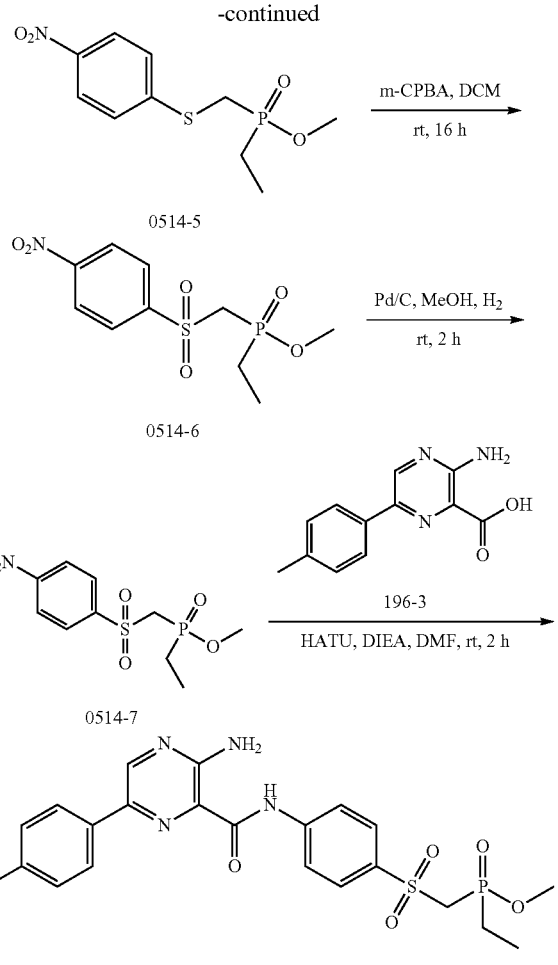

The Synthesis of (ethoxy(hydroxy)phosphoryl)methyl 4-methylbenzenesulfonate (0514-1)

To a solution of 0491-1 (15 g, 46.6 mmol) in MeCN (150 mL) was added Me$_3$SiBr (7.13 g, 46.6 mmol) dropwise at rt. Then it was stirred at 55° C. for 2 hours. The reaction mixture was concentrated to dryness to afford 0514-1(20 g, crude) as a colorless oil.

The Synthesis of (ethoxy(ethyl)phosphoryl)methyl 4-methylbenzenesulfonate (0514-2)

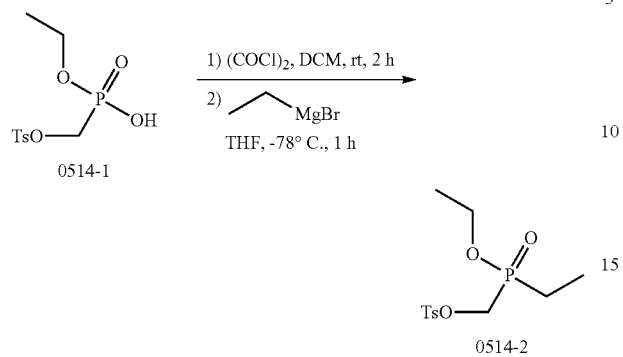

To a solution of 0514-1 (5.0 g, crude) in DCM (50 mL) was added oxalyl dichloride (2.5 mL) dropwise at 0° C. DMF (0.2 mL) was added. The mixture was stirred at rt for 2 h and then concentrated to dryness. The residue was dissolved in THF (50 mL). Then ethylmagnesium bromide (17 mL, 1M, 17 mmol) was added at −78° C. The mixture was stirred at −78° C. for 1 hour. Water (100 mL) was added to quench the reaction. The mixture was extracted with EA (30 mL×3). The combined organic phases were washed with brine (30 mL), dried over anhydrous sodium sulfate, filtered, concentrated and purified by prep-HPLC to give the desired product 0514-2 (850 mg, yield: 16.3%) as a yellow solid.

The Synthesis of ethyl ethyl((4-nitrophenylthio)methyl)phosphinate (0514-3)

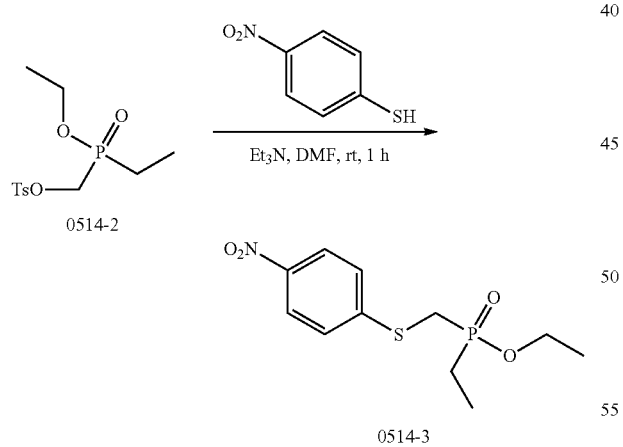

To a stirred solution of 0514-2 (850 mg, 2.78 mmol) in DMF (10 mL) was added 4-nitrobenzenethiol (418 mg, 2.70 mmol) and TEA (1.63 g, 5.00 mmol). The resulting reaction mixture was stirred for 1 h at rt. Then water (60 mL) was added. The aqueous phase was extracted with EA (40 mL×3). The combined organic phases were washed with brine (30 mL), dried over anhydrous sodium sulfate, filtered, and concentrated in vacuo to give the desired product 0514-3 (450 mg, yield: 56.1%) as a yellow solid.

The Synthesis of ethyl((4-nitrophenylthio)methyl)phosphinic acid (0514-4)

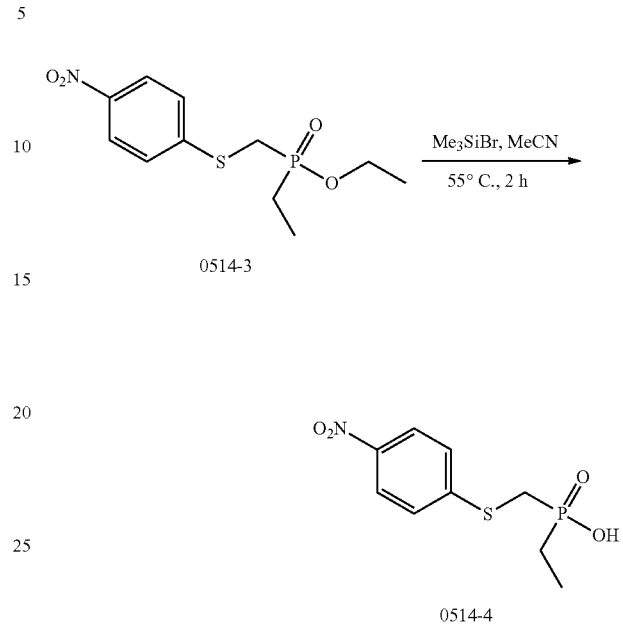

To a solution of 0514-3 (400 mg, 1.38 mmol) in MeCN (5 mL) was added Me₃SiBr (230 mg, 1.5 mmol) dropwise at rt. Then it was stirred at 55° C. for 2 hours. The reaction mixture was concentrated to dryness to afford 0514-4 (750 mg, crude) as a yellow solid.

The Synthesis of methyl ethyl((4-nitrophenylthio)methyl)phosphinate (0514-5)

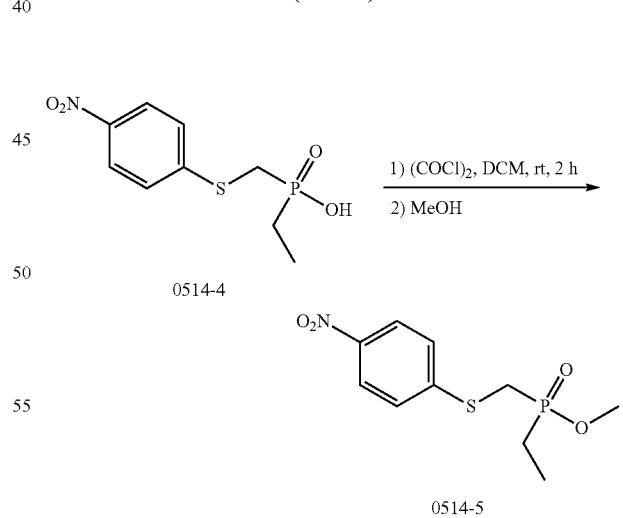

To a solution of 0514-4 (750 mg, crude) in DCM (8 mL) was added oxalyl dichloride (1.0 mL) dropwise at 0° C. DMF (0.1 mL) was added. The mixture was stirred at rt for 2 h and then MeOH (3 mL) was added dropwise. The mixture was concentrated to dryness to afford 0514-5 (1.0 g, crude) as a yellow solid.

The Synthesis of methyl ethyl((4-nitrophenylsulfonyl)methyl)phosphinate (0514-6)

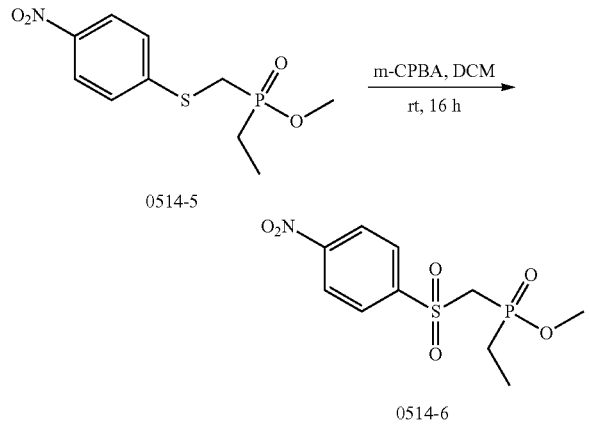

To a stirred solution of compound 0514-5 (1.0 g, crude) in DCM (15 mL) was added 3-chlorobenzenecarboperoxoic acid (863 mg, 5.00 mmol) at 0° C. The resulting reaction mixture was further stirred for 16 h at rt. Then water (50 mL) and Na$_2$SO$_3$ (1.5 g) were added. The aqueous phase was extracted with DCM (25 mL×3). The combined organic phases were dried over anhydrous sodium sulfate, filtered, concentrated and purified by silica-gel column to give the desired product 0514-6 (200 mg, total yield for 3 steps: 47.1%) as a yellow solid.

The Synthesis of methyl (4-aminophenylsulfonyl)methyl(ethyl)phosphinate (0514-7)

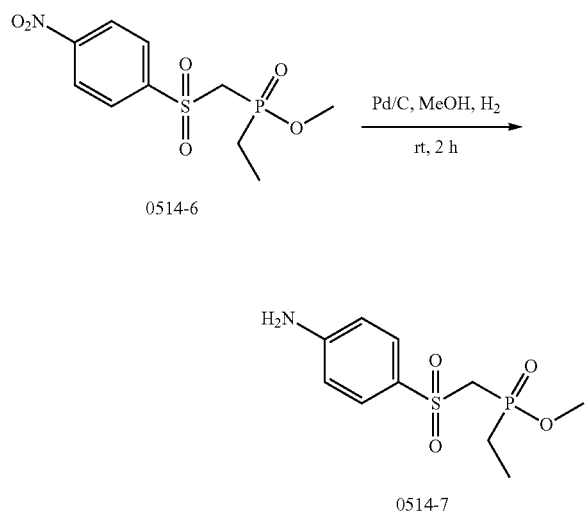

To a solution of 0514-6 (200 mg, 0.65 mmol) in MeOH (6 mL) was added Pd/C (10%, 30 mg). The mixture was stirred at rt for 2 h under H$_2$ atmosphere (1.0 atm). Then it was filtered and concentrated in vacuo to give 0514-7 (150 mg, yield: 84.7%) as an off-white solid.

The Synthesis of methyl (4-(3-amino-6-p-tolylpyrazine-2-carboxamido)phenylsulfonyl)methyl(ethyl) phosphinate (SU20668-0514-01)

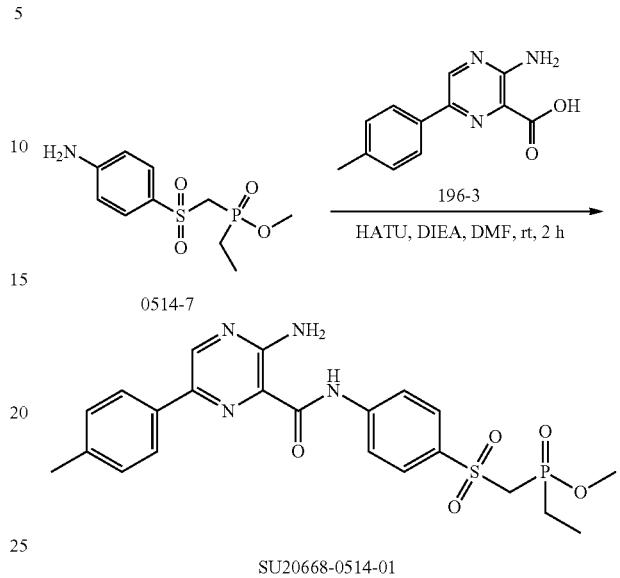

To a solution of compound 0514-7 (150 mg, 0.54 mmol) in DMF (4 mL) was added 196-3 (124 mg, 0.54 mmol), DIEA (129 mg, 1.00 mmol) and HATU (266 mg, 0.70 mmol). The resulting reaction mixture was stirred for 2 hours. Then it was purified by prep-HPLC to give the desired product SU20668-0514-01 (110 mg, yield: 41.8%) as a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=1.987 min; MS Calcd.: 488.1; MS Found: 489.2 [M+H]$^+$. HPLC (Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 100%, Rt=9.433 min. $^1$H NMR (400 MHz, DMSO-d$_6$) δ 10.70 (s, 1H), 8.91 (s, 1H), 8.09-8.11 (m, 4H), 7.94 (d, J=8.8 Hz, 2H), 7.64 (s, 2H), 7.29 (d, J=8.0 Hz, 2H), 4.35 (d, J=13.2 Hz, 2H), 3.53 (d, J=11.2 Hz, 3H), 2.35 (s, 3H), 1.86-1.88 (m, 2H), 0.99-1.07 (m, 3H).

Scheme 72: Route for SU20668-0515-01

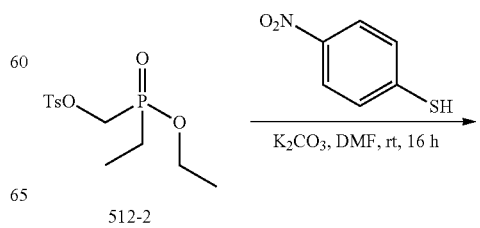

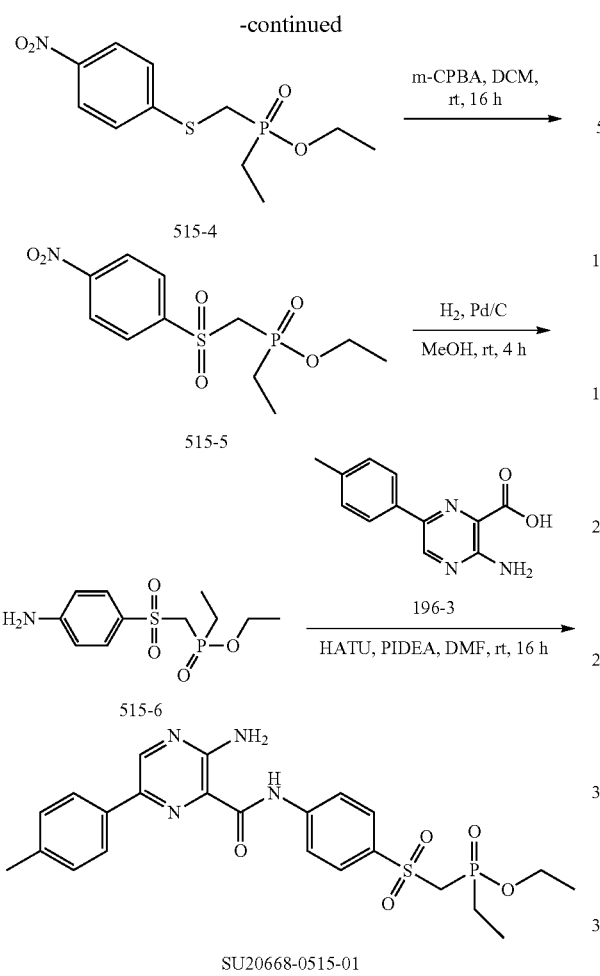

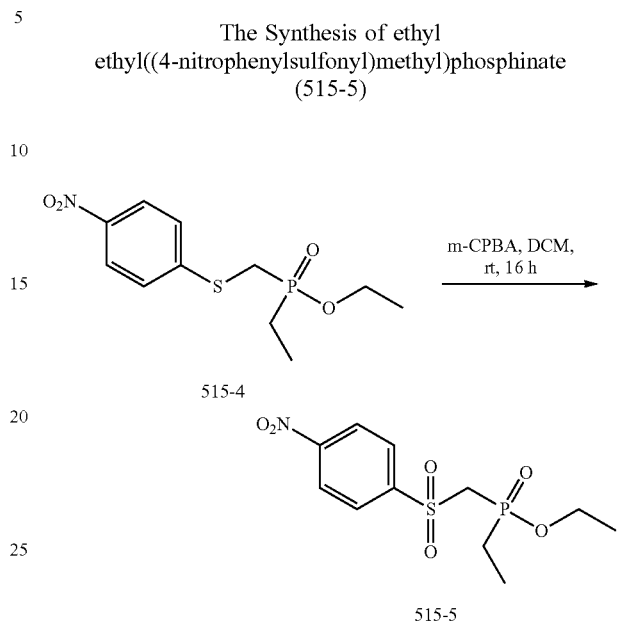

The Synthesis of ethyl ethyl((4-nitrophenylthio)methyl)phosphinate (515-4)

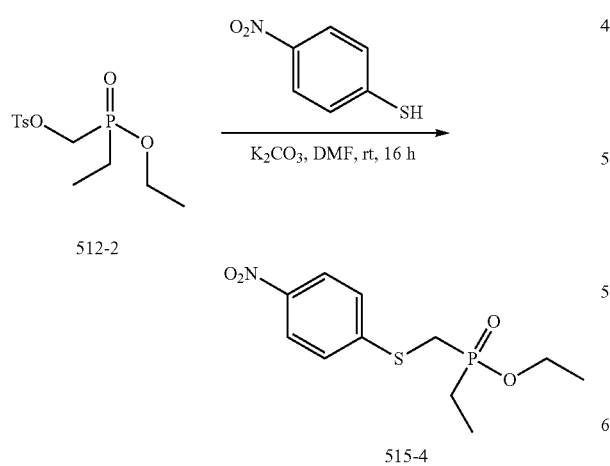

To a stirred solution of 512-2 in DMF (6 mL) was added 4-nitrobenzenethiol (121.58 mg, 783.51 umol) and Potassium carbonate (162.43 mg, 1.18 mmol), the mixture was stirred at rt for 16 h, poured into water, extracted with DCM, dried over anhydrous sodium sulfate, filtered, concentrated and purified with C.C to give 515-4 (176 mg, 608.39 umol) as brown oil.

The Synthesis of ethyl ethyl((4-nitrophenylsulfonyl)methyl)phosphinate (515-5)

To a stirred solution of 515-4 (176 mg, 644.16 umol) in DCM (10 mL) was added 3-Chloroperoxybenzoic acid (166.75 mg, 966.25 umol), the mixture was stirred at rt for 16 h, poured into water, extracted with DCM, washed with Sodium carbonate solution, water, the combined organic phases were dried over anhydrous sodium sulfate, filtered, concentrated in vacuo and purified with pre-HPLC to give 515-5 (196 mg, 610.05 umol, 94.70% yield) as a white solid.

The Synthesis of ethyl (4-aminophenylsulfonyl)methyl(ethyl)phosphinate (515-6)

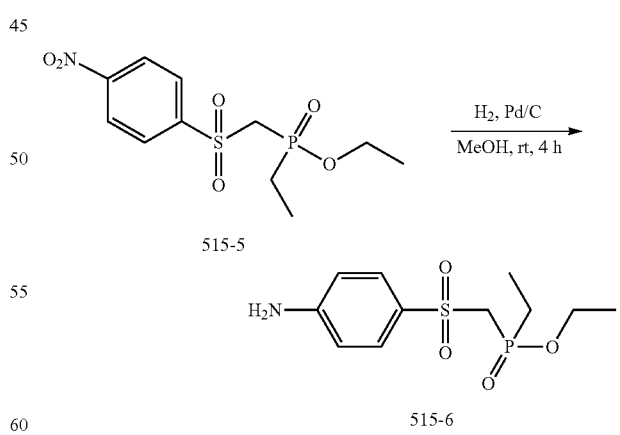

To a solution of 515-5 (120 mg, 373.49 umol) in MeOH (30 mL) was added Pd/C (20 mg), the mixture was stirred under hydrogen atmosphere (1 atm) at room temperature for 4 h, filtrated, concentrated to give 515-6 (104 mg, 95.60% yield) as brown oil.

The Synthesis of ethyl (4-(3-amino-6-p-tolylpyrazine-2-carboxamido)phenylsulfonyl)methyl(ethyl)phosphinate(SU20668-0515-01)

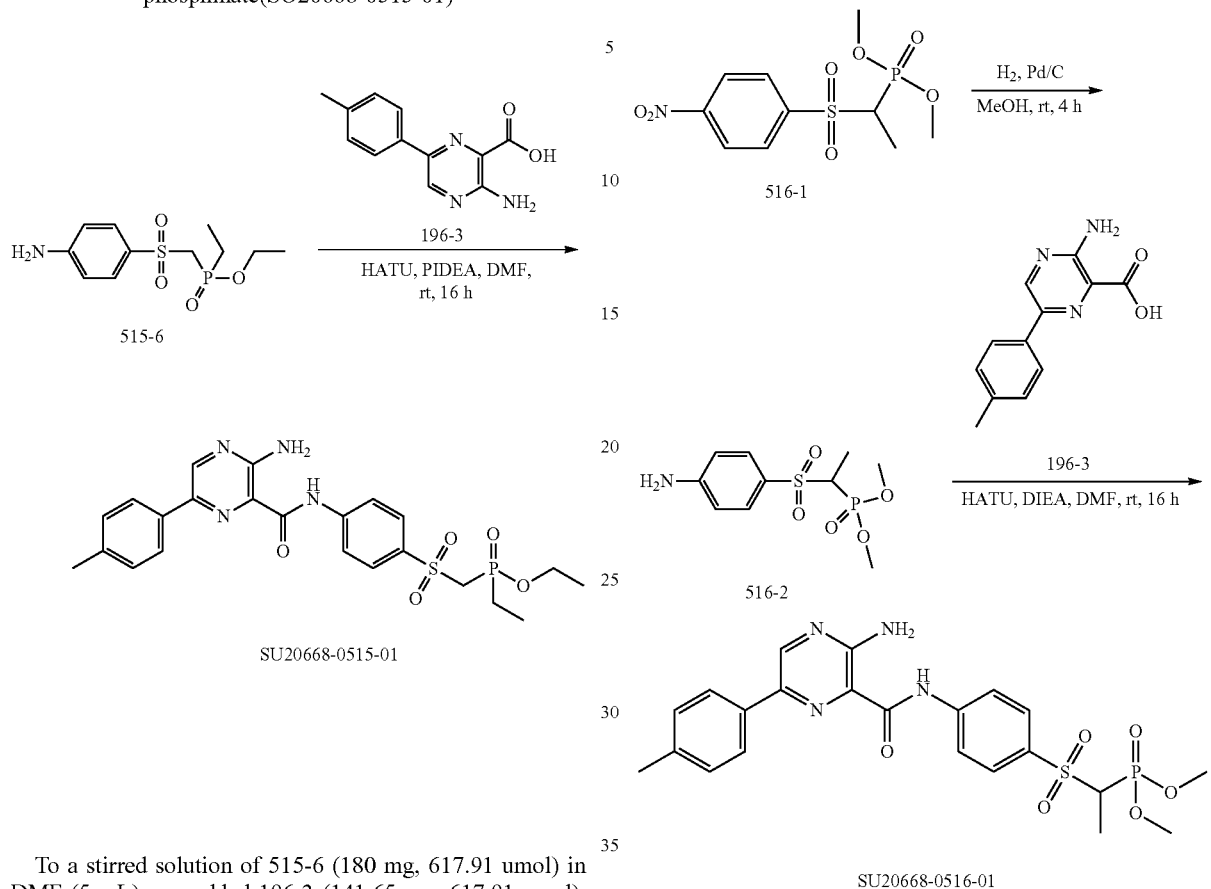

Scheme 73: Route for SU20668-0516-01

SU20668-0515-01

To a stirred solution of 515-6 (180 mg, 617.91 umol) in DMF (5 mL) was added 196-3 (141.65 mg, 617.91 umol), DIPEA (239.58 mg, 1.85 mmol) and HATU (352.42 mg, 926.87 umol). The resulting reaction mixture was stirred at rt for 16 h. Then it was purified by prep-HPLC to give SU20668-0515-01 (178 mg, 57.32% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, R$_t$=2.040 min; MS Calcd.: 502.14; MS Found: 503.1 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM AcONH$_4$) water/CH$_3$CN=900/100 (v/v)] and 10% [total 10 mM AcONH$_4$) water/CH$_3$CN=100/900 (v/v)] to 15% [total 10 mM AcONH$_4$) water/CH$_3$CN=900/100 (v/v)] and 85% [total 10 mM AcONH$_4$) water/CH$_3$CN=100/900 (v/v)] in 5 min, then under this condition for 10 min, finally changed to 90% [(total 10 mM AcONH$_4$) water/CH$_3$CN=900/100 (v/v)] and 10% [total 10 mM AcONH$_4$) water/CH$_3$CN=100/900 (v/v)] in 0.1 min and under this condition for 5 min). Purity: 99.69%, Rt=9.699 min. $^1$H NMR (400 MHz, DMSO-d$_6$) δ 10.70 (s, 1H), 8.91 (s, 1H), 8.09-8.11 (m, 4H), 7.93-7.95 (m, 2H), 7.64 (s, 2H), 7.29 (d, J=7.6 Hz, 2H), 4.33 (d, J=12.8 Hz, 2H), 3.95-4.01 (m, 1H), 3.82-3.88 (m, 1H), 2.35 (s, 3H), 1.82-1.89 (m, 2H), 1.14 (t, J=7.2 Hz, 3H), 0.99-1.08 (m, 3H).

The Synthesis of dimethyl 1-(4-aminophenylsulfonyl)ethylphosphonate (516-2)

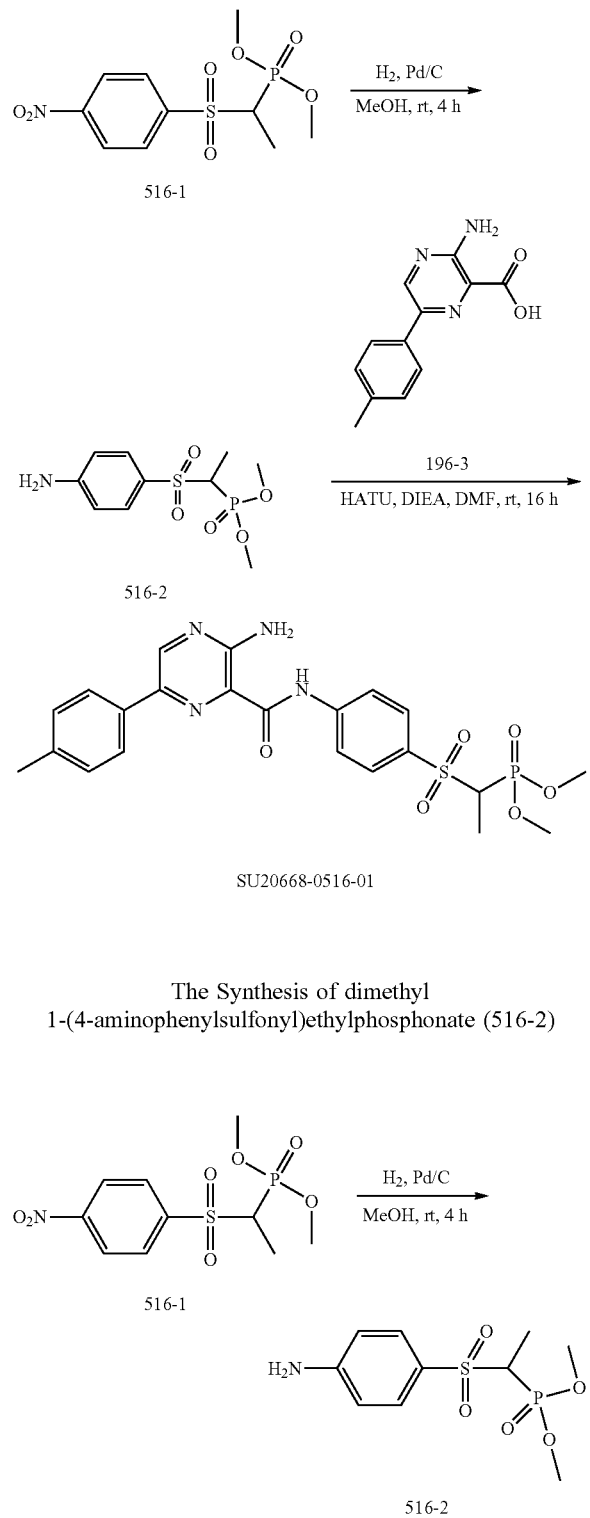

To a solution of 516-1 (100 mg, 309.35 umol) in MeOH (30 mL) was added Pd/C (30 mg), the mixture was stirred under hydrogen atmosphere (1 atm) at room temperature for 4 h, filtrated, concentrated to give 516-2 (84 mg, 92.61% yield) as brown oil.

601

The Synthesis of dimethyl 1-(4-(3-amino-6-p-tolylpyrazine-2-carboxamido)phenylsulfonyl)ethylphosphonate (SU20668-0516-01)

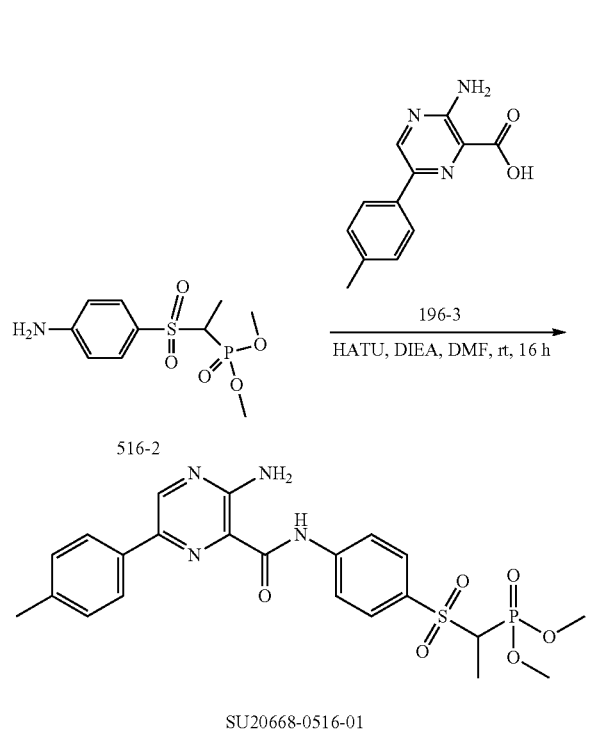

To a stirred solution of 516-2 (84 mg, 286.42 umol) in DMF (4 mL) was added 196-3 (65.66 mg, 286.42 umol), DIPEA (111.05 mg, 859.26 umol) and HATU (163.36 mg, 429.63 umol). The resulting reaction mixture was stirred at rt for 16 h. Then it was purified by prep-HPLC to give SU20668-0516-01 (63 mg, 43.60% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 100%, $R_t$=1.898 min; MS Calcd.: 490.11; MS Found: 491.0 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM $AcONH_4$) water/$CH_3CN$=900/100 (v/v)] and 10% [total 10 mM $AcONH_4$) water/$CH_3CN$=100/900 (v/v)] to 15% [total 10 mM $AcONH_4$) water/$CH_3CN$=900/100 (v/v)] and 85% [total 10 mM $AcONH_4$) water/$CH_3CN$=100/900 (v/v)] in 5 min, then under this condition for 10 min, finally changed to 90% [(total 10 mM $AcONH_4$) water/$CH_3CN$=900/100 (v/v)] and 10% [total 10 mM $AcONH_4$) water/$CH_3CN$=100/900 (v/v)] in 0.1 min and under this condition for 5 min). Purity: 92.67%, Rt=8.939 min. $^1$H NMR (400 MHz, DMSO-$d_6$) δ 10.74 (s, 1H), 8.93 (s, 1H), 8.12-8.14 (m, 4H), 7.91-7.93 (m, 2H), 7.66 (s, 2H), 7.31 (d, J=7.6 Hz, 2H), 4.35-4.46 (m, 1H), 3.67 (t, J=10.4 Hz, 6H), 2.37 (s, 3H) 1.35-1.41 (m, 3H).

602

Scheme 74: Route for SU20668-0519-01

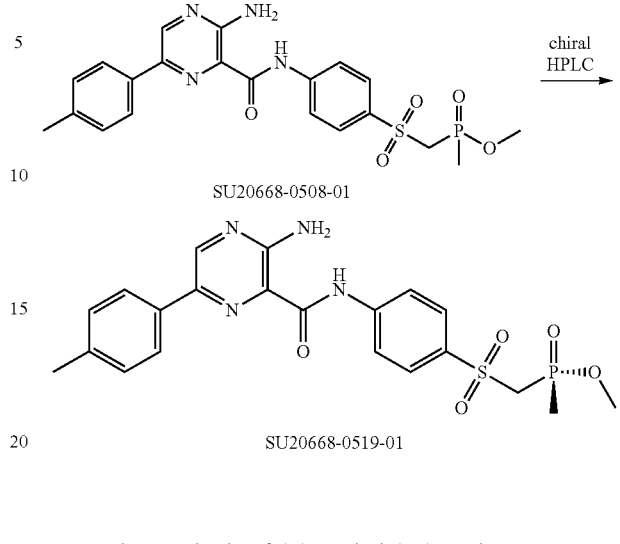

The Synthesis of (R)-methyl (4-(3-amino-6-p-tolylpyrazine-2-carboxamido)phenylsulfonyl)methyl (methyl)phosphinate (0519-1)

SU20668-0508-01 (100 mg) was purified by chiral-HPLC to afford SU20668-0519-01 (19 mg, yield: 19.0%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 97.00%, Rt=1.959 min; MS Calcd.: 474.1; MS Found: 475.2 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 100%, Rt=9.112 min. $^1$H NMR (400 MHz, DMSO-$d_6$) δ 10.70 (s, 1H), 8.91 (s, 1H), 8.10 (d, J=8.8 Hz, 4H), 7.94 (d, J=9.2 Hz, 2H), 7.64 (s, 2H), 7.29 (d, J=8.0 Hz, 2H), 4.38 (d, J=14.0 Hz, 2H), 3.51 (d, J=11.2 Hz, 3H), 2.35 (s, 3H), 1.58 (d, J=15.6 Hz, 3H).

Scheme 75: Route for SU20668-0520-01

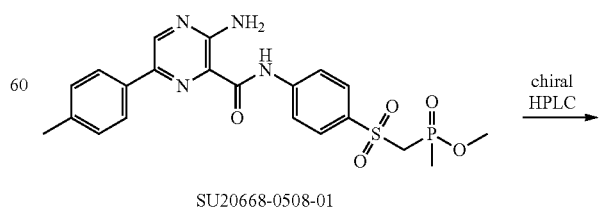

-continued

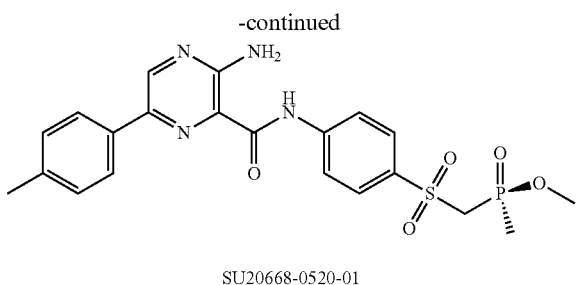

SU20668-0520-01

The Synthesis of (S)-methyl (4-(3-amino-6-p-tolylpyrazine-2-carboxamido)phenylsulfonyl)methyl (methyl)phosphinate (0520-1)

SU20668-0508-01 (100 mg) was purified by chiral-HPLC to afford SU20668-0519-01 (27 mg, yield: 27.0%) as a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 96.35%, Rt=1.954 min; MS Calcd.: 474.1; MS Found: 475.2 [M+H]$^+$. HPLC (Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 100%, Rt=9.111 min. $^1$H NMR (400 MHz, DMSO-d$_6$) δ 10.70 (s, 1H), 8.91 (s, 1H), 8.10 (d, J=8.8 Hz, 4H), 7.94 (d, J=8.8 Hz, 2H), 7.64 (s, 2H), 7.29 (d, J=8.0 Hz, 2H), 4.38 (d, J=14.0 Hz, 2H), 3.51 (d, J=11.2 Hz, 3H), 2.35 (s, 3H), 1.58 (d, J=15.6 Hz, 3H).

Scheme 76: Route for SU20668-0521-01

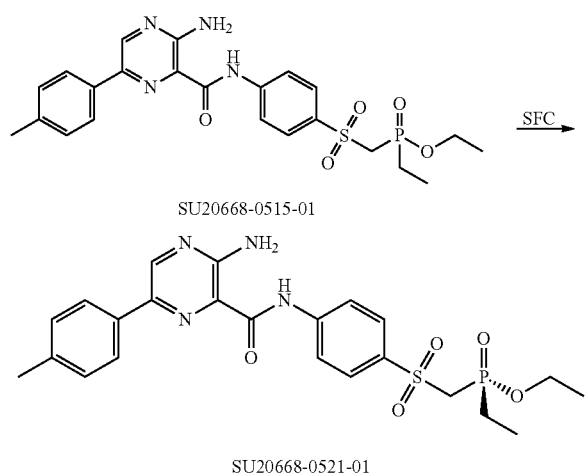

The Synthesis of (R)-ethyl (4-(3-amino-6-p-tolylpyrazine-2-carboxamido)phenylsulfonyl)methyl (ethyl)phosphinate (SU20668-0521-01)

Chiral-HPLC on target SU20668-0515-01 to give SU20668-0521-01 (36 mg) as a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, R$_t$=2.027 min; MS Calcd.: 502.14; MS Found: 502.9 [M+H]$^+$. HPLC (Agilent HPLC 1200, Column: L-column2 ODS (150 mm*4.6 mm*5.0 µm); Column Temperature: 40° C.; Flow Rate: 1.5 mL/min; Mobile Phase: from 90% [(total 10 mM AcONH$_4$) water/CH$_3$CN=900/100 (v/v)] and 10% [total 10 mM AcONH$_4$) water/CH$_3$CN=100/900 (v/v)] to 15% [total 10 mM AcONH$_4$) water/CH$_3$CN=900/100 (v/v)] and 85% [total 10 mM AcONH$_4$) water/CH$_3$CN=100/900 (v/v)] in 5 min, then under this condition for 10 min, finally changed to 90% [(total 10 mM AcONH$_4$) water/CH$_3$CN=900/100 (v/v)] and 10% [total 10 mM AcONH$_4$) water/CH$_3$CN=100/900 (v/v)] in 0.1 min and under this condition for 5 min). Purity: 100%, Rt=9.712 min. $^1$H NMR (400 MHz, DMSO-d$_6$) δ 10.70 (s, 1H), 8.91 (s, 1H), 8.09-8.11 (m, 4H), 7.93-7.95 (m, 2H), 7.64 (s, 2H), 7.29 (d, J=8 Hz, 2H), 4.33 (d, J=12.8 Hz, 2H), 3.95-4.01 (m, 1H), 3.83-3.88 (m, 1H), 2.35 (s, 3H), 1.81-1.90 (m, 2H), 1.14 (t, J=7.2 Hz, 3H), 0.99-1.08 (m, 3H).

Scheme 77: Route for SU20668-0522-01

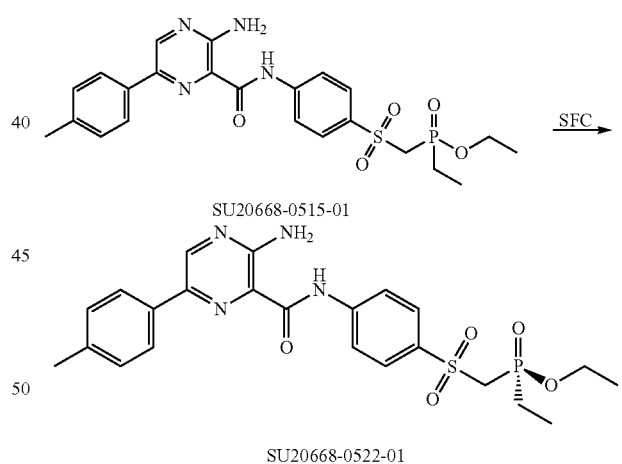

The Synthesis of (S)-ethyl (4-(3-amino-6-p-tolylpyrazine-2-carboxamido)phenylsulfonyl)methyl (ethyl)phosphinate (SU20668-0522-01)

Conducting chiral-HPLC on target SU20668-0515-01 to give SU20668-0522-01 (38 mg) as a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=2.028 min; MS Calcd.: 502.14; MS Found: 502.9 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM AcONH$_4$) water/CH$_3$CN=900/100 (v/v)] and 10% [total 10 mM AcONH$_4$) water/CH$_3$CN=100/900 (v/v)] to 15% [total 10 mM AcONH$_4$) water/CH$_3$CN=900/100 (v/v)] and 85% [total 10 mM AcONH$_4$) water/CH$_3$CN=100/900 (v/v)] in 5 min, then under this condition for 10 min, finally changed to 90% [(total 10 mM AcONH$_4$) water/CH$_3$CN=900/100 (v/v)] and 10% [total 10 mM AcONH$_4$) water/CH$_3$CN=100/900 (v/v)] in 0.1 min and under this condition for 5 min). Purity: 98.81%, Rt=9.714 min. $^1$H NMR (400 MHz, DMSO-d$_6$) δ 10.70 (s, 1H), 8.91 (s, 1H), 8.09-8.11 (m, 4H), 7.93-7.95 (m, 2H), 7.64 (s, 2H), 7.29 (d, J=8.0 Hz, 2H), 4.33 (d, J=12.8 Hz, 2H), 3.95-3.99 (m, 1H), 3.84-3.88 (m, 1H), 2.35 (s, 3H), 1.83-1.90 (m, 2H), 1.14 (t, J=6.8 Hz, 3H), 0.99-1.08 (m, 3H).

The Synthesis of methyl 4-(3-amino-6-p-tolylpyrazine-2-carboxamido)-2-fluorobenzoate (SU20668-0307-01)

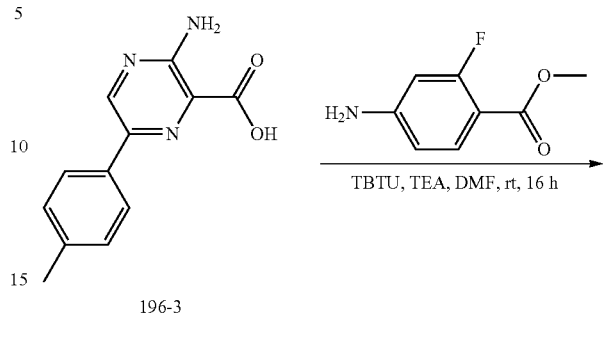

Scheme 78: Route for SU20668-0307-01

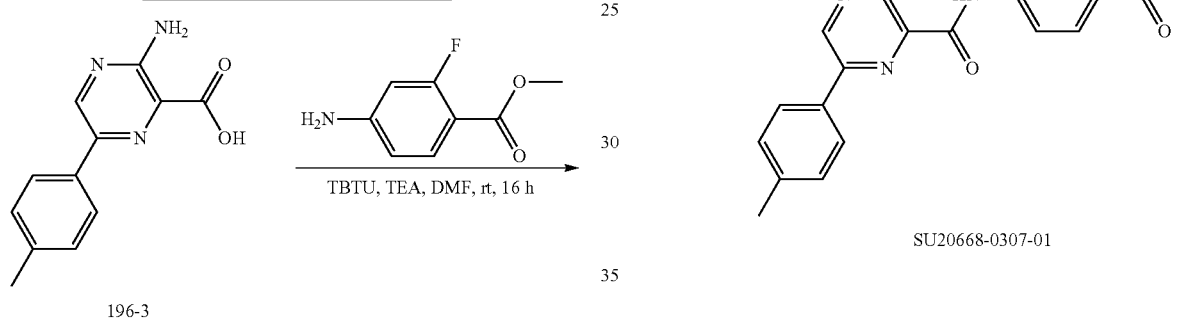

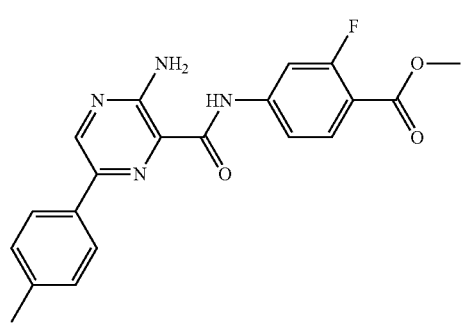

SU20668-0307-01

To a solution of compound 196-3 (200 mg, 0.87 mmol) in DMF (4 mL) was added methyl 4-amino-2-fluorobenzoate (152 mg, 0.90 mmol), DIEA (220 mg, 1.70 mmol) and TBTU (386 mg, 1.20 mmol). The resulting reaction mixture was stirred for 16 h at rt. Then it was purified by prep-HPLC to give the desired product SU20668-0307-01 (30 mg, yield: 9.1%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 97.95%, Rt=2.036 min; MS Calcd.: 380.1; MS Found: 381.0 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 96.76%, Rt=10.955 min. $^1$H NMR (400 MHz, DMSO-d$_6$) δ 10.74 (s, 1H), 8.93 (s, 1H), 8.12 (d, J=8.0 Hz, 2H), 7.79-7.99 (m, 2H), 7.82-7.84 (m, 1H), 7.65 (s. 2H), 7.31 (d, J=8.0 Hz, 2H), 3.85 (s, 3H), 2.37 (s, 3H).

Scheme 79: Route for SU20668-0340-01

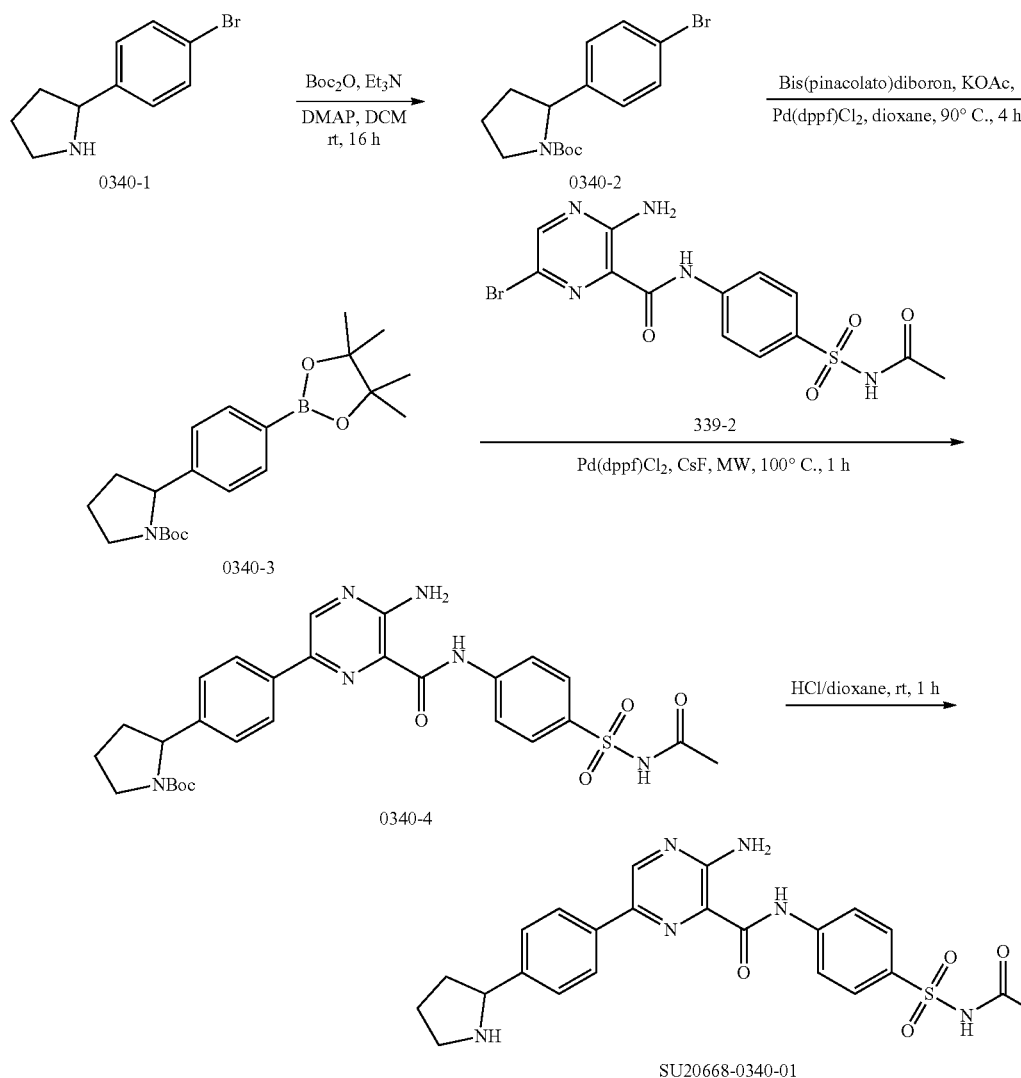

The Synthesis of tert-butyl 2-(4-bromophenyl)pyrrolidine-1-carboxylate (0340-2)

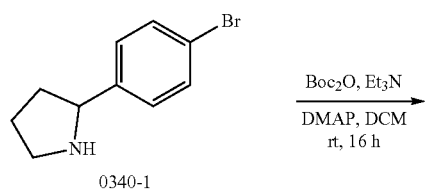

-continued

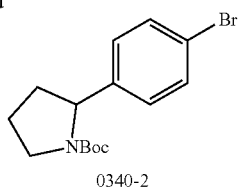

To a stirred solution of compound 0340-1 (300 mg, 1.33 mmol), Et$_3$N (270 mg, 2.66 mmol) and DMAP (16.3 mg, 0.133 mmol) in DCM (10 mL) was added dropwise Boc$_2$O (580 mg, 2.66 mmol). The resulting reaction mixture was stirred at rt overnight. Then added water, the aqueous phase was extracted with dichloromethane, the combined organic phases were dried over anhydrous sodium sulfate, filtered, and concentrated in vacuo to give the desired product 340-2 (400 mg, 92% yield) as yellow oil.

The Synthesis of tert-butyl 2-(4-(4,4,5,5-tetramethyl-1,3,2-dioxaborolan-2-yl)phenyl)pyrrolidine-1-carboxylate (0340-3)

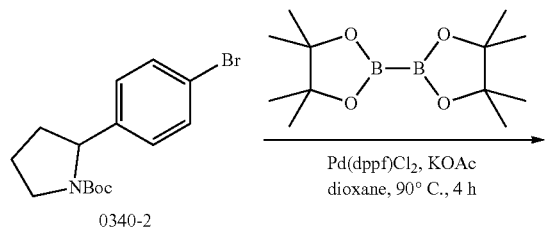

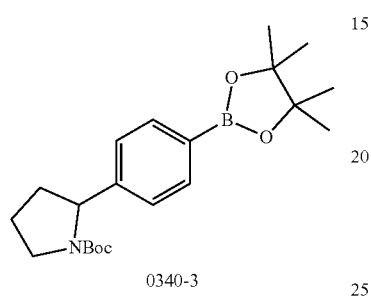

To a stirred solution of compound 0340-2 (400 mg, 1.23 mmol) in dioxane (10 mL), was added bis(pinacolato)diboron (470 mg, 1.85 mmol), KOAc (362 mg, 3.69 mmol) and Pd(dppf)Cl$_2$ (90 mg, 0.123 mmol). The resulting reaction mixture was heated to 90° C. and stirred for 4 h and concentrated in vacuo to remove the solvent, then added water, the aqueous phase was extracted with dichloromethane, the combined organic phases were dried over anhydrous sodium sulfate, filtered, and concentrated, the crude was purified by C.C. to give the desired product 0340-3 (310 mg, 77% yield) as a white solid.

The Synthesis of tert-butyl 2-(4-(6-(4-(N-acetylsulfamoyl)phenylcarbamoyl)-5-aminopyrazin-2-yl)phenyl)pyrrolidine-1-carboxylate (0340-4)

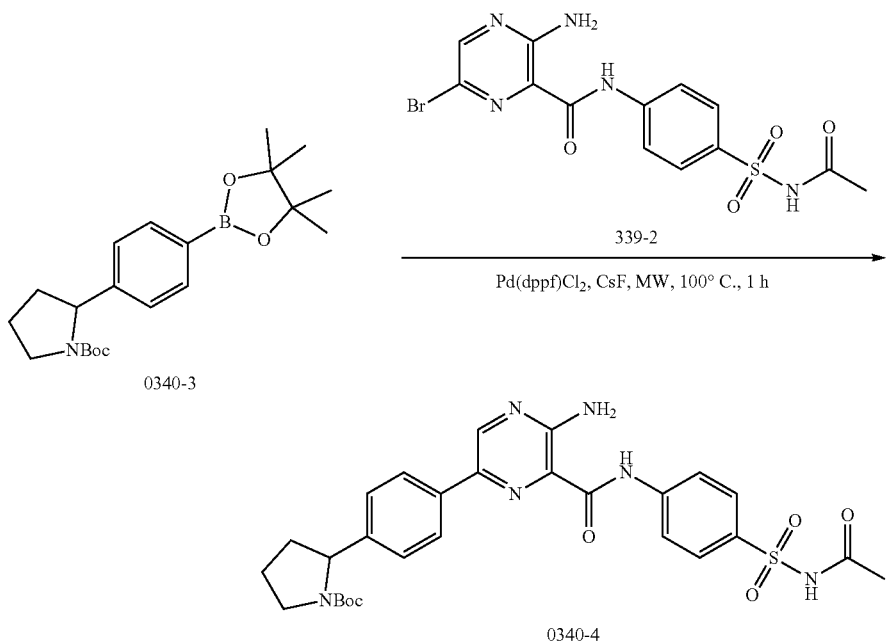

To a stirred solution of compound 0339-2 (300 mg, 0.73 mmol), 0340-3 (325 mg, 0.87 mmol) and CsF (332 mg, 2.19 mmol) in MeOH (4 mL), was added Pd(dppf)Cl$_2$ (10%, 53 mg). The resulting reaction mixture was irradiated with microwave radiation at 120° C. for 1 h under Ar atmosphere (1.0 atm). After the consumption of starting material (by LCMS), the mixture was filtered, and the filtrate was concentrated in vacuo, purified by prep-HPLC to give the desired product 340-4 (50 mg, 10% yield) as a yellow solid.

The Synthesis of N-(4-(N-acetylsulfamoyl)phenyl)-3-amino-6-(4-(pyrrolidin-2-yl)phenyl)pyrazine-2-carboxamide (SU20668-0340-01)

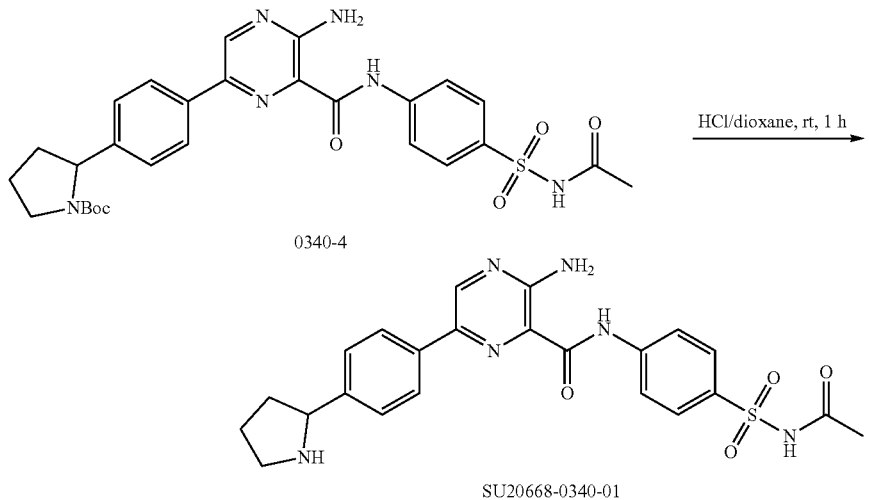

The mixture of 340-4 (50 mg, 0.086 mmol) in HCl/dioxane (4M, 5 mL) was stirred at rt for 1 h. Then the mixture was concentrated. The residue was purified by Prep-HPLC to give SU20668-0340-01 (5 mg, 12% yield) as a yellow solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 97.37%, Rt=1.324 min; MS Calcd.: 480.54; MS Found: 481.3 [M+H]$^+$. Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 95.45%, R$_t$=5.429 min. $^1$H NMR (400 MHz, DMSO-d$_6$) δ 10.53 (s, 1H), 8.97 (s, 1H), 8.28 (d, J=8.4 Hz, 2H), 8.24 (s, 1H), 7.84 (d, J=8.8 Hz, 2H), 7.31-7.76 (m, 4H), 7.57 (d, J=8.4 Hz, 2H), 4.52-4.56 (m, 1H), 3.23-3.38 (m, 2H), 2.34-2.38 (m, 1H), 1.96-2.06 (m, 3H), 1.71 (s, 3H).

Scheme 80: Route for SU20668-0341-01

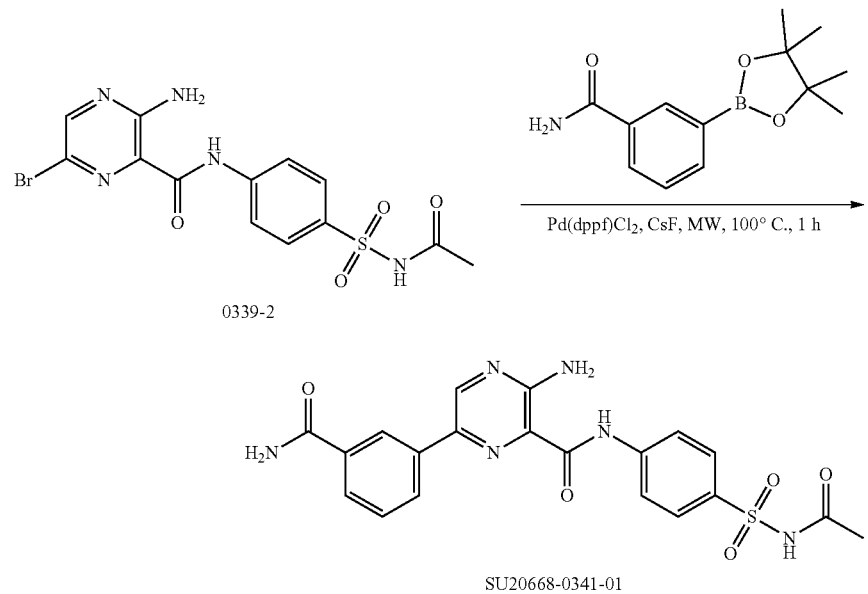

The Synthesis of N-(4-(N-acetylsulfamoyl)phenyl)-3-amino-6-(3-carbamoylphenyl)pyrazine-2-carboxamide (SU20668-0341-01)

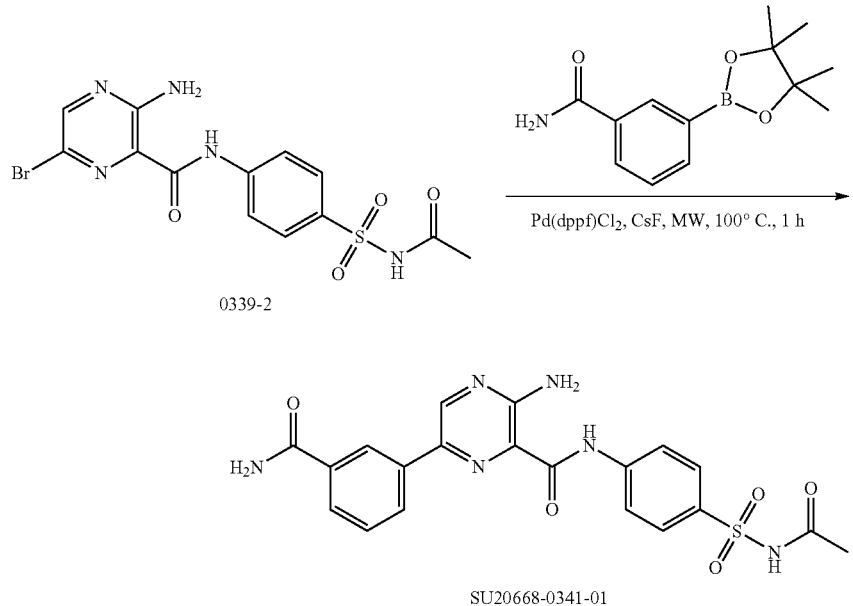

To a stirred solution of compound 0339-2 (140 mg, 0.34 mmol), 3-carbamoylphenylboronic acid pinacol ester (101 mg, 0.41 mmol) and CsF (150 mg, 1.02 mmol) in MeOH (4 mL) was added Pd(dppf)Cl$_2$ (10%, 25 mg). The resulting reaction mixture was irradiated with microwave radiation at 100° C. for 1 h under Ar atmosphere (1.0 atm). After the consumption of starting material (by LCMS), the mixture was filtered, and the filtrate was concentrated in vacuo, purified by prep-HPLC to give the desired product SU20668-0341-01 (45 mg, 29% yield) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 100%, R$_t$=1.211 min; MS Calcd.: 454.46; MS Found: 455.2 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 96.22%, Rt=5.054 min. $^1$H NMR (400 MHz, DMSO-d$_6$) δ 10.72 (s, 1H), 9.02 (s, 1H), 8.61 (s, 1H), 8.41 (d, J=8.0 Hz, 1H), 8.15 (s, 1H), 8.04 (d, J=9.2 Hz, 2H), 7.89-7.92 (m, 3H), 7.76 (s, 2H), 7.60 (t, J=7.6 Hz, 1H), 7.49 (s, 1H), 1.88 (s, 3H).

Scheme 81: Route for SU20668-0342-01

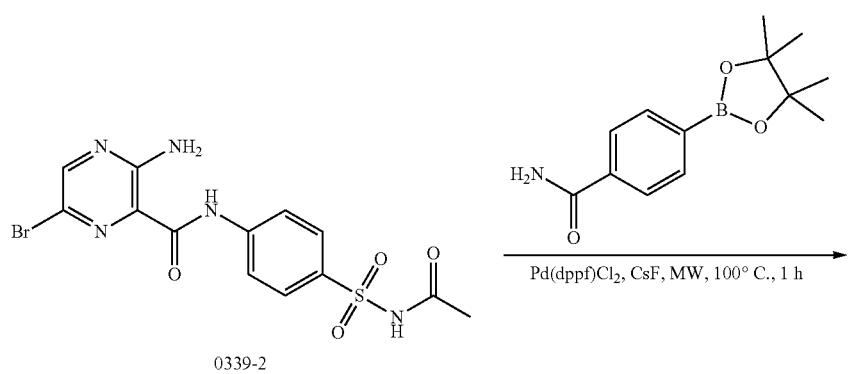

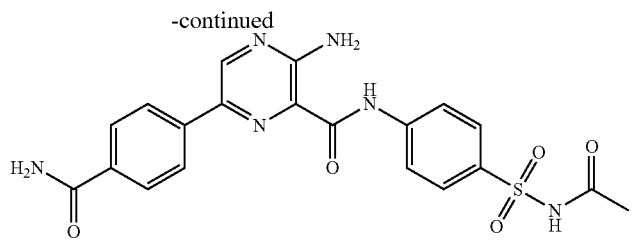

The Synthesis of N-(4-(N-acetylsulfamoyl)phenyl)-3-amino-6-(4-carbamoylphenyl)pyrazine-2-carboxamide (SU20668-0342-01)

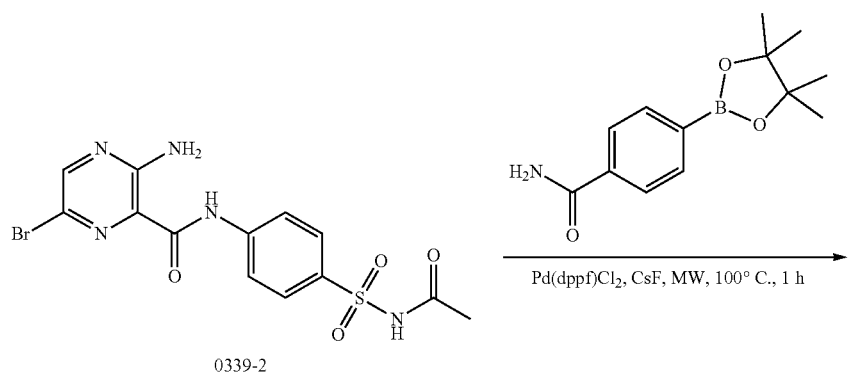

To a stirred solution of compound 0339-2 (140 mg, 0.34 mmol), 4-(4,4,5,5-tetramethyl-1,3,2-dioxaborolan-2-yl)benzamide (101 mg, 0.41 mmol) and CsF (150 mg, 1.02 mmol) in MeOH (4 mL) was added Pd(dppf)Cl$_2$(10%, 25 mg). The resulting reaction mixture was irradiated with microwave radiation at 100° C. for 1 h under Ar atmosphere (1.0 atm). After the consumption of starting material (by LCMS), the mixture was filtered, and the filtrate was concentrated in vacuo, purified by prep-HPLC to give the desired product SU20668-0342-01 (13 mg, 8% yield) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 99.13%, Rt=1.183 min; MS Calcd.: 454.46; MS Found: 455.2 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 100%, Rt=4.937 min. $^1$H NMR (400 MHz, DMSO-d$_6$) δ 10.69 (s, 1H), 9.02 (s, 1H), 8.32 (d, J=8.4 Hz, 2H), 7.98-8.07 (m, 5H), 7.88 (d, J=8.8 Hz, 2H), 7.78 (s, 2H), 7.42 (s, 1H), 1.85 (s, 3H).

Scheme 82: Route for SU20668-0343-01

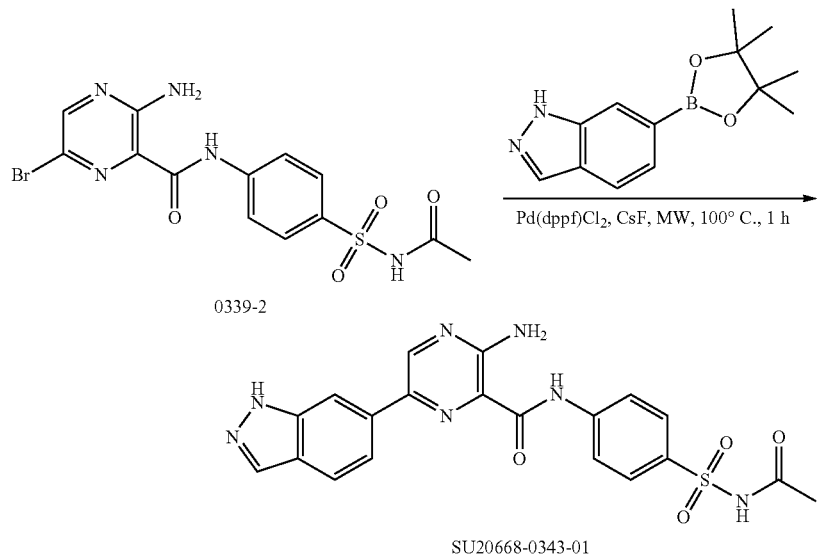

The Synthesis of N-(4-(N-acetylsulfamoyl)phenyl)-3-amino-6-(1H-indazol-6-yl)pyrazine-2-carboxamide (SU20668-0343-01)

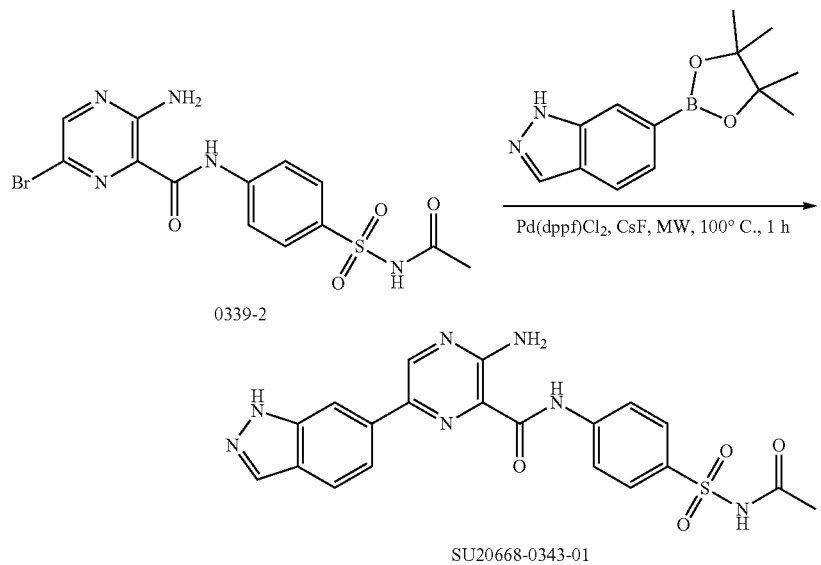

To a stirred solution of compound 0339-2 (140 mg, 0.34 mmol), 6-(4,4,5,5-tetramethyl-1,3,2-dioxaborolan-2-yl)-1H-indazole (101 mg, 0.41 mmol) and CsF (155 mg, 1.02 mmol) in MeOH (4 mL) was added Pd(dppf)Cl$_2$ (10%, 25 mg). The resulting reaction mixture was irradiated with microwave radiation at 100° C. for 1 h under Ar atmosphere (1.0 atm). After the consumption of starting material (by LCMS), the mixture was filtered, and the filtrate was concentrated in vacuo, purified by prep-HPLC to give the desired product SU20668-0343-01 (13 mg, 8% yield) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 95.83%, Rt=1.289 min; MS Calcd.: 451.46; MS Found: 452.3 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 100%, Rt=5.612 min. $^1$H NMR (400 MHz, DMSO-d$_6$) δ 13.22 (s, 1H), 10.76 (s, 1H), 9.03 (s, 1H), 8.32 (s, 1H), 8.11 (s, 1H), 8.00-8.05 (m, 3H), 7.86-7.90 (m, 3H), 7.70 (s, 2H), 1.86 (s, 3H)

Scheme 83: Route for SU20668-0344-01

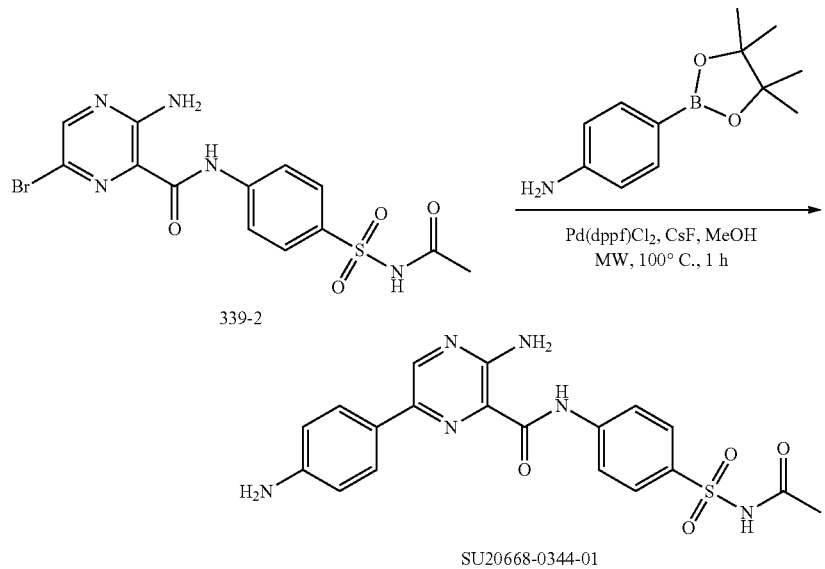

The Synthesis of N-(4-(N-acetylsulfamoyl)phenyl)-3-amino-6-(4-aminophenyl)pyrazine-2-carboxamide (SU20668-0344-01)

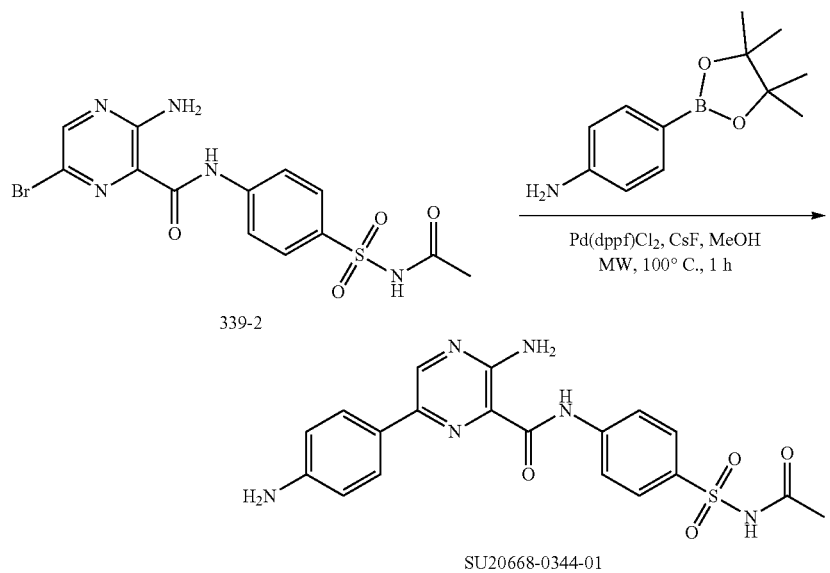

The mixture of 339-2 (150 mg, 0.36 mmol), 4-(4,4,5,5-tetramethyl-1,3,2-dioxaborolan-2-yl)aniline (88 mg, 0.40 mmol), Pd(dppf)Cl$_2$ (25 mg) and K$_2$CO$_3$ (100 mg, 0.72 mmol) in MeOH (3 mL) was heated to 100° C. by microwave and stirred under N$_2$ atmosphere for 1 hours. Then mixture was concentrated to dryness. The residue was purified by prep-HPLC to give SU20668-0344-01 (62 mg, yield: 43.1%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 98.43%, Rt=1.250 min; MS Calcd.: 426.1; MS Found: 427.3 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 98.60%, Rt=5.389 min. $^1$H NMR (400 MHz, DMSO-d$_6$) δ10.60 (s, 1H), 8.79 (s, 1H), 8.03 (d, J=8.8 Hz, 2H), 7.89 (t, J=8.4 Hz, 4H), 7.45 (s, 2H), 6.66 (d, J=8.4 Hz, 2H), 5.38 (bs, 2H), 1.88 (s, 3H).

Scheme 84: Route for SU20668-0345-01

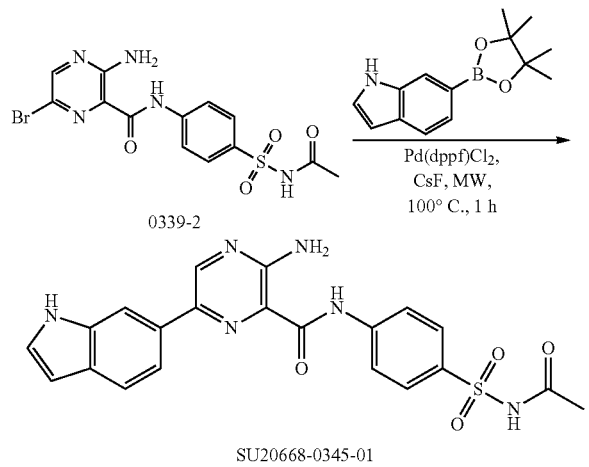

SU20668-0345-01

The Synthesis of N-(4-(N-acetylsulfamoyl)phenyl)-3-amino-6-(1H-indol-6-yl)pyrazine-2-carboxamide (SU20668-0345-01)

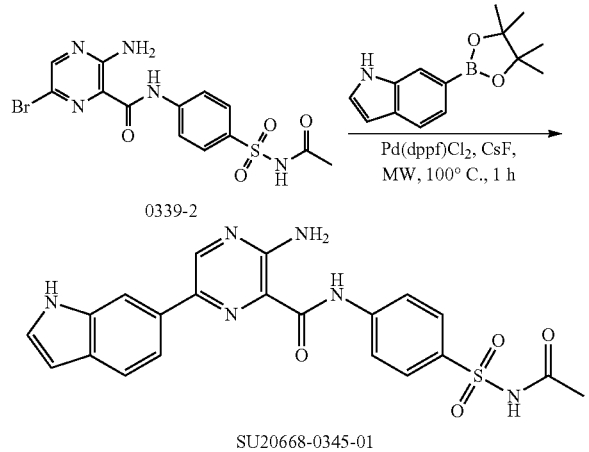

SU20668-0345-01

To a stirred solution of compound 0339-2 (140 mg, 0.34 mmol), 6-(4,4,5,5-tetramethyl-1,3,2-dioxaborolan-2-yl)-1H-indole (100 mg, 0.41 mmol) and CsF (150 mg, 1.02 mmol) in MeOH (4 mL) was added Pd(dppf)Cl$_2$(10%, 25 mg). The resulting reaction mixture was irradiated with microwave radiation at 100° C. for 1 h under Ar atmosphere (1.0 atm). After the consumption of starting material (by LCMS), the mixture was filtered, and the filtrate was concentrated in vacuo, purified by prep-HPLC to give the desired product SU20668-0345-01 (11 mg, 8% yield) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 100%, Rt=1.433 min; MS Calcd.: 450.47; MS Found: 451.2 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 100%, Rt=6.444 min. $^1$H NMR (400 MHz, DMSO-d$_6$) δ 11.23 (s, 1H), 10.76 (s, 1H), 8.95 (s, 1H), 8.18 (s, 1H), 8.07 (d, J=8.8 Hz, 2H), 7.85-7.92 (m, 3H), 7.65 (d, J=8.4 Hz, 1H), 7.56 (s, 2H), 7.41 (s, 1H), 6.47 (s, 1H), 1.90 (s, 3H).

Scheme 85: Route for SU20668-0346-01

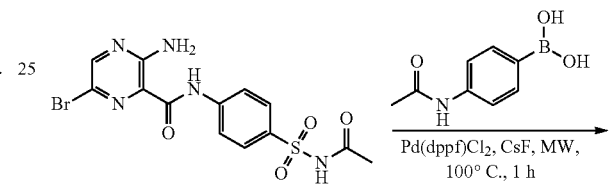

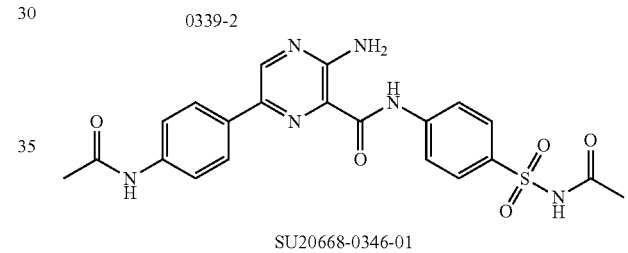

SU20668-0346-01

The Synthesis of 6-(4-acetamidophenyl)-N-(4-(N-acetylsulfamoyl)phenyl)-3-aminopyrazine-2-carboxamide (SU20668-0346-01)

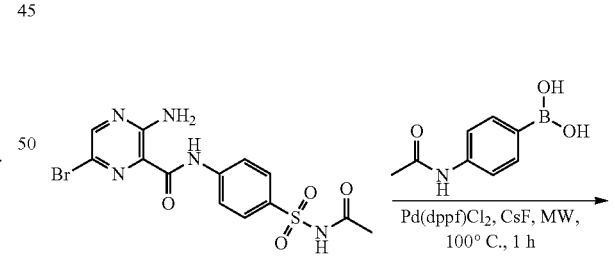

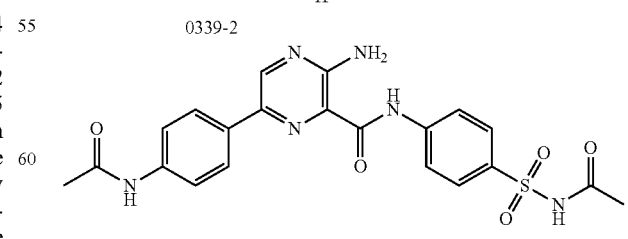

SU20668-0346-01

To a stirred solution of compound 0339-2 (140 mg, 0.34 mmol), 4-acetamidophenylboronic acid (74 mg, 0.41 mmol)

and CsF (150 mg, 1.02 mmol) in MeOH (4 mL) was added Pd(dppf)Cl$_2$ (10%, 25 mg). The resulting reaction mixture was irradiated with microwave radiation at 100° C. for 1 h under Ar atmosphere (1.0 atm). After the consumption of starting material (by LCMS), the mixture was filtered, and the filtrate was concentrated in vacuo, purified by prep-HPLC to give the desired product SU20668-0346-01 (11 mg, 8% yield) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 100%, Rt=1.254 min; MS Calcd.: 468.49; MS Found: 469.2 [M+H]$^+$. Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 100%, Rt=5.404 min. $^1$H NMR (400 MHz, DMSO-d$_6$) δ 10.59 (s, 1H), 10.08 (s, 1H), 8.91 (s, 1H), 8.17 (d, J=8.8 Hz, 2H), 7.99 (d, J=8.8 Hz, 2H), 7.85 (d, J=8.8 Hz, 2H), 7.72 (d, J=8.8 Hz, 2H), 7.64 (s, 2H), 2.08 (s, 3H), 1.82 (s, 3H).

Scheme 86: Route for SU20668-0347-01

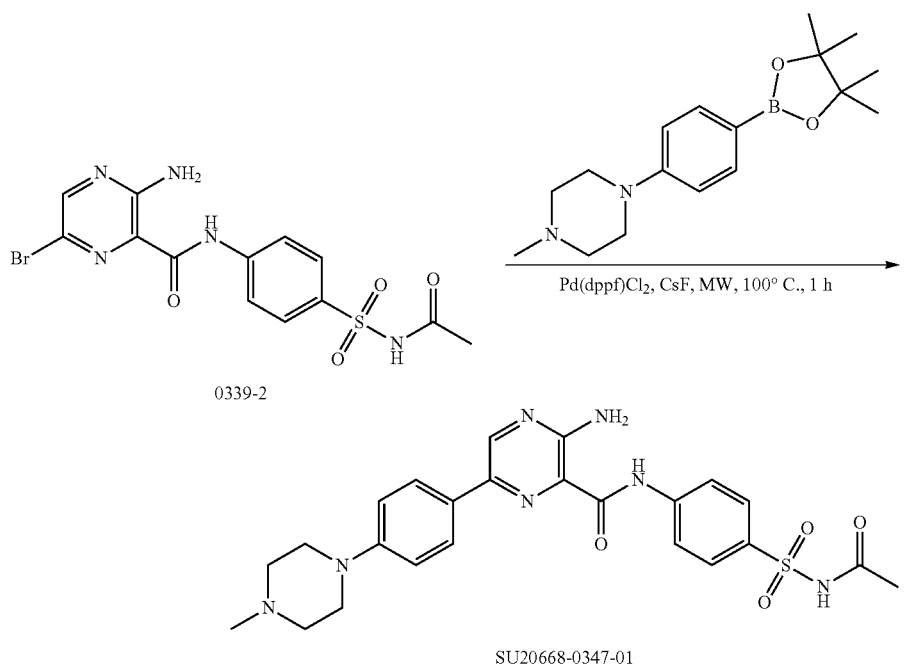

The Synthesis of N-(4-(N-acetylsulfamoyl)phenyl)-3-amino-6-(4-(4-methylpiperazin-1-yl)phenyl)pyrazine-2-carboxamide (SU20668-0347-01)

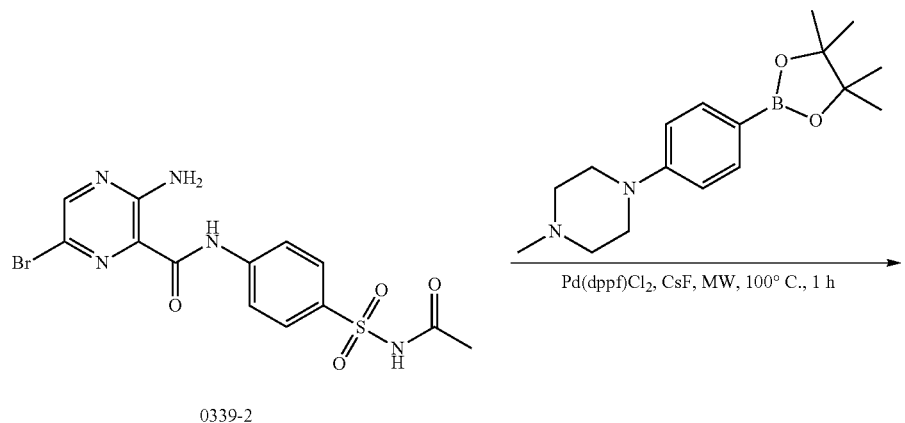

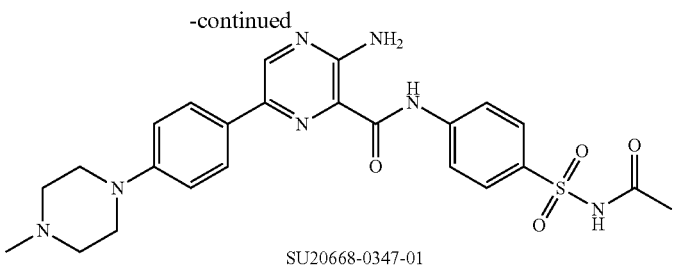

To a stirred solution of compound 0339-2 (140 mg, 0.34 mmol), 1-methyl-4-(4-(4,4,5,5-tetramethyl-1,3,2-dioxaborolan-2-yl)phenyl)piperazine (124 mg, 0.41 mmol) and CsF (150 mg, 1.02 mmol) in MeOH (4 mL) was added Pd(dppf)Cl$_2$ (10%, 25 mg). The resulting reaction mixture was irradiated with microwave radiation at 100° C. for 1 h under Ar atmosphere (1.0 atm). After the consumption of starting material (by LCMS), the mixture was filtered, and the filtrate was concentrated in vacuo, purified by prep-HPLC to give the desired product SU20668-0347-01 (70 mg, 40% yield) as a yellow solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 100%, Rt=1.329 min; MS Calcd.: 509.58; MS Found: 510.4 [M+H]$^+$. Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 100%, Rt=5.882 min. $^1$H NMR (400 MHz, DMSO-d$_6$) δ 10.66 (s, 1H), 8.87 (s, 1H), 8.02-8.09 (m, 4H), 7.90 (d, J=8.8 Hz, 2H), 7.55 (s, 2H), 7.05 (d, J=8.8 Hz, 2H), 3.25-3.26 (m, 4H), 2.57-2.60 (m, 4H), 2.32 (3H, s), 1.89 (3H, s).

Scheme 87: Route for SU20668-0348-01

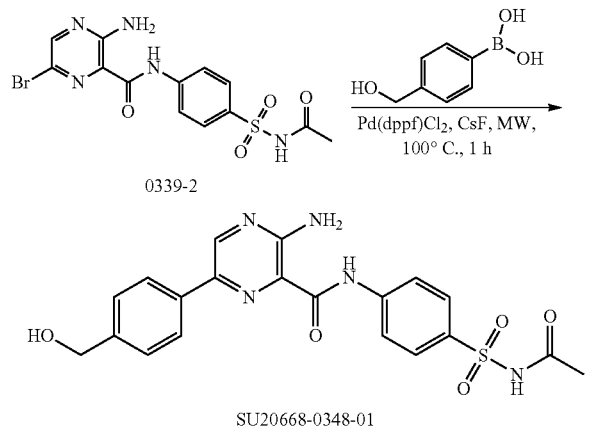

The Synthesis of N-(4-(N-acetylsulfamoyl)phenyl)-3-amino-6-(4-(hydroxymethyl)phenyl)pyrazine-2-carboxamide (SU20668-0348-01)

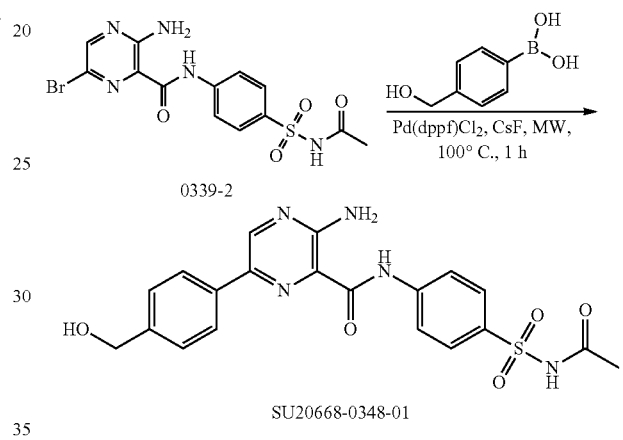

To a stirred solution of compound 0339-2 (140 mg, 0.34 mmol), 4-(hydroxymethyl)phenylboronic acid (63 mg, 0.41 mmol) and CsF (150 mg, 1.02 mmol) in MeOH (4 mL) was added Pd(dppf)Cl$_2$(10%, 25 mg). The resulting reaction mixture was irradiated with microwave radiation at 100° C. for 1 h under Ar atmosphere (1.0 atm). After the consumption of starting material (by LCMS), the mixture was filtered, and the filtrate was concentrated in vacuo, purified by prep-HPLC to give the desired product SU20668-0348-01 (72 mg, 50% yield) as a yellow solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 100%, Rt=1.245 min; MS Calcd.: 441.46; MS Found: 442.2 [M+H]$^+$. Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 100%, Rt=5.287 min. $^1$H NMR (400 MHz, DMSO-d$_6$) δ 10.62 (s, 1H), 8.94 (s, 1H), 8.19 (d, J=8.0 Hz, 2H), 7.98 (d, J=8.8 Hz, 2H), 7.85 (d, J=8.8 Hz, 2H), 7.67 (s, 2H), 7.44 (d, J=8.0 Hz, 2H), 5.25 (s, 1H), 4.56 (s, 2H), 1.82 (s, 3H).

Scheme 88: Route for SU20668-0349-01

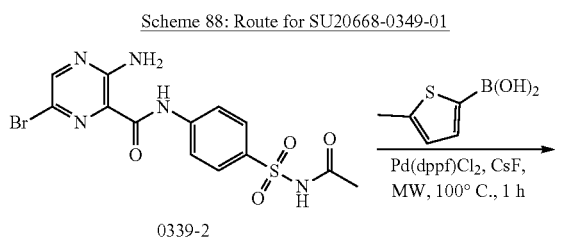

The Synthesis of N-(4-(N-acetylsulfamoyl)phenyl)-3-amino-6-(5-methylthiophen-2-yl)pyrazine-2-carboxamide (SU20668-0349)

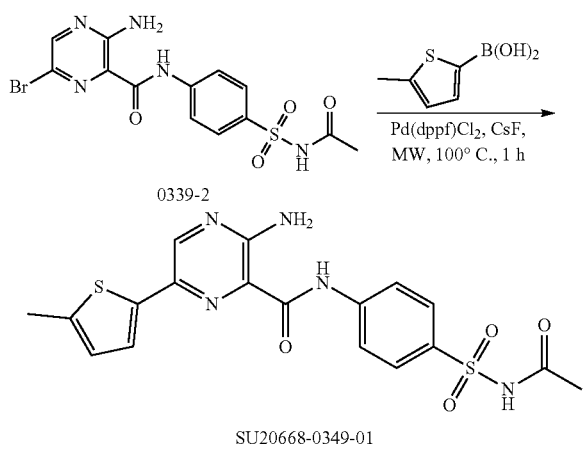

To a stirred solution of compound 0339-2 (140 mg, 0.34 mmol), 5-methylthiophen-2-ylboronic acid (59 mg, 0.41 mmol) and CsF (150 mg, 1 mmol) in MeOH (4 mL) was added Pd(dppf)Cl$_2$ (10%, 25 mg). The resulting reaction mixture was irradiated with microwave radiation at 100° C. for 1 h under Ar atmosphere (1.0 atm). After the consumption of starting material (by LCMS), the mixture was filtered, and the filtrate was concentrated in vacuo, purified by prep-HPLC to give the desired product SU20668-0349-01 (30 mg, 20.5% yield) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 100%, Rt=1.459 min; MS Calcd.: 431.49; MS Found: 432.2 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 97.63%, Rt=6.747 min. $^1$H NMR (400 MHz, DMSO-d$_6$) δ 12.04 (s, 1H), 10.46 (s, 1H), 8.79 (s, 1H), 8.02 (d, J=8.8 Hz, 2H), 7.92 (d, J=8.8 Hz, 2H), 7.65 (s, 1H), 7.64 (s, 2H), 6.86 (s, 1H), 1.92 (s, 3H).

Scheme 89: Route for SU20668-0350-01

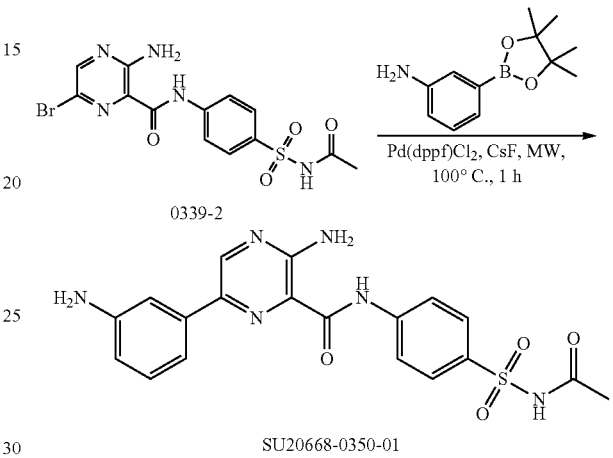

The Synthesis of N-(4-(N-acetylsulfamoyl)phenyl)-3-amino-6-(3-aminophenyl)pyrazine-2-carboxamide (SU20668-0350-01)

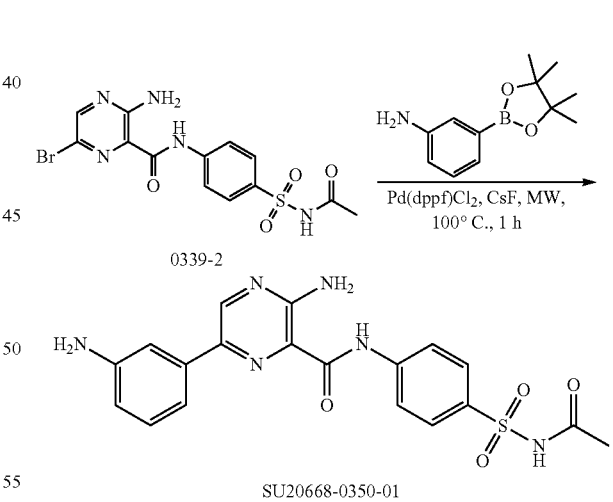

To a stirred solution of compound 0339-2 (140 mg, 0.34 mmol), 3-(4,4,5,5-tetramethyl-1,3,2-dioxaborolan-2-yl)aniline (90 mg, 0.41 mmol) and CsF (150 mg, 1.02 mmol) in MeOH (4 mL) was added Pd(dppf)Cl$_2$ (10%, 25 mg). The resulting reaction mixture was irradiated with microwave radiation at 100° C. for 1 h under Ar atmosphere (1.0 atm). After the consumption of starting material (by LCMS), the mixture was filtered, and the filtrate was concentrated in vacuo, purified by prep-HPLC to give the desired product SU20668-0350-01 (30 mg, 20% yield) as a yellow solid.

Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 100%, Rt=1.283 min; MS Calcd.: 426.45; MS Found: 427.2 [M+H]$^+$. Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 100%, Rt=5.530 min. $^1$H NMR (400 MHz, DMSO-d$_6$) δ 10.59 (s, 1H), 8.79 (s, 1H), 8.02 (d, J=8.8 Hz, 2H), 7.88 (d, J=8.8 Hz, 2H), 7.61 (s, 2H), 7.29-7.35 (m, 2H), 7.14 (t, J=7.6 Hz, 1H), 6.60-6.63 (m, 1H), 5.14 (brs, 2H), 1.86 (s, 3H).

Scheme 90: Route for SU20668-0351-01

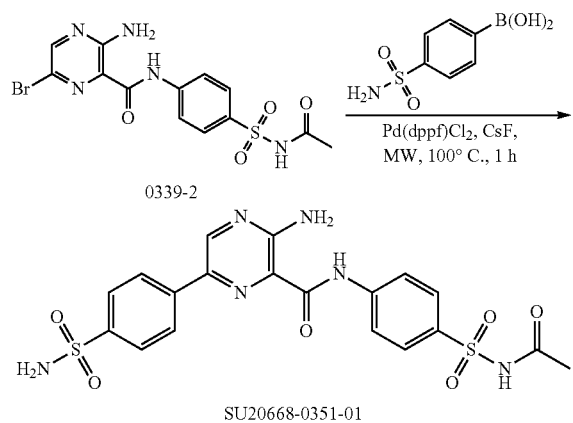

The Synthesis of N-(4-(N-acetylsulfamoyl)phenyl)-3-amino-6-(4-sulfamoylphenyl)pyrazine-2-carboxamide (SU20668-0351-01)

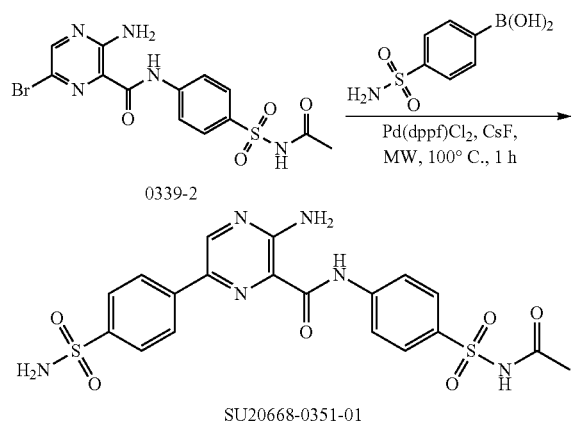

To a stirred solution of compound 0339-2 (140 mg, 0.34 mmol), 4-sulfamoylphenylboronic acid (83 mg, 0.41 mmol) and CsF (150 mg, 1.02 mmol) in MeOH (4 mL) was added Pd(dppf)Cl$_2$ (10%, 25 mg). The resulting reaction mixture was irradiated with microwave radiation at 100° C. for 1 h under Ar atmosphere (1.0 atm). After the consumption of starting material (by LCMS), the mixture was filtered, and the filtrate was concentrated in vacuo, purified by prep-HPLC to give the desired product SU20668-0351-01 (15 mg, 9% yield) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 99.10%, Rt=1.212 min; MS Calcd.: 490.51; MS Found: 491.3 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 98.76%, Rt=5.135 min. H NMR (400 MHz, DMSO-d$_6$) δ 10.70 (s, 1H), 9.03 (s, 1H), 8.43 (d, J=8.4 Hz, 2H), 8.03 (d, J=8.8 Hz, 2H), 7.89-7.92 (m, 4H), 7.84 (s, 2H), 7.44 (s, 2H), 1.88 (s, 3H).

Scheme 91: Route for SU20668-3052-01

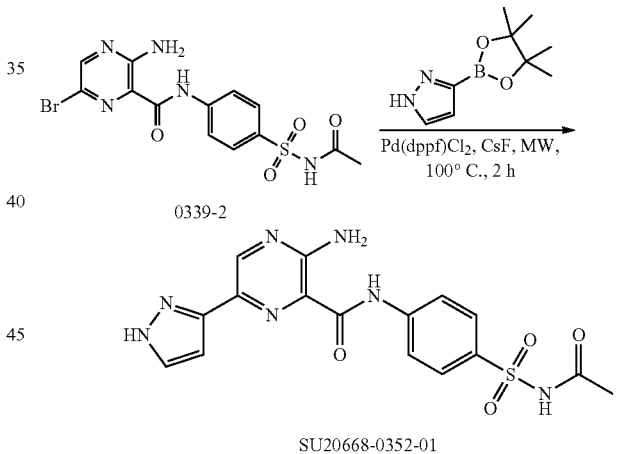

The Synthesis of N-(4-(N-acetylsulfamoyl)phenyl)-3-amino-6-(1H-pyrazol-3-yl)pyrazine-2-carboxamide (SU20668-0352-01)

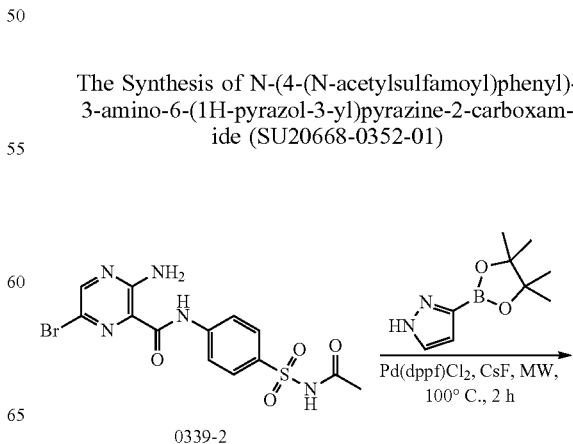

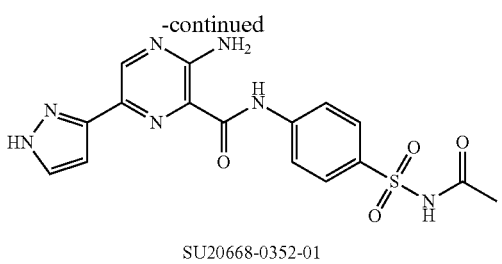

SU20668-0352-01

To a stirred solution of compound 0339-2 (140 mg, 0.34 mmol), 3-(4,4,5,5-tetramethyl-1,3,2-dioxaborolan-2-yl)-1H-pyrazole (80 mg, 0.41 mmol) and CsF (150 mg, 1.02 mmol) in MeOH (4 mL) was added Pd(dppf)Cl$_2$ (10%, 25 mg). The resulting reaction mixture was irradiated with microwave radiation at 100° C. for 2 h under Ar atmosphere. After the consumption of starting material (by LCMS), the mixture was filtered, and the filtrate was concentrated in vacuo, purified by prep-HPLC to give the desired product SU20668-0352-01 (29 mg, 21% yield) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 99.39%, Rt=1.188 min; MS Calcd.: 401.40; MS Found: 402.2 [M+H]$^+$. Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 100%, Rt=4.872 min. $^1$H NMR (400 MHz, DMSO-d$_6$) δ 13.00-13.76 (m, 1H), 10.73-10.78 (m, 1H), 8.86 (s, 1H), 7.61-8.03 (m, 7H), 6.94 (s, 1H), 1.89 (s, 3H).

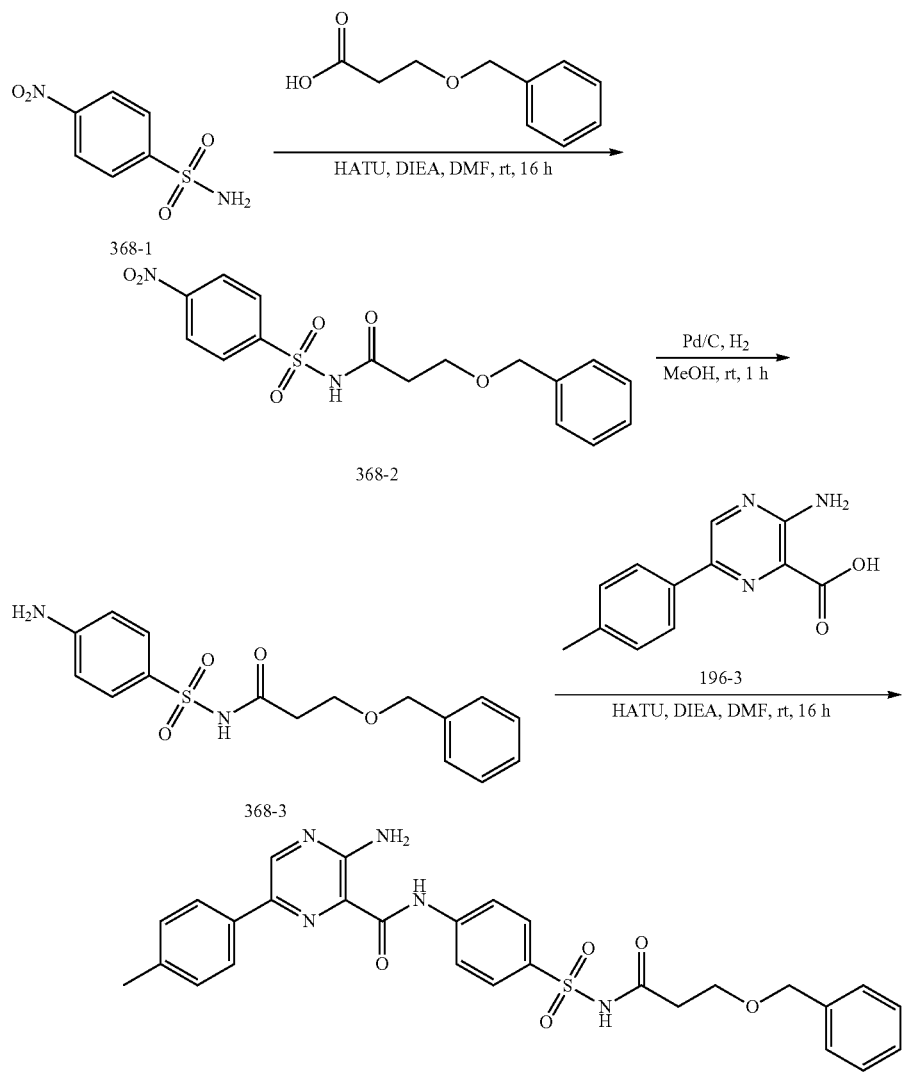

633
The Synthesis of 3-(benzyloxy)-N-(4-nitrophenylsulfonyl)propanamide (368-2)

634
The Synthesis of N-(4-aminophenylsulfonyl)-3-(benzyloxy)propanamide (368-3)

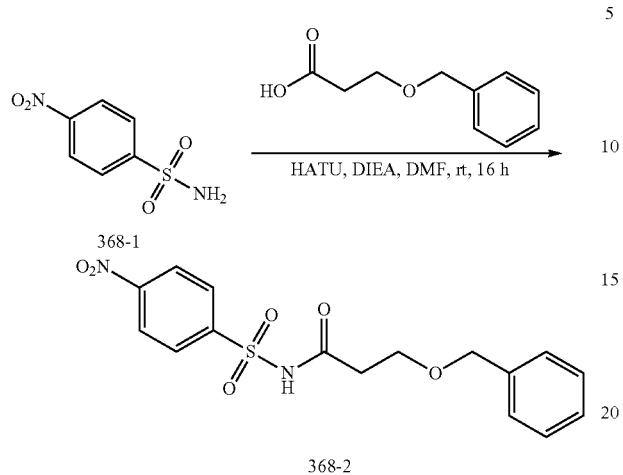

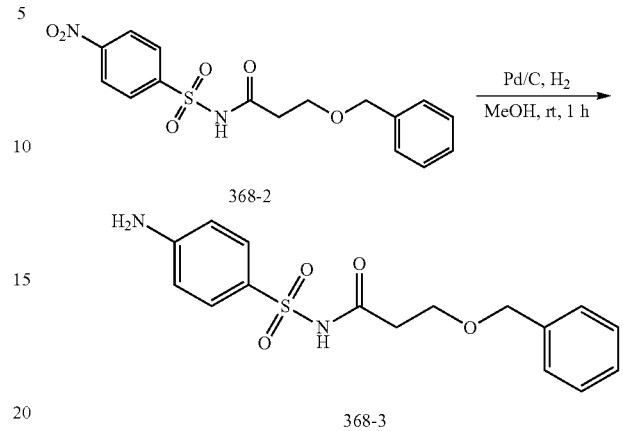

To a stirred solution of compound 368-1 (300 mg, 1.48 mmol) in DMF (15 ml) was added 3-(benzyloxy)propanoic acid (221 mg, 1.23 mmol), HATU (843 mg, 2.22 mmol) and DIEA (572 mg, 4.44 mmol). The resulting reaction mixture was stirred at rt for 16 h. Then added water, the aqueous phase was extracted with dichloromethane, the combined organic phases were dried over anhydrous sodium sulfate, filtered, and concentrated in vacuo, thus was further purified by C.C. to give 368-2 (100 mg, yield: 18%) as a white solid.

To a solution of 368-2 (100 mg, 0.27 mmol) in MeOH (10 mL) was added Pd/C (10%, 10 mg), the mixture was stirred at rt for 1 h under $H_2$ atmosphere (1.0 atm). The mixture was filtered and concentrated in vacuo to give 368-3 (80 mg, 88% yield) as yellow oil.

The Synthesis of 3-amino-N-(4-(N-(3-(benzyloxy)propanoyl)sulfamoyl)phenyl)-6-p-tolylpyrazine-2-carboxamide (SU20668-0368)

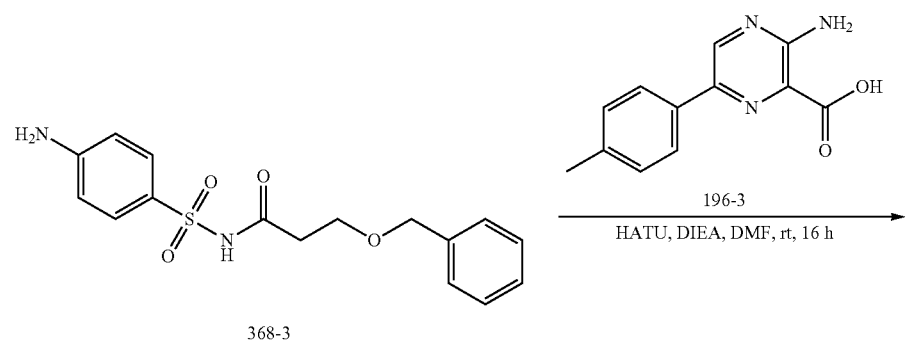

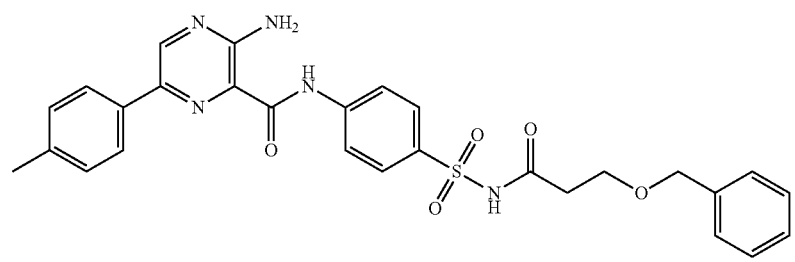

To a stirred solution of compound 368-3 (80 mg, 0.24 mmol) in DMF (5 ml) was added 196-3 (46 mg, 0.20 mmol), HATU (137 mg, 0.36 mmol) and DIEA (93 mg, 0.72 mmol). The resulting reaction mixture was stirred at rt for 16 h. Then added water, the aqueous phase was extracted with dichloromethane, the combined organic phases were dried over anhydrous sodium sulfate, filtered, and concentrated in vacuo, thus was further purified by prep-HPLC to give SU20668-0368 (25 mg, yield: 19%) as a yellow solid. LC-MS (LC-MS (Agilent LCMS 1200-6120, Column: Waters X-Bridge C18 (30 mm×4.6 mm×2.7 μm); Column Temperature: 40° C.; Flow Rate: 3.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 0.8 min, then under this condition for 0.4 min, finally changed to 95% [water+0.05% TFA] and 5% [CH$_3$CN+0.05%] in 0.01 min.). Purity: 98.44%, Rt=1.784 min; MS Calcd.: 545.1; MS Found: 546.3 [M+H]$^+$. HPLC (Agilent HPLC 1200; Column: L-column2 ODS (150 mm*4.6 mm*5.0 m); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min). Purity: 100%, Rt=7.907 min. $^1$H NMR (400 MHz, DMSO-d$_6$) δ 12.07 (s, 1H), 10.68 (s, 1H), 8.93 (s, 1H), 8.11 (d, J=8.4 Hz, 2H), 8.06 (d, J=9.2 Hz, 2H), 7.91 (d, J=8.8 Hz, 2H), 7.64 (s, 2H), 7.18-7.32 (m, 7H), 4.37 (s, 2H), 3.57 (t, J=6 Hz, 2H), 2.49-2.50 (m, 2H), 2.37 (s, 3H).

Scheme 93 Route for SU20668-0369-01

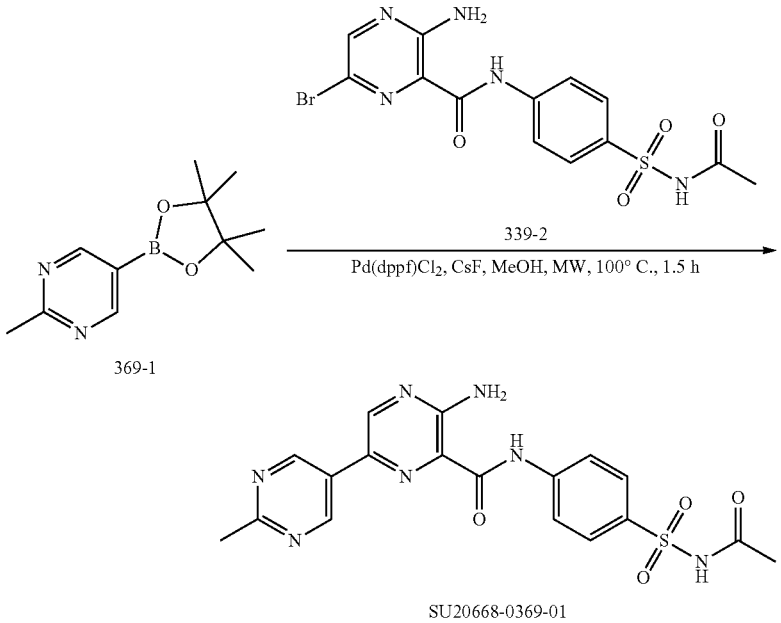

The Synthesis of N-(4-(N-acetylsulfamoyl)phenyl)-3-amino-6-(2-methylpyrimidin-5-yl)pyrazine-2-carboxamide (SU20668-0369-01)

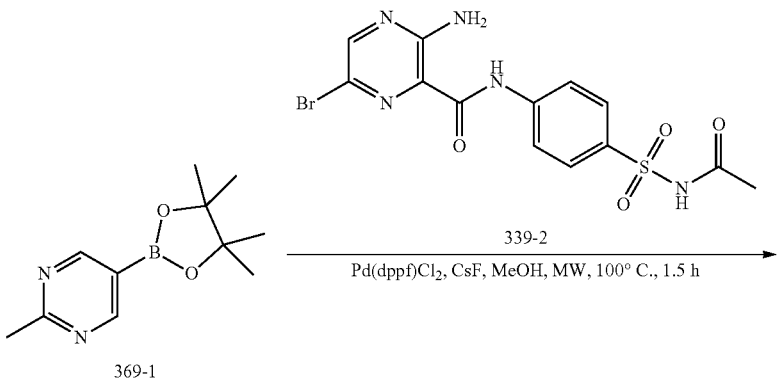

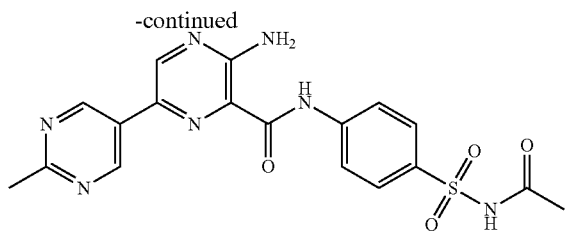

SU20668-0369-01

To a stirred solution of 339-2 (120 mg, 0.2897 mmol) in MeOH (10 mL) was added 369-1 (75 mg, 0.2897 mmol), Pd(dppf)Cl$_2$ (24 mg, 28.97 umol) and CsF (89 mg, 0.5794 mmol) at rt, the mixture was irradiated with microwave at 100° C. for 1.5 h, cooled to rt, filtered, purified by prep-HPLC to give SU20668-0369-01 (20 mg, 16.3% yield) as a white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, R$_t$=1.133 min; MS Calcd.: 427.11; MS Found: 428.1 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM AcONH$_4$) water/CH$_3$CN=900/100 (v/v)] and 10% [total 10 mM AcONH$_4$) water/CH$_3$CN=100/900 (v/v)] to 15% [total 10 mM AcONH$_4$) water/CH$_3$CN=900/100 (v/v)] and 85% [total 10 mM AcONH$_4$) water/CH$_3$CN=100/900 (v/v)] in 5 min, then under this condition for 10 min, finally changed to 90% [(total 10 mM AcONH$_4$) water/CH$_3$CN=900/100 (v/v)] and 10% [total 10 mM AcONH$_4$) water/CH$_3$CN=100/900 (v/v)] in 0.1 min and under this condition for 5 min). Purity: 98.67%, Rt=5.247 min. $^1$H NMR (400 MHz, DMSO-d$_6$) δ 12.05 (bs, 1H), 10.74 (s, 1H), 9.53 (s, 2H), 9.04 (s, 1H), 8.03-8.05 (m, 2H), 7.87-7.91 (m, 4H), 2.69 (s, 3H), 1.89 (s, 3H).

Scheme 94: Route for SU20668-0372-01

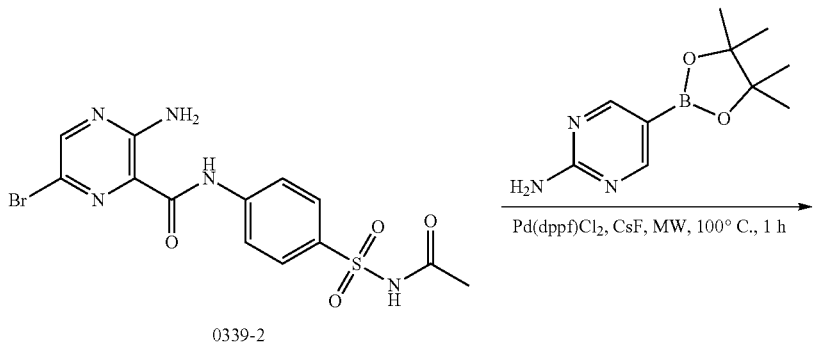

0339-2

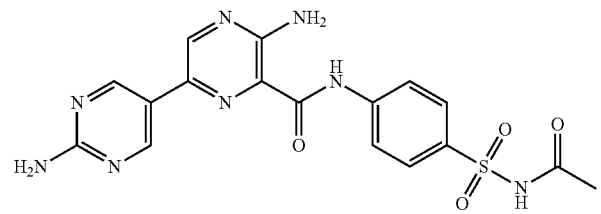

SU20668-0372-01

The Synthesis of N-(4-(N-acetylsulfamoyl)phenyl)-3-amino-6-(2-aminopyrimidin-5-yl)pyrazine-2-carboxamide (SU20668-0372-01)

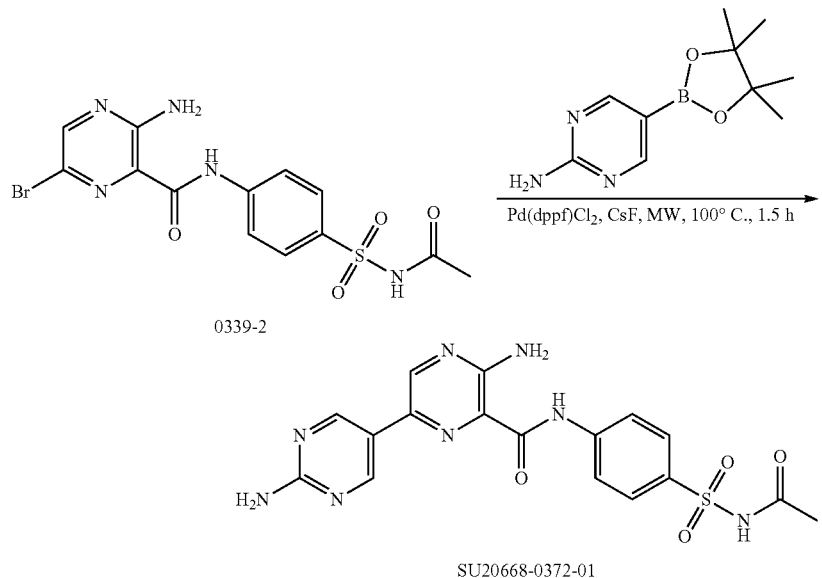

To a stirred solution of compound 0339-2 (140 mg, 0.34 mmol), 5-(4,4,5,5-tetramethyl-1,3,2-dioxaborolan-2-yl)pyrimidin-2-amine (98 mg, 0.41 mmol) and CsF (150 mg, 1.02 mmol) in MeOH (4 mL) was added Pd(dppf)Cl$_2$ (10%, 25 mg). The resulting reaction mixture was irradiated with microwave radiation at 120° C. for 1.5 h under Ar atmosphere. After the consumption of starting material (by LCMS), the mixture was filtered, and the filtrate was concentrated in vacuo, purified by prep-HPLC to give the desired product SU20668-0372-01 (11 mg, 7.6% yield) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 100%, Rt=1.305 min; MS Calcd.: 428.43; MS Found: 429.2 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 94.44%, Rt=5.402 min. $^1$H NMR (400 MHz, DMSO-d$_6$) δ 10.66 (s, 1H), 9.09 (s, 2H), 8.67 (s, 1H), 8.02 (d, J=8.8 Hz, 2H), 7.88 (d, J=8.8 Hz, 2H), 7.63 (s, 2H), 6.92 (s, 2H), 1.87 (s, 3H).

Scheme 95 Route for SU20668-0373

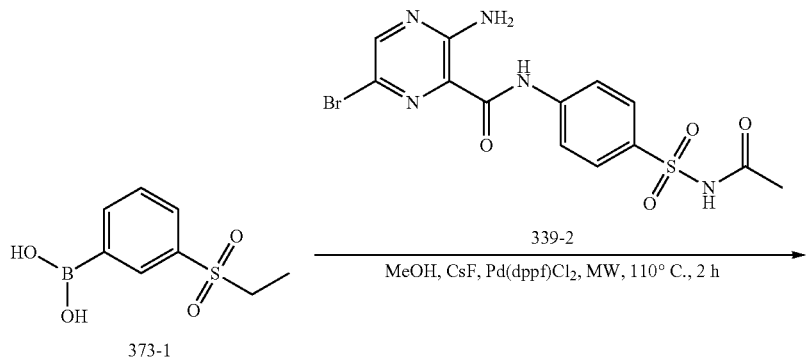

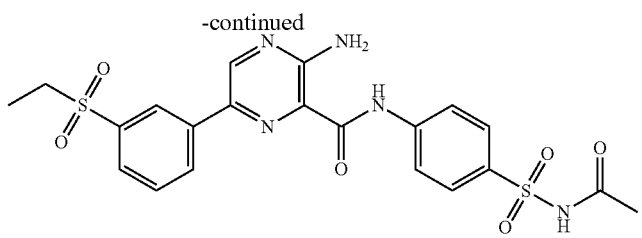

SU20668-0373

The Synthesis of N-(4-(N-acetylsulfamoyl)phenyl)-3-amino-6-(3-(ethylsulfonyl)phenyl)pyrazine-2-carboxamide (SU20668-0373)

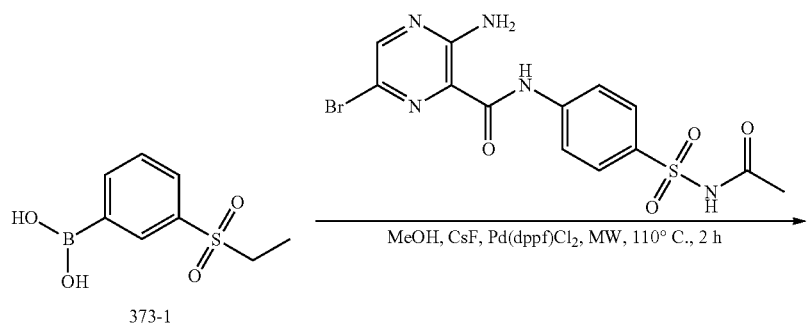

373-1

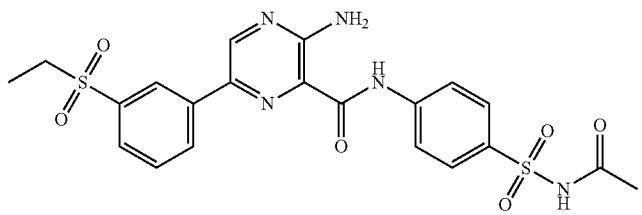

SU20668-0373

To a stirred solution of compound 373-1 (226 mg, 1.05 mmol) in MeOH (4 mL) was added N-(4-(N-acetylsulfamoyl)phenyl)-3-amino-6-bromopyrazine-2-carboxamide (200 mg, 0.48 mmol), CsF (328 mg, 2.16 mmol), Pd(dppf)Cl$_2$ (38 mg, 0.05 mmol). The resulting reaction mixture was heated to 110° C. in M.W. and stirred for 2 h and concentrated in vacuo to remove the solvent, then added water, the aqueous phase was extracted with dichloromethane, the combined organic phases were dried over anhydrous sodium sulfate, filtered, and concentrated, the crude was purified by prep-HPLC to give the desired product SU20668-0373 (31 mg, yield: 5.8%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 98.44%, Rt=1.475 min; MS Calcd.: 503.09; MS Found: 504.2 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 97.35%, Rt=5.993 min. $^1$H NMR (400 MHz, DMSO-d$_6$) δ 12.05 (s, 1H), 10.81 (s, 1H), 9.07 (s, 1H), 8.58-8.65 (m, 2H), 8.05 (d, J=8.8 Hz, 2H), 7.77-7.94 (m, 6H), 3.41-3.47 (m, 2H), 1.92 (s, 3H), 1.16 (t, J=7.2 Hz, 3H).

Scheme 96 Route for SU20668-0374-01

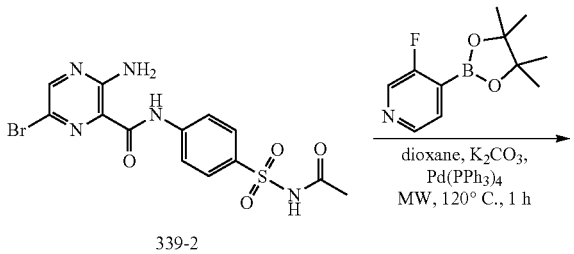

339-2

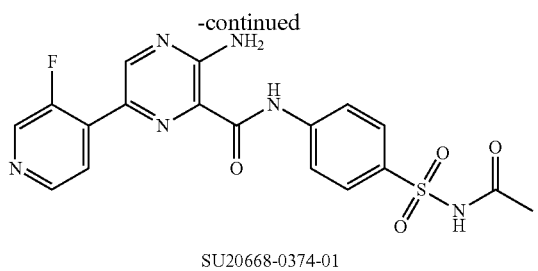

SU20668-0374-01

The Synthesis of N-(4-(N-acetylsulfamoyl)phenyl)-3-amino-6-(3-fluoropyridin-4-yl)pyrazine-2-carboxamide (SU20668-0374-01)

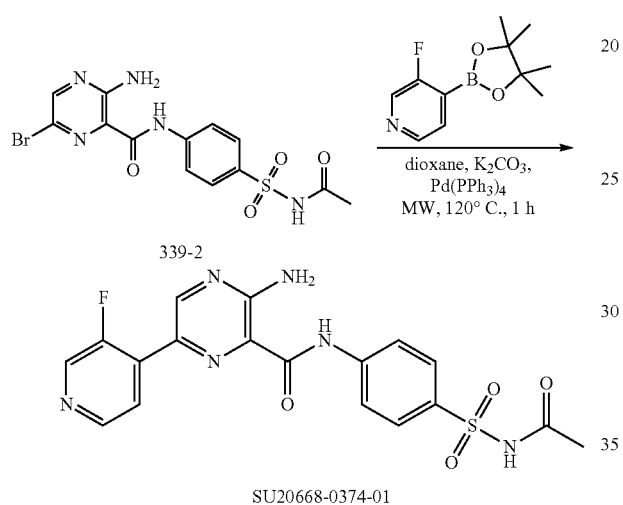

The mixture of 339-2 (150 mg, 0.36 mmol), 3-fluoro-4-(4,4,5,5-tetramethyl-1,3,2-dioxaborolan-2-yl)pyridine (89 mg, 0.40 mmol), Pd(PPh$_3$)$_4$ (25 mg, 0.02 mmol) and K$_2$CO$_3$ (100 mg, 0.72 mmol) in dioxane/H$_2$O (4 mL, 4/1) was heated to 120° C. by microwave and stirred under under N$_2$ atmosphere for 1 hours. Then mixture was concentrated to dryness. The residue was purified by prep-HPLC to give SU20668-0374-01 (17 mg, yield: 10.1%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=1.358 min; MS Calcd.: 430.1; MS Found: 431.2 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 100%, Rt=5.728 min. $^1$H NMR (400 MHz, DMSO-d$_6$) δ 12.05 (s, 1H), 10.76 (s, 1H), 8.85 (d, J=2.0 Hz, 1H), 8.70 (d, J=3.2 Hz, 1H), 8.57 (d, J=4.0 Hz, 1H), 8.38-8.41 (m, 1H), 8.02-8.07 (m, 4H), 7.92-7.94 (m, 2H), 1.93 (s, 3H).

Scheme 97 Route for SU20668-0529-01

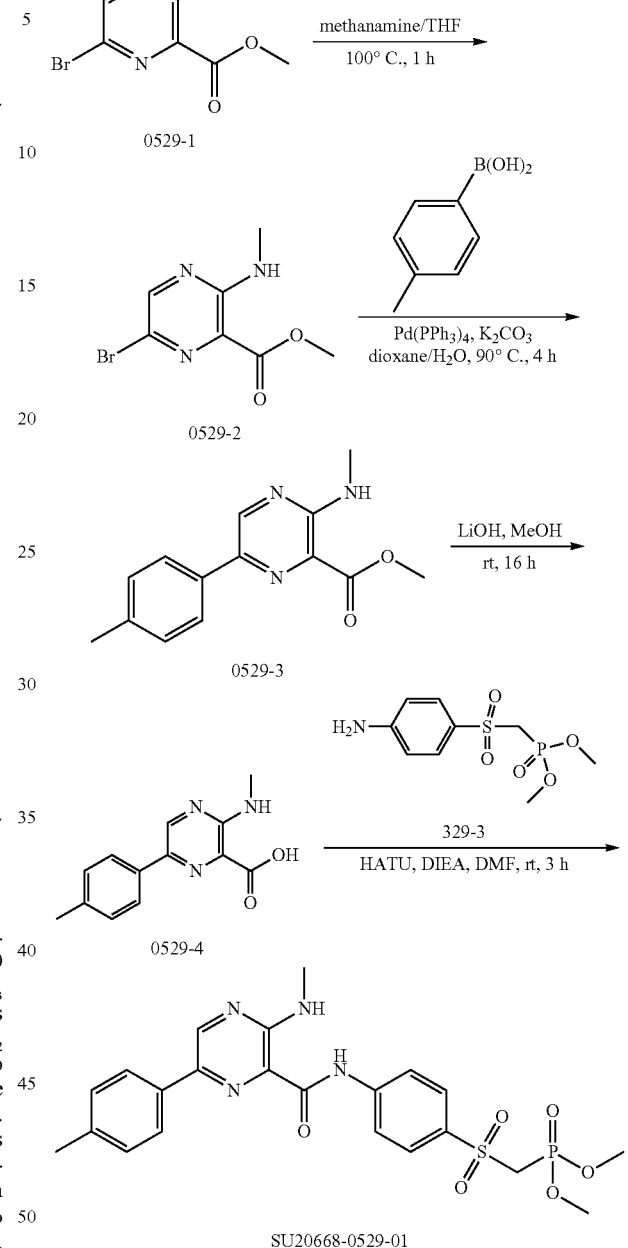

The Synthesis of methyl 6-bromo-3-(methylamino)pyrazine-2-carboxylate (0529-2)

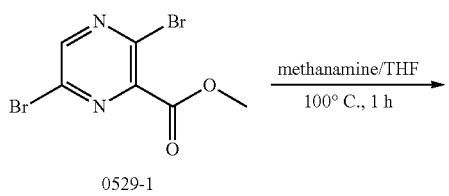

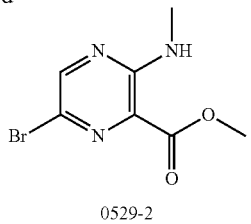

0529-2

The mixture of 0529-1 (1.4 g, 4.7 mmol) in methanamine/THF (1M, 20 mL) was stirred at 100° C. for 1 h. Then the reaction mixture was concentrated to dryness and purified by silica-gel column (DCM) to afford 0529-2 (430 mg, yield: 37.2%) as a yellow solid.

The Synthesis of methyl 3-(methylamino)-6-p-tolylpyrazine-2-carboxylate (0529-3)

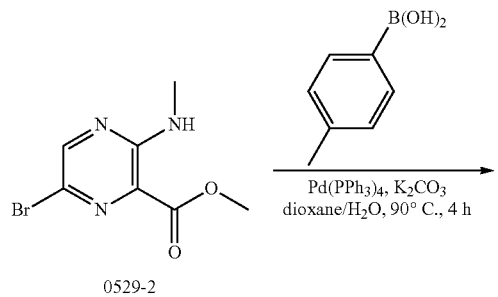

0529-2

0529-3

The mixture of 0529-2 (420 mg, 1.7 mmol), p-tolylboronic acid (272 mg, 2.0 mmol), Pd(PPh$_3$)$_4$ (50 mg) and K$_2$CO$_3$ (408 mg, 3.0 mmol) in dioxane/water (4:1, 10 mL) was stirred at 90° C. under argon atmosphere for 4 hours. Then the mixture was concentrated to dryness. The residue was purified by silica-gel column (DCM) to give 0529-3 (350 mg, yield: 80.1%) as a yellow solid.

The Synthesis of 3-(methylamino)-6-p-tolylpyrazine-2-carboxylic acid (0529-4)

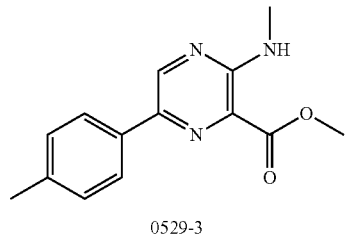

0529-3

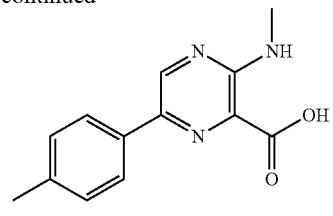

0529-4

The mixture of 0529-3 (350 mg, 1.4 mmol) and LiOH (168 mg, 4.0 mmol) in methanol (6 mL) was stirred at room temperature for 16 hours. Then the reaction mixture was concentrated to ~1 mL and acidified with HCl (1N) till pH=3~4. The solid was collected by filtration to afford 0529-4 (300 mg, yield: 88.2%) as a yellow solid.

The Synthesis of dimethyl (4-(3-(methylamino)-6-p-tolylpyrazine-2-carboxamido)phenylsulfonyl)methylphosphonate (SU20668-0529-01)

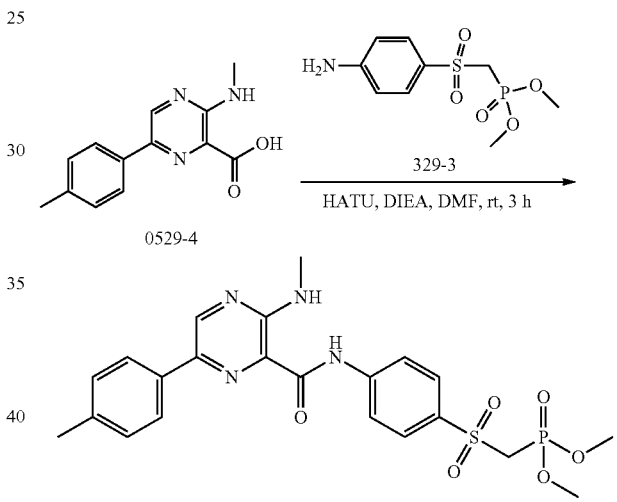

0529-4

SU20668-0529-01

To a solution of compound 0529-4 (200 mg, 0.82 mmol) in DMF (4 mL) was added 329-3 (251 mg, 0.90 mmol), DIEA (258 mg, 2.0 mmol) and HATU (456 mg, 1.2 mmol). The resulting reaction mixture was stirred for 3 h at rt. Then the mixture was purified by prep-HPLC to give the desired product SU20668-0529-01 (25 mg, yield: 6.1%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 98.86%, Rt=2.219 min; MS Calcd.: 504.1; MS Found: 505.3 [M+H]$^+$. HPLC (Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH₄HCO₃] and 5% [CH₃CN] in 0.1 min and under this condition for 5 min). Purity: 100%, Rt=10.552 min. ¹H NMR (400 MHz, DMSO-d₆) δ 10.76 (s, 1H), 8.99 (s, 1H), 8.43-8.45 (m, 1H), 8.12 (d, J=8.4 Hz, 4H), 7.96 (d, J=8.8 Hz, 2H), 7.31 (d, J=8.0 Hz, 2H), 4.50 (d, J=17.2 Hz, 2H), 3.63 (d, J=11.2 Hz, 6H), 3.04 (d, J=4.8 Hz, 3H), 2.37 (s, 3H).

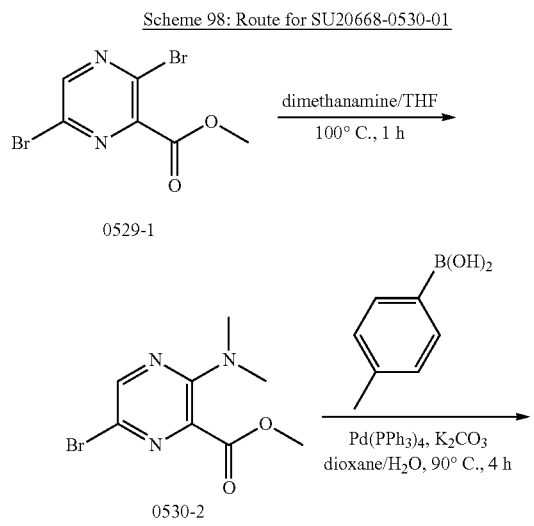

The Synthesis of methyl methyl 6-bromo-3-(dimethylamino)pyrazine-2-carboxylate (0530-2)

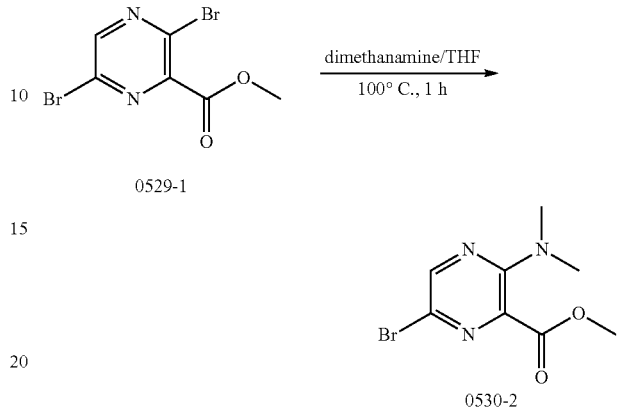

The mixture of 0529-1 (1.5 g, 5.1 mmol) in dimethanamine/THF (1M, 20 mL) was stirred at 100° C. for 1 h. Then the reaction mixture was concentrated to dryness and purified by silica-gel column (DCM) to afford 0530-2 (400 mg, yield: 30.4%) as a yellow solid.

The Synthesis of methyl 3-(dimethylamino)-6-p-tolylpyrazine-2-carboxylate (0530-3)

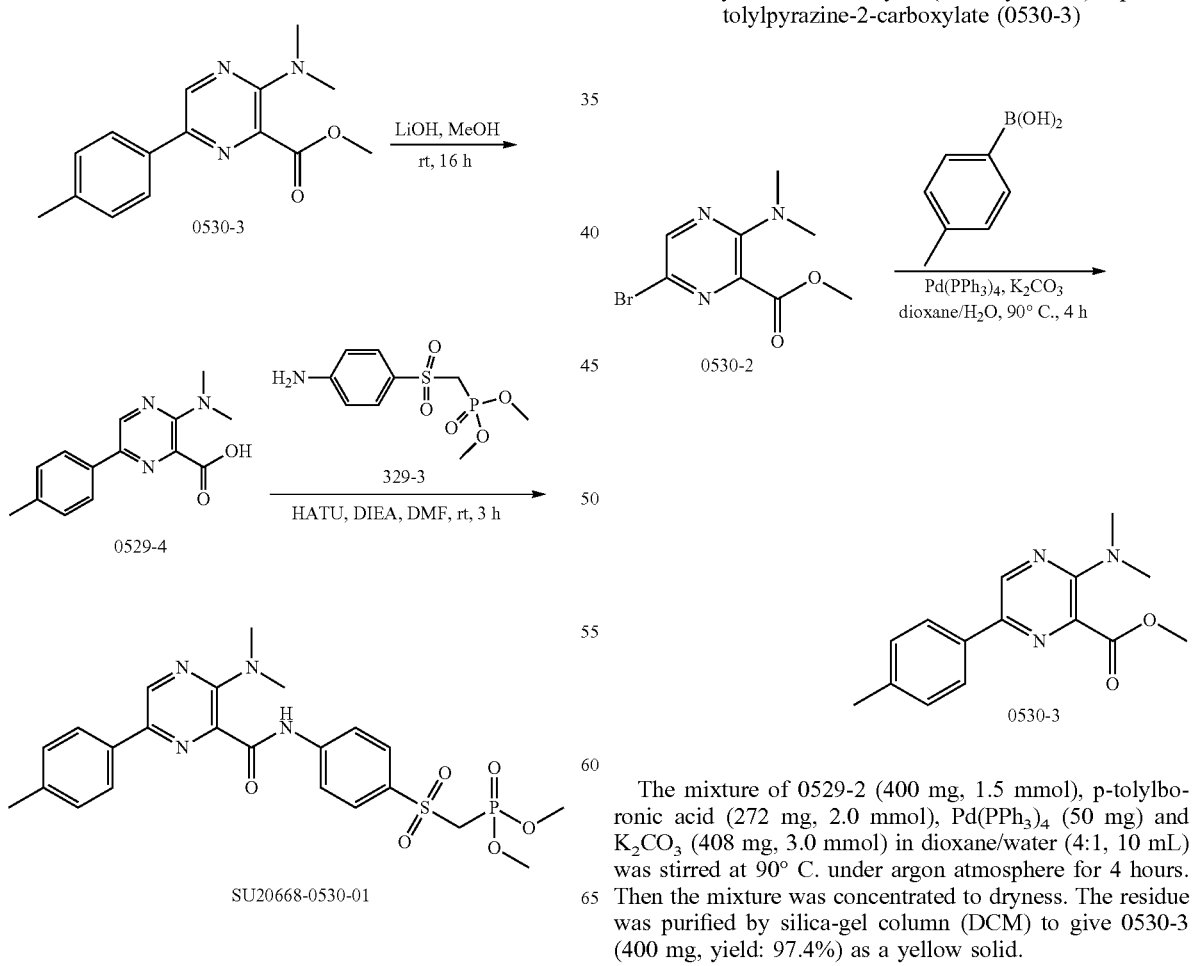

The mixture of 0529-2 (400 mg, 1.5 mmol), p-tolylboronic acid (272 mg, 2.0 mmol), Pd(PPh₃)₄ (50 mg) and K₂CO₃ (408 mg, 3.0 mmol) in dioxane/water (4:1, 10 mL) was stirred at 90° C. under argon atmosphere for 4 hours. Then the mixture was concentrated to dryness. The residue was purified by silica-gel column (DCM) to give 0530-3 (400 mg, yield: 97.4%) as a yellow solid.

The Synthesis of 3-(dimethylamino)-6-p-tolylpyrazine-2-carboxylic acid (0530-4)

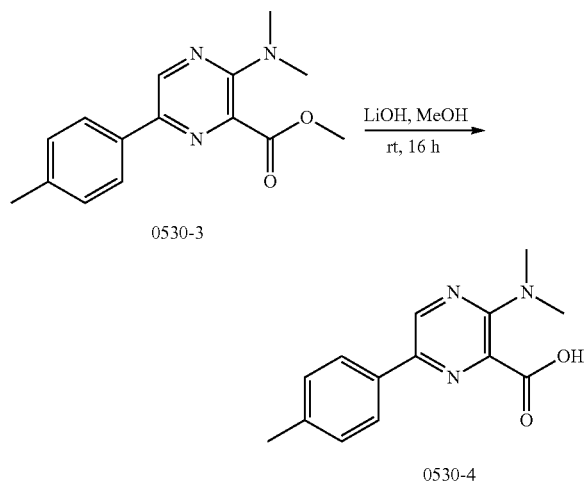

The mixture of 0530-3 (400 mg, 1.5 mmol) and LiOH (190 mg, 4.5 mmol) in methanol (6 mL) was stirred at room temperature for 16 hours. Then the reaction mixture was concentrated to 1 mL and acidified with HCl (1N) till pH=3~4. The solid was collected by filtration to afford 0530-4 (320 mg, yield: 84.7%) as a yellow solid.

The Synthesis of dimethyl (4-(3-(dimethylamino)-6-p-tolylpyrazine-2-carboxamido)phenylsulfonyl)methylphosphonate (SU20668-0530-01)

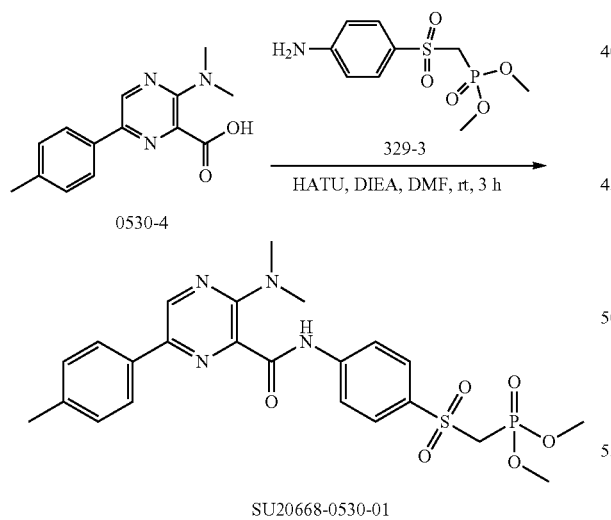

To a solution of compound 0530-4 (200 mg, 0.78 mmol) in DMF (4 mL) was added 329-3 (251 mg, 0.90 mmol), DIEA (258 mg, 2.0 mmol) and HATU (456 mg, 1.2 mmol). The resulting reaction mixture was stirred for 3 h at rt. Then the mixture was purified by prep-HPLC to give the desired product SU20668-0530-01 (25 mg, yield: 6.2%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 99.52%, Rt=2.114 min; MS Calcd.: 518.1; MS Found: 519.3 [M+H]$^+$. HPLC (Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min). Purity: 99.00%, Rt=9.985 min. $^1$H NMR (400 MHz, DMSO-$d_6$) δ 11.16 (s, 1H), 8.82 (s, 1H), 8.03-8.05 (m, 2H), 7.93-7.99 (m, 4H), 7.29 (d, J=8.0 Hz, 2H), 4.47 (d, J=17.2 Hz, 2H), 3.65 (d, J=11.2 Hz, 6H), 3.08 (s, 6H), 2.35 (s, 3H).

Scheme 99: Route for SU20668-0531-01

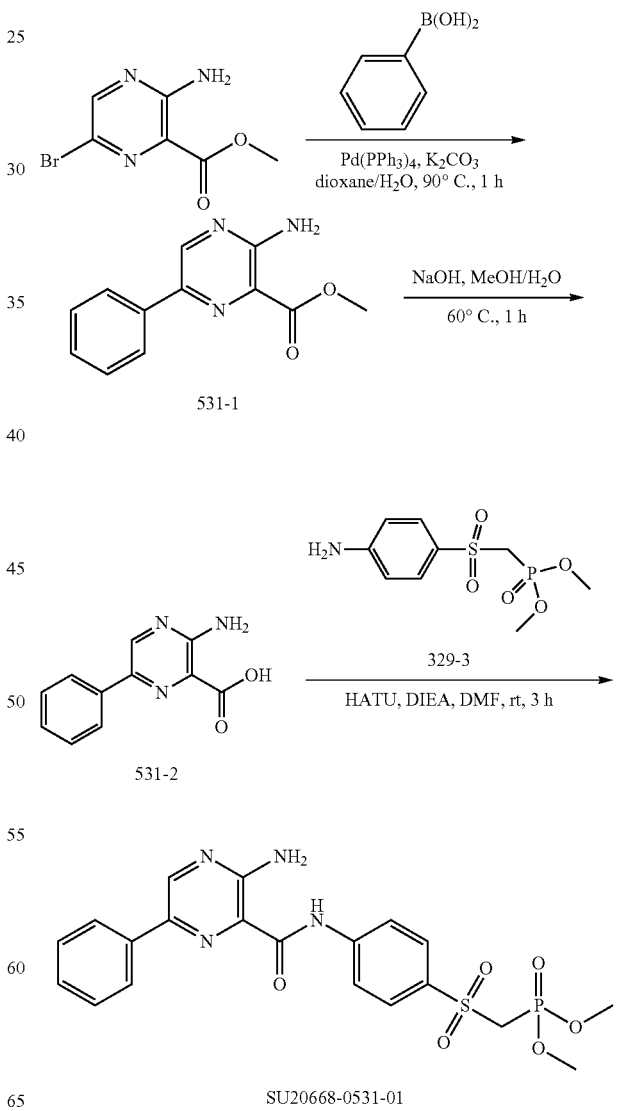

The Synthesis of methyl 3-amino-6-phenylpyrazine-2-carboxylate (531-1)

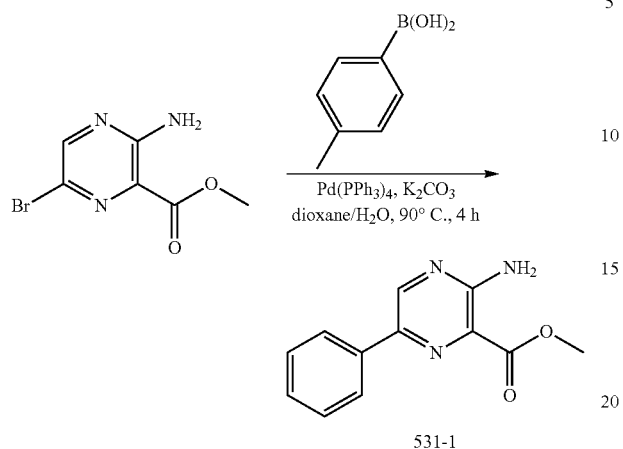

531-1

To a solution of methyl 3-amino-6-bromo-pyrazine-2-carboxylate (1.5 g, 6.46 mmol) in dioxane (40 mL) and water (10 mL) was added phenylboronic acid (945.86 mg, 7.76 mmol), $K_2CO_3$ (1.79 g, 12.93 mmol), $Pd(PPh_3)_4$ (746.66 mg, 646.46 umol). The resulting reaction mixture was heated to 90° C. and stirred for 1 h, concentrated and water was added, the solid was collected by filtration, washed with water, dried to give 531-1 (1.17 g, 79.22% yield) as a brown solid.

The Synthesis of 3-amino-6-phenylpyrazine-2-carboxylic acid (531-2)

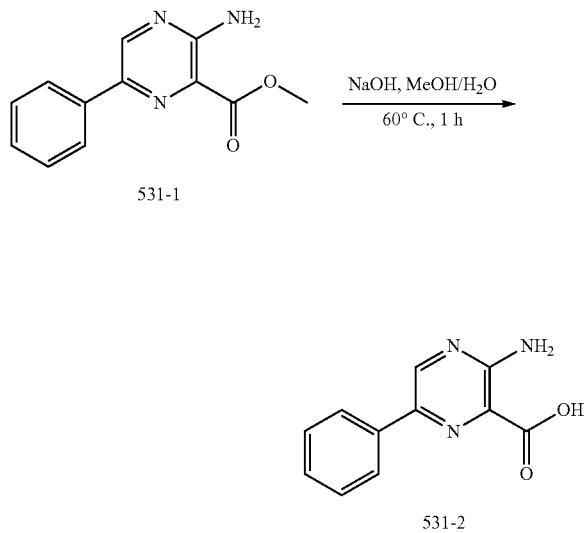

To a stirred solution of methyl 531-1 (1.17 g, 5.12 mmol) in MeOH (48 mL) was added NaOH (245.83 mg, 6.15 mmol) dissolved in $H_2O$ (6 mL), the solution was heated to 60° C. and stirred for 1 h, concentrated and added water, the solution was added HCl (1 N) until pH=4, the solid was collected by filtration and washed with water, dried to give 531-2 (0.994 g, 90.19% yield) as a yellow solid.

The Synthesis of dimethyl (4-(3-amino-6-phenylpyrazine-2-carboxamido)phenylsulfonyl)methylphosphonate (SU20668-0531-01)

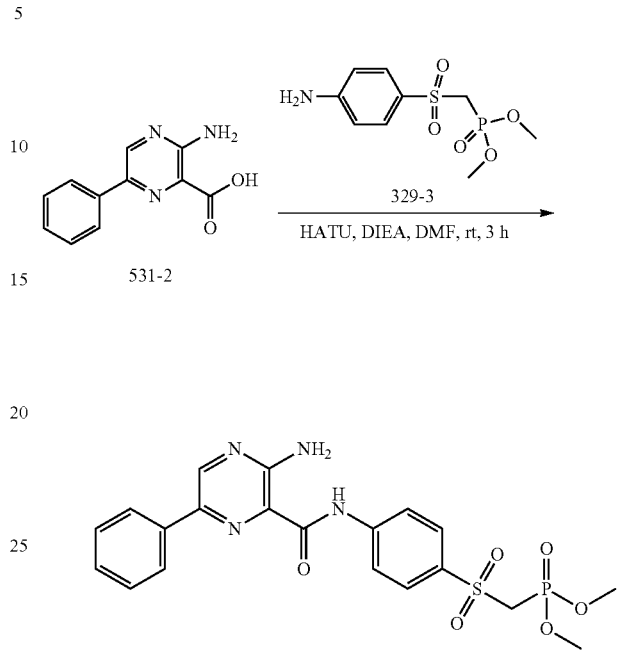

SU20668-0531-01

To a stirred solution of 531-2 (154.13 mg, 716.21 umol) in DMF (4 mL) was added 329-3 (200 mg, 716.21 umol), DIEA (277.69 mg, 2.15 mmol) and HATU (408.48 mg, 1.07 mmol). The resulting reaction mixture was stirred at rt for 3 h, purified by prep-HPLC to give SU20668-0531-01 (170 mg, 49.82% yield) as a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 100%, $R_t$=1.844 min; MS Calcd.: 476.09; MS Found: 477.1 [M+H]$^+$. HPLC (Agilent HPLC 1200, Column: L-column2 ODS (150 mm*4.6 mm*5.0 µm); Column Temperature: 40° C.; Flow Rate: 1.5 mL/min; Mobile Phase: from 90% [(total 10 mM $AcONH_4$) water/$CH_3CN$=900/100 (v/v)] and 10% [total 10 mM $AcONH_4$) water/$CH_3CN$=100/900 (v/v)] to 15% [total 10 mM $AcONH_4$) water/$CH_3CN$=900/100 (v/v)] and 85% [total 10 mM $AcONH_4$) water/$CH_3CN$=100/900 (v/v)] in 5 min, then under this condition for 10 min, finally changed to 90% [(total 10 mM $AcONH_4$) water/$CH_3CN$=900/100 (v/v)] and 10% [(total 10 mM $AcONH_4$) water/$CH_3CN$=100/900 (v/v)] in 0.1 min and under this condition for 5 min). Purity: 100%, Rt=8.850 min. $^1$H NMR (400 MHz, DMSO-$d_6$) δ 10.75 (s, 1H), 8.97 (s, 1H), 8.23-8.25 (m, 2H), 8.12-8.14 (m, 2H), 7.95-7.97 (m, 2H), 7.72 (s, 2H), 7.40-7.53 (m, 3H), 4.50 (d, J=17.2 Hz, 2H), 3.64 (d, J=11.6 Hz, 6H).

Scheme 100: Route for SU20668-0532-01

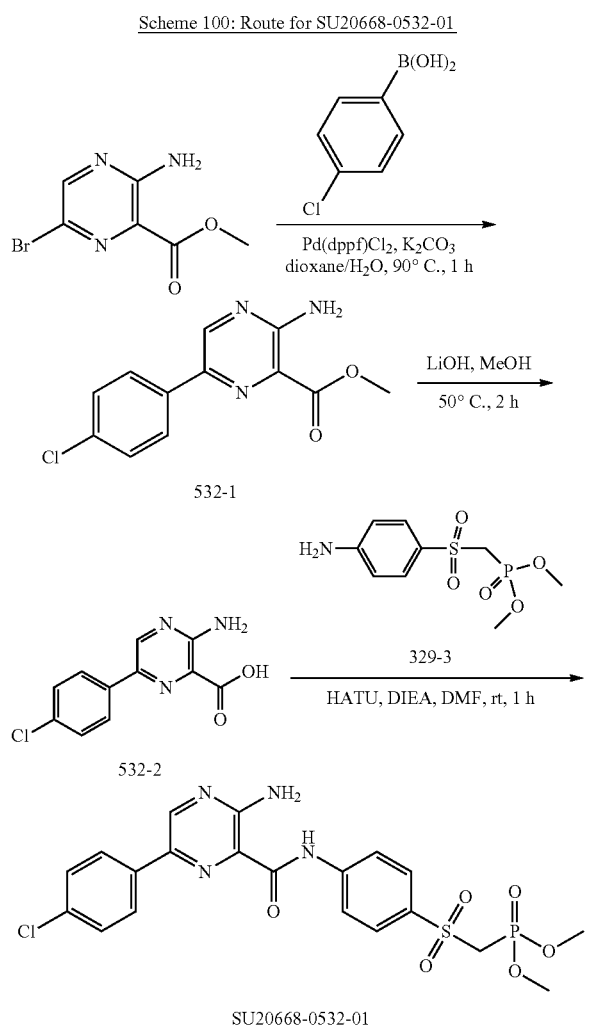

The Synthesis of methyl
3-amino-6-bromopyrazine-2-carboxylate (532-1)

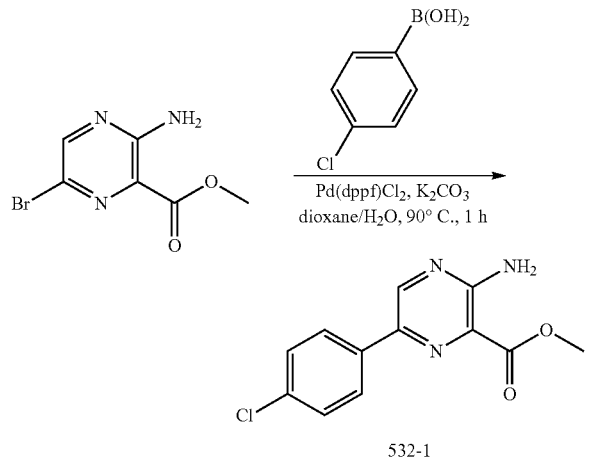

To a stirred solution of compound methyl 3-amino-6-bromopyrazine-2-carboxylate (3.0 g, 12.93 mmol) in dioxane/water (30 mL/3 mL) was added 4-chlorophenylboronic acid (2.5 g, 15.99 mmol), K₂CO₃ (5.0 g, 36.18 mmol), Pd(dppf)Cl₂(300 mg, 410 μmol). The resulting reaction mixture was heated to 90° C. under nitrogen and stirred for 1 h and concentrated in vacuo to remove the solvent, then added water, the aqueous phase was extracted with ethyl acetate, the combined organic phases was dried over anhydrous sodium sulfate, filtered, and concentrated, the crude was purified by prep-HPLC to give the desired product 532-1 (2.4 g, yield: 70%) as a white solid.

The Synthesis of 3-amino-6-(4-chlorophenyl)pyrazine-2-carboxylic acid (532-2)

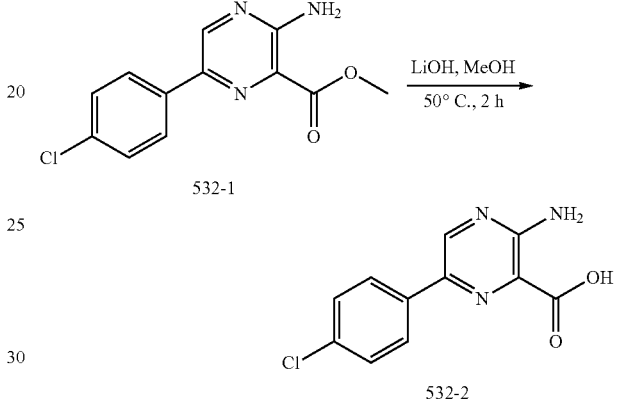

The mixture of 532-1 (2.4 g, 9.10 mmol) and LiOH (1.5 g, 35.75 mmol) in Methanol (25 mL) was stirred at 50° C. for 2 h. Then the reaction mixture was acidified with 1M HCl aq till pH reached to 2.0. The resulting mixture was extracted with ethyl acetate (50 mL×3). The organic layers were washed with brine, dried over Na₂SO₄ and concentrated to give 532-2 (2.0 g, 88% yield) as a yellow solid.

The Synthesis of dimethyl (4-(3-amino-6-(4-chlorophenyl)pyrazine-2-carboxamido)phenylsulfonyl)methylphosphonate (SU20668-0532-01)

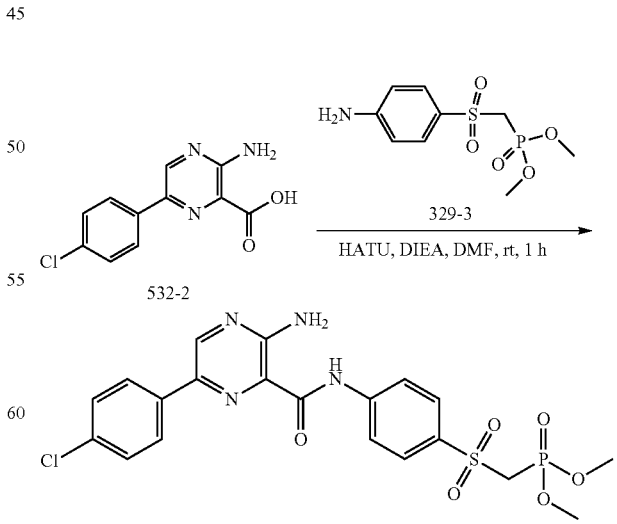

To a solution of compound 532-2 (200 mg, 801 µmol) in DMF (3 mL) was added HATU (350 mg, 915 µmol), DIEA (223 mg, 1.7 mmol) and 329-3 (250 mg, 895 µmol). The mixture was stirred at rt for 1 h. After the reaction was finished (by LCMS), the reaction solvent was removed in vacuo, the crude was purified directly by prep-HPLC to get the desired product SU20668-0532-01 (70 mg, yield: 17%) as a yellow solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min, Purity: 100.00%, Rt=2.000 min; MS Calcd.: 510.1; MS Found: 511.0 [M+H]$^+$. Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min, Purity:98.57%, Rt=9.513 min. $^1$H NMR (400 MHz, DMSO-d$_6$) δ 10.76 (s, 1H), 8.99 (s, 1H), 8.29 (d, J=8.4 Hz, 2H), 8.12 (d, J=8.8 Hz, 2H), 7.96 (d, J=9.2 Hz, 2H), 7.77 (s, 2H), 7.55 (d, J=8.8 Hz, 2H), 4.50 (d, J=17.2 Hz, 2H), 3.64 (d, J=11.2 Hz, 6H).

Scheme 101: Route for SU20668-0533-01

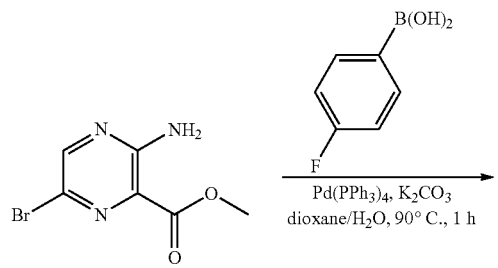

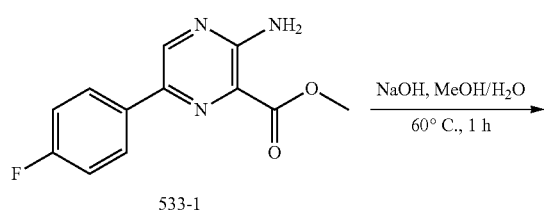

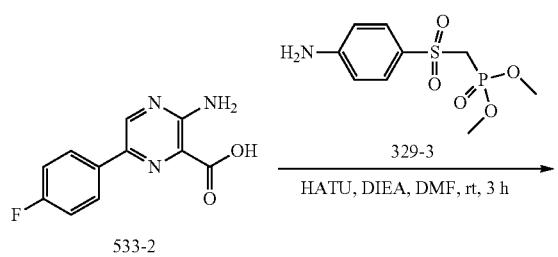

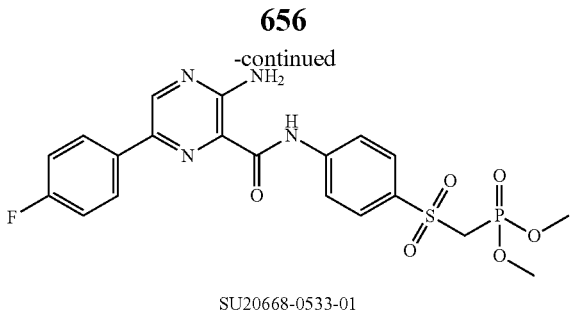

SU20668-0533-01

The Synthesis of methyl 3-amino-6-(4-fluorophenyl)pyrazine-2-carboxylate (533-1)

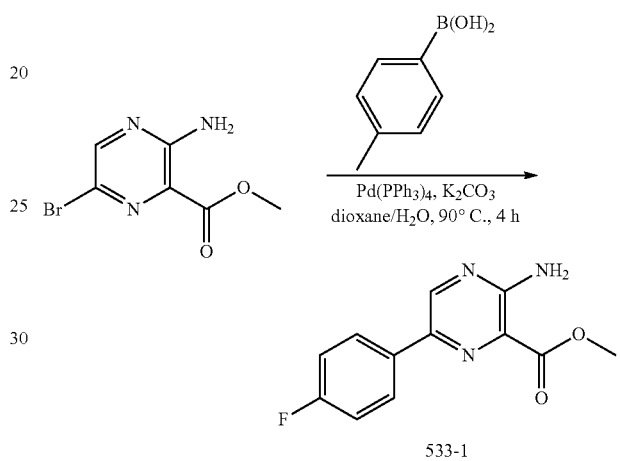

To a solution of methyl 3-amino-6-bromo-pyrazine-2-carboxylate (1.5 g, 6.46 mmol) in dioxane (40 mL) and Water (10 mL) was added (4-fluorophenyl)boronic acid (1.09 g, 7.76 mmol), K$_2$CO$_3$ (1.79 g, 12.93 mmol) and Pd(PPh$_3$)$_4$ (746.66 mg, 646.46 umol). The resulting reaction mixture was heated to 90° C. and stirred for 1 h, concentrated and water was added, the solid was collected by filtration, washed with water, dried to give 533-1 (1.33 g, 83.28% yield) as a brown solid.

The Synthesis of 3-amino-6-(4-fluorophenyl)pyrazine-2-carboxylic acid (533-2)

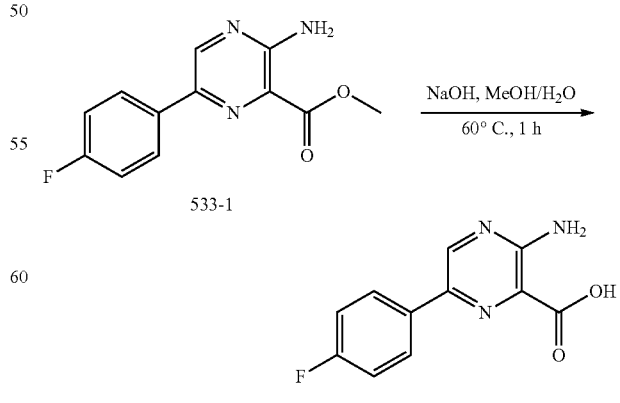

To a stirred solution of 533-1(1.33 g, 5.38 mmol) in MeOH (56 mL) was added NaOH (258.42 mg, 6.46 mmol) dissolved in H₂O (7 mL), the solution was heated to 60° C. and stirred for 1 h, concentrated and added water, the solution was added HCl (1 N) until pH=4, the solid was collected by filtration and washed with water, dried to give 533-2 (1.24 g, 98.37% yield) as a yellow solid.

The Synthesis of dimethyl (4-(3-amino-6-(4-fluoro-phenyl)pyrazine-2-carboxamido)phenylsulfonyl)methylphosphonate (SU20668-0533-01)

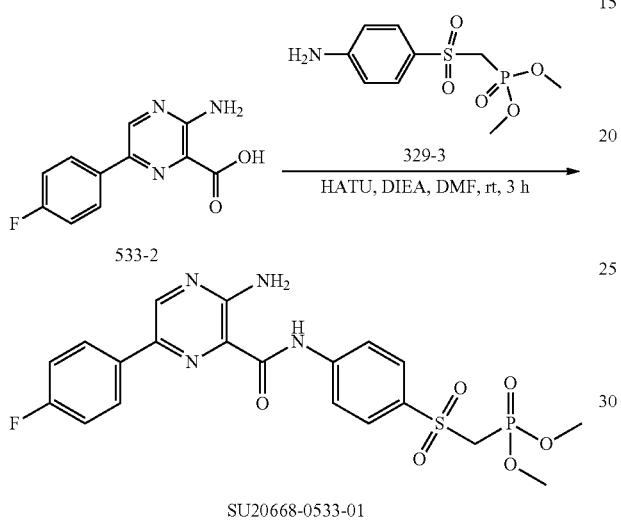

To a stirred solution of 329-3 (200 mg, 716.21 umol) in DMF (3 mL) was added 533-2 (167.02 mg, 716.21 umol), DIPEA (277.69 mg, 2.15 mmol) and HATU (408.48 mg, 1.07 mmol). The resulting reaction mixture was stirred at rt for 3 h, purified with prep-HPLC to give SU20668-0533-01 (157 mg, 44.34% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 100%, R$_t$=1.875 min; MS Calcd.: 494.08; MS Found: 495.1 [M+H]⁺. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM AcONH₄) water/CH₃CN=900/100 (v/v)] and 10% [total 10 mM AcONH₄) water/CH₃CN=100/900 (v/v)] to 15% [total 10 mM AcONH₄) water/CH₃CN=900/100 (v/v)] and 85% [total 10 mM AcONH₄) water/CH₃CN=100/900 (v/v)] in 5 min, then under this condition for 10 min, finally changed to 90% [(total 10 mM AcONH₄) water/CH₃CN=900/100 (v/v)] and 10% [total 10 mM AcONH₄) water/CH₃CN=100/900 (v/v)] in 0.1 min and under this condition for 5 min). Purity: 99.73%, Rt=8.990 min. ¹H NMR (400 MHz, DMSO-d₆) δ 10.76 (s, 1H), 8.95 (s, 1H), 8.29-8.33 (m, 2H), 8.12-8.14 (m, 2H), 7.95-7.97 (m, 2H), 7.72 (s, 2H), 7.34 (t, J=8.8 Hz, 2H), 4.50 (d, J=17.2 Hz, 2H), 3.64 (d, J=11.2 Hz, 6H).

Scheme 102: Route for SU20668-0534-01

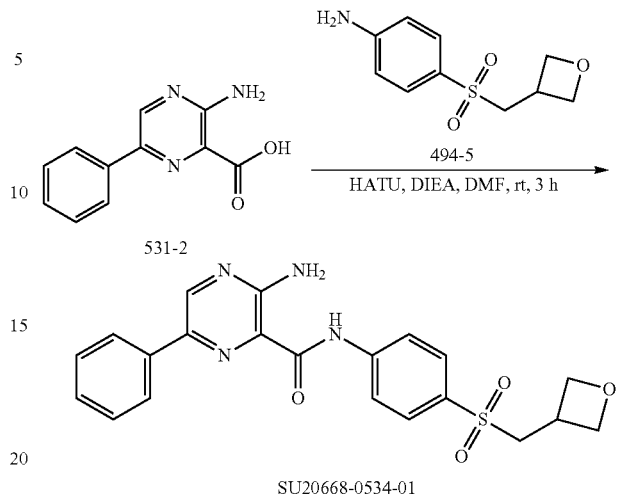

The Synthesis of 3-amino-N-(4-(oxetan-3-ylmethyl-sulfonyl)phenyl)-6-phenylpyrazine-2-carboxamide (SU20668-0534-01)

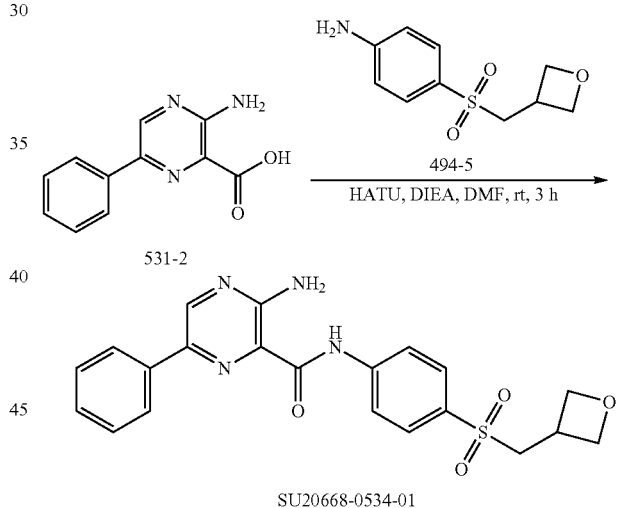

To a stirred solution of 531-2 (236.72 mg, 1.10 mmol) in DMF (4 mL) was added 494-5 (250 mg, 1.10 mmol), DIEA (426.48 mg, 3.30 mmol) and HATU (627.36 mg, 1.65 mmol). The resulting reaction mixture was stirred at rt for 3 h, purified by prep-HPLC to give SU20668-0534-01 (147 mg, 31.48% yield) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 100%, R$_t$=1.918 min; MS Calcd.: 424.12; MS Found: 425.1 [M+H]⁺. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM AcONH₄) water/CH₃CN=900/100 (v/v)] and 10% [total 10 mM AcONH₄) water/CH₃CN=100/900 (v/v)] to 15% [total 10 mM AcONH₄) water/CH₃CN=900/100 (v/v)] and 85% [total 10 mM AcONH₄) water/CH₃CN=100/900 (v/v)] in 5 min, then under this condition for 10 min, finally changed to 90% [(total 10 mM AcONH₄) water/CH₃CN=900/100 (v/v)] and 10% [total 10 mM AcONH₄) water/CH₃CN=100/900 (v/v)] in 0.1 min and under this condition for 5 min). Purity: 98.08%, Rt=9.212 min. $^1$H NMR (400 MHz, DMSO-$d_6$) δ 10.77 (s, 1H), 8.97 (s, 1H), 8.23-8.25 (m, 2H), 8.14-8.17 (m, 2H), 7.88-7.90 (m, 2H), 7.71 (s, 2H), 7.49-7.53 (m, 2H), 7.40-7.44 (m, 1H), 4.54 (t, J=6.0 Hz, 2H), 4.31 (t, J=6.8 Hz, 2H), 3.75 (d, J=7.6 Hz, 2H), 3.27-3.33 (m, 1H).

Scheme 103: Route for SU20668-0535-01

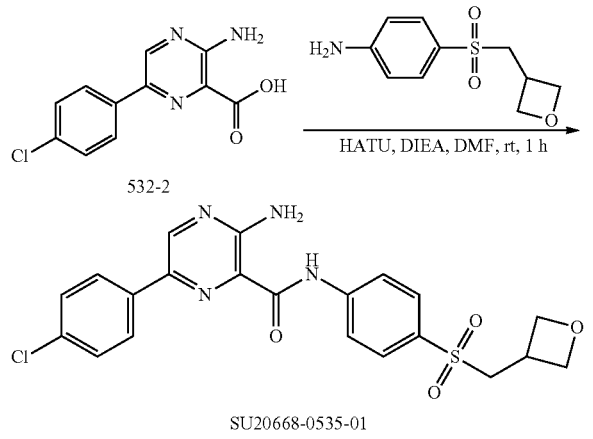

The Synthesis of methyl 3-amino-6-(4-chlorophenyl)-N-(4-(oxetan-3-ylmethylsulfonyl)phenyl)pyrazine-2-carboxamide (SU20668-0535-01)

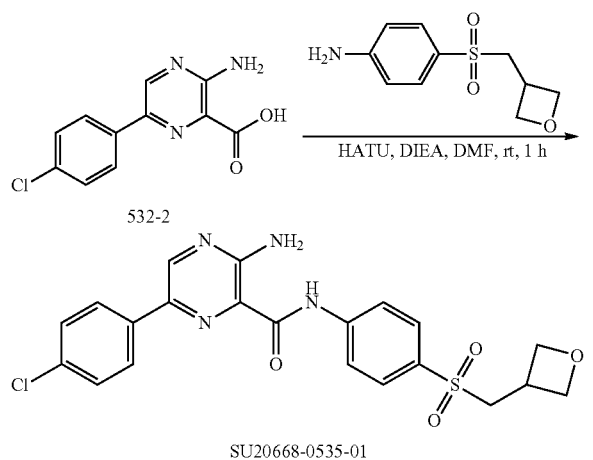

To a solution of compound 532-2 (200 mg, 801 μmol) in DMF (3 mL) was added HATU (350 mg, 915 μmol), DIEA (223 mg, 1.7 mmol) and 329-3 (200 mg, 895 μmol). The mixture was stirred at rt for 1 h. After the reaction was finished (by LCMS), the reaction solvent was removed in vacuo, the crude was purified directly by prep-HPLC to get the desired product SU20668-0535-01 (50 mg, yield: 17%) as a yellow solid. Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05% TFA] in 1.6 min, then under this condition for 1.4 min, finally changed to 95% [water+0.05% TFA] and 5% [CH₃CN+0.05% TFA] in 0.05 min and under this condition for 0.7 min, Purity: 97.32%, Rt=1.839 min; MS Calcd.: 458.1; MS Found: 459.0 [M+H]⁺. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min, Purity:100.00%, Rt=9.882 min. $^1$H NMR (400 MHz, DMSO-$d_6$) δ 10.78 (s, 1H), 8.99 (s, 1H), 8.29 (d, J=8.8 Hz, 2H), 8.14 (d, J=8.8 Hz, 2H), 7.89 (d, J=8.8 Hz, 2H), 7.77 (s, 2H), 7.56 (d, J=8.8 Hz, 2H), 8.14 (d, J=8.8 Hz, 2H), 4.31 (t, J=6.4 Hz, 2H), 3.75 (d, J=7.2 Hz, 2H), 3.26-3.33 (m, 1H).

Scheme 104: Route for SU20668-0536-01

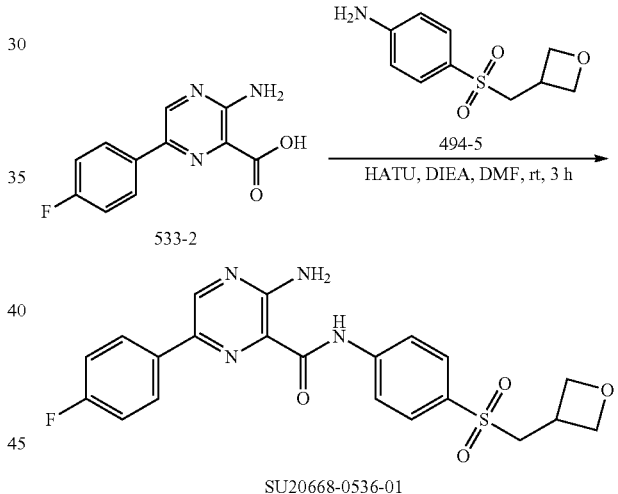

The Synthesis of 3-amino-6-(4-fluorophenyl)-N-(4-(oxetan-3-ylmethylsulfonyl)phenyl)pyrazine-2-carboxamide (SU20668-0536-01)

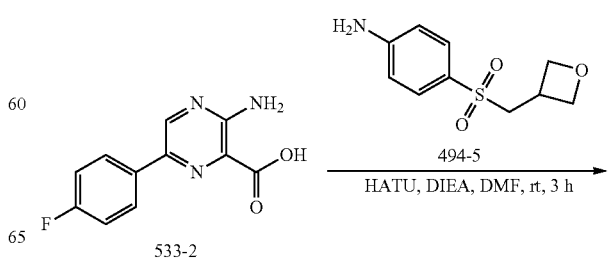

-continued

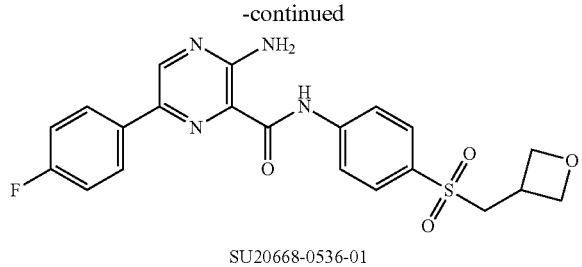

SU20668-0536-01

To a stirred solution of 533-2 (256.51 mg, 1.10 mmol) in DMF (4 mL) was added 494-5 (250 mg, 1.10 mmol), DIEA (426.48 mg, 3.30 mmol) and HATU (627.36 mg, 1.65 mmol). The resulting reaction mixture was stirred at rt for 3 h, purified by pre-HPLC to give SU20668-0536-01 (233 mg, 47.87% yield) as a yellow solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, R$_t$=1.944 min; MS Calcd.: 442.11; MS Found: 443.1 [M+H]$^+$. HPLC (Agilent HPLC 1200, Column: L-column2 ODS (150 mm*4.6 mm*5.0 µm); Column Temperature: 40° C.; Flow Rate: 1.5 mL/min; Mobile Phase: from 90% [(total 10 mM AcONH$_4$) water/CH$_3$CN=900/100 (v/v)] and 10% [total 10 mM AcONH$_4$) water/CH$_3$CN=100/900 (v/v)] to 15% [total 10 mM AcONH$_4$) water/CH$_3$CN=900/100 (v/v)] and 85% [total 10 mM AcONH$_4$) water/CH$_3$CN=100/900 (v/v)] in 5 min, then under this condition for 10 min, finally changed to 90% [(total 10 mM AcONH$_4$) water/CH$_3$CN=900/100 (v/v)] and 10% [total 10 mM AcONH$_4$) water/CH$_3$CN=100/900 (v/v)] in 0.1 min and under this condition for 5 min). Purity: 99.35%, Rt=9.318 min. $^1$H NMR (400 MHz, DMSO-d$_6$) δ 10.77 (s, 1H), 8.96 (s, 1H), 8.29-8.32 (m, 2H), 8.14-8.16 (m, 2H), 7.88-7.90 (m, 2H), 7.71 (s, 2H), 7.34 (t, J=8.8 Hz, 2H), 4.54 (t, J=6.0 Hz, 2H), 4.31 (t, J=6.4 Hz, 2H), 3.75 (d, J=7.2 Hz, 2H), 3.27-3.31 (m, 1H).

Scheme 105: Route for SU20668-0538-01

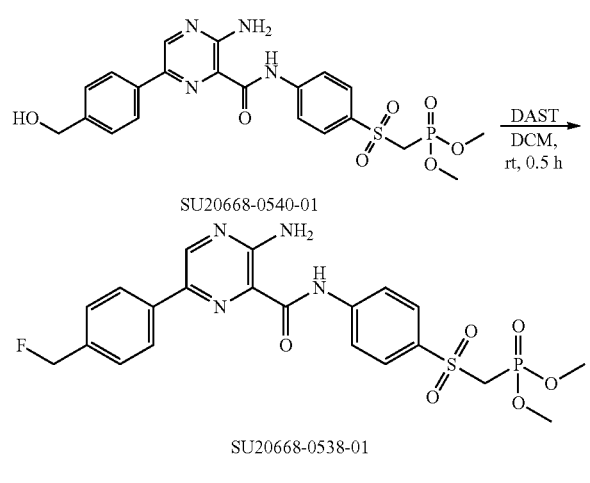

The Synthesis of dimethyl (4-(3-amino-6-(4-(fluoromethyl)phenyl)pyrazine-2-carboxamido)phenylsulfonyl)methylphosphonate (SU20668-0538-01)

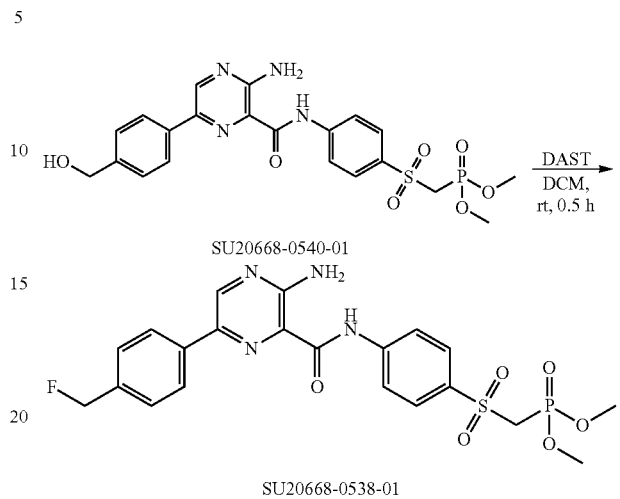

To a solution of SU20668-0540-01 (130 mg, 256.68 µmol) in DCM (1 mL) was added in DAST (530 mg, 3.29 mmol, 0.4 mL) at rt. After the reaction was finished (by LCMS), the reaction solvent was removed in vacuo, the crude was purified directly by prep-HPLC to get the desired product SU20668-0538-01 (30 mg, yield: 23%) as a yellow solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min, Purity: 100.00%, Rt=1.841 min; MS Calcd.: 508.1; MS Found: 509.2 [M+H]$^+$. Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min, Purity:100.00%, Rt=8.858 min. $^1$H NMR (400 MHz, DMSO-d$_6$) δ 10.76 (s, 1H), 9.00 (s, 1H), 8.29 (d, J=8.0 Hz, 2H), 8.13 (d, J=8.4 Hz, 2H), 7.96 (d, J=8.8 Hz, 2H), 7.76 (s, 2H), 7.56 (d, J=7.6 Hz, 2H), 5.50 (d, J=48.0 Hz, 2H), 4.51 (d, J=17.2 Hz, 2H), 3.64 (d, J=11.6 Hz, 6H).

Scheme 106: Route for SU20668-0539-01

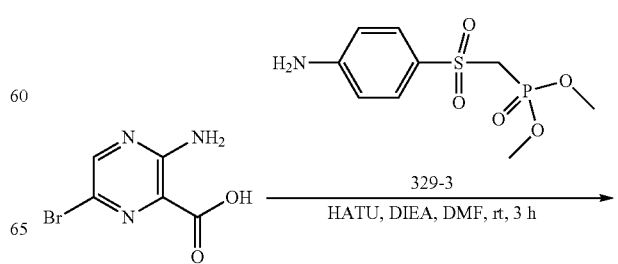

663

-continued

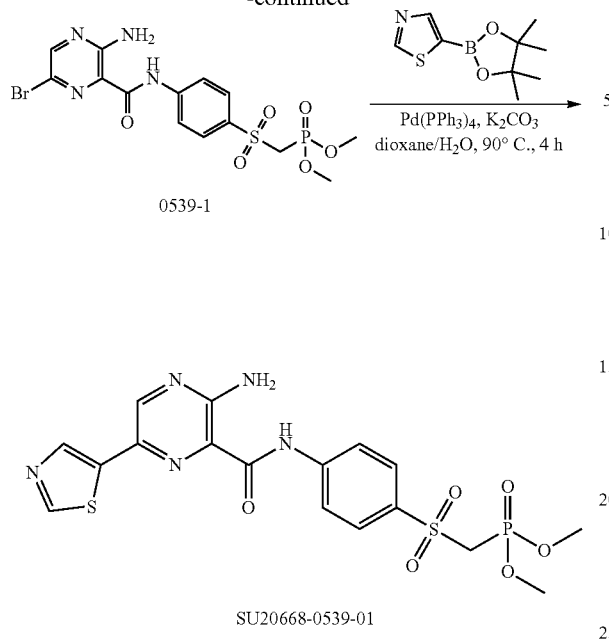

The Synthesis of dimethyl (4-(3-amino-6-bromopyrazine-2-carboxamido)phenylsulfonyl)methylphosphonate (0539-1)

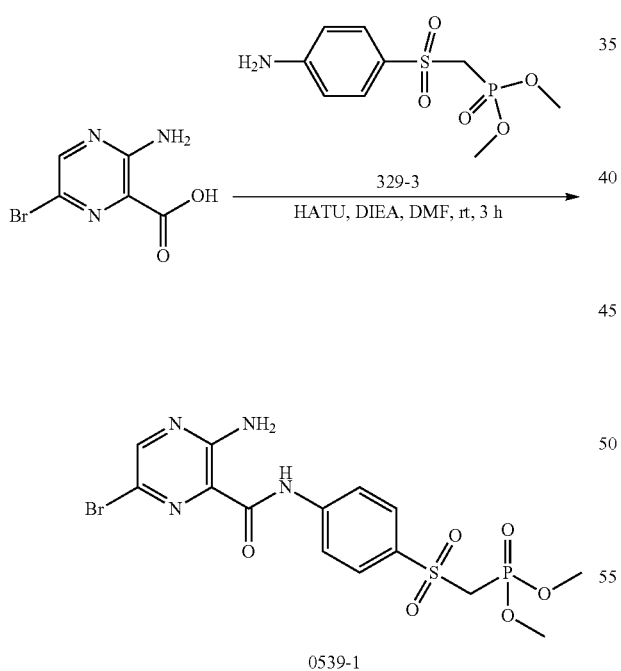

To a solution of 3-amino-6-bromopyrazine-2-carboxylic acid (500 mg, 2.3 mmol) in DMF (6 mL) was added 329-3 (642 mg, 2.3 mmol), DIEA (645 mg, 5.0 mmol) and HATU (1140 mg, 3.0 mmol). The resulting reaction mixture was stirred for 3 h at rt. Then the mixture was purified by prep-HPLC to give the desired product 0539-01 (500 mg, yield: 45.5%) as a yellow solid.

664

The Synthesis of dimethyl (4-(3-amino-6-(thiazol-5-yl)pyrazine-2-carboxamido)phenylsulfonyl)methylphosphonate (SU20668-0539-01)

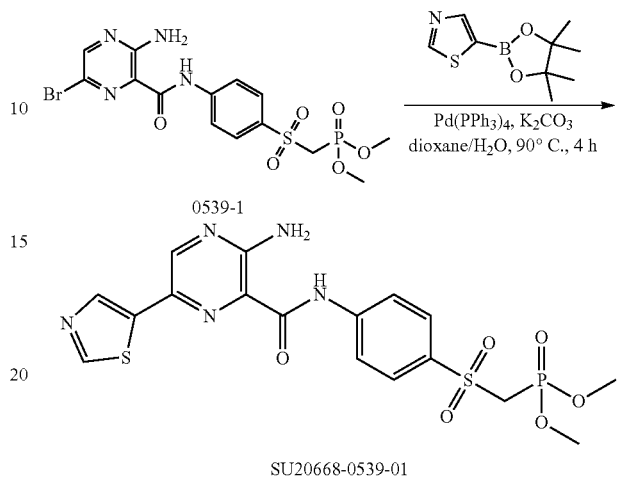

The mixture of methyl 0539-1 (450 mg, 0.94 mmol), 5-(4,4,5,5-tetramethyl-1,3,2-dioxaborolan-2-yl)thiazole (163 mg, 1.2 mmol), Pd(PPh$_3$)$_4$ (50 mg) and K$_2$CO$_3$ (272 mg, 2.0 mmol) in dioxane/water (4:1, 6 mL) was stirred at 90° C. under argon atmosphere for 4 hours. Then the mixture was concentrated to dryness. The residue was purified by prep-HPLC to give SU20668-0539-01 (20 mg, yield: 4.5%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 97.21%, Rt=1.549 min; MS Calcd.: 483.0; MS Found: 484.2 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 96.22%, Rt=7.036 min. $^1$H NMR (400 MHz, DMSO-d$_6$) δ 10.61 (s, 1H), 9.14 (s, 1H), 8.90 (s, 1H), 8.67 (s, 1H), 8.08 (d, J=8.8 Hz, 2H), 7.95 (d, J=8.8 Hz, 2H), 7.82 (s, 2H), 4.50 (d, J=17.2 Hz, 2H), 3.63 (d, J=11.2 Hz, 6H).

Scheme 107: Route for SU20668-0540-01

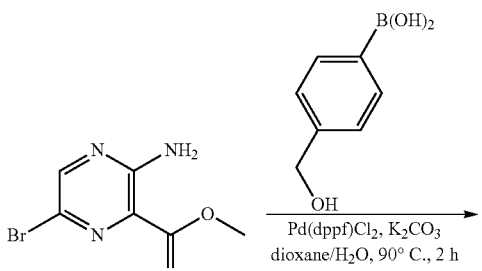

665

-continued

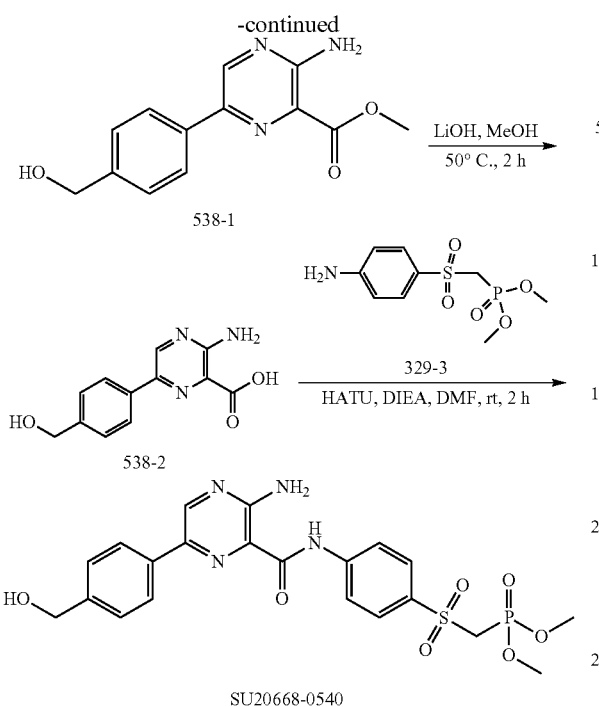

538-1

538-2

SU20668-0540

The Synthesis of methyl 3-amino-6-(4-(hydroxymethyl)phenyl)pyrazine-2-carboxylate (538-1)

538-1

To a stirred solution of compound methyl 3-amino-6-bromopyrazinate-2-carboxylate (2.0 g, 8.62 mmol) in dioxane/water (20 mL/2 mL) was added 4-(hydroxymethyl)phenylboronic acid (1.5 g, 9.87 mmol), K$_2$CO$_3$ (3.0 g, 21.71 mmol), Pd(dppf)Cl$_2$(200 mg, 273 μmol). The resulting reaction mixture was heated to 90° C. under nitrogen and stirred for 2 h and concentrated in vacuo to remove the solvent, then added water, the aqueous phase was extracted with ethyl acetate, the combined organic phases was dried over anhydrous sodium sulfate, filtered, and concentrated, the crude was purified by prep-HPLC to give the desired product 538-1 (1.0 g, yield: 45%) as a yellow solid.

666

The Synthesis of 3-amino-6-(4-(hydroxymethyl)phenyl)pyrazine-2-carboxylic acid (538-2)

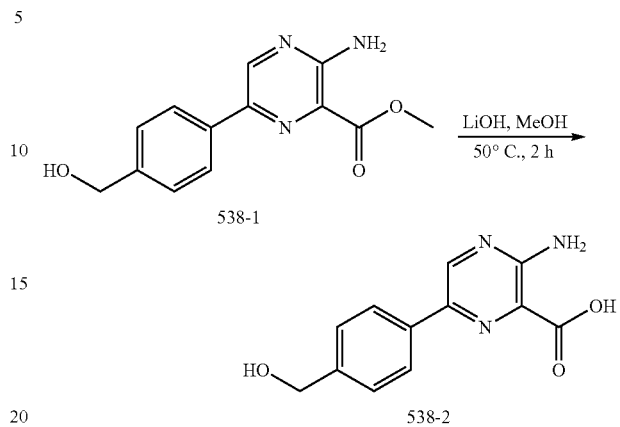

The mixture of 538-1 (1.0 g, 3.86 mmol) and LiOH (1.0 g, 23.83 mmol) in Methanol (10 mL) was stirred at 50° C. for 2 h. Then the reaction mixture was acidified with 1M HCl aq till pH reached to 2.0. The resulting mixture was extracted with ethyl acetate (50 mL×3). The organic layers were washed with brine, dried over Na$_2$SO$_4$ and concentrated to give 538-2 (900 mg, 95% yield) as a yellow solid.

The Synthesis of dimethyl (4-(3-amino-6-(4-(hydroxymethyl)phenyl)pyrazine-2-carboxamido)phenylsulfonyl)methylphosphonate (SU20668-0540-01)

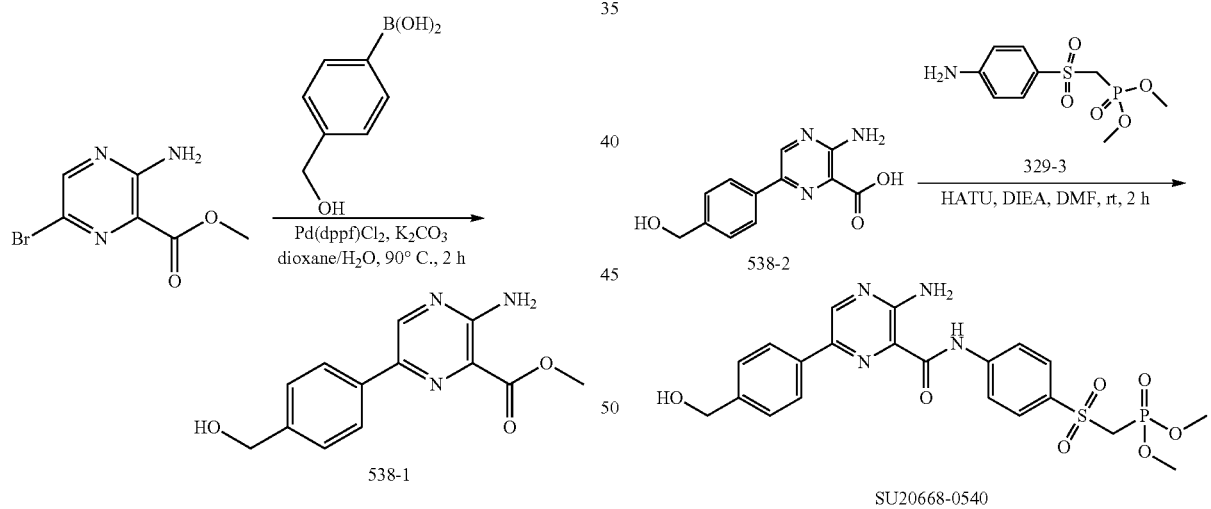

To a solution of compound 538-2 (300 mg, 1.2 mmol) in DMF (5 mL) was added HATU (500 mg, 1.31 mmol), DIPEA (371 mg, 2.87 mmol) and 329-3 (350 mg, 1.25 mmol). The mixture was stirred at rt for 2 h. After the reaction was finished (by LCMS), the reaction solvent was removed in vacuo, the crude was purified directly by prep-HPLC to get the desired product SU20668-0540-01 (300 mg, yield: 48%) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100%

[CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min, Purity: 100.00%, Rt=1.533 min; MS Calcd.: 506.1; MS Found: 507.0 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min, Purity:100.00%, Rt=7.249 min. $^1$H NMR (400 MHz, DMSO-d$_6$) δ 10.74 (s, 1H), 8.96 (s, 1H), 8.21 (d, J=7.2 Hz, 2H), 8.14 (d, J=7.6 Hz, 2H), 7.97 (d, J=7.6 Hz, 2H), 7.70 (s, 2H), 7.45 (d, J=7.6 Hz, 2H), 5.26-5.29 (m, 1H), 4.58 (d, J=5.6 Hz, 2H), 4.50 (d, J=17.2 Hz, 2H), 3.64 (d, J=11.2 Hz, 6H).

Scheme 155: Route for SU20668-0371

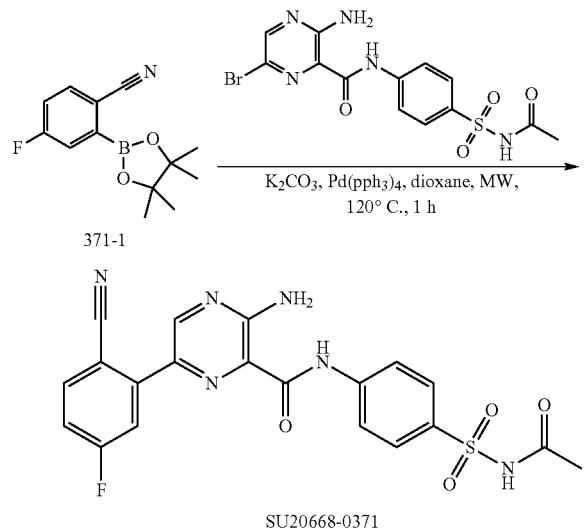

The Synthesis of N-(4-(N-acetylsulfamoyl)phenyl)-3-amino-6-(2-cyano-5-fluorophenyl)pyrazine-2-carboxamide (SU20668-0371)

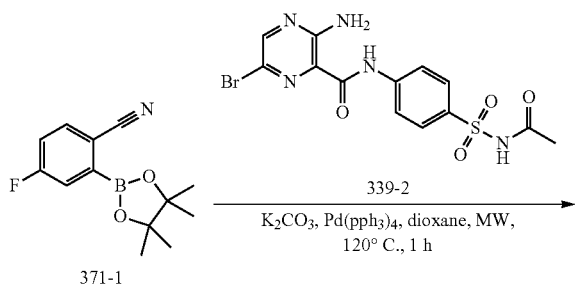

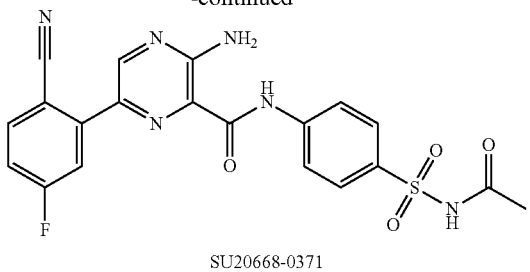

SU20668-0371

To a stirred solution of compound 371-1 (106 mg, 0.43 mmol) in dioxane (5 mL) was added 339-2 (150 mg, 0.36 mmol), K$_2$CO$_3$ (124 mg, 0.9 mmol), Pd(pph$_3$)$_4$ (15 mg, 0.10 mmol). The resulting reaction mixture was irradiated with microwave radiation at 120° C. for 1 h under Ar atmosphere, then concentrated in vacuo to remove the solvent, added water, the aqueous phase was extracted with dichloromethane, the combined organic phases were dried over anhydrous sodium sulfate, filtered, and concentrated, the crude was purified by prep-HPLC to give the desired product SU20668-0371 (20 mg, yield: 10.2%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 98.20%, Rt=1.508 min; MS Calcd.: 454.0; MS Found: 455.2 [M+H]$^+$. HPLC (Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 98.53%, Rt=6.575 min. $^1$H NMR (400 MHz, DMSO-d$_6$) δ 12.04 (s, 1H), 10.47 (s, 1H), 9.05 (s, 1H), 8.08-8.21 (m, 4H), 7.90-8.00 (m, 4H), 7.48-7.52 (m, 1H), 1.89 (s, 3H).

Example 2: Synthetic Methods for PYP Analogs

Scheme 108: Route for SU20668-0264-01

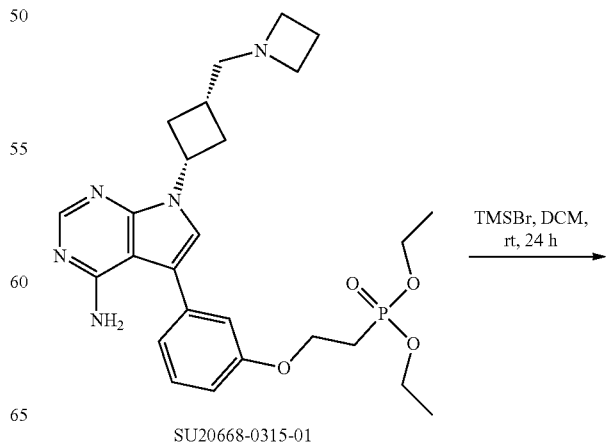

SU20668-0315-01

-continued

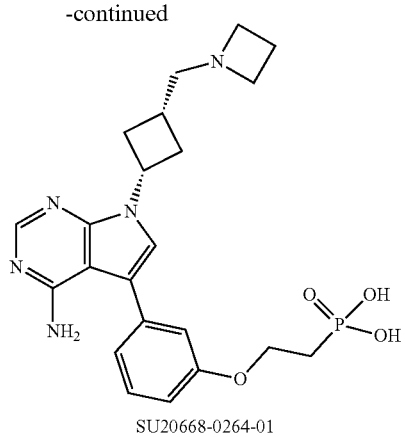

SU20668-0264-01

The Synthesis of(2-(3-(4-amino-7-(cis-3-(azetidin-1-ylmethyl)cyclobutyl)-7H-pyrrolo[2,3-d]pyrimidin-5-yl)phenoxy)ethyl)phosphonic acid (SU20668-0264-01)

To a solution of SU20668-0315-01 (150 mg, 0.29 mmol) in DCM (3.0 mL) was added TMSBr (134 mg, 0.87 mmol) dropwise. Then it was stirred at rt for 24 h. Remove the solvent in vacuo. The residue was purified by prep-HPLC to afford SU20668-0264-01 (12 mg, yield: 9.1%) as a white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 98.32%, Rt=1.022 min; MS Calcd.: 457.1; MS Found: 458.2 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 97.76%, Rt=3.752 min. $^1$H NMR (400 MHz, MeOD-d$_4$) δ 8.03 (s, 1H), 7.38 (s, 1H), 7.26 (t, J=8.0 Hz, 1H), 6.99-7.00 (m, 1H), 6.94 (d, J=7.2 Hz, 1H), 6.85 (dd, J=8.4 Hz, J=2.0 Hz, 1H), 5.04-5.06 (m, 1H), 4.20-4.26 (m, 2H), 4.03 (t, J=8.0 Hz, 4H), 3.25-3.27 (m, 2H), 2.61-2.64 (m, 2H), 2.29-2.42 (m, 5H), 2.00-2.09 (m, 2H).

Scheme 109: Route for SU20668-0265

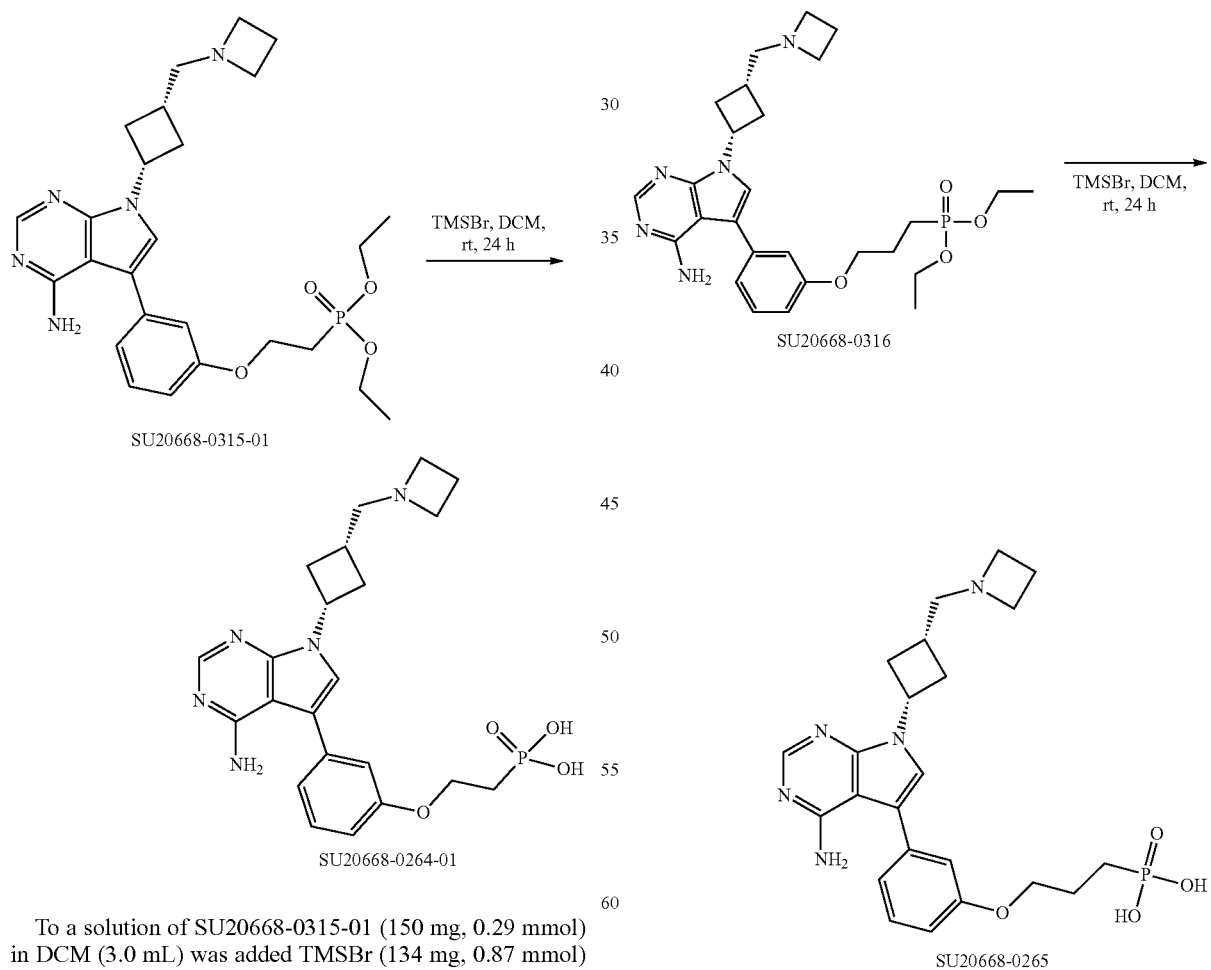

The Synthesis of 3-(3-(4-amino-7-((1s,3s)-3-(azetidin-1-ylmethyl)cyclobutyl)-7H-pyrrolo[2,3-d]pyrimidin-5-yl)phenoxy)propylphosphonic acid (SU20668-0265)

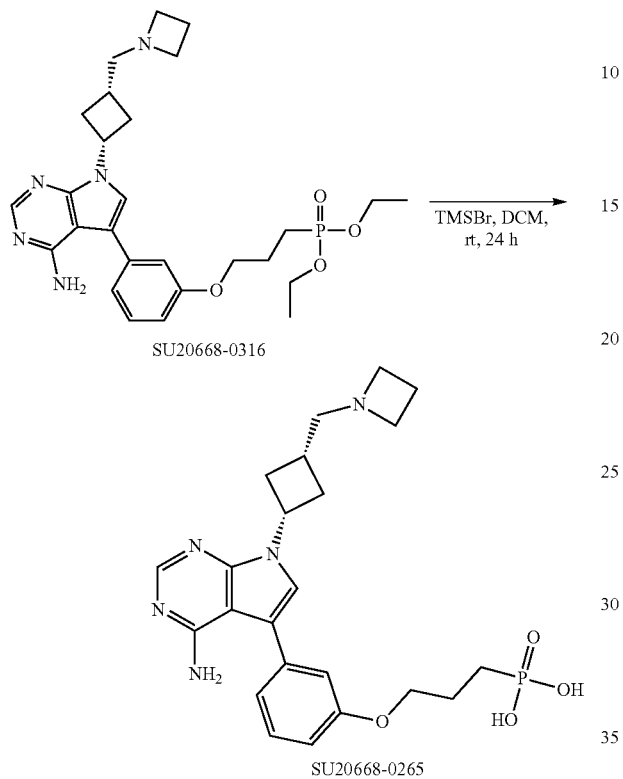

Scheme 110: Route for SU20668-0266-01

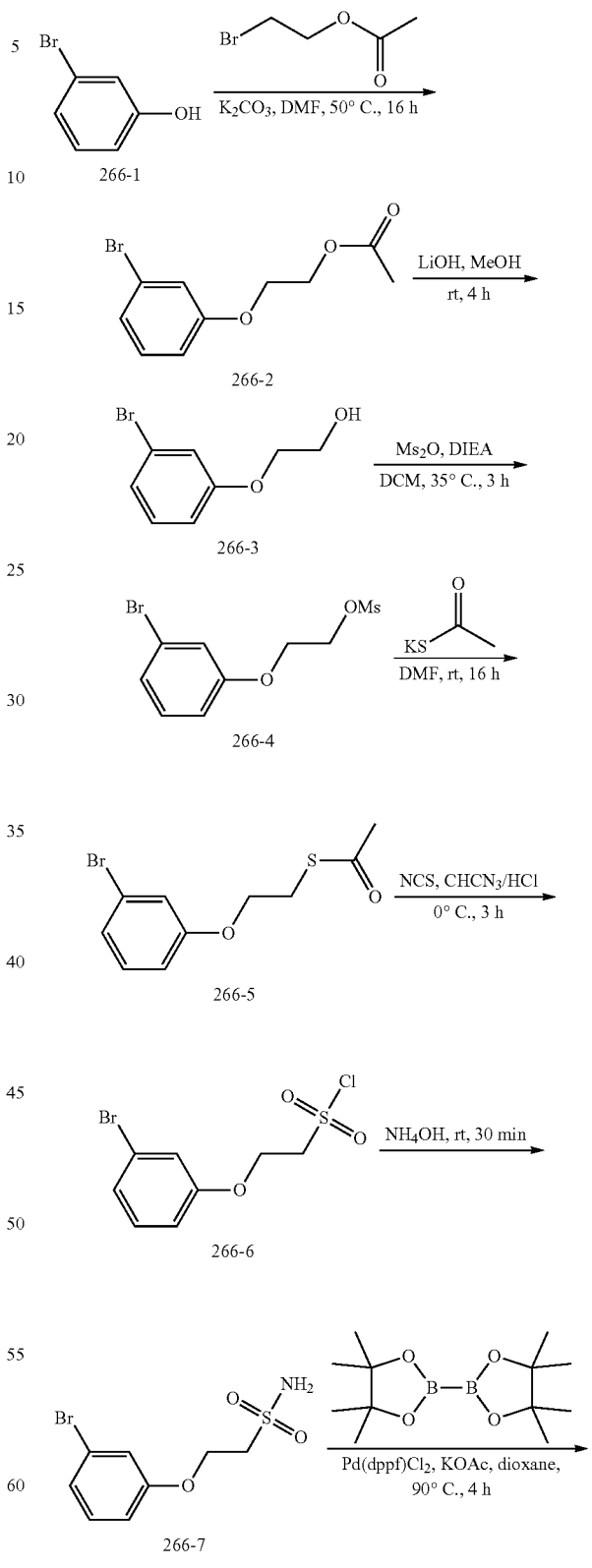

To a solution of SU20668-0316 (50 mg, 0.095 mmol) in DCM (3.00 mL), was added TMSBr (43.5 mg, 0.285 mmol). The mixture was stirred for 24 h. The solvent was removed. The residue was purified by pre-HPLC to give SU20668-0265 (15 mg, yield: 34%) as white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+0.10% NH4OH] and 5% [CH3CN] to 0% [water+0.1% NH4OH] and 100% [CH3CN] in 1.6 min, then under this condition for 1.4 min, finally changed to 95% [water+0.1% NH4OH] and 5% [CH$_3$CN] in 0.1 min and under this condition for 0.7 min), Purity: 97.76%, Rt=1.049 min; MS Calcd.: 471.2; MS Found: 472.3 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min), Purity: 100.0%, Rt=4.675 min. 1H NMR (400 MHz, MeOD+HCl (aq.)) δ 8.37 (s, 1H), 7.85-7.86 (m, 1H), 7.46 (t, J=8.0 Hz, 1H), 7.12-7.14 (m, 2H), 7.04-7.06 (m, 1H), 5.28-5.36 (m, 1H), 4.24-4.31 (m, 2H), 4.15-4.22 (m, 4H), 3.47 (d, J=5.2 Hz, 2H), 2.74-2.82 (m, 2H), 2.61-2.71 (m, 1H), 2.40-2.58 (m, 4H), 2.07-2.17 (m, 2H), 1.92-2.00 (m, 2H).

The Synthesis of 2-(3-bromophenoxy)ethanol (266-3)

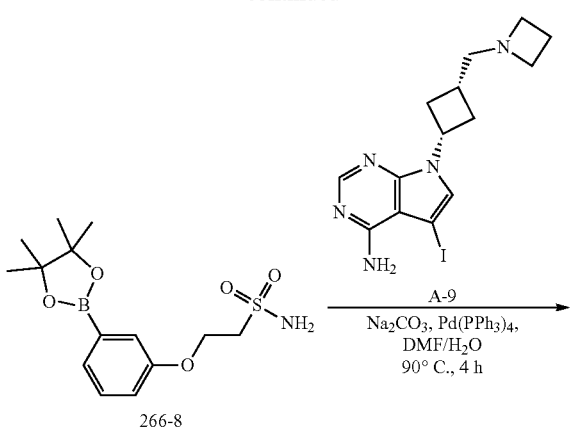

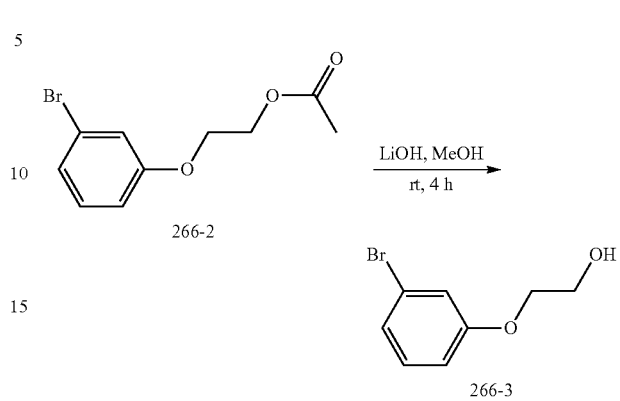

The mixture of 266-2 (7 g, 27.1 mmol) and LiOH (5.7 g, 135.5 mmol) in MeOH (50 mL) was stirred at room temperature for 4 h. After the consumption of starting material (by LCMS), the mixture was filtered, and the filtrate was concentrated in vacuo, purified by column chromatography (petroleum ether/ethyl acetate=5/1) to give the desired product 266-3 (4.9 g, 82.7% yield) as yellow oil.

The Synthesis of 2-(3-bromophenoxy)ethyl methanesulfonate (266-4)

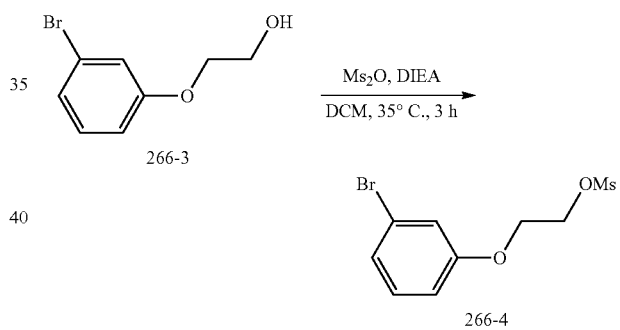

To a stirred solution of compound 266-3 (7 g, 27.1 mmol) and DIEA (17.5 g, 135.5 mmol) in DCM (50 ml) was added Ms₂O (14.2 g, 81.3 mmol) at 0° C. The resulting reaction mixture was stirred for 2 h at room temperature. After the consumption of starting material (by LCMS), added water, the aqueous phase was extracted with dichloromethane, the combined organic phases were dried over anhydrous sodium sulfate, filtered, and concentrated in vacuo to give the desired product 266-4 (10 g, crude) as brown oil.

The Synthesis of S-2-(3-bromophenoxy)ethyl ethanethioate (266-5)

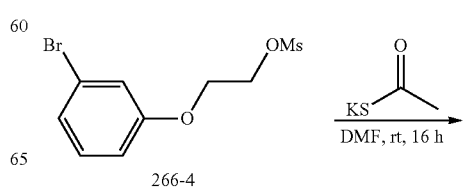

The Synthesis of 2-(3-bromophenoxy)ethyl acetate (266-2)

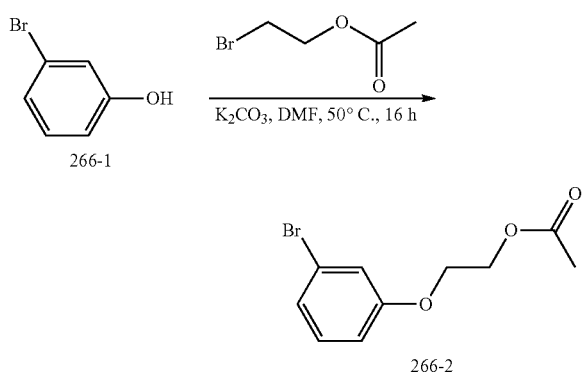

To a stirred solution of compound 266-1 (7 g, 40.7 mmol) and 2-bromoethyl acetate (8.1 g, 48.8 mmol) in DMF (50 mL) was added K₂CO₃ (16.9 g, 122.1 mmol). The resulting reaction mixture was stirred at 50° C. overnight. After the consumption of starting material (by LCMS), Then added water, the aqueous phase was extracted with ethyl acetate, the combined organic phases were dried over anhydrous sodium sulfate, filtered, and concentrated in vacuo to give the desired product 266-2 (13 g, crude) as yellow oil.

-continued

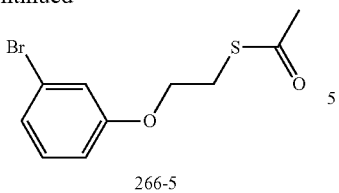

266-5

The mixture of potassium ethanethioate (4.3 g, 37.4 mmol) in DMF (50 mL) was stirred at 0° C. 266-4 (10 g, 34 mmol) dissolved in DMF (20 mL) was added dropwise to the mixture. Then the mixture was stirred at 35° C. for 3 h. After the consumption of starting material (by LCMS), the mixture was added water, the aqueous phase was extracted with Et$_2$O, the combined organic phases were dried over anhydrous sodium sulfate, filtered, and concentrated in vacuo to give the desired product 266-4 (8 g, crude) as brown oil.

The Synthesis of 2-(3-bromophenoxy)ethanesulfonyl chloride (266-6)

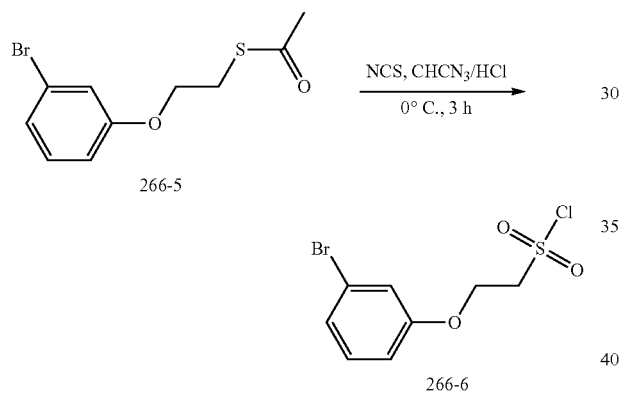

The mixture of NCS (15.6 g, 116.8 mmol) in CH$_3$CN/2M HCl (5/1, 100 mL) was stirred at 0° C. 266-5 (8 g, 29.2 mmol) dissolved in CH$_3$CN/2M HCl (5/1, 20 mL) was added dropwise to the mixture. Then the mixture was stirred at 0° C. for 3 h. After the consumption of starting material (by LCMS), the mixture was added water, the aqueous phase was extracted with Et$_2$O, the combined organic phases were dried over anhydrous sodium sulfate, filtered, and concentrated in vacuo to give the desired product 266-4 (8.5 g, crude) as colorless oil.

The Synthesis of 2-(3-bromophenoxy)ethanesulfonamide (266-7)

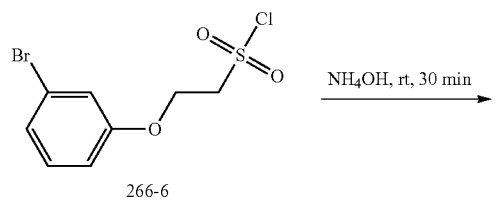

-continued

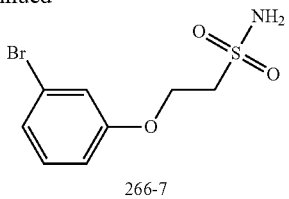

266-7

The solution of 266-6 (1 g, 13.4 mmol) in NH$_4$OH (50 mL) was stirred at room temperature for 30 min. After the consumption of starting material (by LCMS), the mixture was concentrated in vacuo to give the desired product 266-7 (700 mg, crude) as yellow oil.

The Synthesis of 2-(3-(4,4,5,5-tetramethyl-1,3,2-dioxaborolan-2-yl)phenoxy)ethanesulfonamide (266-8)

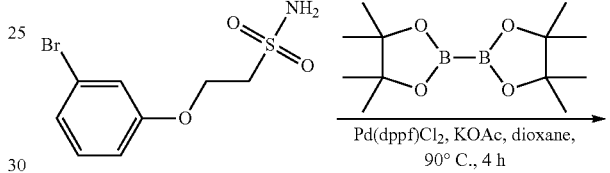

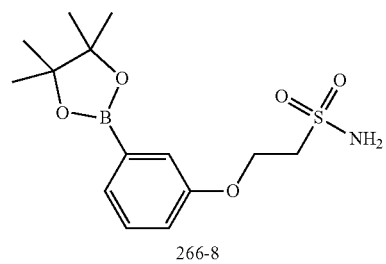

266-8

To a stirred solution of 266-7 (400 mg, 1.4 mmol) in dioxane (10 mL) was added bis(pinacolato)diboron (550 mg, 2.1 mmol), KOAc (420 mg, 4.3 mmol), Pd(dppf)Cl$_2$ (102 mg, 0.14 mmol). The resulting reaction mixture was heated to 90° C. and stirred for 4 h. After the consumption of starting material (by LCMS), the mixture was concentrated in vacuo to remove the solvent, then purified by prep-HPLC to give the desired product 266-8 (250 mg, 62.6% yield) as a colorless oil.

The Synthesis of 2-(3-(4-amino-7-(cis-3-(azetidin-1-ylmethyl)cyclobutyl)-7H-pyrrolo[2,3-d]pyrimidin-5-yl)phenoxy)ethanesulfonamide (SU20668-0266-01)

2H), 3.11-3.15 (m, 4H), 2.10-2.20 (m, 4H), 1.92-1.99 (m, 2H), 1.23-1.35 (m, 2H), 0.85-0.89 (m, 1H).

Scheme 111: Route for SU20668-0267-01

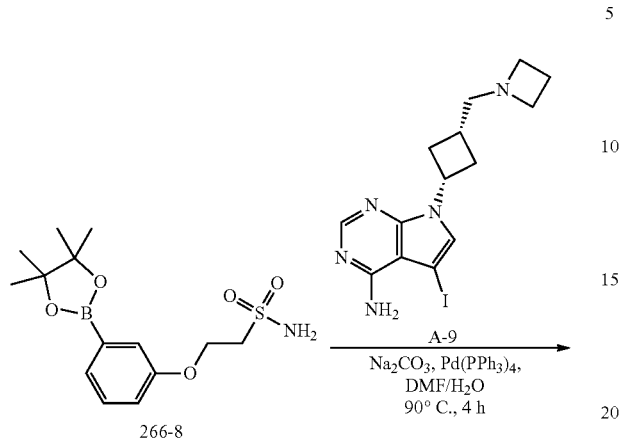

The mixture of 266-8 (200 mg, 0.61 mmol), A-9 (195 mg, 0.51 mmol), Pd(PPh$_3$)$_4$ (58 mg, 0.051 mmol), and Na$_2$CO$_3$ (108 mg, 1.02 mmol) in DMF/H$_2$O (10 mL, 4/1) was stirred at 90° C. under N$_2$ atmosphere for 4 h. After the consumption of starting material (by LCMS), the mixture was concentrated in vacuo to remove the solvent, then purified by prep-HPLC to give the desired product SU20668-0266-01 (20 mg, 6.6% yield) as a white solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 98.55%, Rt=1.369 min; MS Calcd.: 456.56; MS Found: 457.4 [M+H]$^+$. Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 100%, Rt=6.195 min. $^1$H NMR (400 MHz, DMSO-d$_6$) δ 8.12 (s, 1H), 7.63 (s, 1H), 7.41 (t, J=8.0 Hz, 1H), 7.07-7.10 (m, 2H), 6.90-6.99 (m, 3H), 6.12 (brs, 2H), 5.01-5.10 (m, 1H), 4.41 (t, J=6.4 Hz, 2H), 3.51 (t, J=6.4 Hz,

The Synthesis of N-(2-(3-(4,4,5,5-tetramethyl-1,3,2-dioxaborolan-2-yl)phenoxy)ethyl)methanesulfonamide (0267-2)

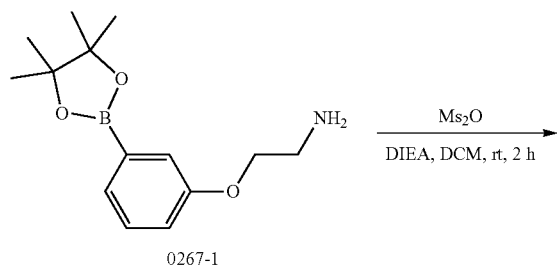

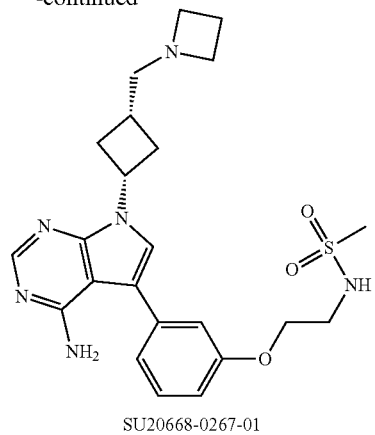

SU20668-0267-01

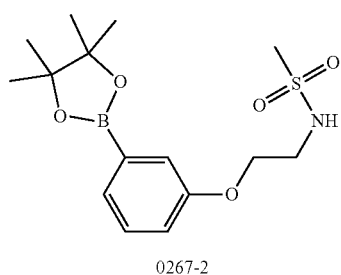

0267-2

To a solution of 0267-1 (1.1 g, 4.2 mmol) and DIEA (1.3 g, 10 mmol) in DCM (20 mL) was added Ms₂O (1.2 g, 7.0 mmol) in several batches. Then it was stirred at rt for 2 h. Remove the solvent in vacuo. The residue was purified by silica-gel column (DCM) to afford 0267-2 (230 mg, yield: 16.1%) as a yellow solid.

The Synthesis of N-(2-(3-(4-amino-7-(cis-3-(azetidin-1-ylmethyl)cyclobutyl)-7H-pyrrolo[2,3-d]pyrimidin-5-yl)phenoxy)ethyl)methanesulfonamide (SU20668-0267-01)

The mixture of A-9 (247 mg, 0.65 mmol), 0264-4 (220 mg, 0.65 mmol), Pd(PPh₃)₄ (40 mg) and Na₂CO₃ (140 mg, 1.3 mmol) in DMF/H₂O (4 mL, 4/1) was stirred at 90° C. for 16 hours. Then the mixture was concentrated to dryness. The residue was purified by silica-gel column (DCM:MeOH=50:1) and prep-HPLC to give SU20668-0267-01 (8 mg, yield: 2.6%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 98.12%, Rt=1.444 min; MS Calcd.: 470.2; MS Found: 471.4 [M+H]⁺. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min). Purity: 94.71%, Rt=6.018 min. ¹H NMR (400 MHz, MeOD-d₄) δ 8.03 (s, 1H), 7.34 (s, 1H), 7.29 (t, J=8.0 Hz, 1H), 6.99-7.00 (m, 2H), 6.86-6.89 (m, 1H), 4.96-5.00 (m, 1H), 4.06 (t, J=5.6 Hz, 2H), 3.32-3.40 (m, 6H), 2.89 (s, 3H), 2.65-2.67 (m, 2H), 2.53-2.59 (m, 2H), 2.10-2.18 (m, 5H).

Scheme 112: Route for SU20668-0273

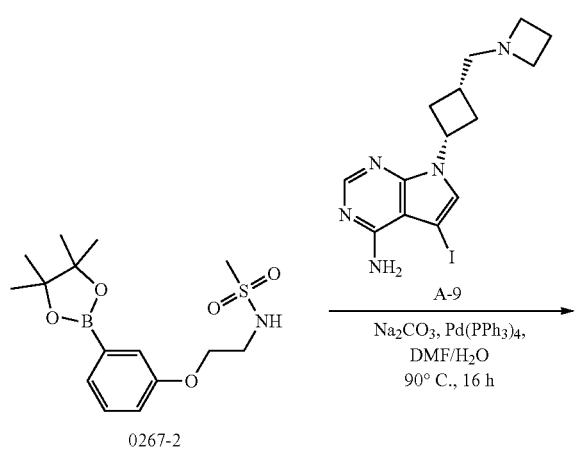

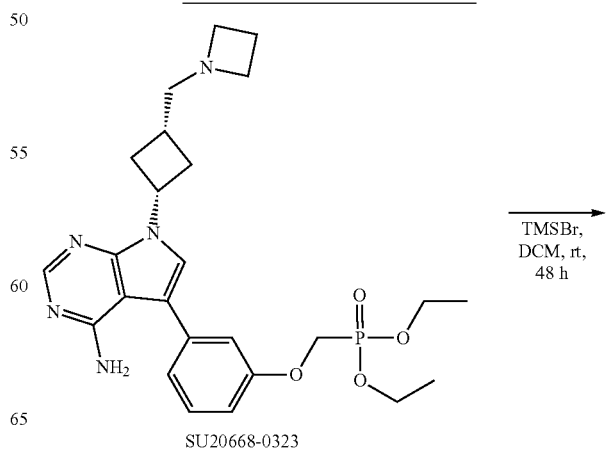

SU20668-0323

-continued

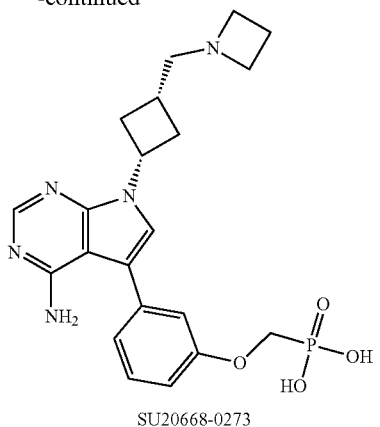

SU20668-0273

The Synthesis of (3-(4-amino-7-((1s,3s)-3-(azetidin-1-ylmethyl)cyclobutyl)-7H-pyrrolo[2,3-d]pyrimidin-5-yl)phenoxy)methylphosphonic acid (SU20668-0273)

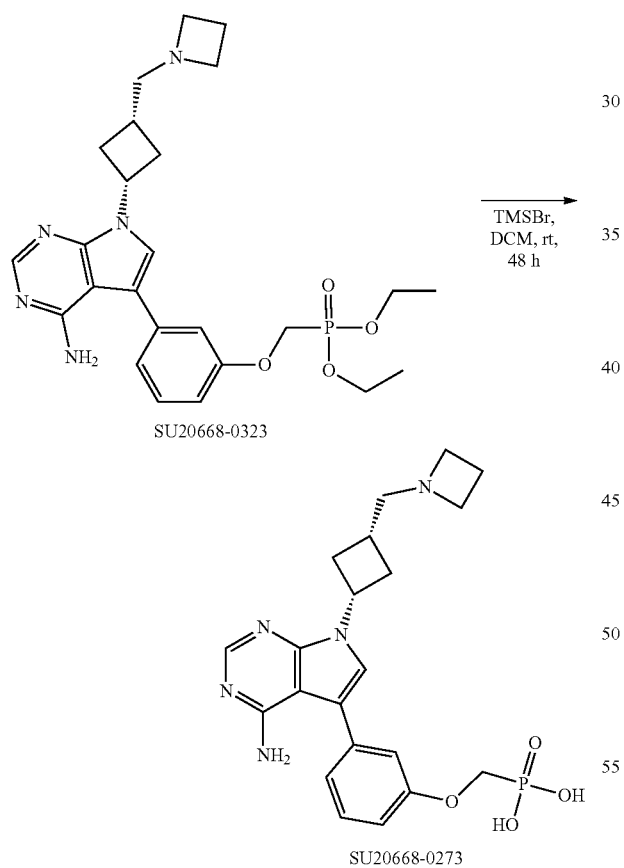

To a solution of SU20668-0323 (40 mg, 0.08 mmol) in DCM (3.00 mL), was added TMSBr (36.8 mg, 0.24 mmol). The mixture was stirred for 48 h at room temperature. The solvent was removed. The residue was purified by pre-HPLC to give SU20668-0273 (8 mg, yield: 23%) as white solid. LC-MS (Agilent LCMS 1200-6120, Column: Waters X-Bridge C18 (50 mm*4.6 mm*3.5 μm); Column Tempera- ture: 40° C.; Flow Rate: 2.0 mL/min; Mobile Phase: from 95% [water+0.1% NH4OH] and 5% [CH3CN] to 0% [water+0.1% NH4OH] and 100% [CH3CN] in 1.6 min, then under this condition for 1.4 min, finally changed to 95% [water+0.1% NH4OH] and 5% [CH$_3$CN] in 0.1 min and under this condition for 0.7 min), Purity: 95.95%, Rt=0.992 min; MS Calcd.: 443.2; MS Found: 444.3 [M+H]$^+$. HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min), Purity: 96.58%, Rt=4.101 min. $^1$H NMR (400 MHz, MeOD+HCl (aq.)) δ 8.37 (s, 1H), 7.87 (s, 1H), 7.49 (t, J=8.0 Hz, 1H), 7.12-7.24 (m, 3H), 5.30-5.34 (m, 1H), 4.36 (d, J=10.4 Hz, 2H), 4.24-4.31 (m, 2H), 4.15-4.22 (m, 2H), 3.48 (d, J=5.6 Hz, 2H), 2.79-2.82 (m, 2H), 2.61-2.71 (m, 1H), 2.50-2.58 (m, 3H), 2.40-2.49 (m, 1H).

Scheme 113: Route for SU20668-0315-01

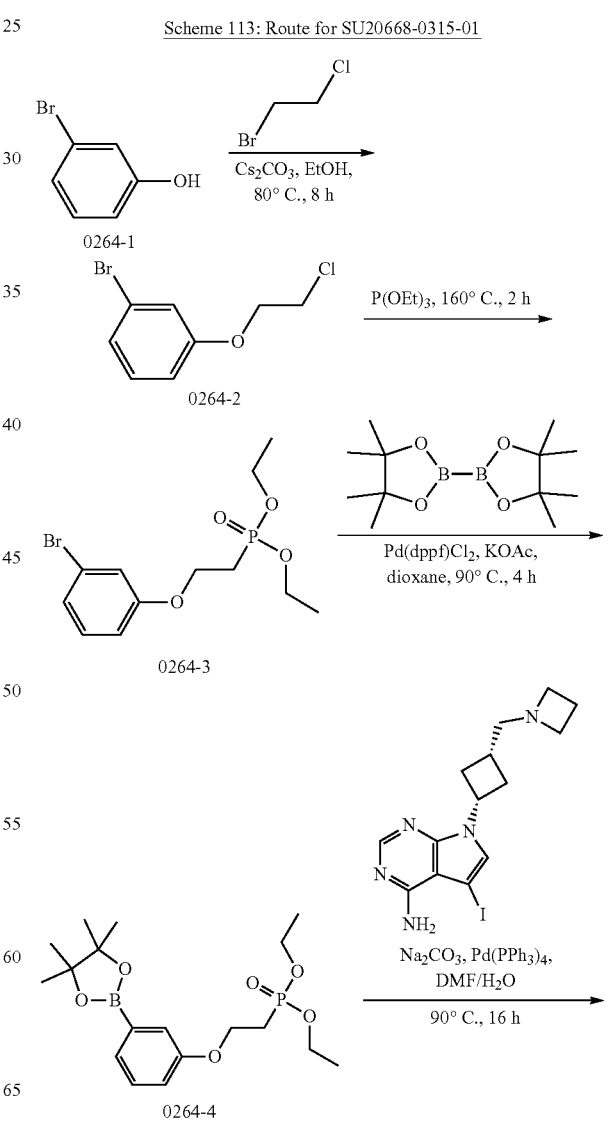

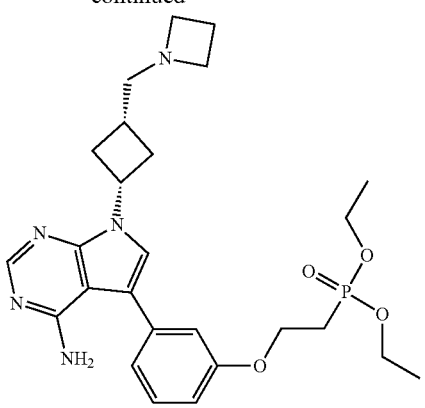

SU20668-0315-01

The Synthesis of
1-bromo-3-(2-chloroethoxy)benzene (0264-2)

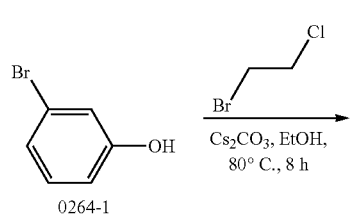

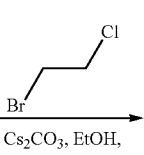

To a mixture of 0264-1 (2.0 g, 11.6 mmol) and $Cs_2CO_3$ (6.5 g, 20 mmol) in EtOH (30 mL) was added 1-bromo-2-chloroethane (2.4 g, 15.0 mmol). The mixture was stirred at 80° C. for 8 h. Then it was filtered. The filtrate was concentrated to dryness and purified by silica-gel column (PE:EA=10:1) to give 0264-2 (1.8 g, yield: 66.0%) as an off-white solid.

The Synthesis of diethyl
2-(3-bromophenoxy)ethylphosphonate (0264-3)

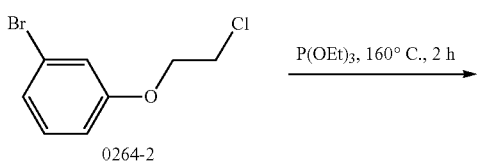

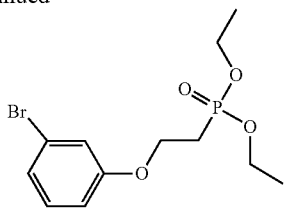

The solution of 0264-2 (1.8 g, 7.7 mmol) in $P(OEt)_3$ (10 mL) was stirred at 160° C. for 2 hours. Then it was purified by prep-HPLC to afford 0264-3 (500 mg, 19.4%) as an off-white solid.

The Synthesis of diethyl 2-(3-(4,4,5,5-tetramethyl-1,3,2-dioxaborolan-2-yl)phenoxy)ethylphosphonate (0264-4)

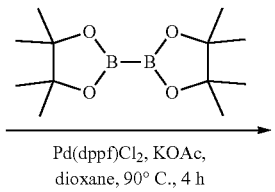

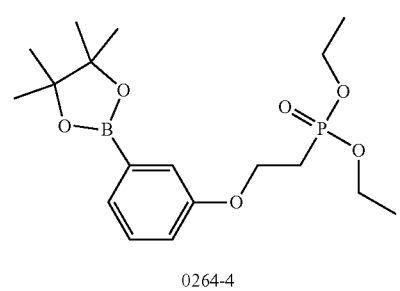

The mixture of 0264-3 (500 mg, 1.5 mmol), 4,4,4',4',5,5,5',5'-octamethyl-2,2'-bi(1,3,2-dioxaborolane) (760 mg, 3.0 mmol), $Pd(dppf)Cl_2$ (50 mg) and KOAC (440 mg, 4.5 mmol) in dioxane (10 mL) was stirred at 90° C. under $N_2$ atmosphere for 4 hours. Then the mixture was concentrated to dryness. The residue was purified by silica-gel column (PE:EA=10:1) to give 0264-4 (450 mg, yield: 78.1%) as an off-white solid.

The Synthesis of diethyl 2-(3-(4-amino-7-(cis-3-(azetidin-1-ylmethyl)cyclobutyl)-7H-pyrrolo[2,3-d]pyrimidin-5-yl)phenoxy)ethylphosphonate (SU20668-0315-01)

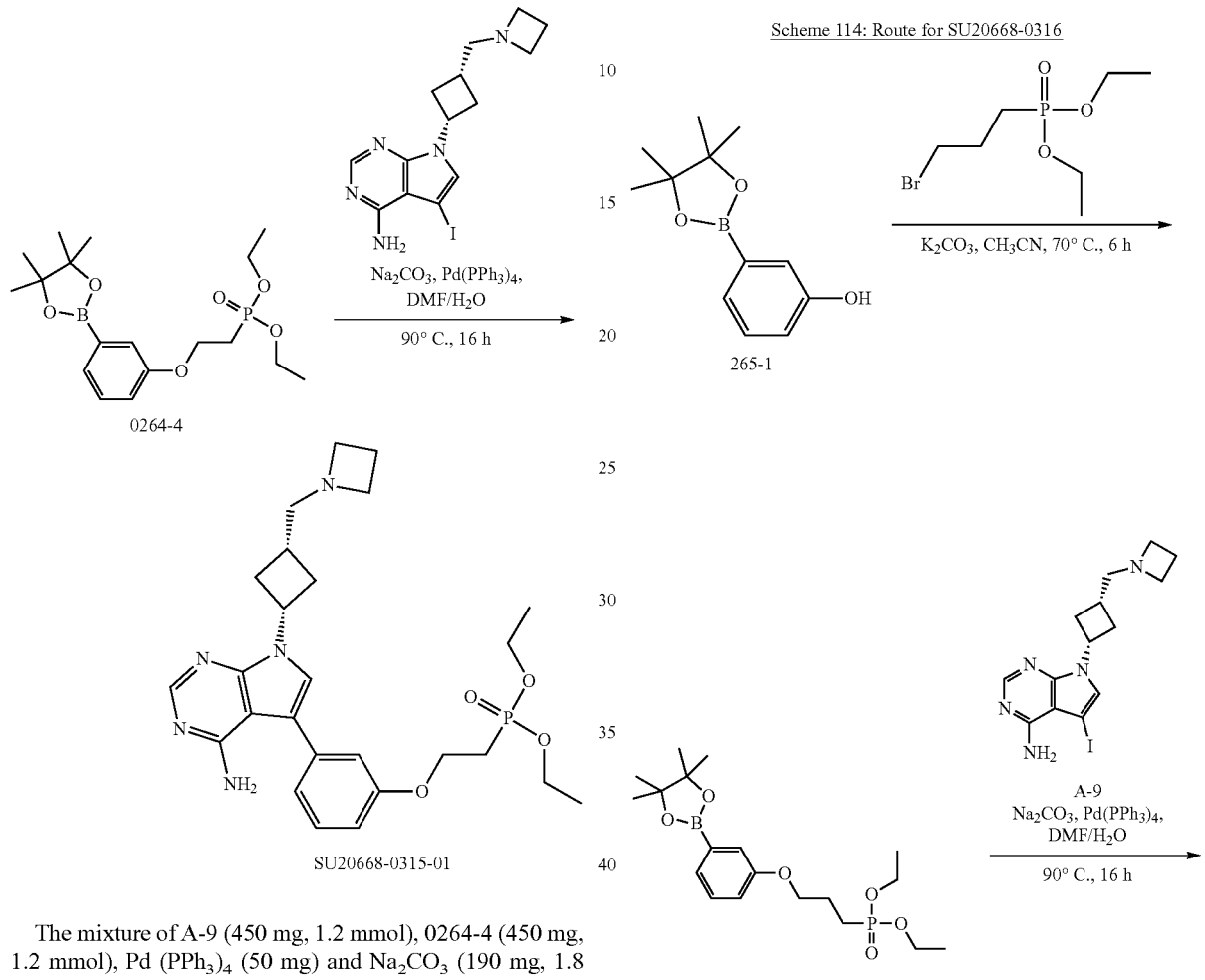

The mixture of A-9 (450 mg, 1.2 mmol), 0264-4 (450 mg, 1.2 mmol), Pd (PPh$_3$)$_4$ (50 mg) and Na$_2$CO$_3$ (190 mg, 1.8 mmol) in DMF/H$_2$O (5 mL, 4/1) was stirred at 90° C. for 16 hours. Then the mixture was concentrated to dryness. The residue was purified by silica-gel column (DCM:MeOH=50:1) and prep-HPLC to give SU20668-0315-01 (168 mg, yield: 27.8%) as a white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=1.511 min; MS Calcd.: 513.2; MS Found: 514.4 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 100%, Rt=6.754 min. $^1$H NMR (400 MHz, DMSO-d$_6$) δ 8.12 (s, 1H), 7.62 (s, 1H), 7.39 (t, J=8.0 Hz, 1H), 7.07 (d, J=7.6 Hz, 1H), 7.02-7.03 (m, 1H), 6.92 (dd, J=8.0 Hz, J=2.4 Hz, 1H), 6.06 (brs, 2H), 5.03-5.05 (m, 1H), 4.19-4.26 (m, 2H), 4.00-4.07 (m, 4H), 3.09 (t, J=7.2 Hz, 4H), 2.47-2.51 (m, 4H), 2.27-2.35 (m, 3H), 2.09-2.17 (m, 2H), 1.92-1.95 (m, 2H), 1.24 (t, J=7.2 Hz, 6H).

Scheme 114: Route for SU20668-0316

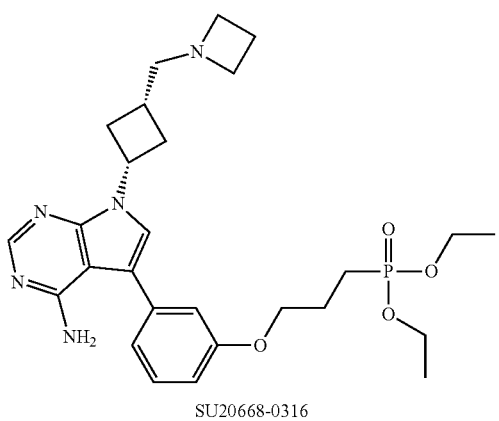

687

The Synthesis of diethyl 3-(3-(4,4,5,5-tetramethyl-1,3,2-dioxaborolan-2-yl)phenoxy)propylphosphonate (265-2)

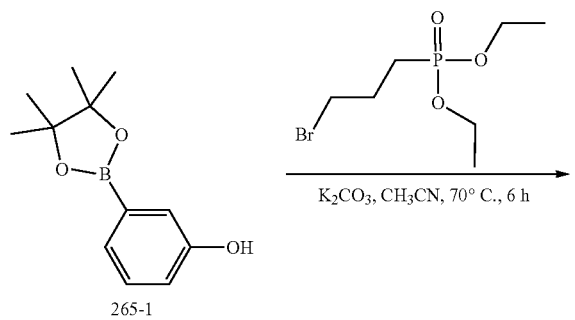

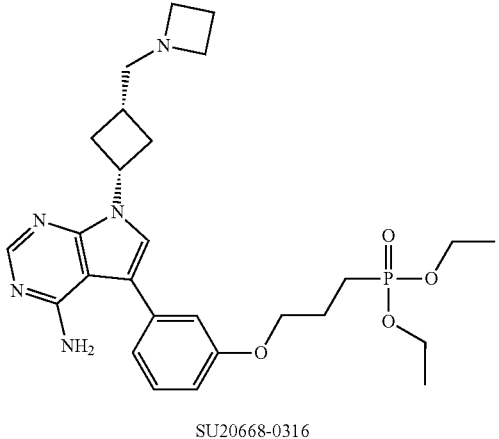

SU20668-0316

To a solution of 265-1 (500 mg, 2.27 mmol) and diethyl 3-bromopropylphosphonate (645 mg, 2.50 mmol) in acetonitrile (20.0 mL), was added K$_2$CO$_3$ (940 mg, 6.81 mmol). The mixture was stirred at 70° C. for 6 h and cooled down to room temperature. Water (50 mL) and EA (50 mL) were added. The organic layer was separated. The aqueous layer was extracted with EA (2×50 mL). The combined organic layers were washed with brine (2×30 mL), dried over anhydrous Na$_2$SO$_4$ and evaporated to give crude product which was purified by c.c (PE/EA=1:1) to give 265-2 (560 mg, yield: 62%) as a yellow oil.

The Synthesis of diethyl 3-(3-(4-amino-7-((1s,3s)-3-(azetidin-1-ylmethyl)cyclobutyl)-7H-pyrrolo[2,3-d]pyrimidin-5-yl)phenoxy)propylphosphonate (SU20668-0316)

To a solution of 265-2 (150 mg, 0.377 mmol), Na$_2$CO$_3$ (80.0 mg, 0.754 mol) and A-9 (144 mg, 0.377 mol) in DMF (5 mL) and water (1 mL), was added Pd(PPh$_3$)$_4$ (20 mg). The mixture was purged by nitrogen gas for several times and then reacted at 90° C. for 16 h. Water (50 mL) was added. The mixture was extracted with EA (3×50 mL). The combined organic layers were washed with brine (2×50 mL), dried over Na$_2$SO$_4$, filtered, and concentrated. The residue was purified by prep-HPLC to give SU20668-0316 (50 mg, yield: 25%) as white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min), Purity: 96.78%, Rt=1.962 min; MS Calcd.: 527.3; MS Found: 528.3 [M+H]$^+$. HPLC (Agilent HPLC 1200, Column: Waters X-Bridge C18 (150 mm*4.6 mm*3.5 m); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min), Purity: 98.72%, Rt=7.039 min. $^1$H NMR (400 MHz, DMSO-d$_6$) δ 8.12 (s, 1H), 7.61 (s, 1H), 7.38 (t, J=8.0 Hz, 1H), 7.04-7.06 (m, 2H), 6.90-6.93 (m, 1H), 6.10 (brs, 2H), 5.01-5.10 (m, 1H), 3.95-4.09 (m, 6H), 3.09 (t, J=7.2 Hz, 4H), 2.46-2.50 (m, 4H), 2.05-2.20 (m, 3H), 1.84-1.97 (m, 6H), 1.23 (t, J=6.8 Hz, 6H).

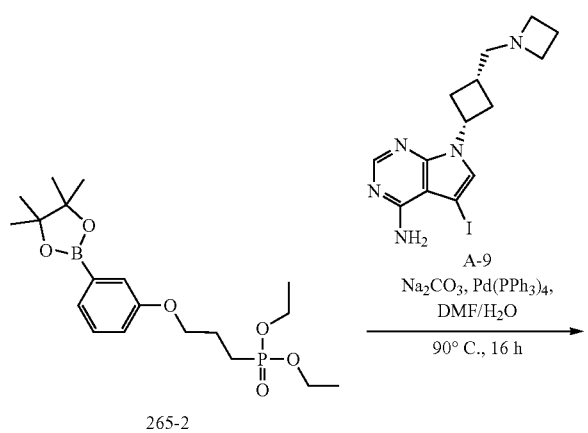

Scheme 115: Route SU20668-0323

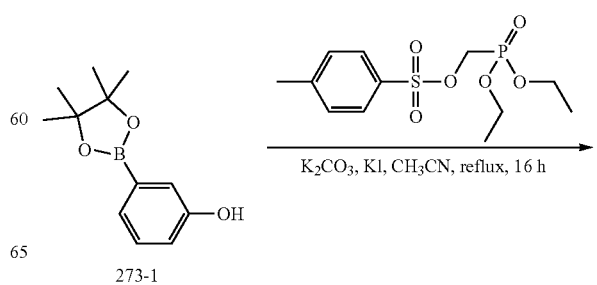

-continued

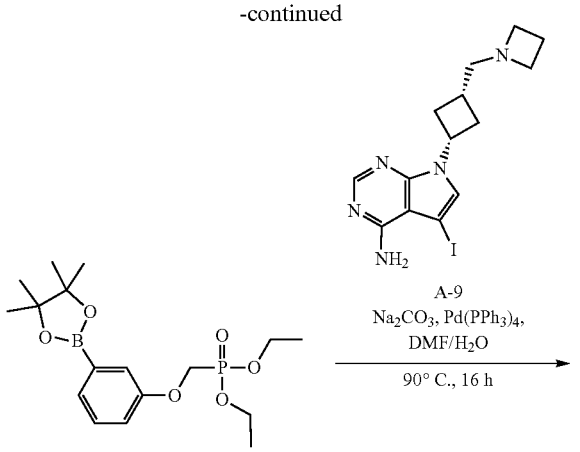

The Synthesis of diethyl (3-(4,4,5,5-tetramethyl-1,3,2-dioxaborolan-2-yl)phenoxy)methylphosphonate (273-2)

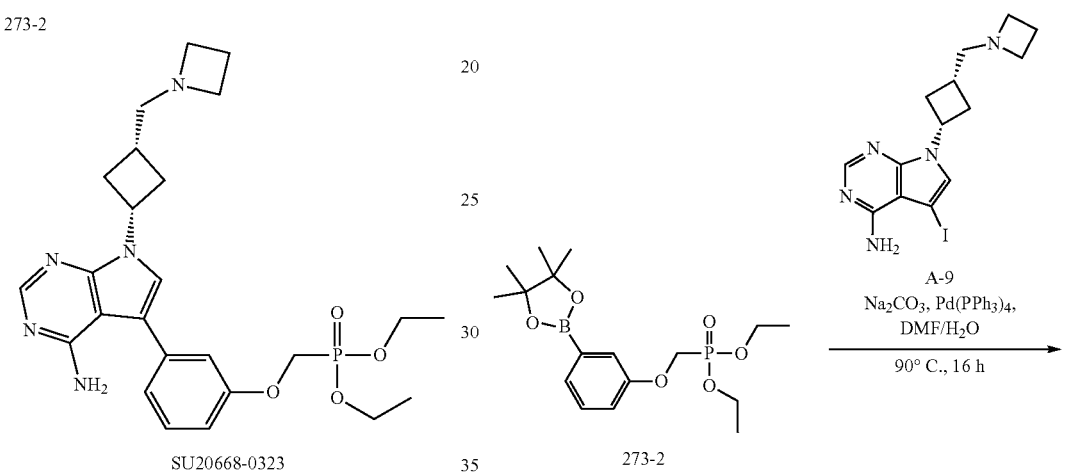

To a solution of 273-1 (2.0 g, 9.09 mmol), (diethoxyphosphoryl)methyl 4-methylbenzenesulfonate (3.51 g. 10.9 mmol) and KI (14.9 mg. 0.09 mmol) in acetonitrile (20.0 mL), was added $K_2CO_3$ (2.51 g, 18.2 mmol). The mixture was refluxed for 16 h and cooled down to room temperature. Water (50 mL) and EA (50 mL) was added. The organic layer was separated. The aqueous layer was extracted with EA (2×50 mL). The combined organic layers were washed with brine (2×30 mL), dried over anhydrous $Na_2SO_4$ and evaporated to give crude product which was purified by c.c (PE/EA=1:1) to give 273-2 (700 mg, yield: 21%) as yellow oil.

The Synthesis of diethyl (3-(4-amino-7-((1s,3s)-3-(azetidin-1-ylmethyl)cyclobutyl)-7H-pyrrolo[2,3-d]pyrimidin-5-yl)phenoxy)methylphosphonate (SU20668-0323)

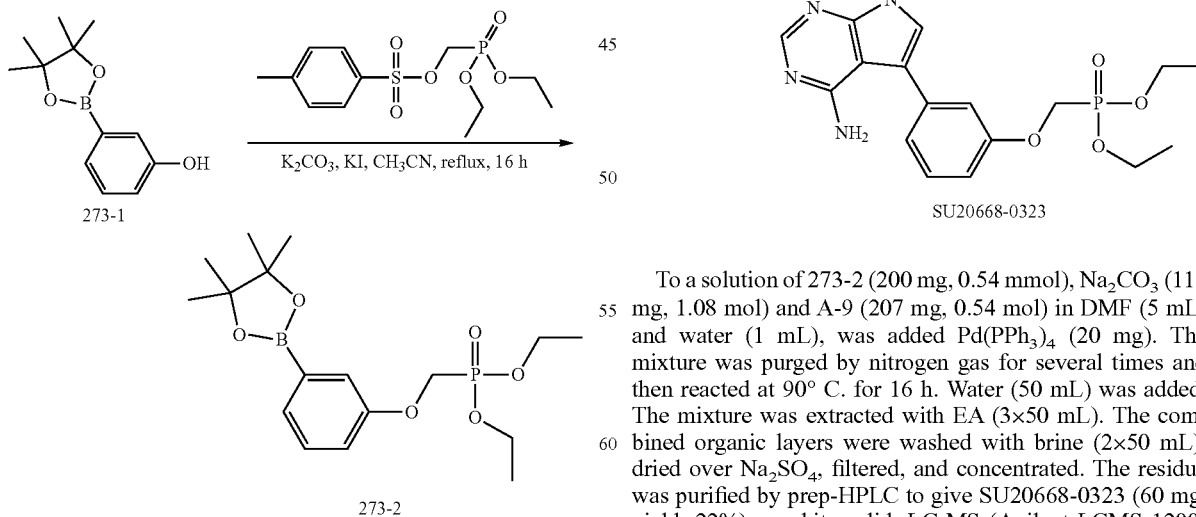

To a solution of 273-2 (200 mg, 0.54 mmol), $Na_2CO_3$ (115 mg, 1.08 mol) and A-9 (207 mg, 0.54 mol) in DMF (5 mL) and water (1 mL), was added $Pd(PPh_3)_4$ (20 mg). The mixture was purged by nitrogen gas for several times and then reacted at 90° C. for 16 h. Water (50 mL) was added. The mixture was extracted with EA (3×50 mL). The combined organic layers were washed with brine (2×50 mL), dried over $Na_2SO_4$, filtered, and concentrated. The residue was purified by prep-HPLC to give SU20668-0323 (60 mg, yield: 22%) as white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+0.1% NH4OH] and 5% [CH3CN] to 0% [water+0.1% NH4OH] and 100%

[CH3CN] in 1.6 min, then under this condition for 1.4 min, finally changed to 95% [water+0.1% NH4OH] and 5% [CH₃CN] in 0.1 min and under this condition for 0.7 min), Purity: 94.65%, Rt=1.997 min; MS Calcd.: 499.2; MS Found: 500.3 [M+H]⁺. HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH₃CN+0.1% TFA] to 0% [water+0.1% TFA] and 100% [CH₃CN+0.1% TFA] in 10 min, then under this condition for 5 min, finally changed to 95% [water+0.1% TFA] and 5% [CH₃CN+0.1% TFA] in 0.1 min and under this condition for 5 min), Purity: 100.0%, Rt=5.266 min. ¹H NMR (400 MHz, DMSO-d₆) δ 8.13 (s, 1H), 7.63 (s, 1H), 7.40 (t, J=8.0 Hz, 1H), 7.10-7.16 (m, 2H), 6.99-7.02 (m, 1H), 6.13 (brs, 2H), 5.04-5.08 (m, 1H), 4.49 (d, J=10.0 Hz, 2H), 4.10-4.17 (m, 4H), 3.09 (t, J=6.8 Hz, 4H), 2.46-2.51 (m, 4H), 2.07-2.19 (m, 3H), 1.91-1.98 (m, 2H), 1.27 (t, J=7.2 Hz, 6H).

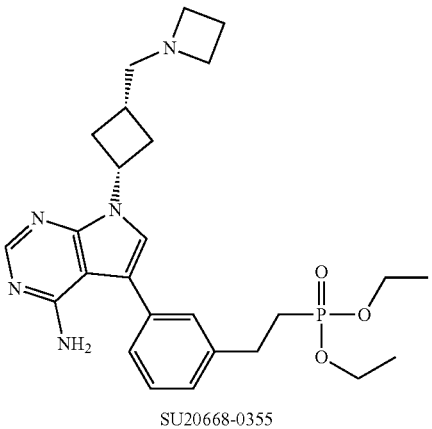

SU20668-0355

The Synthesis of diethyl 3-bromophenethylphosphonate (355-2)

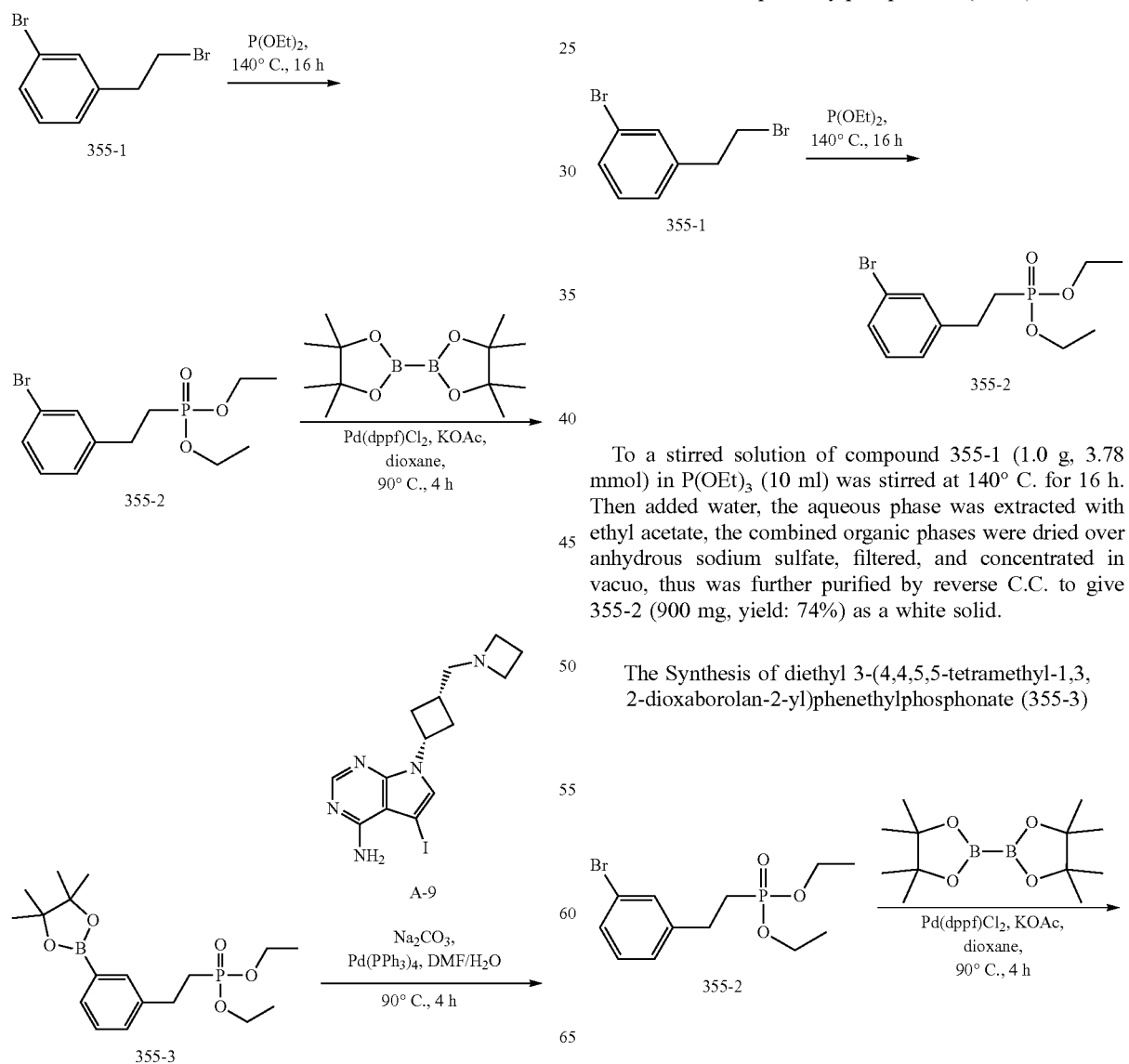

To a stirred solution of compound 355-1 (1.0 g, 3.78 mmol) in P(OEt)₃ (10 ml) was stirred at 140° C. for 16 h. Then added water, the aqueous phase was extracted with ethyl acetate, the combined organic phases were dried over anhydrous sodium sulfate, filtered, and concentrated in vacuo, thus was further purified by reverse C.C. to give 355-2 (900 mg, yield: 74%) as a white solid.

The Synthesis of diethyl 3-(4,4,5,5-tetramethyl-1,3,2-dioxaborolan-2-yl)phenethylphosphonate (355-3)

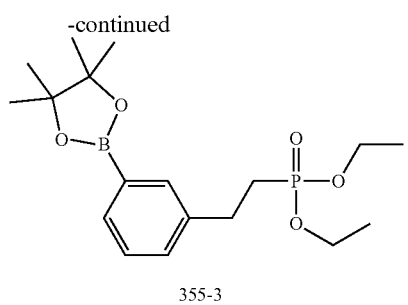

355-3

To a stirred solution of compound 355-2 (500 mg, 1.56 mmol) in dioxane (8 mL) was added 4,4,4',4',5,5,5',5'-octamethyl-2,2'-bi(1,3,2-dioxaborolane) (396 mg, 1.56 mmol), KOAc (313 mg, 3.2 mmol), Pd(dppf)Cl$_2$(57 mg, 0.078 mmol). The resulting reaction mixture was heated to 90° C. and stirred for 4 h and concentrated in vacuo to remove the solvent, then added water, the aqueous phase was extracted with dichloromethane, the combined organic phases were dried over anhydrous sodium sulfate, filtered, and concentrated, the crude was purified by reverse C.C. to give 355-3 (350 mg, yield: 60.9%) as a yellow solid.

The Synthesis of diethyl 3-(4-amino-7-(cis-3-(azetidin-1-ylmethyl)cyclobutyl)-7H-pyrrolo[2,3-d]pyrimidin-5-yl)phenethylphosphonate (SU20668-0355)

(15 mg, 0.013 mmol). The resulting reaction mixture was heated to 90° C. and stirred for 4 h and concentrated in vacuo to remove the solvent, then added water, the aqueous phase was extracted with dichloromethane, the combined organic phases were dried over anhydrous sodium sulfate, filtered, and concentrated, the crude was purified by prep-HPLC to give the desired product SU20668-0355 (100 mg, yield: 43.1%) as a yellow solid. LC-MS (LC-MS (Agilent LCMS 1200-6120, Column: Waters X-Bridge C18 (30 mm×4.6 mm×2.7 m); Column Temperature: 40° C.; Flow Rate: 3.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 0.8 min, then under this condition for 0.4 min, finally changed to 95% [water+0.05% TFA] and 5% [CH$_3$CN+0.05%] in 0.01 min.). Purity: 97.35%, Rt=1.035 min; MS Calcd.: 497.26; MS Found: 498.3 [M+H]$^+$. HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min). Purity: 99.08%, Rt=6.962 min. $^1$H NMR (400 MHz, MeOD-d$_4$) δ 8.25 (s, 1H), 7.69 (s, 1H), 7.26-7.42 (m, 4H), 5.19-5.23 (m, 1H), 3.95-4.08 (m, 8H), 3.34 (d, J=5.6 Hz, 2H), 2.86-2.93 (m, 2H), 2.67-2.69 (m, 2H), 2.49-2.56 (m, 1H), 2.31-2.43 (m, 4H), 2.07-2.16 (m, 2H), 1.20 (t, J=7.6 Hz, 6H).

Scheme 117: Route for SU20668-0356

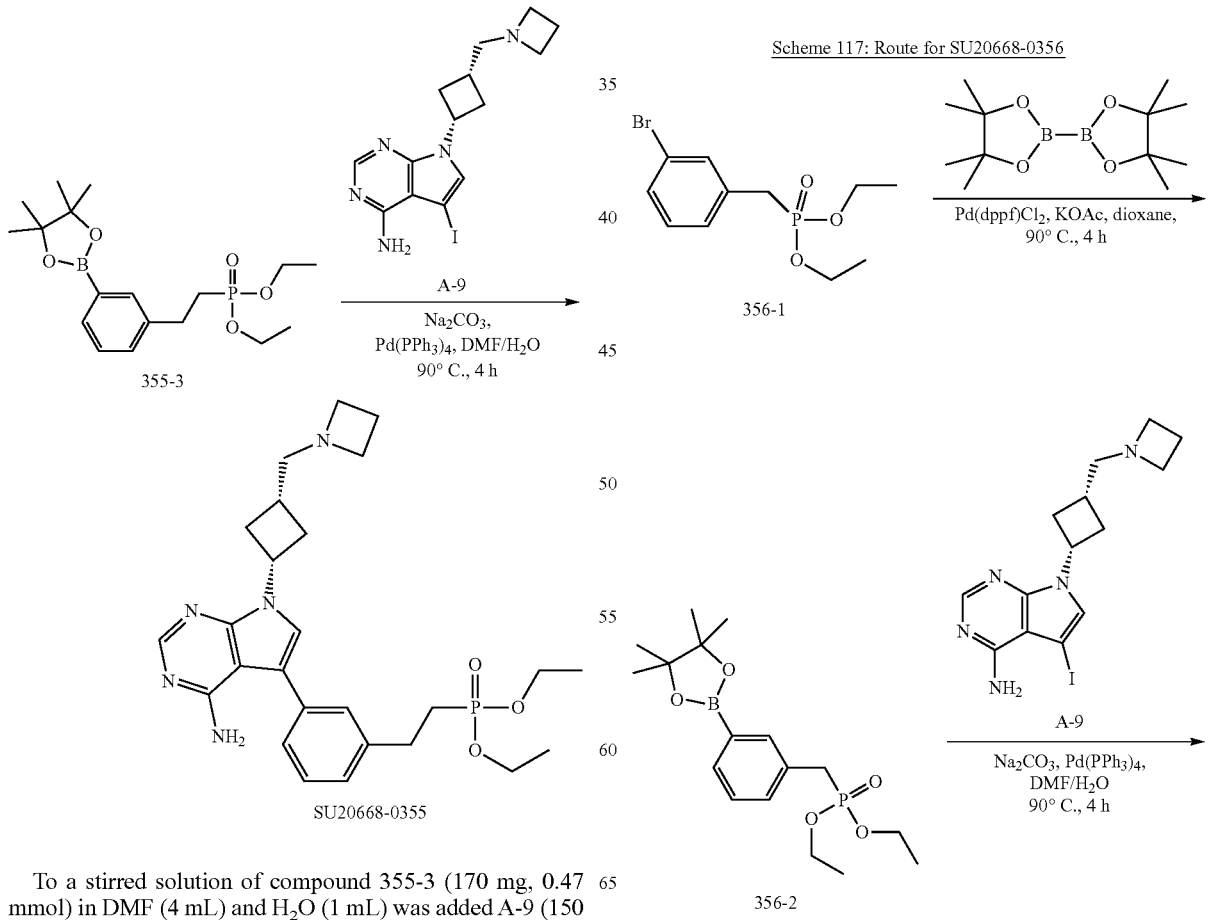

To a stirred solution of compound 355-3 (170 mg, 0.47 mmol) in DMF (4 mL) and H$_2$O (1 mL) was added A-9 (150 mg, 0.39 mmol), Na$_2$CO$_3$ (103 mg, 0.98 mmol), Pd(PPh$_3$)$_4$

The Synthesis of diethyl 3-(4,4,5,5-tetramethyl-1,3,2-dioxaborolan-2-yl)benzylphosphonate (356-2)

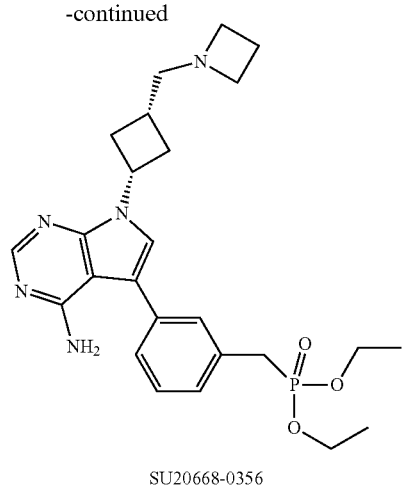

To a stirred solution of compound 356-1 (1.0 mg, 3.25 mmol) in dioxane (15 mL) was added 4,4,4',4',5,5,5',5'-octamethyl-2,2'-bi(1,3,2-dioxaborolane) (825 mg, 3.25 mmol), KOAc (626 mg, 6.4 mmol), Pd(dppf)Cl$_2$(114 mg, 0.156 mmol). The resulting reaction mixture was heated to 90° C. and stirred for 4 h and concentrated in vacuo to remove the solvent, then added water, the aqueous phase was extracted with dichloromethane, the combined organic phases were dried over anhydrous sodium sulfate, filtered, and concentrated, the crude was purified by reverse C.C. to give 356-2 (700 mg, yield: 60.9%) as a yellow solid.

The Synthesis of diethyl 3-(4-amino-7-(cis-3-(azetidin-1-ylmethyl)cyclobutyl)-7H-pyrrolo[2,3-d]pyrimidin-5-yl)benzylphosphonate (SU20668-0356)

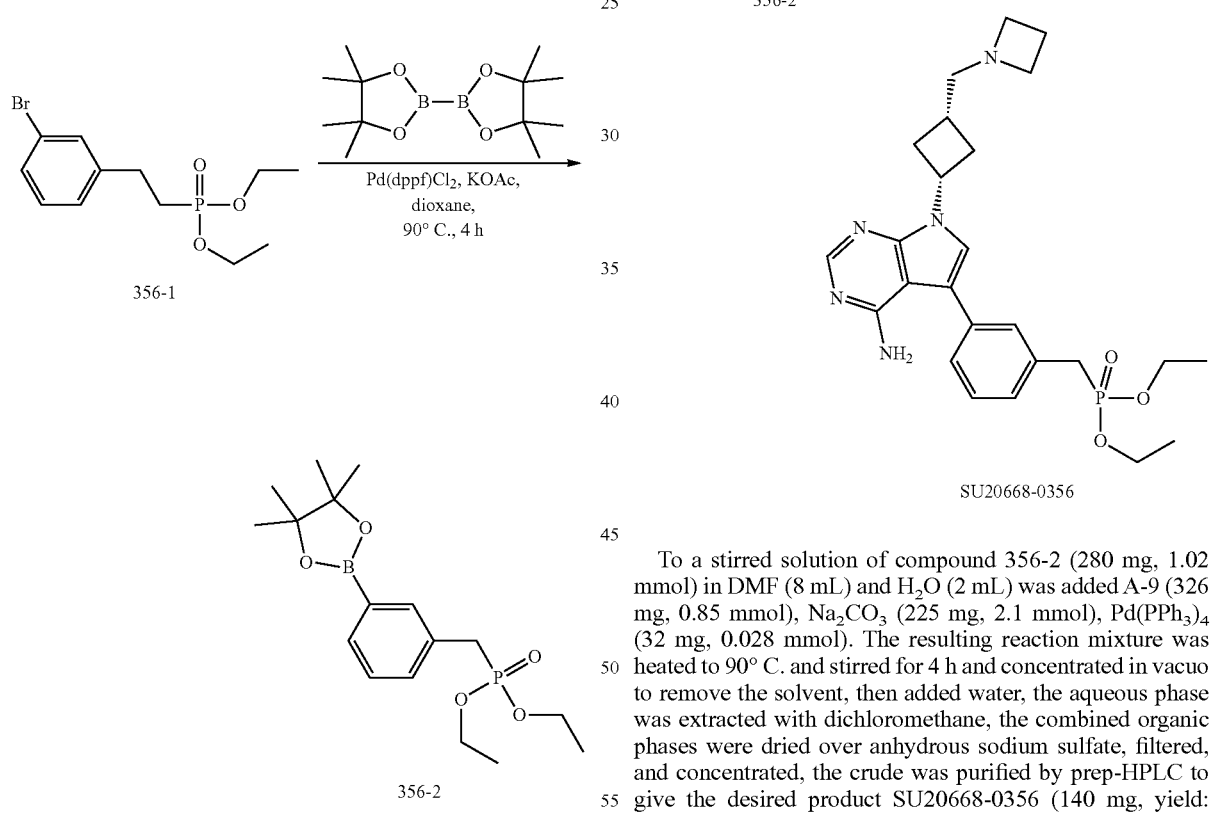

To a stirred solution of compound 356-2 (280 mg, 1.02 mmol) in DMF (8 mL) and H$_2$O (2 mL) was added A-9 (326 mg, 0.85 mmol), Na$_2$CO$_3$ (225 mg, 2.1 mmol), Pd(PPh$_3$)$_4$ (32 mg, 0.028 mmol). The resulting reaction mixture was heated to 90° C. and stirred for 4 h and concentrated in vacuo to remove the solvent, then added water, the aqueous phase was extracted with dichloromethane, the combined organic phases were dried over anhydrous sodium sulfate, filtered, and concentrated, the crude was purified by prep-HPLC to give the desired product SU20668-0356 (140 mg, yield: 28.4%) as a yellow oil. LC-MS (LC-MS (Agilent LCMS 1200-6120, Column: Waters X-Bridge C18 (30 mm×4.6 mm×2.7 m); Column Temperature: 40° C.; Flow Rate: 3.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 0.8 min, then under this condition for 0.4 min, finally changed to 95% [water+0.05% TFA] and 5% [CH$_3$CN+0.05%] in 0.01 min). Purity: 99.85%, Rt=1.614 min; MS Calcd.: 483.24; MS Found: 484.4 [M+H]$^+$. HPLC (Agilent HPLC 1200; Column: L-column2 ODS (150 mm*4.6 mm*5.0 µm); Column Temperature: 40° C.; Flow Rate: 1.0 mL/min; Mobile Phase: from 95% [water+0.1% TFA] and 5% [CH₃CN+0.1% TFA] to 0% [water+0.1% TFA] and 100% [CH₃CN+0.1% TFA] in 10 min, then under this condition for 5 min, finally changed to 95% [water+0.1% TFA] and 5% [CH₃CN+0.1% TFA] in 0.1 min and under this condition for 5 min). Purity: 96.88%, Rt=5.780 min. ¹H NMR (400 MHz, MeOD-d₄) δ 8.03 (s, 1H), 7.38 (s, 1H), 7.33-7.35 (m, 3H), 7.22-7.23 (m, 1H), 4.97-5.02 (m, 1H), 3.95-4.00 (m, 4H), 3.20-3.26 (m, 6H), 2.57-2.58 (m, 4H), 2.13-2.15 (m, 3H), 2.02-2.06 (m, 2H), 1.18 (t, J=7.2 Hz, 6H).

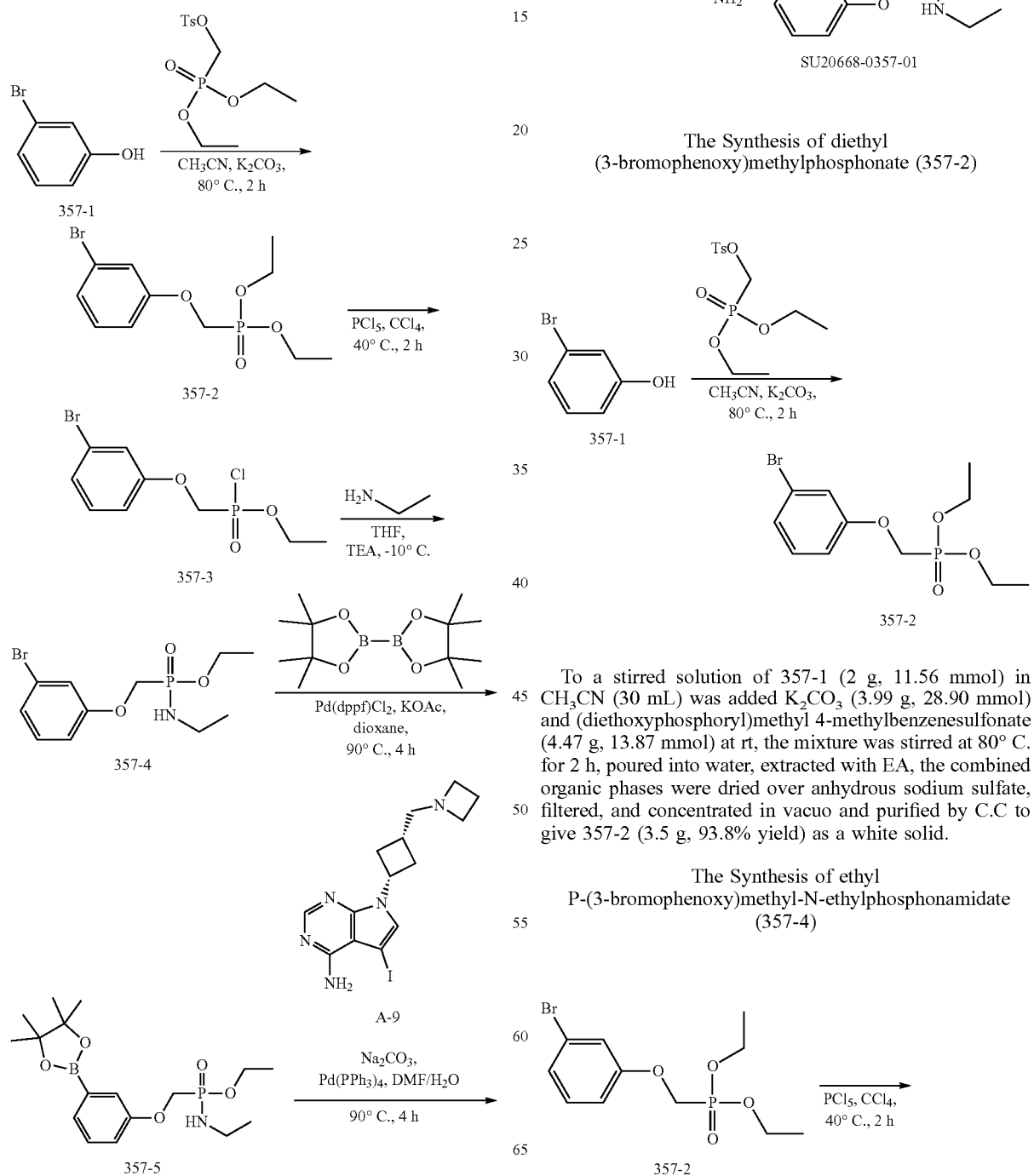

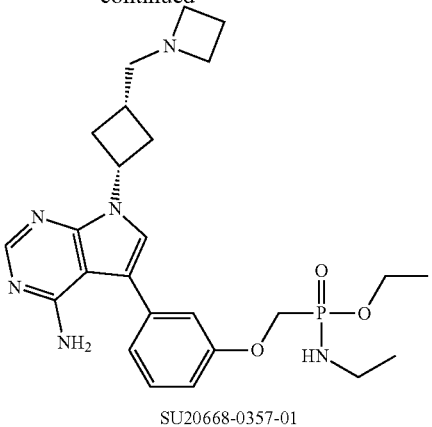

The Synthesis of diethyl (3-bromophenoxy)methylphosphonate (357-2)

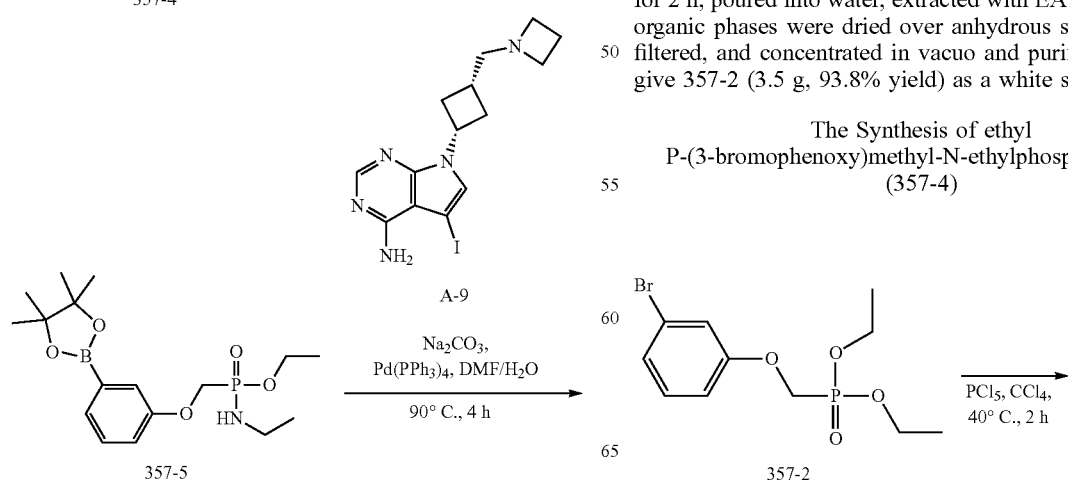

To a stirred solution of 357-1 (2 g, 11.56 mmol) in CH₃CN (30 mL) was added K₂CO₃ (3.99 g, 28.90 mmol) and (diethoxyphosphoryl)methyl 4-methylbenzenesulfonate (4.47 g, 13.87 mmol) at rt, the mixture was stirred at 80° C. for 2 h, poured into water, extracted with EA, the combined organic phases were dried over anhydrous sodium sulfate, filtered, and concentrated in vacuo and purified by C.C to give 357-2 (3.5 g, 93.8% yield) as a white solid.

The Synthesis of ethyl P-(3-bromophenoxy)methyl-N-ethylphosphonamidate (357-4)

-continued

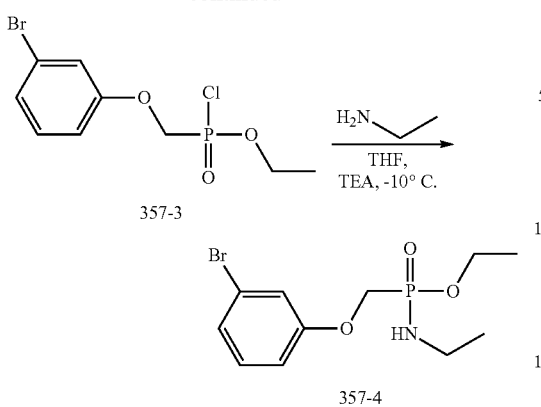

To a stirred solution of 357-2 (1.2 g, 3.714 mmol) in Carbon tetrachloride (25 mL) was added Phosphorus pentachloride (1.16 g, 5.571 mmol), the solution was stirred at 40° C. for 2 h, the solvent was removed by concentration, the residue was dissolved in THF (20 mL), added triethylamine (1.5 g, 14.856 mmol), cooled to −10° C., ethanamine (0.501 g, 11.142 mmol) solution of THF (2 N) was dropwised in, the mixture was warmed to rt, stirred for 16 h, concentrated to give 357-4 (1.5 g, crude) as a brown oil.

The Synthesis of ethyl N-ethyl-P-((3-(4,4,5,5-tetramethyl-1,3,2-dioxaborolan-2-yl)phenoxy)methyl)phosphonamidate(357-5)

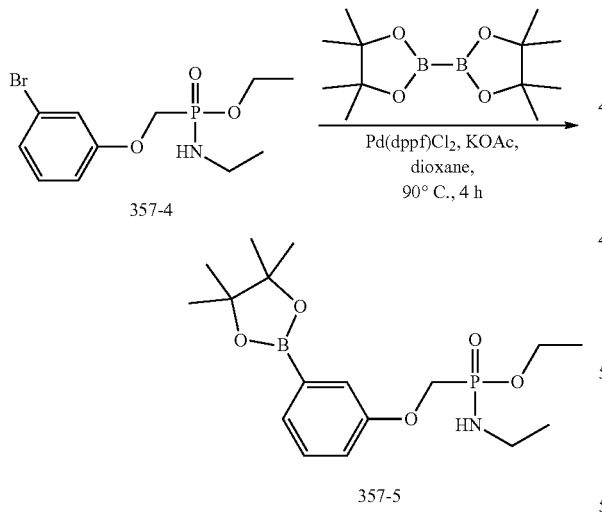

To a stirred solution of 357-4 (500 mg, 1.552 mmol) in dioxane (8 mL) was added bis(pinacolato)diboron (788 mg, 3.104 mmol), KOAc (380.6 mg, 3.88 mmol), Pd(dppf)Cl$_2$ (227 mg, 0.310 mmol). The resulting reaction mixture was heated to 90° C. and stirred for 4 h and concentrated in vacuo to remove the solvent, then added water, the aqueous phase was extracted with EA, the combined organic phases were dried over anhydrous sodium sulfate, filtered, and concentrated, the crude was purified by prep-HPLC to give 357-5 (300 mg, yield: 52.4%) as brown oil.

The Synthesis of 7-((1s,3s)-3-(azetidin-1-ylmethyl)cyclobutyl)-5-(3-(pyrazin-2-ylmethoxy)phenyl)-7H-pyrrolo[2,3-d]pyrimidin-4-amine (SU20668-0357-01)

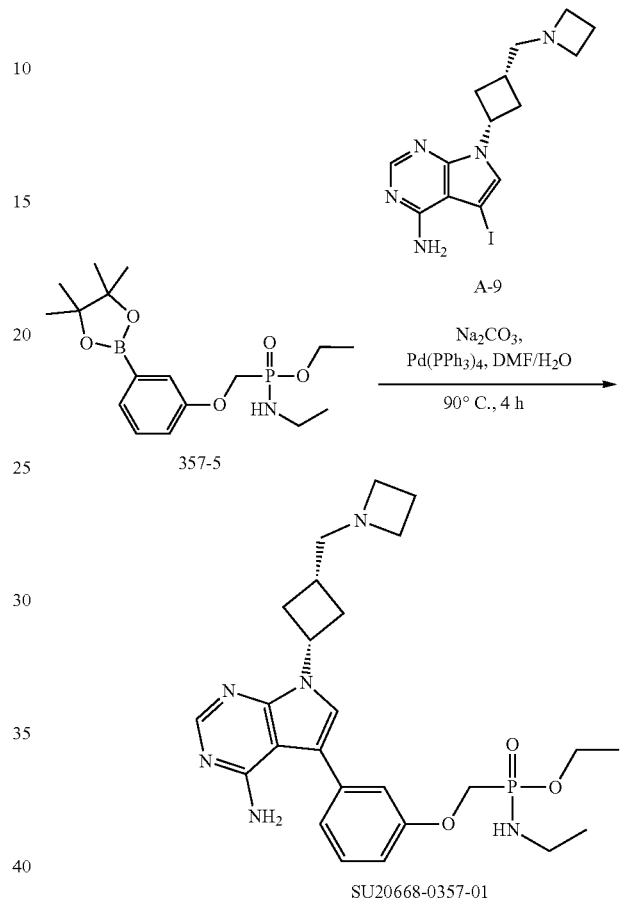

To a stirred solution of 357-5 (235 mg, 0.637 mmol) in DMF/water (12 mL/3 mL) was added A-9 (200 mg, 0.522 mmol), Na$_2$CO$_3$ (115 mg, 1.085 mmol), Pd(PPh$_3$)$_4$ (120 mg, 0.104 mmol). The resulting reaction mixture was heated to 90° C. and stirred for 4 h, filtered and purified by prep-HPLC to give SU20668-0357-01 (29 mg, yield: 8.9%) as a white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 99.30%, R$_t$=1.420 min; MS Calcd.: 498.25; MS Found: 499.2 [M+H]$^+$. HPLC (Agilent HPLC 1200, Column: L-column2 ODS (150 mm*4.6 mm*5.0 m); Column Temperature: 40° C.; Flow Rate: 1.5 mL/min; Mobile Phase: from 90% [(total 10 mM AcONH$_4$) water/CH$_3$CN=900/100 (v/v)] and 10% [total 10 mM AcONH$_4$) water/CH$_3$CN=100/900 (v/v)] to 15% [total 10 mM AcONH$_4$) water/CH$_3$CN=900/100 (v/v)] and 85% [total 10 mM AcONH$_4$) water/CH$_3$CN=100/900 (v/v)] in 5 min, then under this condition for 10 min, finally changed to 90% [(total 10 mM AcONH$_4$) water/CH$_3$CN=900/100 (v/v)]

and 10% [total 10 mM AcONH$_4$) water/CH$_3$CN=100/900 (v/v)] in 0.1 min and under this condition for 5 min). Purity: 92.23%, Rt=6.503 min. $^1$H NMR (400 MHz, DMSO-d$_6$) δ 8.13 (s, 1H), 7.63 (s, 1H), 7.39 (t, J=7.6 Hz, 1H), 7.08-7.13 (m, 2H), 6.97-7.00 (m, 1H), 6.13 (brs, 2H), 5.06-5.08 (m, 1H), 4.89-4.95 (m, 1H), 4.21-4.32 (m, 2H), 3.98-4.02 (m, 2H), 3.12 (t, J=6.8 Hz, 4H), 2.88-2.94 (m, 2H), 2.50-2.51 (m, 4H), 2.13-2.18 (m, 3H), 1.93-1.97 (m, 2H), 1.24 (t, J=6.8 Hz, 3H), 1.05 (t, J=7.2 Hz, 3H).

Scheme 119: Route for SU20668-0358-01

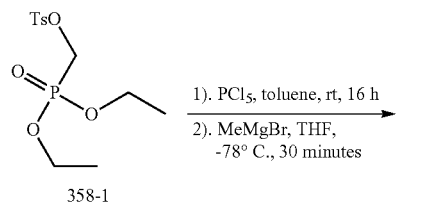

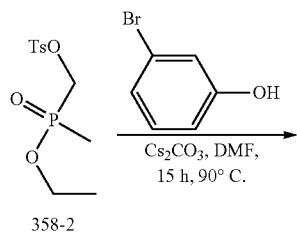

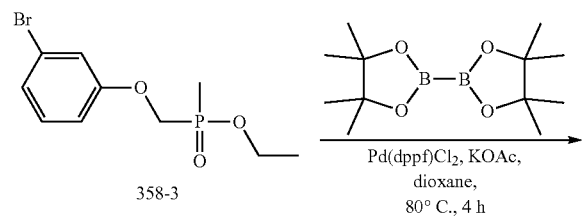

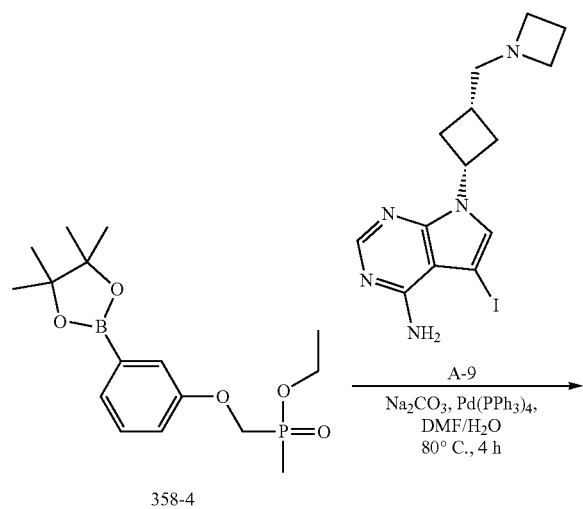

-continued

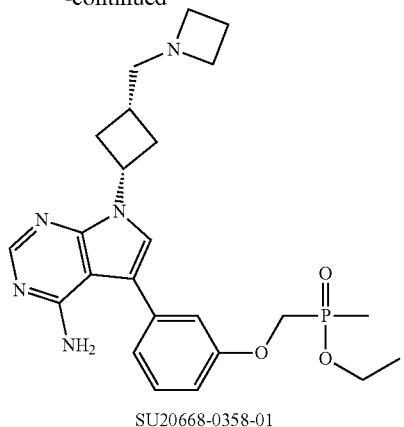

SU20668-0358-01

The Synthesis of (ethoxy(methyl)phosphoryl)methyl 4-methylbenzenesulfonate (358-2)

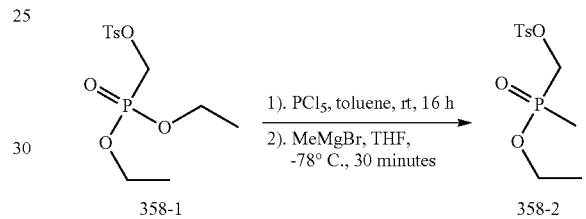

To a stirred solution of 358-1 (5 g, 15.5 mmol) in toluene (30 mL) was added PCS (4.85 g, 23.3 mmol) and the reaction mixture was stirred at 70° C. until homogenous, then stirred at rt overnight. The solvent was removed. To the crude in dry THF (25 mL) at −78° C. was added MeMgBr (5.6 mL, 3.0M in diethyl ether). The mixture solution was stirred for 30 min. The reaction was quenched with aqueous NH$_4$Cl. The mixture was diluted with ethyl acetate and H$_2$O, the organic layer was washed with H$_2$O. The organic layer was concentrated, purified by column to afford the product 358-2 (2 g, 44% yield) as a white solid.

The Synthesis of ethyl (3-bromophenoxy)methyl(methyl)phosphinate (358-3)

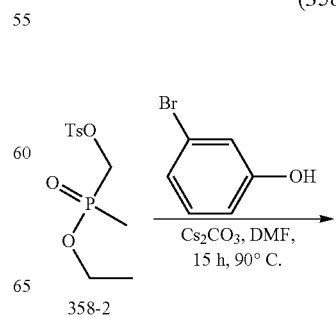

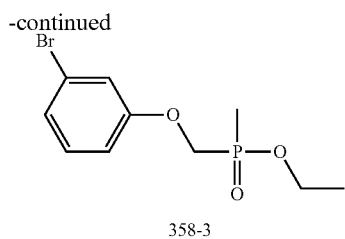

358-3

To a stirred solution of 358-2 (750 mg, 2.56 mmol) and 3-bromophenol (530 mg, 3.07 mmol) in DMF (20 mL) was added Cs$_2$CO$_3$ (1.0 g, 3.07 mmol). The mixture was stirred at 90° C. overnight. After the consumption of starting material (by LCMS), the mixture was concentrated, purified by column to afford the product 358-3 (500 mg, 67% yield) as yellow oil.

The Synthesis of ethyl methyl((3-(4,4,5,5-tetramethyl-1,3,2-dioxaborolan-2-yl)phenoxy)methyl)phosphinate (358-4)

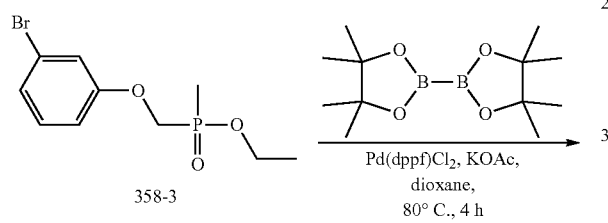

To a stirred solution of 358-3 (500 mg, 1.7 mmol) in dioxane (10 mL) was added bis(pinacolato)diboron (650 mg, 2.6 mmol), KOAc (500 mg, 5.1 mmol), Pd(dppf)Cl$_2$ (125 mg, 0.17 mmol). The resulting reaction mixture was heated to 80° C. and stirred for 4 h. After the consumption of starting material (by LCMS), the mixture was concentrated in vacuo to remove the solvent, then purified by prep-HPLC to give the desired product 358-4 (400 mg, 69% yield) as brown oil.

The Synthesis of ethyl (3-(4-amino-7-(cis-3-(azetidin-1-ylmethyl)cyclobutyl)-7H-pyrrolo[2,3-d]pyrimidin-5-yl)phenoxy)methyl(methyl)phosphinate (SU20668-0358-01)

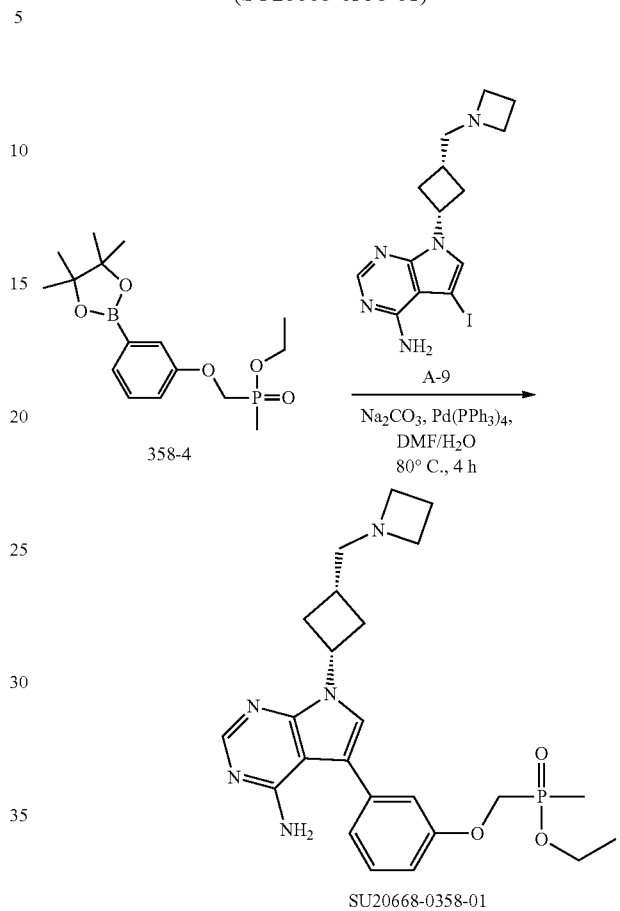

The mixture of 358-4 (250 mg, 0.74 mmol), A-9 (234 mg, 0.61 mmol), Pd(PPh$_3$)$_4$ (71 mg, 0.061 mmol), and Na$_2$CO$_3$ (120 mg, 1.22 mmol) in DMF/H$_2$O (10 mL, 4/1) was stirred at 80° C. under N$_2$ atmosphere for 4 h. After the consumption of starting material (by LCMS), the mixture was concentrated in vacuo to remove the solvent, then purified by prep-HPLC to give the desired product SU20668-0358-01 (55 mg, 19% yield) as a white solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 98.82%, Rt=1.536 min; MS Calcd.: 469.52; MS Found: 470.2 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 99.31%, Rt=6.176 min. $^1$H NMR (400 MHz, DMSO-d$_6$) δ 8.12 (s, 1H), 7.63 (s, 1H), 7.41 (t, J=8.0 Hz, 1H), 7.15-7.16 (m, 1H), 7.10 (d, J=7.6 Hz, 1H), 7.01 (dd, J=8.0 Hz, J=2.4 Hz, 1H), 6.17 (brs, 2H), 5.01-5.10 (m, 1H), 4.35-4.47 (m, 2H), 4.03-4.08 (m, 2H), 3.09 (t, J=6.8 Hz, 4H), 2.43-2.50 (m, 4H), 2.05-2.19 (m, 3H), 1.90-1.97 (m, 2H), 1.55 (d, J=14.4 Hz, 3H), 1.24 (t, J=7.2 Hz, 3H).

Scheme 120: Route for SU20668-0359-01

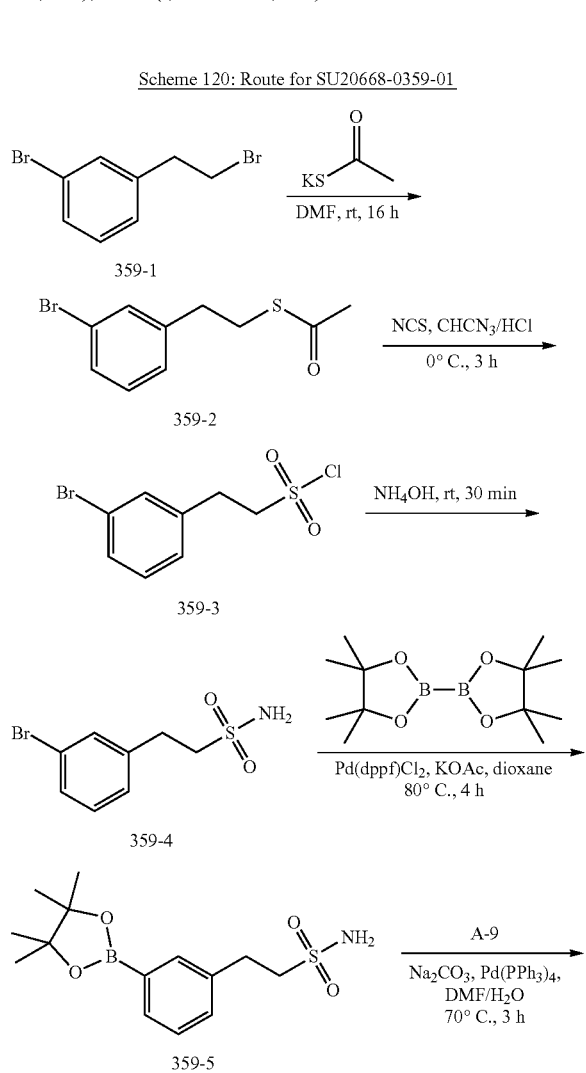

The Synthesis of S-3-bromophenethyl ethanethioate (359-2)

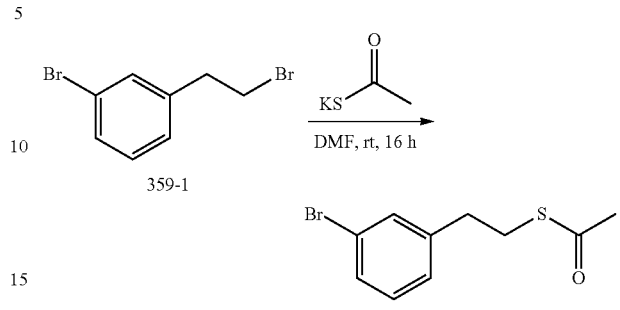

The mixture of potassium ethanethioate (0.48 g, 4.2 mmol) in DMF (15 mL) was stirred at 0° C. 359-1 (1 g, 3.8 mmol) dissolved in DMF (5 mL) was added dropwise to the mixture. Then the mixture was stirred at room temperature for 16 h. After the consumption of starting material (by LCMS), the mixture was added water, the aqueous phase was extracted with Et₂O, the combined organic phases were dried over anhydrous sodium sulfate, filtered, and concentrated in vacuo to give the desired product 359-2 (1 g, crude) as brown oil.

The Synthesis of 2-(3-bromophenyl)ethanesulfonyl chloride (359-3)

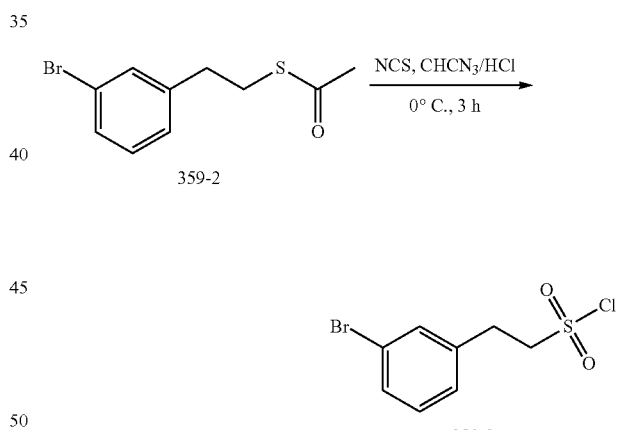

The mixture of NCS (2.03 g, 15.2 mmol) in CH₃CN/2M HCl (5/1, 40 mL) was stirred at 0° C. 359-2 (1 g, 3.8 mmol) dissolved in CH₃CN/2M HCl (5/1, 5 mL) was added dropwise to the mixture. Then the mixture was stirred at 0° C. for 3 h. After the consumption of starting material (by LCMS), the mixture was added water, the aqueous phase was extracted with Et₂O, the combined organic phases were dried over anhydrous sodium sulfate, filtered, and concentrated in vacuo to give the desired product 359-3 (1.1 g, crude) as a white solid.

The Synthesis of 2-(3-bromophenyl)ethanesulfonamide (359-4)

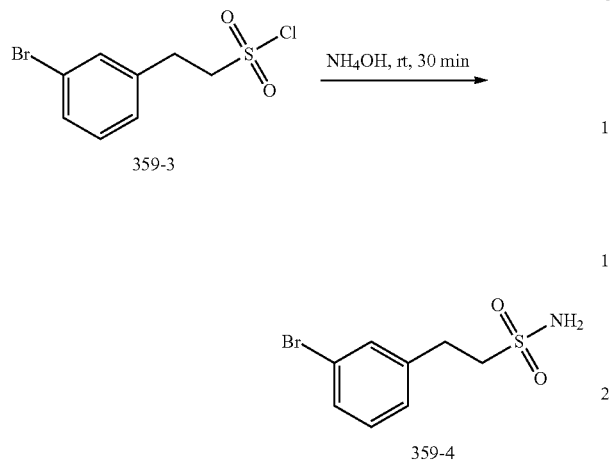

The solution of 359-3 (1.1 g, 3.8 mmol) in NH₄OH (20 mL) was stirred at room temperature for 30 min. After the consumption of starting material (by LCMS), the mixture was concentrated in vacuo to give the desired product 359-4 (320 mg, 32% yield) as a white solid.

The Synthesis of 2-(3-(4,4,5,5-tetramethyl-1,3,2-dioxaborolan-2-yl)phenyl)ethanesulfonamide (359-5)

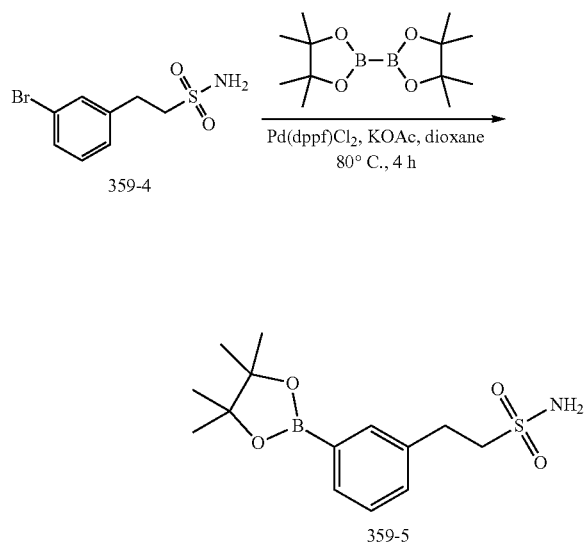

To a stirred solution of 359-4 (300 mg, 1.14 mmol) in dioxane (10 mL) was added bis(pinacolato)diboron (435 mg, 1.71 mmol), KOAc (335 mg, 3.42 mmol), Pd(dppf)Cl₂ (88 mg, 0.12 mmol). The resulting reaction mixture was heated to 80° C. and stirred for 4 h. After the consumption of starting material (by LCMS), the mixture was concentrated in vacuo to remove the solvent, then purified by prep-HPLC to give the desired product 359-5 (130 mg, 37% yield) as a white solid.

The Synthesis of 2-(3-(4-amino-7-(cis-3-(azetidin-1-ylmethyl)cyclobutyl)-7H-pyrrolo[2,3-d]pyrimidin-5-yl)phenyl)ethanesulfonamide (SU20668-0359-01)

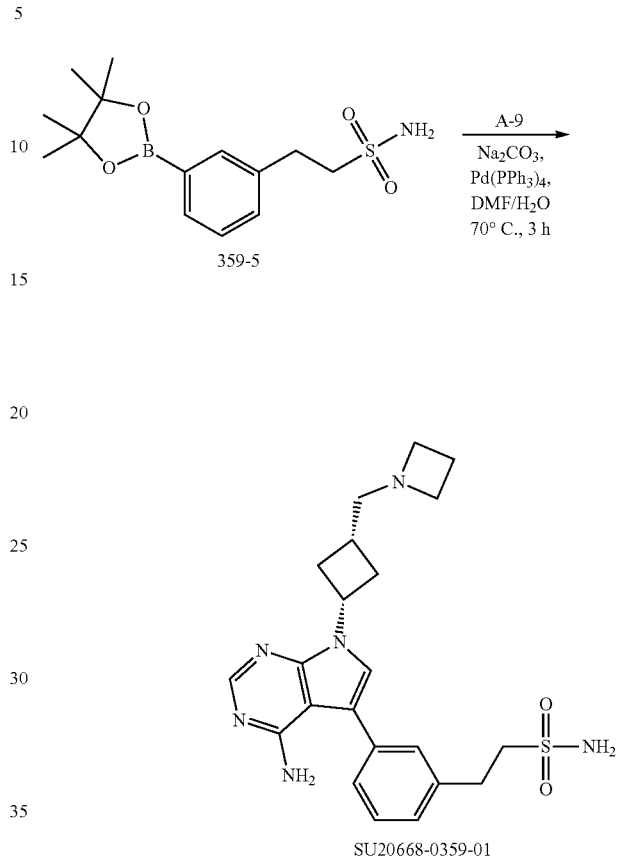

The mixture of 359-5 (100 mg, 0.32 mmol), A-9 (100 mg, 0.26 mmol), Pd(PPh₃)₄ (30 mg, 0.026 mmol), and Na₂CO₃ (70 mg, 0.52 mmol) in DMF/H₂O (5 mL, 4/1) was stirred at 70° C. under N₂ atmosphere 3 h. After the consumption of starting material (by LCMS), the mixture was concentrated in vacuo to remove the solvent, then purified by prep-HPLC to give the desired product SU20668-0359-01 (12 mg, 8.5% yield) as a yellow solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Purity: 100%, Rt=1.356 min; MS Calcd.: 440.56; MS Found: 441.3 [M+H]⁺. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min. Purity: 97.14%, Rt=5.824 min. ¹H NMR (400 MHz, MeOD-d₄) δ 8.15 (s, 1H), 7.44-7.47 (m, 3H), 7.39-7.41 (m, 1H), 7.32 (d, J=7.6 Hz, 1H), 5.09-5.16 (m, 1H), 3.42-3.51 (m, 6H), 3.19-3.23 (m, 3H), 2.82 (brs, 2H), 2.66-2.70 (m, 2H), 2.21-2.30 (m, 6H).

Scheme 121: Route for SU20668-0360

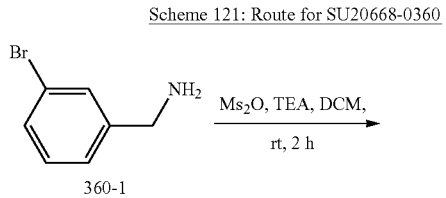

To a stirred solution of compound 360-1 (900 mg, 4.04 mmol) in DCM (15 ml) was added Ms$_2$O (844 mg, 4.85 mmol) and TEA (1.24 g, 12.12 mmol). The resulting reaction mixture was stirred at rt for 2 h. Then concentrated in vacuo, thus was further purified by C.C. to give 360-2 (950 mg, yield: 84%) as yellow oil.

The Synthesis of diethyl N-(3-(4,4,5,5-tetramethyl-1,3,2-dioxaborolan-2-yl)benzyl)methanesulfonamide (360-3)

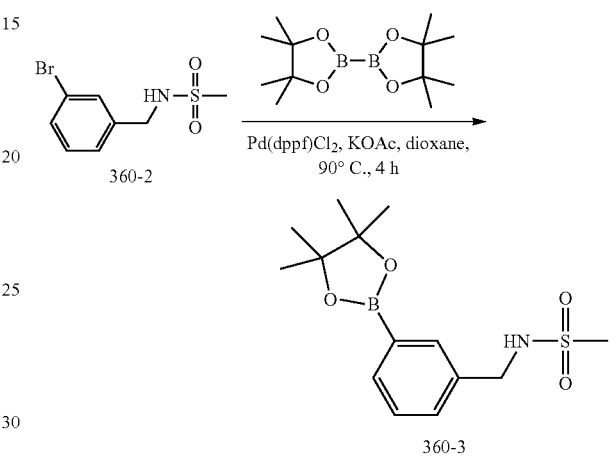

To a stirred solution of compound 360-2 (500 mg, 1.89 mmol) in dioxane (8 mL) was added 4,4,4',4',5,5,5',5'-octamethyl-2,2'-bi(1,3,2-dioxaborolane) (481 mg, 1.89 mmol), KOAc (372 mg, 3.8 mmol), Pd(dppf)Cl$_2$ (50 mg, 0.07 mmol). The resulting reaction mixture was heated to 90° C. and stirred for 4 h and concentrated in vacuo to remove the solvent, then added water, the aqueous phase was extracted with dichloromethane, the combined organic phases were dried over anhydrous sodium sulfate, filtered, and concentrated, the crude was purified by reverse C.C. to give 360-3 (450 mg, yield: 72.58%) as yellow oil.

The Synthesis of N-(3-(4-amino-7-(cis-3-(azetidin-1-ylmethyl)cyclobutyl)-7H-pyrrolo[2,3-d]pyrimidin-5-yl)benzyl)methanesulfonamide (SU20668-0360)

The Synthesis of N-(3-bromobenzyl)methanesulfonamide (360-2)

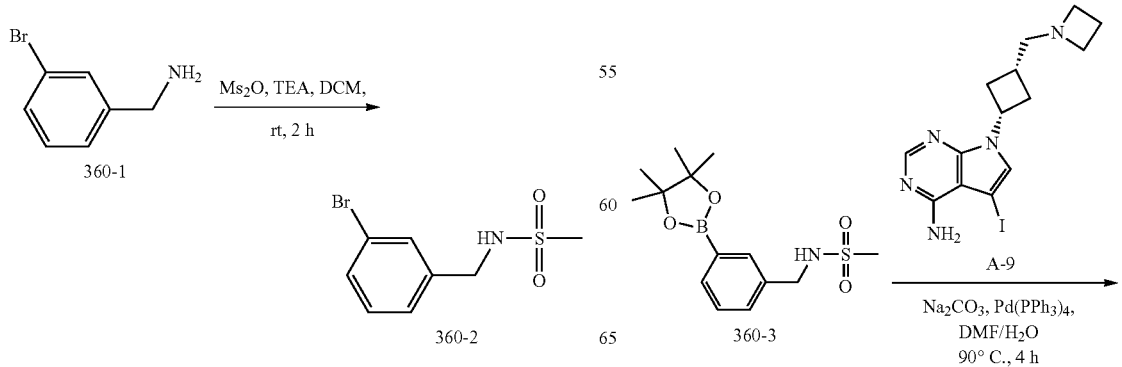

711
-continued

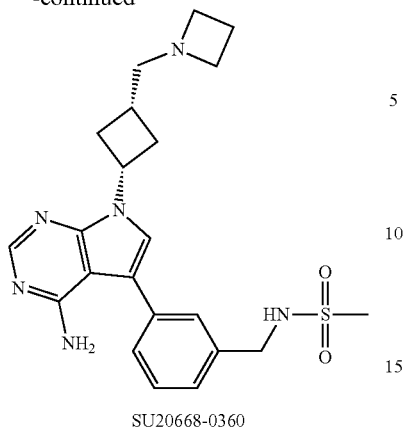

SU20668-0360

To a stirred solution of compound 360-3 (146 mg, 0.47 mmol) in DMF/H₂O (5 mL, 4/1) was added A-9 (150 mg, 0.39 mmol), Na₂CO₃ (104 mg, 0.98 mmol), Pd(PPh₃)₄ (15 mg, 0.013 mmol). The resulting reaction mixture was heated to 90° C. and stirred for 4 h and concentrated in vacuo to remove the solvent, then added water, the aqueous phase was extracted with dichloromethane, the combined organic phases were dried over anhydrous sodium sulfate, filtered, and concentrated, the crude was purified by prep-HPLC to give the desired product SU20668-0360 (70 mg, yield: 33.8%) as a yellow solid. LC-MS (LC-MS (Agilent LCMS 1200-6120, Column: Waters X-Bridge C18 (30 mm×4.6 mm×2.7 m); Column Temperature: 40° C.; Flow Rate: 3.0 mL/min; Mobile Phase: from 95% [water+0.05% TFA] and 5% [CH3CN+0.05% TFA] to 0% [water+0.05% TFA] and 100% [CH3CN+0.05% TFA] in 0.8 min, then under this condition for 0.4 min, finally changed to 95% [water+0.05% TFA] and 5% [CH3CN+0.05%] in 0.01 min.). Purity: 100.00%, Rt=1.354 min; MS Calcd.: 440.20; MS Found: 441.3 [M+H]+. HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH₃CN+0.1% TFA] to 0% [water+0.1% TFA] and 100% [CH₃CN+0.1% TFA] in 10 min, then under this condition for 5 min, finally changed to 95% [water+0.1% TFA] and 5% [CH₃CN+0.1% TFA] in 0.1 min and under this condition for 5 min). Purity: 99.64%, Rt=5.682 min. ¹H NMR (400 MHz, DMSO-d₆) δ 8.12 (s, 1H), 7.57 (s, 1H), 7.41-7.46 (m, 3H), 7.32-7.34 (m, 1H), 6.09 (brs, 2H), 5.01-5.10 (m, 1H), 4.22 (s, 2H), 3.09 (t, J=7.2 Hz, 4H), 2.90 (s, 3H), 2.47-2.51 (m, 5H), 2.08-2.20 (m, 3H), 1.90-1.97 (m, 2H).

Scheme 122: Route for SU20668-0361

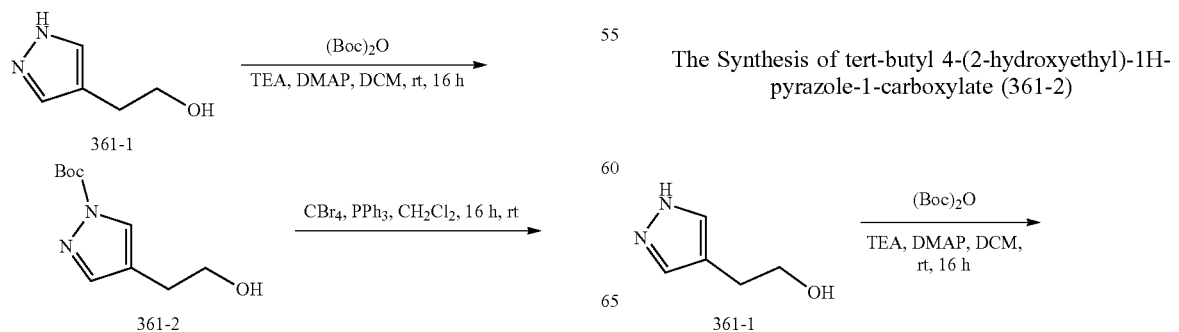

712
-continued

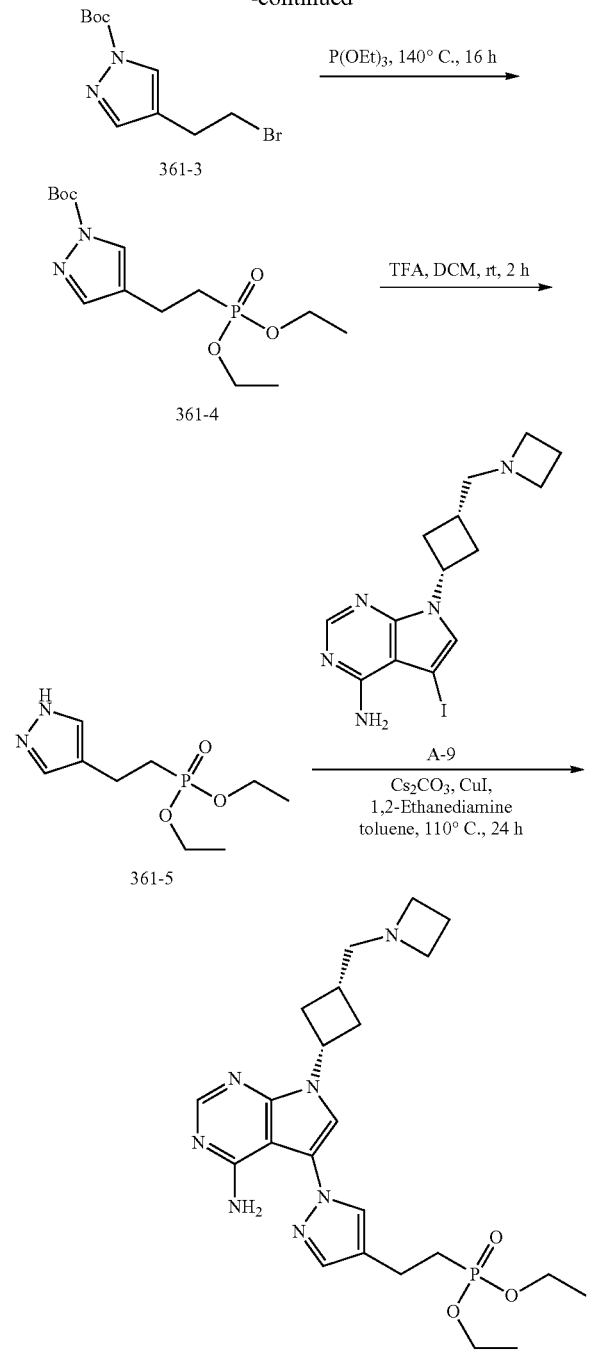

SU20668-0361

The Synthesis of tert-butyl 4-(2-hydroxyethyl)-1H-pyrazole-1-carboxylate (361-2)

-continued

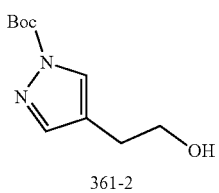

361-2

To a stirred solution of 361-1 (1.0 g, 8.93 mmol) in DCM (15 ml) was added DMAP (108 mg, 0.89 mmol), TEA (3.99 g, 26.79 mmol) and (Boc)$_2$O (2.14 g, 9.8 mmol). The resulting reaction mixture was stirred for 16 h at rt. Then concentrated in vacuo, thus was further purified by C.C. to give 361-2 (1.58 g, yield: 83.6%) as a white solid.

The Synthesis of tert-butyl 4-(2-bromoethyl)-1H-pyrazole-1-carboxylate (361-3)

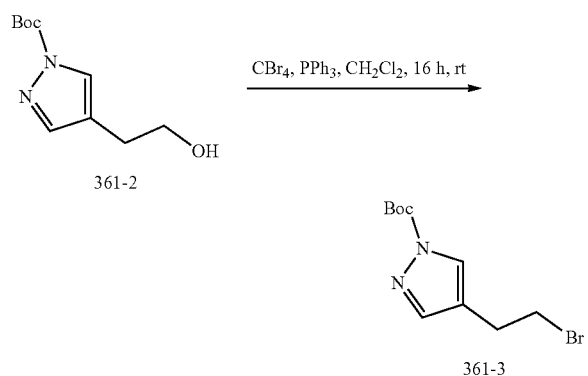

To a stirred solution of 361-2 (1.5 g, 7.07 mmol) in DCM (20 ml) was added PPh$_3$ (2.78 g, 10.6 mmol) and CBr$_4$ (2.34 g, 7.07 mmol). The resulting reaction mixture was stirred for 16 h at rt. Then the reaction mixture was concentrated in vacuo, thus was further purified by C.C. to give 361-3 (1.6 g, yield: 82.3%) as a white solid.

The Synthesis of tert-butyl 4-(2-(diethoxyphosphoryl)ethyl)-1H-pyrazole-1-carboxylate (361-4)

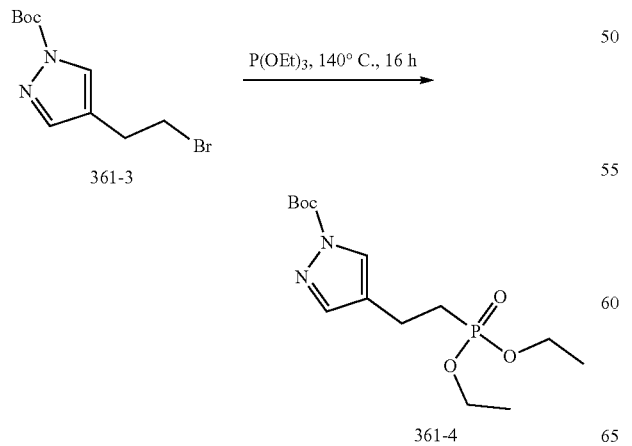

To a stirred solution of compound 361-3 (1.6 g, 5.84 mmol) in P(OEt)$_3$ (20 ml) was stirred at 140° C. for 16 h. Then added water, the aqueous phase was extracted with ethyl acetate, the combined organic phases were dried over anhydrous sodium sulfate, filtered, and concentrated in vacuo, thus was further purified by reverse C.C. to give 361-4 (900 mg, yield: 56%) as a yellow oil.

The Synthesis of diethyl 2-(1H-pyrazol-4-yl)ethylphosphonate (361-5)

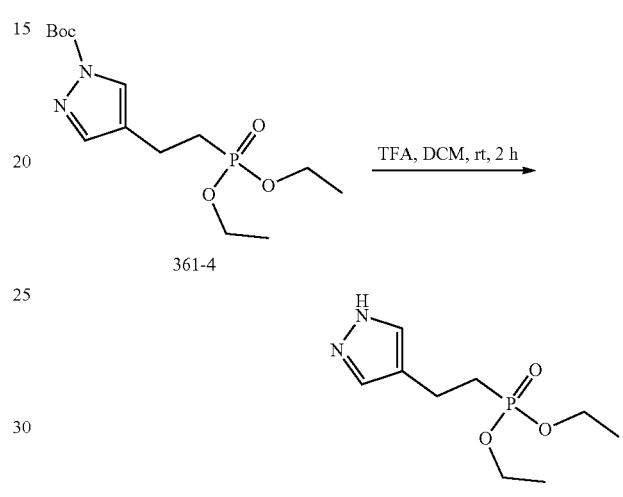

To a stirred solution of compound 361-4 (900 mg, 3.26 mmol) in DCM (15 ml) was added TFA (15 ml). The resulting reaction mixture was stirred for 2 h at rt. Then concentrated in vacuo to give 361-5 (600 mg, yield: 79%) as a yellow oil.

The Synthesis of diethyl 2-(1-(4-amino-7-(cis-3-(azetidin-1-ylmethyl)cyclobutyl)-7H-pyrrolo[2,3-d]pyrimidin-5-yl)-1H-pyrazol-4-yl)ethylphosphonate (SU20668-0361)

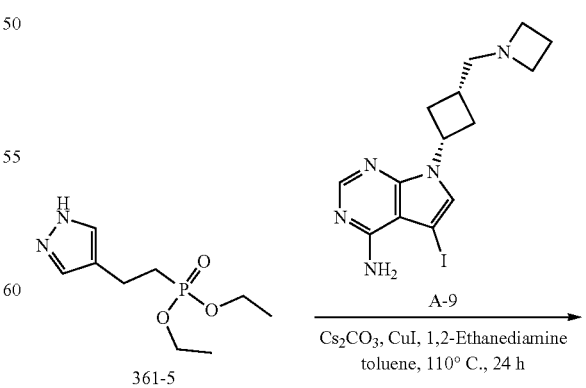

715

-continued

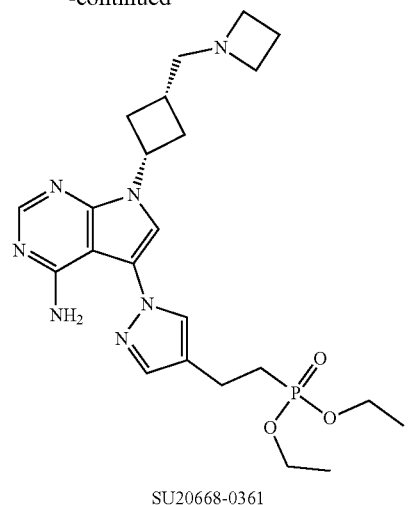

SU20668-0361

To a stirred solution of compound 361-5 (90 mg, 0.39 mmol) in toluene (5 mL) was added A-9 (150 mg, 0.39 mmol), $Cs_2CO_3$ (319 mg, 0.98 mmol), CuI (74 mg, 0.39 mmol), 1,2-Ethanediamine(35 mg, 0.58 mmol). The resulting reaction mixture was heated to 110° C. and stirred for 24 h and concentrated in vacuo to remove the solvent, then added water, the aqueous phase was extracted with dichloromethane, the combined organic phases were dried over anhydrous sodium sulfate, filtered, and concentrated, the crude was purified by prep-HPLC to give the desired product SU20668-0361 (60 mg, yield: 31.6%) as a yellow solid. LC-MS (LC-MS (Agilent LCMS 1200-6120, Column: Waters X-Bridge C18 (30 mm×4.6 mm×2.7 m); Column Temperature: 40° C.; Flow Rate: 3.0 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 0.8 min, then under this condition for 0.4 min, finally changed to 95% [water+0.05% TFA] and 5% [$CH_3CN$+0.05%] in 0.01 min.). Purity: 100.00%, Rt=1.647 min; MS Calcd.: 487.25; MS Found: 488.3 [M+H]$^+$. HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [$CH_3CN$+0.1% TFA] to 0% [water+0.1% TFA] and 100% [$CH_3CN$+0.1% TFA] in 10 min, then under this condition for 5 min, finally changed to 95% [water+0.1% TFA] and 5% [$CH_3CN$+0.1% TFA] in 0.1 min and under this condition for 5 min). Purity: 99.82%, Rt=6.527 min. $^1$H NMR (400 MHz, DMSO-d$_6$) δ 8.32 (s, 1H), 8.06 (s, 1H), 7.92 (s, 1H), 7.72 (s, 1H), 5.06-5.10 (m, 1H), 3.97-4.04 (m, 4H), 3.09-3.12 (m, 4H), 2.68-2.75 (m, 2H), 2.49-2.51 (m, 4H), 2.05-2.14 (m, 5H), 1.92-1.99 (m, 2H), 1.23 (t, J=7.2 Hz, 6H).

Scheme 123: Route for SU20668-0365

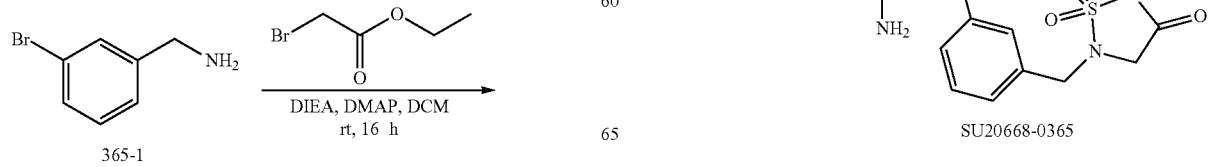

716

-continued

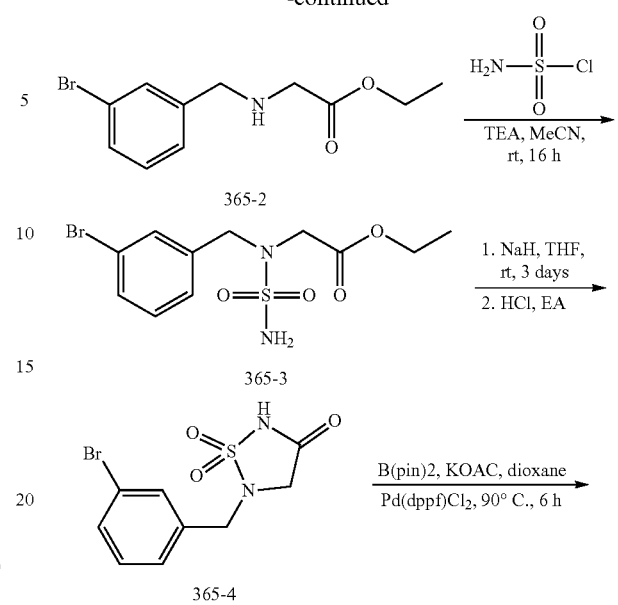

SU20668-0365

The Synthesis of ethyl 2-(3-bromobenzylamino)acetate (365-2)

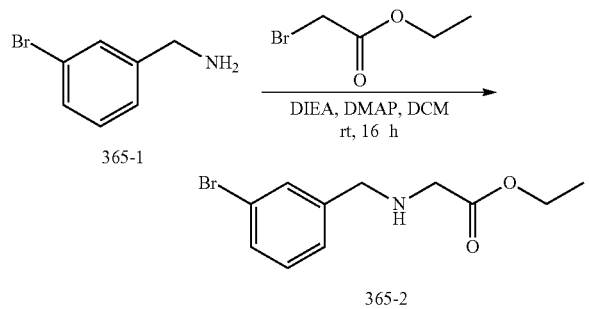

365-1

365-2

To a stirred solution of 365-1 (5.0 g, 26.8 mmol) in DCM (50 ml) was added DMAP (3.9 g, 32.16 mmol), DIEA (6.9 g, 53.6 mmol) and ethyl 2-bromoacetate (4.48 g, 26.8 mmol). The resulting reaction mixture was stirred for 16 h at rt. Then added water, the aqueous phase was extracted with dichloromethane, the combined organic phases were dried over anhydrous sodium sulfate, filtered, and concentrated in vacuo, purified by C.C. to give 365-2 (3.3 g, yield: 45.3%) as a white solid.

The Synthesis of ethyl 2-((3-bromobenzyl)(sulfamoyl)amino)acetate (365-3)

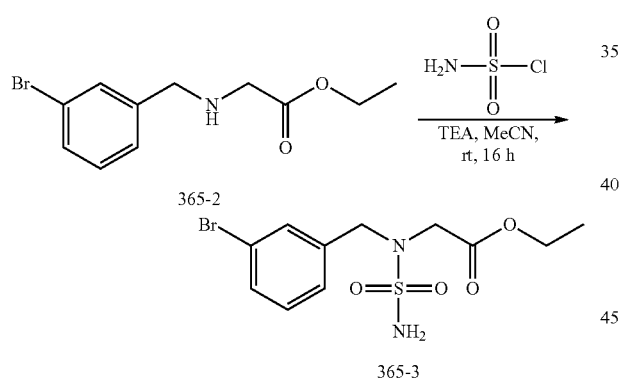

365-2

365-3

To a stirred solution of 365-2 (3 g, 11.03 mmol) in MeCN (30 ml) was added sulfamoyl chloride (1.27 g, 11.03 mmol), TEA (4.9 g, 33.09 mmol). The resulting reaction mixture was stirred for 16 h at rt. Then the reaction mixture was concentrated in vacuo, purified by C.C. to give 365-3 (1.6 g, yield: 41.3%) as a yellow solid.

The Synthesis of 365-4

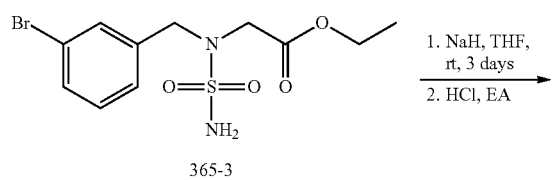

365-3

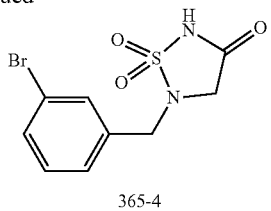

365-4

To a stirred solution of 365-3 (1.4 g, 3.99 mmol) in THF (20 mL) was added NaH (287 mg, 11.9 mmol) and the reaction mixture was stirred at rt for 3 days. The solvent was removed. To the crude in ethyl acetate (20 mL) was added HCl (2 mL). The mixture solution was stirred for 15 min. The mixture was diluted with ethyl acetate and H₂O, the organic layer was washed with H₂O. The organic layer was concentrated, purified by column to afford the product 365-4 (550 mg, 45% yield) as a yellow solid.

The Synthesis of 364-5

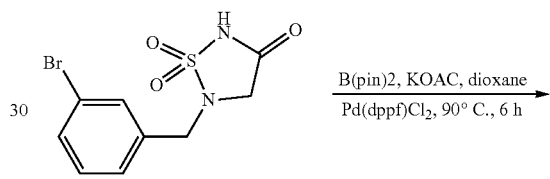

365-4

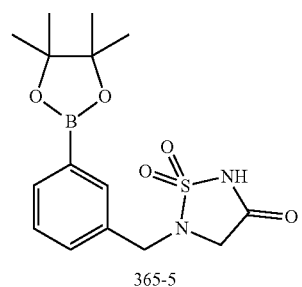

365-5

To a stirred solution of compound 365-4 (100 mg, 0.33 mmol) in dioxane (5 ml) was added KOAc (81 mg, 0.83 mmol), B(pin)₂ (116 mg, 0.39 mmol), Pd(dppf)Cl₂ (12 mg, 0.017 mmol). The resulting reaction mixture was heated to 90° C. and stirred for 6 h. Then concentrated in vacuo and purified by column to afford the product 365-5 (60 mg, 51.7% yield) as a yellow solid.

The Synthesis of SU20668-0365

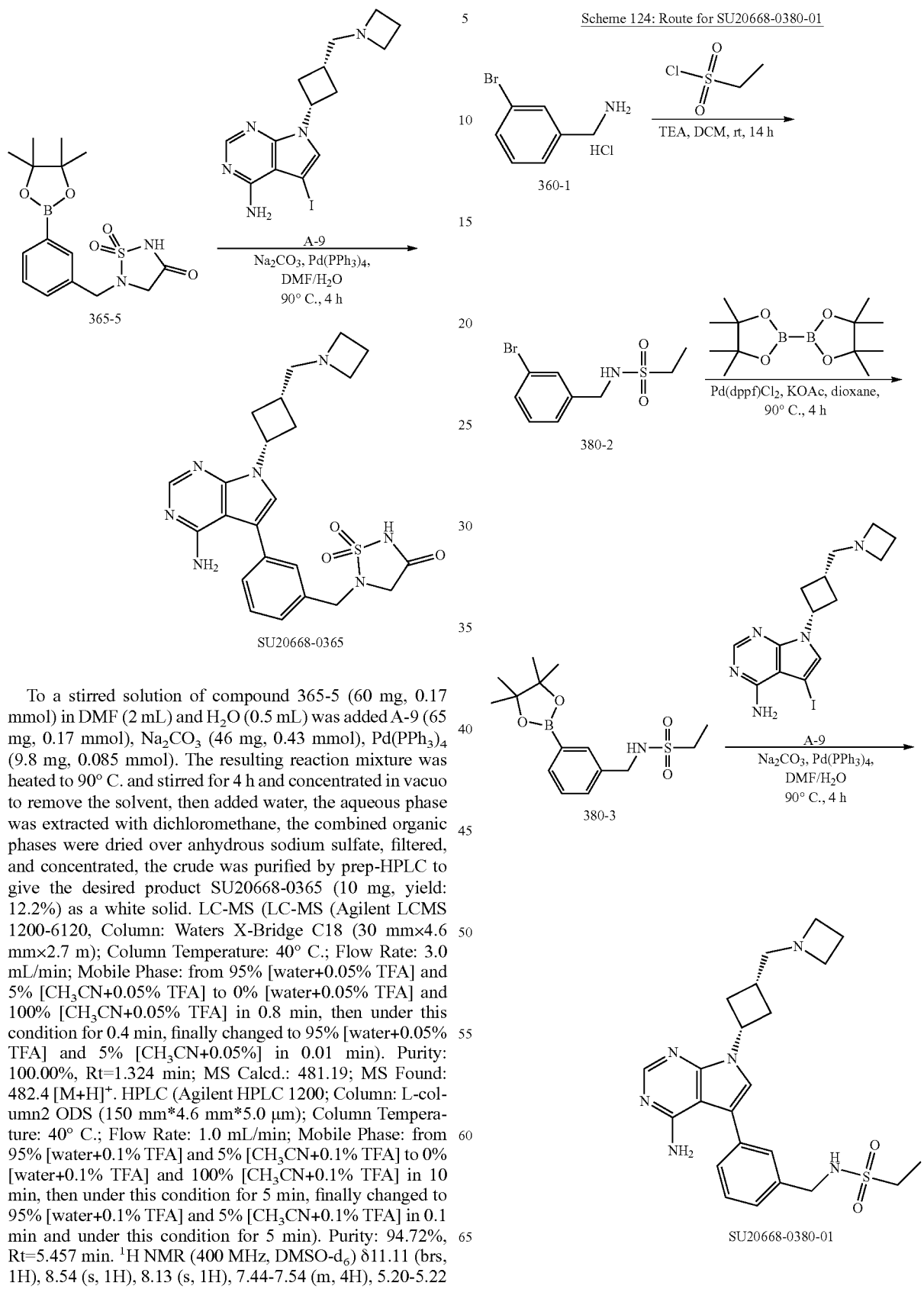

To a stirred solution of compound 365-5 (60 mg, 0.17 mmol) in DMF (2 mL) and H$_2$O (0.5 mL) was added A-9 (65 mg, 0.17 mmol), Na$_2$CO$_3$ (46 mg, 0.43 mmol), Pd(PPh$_3$)$_4$ (9.8 mg, 0.085 mmol). The resulting reaction mixture was heated to 90° C. and stirred for 4 h and concentrated in vacuo to remove the solvent, then added water, the aqueous phase was extracted with dichloromethane, the combined organic phases were dried over anhydrous sodium sulfate, filtered, and concentrated, the crude was purified by prep-HPLC to give the desired product SU20668-0365 (10 mg, yield: 12.2%) as a white solid. LC-MS (LC-MS (Agilent LCMS 1200-6120, Column: Waters X-Bridge C18 (30 mm×4.6 mm×2.7 m); Column Temperature: 40° C.; Flow Rate: 3.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 0.8 min, then under this condition for 0.4 min, finally changed to 95% [water+0.05% TFA] and 5% [CH$_3$CN+0.05%] in 0.01 min). Purity: 100.00%, Rt=1.324 min; MS Calcd.: 481.19; MS Found: 482.4 [M+H]$^+$. HPLC (Agilent HPLC 1200; Column: L-column2 ODS (150 mm*4.6 mm*5.0 µm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min). Purity: 94.72%, Rt=5.457 min. $^1$H NMR (400 MHz, DMSO-d$_6$) δ11.11 (brs, 1H), 8.54 (s, 1H), 8.13 (s, 1H), 7.44-7.54 (m, 4H), 5.20-5.22 (m, 1H), 4.38 (s, 2H), 4.15 (s, 2H), 4.00-4.06 (m, 4H), 2.58-2.63 (m, 3H), 2.25-2.45 (m, 6H).

Scheme 124: Route for SU20668-0380-01

721
The Synthesis of
N-(3-bromobenzyl)ethanesulfonamide (380-2)

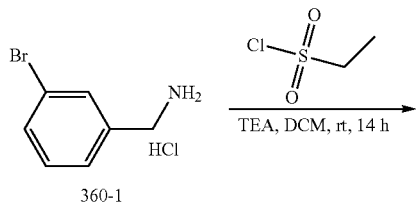

To a stirred solution of 360-1 (400 mg, 1.798 mmol) in DCM (15 ml) was added TEA (454 mg, 4.494 mmol) and ethanesulfonyl chloride (255 mg, 1.978 mmol) at rt. The resulting reaction mixture was stirred for 14 h at rt. Then added water, the aqueous phase was extracted with dichloromethane, the combined organic phases were dried over anhydrous sodium sulfate, filtered, and concentrated in vacuo to give 380-2 (488 mg, yield: 81.7%) as yellow oil.

The Synthesis of N-(3-(4,4,5,5-tetramethyl-1,3,2-dioxaborolan-2-yl)benzyl)ethanesulfonamide (380-3)

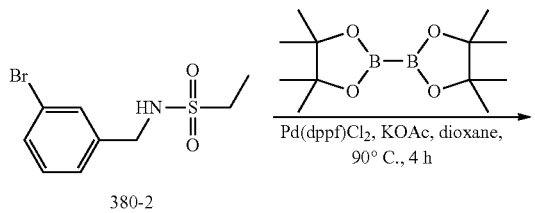

To a stirred solution of 380-2 (448 mg, 1.61 mmol) in dioxane (16 mL) was added bis(pinacolato)diboron (820 mg, 3.23 mmol), KOAc (399 mg, 4.07 mmol), Pd(dppf)Cl$_2$ (237 mg, 0.324 mmol). The resulting reaction mixture was heated to 90° C. and stirred for 4 h and concentrated in vacuo to remove the solvent, the crude was purified by prep-TLC to give 380-3 (460 mg, yield: 87.95%) as a brown solid.

722
The Synthesis of N-(3-(4-amino-7-((s,3s)-3-(azetidin-1-ylmethyl)cyclobutyl)-7H-pyrrolo[2,3-d]pyrimidin-5-yl)benzyl)ethanesulfonamide (SU20668-0380-01)

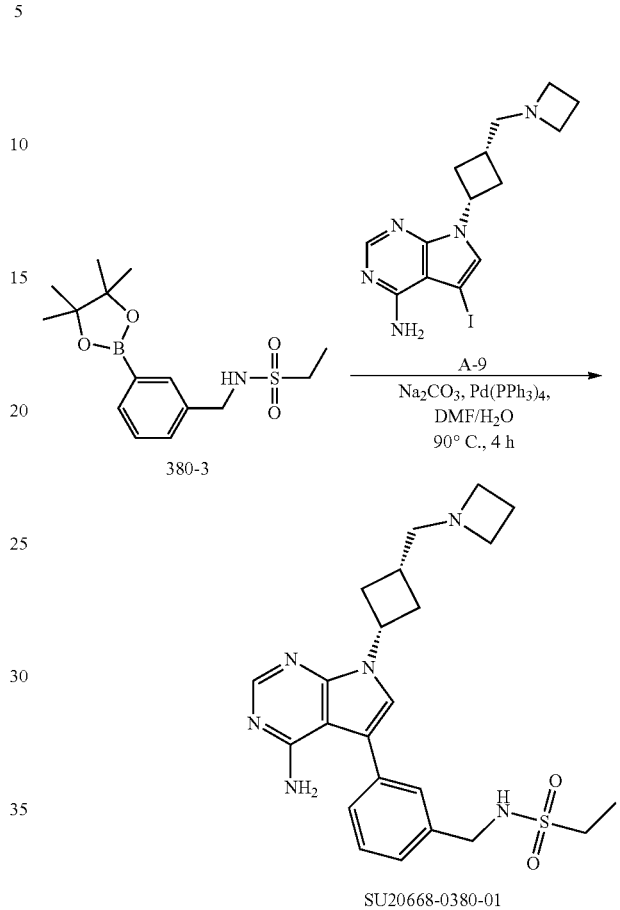

To a stirred solution of 380-3 (168 mg, 0.517 mmol) in DMF/water (8 mL/2 mL) was added A-9 (150 mg, 0.391 mmol), Na$_2$CO$_3$ (85 mg, 0.802 mmol), Pd(PPh$_3$)$_4$ (90 mg, 0.078 mmol). The resulting reaction mixture was heated to 90° C. and stirred for 4 h, filtered and purified by prep-HPLC to give SU20668-0380-01 (30 mg, yield: 16.9%) as a brown solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, R$_t$=1.322 min; MS Calcd.: 454.22; MS Found: 455.2 [M+H]$^+$. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM AcONH$_4$) water/CH$_3$CN=900/100 (v/v)] and 10% [total 10 mM AcONH$_4$) water/CH$_3$CN=100/900 (v/v)] to 15% [total 10 mM AcONH$_4$) water/CH$_3$CN=900/100 (v/v)] and 85% [total 10 mM AcONH$_4$) water/CH$_3$CN=100/900 (v/v)] in 5 min, then under this condition for 10 min, finally changed to 90% [(total 10 mM AcONH$_4$) water/CH$_3$CN=900/100 (v/v)] and 10% [total 10 mM AcONH$_4$) water/CH$_3$CN=100/900 (v/v)] in 0.1 min and under this condition for 5 min). Purity: 97.93%, Rt=6.682 min. $^1$H NMR (400 MHz, DMSO-d$_6$) δ

8.30 (s, 1H), 8.14 (s, 1H), 7.65 (t, J=6 Hz, 1H), 7.59 (s, 1H), 7.42-7.49 (m, 2H), 7.34-7.35 (m, 1H), 6.10 (brs, 2H), 5.07-5.11 (m, 1H), 4.21 (d, J=6.0 Hz, 2H) 3.40-3.44 (m, 3H), 2.97-3.02 (m, 2H), 2.76-2.78 (m, 2H), 2.51 (m, 4H), 2.06-2.25 (m, 4H), 1.19 (t, J=7.2 Hz, 3H).

The Synthesis of N-(3-bromobenzyl)-1-phenylmethanesulfonamide (0382-2)

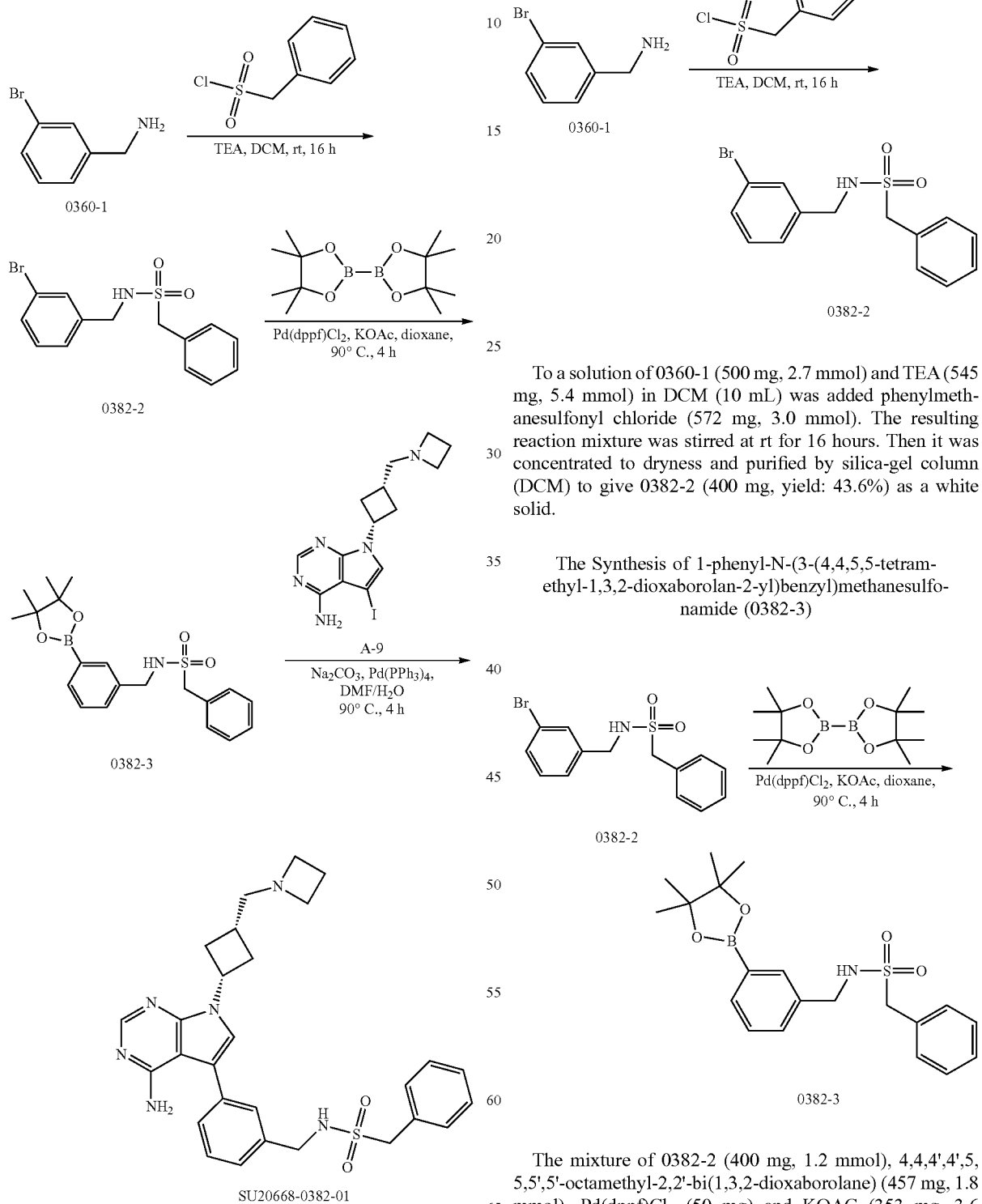

To a solution of 0360-1 (500 mg, 2.7 mmol) and TEA (545 mg, 5.4 mmol) in DCM (10 mL) was added phenylmethanesulfonyl chloride (572 mg, 3.0 mmol). The resulting reaction mixture was stirred at rt for 16 hours. Then it was concentrated to dryness and purified by silica-gel column (DCM) to give 0382-2 (400 mg, yield: 43.6%) as a white solid.

The Synthesis of 1-phenyl-N-(3-(4,4,5,5-tetramethyl-1,3,2-dioxaborolan-2-yl)benzyl)methanesulfonamide (0382-3)

The mixture of 0382-2 (400 mg, 1.2 mmol), 4,4,4',4',5,5,5',5'-octamethyl-2,2'-bi(1,3,2-dioxaborolane) (457 mg, 1.8 mmol), Pd(dppf)Cl$_2$ (50 mg) and KOAC (353 mg, 3.6 mmol) in dioxane (5 mL) was stirred at 90° C. under N$_2$ atmosphere for 4 hours. Then the mixture was concentrated to dryness. The residue was purified by silica-gel column (DCM) to give 0382-3 (260 mg, yield: 56.0%) as a white solid.

The Synthesis of N-(3-(4-amino-7-(cis-3-(azetidin-1-ylmethyl)cyclobutyl)-7H-pyrrolo[2,3-d]pyrimidin-5-yl)benzyl)-1-phenylmethanesulfonamide (SU20668-0382-01)

condition for 5 min). Purity: 94.18%, Rt=7.689 min. $^1$H NMR (400 MHz, DMSO-d$_6$) δ 8.13 (s, 1H), 7.74 (brs, 1H), 7.56 (s, 1H), 7.30-7.47 (m, 9H), 6.10 (brs, 2H), 5.02-5.10 (m, 1H), 4.36 (s, 2H), 4.16 (s, 2H), 3.08 (t, J=6.8 Hz, 4H), 2.47-2.50 (m, 2H), 2.08-2.19 (m, 3H), 1.90-1.95 (m, 2H).

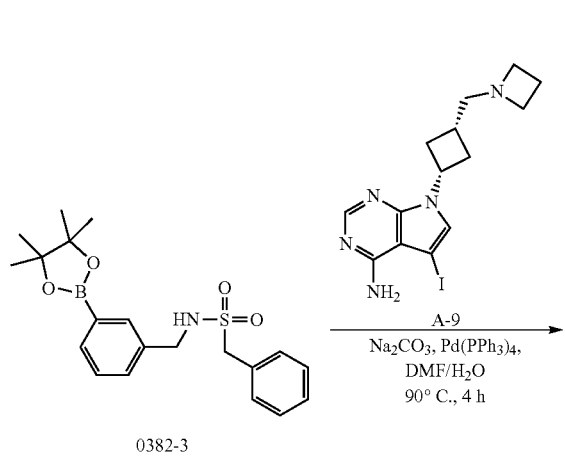

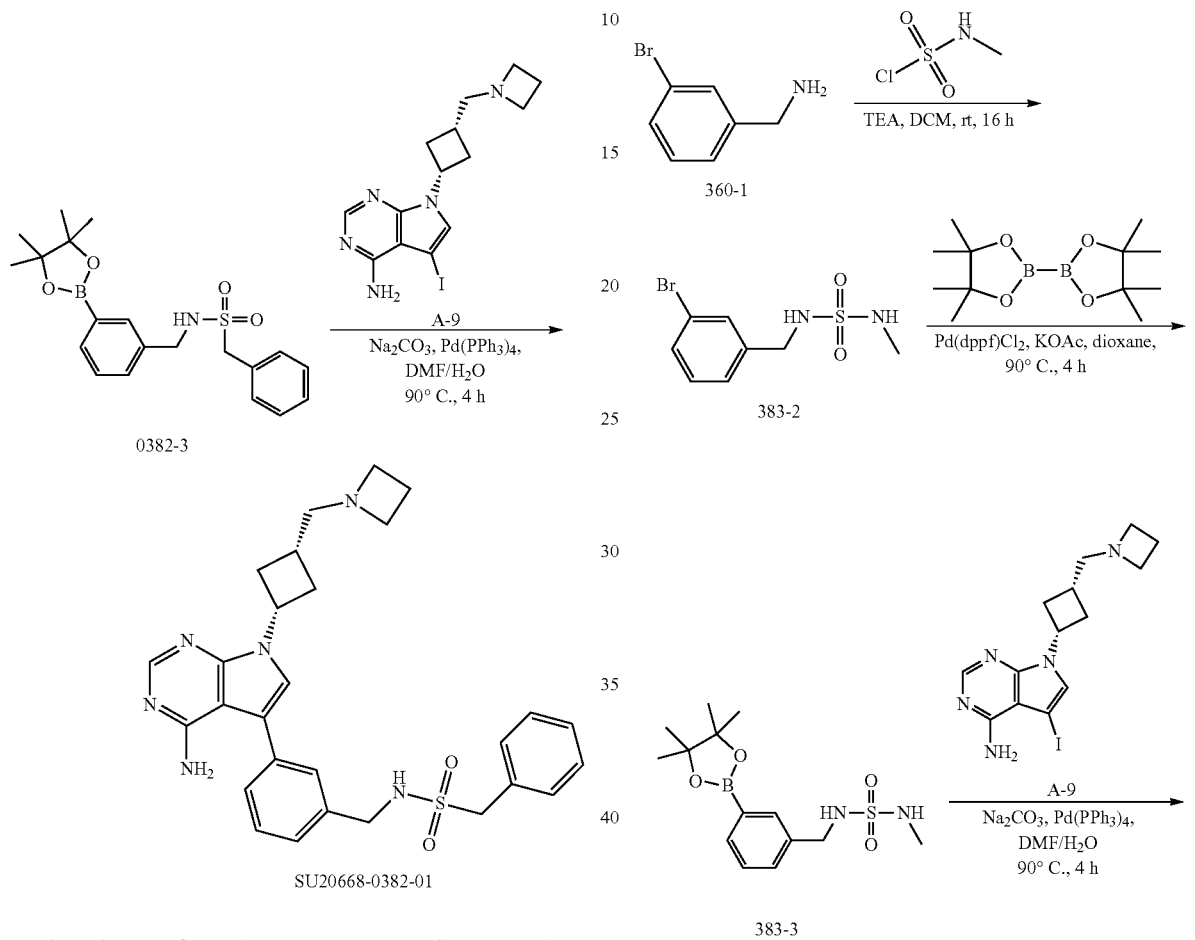

Scheme 126: Route for SU20668-0383-01

The mixture of A-9 (148 mg, 0.39 mmol), 0382-3 (150 mg, 0.39 mmol), Pd (PPh$_3$)$_4$ (20 mg) and Na$_2$CO$_3$ (85 mg, 0.80 mmol) in DMF/H$_2$O (3 mL, 4/1) was stirred at 90° C. for 4 hours. Then the mixture was concentrated to dryness. The residue was purified by silica-gel column (DCM: MeOH=50:1) and prep-HPLC to give SU20668-0382-01 (55 mg, yield: 27.3%) as a white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=1.527 min; MS Calcd.: 516.2; MS Found: 517.2 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this

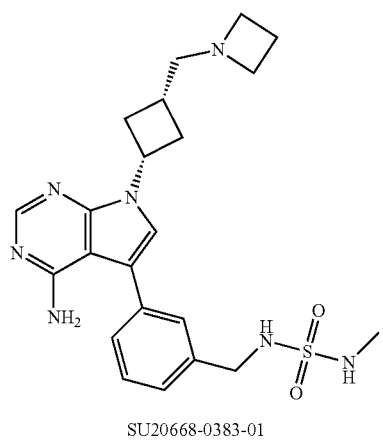

SU20668-0383-01

The Synthesis of Compound (383-2)

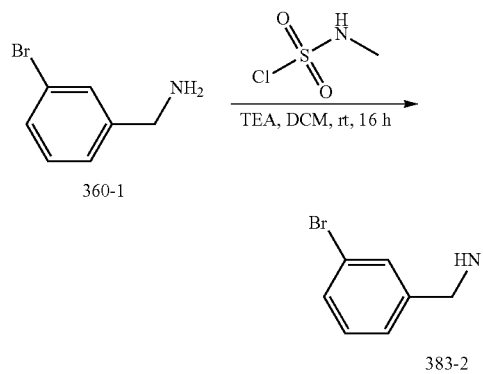

To a stirred solution of 360-1 (500 mg, 2.687 mmol) in DCM (15 ml) was added TEA (543 mg, 5.373 mmol) and methylsulfamoyl chloride (349 mg, 2.687 mmol) at rt. The resulting reaction mixture was stirred for 16 h at rt. Then added water, the aqueous phase was extracted with dichloromethane, the combined organic phases were dried over anhydrous sodium sulfate, filtered, and concentrated in vacuo to give 383-2 (610 mg, yield: 81.3%) as a white solid.

The Synthesis of Compound (383-3)

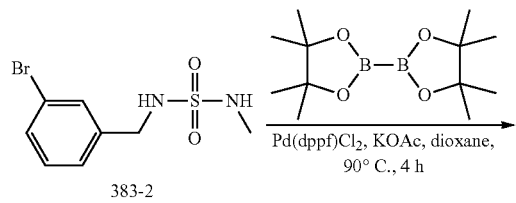

To a stirred solution of 383-2 (722 mg, 2.586 mmol) in dioxane (24 mL) was added bis(pinacolato)diboron (1314 mg, 5.173 mmol), KOAc (636 mg, 6.483 mmol), Pd(dppf)Cl$_2$ (383 mg, 0.523 mmol). The resulting reaction mixture was heated to 90° C. and stirred for 4 h and concentrated in vacuo to remove the solvent, then added water, the aqueous phase was extracted with EA, the combined organic phases were dried over anhydrous sodium sulfate, filtered, and concentrated, the crude was purified by prep-TLC to give 383-3 (420 mg, yield: 73%) as a white solid.

The Synthesis of Compound (SU20668-0383-01)

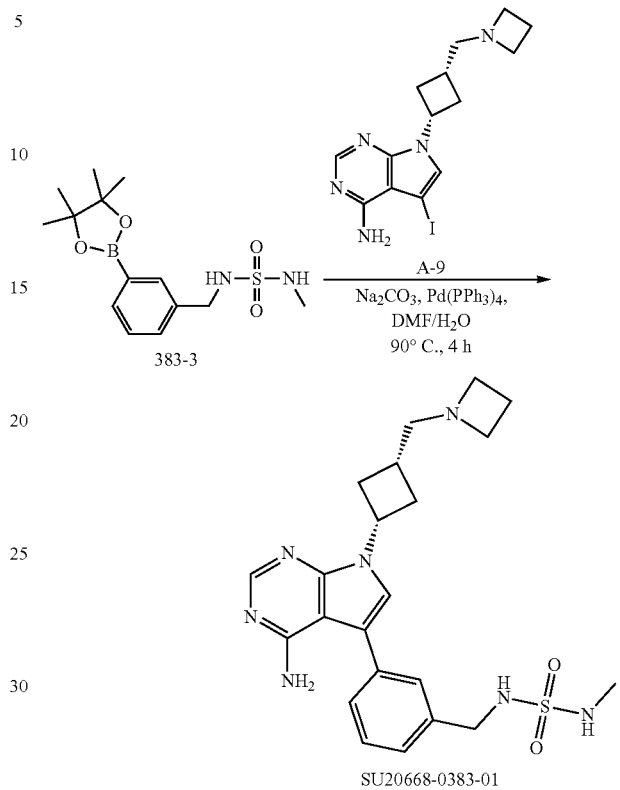

To a stirred solution of 383-3 (195 mg, 0.598 mmol) in DMF/water (8 mL/2 mL) was added A-9 (150 mg, 0.391 mmol), Na$_2$CO$_3$ (85 mg, 0.802 mmol), Pd(PPh$_3$)$_4$ (90 mg, 0.078 mmol).

The resulting reaction mixture was heated to 90° C. and stirred for 4 h, filtered and purified by prep-HPLC to give SU20668-0383-01 (33.7 mg, yield: 12.4%) as a white solid. LC-MS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 95.08%, R$_t$=1.258 min; MS Calcd.: 455.21; MS Found: 456.3 [M+H]$^+$. HPLC (Agilent HPLC 1200, Column: L-column2 ODS (150 mm*4.6 mm*5.0 µm); Column Temperature: 40° C.; Flow Rate: 1.5 mL/min; Mobile Phase: from 90% [(total 10 mM AcONH$_4$) water/CH$_3$CN=900/100 (v/v)] and 10% [total 10 mM AcONH$_4$) water/CH$_3$CN=100/900 (v/v)] to 15% [total 10 mM AcONH$_4$) water/CH$_3$CN=900/100 (v/v)] and 85% [total 10 mM AcONH$_4$) water/CH$_3$CN=100/900 (v/v)] in 5 min, then under this condition for 10 min, finally changed to 90% [(total 10 mM AcONH$_4$) water/CH$_3$CN=900/100 (v/v)] and 10% [total 10 mM AcONH$_4$) water/CH$_3$CN=100/900 (v/v)] in 0.1 min and under this condition for 5 min). Purity: 93.79%, Rt=6.207 min. $^1$H NMR (400 MHz, DMSO-d$_6$) δ 8.13 (s, 1H), 7.57 (s, 1H), 7.39-7.47 (m, 4H), 7.33-7.34 (m, 1H), 6.80-6.84 (m, 1H), 6.11 (brs, 2H), 5.03-5.11 (m, 1H), 4.06 (d, J=6.0 Hz, 2H), 3.10 (t, J=6.8 Hz, 4H), 2.46-2.50 (m, 7H), 2.06-2.17 (m, 3H), 1.91-1.97 (m, 2H).

Scheme 127: Route for SU20668-0384-01

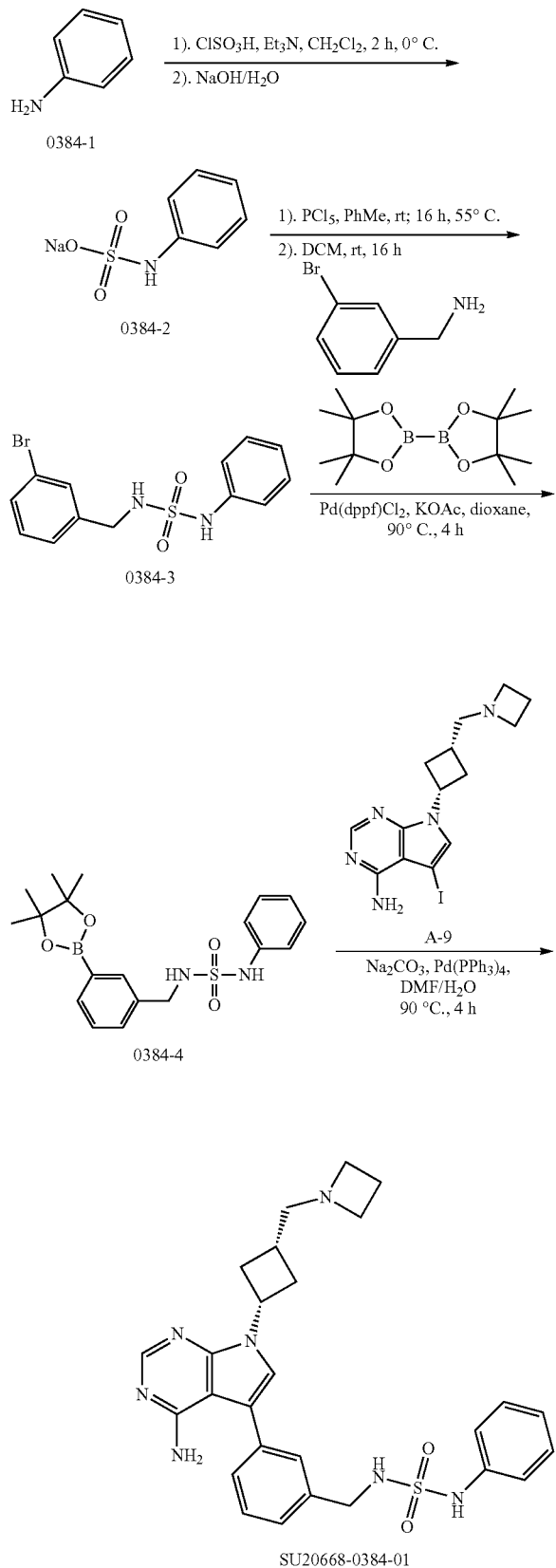

The Synthesis of Sodium Phenylsulfamate (384-2)

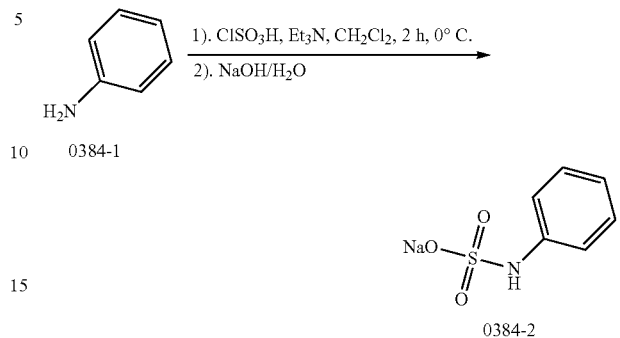

To a stirred solution of 0384-1 (15 g, 161.12 mmol) in DCM (360 ml) was added TEA (40.68 g, 402.79 mmol) and ClSO$_3$H (18.77 g, 161.12 mmol) at 0° C. The resulting reaction mixture was stirred for 2 h at 0° C. Then, the mixture was concentrated in vacuo to give a white solid, this white solid was dissolved in 1N NaOH solution, the solution was concentrated to give a brown solid, to this solid was added EtOH and heated to reflux, this hot mixture was filtrated, washed with hot EtOH, the filtration was concentrated and recrystallzation to give 0384-2 (23 g, yield: 73.2%) as a white crystal.

The Synthesis of Compound (0384-3)

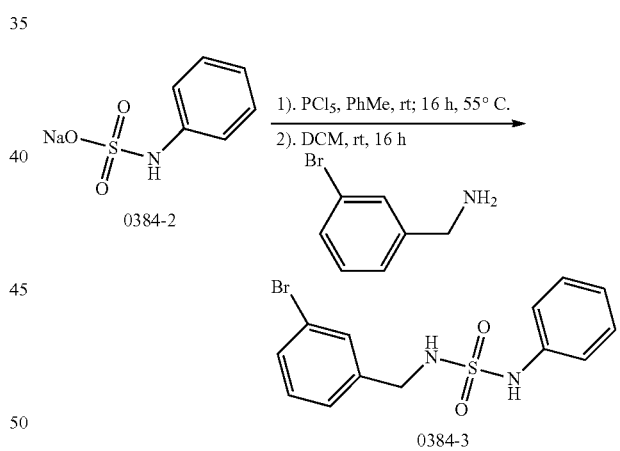

To a solution of 0384-2 (2 g, 10.25 mmol) in toluene (40 mL) was added pentachloro-phosphane (2.13 g, 10.25 mmol), the mixture was heated to 55° C. and stirred for 16 h, the mixture was cooled to rt, filtrated, the filtration was concentrated to give a brown solid, this solid was dissolved in DCM. To a stirred solution of (3-bromophenyl)methanamine (1907 mg, 10.25 mmol) in DCM (30 mL) was added TEA (3.106 g, 30.75 mmol) and the obtained sulfochlorides solution at rt, The resulting reaction mixture was stirred at rt for 16 h. Then added water, the aqueous phase was extracted with DCM, the combined organic phases were dried over anhydrous sodium sulfate, filtered, and concentrated to give 0384-3 (660 mg, yield: 18.88%) as an off-white solid.

The Synthesis of Compound (0384-4)

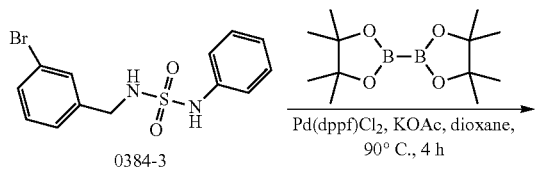

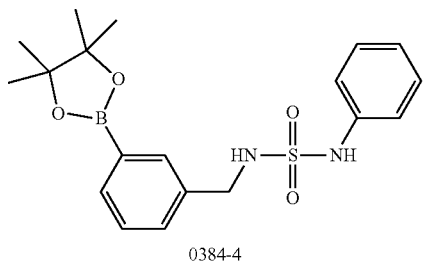

To a stirred solution of 0384-3 (300 mg, 879.19 umol) in 1,4-Dioxane (18 mL) was added 4,4,4',4',5,5,5',5'-octamethyl-2,2'-bi(1,3,2-dioxaborolane) (446.52 mg, 1.76 mmol), KOAc (215.71 mg, 2.20 mmol) and Pd(dppf)Cl₂ (64.33 mg, 87.92 umol). The resulting reaction mixture was heated to 90° C. and stirred for 4 h and concentrated in vacuo to remove the solvent, then added water, the aqueous phase was extracted with EA, the combined organic phases were dried over anhydrous sodium sulfate, filtered, and concentrated, the crude was purified by C.C. to give 0384-4 (140 mg, 41.01% yield) as a light yellow solid.

The Synthesis of Compound (SU20668-0384-01)

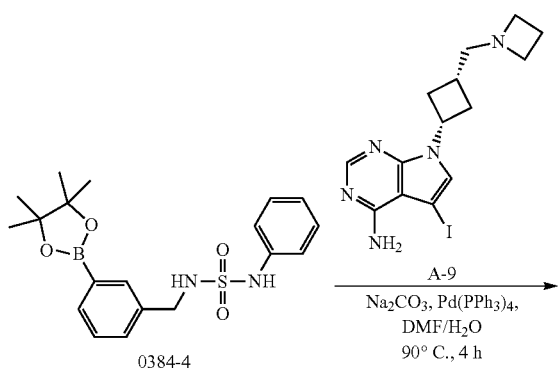

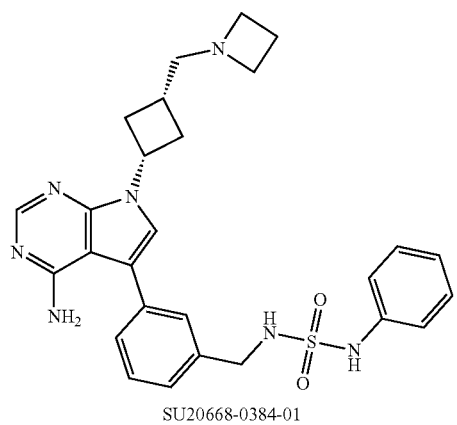

To a stirred solution of A-9 (50 mg, 130.47 umol) in DMF/H₂O (4 mL/1 mL) was added 0384-4 (65.86 mg, 169.61 umol), Na₂CO₃ (27.66 mg, 260.94 umol), Pd(PPh₃)₄ (15.08 mg, 13.05 umol). The resulting reaction mixture was heated to 90° C. and stirred for 4 h and concentrated in vacuo to remove the solvent, then purified by prep-HPLC to give SU20668-0384-01 (35 mg, 51.85%) as a white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 98.88%, $R_t$=1.653 min; MS Calcd.: 517.23; MS Found: 518.3 [M+H]⁺. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM AcONH₄) water/CH₃CN=900/100 (v/v)] and 10% [total 10 mM AcONH₄) water/CH₃CN=100/900 (v/v)] to 15% [total 10 mM AcONH₄) water/CH₃CN=900/100 (v/v)] and 85% [total 10 mM AcONH₄) water/CH₃CN=100/900 (v/v)] in 5 min, then under this condition for 10 min, finally changed to 90% [(total 10 mM AcONH₄) water/CH₃CN=900/100 (v/v)] and 10% [total 10 mM AcONH₄) water/CH₃CN=100/900 (v/v)] in 0.1 min and under this condition for 5 min). Purity: 98.63%, Rt=7.447 min. ¹H NMR (400 MHz, DMSO-d₆) δ 9.77 (s, 1H), 8.13 (s, 1H), 8.01 (t, J=6 Hz, 1H), 7.46 (s, 1H), 7.31-7.35 (m, 3H), 7.16-7.25 (m, 5H), 6.94 (t, J=7.2 Hz, 1H), 6.05 (brs., 2H), 5.03-5.07 (m, 1H), 4.09 (d, J=6.0 Hz, 2H), 3.10 (t, J=7.2 Hz, 4H), 2.48-2.50 (m, 4H), 2.12-2.16 (m, 3H), 1.93-1.96 (m, 2H).

Scheme 128: Route for SU20668-0385-01

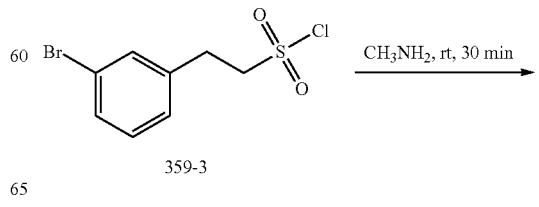

-continued

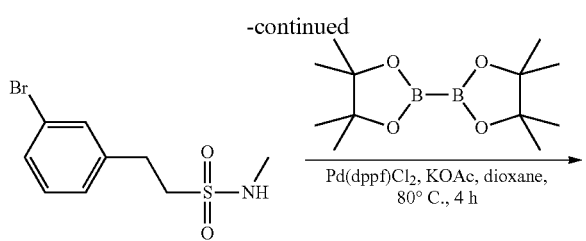

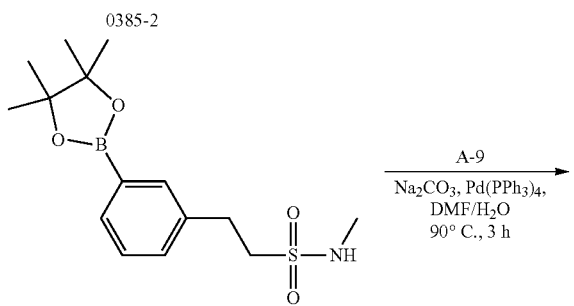

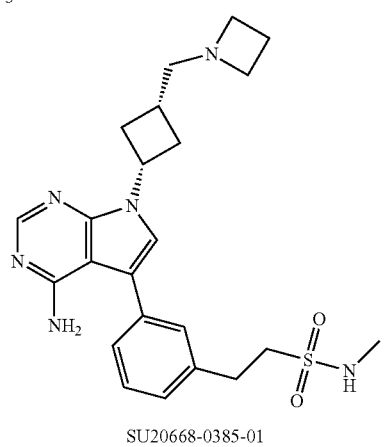

SU20668-0385-01

The Synthesis of 2-(3-bromophenyl)-N-methylethanesulfonamide (385-2)

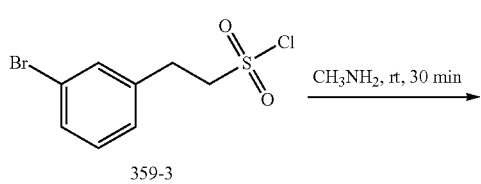

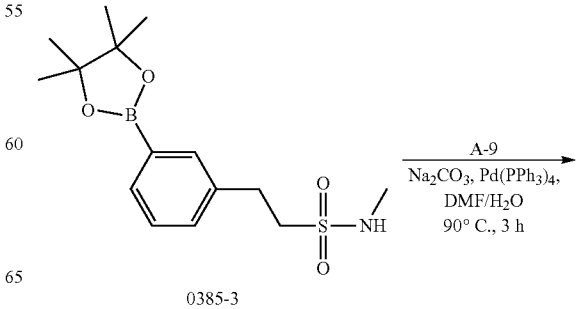

To a stirred solution of 359-3 (1.1 g, 3.8 mmol) in TH was added CH₃NH₂ (3.6 mL, 2M in THF). The mixture was stirred at room temperature for 30 min. After the consumption of starting material (by LCMS), the mixture was concentrated in vacuo, then purified by prep-HPLC to give the desired product 385-2 (800 mg, 76% yield) as a white solid.

The Synthesis of N-methyl-2-(3-(4,4,5,5-tetramethyl-1,3,2-dioxaborolan-2-yl)phenyl)ethanesulfonamide (385-3)

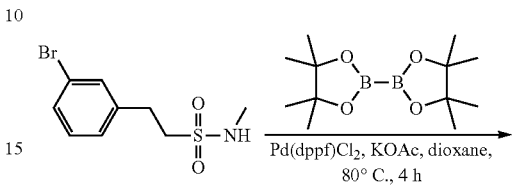

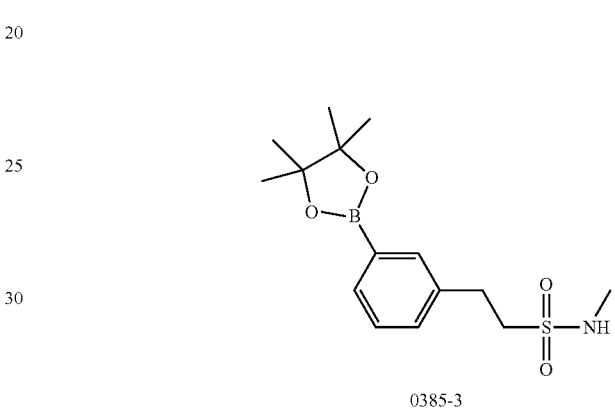

To a stirred solution of 385-2 (400 mg, 1.45 mmol) in dioxane (10 mL) was added bis(pinacolato)diboron (553 mg, 2.2 mmol), KOAc (427 mg, 4.35 mmol), Pd(dppf)Cl₂ (106 mg, 0.15 mmol). The resulting reaction mixture was heated to 90° C. and stirred for 4 h. After the consumption of starting material (by LCMS), the mixture was concentrated in vacuo to remove the solvent, then purified by prep-HPLC to give the desired product 385-3 (310 mg, 65% yield) as a white solid.

The Synthesis of 2-(3-(4-amino-7-(cis-3-(azetidin-1-ylmethyl)cyclobutyl)-7H-pyrrolo[2,3-d]pyrimidin-5-yl)phenyl)-N-methylethanesulfonamide (SU20668-0385-01)

-continued

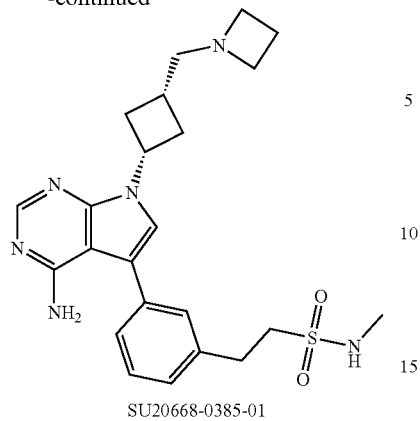

SU20668-0385-01

-continued

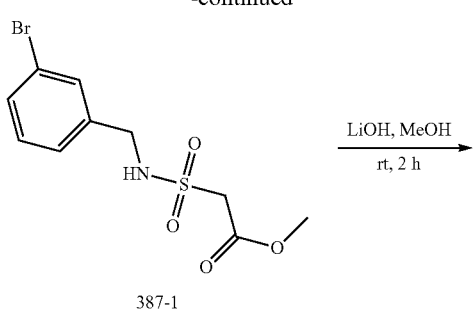

387-1

The mixture of 385-3 (310 mg, 0.95 mmol), A-9 (300 mg, 0.79 mmol), Pd(PPh₃)₄ (91 mg, 0.079 mmol), and Na₂CO₃ (167 mg, 1.58 mmol) in DMF/H₂O (10 mL, 4/1) was stirred at 90° C. under N₂ atmosphere 3 h. After the consumption of starting material (by LCMS), the mixture was concentrated in vacuo to remove the solvent, then purified by prep-HPLC to give the desired product SU20668-0385-01 (80 mg, 22% yield) as a white solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Purity: 99.72%, Rt=1.617 min; MS Calcd.: 454.59; MS Found: 455.4 [M+H]⁺. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min. Purity: 94.24%, Rt=6.426 min. ¹H NMR (400 MHz, DMSO-d₆) δ 8.12 (s, 1H), 7.60 (s, 1H), 7.39-7.43 (m, 2H), 7.34-7.36 (m, 1H), 7.27 (d, J=7.2 Hz, 1H), 7.01 (brs, 1H), 6.09 (brs, 2H), 5.02-5.10 (m, 1H), 3.34-3.38 (m, 2H), 3.09 (t, J=6.8 Hz, 4H), 2.99-3.03 (m, 2H), 2.61 (s, 3H), 2.45-2.51 (m, 4H), 2.05-2.19 (m, 3H), 1.90-1.97 (m, 2H).

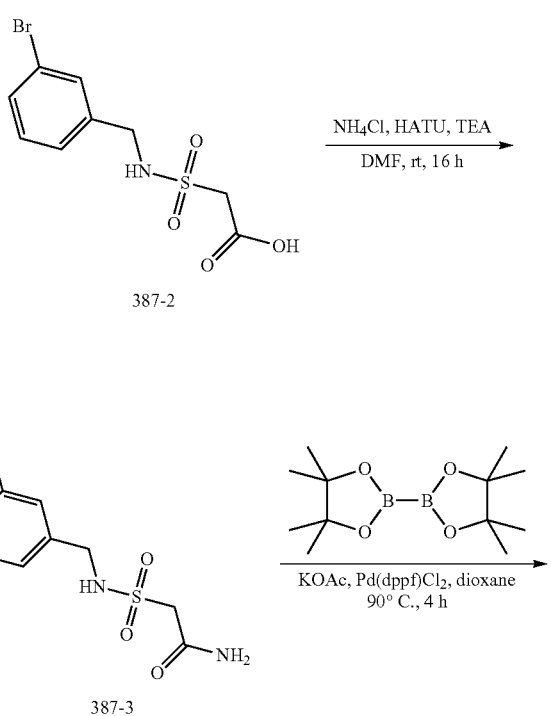

387-2

387-3

387-4

Scheme 129: Route for SU20668-0387-01

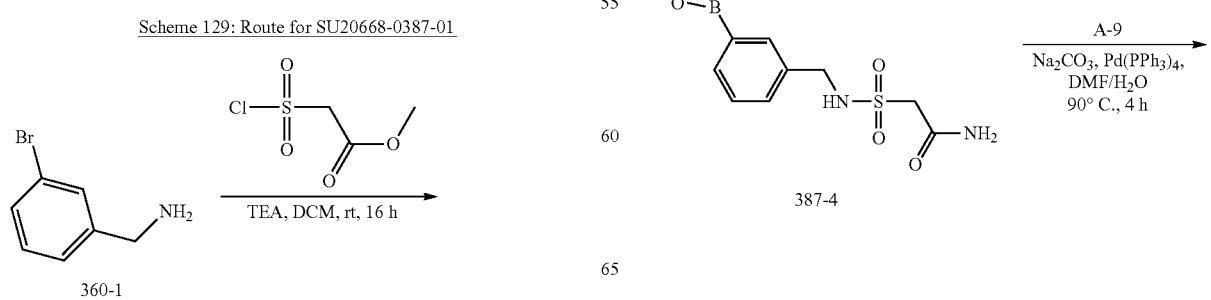

737
-continued

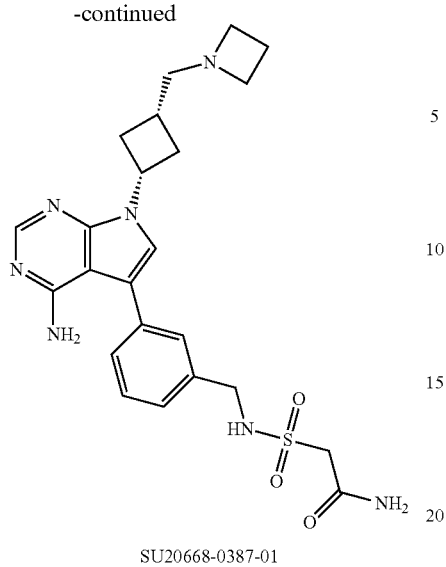

SU20668-0387-01

The Synthesis of methyl
2-(N-(3-bromobenzyl)sulfamoyl)acetate (387-1)

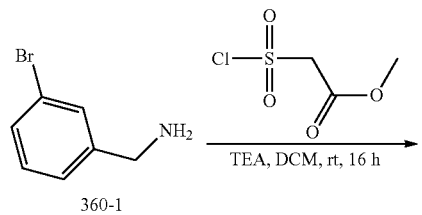

To a stirred solution of 360-1 (2.0 g, 10.75 mmol) in DCM (20 ml) was added TEA (1.6 g, 16.12 mmol) and SM-1 (2.0 g, 11.82 mmol). The resulting reaction mixture was stirred at rt overnight. Then added water, the aqueous phase was extracted with EtOAc, the combined organic phases were dried over anhydrous sodium sulfate, filtered, and concentrated. The residue was purified by Prep-HPLC to give the desired product 387-1 (1.7 g, 50% yield) as a white solid.

738

The Synthesis of
2-(N-(3-bromobenzyl)sulfamoyl)acetic acid (387-2)

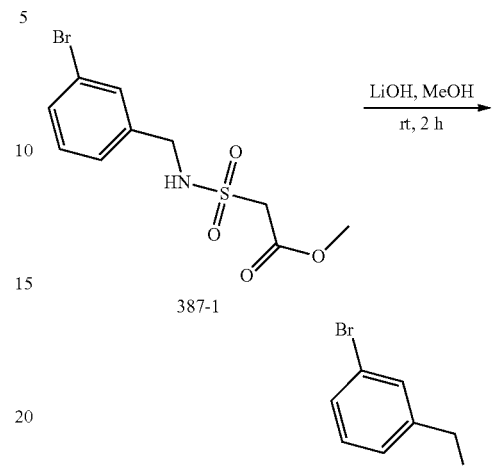

To a stirred solution of 387-1 (1.7 g, 5.28 mmol) in MeOH (20 ml) was added LiOH (13 mg, 0.53 mmol). The resulting reaction mixture was stirred for 2 h at rt. Then the mixture was acidized with 1N HCl until pH reached to 5-6. The aqueous phase was extracted with EtOAc, the combined organic phases were dried over anhydrous sodium sulfate, filtered, and concentrated. The residue was purified by Prep-HPLC to give the desired product 387-2 (1.1 g, 67% yield) as a white solid.

The Synthesis of
2-(N-(3-bromobenzyl)sulfamoyl)acetamide (387-3)

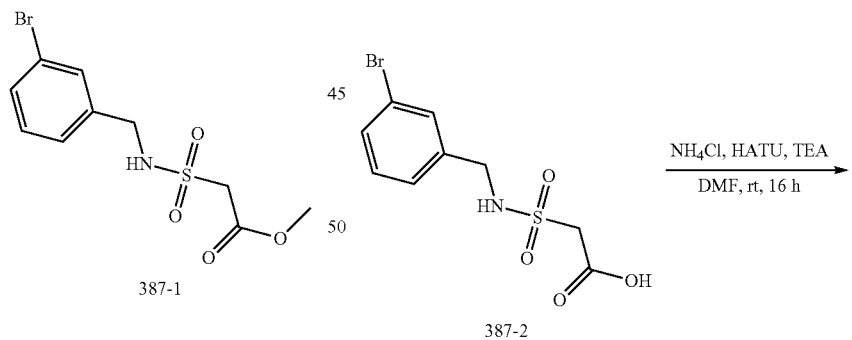

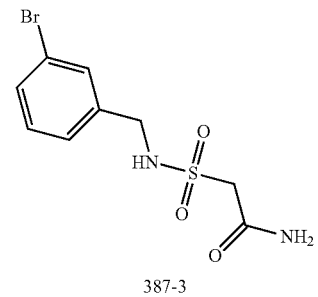

To a stirred solution of 387-2 (1.1 g, 3.57 mmol) in DMF (10 mL) was added HATU (2.71 g, 7.14 mmol), TEA (2.17 g, 21.42 mmol) and NH₄Cl (954 mg, 17.85 mmol) at rt. The resulting reaction mixture was stirred at rt overnight. Then added water, the aqueous phase was extracted with ethyl acetate, the combined organic phases were dried over anhydrous sodium sulfate, filtered, and concentrated. The residue was purified by Prep-HPLC to give the desired product 387-3 (650 mg, 60% yield) as a white solid.

The Synthesis of 2-(N-(3-(4,4,5,5-tetramethyl-1,3,2-dioxaborolan-2-yl)benzyl) sulfamoyl)acetamide (387-4)

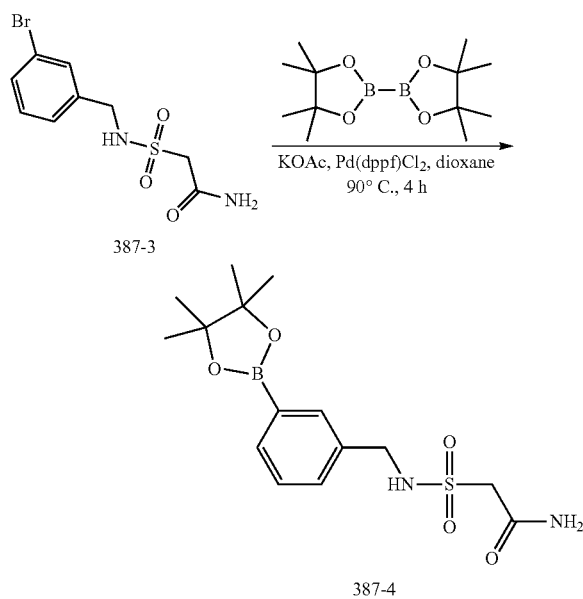

To a stirred solution of 387-3 (700 mg, 2.28 mmol) in dioxane (10 mL) was added bis(pinacolato)diboron (1.15 g, 4.56 mmol), Pd(dppf)Cl₂ (161 mg, 0.22 mmol) and KOAc (671 mg, 6.84 mmol) at rt. The resulting reaction mixture was stirred at 90° C. for 4 h. Then added water, the aqueous phase was extracted with ethyl acetate, the combined organic phases were dried over anhydrous sodium sulfate, filtered, and concentrated. The residue was purified by Prep-HPLC to give the desired product 387-4 (450 mg, 56% yield) as a white solid.

The Synthesis of 2-(N-(3-(4-amino-7-(cis-3-(azetidin-1-ylmethyl)cyclobutyl)-7H-pyrrolo[2,3-d]pyrimidin-5-yl)benzyl)sulfamoyl)acetamide (SU20668-0387-01)

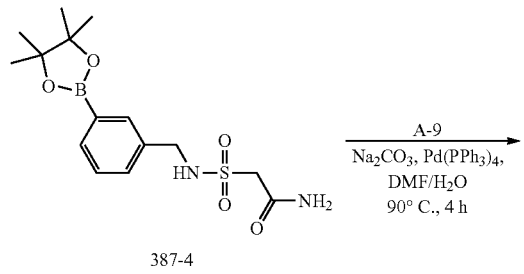

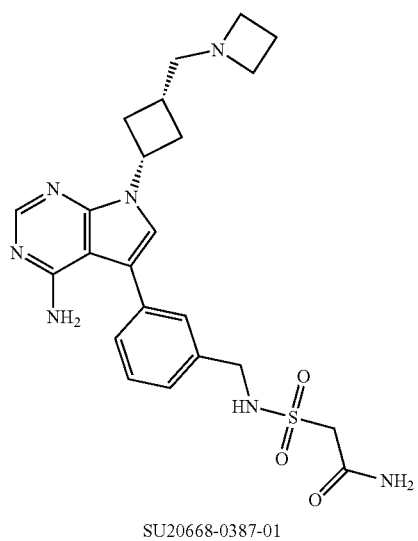

The mixture of 387-4 (200 mg, 0.56 mmol), A-9 (180 mg, 0.47 mmol), Pd(PPh₃)₄ (54 mg, 0.047 mmol), and Na₂CO₃ (100 mg, 0.94 mmol) in DMF/H₂O (10 mL, 4/1) was stirred at 90° C. under N₂ atmosphere for 4 h. After the consumption of starting material (by LCMS), the mixture was concentrated in vacuo to remove the solvent, then purified by prep-HPLC to give the desired product SU20668-0387-01 (40 mg, 17.6% yield) as a white solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Purity: 98.84%, Rt=1.358 min; MS Calcd.: 483.59; MS Found: 484.4 [M+H]⁺. Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min. Purity: 100%, Rt=5.993 min. ¹H NMR (400 MHz, DMSO-d₆) δ 8.12 (s, 1H), 7.63 (s, 1H), 7.58 (s, 1H), 7.39-7.46 (m, 4H), 7.33 (d, J=7.2 Hz, 1H), 6.09 (brs, 2H), 5.01-5.10 (m, 1H), 4.25 (s, 2H), 3.94 (s, 2H), 3.09 (t, J=6.8 Hz, 4H), 2.45-2.51 (m, 4H), 2.05-2.20 (m, 3H), 1.90-1.95 (m, 2H).

Scheme 130: Route for SU20668-0388-01

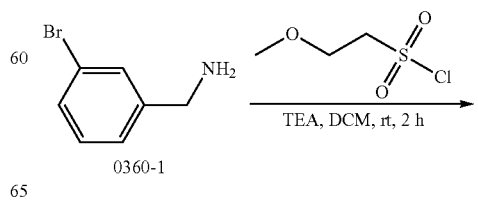

-continued

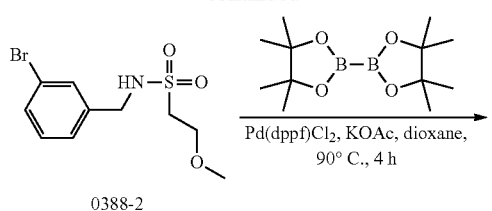

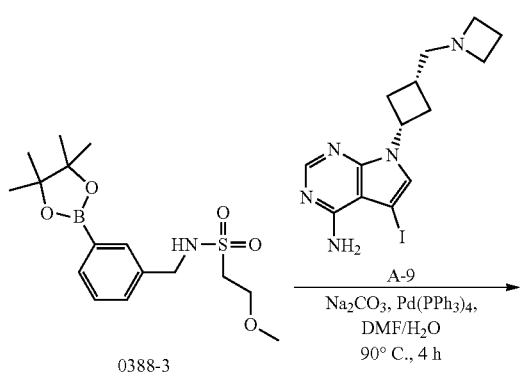

The Synthesis of N-(3-bromobenzyl)-2-methoxyethanesulfonamide (0388-2)

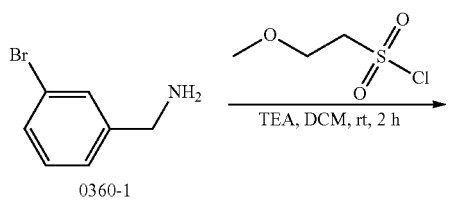

-continued

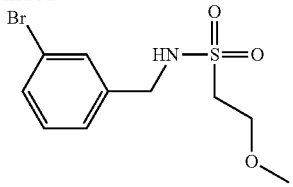

To a solution of 0360-1 (500 mg, 2.7 mmol) and TEA (545 mg, 5.4 mmol) in DCM (10 mL) was added 2-methoxy-ethanesulfonyl chloride (474 mg, 3.0 mmol). The resulting reaction mixture was stirred at rt for 2 hours. Then it was concentrated to dryness and purified by silica-gel column (DCM) to give 0388-2 (500 mg, yield: 60.1%) as a white solid.

The Synthesis of 2-methoxy-N-(3-(4,4,5,5-tetramethyl-1,3,2-dioxaborolan-2-yl)benzyl)ethanesulfonamide (0388-3)

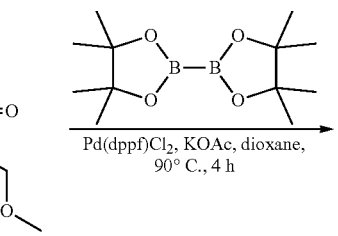

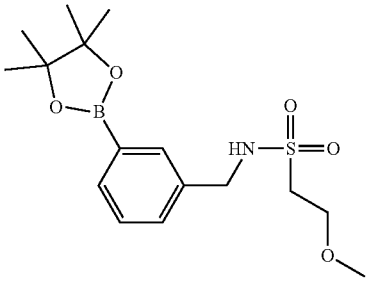

The mixture of 0388-2 (500 mg, 1.6 mmol), 4,4,4',4',5,5,5',5'-octamethyl-2,2'-bi(1,3,2-dioxaborolane) (635 mg, 2.5 mmol), Pd(dppf)Cl$_2$ (50 mg) and KOAc (392 mg, 4.0 mmol) in dioxane (10 mL) was stirred at 90° C. under N$_2$ atmosphere for 4 hours. Then the mixture was concentrated to dryness. The residue was purified by silica-gel column (DCM) to give 0388-3 (350 mg, yield: 62.4%) as a white solid.

The Synthesis of N-(3-(4-amino-7-(cis-3-(azetidin-1-ylmethyl)cyclobutyl)-7H-pyrrolo[2,3-d]pyrimidin-5-yl)benzyl)-2-methoxyethanesulfonamide (SU20668-0388-01)

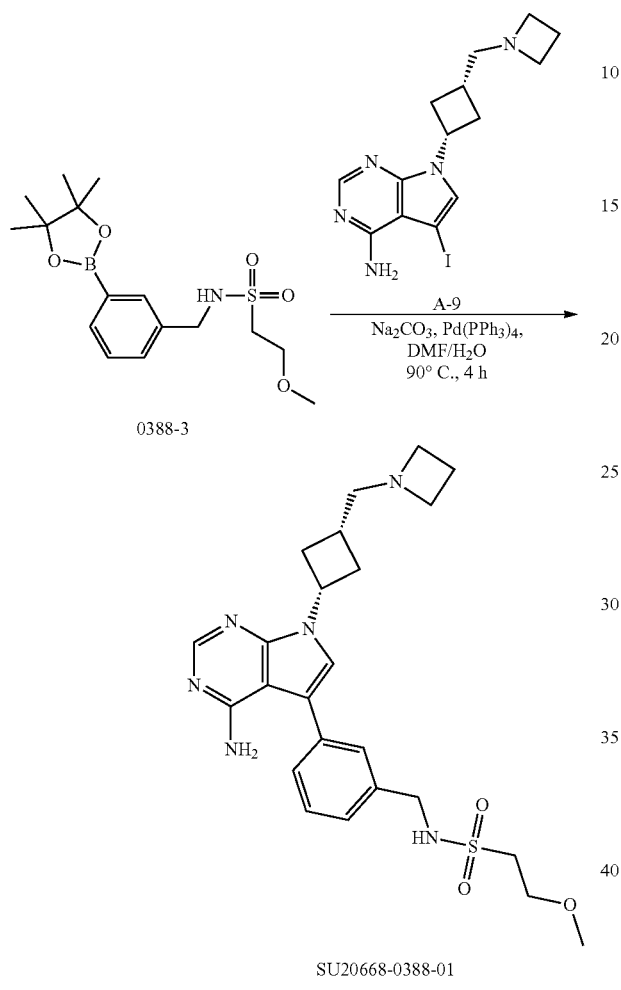

The mixture of A-9 (344 mg, 0.9 mmol), 0388-3 (350 mg, 0.99 mmol), Pd(PPh$_3$)$_4$ (40 mg) and Na$_2$CO$_3$ (191 mg, 1.8 mmol) in DMF/H$_2$O (5 mL, 4/1) was stirred at 90° C. for 4 hours. Then the mixture was concentrated to dryness. The residue was purified by silica-gel column (DCM:MeOH=50: 1) and prep-HPLC to give SU20668-0388-01 (40 mg, yield: 9.2%) as a white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100%, Rt=1.600 min; MS Calcd.: 484.2; MS Found: 485.4 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 97.15%, Rt=6.372 min. $^1$H NMR (400 MHz, DMSO-d$_6$) δ 8.13 (s, 1H), 7.65-7.67 (m, 1H), 7.57 (s, 1H), 7.39-7.48 (m, 3H), 7.33 (d, J=7.6 Hz, 1H), 6.10 (brs, 2H), 5.03-5.07 (m, 1H), 4.21 (d, J=5.6 Hz, 2H), 3.64 (t, J=6.4 Hz, 2H), 3.27-3.31 (m, 2H), 3.23 (s, 3H), 3.11-3.14 (m, 4H), 2.48-2.51 (m, 4H), 2.13-2.18 (m, 3H), 1.93-1.97 (m, 2H).

Scheme 131: Route for SU20668-0389-01

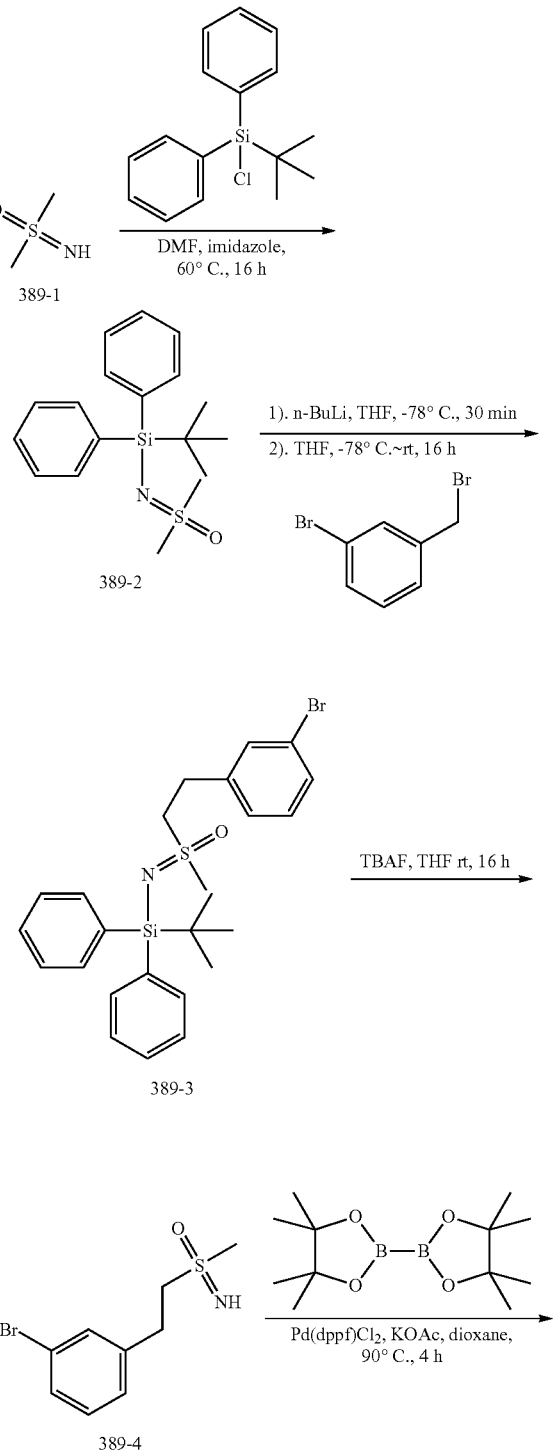

-continued

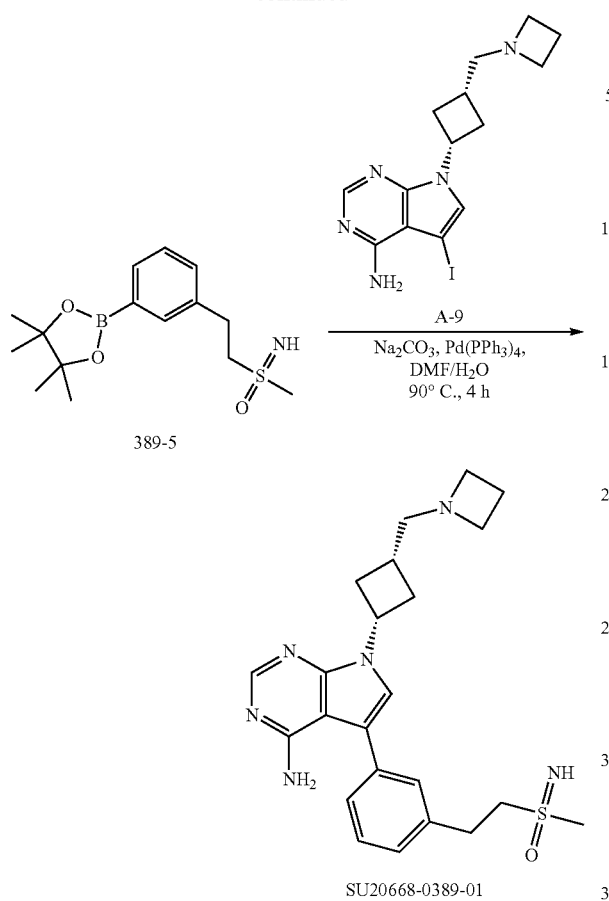

389-5

A-9
Na₂CO₃, Pd(PPh₃)₄,
DMF/H₂O
90° C., 4 h

SU20668-0389-01

The Synthesis of Compound (389-2)

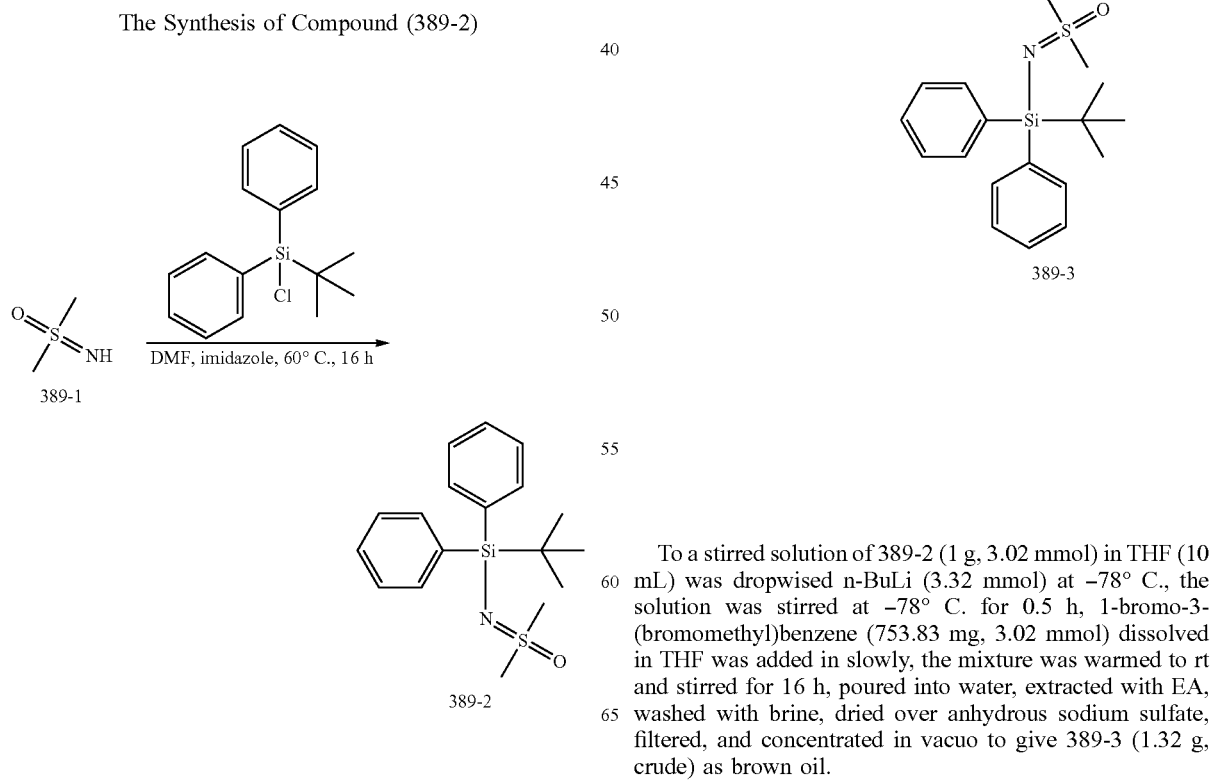

To a stirred solution of 389-1 (0.5 g, 5.37 mmol) in DMF (10 mL) was added tert-butyl-chloro-diphenyl-silane (1.77 g, 6.44 mmol), imidazole (548.16 mg, 8.05 mmol), the solution was heated to 60° C. and stirred for 16 h, the mixture was poured into water, the aqueous phase was extracted with DCM, the combined organic phases were washed with water, dried over anhydrous sodium sulfate, filtered, concentrated and purified with C.C to give 389-2 (2.3 g, crude) as a white solid.

The Synthesis of Compound (389-3)

To a stirred solution of 389-2 (1 g, 3.02 mmol) in THF (10 mL) was dropwised n-BuLi (3.32 mmol) at −78° C., the solution was stirred at −78° C. for 0.5 h, 1-bromo-3-(bromomethyl)benzene (753.83 mg, 3.02 mmol) dissolved in THF was added in slowly, the mixture was warmed to rt and stirred for 16 h, poured into water, extracted with EA, washed with brine, dried over anhydrous sodium sulfate, filtered, and concentrated in vacuo to give 389-3 (1.32 g, crude) as brown oil.

The Synthesis of Compound (389-4)

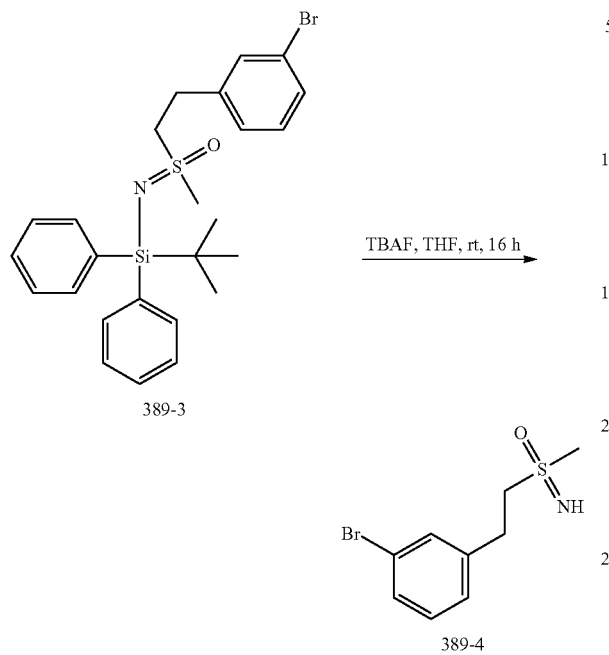

To a solution of 389-3 (7.8 g, 15.58 mmol) in THF (80 mL) was added TBAF (4.07 g, 15.58 mmol), the solution was stirred at rt for 16 h, poured into water, extracted with EA, washed with brine, dried over anhydrous sodium sulfate, filtered, concentrated in vacuo and purified by prep-HPLC to give 389-4 (0.85 g, 20.81% yield) as a white solid.

The Synthesis of Compound (389-5)

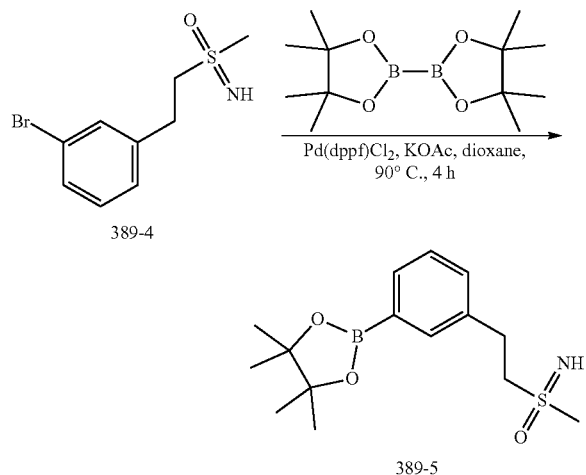

To a stirred solution of compound 389-4 (0.7 g, 2.67 mmol) in 1,4-Dioxane (11 mL) was added 4,4,4',4',5,5,5',5'-octamethyl-2,2'-bi(1,3,2-dioxaborolane) (1.36 g, 5.34 mmol), KOAc (655.11 mg, 6.68 mmol) and Pd(dppf)Cl$_2$ (195.37 mg, 267.01 umol). The resulting reaction mixture was heated to 90° C. and stirred for 4 h and concentrated in vacuo to remove the solvent, then added water, the aqueous phase was extracted with EA, the combined organic phases were dried over anhydrous sodium sulfate, filtered, and concentrated, the crude was purified by prep-HPLC to give 389-5 (0.6 g, 72.67% yield) as a light yellow solid.

The Synthesis of Compound (SU20668-0389-01)

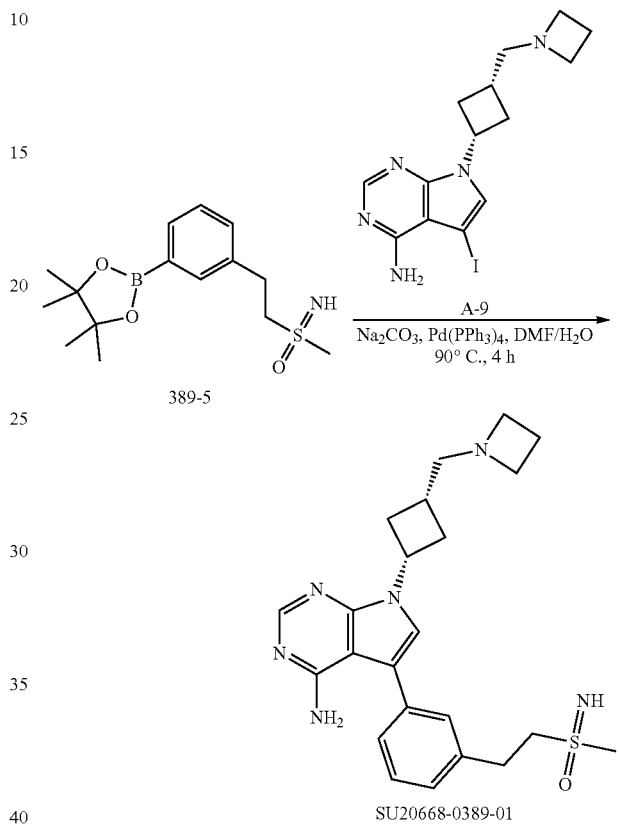

To a mixture of 389-5 (136.37 mg, 440.99 umol) and A-9 (130 mg, 339.22 umol) in DMF/H$_2$O (10 mL/2.5 mL) was added Na$_2$CO$_3$ (71.92 mg, 678.44 umol) and Pd(PPh$_3$)$_4$ (39.20 mg, 33.92 umol) at rt, the mixture was stirred at 90° C. for 4 h under argon atmosphere, concentrated and purified with prep-HPLC to give SU20668-0389-01 (29 mg, 19.49% yield) as a white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 99.11%, R$_t$=1.219 min; MS Calcd.: 438.22; MS Found: 439.3 [M+H]$^+$. HPLC (Agilent HPLC 1200, Column: L-column2 ODS (150 mm*4.6 mm*5.0 m); Column Temperature: 40° C.; Flow Rate: 1.5 mL/min; Mobile Phase: from 90% [(total 10 mM AcONH$_4$) water/CH$_3$CN=900/100 (v/v)] and 10% [total 10 mM AcONH$_4$) water/CH$_3$CN=100/900 (v/v)] to 15% [total 10 mM AcONH$_4$) water/CH$_3$CN=900/100 (v/v)] and 85% [total 10 mM AcONH$_4$) water/CH$_3$CN=100/900 (v/v)] in 5 min, then under this condition for 10 min, finally changed to 90% [(total 10 mM AcONH$_4$) water/CH$_3$CN=900/100 (v/v)] and 10% [total 10 mM AcONH₄) water/CH₃CN=100/900 (v/v)] in 0.1 min and under this condition for 5 min). Purity: 92.39%, Rt=5.285 min. ¹H NMR (400 MHz, DMSO-d₆) δ 8.13 (s, 1H), 7.60 (s, 1H), 7.27-7.43 (m, 4H), 6.09 (brs, 2H), 5.04-5.08 (m, 1H), 3.73 (s, 1H), 3.35-3.39 (m, 2H), 3.09 (t, J=6.4 Hz, 6H), 2.92 (s, 3H), 2.48-2.50 (m, 4H), 2.08-2.19 (m, 3H), 1.92-1.96 (m, 2H).

Scheme 132: Route for SU20668-0397-01

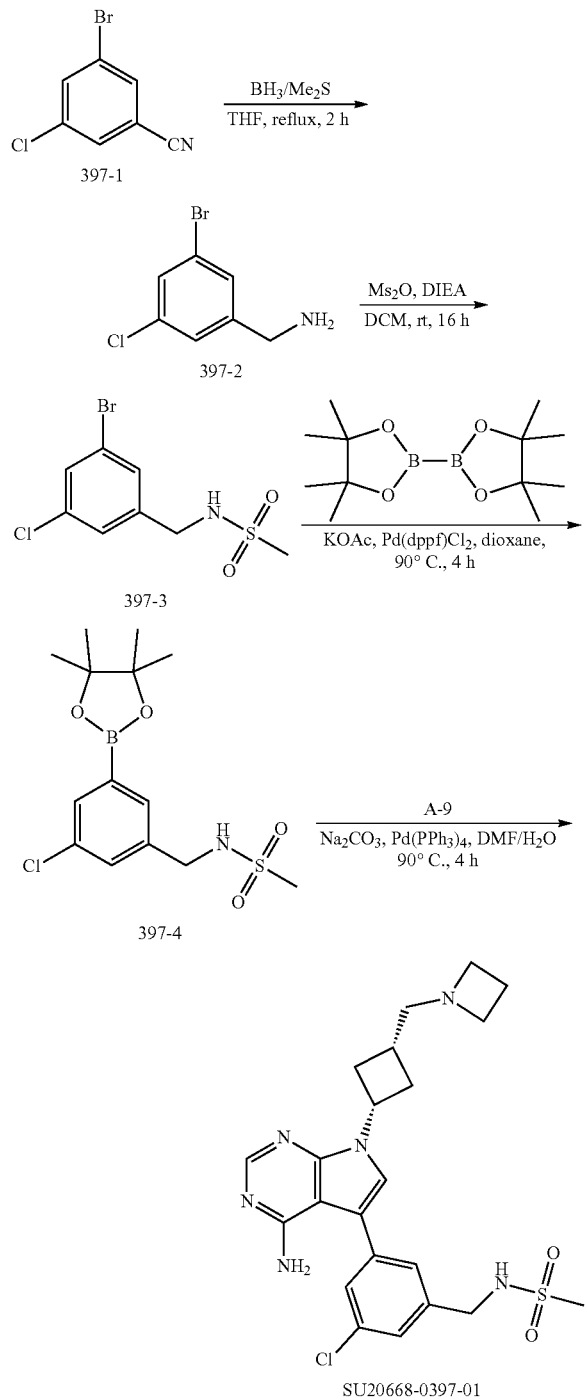

The Synthesis of (3-bromo-5-chlorophenyl)methanamine (0397-2)

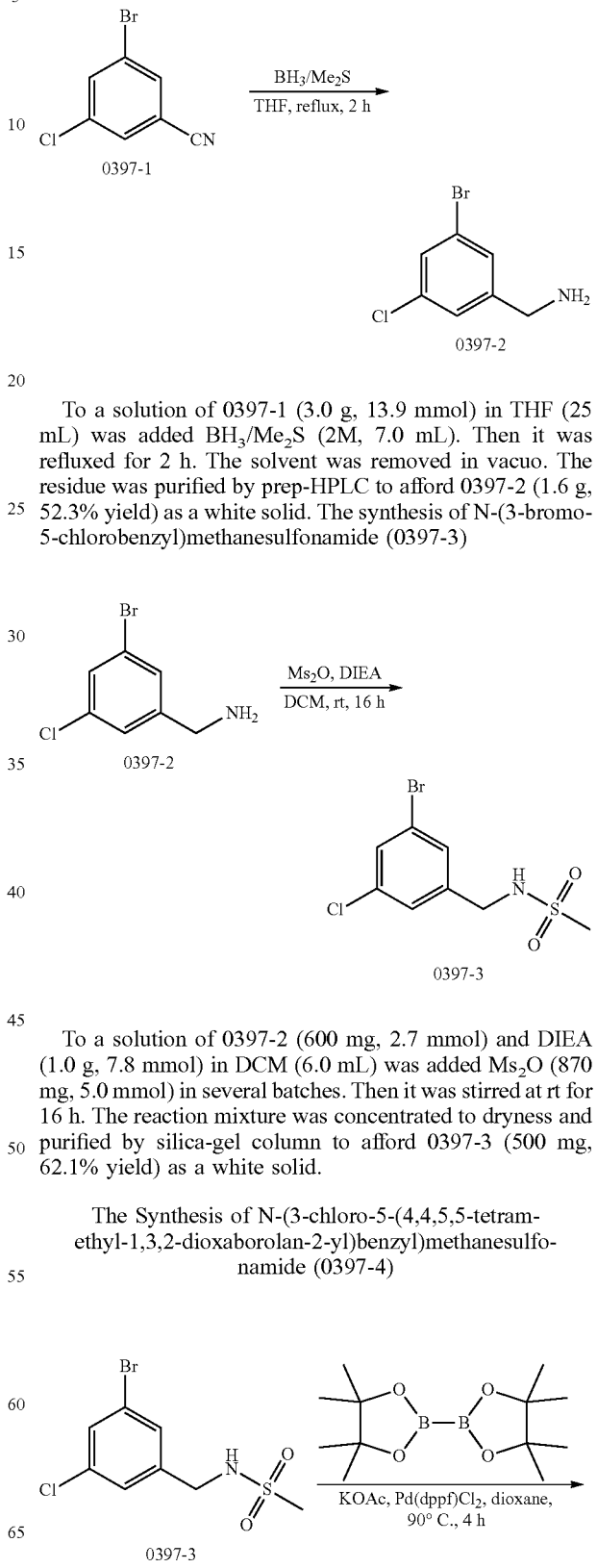

To a solution of 0397-1 (3.0 g, 13.9 mmol) in THF (25 mL) was added BH₃/Me₂S (2M, 7.0 mL). Then it was refluxed for 2 h. The solvent was removed in vacuo. The residue was purified by prep-HPLC to afford 0397-2 (1.6 g, 52.3% yield) as a white solid. The synthesis of N-(3-bromo-5-chlorobenzyl)methanesulfonamide (0397-3)

To a solution of 0397-2 (600 mg, 2.7 mmol) and DIEA (1.0 g, 7.8 mmol) in DCM (6.0 mL) was added Ms₂O (870 mg, 5.0 mmol) in several batches. Then it was stirred at rt for 16 h. The reaction mixture was concentrated to dryness and purified by silica-gel column to afford 0397-3 (500 mg, 62.1% yield) as a white solid.

The Synthesis of N-(3-chloro-5-(4,4,5,5-tetramethyl-1,3,2-dioxaborolan-2-yl)benzyl)methanesulfonamide (0397-4)

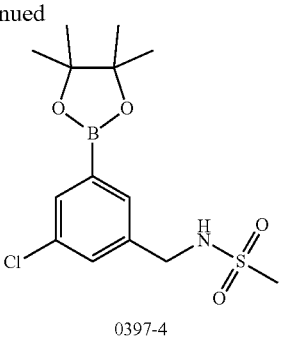

0397-4

The mixture of 0397-3 (500 mg, 1.7 mmol), bis(pinacolato)diboron (635 mg, 2.5 mmol), Pd(dppf)Cl$_2$ (50 mg) and KOAC (392 mg, 4.0 mmol) in dioxane (10 mL) was stirred at 90° C. under N$_2$ atmosphere for 4 h. Then the mixture was concentrated to dryness. The residue was purified by prep-HPLC to give 0397-4 (260 mg, 44.3% yield) as a white solid.

The Synthesis of N-(3-(4-amino-7-(cis-3-(azetidin-1-ylmethyl)cyclobutyl)-7H-pyrrolo[2,3-d]pyrimidin-5-yl)-5-chlorobenzyl)methanesulfonamide (SU20668-0397-01)

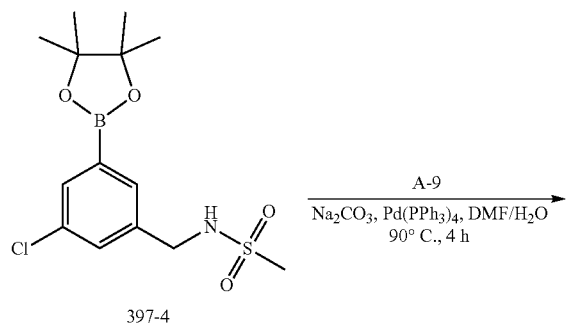

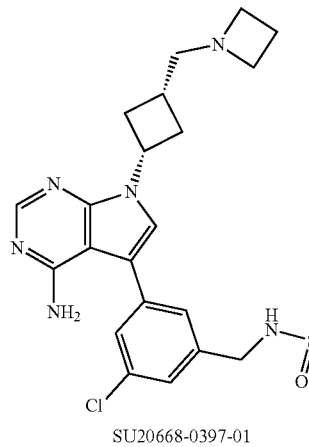

SU20668-0397-01

The mixture of 397-4 (100 mg, 0.29 mmol), A-9 (93 mg, 0.24 mmol), Pd(PPh$_3$)$_4$ (28 mg, 0.024 mmol), and Na$_2$CO$_3$ (51 mg, 0.48 mmol) in DMF/H$_2$O (5 mL, 4/1) was stirred at 90° C. under N$_2$ atmosphere for 4 h. After the consumption of starting material (by LCMS), the mixture was concentrated in vacuo to remove the solvent, then purified by prep-HPLC to give the desired product SU20668-0397-01 (38 mg, 33% yield) as a white solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 98.88%, Rt=1.564 min; MS Calcd.: 475.01; MS Found: 475.3 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 100%, Rt=6.993 min. $^1$H NMR (400 MHz, DMSO-d$_6$) δ 8.13 (s, 1H), 7.72 (s, 1H), 7.64 (brs, 1H), 7.49 (s, 1H), 7.38 (d, J=10.4 Hz, 2H), 6.21 (brs, 2H), 5.02-5.11 (m, 1H), 4.22 (s, 2H), 3.09 (t, J=6.8 Hz, 4H), 2.94 (s, 3H), 2.45-2.50 (m, 4H), 2.05-2.19 (m, 3H), 1.90-1.97 (m, 2H).

Scheme 133: Route for SU20668-0398-01

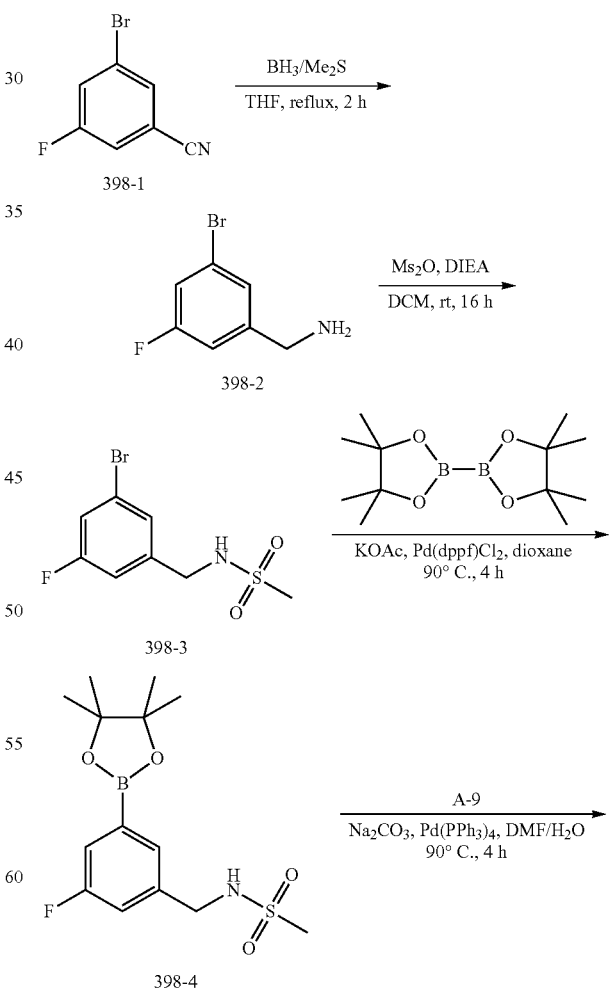

-continued

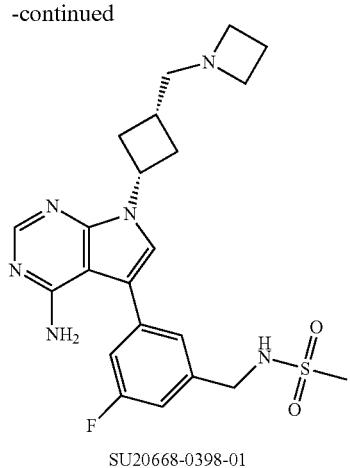

SU20668-0398-01

The Synthesis of (3-bromo-5-fluorophenyl)methanamine (0398-2)

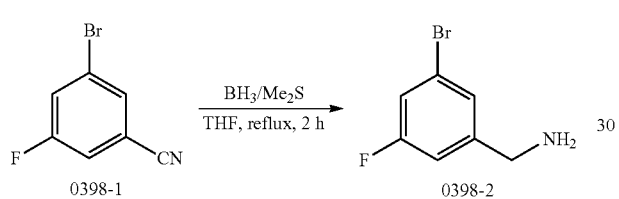

To a solution of 0398-1 (5.0 g, 25 mmol) in THF (50 mL) was added BH$_3$/Me$_2$S (2M, 15 mL). Then it was refluxed for 2 h. The solvent was removed in vacuo. The residue was purified by prep-HPLC to afford 0398-2 (3.0 g, 58.8% yield) as a white solid.

The Synthesis of N-(3-bromo-5-fluorobenzyl)methanesulfonamide (0398-3)

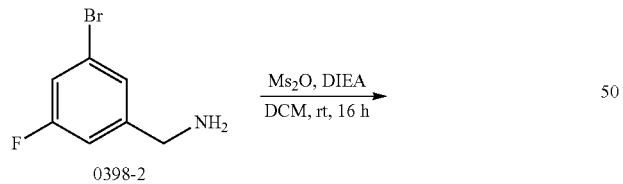

To a solution of 0398-2 (1.2 g, 5.9 mmol) and DIEA (2.0 g, 15.5 mmol) in DCM (20 mL) was added Ms$_2$O (1.6 g, 9.0 mmol) in several batches. Then it was stirred at rt for 16 h. The reaction mixture was concentrated to dryness and purified by silica-gel column (DCM) to afford 0398-3 (800 mg, 48.1% yield) as a white solid.

The Synthesis of N-(3-fluoro-5-(4,4,5,5-tetramethyl-1,3,2-dioxaborolan-2-yl)benzyl)methanesulfonamide (0398-4)

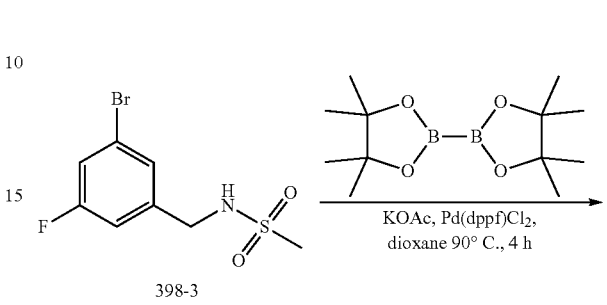

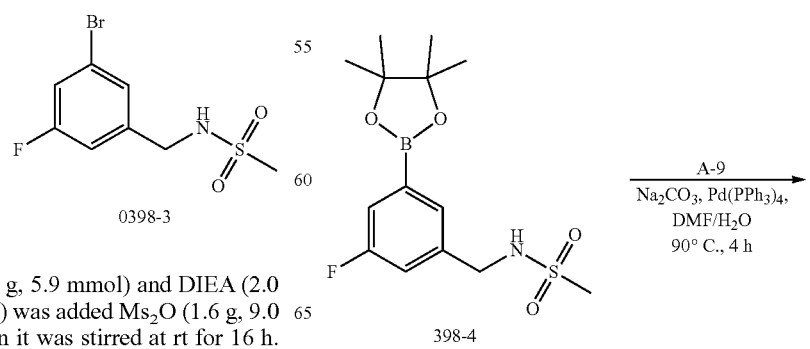

The mixture of 0398-3 (300 mg, 1.1 mmol), bis(pinacolato)diboron (457 mg, 1.8 mmol), Pd(dppf)Cl$_2$ (50 mg) and KOAC (294 mg, 3.0 mmol) in dioxane (6.0 mL) was stirred at 90° C. under N$_2$ atmosphere for 4 h. Then the mixture was concentrated to dryness. The residue was purified by prep-HPLC to give 0398-4 (240 mg, 66.3% yield) as a white solid.

The Synthesis of N-(3-(4-amino-7-(cis-3-(azetidin-1-ylmethyl)cyclobutyl)-7H-pyrrolo[2,3-d]pyrimidin-5-yl)-5-fluorobenzyl)methanesulfonamide (SU20668-0398-01)

755

-continued

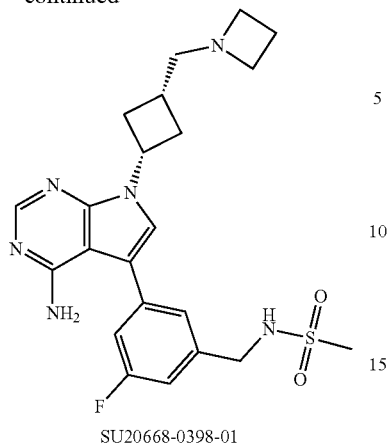

SU20668-0398-01

The mixture of 398-4 (70 mg, 0.21 mmol), A-9 (67 mg, 0.18 mmol), Pd(PPh₃)₄ (21 mg, 0.018 mmol), and Na₂CO₃ (38 mg, 0.36 mmol) in DMF/H₂O (2 mL, 4/1) was stirred at 90° C. under N₂ atmosphere for 4 h. After the consumption of starting material (by LCMS), the mixture was concentrated in vacuo to remove the solvent, then purified by prep-HPLC to give the desired product SU20668-0398-01 (20 mg, 24% yield) as a white solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Purity: 99.16%, Rt=1.467 min; MS Calcd.: 458.55; MS Found: 459.3 [M+H]⁺. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min. Purity: 99.06%, Rt=6.364 min. ¹H NMR (400 MHz, DMSO-d₆) δ 8.13 (s, 1H), 7.69 (s, 1H), 7.65 (brs, 1H), 7.29 (s, 1H), 7.24 (d, J=9.6 Hz, 1H), 7.14 (d, J=9.6 Hz, 1H), 6.22 (brs, 2H), 5.02-5.10 (m, 1H), 4.24 (s, 2H), 3.09 (t, J=6.8 Hz, 4H), 2.93 (s, 3H), 2.45-2.50 (m, 4H), 2.06-2.19 (m, 3H), 1.90-1.97 (m, 2H).

Scheme 134: Route for SU20668-0399-01

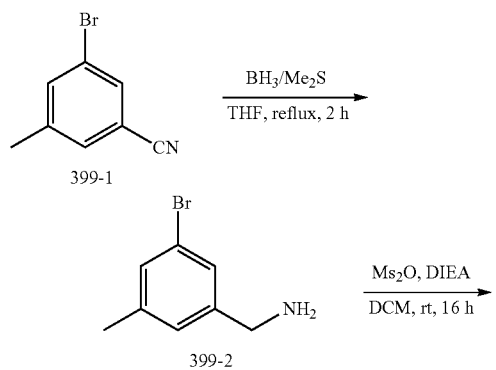

756

-continued

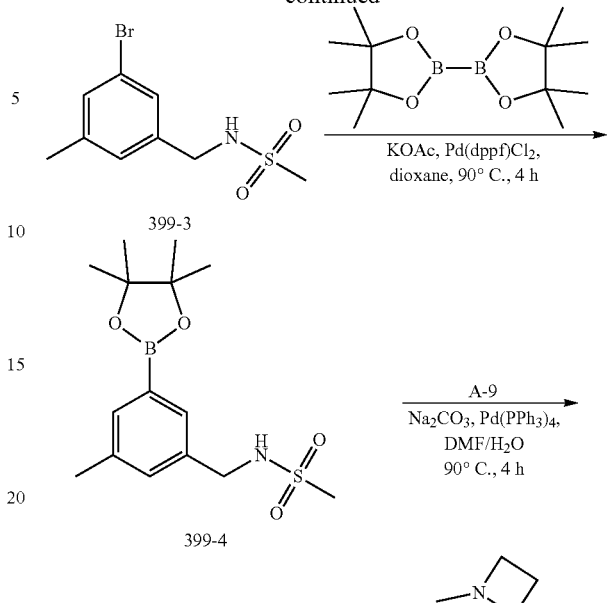

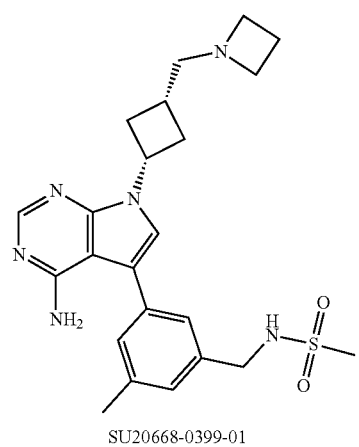

SU20668-0399-01

The Synthesis of (3-bromo-5-methylphenyl)methanamine (0399-2)

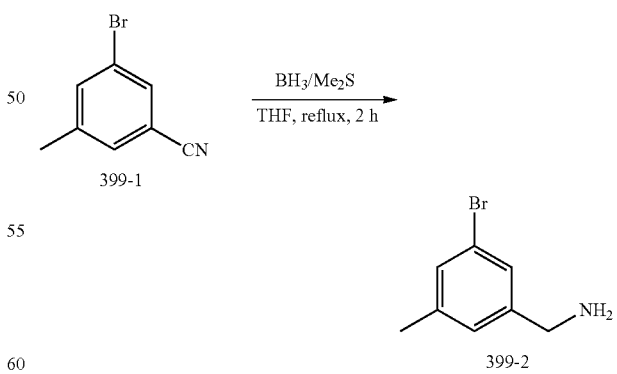

To a solution of 0399-1 (3.0 g, 15.3 mmol) in THF (30 mL) was added BH₃/Me₂S (2M, 10 mL). Then it was refluxed for 2 h. The solvent was removed in vacuo. The residue was purified by prep-HPLC to afford 0399-2 (1.5 g, 49.0% yield) as a white solid.

The Synthesis of N-(3-bromo-5-methylbenzyl)methanesulfonamide (0399-3)

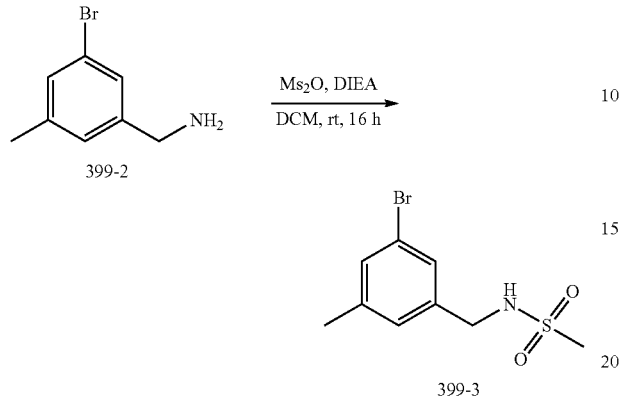

To a solution of 0399-2 (500 mg, 2.5 mmol) and DIEA (645 mg, 5.0 mmol) in DCM (8.0 mL) was added Ms₂O (610 mg, 3.5 mmol) in several batches. Then it was stirred at rt for 16 h. The reaction mixture was concentrated to dryness and purified by silica-gel column to afford 0399-3 (520 mg, 74.8% yield) as a white solid.

The Synthesis of N-(3-methyl-5-(4,4,5,5-tetramethyl-1,3,2-dioxaborolan-2-yl)benzyl)methanesulfonamide (399-4)

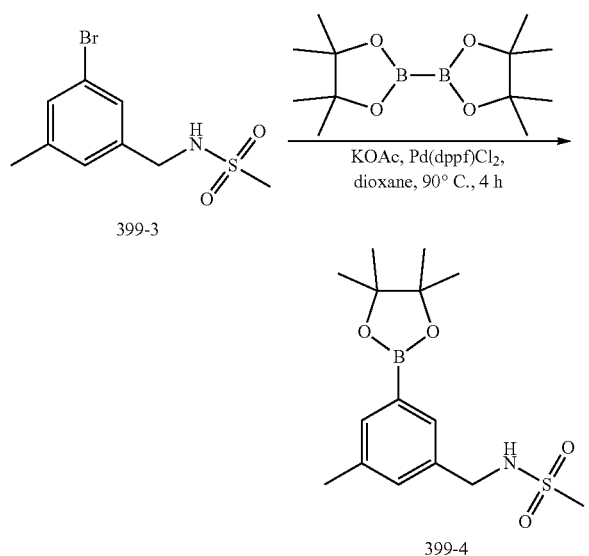

To a stirred solution of 399-3 (300 mg, 0.88 mmol) in dioxane (10 mL) was added bis(pinacolato)diboron (270 mg, 1.06 mmol), KOAc (260 mg, 2.64 mmol), Pd(dppf)Cl₂ (65 mg, 0.09 mmol). The resulting reaction mixture was heated to 90° C. and stirred for 4 h. After the consumption of starting material (by LCMS), the mixture was concentrated in vacuo to remove the solvent, then purified by prep-HPLC to give the desired product 399-4 (200 mg, 50% yield) as a yellow solid.

The Synthesis of N-(3-(4-amino-7-(cis-3-(azetidin-1-ylmethyl)cyclobutyl)-7H-pyrrolo[2,3-d]pyrimidin-5-yl)-5-methylbenzyl)methanesulfonamide (SU20668-0399-01)

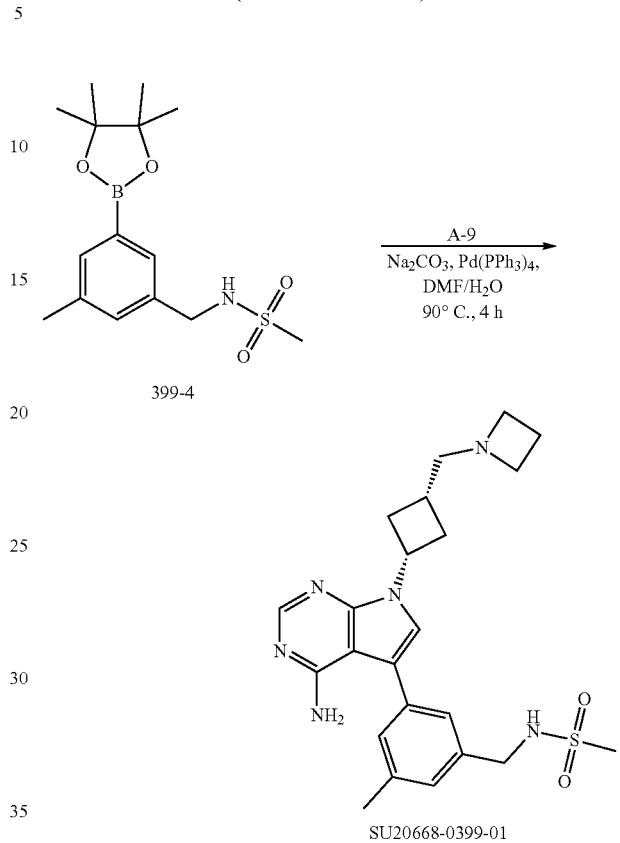

The mixture of 399-4 (100 mg, 0.31 mmol), A-9 (98 mg, 0.26 mmol), Pd(PPh₃)₄ (30 mg, 0.026 mmol), and Na₂CO₃ (55 mg, 0.52 mmol) in DMF/H₂O (5 mL, 4/1) was stirred at 90° C. under N₂ atmosphere for 4 h. After the consumption of starting material (by LCMS), the mixture was concentrated in vacuo to remove the solvent, then purified by prep-HPLC to give the desired product SU20668-0399-01 (63 mg, 53% yield) as a white solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Purity: 100%, Rt=1.515 min; MS Calcd.: 454.59; MS Found: 455.4 [M+H]⁺. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min. Purity: 100%, Rt=6.807 min. ¹H NMR (400 MHz, DMSO-d₆) δ 8.12 (s, 1H), 7.57 (s, 1H), 7.24 (s, 2H), 7.14 (s, 1H), 6.56 (s, 1H), 6.09 (brs, 2H), 5.02-5.10 (m, 1H), 4.17 (s, 2H), 4.00 (s, 1H), 3.09 (t, J=6.8 Hz, 4H), 2.90 (s, 3H), 2.83 (s, 2H), 2.37 (s, 3H), 2.09-2.20 (m, 5H), 1.92-1.97 (m, 2H).

Scheme 135: Route for SU20668-0400-01

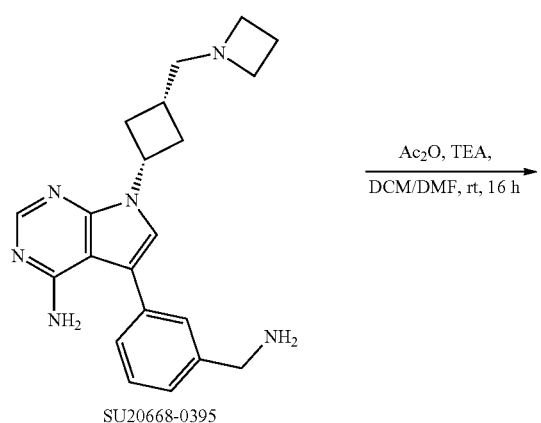

SU20668-0395

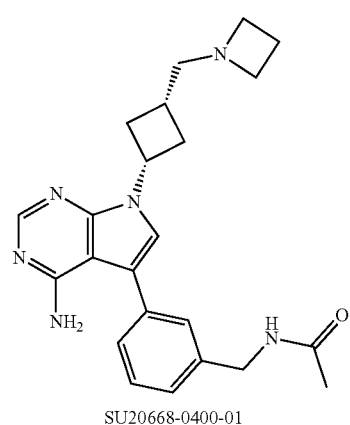

SU20668-0400-01

The Synthesis of N-(3-(4-amino-7-((s,3s)-3-(azetidin-1-ylmethyl)cyclobutyl)-7H-pyrrolo[2,3-d]pyrimidin-5-yl)benzyl)acetamide (SU20668-0400-01)

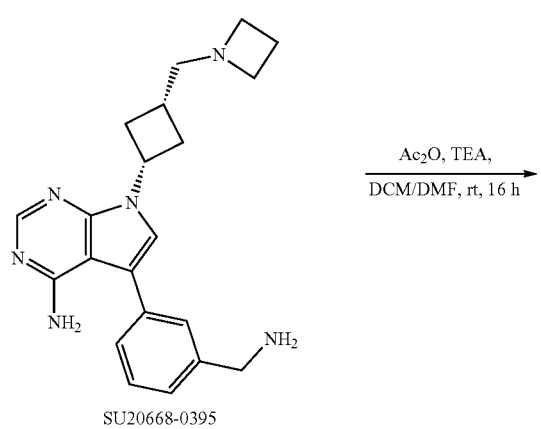

SU20668-0395

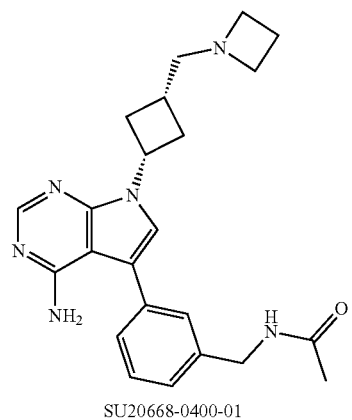

SU20668-0400-01

To a solution of SU20668-0395 in DCM/DMF (4 mL/12 mL) was added TEA (104.69 mg, 1.03 mmol), after stirred for 5 min, Ac₂O (42.25 mg, 413.83 umol) was added dropwisely in at rt, the solution was stirred at rt for 16 h, concentrated and purified with prep-HPLC to give SU20668-0400-01 (10 mg, 5.97% yield) as a white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 100%, $R_f$=1.279 min; MS Calcd.: 404.23; MS Found: 405.3 [M+H]⁺. HPLC (Agilent HPLC 1200, Column: L-column2 ODS (150 mm*4.6 mm*5.0 μm); Column Temperature: 40° C.; Flow Rate: 1.5 mL/min; Mobile Phase: from 90% [(total 10 mM AcONH₄) water/CH₃CN=900/100 (v/v)] and 10% [total 10 mM AcONH₄) water/CH₃CN=100/900 (v/v)] to 15% [total 10 mM AcONH₄) water/CH₃CN=900/100 (v/v)] and 85% [total 10 mM AcONH₄) water/CH₃CN=100/900 (v/v)] in 5 min, then under this condition for 10 min, finally changed to 90% [(total 10 mM AcONH₄) water/CH₃CN=900/100 (v/v)] and 10% [total 10 mM AcONH₄) water/CH₃CN=100/900 (v/v)] in 0.1 min and under this condition for 5 min). Purity: 97.25%, Rt=6.093 min. ¹H NMR (400 MHz, DMSO-d₆) δ 8.41-8.44 (m, 1H), 8.13 (s, 1H), 7.59 (s, 1H), 7.38-7.45 (m, 3H), 7.23-7.24 (m, 1H), 6.10 (brs, 2H), 5.03-5.09 (m, 1H), 4.30 (d, J=6.0 Hz, 2H), 3.23 (t, J=7.2 Hz, 4H), 2.60-2.62 (m, 2H), 2.50 (s, 4H), 2.14-2.21 (m, 3H), 1.98-2.02 (m, 2H), 1.88 (s, 3H).

Scheme 136: Route for SU20668-0401-01

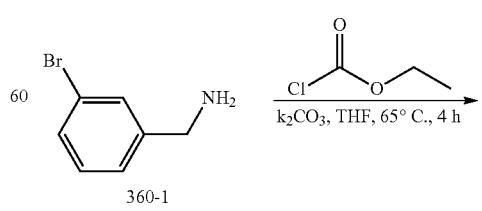

360-1

-continued

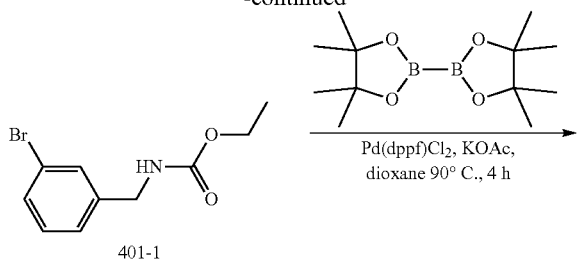

401-1

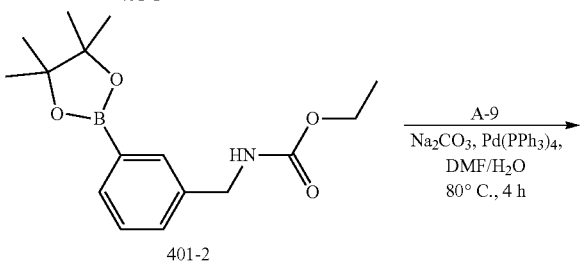

401-2

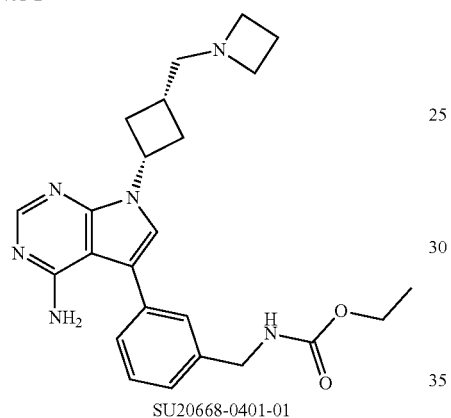

SU20668-0401-01

The Synthesis of (3-bromophenyl)methanamine (401-1)

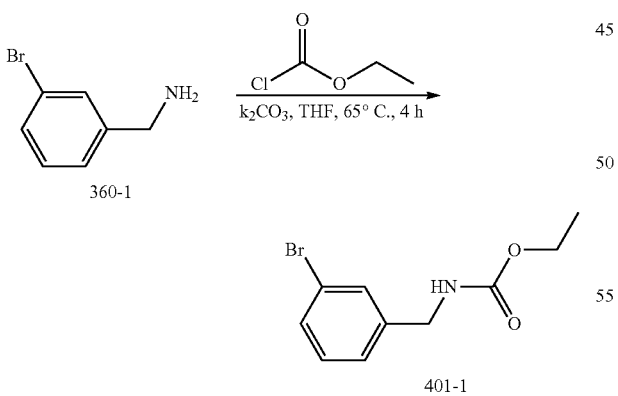

To a stirred solution of 360-1 (3.65 g, 19.6 mmol) and K₂CO₃ (5.4 g, 39.2 mmol) in THF (50 mL) was added dropwise ethyl carbonochloridate (2.34 g, 21.6 mmol) and the reaction mixture was stirred at 65° C. for 4 h. After the consumption of starting material (by LCMS), Then added water, the aqueous phase was extracted with ethyl acetate, the combined organic phases were dried over anhydrous sodium sulfate, filtered, and concentrated in vacuo, purified by column chromatography (petroleum ether/ethyl acetate=10/1) to give the desired product 401-1 (2.9 g, 57.6% yield) as colorless oil.

The Synthesis of ethyl 3-bromobenzylcarbamate (401-2)

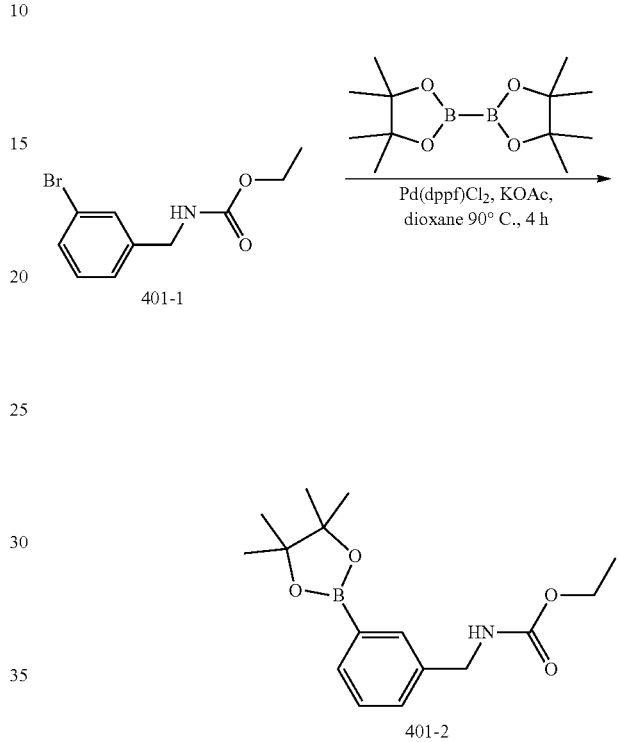

401-2

To a stirred solution of 401-1 (500 mg, 1.9 mmol) in dioxane (10 mL) was added bis(pinacolato)diboron (580 mg, 2.3 mmol), KOAc (560 mg, 5.7 mmol), Pd(dppf)Cl₂ (140 mg, 0.19 mmol). The resulting reaction mixture was heated to 90° C. and stirred for 4 h. After the consumption of starting material (by LCMS), the mixture was concentrated in vacuo to remove the solvent, then purified by prep-HPLC to give the desired product 401-2 (500 mg, 84.6% yield) as a colorless oil.

The Synthesis of ethyl 3-(4-amino-7-(cis-3-(azetidin-1-ylmethyl)cyclobutyl)-7H-pyrrolo[2,3-d]pyrimidin-5-yl)benzylcarbamate (SU20668-0401-01)

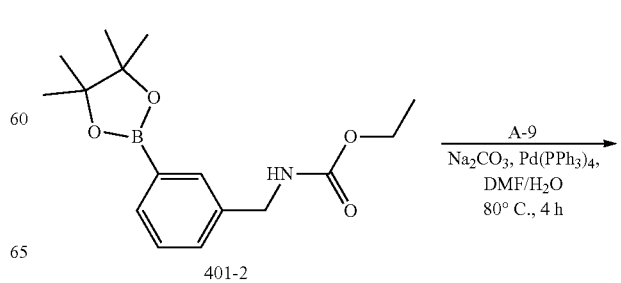

401-2

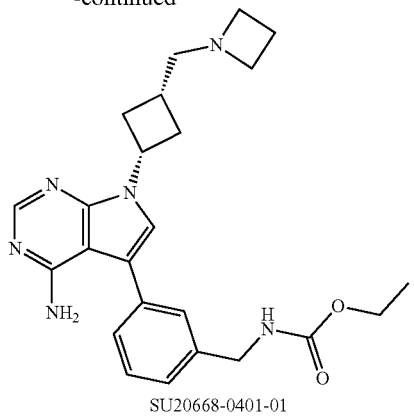

SU20668-0401-01

The mixture of 401-2 (150 mg, 0.49 mmol), A-9 (156 mg, 0.41 mmol), Pd(PPh₃)₄ (57 mg, 0.049 mmol), and Na₂CO₃ (104 mg, 0.98 mmol) in DMF/H₂O (5 mL, 4/1) was stirred at 80° C. under N₂ atmosphere for 4 h. After the consumption of starting material (by LCMS), the mixture was concentrated in vacuo to remove the solvent, then purified by prep-HPLC to give the desired product SU20668-0401-01 (20 mg, 19% yield) as a white solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Purity: 99.58%, Rt=1.559 min; MS Calcd.: 434.53; MS Found: 435.2 [M+H]⁺. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min. Purity: 100%, Rt=7.049 min. ¹H NMR (400 MHz, DMSO-d₆) δ 8.13 (s, 1H), 7.69 (t, J=6 Hz, 1H), 7.57 (s, 1H), 7.36-7.45 (m, 3H), 7.23 (d, J=7.2 Hz, 1H), 6.07 (brs, 2H), 5.02-5.11 (m, 1H), 4.24 (d, J=6 Hz, 2H), 4.01 (q, J=6.8 Hz, 2H), 3.13 (t, J=6.8 Hz, 4H), 2.46-2.51 (m, 4H), 2.07-2.20 (m, 3H), 1.92-1.99 (m, 2H), 1.16 (t, J=7.2 Hz, 3H).

Scheme 137: Route for SU20668-0402-01

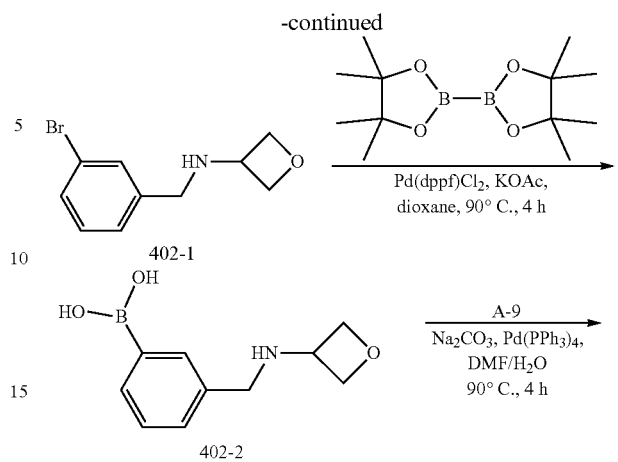

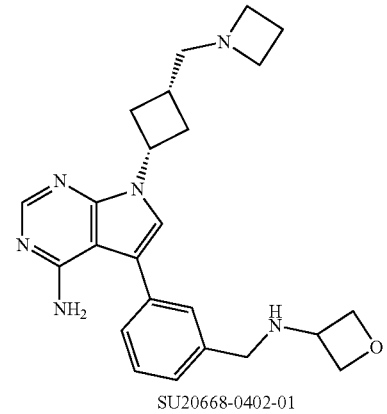

SU20668-0402-01

The Synthesis of N-(3-bromobenzyl)oxetan-3-amine (402-1)

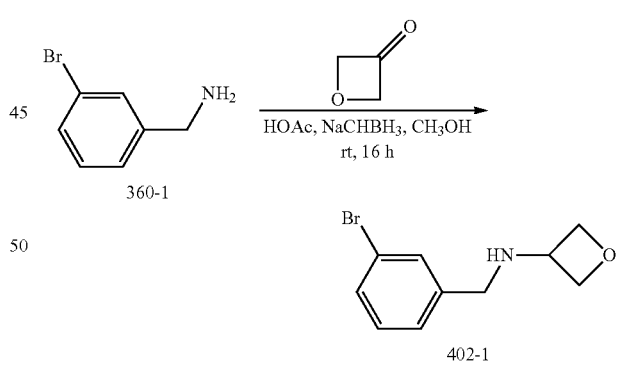

The mixture of 360-1 (2 g, 10.8 mmol), oxetan-3-one (0.93 g, 13 mmol) and AcOH (324 mg, 5.4 mmol) in CH₃OH (20 mL) was stirred at room temperature for 30 min. Then NaCNBH₃ (1 g, 16.2 mmol) was added to the mixture, and the reaction mixture was stirred at room temperature overnight. After the consumption of starting material (by LCMS), added water, the aqueous phase was extracted with ethyl acetate, the combined organic phases were dried over anhydrous sodium sulfate, filtered, and concentrated in vacuo, purified by prep-HPLC to give the desired product 402-1 (1.1 g, 42.3% yield) as colorless oil.

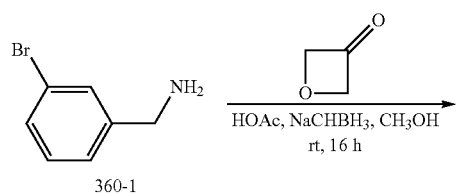

The Synthesis of 3-((oxetan-3-ylamino)methyl)phenylboronic acid (402-2)

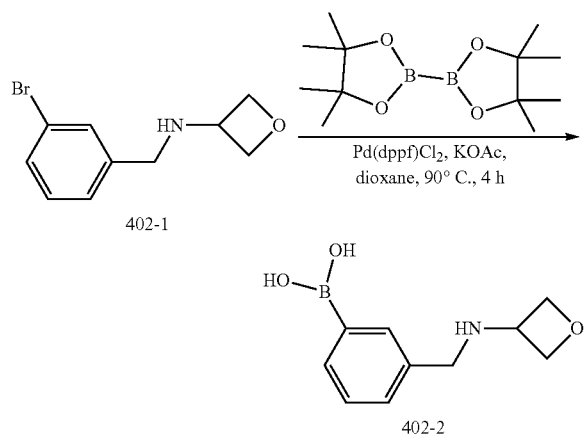

To a stirred solution of 402-1 (1.1 g, 4.6 mmol) in dioxane (20 mL) was added bis(pinacolato)diboron (1.75 g, 6.9 mmol), KOAc (1.35 g, 13.8 mmol), Pd(dppf)Cl$_2$ (468 mg, 0.46 mmol). The resulting reaction mixture was heated to 90° C. and stirred for 4 h. After the consumption of starting material (by LCMS), the mixture was concentrated in vacuo to remove the solvent, then purified by prep-HPLC to give the desired product 402-2 (600 mg, 63% yield) as colorless oil.

The Synthesis of 7-(cis-3-(azetidin-1-ylmethyl)cyclobutyl)-5-(3-((oxetan-3-ylamino)methyl)phenyl)-7H-pyrrolo[2,3-d]pyrimidin-4-amine (SU20668-0402-01)

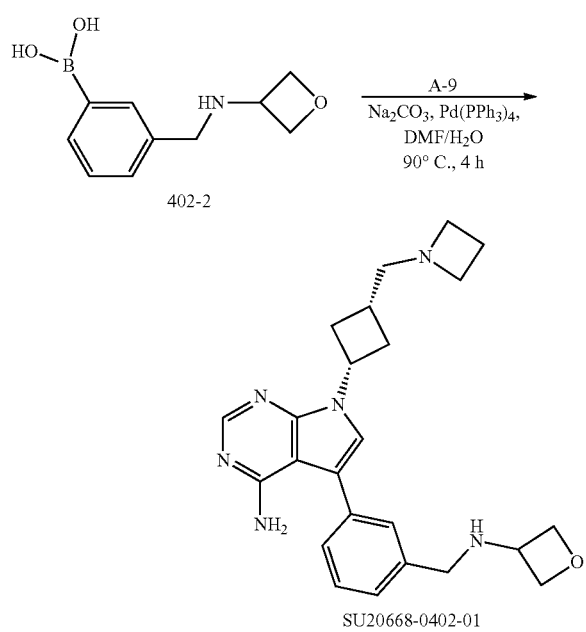

The mixture of 402-2 (200 mg, 0.97 mmol), A-9 (310 mg, 0.81 mmol), Pd(PPh$_3$)$_4$ (94 mg, 0.081 mmol), and Na$_2$CO$_3$ (171 mg, 1.62 mmol) in DMF/H$_2$O (10 mL, 4/1) was stirred at 90° C. under N$_2$ atmosphere for 4 h. After the consumption of starting material (by LCMS), the mixture was concentrated in vacuo to remove the solvent, then purified by prep-HPLC to give the desired product SU20668-0402-01 (5 mg, 1.5% yield) as a white solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 94.16%, Rt=1.253 min; MS Calcd.: 418.53; MS Found: 419.3 [M+H]$^+$. Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 89.75%, Rt=5.608 min. $^1$H NMR (400 MHz, MeOD-d$_4$) δ 8.16 (s, 1H), 7.43-7.52 (m, 4H), 7.37-7.39 (m, 1H), 5.10-5.16 (m, 1H), 4.76 (t, J=6.8 Hz, 2H), 4.48 (t, J=6.4 Hz, 2H), 4.03-4.10 (m, 1H), 3.79 (s, 2H), 3.50 (br, 4H), 2.82 (br, 2H), 2.67-2.71 (m, 2H), 2.21-2.30 (m, 5H).

Scheme 138: Route for SU20668-0405-01

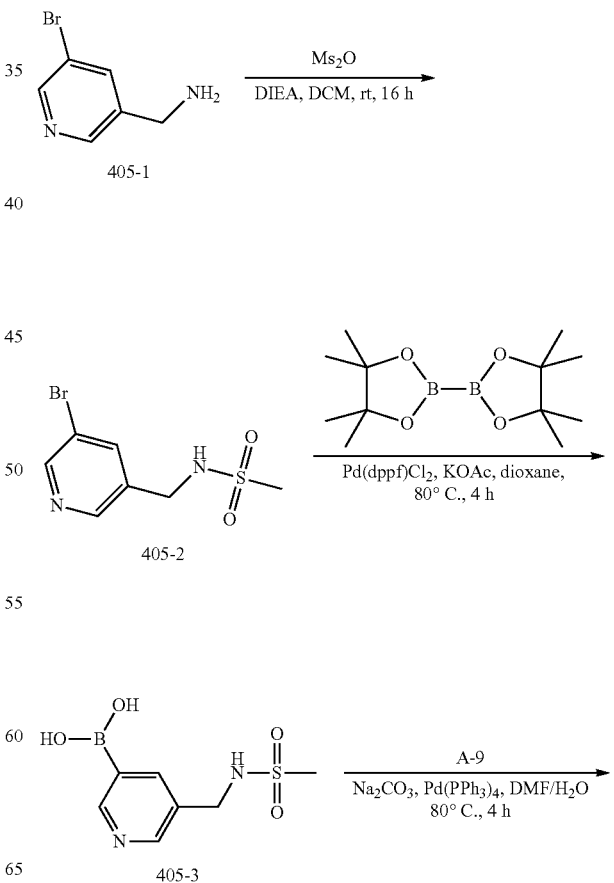

-continued

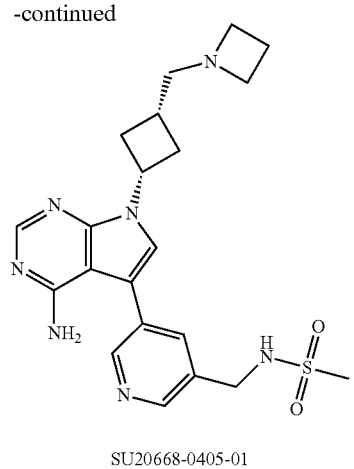

SU20668-0405-01

The Synthesis of N-((5-bromopyridin-3-yl)methyl)methanesulfonamide (405-2)

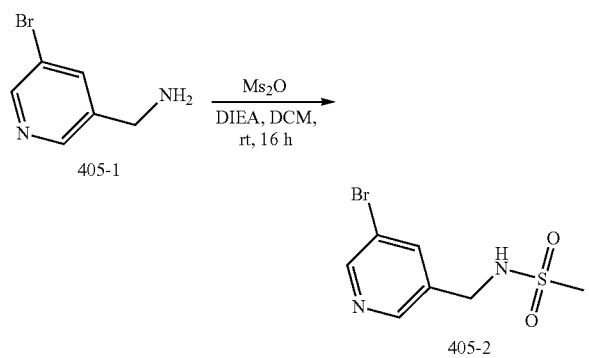

To a stirred solution of compound 405-1 (250 mg, 1.34 mmol) and DIEA (864 mg, 6.7 mmol) in DCM (10 ml) was added Ms₂O (700 mg, 4.02 mmol) at 0° C. The resulting reaction mixture was stirred for 2 h at room temperature. After the consumption of starting material (by LCMS), added water, the aqueous phase was extracted with dichloromethane, the combined organic phases were dried over anhydrous sodium sulfate, filtered, and concentrated in vacuo, purified by column chromatography to give the desired product 405-2 (110 mg, 31% yield) as yellow oil.

The Synthesis of N-((5-(4,4,5,5-tetramethyl-1,3,2-dioxaborolan-2-yl)pyridin-3-yl)methyl)methanesulfonamide (405-3)

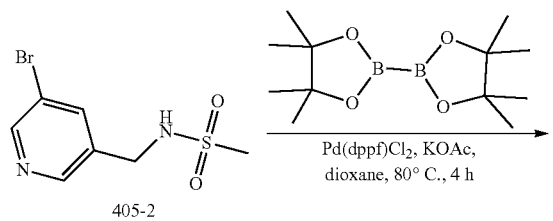

-continued

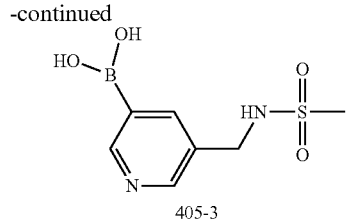

405-3

To a stirred solution of 405-2 (110 mg, 0.42 mmol) in dioxane (5 mL) was added bis(pinacolato)diboron (160 mg, 0.63 mmol), KOAc (124 mg, 1.26 mmol), Pd(dppf)Cl₂(31 mg, 0.042 mmol). The resulting reaction mixture was heated to 80° C. and stirred for 4 h. After the consumption of starting material (by LCMS), the mixture was concentrated in vacuo to remove the solvent, then purified by prep-HPLC to give the desired product 405-3 (50 mg, 51.7% yield) as a colorless oil.

The Synthesis of N-((5-(4-amino-7-(cis-3-(azetidin-1-ylmethyl)cyclobutyl)-7H-pyrrolo[2,3-d]pyrimidin-5-yl)pyridin-3-yl)methyl)methanesulfonamide (SU20668-0405-01)

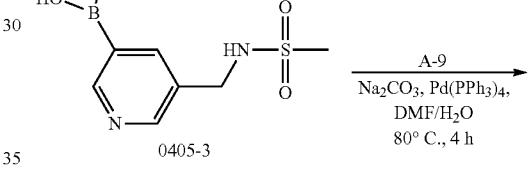

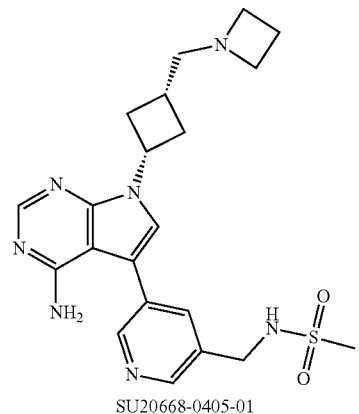

SU20668-0405-01

The mixture of 405-3 (50 mg, 0.22 mmol), A-9 (70 mg, 0.18 mmol), Pd(PPh₃)₄ (21 mg, 0.018 mmol), and Na₂CO₃ (38 mg, 0.36 mmol) in DMF/H₂O (2 mL, 4/1) was stirred at 80° C. under N₂ atmosphere for 4 h. After the consumption of starting material (by LCMS), the mixture was concentrated in vacuo to remove the solvent, then purified by prep-HPLC to give the desired product SU20668-0405-01 (20 mg, 25.3% yield) as a white solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min. Purity: 98.35%, Rt=1.338 min; MS Calcd.: 441.55; MS Found: 442.2 [M+H]⁺. Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 96.26%, Rt=6.050 min. ¹H NMR (400 MHz, DMSO-$d_6$) δ 8.65 (s, 1H), 8.50 (s, 1H), 8.15 (s, 1H), 7.82 (s, 1H), 7.73 (s, 1H), 7.63 (t, J=6 Hz, 1H), 6.22 (brs, 2H), 5.03-5.12 (m, 1H), 4.27 (d, J=6 Hz, 2H), 3.10 (t, J=7.2 Hz, 4H), 2.96 (s, 3H), 2.44-2.49 (m, 4H), 2.09-2.20 (m, 3H), 1.91-1.98 (m, 2H).

The Synthesis of N-(3-(4-amino-7-(cis-3-formylcyclobutyl)-7H-pyrrolo[2,3-d]pyrimidin-5-yl)benzyl)methanesulfonamide (408-3)

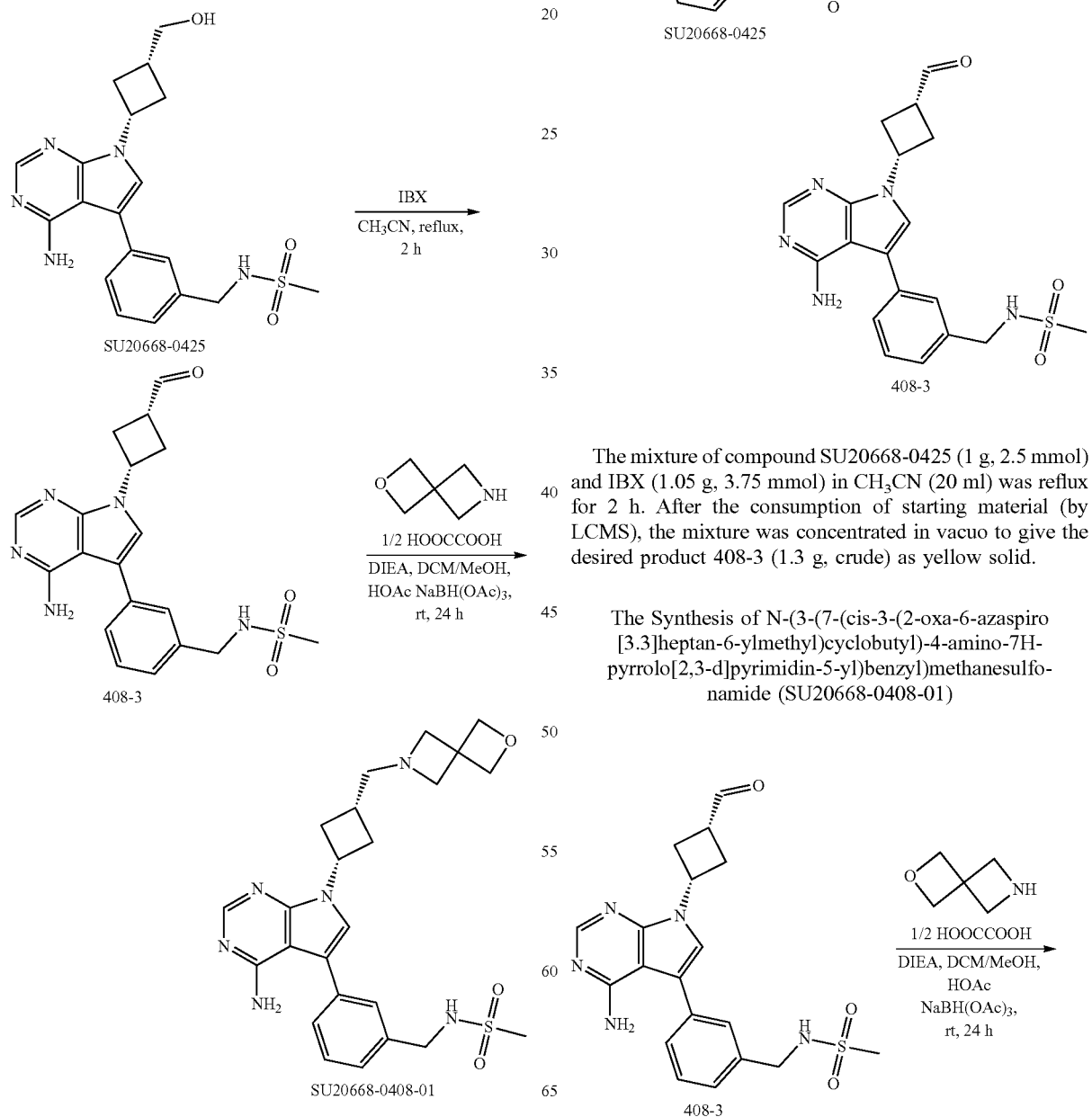

The mixture of compound SU20668-0425 (1 g, 2.5 mmol) and IBX (1.05 g, 3.75 mmol) in $CH_3CN$ (20 ml) was reflux for 2 h. After the consumption of starting material (by LCMS), the mixture was concentrated in vacuo to give the desired product 408-3 (1.3 g, crude) as yellow solid.

The Synthesis of N-(3-(7-(cis-3-(2-oxa-6-azaspiro[3.3]heptan-6-ylmethyl)cyclobutyl)-4-amino-7H-pyrrolo[2,3-d]pyrimidin-5-yl)benzyl)methanesulfonamide (SU20668-0408-01)

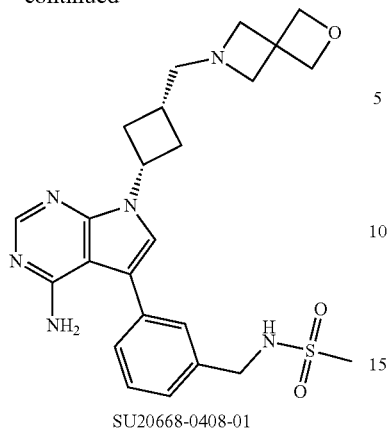

SU20668-0408-01

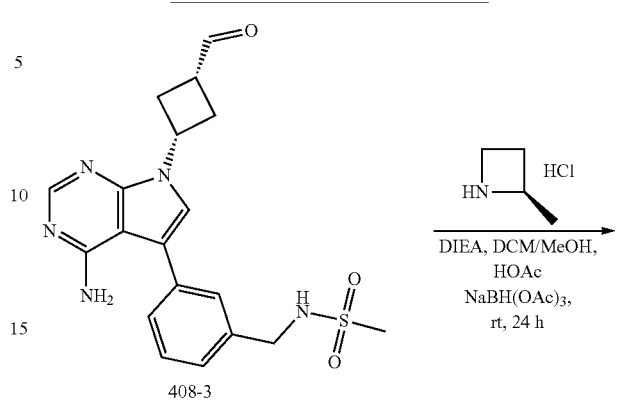

Scheme 140: Route for SU20668-0411-01

The mixture of 2-oxa-6-azaspiro[3,3]heptane oxalic acid salt (173 mg, 0.6 mmol) and DIEA (97 mg, 0.75 mmol) in MeOH/DCM (10 mL, 4/1) was stirred at rt for 5 min. 408-3 (200 mg, 0.5 mmol) and AcOH (15 mg, 0.25 mmol) were added to the solution. After stirring for 30 min at rt, NaBH(OAc)$_3$ (212 mg, 1.0 mmol) was added to the solution. The mixture solution was stirred at rt for overnight. After the consumption of starting material (by LCMS), the mixture was concentrated in vacuo to remove the solvent, then purified by prep-HPLC to give the desired product SU20668-0408-01 (30 mg, 8.3% yield) as a white solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 100%, Rt=1.424 min; MS Calcd.: 482.60; MS Found: 483.2 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 97.03%, Rt=6.534 min. $^1$H NMR (400 MHz, DMSO-d$_6$) δ 8.13 (s, 1H), 7.57-7.60 (m, 2H), 7.35-7.48 (m, 3H), 7.32-7.35 (m, 1H), 6.11 (brs, 2H), 5.02-5.10 (m, 1H), 4.59-4.60 (m, 4H), 4.22 (d, J=6.4 Hz, 2H), 3.27-3.34 (m, 5H), 2.91 (s, 3H), 2.45-2.53 (m, 3H), 2.09-2.19 (m, 3H).

SU20668-0411-01

The Synthesis of N-(3-(4-amino-7-(cis-3-(((R)-2-methylazetidin-1-yl)methyl)cyclobutyl)-7H-pyrrolo[2,3-d]pyrimidin-5-yl)benzyl)methanesulfonamide (SU20668-0411-01)

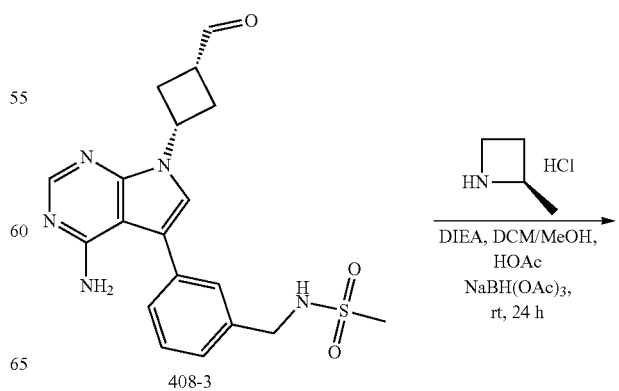

773
-continued

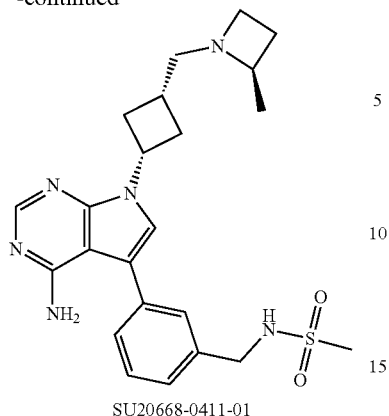

SU20668-0411-01

The mixture of 2-Methylazetidine HCl (64 mg, 0.6 mmol) and DIEA (97 mg, 0.75 mmol) in MeOH/DCM (10 mL, 4/1) was stirred at rt for 5 min. 408-3 (200 mg, 0.5 mmol) and AcOH (15 mg, 0.25 mmol) were added to the solution. After stirring for 30 min at rt, NaBH(OAc)$_3$ (212 mg, 1.0 mmol) was added to the solution. Then the mixture solution was stirred at rt for 24 h. After the consumption of starting material (by LCMS), the mixture was concentrated in vacuo to remove the solvent, then purified by prep-HPLC to give the desired product SU20668-0411-01 (20 mg, 8.8% yield) as a white solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 99.42%, Rt=1.350 min; MS Calcd.: 454.59; MS Found: 455.3 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 97.38%, Rt=6.492 min. $^1$H NMR (400 MHz, DMSO-d$_6$) δ 8.13 (s, 1H), 7.57-7.61 (m, 2H), 7.40-7.48 (m, 3H), 7.33-7.35 (m, 1H), 6.09 (brs, 2H), 5.03-5.11 (m, 1H), 4.27 (d, 5.6 Hz, 2H), 3.21-3.33 (m, 1H), 3.02-3.11 (m, 1H), 2.91 (s, 3H), 2.63-2.72 (m, 2H), 2.33-2.46 (m, 3H), 2.10-2.21 (m, 3H), 1.95-2.01 (m, 1H), 1.59-1.68 (m, 1H), 1.09-1.11 (m, 3H).

Scheme 141: Route for SU20668-0414-01

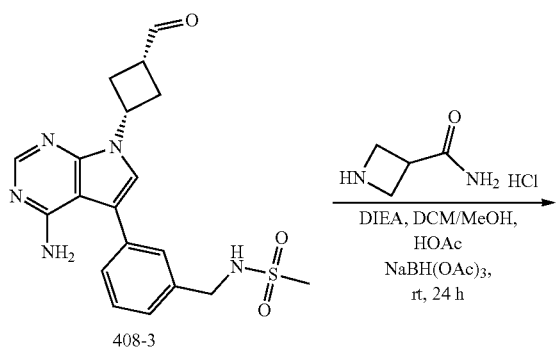

774
-continued

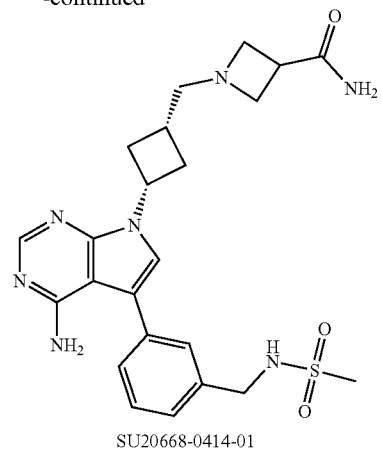

SU20668-0414-01

The Synthesis of 1-(cis-3-(4-amino-5-(3-(methyl-sulfonamidomethyl)phenyl)-7H-pyrrolo[2,3-d]pyrimidin-7-yl)cyclobutyl)methyl)azetidine-3-carboxamide (SU20668-0414-01)

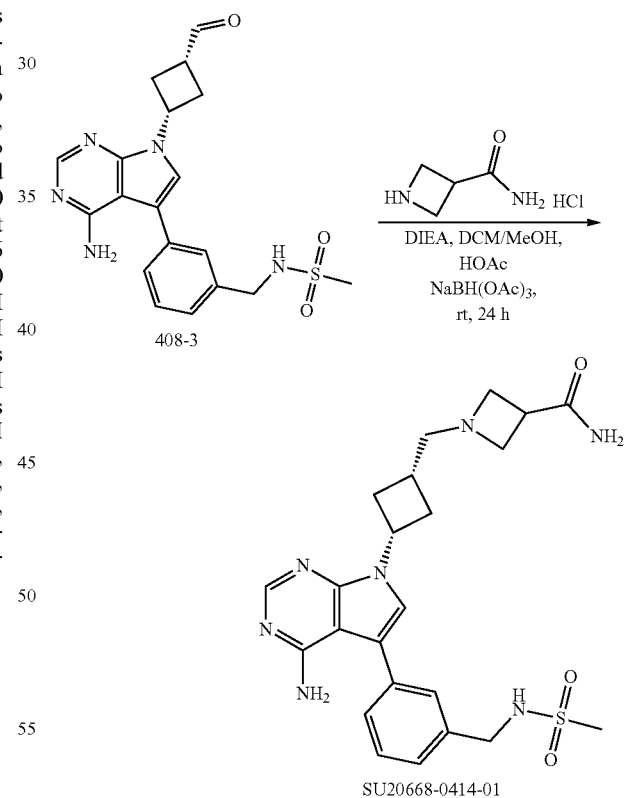

The mixture of 3-AzetidinecarboxaMide HCl (84 mg, 0.6 mmol) and DIEA (97 mg, 0.75 mmol) in MeOH/DCM (10 mL, 4/1) was stirred at rt for 5 min. 408-3 (200 mg, 0.5 mmol) and AcOH (15 mg, 0.25 mmol) were added to the solution. After stirring for 30 min at rt, NaBH(OAc)$_3$ (212 mg, 1.0 mmol) was added to the solution. Then The mixture solution was stirred at rt for 24 h. After the consumption of starting material (by LCMS), the mixture was concentrated in vacuo to remove the solvent, then purified by prep-HPLC to give the desired product SU20668-0414-01 (23 mg, 9.5% yield) as a white solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 100%, Rt=1.272 min; MS Calcd.: 483.59; MS Found: 484.4 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 100%, Rt=5.552 min. $^1$H NMR (400 MHz, DMSO-d$_6$) δ 8.11 (s, 1H), 7.55-7.58 (m, 2H), 7.38-7.46 (m, 3H), 7.30-7.32 (m, 1H), 7.23 (s, 1H), 6.81 (s, 1H), 6.05 (brs, 2H), 5.00-5.09 (m, 1H), 4.20 (d, J=6.4 Hz, 2H), 3.33-3.35 (m, 3H), 3.05-3.08 (m, 3H), 2.88 (s, 3H), 2.27-2.35 (m, 2H), 2.05-2.19 (m, 4H).

Scheme 142: Route for SU20668-0415

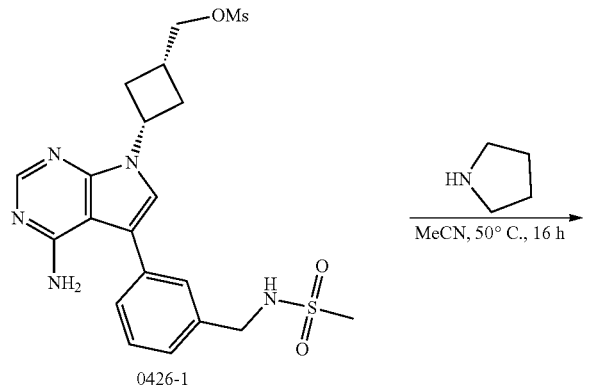

The Synthesis of N-(3-(4-amino-7-(cis-3-(pyrrolidin-1-ylmethyl)cyclobutyl)-7H-pyrrolo[2,3-d]pyrimidin-5-yl)benzyl)methanesulfonamide (SU20668-0415)

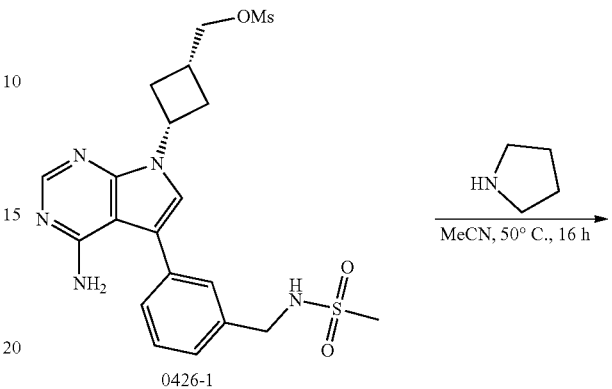

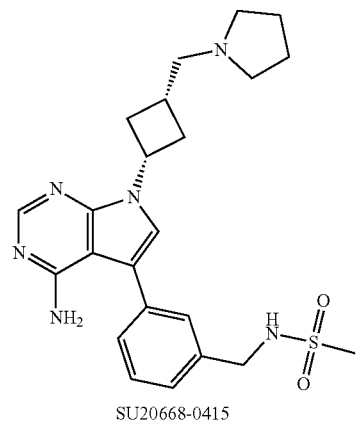

To a stirred solution of compound 0426-1 (270 mg, 0.56 mmol) in MeCN (4 mL) was added pyrrolidine (200 mg, 2.8 mmol) and the reaction mixture was stirred at 50° C. for 16 h. The reaction mixture was concentrated in vacuo to remove the solvent, then the crude was purified by prep-HPLC to give the desired product SU20668-0415 (90 mg, yield: 35.4%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH4HCO3] and 5% [CH3CN] to 0% [water+10 mM NH4HCO3] and 100% [CH3CN] in 1.6 min, then under this condition for 1.4 min, finally changed to 95% [water+10 mM NH4HCO3] and 5% [CH3CN] in 0.1 min and under this condition for 0.7 min), Purity: 100.00%, Rt=1.431 min; MS Calcd.: 454.22; MS Found: 455.2 [M+H]+. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH4HCO3] and 5% [CH3CN] to 0% [water+10 mM NH4HCO3] and 100% [CH3CN] in 10 min, then under this condition for 5 min, finally changed to 95% [water+10 mM NH4HCO3] and 5% [CH3CN] in 0.1 min and under this condition for 5 min), Purity: 99.69%, Rt=6.826 min. $^1$H NMR (400 MHz, DMSO-d$_6$) δ 8.13 (s, 1H), 7.60 (s, 2H), 7.40-7.48 (m, 3H), 7.33 (d, J=7.6 Hz, 1H), 6.05 (brs, 2H), 5.06-5.11 (m, 1H), 4.22 (s, 2H), 2.90 (s, 3H), 2.54-2.58 (m, 4H), 2.41-2.44 (m, 4H), 2.26-2.30 (m, 1H), 2.16-2.21 (m, 2H), 1.65-1.67 (m, 4H).

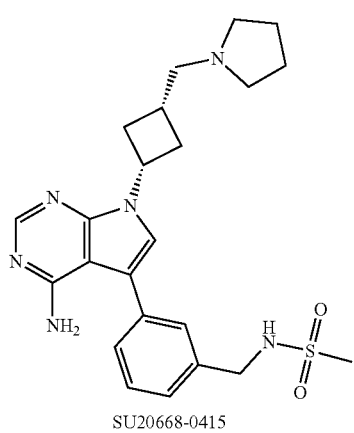

Scheme 143: Route for SU20668-0416

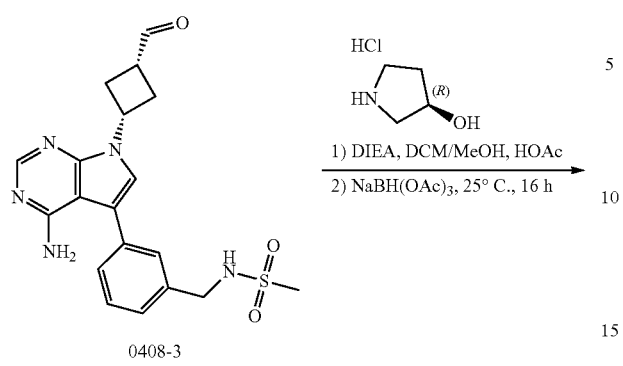

The Synthesis of N-(3-(4-amino-7-(cis-3-(((R)-3-hydroxypyrrolidin-1-yl)methyl)cyclobutyl)-7H-pyrrolo[2,3-d]pyrimidin-5-yl)benzyl)methanesulfonamide (SU20668-0416)

To a stirred solution of 0408-3 (178 mg, 0.45 mmol) in DCM (1 mL) and MeOH (4 mL) was added DIEA (104 mg, 0.81 mmol), HOAc (0.2 mL) and the reaction mixture was stirred at 25° C. for 0.5 h, then was added NaBH(OAc)$_3$ (1.88 g, 8.9 mmol) stirred at 25° C. for 16 h. The solvent was removed in vacuo. Then added water, the aqueous phase was extracted with ethyl acetate, the combined organic phases were dried over anhydrous sodium sulfate, filtered, and concentrated. The organic layer was concentrated, purified by column to afford the product SU20668-416 (15 mg, 7.1% yield) as a white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH4HCO3] and 5% [CH3CN] to 0% [water+10 mM NH4HCO3] and 100% [CH3CN] in 1.6 min, then under this condition for 1.4 min, finally changed to 95% [water+10 mM NH4HCO3] and 5% [CH3CN] in 0.1 min and under this condition for 0.7 min), Purity: 100.00%, Rt=1.499 min; MS Calcd.: 470.21; MS Found: 471.2 [M+H]+. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH4HCO3] and 5% [CH3CN] to 0% [water+10 mM NH4HCO3] and 100% [CH3CN] in 10 min, then under this condition for 5 min, finally changed to 95% [water+10 mM NH4HCO3] and 5% [CH3CN] in 0.1 min and under this condition for 5 min), Purity: 100.00%, Rt=6.943 min. $^1$H NMR (400 MHz, DMSO-d$_6$) δ 8.13 (s, 1H), 7.60 (s, 1H), 7.40-7.48 (m, 3H), 7.33 (d, J=7.2 Hz, 1H), 6.07 (brs, 2H), 5.06-5.11 (m, 1H), 4.66-4.68 (m, 1H), 4.22 (s, 2H), 4.17 (brs, 1H), 2.93 (s, 3H), 2.65-2.72 (m, 2H), 2.50-2.57 (m, 4H), 2.32-2.44 (m, 2H), 2.13-2.29 (m, 4H), 1.91-2.00 (m, 1H), 1.51-1.54 (m, 1H).

Scheme 144: Route for SU20668-0417

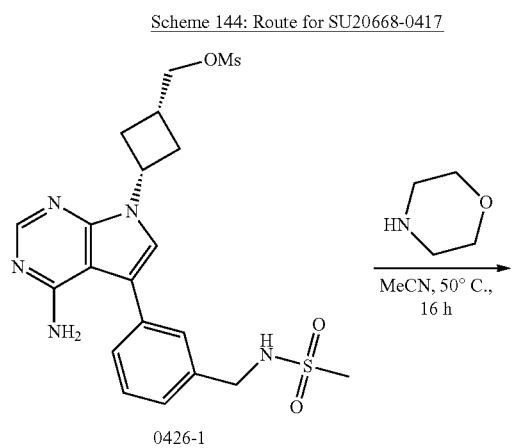

0426-1

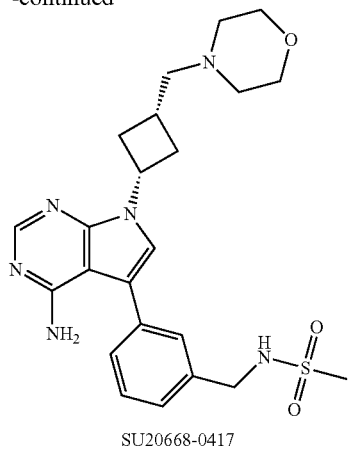

SU20668-0417

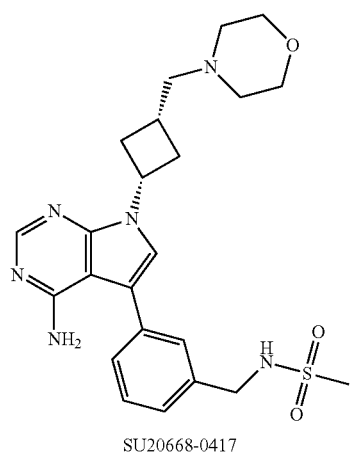

SU20668-0417

The Synthesis of N-(3-(4-amino-7-(cis-3-(morpholinomethyl)cyclobutyl)-7H-pyrrolo[2,3-d]pyrimidin-5-yl)benzyl)methanesulfonamide (SU20668-0417)

To a stirred solution of compound 0426-1 (160 mg, 0.33 mmol) in MeCN (4 mL) was added morpholine (143.5 mg, 1.65 mmol) and the reaction mixture was stirred at 50° C. for 16 h. The reaction mixture was concentrated in vacuo to remove the solvent, then the crude was purified by prep-HPLC to give the desired product SU20668-0417 (20 mg, yield: 12.9%) as a white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH4HCO3] and 5% [CH3CN] to 0% [water+10 mM NH4HCO3] and 100% [CH3CN] in 1.6 min, then under this condition for 1.4 min, finally changed to 95% [water+10 mM NH4HCO3] and 5% [CH3CN] in 0.1 min and under this condition for 0.7 min), Purity: 100.00%, Rt=1.505 min; MS Calcd.: 470.21; MS Found: 471.2 [M+H]+. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH4HCO3] and 5% [CH3CN] to 0% [water+10 mM NH4HCO3] and 100% [CH3CN] in 10 min, then under this condition for 5 min, finally changed to 95% [water+10 mM NH4HCO3] and 5% [CH$_3$CN] in 0.1 min and under this condition for 5 min), Purity: 99.54%, R$_t$=6.904 min. $^1$H NMR (400 MHz, DMSO-d$_6$) δ 8.13 (s, 1H), 7.57-7.61 (m, 2H), 7.40-7.47 (m, 3H), 7.33 (d, J=7.6 Hz, 1H), 6.11 (brs, 2H), 5.07-5.12 (m, 1H), 4.22 (d, J=6.0 Hz, 2H), 3.56 (t, J=4.8 Hz, 4H), 2.90 (s, 3H), 2.48-2.54 (m, 3H), 2.32-2.36 (m, 6H), 2.14-2.22 (m, 2H).

Scheme 145: Route for SU20668-0418

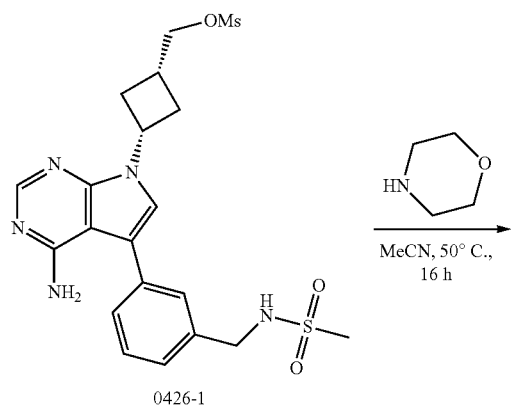

0426-1

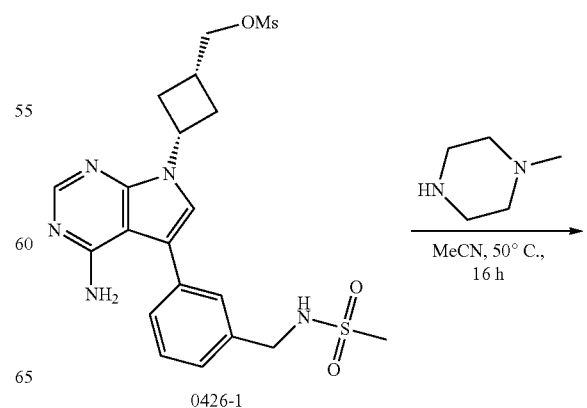

0426-1

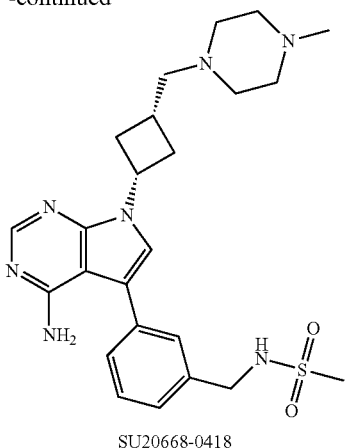

SU20668-0418

The Synthesis of N-(3-(4-amino-7-(cis-3-((4-methylpiperazin-1-yl)methyl)cyclobutyl)-7H-pyrrolo[2,3-d]pyrimidin-5-yl)benzyl)methanesulfonamide (SU20668-0418)

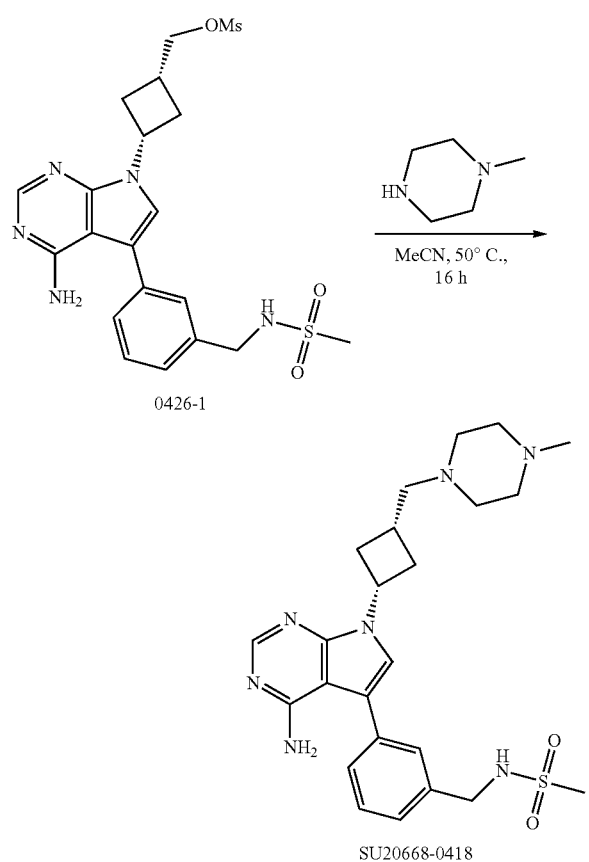

To a stirred solution of compound 0426-1 (160 mg, 0.33 mmol) in MeCN (4 mL) was added 1-methylpiperazine (165 mg, 1.65 mmol) and the reaction mixture was stirred at 50° C. for 16 h. The reaction mixture was concentrated in vacuo to remove the solvent, then the crude was purified by prep-HPLC to give the desired product SU20668-0418 (27 mg, yield: 16.9%) as a white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH4HCO3] and 5% [CH3CN] to 0% [water+10 mM NH4HCO3] and 100% [CH3CN] in 1.6 min, then under this condition for 1.4 min, finally changed to 95% [water+10 mM NH4HCO3] and 5% [CH3CN] in 0.1 min and under this condition for 0.7 min), Purity: 100.00%, Rt=1.446 min; MS Calcd.: 483.24; MS Found: 484.3 [M+H]+. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH4HCO3] and 5% [CH3CN] to 0% [water+10 mM NH4HCO3] and 100% [CH3CN] in 10 min, then under this condition for 5 min, finally changed to 95% [water+10 mM NH4HCO3] and 5% [CH3CN] in 0.1 min and under this condition for 5 min), Purity: 99.60%, Rt=6.319 min. $^1$H NMR (400 MHz, DMSO-$d_6$) δ 8.13 (s, 1H), 7.57-7.60 (m, 2H), 7.40-7.48 (m, 3H), 7.33 (d, J=7.2 Hz, 1H), 6.11 (brs, 2H), 5.06-5.13 (m, 1H), 4.22 (d, J=6.0 Hz, 2H), 2.90 (s, 3H), 2.45-2.55 (m, 5H), 2.29-2.37 (m, 7H), 2.13-2.20 (m, 6H).

Scheme 146: Route for SU20668-0419

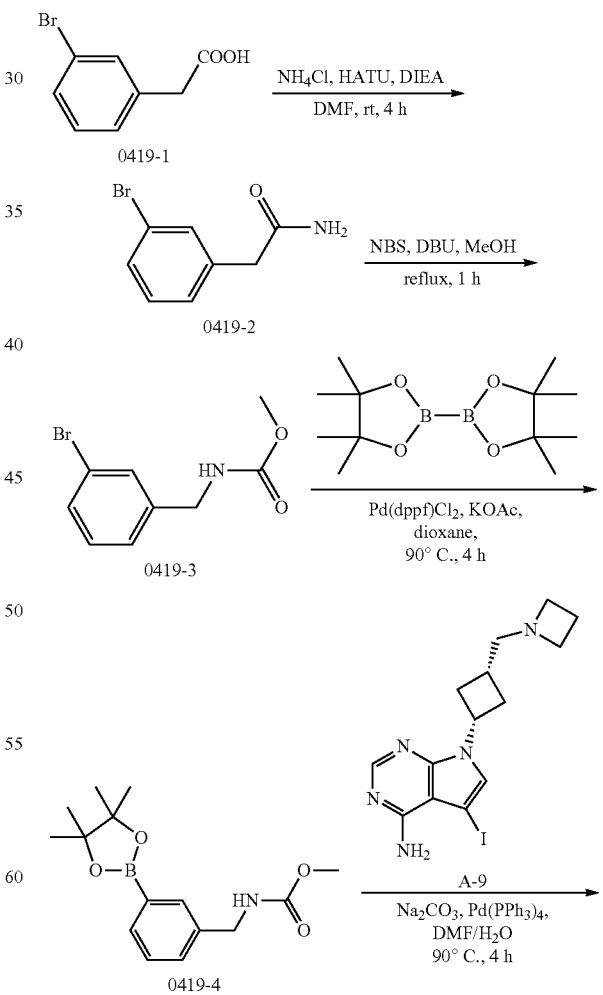

-continued

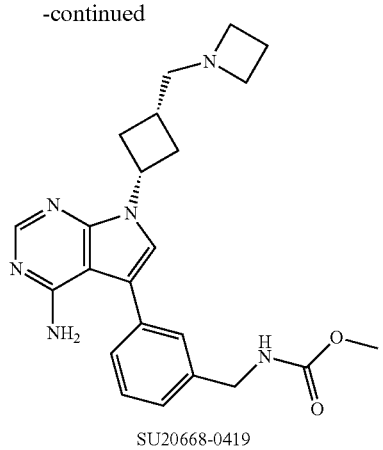

SU20668-0419

The Synthesis of 2-(3-bromophenyl)acetamide (0419-2)

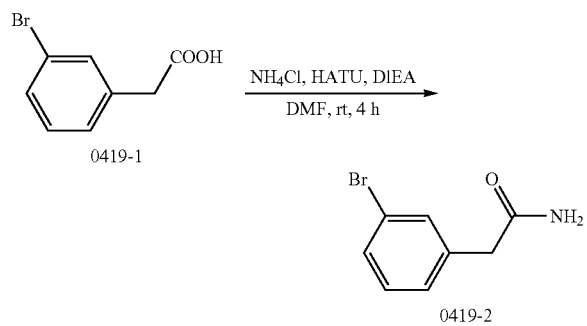

To a stirred solution of compound 0419-1 (2.0 g, 9.3 mmol) in DMF (25 ml) was added NH₄Cl (497 mg, 9.3 mmol), HATU (5.3 g, 13.95 mmol), and DIEA (3.6 g, 27.9 mmol) was stirred at rt for 4 h. Then added water, the aqueous phase was extracted with dichloromethane, the combined organic phases were dried over anhydrous sodium sulfate, filtered, and concentrated in vacuo, purified by C.C. to give 419-2 (1.5 g, yield: 75.4%) as a white solid.

The Synthesis of methyl 3-bromobenzylcarbamate (0419-3)

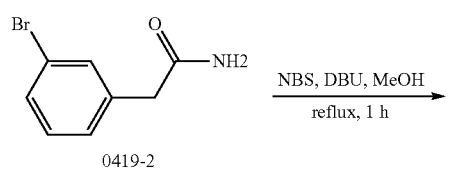

To a stirred solution of compound 0419-2 (1.3 g, 6.07 mmol) in MeOH (20 mL) was added DBU (92 mg, 0.607 mmol), NBS (1.08 g, 6.07 mmol). The resulting reaction mixture was heated to 70° C. and stirred for 1 h and concentrated in vacuo to remove the solvent, the crude was purified by reverse C.C. to give 0419-3 (600 mg, yield: 40.5%) as a yellow oil.

The Synthesis of methyl 3-(4,4,5,5-tetramethyl-1,3,2-dioxaborolan-2-yl)benzylcarbamate (0419-4)

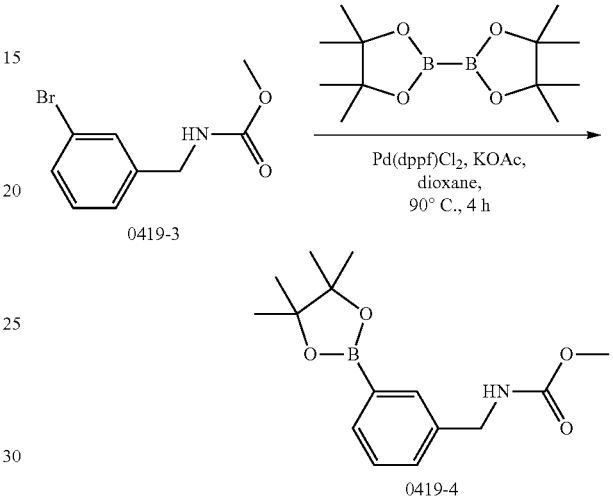

To a stirred solution of compound 0419-3 (600 mg, 2.46 mmol) in dioxane (10 mL) was added 4,4,4',4',5,5,5',5'-octamethyl-2,2'-bi(1,3,2-dioxaborolane) (624.8 mg, 2.46 mmol), KOAc (602 mg, 6.15 mmol), Pd(dppf)Cl₂(90 mg, 0.123 mmol). The resulting reaction mixture was heated to 90° C. and stirred for 4 h and concentrated in vacuo to remove the solvent, then added water, the aqueous phase was extracted with dichloromethane, the combined organic phases were dried over anhydrous sodium sulfate, filtered, and concentrated, the crude was purified by reverse C.C. to give 0419-4 (400 mg, yield: 55.9%) as a yellow oil.

The Synthesis of methyl 3-(4-amino-7-(cis-3-(azetidin-1-ylmethyl)cyclobutyl)-7H-pyrrolo[2,3-d]pyrimidin-5-yl)benzylcarbamate (SU20668-0419)

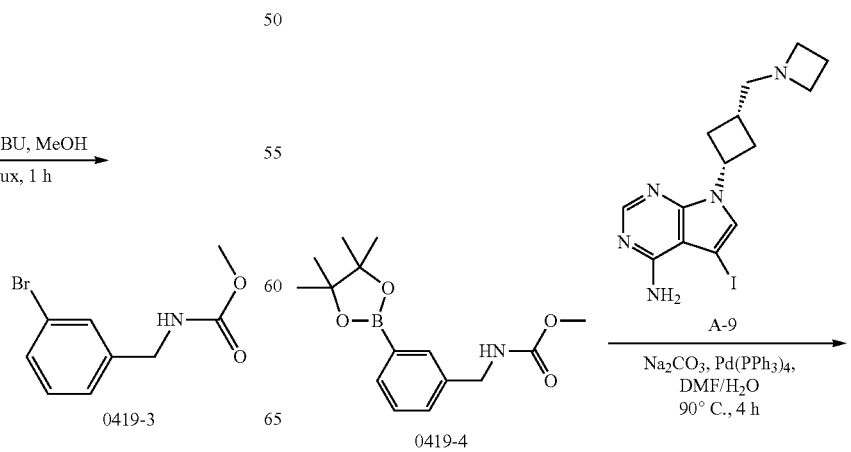

-continued

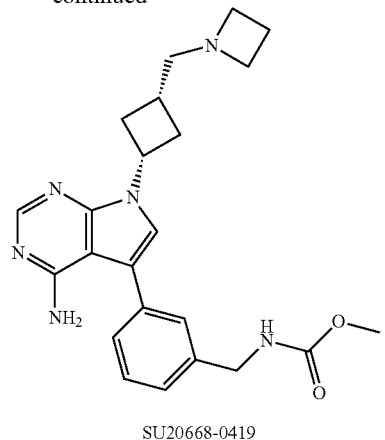

SU20668-0419

To a stirred solution of compound 0419-4 (150 mg, 0.52 mmol) in DMF (4 mL) and H$_2$O (1 mL) was added A-9 (199 mg, 0.52 mmol), Na$_2$CO$_3$ (138 mg, 1.3 mmol), Pd(PPh$_3$)$_4$ (30 mg, 0.026 mmol). The resulting reaction mixture was heated to 90° C. and stirred for 4 h and concentrated in vacuo to remove the solvent, then added water, the aqueous phase was extracted with ethyl acetate, the combined organic phases were dried over anhydrous sodium sulfate, filtered, and concentrated, the crude was purified by prep-HPLC to give the desired product SU20668-0419 (30 mg, yield: 13.8%) as a yellow solid. LC-MS (LC-MS (Agilent LCMS 1200-6120, Column: Waters X-Bridge C18 (30 mm×4.6 mm×2.7 m); Column Temperature: 40° C.; Flow Rate: 3.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 0.8 min, then under this condition for 0.4 min, finally changed to 95% [water+0.05% TFA] and 5% [CH$_3$CN+0.05%] in 0.01 min.). Purity: 100.00%, Rt=1.494 min; MS Calcd.: 420.23; MS Found: 421.2 [M+H]$^+$. HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.1% TFA] and 5% [CH$_3$CN+0.1% TFA] to 0% [water+0.1% TFA] and 100% [CH$_3$CN+0.1% TFA] in 10 min, then under this condition for 5 min, finally changed to 95% [water+0.1% TFA] and 5% [CH$_3$CN+0.1% TFA] in 0.1 min and under this condition for 5 min). Purity: 100.00%, Rt=6.686 min. $^H$ NMR (400 MHz, DMSO-d$_6$) δ 8.12 (s, 1H), 7.71-7.74 (m, 1H), 7.57 (s, 1H), 7.36-7.45 (m, 3H), 7.23 (d, J=7.6 Hz, 1H), 6.06 (brs, 2H), 5.01-5.10 (m, 1H), 4.24 (d, J=6.0 Hz, 2H), 3.55 (s, 3H), 3.09 (t, J=6.8 Hz, 4H), 2.45-2.50 (m, 4H), 2.08-2.19 (m, 3H), 1.90-1.97 (m, 2H).

Scheme 147: Route for SU20668-0420

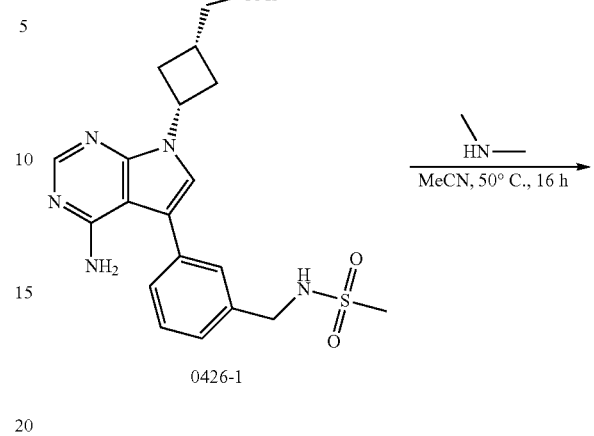

0426-1

The Synthesis of N-(3-(4-amino-7-(cis-3-((dimethylamino)methyl)cyclobutyl)-7H-pyrrolo[2,3-d]pyrimidin-5-yl)benzyl)methanesulfonamide (SU20668-0420)

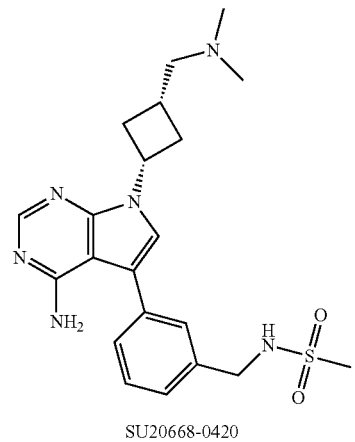

SU20668-0420

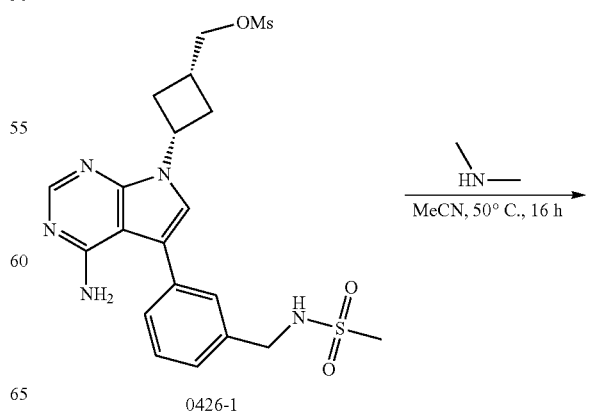

0426-1

787
-continued

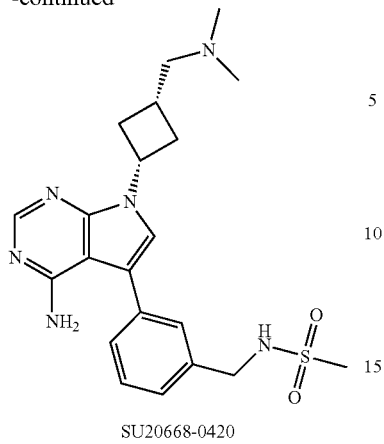

SU20668-0420

To a stirred solution of compound 0426-1 (160 mg, 0.33 mmol) in MeCN (4 mL) was added dimethylamine (74 mg, 1.65 mmol) and the reaction mixture was stirred at 50° C. for 16 h. The reaction mixture was concentrated in vacuo to remove the solvent, then the crude was purified by prep-HPLC to give the desired product SU20668-0420 (25 mg, yield: 17.7%) as a yellow solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH4HCO3] and 5% [CH3CN] to 0% [water+10 mM NH4HCO3] and 100% [CH3CN] in 1.6 min, then under this condition for 1.4 min, finally changed to 95% [water+10 mM NH4HCO3] and 5% [CH3CN] in 0.1 min and under this condition for 0.7 min), Purity: 99.47%, Rt=1.432 min; MS Calcd.: 428.20; MS Found: 429.3 [M+H]+. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH4HCO3] and 5% [CH3CN] to 0% [water+10 mM NH4HCO3] and 100% [CH3CN] in 10 min, then under this condition for 5 min, finally changed to 95% [water+10 mM NH4HCO3] and 5% [CH3CN] in 0.1 min and under this condition for 5 min), Purity: 97.36%, Rt=6.315 min. $^1$H NMR (400 MHz, DMSO-$d_6$) δ 8.13 (s, 1H), 7.55-7.61 (m, 2H), 7.40-7.48 (m, 3H), 7.33 (d, J=7.6 Hz, 1H), 6.09 (brs, 2H), 5.07-5.11 (m, 1H), 4.22 (s, 2H), 2.90 (s, 3H), 2.39-2.41 (m, 3H), 2.26-2.31 (m, 2H), 2.12-2.17 (m, 8H).

Scheme 148: Route for SU20668-0421-01

788
-continued

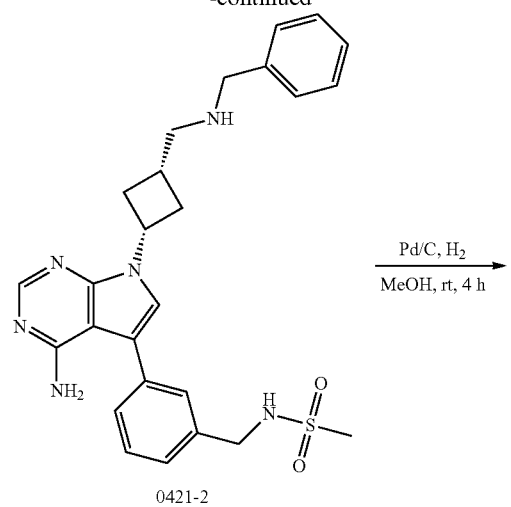

0421-2

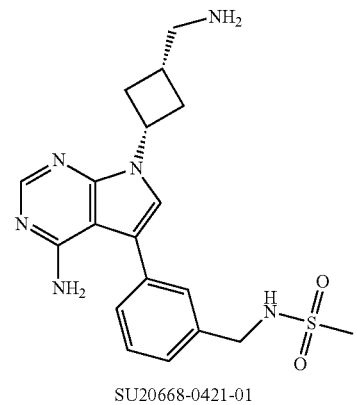

SU20668-0421-01

The Synthesis of N-(3-(4-amino-7-(cis-3-((benzylamino)methyl)cyclobutyl)-7H-pyrrolo[2,3-d]pyrimidin-5-yl)benzyl)methanesulfonamide (0421-2)

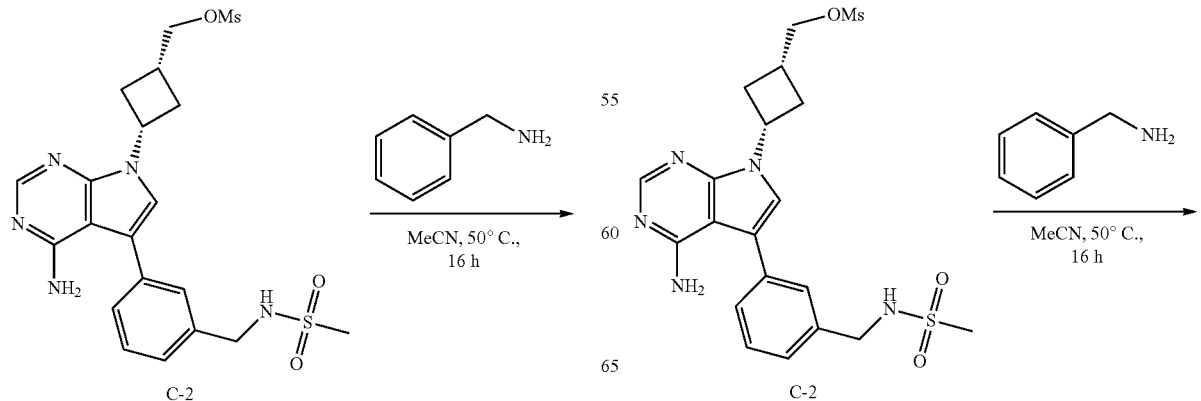

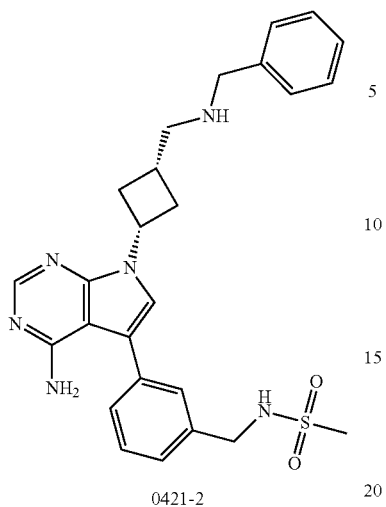

0421-2

To a mixture of C-2 (70 mg, 0.15 mmol) in MeCN (3 mL) was added phenylmethanamine (0.2 mL). Then it was stirred in a sealed tube at 50° C. for 16 hours. Remove the solvent in vacuo. The residue was purified by silica-gel column (DCM:MeOH=40:1) to afford 0421-2 (50 mg, yield: 68.0%) as a white solid.

The Synthesis of N-(3-(4-amino-7-(cis-3-(aminomethyl)cyclobutyl)-7H-pyrrolo[2,3-d]pyrimidin-5-yl)benzyl)methanesulfonamide (SU20668-0421-01)

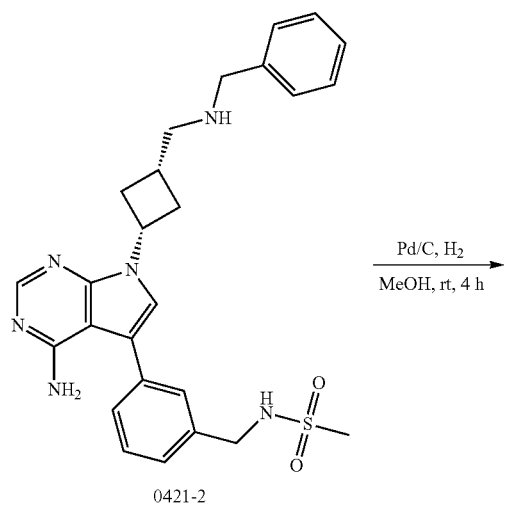

0421-2

Pd/C, H₂
MeOH, rt, 4 h
→

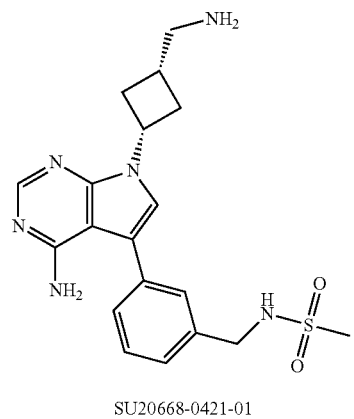

SU20668-0421-01

To a solution of 0421-2 (50 mg, 0.10 mmol) in MeOH (5 mL) was added Pd/C (10%, 10 mg). The mixture was stirred at rt for 4 h under H₂ atmosphere (1.0 atm). Then it was filtered and concentrated in vacuo. The residue was purified by prep-HPLC to afford SU20668-0421-01 (8 mg, yield: 20.0%) as a white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 99.40%, Rt=1.509 min; MS Calcd.: 400.1; MS Found: 401.2 [M+H]⁺. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min). Purity: 98.29%, Rt=7.147 min. ¹H NMR (400 MHz, MeOD-d₄) δ 8.16 (s, 1H), 7.56 (s, 1H), 7.41-7.50 (m, 4H), 5.11-5.16 (m, 1H), 4.34 (s, 2H), 2.92-2.94 (m, 5H,) 2.70-2.73 (m, 2H), 2.30-2.37 (m, 3H).

Scheme 149: Route for SU20668-0425

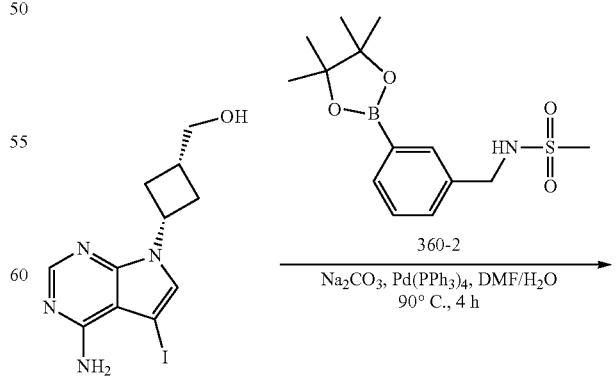

A-7      360-2

Na₂CO₃, Pd(PPh₃)₄, DMF/H₂O
90° C., 4 h
→

The Synthesis of N-(3-(4-amino-7-(cis-3-(hydroxymethyl)cyclobutyl)-7H-pyrrolo[2,3-d]pyrimidin-5-yl)benzyl)methanesulfonamide (SU20668-0425)

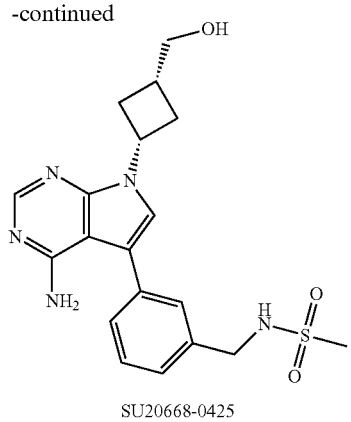

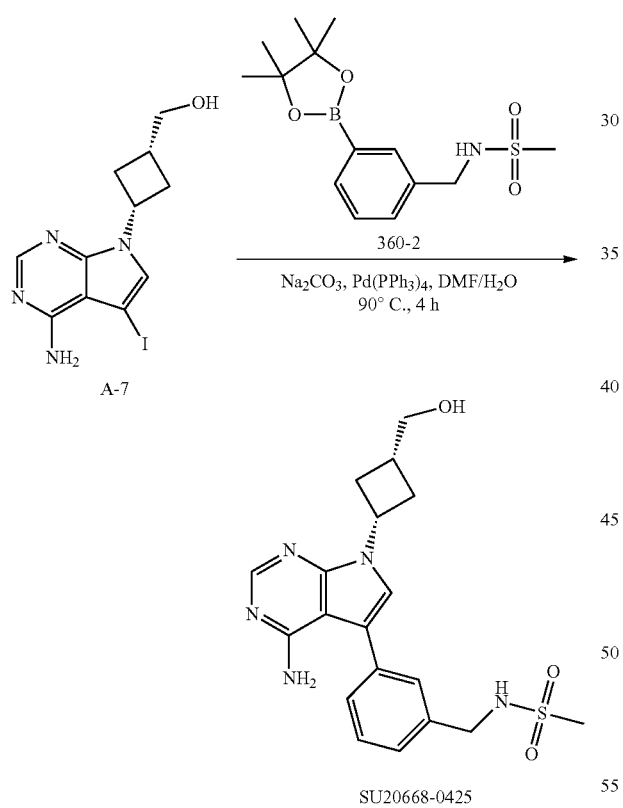

To a stirred solution of compound A-7 (200 mg, 0.58 mmol) in DMF (4 mL) and H₂O (1 mL) was added 360-2 (217 mg, 0.69 mmol), Na₂CO₃ (154 mg, 1.45 mmol), Pd(PPh₃)₄ (33 mg, 0.029 mmol). The resulting reaction mixture was heated to 90° C. and stirred for 4 h and concentrated in vacuo to remove the solvent, then added water, the aqueous phase was extracted with dichloromethane, the combined organic phases were dried over anhydrous sodium sulfate, filtered, and concentrated, the crude was purified by prep-HPLC to give the desired product SU20668-0425 (150 mg, yield: 64.7%) as a white solid. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH4HCO3] and 5% [CH3CN] to 0% [water+10 mM NH4HCO3] and 100% [CH3CN] in 1.6 min, then under this condition for 1.4 min, finally changed to 95% [water+10 mM NH4HCO3] and 5% [CH3CN] in 0.1 min and under this condition for 0.7 min), Purity: 100.00%, Rt=1.547 min; MS Calcd.: 401.15; MS Found: 402.2 [M+H]+. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH4HCO3] and 5% [CH3CN] to 0% [water+10 mM NH4HCO3] and 100% [CH3CN] in 10 min, then under this condition for 5 min, finally changed to 95% [water+10 mM NH4HCO3] and 5% [CH3CN] in 0.1 min and under this condition for 5 min), Purity: 100.00%, Rt=6.781 min. ¹H NMR (400 MHz, DMSO-d₆) δ 8.13 (s, 1H), 7.52 (s, 1H), 7.45-7.47 (m, 2H), 7.39-7.41 (m, 1H), 7.33 (d, J=7.6 Hz, 1H), 6.07 (brs, 2H), 5.06-5.12 (m, 1H), 4.62 (t, J=5.2 Hz, 1H), 4.22 (s, 2H), 3.49 (t, J=4.4 Hz, 2H), 2.90 (s, 3H), 2.45-2.47 (m, 2H), 2.25-2.28 (m, 3H).

Scheme 150: Route for SU20668-0451-01

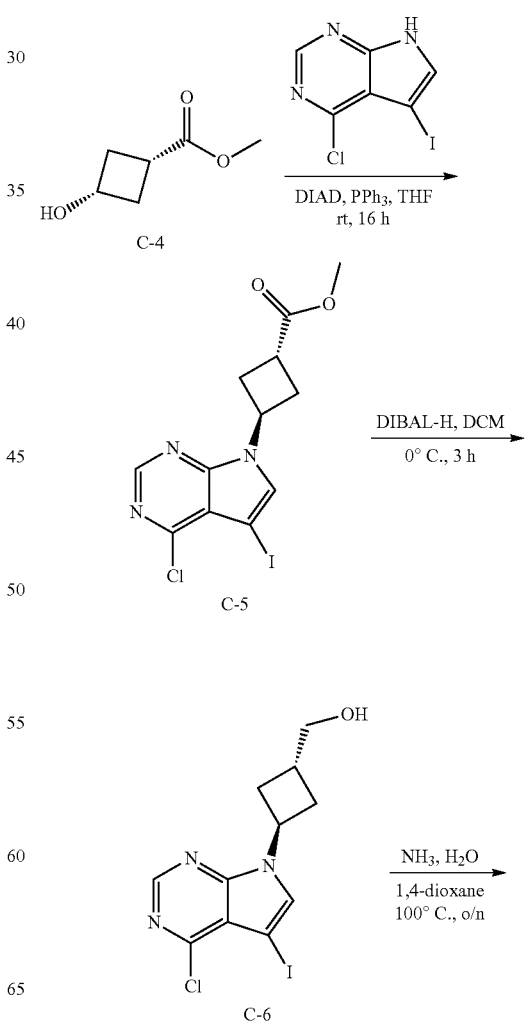

The Synthesis of trans-methyl 3-(4-chloro-5-iodo-7H-pyrrolo[2,3-d]pyrimidin-7-yl)cyclobutanecarboxylate (C-5)

To a solution of C-4 (1.3 g, 10 mmol), 4-chloro-5-iodo-7H-pyrrolo[2,3-d]pyrimidine (3.0 g, 11 mmol) and PPh3 (3.9 g, 15 mmol) in dry THF (20 mL) was added DIAD (4.1 g, 20 mmol) dropwise at −20° C. Then it was stirred at rt for 16 h. Remove the solvent in vacuo. The residue was stirred in methanol (10 mL) at 0° C. for 20 minutes. Then it was filtered. The solid was washed with methanol (10 mL) to afford C-5 (2.5 g, 63.9% yield) as an off-white solid.

The Synthesis of (trans-3-(4-chloro-5-iodo-7H-pyrrolo[2,3-d]pyrimidin-7-yl)cyclobutyl)methanol (C-6)

-continued

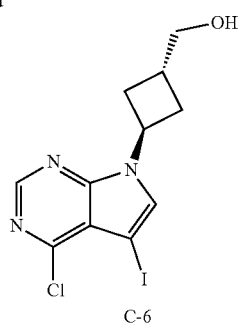

C-6

To a solution of C-5 (2.5 g, 6.4 mmol) in DCM (30 mL) was added DIBAL-H (1M, 10 mL) dropwise at 0° C. Then it was stirred at 0° C. for 3 h. Sodium sulfate decahydrate (5.0 g) was added to quench the reaction. DCM (200 mL) was added. Then it was washed with water (30 mL), dried and concentrated to dryness to afford C-6 (3.1 g, crude) as a yellow solid.

The Synthesis of (trans-3-(4-amino-5-iodo-7H-pyrrolo[2,3-d]pyrimidin-7-yl)cyclobutyl)methanol (C-7)

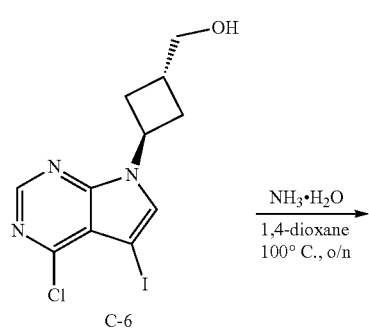

C-6

NH$_3$·H$_2$O
1,4-dioxane
100° C., o/n

To a mixture of C-6 (3.1 g, crude) in dioxane (15 mL) was added ammonium hydroxide (15 mL). Then it was stirred in a sealed tube at 100° C. for 16 hours. Remove the solvent in vacuo. The residue was purified by silica-gel column (DCM:MeOH=40:1) to afford C-7 (1.1 g, total yield for 2 steps: 50.0% yield) as a yellow solid.

The Synthesis of N-(3-(4-amino-7-(trans-3-(hydroxymethyl)cyclobutyl)-7H-pyrrolo[2,3-d]pyrimidin-5-yl)benzyl)methanesulfonamide (0408-2)

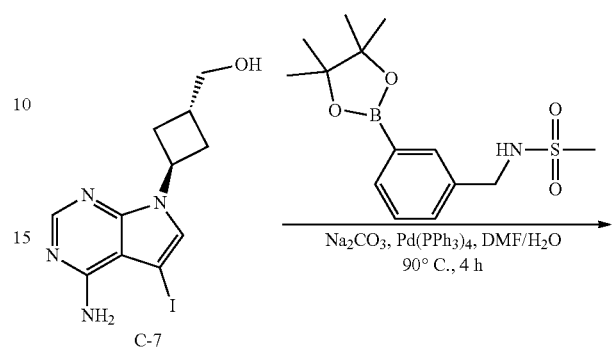

C-7

Na$_2$CO$_3$, Pd(PPh$_3$)$_4$, DMF/H$_2$O
90° C., 4 h

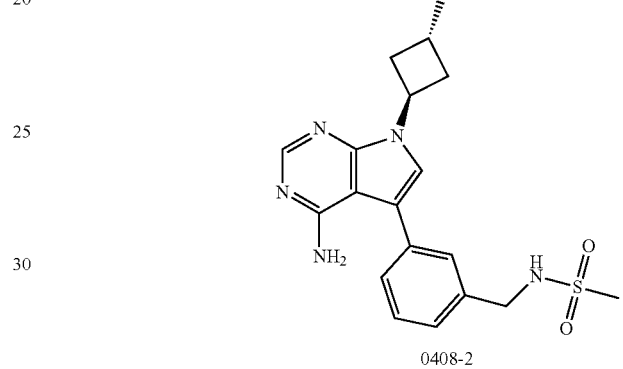

0408-2

The mixture of C-7 (2.5 g, 7.3 mmol), N-(3-(4,4,5,5-tetramethyl-1,3,2-dioxaborolan-2-yl)benzyl)methanesulfonamide (2.73 g, 8.76 mmol), Pd(PPh$_3$)$_4$ (844 mg, 0.73 mmol), and Na$_2$CO$_3$ (2.32 g, 21.9 mmol) in DMF/H$_2$O (50 mL, 4/1) was stirred at 90° C. under N$_2$ atmosphere for 4 h. After the consumption of starting material (by LCMS), the mixture was concentrated in vacuo to remove the solvent, then purified by prep-HPLC to give the desired product 0408-2 (1.3 g, 44.3% yield) as a yellow solid.

The Synthesis of N-(3-(4-amino-7-(trans-3-formylcyclobutyl)-7H-pyrrolo[2,3-d]pyrimidin-5-yl)benzyl)methanesulfonamide (0408-3a)

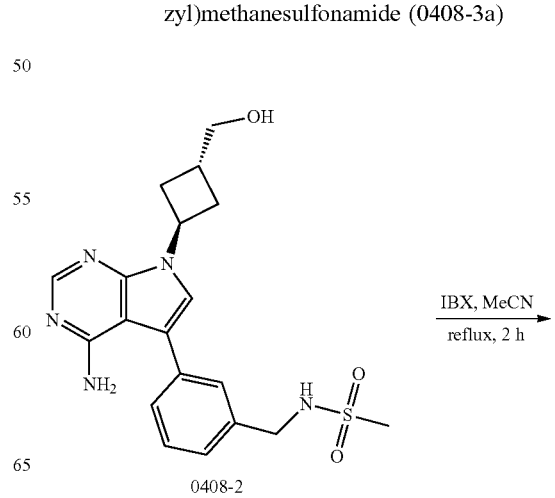

0408-2

IBX, MeCN
reflux, 2 h

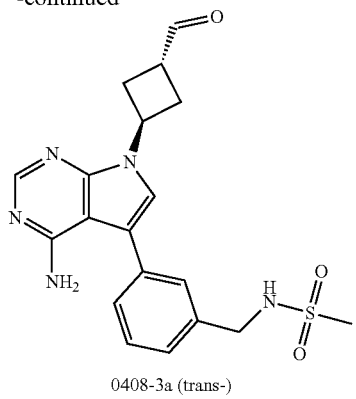

0408-3a (trans-)

The mixture of compound 0408-2 (1.3 g, 3.3 mmol) and IBX (1.36 g, 4.9 mmol) in CH$_3$CN (20 ml) was reflux for 2 h. After the consumption of starting material (by LCMS), the mixture was concentrated in vacuo to give the desired product 408-3a (1.5 g, crude) as a yellow solid.

The Synthesis of N-(3-(4-amino-7-(trans-3-((3-fluoroazetidin-1-yl)methyl)cyclobutyl)-7H-pyrrolo[2,3-d]pyrimidin-5-yl)benzyl)methanesulfonamide (SU20668-0451-01)

The mixture of 3-fluoroazetidine hydrochloride (100 mg, 0.9 mmol) and DIEA (145 mg, 1.13 mmol) in MeOH/DCM (10 mL, 4/1) was stirred at rt for 5 min. 0408-3a (trans-) (300 mg, 0.75 mmol) and AcOH (23 mg, 0.38 mmol) were added to the solution. After stirring for 30 min at rt, NaBH(OAc)$_3$ (318 mg, 1.5 mmol) was added to the solution. The mixture solution was stirred at rt overnight. After the consumption of starting material (by LCMS), the mixture was concentrated in vacuo, then purified by prep-HPLC to give the desired product SU20668-0451-01 (12 mg, 3.5% yield) as a white solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 96.33%, Rt=1.605 min; MS Calcd.: 458.55; MS Found: 459.4 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 96.08%, Rt=7.418 min. $^1$H NMR (400 MHz, DMSO-d$_6$) δ 8.13 (s, 1H), 7.57-7.61 (m, 2H), 7.39-7.48 (m, 3H), 7.32-7.34 (m, 1H), 6.11 (brs, 2H), 5.09-5.35 (m, 2H), 4.22 (d, J=6.4 Hz, 2H), 3.60 (brs, 2H), 3.02-3.15 (m, 2H), 2.90 (s, 3H), 2.59-2.68 (m, 3H), 2.20-2.33 (m, 4H).

Scheme 151: Route for SU20668-0453-01

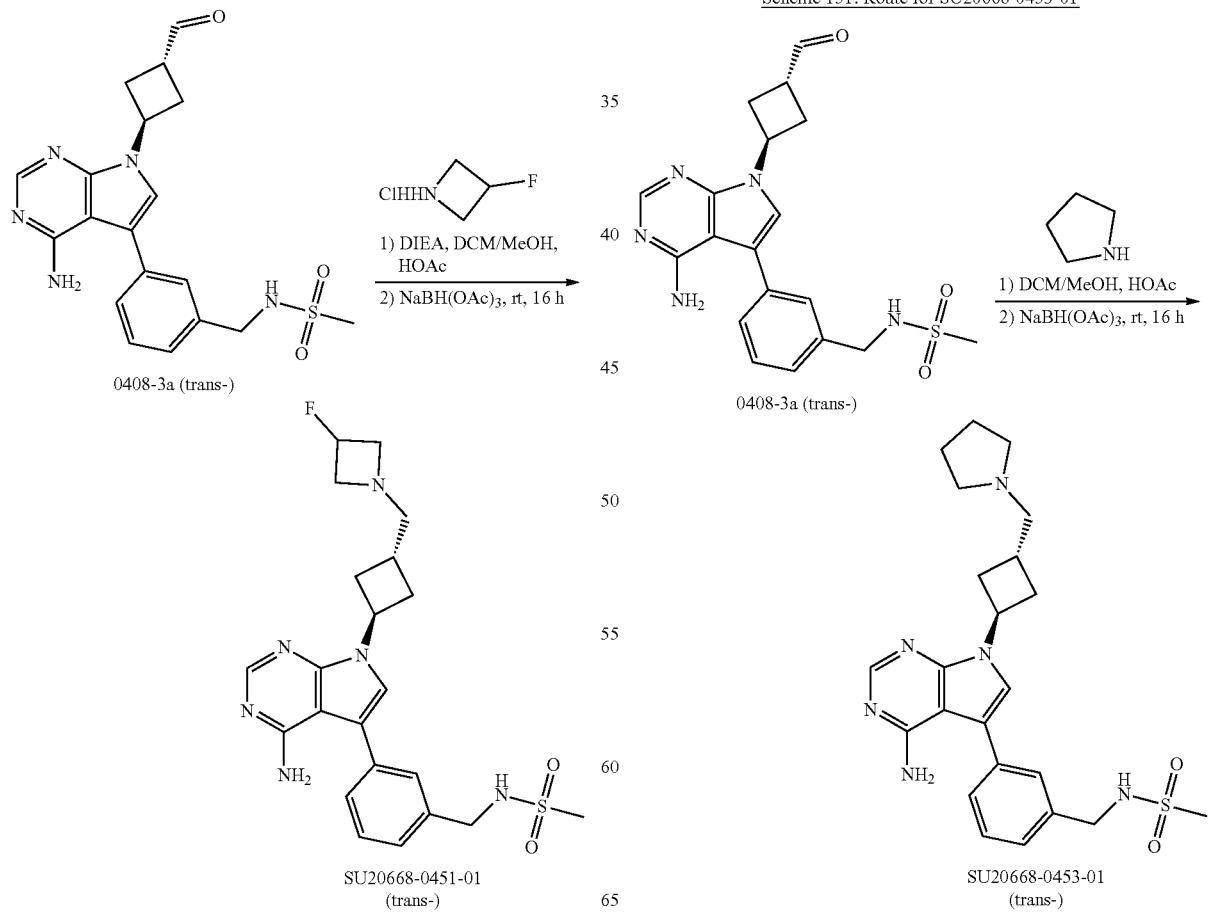

The Synthesis of N-(3-(4-amino-7-(trans-3-(pyrrolidin-1-ylmethyl)cyclobutyl)-7H-pyrrolo[2,3-d]pyrimidin-5-yl)benzyl)methanesulfonamide (SU20668-0453-01)

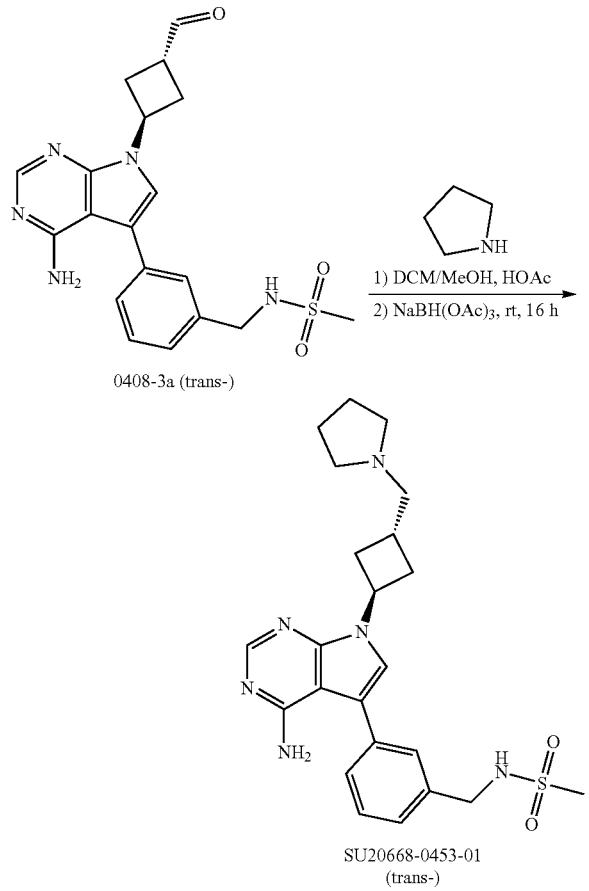

The mixture of pyrrolidine (64 mg, 0.9 mmol) and in MeOH/DCM (10 mL, 4/1),0408-3a (trans-) (300 mg, 0.75 mmol) and AcOH (23 mg, 0.38 mmol) were added to the solution. After stirring for 30 min at rt, NaBH(OAc)$_3$ (318 mg, 1.5 mmol) was added to the solution. The mixture solution was stirred at rt overnight. After the consumption of starting material (by LCMS), the mixture was concentrated in vacuo to remove the solvent, then purified by prep-HPLC to give the desired product SU20668-0453-01 (13 mg, 3.8% yield) as a white solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 100%, Rt=1.400 min; MS Calcd.: 454.59; MS Found: 455.4 [M+H]$^+$. Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+ 10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 100%, Rt=6.287 min. $^1$H NMR (400 MHz, DMSO-d$_6$) δ 8.11 (s, 1H), 7.55-7.60 (m, 2H), 7.38-7.46 (m, 3H), 7.30-7.32 (m, 1H), 6.07 (brs, 2H), 5.03-5.11 (m, 1H), 4.20 (d, J=6 Hz, 2H), 2.48 (s, 3H), 2.47-2.65 (m, 4H), 3.29-2.43 (m, 4H), 2.15-2.31 (m, 3H), 1.63-1.66 (m, 4H).

Scheme 152: Route for SU20668-0455-01

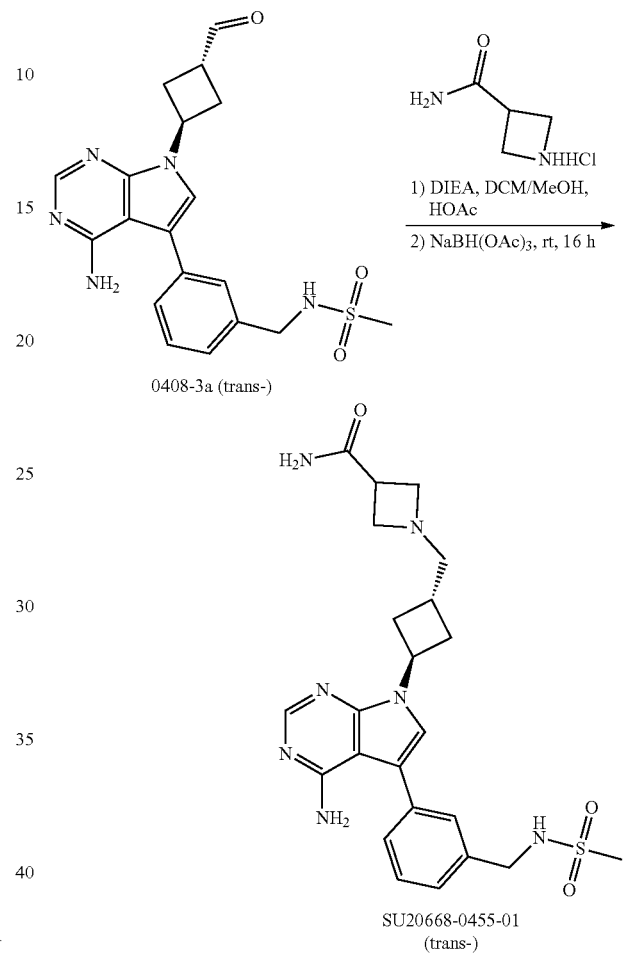

The Synthesis of 1-((trans-3-(4-amino-5-(3-(methylsulfonamidomethyl)phenyl)-7H-pyrrolo[2,3-d]pyrimidin-7-yl)cyclobutyl)methyl)azetidine-3-carboxamide (SU20668-0455-01)

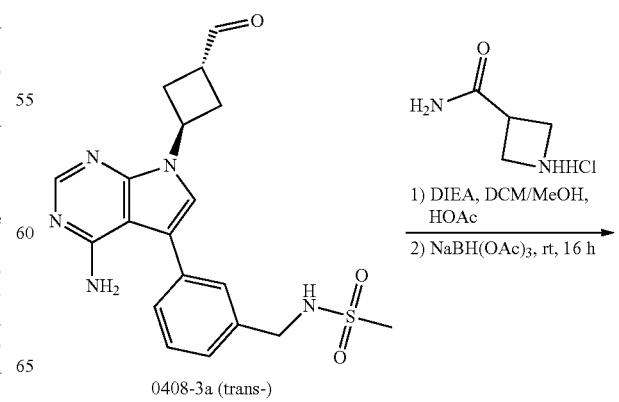

801

-continued

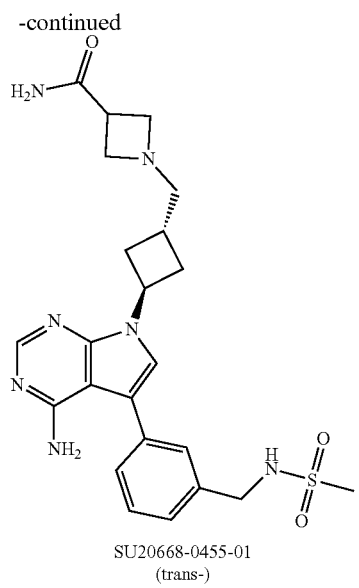

SU20668-0455-01
(trans-)

The mixture of azetidine-3-carboxamide hydrochloride (123 mg, 0.9 mmol) and DIEA (145 mg, 1.13 mmol) in MeOH/DCM (10 mL, 4/1) was stirred at rt for 5 min. 0408-3a (trans-) (300 mg, 0.75 mmol) and AcOH (23 mg, 0.38 mmol) were added to the solution. After stirring for 30 min at rt, NaBH(OAc)$_3$ (318 mg, 1.5 mmol) was added to the solution. The mixture solution was stirred at rt overnight. After the consumption of starting material (by LCMS), the mixture was concentrated in vacuo to remove the solvent, then purified by prep-HPLC to give the desired product SU20668-0455-01 (15 mg, 4.1% yield) as a white solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 100%, Rt=1.314 min; MS Calcd.: 483.59; MS Found: 484.4 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 100%, Rt=5.867 min. $^1$H NMR (400 MHz, DMSO-d$_6$) δ 8.11 (s, 1H), 7.58 (s, 1H), 7.37-7.46 (m, 3H), 7.30-7.32 (m, 1H), 7.25 (s, 1H), 6.83 (s, 1H), 6.07 (brs, 2H), 5.23-5.31 (m, 1H), 4.20 (s, 2H), 3.08-3.11 (m, 3H), 2.88 (s, 3H), 2.49-2.65 (m, 4H), 2.17-2.47 (m, 4H).

802

Scheme 153: Route for SU20668-0457-01

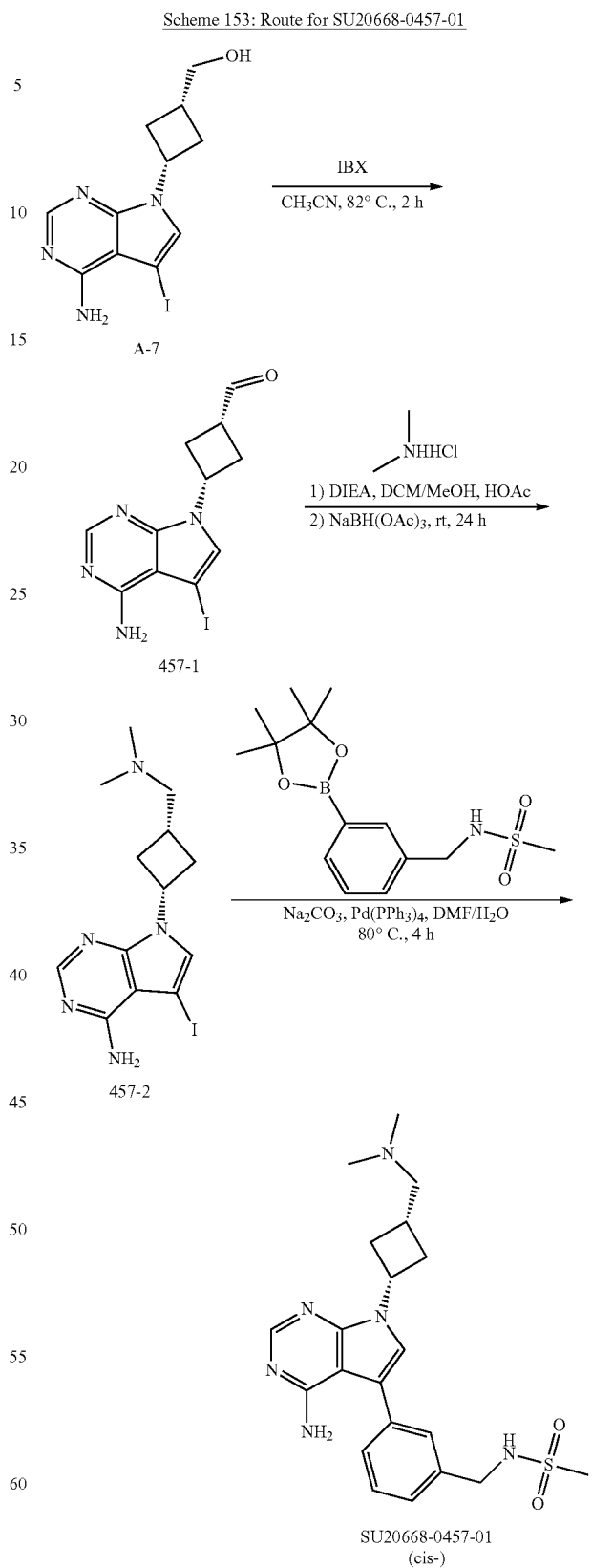

The Synthesis of (cis)-3-(4-amino-5-iodo-7H-pyrrolo[2,3-d]pyrimidin-7-yl)cyclobutanecarbaldehyde (457-1)

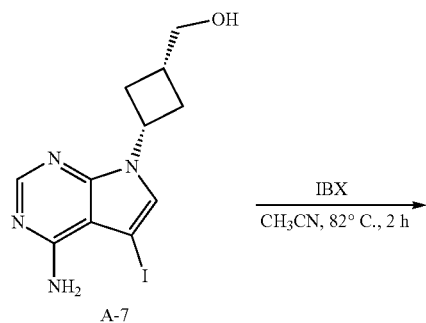

The mixture of compound A-7 (400 mg, 1.2 mmol) and IBX (504 mg, 1.8 mmol) in CH₃CN (10 ml) was stirred for 2 h at 82° C. After the consumption of starting material (by LCMS), the mixture was concentrated in vacuo to give the desired product 457-1 (500 mg, crude) as a yellow solid.

The Synthesis of 7-(cis-3-((dimethylamino)methyl)cyclobutyl)-5-iodo-7H-pyrrolo[2,3-d]pyrimidin-4-amine (457-2)

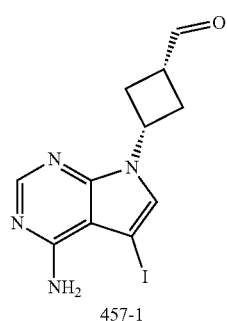

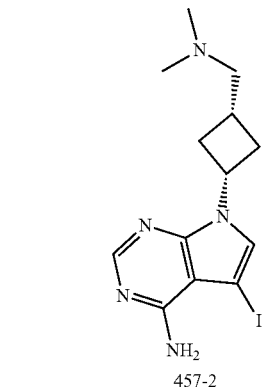

The mixture of Dimethylamine hydrochloride (143 mg, 1.75 mmol) and DIEA (283 mg, 2.19 mmol) in MeOH/DCM (20 mL, 4/1) was stirred at rt for 5 min. 457-1 (500 mg, 1.46 mmol) and AcOH (44 mg, 0.73 mmol) were added to the solution. After stirring for 30 min at rt, NaBH(OAc)₃ (619 mg, 2.92 mmol) was added to the solution. The mixture solution was stirred at rt for 24 h. After the consumption of starting material (by LCMS), the mixture was concentrated in vacuo to remove the solvent, then purified by prep-HPLC to give the desired product 457-2 (200 mg, 36.9% yield) as a yellow solid.

The Synthesis of N-(3-(4-amino-7-(cis-3-((dimethylamino)methyl)cyclobutyl)-7H-pyrrolo[2,3-d]pyrimidin-5-yl)benzyl)methanesulfonamide (SU20668-0457-01)

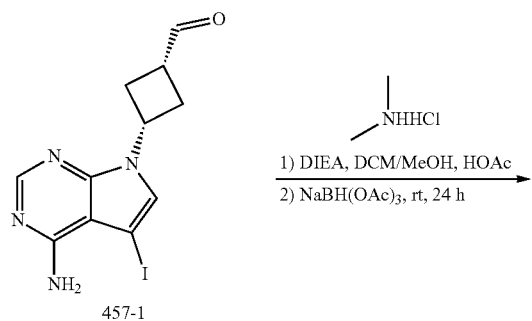
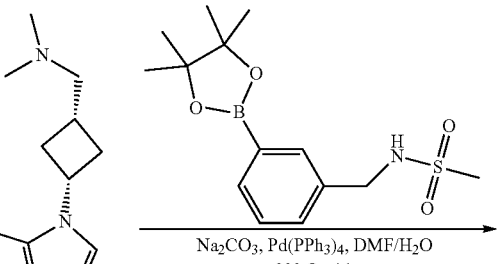

805

-continued

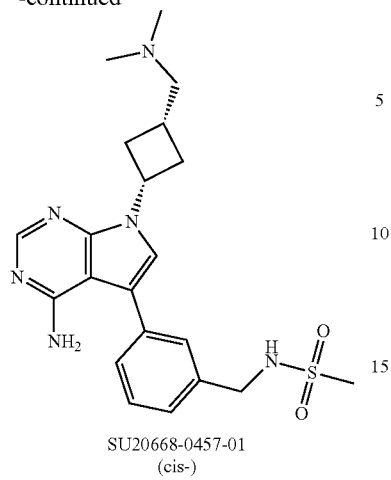

SU20668-0457-01
(cis-)

The mixture of 457-2 (200 mg, 0.54 mmol), N-(3-(4,4,5,5-tetramethyl-1,3,2-dioxaborolan-2-yl)benzyl)methanesulfonamide (202 mg, 0.65 mmol), Pd(PPh$_3$)$_4$ (62 mg, 0.054 mmol), and Na$_2$CO$_3$ (115 mg, 1.08 mmol) in DMF/H2O (10 mL, 4/1) was stirred at 80° C. under N$_2$ atmosphere for 4 h. After the consumption of starting material (by LCMS), the mixture was concentrated in vacuo to remove the solvent, then purified by prep-HPLC to give the desired product SU20668-0457-01 (35 mg, 15% yield) as a white solid. Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 99.09%, Rt=1.371 min; MS Calcd.: 428.55; MS Found: 429.4 [M+H]$^+$. Agilent HPLC 1200, Column: Waters X-Bridge C18 (150 mm*4.6 mm*3.5 µm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 99.65%, Rt=6.139 min. $^1$H NMR (400 MHz, DMSO-d$_6$) δ 8.11 (s, 1H), 7.57 (s, 2H), 7.38-7.46 (m, 3H), 7.31 (d, J=7.2 Hz, 1H), 6.05 (brs, 2H), 5.03-5.12 (m, 1H), 4.20 (s, 2H), 2.88 (s, 3H), 2.49-2.56 (m, 2H), 2.37-2.47 (m, 2H), 2.24-2.31 (m, 1H), 2.18-2.13 (m, 2H), 2.11 (s, 6H).

806

-continued

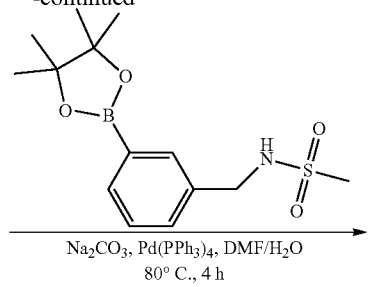

Na$_2$CO$_3$, Pd(PPh$_3$)$_4$, DMF/H$_2$O
80° C., 4 h 465-1

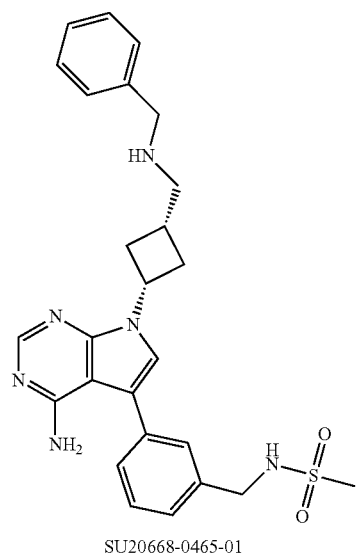

SU20668-0465-01

The Synthesis of 7-(cis-3-((benzylamino)methyl)cyclobutyl)-5-iodo-7H-pyrrolo[2,3-d]pyrimidin-4-amine (465-1)

Scheme 154: Route for SU20668-0465-01

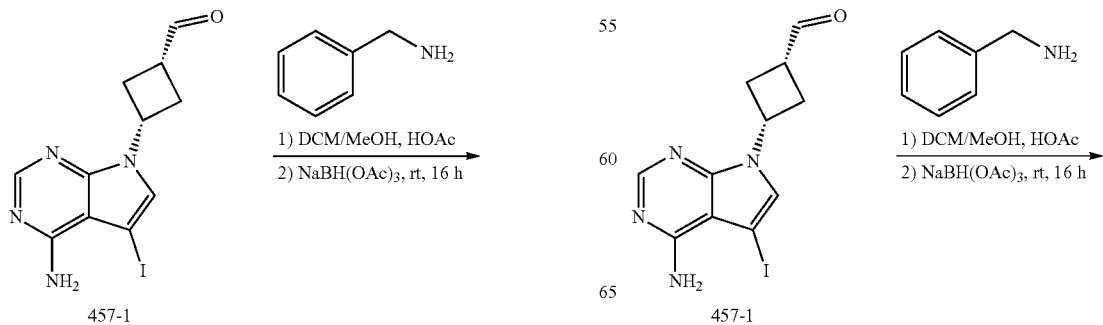

457-1

1) DCM/MeOH, HOAc
2) NaBH(OAc)$_3$, rt, 16 h 457-1

1) DCM/MeOH, HOAc
2) NaBH(OAc)$_3$, rt, 16 h

807
-continued

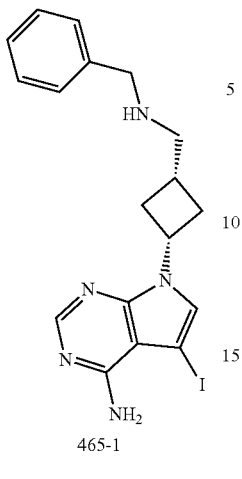
465-1

808
-continued

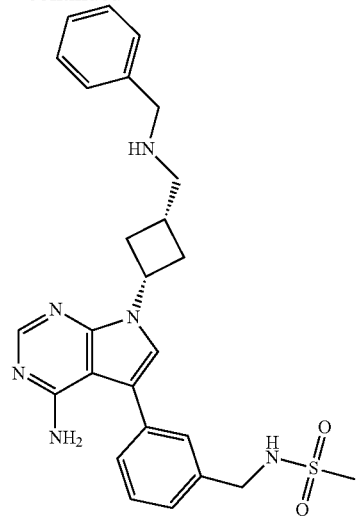
SU20668-0465-01

The mixture of phenylmethanamine (0.56 g, 5.3 mmol) 457-1 (1.5 g, 4.4 mmol) and AcOH (80 mg, 1.32 mmol) in MeOH/DCM (20 mL, 4/1) was stirred for 30 min at rt, Then NaBH(OAc)$_3$ (1.87 g, 8.8 mmol) was added to the solution. The mixture solution was stirred at rt for overnight. After the consumption of starting material (by LCMS), the mixture was concentrated in vacuo to remove the solvent, then purified by prep-HPLC to give the desired product 465-1 (800 mg, 42.1% yield) as a yellow solid.

The Synthesis of N-(3-(4-amino-7-(cis-3-((benzylamino)methyl)cyclobutyl)-7H-pyrrolo[2,3-d]pyrimidin-5-yl)benzyl)methanesulfonamide (SU20668-0465-01)

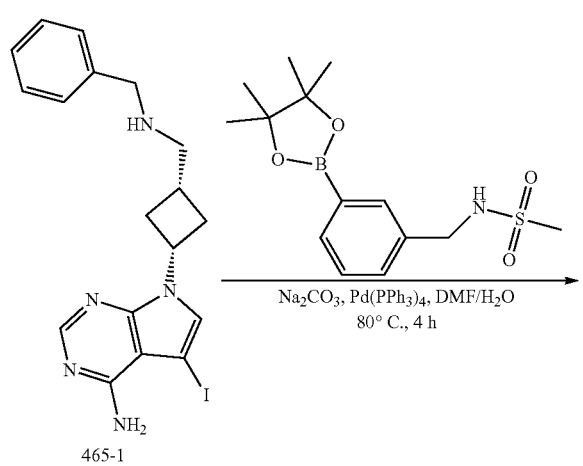

The mixture of 465-1 (200 mg, 0.46 mmol), N-(3-(4,4,5,5-tetramethyl-1,3,2-dioxaborolan-2-yl)benzyl)methanesulfonamide (171 mg, 0.55 mmol), Pd(PPh$_3$)$_4$ (53 mg, 0.046 mmol), and Na$_2$CO$_3$ (115 mg, 1.08 mmol) in DMF/H$_2$O (10 mL, 4/1) was stirred at 80° C. under N$_2$ atmosphere for 4 h. After the consumption of starting material (by LCMS), the mixture was concentrated in vacuo to remove the solvent, then purified by prep-HPLC to give the desired product SU20668-0465-01 (25 mg, 11.1% yield) as a white solid. Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min. Purity: 96.44%, Rt=1.761 min; MS Calcd.: 490.62; MS Found: 491.4 [M+H]$^+$. Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min. Purity: 96.05%, Rt=7.791 min. $^1$H NMR (400 MHz, DMSO-d$_6$) δ 8.12 (s, 1H), 7.52-7.57 (m, 2H), 7.39-7.48 (m, 3H), 7.28-7.35 (m, 5H), 7.19-7.23 (m, 1H), 6.08 (brs, 2H), 5.06-5.11 (m, 1H), 4.22 (s, 2H), 3.71 (s, 2H), 2.90 (s, 3H), 2.64-2.67 (m, 2H), 2.11-2.33 (m, 5H).

Example 3: Biological Data for APA Series

TABLE 1

Biologicial Data for select APA Analogs

| STRUCTURE | Compound # | LKB1 % Act. Increase | Cell Activity | MW |
|---|---|---|---|---|
| 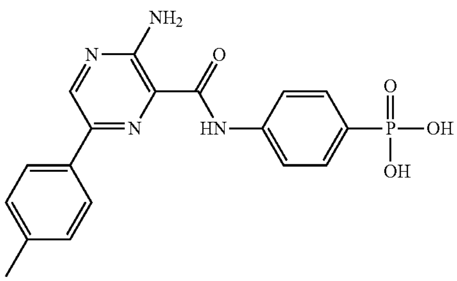 [SMILES: Cc1ccc(-c2cnc(N)c(C(=O)Nc3ccc(P(=O)(O)O)cc3)n2)cc1] | SU20668-0196 | C | nd | 384.33 |
| 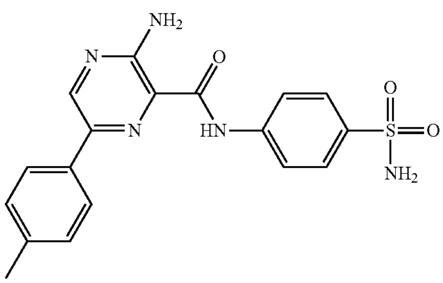 [SMILES: Cc1ccc(-c2cnc(N)c(C(=O)Nc3ccc(S(N)(=O)=O)cc3)n2)cc1] | SU20668-0197 | B | I | 383.42 |
| 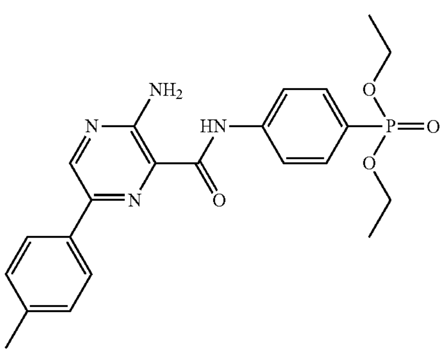 [SMILES: CCOP(=O)(OCC)c1ccc(NC(=O)c2nc(-c3ccc(C)cc3)cnc2N)cc1] | SU20668-0211 | D | nd | 440.43 |
| 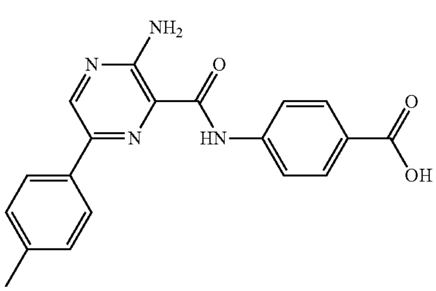 [SMILES: Cc1ccc(-c2cnc(N)c(C(=O)Nc3ccc(C(=O)O)cc3)n2)cc1] | SU20668-0279 | C | nd | 348.36 |

TABLE 1-continued

Biologicial Data for select APA Analogs

| STRUCTURE | Compound # | LKB1 % Act. Increase | Cell Activity | MW |
|---|---|---|---|---|
| 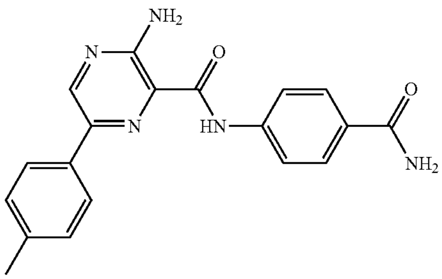 [SMILES: Cc1ccc(-c2cnc(N)c(C(=O)Nc3ccc(C(N)=O)cc3)n2)cc1] | SU20668-0280 | D | nd | 347.37 |
| 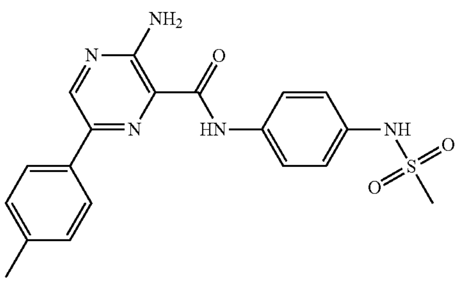 [SMILES: Cc1ccc(-c2cnc(N)c(C(=O)Nc3ccc(NS(C)(=O)=O)cc3)n2)cc1] | SU20668-0281 | D | nd | 397.45 |
| 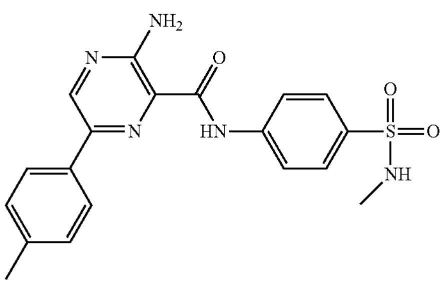 [SMILES: CNS(=O)(=O)c1ccc(NC(=O)c2nc(-c3ccc(C)cc3)cnc2N)cc1] | SU20668-0286 | C | nd | 397.45 |
| 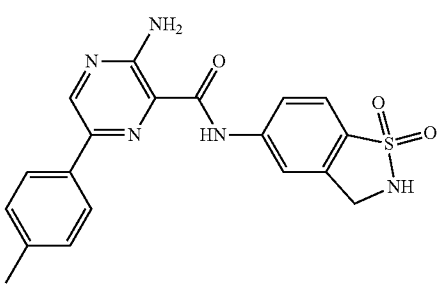 [SMILES: Cc1ccc(-c2cnc(N)c(C(=O)Nc3ccc4c(c3)CNS4(=O)=O)n2)cc1] | SU20668-0288 | D | nd | 395.43 |
| 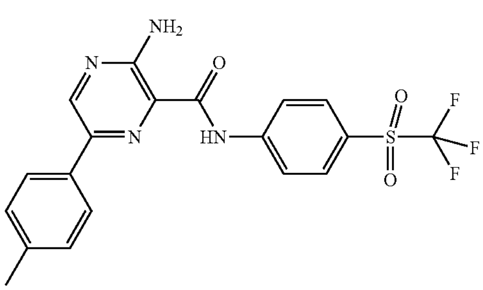 [SMILES: Cc1ccc(-c2cnc(N)c(C(=O)Nc3ccc(S(=O)(=O)C(F)(F)F)cc3)n2)cc1] | SU20668-0292 | D | nd | 436.41 |

TABLE 1-continued

Biologicial Data for select APA Analogs

| STRUCTURE | Compound # | LKB1 % Act. Increase | Cell Activity | MW |
|---|---|---|---|---|
| 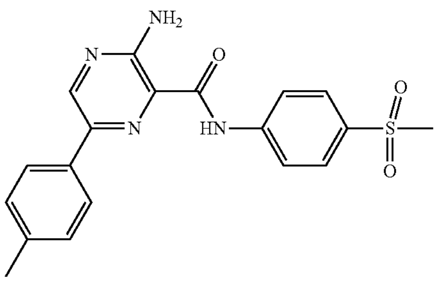 [SMILES: Cc1ccc(-c2cnc(N)c(C(=O)Nc3ccc(S(C)(=O)=O)cc3)n2)cc1] | SU20668-0293 | C | nd | 382.44 |
| 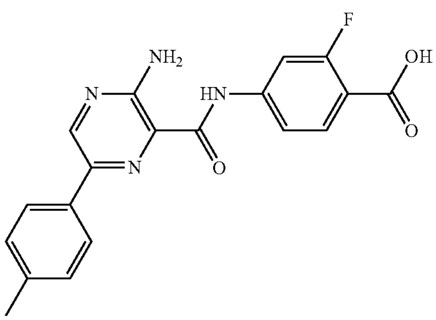 [SMILES: Cc1ccc(-c2cnc(N)c(C(=O)Nc3ccc(C(=O)O)c(F)c3)n2)cc1] | SU20668-0299 | D | nd | 366.35 |
| 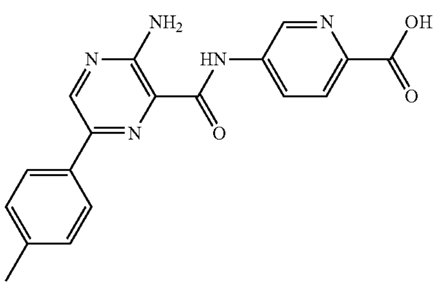 [SMILES: Cc1ccc(-c2cnc(N)c(C(=O)Nc3ccc(C(=O)O)nc3)n2)cc1] | SU20668-0300 | D | nd | 349.34 |
| 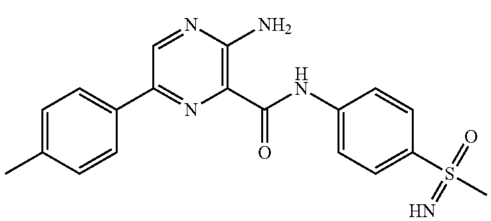 | SU20668-0302 | | nd | 381.45 |
| 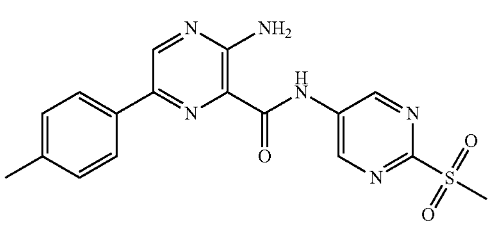 | SU20668-0303 | D | nd | 384.41 |

TABLE 1-continued

Biologicial Data for select APA Analogs

| STRUCTURE | Compound # | LKB1 % Act. Increase | Cell Activity | MW |
|---|---|---|---|---|
| 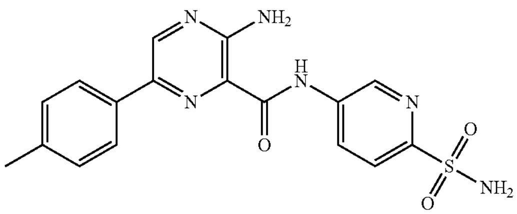 [SMILES: Cc1ccc(-c2cnc(N)c(C(=O)Nc3ccc(S(N)(=O)=O)nc3)n2)cc1] | SU20668-0304 | D | nd | 384.41 |
| 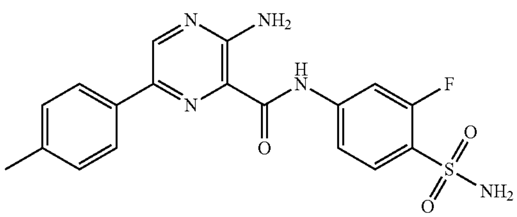 [SMILES: Cc1ccc(-c2cnc(N)c(C(=O)Nc3ccc(S(N)(=O)=O)c(F)c3)n2)cc1] | SU20668-0305 | C | I | 401.41 |
| 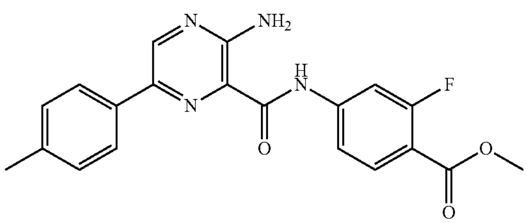 | SU20668-0307 | D | nd | 380.37 |
| 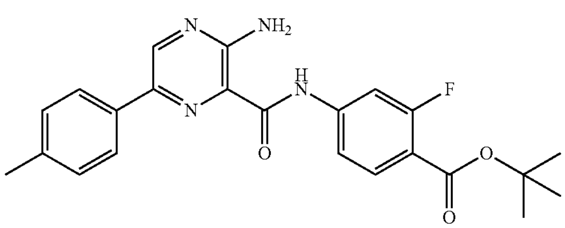 [SMILES: Cc1ccc(-c2cnc(N)c(C(=O)Nc3ccc(C(=O)OC(C)(C)C)c(F)c3)n2)cc1] | SU20668-0308 | C | nd | 422.45 |
| 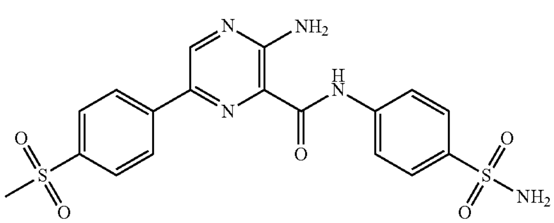 [SMILES: CS(=O)(=O)c1ccc(-c2cnc(N)c(C(=O)Nc3ccc(S(N)(=O)=O)cc3)n2)cc1] | SU20668-0309 | C | nd | 447.49 |
| 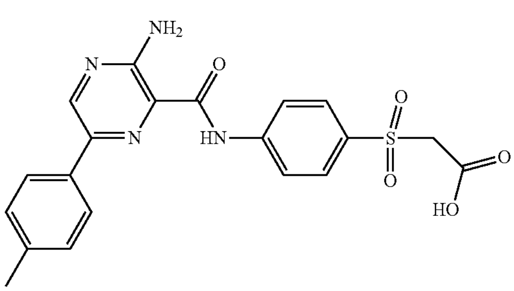 [SMILES: Cc1ccc(-c2cnc(N)c(C(=O)Nc3ccc(S(=O)(=O)CC(=O)O)cc3)n2)cc1] | SU20668-0310 | D | nd | 426.45 |

TABLE 1-continued

Biologicial Data for select APA Analogs

| STRUCTURE | Compound # | LKB1 % Act. Increase | Cell Activity | MW |
|---|---|---|---|---|
| 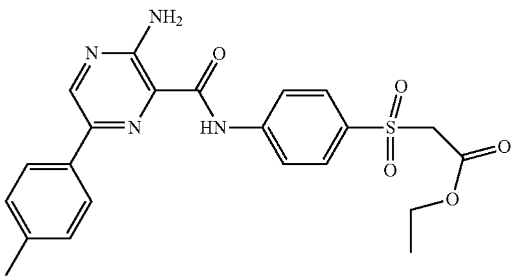 [SMILES: CCOC(=O)CS(=O)(=O)c1ccc(NC(=O)c2nc(-c3ccc(C)cc3)cnc2N)cc1] | SU20668-0311 | C | nd | 454.5 |
| 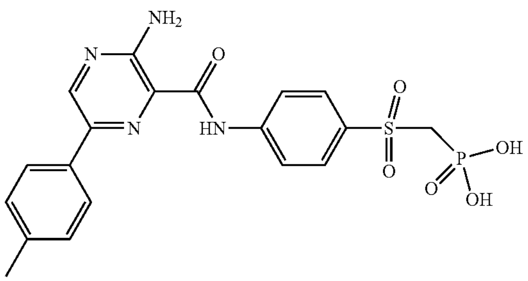 [SMILES: Cc1ccc(-c2cnc(N)c(C(=O)Nc3ccc([S@SP3](=O)(=O)CP(=O)(O)O)cc3)n2)cc1] | SU20668-0312 | C | nd | 462.42 |
| 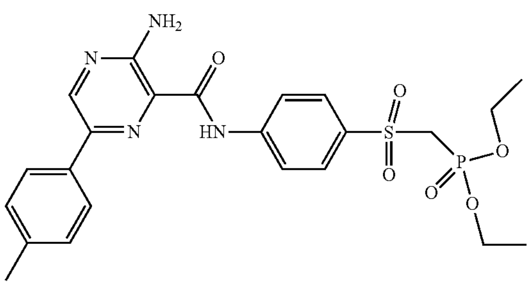 [SMILES: CCOP(=O)(C[S@SP3](=O)(=O)c1ccc(NC(=O)c2nc(-c3ccc(C)cc3)cnc2N)cc1)OCC] | SU20668-0313 | C | I | 518.52 |
| 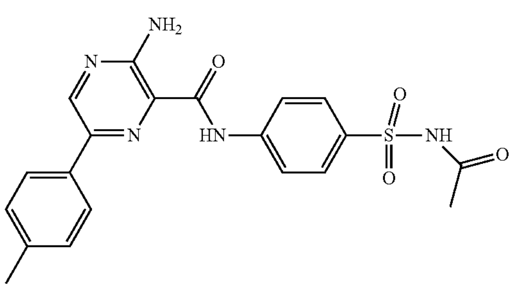 [SMILES: CC(=O)N[S@SP3](=O)(=O)c1ccc(NC(=O)c2nc(-c3ccc(C)cc3)cnc2N)cc1] | SU20668-0314 | C | II | 425.46 |
| 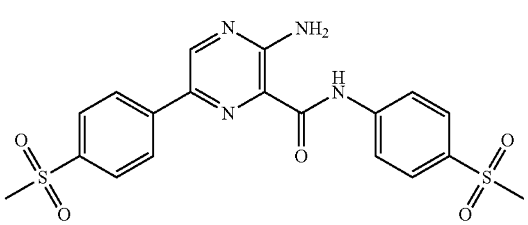 | SU20668-0317 | C | nd | 446.5 |

TABLE 1-continued

Biologicial Data for select APA Analogs

| STRUCTURE | Compound # | LKB1 % Act. Increase | Cell Activity | MW |
|---|---|---|---|---|
| 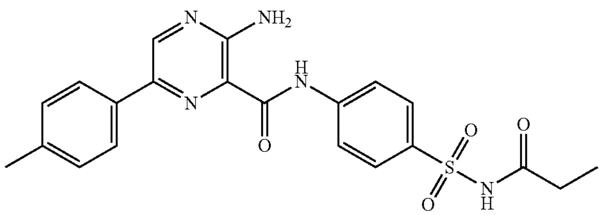 [SMILES: CCC(=O)NS(=O)(=O)c1ccc(NC(=O)c2nc(-c3ccc(C)cc3)cnc2N)cc1] | SU20668-0325 | C | nd | 439.49 |
| 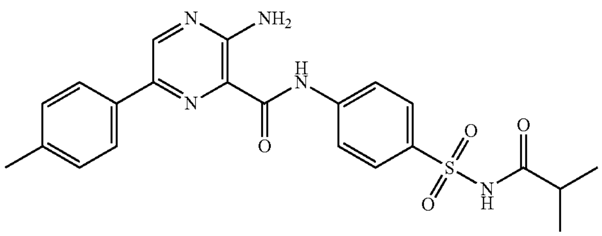 [SMILES: Cc1ccc(-c2cnc(N)c(C(=O)Nc3ccc(S(=O)(=O)NC(=O)C(C)C)cc3)n2)cc1] | SU20668-0327 | D | nd | 453.51 |
| 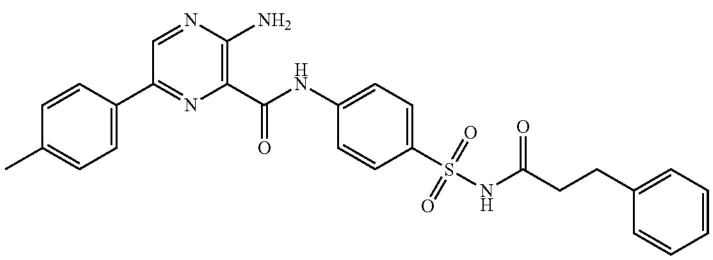 [SMILES: Cc1ccc(-c2cnc(N)c(C(=O)Nc3ccc(S(=O)(=O)NC(=O)CCc4ccccc4)cc3)n2)cc1] | SU20668-0328 | D | nd | 515.58 |
| 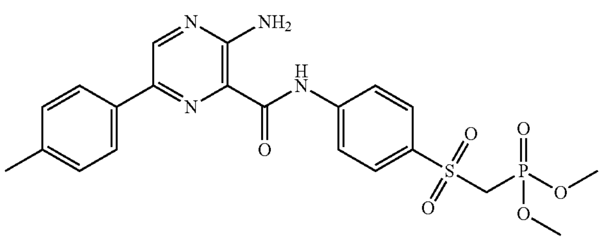 | SU20668-0329 | A | I | 490.47 |
| 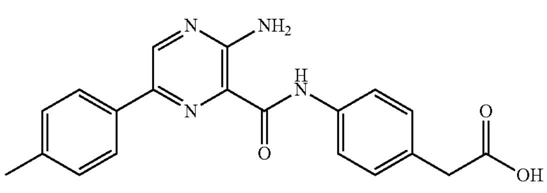 [SMILES: Cc1ccc(-c2cnc(N)c(C(=O)Nc3ccc(CC(=O)O)cc3)n2)cc1] | SU20668-0330 | C | nd | 362.38 |
| 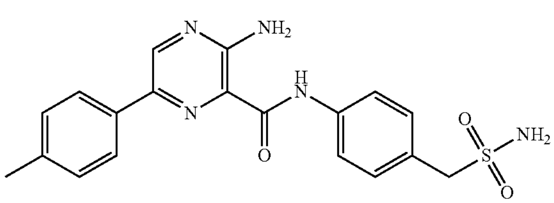 [SMILES: Cc1ccc(-c2cnc(N)c(C(=O)Nc3ccc(CS(N)(=O)=O)cc3)n2)cc1] | SU20668-0331 | C | nd | 397.45 |

TABLE 1-continued

Biologicial Data for select APA Analogs

| STRUCTURE | Compound # | LKB1 % Act. Increase | Cell Activity | MW |
|---|---|---|---|---|
| 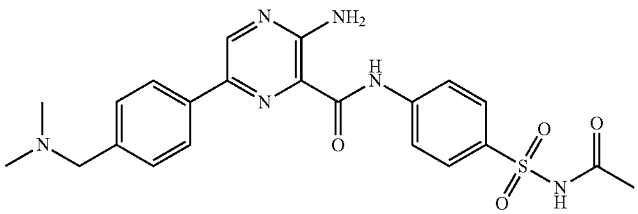 [SMILES: CC(=O)NS(=O)(=O)c1ccc(NC(=O)c2nc(-c3ccc(CN(C)C)cc3)cnc2N)cc1] | SU20668-0339 | C | nd | 468.53 |
| 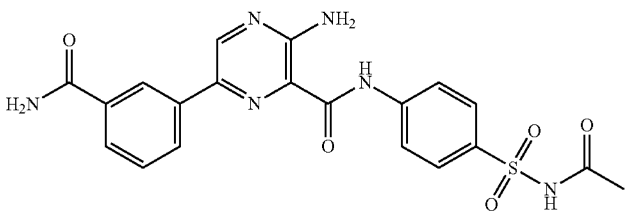 [SMILES: CC(=O)NS(=O)(=O)c1ccc(NC(=O)c2nc(-c3cccc(C(N)=O)c3)cnc2N)cc1] | SU20668-0341 | D | nd | 454.46 |
| 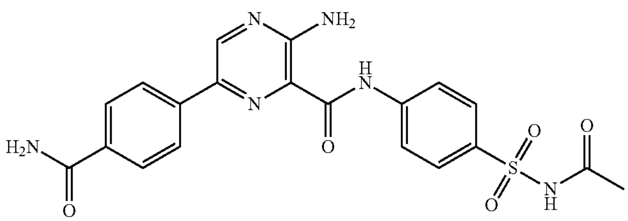 [SMILES: CC(=O)NS(=O)(=O)c1ccc(NC(=O)c2nc(-c3ccc(C(N)=O)cc3)cnc2N)cc1] | SU20668-0342 | D | nd | 454.46 |
| 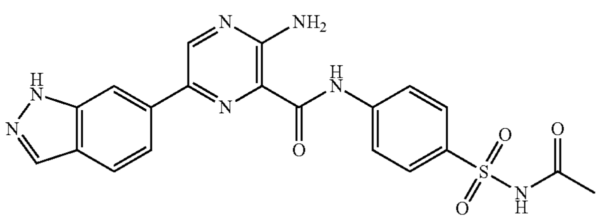 [SMILES: CC(=O)NS(=O)(=O)c1ccc(NC(=O)c2nc(-c3ccc4cn[nH]c4c3)cnc2N)cc1] | SU20668-0343 | C | E | 451.46 |
| 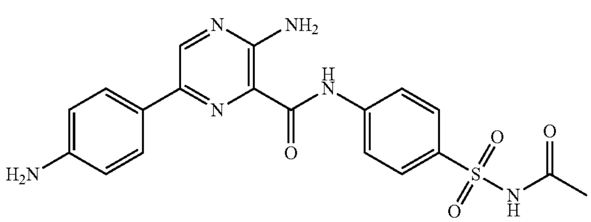 [SMILES: CC(=O)NS(=O)(=O)c1ccc(NC(=O)c2nc(-c3ccc(N)cc3)cnc2N)cc1] | SU20668-0344 | C | nd | 426.45 |
| 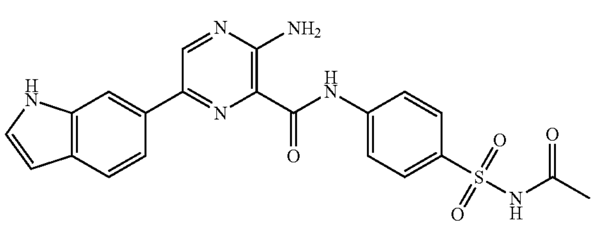 [SMILES: CC(=O)NS(=O)(=O)c1ccc(NC(=O)c2nc(-c3ccc4cc[nH]c4c3)cnc2N)cc1] | SU20668-0345 | C | nd | 450.47 |
| 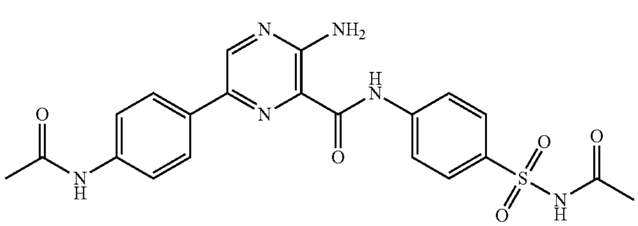 [SMILES: CC(=O)Nc1ccc(-c2cnc(N)c(C(=O)Nc3ccc(S(=O)(=O)NC(C)=O)cc3)n2)cc1] | SU20668-0346 | C | nd | 468.49 |

TABLE 1-continued

Biologicial Data for select APA Analogs

| STRUCTURE | Compound # | LKB1 % Act. Increase | Cell Activity | MW |
|---|---|---|---|---|
| 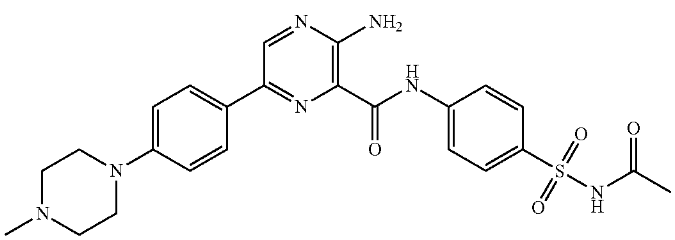 [SMILES: CC(=O)NS(=O)(=O)c1ccc(NC(=O)c2nc(-c3ccc(N4CCN(C)CC4)cc3)cnc2N)cc1] | SU20668-0347 | C | E | 509.58 |
| 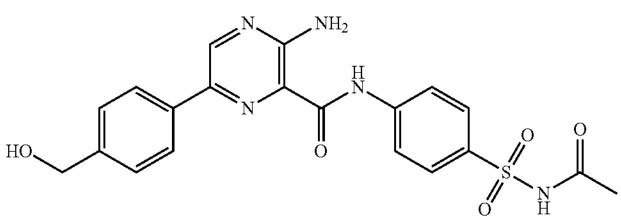 [SMILES: CC(=O)NS(=O)(=O)c1ccc(NC(=O)c2nc(-c3ccc(CO)cc3)cnc2N)cc1] | SU20668-0348 | C | nd | 441.46 |
| 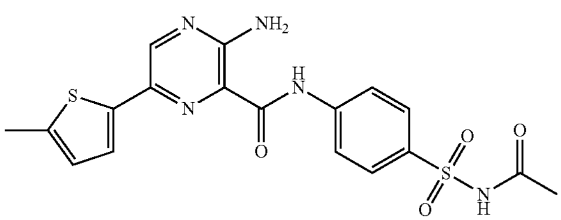 [SMILES: CC(=O)NS(=O)(=O)c1ccc(NC(=O)c2nc(-c3ccc(C)s3)cnc2N)cc1] | SU20668-0349 | C | II | 431.49 |
| 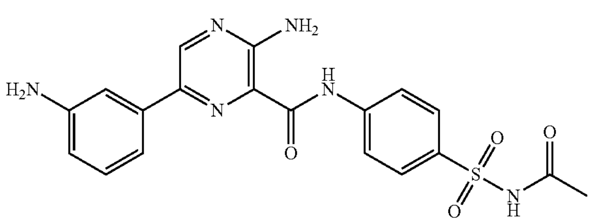 [SMILES: CC(=O)NS(=O)(=O)c1ccc(NC(=O)c2nc(-c3cccc(N)c3)cnc2N)cc1] | SU20668-0350 | D | nd | 426.45 |
| 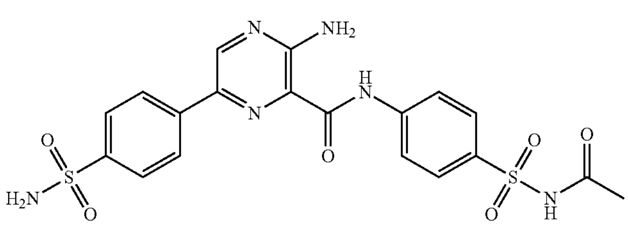 [SMILES: CC(=O)NS(=O)(=O)c1ccc(NC(=O)c2nc(-c3ccc(S(N)(=O)=O)cc3)cnc2N)cc1] | SU20668-0351 | C | nd | 490.51 |
| 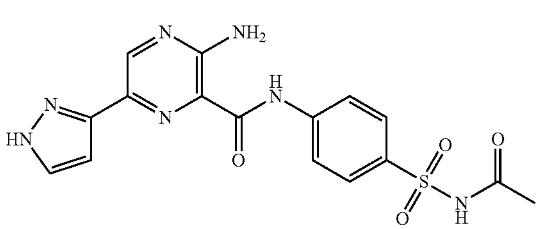 [SMILES: CC(=O)NS(=O)(=O)c1ccc(NC(=O)c2nc(-c3cc[nH]n3)cnc2N)cc1] | SU20668-0352 | C | nd | 401.4 |

TABLE 1-continued

Biologicial Data for select APA Analogs

| STRUCTURE | Compound # | LKB1 % Act. Increase | Cell Activity | MW |
|---|---|---|---|---|
| 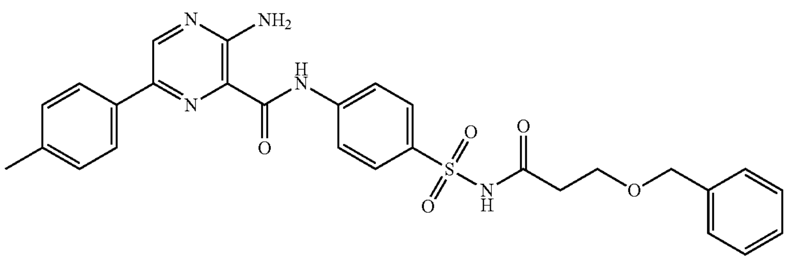 [SMILES: Cc1ccc(-c2cnc(N)c(C(=O)Nc3ccc(S(=O)(=O)NC(=O)CCOCc4ccccc4)cc3)n2)cc1] | SU20668-0368 | D | nd | 545.61 |
| 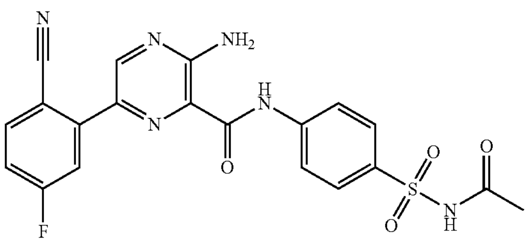 [SMILES: CC(=O)NS(=O)(=O)c1ccc(NC(=O)c2nc(-c3cc(F)ccc3C#N)cnc2N)cc1] | SU20668-0371 | A | II | 454.43 |
| 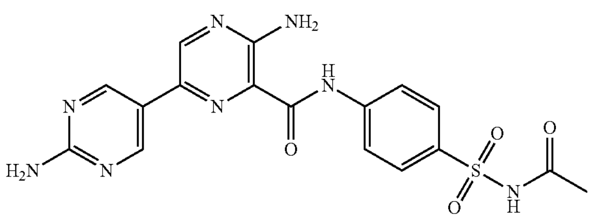 [SMILES: CC(=O)NS(=O)(=O)c1ccc(NC(=O)c2nc(-c3cnc(N)nc3)cnc2N)cc1] | SU20668-0372 | D | nd | 428.43 |
| 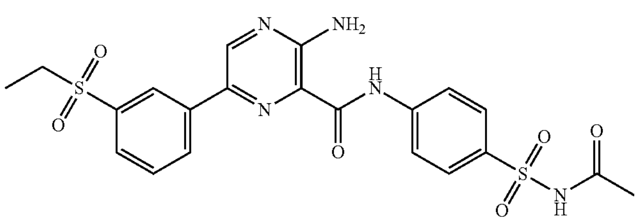 [SMILES: CCS(=O)(=O)c1cccc(-c2cnc(N)c(C(=O)Nc3ccc(S(=O)(=O)NC(C)=O)cc3)n2)c1] | SU20668-0373 | C | nd | 503.55 |
| 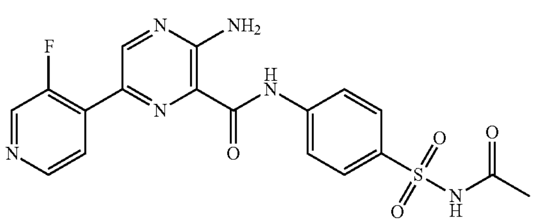 [SMILES: CC(=O)NS(=O)(=O)c1ccc(NC(=O)c2nc(-c3ccncc3F)cnc2N)cc1] | SU20668-0374 | C | nd | 430.41 |
| 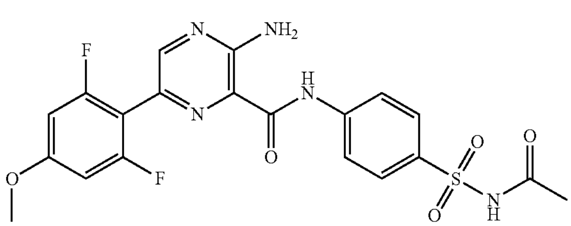 [SMILES: COc1cc(F)c(-c2cnc(N)c(C(=O)Nc3ccc(S(=O)(=O)NC(C)=O)cc3)n2)c(F)c1] | SU20668-0375 | D | nd | 477.44 |

TABLE 1-continued

Biologicial Data for select APA Analogs

| STRUCTURE | Compound # | LKB1 % Act. Increase | Cell Activity | MW |
|---|---|---|---|---|
| (structure) | SU20668-0376 | C | nd | 467.52 |
| (structure) | SU20668-0377 | D | nd | 496.54 |
| (structure) | SU20668-0390 | D | nd | 443.45 |
| (structure) | SU20668-0391 | D | nd | 445.88 |
| (structure) | SU20668-0392 | D | nd | 495.43 |
| (structure) | SU20668-0446 | D | nd | 519.44 |

TABLE 1-continued

Biological Data for select APA Analogs

| STRUCTURE | Compound # | LKB1 % Act. Increase | Cell Activity | MW |
|---|---|---|---|---|
| 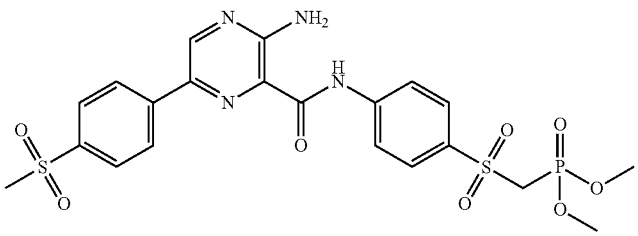 | SU20668-0447 | D | nd | 554.53 |
| 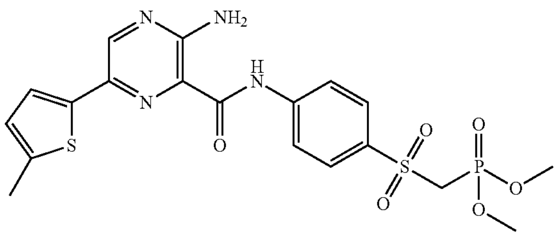 [SMILES: COP(=O)(CS(=O)(=O)c1ccc(NC(=O)c2nc(-c3ccc(C)s3)cnc2N)cc1)OC] | SU20668-0448 | C | nd | 496.5 |
| 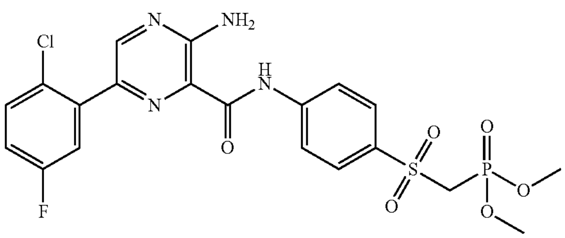 [SMILES: COP(=O)(CS(=O)(=O)c1ccc(NC(=O)c2nc(-c3cc(F)ccc3Cl)cnc2N)cc1)OC] | SU20668-0449 | C | nd | 528.88 |
| 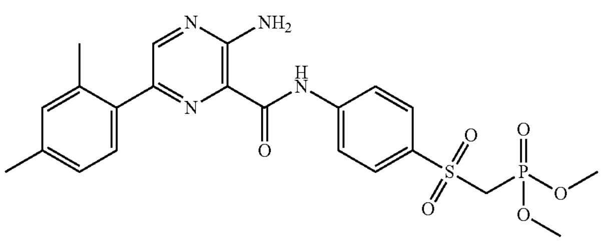 | SU20668-0450 | D | nd | 504.5 |
| 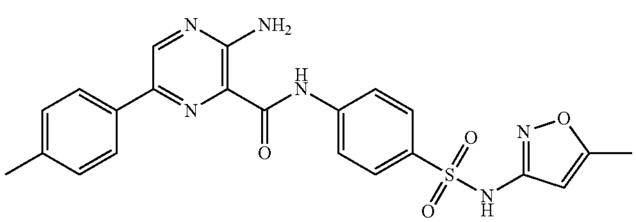 | SU20668-0467 | C | nd | 464.5 |
| 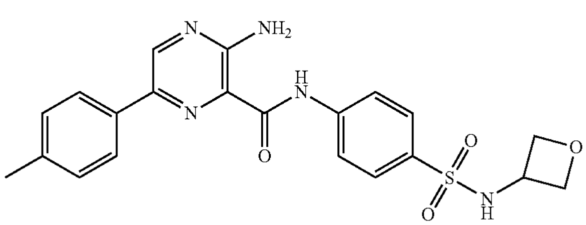 [SMILES: Cc1ccc(-c2cnc(N)c(C(=O)Nc3ccc(S(=O)(=O)NC4COC4)cc3)n2)cc1] | SU20668-0468 | C | I | 439.49 |

TABLE 1-continued

Biologicial Data for select APA Analogs

| STRUCTURE | Compound # | LKB1 % Act. Increase | Cell Activity | MW |
|---|---|---|---|---|
| 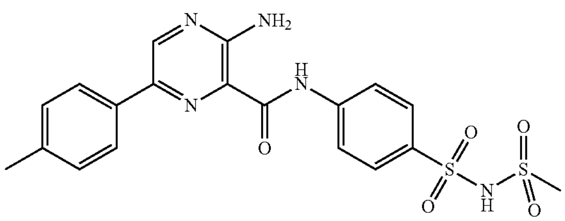 | SU20668-0470 | D | nd | 461.51 |
| 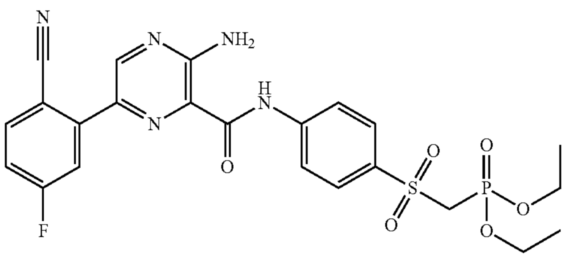 [SMILES: CCOP(=O)(CS(=O)(=O)c1ccc(NC(=O)c2nc(-c3cc(F)ccc3C#N)cnc2N)cc1)OCC] | SU20668-0471 | D | nd | 547.5 |
| 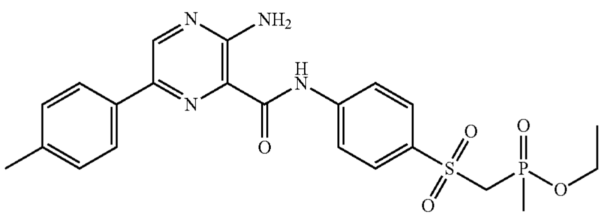 [SMILES: CCOP(C)(=O)CS(=O)(=O)c1ccc(NC(=O)c2nc(-c3ccc(C)cc3)cnc2N)cc1] | SU20668-0472 | A | I | 488.5 |
| 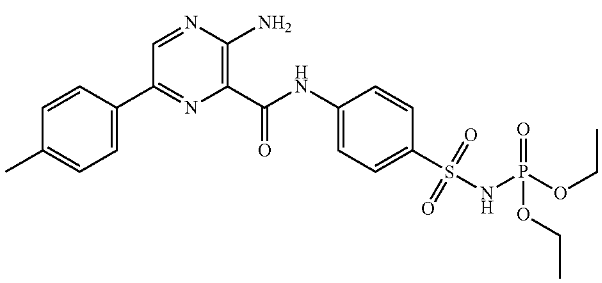 [SMILES: CCOP(=O)(NS(=O)(=O)c1ccc(NC(=O)c2nc(-c3ccc(C)cc3)cnc2N)cc1)OCC] | SU20668-0475 | B | nd | 519.51 |
| 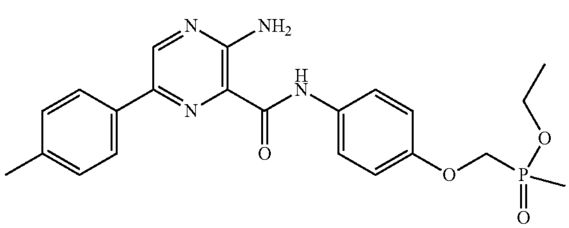 | SU20668-0476 | D | nd | 440.43 |
| 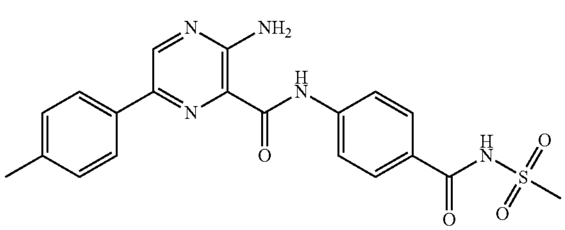 | SU20668-0478 | D | nd | 425.46 |

TABLE 1-continued
Biologicial Data for select APA Analogs
| STRUCTURE | Compound # | LKB1 % Act. Increase | Cell Activity | MW |
|---|---|---|---|---|
| 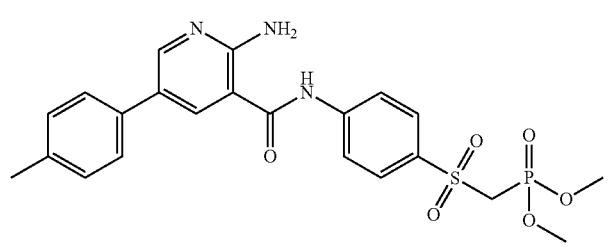 | SU20668-0479 | | nd | 489.48 |
| 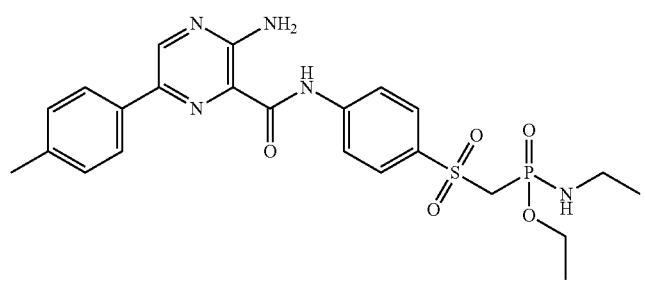 [SMILES: CCNP(=O)(CS(=O)(=O)c1ccc(NC(=O)c2nc(-c3ccc(C)cc3)cnc2N)cc1)OCC] | SU20668-0480 | D | nd | 517.54 |
| 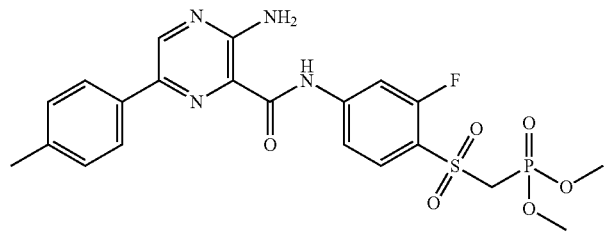 | SU20668-0481 | | nd | 508.46 |
| 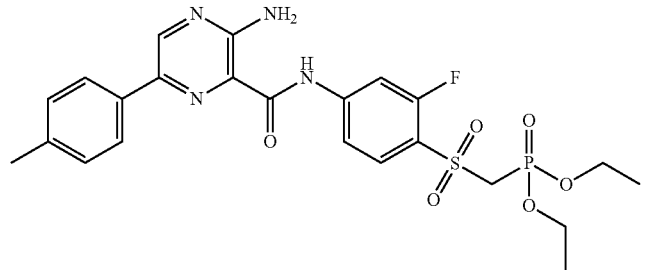 [SMILES: CCOP(=O)(CS(=O)(=O)c1ccc(NC(=O)c2nc(-c3ccc(C)cc3)cnc2N)cc1F)OCC] | SU20668-0482 | D | nd | 536.51 |
| 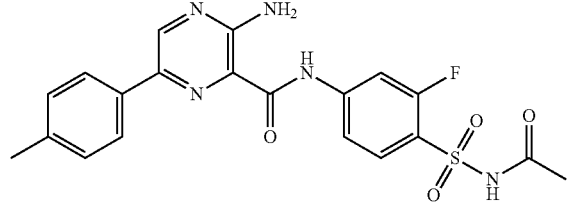 [SMILES: CC(=O)NS(=O)(=O)c1ccc(NC(=O)c2nc(-c3ccc(C)cc3)cnc2N)cc1F] | SU20668-0483 | D | nd | 443.45 |

TABLE 1-continued

Biological Data for select APA Analogs

| STRUCTURE | Compound # | LKB1 % Act. Increase | Cell Activity | MW |
|---|---|---|---|---|
| 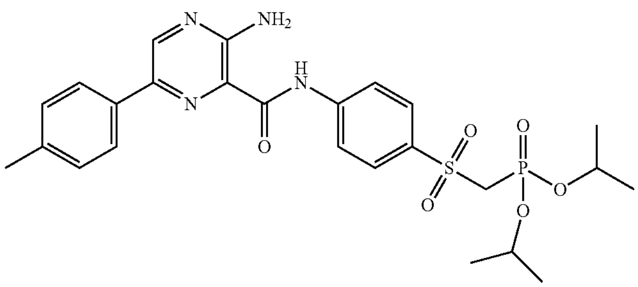 [SMILES: Cc1ccc(-c2cnc(N)c(C(=O)Nc3ccc(S(=O)(=O)CP(=O)(OC(C)C)OC(C)C)cc3)n2)cc1] | SU20668-0484 | D | nd | 546.58 |
| | SU20668-0485 C | C | I | 536.51 |
| | SU20668-0485 B | B | nd | 536.51 |
| 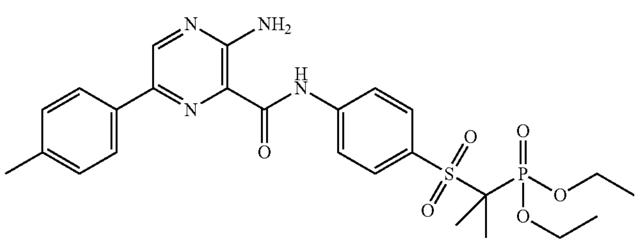 [SMILES: CCOP(=O)(OCC)C(C)(C)S(=O)(=O)c1ccc(NC(=O)c2nc(-c3ccc(C)cc3)cnc2N)cc1] | SU20668-0486 | B | nd | 546.58 |
| 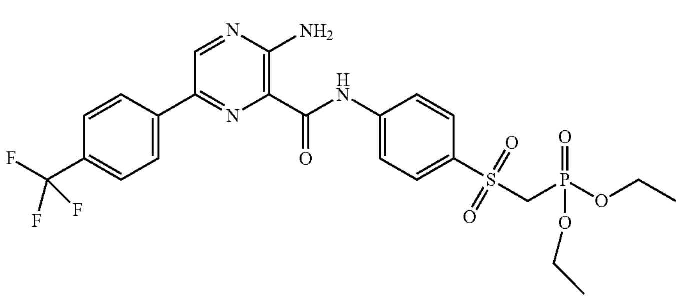 [SMILES: CCOP(=O)(CS(=O)(=O)c1ccc(NC(=O)c2nc(-c3ccc(C(F)(F)F)cc3)cnc2N)cc1)OCC] | SU20668-0488 | D | nd | 572.49 |

TABLE 1-continued

Biologicial Data for select APA Analogs

| STRUCTURE | Compound # | LKB1 % Act. Increase | Cell Activity | MW |
|---|---|---|---|---|
| 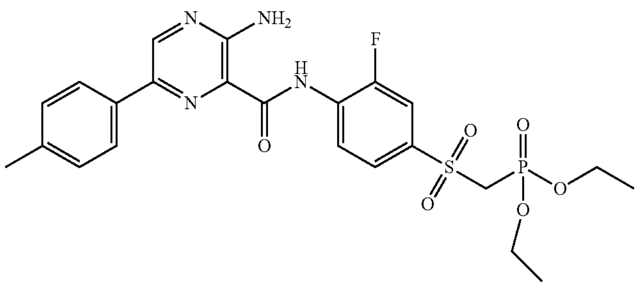 [SMILES: CCOP(=O)(CS(=O)(=O)c1ccc(NC(=O)c2nc(-c3ccc(C)cc3)cnc2N)c(F)c1)OCC] | SU20668-0489 | | nd | 536.51 |
| 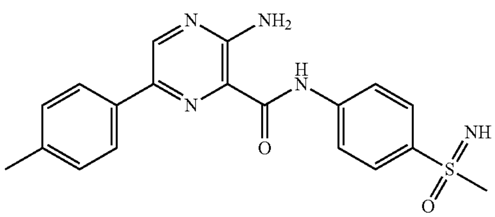 | SU20668-0490 | C | nd | 381.45 |
| 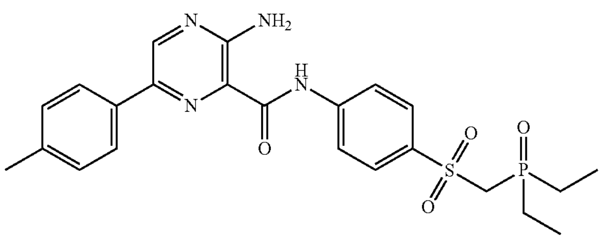 [SMILES: CCP(=O)(CC)CS(=O)(=O)c1ccc(NC(=O)c2nc(-c3ccc(C)cc3)cnc2N)cc1] | SU20668-0491 | B | nd | 486.52 |
| 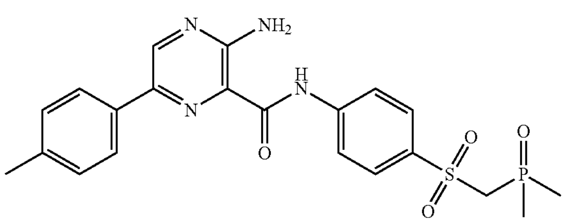 | SU20668-0492 | B | nd | 458.47 |
| 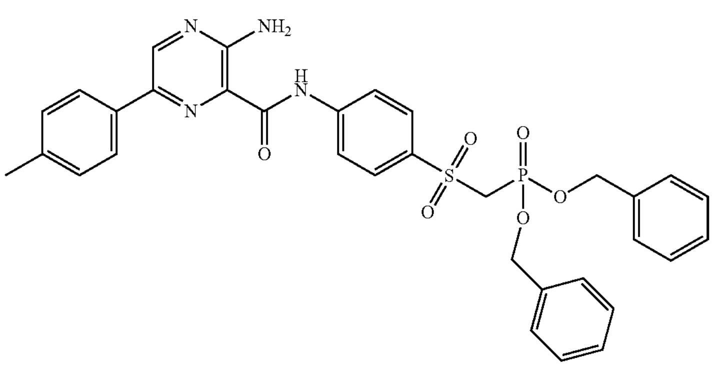 [SMILES: Cc1ccc(-c2cnc(N)c(C(=O)Nc3ccc(S(=O)(=O)CP(=O)(OCc4ccccc4)OCc4ccccc4)cc3)n2)cc1] | SU20668-0493 | nd | nd | 642.66 |

TABLE 1-continued

Biologicial Data for select APA Analogs

| STRUCTURE | Compound # | LKB1 % Act. Increase | Cell Activity | MW |
|---|---|---|---|---|
| 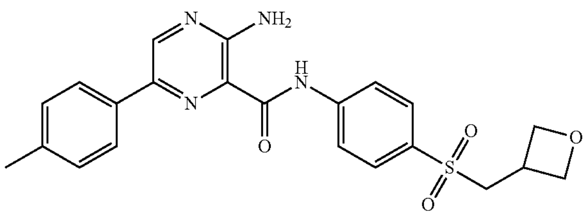 [SMILES: Cc1ccc(-c2cnc(N)c(C(=O)Nc3ccc(S(=O)(=O)CC4COC4)cc3)n2)cc1] | SU20668-0494 | A | I | 438.5 |
| 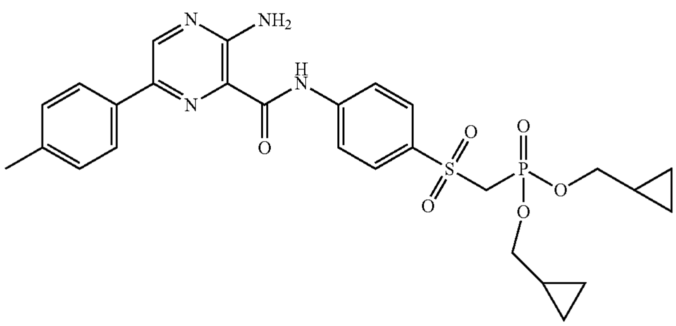 [SMILES: Cc1ccc(-c2cnc(N)c(C(=O)Nc3ccc(S(=O)(=O)CP(=O)(OCC4CC4)OCC4CC4)cc3)n2)cc1] | SU20668-0495 | | nd | 570.6 |
| 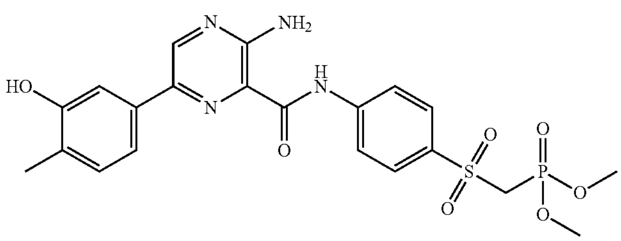 | SU20668-0496 | C | nd | 506.47 |
| 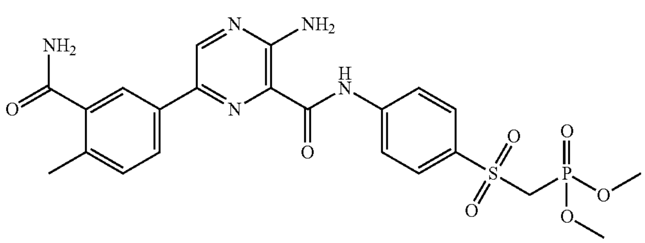 [SMILES: COP(=O)(CS(=O)(=O)c1ccc(NC(=O)c2nc(-c3ccc(C)c(C(N)=O)c3)cnc2N)cc1)OC] | SU20668-0497 | | nd | 533.49 |
| 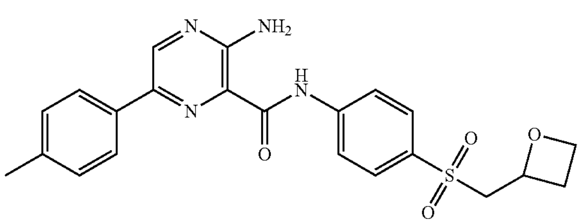 [SMILES: Cc1ccc(-c2cnc(N)c(C(=O)Nc3ccc(S(=O)(=O)CC4CCO4)cc3)n2)cc1] | SU20668-0500 | B | nd | 438.5 |
| 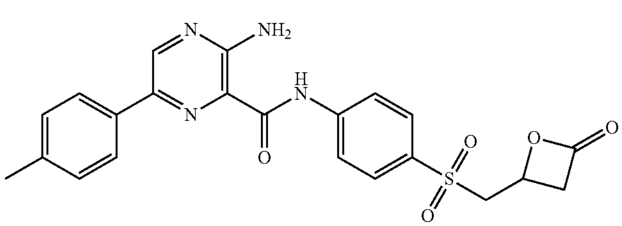 [SMILES: Cc1ccc(-c2cnc(N)c(C(=O)Nc3ccc(S(=O)(=O)CC4CC(=O)O4)cc3)n2)cc1] | SU20668-0501 | | nd | 452.48 |

TABLE 1-continued

Biologicial Data for select APA Analogs

| STRUCTURE | Compound # | LKB1 % Act. Increase | Cell Activity | MW |
|---|---|---|---|---|
| 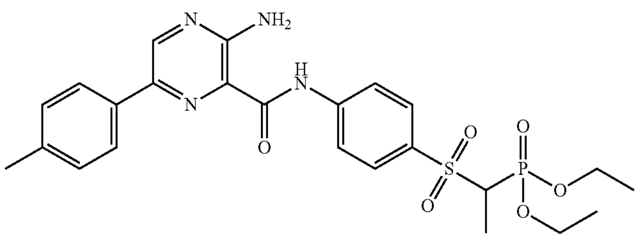 [SMILES: CCOP(=O)(OCC)C(C)S(=O)(=O)c1ccc(NC(=O)c2nc(-c3ccc(C)cc3)cnc2N)cc1] | SU20668-0505 | A | nd | 532.55 |
| 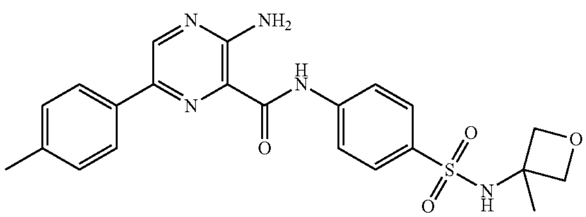 [SMILES: Cc1ccc(-c2cnc(N)c(C(=O)Nc3ccc(S(=O)(=O)NC4(C)COC4)cc3)n2)cc1] | SU20668-0510 | B | nd | 453.51 |
| 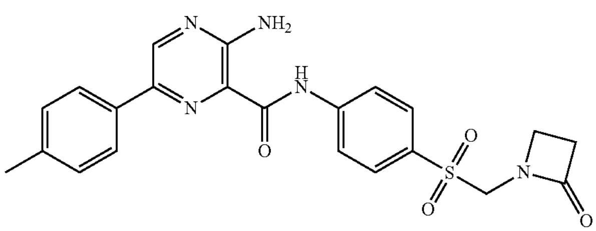 [SMILES: Cc1ccc(-c2cnc(N)c(C(=O)Nc3ccc(S(=O)(=O)CN4CCC4=O)cc3)n2)cc1] | SU20668-0512 | | nd | 451.5 |
| 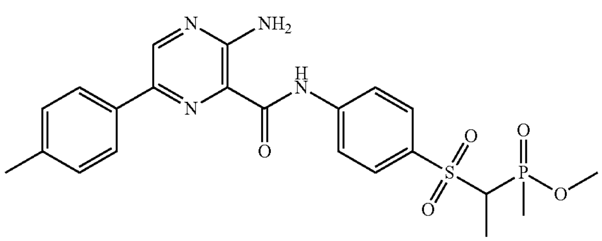 | SU20668-0513 | | nd | 488.5 |
| 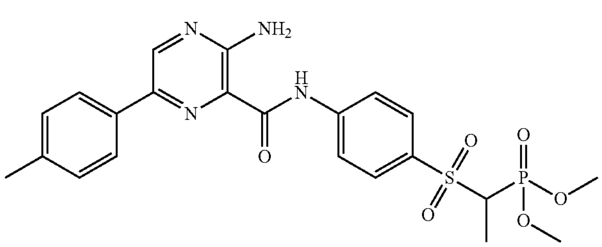 | SU20668-0516 | A | nd | 504.5 |
| 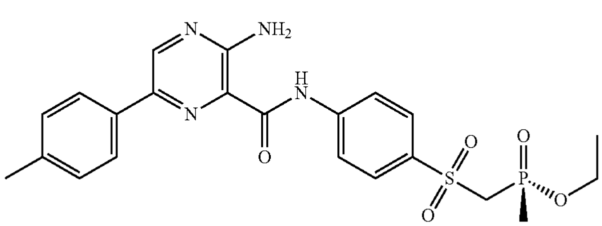 [SMILES: CCO[P@@](C)(=O)CS(=O)(=O)c1ccc(NC(=O)c2nc(-c3ccc(C)cc3)cnc2N)cc1] | SU20668-0517 | B | nd | 488.5 |

TABLE 1-continued

Biologicial Data for select APA Analogs

| STRUCTURE | Compound # | LKB1 % Act. Increase | Cell Activity | MW |
|---|---|---|---|---|
| 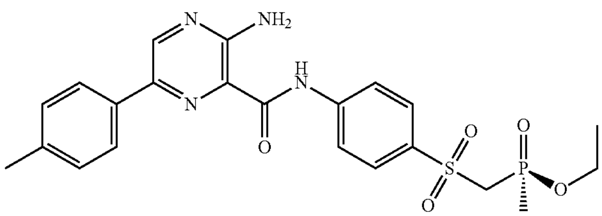 [SMILES: CCO[P@](C)(=O)CS(=O)(=O)c1ccc(NC(=O)c2nc(-c3ccc(C)cc3)cnc2N)cc1] | SU20668-0518 | B | nd | 488.5 |
| 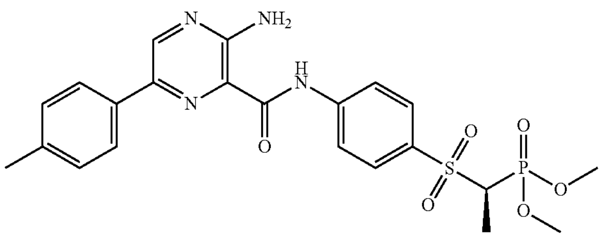 | SU20668-0525 | | nd | 504.5 |
| 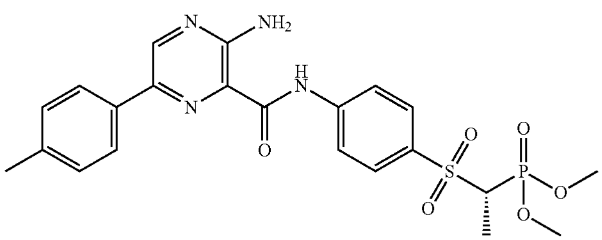 | SU20668-0526 | | nd | 504.5 |
| 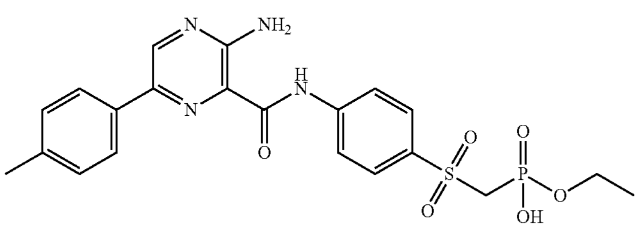 [SMILES: CCOP(=O)(O)CS(=O)(=O)c1ccc(NC(=O)c2nc(-c3ccc(C)cc3)cnc2N)cc1] | SU20668-0338 | D | nd | 490.47 |
| 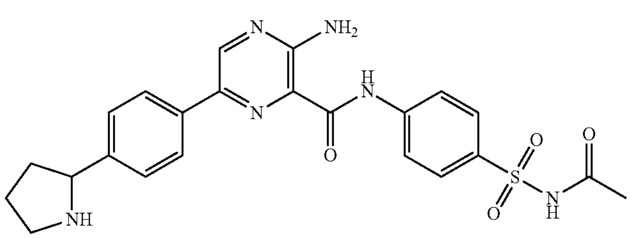 [SMILES: CC(=O)NS(=O)(=O)c1ccc(NC(=O)c2nc(-c3ccc(C4CCCN4)cc3)cnc2N)cc1] | SU20668-0340 | D | nd | 480.54 |
| 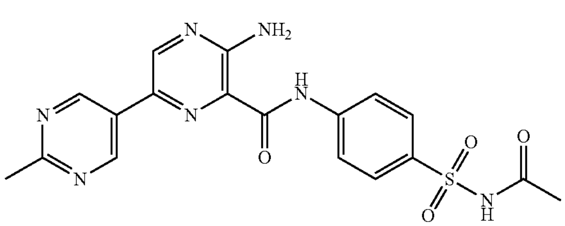 [SMILES: CC(=O)NS(=O)(=O)c1ccc(NC(=O)c2nc(-c3cnc(C)nc3)cnc2N)cc1] | SU20668-0369 | C | nd | 427.44 |

TABLE 1-continued

Biologicial Data for select APA Analogs

| STRUCTURE | Compound # | LKB1 % Act. Increase | Cell Activity | MW |
|---|---|---|---|---|
| 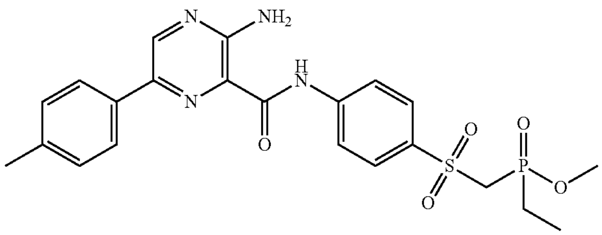 | SU20668-0514 | B | | 588.5 |
| 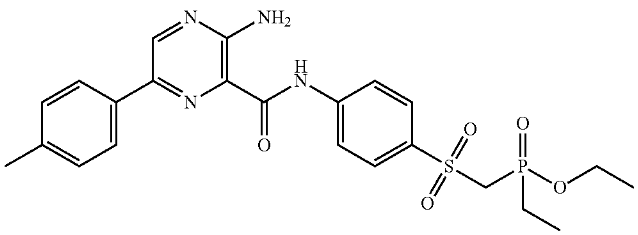 [SMILES: CCOP(=O)(CC)CS(=O)(=O)c1ccc(NC(=O)c2nc(-c3ccc(C)cc3)cnc2N)cc1] | SU20668-0515 | B | I | 502.53 |
| 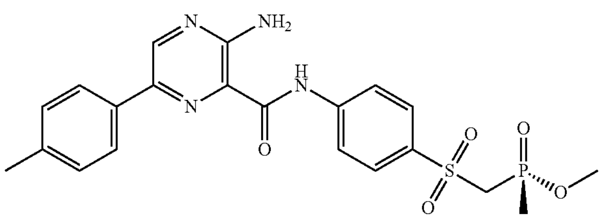 | SU20668-0519 | A | I | 474.47 |
| 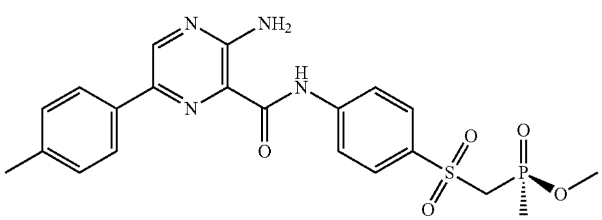 | SU20668-0520 | A | I | 474.47 |
| 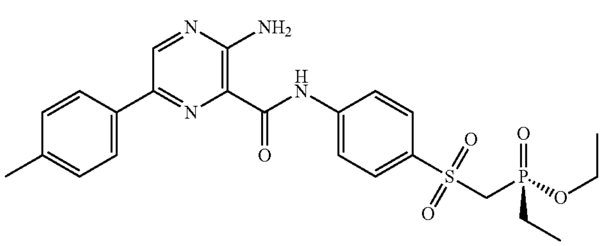 [SMILES: CCO[P@](=O)(CC)CS(=O)(=O)c1ccc(NC(=O)c2nc(-c3ccc(C)cc3)cnc2N)cc1] | SU20668-0521 | A | I | 502.53 |
| 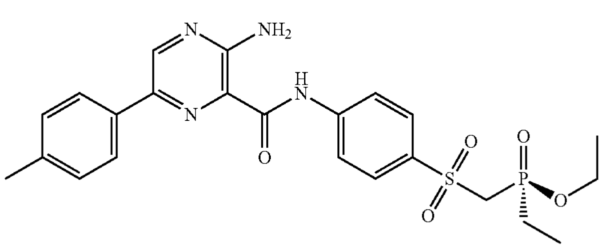 [SMILES: CCO[P@@](=O)(CC)CS(=O)(=O)c1ccc(NC(=O)c2nc(-c3ccc(C)cc3)cnc2N)cc1] | SU20668-0522 | B | I | 502.53 |

For in vitro LKB1 functional activity, the % activity increase is defined as follows: A=>4000%, B=399-2000%, C=199-1000%, and D=<1000%. Blank cells mean the compound has not been tested. For cell activity (CTG antiproliferation in most sensitive cancer cell line), the $IC_{50}$ is defined as follows: I=<3 uM II=3-50 uM, and III=>50 uM.

Example 4: Biological Data for PYP Series

TABLE 2

Biologicial Data for select PYP Analogs

| Structure | Compound # | LKB1 % Act. Increase | MW |
|---|---|---|---|
| 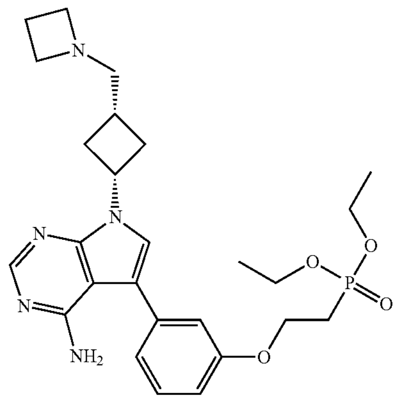 [SMILES: CCOP(=O)(CCOc1cccc(-c2cn([C@H]3C[C@@H](CN4CCC4)C3)c3ncnc(N)c23)c1)OCC] | SU20668-0315 | C | 513.6 |
| 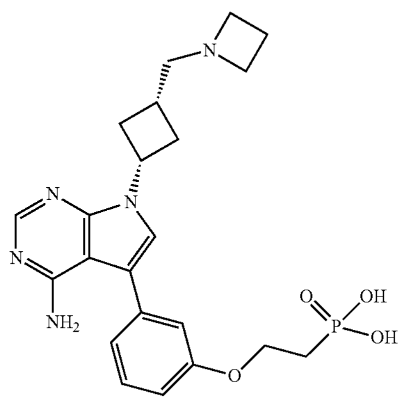 [SMILES: Nc1ncnc2c1c(-c1cccc(OCCP(=O)(O)O)c1)cn2[C@H]1C[C@@H](CN2CCC2)C1] | SU20668-0264 | D | 457.5 |
| 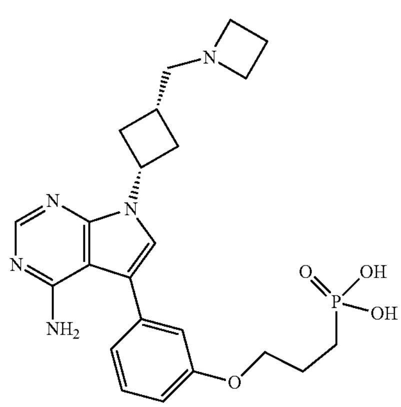 [SMILES: Nc1ncnc2c1c(-c1cccc(OCCCP(=O)(O)O)c1)cn2[C@H]1C[C@@H](CN2CCC2)C1] | SU20668-0265 | D | 471.5 |

TABLE 2-continued

Biologicial Data for select PYP Analogs

| Structure | Compound # | LKB1 % Act. Increase | MW |
|---|---|---|---|
| 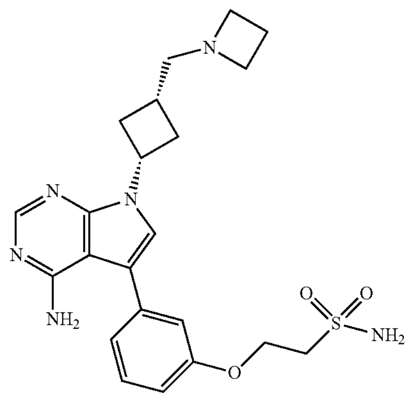 [SMILES: Nc1ncnc2c1c(-c1cccc(OCCS(N)(=O)=O)c1)cn2[C@H]1C[C@@H](CN2CCC2)C1] | SU20668-0266 | C | 456.6 |
| 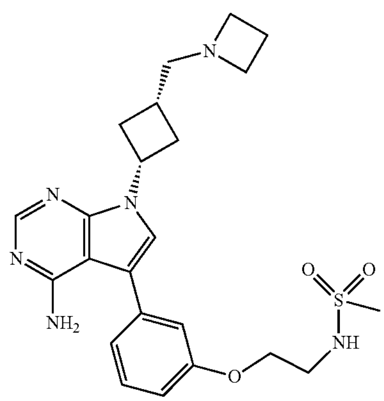 [SMILES: CS(=O)(=O)NCCOc1cccc(-c2cn([C@H]3C[C@@H](CN4CCC4)C3)c3ncnc(N)c23)c1] | SU20668-0267 | C | 470.6 |
| 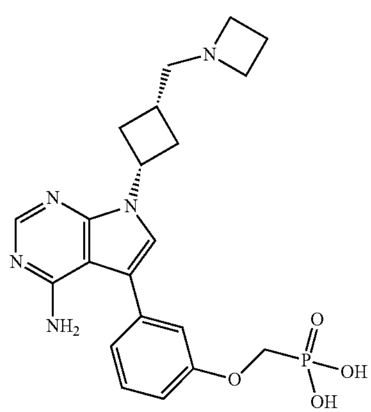 [SMILES: Nc1ncnc2c1c(-c1cccc(OCP(=O)(O)O)c1)cn2[C@H]1C[C@@H](CN2CCC2)C1] | SU20668-0273 | C | 443.4 |

TABLE 2-continued

Biologicial Data for select PYP Analogs

| Structure | Compound # | LKB1 % Act. Increase | MW |
|---|---|---|---|
| 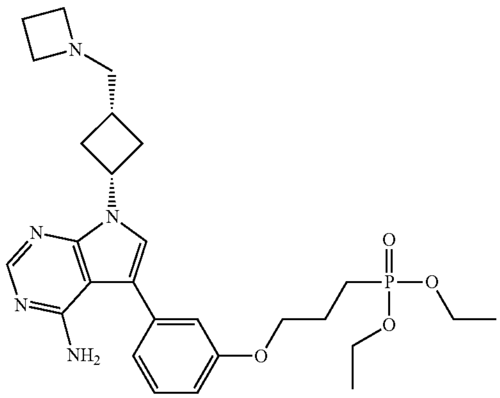 [SMILES: CCOP(=O)(CCCOc1cccc(-c2cn([C@H]3C[C@@H](CN4CCC4)C3)c3ncnc(N)c23)c1)OCC] | SU20668-0316 | C | 527.6 |
| 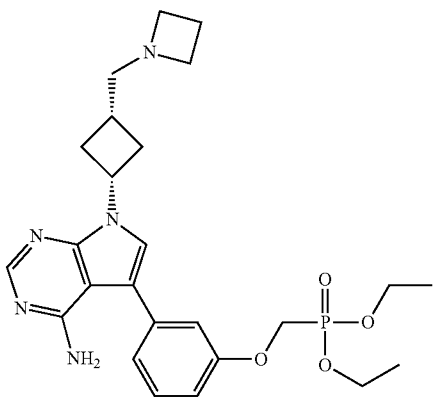 | SU20668-0323 | A | 499.6 |
| 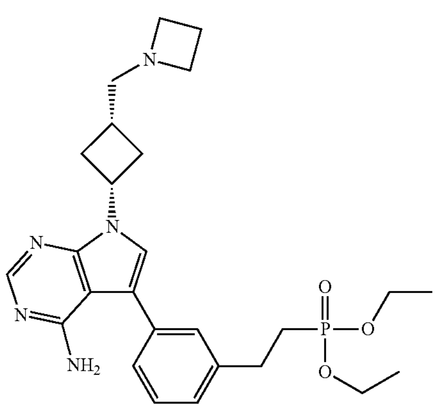 [SMILES: CCOP(=O)(CCc1cccc(-c2cn([C@H]3C[C@@H](CN4CCC4)C3)c3ncnc(N)c23)c1)OCC] | SU20668-0355 | B | 497.6 |

TABLE 2-continued
Biologicial Data for select PYP Analogs
| Structure | Compound # | LKB1 % Act. Increase | MW |
|---|---|---|---|
| 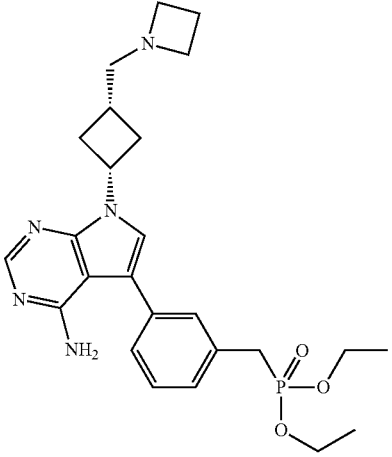 [SMILES: CCOP(=O)(Cc1cccc(-c2cn([C@H]3C[C@@H](CN4CCC4)C3)c3ncnc(N)c23)c1)OCC] | SU20668-0356 | B | 483.6 |
| 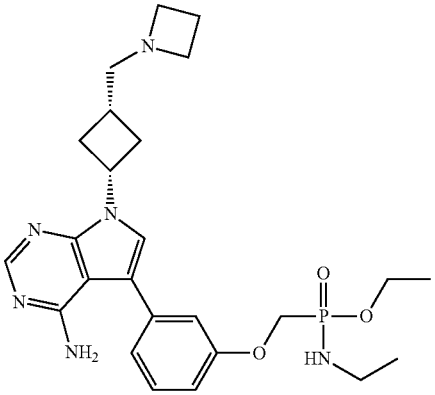 [SMILES: CCNP(=O)(COc1cccc(-c2cn([C@H]3C[C@@H](CN4CCC4)C3)c3ncnc(N)c23)c1)OCC] | SU20668-0357 | B | 498.6 |
| 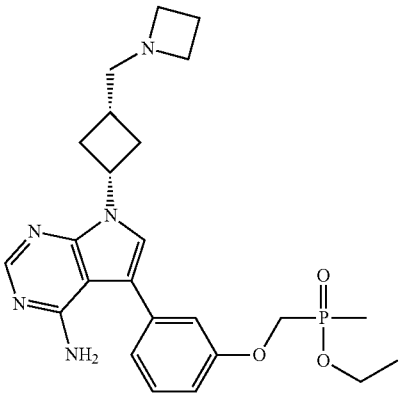 [SMILES: CCOP(C)(=O)COc1cccc(-c2cn([C@H]3C[C@@H](CN4CCC4)C3)c3ncnc(N)c23)c1] | SU20668-0358 | A | 469.5 |

TABLE 2-continued
Biologicial Data for select PYP Analogs
| Structure | Compound # | LKB1 % Act. Increase | MW |
|---|---|---|---|
| 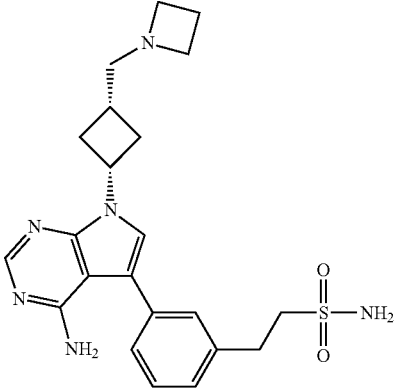 [SMILES: Nc1ncnc2c1c(-c1cccc(CCS(N)(=O)=O)c1)cn2[C@H]1C[C@@H](CN2CCC2)C1] | SU20668-0359 | C | 440.6 |
| 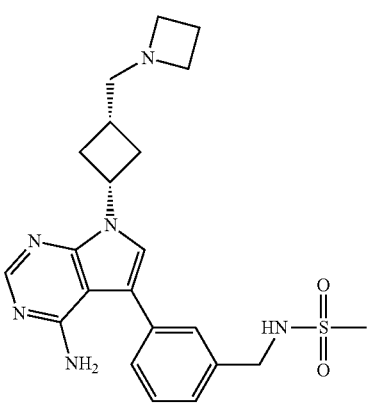 [SMILES: CS(=O)(=O)NCc1cccc(-c2cn([C@H]3C[C@@H](CN4CCC4)C3)c3ncnc(N)c23)c1] | SU20668-0360 | A | 440.6 |
| 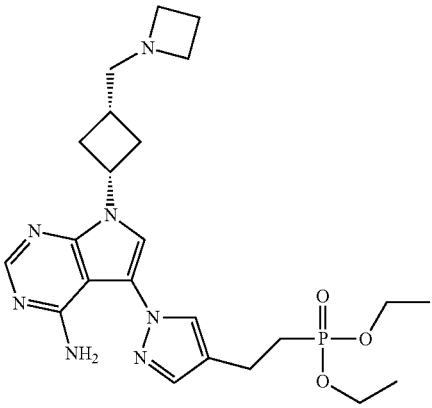 [SMILES: CCOP(=O)(CCc1cnn(-c2cn([C@H]3C[C@@H](CN4CCC4)C3)c3ncnc(N)c23)c1)OCC] | SU20668-0361 | B | 487.5 |

TABLE 2-continued

Biological Data for select PYP Analogs

| Structure | Compound # | LKB1 % Act. Increase | MW |
|---|---|---|---|
| 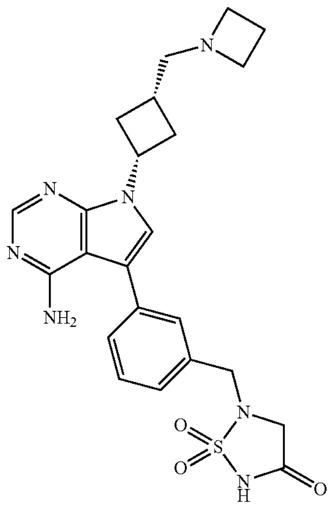 [SMILES: Nc1ncnc2c1c(-c1cccc(CN3CC(=O)NS3(=O)=O)c1)cn2[C@H]1C[C@@H](CN2CCC2)C1] | SU20668-0365 | C | 481.6 |
| 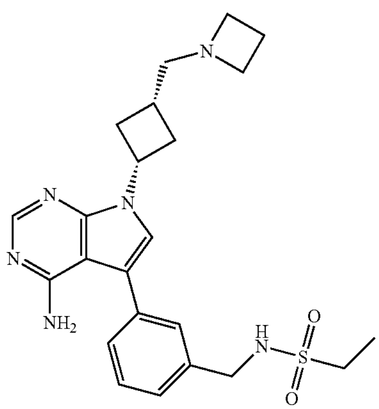 [SMILES: CCS(=O)(=O)NCc1cccc(-c2cn([C@H]3C[C@@H](CN4CCC4)C3)c3ncnc(N)c23)c1] | SU20668-0380 | C | 454.6 |
| 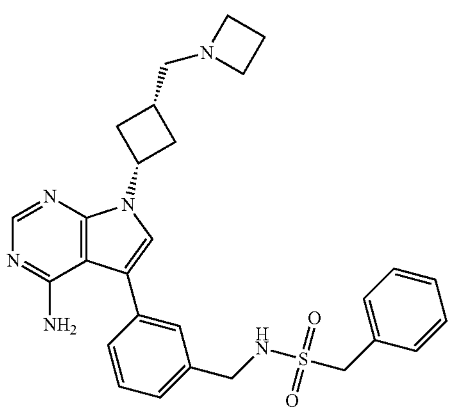 [SMILES: Nc1ncnc2c1c(-c1cccc(CNS(=O)(=O)Cc3ccccc3)c1)cn2[C@H]1C[C@@H](CN2CCC2)C1] | SU20668-0382 | D | 516.7 |

TABLE 2-continued

Biologicial Data for select PYP Analogs

| Structure | Compound # | LKB1 % Act. Increase | MW |
|---|---|---|---|
| 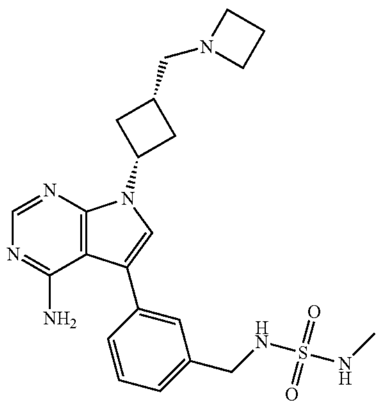 [SMILES: CNS(=O)(=O)NCc1cccc(-c2cn([C@H]3C[C@@H](CN4CCC4)C3)c3ncnc(N)c23)c1] | SU20668-0383 | C | 455.6 |
| 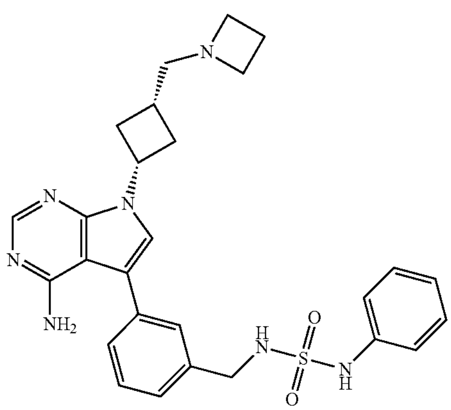 [SMILES: Nc1ncnc2c1c(-c1cccc(CNS(=O)(=O)Nc3ccccc3)c1)cn2[C@H]1C[C@@H](CN2CCC2)C1] | SU20668-0384 | D | 517.7 |
| 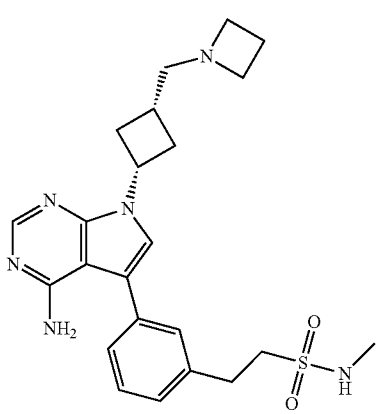 [SMILES: CNS(=O)(=O)CCc1cccc(-c2cn([C@H]3C[C@@H](CN4CCC4)C3)c3ncnc(N)c23)c1] | SU20668-0385 | B | 454.6 |

TABLE 2-continued

Biologicial Data for select PYP Analogs

| Structure | Compound # | LKB1 % Act. Increase | MW |
|---|---|---|---|
| 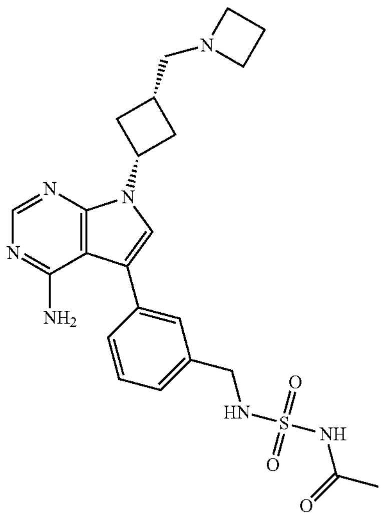 [SMILES: CC(=O)NS(=O)(=O)NCc1cccc(-c2cn([C@H]3C[C@@H](CN4CCC4)C3)c3ncnc(N)c23)c1] | SU20668-0386 | C | 483.6 |
| 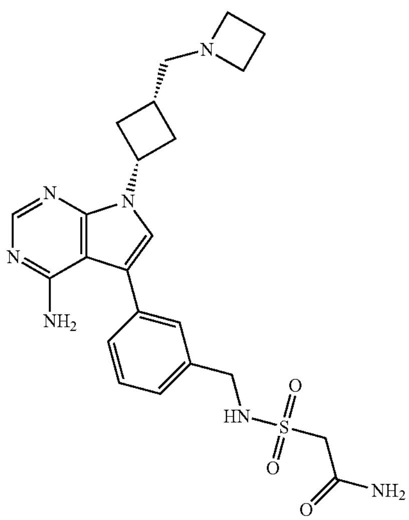 [SMILES: NC(=O)CS(=O)(=O)NCc1cccc(-c2cn([C@H]3C[C@@H](CN4CCC4)C3)c3ncnc(N)c23)c1] | SU20668-0387 | D | 483.6 |
| 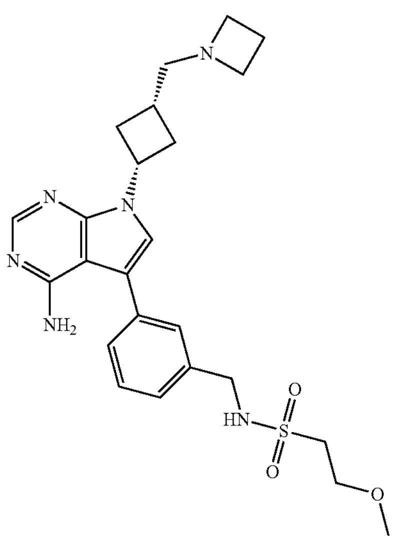 [SMILES: COCCS(=O)(=O)NCc1cccc(-c2cn([C@H]3C[C@@H](CN4CCC4)C3)c3ncnc(N)c23)c1] | SU20668-0388 | C | 484.6 |

TABLE 2-continued
Biologicial Data for select PYP Analogs
| Structure | Compound # | LKB1 % Act. Increase | MW |
|---|---|---|---|
| 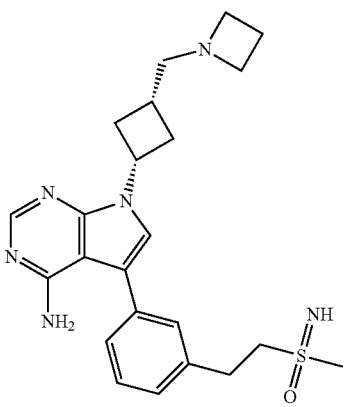 [SMILES: CS(=N)(=O)CCc1cccc(-c2cn([C@H]3C[C@@H](CN4CCC4)C3)c3ncnc(N)c23)c1] | SU20668-0389 | A | 438.6 |
| 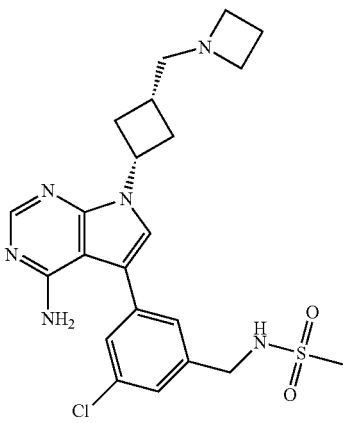 [SMILES: CS(=O)(=O)NCc1cc(Cl)cc(-c2cn([C@H]3C[C@@H](CN4CCC4)C3)c3ncnc(N)c23)c1] | SU20668-0397 | D | 475 |
| 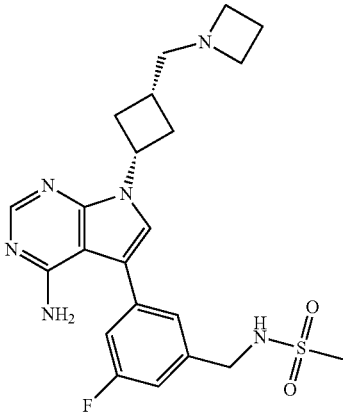 [SMILES: CS(=O)(=O)NCc1cc(F)cc(-c2cn([C@H]3C[C@@H](CN4CCC4)C3)c3ncnc(N)c23)c1] | SU20668-0398 | C | 458.6 |

TABLE 2-continued

Biologicial Data for select PYP Analogs

| Structure | Compound # | LKB1 % Act. Increase | MW |
|---|---|---|---|
| 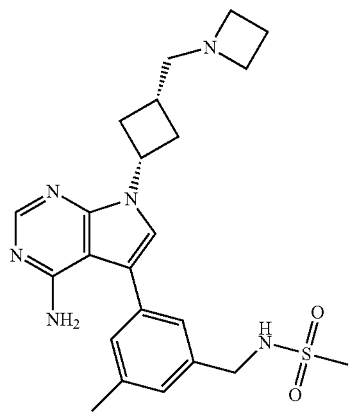 [SMILES: Cc1cc(CNS(C)(=O)=O)cc(-c2cn([C@H]3C[C@@H](CN4CCC4)C3)c3ncnc(N)c23)c1] | SU20668-0399 | B | 454.6 |
| 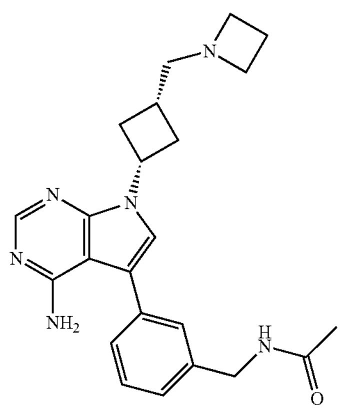 [SMILES: CC(=O)NCc1cccc(-c2cn([C@H]3C[C@@H](CN4CCC4)C3)c3ncnc(N)c23)c1] | SU20668-0400 | A | 404.5 |
| 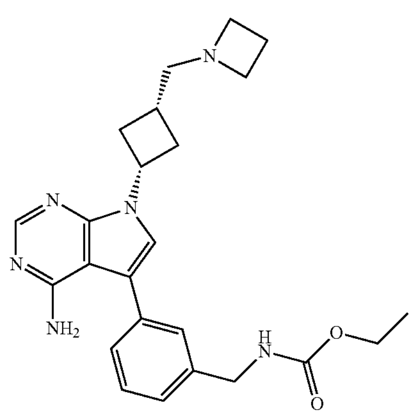 [SMILES: CCOC(=O)NCc1cccc(-c2cn([C@H]3C[C@@H](CN4CCC4)C3)c3ncnc(N)c23)c1] | SU20668-0401 | A | 434.5 |

TABLE 2-continued
Biologicial Data for select PYP Analogs
| Structure | Compound # | LKB1 % Act. Increase | MW |
|---|---|---|---|
| 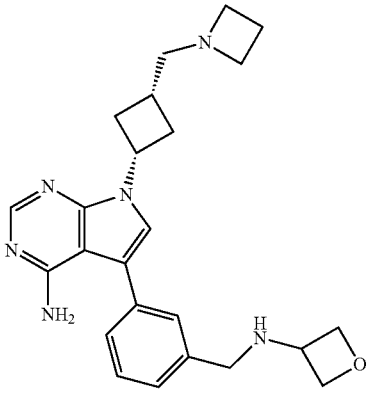 [SMILES: Nc1ncnc2c1c(-c1cccc(CNC3COC3)c1)cn2[C@H]1C[C@@H](CN2CCC2)C1] | SU20668-0402 | B | 418.6 |
| 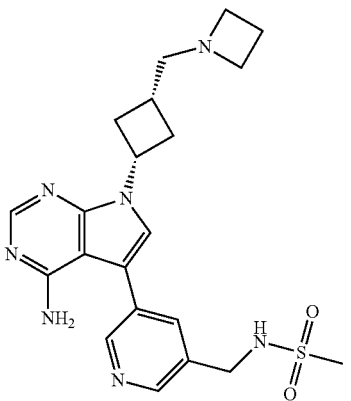 [SMILES: CS(=O)(=O)NCc1cncc(-c2cn([C@H]3C[C@@H](CN4CCC4)C3)c3ncnc(N)c23)c1] | SU20668-0405 | A | 441.6 |
| 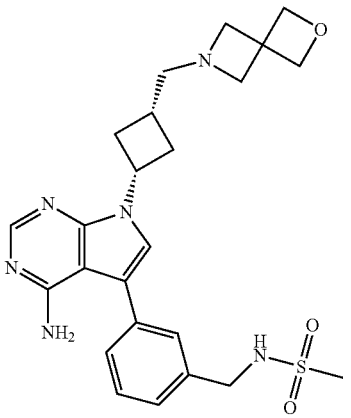 [SMILES: CS(=O)(=O)NCc1cccc(-c2cn([C@H]3C[C@@H](CN4CC5(COC5)C4)C3)c3ncnc(N)c23)c1] | SU20668-0408 | D | 482.6 |

TABLE 2-continued

Biologicial Data for select PYP Analogs

| Structure | Compound # | LKB1 % Act. Increase | MW |
|---|---|---|---|
| 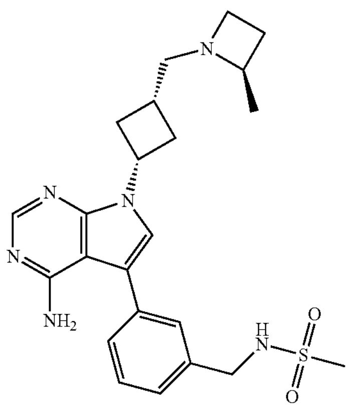 [SMILES: C[C@@H]1CCN1C[C@H]1C[C@@H](n2cc(-c3cccc(CNS(C)(=O)=O)c3)c3c(N)ncnc32)C1] | SU20668-0411 | D | 454.6 |
| 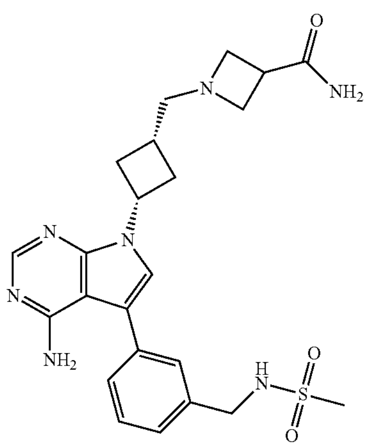 [SMILES: CS(=O)(=O)NCc1cccc(-c2cn([C@H]3C[C@@H](CN4CC(C(N)=O)C4)C3)c3ncnc(N)c23)c1] | SU20668-0414 | C | 483.6 |
| 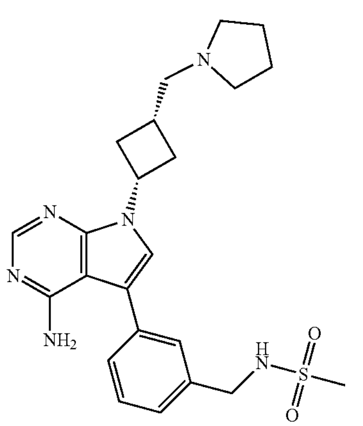 [SMILES: CS(=O)(=O)NCc1cccc(-c2cn([C@H]3C[C@@H](CN4CCCC4)C3)c3ncnc(N)c23)c1] | SU20668-0415 | D | 454.6 |

TABLE 2-continued
Biologicial Data for select PYP Analogs
| Structure | Compound # | LKB1 % Act. Increase | MW |
|---|---|---|---|
| 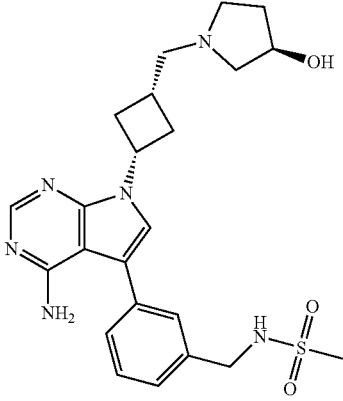 [SMILES: CS(=O)(=O)NCc1cccc(-c2cn([C@H]3C[C@@H](CN4CC[C@@H](O)C4)C3)c3ncnc(N)c23)c1] | SU20668-0416 | D | 470.6 |
| 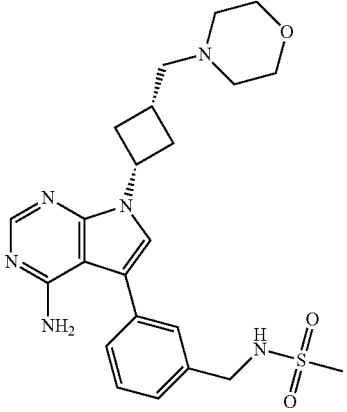 [SMILES: CS(=O)(=O)NCc1cccc(-c2cn([C@H]3C[C@@H](CN4CCOCC4)C3)c3ncnc(N)c23)c1] | SU20668-0417 | D | 470.6 |
| 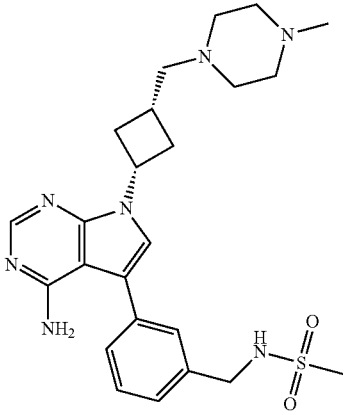 [SMILES: CN1CCN(C[C@H]2C[C@@H](n3cc(-c4cccc(CNS(C)(=O)=O)c4)c4c(N)ncnc43)C2)CC1] | SU20668-0418 | D | 483.6 |

TABLE 2-continued

Biologicial Data for select PYP Analogs

| Structure | Compound # | LKB1 % Act. Increase | MW |
|---|---|---|---|
| 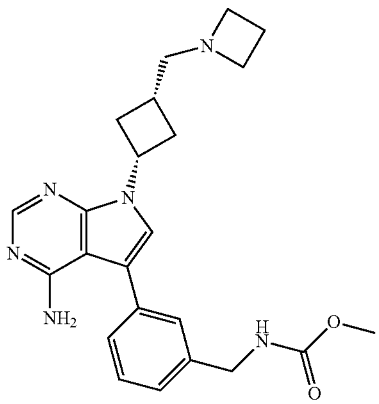 [SMILES: COC(=O)NCc1cccc(-c2cn([C@H]3C[C@@H](CN4CCC4)C3)c3ncnc(N)c23)c1] | SU20668-0419 | B | 420.5 |
| 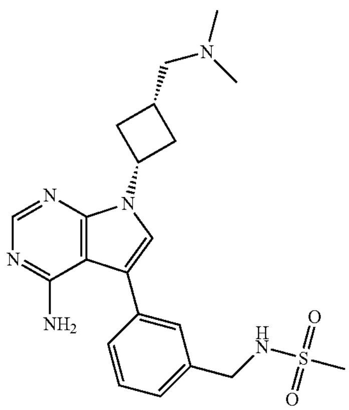 [SMILES: CN(C)C[C@H]1C[C@@H](n2cc(-c3cccc(CNS(C)(=O)=O)c3)c3c(N)ncnc32)C1] | SU20668-0420 | C | 428.6 |
| 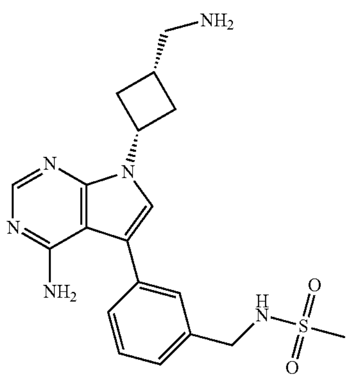 [SMILES: CS(=O)(=O)NCc1cccc(-c2cn([C@H]3C[C@@H](CN)C3)c3ncnc(N)c23)c1] | SU20668-0421 | D | 400.5 |
| 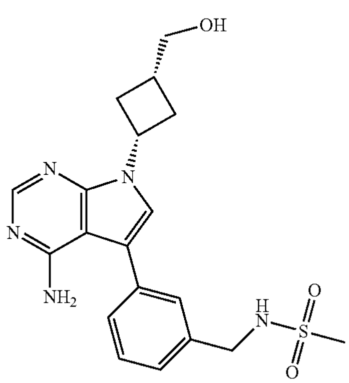 [SMILES: CS(=O)(=O)NCc1cccc(-c2cn([C@H]3C[C@@H](CO)C3)c3ncnc(N)c23)c1] | SU20668-0425 | D | 401.5 |

TABLE 2-continued

Biological Data for select PYP Analogs

| Structure | Compound # | LKB1 % Act. Increase | MW |
|---|---|---|---|
| (structure) | SU20668-0451 | C | 458.6 |
| (structure) | SU20668-0453 | C | 454.6 |
| (structure) | SU20668-0455 | D | 483.6 |

TABLE 2-continued
Biologicial Data for select PYP Analogs
| Structure | Compound # | LKB1 % Act. Increase | MW |
|---|---|---|---|
| 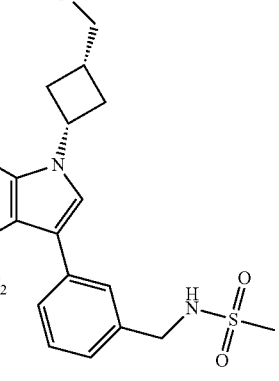 | SU20668-0457 | D | 428.6 |
| 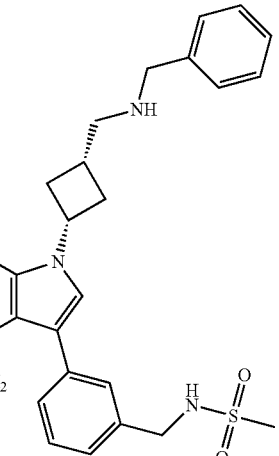 | SU20668-0465 | D | 490.6 |
| 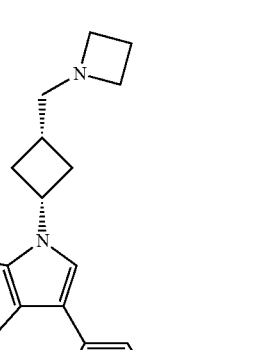 | SU20668-0363 | C | 515.6 |

TABLE 2-continued

Biologicial Data for select PYP Analogs

| Structure | Compound # | LKB1 % Act. Increase | MW |
|---|---|---|---|
| (structure) | SU20668-0407 | A | 363.5 |
| (structure) | SU20668-0424 | D | 400.5 |
| (structure) | SU20668-0428 | C | 375.5 |

For in vitro LKB1 functional activity, the $EC_{50}$ is defined as follows: A=<500 nM, B=500 nM-5.0 uM, C=5.0 uM-25 uM, and D=>25 uM.

Example 5: Drug Screen of the SelleckChem Kinase Inhibitor Library

Figure 8:
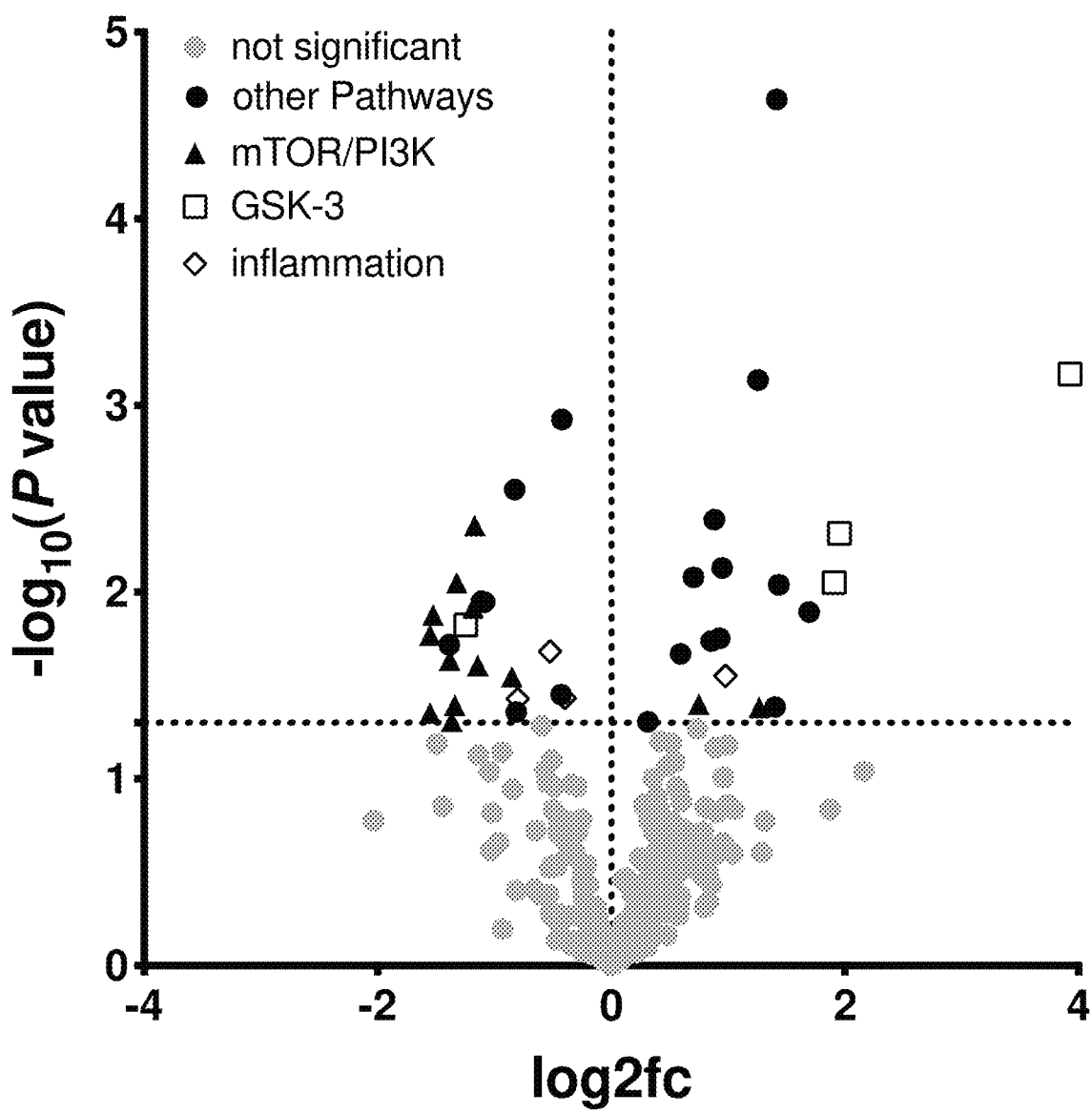
FIG. 8. Drug screen identifies signaling pathways that affect the impact of LKB1 activation. Drug screen of the SelleckChem kinase inhibitor library was performed in the ACHN cell line. Sensitivity to kinase inhibitors used at 200 nM with and without 5 μM of SU-329 was measured after 5 days with Cell-Titer Glo. Inhibition of mTOR and components of the PI3K attenuated the response of LKB1 stimulation. Inhibition of GSK-3 reduced the response of LKB1 stimulation. The terms SU-329 and SU20668-0329-01 refer to the same compound.

Drug screen of the SelleckChem kinase inhibitor library was performed in the ACHN cell line. Sensitivity to kinase inhibitors used at 200 nM with and without 5 μM of SU-329 was measured after 5 days with Cell-Titer Glo (FIG. 8). Inhibition of mTOR and components of the PI3K attenuated the response of LKB1 stimulation. Inhibition of GSK-3 reduced the response of LKB1 stimulation. Not all compounds in the noted pathways had significant synergy or antagonism in combination with SU-329, as can be seen in Table 3. The target and/or compound class, as indicated in Table 3, is provided by Selleckchem.

TABLE 3

Compound combinations for drug screen of the SelleckChem kinase inhibitor library.

| | | 5 uM SU329 | |
|---|---|---|---|
| Product Name | Target | log2fc | p value |
| PF-477736 | Chk | −2.03474 | 0.1667821 |
| Rapamycin (Sirolimus) | Autophagy, mTOR | −1.5520194 | 0.01689784 |

TABLE 3-continued

Compound combinations for drug screen of the SelleckChem kinase inhibitor library.

|  |  | 5 uM SU329 | |
| --- | --- | --- | --- |
| Product Name | Target | log2fc | p value |
| KU-0063794 | mTOR | −1.5510716 | 0.04439411 |
| Temsirolimus (CCI-779, NSC 683864) | mTOR | −1.5242572 | 0.01322247 |
| OSI-027 | mTOR | −1.4944444 | 0.06517293 |
| Momelotinib (CYT387) | JAK | −1.4408581 | 0.13998394 |
| Uprosertib (GSK2141795) | Akt | −1.3872917 | 0.01912676 |
| Ridaforolimus (Deforolimus, MK-8669) | mTOR | −1.3836337 | 0.02315395 |
| Everolimus (RAD001) | mTOR | −1.364331 | 0.04914098 |
| Zotarolimus (ABT-578) | mTOR | −1.340416 | 0.04031819 |
| WAY-600 | mTOR | −1.3223936 | 0.00888656 |
| Indirubin | GSK-3 | −1.2472992 | 0.01500026 |
| Buparlisib (BKM120, NVP-BKM120) | PI3K | −1.1833411 | 0.01213918 |
| Pictilisib (GDC-0941) | PI3K | −1.1696079 | 0.00439813 |
| WYE-354 | mTOR | −1.1431374 | 0.02466218 |
| BMS-754807 | c-Met, IGF-1R, Trk receptor | −1.1385549 | 0.07424333 |
| GSK2334470 | PDK | −1.1114985 | 0.01120904 |
| AT7519 | CDK | −1.0854175 | 0.01128625 |
| CH5132799 | mTOR, PI3K | −1.0438836 | 0.09129746 |
| SNS-032 (BMS-387032) | CDK | −1.0283809 | 0.2417302 |
| PI-103 | Autophagy, DNA-PK, mTOR, PI3K | −1.0210264 | 0.15146812 |
| PHA-767491 | CDK | −0.9628928 | 0.21866462 |
| AT7867 | Akt, S6 Kinase | −0.935013 | 0.07192551 |
| PFK15 | Others | −0.9312472 | 0.63501695 |
| ZSTK474 | PI3K | −0.850892 | 0.028351 |
| RKI-1447 | ROCK | −0.8453064 | 0.11356273 |
| Semaxanib (SU5416) | VEGFR | −0.8277161 | 0.00281923 |
| CYC116 | Aurora Kinase, VEGFR | −0.814 | 0.04379265 |
| Vistusertib (AZD2014) | mTOR | −0.8126986 | 0.39652238 |
| Skepinone-L | p38 MAPK | −0.799724 | 0.03730847 |
| Apitolisib (GDC-0980, RG7422) | mTOR, PI3K | −0.6580163 | 0.38811669 |
| A-674563 | Akt, CDK, PKA | −0.6438316 | 0.1890898 |
| CEP-33779 | JAK | −0.6077588 | 0.41759682 |
| GSK690693 | Akt | −0.5999266 | 0.05187664 |
| PH-797804 | p38 MAPK | −0.5678338 | 0.08952618 |
| Doramapimod (BIRB 796) | p38 MAPK | −0.5476963 | 0.10493087 |
| Tyrphostin 9 | EGFR | −0.5357899 | 0.41705261 |
| YM201636 | PI3K | −0.5268304 | 0.30059603 |
| Losmapimod (GW856553X) | p38 MAPK | −0.5235593 | 0.02078755 |
| PP121 | DNA-PK, mTOR, PDGFR | −0.5205523 | 0.52612284 |
| PF-04691502 | Akt, mTOR, PI3K | −0.5101229 | 0.53803249 |
| BMS-777607 | TAM Receptor, c-Met | −0.5094963 | 0.29179825 |
| Ipatasertib (GDC-0068) | Akt | −0.5082452 | 0.07904882 |
| AZD1208 | Pim | −0.4967223 | 0.10988041 |
| Thiazovivin | ROCK | −0.4963238 | 0.14643894 |
| ALK-IN-1 | ALK | −0.4692398 | 0.29273623 |
| BGT226 (NVP-BGT226) | mTOR, PI3K | −0.4637553 | 0.72735312 |
| WP1066 | JAK | −0.4550812 | 0.19361809 |
| BX-912 | PDK | −0.4536473 | 0.16543381 |
| Quercetin | Src, Sirtuin, PKC, PI3K | −0.4489992 | 0.53014074 |
| Ponatinib (AP24534) | Bcr-Abl, FGFR, PDGFR, VEGFR | −0.4485294 | 0.60078022 |
| Vatalanib (PTK787) 2HCl | c-Kit, VEGFR | −0.4288534 | 0.03532674 |
| DDR1-IN-1 | Others | −0.422809 | 0.00118681 |
| PHA-680632 | Aurora Kinase | −0.4047874 | 0.20717177 |
| U0126-EtOH | MEK | −0.3987978 | 0.16699054 |
| SB202190 (FHPI) | p38 MAPK | −0.3986101 | 0.03685473 |
| MK-8745 | Aurora Kinase | −0.3778744 | 0.25666859 |
| VS-5584 (SB2343) | PI3K | −0.3678913 | 0.73307499 |
| AG-1024 | IGF-1R | −0.3636223 | 0.22814787 |
| Dovitinib (TKI-258) Dilactic Acid | c-Kit, FGFR, FLT3, PDGFR, VEGFR | −0.3597504 | 0.76072792 |
| CX-6258 HCl | Pim | −0.3549962 | 0.76695954 |
| BX-795 | IκB/IKK, PDK | −0.3475652 | 0.54044666 |
| TGX-221 | PI3K | −0.3414792 | 0.10651965 |
| Torkinib (PP242) | Autophagy, mTOR | −0.3157342 | 0.73562469 |
| Lenvatinib (E7080) | VEGFR | −0.3139866 | 0.24446152 |
| Dabrafenib (GSK2118436) | Raf | −0.3139628 | 0.75270759 |
| VX-745 | p38 MAPK | −0.2953304 | 0.10986837 |
| SL-327 | MEK | −0.2882334 | 0.19485522 |
| Amuvatinib (MP-470) | c-Kit, FLT3, PDGFR | −0.2593713 | 0.8362147 |
| Sorafenib Tosylate | PDGFR, Raf, VEGFR | −0.2532671 | 0.72942605 |
| CNX-774 | BTK | −0.2518652 | 0.16451285 |
| Orantinib (TSU-68, SU6668) | FGFR, PDGFR, VEGFR | −0.2486821 | 0.35355774 |
| Linifanib (ABT-869) | CSF-1R, PDGFR, VEGFR | −0.2483204 | 0.5554538 |
| NU6027 | CDK | −0.2463328 | 0.31426337 |
| MK-5108 (VX-689) | Aurora Kinase | −0.2429462 | 0.38229423 |
| CCT128930 | Akt | −0.2363776 | 0.43398402 |

TABLE 3-continued

Compound combinations for drug screen of the SelleckChem kinase inhibitor library.

|  |  | 5 uM SU329 | |
| --- | --- | --- | --- |
| Product Name | Target | log2fc | p value |
| Bisindolylmaleimide I (GF109203X) | PKC | −0.2331945 | 0.55617177 |
| OSI-930 | c-Kit, CSF-1R, VEGFR | −0.2272917 | 0.39542061 |
| CC-292 (AVL-292) | BTK | −0.2141805 | 0.74364352 |
| Duvelisib (IPI-145, INK1197) | PI3K | −0.2127843 | 0.28763495 |
| INK 128 (MLN0128) | mTOR | −0.2017737 | 0.73416446 |
| Aurora A Inhibitor I | Aurora Kinase | −0.1962424 | 0.37341982 |
| Dasatinib | Bcr-Abl, c-Kit, Src | −0.1960315 | 0.7081523 |
| PD173955 | Bcr-Abl | −0.1932225 | 0.83483205 |
| Chrysophanic Acid | EGFR, mTOR | −0.1902275 | 0.59496316 |
| S-Ruxolitinib (INCB018424) | JAK | −0.1854936 | 0.58477041 |
| BIO | GSK-3 | −0.1794908 | 0.55418452 |
| LY2603618 | Chk | −0.1738891 | 0.86725607 |
| XL019 | JAK | −0.1668725 | 0.57293977 |
| Bosutinib (SKI-606) | Src | −0.158336 | 0.59223635 |
| MK-2206 2HCl | Akt | −0.157505 | 0.77509004 |
| TG101209 | c-RET, FLT3, JAK | −0.1573133 | 0.83733576 |
| AS-252424 | PI3K | −0.1562537 | 0.50580738 |
| Danusertib (PHA-739358) | Aurora Kinase, Bcr-Abl, c-RET, FGFR | −0.1536853 | 0.66198782 |
| WZ4003 | AMPK | −0.1404935 | 0.57480525 |
| Foretinib (GSK1363089) | c-Met, VEGFR | −0.1359289 | 0.77584408 |
| Alpelisib (BYL719) | PI3K | −0.1348678 | 0.62745697 |
| Golvatinib (E7050) | c-Met, VEGFR | −0.1341046 | 0.71865449 |
| Degrasyn (WP1130) | Bcr-Abl, DUB | −0.1319801 | 0.66647274 |
| Pazopanib | c-Kit, PDGFR,VEGFR | −0.1315945 | 0.47899653 |
| BAY 11-7082 | E2 conjugating, IκB/IKK | −0.1258155 | 0.5781531 |
| Ruxolitinib (INCB018424) | JAK | −0.1253476 | 0.70938538 |
| Sunitinib Malate | c-Kit, PDGFR, VEGFR | −0.1248583 | 0.77222799 |
| PHA-793887 | CDK | −0.1187291 | 0.7827437 |
| IKK-16 (IKK Inhibitor VII) | IκB/IKK | −0.1182574 | 0.55139882 |
| VX-702 | p38 MAPK | −0.1167533 | 0.75757681 |
| Motesanib Diphosphate (AMG-706) | VEGFR, PDGFR, c-Kit | −0.1117549 | 0.78465177 |
| AZD6482 | PI3K | −0.1097822 | 0.78222118 |
| BMS-265246 | CDK | −0.1077301 | 0.88248455 |
| XMD8-92 | ERK | −0.0990086 | 0.8158244 |
| NVP-BSK805 2HCl | JAK | −0.0949883 | 0.82698997 |
| SB203580 | p38 MAPK | −0.0942405 | 0.82064272 |
| GW441756 | Trk receptor | −0.0933262 | 0.84922902 |
| TPCA-1 | IκB/IKK | −0.0892828 | 0.67755441 |
| TAE226 (NVP-TAE226) | FAK | −0.0889668 | 0.874677 |
| Tie2 kinase inhibitor | Tie-2 | −0.0869655 | 0.64086704 |
| BIX 02189 | MEK | −0.0824788 | 0.75665495 |
| WZ4002 | EGFR | −0.0754535 | 0.8568359 |
| KN-62 | CaMK | −0.0725798 | 0.87387953 |
| FRAX597 | PAK | −0.0717981 | 0.93499594 |
| AZD3463 | ALK | −0.0632847 | 0.93815218 |
| KW-2449 | Aurora Kinase, Bcr-Abl, FLT3 | −0.0564016 | 0.92202849 |
| PLX-4720 | Raf | −0.0506592 | 0.806923 |
| LDC000067 | CDK | −0.050493 | 0.83464961 |
| OSI-420 | EGFR | −0.0484574 | 0.79914393 |
| BMS-794833 | C-Met, VEGFR | −0.0440533 | 0.86042966 |
| GSK429286A | ROCK | −0.0393864 | 0.95171009 |
| GSK1838705A | ALK, IGF-1R | −0.0308107 | 0.71670081 |
| PHT-427 | Akt, PDK | −0.0286102 | 0.87509649 |
| SGI-1776 free base | Pim | −0.0253992 | 0.96920412 |
| AZ20 | ATWW/ATR | −0.0152842 | 0.98874953 |
| AG-490 (Tyrphostin B42) | EGFR,JAK | −0.01509 | 0.96745757 |
| H 89 2HCl | PKA, S6 Kinase | −0.0140427 | 0.94434125 |
| Osimertinib (AZD9291) | EGFR | −0.0128647 | 0.98487568 |
| PP2 | Src | −0.0108797 | 0.96938836 |
| Y-27632 2HCl | Autophagy, ROCK | −0.0100285 | 0.97621176 |
| Tideglusib | GSK-3 | −0.007073 | 0.95243006 |
| Fedratinib (SAR302503, TG101348) | JAK | −0.0034438 | 0.99544108 |
| Rociletinib (CO-1686, AVL-301) | EGFR | −0.0018993 | 0.99224404 |
| Cabozantinib (XL184, BMS-907351) | TAM Receptor, c-Kit, c-Met, FLT3, Tie- | 0.00119651 | 0.99850558 |
| Axitinib | c-Kit, PDGFR, VEGFR | 0.00154998 | 0.99304502 |
| Bay 11-7085 | IκB/IKK | 0.00415338 | 0.98923157 |
| Rebastinib (DCC-2036) | Bcr-Abl | 0.00771546 | 0.99393774 |
| Vemurafenib (PLX4032, RG7204) | Raf | 0.00915408 | 0.98552555 |
| Cediranib (AZD2171) | VEGFR | 0.01223764 | 0.96921521 |
| WZ8040 | EGFR | 0.02091638 | 0.94492029 |
| NVP-BHG712 | Bcr-Abl, Ephrin receptor, Raf, Src | 0.02395922 | 0.9136084 |
| TAK-715 | p38 MAPK | 0.02438533 | 0.89586439 |
| KN-93 Phosphate | CaMK | 0.02491343 | 0.85443407 |
| KRN 633 | PDGFR, VEGFR | 0.02523814 | 0.86550094 |

TABLE 3-continued

Compound combinations for drug screen of the SelleckChem kinase inhibitor library.

| | | 5 uM SU329 | |
|---|---|---|---|
| Product Name | Target | log2fc | p value |
| JNJ-38877605 | c-Met | 0.0290681 | 0.93126618 |
| AMG-458 | c-Met | 0.03949632 | 0.91426614 |
| Tepotinib (EMD 1214063) | c-Met | 0.04059348 | 0.82227753 |
| Afatinib (BIBW2992) | EGFR, HER2 | 0.04312949 | 0.89600405 |
| Brivanib Alaninate (BMS-582664) | FGFR, VEGFR | 0.04321174 | 0.84172677 |
| PIK-294 | PI3K | 0.04742468 | 0.74841665 |
| WYE-125132 (WYE-132) | mTOR | 0.04946179 | 0.91955813 |
| Genistein | EGFR, Topoisomerase | 0.0526234 | 0.78231439 |
| Sotrastaurin | PKC | 0.05399865 | 0.8812185 |
| WZ3146 | EGFR | 0.05458962 | 0.93385305 |
| AST-1306 | EGFR | 0.05839998 | 0.88656314 |
| SKI II | S1P Receptor | 0.0656408 | 0.87797321 |
| SP600125 | JNK | 0.06822629 | 0.84139485 |
| MLN8054 | Aurora Kinase | 0.07059357 | 0.88132574 |
| AEE788 (NVP-AEE788) | EGFR, HER2, VEGFR | 0.07426899 | 0.84992917 |
| Triciribine | Akt | 0.08156849 | 0.92496437 |
| TAK-733 | MEK | 0.08617907 | 0.82214515 |
| RN486 | BTK | 0.08694777 | 0.81247786 |
| Daphnetin | PKA, EGFR, PKC | 0.08794284 | 0.64655097 |
| Linsitinib (OSI-906) | IGF-1R | 0.08978439 | 0.83942354 |
| Go 6983 | PKC | 0.08991642 | 0.65238125 |
| MK-2461 | c-Met, FGFR, PDGFR | 0.09191689 | 0.71296513 |
| BS-181 HCl | CDK | 0.09476011 | 0.72131448 |
| Honokiol | Akt, MEK | 0.09483559 | 0.34835892 |
| Idelalisib (CAL-101, GS-1101) | PI3K | 0.0983792 | 0.86033252 |
| Hesperadin | Aurora Kinase | 0.1005556 | 0.73122565 |
| Ki8751 | c-Kit, PDGFR,VEGFR | 0.10107054 | 0.89930676 |
| SU11274 | c-Met | 0.10133225 | 0.59710446 |
| AZD8055 | mTOR | 0.10242497 | 0.85727771 |
| ERK5-IN-1 | ERK | 0.10311499 | 0.82549151 |
| PD173074 | FGFR, VEGFR | 0.1032418 | 0.85526241 |
| EHop-016 | Rho | 0.11562143 | 0.6920156 |
| Icotinib | EGFR | 0.11822974 | 0.82483643 |
| Brivanib (BMS-540215) | FGFR,VEGFR | 0.11943647 | 0.7214741 |
| CNX-2006 | EGFR | 0.12179491 | 0.84090102 |
| PIK-293 | PI3K | 0.12488528 | 0.7066518 |
| CUDC-101 | EGFR, HDAC, HER2 | 0.12688017 | 0.84590946 |
| AR-A014418 | GSK-3 | 0.12929783 | 0.78085284 |
| GNF-2 | Bcr-Abl | 0.13365972 | 0.33950879 |
| Fasudil (HA-1077) HCl | Autophagy, ROCK | 0.14570208 | 0.6282251 |
| Asiatic Acid | p38 MAPK | 0.15054021 | 0.78131399 |
| Imatinib Mesylate (STI571) | Bcr-Abl, c-Kit, PDGFR | 0.15359551 | 0.79210335 |
| TDZD-8 | GSK-3 | 0.15520908 | 0.75134289 |
| abemaciclib (LY2835219) | CDK | 0.1618296 | 0.81109267 |
| ZM 323881 HCl | VEGFR | 0.17646323 | 0.4065131 |
| PHA-665752 | C-Met | 0.1781042 | 0.57798622 |
| A-769662 | AMPK | 0.17975476 | 0.72614042 |
| JNK Inhibitor IX | JNK | 0.18142065 | 0.66117314 |
| Pazopanib HCl (GW786034 HCl) | c-Kit, PDGFR, VEGFR | 0.18169951 | 0.77176138 |
| Masitinib (AB1010) | c-Kit, PDGFR | 0.18735952 | 0.5130453 |
| A66 | PI3K | 0.1890388 | 0.71051282 |
| CGK 733 | ATWWATR | 0.19231144 | 0.67378605 |
| Crizotinib (PF-02341066) | ALK, c-Met | 0.19603015 | 0.71133283 |
| AZD2858 | GSK-3 | 0.19913117 | 0.75895961 |
| IMD 0354 | IκB/IKK | 0.20860592 | 0.85317572 |
| SB590885 | Raf | 0.2113252 | 0.52560836 |
| Lapatinib (GW-572016) Ditosylate | EGFR, HER2 | 0.21199009 | 0.76858643 |
| CZC24832 | PI3K | 0.21390326 | 0.46738021 |
| ZM 336372 | Raf | 0.21768299 | 0.72388706 |
| PF-04217903 | c-Met | 0.21769337 | 0.53429069 |
| NVP-AEW541 | IGF-1R | 0.21788503 | 0.65322647 |
| BIX 02188 | MEK | 0.22157093 | 0.59081577 |
| Mubritinib (TAK 165) | HER2 | 0.22500687 | 0.50875535 |
| TG100-115 | PI3K | 0.23342224 | 0.48132809 |
| Sorafenib | Raf | 0.24621583 | 0.71835086 |
| 10058-F4 | c-Myc | 0.2471754 | 0.37787713 |
| HMN-214 | PLK | 0.24770336 | 0.26657507 |
| Telatinib | c-Kit, PDGFR, VEGFR | 0.24786648 | 0.66404664 |
| Apatinib | VEGFR | 0.25696035 | 0.55513245 |
| Tivantinib (ARQ 197) | c-Met | 0.27094546 | 0.63658376 |
| SB415286 | GSK-3 | 0.27362562 | 0.4358106 |
| Quizartinib (AC220) | FLT3 | 0.27801115 | 0.13766739 |
| TAK-901 | Aurora Kinase | 0.28177684 | 0.45703981 |
| CP-724714 | EGFR, HER2 | 0.2836131 | 0.51076856 |

TABLE 3-continued

Compound combinations for drug screen of the SelleckChem kinase inhibitor library.

| | | 5 uM SU329 | |
|---|---|---|---|
| Product Name | Target | log2fc | p value |
| AG-1478 (Tyrphostin AG-1478) | EGFR | 0.29025088 | 0.43647647 |
| PP1 | Src | 0.29559714 | 0.2857922 |
| Ceritinib (LDK378) | ALK | 0.29881476 | 0.35854556 |
| KU-55933 (ATM Kinase Inhibitor) | ATWWATR | 0.30532166 | 0.4982007 |
| VE-822 | ATWWATR | 0.30830717 | 0.78973589 |
| GNE-0877 | LRRK2 | 0.3097934 | 0.58081914 |
| HTH-01-015 | AMPK | 0.31409664 | 0.04944285 |
| PIK-93 | PI3K | 0.3161707 | 0.66855421 |
| TIC10 Analogue | Akt | 0.31757665 | 0.43333272 |
| Palomid 529 (P529) | mTOR | 0.31915715 | 0.16654399 |
| GSK650394 | Others | 0.32054047 | 0.5017077 |
| 3-Methyladenine (3-MA) | Autophagy, PI3K | 0.3231856 | 0.45676685 |
| Pimasertib (AS-703026) | MEK | 0.32521263 | 0.44893316 |
| PD184352 (CI-1040) | MEK | 0.32566863 | 0.16287281 |
| Nilotinib (AMN-107) | Bcr-Abl | 0.33100879 | 0.72908352 |
| PD98059 | MEK | 0.33688524 | 0.52559224 |
| Tyrphostin AG 879 | HER2 | 0.33914525 | 0.39982806 |
| Voxtalisib (SAR245409, XL765) Analogue | mTOR, PI3K | 0.34224283 | 0.68183954 |
| SSR128129E | FGFR | 0.34733247 | 0.38620314 |
| Tofacitinib (CP-690550) Citrate | JAK | 0.35117979 | 0.50454942 |
| URMC-099 | LRRK2 | 0.35150064 | 0.61679675 |
| Selumetinib (AZD6244) | MEK | 0.3569868 | 0.1882362 |
| Sapitinib (AZD8931) | EGFR, HER2 | 0.358036 | 0.09946418 |
| GDC-0879 | Raf | 0.35919291 | 0.51125288 |
| Crenolanib (CP-868596) | PDGFR | 0.36661123 | 0.28525285 |
| SAR131675 | VEGFR | 0.37402377 | 0.4461683 |
| CAY10505 | PI3K | 0.38283679 | 0.43430172 |
| JNJ-7706621 | Aurora Kinase, CDK | 0.38568143 | 0.68303587 |
| TAK-285 | EGFR, HER2 | 0.38759053 | 0.46818469 |
| KX2-391 | Src | 0.38918832 | 0.2457403 |
| PD0325901 | MEK | 0.39251052 | 0.12454569 |
| Dacomitinib (PF299804, PF299) | EGFR | 0.39971187 | 0.2019645 |
| Saracatinib (AZD0530) | Bcr-Abl, Src | 0.40093257 | 0.36079637 |
| GW5074 | Raf | 0.40705145 | 0.20958922 |
| GNE-9605 | LRRK2 | 0.40924847 | 0.14420162 |
| BMS-536924 | IGF-1R | 0.4161103 | 0.16162184 |
| TG003 | CDK | 0.41630252 | 0.45162974 |
| PD318088 | MEK | 0.41841163 | 0.06298056 |
| CP-673451 | PDGFR | 0.42337062 | 0.32516768 |
| Ro3280 | PLK | 0.42687659 | 0.19610466 |
| MGCD-265 | c-Met, Tie-2, VEGFR | 0.43112879 | 0.41581283 |
| AZ 628 | Raf | 0.43190183 | 0.22743768 |
| PF-573228 | FAK | 0.43246828 | 0.27429495 |
| AZD2932 | PDGFR, VEGFR, FLT3, c-Kit | 0.44283806 | 0.40005244 |
| SNS-314 Mesylate | Aurora Kinase | 0.44686531 | 0.36867551 |
| SB216763 | GSK-3 | 0.47081422 | 0.52258583 |
| HS-173 | PI3K | 0.47173535 | 0.31350436 |
| AZD4547 | FGFR | 0.4724736 | 0.29688575 |
| TAK-632 | Raf | 0.47319961 | 0.08534439 |
| Dovitinib (TKI-258, CHIR-258) | c-Kit, FGFR, FLT3, PDGFR, VEGFR | 0.47462288 | 0.68976949 |
| Trametinib (GSK1120212) | MEK | 0.48030119 | 0.2660598 |
| AZD1480 | JAK | 0.48133877 | 0.39839181 |
| Refametinib (RDEA119, Bay 86-9766) | MEK | 0.48673163 | 0.31852586 |
| AS-604850 | PI3K | 0.48759136 | 0.3713171 |
| Gefitinib (ZD1839) | EGFR | 0.49053116 | 0.42060321 |
| R406 | FLT3,Syk | 0.49426667 | 0.34925273 |
| SC-514 | IκB/IKK | 0.50236005 | 0.24559674 |
| WHI-P154 | EGFR, JAK | 0.51102371 | 0.06432287 |
| IPA-3 | PAK | 0.51684117 | 0.23555597 |
| PF-4708671 | S6 Kinase | 0.51870609 | 0.4165124 |
| ZM 447439 | Aurora Kinase | 0.52000109 | 0.30161071 |
| TWS119 | GSK-3 | 0.52000509 | 0.16726176 |
| LY294002 | Autophagy, PI3K | 0.53374396 | 0.48223561 |
| Omipalisib (GSK2126458, GSK458) | mTOR,PI3K | 0.53417686 | 0.34977141 |
| Binimetinib (MEK162, ARRY-162, ARRY-438) | MEK | 0.54336633 | 0.08093223 |
| Piceatannol | Syk | 0.54471495 | 0.32160288 |
| R547 | CDK | 0.56175401 | 0.10987323 |
| Schisandrin B (Sch B) | ATWWATR | 0.56736497 | 0.44620504 |
| JNK-IN-8 | JNK | 0.56956177 | 0.21077653 |
| Cabozantinib malate (XL184) | TAM Receptor, VEGFR | 0.57134854 | 0.53596752 |
| ZM 306416 | VEGFR | 0.58069215 | 0.11767865 |
| Enzastaurin (LY317615) | PKC | 0.58136204 | 0.47258107 |
| NVP-BVU972 | C-Met | 0.5845652 | 0.29750227 |
| CUDC-907 | HDAC, PI3K | 0.58954676 | 0.18307617 |

TABLE 3-continued

Compound combinations for drug screen of the SelleckChem kinase inhibitor library.

| | | 5 uM SU329 | |
|---|---|---|---|
| Product Name | Target | log2fc | p value |
| MLN2480 | Raf | 0.59164298 | 0.4255948 |
| AZD8330 | MEK | 0.59348871 | 0.28698749 |
| Phenformin HCl | AMPK | 0.59453208 | 0.02135144 |
| PD168393 | EGFR | 0.59906913 | 0.13195639 |
| Roscovitine (Seliciclib, CYC202) | CDK | 0.59933709 | 0.19821463 |
| GSK1904529A | IGF-1R | 0.62110747 | 0.30401514 |
| Volasertib (BI 6727) | PLK | 0.63720741 | 0.19069446 |
| Tofacitinib (CP-690550, Tasocitinib) | JAK | 0.6420581 | 0.29939274 |
| Rigosertib (ON-01910) | PLK | 0.66431451 | 0.19944437 |
| ENMD-2076 | Aurora Kinase, FLT3, VEGFR | 0.67990033 | 0.28402504 |
| AC480 (BMS-599626) | EGFR, HER2 | 0.68063834 | 0.25191266 |
| Fingolimod (FTY720) HCl | S1P Receptor | 0.70513231 | 0.22253429 |
| Alisertib (MLN8237) | Aurora Kinase | 0.7052251 | 0.00830065 |
| AICAR (Acadesine) | AMPK | 0.71638356 | 0.28723812 |
| Fostamatinib (R788) | Syk | 0.72424376 | 0.27009866 |
| Barasertib (AZD1152-HQPA) | Aurora Kinase | 0.73868104 | 0.05386215 |
| BI-D1870 | S6 Kinase | 0.74985927 | 0.03971614 |
| Nintedanib (BIBF 1120) | FGFR, PDGFR, VEGFR | 0.78587866 | 0.19157036 |
| OSU-03012 (AR-12) | PDK | 0.79107621 | 0.33549613 |
| Tivozanib (AV-951) | c-Kit, PDGFR, VEGFR | 0.79800925 | 0.48816284 |
| Varlitinib | EGFR | 0.79992739 | 0.14181112 |
| PF-562271 | FAK | 0.82576933 | 0.22867221 |
| PF-00562271 | FAK | 0.82743339 | 0.34655924 |
| PF-3758309 | PAK | 0.82833793 | 0.31796958 |
| Regorafenib (BAY 73-4506) | c-RET, VEGFR | 0.83334818 | 0.45451575 |
| R406 (free base) | Syk | 0.83335128 | 0.14390525 |
| AZD7762 | Chk | 0.85679817 | 0.01829763 |
| PF-543 | S1P Receptor | 0.85977377 | 0.36794333 |
| AMG-900 | Aurora Kinase | 0.88303368 | 0.00408953 |
| KU-60019 | ATIWATR | 0.88599796 | 0.06809373 |
| CGI1746 | BTK | 0.89388648 | 0.25386514 |
| RAF265 (CHIR-265) | Raf, VEGFR | 0.90011722 | 0.15121397 |
| Tozasertib (VX-680, MK-0457) | Aurora Kinase | 0.92650942 | 0.01761105 |
| Lapatinib | EGFR, HER2 | 0.9498671 | 0.0074109 |
| CHIR-99021 (CT99021) HCl | GSK-3 | 0.95765514 | 0.09821831 |
| Pelitinib (EKB-569) | EGFR | 0.96000363 | 0.21908382 |
| AZ 960 | JAK | 0.97895788 | 0.02804297 |
| GSK461364 | PLK | 0.99254999 | 0.0658261 |
| Milciclib (PHA-848125) | CDK | 0.99859381 | 0.13801329 |
| Gandotinib (LY2784544) | JAK | 1.04007241 | 0.25148766 |
| Flavopiridol (Alvocidib) | CDK | 1.05049963 | 0.14598257 |
| CHIR-124 | Chk | 1.2568828 | 0.00072957 |
| Torin 2 | ATIWATR, mTOR | 1.26723187 | 0.04138747 |
| Ibrutinib (PCI-32765) | BTK | 1.28855098 | 0.24615941 |
| CHIR-99021 (CT99021) | GSK-3 | 1.3155166 | 0.16763477 |
| Dinaciclib (SCH727965) | CDK | 1.4022662 | 0.04113832 |
| BI 2536 | PLK | 1.41535047 | 2.2972E-05 |
| GZD824 Dimesylate | Bcr-Abl | 1.43376323 | 0.00912023 |
| Flavopiridol HCl | CDK | 1.69272191 | 0.01277002 |
| AZD5438 | CDK | 1.87106666 | 0.14622764 |
| LY2090314 | GSK-3 | 1.90982837 | 0.00889679 |
| AZD1080 | GSK-3 | 1.95297659 | 0.00483577 |
| AT9283 | Aurora Kinase, Bcr-Abl, JAK | 2.16315015 | 0.09123815 |
| CHIR-98014 | GSK-3 | 3.92835163 | 0.0006772 |

The terms SU-329 and SU20668-0329-01 refer to the same compound.

REFERENCES

1. Cokorinos E C, Delmore J, Reyes A R, Albuquerque B, Kjøbsted R, Jørgensen N O, Tran J L, Jatkar A, Cialdea K, Esquejo R M, Meissen J, Calabrese M F, Cordes J, Moccia R, Tess D, Salatto C T, Coskran T M, Opsahl A C, Flynn D, Blatnik M, Li W, Kindt E, Foretz M, Viollet B, Ward J, Kurumbail R G, Kalgutkar A S, Wojtaszewski J F P, Cameron K O, Miller R A. Activation of Skeletal Muscle AMPK Promotes Glucose Disposal and Glucose Lowering in Non-human Primates and Mice. Cell Metab. 2017 May 2; 25(5):1147-1159.e10. doi: 10.1016/j.cmet.2017.04.010. PubMed PMID: 28467931.

2. Myers R W, Guan H P, Ehrhart J, Petrov A, Prahalada S, Tozzo E, Yang X, Kurtz M M, Trujillo M, Gonzalez Trotter D, Feng D, Xu S, Eiermann G, Holahan M A, Rubins D, Conarello S, Niu X, Souza S C, Miller C, Liu J, Lu K, Feng W, Li Y, Painter R E, Milligan J A, He H, Liu F, Ogawa A, Wisniewski D, Rohm R J, Wang L, Bunzel M, Qian Y, Zhu W, Wang H, Bennet B, LaFranco Scheuch L, Fernandez G E, Li C, Klimas M, Zhou G, van Heek M, Biftu T, Weber A, Kelley D E, Thornberry N, Erion M D, Kemp D M, Sebhat I K. Systemic pan-AMPK activator M K-8722 improves glucose homeostasis but induces cardiac hypertrophy. Science. 2017 Aug. 4; 357

(6350): 507-511. doi:10.1126/science.aah5582. Epub 2017 Jul. 13. PubMed PMID: 28705990.
3. Jeppesen J, Maarbjerg S J, Jordy A B, Fritzen A M, Pehmoller C, Sylow L, Serup A K, Jessen N, Thorsen K, Prats C, Qvortrup K, Dyck J R, Hunter R W, Sakamoto K, Thomson D M, Schjerling P, Wojtaszewski J F, Richter E A, Kiens B. LKB1 regulates lipid oxidation during exercise independently of AMPK. Diabetes. 2013 May; 62(5): 1490-9. doi: 10.2337/db12-1160. Epub 2013 Jan. 24. PubMed PMID: 23349504; PubMed Central PMCID: PMC3636614.
4. Zequiraj et al. Science, PLOS Biology, 2009.
5. van Aalten, 2009
6. U.S. Pat. No. 8,841,308

What is claimed is:

1. A compound having the formula:

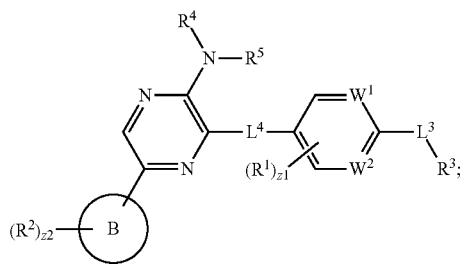

(I)

wherein,

W¹ is N, CH, or CR¹;
W² is N, CH, or CR¹;

R¹ is independently halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1D}$, $-SO_{v1}NR^{1A}R^{1B}$, $-NR^{1C}NR^{1A}R^{1B}$, $-ONR^{1A}R^{1B}$, $-NHC(O)NR^{1C}NR^{1A}R^{1B}$, $-NHC(O)NR^{1A}R^{1B}$, $-N(O)_{m1}$, $-NR^{1A}R^{1B}$, $-C(O)R^{1C}$, $-C(O)-OR^{1C}$, $-C(O)NR^{1A}R^{1B}$, $-OR^{1D}$, $-NR^{1A}SO_2R^{1D}$, $-NR^{1A}C(O)R^{1C}$, $-NR^{1A}C(O)OR^{1C}$, $-NR^{1A}OR^{1C}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R¹ substituents may optionally be joined to form a substituted or unsubstituted cycloalkyl, substituted or unsubstituted heterocycloalkyl, substituted or unsubstituted aryl, or substituted or unsubstituted heteroaryl;

z1 is an integer from 0 to 4;

Ring B is aryl or heteroaryl;

R² is independently oxo, halogen, $-CX^2_3$, $-CHX^2_2$, $-CH_2X^2$, $-OCX^2_3$, $-OCH_2X^2$, $-OCHX^2_2$, $-CN$, —SO$_{n2}$R$^{2D}$, —SO$_{v2}$NR$^{2A}$R$^{2B}$, —NR$^{2C}$NR$^{2A}$R$^{2B}$, —ONR$^{2A}$R$^{2B}$, —NHC(O)NR$^{2C}$NR$^{2A}$R$^{2B}$, —NHC(O)NR$^{2A}$R$^{2B}$, —N(O)$_{m2}$, —NR$^{2A}$R$^{2B}$, —C(O)R$^{2C}$, —C(O)—OR$^{2C}$, —C(O)NR$^{2A}$R$^{2B}$, —OR$^{2D}$, —NR$^{2A}$SO$_2$R$^{2D}$, —NR$^{2A}$C(O)R$^{2C}$, —NR$^{2A}$C(O) OR$^{2C}$, —NR$^{2A}$OR$^{2C}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^2$ substituents may optionally be joined to form a substituted or unsubstituted cycloalkyl, substituted or unsubstituted heterocycloalkyl, substituted or unsubstituted aryl, or substituted or unsubstituted heteroaryl;

z2 is an integer from 0 to 6;

L$^3$ is a bond, —NH—, —O—, —C(O)—, —C(O)NH—, —NHC(O)—, —NHC(O)NH—, —C(O)O—, —OC(O)—, substituted or unsubstituted alkylene, or substituted or unsubstituted heteroalkylene;

R$^3$ is —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO$_2$R$^{3D}$, —NR$^{3C}$SO$_2$NR$^{3A}$R$^{3B}$, —NR$^{3A}$C(O)R$^{3C}$, —NR$^{3A}$C(O) OR$^{3C}$, —SO$_2$R$^{3C}$, —SO$_2$-L$^{3A}$-R$^{3C}$, —SO$_2$NR$^{3A}$R$^{3B}$, —SO$_2$NR$^{3A}$SO$_2$R$^{3C}$, —SO$_2$NR$^{3A}$P(O)(OR$^{3C}$)(OR$^{3D}$), —SO$_2$P(O)(OR$^{3C}$)(OR$^{3D}$), —SO$_2$CH$_2$P(O)(OR$^{3C}$)(OR$^{3D}$), —SO$_2$P(O)(OR$^{3D}$)(NR$^{3A}$R$^{3B}$), —SO$_2$P(O)(R$^{3C}$)(OR$^{3D}$), —SO$_2$P(O)(R$^{3C}$)(R$^{3D}$), —SO$_2$-L$^{3A}$-P(O)(OR$^{3C}$)(OR$^{3D}$), —SO$_2$-L$^{3A}$-P(O)(OR$^{3D}$)(NR$^{3A}$R$^{3B}$), —SO$_2$-L$^{3A}$-P(O)(R$^{3C}$)(OR$^{3D}$), —SO$_2$-L$^{3A}$-P(O)(R$^{3C}$)(R$^{3D}$), —S(O)(NR$^{3A}$)R$^{3C}$, —C(O)OR$^{3C}$, —C(O)NR$^{3A}$R$^{3B}$, —NR$^{3A}$C(O)OR$^{3C}$ substituted or unsubstituted cycloalkyl, substituted or unsubstituted heterocycloalkyl, substituted or unsubstituted aryl, or substituted or unsubstituted heteroaryl;

L$^{3A}$ is —CH$_2$—, —CH(CH$_3$)—, —C(CH$_3$)$_2$—, —CH(X$^{3A}$)—, or —C(X$^{3A}$)$_2$—;

L$^4$ is —C(O)NH— or —NHC(O)—;

R$^4$ and R$^5$ are independently hydrogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^4$ and R$^5$ substituents bonded to the same nitrogen may optionally be joined to form a substituted or unsubstituted heterocycloalkyl or substituted or unsubstituted heteroaryl;

R$^{1A}$, R$^{1B}$, R$^{1C}$, R$^{1D}$, R$^{2A}$, R$^{2B}$, R$^{2C}$, and R$^{2D}$ are independently hydrogen, —CCl$_3$, —CBr$_3$, —CF$_3$, —CI$_3$, CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl;

R$^{3A}$, R$^{3B}$, R$^{3C}$, and R$^{3D}$ are independently hydrogen, oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —N$_3$, —SO$_2$CH$_3$, —NHC(O)CH$_3$, —C(O)CH$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{3A}$ and R$^{3B}$ substituents bonded to the same nitrogen atom may optionally be joined to form a substituted or unsubstituted heterocycloalkyl or substituted or unsubstituted heteroaryl; R$^{3A}$ and R$^{3D}$ substituents may optionally be joined to form a substituted or unsubstituted heterocycloalkyl or substituted or unsubstituted heteroaryl;

X$^1$, X$^2$, and X$^{3A}$ are independently —F, —Cl, —Br, or —I;

n1 and n2 are independently an integer from 0 to 4; and m1, m2, v1, and v2 are independently 1 or 2;

wherein Ring B is not pyridyl.

2. The compound of claim 1, having the formula:

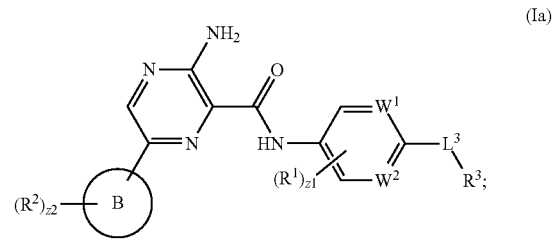

(Ia)

wherein,

R$^1$ is independently halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1D}$, —SO$_{v1}$NR$^{1A}$R$^{1B}$, —NR$^{1C}$NR$^{1A}$R$^{1B}$, ONR$^{1A}$R$^{1B}$, —NHC(O)NR$^{1C}$NR$^{1A}$R$^{1B}$, —NHC(O)NR$^{1A}$R$^{1B}$, —N(O)$_{m1}$, —NR$^{1A}$R$^{1B}$, —C(O)R$^{1C}$, —C(O)—OR$^{1C}$, —C(O)NR$^{1A}$R$^{1B}$, —OR$^{1D}$, —NR$^{1A}$SO$_2$R$^{1D}$, —NR$^{1A}$C(O)R$^{1C}$, —NR$^{1A}$C(O)OR$^{1C}$, —NR$^{1A}$OR$^{1C}$, —N$_3$, substituted or unsubstituted C$_1$-C$_6$ alkyl, substituted or unsubstituted 2 to 6 membered heteroalkyl, substituted or unsubstituted C$_3$-C$_6$ cycloalkyl, substituted or unsubstituted 3 to 6 membered heterocycloalkyl, substituted or unsubstituted C$_6$-C$_{10}$ aryl, or substituted or unsubstituted 5 to 10 membered heteroaryl; two adjacent R$^1$ substituents may optionally be joined to form a substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl;

Ring B is phenyl or 5 to 10 membered heteroaryl;

$R^2$ is independently oxo, halogen, —$CX^2_3$, —$CHX^2_2$, —$CH_2X^2$, —$OCX^2_3$, —$OCH_2X^2$, —$OCHX^2_2$, —CN, —$SO_{n2}R^{2D}$, —$SO_2NR^{2A}R^{2B}$, —$NR^{2C}NR^{2A}R^{2B}$, —$ONR^{2A}R^{2B}$, —NHC(O)$NR^{2C}NR^{2A}R^{2B}$, —NHC(O)$NR^{2A}R^{2B}$, —$N(O)_{m2}$, —$NR^{2A}R^{2B}$, —C(O)$R^{2C}$, —C(O)—$OR^{2C}$, —C(O)$NR^{2A}R^{2B}$, —$OR^{2D}$, —$NR^{2A}SO_2R^{2D}$, —$NR^{2A}C(O)R^{2C}$, —$NR^{2A}C(O)OR^{2C}$, —$NR^{2A}OR^{2C}$, —$N_3$, substituted or unsubstituted $C_1$-$C_6$ alkyl, substituted or unsubstituted 2 to 6 membered heteroalkyl, substituted or unsubstituted $C_3$-$C_6$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl; two adjacent $R^2$ substituents may optionally be joined to form a substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl; and $L^3$ is a bond, —NH—, —O—, —C(O)—, —C(O)NH—, —NHC(O)—, —NHC(O)NH—, —C(O)O—, —OC(O)—, substituted or unsubstituted $C_1$-$C_6$ alkylene, or substituted or unsubstituted 2 to 6 membered heteroalkylene.

3. The compound of claim 1, having the formula:

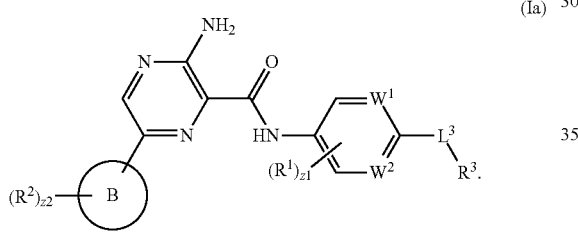

(Ia)

4. The compound of claim 1, wherein $R^3$ is —P(O)(OR$^{3C}$)(OR$^{3D}$), —P(O)(OR$^{3D}$)(NR$^{3A}$R$^{3B}$), —P(O)(R$^{3C}$)(OR$^{3D}$), —P(O)(R$^{3C}$)(R$^{3D}$), —P(S)(OR$^{3C}$)(OR$^{3D}$), —P(S)(OR$^{3D}$)(NR$^{3A}$R$^{3B}$), —P(S)(R$^{3C}$)(OR$^{3D}$), —P(S)(R$^{3C}$)(R$^{3D}$), —NR$^{3A}$SO$_2$R$^{3D}$, —NR$^{3C}$SO$_2$NR$^{3A}$R$^{3B}$, —NR$^{3A}$C(O)R$^{3C}$, —NR$^{3A}$C(O)OR$^{3C}$, —SO$_2$R$^{3C}$, —SO$_2$-L$^{3A}$-R$^{3C}$, —SO$_2$NR$^{3A}$R$^{3B}$, —SO$_2$NR$^{3A}$SO$_2$R$^{3C}$, —SO$_2$NR$^{3A}$P(O)(OR$^{3C}$)(OR$^{3D}$), —SO$_2$P(O)(OR$^{3C}$)(OR$^{3D}$), —SO$_2$CH$_2$P(O)(OR$^{3C}$)(OR$^{3D}$), —SO$_2$P(O)(OR$^{3D}$)(NR$^{3A}$R$^{3B}$), —SO$_2$P(O)(R$^{3C}$)(OR$^{3D}$), —SO$_2$P(O)(R$^{3C}$)(R$^{3D}$), —SO$_2$-L$^{3A}$-P(O)(OR$^{3C}$)(OR$^{3D}$), —SO$_2$-L$^{3A}$-P(O)(OR$^{3D}$)(NR$^{3A}$R$^{3B}$), —SO$_2$-L$^{3A}$-P(O)(R$^{3C}$)(OR$^{3D}$), —SO$_2$-L$^{3A}$-P(O)(R$^{3C}$)(R$^{3D}$), —S(O)(NR$^{3A}$)R$^{3C}$, —C(O)OR$^{3C}$, —C(O)NR$^{3A}$R$^{3B}$, or —NR$^{3A}$C(O)OR$^{3C}$.

5. A pharmaceutical composition comprising the compound of claim 1 and a pharmaceutically acceptable excipient.

6. A method of treating a cancer in a subject in need thereof, said method comprising administering to the subject in need thereof an effective amount of a compound of claim 1.

7. A method of treating diabetes in a subject in need thereof, said method comprising administering to the subject in need thereof an effective amount of a compound of claim 1.

8. The compound of claim 1, wherein $W^1$ and $W^2$ are CH.

9. The compound of claim 1, wherein $R^3$ is —SO$_2$CH$_2$P(O)(OR$^{3C}$)(OR$^{3D}$), and R$^{3C}$ and R$^{3D}$ are independently substituted or unsubstituted $C_1$-$C_6$ alkyl.

10. The compound of claim 1, wherein $R^3$ is

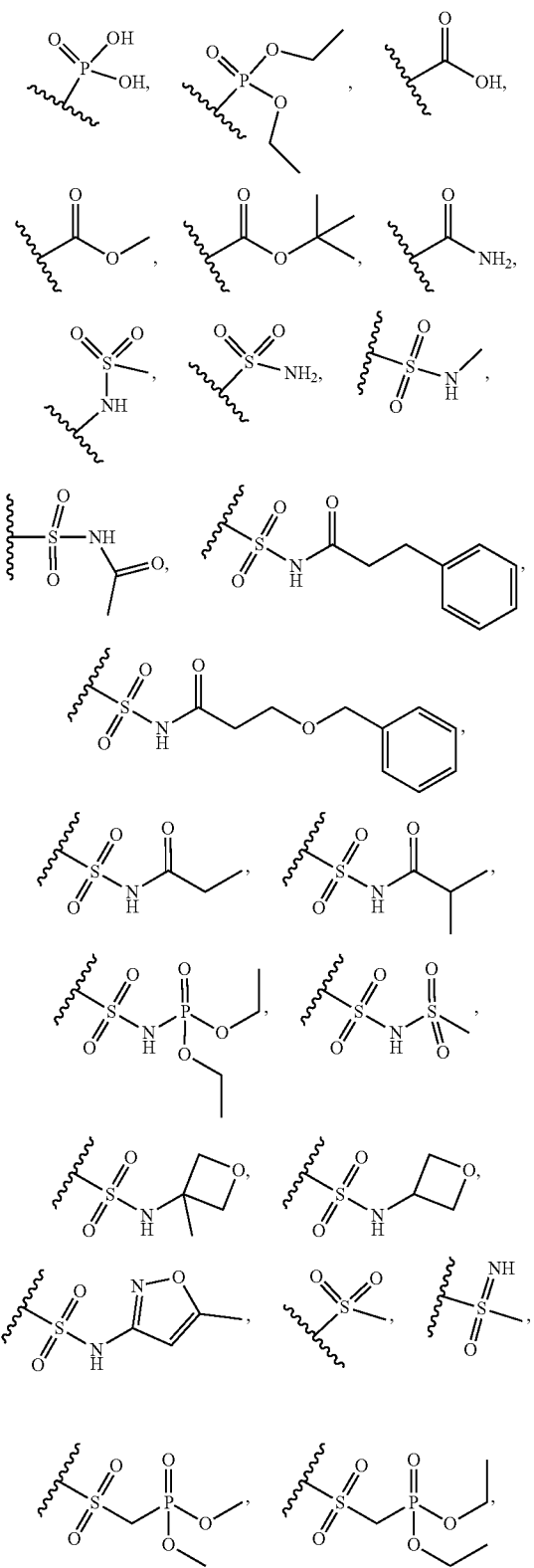

-continued
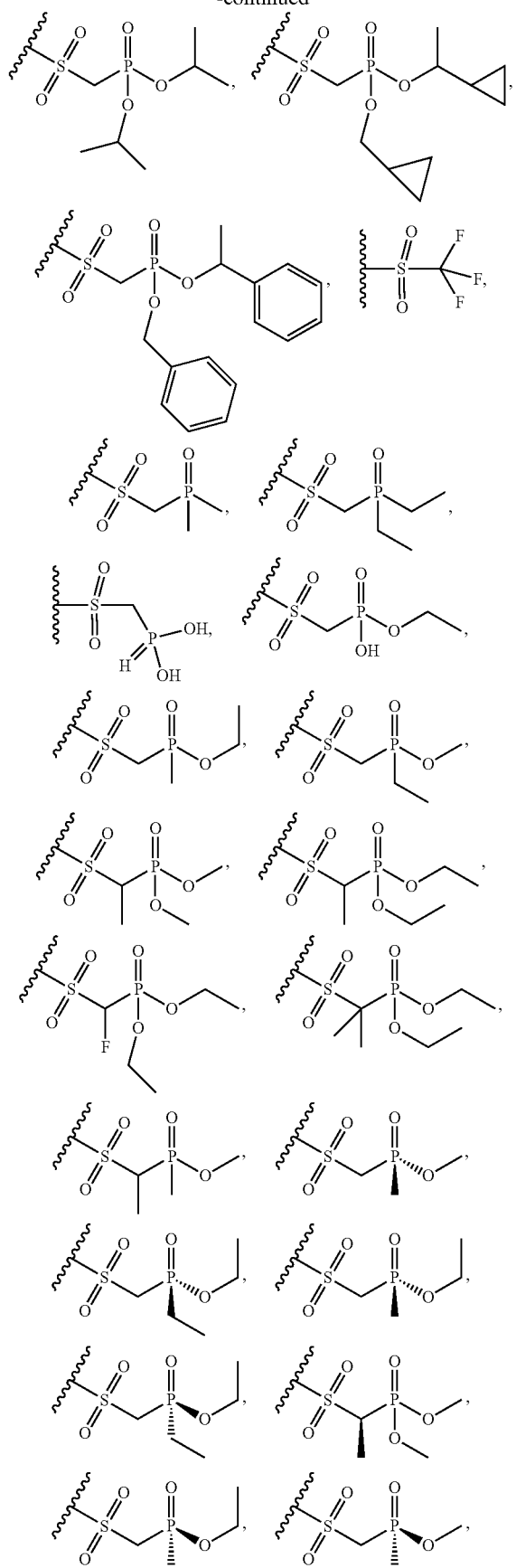
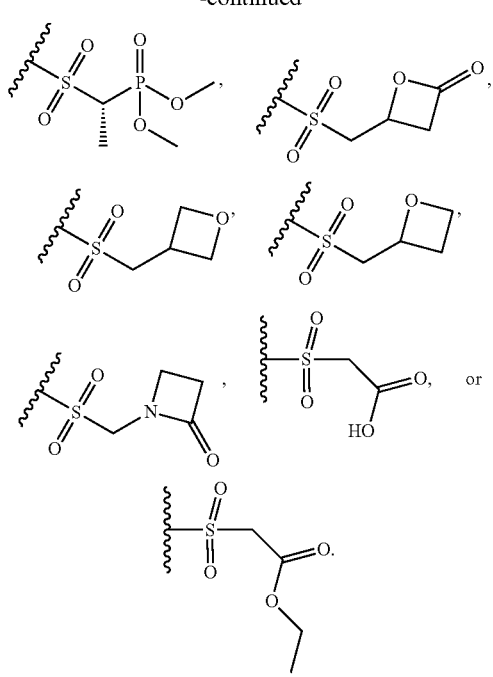
11. The compound of claim 1, wherein $L^3$ is a bond or —CH$_2$—.
12. The compound of claim 1, wherein Ring B is phenyl, thienyl, indazolyl, indolyl, pyrazolyl, pyrimidinyl, or benzothienyl.
13. The compound of claim 1, having the formula:
(Ib)
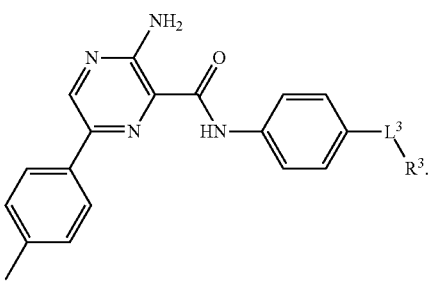
14. The compound of claim 1, having the formula:
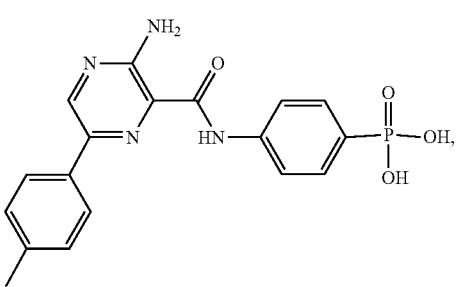

917
-continued
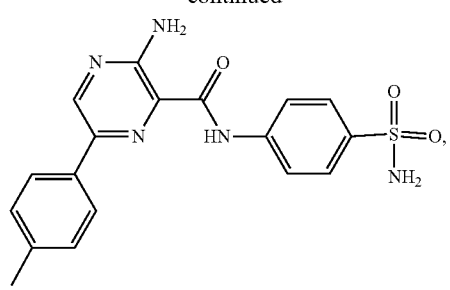
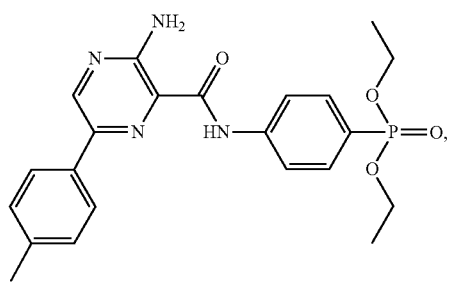
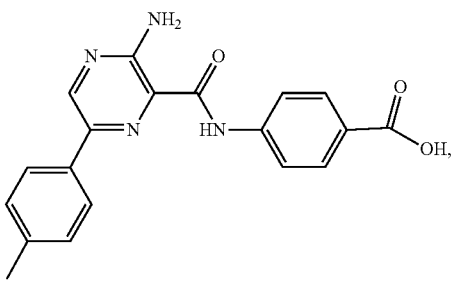
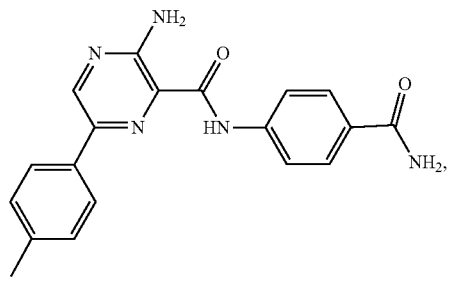
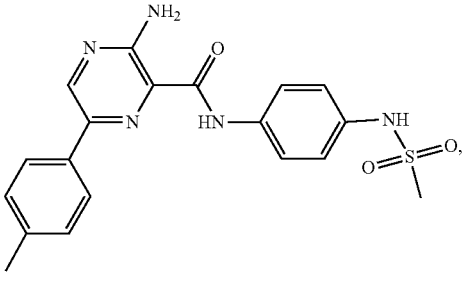
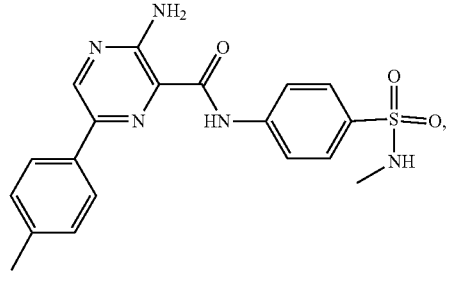
918
-continued
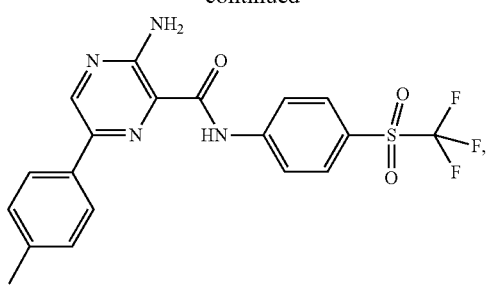
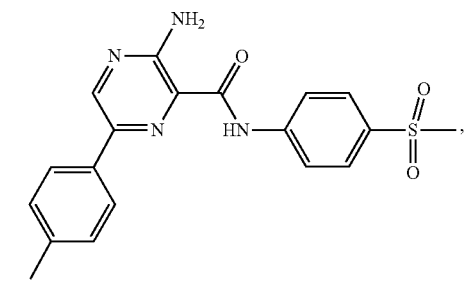
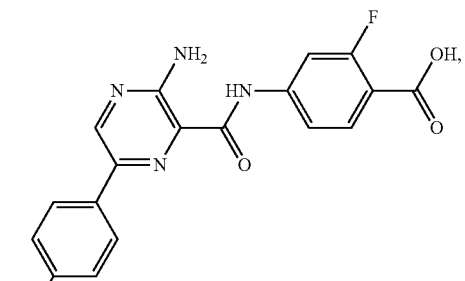
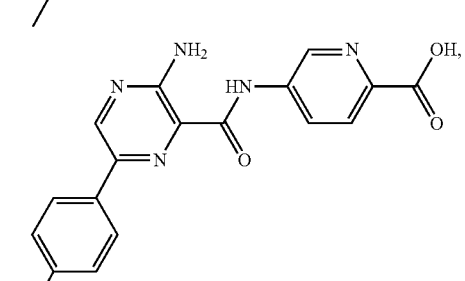
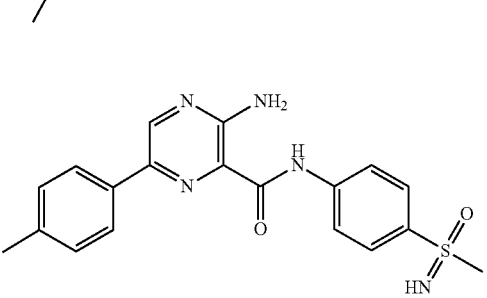
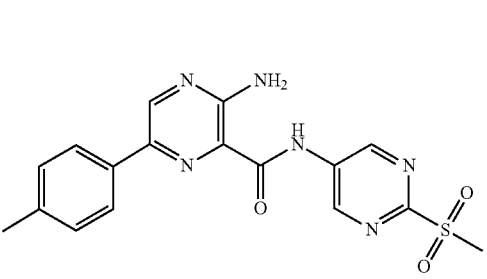

919
-continued
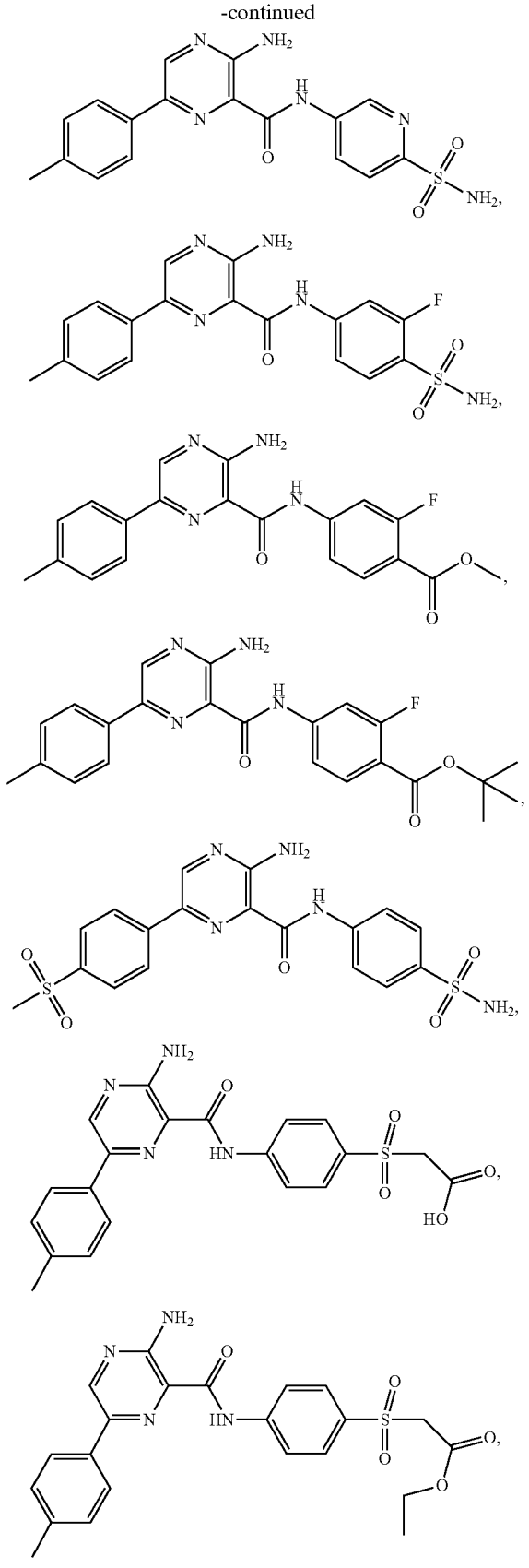
920
-continued
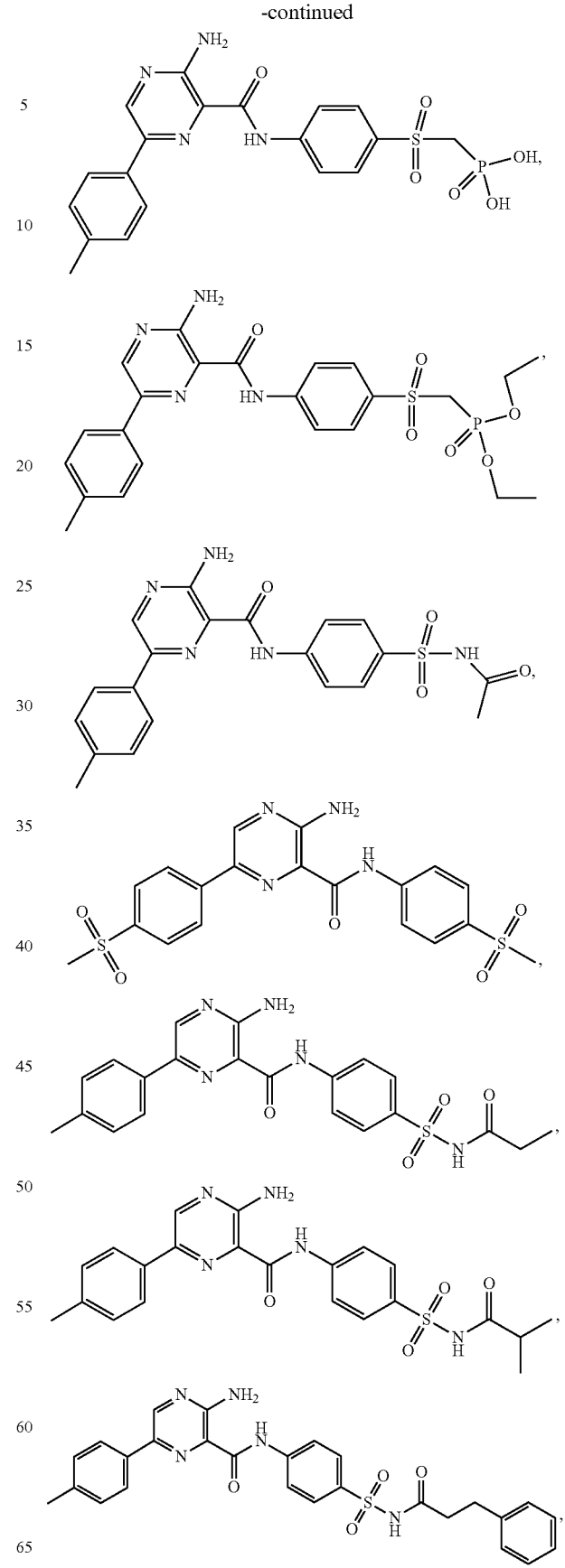

-continued
921
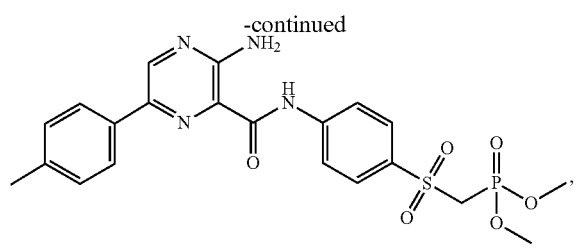
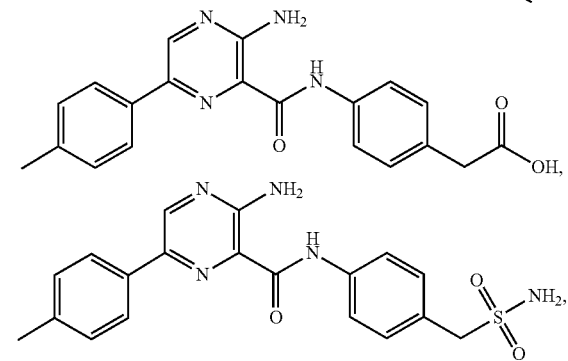
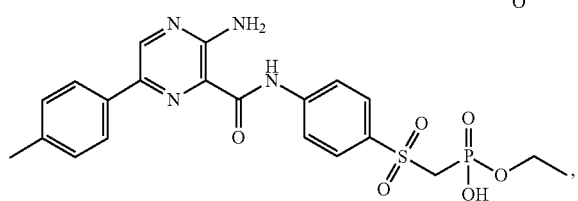
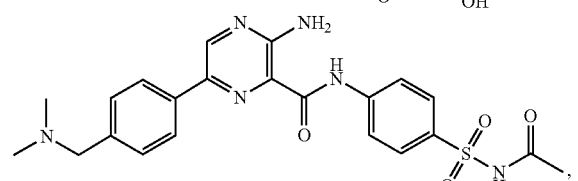
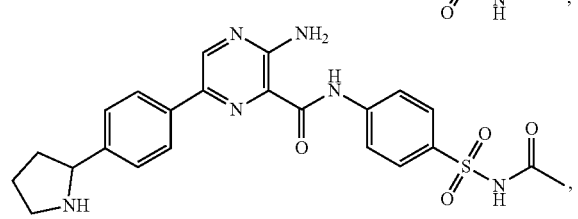
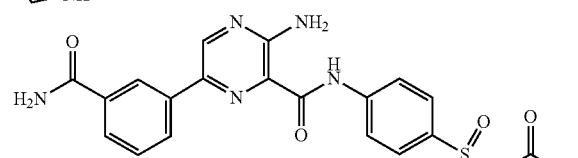
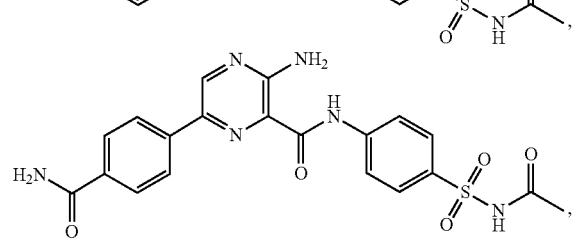
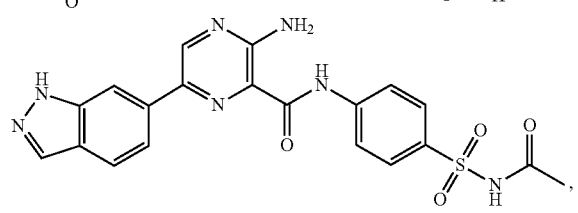
922
-continued
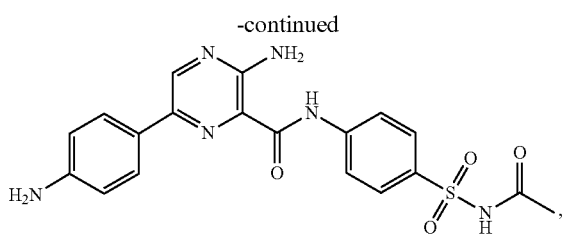
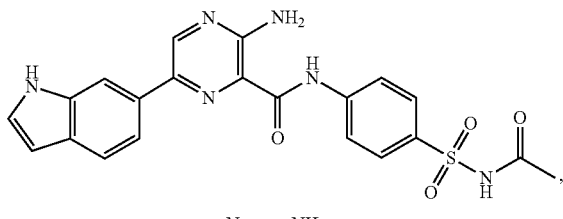
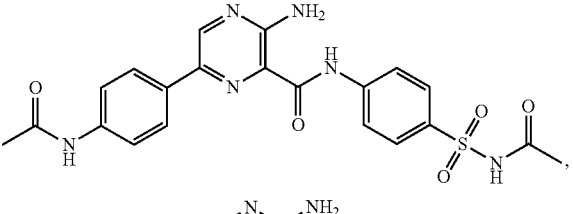
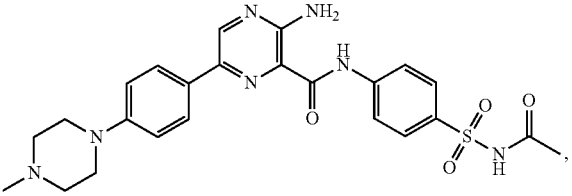
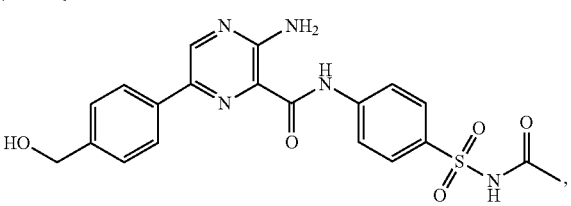
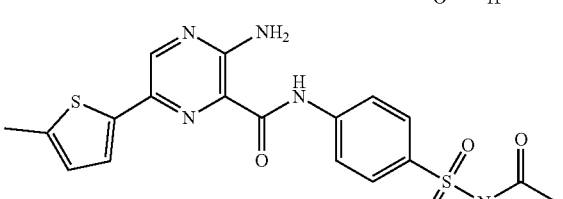
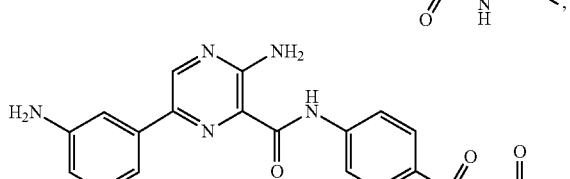
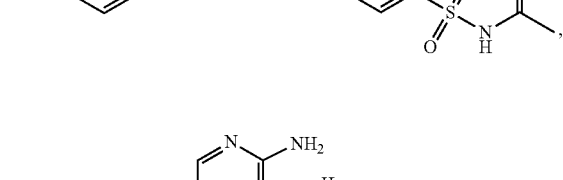
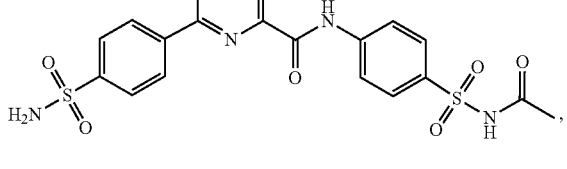

923
-continued
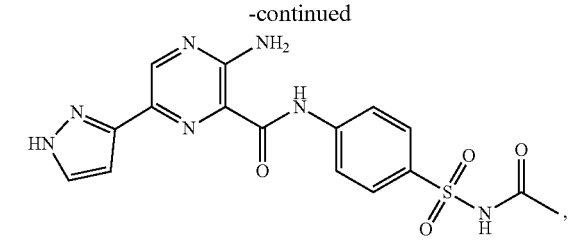
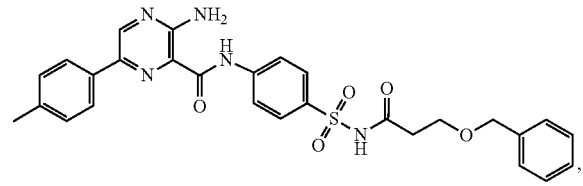
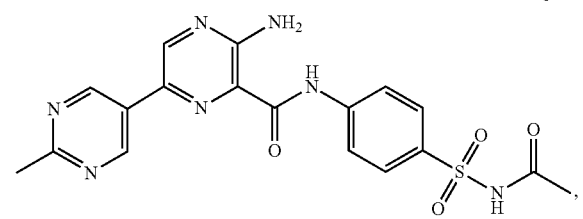
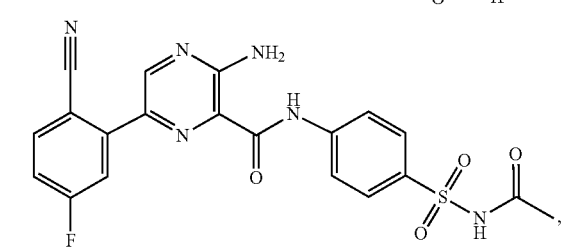
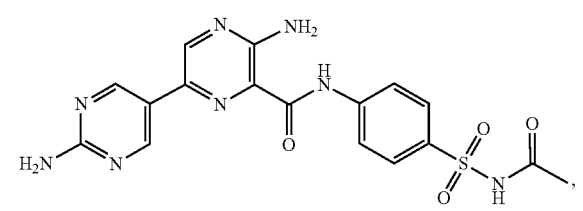
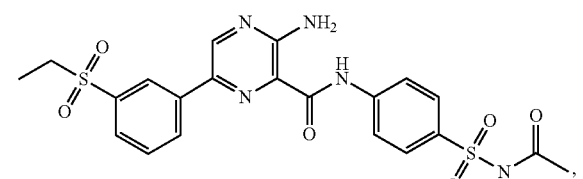
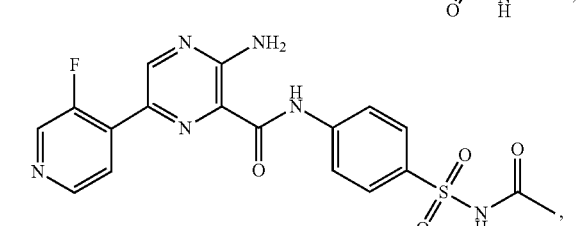
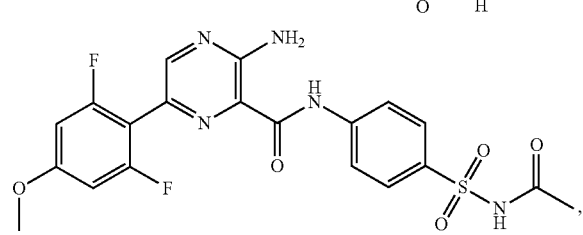
924
-continued
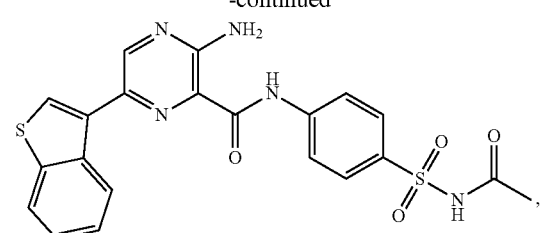
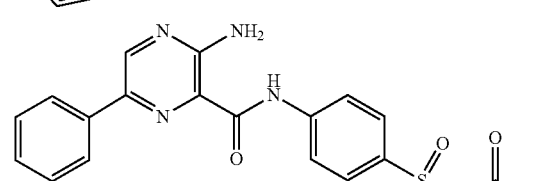
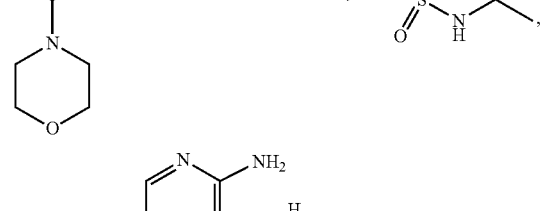
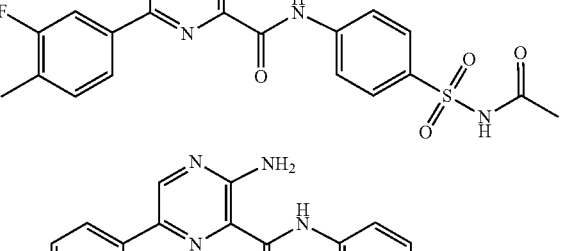
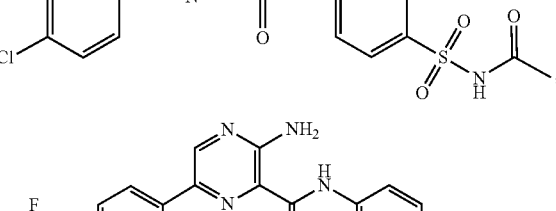
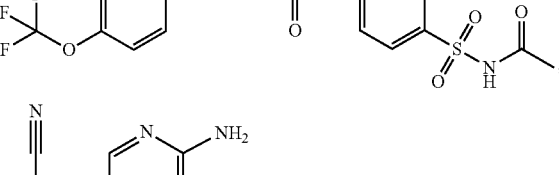
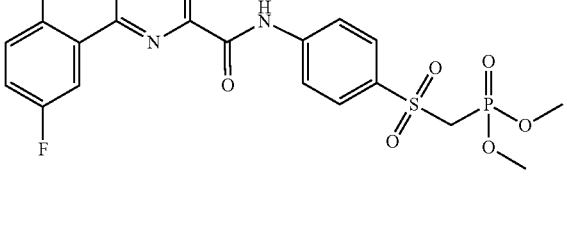
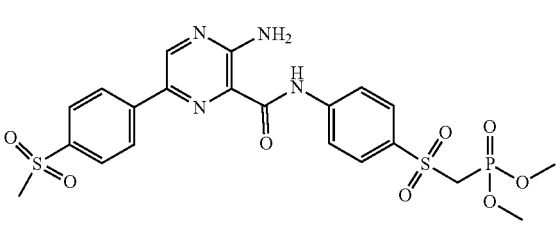

925
-continued
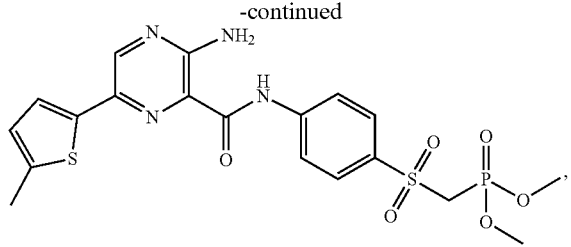
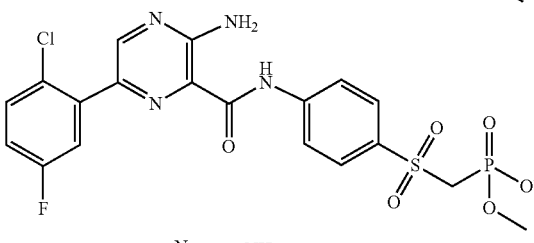
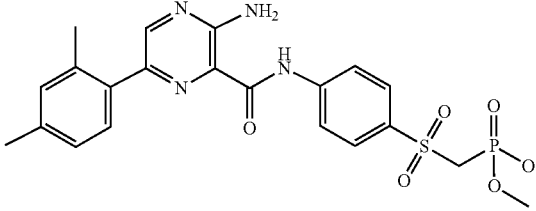
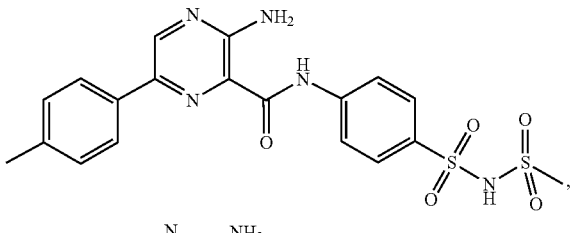
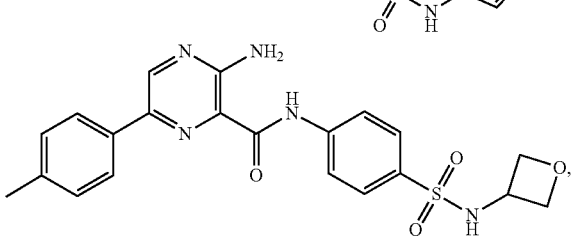
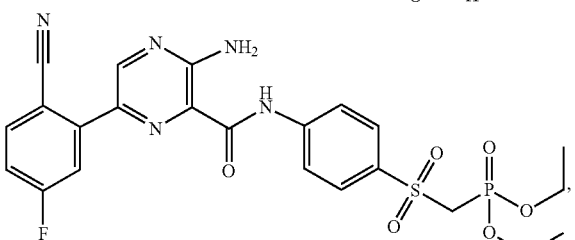
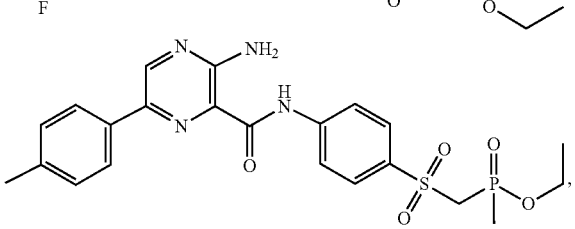
926
-continued
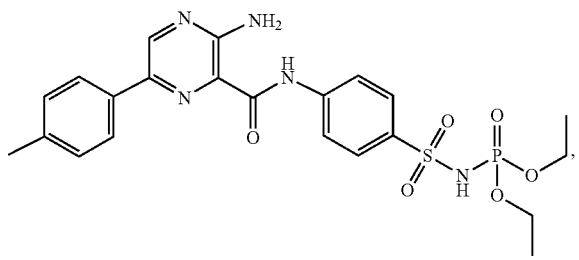
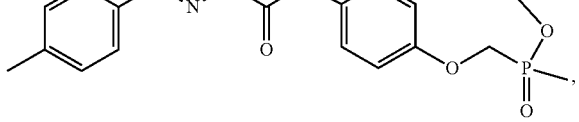
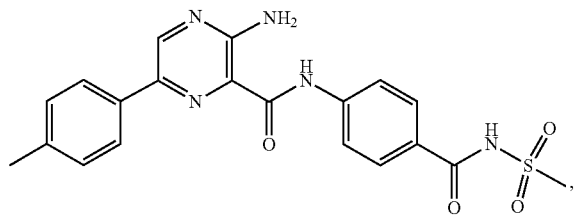
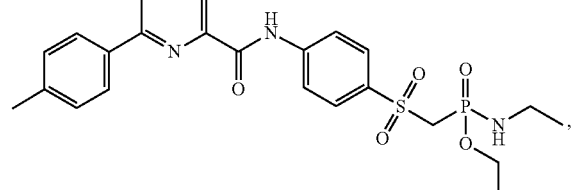
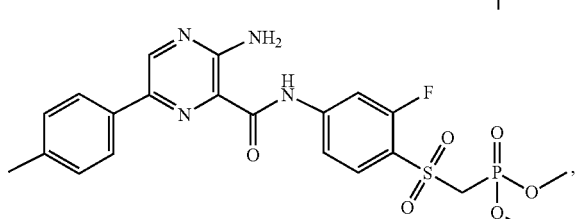
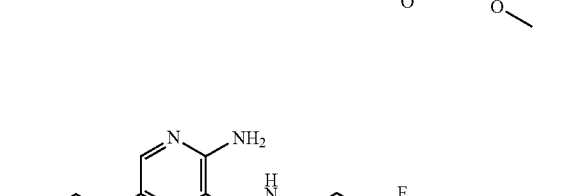
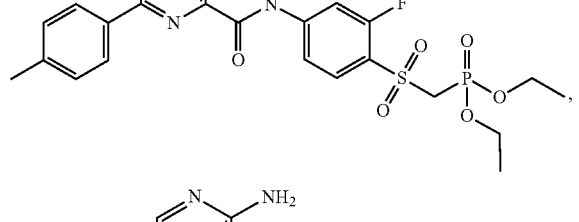
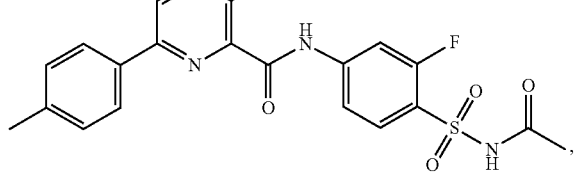

927
-continued
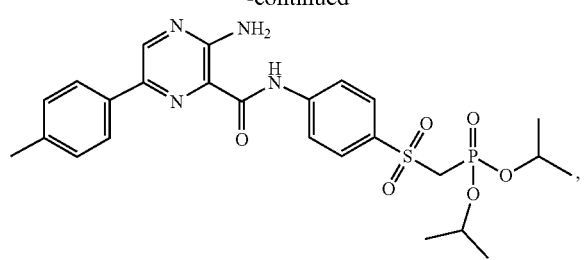
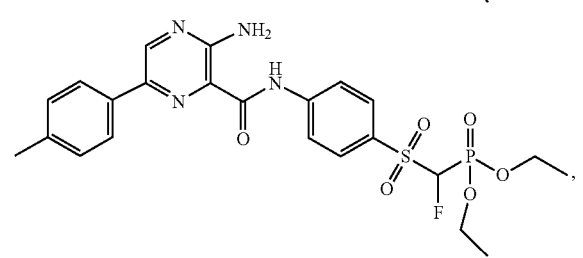
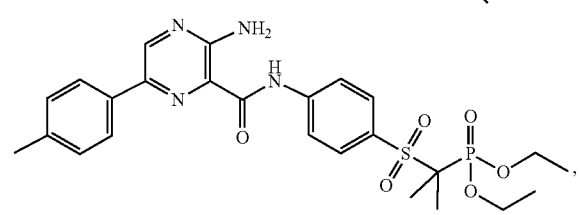
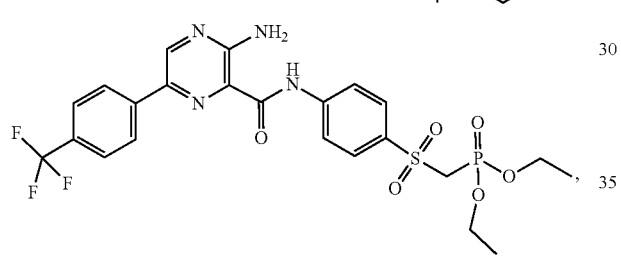
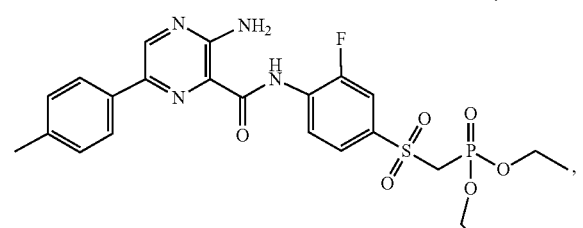
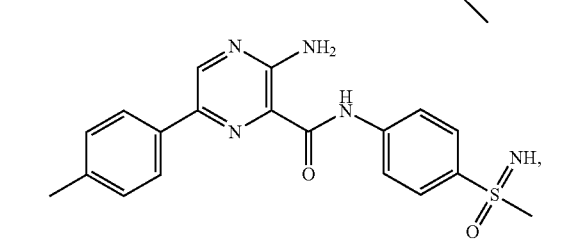
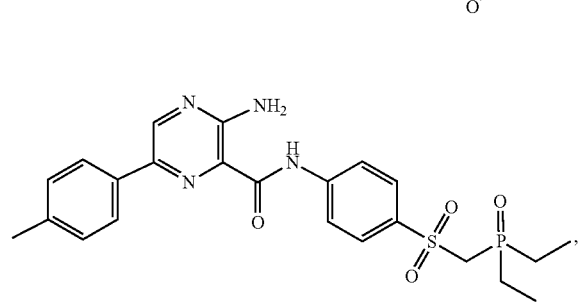
928
-continued
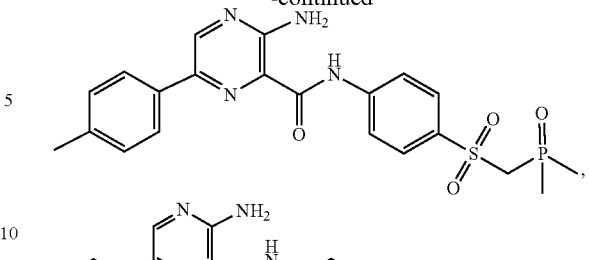
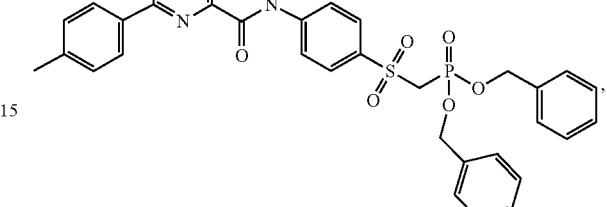
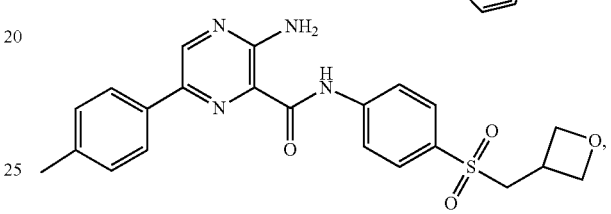
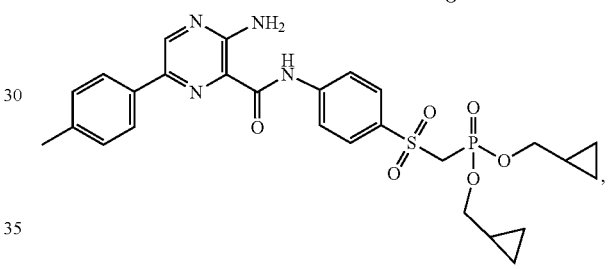
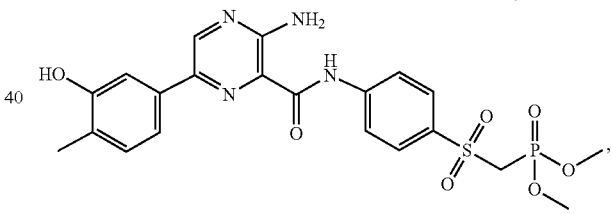
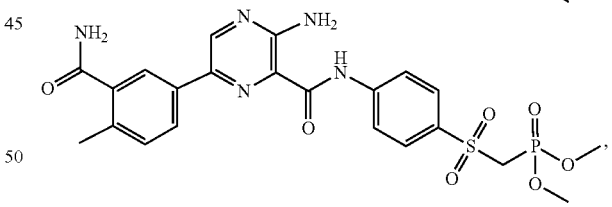
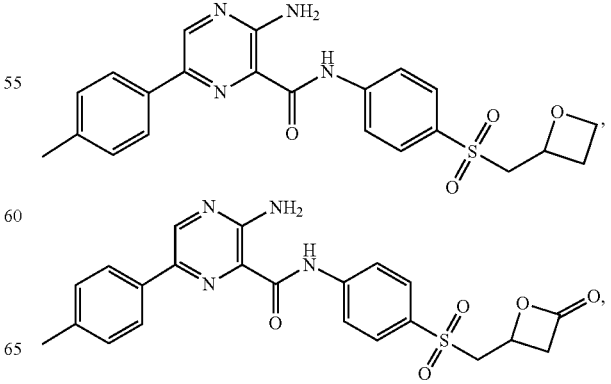

929
-continued
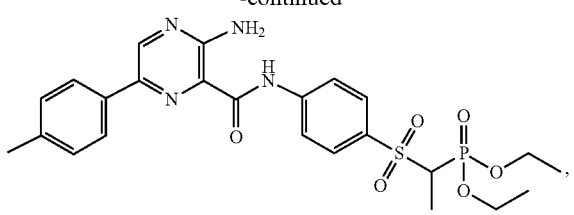
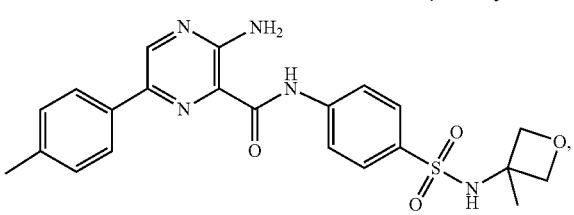
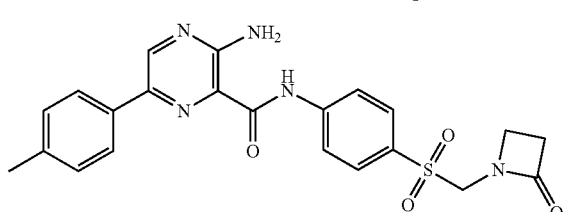
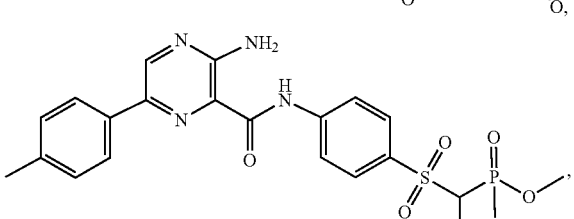
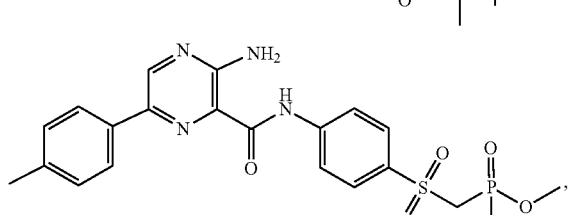
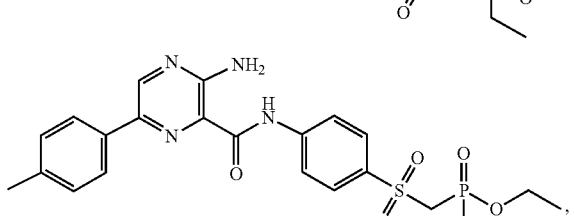
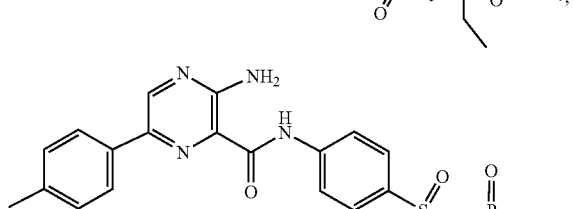
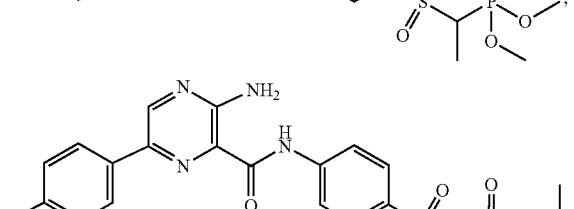
930
-continued
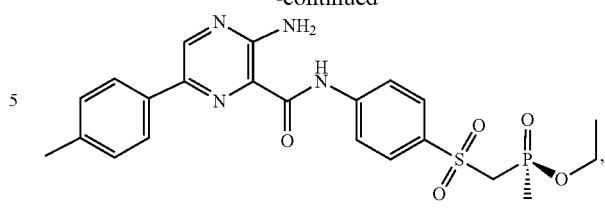
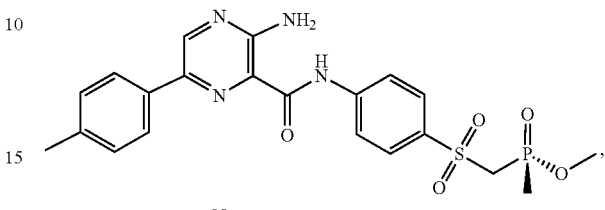
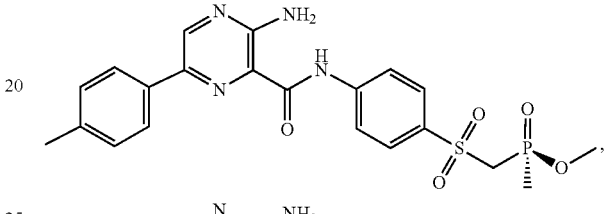
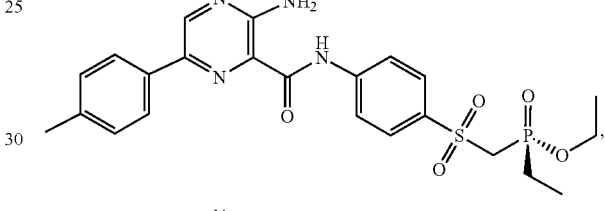
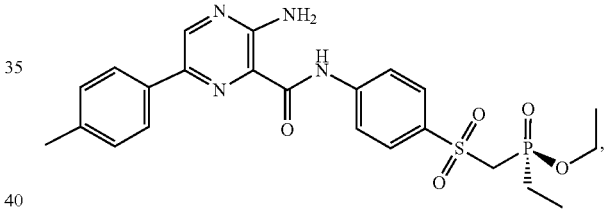
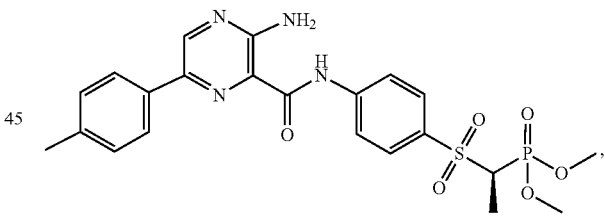
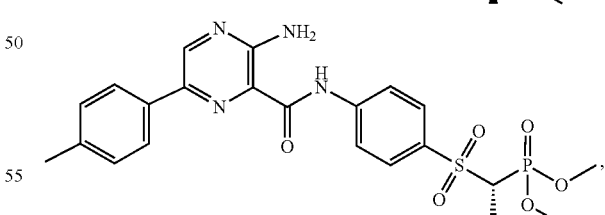
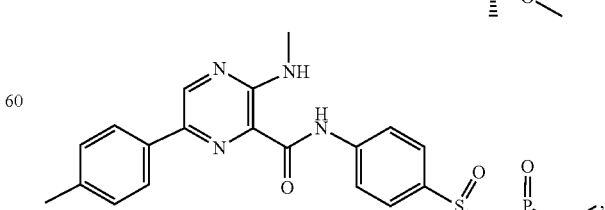

931
-continued
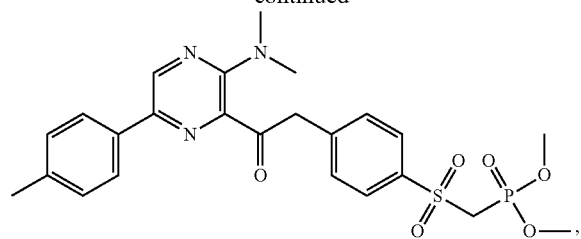
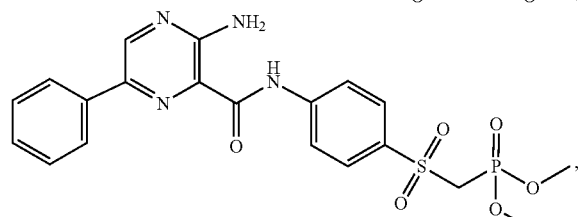
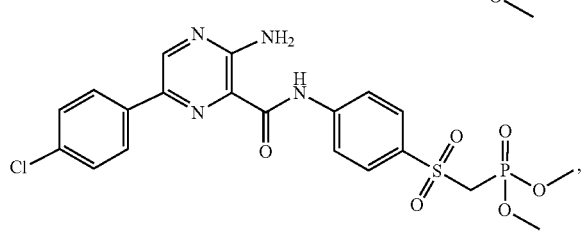
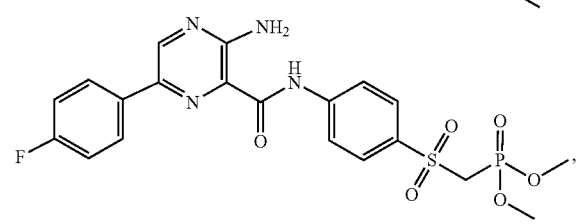
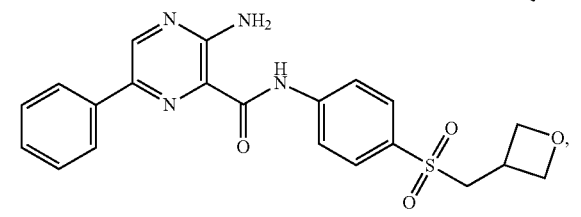
932
-continued
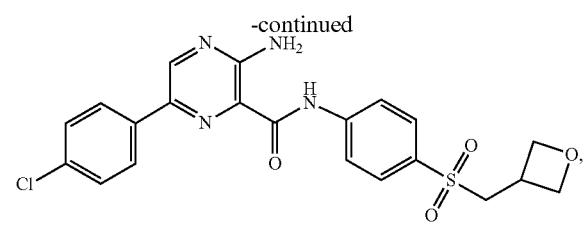
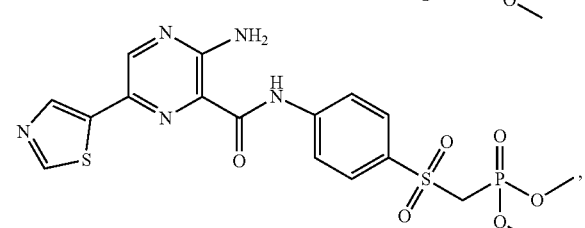
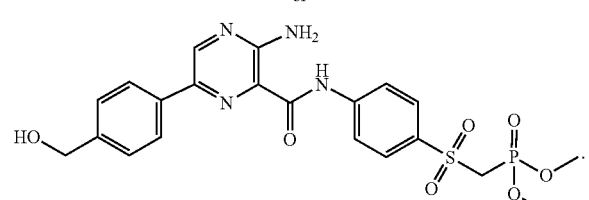
or
* * * * *

SEQUENCE LISTING

```
<160> NUMBER OF SEQ ID NOS: 7

<210> SEQ ID NO 1
<211> LENGTH: 429
<212> TYPE: PRT
<213> ORGANISM: Artificial Sequence
<220> FEATURE:
<223> OTHER INFORMATION: Synthetic polypeptide

<400> SEQUENCE: 1

Met Ser Phe Leu Val Ser Lys Pro Glu Arg Ile Arg Arg Trp Val Ser
1               5                   10                  15

Glu Lys Phe Ile Val Glu Gly Leu Arg Asp Leu Glu Leu Phe Gly Glu
            20                  25                  30

Gln Pro Pro Gly Asp Thr Arg Arg Lys Thr Asn Asp Ala Ser Ser Glu
        35                  40                  45

Ser Ile Ala Ser Phe Ser Lys Gln Glu Val Met Ser Ser Phe Leu Pro
    50                  55                  60

Glu Gly Gly Cys Tyr Glu Leu Leu Thr Val Ile Gly Lys Gly Phe Glu
65                  70                  75                  80

Asp Leu Met Thr Val Asn Leu Ala Arg Tyr Lys Pro Thr Gly Glu Tyr
                85                  90                  95

Val Thr Val Arg Arg Ile Asn Leu Glu Ala Cys Ser Asn Glu Met Val
            100                 105                 110

Thr Phe Leu Gln Gly Glu Leu His Val Ser Lys Leu Phe Asn His Pro
        115                 120                 125

Asn Ile Val Pro Tyr Arg Ala Thr Phe Ile Ala Asp Asn Glu Leu Trp
    130                 135                 140

Val Val Thr Ser Phe Met Ala Tyr Gly Ser Ala Lys Asp Leu Ile Cys
145                 150                 155                 160

Thr His Phe Met Asp Gly Met Asn Glu Leu Ala Ile Ala Tyr Ile Leu
                165                 170                 175

Gln Gly Val Leu Lys Ala Leu Asp Tyr Ile His His Met Gly Tyr Val
            180                 185                 190

His Arg Ser Val Lys Ala Ser His Ile Leu Ile Ser Val Asp Gly Lys
        195                 200                 205

Val Tyr Leu Ser Gly Leu Arg Ser Asn Leu Ser Met Ile Ser His Gly
    210                 215                 220

Gln Arg Gln Arg Val Val His Asp Phe Pro Lys Tyr Ser Val Lys Val
225                 230                 235                 240

Leu Pro Trp Leu Ser Pro Glu Val Leu Gln Gln Asn Leu Gln Gly Tyr
                245                 250                 255

Asp Ala Lys Ser Asp Ile Tyr Ser Val Gly Ile Thr Ala Cys Glu Leu
            260                 265                 270

Ala Asn Gly His Val Pro Phe Lys Asp Met Pro Ala Thr Gln Met Leu
        275                 280                 285

Leu Glu Lys Leu Asn Gly Thr Val Pro Cys Leu Leu Asp Thr Ser Thr
    290                 295                 300
```

```
Ile Pro Ala Glu Glu Leu Thr Met Ser Pro Ser Arg Ser Val Ala Asn
305                 310                 315                 320

Ser Gly Leu Ser Asp Ser Leu Thr Thr Ser Thr Pro Arg Pro Ser Asn
            325                 330                 335

Gly Asp Ser Pro Ser His Pro Tyr His Arg Thr Phe Pro His Phe His
            340                 345                 350

His Phe Val Glu Gln Cys Leu Gln Arg Asn Pro Asp Ala Arg Pro Ser
            355                 360                 365

Ala Ser Thr Leu Leu Asn His Ser Phe Phe Lys Gln Ile Lys Arg Arg
370                 375                 380

Ala Ser Glu Ala Leu Pro Glu Leu Leu Arg Pro Val Thr Pro Ile Thr
385                 390                 395                 400

Asn Phe Glu Gly Ser Gln Ser Gln Asp His Ser Gly Ile Phe Gly Leu
            405                 410                 415

Val Asn Leu Glu Glu Leu Glu Val Asp Asp Trp Glu Phe
            420                 425

<210> SEQ ID NO 2
<211> LENGTH: 431
<212> TYPE: PRT
<213> ORGANISM: Artificial Sequence
<220> FEATURE:
<223> OTHER INFORMATION: Synthetic polypeptide

<400> SEQUENCE: 2

Met Ser Phe Leu Val Ser Lys Pro Glu Arg Ile Arg Arg Trp Val Ser
1               5                   10                  15

Glu Lys Phe Ile Val Glu Gly Leu Arg Asp Leu Glu Leu Phe Gly Glu
            20                  25                  30

Gln Pro Pro Gly Asp Thr Arg Arg Lys Thr Asn Asp Ala Ser Ser Glu
        35                  40                  45

Ser Ile Ala Ser Phe Ser Lys Gln Glu Val Met Ser Ser Phe Leu Pro
50                  55                  60

Glu Gly Gly Cys Tyr Glu Leu Leu Thr Val Ile Gly Lys Gly Phe Glu
65                  70                  75                  80

Asp Leu Met Thr Val Asn Leu Ala Arg Tyr Lys Pro Thr Gly Glu Tyr
            85                  90                  95

Val Thr Val Arg Arg Ile Asn Leu Glu Ala Cys Ser Asn Glu Met Val
            100                 105                 110

Thr Phe Leu Gln Gly Glu Leu His Val Ser Lys Leu Phe Asn His Pro
        115                 120                 125

Asn Ile Val Pro Tyr Arg Ala Thr Phe Ile Ala Asp Asn Glu Leu Trp
130                 135                 140

Val Val Thr Ser Phe Met Ala Tyr Gly Ser Ala Lys Asp Leu Ile Cys
145                 150                 155                 160

Thr His Phe Met Asp Gly Met Asn Glu Leu Ala Ile Ala Tyr Ile Leu
            165                 170                 175

Gln Gly Val Leu Lys Ala Leu Asp Tyr Ile His His Met Gly Tyr Val
            180                 185                 190

His Arg Ser Val Lys Ala Ser His Ile Leu Ile Ser Val Asp Gly Lys
        195                 200                 205

Val Tyr Leu Ser Gly Leu Arg Ser Asn Leu Ser Met Ile Ser His Gly
210                 215                 220

Gln Arg Gln Arg Val Val His Asp Phe Pro Lys Tyr Ser Val Lys Val
225                 230                 235                 240
```

```
Leu Pro Trp Leu Ser Pro Glu Val Leu Gln Gln Asn Leu Gln Gly Tyr
                245                 250                 255

Asp Ala Lys Ser Asp Ile Tyr Ser Val Gly Ile Thr Ala Cys Glu Leu
            260                 265                 270

Ala Asn Gly His Val Pro Phe Lys Asp Met Pro Ala Thr Gln Met Leu
        275                 280                 285

Leu Glu Lys Leu Asn Gly Thr Val Pro Cys Leu Leu Asp Thr Ser Thr
    290                 295                 300

Ile Pro Ala Glu Glu Leu Thr Met Ser Pro Ser Arg Ser Val Ala Asn
305                 310                 315                 320

Ser Gly Leu Ser Asp Ser Leu Thr Thr Ser Thr Pro Arg Pro Ser Asn
                325                 330                 335

Gly Asp Ser Pro Ser His Pro Tyr His Arg Thr Phe Ser Pro His Phe
            340                 345                 350

His His Phe Val Glu Gln Cys Leu Gln Arg Asn Pro Asp Ala Arg Pro
        355                 360                 365

Ser Ala Ser Thr Leu Leu Asn His Ser Phe Phe Lys Gln Ile Lys Arg
    370                 375                 380

Arg Ala Ser Glu Ala Leu Pro Glu Leu Leu Arg Pro Val Thr Pro Ile
385                 390                 395                 400

Thr Asn Phe Glu Gly Ser Gln Ser Gln Asp His Ser Gly Ile Phe Gly
                405                 410                 415

Leu Val Thr Asn Leu Glu Glu Leu Glu Val Asp Asp Trp Glu Phe
            420                 425                 430

<210> SEQ ID NO 3
<211> LENGTH: 433
<212> TYPE: PRT
<213> ORGANISM: Artificial Sequence
<220> FEATURE:
<223> OTHER INFORMATION: Synthetic polypeptide

<400> SEQUENCE: 3

Met Glu Val Val Asp Pro Gln Gln Leu Gly Met Phe Thr Glu Gly Glu
1               5                   10                  15

Leu Met Ser Val Gly Met Asp Thr Phe Ile His Arg Ile Asp Ser Thr
                20                  25                  30

Glu Val Ile Tyr Gln Pro Arg Arg Lys Arg Ala Lys Leu Ile Gly Lys
            35                  40                  45

Tyr Leu Met Gly Asp Leu Leu Gly Glu Gly Ser Tyr Gly Lys Val Lys
        50                  55                  60

Glu Val Leu Asp Ser Glu Thr Leu Cys Arg Arg Ala Val Lys Ile Leu
65                  70                  75                  80

Lys Lys Lys Lys Leu Arg Arg Ile Pro Asn Gly Glu Ala Asn Val Lys
                85                  90                  95

Lys Glu Ile Gln Leu Leu Arg Arg Leu Arg His Lys Asn Val Ile Gln
            100                 105                 110

Leu Val Asp Val Leu Tyr Asn Glu Glu Lys Gln Lys Met Tyr Met Val
        115                 120                 125

Met Glu Tyr Cys Val Cys Gly Met Gln Glu Met Leu Asp Ser Val Pro
    130                 135                 140

Glu Lys Arg Phe Pro Val Cys Gln Ala His Gly Tyr Phe Cys Gln Leu
145                 150                 155                 160

Ile Asp Gly Leu Glu Tyr Leu His Ser Gln Gly Ile Val His Lys Asp
                165                 170                 175
```

-continued

```
Ile Lys Pro Gly Asn Leu Leu Leu Thr Thr Gly Gly Thr Leu Lys Ile
            180                 185                 190

Ser Asp Leu Gly Val Ala Glu Ala Leu His Pro Phe Ala Ala Asp Asp
        195                 200                 205

Thr Cys Arg Thr Ser Gln Gly Ser Pro Ala Phe Gln Pro Pro Glu Ile
    210                 215                 220

Ala Asn Gly Leu Asp Thr Phe Ser Gly Phe Lys Val Asp Ile Trp Ser
225                 230                 235                 240

Ala Gly Val Thr Leu Tyr Asn Ile Thr Thr Gly Leu Tyr Pro Phe Glu
                245                 250                 255

Gly Asp Asn Ile Tyr Lys Leu Phe Glu Asn Ile Gly Lys Gly Ser Tyr
            260                 265                 270

Ala Ile Pro Gly Asp Cys Gly Pro Pro Leu Ser Asp Leu Leu Lys Gly
        275                 280                 285

Met Leu Glu Tyr Glu Pro Ala Lys Arg Phe Ser Ile Arg Gln Ile Arg
    290                 295                 300

Gln His Ser Trp Phe Arg Lys His Pro Pro Ala Glu Ala Pro Val
305                 310                 315                 320

Pro Ile Pro Pro Ser Pro Asp Thr Lys Asp Arg Trp Arg Ser Met Thr
                325                 330                 335

Val Val Pro Tyr Leu Glu Asp Leu His Gly Ala Asp Glu Asp Glu Asp
            340                 345                 350

Leu Phe Asp Ile Glu Asp Asp Ile Ile Tyr Thr Gln Asp Phe Thr Val
        355                 360                 365

Pro Gly Gln Val Pro Glu Glu Ala Ser His Asn Gly Gln Arg Arg
    370                 375                 380

Gly Leu Pro Lys Ala Val Cys Met Asn Gly Thr Glu Ala Ala Gln Leu
385                 390                 395                 400

Ser Thr Lys Ser Arg Ala Glu Gly Arg Ala Pro Asn Pro Ala Arg Lys
                405                 410                 415

Ala Cys Ser Ala Ser Ser Lys Ile Arg Arg Leu Ser Ala Cys Lys Gln
            420                 425                 430

Gln

<210> SEQ ID NO 4
<211> LENGTH: 341
<212> TYPE: PRT
<213> ORGANISM: Artificial Sequence
<220> FEATURE:
<223> OTHER INFORMATION: Synthetic polypeptide

<400> SEQUENCE: 4

Met Pro Phe Pro Phe Gly Lys Ser His Lys Ser Pro Ala Asp Ile Val
1               5                   10                  15

Lys Asn Leu Lys Glu Ser Met Ala Val Leu Glu Lys Gln Asp Ile Ser
            20                  25                  30

Asp Lys Lys Ala Glu Lys Ala Thr Glu Glu Val Ser Lys Asn Leu Val
        35                  40                  45

Ala Met Lys Glu Ile Leu Tyr Gly Thr Asn Glu Lys Glu Pro Gln Thr
    50                  55                  60

Glu Ala Val Ala Gln Leu Ala Gln Glu Leu Tyr Asn Ser Gly Leu Leu
65                  70                  75                  80

Ser Thr Leu Val Ala Asp Leu Gln Leu Ile Asp Phe Glu Gly Lys Lys
                85                  90                  95

Asp Val Ala Gln Ile Phe Asn Asn Ile Leu Arg Arg Gln Ile Gly Thr
```

```
                    100                 105                 110
Arg Thr Pro Thr Val Glu Tyr Ile Cys Thr Gln Gln Asn Ile Leu Phe
            115                 120                 125

Met Leu Leu Lys Gly Tyr Glu Ser Pro Glu Ile Ala Leu Asn Cys Gly
        130                 135                 140

Ile Met Leu Arg Glu Cys Ile Arg His Glu Pro Leu Ala Lys Ile Ile
145                 150                 155                 160

Leu Trp Ser Glu Gln Phe Tyr Asp Phe Arg Tyr Val Glu Met Ser
                    165                 170                 175

Thr Phe Asp Ile Ala Ser Asp Ala Phe Ala Thr Phe Lys Asp Leu Leu
            180                 185                 190

Thr Arg His Lys Leu Leu Ser Ala Glu Phe Leu Glu Gln His Tyr Asp
        195                 200                 205

Arg Phe Phe Ser Glu Tyr Glu Lys Leu Leu His Ser Glu Asn Tyr Val
        210                 215                 220

Thr Lys Arg Gln Ser Leu Lys Leu Leu Gly Glu Leu Leu Asp Arg
225                 230                 235                 240

His Asn Phe Thr Ile Met Thr Lys Tyr Ile Ser Lys Pro Glu Asn Leu
                    245                 250                 255

Lys Leu Met Met Asn Leu Leu Arg Asp Lys Ser Arg Asn Ile Gln Phe
            260                 265                 270

Glu Ala Phe His Val Lys Val Phe Val Ala Asn Pro Asn Lys Thr
        275                 280                 285

Gln Pro Ile Leu Asp Ile Leu Leu Lys Asn Gln Ala Lys Leu Ile Glu
        290                 295                 300

Phe Leu Ser Lys Phe Gln Asn Asp Arg Thr Glu Asp Glu Gln Phe Asn
305                 310                 315                 320

Asp Glu Lys Thr Tyr Leu Val Lys Gln Ile Arg Asp Leu Lys Arg Pro
                    325                 330                 335

Ala Gln Gln Glu Ala
            340

<210> SEQ ID NO 5
<211> LENGTH: 693
<212> TYPE: PRT
<213> ORGANISM: Artificial Sequence
<220> FEATURE:
<223> OTHER INFORMATION: Synthetic polypeptide

<400> SEQUENCE: 5

Met Ala Thr Ser Gly Ala Asn Gly Pro Gly Ser Ala Thr Ala Ser Ala
1               5                   10                  15

Ser Asn Pro Arg Lys Phe Ser Glu Lys Ile Ala Leu Gln Lys Gln Arg
            20                  25                  30

Gln Ala Glu Glu Thr Ala Ala Phe Glu Glu Val Met Met Asp Ile Gly
        35                  40                  45

Ser Thr Arg Leu Gln Ala Gln Lys Leu Arg Leu Ala Tyr Thr Arg Ser
    50                  55                  60

Ser His Tyr Gly Gly Ser Leu Pro Asn Val Asn Gln Ile Gly Ser Gly
65                  70                  75                  80

Leu Ala Glu Phe Gln Ser Pro Leu His Ser Pro Leu Asp Ser Ser Arg
                85                  90                  95

Ser Thr Arg His His Gly Leu Val Glu Arg Val Gln Arg Asp Pro Arg
            100                 105                 110

Arg Met Val Ser Pro Leu Arg Arg Tyr Thr Arg His Ile Asp Ser Ser
```

-continued

```
            115                 120                 125
Pro Tyr Ser Pro Ala Tyr Leu Ser Pro Pro Glu Ser Ser Trp Arg
    130                 135                 140
Arg Thr Met Ala Trp Gly Asn Phe Pro Ala Glu Lys Gly Gln Leu Phe
145                 150                 155                 160
Arg Leu Pro Ser Ala Leu Asn Arg Thr Ser Asp Ser Ala Leu His
                165                 170                 175
Thr Ser Val Met Asn Pro Ser Pro Gln Asp Thr Tyr Pro Gly Pro Thr
                180                 185                 190
Pro Pro Ser Ile Leu Pro Ser Arg Arg Gly Gly Ile Leu Asp Gly Glu
            195                 200                 205
Met Asp Pro Lys Val Pro Ala Ile Glu Glu Asn Leu Leu Asp Asp Lys
    210                 215                 220
His Leu Leu Lys Pro Trp Asp Ala Lys Lys Leu Ser Ser Ser Ser Ser
225                 230                 235                 240
Arg Pro Arg Ser Cys Glu Val Pro Gly Ile Asn Ile Phe Pro Ser Pro
                245                 250                 255
Asp Gln Pro Ala Asn Val Pro Val Leu Pro Pro Ala Met Asn Thr Gly
                260                 265                 270
Gly Ser Leu Pro Asp Leu Thr Asn Leu His Phe Pro Pro Leu Pro
            275                 280                 285
Thr Pro Leu Asp Pro Glu Glu Thr Ala Tyr Pro Ser Leu Ser Gly Gly
            290                 295                 300
Asn Ser Thr Ser Asn Leu Thr His Thr Met Thr His Leu Gly Ile Ser
305                 310                 315                 320
Arg Gly Met Gly Leu Gly Pro Gly Tyr Asp Ala Pro Gly Leu His Ser
                325                 330                 335
Pro Leu Ser His Pro Ser Leu Gln Ser Ser Leu Ser Asn Pro Asn Leu
                340                 345                 350
Gln Ala Ser Leu Ser Ser Pro Gln Pro Gln Leu Gln Gly Ser His Ser
            355                 360                 365
His Pro Ser Leu Pro Ala Ser Ser Leu Ala Arg His Val Leu Pro Thr
            370                 375                 380
Thr Ser Leu Gly His Pro Ser Leu Ser Ala Pro Ala Leu Ser Ser Ser
385                 390                 395                 400
Ser Ser Ser Ser Ser Thr Ser Ser Pro Val Leu Gly Ala Pro Ser Tyr
                405                 410                 415
Pro Ala Ser Thr Pro Gly Ala Ser Pro His His Arg Arg Val Pro Leu
                420                 425                 430
Ser Pro Leu Ser Leu Leu Ala Gly Pro Ala Asp Ala Arg Arg Ser Gln
            435                 440                 445
Gln Gln Leu Pro Lys Gln Phe Ser Pro Thr Met Ser Pro Thr Leu Ser
            450                 455                 460
Ser Ile Thr Gln Gly Val Pro Leu Asp Thr Ser Lys Leu Ser Thr Asp
465                 470                 475                 480
Gln Arg Leu Pro Pro Tyr Pro Tyr Ser Ser Pro Ser Leu Val Leu Pro
                485                 490                 495
Thr Gln Pro His Thr Pro Lys Ser Leu Gln Pro Gly Leu Pro Ser
                500                 505                 510
Gln Ser Cys Ser Val Gln Ser Ser Gly Gln Pro Pro Gly Arg Gln
            515                 520                 525
Ser His Tyr Gly Thr Pro Tyr Pro Pro Gly Pro Ser Gly His Gly Gln
            530                 535                 540
```

```
Gln Ser Tyr His Arg Pro Met Ser Asp Phe Asn Leu Gly Asn Leu Glu
545                 550                 555                 560

Gln Phe Ser Met Glu Ser Pro Ser Ala Ser Leu Val Leu Asp Pro Pro
            565                 570                 575

Gly Phe Glu Gly Pro Gly Phe Leu Gly Gly Glu Gly Pro Met Gly
        580                 585                 590

Gly Pro Gln Asp Pro His Thr Phe Asn His Gln Asn Leu Thr His Cys
            595                 600                 605

Ser Arg His Gly Ser Gly Pro Asn Ile Ile Leu Thr Gly Asp Ser Ser
    610                 615                 620

Pro Gly Phe Ser Lys Glu Ile Ala Ala Leu Ala Gly Val Pro Gly
625                 630                 635                 640

Phe Glu Val Ser Ala Ala Gly Leu Glu Leu Gly Leu Gly Leu Glu Asp
                645                 650                 655

Glu Leu Arg Met Glu Pro Leu Gly Leu Glu Gly Leu Asn Met Leu Ser
            660                 665                 670

Asp Pro Cys Ala Leu Leu Pro Asp Pro Ala Val Glu Glu Ser Phe Arg
            675                 680                 685

Ser Asp Arg Leu Gln
        690

<210> SEQ ID NO 6
<211> LENGTH: 650
<212> TYPE: PRT
<213> ORGANISM: Artificial Sequence
<220> FEATURE:
<223> OTHER INFORMATION: Synthetic polypeptide

<400> SEQUENCE: 6

Met Ala Thr Ser Asn Asn Pro Arg Lys Phe Ser Glu Lys Ile Ala Leu
1               5                   10                  15

His Asn Gln Lys Gln Ala Glu Glu Thr Ala Ala Phe Glu Glu Val Met
            20                  25                  30

Lys Asp Leu Ser Leu Thr Arg Ala Ala Arg Leu Gln Leu Gln Lys Ser
        35                  40                  45

Gln Tyr Leu Gln Leu Gly Pro Ser Arg Gly Gln Tyr Tyr Gly Gly Ser
    50                  55                  60

Leu Pro Asn Val Asn Gln Ile Gly Ser Gly Thr Met Asp Leu Pro Phe
65                  70                  75                  80

Gln Pro Ser Gly Phe Leu Gly Glu Ala Leu Ala Ala Ala Pro Val Ser
                85                  90                  95

Leu Thr Pro Phe Gln Ser Ser Gly Leu Asp Thr Ser Arg Thr Thr Arg
            100                 105                 110

His His Gly Leu Val Asp Arg Val Tyr Arg Glu Arg Gly Arg Leu Gly
        115                 120                 125

Ser Pro His Arg Arg Pro Leu Ser Val Asp Lys His Gly Arg Gln Ala
    130                 135                 140

Asp Ser Cys Pro Tyr Gly Thr Met Tyr Leu Ser Pro Pro Ala Asp Thr
145                 150                 155                 160

Ser Trp Arg Arg Thr Asn Ser Asp Ser Ala Leu His Gln Ser Thr Met
                165                 170                 175

Thr Pro Thr Gln Pro Glu Ser Phe Ser Ser Gly Ser Gln Asp Val His
            180                 185                 190

Gln Lys Arg Val Leu Leu Leu Thr Val Pro Gly Met Glu Glu Thr Thr
        195                 200                 205
```

-continued

```
Ser Glu Ala Asp Lys Asn Leu Ser Lys Gln Ala Trp Asp Thr Lys Lys
    210                 215                 220
Thr Gly Ser Arg Pro Lys Ser Cys Glu Val Pro Gly Ile Asn Ile Phe
225                 230                 235                 240
Pro Ser Ala Asp Gln Glu Asn Thr Thr Ala Leu Ile Pro Ala Thr His
                245                 250                 255
Asn Thr Gly Gly Ser Leu Pro Asp Leu Thr Asn Ile His Phe Pro Ser
            260                 265                 270
Pro Leu Pro Thr Pro Leu Asp Pro Glu Glu Pro Thr Phe Pro Ala Leu
        275                 280                 285
Ser Ser Ser Ser Ser Thr Gly Asn Leu Ala Ala Asn Leu Thr His Leu
    290                 295                 300
Gly Ile Gly Gly Ala Gly Gln Gly Met Ser Thr Pro Gly Ser Ser Pro
305                 310                 315                 320
Gln His Arg Pro Ala Gly Val Ser Pro Leu Ser Leu Ser Thr Glu Ala
                325                 330                 335
Arg Arg Gln Gln Ala Ser Pro Thr Leu Ser Pro Leu Ser Pro Ile Thr
            340                 345                 350
Gln Ala Val Ala Met Asp Ala Leu Ser Leu Glu Gln Gln Leu Pro Tyr
        355                 360                 365
Ala Phe Phe Thr Gln Ala Gly Ser Gln Gln Pro Pro Pro Gln Pro Gln
    370                 375                 380
Pro Pro Pro Pro Pro Pro Ala Ser Gln Gln Pro Pro Pro Pro Pro Pro
385                 390                 395                 400
Pro Pro Gln Ala Pro Val Arg Leu Pro Pro Gly Gly Pro Leu Leu Pro
                405                 410                 415
Ser Ala Ser Leu Thr Arg Gly Pro Gln Pro Pro Leu Ala Val Thr
            420                 425                 430
Val Pro Ser Ser Leu Pro Gln Ser Pro Pro Glu Asn Pro Gly Gln Pro
        435                 440                 445
Ser Met Gly Ile Asp Ile Ala Ser Ala Pro Ala Leu Gln Gln Tyr Arg
    450                 455                 460
Thr Ser Ala Gly Ser Pro Ala Asn Gln Ser Pro Thr Ser Pro Val Ser
465                 470                 475                 480
Asn Gln Gly Phe Ser Pro Gly Ser Ser Pro Gln His Thr Ser Thr Leu
                485                 490                 495
Gly Ser Val Phe Gly Asp Ala Tyr Tyr Glu Gln Gln Met Ala Ala Arg
            500                 505                 510
Gln Ala Asn Ala Leu Ser His Gln Leu Glu Gln Phe Asn Met Met Glu
        515                 520                 525
Asn Ala Ile Ser Ser Ser Ser Leu Tyr Ser Pro Gly Ser Thr Leu Asn
    530                 535                 540
Tyr Ser Gln Ala Ala Met Met Gly Leu Thr Gly Ser His Gly Ser Leu
545                 550                 555                 560
Pro Asp Ser Gln Gln Leu Gly Tyr Ala Ser His Ser Gly Ile Pro Asn
                565                 570                 575
Ile Ile Leu Thr Val Thr Gly Glu Ser Pro Pro Ser Leu Ser Lys Glu
            580                 585                 590
Leu Thr Ser Ser Leu Ala Gly Val Gly Asp Val Ser Phe Asp Ser Asp
        595                 600                 605
Ser Gln Phe Pro Leu Asp Glu Leu Lys Ile Asp Pro Leu Thr Leu Asp
    610                 615                 620
```

```
Gly Leu His Met Leu Asn Asp Pro Asp Met Val Leu Ala Asp Pro Ala
625                 630                 635                 640

Thr Glu Asp Thr Phe Arg Met Asp Arg Leu
                645                 650

<210> SEQ ID NO 7
<211> LENGTH: 619
<212> TYPE: PRT
<213> ORGANISM: Artificial Sequence
<220> FEATURE:
<223> OTHER INFORMATION: Synthetic polypeptide

<400> SEQUENCE: 7

Met Ala Ala Ser Pro Gly Ser Gly Ser Ala Asn Pro Arg Lys Phe Ser
1               5                   10                  15

Glu Lys Ile Ala Leu His Thr Gln Arg Gln Ala Glu Glu Thr Arg Ala
                20                  25                  30

Phe Glu Gln Leu Met Thr Asp Leu Thr Leu Ser Arg Val Gln Phe Gln
                35                  40                  45

Lys Leu Gln Gln Leu Arg Leu Thr Gln Tyr His Gly Gly Ser Leu Pro
50                  55                  60

Asn Val Ser Gln Leu Arg Ser Ser Ala Ser Glu Phe Gln Pro Ser Phe
65                  70                  75                  80

His Gln Ala Asp Asn Val Arg Gly Thr Arg His His Gly Leu Val Glu
                85                  90                  95

Arg Pro Ser Arg Asn Arg Phe His Pro Leu His Arg Arg Ser Gly Asp
                100                 105                 110

Lys Pro Gly Arg Gln Phe Asp Gly Ser Ala Phe Gly Ala Asn Tyr Ser
                115                 120                 125

Ser Gln Pro Leu Asp Glu Ser Trp Pro Arg Gln Gln Pro Pro Trp Lys
130                 135                 140

Asp Glu Lys His Pro Gly Phe Arg Leu Thr Ser Ala Leu Asn Arg Thr
145                 150                 155                 160

Asn Ser Asp Ser Ala Leu His Thr Ser Ala Leu Ser Thr Lys Pro Gln
                165                 170                 175

Asp Pro Tyr Gly Gly Gly Gln Ser Ala Trp Pro Ala Pro Tyr Met
                180                 185                 190

Gly Phe Cys Asp Gly Glu Asn Asn Gly His Gly Glu Val Ala Ser Phe
                195                 200                 205

Pro Gly Pro Leu Lys Glu Glu Asn Leu Asn Val Pro Lys Pro Leu
210                 215                 220

Pro Lys Gln Leu Trp Glu Thr Lys Glu Ile Gln Ser Leu Ser Gly Arg
225                 230                 235                 240

Pro Arg Ser Cys Asp Val Gly Gly Asn Ala Phe Pro His Asn Gly
                245                 250                 255

Gln Asn Leu Gly Leu Ser Pro Phe Leu Gly Thr Leu Asn Thr Gly Gly
                260                 265                 270

Ser Leu Pro Asp Leu Thr Asn Leu His Tyr Ser Thr Pro Leu Pro Ala
                275                 280                 285

Ser Leu Asp Thr Thr Asp His His Phe Gly Ser Met Ser Val Gly Asn
                290                 295                 300

Ser Val Asn Asn Ile Pro Ala Ala Met Thr His Leu Gly Ile Arg Ser
305                 310                 315                 320

Ser Ser Gly Leu Gln Ser Ser Arg Ser Asn Pro Ser Ile Gln Ala Thr
                325                 330                 335
```

-continued

```
Leu Asn Lys Thr Val Leu Ser Ser Ser Leu Asn Asn His Pro Gln Thr
            340                 345                 350

Ser Val Pro Asn Ala Ser Ala Leu His Pro Ser Leu Arg Leu Phe Ser
            355                 360                 365

Leu Ser Asn Pro Ser Leu Ser Thr Thr Asn Leu Ser Gly Pro Ser Arg
            370                 375                 380

Arg Arg Gln Pro Pro Val Ser Pro Leu Thr Leu Ser Pro Gly Pro Glu
385                 390                 395                 400

Ala His Gln Gly Phe Ser Arg Gln Leu Ser Thr Ser Pro Leu Ala
                405                 410                 415

Pro Tyr Pro Thr Ser Gln Met Val Ser Ser Asp Arg Ser Gln Leu Ser
            420                 425                 430

Phe Leu Pro Thr Glu Ala Gln Ala Gln Val Ser Pro Pro Pro Tyr
            435                 440                 445

Pro Ala Pro Gln Glu Leu Thr Gln Pro Leu Leu Gln Gln Pro Arg Ala
        450                 455                 460

Pro Glu Ala Pro Ala Gln Gln Pro Gln Ala Ala Ser Ser Leu Pro Gln
465                 470                 475                 480

Ser Asp Phe Gln Leu Leu Pro Ala Gln Gly Ser Ser Leu Thr Asn Phe
                485                 490                 495

Phe Pro Asp Val Gly Phe Asp Gln Gln Ser Met Arg Pro Gly Pro Ala
            500                 505                 510

Phe Pro Gln Gln Val Pro Leu Val Gln Gln Gly Ser Arg Glu Leu Gln
            515                 520                 525

Asp Ser Phe His Leu Arg Pro Ser Pro Tyr Ser Asn Cys Gly Ser Leu
    530                 535                 540

Pro Asn Thr Ile Leu Pro Glu Asp Ser Ser Thr Ser Leu Phe Lys Asp
545                 550                 555                 560

Leu Asn Ser Ala Leu Ala Gly Leu Pro Glu Val Ser Leu Asn Val Asp
                565                 570                 575

Thr Pro Phe Pro Leu Glu Glu Glu Leu Gln Ile Glu Pro Leu Ser Leu
            580                 585                 590

Asp Gly Leu Asn Met Leu Ser Asp Ser Ser Met Gly Leu Leu Asp Pro
            595                 600                 605

Ser Val Glu Glu Thr Phe Arg Ala Asp Arg Leu
            610                 615
```